US012576040B2

(12) United States Patent
Buschmann et al.

(10) Patent No.: US 12,576,040 B2
(45) Date of Patent: Mar. 17, 2026

(54) IONIZABLE LIPIDS AND METHODS OF MANUFACTURE AND USE THEREOF

(71) Applicants: George Mason Research Foundation, Inc., Fairfax, VA (US); The Trustees of the University of Pennsylvania, Philadelphia, PA (US)

(72) Inventors: Michael Daro Buschmann, Fairfax, VA (US); Mikell Paige, Fairfax, VA (US); Suman Alishetty, Fairfax, VA (US); Manuel Carrasco, Fairfax, VA (US); Mohamad Gabriel Alameh, Fairfax, VA (US); Drew Weissman, Fairfax, VA (US)

(73) Assignees: The Trustees of the University of Pennsylvania, Philadelphia, PA (US); George Mason Research Foundation, Inc., Fairfax, VA (US)

( * ) Notice: Subject to any disclaimer, the term of this patent is extended or adjusted under 35 U.S.C. 154(b) by 566 days.

(21) Appl. No.: 17/500,486

(22) Filed: Oct. 13, 2021

(65) Prior Publication Data

US 2022/0218622 A1 Jul. 14, 2022

Related U.S. Application Data

(60) Provisional application No. 63/179,885, filed on Apr. 26, 2021, provisional application No. 63/179,872, filed on Apr. 26, 2021, provisional application No. 63/091,616, filed on Oct. 14, 2020, provisional application No. 63/091,603, filed on Oct. 14, 2020.

(51) Int. Cl.

| | |
|---|---|
| ***C07D 295/13*** | (2006.01) |
| ***A61K 9/127*** | (2006.01) |
| ***A61K 9/51*** | (2006.01) |
| ***A61K 31/7088*** | (2006.01) |
| ***A61K 31/7105*** | (2006.01) |
| ***A61K 47/18*** | (2017.01) |
| ***A61K 47/28*** | (2006.01) |
| ***A61P 37/04*** | (2006.01) |
| ***B82Y 5/00*** | (2011.01) |
| ***C07C 229/16*** | (2006.01) |
| ***C07D 207/09*** | (2006.01) |
| ***C07D 211/26*** | (2006.01) |
| ***C12N 15/88*** | (2006.01) |
| *A61K 48/00* | (2006.01) |

(52) U.S. Cl.

CPC ............ *A61K 9/5123* (2013.01); *A61K 9/127* (2013.01); *A61K 31/7088* (2013.01); *A61K 31/7105* (2013.01); *A61K 47/18* (2013.01); *A61K 47/28* (2013.01); *A61P 37/04* (2018.01); *B82Y 5/00* (2013.01); *C07C 229/16* (2013.01); *C07D 207/09* (2013.01); *C07D 211/26* (2013.01); *C07D 295/13* (2013.01); *C12N 15/88* (2013.01); *A61K 48/00* (2013.01)

(58) Field of Classification Search

CPC .................................................. C07D 295/13

USPC ........................................................ 544/402

See application file for complete search history.

(56) References Cited

U.S. PATENT DOCUMENTS

| | | | |
|---|---|---|---|
| 4,987,071 | A | 1/1991 | Cech et al. |
| 5,589,332 | A | 12/1996 | Shih et al. |
| 5,741,679 | A | 4/1998 | George et al. |
| 5,834,186 | A | 11/1998 | George et al. |
| 5,837,282 | A | 11/1998 | Fenske et al. |
| 5,849,902 | A | 12/1998 | Arrow et al. |
| 5,871,914 | A | 2/1999 | Nathan |
| 5,989,912 | A | 11/1999 | Arrow et al. |
| 6,197,553 | B1 | 3/2001 | Lee et al. |
| 7,074,596 | B2 | 7/2006 | Darzynkiewicz et al. |
| 7,745,651 | B2 | 6/2010 | Heyes et al. |
| 7,811,602 | B2 | 10/2010 | Cullis et al. |
| 8,058,069 | B2 | 11/2011 | Yaworski et al. |
| 8,278,036 | B2 | 10/2012 | Kariko et al. |
| 8,329,070 | B2 | 12/2012 | Maclachlan et al. |

(Continued)

FOREIGN PATENT DOCUMENTS

| | | | |
|---|---|---|---|
| AU | 2010326132 | A1 | 7/2012 |
| AU | 2012267531 | A1 | 12/2013 |

(Continued)

OTHER PUBLICATIONS

Zhu et al. Polymer Chemistry (2011), 2(8), 1761-1768.*

(Continued)

*Primary Examiner* — Kahsay Habte

(74) *Attorney, Agent, or Firm* — Choate, Hall & Stewart LLP; Michael A. Shinall; Lauren E. Markham

(57) ABSTRACT

The invention encompasses novel ionizable lipids compounds and their use in lipid nanoparticles delivery systems that are useful in the delivery of nucleic acids to a mammalian subject that can be included for use, for example, as cancer vaccines, gene editing therapeutics, delivery of nucleic acid (e.g., mRNA) encoding antibodies, vaccines for infectious disease, and protein replacement therapeutics. Additionally, the invention encompasses compositions and therapeutics comprising the ionizable lipids in the lipid nanoparticles and the use of the composition and therapeutics for the preparation of a pharmaceutical composition, especially a vaccine, (e.g., for use in the prophylaxis or treatment of infectious diseases, tumor or cancer diseases, rare diseases, allergies, or autoimmune diseases). The invention encompasses methods of treatment or prophylaxis of the aforementioned diseases.

13 Claims, 142 Drawing Sheets

Specification includes a Sequence Listing.

(56) References Cited

U.S. PATENT DOCUMENTS 8,569,256 B2 10/2013 Heyes et al.
8,702,942 B2 4/2014 Corbett et al.
8,754,062 B2 6/2014 De Fougerolles et al.
8,853,377 B2 10/2014 Guild et al.
8,936,942 B2 1/2015 Heyes et al.
9,018,187 B2 4/2015 Heyes et al.
9,061,021 B2 6/2015 Guild et al.
9,139,554 B2 9/2015 Hope et al.
9,181,321 B2 11/2015 Heartlein et al.
9,227,917 B2 1/2016 Anderson et al.
9,308,281 B2 4/2016 Guild et al.
9,352,042 B2 5/2016 Heyes et al.
9,364,435 B2 6/2016 Yaworski et al.
9,428,751 B2 8/2016 Macdonald et al.
9,439,968 B2 9/2016 Anderson et al.
9,522,176 B2 12/2016 Derosa et al.
9,567,296 B2 2/2017 Payne et al.
9,580,708 B2 2/2017 Uhlmann et al.
9,597,413 B2 3/2017 Guild et al.
9,629,804 B2 4/2017 Heartlein et al.
9,668,980 B2 6/2017 Derosa et al.
9,713,626 B2 7/2017 Heartlein et al.
9,717,690 B2 8/2017 Guild et al.
9,732,340 B2 8/2017 Uhlmann et al.
9,732,341 B2 8/2017 Uhlmann et al.
9,738,593 B2 8/2017 Ansell et al.
9,790,494 B2 10/2017 Uhlmann et al.
9,850,269 B2 12/2017 Derosa et al.
9,868,692 B2 1/2018 Benenato
9,872,900 B2 1/2018 Ciaramella et al.
9,925,277 B2 3/2018 Almarsson et al.
9,926,560 B2 3/2018 Maclachlan et al.
9,943,595 B2 4/2018 Derosa et al.
9,950,068 B2 4/2018 De Fougerolles et al.
9,956,271 B2 5/2018 Guild et al.
9,957,499 B2 5/2018 Heartlein et al.
9,970,047 B2 5/2018 Heartlein et al.
10,022,455 B2 7/2018 Derosa et al.
10,041,074 B2 8/2018 Ozsolak
10,041,091 B2 8/2018 Cullis et al.
10,052,284 B2 8/2018 Heartlein et al.
10,058,623 B2 8/2018 Krieg et al.
10,059,941 B2 8/2018 Krieg et al.
10,064,959 B2 9/2018 Schrum et al.
10,072,057 B2 9/2018 Hoge et al.
10,093,924 B2 10/2018 Uhlmann et al.
10,106,490 B2 10/2018 Du
10,137,087 B2 11/2018 Derosa et al.
10,138,213 B2 11/2018 Derosa et al.
10,143,758 B2 12/2018 Guild et al.
10,144,942 B2 12/2018 Strack-Logue et al.
10,155,785 B2 12/2018 Derosa et al.
10,172,924 B2 1/2019 Derosa et al.
10,174,315 B2 1/2019 Krieg et al.
10,174,323 B2 1/2019 Krieg et al.
10,174,328 B2 1/2019 Krieg et al.
10,208,295 B2 2/2019 Derosa et al.
10,221,127 B2 3/2019 Du et al.
10,232,055 B2 3/2019 Kariko et al.
10,238,754 B2 3/2019 Guild et al.
10,245,229 B2 4/2019 Heartlein et al.
10,258,698 B2 4/2019 Hoge et al.
10,266,485 B2 4/2019 Benenato
10,266,559 B2 4/2019 Derosa et al.
10,266,843 B2 4/2019 Derosa et al.
10,286,082 B2 5/2019 Derosa et al.
10,286,083 B2 5/2019 Derosa et al.
10,293,057 B2 5/2019 Derosa et al.
10,350,303 B1 7/2019 Guild et al.
10,413,618 B2 9/2019 Guild et al.
10,420,791 B2 9/2019 Heartlein et al.
10,428,349 B2 10/2019 Derosa et al.
10,442,756 B2 10/2019 Benenato et al.
10,471,153 B2 11/2019 DeROSA et al.
10,485,885 B2 11/2019 Besin et al.
10,493,031 B2 12/2019 Heartlein et al.
10,493,166 B2 12/2019 Derosa et al.
10,507,183 B2 12/2019 Guild et al.
10,507,249 B2 12/2019 Guild et al.
10,556,855 B1 2/2020 Angel et al.
10,561,732 B2 2/2020 Heyes et al.
10,576,166 B2 3/2020 Derosa et al.
10,577,403 B2 3/2020 De et al.
10,584,165 B2 3/2020 Heartlein et al.
10,626,393 B2 4/2020 Lee et al.
10,646,504 B2 5/2020 DeRosa et al.
10,653,767 B2 5/2020 Ciaramella et al.
10,702,600 B1 7/2020 Ciaramella et al.
10,703,789 B2 7/2020 De et al.
2002/0182643 A1 12/2002 Marks et al.
2003/0077829 A1 4/2003 Maclachlan
2003/0236266 A1 12/2003 Friebe et al.
2005/0118253 A1 6/2005 Maclachlan et al.
2006/0051405 A1 3/2006 Maclachlan et al.
2007/0042031 A1 2/2007 Maclachlan et al.
2007/0049581 A1 3/2007 Mueller et al.
2010/0021713 A1 1/2010 Lane et al.
2010/0055169 A1 3/2010 Dande et al.
2010/0166714 A1 7/2010 Chien et al.
2011/0003327 A1 1/2011 Chien et al.
2011/0033430 A1 2/2011 Chien et al.
2011/0244026 A1 10/2011 Guild et al.
2012/0009222 A1 1/2012 Nguyen
2012/0142756 A1 6/2012 Guild et al.
2012/0251618 A1 10/2012 Schrum et al.
2012/0276209 A1 11/2012 Cullis et al.
2013/0017223 A1 1/2013 Hope et al.
2013/0079383 A1 3/2013 Bennett et al.
2013/0090372 A1 4/2013 Budzik et al.
2013/0195967 A1 8/2013 Guild et al.
2014/0045913 A1 2/2014 Kuboyama et al.
2014/0206753 A1 7/2014 Guild et al.
2014/0288160 A1 9/2014 Guild et al.
2014/0294938 A1 10/2014 Guild et al.
2014/0294939 A1 10/2014 Guild et al.
2014/0294940 A1 10/2014 Guild et al.
2014/0371302 A1 12/2014 Afeyan et al.
2015/0004217 A1 1/2015 Guild et al.
2015/0030576 A1 1/2015 Bancel
2015/0038556 A1 2/2015 Heartlein et al.
2015/0099791 A1 4/2015 Krieg et al.
2015/0110857 A1 4/2015 DeRosa et al.
2015/0110858 A1 4/2015 DeRosa et al.
2015/0110859 A1 4/2015 Heartlein et al.
2015/0133362 A1 5/2015 Krieg et al.
2015/0133528 A1 5/2015 Krieg et al.
2015/0140070 A1 5/2015 Heartlein et al.
2015/0157565 A1 6/2015 Heartlein et al.
2015/0159160 A1 6/2015 Krieg et al.
2015/0218560 A1 8/2015 Krieg et al.
2015/0232858 A1 8/2015 Ozsolak
2015/0239926 A1 8/2015 Payne et al.
2015/0247141 A1 9/2015 Uhlmann et al.
2015/0252364 A1 9/2015 Krieg et al.
2015/0267192 A1 9/2015 Heartlein et al.
2015/0299695 A1 10/2015 Uhlmann et al.
2015/0315585 A1 11/2015 Uhlmann et al.
2015/0315586 A1 11/2015 Uhlmann et al.
2015/0315587 A1 11/2015 Uhlmann et al.
2015/0315588 A1 11/2015 Uhlmann et al.
2015/0366997 A1 12/2015 Guild et al.
2015/0376144 A1 12/2015 Derosa et al.
2015/0376220 A1 12/2015 Derosa et al.
2016/0002705 A1 1/2016 Heartlein et al.
2016/0031928 A1 2/2016 Derosa et al.
2016/0032356 A1 2/2016 Heartlein et al.
2016/0038612 A1 2/2016 Hoge et al.
2016/0040154 A1 2/2016 Heartlein et al.
2016/0101160 A1 4/2016 Guild et al.
2016/0106772 A1 4/2016 Heartlein et al.
2016/0122727 A1 5/2016 Heartlein et al.
2016/0158354 A1 6/2016 Derosa et al.
2016/0184458 A1 6/2016 Heartlein
2016/0222391 A1 8/2016 Krieg et al.

(56) References Cited

U.S. PATENT DOCUMENTS

| | | | |
|---|---|---|---|
| 2016/0243259 | A1 | 8/2016 | Almarsson et al. |
| 2016/0287725 | A1 | 10/2016 | Derosa et al. |
| 2016/0324940 | A1 | 11/2016 | Derosa et al. |
| 2016/0376224 | A1 | 12/2016 | Du et al. |
| 2017/0073648 | A1 | 3/2017 | Derosa et al. |
| 2017/0143848 | A1 | 5/2017 | Calias et al. |
| 2017/0159093 | A1 | 6/2017 | Strack-Logue et al. |
| 2017/0210697 | A1 | 7/2017 | Benenato et al. |
| 2017/0211065 | A1 | 7/2017 | Uhlmann et al. |
| 2017/0239371 | A1 | 8/2017 | Guild et al. |
| 2017/0246319 | A1 | 8/2017 | Derosa et al. |
| 2017/0281542 | A1 | 10/2017 | Heartlein et al. |
| 2017/0314041 | A1 | 11/2017 | Derosa et al. |
| 2018/0008543 | A1 | 1/2018 | Guild et al. |
| 2018/0008680 | A1 | 1/2018 | Derosa et al. |
| 2018/0015116 | A1 | 1/2018 | Heartlein et al. |
| 2018/0028445 | A1 | 2/2018 | Derosa et al. |
| 2018/0028557 | A1 | 2/2018 | Ozsolak |
| 2018/0030444 | A1 | 2/2018 | Uhlmann et al. |
| 2018/0030452 | A1 | 2/2018 | Ozsolak |
| 2018/0085474 | A1 | 3/2018 | Almarsson et al. |
| 2018/0092971 | A1 | 4/2018 | Manoharan et al. |
| 2018/0112234 | A9 | 4/2018 | Dombrowski et al. |
| 2018/0125937 | A1 | 5/2018 | De et al. |
| 2018/0125989 | A1 | 5/2018 | DeRosa et al. |
| 2018/0127449 | A1 | 5/2018 | Derosa et al. |
| 2018/0148719 | A1 | 5/2018 | Lee et al. |
| 2018/0153822 | A1 | 6/2018 | Karve et al. |
| 2018/0169020 | A1 | 6/2018 | Guild et al. |
| 2018/0185516 | A1 | 7/2018 | Ansell et al. |
| 2018/0214579 | A1 | 8/2018 | Almarsson et al. |
| 2018/0236047 | A1 | 8/2018 | Guild et al. |
| 2018/0237766 | A1 | 8/2018 | Heartlein et al. |
| 2018/0251754 | A1 | 9/2018 | Derosa et al. |
| 2018/0251755 | A1 | 9/2018 | Abysalh et al. |
| 2018/0256741 | A1 | 9/2018 | Dias et al. |
| 2018/0256750 | A1 | 9/2018 | Butora et al. |
| 2018/0271938 | A1 | 9/2018 | Bancel et al. |
| 2018/0272002 | A1 | 9/2018 | Derosa et al. |
| 2018/0272003 | A1 | 9/2018 | Derosa et al. |
| 2018/0272004 | A1 | 9/2018 | Derosa et al. |
| 2018/0272005 | A1 | 9/2018 | Derosa et al. |
| 2018/0291425 | A1 | 10/2018 | Heartlein et al. |
| 2018/0298384 | A1 | 10/2018 | Krieg et al. |
| 2018/0311176 | A1 | 11/2018 | Ozsolak et al. |
| 2018/0311336 | A1 | 11/2018 | Ciaramella et al. |
| 2018/0312839 | A1 | 11/2018 | Bhat et al. |
| 2018/0333457 | A1 | 11/2018 | Heartlein et al. |
| 2018/0353616 | A1 | 12/2018 | Guild et al. |
| 2018/0360961 | A1 | 12/2018 | Derosa et al. |
| 2018/0369144 | A1 | 12/2018 | Heartlein et al. |
| 2018/0369413 | A1 | 12/2018 | Heartlein et al. |
| 2018/0369419 | A1 | 12/2018 | Benenato et al. |
| 2019/0000932 | A1 | 1/2019 | Martini et al. |
| 2019/0000933 | A1 | 1/2019 | Martini et al. |
| 2019/0002890 | A1 | 1/2019 | Martini et al. |
| 2019/0015501 | A1 | 1/2019 | Ciaramella et al. |
| 2019/0022247 | A1 | 1/2019 | Ansell et al. |
| 2019/0032087 | A1 | 1/2019 | Cullis et al. |
| 2019/0054112 | A1 | 2/2019 | Gregoire |
| 2019/0055553 | A1 | 2/2019 | Barsoum et al. |
| 2019/0062743 | A1 | 2/2019 | Uhlmann et al. |
| 2019/0100753 | A1 | 4/2019 | Heartlein et al. |
| 2019/0111153 | A1 | 4/2019 | Stephan et al. |
| 2019/0127708 | A1 | 5/2019 | Heartlein et al. |
| 2019/0134164 | A1 | 5/2019 | Derosa et al. |
| 2019/0142971 | A1 | 5/2019 | Hoge et al. |
| 2019/0144480 | A1 | 5/2019 | Derosa et al. |
| 2019/0151461 | A1 | 5/2019 | Brown et al. |
| 2019/0175517 | A1 | 6/2019 | Martini et al. |
| 2019/0175761 | A1 | 6/2019 | Guild et al. |
| 2019/0185435 | A1 | 6/2019 | Derosa et al. |
| 2019/0192688 | A1 | 6/2019 | Askew et al. |
| 2019/0192689 | A1 | 6/2019 | Guild et al. |
| 2019/0192690 | A1 | 6/2019 | Guild et al. |
| 2019/0211314 | A1 | 7/2019 | Derosa et al. |
| 2019/0216730 | A1 | 7/2019 | Heartlein et al. |
| 2019/0216843 | A1 | 7/2019 | DeRosa et al. |
| 2019/0224326 | A1 | 7/2019 | Bhat et al. |
| 2019/0240339 | A1 | 8/2019 | Yaworski et al. |
| 2019/0249191 | A1 | 8/2019 | Derosa et al. |
| 2019/0263850 | A1 | 8/2019 | Derosa et al. |
| 2019/0274968 | A1 | 9/2019 | Weissman et al. |
| 2019/0298657 | A1 | 10/2019 | Martini et al. |
| 2019/0298755 | A1 | 10/2019 | Karve et al. |
| 2019/0314284 | A1 | 10/2019 | Guild et al. |
| 2019/0314291 | A1 | 10/2019 | Besin et al. |
| 2019/0314527 | A1 | 10/2019 | De et al. |
| 2019/0316121 | A1 | 10/2019 | Smith et al. |
| 2019/0321489 | A1 | 10/2019 | Guild et al. |
| 2019/0359556 | A1 | 11/2019 | Du et al. |
| 2019/0388562 | A1 | 12/2019 | Payne et al. |
| 2019/0388563 | A1 | 12/2019 | Heartlein |
| 2020/0016274 | A1 | 1/2020 | Karve et al. |
| 2020/0022921 | A1 | 1/2020 | Karve et al. |
| 2020/0032274 | A1 | 1/2020 | Mauger et al. |
| 2020/0038515 | A1 | 2/2020 | DeRosa et al. |
| 2020/0040333 | A9 | 2/2020 | Krieg et al. |
| 2020/0046752 | A1 | 2/2020 | Heartlein et al. |
| 2020/0046830 | A1 | 2/2020 | Hooper et al. |
| 2020/0069599 | A1 | 3/2020 | Smith et al. |
| 2020/0078299 | A1 | 3/2020 | Heartlein et al. |
| 2020/0078313 | A1 | 3/2020 | Roy et al. |
| 2020/0085973 | A1 | 3/2020 | Guild et al. |
| 2020/0093936 | A1 | 3/2020 | Muzykantov et al. |
| 2020/0109113 | A1 | 4/2020 | Payne et al. |
| 2020/0113832 | A1 | 4/2020 | Yaworski et al. |
| 2020/0121809 | A1 | 4/2020 | Hope et al. |
| 2020/0129445 | A1 | 4/2020 | Patel et al. |
| 2020/0155691 | A1 | 5/2020 | DeRosa et al. |
| 2020/0157157 | A1 | 5/2020 | Karve et al. |
| 2020/0157205 | A1 | 5/2020 | Heartlein et al. |
| 2020/0163878 | A1 | 5/2020 | Baumhof et al. |
| 2020/0172472 | A1 | 6/2020 | Du |
| 2020/0206362 | A1 | 7/2020 | Besin et al. |
| 2020/0237671 | A1 | 7/2020 | Guild et al. |
| 2020/0247861 | A1 | 8/2020 | De et al. |
| 2020/0254086 | A1 | 8/2020 | Hoge et al. |
| 2020/0283372 | A1 | 9/2020 | Du |
| 2020/0306191 | A1 | 10/2020 | Schariter et al. |
| 2020/0385721 | A1 | 12/2020 | Lee et al. |
| 2021/0161818 | A1 | 6/2021 | Haas et al. |
| 2021/0169804 | A1 | 6/2021 | Patwardhan et al. |
| 2021/0222173 | A1 | 7/2021 | Dymek et al. |
| 2021/0230112 | A1 | 7/2021 | Hamilton et al. |
| 2021/0236647 | A1 | 8/2021 | Wu et al. |
| 2021/0244675 | A1 | 8/2021 | Landfester et al. |
| 2021/0252163 | A1 | 8/2021 | Payne et al. |
| 2021/0254097 | A1 | 8/2021 | O'Dea et al. |
| 2021/0290756 | A1 | 9/2021 | Sullivan et al. |
| 2021/0292303 | A1 | 9/2021 | Brown |
| 2021/0299172 | A1 | 9/2021 | Getts et al. |
| 2021/0299261 | A1 | 9/2021 | Rajeev et al. |
| 2021/0317468 | A1 | 10/2021 | Limphong et al. |
| 2022/0218612 | A1 | 7/2022 | Karve et al. |
| 2022/0235377 | A1 | 7/2022 | Buschmann et al. |

FOREIGN PATENT DOCUMENTS

| | | | |
|---|---|---|---|
| AU | 2010326132 | B2 | 8/2014 |
| AU | 2010326132 | B9 | 10/2014 |
| AU | 2014250713 | A1 | 11/2014 |
| AU | 2013262649 | A1 | 1/2015 |
| AU | 2013262656 | A1 | 1/2015 |
| AU | 2013262663 | A1 | 1/2015 |
| AU | 2013262699 | A1 | 1/2015 |
| AU | 2013262700 | A1 | 1/2015 |
| AU | 2013271392 | A1 | 1/2015 |
| AU | 2014239250 | A1 | 8/2015 |
| AU | 2014239264 | A1 | 8/2015 |
| AU | 2014340149 | A1 | 5/2016 |
| AU | 2014340155 | A1 | 5/2016 |
| AU | 2014250713 | B2 | 7/2016 |
| AU | 2016250459 | A1 | 11/2016 |

(56) References Cited

FOREIGN PATENT DOCUMENTS

| | | | |
|---|---|---|---|
| AU | 2015279968 | A1 | 1/2017 |
| AU | 2012267578 | B2 | 4/2017 |
| AU | 2012267531 | B2 | 6/2017 |
| AU | 2015357562 | A1 | 6/2017 |
| AU | 2017204509 | A1 | 7/2017 |
| AU | 2012308320 | B2 | 2/2018 |
| AU | 2013271392 | B2 | 2/2018 |
| AU | 2016338559 | A1 | 5/2018 |
| AU | 2014239562 | B2 | 7/2018 |
| AU | 2013315225 | B2 | 11/2018 |
| AU | 2014340155 | B2 | 11/2018 |
| AU | 2017266932 | A1 | 11/2018 |
| AU | 2017266948 | A1 | 12/2018 |
| AU | 2017268396 | A1 | 12/2018 |
| AU | 2017283479 | A1 | 12/2018 |
| AU | 2014236305 | B2 | 1/2019 |
| AU | 2019200474 | A1 | 2/2019 |
| AU | 2017204509 | B2 | 4/2019 |
| AU | 2019201924 | A1 | 4/2019 |
| AU | 2017356190 | A1 | 5/2019 |
| AU | 2017357748 | A1 | 6/2019 |
| AU | 2017204509 | C1 | 7/2019 |
| AU | 2014340083 | B2 | 8/2019 |
| AU | 2017266932 | A9 | 8/2019 |
| AU | 2014340092 | B2 | 9/2019 |
| AU | 2018203985 | B2 | 9/2019 |
| AU | 2018224318 | A1 | 9/2019 |
| AU | 2018224326 | A1 | 9/2019 |
| AU | 2019240643 | A1 | 10/2019 |
| AU | 2015266764 | B2 | 11/2019 |
| AU | 2015279968 | B2 | 11/2019 |
| AU | 2018268859 | A1 | 12/2019 |
| AU | 2020200489 | A1 | 2/2020 |
| AU | 2020200576 | A1 | 2/2020 |
| AU | 2020202322 | A1 | 4/2020 |
| AU | 2018203310 | B2 | 5/2020 |
| AU | 2018202634 | B2 | 10/2020 |
| AU | 2017248189 | B2 | 4/2021 |
| AU | 2019200789 | B2 | 4/2021 |
| AU | 2021201646 | A1 | 4/2021 |
| AU | 2019202582 | B2 | 5/2021 |
| AU | 2015249312 | B2 | 7/2021 |
| AU | 2016233135 | B2 | 7/2021 |
| AU | 2016219052 | B2 | 6/2022 |
| BR | 112014028634 | A2 | 6/2017 |
| BR | 112016009014 | A2 | 9/2017 |
| BR | 112014028631 | A2 | 10/2017 |
| BR | 112015022505 | A2 | 10/2017 |
| BR | 112015022507 | A2 | 10/2017 |
| BR | 112015022660 | A2 | 10/2017 |
| BR | 112015022868 | A2 | 11/2017 |
| BR | 112016024632 | A2 | 1/2018 |
| BR | 112016027705 | A2 | 1/2018 |
| BR | 112016030292 | A2 | 1/2018 |
| BR | 112014030677 | A2 | 7/2022 |
| CA | 2782676 | A1 | 6/2011 |
| CA | 2838063 | A1 | 12/2012 |
| CA | 2838069 | A1 | 12/2012 |
| CA | 2853689 | A1 | 6/2013 |
| CA | 2873766 | A1 | 11/2013 |
| CA | 2873769 | A1 | 11/2013 |
| CA | 2873794 | A1 | 11/2013 |
| CA | 2873797 | A1 | 11/2013 |
| CA | 2873809 | A1 | 11/2013 |
| CA | 2876155 | A1 | 12/2013 |
| CA | 2884608 | A1 | 3/2014 |
| CA | 2902892 | A1 | 9/2014 |
| CA | 2903487 | A1 | 9/2014 |
| CA | 2903488 | A1 | 9/2014 |
| CA | 2904151 | A1 | 9/2014 |
| CA | 2921459 | A1 | 2/2015 |
| CA | 2928040 | A1 | 4/2015 |
| CA | 2928078 | A1 | 4/2015 |
| CA | 2928186 | A1 | 4/2015 |
| CA | 2928188 | A1 | 4/2015 |
| CA | 2944800 | A1 | 10/2015 |
| CA | 2949106 | A1 | 12/2015 |
| CA | 2952824 | A1 | 12/2015 |
| CA | 2976576 | A1 | 8/2016 |
| CA | 2979695 | A1 | 9/2016 |
| CA | 3001852 | A1 | 4/2017 |
| CA | 3020343 | A1 | 10/2017 |
| CA | 3024507 | A1 | 11/2017 |
| CA | 3024624 | A1 | 11/2017 |
| CA | 3024625 | A1 | 11/2017 |
| CA | 3027312 | A1 | 12/2017 |
| CA | 3034681 | A1 | 1/2018 |
| CA | 3041350 | A1 | 5/2018 |
| CA | 3043033 | A1 | 5/2018 |
| CA | 3054062 | A1 | 8/2018 |
| CA | 3054321 | A1 | 8/2018 |
| CA | 3054323 | A1 | 8/2018 |
| CA | 3063531 | A1 | 11/2018 |
| CA | 3063989 | A1 | 12/2018 |
| CA | 2902884 | C | 5/2021 |
| CA | 2848753 | C | 7/2022 |
| CN | 102525926 | A | 7/2012 |
| CN | 103906527 | A | 7/2014 |
| CN | 104519915 | A | 4/2015 |
| CN | 104540946 | A | 4/2015 |
| CN | 104540947 | A | 4/2015 |
| CN | 104583398 | A | 4/2015 |
| CN | 104583399 | A | 4/2015 |
| CN | 104583401 | A | 4/2015 |
| CN | 105026411 | A | 11/2015 |
| CN | 105051190 | A | 11/2015 |
| CN | 105051213 | A | 11/2015 |
| CN | 105209633 | A | 12/2015 |
| CN | 105658242 | A | 6/2016 |
| CN | 105658800 | A | 6/2016 |
| CN | 105813656 | A | 7/2016 |
| CN | 103748078 | B | 11/2016 |
| CN | 106413811 | A | 2/2017 |
| CN | 106659731 | A | 5/2017 |
| CN | 106795142 | A | 5/2017 |
| CN | 107095849 | A | 8/2017 |
| CN | 109312313 | A | 2/2019 |
| CN | 110114058 | A | 8/2019 |
| CN | 106164248 | B | 10/2019 |
| CN | 110511927 | A | 11/2019 |
| CN | 105142676 | B | 6/2022 |
| CN | 108473969 | B | 9/2022 |
| CN | 109072223 | B | 10/2022 |
| EP | 0250358 | A2 | 12/1987 |
| EP | 1781593 | B1 | 12/2011 |
| EP | 2506857 | A1 | 10/2012 |
| EP | 2506857 | A4 | 4/2014 |
| EP | 2717893 | A1 | 4/2014 |
| EP | 2858679 | A1 | 4/2015 |
| EP | 2929035 | A1 | 10/2015 |
| EP | 2850185 | A4 | 12/2015 |
| EP | 2850182 | A4 | 1/2016 |
| EP | 2850188 | A4 | 1/2016 |
| EP | 2970940 | A1 | 1/2016 |
| EP | 2971010 | A1 | 1/2016 |
| EP | 3008191 | A2 | 4/2016 |
| EP | 2859102 | A4 | 5/2016 |
| EP | 3043826 | A1 | 7/2016 |
| EP | 3060257 | A1 | 8/2016 |
| EP | 3060258 | A1 | 8/2016 |
| EP | 3060671 | A1 | 8/2016 |
| EP | 3052632 | A4 | 3/2017 |
| EP | 3043826 | A4 | 5/2017 |
| EP | 3160959 | A1 | 5/2017 |
| EP | 3033422 | A4 | 8/2017 |
| EP | 2970351 | B1 | 9/2017 |
| EP | 1937213 | B1 | 10/2017 |
| EP | 3226912 | A1 | 10/2017 |
| EP | 2718269 | B1 | 1/2018 |
| EP | 2506857 | B1 | 2/2018 |
| EP | 3160959 | A4 | 2/2018 |
| EP | 3318248 | A1 | 5/2018 |
| EP | 2971102 | B1 | 6/2018 |
| EP | 3338765 | A1 | 6/2018 |

(56) References Cited

FOREIGN PATENT DOCUMENTS

| | | | |
|---|---|---|---|
| EP | 2968586 | B1 | 7/2018 |
| EP | 2970940 | B1 | 7/2018 |
| EP | 3256591 | A4 | 8/2018 |
| EP | 3354644 | A1 | 8/2018 |
| EP | 3362565 | A1 | 8/2018 |
| EP | 3256592 | A4 | 9/2018 |
| EP | 3368671 | A1 | 9/2018 |
| EP | 3122878 | B1 | 10/2018 |
| EP | 3256590 | A4 | 10/2018 |
| EP | 2850189 | B1 | 11/2018 |
| EP | 2970955 | B1 | 11/2018 |
| EP | 2971098 | B1 | 11/2018 |
| EP | 3060303 | B1 | 11/2018 |
| EP | 3403647 | A1 | 11/2018 |
| EP | 2850186 | B1 | 12/2018 |
| EP | 3338765 | B1 | 12/2018 |
| EP | 3431592 | A1 | 1/2019 |
| EP | 2756080 | B1 | 2/2019 |
| EP | 3446712 | A1 | 2/2019 |
| EP | 3458081 | A1 | 3/2019 |
| EP | 3458104 | A1 | 3/2019 |
| EP | 3458590 | A1 | 3/2019 |
| EP | 3318248 | B1 | 4/2019 |
| EP | 3467108 | A1 | 4/2019 |
| EP | 2717893 | B1 | 5/2019 |
| EP | 3495505 | A1 | 6/2019 |
| EP | 3501605 | A1 | 6/2019 |
| EP | 3148552 | B1 | 7/2019 |
| EP | 3511416 | A1 | 7/2019 |
| EP | 3134506 | B1 | 8/2019 |
| EP | 3533873 | A1 | 9/2019 |
| EP | 3536787 | A1 | 9/2019 |
| EP | 3538068 | A1 | 9/2019 |
| EP | 3538136 | A1 | 9/2019 |
| EP | 2895200 | B1 | 11/2019 |
| EP | 3565535 | A1 | 11/2019 |
| EP | 3567112 | A1 | 11/2019 |
| EP | 3450553 | B1 | 12/2019 |
| EP | 3574923 | A1 | 12/2019 |
| EP | 3586861 | A1 | 1/2020 |
| EP | 3301102 | B1 | 4/2020 |
| EP | 3336082 | B1 | 4/2020 |
| EP | 3558271 | A4 | 7/2020 |
| EP | 3440206 | B1 | 10/2020 |
| EP | 3469074 | B1 | 12/2020 |
| EP | 3362555 | B1 | 1/2021 |
| EP | 2858679 | B1 | 2/2021 |
| EP | 3270894 | B1 | 2/2021 |
| EP | 3585891 | B1 | 10/2021 |
| EP | 3585892 | B1 | 6/2022 |
| EP | 3587409 | B8 | 7/2022 |
| ES | 2647832 | T3 | 12/2017 |
| ES | 2663360 | T3 | 4/2018 |
| ES | 2666559 | T3 | 5/2018 |
| ES | 2680595 | T3 | 9/2018 |
| ES | 2689523 | T3 | 11/2018 |
| ES | 2692363 | T3 | 12/2018 |
| ES | 2707966 | T3 | 4/2019 |
| ES | 2707969 | T3 | 4/2019 |
| ES | 2708561 | T3 | 4/2019 |
| ES | 2708562 | T3 | 4/2019 |
| ES | 2713852 | T3 | 5/2019 |
| ES | 2734973 | T3 | 12/2019 |
| ES | 2740248 | T3 | 2/2020 |
| HK | 1199206 | A1 | 6/2015 |
| HK | 1200484 | A1 | 8/2015 |
| HK | 1208352 | A1 | 3/2016 |
| HK | 1208618 | A1 | 3/2016 |
| HK | 1208700 | A1 | 3/2016 |
| HK | 1218068 | A1 | 2/2017 |
| HK | 1219955 | A1 | 4/2017 |
| HK | 1220137 | A1 | 4/2017 |
| IL | 240982 | B | 11/2018 |
| IL | 276122 | A | 8/2020 |
| IL | 229699 | B | 2/2021 |
| JP | 2014-101357 | A | 6/2014 |
| JP | 2014523411 | A | 9/2014 |
| JP | 2014523870 | A | 9/2014 |
| JP | 2014527819 | A | 10/2014 |
| JP | 2015518710 | A | 7/2015 |
| JP | 2015518713 | A | 7/2015 |
| JP | 2015518714 | A | 7/2015 |
| JP | 2015520195 | A | 7/2015 |
| JP | 2015523853 | A | 8/2015 |
| JP | 2015523854 | A | 8/2015 |
| JP | 2015529469 | A | 10/2015 |
| JP | 2016513470 | A | 5/2016 |
| JP | 2016513973 | A | 5/2016 |
| JP | 2016514970 | A | 5/2016 |
| JP | 2016515216 | A | 5/2016 |
| JP | 2016517437 | A | 6/2016 |
| JP | 2016531570 | A | 10/2016 |
| JP | 6022557 | B2 | 11/2016 |
| JP | 2016534035 | A | 11/2016 |
| JP | 2016534992 | A | 11/2016 |
| JP | 2016535729 | A | 11/2016 |
| JP | 2016535738 | A | 11/2016 |
| JP | 2016539916 | A | 12/2016 |
| JP | 2017014278 | A | 1/2017 |
| JP | 2017019857 | A | 1/2017 |
| JP | 6129844 | B2 | 5/2017 |
| JP | 2017127325 | A | 7/2017 |
| JP | 2017518371 | A | 7/2017 |
| JP | 2017518734 | A | 7/2017 |
| JP | 2017520563 | A | 7/2017 |
| JP | 6184945 | B2 | 8/2017 |
| JP | 2017203045 | A | 11/2017 |
| JP | 2017206567 | A | 11/2017 |
| JP | 2018500303 | A | 1/2018 |
| JP | 6316930 | B2 | 4/2018 |
| JP | 2018511588 | A | 4/2018 |
| JP | 2018100307 | A | 6/2018 |
| JP | 2018115164 | A | 7/2018 |
| JP | 6372042 | B2 | 8/2018 |
| JP | 2018141006 | A | 9/2018 |
| JP | 2018531017 | A | 10/2018 |
| JP | 2018174942 | A | 11/2018 |
| JP | 2019014742 | A | 1/2019 |
| JP | 6463810 | B2 | 2/2019 |
| JP | 2019048900 | A | 3/2019 |
| JP | 6506749 | B2 | 4/2019 |
| JP | 2019065047 | A | 4/2019 |
| JP | 2019065052 | A | 4/2019 |
| JP | 2019073557 | A | 5/2019 |
| JP | 2019513372 | A | 5/2019 |
| JP | 6525435 | B2 | 6/2019 |
| JP | 2019516719 | A | 6/2019 |
| JP | 2019519511 | A | 7/2019 |
| JP | 2019519601 | A | 7/2019 |
| JP | 6557722 | B2 | 8/2019 |
| JP | 6561378 | B2 | 8/2019 |
| JP | 6567494 | B2 | 8/2019 |
| JP | 2019135241 | A | 8/2019 |
| JP | 2019522047 | A | 8/2019 |
| JP | 6571679 | B2 | 9/2019 |
| JP | 2019163322 | A | 9/2019 |
| JP | 6586075 | B2 | 10/2019 |
| JP | 6599373 | B2 | 10/2019 |
| JP | 6608815 | B2 | 11/2019 |
| JP | 2019533708 | A | 11/2019 |
| JP | 2019205472 | A | 12/2019 |
| JP | 2019206545 | A | 12/2019 |
| JP | 6646773 | B2 | 2/2020 |
| KR | 20120138865 | A | 12/2012 |
| KR | 20140044356 | A | 4/2014 |
| KR | 20150030205 | A | 3/2015 |
| KR | 20150127582 | A | 11/2015 |
| KR | 20150128687 | A | 11/2015 |
| KR | 20160010398 | A | 1/2016 |
| KR | 20160073885 | A | 6/2016 |
| KR | 20160074368 | A | 6/2016 |
| KR | 20160091893 | A | 8/2016 |
| KR | 20160145004 | A | 12/2016 |
| KR | 20170021281 | A | 2/2017 |

(56) References Cited

FOREIGN PATENT DOCUMENTS

| | | | |
|---|---|---|---|
| KR | 20190027353 | A | 3/2019 |
| KR | 20190067261 | A | 6/2019 |
| KR | 20190120160 | A | 10/2019 |
| MX | 2013014419 | A | 1/2014 |
| MX | 2014015041 | A | 6/2015 |
| MX | 2015011943 | A | 12/2015 |
| MX | 2015011944 | A | 12/2015 |
| MX | 2015011945 | A | 12/2015 |
| MX | 2015012333 | A | 5/2016 |
| MX | 2015012865 | A | 7/2016 |
| MX | 2016005236 | A | 8/2016 |
| MX | 2016005237 | A | 8/2016 |
| MX | 2016005238 | A | 8/2016 |
| MX | 2016005239 | A | 8/2016 |
| MX | 2016013965 | A | 1/2017 |
| MX | 2017000143 | A | 5/2017 |
| MX | 365409 | B | 5/2019 |
| MX | 367605 | B | 8/2019 |
| NZ | 600616 | A | 11/2014 |
| NZ | 700688 | A | 2/2016 |
| NZ | 618275 | A | 11/2016 |
| NZ | 716192 | A | 7/2017 |
| RU | 2013154295 | A | 7/2015 |
| WO | WO-9508986 | A1 | 4/1995 |
| WO | WO-9512673 | A1 | 5/1995 |
| WO | WO-9521251 | A1 | 8/1995 |
| WO | WO-9521915 | A1 | 8/1995 |
| WO | WO-9827104 | A1 | 6/1998 |
| WO | WO-9929842 | A1 | 6/1999 |
| WO | WO-9932619 | A1 | 7/1999 |
| WO | WO-0024931 | A2 | 5/2000 |
| WO | WO-0026226 | A1 | 5/2000 |
| WO | WO-0044895 | A1 | 8/2000 |
| WO | WO-0129058 | A1 | 4/2001 |
| WO | WO-0202606 | A2 | 1/2002 |
| WO | WO-0234771 | A2 | 5/2002 |
| WO | WO-02098443 | A2 | 12/2002 |
| WO | WO-03018054 | A1 | 3/2003 |
| WO | WO-2005002619 | A2 | 1/2005 |
| WO | WO-2005007196 | A2 | 1/2005 |
| WO | WO-2005032582 | A3 | 11/2005 |
| WO | WO-2005111066 | A2 | 11/2005 |
| WO | WO-2006091517 | A2 | 8/2006 |
| WO | WO-2006110413 | A2 | 10/2006 |
| WO | WO-2006/138380 | A2 | 12/2006 |
| WO | WO-2006138004 | A2 | 12/2006 |
| WO | WO-2007049155 | A2 | 5/2007 |
| WO | WO-2008014979 | A2 | 2/2008 |
| WO | WO-2008016473 | A2 | 2/2008 |
| WO | WO-2008054819 | A2 | 5/2008 |
| WO | WO-2008083949 | A2 | 7/2008 |
| WO | WO-2008157688 | A2 | 12/2008 |
| WO | WO-2009016515 | A2 | 2/2009 |
| WO | WO-2008020330 | A3 | 3/2009 |
| WO | WO-2009031043 | A2 | 3/2009 |
| WO | WO-2009095226 | A2 | 8/2009 |
| WO | WO-2009104092 | A2 | 8/2009 |
| WO | WO-2009109860 | A2 | 9/2009 |
| WO | WO-2009149253 | A2 | 12/2009 |
| WO | WO-2010042856 | A2 | 4/2010 |
| WO | WO-2010042877 | A1 | 4/2010 |
| WO | WO-2010119343 | A2 | 10/2010 |
| WO | WO-2010144678 | A2 | 12/2010 |
| WO | WO-2011005799 | A2 | 1/2011 |
| WO | WO-2011015347 | A1 | 2/2011 |
| WO | WO-2011068810 | A1 | 6/2011 |
| WO | WO-2011076807 | A2 | 6/2011 |
| WO | WO-2012006372 | A1 | 1/2012 |
| WO | WO-2012019780 | A1 | 2/2012 |
| WO | WO-2012075040 | A2 | 6/2012 |
| WO | WO-2012170889 | A1 | 12/2012 |
| WO | WO-2012170930 | A1 | 12/2012 |
| WO | WO-2013040429 | A1 | 3/2013 |
| WO | WO-2013059475 | A1 | 4/2013 |
| WO | WO-2013143700 | A2 | 10/2013 |
| WO | WO-2013149140 | A1 | 10/2013 |
| WO | WO-2013173598 | A1 | 11/2013 |
| WO | WO-2013173599 | A1 | 11/2013 |
| WO | WO-2013173638 | A1 | 11/2013 |
| WO | WO-2013173645 | A1 | 11/2013 |
| WO | WO-2013173652 | A1 | 11/2013 |
| WO | WO-2013185067 | A1 | 12/2013 |
| WO | WO-2013185069 | A1 | 12/2013 |
| WO | WO-2012170930 | A9 | 1/2014 |
| WO | WO-2014/028487 | A1 | 2/2014 |
| WO | WO-2014043544 | A1 | 3/2014 |
| WO | WO-2012075040 | A3 | 4/2014 |
| WO | WO-2014089486 | A1 | 6/2014 |
| WO | WO-2014152211 | A1 | 9/2014 |
| WO | WO-2014152513 | A1 | 9/2014 |
| WO | WO-2014152659 | A1 | 9/2014 |
| WO | WO-2014152673 | A1 | 9/2014 |
| WO | WO-2014152940 | A1 | 9/2014 |
| WO | WO-2014152966 | A1 | 9/2014 |
| WO | WO-2014153052 | A2 | 9/2014 |
| WO | WO-2013173645 | A8 | 12/2014 |
| WO | WO-2015011633 | A1 | 1/2015 |
| WO | WO-2015023941 | A1 | 2/2015 |
| WO | WO-2014201252 | A3 | 3/2015 |
| WO | WO-2015038892 | A1 | 3/2015 |
| WO | WO-2015051283 | A1 | 4/2015 |
| WO | WO-2015061461 | A1 | 4/2015 |
| WO | WO-2015061467 | A1 | 4/2015 |
| WO | WO-2015061491 | A1 | 4/2015 |
| WO | WO-2015061500 | A1 | 4/2015 |
| WO | WO-2014153052 | A9 | 8/2015 |
| WO | WO-2015148247 | A1 | 10/2015 |
| WO | WO-2015164773 | A1 | 10/2015 |
| WO | WO-2015184256 | A2 | 12/2015 |
| WO | WO-2015199952 | A1 | 12/2015 |
| WO | WO-2015200465 | A1 | 12/2015 |
| WO | WO-2015184256 | A3 | 1/2016 |
| WO | WO-2016090262 | A1 | 6/2016 |
| WO | WO-2016097065 | A1 | 6/2016 |
| WO | WO-2016130929 | A1 | 8/2016 |
| WO | WO-2016130943 | A1 | 8/2016 |
| WO | WO-2016130963 | A1 | 8/2016 |
| WO | WO-2016149508 | A1 | 9/2016 |
| WO | WO-2016176330 | A1 | 11/2016 |
| WO | WO-2016197133 | A1 | 12/2016 |
| WO | WO-2017004143 | A1 | 1/2017 |
| WO | WO-2017/049245 | A2 | 3/2017 |
| WO | WO-2017049074 | A1 | 3/2017 |
| WO | WO-2017066573 | A1 | 4/2017 |
| WO | WO-2017066594 | A1 | 4/2017 |
| WO | WO-2017075030 | A1 | 5/2017 |
| WO | WO-2017075531 | A1 | 5/2017 |
| WO | WO-2017177169 | A1 | 10/2017 |
| WO | WO-2017181026 | A1 | 10/2017 |
| WO | WO-2017182524 | A1 | 10/2017 |
| WO | WO-2017186928 | A1 | 11/2017 |
| WO | WO-2017201317 | A1 | 11/2017 |
| WO | WO-2017201328 | A1 | 11/2017 |
| WO | WO-2017201332 | A1 | 11/2017 |
| WO | WO-2017201346 | A1 | 11/2017 |
| WO | WO-2017201349 | A1 | 11/2017 |
| WO | WO-2017218524 | A1 | 12/2017 |
| WO | WO-2018031871 | A1 | 2/2018 |
| WO | WO-2018078053 | A1 | 5/2018 |
| WO | WO-2018081480 | A1 | 5/2018 |
| WO | WO-2018081638 | A1 | 5/2018 |
| WO | WO-2018089790 | A1 | 5/2018 |
| WO | WO-2018089801 | A1 | 5/2018 |
| WO | WO-2018089846 | A1 | 5/2018 |
| WO | WO-2018157133 | A1 | 8/2018 |
| WO | WO-2018157141 | A1 | 8/2018 |
| WO | WO-2018157153 | A1 | 8/2018 |
| WO | WO-2018165257 | A1 | 9/2018 |
| WO | WO-2018170336 | A1 | 9/2018 |
| WO | WO-2018157154 | A3 | 10/2018 |
| WO | WO-2018191719 | A1 | 10/2018 |
| WO | WO-2018213476 | A1 | 11/2018 |
| WO | WO-2018231709 | A1 | 12/2018 |
| WO | WO-2018236849 | A1 | 12/2018 |

(56) References Cited

FOREIGN PATENT DOCUMENTS

| | | | |
|---|---|---|---|
| WO | WO-2019036028 | A1 | 2/2019 |
| WO | WO-2019036030 | A1 | 2/2019 |
| WO | WO-2019040590 | A1 | 2/2019 |
| WO | WO-2019046809 | A1 | 3/2019 |
| WO | WO-2019056098 | A1 | 3/2019 |
| WO | WO-2019077053 | A1 | 4/2019 |
| WO | WO-2019089828 | A1 | 5/2019 |
| WO | WO-2019126593 | A1 | 6/2019 |
| WO | WO-2019131839 | A1 | 7/2019 |
| WO | WO-2019137999 | A1 | 7/2019 |
| WO | WO-2019140102 | A1 | 7/2019 |
| WO | WO-2019140102 | A8 | 8/2019 |
| WO | WO-2019152802 | A1 | 8/2019 |
| WO | WO-2019154985 | A1 | 8/2019 |
| WO | WO-2019191780 | A1 | 10/2019 |
| WO | WO-2019213308 | A1 | 11/2019 |
| WO | WO-2019222277 | A1 | 11/2019 |
| WO | WO-2019222424 | A1 | 11/2019 |
| WO | WO-2019226925 | A1 | 11/2019 |
| WO | WO-2019232095 | A1 | 12/2019 |
| WO | WO-2019232097 | A1 | 12/2019 |
| WO | WO-2019232103 | A1 | 12/2019 |
| WO | WO-2019232208 | A1 | 12/2019 |
| WO | WO-2020002540 | A1 | 1/2020 |
| WO | WO-2020002598 | A1 | 1/2020 |
| WO | WO-2020035609 | A2 | 2/2020 |
| WO | WO-2020041793 | A1 | 2/2020 |
| WO | WO-2020047061 | A1 | 3/2020 |
| WO | WO-2020051223 | A1 | 3/2020 |
| WO | WO-2020061332 | A1 | 3/2020 |
| WO | WO-2020061367 | A1 | 3/2020 |
| WO | WO-2020061426 | A2 | 3/2020 |
| WO | WO-2020061457 | A1 | 3/2020 |
| WO | WO-2020061426 | A3 | 4/2020 |
| WO | WO-2020072605 | A1 | 4/2020 |
| WO | WO-2020081938 | A1 | 4/2020 |
| WO | WO-2020093061 | A1 | 5/2020 |
| WO | WO-2020097493 | A1 | 5/2020 |
| WO | WO-2020097540 | A1 | 5/2020 |
| WO | WO-2020097548 | A1 | 5/2020 |
| WO | WO-2020118041 | A1 | 6/2020 |
| WO | WO-2020121273 | A1 | 6/2020 |
| WO | WO-2020128012 | A1 | 6/2020 |
| WO | WO-2020144295 | A1 | 7/2020 |
| WO | WO-2020146805 | A1 | 7/2020 |
| WO | WO-2020160397 | A1 | 8/2020 |
| WO | WO-2020161224 | A1 | 8/2020 |
| WO | WO-2020191103 | A1 | 9/2020 |
| WO | WO-2020201383 | A1 | 10/2020 |
| WO | WO-2020214946 | A1 | 10/2020 |
| WO | WO-2020219876 | A1 | 10/2020 |
| WO | WO-2020219941 | A1 | 10/2020 |
| WO | WO-2020247382 | A1 | 12/2020 |
| WO | WO-2021026358 | A1 | 2/2021 |
| WO | WO-2021030701 | A1 | 2/2021 |
| WO | WO-2021123332 | A1 | 6/2021 |
| WO | WO-2021129945 | A1 | 7/2021 |
| WO | WO-2021130225 | A1 | 7/2021 |
| WO | WO-2022081750 | A1 | 4/2022 |
| WO | WO-2022081752 | A1 | 4/2022 |
| ZA | 201409228 | B | 7/2016 |
| ZA | 201409229 | B | 7/2016 |
| ZA | 201507605 | B | 1/2017 |

OTHER PUBLICATIONS

Alabi et al. Proceedings of the National Academy of Sciences of the United States of America (2013), 110(32), 12881-12886.*

Abdelaal et al., "Ligand-mediated delivery of RNAi-based therapeutics for the treatment of oncological diseases", NAR Cancer, Jul. 2021, pp. 1-23, vol. 3, No. 3.

ACD/LABS, "ACD/pKa Classic Module Report", Dec. 20, 2020, 4 pages.

Adams, "AstraZeneca's eagerly awaited COVID-19 vaccine passes large test, but confirmation needed," FierceBiotech, Jul. 20, 2020 [online], [retrieved on Mar. 8, 2022]. Retrieved from the Internet URL: https://www.fiercebiotech.com/biotech/astrazeneca-s-eagerly-awaited-covid-vaccine-passes-large-test-but-confirmation-needed, 3 pages.

Adams, B., "China's Sinovac hit by late-stage COVID-19 vaccine halt after reports of a death in Brazilian trial," FierceBiotech, Nov. 10, 2020 [online], [retrieved on Mar. 8, 2022]. Retrieved from the Internet URL: https://www.fiercebiotech.com/biotech/china-s-sinovac-hit-by-late-stage-covd-vaccine-halt-after-reports-a-death-brazilian-trial, 2 pages.

Adams, B., "Pfizer, BioNTech start their COVID-19 vax phase 3, squaring off with Moderna," FierceBiotech, Jul. 28, 2020 [online], [retrieved on Mar. 8, 2022]. Retrieved from the Internet URL: https://www.fiercebiotech.com/biotech/pfizer-biontech-start-their-covid-vax-phase-3-squaring-off-moderna, 5 pages.

Adams, B., "Pfizer, Under pressure, Pfizer, Moderna (and soon AstraZeneca) publish COVID-19 vaccine protocols," FierceBiotech, Sep. 18, 2020 [online], [retrieved on Mar. 8, 2022]. Retrieved from the Internet URL: https://www.fiercebiotech.com/biotech/under-pressure-pfizer-moderna-and-soon-astrazeneca-publish-covid-vaccine-protocols, 2 pages.

Adams, Pfizer, "BioNTech nab fast track tag, prep for major phase 3 COVID-19 vax test this month," FierceBiotech, Jul. 13, 2020 [online], [retrieved on Mar. 8. 2022]. Retrieved from the Internet URL: https://www.fiercebiotech.com/biotech/pfizer-biontech-nab-fast-track-tag-preps-for-major-phase-3-covid-vax-test-month, 2 pages.

Addison, et al., Extracellular matrix mineralization in murine MC3T3-E1 osteoblast cultures: An ultrastructural, compositional and comparative analysis with mouse bone, Bone, Feb. 2015, pp. 244-256, vol. 71.

Ahmad et al., "New multivalent cationic lipids reveal bell curve for transfection efficiency versus membrane charge density: lipid-DNA complexes for gene delivery," The Journal of Gene Medicine, 2005, pp. 739-748, vol. 7.

Ahmed et al, "Preliminary Identification of Potential Vaccine Targets for the COVID-19 Coronavirus (SARS-CoV-2) Based on SARS-COV Immunological Studies," Viruses 12(3):254, pp. 1-15 (2020).

Akinc, et al., Targeted delivery of RNAi therapeutics with endogenous and exogenous ligand-based mechanisms, Molecular Therapy, Jul. 1, 2010, pp. 1357-1364, vol. 18, No. 7.

Al Idrus, "CanSino adds mRNA to COVID-19 vaccine efforts with Precision NanoSystems deal," FierceBiotech, May 20, 2020 [online], [retrieved on Mar. 8, 2022]. Retrieved from the Internet URL: https://www.fiercebiotech.com/biotech/cansino-adds-mrna-to-covid-19-vaccine-efforts-precision-nanosystems-deal, 2 pages.

Al Idrus, "Moderna's COVID-19 vaccine triggers immune response in older adults," FierceBiotech, Aug. 26, 2020 [online], [retrieved on Mar. 8, 2022]. Retrieved from the Internet URL: https://www.fiercebiotech.com/biotech/moderna-s-covid-19-vaccine-triggers-immune-response-older-adults, 4 pages.

Alabi, et al., "Multiparametric approach for the evaluation of lipid nanoparticles for siRNA delivery, Supporting Information", Applied Biological Sciences, Jul. 23, 2013, 4 pages.

Alameh, et al., "siRNA delivery with chitosan: Influence of chitosan molecular weight, degree of deacetylation, and amine to phosphate ratio on in vitro silencing efficiency, hemocompatibility, biodistribution, and in vivo efficacy", Biomacromolecules, 2018, pp. 112-131, vol. 19.

Alameh et al., "Lipid nanoparticles enhance the efficacy of mRNA and protein subunit vaccines by inducing robust T follicular helper cell and humoral responses," Immunity, 2021, pp. 2877-2892, vol. 54, No. 12.

Alameh et al., "Messenger RNA-Based Vaccines Against Infectious Diseases," Current Topics in Microbiology and Immunology, Apr. 17, 2020, pp. 1-35.

Alberer et al., "Safety and immunogenicity of a mRNA rabies vaccine in healthy adults: an open-label, non-randomised, prospective, first-in-human phase 1 clinical trial", Lancet, Sep. 23, 2017, pp. 1511-1520, vol. 390.

(56) References Cited

OTHER PUBLICATIONS

Alberts et al., Cell biology: the endless frontier, Molecular Biology of the Cell, Nov. 15, 2010, pp. 3785-3785, vol. 21, No. 22.
Aldrich et al., "Proof-of-concept of a low-dose unmodified mRNA-based rabies vaccine formulated with lipid nanoparticles in human volunteers: a phase 1 trial", Vaccine, 2021, pp. 1310-1318, vol. 39.
Ali et al., "Design of a new cell penetrating peptide for DNA, siRNA and mRNA delivery", The Journal of Gene Medicine, 2022, pp. 1-31, vol. 24, No. 3.
Alishetty, et al., "Novel lipid nanoparticle provides potent SARS-CoV-2 mRNA vaccine at low dose with low local reactogenicity, high thermostability and limited systemic biodistribution", 2021, 55 pages.
Allen et al., "Efficient Delivery of Macromolecules into Human Cells by Improving the Endosomal Escape Activity of Cell-Penetrating Peptides: Lessons Learned from dfTAT and its Analogs", Biomolecules, 2018, pp. 1-13, vol. 8.
Allen, et al., Liposomal drug delivery systems: from concept to clinical applications, Advanced Drug Delivery Reviews, Jan. 1, 2013, pp. 36-48, vol. 65, No. 1.
Amanat et al., "SARS-CoV-2 Vaccines: Status Report," Immunity, vol. 52, Apr. 14, 2020, pp. 583-589.
An, et al., "Systematic Messenger RNA Therapy as a Treatment for Methylmalonic Acidemia", Cell Reports, Dec. 19, 2017, pp. 3548-3558, vol. 21.
Anderson, B.R. et al., "Incorporation of pseudouridine into mRNA enhances translation by diminishing PKR activation," Nucleic Acids Research, vol. 38(17):5884-5892 (2010).
Anderson, et al., Safety and immunogenicity of SARS-CoV-2 mRNA-1273 vaccine in older adults, Supplemental Appendix, N Engl J Med., 2020, pp. 1-63.
Ando et al., "Enzymatic litigation of an antibody and arginine 9 peptide for efficient and cell-specific siRNA delivery", Scientific Reports, 2021, pp. 1-11, vol. 11.
Armbruster et al., "Advances in RNA Vaccines for Preventative Indications: A Case Study of a Vaccine against Rabies", Vaccines, 2019, pp. 1-12, vol. 7.
Armen et al., "Phospholipid Component Volumes: Determination and Application to Bilayer Structure Calculations," Biophysical Journal, Aug. 1998, pp. 734-744, vol. 75.
Arteta et al., "Supporting Information," PNAS, 2 pages.
Arteta, M.Y., et al., "Successful Reprogramming of Cellular Protein Production Through Mrna Delivered by Functionalized Lipid Nanoparticles," Proceedings of the National Academy of Sciences of the United States of America, 2018, vol. 115(15), pp. E3351-E3360.
Attia, et al., "Modification of Nanoparticles with Transferrin for Targeting Brain Tissues", Peptide Conjugation, Methods in Molecular Biology, 2021, pp. 49-56.
Avanti Polar Lipids, 18:0 PC-d83, No Date, 1 page.
Avanti Polar Lipids, cholesterol-d6, No Date, 1 page.
Avanti Polar Lipids, cholesterol-d7, No Date, 1 page.
Avanti Polar Lipids, "Storage & Handling of Lipids", Oct. 4, 2019, 3 pages. Retrieved from https://avantilipids.com/tech-support/storage-handling-of-lipids#:~:text=SATURATED%20LIPIDStext=These%20lipids%20should%20be%20stored,temperature%20before%20opening%20the%20bottle.
Awasthi et al., "Antibody responses to crucial functional epitopes as a novel approach to assess immunogenicity of vaccine adjuvants", Vaccine, May 2019, pp. 3770-3778, vol. 37, No. 29.
Bachmann et al., "Vaccine delivery: a matter of size, geometry, kinetics and molecular patterns", Nature Reviews, Immunology, Nov. 2010, pp. 787-796, vol. 10.
Baden et al., "A Phase3, Randomized, Stratified, Observer-Blind, Placebo-Controlled Study to Evaluate the Efficacy, Safety, and Immunogenicity of mRNA-1273 SARS CoV-2 Vaccine in Adults Aged 18 Years and Older", Statistical Analysis Plan, Version 1.0, Sep. 10, 2020, pp. 1-307.
Bahl et al., "Preclinical and Clinical demonstration of Immunogenicity by mRNA Vaccines against H10N8 and H7N9 Influenza Viruses", Molecular Therapy, Jun. 2017, pp. 1316-1327, vol. 25, No. 6.
Baiersdorfer et al., "A Facile Method for the Removal of dsRNA Contaminant from In Vitro-Transcribed RNA," Moleculary Therapy Nucleic Acids, Apr. 2019, pp. 26-35, vol. 15.
Baladi et al., "Stealth fluorescence labeling for live microscopy imaging of mRNA delivery", BioRxiv, 2020, pp. 1-45.
Ball et al., "Oral delivery of siRNA lipid nanoparticles: Fate in the GI tract", Scientific Reports, 2018, pp. 1-12, vol. 8.
Bangham, The action of steroids and streptolysin S on the permeability of phospholipid structures to cations, J. Mol. Biol. Aug. 1, 1965, pp. 238-252, vol. 13, No. 1.
Barda et al., "Safety of the BNT162b2 mRNA Covid-19 Vaccine in a Nationwide Setting," The New England Journal of Medicine, Aug. 25, 2021, pp. 1-14.
Barichello, et al., "Complexation of siRNA and pDNA with Cationic Liposomes: The Important Aspects in Lipoplex Preparation," Methods in Molecular Biology, 2010, pp. 461-472, vol. 605.
Bar-On et al., "Protection of BNT162b2 Vaccine Booster against Covid-19 in Israel," The New England Journal of Medicine, Sep. 15, 2021, pp. 1-8.
Bar-Zeev et al., "Encouraging results from phase 1/2 COVID-19 vaccine trials," The Lancet, Jul. 20, 2020, URL https://doi.org/10.1016/S0140-6736(20)31611-1 pp. 1-2.
Basha, et al., Influence of cationic lipid composition on gene silencing properties of lipid nanoparticle formulations of siRNA in antigen-presenting cells, Molecular Therapy, Dec. 1, 2011, pp. 2186-2200, vol. 19, No. 12.
Beckert, Synthesis of RNA by in Vitro Transcription in RNA in Methods in Molecular Biology, InRna, 2011, pp. 29-41.
Belliveau et al., "Microfluidic Synthesis of Highly Potent Limit-size Lipid Nanoparticles for in Vivo Delivery of siRNA," Molecular Therapy-Nucleic Acids, 2012, 1, e37, 9 pages.
Berger, R. et al., "Phase I safety and pharmacokinetic study of CT-011, a humanized antibody interacting with PD-1, in patients with advanced hematologic malignancies," Clinical Cancer Research, 14(10):3044-3051 (May 2008).
Bernstein, P. et al., Poly(A), poly(A) binding protein and the regulation of mRNA stability. Trends Biochem Sci. 198S Sep. ;14(9):373-7.
Berthub et al., "The CureVac Vaccine, and a brief tour through some of the wonders of nature", Mar. 8, 2021, 12 pages.
Bhattacharjee, "DLS and zeta potential—What they are and what they are not?", Journal of Controlled Release, 2016, pp. 337-351, vol. 235.
Bhattacharya et al., "Development of epitope-based peptide vaccine against novel coronavirus 2019 (SARS-COV-2): Immunoinformatics approach," Journal of Medical Virology, 2020, pp. 618-631, vol. 92.
Binder, R. et al., Evidence that the pathway of transferrin receptor mRNA degradation involves an endonucleolytic cleavage within the 3' UTR and does not involve poly(A) tail shortening. EMBO J. Apr. 15, 1994;13(8):1969-80.
Binette, et al., "Tetrapolar measurement of electrical conductivity and thickness of articular cartilage", J. Biomech. Eng., Aug. 2004, pp. 475-484, vol. 126.
Biontech, "Study to Describe the Safety, Tolerability, Immunogenicity, and Potential Efficacy of RNA Vaccine Candidates Against COVID-19 in Healthy Adults," ClinicalTrials, 2020, 2 Pages. Retrieved from the Internet URL: https://clinicaltrials.gov/ct2/show/NCT04368728, pp. 1-16.
Bisht et al., "Severe acute respiratory syndrome coronavirus spike protein expressed by attenuated vaccinia virus protectively immunizes mice," PNAS, Apr. 27, 2004, pp. 6641-6646, vol. 101, No. 17.
Bizet, et al., "The TGF-β co-receptor, CD109, promotes internalization and degradation of TGF-β receptors", Biochimica et Biophysica Acta 1813, Feb. 2, 2011, pp. 742-753.
Blakcenship, "CureVac ties up Wacker to churn out more than 100M does of mRNA coronavirus vaccine", Nov. 25, 2020, 2 pages.
Blanc et al., "Optimal Processing Method to Obtain Four-color Confocal Fluorescent Images of the Cytoskeleton and Nucleus in

(56) References Cited

OTHER PUBLICATIONS

Three-dimensional Chondrocyte Cultures", Journal of Histochemistry and Cytochemistry, May 11, 2005, pp. 1171-1175, vol. 53, No. 9.
Bnyan et al., "Surfactant effects on Lipid-Based Vesicles Properties", Journal of Pharmaceutical Sciences, Jan. 2018, pp. 1237-1246, vol. 107.
Boada et al., "LDL-Based Lipid Nanoparticle Derived for Blood Plasma Accumulates Preferentially in Atherosclerotic Plaque", Frontiers in Bioengineering and Biotechnoogy, Dec. 2021, p. 1-14, vol. 9.
Bolles et al., "A Double-Inactivated Severe Acute Respiratory Syndrome Coronavirus Vaccine Provides Incomplete Protection in Mice and Induces Increased Eosinophilic Proinflammatory Pulmonary Response upon Challenge," Journal of Virology, Dec. 2011, pp. 12201-12215, vol. 85, No. 23.
Boucher et al., "Human corneal epithelial cell response to epidermal growth factor tethered via coiled-coil interactions", Biomaterials, May 27, 2010, pp. 1-11.
Bour-Jordan, H. et al., "Intrinsic and extrinsic control of peripheral T-cell tolerance by costimulatory molecules of the CD28/B7 family," Immunol. Rev. 241(1):180-205 (2011).
Bourquin et al., "Biodistribution, Clearance, and Long-Term Fate of Clinically Relevant Nanomaterials", Advanced Materials, 2018, pp. 1-31, vol. 30.
Bowman et al., "Lack of effects on female fertility and prenatal and postnatal offspring development in rats with BNT162b2, a mRNA-based COVID-19 vaccine," Reproductive Toxicology, 2021, pp. 28-35, vol. 103.
Brader et al., "Encapsulation state of messenger RNA inside lipid nanoparticles", Biophysical Journal, 2021, pp. 1-2, vol. 120.
Brahmer et al., "Safety and Activity of Anti-PD-L1 Antibody in Patients with Advanced Cancer," N Engl J Med., 366:2455-2465 (2012).
Brahmer, J. R. et al., "Phase I study of single-agent anti-programmed death-1 (MDX-1106) in refractory solid tumors: safety, clinical activity, pharmacodynamics, and immunologic correlates," J Clin Oncol. Jul. 1, 2010;28(19):3167-75.
Braun et al., "Supplementary Table," 2020, 7 pages.
Brighman et al., Rapid communication: In vivo transfection of murine lungs with a functioning prokaryotic gene using a liposome vehicle, Am. J. Med. Sci., 2 Oct. 1, 1989, pp. 278-281, vol. 298, No. 4.
Brunelle, et al., In vitro transcription from plasmid or PCR-amplified DNA, InMethods in Enzymology, Jan. 1, 2013, pp. 101-114, vol. 530.
Bulik, B. S., "Pfizer lays out COVID-19 vaccine commercial strategy for pandemic and beyond," FiercePharma, Jul. 29, 2020 [online], [retrieved on Mar. 8, 2022]. Retrieved from the Internet URL: https://www.fiercepharma.com/marketing/pfizer-lays-out-commercial-strategy-for-covid-19-vaccine-during-pandemic-and-beyond, 2 pages.
Buschmann et al., "A Method of Quantitative Autoradiography for the Spatial Localization of Proteoglycan Synthesis Rates in Cartilage", The Journal of Histochemistry and Cytochemistry, Dec. 28, 1995, pp. 423-431, vol. 44 No. 5.
Buschmann et al., "A Molecular Model of Proteoglycan-Associated Electrostatic Forces in Cartilage Mechanics", Journal of Biomechanical Engineering, May 1995, pp. 179-192, vol. 117.
Buschmann et al., "Altered aggrecan synthesis correlates with cell and nucleus structure in statically compressed cartilage", Journal of Cell Science, Nov. 15, 1995, pp. 499-508, vol. 109.
Buschmann et al., "Cartilage Repair with Chitosan-Glycerol Phosphate-Stabilized Blood Clots", Cartilage Repair Strategies, 2007, 85-104.
Buschmann et al., "Chitosans for delivery of nucleic acids", Advanced Drug Delivery Reviews, Jul. 18, 2013, pp. 1234-1270, vol. 65.
Buschmann et al., "Chondrocytes in Agarose Culture Synthesize a Mechanically functional Extracellular Matrix", Journal of Orthopedic Research, 1992, pp. 745-758, vol. 10.
Buschmann et al., "Confined compression of articular cartilage: Linearity in ramp and sinusoidal tests and the importance of interdigitation and incomplete confinement", Journal of Biomechanics, 1998, pp. 171-178, vol. 31.
Buschmann et al., "Mechanical compression modulates matrix biosynthesis in Chondrocyte/agarose culture", Journal of Cell Science, Jan. 6, 1995, pp. 1497-1508, vol. 108.
Buschmann et al., "Nanomaterial Delivery Systems for mRNA Vaccines", Vaccines, Jan. 19, 2021, pp. 1-30, vol. 9, No. 65.
Buschmann et al., "Numerical Conversion of Transient to Harmonic Response Functions for Linear Viscoelastic Materials", Biomechanics, 1997, pp. 197-202, vol. 30 No. 2.
Buschmann et al., "Ruthenium Hexammine Trichloride Chemography for Aggrecan Mapping in Cartilage is a Sensitive Indicator of Matrix Degradation", Journal of Histochemistry and Cytochemistry, 2000, 81-88, vol. 48, No. 1.
Buschmann et al., "Stimulation of Aggrecan Synthesis in Cartilage Explants by Cyclic Loading is Localized to Regions of High Interstitial Fluid Flow", Biochemistry and Biophysics, Feb. 22, 1999, pp. 1-7, vol. 366.
Callow et al., "The time course of the immune response to experimental coronavirus infection of man," Epidemiol. Infect., 1990, pp. 435-446, vol. 105.
Caput, D. et al., Identification of a common nucleotide sequence in the 3'-untranslaled region of mRNA molecules specifying inflammatory mediators. Proc Natl Acad Sci USA. Mar. 1986;83(6):1670-4.
Carrasco et al., "Ionization and Structural Properties of mRNA Lipid Nanoparticles that Influence Expression in Intramuscular and Intravascular Administration", Communications Biology, 2021, pp. 1-36, vol. 4.
Cech et al., Ribozymes and their medical implications, JAMA, Nov. 25, 1988, pp. 3030-3034.
Cevaal et al., "In Vivo T Cell-Targeting Nanoparticle Drug Delivery Systems: Considerations for Rational Design", ACS Nano, 2021, pp. 3736-3753, vol. 15.
Chandrashekar et al., "SARS-CoV-2 infection protects against rechallenge in rhesus macaques," Science, May 20, 2020, DOI: 10.1126/science.abc4776, pp. 1-12.
Changoor et al. "A polarized light microscopy method for accurate and reliable grading of collagen organization in cartilage repair", Osteoarthritis and Cartilage, Oct. 2, 2010, pp. 126-135, vol. 19.
Changoor et al., "Effects of Refrigeration and Freezing on the Electromechanical and Biomechanical Properties of Articular Cartilage", Journal of Biomechanical Engineering, Jun. 2010, pp. 1-6, vol. 132.
Changoor et al., "Streaming Potential-Based Arthroscopic Device is Sensitive to Cartilage Changes Immediately Post-Impact in an Equine Cartilage Injury Model", Journal of Biomechanical Engineering, Jun. 2011, pp. 1-9, vol. 133.
Changoor et al., "Structural characteristics of the collagen network in human normal, degraded and repair articular cartilages observed in polarized light and scanning electron microscopies", Osteoarthritis and Cartilage, Sep. 23, 2011, pp. 1458-1468, vol. 19.
Charlebois et al., "Nonlinear Tensile Properties of Bovine Articular Cartilage and their Variation with Age and Depth", Journal of Biomechanical Engineering, Apr. 2004, pp. 129-137, vol. 26.
Chaudhary et al., "mRNA vaccines for infectious diseases: principles, delivery and clinical translation," Nature Reviews, Aug. 25, 2021, pp. 817-838, vol. 20, No. 11.
Chen et al., "Acute Osteoclast Activity following Subchondral Drilling is Promoted by Chitosan and Associated with Improved Cartilage Repair Tissue Integration", Cartilage, Oct. 11, 2010, pp. 1-14, vol. 2, No. 2.
Chen et al., "Bone marrow stimulation induces greater chondrogenesis in trochlear vs condylar cartilage defects in skeletally mature rabbits", Osteoarthritis and Cartilage, Apr. 14, 2013, pp. 999-1007, vol. 21.
Chen et al., "Bone Marrow Stimulation of the Medial Femoral Condyle Produces Inferior Cartilage and Bone Repair Compared to the Trochlea in a rabbit Surgical Model", Journal of Orthopedic Research, Jul. 10, 2013, pp. 1757-1764, vol. 31, No. 11.

(56) References Cited

OTHER PUBLICATIONS

Chen et al., "Characterization of Subchondral Bone Repair for Marrow-Stimulated Chondral Defects and its Relationship to Articular Cartilage Resurfacing", The American Journal of Sports Medicine, May 31, 2011, pp. 1731-1740, vol. 39 No. 8.
Chen et al., "Depth of Subchondral Perforation Influences the Outcome of Bone Marrow Stimulation Cartilage Repair", Journal of Orthopedic Research, Feb. 24, 2011, pp. 1178-1184, vol. 29, No. 8.
Chen et al., "Drilling and Microfracture Lead to Different Bone Structure and Necrosis during Bone-Marrow Stimulation for Cartilage Repair", Journal of Orthopedic Research, Nov. 2009, pp. 1432-1438, vol. 27, No. 11.
Chen et al., "Influence of particle size on the in vivo potency of lipid nanoparticle formulations of siRNA," Journal of Controlled Release, Aug. 10, 2016, pp. 236-244, vol. 235.
Chen et al., "Nanoparticles targeting tumor-associated macrophages: A novel anti-tumor therapy", Nano Research, Jul. 2021, pp. 1-19.
Cheng et al., "Small Angle Neutron Scattering Study of Conformation of Oligo(ethylene glycol)-Grafted Polystyrene in Dilute Solutions: Effect of the Backbone Length," Macromolecules, 2008, pp. 9831-9836, vol. 41.
Cheng et al., "The role of helper lipids in lipid nanoparticles (LNPs) designed for oligonucleotide delivery", Advanced Drug Delivery Reviews, 2016, pp. 129-137, vol. 99.
Chenite et al., "Monolithic gelation of chitosan solutions via enzymatic hydrolysis of urea", Carbohydrate Polymers, Jan. 20, 2006, pp. 419-424, vol. 64.
Chenite et al., "Novel injectable neutral solutions of chitosan form biodegradable gels in situ", Biomaterials, Apr. 7, 2000, pp. 2155-2161, vol. 21.
Chenite et al., "Rheological characterization of thermogelling chitosan/glycerol-phosphate solutions", Carbohydrate Polymers, Jul. 28, 2000, pp. 39-47, vol. 46.
Chevrier et al., "Chitosan-glycerol phosphate/blood implants increase cell recruitment, transient vascularization and subchondral bone remodeling in drilled cartilage defects", Osteoarthritis and Cartilage, Aug. 10, 2006, pp. 316-327, vol. 15, No. 3.
Chevrier et al., "Injectable chitosan-platelet-rich plasma implants to promote tissue regeneration: in vitro properties, in vivo residence, degradation, cell recruitment and vascularization", Journal of Tissue Engineering and Regenerative Medicine, 2017, pp. 1-12.
Chevrier et al., "Injectable chitosan-platelet-rich plasma implants to promote tissue regeneration: In vitro properties, in vivo residence, degradation cell recruitment and vascularization" Journal of Tissue Engineering and Regenerative Medicine, 2018, pp. 217-228, vol. 12.
Chevrier et al., "Interspecies Comparison of Subchondral Bone Properties Important for Cartilage Repair", Journal of Orthopedic Research, Aug. 25, 2014, pp. 1-8, vol. 33, No. 1.
Chevrier et al., "Meniscus Structure in Human, Sheep, Rabbit, for Animal Models of Meniscus Repair", Journal of Orthopedic Research, Feb. 25, 2009, pp. 1197-1203, vol. 27.
Chevrier et al., "Soluble Recombinant Neprilysin Induces Aggrecanase-Mediated Cleavage of Aggrecan in Cartilage Explant Cultures", Archives of Biochemistry and Biophysics, 2001, pp. 1-9.
Chevrier et al., "Optimization of Histoprocessing Methods to Detect Glycosaminoglycan, Collagen Type II, and Collagen Type I in Decalcified Rabbit Osteochondral Sections", The Journal of Histotechnology, Sep. 2005, pp. 165-175, vol. 28, No. 3.
Chevrier et al., "Temporal and spatial modulation of chondrogenic foci in subchondral microdrill holes by chitosan-glycerol phosphate/blood implants", Osteoarthritis and Cartilage, Jan. 2011, pp. 136-144, vol. 19.
Chibowksi et al., "Zeta potential and surface charge of DPPC and DOPC liposomes in the presence of PLC enzyme", Adsorption, 2016, pp. 755-765, vol. 22.
Chithrani et al., "Polyethylene Glycol Density and Length Affects Nanoparticle Uptake by Cancer Cells", Journal of nanomedicine Research, Oct. 18, 2014, pp. 1-6, vol. 1, Issue 1.
Choi et al., "Safety and immunogenicity of SARS-CoV-2 variant mRNA vaccine boosters in healthy adults: an interim analysis," Nature Medicine, 2021, https://doi.org/10.1038/s41591-021-01527-y, 13 pages.
Clarke, "Characterizing the Zeta Potential & Isoelectric Point of Nanomaterials | Malvern Panalytical," 2013, 195 pages.
Clarke, "Development of Hierarchical Magnetic Nanocomposite Material for Biomedical Applications", Dublin City University, Jan. 2013, pp. 1-195.
Clayton et al., "Physical characterization of nanoparticle size and surface modification using particle scattering diffusometry", Biomicrofluidics, 2016, pp. 1-14, vol. 10.
clinicaltrials.gov, "Safety and Immunogenicity Study of 2019-nCoV Vaccine (mRNA-1273) for Prophylaxis SARS CoV-2 Infection (COVID-19)", 2019, 10 pages.
Cohen, "Vaccine designers take first shots at COVID-19," Science Mag, Apr. 3, 2020, pp. 14-16, vol. 368, Issue 6486.
Cohen, "What went wrong with the CureVac's mRNA vaccine", Science Magazine, 2021, pp. 1381, vol. 372, No. 6549.
Collier et al., "SARS-CoV-2 B.1.1.7 escape from mRNA vaccine-elicited neutralizing antibodies," MedRxiv, Feb. 2, 2021, 32 pages. Retrieved from the internet https://doi.org/10.1101/2021.01.19.21249840.
Collins, F., "Meet the Researcher Leading NIH's COVID-19 Vaccine Development Effort,". NIH Director's Blog, Jul. 9, 2020 [online], [retrieved on Mar. 8, 2022]. Retrieved from the Internet URL: https://directorsblog.nih.gov/2020/07/09/meet-the-researcher-leading-nihs-covid-19-vaccine-development-efforts/, 6 pages.
Collins, "Researchers Publish Encouraging Early Data on COVID-19 Vaccine: NIH Director's Blog", Jul. 16, 2020, 6 pages. Retrieved from the Internet URL: https://directorsblog.nih.gov/2020/07/16/researchers-publish-encouraging-early-data-on-covid-19-vaccine/.
Coon, et al. "Nitinol thin films functionalized with CAR-T cells for the treatment of solid tumours." Nature Biomedical Engineering 4.2, 2020, pp. 95-206.
Corbett et al., "SARS-CoV-2 mRNA vaccine design enabled by prototype pathogen preparedness", Nature, Aug. 5, 2020, pp. 567-571, vol. 586, No. 7830.
Corbett et al., "SARS-CoV-2 mRNA Vaccine Development Enabled by Prototype Pathogen Preparedness," bioRxiv, Jun. 11, 2020, retrieved from the internet https://doi.org/10.1101/2020.06.11.145920, 39 pages.
Corbett, et al., "Evaluation of the mRNA-1273 Vaccine against SARS-CoV-2 in Nonhuman Primate", The New England Journal of Medicine, Jul. 28, 2020, pp. 1-12, vol. 383, No. 16.
Corbett et al., "Evaluation of the mRNA-1273 vaccine against SARS-CoV-2 in nonhuman primates, Supplementary Appendix", The New England Journal of Medicine, Jul. 28, 2020, pp. 1-24.
Corey et al., "A strategic approach to COVID-19 vaccine R&D," Science, May 11, 2020, DOI: 10.1126/science.abc5312, pp. 1-6.
Cott, E. et al., "How Pfizer Makes Its Covid-19 Vaccine," The New York Times, Apr. 28, 2021 [online], [retrieved on Mar. 8, 2022]. Retrieved from the Internet URL: https://www.nytimes.com/interactive/2021/health/pfizer-coronavirus-vaccine.html, 25 pages.
Crobett et al., "Advances in the measurement of protein mobility using laser Doppler electrophoresis—the diffusion barrier technique", Electrophoresis, 2011, pp. 1787-1794, vol. 32.
Cross, Chemical & Engineering News, Aug. 25, 7 pages. Retrieved from the Internet URL: https://cen.acs.org/pharmaceuticals/drug-discovery/Michelle-Lynn-Hall/97/i33.
Cross, "Modeling mastermind is using computational chemistry to help scientists craft mRNA therapies", Drug Discovery, Aug. 25, 2019, 7 pages, vol. 97, Issue 33.
Cugia et al., "Interplay of ion specificity, pH, and buffers: insights from electrophoretic mobility and pH measurements of lysozyme solutions", The Royal Society of Chemistry Advances, 2013, pp. 5882-5888, vol. 3.
Curevac, "About CureVac's activities regarding an mRNA-based vaccine against COVID-19", Apr. 8, 2020, 5 pages.
Curevac, "CureVac Announces Financial Results and Business Updates for the Third Quarter and First Nine Months of 2020", 9 pages.

(56) References Cited

OTHER PUBLICATIONS

Curevac, "CureVac Provides Update on Phase 2b/3 Trial of First-Generation COVID-19 Vaccine Candidate, CVnCoV", Jun. 16, 2021, 4 pages.
Dahlman, James E et al., In vivo endothelial siRNA delivery using polymeric nanoparticles with low molecular weight, Nature Nanotechnology, 2014, No. Vol.#, pp. 1-8.
Dammes et al., "Conformation-sensitive targeting of lipid nanoparticles for RNA therapeutics", nature nanotechnology, Nature nanotechnology, 2021, pp. 1030-1038, vol. 16, No. 9.
Danaei et al., "Impact of particle Size and Polydispersity Index on the Clinical Applications of Lipidic nanocarrier Systems", Pharmaceutics, 2018, pp. 1-17, vol. 10.
Danaei et al., "Probing nanoliposomes using single particle analytical techniques: effect of excipients, solvents, phase transition and zeta potential", Heliyon, Dec. 2018, pp. 1-32.
Darras et al., "Chitosan modified with gadolinium diethylenetriaminepentaacetic acid for magnetic resonance imaging of DNA/chitosan nanoparticles", Carbohydrate Polymers, Jan. 22, 2010, pp. 1137-1146, vol. 80.
Davidson et al., "Fibroblast Growth Factor (FGF) 18 Signals through FGF Receptor 3 to Promote Chondrogenesis", The Journal of Biological Chemistry, Mar. 21, 2005, pp. 20509-20515, vol. 280, No. 21.
Dedeudis, "'Learned a lot last year': After Covid-19 success, Moderna's Stéphane Bancel plans to give rest of pipeline a big push", Endpoint News, 2021, 29 pages.
Demolliens et al., "Tyrosinase-Catalyzed Synthesis of a Universal Coil-Chitosan Bioconjugate for Protein immobilization", Bioconjugate Chemistry, Aug. 14, 2008, pp. 1849-1854, vol. 19, No. 9.
Deng et al., "Primary exposure to SARS-CoV-2 protects against reinfection in rhesus macaques," Science, Jul. 2, 2020, pp. 1-10, DOI: 10.1126/science.abc5343.
Deprés-Tremblay et al., "Chitosan inhibits platelet-mediated clot retraction, increases platelet-derived growth factor release, and increases residence time and bioactivity of platelet-rich plasma in vivo", Biomedical Materials, Nov. 10, 2017, pp. 1-11, vol. 13.
Deprés-Tremblay et al., "Freeze-Dried Chitosan-Platelet-Rich Plasma Implants for Rotator Cuff Tear repair: Pilot Ovine Studies" ACS Biomaterials Science and Engineering, Oct. 13, 2017, pp. 1-10, vol. 4, No. 11.
Deprés-Tremblay et al., "Rotator cuff repair: a review of surgical techniques, animal models, and new technologies under development", Journal of Shoulder and Elbow Surgery, 2016, pp. 2078-2085, vol. 25.
Derosa et al., "Improved Efficacy in a Fabry Disease Model Using a Systemic mRNA Liver Depot System as Compared to Enzyme Replacement Therapy," Molecular Therapy, Apr. 2019, pp. 878-889, vol. 27, Issue No. 4.
Di et al., "When liposomes met antibodies: Drug delivery and beyond", Advanced Drug Delivery Reviews, Sep. 2020, pp. 151-162, vol. 154-155.
Dinnon, "SARS-CoV-2 mRNA Vaccine Design Enabled by Prototype Pathogen Preparedness, Peer review File", Natureresearch, 2020, pp. 12 pages.
Dinpajooh et al., "Mobility of nanometer-size solutes in water riven by electric field", Arizona State University, Jun. 7, 2016, pp. 1-10.
Dipiazza et al., "COVID-19 vaccine mRNA-1273 elicits a protective immune profile in mice that is not associated with vaccine-enhanced disease upon SARS-CoV-2 challenge", Immunity, Jun. 2021, pp. 1869-1882, vol. 54, No. 8.
Doane et al., "Nanoparticle Potentials", Accounts of Chemical Research, 2012, pp. 317-326, vol. 45, No. 3.
Dold et al., "A poly (beta-amino ester) activates macrophages independent of NF-kB signaling", Acta Biomaterialia, 2018, pp. 168-177, vol. 68.
Dolsten, "COVID-19 R&D," Pfizer, No Date, 30 pages.
Doremalen et al., "ChAdOx1 nCOV-19 vaccination prevents SARS-CoV-2 pneumonia in rhesus macaques," bioRxiv, May 13, 2020, retrieved from the internet https://doi.org/10.1101/2020.05.13.093195, 23 pages.
Dreyfus, et al., 2002, The poly(A) tail of mRNAs: Bodyguard in eukaryotes, scavenger in bacteria, Cell, Nov. 27, 2002, pp. 611-613.
Drzymala et al., "Ice/Water interface: Zeta Potential, Point of Zero Charge, and Hydrophobicity", Journal of Colloid and Interface Science, 1999, pp. 229-234, vol. 220.
Dudek et al., "Knockdown of β-catenin with Dicer-Substrate sirRNAs Reduces Liver Tumor Burden in vivo", Molecular Therapy, Jan. 2014, pp. 92-101, vol. 22, No. 1.
Duguay et al., "Lipofection of plasmid DNA into human mast cell lines using lipid nanoparticles generated by microfluidic mixing", Journal of Leukocyte Biology, Mar. 2018, pp. 587-596, vol. 104.
Dumont et al., "Mature Full-thickness Articular Cartilage Explants Attached to Bone are Physiologically Stable over Long-term Culture in Serum-free Media", Connective Tissue Research, Apr. 29, 1999, pp. 259-272, vol. 40, No. 4.
Duval-Valentin et al, "Specific Inhibition of Transcription by Triple Helix-Forming Oligonucleotides," Proc. Natl. Acad. Sci. USA, 89:504-508 (1992).
Dwivedi et al., "Bone Marrow Progenitor Cells Isolated from Young Rabbit Trochlea are More Numerous and Exhibit Greater Clonogenic, Chondrogenic, and Osteogenic Potential than Cells Isolated from Condyles", Cartilage, 2018, pp. 378-390, vol. 9, No. 4.
Dwivedi et al., "Injectable freeze-dried chitosan-platelet-rich-plasma implants improve marrow-stimulated cartilage repair in a chronic-defect rabbit model", Journal of Tissue Engineering and Regenerative Medicine, Jan. 14, 2019, pp. 599-611, vol. 13.
Efrati et al., "Safety and humoral responses to BNT162b2 mRNA vaccination of SARS-CoV-2 previously infected and naïve populations," Scientific Repports, 2021, 7 pages, vol. 11, No. 16543. https://doi.org/10.1038/s41598-021-96129-6.
Egawa et al., "Liposome Adhesion on Mica Surface Studied by Atomic Force Microscopy", Langmuir, Dec. 18, 1998, pp. 1660-1666, vol. 15.
Egholm, et al., PNA hybridizes to complementary oligonucleotides obeying the Watson-Crick hydrogen-bonding rules, Nature, Oct. 1993, pp. 566-568.
Elbashir, et al., Duplexes of 21-nucleotide RNAs mediate RNA interference in cultured mammalian cells, Nature, May 2001, pp. 494-498, vol. 411.
El-Bikai et al., "Perturbation of adhesion molecule-mediated chondrocyte-matrix interactions by 4-hydroxynonenal binding: implication in osteoarthritis pathogenesis", Arthritis research and Therapy, 2010, pp. 1-14, vol. 12.
EMA, "Assessment Report: COVID-19 Vaccine Moderna", European Medicines Agency, Mar. 11, 2021, pp. 1-169.
Espeseth, Supplementary Files, "Supplementary Figure 1. Flow Cytometry of RSV F constructs containing an intact transmembrane domain expressed in Expi293F cells", No Date, 14 pages.
Evans et al., "Endosomolytic Nano-Polyplex Platform Technology for Cytosolic Peptide Delivery to Inhibit Pathological Vasoconstriction", ACS Nano, 2015, pp. 5893-5907, vol. 9 No. 6.
Everton et al., "Transient yet Robust Expression of Proteins in the Mouse Liver via Intravenous Injection of Lipid Nanoparticle-encapsulated Nucleoside-modified mRNA," Bio-protocol, Oct. 15, 2021, pp. 1-15, vol. 11, No. 19.
Ewert et al., "Lipoplex Structures and their Distinct cellular Pathways", Advanced in Genetics, 2005, pp. 119-155, vol. 53.
Fairhurst, "An Overview of the Zeta Potential—Part 2: Measurement," American Pharmaceutical Review, Apr. 1, 2013, 6 pages.
Falsey, et al., "SARS-CoV-2 Neutralization with BNT162b2 Vaccine Dose 3," N Engl J Med, 2021, pp. 1-3.
Falsini, Advances in Lipid-Based Platforms for RNAi Therapeutics, J. Med. Chem., Sep. 18, 2013, pp. 1138-1146, vol. 57, No. 4.
Fan et al., "Analytical characterization of liposomes and other lipid nanoparticles for drug delivery", Journal of Pharmaceutical and Biomedical Analysis, 2021, pp. 1-21, vol. 192.

(56) References Cited

OTHER PUBLICATIONS

Fang et al., "Evidence of the adsorption of hydroxide ion at hexadecane/water interface from second harmonic generation study", The Royal Society of Chemistry Advances, 2015, pp. 23578-23585, vol. 5.

Fehring et al., "Delivery of Therapeutic siRNA to the Lung Endothelium via Novel Lipoplex Formulation DACC", Molecular Therapy, Apr. 2014, pp. 811-820, vol. 22 No. 4.

Feldman et al., "mRNA vaccines against H10N8 and H7N9 influenza viruses of pandemic potential are immunogenic and well tolerated in healthy adults in phase 1 randomized clinical trials", Vaccine, May 2019, pp. 3326-3334, vol. 37.

Felgner, PL Cationic lipid/polynucleotide condensates for in vitro and in vivo polynucleotide delivery—the cytofectins. J. of Liposome Research. 1993; 3(1): 3-16.

Felgner P.L., et al., "Lipofection: A Highly Efficient, Lipid-Mediated DNA—Transfection Procedure," Proceedings of the National Academy of Sciences USA, vol. 84 (21), Nov. 1987, pp. 7413-7417.

Felgner, PL Particulate systems and polymers for in vitro and in vivo delivery of polynucleotides. Adv. Drug Delivery Rev. 1990; 5(3): 163-187.

Fenton et al., "Synthesis and biological Evaluation of lonizable Lipid Materials for the in Vivo Delivery of Messenger RNA to B Lymphocytes", Advanced Materials, Supporting Information, 2017, pp. 1-17.

Ferretti, et al., "COVID-19 Patients Form Memory CD8+ T Cells that Recognize a Small Set of Shared Immunodominant Epitopes in SARS-CoV-2," medRxiv, Jul. 29, 2020, pp. 1-21. retrieved from URL https://doi.org/10.1101/2020.07.24.20161653.

Filion et al., "Chitosan-glycerol-phosphate (GP) gels release freely diffusible GP and possess titratable fixed charge", Carbohydrate Polymers, Jul. 4, 2013, pp. 813-819, vol. 98.

Filion et al., "Ionization and Solubility of Chitosan Solutions related to Thermosensitive Chitosan/Glycerol-Phosphate Systems", Biomacromolecules, Jul. 12, 2007, pp. 3224-3234, vol. 8.

Finn et al.,"A Single Administration of CRISPR/Cas9 Lipid Nanoparticles Achieves Robus and Persistent in Vivo Genome Editing", Cell Reports, 2018, pp. 2227-2235, vol. 22, No. 9.

Fish et al., "Deformable microparticles for shuttling nanoparticles to the vascular wall", Science Advances, Apr. 2021, pp. 1-11, vol. 7.

Fleischmann et al., "General Sites of Nanoparticle Biodistribution as a Novel Opportunity for Nanomedicine", European Journal of Pharmaceutics and Biopharmaceutics, May 2021, pp. 44-60, vol. 166.

Fobian et al., "Smart Lipid-Based Nanosystems for Therapeutic Immune Induction against Cancers: perspectives and Outlooks", Pharmaceutics, Dec. 2021, pp. 1-43, vol. 14.

Fohse et al., "The BNT162b2 mRNA vaccine against SARS-CoV-2 reprograms both adaptive and innate immune responses," medRxiv, May 6, 2021, pp. 1-21. retrieved from URL https://doi.org/10.1101/2021.05.03.2125650.

Folegatti, et al., "Safety and immunogenicity of the ChAdOx1 nCoV-19 vaccine against SARS-CoV-2: a preliminary report of a phase 1/2, single-blind, randomised controlled trial," The Lancet, Jul. 20, 2020, pp. 1-13. retrieved from URL https://doi.org/10.1016/S0140-6736(20)31604-4.

Fong et al., "Biodegradable chitosan microparticles induce delayed STAT-1 activation and lead to distinct cytokine responses in differently polarized human macrophages in vitro", Acta Biomaterialia, Oct. 25, 2014, pp. 183-194, vol. 12.

Food and Drug Administration, "Fact sheet for healthcare providers administering vaccine (vaccination providers): Emergency Use Authorization (EUA) of the Pfizer-BioNTech COVID-19 vaccine to prevent coronavirus disease 2019 (COVID-19), Silver Spring, MD: US Department of Health and Human Services." Food and Drug Administration, 2021, 30 pages.

Fornaguera et al., "mRNA Delivery System for targeting Antigen-Presenting Cells in Vivo", Advanced Healthcare Materials, 2018, pp. 1-11, vol. 7.

Fortin et al., "Dynamic measurement of internal solid displacement in articular cartilage using ultrasound backscatter", Journal of biomechanics, 2003, pp. 443-447, vol. 36.

Fortin et al., "Unconfined Compresion of Articular Cartilage: Nonlinear behavior and Comparison with a Fibril-Reinforced Biphasic Model", Journal of Biomechanical Engineering, Apr. 2000, pp. 189-195, vol. 122.

Foster et al., "Development of GPC2-directed chimeric antigen receptors using mRNA for pediatric brain tumors," bioRxiv, Jul. 7, 2021, 40 pages. retrived from URL https://doi.org/10.1101/2021.07.06.451385.

Foster et al., "Purification of mRNA Encoding Chimeric Antigen Receptor Is Critical for Generation of a Robust T-Cell Response," Human Gene Therapy, 2019, pp. 168-178, vol. 30, No. 2.

Fotin-Mleczek, M., et al., "Messenger RNA-Based Vaccines with Dual Activity Induce Balanced TLR-7 Dependent Adaptive Immune Responses and Provide Antitumor Activity," Journal of Immunotherapy 34(1 ): 1-15, Informa Healthcare, England (2011 ).

Fox, Targeting DNA with triplexes, Current medicinal chemistry, Jan. 1, 2000, pp. 17-37, vol. 7, No. 1.

Franklin et al., "Internal Electrostatic Potentials in Bilayers: Measuring and Controlling Dipole Potentials in Lipid vesicles", Biophysical Journal, Jul. 1993, pp. 289-299, vol. 65.

Freichel et al., "Effects of Linker and Liposome Anchoring on Lactose-functionalized Glycomacromolecules as Multivalent Ligands for Binding Galectin-3", The Royal Society of Chemistry, Supporting Information, 2019, 56 pages.

Friedman, "membrane-Ion Interactions", The Journal of Membrane Biology, 2018, pp. 453-460, vol. 251.

Fuchs et al., "Lipid analysis by thin-layer chromatography—A review of the current state", Journal of Chromatography A, 2011, pp. 2754-2774, vol. 1218.

Gallas, Chemistry and formulations for siRNA therapeutics, Chem. Soci. Rev., 2013, pp. 7983-7997, vol. 42, No. 20.

Gan et al., "The behavior of hydroxide and hydronium ions at the hexadecane-water interface studied with second harmonic generation and zeta potential measurements", Soft Matter, Apr. 2017, pp. 7962-7968, vol. 13.

Ganesh et al., "Direct Pharmacological Inhibition of β-Catenin by RNA Interference in Tumors of Diverse Origin", Molecular Cancer Therapeutics, Sep. 2016, pp. 2143-2154, vol. 15, No. 9.

Gao et al., "Development of an inactivated vaccine candidate for SARS-CoV-2," Science, May 6, 2020, pp. 1-10.

Gao et al., "Mesenchymal Stem Cell Transplantation to Promote Bone Healing", Journal of Orthopedic Research, Jan. 6, 2012, pp. 1183-1189, vol. 30, No. 8.

Garon et al., "Streaming potentials maps are spatially resolved indicators of amplitude frequency and ionic strength dependent response of articular cartilage to load", Journal of Biomechanics, 2002, pp. 207-216, vol. 35.

Gauthier et al., "Degree of crosslinking and mechanical properties of crosslinked poly (vinyl alcohol) beads for use in solid-phase organic synthesis", Polymer, Oct. 12, 2004, pp. 8201-8210, vol. 45.

Geall et al., RNA: the new revolution in nucleic acid vaccines, InSeminars in immunology, Apr. 1, 2013, pp. 152-159, vol. 25, No. 2.

Gessner, "Optimizing nanoparticle design and surface modification toward clinical translation", MRS Bulletin, Jul. 2021, pp. 1-7, vol. 6.

Ghazi et al., "Freeze-Dried Chitosan-PRP Injectable Surgical Implants for Meniscus Repair: Pilot Feasibility Studies in Ovine Models", Regenerative Medicine and Therapeutics, 2017, pp. 16-29, vol. No. 1.

Ghazi et al., "Freeze-dried chitosan-PRP injectable surgical implants for meniscus repair: Pilot feasibility studies in ovine models", The Open Orthopedics Journal, No Date, pp. 1-31.

Ghazi et al., "Multiple platelet-rich plasma preparations can solubilize freeze-dried chitosan formulations t form injectable implants for orthopedic indications", Bio-Medical Materials and Engineering, 2019, pp. 349-364, vol. 30.

(56) References Cited

OTHER PUBLICATIONS

Gigout et a., "Chondrocyte Aggregation in Suspension Culture is GFOGER-GPP- and β1 Integrin-dependent", The Journal of Biological Chemistry, Nov. 14, 2008, pp. 31522-31530, vol. 283, No. 46.

Gigout et al., "CHO Cells Adhering to Nitrogen-Rich Plasma-Polymerised Ethylene Exhibit High Production of a Specific Recombinant Protein", Macromolecular Bioscience, 2009, pp. 979-988, vol. 9.

Gigout et al., "Chondrocytes Cultured in Stirred Suspension with Serum-Free Medium Containing Pluronic-68 Aggregate and Proliferate While Maintaining their Differentiated Phenotype", Tissue Engineering, 2009, pp. 1-12, vol. 15 No. 8.

Gigout et al., "Low calcium levels in serum-free media maintain chondrocyte phenotype in monolayer culture and reduce chondrocyte aggregation in suspension culture", Osteoarthritis and Cartilage, 2005, pp. 1012-1024, vol. 13.

Gigout et al., "The Fate of Pluronic F-68 in Chondrocytes and CHO Cells", Biotechnology and Bioengineering, Aug. 1, 2008, pp. 975-987, vol. 100, No. 5.

Gilleron et al., "Image-based analysis of lipid nanoparticle-mediated siRNA delivery, intracellular trafficking and endosomal escape", Nature Biotechnology, Jul. 2013, pp. 638-670, vol. 13, No. 7.

Gindy et al., "Challenges in the pharmaceutical development of lipid-based short interfering ribonucleic acid therapeutics", Taylor Francis Online, Feb. 1, 2012, pp. 171-182, vol. 9, Issue 2.

Gindy et al., "Stabilization of Ostwald Ripening in Low Molecular Weight Amino Lipid Nanoparticles for Systemic delivery of siRNA Therapeutics, Supporting Information", Molecular Pharmaceutics, 2014, pp. 4143-4153, vol. 11.

Giuliani, et al., A universal vaccine for serogroup B meningococcus, Proc Natl Acad Sci., Jul. 18, 2006, pp. 10834-9, vol. 103, No. 29.

Glaszlou, "Waste in covid-19 research," BMJ, May 12, 2020, pp. 1-2, vol. 369, No. m1847.

Graham et al., "Evaluation of the immunogenicity of prime-boost vaccination with the replication-deficient viral vectored COVID-19 vaccine candidate ChAdOx1 nCoV-19," bioRxiv, Jun. 20, 2020, pp. 1-11. retrieved from URL https://doi.org/10.1101/2020.06.20.159715.

Graham et al., "Rapid COVID-19 vaccine development," Science, May 8, 2020, 5 pages. DOI: 10.1126/science.abb8923.

Graham et al., "Structure-Based Vaccine Antigen Design," Annual Review of Medicine, 2019, pp. 91-104, vol. 70.

Granot-Matok et al., "Therapeutic mRNA delivery to leukocytes", Journal of Controlled Release, May 2019, pp. 165-175, vol. 305.

Greenwood et al., "Partial molecular volumes of lipids and cholesterol", Chemistry and Physics of Lipids, 2006, pp. 1-10, vol. 143.

Grifoni et al., "Targets of T Cell Responses to SARS-CoV-2 Coronavirus in Humans with COVID-19 Disease and Unexposed Individuals," Cell, Supplemental Information, Jun. 25, 2020, 6 pages.

Grit et al., "Determination of phosphatidylcholine, phosphatidylglycerol and their lyso forms from liposome dispersions by high-performance liquid chromatography using high-sensitivity refractive index detection" Journal of Chromatography, May 1991, pp. 239-246, vol. 585.

Grudzien-Nogalska et al., Synthetic mRNAss with superior translation and stability properties in Synthetic Messenger RNA and Cell Metabolism Modulation in Methods in Molecular Biology, 2013, pp. 55-72.

Gubernatorova et al., "IL-6: Relevance for immunopathology of SARS-CoV-2," Cytokine and Growth Factor Reviews, May 20, 2020, pp. 13-24, vol. 53.

Guhaniyogi, J. et al., Regulation of mRNA stability in mammalian cells. Gene. Mar. 7, 2001;265(1-2):11-23.

Guyon et al., "Relevant Physiochemical Methods to Functionalize, Purify, and Characterize Surface-Decorated Lipid-Based Nanocarriers", Molecular Pharmaceutics, 2021, pp. 44-64, vol. 18.

Guzmán-Morales et al., "Subchondral chitosan/blood implant-guided bone plate resorption and woven bone repair is coupled to hyaline cartilage regeneration from microdrill holes in aged rabbit knees", Osteoarthritis and Cartilage, 2014, pp. 323-333, vol. 22.

Hadjab et al., "Electromechanical properties of human osteoarthritic and asymptomatic articular cartilage are sensitive and earl detectors of degeneration", Osteoarthritis and Cartilage, 2018, pp. 405-413, vol. 26.

Hafez, et al., Gene Ther 8:1188-1196, 2001.

Hafez et al., "Tunable pH-Sensitive Liposomes Composed of Mixtures of Cationic and Anionic Lipids", Biophysical Journal, Sep. 2000, pp. 1438-1446, vol. 79.

Hajj et al., "A Potent Branched-Tail Lipid Nanoparticle Enables Multiplexed mRNA Delivery and Gene Editing in Vivo," Nano Letters, 2020, pp. 5167-5175, vol. 20.

Hajj et al., "Branched-Tail Lipid Nanoparticles Potently Deliver mRNA in Vivo due to Enhanced lonization at Endosomal pH," Small, 2019, pp. 1-16, vol. 10.

Hajj et al., "Tools for translation: non-viral materials for therapeutic mRNA delivery," Nature Reviews Material, Sep. 12, 2017, pp. 1-17, vol. 2.

Hamman, et al., Length variation of helix III in a hammerhead ribozyme and its influence on cleavage activity, Antisense and Nucleic Acid Drug Dev., Feb. 1999, pp. 25-31, vol. 9, No. 1.

Han et al., "The Forward Problem of Electroarthrography: Modeling Load-Induced electrical Potentials at the Surface of the Knee", IEEE Transactions on Biomedical Engineering, Jul. 2014, pp. 2020-2027, vol. 61, No. 7.

Hassett et al., "Optimization of Lipid Nanoparticles for Intramuscular Administration of mRNA Vaccines", OMTN, 2019, pp. 1-7, vol. 15.

Heerklotz, "Interactions of surfactants with lipid membranes", Quarterly Reviews of Biophysics, 2008, p. 205-264, vol. 41.

Heilig et al., Large-Scale Preparation of Plasmid DNA, Current Protocols in Molecular Biology, Jan. 1998, pp. 1-7.

Helfand, C., "JPM: How did Pfizer up its COVID-19 vaccine capacity? 'Out of the box manufacturing,' CEO says," FiercePharma, Jan. 13, 2021, 5 pages [online], [retrieved on Mar. 8, 2022]. Retrieved from the Internet URL: https://www.fiercepharma.com/pharma/jpm-how-did-pfizer-up-its-covid-19-vaccine-capacity-out-box-manufacturing-ceo-says.

Heyes, et al., "Genevant Keto Intermediate", American Chemical Society, 2020, 3 pages.

Heyes, et al., Genevant Tail Procedure, American Chemical Society, 2020, 3 pages.

Heyes, J. et al. (2005), "Cationic lipid saturation influences intracellular delivery of encapsulated nucleic acids," Journal of Controlled Release, 107:276-287.

Hill et al., "Electrophoretic Interpretation of PEGylated NP Structure with and without Peripheral Charge", Langmuir, Sep. 2, 2015, pp. 10246-10253, vol. 31.

Hinton et al., "Letter in response to a request from Pfizer Inc. tthat the Food and Drug Administration (FDA) issue an Emergency Use Authorization for emergency use of Pfizer-BioNTech COVID-19 Vaccine," US FDA, Dec. 11, 2020, 9 pages.

Hinton, Letter to Moderna from the Food and Drug Administration, Dec. 18, 2020, 9 pages.

Hoemann et al., "A Multivalent Assay to Detect Glycosaminoglycan, Protein, Collagen, RNA, and DNA Content in Milligram Samples of Cartilage or Hydrogel-based Repair Cartilage", Analytical Biochemistry, 2001, pp. 1-10, vol. 300, No. 1.

Hoemann et al. Appendix to "Chondroinduction is the Main Cartilage Repair Response to Microfracture and Microfracture with BST-CarGel", The American Journal of Sports Medicine, Aug. 10, 2015, 4 pages.

Hoemann et al., "Scaffold-Guided Subchondral Bone Repair", The American Journal of Sports Medicine, 2010, pp. 1-13, vol. 38, No. 9.

Hoemann et al., "Characterization of Initial Microfracture Defects in Human Condyles", The Journal of Knee Surgery, 2013, pp. 1-10, vol. 26, No. 5.

Hoemann et al., "Chitosan Rate of Uptake in HEK293 Cells is Influenced by Soluble versus Microparticle State and Enhanced by

(56) References Cited

OTHER PUBLICATIONS

Serum-Induced Cell Metabolism and Lactate-Based Media Acidification", Molecules, 2013, pp. 1-21, vol. 18.
Hoemann et al., "Chitosan-glycerol phosphate/blood implants elicit hyaline cartilage repair integrated with porous subchondral bone in microdrilled rabbit defects", osteoarthritis and Cartilage, 2007, pp. 78-89, vol. 15.
Hoemann et al., "Chitosan-Glycerol Phosphate/Blood Implants Improve Hyaline Cartilage Repair in Ovine Microfracture Defects", The Journal of Bone and Joint Surgery, Dec. 2005, pp. 2671-2686, vol. 87, No. 12.
Hoemann et al., "Chondroinduction is the Main Cartilage Repair Response to Microfracture and Microfracture with BST-CarGel", The American Journal of Sports Medicine, Aug. 10, 2015, pp. 1-12, vol. XX, No. X.
Hoemann et al., "Cytocompatible gel formation of Chitosan-glycerol phosphate solutions supplemented with hydroxyl ethyl cellulose is due to the presence of glyoxal", Journal of Biomedical Materials Research Part A, Feb. 27, 2007, pp. 521-529, vol. 83, No. 2.
Hoemann et al., "In vitro osteogenesis assays: Influence of the primary cell source on alkaline phosphatase activity and mineralization", Pathologie Biologie, 2008, pp. 1-6, vol. 57, No. 4.
Hoemann et al., "International Cartilage Repair Society (ICRS) Recommended Guidelines for Histological Endpoints for Cartilage Repair Studies in Animal Models and Clinical Trials", Cartilage, 2011, pp. 153-172, vol. 2, No. 2.
Hoemann et al., "The Cartilage-Bone Interface", The Journal of Knee Surgery, 2012, pp. 1-13, vol. 25, No. 2.
Hoemann et al., "Tissue engineering of cartilage using and injectable and adhesive chitosan-based cell delivery vehicle", Osteoarthritis and Cartilage, 2005, pp. 318-329, vol. 13.
Hoemann et al., "Two Distinct Notch1 Mutant Alleles are Involved in the Induction of T-Cell Leukemia in c-myc Transgenic Mice", Molecular and Cellular Biology, Jun. 2000, pp. 3831-3842, vol. 20 No. 11.
Hoemann, "Molecular and Biochemical Assays of Cartilage Components", Cartilage and Osteoarthritis, 2004, pp. 127-156.
Hoerr, I. et al., In vivo application of RNA leads to induction of specific cytotoxic T lymphocytes and antibodies. EurJ Immunol. Jan. 2000;30(1): 1 -7.
Hoffman et al., "Age- and Sex-Graded Data Evaluation of Vaccination Reactions after Initial Injection of the BNT162b2 mRNA Vaccine in a Local Vaccination Center in Germany," Vaccines, Aug. 16, 2021, pp. 1-10, vol. 9, No. 911.
Hoffmann et al., CnCoV protects human ACE2 trangenic mice from ancestral B PavPat1 and emerging B.1.351 SARS-CoV-2, Cell Rep Med, 2021, pp. 1-16, vol. 2.
Hotz et al., "Local delivery of mRNA-encoding cytokines promotes antitumor immunity and tumor eradication across multiple preclinical tumor models," Science Translational Medicine, Sep. 8, 2021, pp. 1-13, vol. 13.
Hu et al., "Polysarcosine as an Alternative to PEG for Therapeutic Protein Conjugation," Bioconjugate Chem, 2018, pp. 2232-2238, vol. 29.
Huang et al., "Priming with Sars Cov S DNA and boosting with Sars CoV S epitopes specific for CD4+ and CD8+ T cells," Vaccine, Jul. 16, 2007, pp. 6981-6991, vol. 25.
Huotari et al., "Endosome Maturation", The EMBO Journal, 2011, pp. 3481-3500, vol. 30.
Hurtig et al., "Preclinical Studies for Cartilage Repair: Recommendations from the International Cartilage Repair Society", Cartilage, 2011, pp. 137-152, vol. 2, No. 2.
Idrus, "Moderna's COVID-19 jab spurs 'robust' immune response in first published data", FierceBiotech, Jul. 14, 2020, 5 Pages. Retrieved from the Internet URL: https://www.fiercebiotech.com/biotech/moderna-s-covid-19-jab-spurs-immune-response-first-published-data.
Idrus, "Moderna COVID-19 vaccine passes FDA reviewers' test, but shares drop anyway", FierceBiotech, Dec. 15, 2020, 7 pages. Retrieved from the Internet URL: https://www.fiercebiotech.com/biotech/moderna-covid-19-shot-passes-muster-at-fda-but-shares-dip.
Iliescu et al., "Ultrastructure of Hybrid Chitosan-Glycerol Phosphate Blood Clots by Environmental Scanning Electron Microscopy", Microscopy Research and Technique, 2008, pp. 236-247, vol. 71.
International Organization for Standardazation, "Particle size analysis—Dynamic light scattering (DLS)," International Organization for Standardization, Feb. 2017, 3 pages.
International Search Report and Written Opinion for Application No. PCT/US2021/054837, mailed Mar. 18, 2022, 12 pages.
International Search Report and Written Opinion for International Application No. PCT/US2021/054839, mailed Feb. 8, 2022, 14 pages.
Invitation to Pay Additional Fees for International Application No. PCT/US2021/054837, mailed Jan. 13, 2022, 2 pages.
Ishida T et al., "A combinatorial approach to producing sterically stabilized (Stealth) immunoliposomal drugs." FEBS Letters, vol. 460, 1999, pp. 129-133. (Year: 1999).
Isho, B. et al., "Persistence of serum and saliva antibody responses to SARS-CoV-2 spike antigens in COVID-19 patients," Science Immunology, Oct. 8, 2020, pp. 1-21. [online], [retrieved on Mar. 8, 2022]. Retrieved from the Internet URL: https://www.science.org/doi/10.1126/sciimmunol.abe5511.
Iyer et al., "Persistence and decay of human antibody responses to the receptor binding domain of SARS-CoV-2 spike protein in COVID-19 patients," Science Immunology, Oct. 8, 2020, pp. 1-13, DOI: 10.1126/sciimmunol.abe0367.
Jackson, et al., "An mRNA Vaccine against SARS-CoV-2—Preliminary Report", The New England Journal of Medicine, Nov. 12, 2020, 6 pages. Retrieved from the Internet URL: https://doi.org/10.1056/NEJMoa2022483.
Jackson, et al., "Experimental COVID-19 vaccine safe, generates immune response", Jul. 14, 2020, 4 pages. Retrieved from the Internet URL: https://www.nih.gov/news-events/news-releases/experimental-covid-19-vaccine-safe-generates-immune-response.
Jackson et al., "The promise of mRNA vaccines: a biotech and industrial perspective," npj Vaccines, Feb. 4, 2020, pp. 1-6, vol. 11.
Jackson et al., "An mRNA Vaccine against SARS-CoV-2 Preliminary Report," The New England Journal of Medicine, pp. 1-12 (2020).
Jahn et al., "Microfluidic Mixing and the Formation of Nanoscale Lipid Vesicles", ACS Nano, Mar. 31, 2010, pp. 2077-2087, vol. 4, No. 4.
Janowski et al., Inhibiting gene expression at transcription start sites in chromosomal DNA with antigene RNAs, Nature Chemical Biology, Sep. 1, 2005, pp. 216-222.
Jansig et al., "Viromers as carriers for mRNA-mediated expression of therapeutic molecules under inflammatory conditions," Scientific Reports, Sep. 15, 2020, 3 pages, vol. 10, retrieved from URL https://doi.org/10.1038/s41598-020-72004-8.
Jarry et al., "Effects of Steam Sterilization on Thermogelling Chitosan-Based Gels", 2000, pp. 127-135, vol. 58, No. 1.
Jayaraman et al., "Maximizing the Potency of siRNA Lipid Nanoparticles for Hepatic Gene Silencing in Vivo," Angew. Chem. Int. Ed. 2012, 51, 8529-8533.
Jean et al., "Chitosan-based therapeutic nanoparticles for combination gene therapy and gene silencing of in vitro cell lines relevant to type 2 diabetes", European Journal of Pharmaceutical Sciences, 2012, pp. 138-149, vol. 45.
Jean et al., "Chitosan-plasmid nanoparticle formulations for IM and SC delivery of recombinant FGF-2 and PDGF-BB or generation of antibodies", Gene Therapy, 2009, pp. 1097-1110, vol. 16.
Jean et al., "Effective and safe gene-based delivery of GLP-1 using chitosan/plasmid-DNA therapeutics nanocomplexes in an animal model of type 2 diabetes", Gene Therapy, 2011, pp. 807-816, vol. 18.
Jeong et al., "Assemblies of putative SARS-CoV-2-spike-enconding mRNA Sequences for Vaccines BNT-162b2 and mRNA-1273", Version 0.1beta, Mar. 23, 2021, pp. 1-4.

(56) References Cited

OTHER PUBLICATIONS

Jiang et al., "Identification of murine antigen-specific T follicular helper cells using an activation-induced marker assay," Journal of Immunological Methods, Feb. 22, 2019, pp. 48-57, vol. 467.
Jiang et al., "Quantitating endosomal Escape of a Library of Polymers for mRNA Delivery", Nano Letters, 2020, pp. 1117-1123, vol. 20.
Jimeno, et al., "Abstract CT032: A phase 1/2, open-label, multi-center, dose escalation and efficacy study of mRNA-2416, a lipid nanoparticle encapsulated mRNA encoding human OX40L, for intratumoral injection alone or in combination with durvalumab for patients with advanced malignancies. AACR", Aug. 2020, 4 pages. Retrieved from the Internet URL: https://cancerres.aacrjournals.org/content/80/16_Supplement/CT032.
Johnson et al., "CureVac, latest experimental coronavirus vaccine, proved just 47 percent effective amid spread of variants, preliminary analysis shows", The Washington Post, 2021, pp. 1-7.
Jorge et al., "Lipid Nanocarriers for Oligonucleotide Delivery to the Brian", Nanoparticles for Brain Drug Delivery, Chapter 8, 2021, pp. 258-287.
Joshi et al., "Microfluidics based manufacture of liposomes simultaneously entrapping hydrophilic and lipophilic drugs", International Journal of Pharmaceutics, Jul. 2016, pp. 160-168, vol. 514.
Jurvelin et al., "Mechanical anisotropy of the human knee articular cartilage in compression", Journal of engineering in Medicine, 2003, pp. 215-219, vol. 217.
Jurvelin et al., Optical and Mechanical Determination of Poisson's Ratio of Adult Bovine Humeral Articular Cartilage, Journal of Biomechanics, 1997, pp. 335-241, vol. 30 No. 3.
Kaczmarek et al., "Polymer-Lipid Nanoparticles for Systemic Delivery of mRNA to the Lungs", Angewandte Chemical International Edition, 2016, pp. 13808-13812, vol. 55.
Kaczmarek et al., "Systemic Delivery of mRNA and DNA to the Lung using Polymer-Lipid Nanoparticles", Biomaterials, Journal Pre-Proof, Jun. 2021, pp. 1-25.
Kallen et al., "A novel, disruptive vaccination technology", Human Vaccines and Immunotherapeutics, 2013, pp. 2263-2276, vol. 9.
Kalnin et al., "Immunogenicity of novel mRNA COVID-19 vaccine MRT5500 in mice and non-human primates," bioXriv, Oct. 14, 2020, pp. 1-28. retrieved from URL https://doi.org/10.1101/2020.10.14.337535.
Kamakaka, In Vitro Transcription, Current Protocols in Cell Biology, Apr. 1999, pp. 11-16, vol. 2, No. 1.
Kansteiner, F., "JPM: BioNTech hikes COVID-19 vaccine output to 2B doses in 2021—and plans a bigger label, too," FiercePharma, Jan. 11, 2021, 2 pages. [online], [retrieved on Mar. 8, 2022]. Retrieved from the Internet URL: https://www.fiercepharma.com/manufacturing/jpm-biontech-raises-covid-19-vaccine-output-to-2b-eyeing-label-extensions-and-higher.
Kapadia et al., "Long-term protection from SARS coronavirus infection conferred by a single immunization with an attenuated VSV-based vaccine," Virology, Jul. 25, 2005, pp. 174-182, vol. 340.
Kariko et al., "Generating the optimal mRNA for therapy: HPLC purification eliminates immune activation and improves translation of nucleoside-modified, protein-encoding mRNA", Nucleic Acids Research, Oxford University Press, GB, vol. 39, No. 21, Nov. 1, 2011 (Nov. 1, 2011), pp. e142-1.
Kariko et al., "Increased Erythropoiesis in Mice Injected With Submicrogram Quantities of Pseudouridine-containing mRNA Encoding Erythropoietin," Molecular Therapy, May 2012, pp. 948-953, vol. 20, No. 5.
Kariko et al., "What does the success of mRNA vaccines tell US about the future of biological therapeutics?" Cell Systems, Aug. 18, 2021, pp. 757-758, vol. 12.
Kariko K. et al., "Incorporation of pseudouridine into mRNA yields superior nonimmunogenic vector with increased translational capacity and biological stability," Molecular Therapy, Nature Publishing Group, vol. 16 (11):1833-1840 (2008).
Kariko, K. et al., "Suppression of RNA Recognition by Toll-like Receptors: The Impact of Nucleoside Modification and the Evolutionary Origin of RNA," Immunity, vol. 23: 165-175 (2005).
Kariko, Katalin, et al. Naturally occurring nucleoside modifications suppress the immunostimulatory activity of RNA: Implication for therapeutic RNA development. Current Opinion in Drug Discovery & Development 2007 10(5) 523-532; The Thomson Corporation ISSN 1367-6733.
Karlin S., et al., "Applications and Statistics for Multiple High-scoring Segments in Molecular Sequences," Proceedings of National Academy of Sciences, Jun. 15, 1993, vol. 90, No. 12, pp. 5873-5877.
Kasiewicz et al., "Lipid nanoparticles incorporating a GalNAc ligand enable in vivo liver ANGPTL3 editing in wild-type and somatic LDLR knockout non-human primates", bioRxiv, Nov. 2021, pp. 1-7.
Kaszuba, "How to Obtain better Data from Zetasizer Measurements", PowerPoint slides, 2017, 22 pages.
Katnelson, "Preventative Cancer Vaccine Based on Neoantigens Gets Put to the Test," ACS Central Science, 2021, 4 pages. retrieved from URL https://doi.org/10.1021/ascsentsci.1c00936.
Kazemi et al., "Greep behavior of the intact and meniscectomy knee joints", Journal of the Mechanical behavior of Biomedical Materials, 2011, pp. 1351-1358, vol. 4.
Kazemi et al., "Partial Meniscectomy Changes Fluid Pressurization in Articular cartilage in Human Knees", Journal of Biomechanical Engineering, Feb. 2012, pp. 1-10, vol. 134.
Ke et al., "Surface-Functionalized PEGylated Nanoparticles Deliver Messenger RNA to Pulmonary Immune Cells", ACS Applied Materials Interfaces, 2020, pp. 35835-35844, vol. 12.
Kedmi et al., "A modular platform for targeted RNAi therapeutics", Nature Nanotechnology, Supplementary Information, 2018, 13 pages.
Keech et al., "Phase 1-2 Trial of a SARS-CoV-2 Recombinant Spike Protein Nanoparticle Vaccine," N Engl J Med, Sep. 2, 2020, pp. 1-13.
Kenworthy et al., "Range and Magnitude of the Steric Pressure Between Bilayers Containing Phospholipids with Covalently Attached Poly (ethylene glycol)", Biophysical Journal, May 1995, pp. 1921-1936, vol. 68.
Khalil et al., "Phosphonodithioformate-amine coupling reaction: from basic discovery to application for the functionalization of liposomes", Taylor Francis Online, Dec. 2021, 4 pages.
Khalil et al., "Recent Advances in Research on Particulate Formulations such as Lipoproteins, Liposomes, Extracellular Vesicles, and iPS-Derived Cells", Biol. Pharm. Bulletin, 2020, pp. 584-595, vol. 43, No. 4.
Khillari, "mRNA Vaccine and Therapeutics Market Growth, Trends and Forecast Report", from the SelectedWorks of Shweta Khillari, 2020, pp. 1-3.
Kilchrist et al., "Gal8 Visualization of Endosome disruption Predicts Carrier-Mediated Biologic Drug Intracellular Bioavailability", ACS Nano, 2019, pp. 1136-1152, vol. 13.
Kim et al., "Cuboplexes: topologically Active siRNA Delivery", ACS Nano, 2015, pp. 10214-10226, vol. 9 No. 10.
Kim et al., "Microfluidics Synthesis of gene Silencing Cubosomes", ACS Nano, 2018, pp. 9196-9205, vol. 12.
Kirk et al., "Electrophoretic mobility of weakly-charged (dipolar) hydrogels in water: Contribution of hydrogen-bonding in the solvent dipole layer", Journal of Colloid and Interface Science, 2014, pp. 294-305, vol. 416.
Klasczyk et al., "Interactions of alkali metal chlorides with phosphatidylcholine vesicles", Supporting Information, 2010, 1 page.
Klauda, "Considerations of Recent All-Atom Lipid Force Field Development", The Journal of Physical Chemistry, May 28, 2021, pp. 5676-5682, vol. 125, No. 22.
Knecht et al., "Electrophoresis of neutral oil in water", Journal of Colloid and Interface Science, 2010, pp. 223-231, vol. 352.
Knecht et al., "Electrophoretic mobility does not always reflect the charge on an oil droplet", Journal of Colloid and Interface Science, 2008, pp. 477-486, vol. 318.
Knudson, et al., "Lipid-nanoparticle encapsulated mRNA vaccines induce protective memory CD8 T cells against a lethal viral

(56) References Cited

OTHER PUBLICATIONS infection", ScienceDirect, May 14, 2021. 5 pages. Retrieved from the Internet: URL: https://www.sciencedirect.com/science/article/pii/S152500162100263X.

Knudson et al., "Lipid-nanoparticle-encapsulated mRNA vaccines induce protective memory CDS T cells against a lethal viral infection," Molecular Therapy, Sep. 2021, pp. 1-13, vol. 29, No. 9.

Koerner et al., "Electrodynamics of Lipid Membrane Interactions in the Presence of Zwitterionic Buffers", Biophysical Journal, Jul. 2011, pp. 362-369, vol. 101.

Kore, A.R. et al., "Synthesis and biological validation of N7-(4-chlorophenoxyethyl) substituted dinucleotide cap analogs for mRNA translation," Bioorganic & Medicinal Chemistry, vol. 21:4570-4574 (2013).

Kose et al., "A Lipid-encapsulated mRNA Encoding a Potently Neutralizing Human Monoclonal Antibody Protects Against Chikungunya Infection," Science Immunology (2019) 4(35): eaaw6647, 28 pages.

Kowalski et al., "ionizable Amino-Polyesters Synthesized via Ring Opening Polymerization of Tertiary Amino-Alcohols for Tissue Selective mRNA Delivery", Advanced Materials, 2018, pp. 1-10, vol. 30.

Kranz, et al., RNA delivery to dendritic cells exploits antiviral defence for cancer immunotherapy, Nature, Jun. 2016, pp. 396-401.

Kremsner et al., "Phase 1 Assessment of the Safety and Immunogenicity of an mRNA-Lipid Nanoparticle Vaccine Candidate Against SARS-VoV-2 in Human Volunteers", MedRxiv, 2020, pp. 1-38.

Krienke et al., "A noninflammatory mRNA vaccine for treatment of experimental autoimmune encephalomyelitis," Science, Jan. 8, 2021, pp. 1-9, vol. 371.

Kuhn et al., "Phosphorothioate cap analogs increase stability and translational efficiency of RNA vaccines in immature dendritic cells and induce superior immune reponses in vivo," Gene Therapy, Apr. 22, 2010, pp. 961-971, vol. 17.

Kulkarni et al., "Lipid Nanoparticle Technology for Clinical Translation of siRNA Therapeutics", Accounts of Chemical Research, 2019, pp. 2435-2444, vol. 52.

Laczko et al., "A Single Immunization with Nucleoside-Modified mRNA Vaccines Elicits Strong Cellular and Humoral Immune Responses against SARS-CoV-2 in Mice," Immunity, Oct. 13, 2020, pp. 724-732, vol. 53.

Lafantaisie-Favreau et al., "Subchondral pre-solidified chitosan/blood implants elicit reproducible early osteochondral wound-repair responses including neutrophil and stromal cell chemotaxis, bone resorption and repair, enhanced repair tissue integration and delayed matrix deposition", BMC Musculoskeletal Disorders, 2013, pp. 1-16, vol. 14.

Lakdawala et al., "The search for a COVID-19 animal model," Science, May 29, 2020, pp. 942-943, vol. 368, Issue 6494.

Langelier et al., "Increasing strain and strain rate strengthen transient stiffness but weaken the response to subsequent compression for articular cartilage in unconfined compression", Journal of Biomechanics, 2003, pp. 853-859, vol. 36.

Langelier et al., "The Chondrocyte Cytoskeleton in Mature Articular Cartilage: Structure and Distribution of Actin, Tubulin, and Vimentin Filaments", The Journal of Histochemistry and Cytochemistry, 2000, pp. 1307-1320, vol. 48, No. 10.

Latourette, II et al., "Protection against herpes simplex virus type 2 infection in a neonatal murine model using a trivalent nucleoside-modified mRNA in lipid nanoparticle vaccine," Vaccine, 2020, pp. 7409-7413, vol. 38.

Lavertu et al., "A validated 1H NMR method for the determination o the degree of deacetylation of chitosan", Journal of Pharmaceuticals and Biomedical Analysis, 2003, pp. 1149-1158, vol. 32.

Lavertu et al., "Heat-Induced Transfer of Protons from Chitosan to Glycerol Phosphate Produces Chitosan Precipitation and Gelation" Biomacromolecules, 2008, pp. 640-650, vol. 9.

Lavertu et al., "High efficiency gene transfer using chitosan/DNA nanoparticles with specific combinations of molecular weight and degree of deacetylation", Biomaterials, 2006, pp. 4815-4824, vol. 27.

Lavertu et al., "Kinetics and efficiency of chitosan reacetylation", Carbohydrate Polymers, 2012, pp. 1192-1198, vol. 87.

Le Bert et al., "SARS-CoV-2-specific T cell immunity in cases of COVID-19 and SARS, and uninfected controls," Nature, Jul. 15, 2020, 25 pages. retrieved from URL https://doi.org/10.1038/ss41586-020-2550-z.

Le et al., "The COVID-19 vaccine development landscape," Nature Reviews Drug Delivery, May 2020, pp. 305-306, vol. 19.

Lederer et al., "SARS-CoV-2 mRNA Vaccines Foster Potent Antigen-Specific Germinal Center Responses Associated with Neutralizing Antibody Generation," Immunity, Dec. 15, 2020, pp. 1281-1295, vol. 53.

Lee, Justin B. et al., Lipid Nanoparticle siRNA Systems for Silencing the Androgen Receptor in Human Prostate Cancer in Vivo, International Journal of Cancer, 2012, vol. 131, pp. 781-790.

Leslie, "T cells found in coronavirus patients 'bode well' for long-term immunity," Science, May 22, 2020, pp. 809-810, vol. 368, Issue 6493.

Leung et al., "Lipid Nanoparticles Containing siRNA Synthesized by Microfluidic Mixing Exhibit an Electron-Dense Nanostructured Core," The Journal of Physical Chemistry C, 2012, 116:18440-18450.

Leung et al., "Microfluidic Mixing: A General Method for Encapsulating macromolecules in Lipid Nanoparticle Systems", The Journal of Physical Chemistry, Jun. 18, 2015, pp. 8698-8706, vol. 8.

Légaré et al., "Detection and analysis of cartilage degeneration by spatially resolved streaming potentials", Journal of Orthopedic Research, 2002, pp. 819-826, vol. 20.

Li et al., "A fibril reinforced nonhomogeneous poroelastic model for articular cartilage: inhomogeneous response in unconfined compression", Journal of Biomechanics, 2000, pp. 1533-1541, vol. 33.

Li et al., "BBB pathophysiology-independent delivery of siRNA in traumatic brain injury", Science Advances, Jan. 2021, pp. 1-16, vol. 7.

Li et al., "Simultaneous separation of small interfering RNA and lipids sing ion-pair reversed-phase liquid chromatography", Journal of Chromatography A, Apr. 2019, pp. 145-154, vol. 1601.

Li et al., "Investigation of mechanical behavior of articular cartilage by fibril reinforced poroelastic models", Biorheology, pp. 227-233, vol. 40.

Li et al., "Nonlinear analysis of cartilage in unconfined ramp compression using a fibril reinforced poroelastic model", Clinical Biomechanics, 1999, pp. 673-682, vol. 14.

Li et al., "The Asymmetry of transient Response in Compression Versus Release for Cartilage in Unconfined Compression", Journal of Biomechanical Engineering, Oct. 2001, pp. 519-522, vol. 123.

Li et al., "The role of fibril reinforcement in the mechanical behavior of cartilage", Biorheology, 2002, pp. 89-96, vol. 39.

Li et al., "Strain-rate Dependent Stiffness of Articular Cartilage in Unconfined Compression", Journal of Biomechanical Engineering, Apr. 2003, pp. 161-168, vol. 125.

Liang et al, Design and Synthesis of Lipidic Organoalkoxysilanes for the Self-Assembly of Liposomal Nanohybrid Cerasomes with Controlled Drug Release Properties, Chemistry: A European Journal, 2013, pp. 16113-16121, vol. 19.

Liang et al., "Dissociation of skeletal muscle for flow cytometric characterization of immune cell in macaques", Journal of Immunological Methods, 2015, pp. 69-78, vol. 425.

Liang et al., "Efficient targeting and Activation of Antigen-Presenting Cells in Vivo after Modified mRNA Vaccine Administration in Rhesus Macaques", Molecular Therapy, Dec. 2017, pp. 1-13, vol. 25 No. 12.

Lin et al., "Three-Dimensional Imaging of Lipid Gene-Carriers: Membrane Charge Density Controls Universal Transfection Behavior in Lamellar Cationic Liposome-DNA Complexes," Biophysical Journal, May 2003, pp. 3307-3316, vol. 84, No. 5.

(56) References Cited

OTHER PUBLICATIONS

Linpinsel, et al., General protocols for preparation of plasmid DNA template, RNA in vitro transcription, and RNA purification by denaturing Page, InRecombinant and in vitro RNA synthesis, 2013, pp. 43-58.

Liu et al., "BNT162b2-Elicited Neutralization against New SARS-CoV-2 Spike Variants," N Engl J Med, May 12, 2021, pp. 1-2.

Liu et al., "BNT162b2-elicited neutralization of B.1.617 and other SARS-CoV-2 variants," Nature, Jun. 10, 2021, 12 pages. retrived from URL https://doi.org/10.1038/s41586-021-03693-y.

Liu et al., "Chimeric severe acute respiratory syndrome coronavirus (SARS-CoV) S glycoprotein and influenza matrix 1 efficiently form virus-like particles (VLPs) that protect mice against challenge with SARS-CoV," Vaccine, Jul. 14, 2011, pp. 6606-6613, vol. 29.

Liu et al., "Neutralizing Activity of BNT162b2-Elicited Serum—Preliminary Report," N Engl J Med, Feb. 19, 2021, pp. 1-3.

Liu et al., "Two-Year Prospective Study of the Humoral Immune Response of Patients with Severe Acute Respiratory Syndrome," JID, Mar. 15, 2006, pp. 792-795, vol. 193.

Liu, "Feds consider half-doses of Moderna COVID-19 vaccine to stretch supplies, as U.K. spaces out Pfizer, AstraZeneca shots", FiercePharma, Jan. 4, 2021, 4 pages. Retrieved from the Internet URL: https://www.fiercepharma.com/pharma/feds-consider-half-dose-moderna-covid-19-vaccine-as-u-k-spaces-out-pfizer-astrazeneca-shots.

Liu, "mRNA Latecomer CureVac recruits Bayer to speed COVID-19 vaccine to market", FiercePharma, 2021, pp. 1-2.

Lönn et al., "Enhancing Endosomal Escape for Intracellular Delivery of Macromolecular Biologic Therapeutics", Scientific Reports, Sep. 2016, pp. 1-9, vol. 6.

Lo et al., "Evaluation of a Single-Dose Nucleoside-Modified Messenger RNA Vaccine Encoding Hendra Virus-Soluble Glycoprotein Against Lethal Nipah virus Challenge in Syrian Hamsters," The Journal of Infectious Diseases, Supplemental 4, 2020, pp. S493-S498.

Loftus, "Moderna Vows to Not Enforce Covid-19 Vaccine Patents During Pandemic", The Wall Street Journal, Oct. 8, 2020, 2 pages. Retrieved from the Internet URL: https://www.wsj.com/articles/moderna-vows-to-not-enforce-covid-19-vaccine-patents-during-pandemic-11602154805.

Lood et al., "TLR7/8 activation in neutrophils impairs immune complex phagocytosis through shedding of FcgRIIA", The Journal of Experimental Medicine, pp. 2103-2119, vol. 214, No. 7.

Lopes De Menezes et al., "Cellular Trafficking and Cytotoxicity of Anti-CD19-Targeted Liposomal Doxorubicin in B Lymphoma Cells", Journal of Liposome Research, 1999, pp. 199-228, vol. 9, No. 2.

Losick, In vitro transcription, Ann Rev Biochem., Jul. 1972, pp. 409-446.

Lou et al., "mRNA Polyplexes with Post-Conjugated GALA Peptides Efficiently Target, Transfect, and Activate Antigen Presenting Cells", Bioconjugate Chemistry, 2019, pp. 461-475, vol. 30.

Loughrey et al., "Non-liver mRNA Delivery", Accounts of Chemical Research, Sep. 2021, pp. 13-23, vol. 55.

Lovelace, Moderna says new data shows its Covid vaccine is more than 90% effective against virus six months after second shot:, CNBC, Apr. 13, 2021, 9 pages. Retrieved from the Internet URL: https://www.cnbc.com/2021/04/13/covid-vaccine-moderna-says-new-data-shows-its-90percent-effective-six-months-after-second-dose.html.

Lowry et al., "Guidance to improve the scientific value of zeta-potential measurements in nanoEHS", Environmental Science Nano, 2016, pp. 953-965, vol. 3.

López-Vidal et al., "Deep Learning Enables Discovery of a Short Nuclear Targeting Peptide for efficient Delivery of Antisense Oligomers", An Open Access Journal of the American Chemical Society, Oct. 6, 2021, pp. 1-12, vol. 1, No. 11.

Lu et al., "Chemical Conjugation Strategies for the Development of Protein-Based Subunit Nanovaccines", Vaccines, 2021, pp. 1-24, vol. 9, No. 563.

Lu et al., "Genomic characterisation and epidemiology of 2019 novel coronavirus: implications for virus origins and receptor binding," The Lancet, Jan. 29, 2020, retrieved from URL https://doi.org/10.1016/S0140-6736(20)30251-8, pp. 1-10.

Luksasky, et al., Large-scale preparation and purification of polyacrylamide-free RNA oligonucleotides, RNA, May 1, 2004, pp. 889-893.

Lutz, "Supplementary Figure 1", No Date, 1 page.

Ma et al., "Complete Physiochemical Characterization of DNA/Chitosan Complexes by Multiple Detection Using Asymmetrical Flow Field-Flow Fractionation", Analytical Chemistry, Dec. 10, 2010, pp. 9636-9643, vol. 82 No. 23.

Ma et al., "New Insights into Chitosan—DNA Interactions Using isothermal Titration Microcalorimetry", Biomacromolecules, 2009, pp. 1490-1499, vol. 10.

Ma et al., "One-Step Analysis of DNA/Chitosan Complexes by Field-Flow Fractionation Reveals Particle Size and Free Chitosan Content", Biomacromolecules, 2010, pp. 549-554, vol. 11.

Ma et al., "Precise derivatization of structurally distinct chitosans with rhodamine B isothiocyanate", Carbohydrate Polymers, 2008, pp. 616-624, vol. 72.

Ma et al., "Stability and binding affinity of DNA/Chitosan complexes by polyanion competition", Carbohydrate Polymers, 2017, pp. 167-176, vol. 176.

Maass et al., "The Effect of Radiofrequency Energy in Tissue", Histologic Technical Bulletin for Histotechnology, 2005, pp. 21-40, vol. 38.

Macqueen et al., "Electro-manipulation of Biological Cells in Microdevices", IEEE Transactions on Dielectrics and Electrical Insulation, Aug. 2012, pp. 1261-1268, vol. 19 No. 4.

Macqueen et al., "Electromechanical deformation of mammalian cells in suspension depends on their cortical actin thickness", Journal of Biometrics, 2012, pp. 2797-2803, vol. 45.

Macqueen et al., "Gene delivery by electroporation after dielectrophoretic positioning of cells in a non-uniform electric field", Bioelectrochemistry, 2008, pp. 141-148, vol. 72.

Macqueen et al., "Mechanical properties of mammalian cells in suspension measured by electro-deformation", Journal of Micromechanics and Microengineering, 2010, pp. 1-11, vol. 20.

Madrigal et al., "Biomaterial-Guided gene delivery for Musculoskeletal Tissue Repair", Tissue Engineering: Part B, 2017, pp. 347-361, vol. 23, No. 4.

Maeki et al., "Understanding the formation mechanism of lipid nanoparticles in microfluidic devices with chaotic micromixers", PLOS ONE, 2017, pp. 1-16, vol. 12, No. 11.

Mai et al., "Advances in engineering and synthetic biology toward improved therapeutic immune cells", Current Opinion in Biomedical Engineering, 2021, 9 pages.

Maier, et al., Biodegradable lipids enabling rapidly eliminated lipid nanoparticles for systemic delivery of RNAi therapeutics, Molecular Therapy, Aug. 1, 2013, pp. 1570-1578, vol. 21, No. 8.

Majzoub et al., "Quantitative intracellular localization of cationic lipid-nucleic acid nanoparticles with fluorescence microscopy", Methods of Molecular Biology, Jan. 2017, pp. 1-32.

Makino, et al., "Temperature- and ionic strength-induced conformational changes in the lipid head group region of liposomes as suggested by zeta potential data," ScienceDirect, Nov. 1991, 2 pages.

Makino et al., "Temperature-and-ionic strength-induced confrontational changes in the lipid head group region of liposomes as suggested by zeta potential data", Biophysical Chemistry, Nov. 1991, pp. 175-183, vol. 41, No. 2.

Malven Instruments Limited, "Dynamic light Scattering: an introduction," 2017, 17 pages.

Malvern Instruments, "How is the frequency shift measured in electrophoretic light scattering?", No Date, 3 pages.

Malvern Instruments, "What is a Frequency Plot?", No Date, 2 pages.

Malvern Instruments, "What is a Voltage and Current Plot?", No Date, 3 pages.

Malvern Instruments, "What is the Wall Zeta Potential?", No Date, 2 pages.

Malvern Instruments, "What is Zeta Potential and what value is it?", No Date, 1 pages.

(56) References Cited

OTHER PUBLICATIONS

Malvern Instruments Worldwide, "Zetasizer nano series, user manual," 2017, 4 pages.
Malvern Instruments Worldwide, "Zetasizer Nano Specifications Zeta Potential Mximum Concentration Limit 40% with v, Technical Note," 2017, 4 pages.
Malvern, The diffusion barrier technique, Practical aspects and data interpretation, 2017, 5 pages.
Malvern, Zetasizer Nano Series User Manual, Apr. 2013, 250 pages, Issue 1.1.
Manolova et al., "Nanoparticles target distinct dendritic cell populations according to their size", European Journal of Immunology, 2008, pp. 1404-1413, vol. 38.
Marchand et al., "C3, C5, and factor B bind to Chitosan without Complement Activation", Journal of Biomedical Materials Research Part A, 2009, pp. 1429-1441, vol. 93, No. 4.
Marchand et al., "Microdrilled Cartilage Defects treated with Thrombin-Solidified Chitosan/Blood Implant Regenerate a more Hyaline, Stable, and Structurally Integrated Osteochondral Unit Compared to Drilled Controls", Tissue Engineering, 2011, pp. 1-12, vol. 18.
Marchand et al., "Solidification mechanisms of chitosan-glycerol phosphate/blood implant for articular cartilage repair", Osteoarthritis and Cartilage, 2009, pp. 950-960, vol. 17.
Marcos-Contreras et al., "Selective targeting of nanomedicine to inflamed cerebral vasculature to enhance the blood-brain barrier," PNAS, 2020, pp. 1-23, vol. 117, No. 7.
Marsh et al., "Lipid membranes with grafted polymers: physicochemical aspects," Biochimica et Biophysica Acta, 2003, pp. 33-59, vol. 1615.
Maruggi, et al., "mRNA as a Transformative Technology for Vaccine Development to Control Infectious Diseases," Molecular Therapy, Apr. 2019, pp. 757-772, vol. 27.
Mattern-Schain et al., "Cell mimetic liposomal nanocarriers for tailored delivery of vascular therapeutics", Chemistry and Physics of Lipids, 2019, pp. 149-157, vol. 218.
Matyushov, "Electrophoretic mobility without charge driven by polarization of the nanoparticle—water interface", Molecular Physics, 2014, pp. 2029-2039, vol. 112, No. 15.
Maugeri et al., "Linkage between endosomal escape of LNP-mRNA and loading into Evs for transport to other cells," Nature Communications, 2019, pp. 1-15, with supplemental data, vol. 10, No. 4333.
Mcdaniel et al., "Electrostatic potential distribution of a soft spherical particle with a charged core and pH-dependent charge density", Colloids and Surfaces B: Biointerfaces, 2015, pp. 143-147, vol. 127.
Mckay et al., "Self-amplifying RNA SARS-CoV-2 lipid nanoparticle vaccine candidate induces high neutralizing antibody titers in mice," Nature Communications, 2020, pp. 1-7, vol. 11, No. 3523.
Mckay et al., "Self-amplifying Rna SARS-CoV-2 lipid nanoparticle vaccine induces equivalent preclinical antibody titers and viral neutralization to recovered COVID-19 patients," bioRxiv, Apr. 25, 2020, pp. 1-14. retrieved from URL https://doi.org/10.1101/2020.04.22.055608.
Mercado, et al., "Single-shot Ad26 vaccine protects against SARS-CoV-2 in rhesus macaques," Nature, Jul. 30, 2020, 27 pages. retrieved from URL https://doi.org/10.1038/s41586-020-2607-z.
Merzouki et al., "Adva-27a, a Novel Podophyllotoxin Derivative Found to Be Effective against Multidrug Resistant Human Cancer Cells", Anticancer Research, 2012, pp. 4423-4432, vol. 32.
Merzouki et al., "Chitosanase-based method for RNA isolation form cells transfected with chitosan/siRNA nanocomplexes for real-time RT-PCR in gene silencing", International Journal of Nanomedicine, 2010 pp. 473-481, vol. 5.
Merzouki et al., "Low Molecular Weight Chitosan Nanoparticulate System at Low N:P Ratio for Nontoxic Polynucleotide Delivery", International Journal of Nanomedicine, 2012, pp. 1399-1414, vol. 7.
Milicevic et al., "Establishing conditions for simulating hydrophobic solutes in electric fields by molecular dynamics", Journal of Molecular Model, Aug. 2014, pp. 1-11, vol. 20.
Miller, "mRNA-1273 Clinical Development Program" Moderna, Aug. 26, 2020, pp. 1-18.
Šmisterová et al., "Molecular Shape of the Cationic Lipid Controls the Structure of Cationic Lipid/Dioleylphosphatidylethanolamine-DNA Complexes and the Efficiency of Gene Delivery", The Journal of Biological Chemistry, Dec. 2001, pp. 47615-47622, vol. 276, No. 50.
Miyoshi et al., "A detailed analysis of partial molecular volumes in DPPC/cholesterol binary bilayers", Biochimica et Biophysica Acta, 2014, pp. 3069-3077, vol. 1838.
Modern Instruments Limited, Comparisons between the Folded Capillary Cell (DTS1060/DTS1061), the 'dip' cell (ZEN1002) and the high concentration cell (ZEN1010), 2017, 3 pages.
Modern Instruments Limited, "Dynamic light scattering—definition of terms", 2017, 17 pages.
Moderna, I. "Safety, Tolerability, and Immunogenicity of VAL-506440 in Healthy Adult Subjects", Dec. 2015, 6 pages. Retrieved from the Internet URL: https://clinicaltrials.gov/ct2/show/NCT03076385.
Moderna, "Moderna Advances Late-Stage Development of its Vaccine (mRNA-1273) Against COVID-19," Jun. 11, 2020, 7 pages. Retrieved from the Internet URL: https://investors.modernatx.com/news-releases/news-release-details/moderna-advances-late-stage-development-its-vaccine-mrna-1273/.
Moderna, "Moderna Announces First Participants in Each Age Cohort Dosed in Phase 2 Study of mRNA Vaccine (mRNA-1273) Against Novel Coronavirus", Yahoo Business, May 29, 2020, 11 pages. Retrieved from the Internet URL: https://ca.finance.yahoo.com/quote/MRNA/.
Moderna, "Moderna Announces Positive Interim Phase 1 Data for its mRNA Vaccine (mRNA-1273) Against Novel Coronavirus", May 18, 2020, 7 pages. Retrieved from the Internet URL: https://investors.modernatx.com/news-releases/news-release-details/moderna-announces-positive-interim-phase-1-data-its-mrna-vaccine/.
Moderna, "Moderna's COVID-19 Vaccine Candidate Meets its Primary Efficacy Endpoint in the First Interim Analysis of the Phase 3 Cove Study", Nov. 16, 2020, 6 pages. Retrieved from the Internet URL: https://investors.modernatx.com/news-releases/news-release-details/modernas-covid-19-vaccine-candidate-meets-its-primary-efficacy/.
Moderna, "Moderna Provides COVID-19 Vaccine Supply Update", Jan. 4, 2021, 5 pages. Retrieved from the Internet URL: https://investors.modernatx.com/news-releases/news-release-details/moderna-provides-covid-19-vaccine-supply-update/.
Mole, "Shkreli Award" goes to Moderna for "blatantly greedy" COVID vaccine price Ars Technica, Jan. 6, 2021 5 pages. Retrieved from the Internet URL: https://arstechnica.com/science/2021/01/moderna-shamed-with-shkreli-award-over-high-covid-vaccine-prices/.
Monslow et al., "Immunogenicity generated by mRNA vaccine encoding VZV gE antigen is comparable to adjuvanted subunit vaccine and better than live attenuated vaccine in nonhuman primates", Vaccine, Jul. 2020, pp. 5793-5802, vol. 38.
Moore, L., "Pfizer ramps up vaccine production to 2 billion doses for 2021," MLive [online], [retrieved on Mar. 8, 2022]. Retrieved from the Internet URL: https://www.mlive.com/coronavirus/2021/01/pfizer-ramps-up-vaccine-production-to-2-billion-doses-for-2021.html, 3 pages.
Morrissey, et al., Potent and persistent in vivo anti-HBV activity of chemically modified siRNAs, Nat. Biotech., Aug. 2005, pp. 1002-1007, vol. 23, No. 8.
Moyo et al., "Tetravalent Immunogen Assembled from Conserved Regions of HIV-1 and Delivered as mRNA Demonstrates Potent Preclinical T-Cell Immunogenicity and Breadth", Vaccines, 2020, pp. 1-10, vol. 8.
Méthot et al., "Osteochondral Biopsy Analysis Demonstrates that BST-CarGel treatment Improves Structural and Cellular Characteristics of Cartilage repair Tissue Compared with Microfracture", Cartilage, 2015, pp. 1-13, vol. 7, No. 1.
Mui, et al., Influence of polyethylene glycol lipid desorption rates on pharmacokinetics and pharmacodynamics of siRNA lipid nanoparticles, Molecular Therapy-Nucleic Acids, Jan. 1, 2013, e139.
Mulligan et al., "Phase 1/2 Study to Describe the Safety and Immunogenicity of a COVID-19 RNA Vaccine Candidate (BNT162b1)

(56) References Cited

OTHER PUBLICATIONS in Adults 18 to 55 Years of Age: Interim Report," medRxiv, Jul. 1, 2020, pp. 1-16. retrieved from URL https://doi.org/10.1101/2020.06.03.20142570.
Mulligan et al., "Phase I/II study of COVID-19 RNA vaccine BNT162b1 in adults," Nature Research Supplementary Information, PF-07302048 (BNT162 RNA-Based COVID-19 Vaccines), Protocol C4591001, Protocol Amendment 3, Jun. 10, 2020, 131 pages.
Naito et al., "Real-world evidence for the effectiveness and breakthrough of BNT162b2 mRNA COVID-19 vaccine at a medical center in Japan," Human Vaccines & Immunotherapeutics, Oct. 6, 2021, retrieved from URL https://doi.org/10.1080/21645515.2021.1984124, pp. 1-2.
National Institutes of Health, "Safety and Immunogenicity Study of 2019-nCoV Vaccine (mRNA-1273) for Prophylaxis Sars CoV-2 Infection (COVID-19)", ClinicalTrials, Apr. 13, 2020, 19 pages. Retrieved from the Internet URL: https://clinicaltrials.gov/ct2/show/NCT04283461.
National Institutes of Health, "Phase 3 clinical trial of investigational vaccine for COVID-19 begins", NIH, Jul. 27, 2020, 3 pages. Retrieved from the Internet URL: https://www.nih.gov/news-events/news-releases/phase-3-clinical-trial-investigational-vaccine-covid-19-begins.
National Institutes of Health, "Promising Interim Results from Clinical Trial of NIH-Moderna COVID-19 Vaccine", Nov. 16, 2020, 6 pages. Retrieved from the Internet URL: https://www.nih.gov/news-events/news-releases/promising-interim-results-clinical-trial-nih-moderna-covid-19-vaccine.
Ndeupen et al., "The mRNA-LNP platform's lipid nanoparticle component ussed in preclinical vaccine studies is highly inflammatory," bioRxiv, Mar. 4, 2021, pp. 1-24.
Neidleman et al., "mRNA vaccine-induced SARS-CoV-2-specific T cells recognize B.1.1.7 and B.1.351 variants but differ in longevity and homing properties depending on prior infection status", bioRxiv, May 12, 2021 pp. 1-62.
Nelson et al., "Human Cytomegalovirus Glycoprotein B Nucleoside-Modified mRNA Vaccine Elicits Antibody Responses with Greater Durability and Breadth than MF59-Adjuvanted gB Protein Immunization," Journal of Virology, Apr. 16, 2020, pp. 1-19, vol. 94, No. 9.
Nelson et al., "Impact of mRNA chemistry and manufacturing process on innate immune activation", Science Advances, 2020, pp. 1-13, vol. 6.
Netea et al., "Trained Immunity: a Tool for Reducing Susceptibility to and the Severity of SARS-CoV-2 Infection," Cell, May 28, 2020, pp. 969-977, vol. 181.
Nguyen et al., "Fractionation and characterization of chitosan by analytical SEC and 1H NMR after semi-preparative SEC", Carbohydrate Polymers, 2009, pp. 636-645, vol. 75.
Nguyen et al., "Improved reproducibility in the determination of the molecular weight of chitosan by analytical size exclusion chromatography", Carbohydrate Polymers, 2009, pp. 528-533, vol. 75.
Nguyen et al., "Lipid-derived nanoparticles for immunostimulatory RNA adjuvent delivery," Proc. Natl. Acad. Sci., Mar. 15, 2012, pp. E797-E803, vol. 109, No. 14.
Nimesh et al., "Enhanced Gene Delivery Mediated by Low Molecular Weight Chitosan/DNA Complexes: effect of pH and Serum", Molecular Biotechnology, 2010, pp. 182-196, vol. 46.
Nittner-Marszalska et al., "Pfizer-BioNTech COVID-19 Vaccine Tolerance in Allergic versus Non-Allergic Individuals," Vaccines, May 25, 2021, 8 pages, vol. 9, No. 553.
No Author, "Example for Diffusion Barrier Method SOP," No Date, 1 page.
No Author, "Vaccines and Related Biological Advisory Committee Meeting, FDA Briefing Document, Pfizer-BioNTech COVID-19 Vaccine", Dec. 10, 2020, 53 pages.
Nogueira et al., "Polysarcosine-Functionalized Lipid Nanoparticles for Therapeutic mRNA Delivery," ACS Appl. Nano Mater., Sep. 25, 2020, pp. 10634-10645, vol. 3.
O'Brien et al., "The electrophoretic mobility of an uncharged particle", Journal of Colloid and Interface Science, 2014, pp. 70-73, vol. 420.
O'Callaghan et al., "Developing a SARS-CoV-2 Vaccine at Warp Speed," JAMA, Aug. 4, 2020, pp. 437-438, vol. 324, No. 5.
Oesterhelt et al., S4 Appendix, Estimating the contour lengths of PEG and ddFLN4, No Date, 1 page.
Ohshima, "A Simple Expression for Henry's Function for the Retardation Effect in Electrophoresis of Spherical Colloidal Particles", Journal of Colloid and Interface Science, Nov. 1994, pp. 269-271, vol. 168, Issue 1.
Ohshima, "Donnan potential and surface potential of a spherical soft particle in an electrolyte solution", Journal of Colloid and Interface Science, 2008, pp. 92-97, vol. 323.
Ohshima et al., "Donnan Potential and Surface Potential of a Charged Membrane", Biophysical Journal, May 1985, pp. 673-678, vol. 47.
Ohshima, "Limiting electrophoretic mobility of a highly charged soft particle in an electrolyte solution; solidification effect", Journal of Colloid and Interface Science, 2010, pp. 641-644, vol. 349.
Ohshima, "Theory of electrostatics and electrokinetics of soft particles", Science and technology of Advanced Materials, 2009, pp. 1-13, vol. 10.
Oswald et al., "HPLC analysis as a tool for assessing targeted liposome composition", International Journal of Pharmaceutics, 2016, pp. 293-300, vol. 497.
Pallesen et al., "Immunogenicity and structures of a rationally designed prefusion MERS-CoV spike antigen," PNAS E7348-E7357 (2017).
Parayath et al., "In vitro-transcribed antigen receptor mRNA nanocarriers for transient expression in circulating T cells in vivo", Supplementary Information, 2020, 9 pages.
Pardi et al., "Administration of nucleoside-modified mRNA encoding broadly neutralizing antibody protects humanized mice from HIV-1 challenge," Nature Communications, Mar. 2, 2017, pp. 1-8, vol. 8, Article No. 14630.
Pardi et al., "Expression kinetics of nucleoside-modified mRNA delivered in lipid nanoparticles to mice by various routes," Journal of Controlled Release, 217, 2015, 345-351.
Pardi et al., In vitro transcription of long RNA containing modified nucleosides in Synthetic Messenger RNA and Cell Metabolism Modulation in Methods in Molecular Biology, 2013, pp. 29-42.
Pardi et al., "mRNA vaccines—a new era in vaccinology," Nature Reviews, 2018, pp. 261-279, vol. 17.
Pardi et al., "Nucleoside-modified mRNA immunization elicits influenza virus hemagglutinin stalk-specific antibodies," Nature Communications, Aug. 22, 2018, pp. 1-12, vol. 9, Article No. 3361.
Pardi et al., "Nucleoside-modified mRNA vaccines induce potent T follicular helper and germinal center B cell responses," Journal of Experimental Medicine, May 8, 2018, pp. 1571-1588, vol. 215, No. 6.
Pardi et al., "Zika virus protection by a single low-dose nucleoside-modified mRNA vaccination," Nature, May 9, 2017, pp. 248-251, vol. 543.
Parhiz et al., "Added to pre-existing inflammation, mRNA-lipid nanoparticles induce inflammation exacerbation (IE)," Journal of Controlled Release, 2022, pp. 50-61, vol. 344.
Parhiz et al., "PECAM-1 directed re-targeting of exogenous mRNA providing two orders of magnitude enhancement of vascular delivery an expression in lungs independent of apolipoprotein E-mediated uptake", Journal of Controlled Release, 2018, pp. 106-115, vol. 291.
Park et al., "Endocytosis and exocytosis of nanoparticles in mammalian cells", International Journal of Nanomedicine, 2014, pp. 51-63, vol. 201.
Patel et al., "Boosting Intracellular Delivery of Lipid Nanoparticle-Encapsulated mRNA", Nano Letters, 2017, pp. 5711-5718, vol. 17.
Patel et al., "Brief update on endocytosis of nanomedicines", Advanced Drug Delivery Reviews, 2019, pp. 90-111, vol. 144.
Patel et al., "Naturally-occurring cholesterol analogues in lipid nanoparticles induce polymorphic shape and enhance intracellular delivery of mRNA", Nature Communications, 2020, pp. 1-13.

(56) References Cited

OTHER PUBLICATIONS

Pepini et al., "Induction of an IFN-Mediated Antiviral Response by a Self-Amplifying RNA Vaccine: Implications for Vaccine Design," The Journal of Immunology, 2017, pp. 4012-4024, vol. 198.
Perche, et al., "Selective gene delivery in dendritic cells with mannosylated and histidylated lipopolyplexes", Journal of Drug Targeting, 2011, pp. 315-325, vol. 19, No. 5.
Perche et al., "Selective gene delivery in dendritic cells with mannosylated and histidylated lipopolyplexes", Journal on Drug Targeting, Jul. 2010, 3 pages.
Perche, F., et al., Enhancement of dendritic cells transfection in vivo and of vaccination against B16F10 melanoma with mannosylated histidylated lipopolyplexes loaded with tumor antigen messenger RNA. Nanomed: Nanotech, Bio, and Med. Aug. 2011; 7(4): 445-453.
Pfizer, "BNT162b2 VRBPAC Briefing Document," Sep. 17, 2021, 53 pages.
Pfizer, et al., "Vaccines and Related Biological Products Advisory Committee Dec. 17, 2020 Meeting Announcement", U.S. Food & Drug Administration, Dec. 17, 2020, 53 pages. Retrieved from the Internet URL: https://www.fda.gov/advisory-committees/advisory-committee-calendar/vaccines-and-related-biological-products-advisory-committee-december-17-2020-meeting-announcement.
Pfizer, "Pfizer-BioNTech COVID-19 Vaccine: VRBPAC Briefing Document," Dec. 10, 2020, pp. 1-92.
Philipse et al., "The Donnan Equilibrium: I. On the Thermodynamic Foundation of the Donnan Equation of State", Journal of Physics: Condensed Matter, 2011, pp. 1-12, vol. 23.
Pickenhahn et al., "Regioselective thioacetylation of chitosan end-groups for nanoparticle gene delivery system", Chemical Science, 2015, pp. 4650-4664, vol. 6.
Pincet et al., "Bilayers of neutral lipids bear a small but significant charge", The European Physical Journal B, 1999, pp. 127-130, vol. 11.
Player et al., The 2-5 A system: Modulation of viral and cellular processes through acceleration of RNA degradation, Pharmacology & therapeutics, May 1, 1998, pp. 55-113, vol. 78, No. 2.
Polack et al., "Safety and Efficacy of the BNT162b2 mRNA Covid-19 Vaccine," N Engl J Med, Dec. 31, 2020, pp. 2603-2615, vol. 383, No. 27.
Polack et al., "Safety and Efficacy of the BNT162b2 mRNA Covid-19 Vaccine," N Engl J Med, Dec. 10, 2020, pp. 1-13.
Polvere et al., "A Peptide-Based Assay Discriminates Individual Antibody Response to the COVID-19 Pfizer/BioNTech mRNA Vaccine," Vaccines, Sep. 3, 2021, 8 pages, vol. 9, No. 987.
Poole et al., "Recommendations for the use of preclinical models in the study and treatment of osteoarthritis", osteoarthritis and Cartilage, 2010, pp. 510-516, vol. 18.
Pozzi et al., "Transfection efficiency boost of Cholesterol-containing lipoplexes", Biochimica et Biophysica Acta, 2012, pp. 2335-2343, vol. 1818.
Praseuth, et al., Triple helix formation and the antigene strategy for sequence-specific control of gene expression, Biochim Biophys Acta., Dec. 10, 1999, pp. 181-206, vol. 1489, No. 1.
Prompetchara et al., "Immune responses in COVID-19 and potential vaccines: Lessons learned from SARS and MERS epidemic," Asian Pacific Journal of Allergy and Immunology, 2020, pp. 1-9, vol. 38.
Préville et al., "Electroarthrography: a novel method to assess articular cartilage and diagnose osteoarthritis by non-invasive measurement of load-induced electrical potentials at the surface of the knee", Osteoarthritis and Cartilage, 2013, pp. 1731-1737, vol. 21.
Pu et al., "An in-depth investigation of the safety and immunogenicity of an inactivated SARS-CoV-2 vaccine," medRxiv, Oct. 6, 2020, pp. 1-27. retrieved from URL https://doi.org/10.1101/2020.09.27.20189548.
Puranik et al., "Comparison of two highly-effective mRNA vaccines for COVID-19 during periods of Alpha and Delta variant prevalence," medRxiv, Aug. 8, 2021, pp. 1-29. retrieved from URL https://doi.org/10.1101/2021.08.06.21261707.
Quenneville et al., "A transport model of electrolyte convection through a charged membrane predicts generation of net charge at membrane/electrolyte interfaces", Journal of Membrane Science, 2005, pp. 60-73, vol. 265.
Quenneville et al., "Fabrication and Characterization on Nonplanar Microelectrode Array Circuits for Use in Arthroscopic Diagnosis of Cartilage Diseases", IEEE Transactions on Biomedical Engineering, Dec. 2004, pp. 2164-2173, vol. 51 No. 12.
Quinn et al., "Mechanical compression alters proteoglycan deposition and matrix deformation around individual cells in cartilage explants", Journal of Cell Science, 1998, pp. 573-583, vol. 111.
Rajappan et al., "Property-Driven Design and Development of Lipids for Efficient Delivery of siRNA," Journal of Medicinal Chemistry, Oct. 29, 2020, pp. 12992-13012, vol. 63.
Rajesh, et al., "Dramatic Influence of the Orientation of Linker between Hydrophilic and Hydrophobic Lipid Moiety in Liposomal Gene Delivery," J. Am. Chem. Soc., 2007, pp. 11408-11420, vol. 129.
Ramaswamy et al., "Systemic delivery of factor IX messenger RNA for protein replacement therapy," PNAS, Feb. 15, 2017, pp. E1941-E1950.
Ramishett et al., "A Combinatorial Library of Lipid Nanoparticles for RNA Delivery to Leukocytes", Advanced Materials, 2020, pp. 1-8, vol. 32.
Ramishetti et al., "Systemic Gene Silencing in Primary T Lymphocytes Using Targeted Lipid Nanoparticles", ACS Nano, 2015, pp. 6706-6716, vol. 9, No. 7.
Rauch et al., "mRNA-based SARS-CoV-2 vaccine candidate CVnCoV induces high levels of virus neutralizing antibodies and mediates protection in rodents", BioRxiv, 2020, pp. 1-18, vol. 6, No. 1.
Rauch, "Supplementary Materials", No Date, 2 pages.
Reddy et al., "In vivo targeting of dendritic cells in lymph nodes with poly (propylene sulfide) nanoparticles", Journal of Controlled Release, 2006, pp. 26-34, vol. 112.
Regalado, "What are the ingredients of Pfizer's Covid-19 vaccine?" MIT Technology Review, Dec. 9, 2020, pp. 1-5.
Rehman et al., "Mechanism of Polyplex-and Lipoplex-Mediated delivery of Nucleic Acids: Real-Time Visualization of Transient Membrane Destabilization without Endosomal Lysis", ACS Nano, 2013, pp. 3767-3777, vol. 7 No. 5.
Reichmuth, et al., "mRNA Vaccine Delivery Using Lipid Nanoparticles," Therapeutic Delivery (2016), v. 7, No. 5, pp. 319-334.
Reinhard et al., "Carriers for Nucleic Acid Delivery to the Brain", Nanoparticles for Brain Drug Delivery, Chapter 9, 2021, pp. 289-316.
Restrepo et al., "Challenges in Designing randomized Clinical Trials for Cartilage Repair: the BST-CarGel Experience", Osteoarthritis and Cartilage, Supplement 1, 2009, pp. S177-S178, vol. 17.
Rheosense, Inc., "Viscosity of Two Component Mixtures", 2020, 5 pages.
Ribeiro et al., "Use of nanoparticle concentration as a tool to understand the structural properties of colloids" Scientific Reports, 2018, pp. 1-8, vol. 8.
Richard et al., "Ionization Behavior of Chitosan and Chitosan-DNA Polyplexes Indicate that Chitosan has a Similar Capability to Induce a proton-Sponge Effect as PEI", Biomacromolecules,2013, pp. 1732-1740, vol. 14.
Richner et al., "Modified mRNA Vaccines Protect against Zika Virus Infection", Cell, 2017, pp. 1-23.
Rizvi et al., "Murine liver repair via transient activation of regenerative pathways in hepatocytes using lipid nanoparticle-complexed nucleoside-modified mRNA," Nature Communications, Jan. 27, 2021, pp. 1-10, vol. 12, Article No. 613.
Rockx et al., "Comparative Pathogenesis of COVID-19, MERS, and SARS in a nonhuman primate model," Science, Apr. 17, 2020, pp. 1-10.
Roltgen et al., "mRNA vaccination compared to infection elicits an IgG-predominant response with greater SARS-CoV-2 specificity and similar decrease in variant spike recognition," medRxiv, Apr. 7, 2021, pp. 1-33. retrieved from URL https://doi.org/10.1101/2021.04.05.21254952.

(56) References Cited

OTHER PUBLICATIONS

Rossomacha et al., "Simple Methods for Staining Chitosan in Biotechnological Applications", Biosyntech Canada Inc., 2004, pp. 1-19, vol. 27, No. 1.
Rothgangl et al., "In vivo adenine base editing of PCSK9 in macaques reduces LDL cholesterol levels," Nature Biotechnology, May 19, 2021, pp. 949-957, vol. 39.
Rothwell, et al., "The mRNA IP and Competitive Landscape: Translate BIO; Arcturus; eTheRNA and Other Startups; and LNP Technology (Part II)," JDSUPRA, May 3, 2021, 10 pages.
Roughley et al., "The potential of chitosan-based gels containing intervertebral disc cells for nucleus pulposus supplementation", Biomaterials, 2006, pp. 388-396, vol. 27.
Rowland, C. et al., "Drug companies defend vaccine monopolies in face of global outcry," The Washington Post, Mar. 20, 2021 [online], [retrieved on Mar. 8, 2022]. Retrieved from the Internet URL: https://www.washingtonpost.com/business/2021/03/20/covid-vaccine-global-shortages/, 13 pages.
Rowland, C., "Inside Pfizer's race to produce the world's biggest supply of covid vaccine." The Washington Post, Jun. 16, 2021 [online], [retrieved on Mar. 8, 2022]. Retrieved from the Internet URL: https://www.washingtonpost.com/business/2021/06/16/pfizer-vaccine-engineers-supply/, 15 pages.
Rowland, C., "Why grandparents can't find vaccines: Scarcity of niche biotech ingredients," The Washington Post, Feb. 18, 2021 [online], [retrieved on Mar. 8, 2022]. Retrieved from the Internet URL: https://www.washingtonpost.com/business/2021/02/18/vaccine-fat-lipids-supply/, 10 pages.
Rozkov et al., Large-scale production of endotxoin-frree plasmids for transient expression in mammalian cell culture, Biotechnol. Bioeng., 2008, pp. 557-566.
Rurik et al., "CAR T cells produced in vivo to treat cardiac injury," Science, Jan. 7, 2022, pp. 91-96, vol. 375.
Sabnis et al., "A Novel Amino Lipid Series for mRNA Delivery: Improved Endosomal Escape and Sustained Pharmacology and Safety in Non-human Primates," Molecular Therapy, Jun. 2018, vol. 26, No. 6, pp. 1509-1519.
Sadoff et al., "Safety and immunogenicity of the Ad26.COV2.S COVID-19 vaccine candidate: interim results of a phase 1/2a, double-blind, randomized, placebo-controlled trial," medRxiv, Sep. 25, 2020, pp. 1-28. retrieved from URL https://doi.org/10.1101/2020.09.23.20199604.
Sago et al., "High-throughput in vivo screen of functional mRNA delivery identifies nanoparticles for endothelial cell gene editing", PNAS, Oct. 16, 2018, pp. 1-10, vol. 115, No. 42.
Sagonowsky, "BIO: Moderna, Merck execs see possible speed bumps in COVID-19 vaccine manufacturing. FiercePharma", Jun. 11, 2020, 5 pages. Retrieved from the Internet URL: https://www.fiercepharma.com/manufacturing/bio-moderna-merck-execs-see-possible-speed-bumps-covid-19-vaccine-manufacturing.
Sagonowsky, "CureVac's mRNA coronavirus shot boasts one advantage over Pfizer and Moderna counterparts—refrigerated storage," FiercePharma, Nov. 12, 2020 [online], [retrieved on Mar. 8, 2022]. Retrieved from the Internet URL: https://www.fiercepharma.com/pharma/curevac-s-mrna-coronavirus-shot-holds-edge-over-pfizer-and-moderna-counterparts-refrigerated, 3 pages.
Sagonowsky, E., "Pfizer and BioNTech, scaling up for 2B coronavirus vaccine doses, temporarily cut deliveries in EU, Canada," FiercePharma, Jan. 19, 2021 [online], [retrieved on Mar. 8, 2022]. Retrieved from the Internet URL: https://www.fiercepharma.com/pharma/pfizer-and-biontech-pushing-for-2b-coronavirus-vaccine-doses-2021-temporarily-reduce, 3 pages.
Sagonowsky, "FDA will require 50% efficacy for COVID-19 vaccines, WSJ says. How high is that bar?" FiercePharma, Jun. 30, 2020, 3 pages. [online], [retrieved on Mar. 8, 2022]. Retrieved from the Internet URL: https://www.fiercepharma.com/vaccines/fda-to-require-at-least-50-efficacy-for-covid-19-vaccines-wsj.
Sagonowsky, "Johnson & Johnson gears up for 60,000-person COVID-19 vaccine trial, the industry's biggest yet," FiercePharma, Aug. 21, 2020 [online], [retrieved on Mar. 8, 2022]. Retrieved from the Internet URL: https://www.fiercepharma.com/vaccines/johnson-johnson-gears-up-for-60-000-person-covid-vaccine-trial-next-month, 2 pages.
Sahin et al., "BNT162b2 vaccine induces neutralizing antibodies and poly-specific T cells in humans," Nature, May 27, 2021, 30 pages. retrieved from URL https://doi.org/10.1038/s41586-021-03653-6.
Sahin et al., "Concurrent human anitbody and TH1 type T-cell responses elicited by a COVID-19 RNA vaccine," medRxiv, Jul. 20, 2020, pp. 1-27. retrieved from URL https://doi.org/10.1101/2020.07.17.20140533.
Sahin, "Reporting Summary," Nature Research, Dec. 30, 2020, pp. 1-6.
Sahin, U. et al., "mRNA-based therapeutics—developing a new class of drugs," Nature Reviews Drug Discovery, vol. 13(10)759-780 (2014).
Samanovic et al., "Poor antigen-specific responses to the second BNT162b2 mRNA vaccine dose in SARS-CoV-2-experienced individuals," medRxiv, Feb. 9, 2021, retrieved from URL https://doi.org/10.1101/2021.02.07.21251311, 9 pages.
Samaridou, et al., "Lipid nanoparticles for nucleic acid delivery: Current perspectives." Advanced drug delivery reviews, 2020, pp. 37-63, vol. 154.
Sample, "Delay in giving second jabs of Pfizer vaccine improves immunity," The Guardian, May 13, 2021, 4 pages. [online], [retrieved on Mar. 8, 2022]. Retrieved from the Internet URL: http://www.theguardian.com/science/2021/May 14/delay-in-giving-second-jabs-of-pfizer-vaccine-improves-immunity.
Samsa et al, "Self-Amplifying RNA Vaccines for Venezuelan Equine Encephalitis Virus Induce Robust Protective Immunogenicity in Mice," Molecular Therapy, Apr. 2019, pp. 850-865, vol. 27.
Saslow, "'We're all starved for hope'", The Washington Post, Jul. 6, 2020.
Satapathy et al., "Solid Lipid Nanoparticles (SLNs): An Advanced Drug Delivery System Targeting Brain Through BBB", Pharmaceutics, 2021, pp. 1-36, vol. 13.
Sato et al., "Highly specific delivery of siRNA to hepatocytes circumvents endothelial cell-mediated lipid nanoparticle-associated toxicity leading to the safe and efficacious decrease on the hepatitis B virus", Journal of Controlled Release, Nov. 2017, pp. 216-225, vol. 266.
Sato et al., "Relationship Between the Physicochemical Properties of Lipid Nanoparticles and the Quality of siRNA Delivery to Liver Cells", Molecular Therapy, Apr. 2016, pp. 788-795, vol. 24, No. 4.
Sato, et al., "Understanding structure-activity relationships of pH-sensitive cationic lipids facilitates the rational identification of promising lipid nanoparticles for delivering siRNAs in vivo", Journal of Controlled Release, 2019 pp. 140-152, vol. 295.
Saunders et al., "A Nanoprimer to Improve the Systemic Delivery of siRNA and mRNA", Nano Letters, 2020, pp. 4264-4269, vol. 20.
Saunders et al., "Neutralizing antibody vaccine for pandemic and pre-emergent coronaviruses," Supplementary Figures, Nature, May 10, 2021, 28 pages.
Scheel et al., "Immunostimulating capacities of stabilized RNA molecules", Immunology, 2004, pp. 537-547, vol. 34.
Schlothauer et al., "Novel human lgG1 and lgG4 Fc-engineered antibodies with completely abolished immune effector functions", Protein Engineering Design and Selection, 2016, pp. 457-466, vol. 29, No. 10.
Schmidt et al., "Prevalence of serum lgG antibodies against SARS-CoV-2 among clinic staff," PLOS ONE, Jun. 25, 2020, pp. 1-8, vol. 15, No. 6.
Schnee et al., "An mRNA Vaccine Encoding Rabies Virus Glycoprotein Induces Protection against Lethal Infection in Mice and Correlates of Protection in Adult and Newborn Pigs", PLOS Neglected Tropical Diseases, 2016, pp. 1-20, vol. 10, No. 6.
Schulze et al., "A Liposomal Platform for Delivery of a Protein Antigen to Langerin-Expressing Cells", Supporting Information, May 2019, pp. 2576-80, vol. 58, No. 21.
Sciex, "Thousands of Lipids. One name to remember: Lipidyzer" Broucher, 2016, 8 pages.

(56) References Cited

OTHER PUBLICATIONS

Scudellari, "Attack of the killer clones: the next generation of modified T-cell therapies is taking on solid tumors—but it's an uphill fight", Nature, Dec. 2017, pp. 1-3, vol. 552.
Sedic et al., "Safety Evauation of Lipid Nanoaprticle-Formulated Midfied mRNA in the Sprague-Dawley Rat and Cynomolgus Monkey", Veterinary Pathology, 2017, pp. 341-354, vol. 55, No. 2.
Self et al., "Comparative Effectiveness of Moderna, Pfizer-BioNTech, and Janssen (Johnson & Johnson) Vaccines in Preventing COVID-19 Hospitalizations Among Adults Without Immunocompromising Conditions—United States, Mar.-Aug. 2021," Morbidity and Mortality Weekly Report, Sep. 24, 2021, pp. 1337-1343, vol. 70, No. 38.
Semple, et al., Interactions of liposomes and lipid-based carrier systems with blood proteins: Relation to clearance behaviour in vivo, Advanced drug delivery reviews, Jun. 8, 1998, pp. 3-17, vol. 32.
Semple, S.C., et al., "Rational design of cationic lipids for siRNA delivery", Nature Biotechnology, 2010, vol. 28, No. 2, 172-176.
Seow et al., "Longitudinal evaluation and decline of antibody responses in SARS-CoV-2 infection," medRxiv, Jul. 11, 2020, pp. 1-24. retrieved from URL https://doi.org/10.1101/2020.07.09.20148429.
Shahzad et al., "Drug Delivery Using Nanomaterials", Emerging Materials and Technologies, 2021, pp. 1-431.
Shang et al., "The outbreak of SARS-CoV-2 pneumonia calls for viral vaccines," npj Vaccines, Mar. 6, 2020, pp. 1-3, vol. 5, No. 18.
Shaw et al., "Safety and immunogenicity of a mRNA-based chikungunya in a phase 1 dose-ranging trial", International Journal of Infectious Diseases (Abstracts), 2019, pp. 1, vol. 79, No. S1.
Shimizu et al., "Simultaneous quantification of components of neoglycolipid-coated liposomes using high-performance liquid chromatography with evaporative light scattering detection", Journal of Chromatography B, 2001, pp. 127-133, vol. 754.
Shin et al., "COVID-19 vaccine development and a potential nanomaterial path forward," Nature Nanotechnology, Aug. 2020, pp. 646-655, vol. 15.
Shive et al., "BST-CarGel: In Situ ChondroInduction for Cartilage Repair", Operative Techniques in Orthapedics, 2006, pp. 271-278, vol. 16, No. 4.
Shobaki et al., "Mixing lipids to manipulate the ionization status of lipid nanoparticles for specific tissue targeting", International Journal of Nanomedicine, 2018, pp. 8395-8410, vol. 13.
Shrock et al., Viral epitope profiling of COVID-19 patients reveals cross-reactivity and correlates of severity, Science, Nov. 27, 2020, vol. 370, No. 6520.
Si et al., "Targeted Exosomes for Drug Delivery: Biomanufacturing, Surface Tagging, and Validation", Biotechnology Journal, 2019, pp. 1-12, vol. 15, No. 1.
Siengra et al., "Lipid Nanoparticle Spherical Nucleic Acids for Intracellular DNA and RNA Delivery", Nano Letters, Jul. 21, 2021, pp. 6584-6591, vol. 21, No. 15.
Silverman, et al., Selective RNA cleavage by isolated RNase L activated with 2-5A antisense chimeric oligonucleotides, InMethods in Enzymol., Jan. 1, 2000, pp. 522-533.
Sim et al., "Development of an Electromechanical Grade to Assess Human Knee Articular Cartilage Quality", Annals of Biomedical Engineering, Oct. 2017, pp. 2410-2421, vol. 45 No. 10.
Sim et al., "Electromechanical Probe and Automated Indentation Maps are Sensitive techniques in Assessing Early Degenerated Human Articular Cartilage", Journal of orthopedic Research, 2016, pp. 1-10, vol. 35, No. 4.
Sim et al., "Non-destructive electromechanical assessment (Arthro-BST) of human articular cartilage correlates with histological scores and biomechanical properties", osteoarthritis and Cartilage,2014, pp. 1926-1935, vol. 22.
Singh et al., "A rapid isocratic high-performance liquid chromatography method for determination of cholesterol and 1,2-dioleoyl-sn-glycero-3-phosphocholine in liposome-based drug formulations", Journal of Chromatography A, 2005, pp. 347-353.
Smith et al., "In situ programming of leukemia-specific T cells using synthetic DNA nanocarriers", Nature Nanotechnology, Aug. 2017, pp. 813-823, vol. 12.
Smith, et al., "Tertiary Amine Esters for Carbon Dioxide Based Emulsions", ACS, Mar. 15, 2007, 6 pages. Retrieved from the Internet <URL: <a= href=>https://pubs.acs.org/doi/10.1021/ie060934h. </url:>.
Smith et al., "The endosomal Escape of Nanoparticles: Toward More Efficient Cellular Delivery", Bioconjugate Chemistry, 2019, pp. 263-272, vol. 30.
Soulhat et al., "A Fibril-Network-Reinforced Biphasic Model of Cartilage in Unconfined Compression", Journal of Biomechanical Engineering, Jun. 1999, pp. 340-347, vol. 121.
Steensels et al., "Comparison of SARS-CoV-2 Antibody Response Following Vaccination with BNT162b2 and mRNA-1273," JAMA, Aug. 30, 2021, pp. E1-E3.
Stein, et al., Antisense oligonucleotides as therapeutic agents—is the bullet really magical?, Science, Aug. 20, 1993, pp. 1004-1012, vol. 261, No. 5124.
Stetefeld et al., "Dynamic light scattering: a practical guide and applications in biomedical sciences", Biophysics Review, 2016, pp. 409-427, vol. 8.
Studer et al., "Vitrification of articular cartilage by high-pressure freezing", Journal of Microscopy, Pt. 3, Sep. 1995, pp. 321-332, vol. 179.
Subbarao, et al., "Respiratory Virus Infections: Understanding COVID-19," Immunity, vol. 52, Jun. 16, 2020, pp. 905-909.
Sultana et al., "Optimizing Cardiac Delivery of Modified mRNA," Molecular Therapy, Jun. 2017, pp. 1306-1315, vol. 25.
Swaminathan et al., "A novel lipid nanoparticle adjuvant significantly enhances B Cell and T Cell responses to sub-unit vaccine antigens", Vaccine, 2016, pp. 110-119, vol. 34.
Swaminathan et al., "A Tetravalent Sub-Unit Dengue Vaccine Formulated with Ionizable Cationic Lipid Nanoparticle induces Significant Immune Responses in Rodents and Non-Human Primates", Scientific Reports, Oct. 2016, pp. 1-17, vol. 6.
Swan et al., "A simpler expression for henry's function describing the electrophoretic mobility f spherical colloids", Journal of Colloid and interface Science, 2012, pp. 92-94, vol. 388.
Tabernero et al., "First-in-Humans Trial of an RNA Interference Therapeutic Targeting VEGF and KSP in Cancer Patients with Liver Involvement", Cancer Discovery, Jan. 28, 2013, pp. 406-417.
Tam, et al., Small molecule ligands for enhanced intracellular delivery of lipid nanoparticle formulations of siRNA, Nanomedicine: Nanotechnology, Biology and Medicine, Jul. 1, 2013, pp. 665-674, vol. 9, No. 5.
Tanaka et al., "Development of Lipid-like materials for RNA delivery based on intracellular environment-responsive membrane destabilization and spontaneous collapse", Advanced Drug Delivery Reviews, 2020, pp. 1-17, vol. 154.
Tavakoli Naeini, A. et al. (Apr. 7, 2017) "Automated in-line mizing system for large scale produciton of chitosan-based polyplexes" J Colloid Interface Sci, 500:253-263.
Taylor, "CureVac links COVID-19 vaccine to immune response, setting it up to enter pivotal trial" FierceBiotech, 2020, 2 pages.
Taylor, "Moderna finalizes design of phase 3 COVID-19 vaccine trial ahead of July start", FierceBiotech, Jun. 11, 2020, 5 pages. Retrieved from the Internet URL: https://www.fiercebiotech.com/biotech/moderna-finalizes-design-phase-3-covid-19-vaccine-trial-ahead-july-start.
Taylor, N. P., "AstraZeneca's COVID-19 vaccine 70% effective, shares fall," FierceBiotech, Nov. 23, 2020 [online], [retrieved on Mar. 8, 2022]. Retrieved from the Internet URL: https://www.fiercebiotech.com/biotech/astrazeneca-s-covid-19-vaccine-70-effective-phase-3, 2 pages.
Taylor, N. P., "CureVac gets Ok to start testing mRNA COVID-19 vaccine in humans," FierceBiotech, Jun. 17, 2020 [online], [retrieved on Mar. 8, 2022]. Retrieved from the Internet URL: https://www.fiercebiotech.com/biotech/curevac-gets-ok-to-start-testing-mrna-covid-19-vaccine-humans, 2 pages.
Taylor, N. P., "Moderna stock sinks as patent case spurs concern for COVID-19 vaccine," FierceBiotech, Jul. 24, 2020 [online], [retrieved on Mar. 8, 2022]. Retrieved from the Internet URL: https://www.

(56) References Cited

OTHER PUBLICATIONS fiercebiotech.com/biotech/moderna-stock-sinks-as-patent-case-spurs-concern-for-covid-19-vaccine, 6 pages.
Taylor, N. P., "Pfizer, BioNTech share clinical data linking favored COVID-19 vaccine to improved tolerability," FierceBiotech, Aug. 21, 2020 [online], [retrieved on Mar. 8, 2022]. Retrieved from the Internet URL: https://www.fiercebiotech.com/biotech/pfizer-biontech-share-clinical-data-linking-favored-covid-19-vaccine-to-improved, 2 pages.
Taylor, N. P., "Pfizer passes COVID-19 vaccine safety milestone, reveals 95% efficacy ahead of EUA," FierceBiotech, Nov. 18, 2020 [online], [retrieved on Mar. 8, 2022]. Retrieved from the Internet URL: https://www.fiercebiotech.com/biotech/pfizer-passes-covid-19-vaccine-safety-milestone-readies-for-eua 2 pages.
Taylor, N. P., "Pfizer reports strong T-cell response to COVID-19 vaccine," FierceBiotech, Jul. 20, 2020 [online], [retrieved on Mar. 8, 2022]. Retrieved from the Internet URL: https://www.fiercebiotech.com/biotech/pfizer-reports-strong-t-cell-response-to-covid-19-vaccine, 2 pages.
Taylor, N. P., "'Positive news' on AstraZeneca's COVID-19 vaccine is imminent: report," FierceBiotech, Jul. 15, 2020 [online], [retrieved on Mar. 8, 2022]. Retrieved from the Internet URL: https://www.fiercebiotech.com/biotech/positive-news-astrazeneca-s-covid-19-vaccine-imminent-report, 2 pages.
Taylor, N. P., "Weak clinical data force Sanofi, GSK to delay COVID-19 vaccine," FierceBiotech, Dec. 11, 2020 [online], [retrieved on Mar. 8, 2022]. Retrieved from the Internet URL: https://www.fiercebiotech.com/biotech/weak-clinical-data-force-sanofi-gsk-to-delay-covid-19-vaccine, 3 pages.
Tenchov et al., "Cubic Phases in Phosphatidylcholine-Cholesterol Mixtures: Cholesterol as Membrane 'Fusogen'", Biophysical Journal, Oct. 2006, pp. 2508-2516, vol. 91.
Ter Meulen et al., "Human monoclonal antibody as prophylaxis for SARS coronavirus infection in ferrets," The Lancet, Jun. 26, 2004, pp. 2139-2141, vol. 363.
Thess et al., "Sequence-engineered mRNA Without Chemical Nucleosside Modifications Enables an Effective Protein Therapy in Large Animals," Molecular Therapy, Jun. 30, 2015, pp. 1-9, with supplemental data, vol. 23, No. 9.
Thibault et al., "Cyclic compression of cartilage/bone explants in vitro leads to physical weakening, mechanical breakdown of collagen and release of matrix fragments", Journal of Orthopedic Research, 2002, pp. 1265-1273, vol. 20.
Thibault et al., "Excess Polycation Mediates efficient chitosan-based gene transfer by promoting lysosomal release of the polyplexes", Biomaterials, 2011, pp. 4639-4646, vol. 32.
Thibault et al., "Fibronectin, Vitronectin, and Collagen I Induce Chemotaxis and Haptotaxis of Human and Rabbit Mesenchymal Stem Cells in a Standardized Transmembrane Assay", Stem Cells and Development, 2007, pp. 489-502, vol. 16.
Thibault et al., "Intracellular Trafficking and Decondensation Kinetics of Chitosan-pDNA Polyplexes", Molecular Therapy, Oct. 2010, pp. 1787-1795, vol. 18, No. 10.
Thibault et al., "Migration of Bone Marrow Stromal Cells in 3D: 4 Color Methodology Reveals Spatially and temporally Coordinated Events", Cell Motility and the Cytoskeleton, 2006, pp. 725-740, vol. 63.
Thibault et al., "Structure Dependence of Lysosomal Transit of Chitosan-Based Polyplexes for Gene Delivery", Molecular Biotechnology, 2016, pp. 1-11, vol. 58, No. 10.
Thomas et al., "Safety and Efficacy of the BNT162b2 mRNA Covid-19 Vaccine through 6 Months," N Engl J Med, Sep. 15, 2021, pp. 1-13.
Thran et al., "mRNA mediates passive vaccination against infectious agents, toxins, and tumors", EMBO Molecular Medicine, 2017, pp. 1434-1447, vol. 9, No. 10.
Tombacz et al., "Highly efficient CD4+ T cell targeting and genetic recombination using engineered CD4+ cell-homing mRNA-LNP," Molecular therapy, 2021, pp. 3293-3304, vol. 9, No. 11.
Tombácz et al., "Hughly efficient CD4+ T cell targeting and genetic recombination using engineered CD4+ cell-homing mRNA-LNP", Molecular Therapy, Jun. 3, 2021, pp. 1-28, vol. 29.
Torjesen, "Covid-19: Norway investigates 23 deaths in frail elderly patients after vaccination," BMJ, Jan. 15, 2021, 1 page, vol. 372, No. n149.
Torrence et al., Targeting RNA for degradation with a (2'-5') oligoadenylate-antisense chimera, Proc. Natl. Acad. Sci., Feb. 15, 1993, pp. 1300-1304.
Tran-Khanh et al., "Aged bovine chondrocytes display a diminished capacity to produce a collagen-rich, mechanically functional cartilage extracellular matrix", Journal of orthopedic Research, 2005, pp. 1354-1362, vol. 23.
Tran-Khanh et al., "Young Adult Chondrocytes Proliferate Rapidly and Produce a Cartilaginous Tissue at the Gel-Media Interface in Agarose Cultures", Connective Tissue Research, 2010, pp. 216-223, vol. 51.
Translate Bio, Translate Bio Announces FDA Clearance to Proceed with a Single-ascending Dose (SAD) Phase 1/2 Clinical Trial for Ornithine Transcarbamylase (OTC) Deficiency, Translate Bio, Inc., Jun. 26, 2019, 4 pages. Retrieved from the Internet URL: http://www.globenewswire.com/news-release/2019/06/26/1874354/0/en/Translate-Bio-Announces-FDA-Clearance-to-Proceed-with-a-Single-ascending-Dose-SAD-Phase-1-2-Clinical-Trial-for-Ornithine-Transcarbamylase-OTC-Deficiency.html.
Tureci et al., "Racing for a SARS-CoV-2 vaccine," BioNTech, 2021, 7 pages, DOI: 10.15252/emmm.202115145.
Tuzimski, "Application of different modes of thin-layer chromatography and mass spectrometry for the separation and detection of large and small biomolecules", Journal of Chromatography A, 2011, pp. 8799-8812, vol. 1218.
Uebbing et al., "Investigation of pH-responsiveness inside lipid nanoparticles for parenteral mRNA application using small angle X-ray scattering," Supporting Information, 2020, pp. S1-S11.
United States Patent and Trademark Office, Inter Partes Review of U.S. Pat. No. 9,404,127, Feb. 21, 2018, 75 pages.
United States Securities and Exchange Commission, "Annual Report Pursuant to Section 13 or 15(d) of the Securities Exchange Act of 1934", Dec. 31, 2020, 355 pages. Retrieved from the Internet URL: https://www.sec.gov/ix?doc=/Archives/edgar/data/1682852/000168285221000006/mrna-20201231.htm.
Unknown Author, 18:1-d7-cholesterol | Avanti Polar Lipids, retrieved on Nov. 2, 2022, 2 pages. https://avantilipids.com/product/791645?utm_source=behavioral-VT.
Unknown Author, Arcturus Therapeutics Announces Positive Interim ARCT-021 (LUNAR-COV19) Phase 1/2 Study Results for Both Single Shot and Prime-boost Regimens, and Up to $220 Million in Additional Financial Commitments from Singapore. MarketWatch, Nov. 9, 2020 [online], 2 pages [retrieved on Mar. 7, 2022]. Retrieved from the Internet <URL: <a= href=>https://www.marketwatch.com/press-release/arcturus-therapeutics-announces-positive-interim-arct-021-lunar-cov19-phase-12-study-results-for-both-single-shot-and-prime-boost-regimens-and-up-to-220-million-in-additional-financial-commitments-from-singapore-2020-11-09.</url:>.
Unknown Author, Arcturus Therapeutics, "Building the Next Generation of RNA Medicines: Development of a self-transcribing and replicating (STARRtm) mRNA vaccine candidate against SARS-CoV-2," Sep. 2020, 35 pages.
Unknown Author, "Background document on the mRNA vaccine BNT162b2 (Pfizer-BioNTech) against COVID-19," World Health Organization, Jan. 14, 2021, 44 pages.
Unknown Author, BioNTech, "BioNTech and Pfizer announce regulatory approval from German authority Paul-Ehrlich-Institut to commence first clinical trial of COVID-19 vaccine candidates," Apr. 22, 2020, 3 pages.
Unknown Author, BioNTech, Lipid Structures, Dec. 12, 2020, 2 pages.
Unknown Author, BioNTech, "Pfizer and BioNTech Conclude Phase 3 Study of COVID-19 Vaccine Candidate, Meeting All Primary Efficacy Endpoints," Nov. 18, 2020, 3 pages.

(56) References Cited

OTHER PUBLICATIONS

Unknown Author, "COVID-19 mRNA Vaccine BNT162b2 (BNT162b2 RNA) concentrate for solution for injection," Medicines & Healthcare products Regulatory Agency, Public Assessment Report, 2020, pp. 1-51.
Unknown Author, "COVID-19 vaccine AZD1222 showed robust immune responses in all participants in Phase I/II trial," AstraZeneca, Jul. 20, 2020, 5 pages. [online], [retrieved on Mar. 8, 2022]. Retrieved from the Internet URL: https://www.astrazeneca.com/media-centre/press-releases/2020/covid-19-vaccine-azd1222-showed-robust-immune-responses-in-all-participants-in-phase-i-ii-trial.html.
Unknown Author, Curevac Covid 19 Activities. CureVac, Apr. 8, 2020 [online], [retrieved on Mar. 8, 2022], 5 pages. Retrieved from the Internet <url: <a=href=>https://www.curevac.com/covid-19.</url:>.
Unknown Author, Emergency Use Authorization for Pfizer-BioNTech COVID-19 Vaccine, May 10, 2021 (accessed Dec. 14, 2020), 10 pages.
Unknown Author, European Medicines Agency, Assessment report of COVID-19 mRNA vaccine (nucleoside-modified), Feb. 19, 2021, 140 pages.
Unknown Author, "Imperial College London gets UK funding for Covid-19 vaccine," Clinical Trials Arena, Apr. 23, 2020 [online], [retrieved on Mar. 8, 2022]. Retrieved from the Internet URL: https://www.clinicaltrialsarena.com/news/imperial-covid-19-vaccine-trial/, 9 pages.
Unknown Author, "Industry News: Pfizer and BioNTech to start human trials of COVID-19 vaccine," SelectScience, Apr. 24, 2020 [online], [retrieved on Mar. 8, 2022]. Retrieved from the Internet URL: http://www.selectscience.net/industry-news/pfizer-and-biontech-to-start-human-trials-of-covid-19-vaccine/?artID=51330, 4 pages.
Unknown Author, "Moderna's COVID-19 Vaccine Candidate Meets its Primary Efficacy Endpoint in the First Interim Analysis of the Phase 3 COVE Study," Moderna, Nov. 16, 2020 [online], [retrieved on Mar. 8, 2022]. Retrieved from the Internet URL: https://investors.modernatx.com/news-releases/news-release-details/modernas-covid-19-vaccine-candidate-meets-its-primary-efficacy/, 6 pages.
Unknown Author, "Moderna Loses Challenge of Arbutus Patent on Vaccine Technology," Bloomberg, Jul. 23, 2020, 9 pages.
Unknown Author, "Moderna's Work on a Potential Vaccine Against COVID-19," Moderna, Apr. 16, 2020 [online], [retrieved on Mar. 8, 2022]. Retrieved from the Internet URL: https://www.modernatx.com/modernas-work-potential-vaccine-against-covid-19, 3 pages.
Unknown Author, "Novavax Announces Positive Phase 1 Data for its COVID-19 Vaccine Candidate," Novavax, Aug. 4, 2020 [online], [retrieved on Mar. 8, 2022]. Retrieved from the Internet URL: https://ir.novavax.com/news-releases/news-release-details/novavax-announces-positive-phase-1-data-its-covid-19-vaccine , 5 pages.
Unknown Author "Pfizer and Biontech Announce Vaccine Candidate Against COVID-19 Achieved Success in First Interim Analysis From Phase 3 Study," Pfizer Inc., Nov. 9, 2020 [online], 7 pages. [retrieved on Mar. 8, 2022]. Retrieved from the Internet <url: <a=href=>https://www.pfizer.com/news/press-release/press-release-detail/pfizer-and-biontech-announce-vaccine-candidate-against.</url:>.
Unknown Author, "Start of Production in Record Time: Evonik Delivers First Lipids From German Facility to Biontech," Evonik, , 1 page. [online], [retrieved on Mar. 8, 2022]. Retrieved from the Internet URL: https://corporate.evonik.com/en/start-of-production-in-record-time-evonik-delivers-first-lipids-from-german-facility-to-biontech-157147.html.
Unknown Author, Trilink Biotechnologies CleanCap Technology, 2022, 4 pages. https://www.trilinkbiotech.com/cleancap.
Unknown Author, Which animals are being used to develop a COVID-19 Vaccine?AnimalResearch.info, Jun. 15, 2020 [online], [retrieved on Mar. 8, 2022]. Retrieved from the Internet URL: http://www.animalresearch.info/en/medical-advances/diseases-research/sars-cov-2/, 14 pages.
Unkown Author, "Clinical Trial Protocol Including Amendments Nos. 01 to 04 BNT162-01," BioNTech, Version 7.0, Jun. 26, 2020, pp. 1-137.
US Dept. of Health and Human Services, "Development and Licensure of Vaccines to Prevent COVID-19: Guidance for Industry," Jun. 2020, 24 pages.
Uster et al., "Insertion of poly (ethylene glycol) derivatized phospholipid into pre-formed liposomes results in prolonged in vivo circulation time", FEBS Letters, 1996, pp. 243-246, vol. 386.
Vabret et al., "Immunology of COVID-19: Current State of the Science," Immunity, Jun. 16, 2020, pp. 910-941, vol. 52.
Vacha et al., "The Orientation and Charge of Water at the Hydrophobic Oil droplet—water Interface", The Journal of the American Chemical Society, 2011, pp. 10204-10210, vol. 133.
Valverde-Franco et al., "Defects in articular cartilage metabolism and early arthritis in fibroblast growth factor receptor 3 deficient mice", Human Molecular Genetics, 2006, pp. 1783-1792, vol. 15 no. 11.
Van Der Meel et al., "Nanotechnology for organ-tunable gene editing", Nature Nanotechnology, Apr. 2020, pp. 252-255, vol. 15.
Van Meer et al., "Membrane lipids: where they are and how they behave" Nature, Feb. 2008, pp. 112-124, , vol. 9.
Veiga et al., "Cell Specific delivery of modified mRNA expressing therapeutic proteins to leukocytes", Nature Communications, Oct. 2018, pp. 1-9, vol. 9.
Veilleux et al., "Lyophilisation and concentration of chitosan/siRNA polyplexes: Influence of buffer composition, oligonucleotide sequence, and hyaluronic acid coating", Journal of Colloid and Interface Science, 2018, pp. 335-345, vol. 512.
Veilleux et al., "Preparation of Concentrated Chitosan/DNA Nanoparticle Formulations by Lyophilization for Gene Delivery at Clinically Relevant Dosages", Journal of Pharmaceutical Sciences, 2016, pp. 88-96, vol. 105.
Vermeulen et al., "Endosomal Size and membrane leakiness Influence Proton Sponge-Based Rupture of Endosomal Vesicles, Suporting Information", ACS nano, 2018, 8 pages.
Viger-Gravel et al., "Structure of Lipid Nanoparticles Containing siRNA or mRNA by Dynamic Nuclear Polarization Enhanced NMR Spectroscopy," Supporting Information, 2018, pp. S1-S32.
Villaverde et al., "Targeting strategies for improving the efficacy of nanomedicine in oncology", Journal of Nanotechnology, 2019, pp. 168-181, vol. 10.
Vogel et al., "A prefusion SARS-CoV-2 spike RNA vaccine is highly immunogenic and prevents lung infection in non-human primates," bioRxiv, Sep. 8, 2020, pp. 1-38. retrieved from URL https://doi.org/10.1101/2020.09.08.280818.
Vogel et al., "BNT162b vaccines protect rhesus macaques from SARS-CoV-2," Nature, Apr. 8, 2021, pp. 283-289, vol. 592.
Vogel et al., "Self-Amplifying RNA Vaccines Give Equivalent Protection against Influenza to mRNA Vaccines but at Much Lower Doses," Molecular Therapy, Feb. 2018, pp. 446-455, vol. 26, No. 2.
Vogel et al., "High-Resolution Single Particle Zeta Potential Characterization of Biological Nanoparticles using Tunable Resistive Pulse Sensing", Scientific Reports, Dec. 2017, pp. 1-13, vol. 7.
Voss et al., "Calculation of Standard Atomic Volumes for RNA and Comparison with Proteins: RNA is Packed More Tightly", Journal of Molecular Biology, 2005, pp. 477-492, vol. 346.
Voysey et al., "Single-dose administration and the influence of the timing of the booster dose on immunogenicity and efficacy of ChAdOx1 nCoV-19 (AZD1222) vaccine: a pooled analysis of four randomised trials," The Lancet, Mar. 6, 2021, pp. 881-891, vol. 397.
Vuong et al., "Feline coronavirus drug inhibits the main protease of SARS-CoV-2 and blocks virus replication," Nature Communications, 2020, pp. 1-8, vol. 11, No. 4282.
Wadman et al., "A Rampage through the body: The lungs are ground zero, but COVID-19 also tears through organ systems from brain to blood vessels," Science, Apr. 24, 2020, pp. 356-360, vol. 368, Issue 6489.
Walls et al., "Structure, Function, and Antigenicity of the SARS-CoV-2 Spike Glycoprotein," Cell, Mar. 19, 2020, pp. 1-12, vol. 180.

(56) References Cited

OTHER PUBLICATIONS

Walsh et al., "Protocol: Safety and Immunogenicity of Two RNA-Based COVID-19 Vaccine Candidates," Pfizer, PF-07302048 (BNT162 RNA-Based COVID-19 Vaccines), Protocol C4591001, Final Protocol, Apr. 15, 2020, 314 pages.
Walsh et al., "RNA-Based COVID-19 Vaccine BNT162b2 Selected for a Pivotal Efficacy Study," medRxiv, Aug. 20, 2020, pp. 1-20. retrieved from URL https://doi.org/10.1101/2020.08.17.20176651.
Wamhoff et al., "A specific glycomimetic Langerin ligand for human Langerhans cell targeting", Supporting Information, ACS Central Science, 2019, pp. 808-820, vol. 5, No. 5.
Wang et al., "An Evidence Based Perspective on mRNA-SARS-CoV-2 Vaccine Development," Medical Science Monitor, 2020, pp. e924700-1-e924700-8, vol. 26.
Wang et al., targeting Liver Sinusoidal Endothelial Cells: An Attractive Therapeutic Strategy to Control Inflammation in Nonalcoholic Fatty Liver Disease, Frontiers in Pharmacology, Apr. 5, 2021, pp. 1-16, vol. 12.
Watanabe et al., "Site-Specific glycan analysis of the SARS-CoV-2 spike," Science, May 4, 2020, pp. 1-9, DOI: 10.1126/science. abb9983.
Weber, Immune checkpoint proteins: a new therapeutic paradigm for cancer-preclinical background: CTLA-4 and PD-1 blockade, Semin. Oncol., Oct. 1, 2010, pp. 430-439, . Vol. 37, No. 5.
Weinberg et al., Anti-OX40 (CD134) administration to nonhuman primates: immunostimulatory effects and toxicokinetic study, J. Immunother, Nov. 1, 2006, pp. 575-585, vol. 29, No. 6.
Weintraub, A., "It Could Be Several Years for 2 Leading COVID-19 Vaccines to Debut", Wall Street Analysts, Global Research, Apr. 22, 2020, 3 pages. Retrieved from the Internet URL: https://www.globalresearch.ca/it-could-take-5-years-covid-19-vaccines-debut-ai-analysis-finds/5710239.
Weintraub, A., "J&J COVID-19 vaccine candidate protects monkeys after single dose," FiercePharma, Jul. 30, 2020 [online], [retrieved on Mar. 8, 2022]. Retrieved from the Internet URL: https://www.fiercebiotech.com/research/j-j-covid-19-vaccine-candidate-protects-monkeys-after-single-dose, 4 pages.
Weintraub, A., "Pfizer's COVID vaccine data raise some flags, analysts say, but not enough to scuttle an FDA nod," FiercePharma, Dec. 9, 2020 [online], [retrieved on Mar. 8, 2022]. Retrieved from the Internet URL: https://www.fiercepharma.com/pharma/pfizer-s-covid-vaccine-data-raise-some-questions-but-shouldn-t-scuttle-fda-nod-analysts, 2 pages.
Weintraub, "It's too soon to assume success for Moderna's COVID-19 vaccine: analyst", FierceBiotech, May 20, 2020, 5 pages. Retrieved from the Internet URL: https://www.fiercebiotech.com/biotech/it-s-too-soon-to-assume-success-for-moderna-s-covid-19-vaccine-analyst.
Weissman, D., "mRNA transcript therapy," Expert Review of Vaccines, vol. 14(2): 265-281 (2015).
Weissman et al., "D614G Spike Mutation Increases SARS CoV-2 Susceptibility to Neutralization," Cell Host & Microbe, Jan. 13, 2021, pp. 23-31, vol. 29.
Weissman et al., "D614G Spike Mutation Increases SARS CoV-2 Susceptibility to Neutralization," medRxiv, Jul. 24, 2020, pp. 1-16.
Wener, et al., The effect of base mismatches in the substrate recognition helices of hammerhead ribozymes on binding and catalysis, Nucleic Acids Research, Jun. 1995, 2092-2096, vol. 23, No. 12.
Widge, "Durability of responses after SARS-CoV-2 mRNA-1273 Vaccination", The New England Journal of Medicine, Correspondence, Dec. 2020, pp. 1-4.
Willis et al., "Nucleoside-modified mRNA vaccination partially overcomes maternal antibody inhibition of de novo immune responses in mice," Science Translational Medicine, Jan. 8, 2020, pp. 1-12, vol. 12.
Wilson et al., "Biodegradable PLGA-b-PEG Nanoparticles Induce T Helper 2 (Th2) Immune Responses and Sustained Antibody Titers via TLR9 Stimulation", Vaccines, May 29, 2020, pp. 1-14, vol. 8.
Wittrup et al., "Visualizing lipid-formulated siRNA release from endosomes and target gene knockdown", Nature Biotechnology, Aug. 2015, pp. 870-885, vol. 33, No. 8.
Wolfe, "Moderna loses challenge to Arbutus patent on vaccine technology", Jul. 23, 2020, 9 pages. Retrieved from the Internet URL: https://www.reuters.com/article/us-moderna-patent/moderna-loses-challenge-to-arbutus-patent-on-vaccine-technology-idUSKCN2402XY.
Wong et al., "Chondrocyte Biosynthesis Correlates with Local Tissue Strain in Statically Compressed Adult Articular Cartilage", Journal of orthopedic Research, 1997, pp. 186-196, vol. 15.
Wu et al., "Progress and Concept for COVID-19 Vaccine Development," Biotechnology Journal, 2000147, 2020, pp. 1-3.
Xia et al., "Effect of an Inactivated Vaccine Against SARS-CoV-2 on Safety and Immunogenicity Outcomes," JAMA, Aug. 13, 2020, pp. E1-E10.
Xiao et al., "Regulation of microglia polarization via mannose receptor-mediated delivery of siRNA by ligand-functionalized DoGo LNP", Royal Society of Chemistry Advances, 2021, pp. 32549-32558, vol. 11.
Xie et al., "Neutralization of N501Y mutant SARS-CoV-2 by BNT162b2 vaccine-elicited sera," bioRxiv, Jan. 7, 2021, 6 pages. retrieved from URL https://doi.org/10.1101/2021.01.07.425740.
Xu et al., "Cholesterol domains in cationic lipid/DNA complexes improve transfection", Biochimica et Biophysica Acta, Apr. 2008, pp. 2177-2181, vol. 1778.
Yan et al., "Systemic mRNA Delivery to the Lungs by Functional Polyester-based Carriers", Biomacromolecules, 2017, pp. 4307-4315, vol. 18.
Yang et al., "Measurement of the Zeta Potential of Gas Bubbles in Aqueous Solutions by Microelectrophoresis Method", Journal of Colloid and Interface Science, 2001, pp. 128-135, vol. 243.
Yu et al., "DNA vaccine protection against SARS-CoV-2 in rhesus macaques," Science 369(6505) pp. 806-811 (2020).
Yu et al., "Hydrophobic Optimization of Functional Poly (TPAE-co-suberoyl chloride) for Extrahepatic mRNA Delivery following Intravenous Administration", Pharmaceutics, 2021, pp. 1-13, vol. 13.
Zadeh, et al., "Augmentation Techniques for Meniscus Repair", The Journal of Knee Surgery, Mar. 9, 2017, pp. 1-18.
Zagato et al., Quantifying the average number of nucleic acid therapeutics per nanocarrier by single particle tracking microscopy, Supporting Information, Molecular Pharmaceutics, 2018, pp. 1142-1149, vol. 15, No. 3.
Zak et al., "Lipid Nanoparticles for Organ-Specific mRNA Therapeutic Delivery", Pharmaceutics, 2021, pp. 1-13, vol. 13.
Zamore, et al., Ribo-gnome: the big world of small RNAs, Science, Sep. 2, 2005, pp. 1519-1524.
Zamore et al., "RNAi: double-stranded RNA directs the ATP-dependent cleavage of mRNA at 21 to 23 nucleotide intervals," 2000, Cell, 101, 25-33.
Zeng et al., "Scalable Production of Therapeutic protein Nanoparticles Using Flash Nanoprecipitation", Advanced Healthcare Materials, Supporting Information, 2019, 10 pages.
Zeng et al., "Leveraging mRNAs sequences to express SARS-CoV-2 antigens in vivo," bioRxiv, Apr. 5, 2020, 16 pages. retrieved from URL https://doi.org/10.1101/2020.04.01.019877.
Zetaview, Particle Metrix GmbH, Mar. 2014, 132 pages.
Zhang et al., "A thermostable mRNA vaccine against COVID-19," Cell, Journal Pre-proof, 2020, 48 pages.
Zhang et al, "Advances in mRNA Vaccines for Infectious Diseases," Frontiers in Immunology, Mar. 27, 2019, pp. 1-13, vol. 10.
Zhang et al., "Assessing the Heterogeneity Level in Lipid Nanoparticles for siRNA Delivery: Size-Based Separation, Compositional heterogeneity, and Impact of Bioperformance", Molecular Pharmaceutics, 2013, pp. 397-405, vol. 10.
Zhang et al., "Fluorescence Correlation Spectroscopy to find the critical balance between extracellular association and intracellular dissociation of mRNA", Acta Biomaterialia, May 2018, pp. 358-370, vol. 75.
Zhang et al., "In situ repurposing of dendritic cells with CRISPR/Cas9-based nanomedicine to induce transplant tolerance", Biomaterials, Jun. 2019, pp. 1-11, vol. 217.

(56) References Cited

OTHER PUBLICATIONS

Zhang et al., "Lipids and Lipid Derivative for RNA Delivery", Chemical Reviews, 2021, pp. 12181-12277, vol. 121,No. 20.
Zhang et al., "Nanoparticles that Reshape the Tumor Milieu Create a Therapeutic Window for Effective T-cell Therapy in Solid Malignancies", Cancer Research, Jul. 1, 2018, pp. 3718-3731, vol. 78, No. 13.
Zhang et al., "Polydispersity Characterization of Lipid Nanoparticles for siRNA Delivery Using Multiple Detection Size-Exclusion Chromatography", Supporting Information, [figures S1, S2, S3, and S4], Jul. 17, 2012, vol. 84, No. 14.
Zhang et al., "targeted Delivery of mRNA with One-Component lonizable Amphiphilic Janus Dendrimers", Journal of the American Chemical Society, Oct. 21, 2021, pp. 1-8, vol. 143.
Zhang et al., "The development of an in vitro assay to screen lipid based nanoparticles for siRNA delivery", Journal of Controlled Release, Nov. 2013, pp. 7-14, vol. 174.
Zhang, "What the Vaccine's Side Effects Feel Like", The Atlantic, Dec. 18, 2020, 3 pages. Retrieved from the Internet URL: https://www.theatlantic.com/health/archive/2020/12/what-expect-when-you-get-covid-19-vaccine/617428/.
Zhao, Y., et al., "Lipid Nanoparticles for Gene Delivery," Advances in genetics, 2014, vol. 88, pp. 13-36.
Zheng et al., "Novel antibody epitopes dominate the antigenicity of spike glycoprotein in SARS-CoV-2 compared to SARS-CoV," Cellular & Molecular Immunology, Mar. 4, 2020, pp. 536-538, vol. 17.
Zhou et al., "pH-Sensitive Nanomicelles for High-Efficiency siRNA Delivery in Vitro and in Vivo: An Insight into the Design of Polycations with Robust Cytosolic Release", Nano Letters, 2016, pp. 6916-6923, vol. 16.
Zhu et al., "Decrease of the electrical potentials measured on the surface of the knee produced by cartilage compression during successive loading cycles", Journal of Biomechanics, 2016, pp. 3587-3591, vol. 49.
Zhu et al., "Electrical potentials measured on the surface of the knee reflect the changes of the contact force in the knee joint produced by postural sway", Gait and Posture, 2017, pp. 159-164, vol. 52.
Zhu et al., "Polyelectrolyte Stabilized Drug Nanoparticles via Flash Nanoprecipitation: A Model Study with β-Carotene", Journal of Pharmaceutical Sciences, Oct. 2010, pp. 4295-4306, vol. 99, No. 10.
Zimmer, C. et al., "Coronavirus Vaccine Tracker," Nov. 27, 2020 [online], [retrieved on Mar. 8, 2022]. Retrieved from the Internet URL: https://www.nytimes.com/interactive/2020/science/coronavirus-vaccine-tracker.html, 38 pages.
Zimmerman, et al., RNAi-mediated gene silencing in non-human primates, Nature, May 2006, pp. 111-114, vol. 441.
Ziyi et al., "DNA nanotechnology-facilitated ligand manipulation for targeted therapeutics and diagnostics", Journal of Controlled Release, Dec. 10, 2021, pp. 292-307, vol. 340.
Zukancic et al., "The Importance of Poly (ethylene glycol) and Lipid Structure in targeted Gene Delivery to Lymph Nodes by Lipid nanoparticles", Pharmaceutics, Nov. 9, 2020, pp. 1-16, vol. 12.
Extended European Search Report for EP21881024, 138 pages (Jan. 22, 2025).
Hromatka, O., et al., Untersuchungen über Phenthiazinderivate, 19. Mitt. Neue piperazinsubstituierte Phenthiazine, Monatshefte für Chemie und verwandte Teile anderer Wissenschaften, 93: 807-813 (1962) Non-English—English Abstract Only.
Peeters, A., et al., Carbon dioxide as a reversible amine-protecting agent in selective Michael additions and acylations, Green chemistry 15(6): 1550-1557 (2013).

* cited by examiner

Figure 1: A comprehensive approach to improve mRNA LNP potency 4 hour in-vivo imaging. IVIS I.M. injections (left group 1, right group 2). From left to right (MC3 / DL-ADDE-C2C2-4Me-PipZ / BODD-ADDE-C2C4-4Me-PipZ)

24 hour in-vivo imaging

I.M. injections (left group 1, right group 2). From left to right (MC3 / DL-ADDE-C2C2-4Me-PipZ / BODD-ADDE-C2C4-4Me-PipZ)

24 hr

3. Group 3 = 5 ug dose (4, 24, 48, 72, 120 hours) longevity. Left to Right = MC3-SR/MC3-HO/BODD-HO 4 hr 1 BODDC2C2PipZ 4(1,5)
2 BODDC2C4PipZ 4(1,5)
3 BODDC2C2DMA 4(1,5)
4 BODDC2C4Pyr 4(1,5)
5 BODDC2C2 1Me 2Pyr 4(1,5)

6 BODDC2C0 1Me PipD 4(1,5)
7 SL-C2PipZ 4(1,5)
8 BODDC2C2Pyr 4(1,5)
9 BHDC2C2PipZ 4(1,5)
10 BHDC2C2 1Me 2Pyr 4(1,5)

11 BHDC2C4Pyr 4(1,5)
12 BODDC4C4BA 4(1,5)
13 BODDC2C1 1Me PipD 4(1,5)
14 BODDC2C1 1Me 3PipD 4(1,5)
15 DHC2C4PipZ 4(1,5)

C24

C24-WSA

MC3

MC3-WSA

| Ionizable Lipid | pKa, ACD Classic | pKa, NMR | pKa, TNS | pKa, ZP | pI, ZP | ΔTNS 6-7.4 (RFU) | ΔZP 4.5-7.4 (mV) |
|---|---|---|---|---|---|---|---|
| C24 | 7.8, 4.1, 7.7 | 8.1, 3.7, 7.5 | 6.77 | 5.21 | 6.12 | 4517 | 25.1 |
| MC3 | 9.4 | 9.5 | 6.55 | 5.33 | 5.57 | 2559 | 14.3 |

FIG. 84F

SEQUENCE LISTING

```
<160> NUMBER OF SEQ ID NOS: 4

<210> SEQ ID NO 1
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

gcggctcggc catgtcccag tacagtccgg aggctgcggc tgcagaagta ccgcctgcgg     60

agtaactgca aag                                                        73


<210> SEQ ID NO 2
<211> LENGTH: 15
<212> TYPE: PRT
<213> ORGANISM: Clostridium tetani

<400> SEQUENCE: 2

Gln Tyr Ile Lys Ala Asn Ser Lys Phe Ile Gly Ile Thr Glu Leu
1               5                   10                  15


<210> SEQ ID NO 3
<211> LENGTH: 16
<212> TYPE: PRT
<213> ORGANISM: Clostridium tetani

<400> SEQUENCE: 3

Ala Gln Tyr Ile Lys Ala Asn Ser Lys Phe Ile Gly Ile Thr Glu Leu
1               5                   10                  15


<210> SEQ ID NO 4
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 4

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa a                        101
```

IONIZABLE LIPIDS AND METHODS OF MANUFACTURE AND USE THEREOF

I. CROSS-REFERENCE TO RELATED APPLICATIONS

This application claims the benefit of U.S. provisional application No. 63/091,616, which was filed on Oct. 14, 2020; U.S. provisional application No. 63/179,885, which was filed on Apr. 26, 2021; U.S. provisional application No. 63/091,603, which was filed on Oct. 14, 2020; and U.S. provisional application No. 63/179,872, which was filed on Apr. 26, 2021, each of which is incorporate herein by reference in its entirety.

SEQUENCE LISTING

The instant application contains a Sequence Listing which has been submitted electronically in ASCII format and is hereby incorporated by reference in its entirety. Said ASCII copy, created on Dec. 21, 2021, is named AEXR-001-02US-343269-2014_SL.txt and is 1,460 bytes in size.

II. FIELD OF THE INVENTION

The invention encompasses novel ionizable lipids compounds and their use in lipid nanoparticles delivery systems that are useful in the delivery of nucleic acids to a mammalian subject that can be included for use, for example, as cancer vaccines, delivering gene editing therapies, in the delivery of nucleic acid (e.g., mRNA) encoding antibodies, vaccines for infectious disease, and protein replacement therapeutics. Additionally, the invention encompasses compositions and therapeutics comprising ionizable lipids in the lipid nanoparticles and the use of the composition and therapeutics for the preparation of a pharmaceutical composition, especially a vaccine (e.g., for use in the prophylaxis or treatment of infectious diseases, tumor or cancer diseases, rare diseases, allergies, or autoimmune diseases). The invention also encompasses methods of treatment or prophylaxis of the aforementioned diseases.

II. BACKGROUND OF THE INVENTION

Gene therapy and genetic vaccination belong to the most promising and quickly developing methods of modern medicine. They may provide highly specific and individual options for therapy of a large variety of diseases. As a fundamental biological concept, the cellular machinery exploits mRNA as a transient carrier of information for synthesizing genetically encoded proteins. Hence, from a theoretical standpoint, mRNA should be capable of replacing DNA or recombinant proteins for therapeutic purposes. For example, RNA-interference (RNAi) agents such as small-interfering RNA (siRNA) and micro-RNA (miRNA) have strong potential as therapeutic agents for the treatment of a broad range of diseases such as malignancies, infections, autoimmune diseases and neurological diseases that are associated with undesirable gene expression.

For systemic administration of these poorly permeable and easily degradable macromolecules, a safe and efficient delivery platform is highly desirable. Because of high biocompatibility, biodegradability and a solid track record for clinical use, nanocarriers made of lipids and/or phospholipids have been commonly employed to facilitate RNA delivery (e.g. liposomes, lipid nanoparticles, and lipid nanoemulsions).

Genetic vaccination evokes a desired immune response to selected antigens, such as characteristic components of bacterial surfaces, viral particles, tumor antigens or the like. Genetic vaccines (i.e., vaccines for genetic vaccination) typically composed of genetically engineered nucleic acid molecules which allow expression of peptide or protein (i.e., antigen) fragments characteristic for a pathogen or a tumor antigen in vivo. Genetic vaccines are expressed upon administration to a patient after uptake by target cells. Expression of the administered nucleic acids results in production of the encoded proteins. In the event these proteins are recognized as foreign by the patient's immune system, an immune response is triggered.

DNA, as well as RNA, may be used as nucleic acid molecules for administration in the context of genetic vaccination. DNA is known to be relatively stable and easy to handle. However, the use of DNA bears the risk of undesired insertion of the administered DNA-fragments into the patient's genome potentially resulting in mutagenic events such as in loss of function of the impaired genes. As a further risk, the undesired generation of anti-DNA antibodies may emerge. Another drawback is the limited expression level of the encoded peptide or protein that is achievable upon DNA administration because the DNA must enter the nucleus in order to be transcribed before the resulting mRNA can be translated. Among other reasons, the expression level of the administered DNA will be dependent on the presence of specific transcription factors which regulate DNA transcription. In the absence of such factors, DNA transcription will not yield satisfying amounts of RNA. As a result, the level of translated peptide or protein obtained is limited.

By using RNA instead of DNA for gene therapy and genetic vaccination, the risk of undesired genomic integration and generation of anti-DNA antibodies is minimized or avoided. However, RNA is considered to be a rather unstable molecular species which may readily be degraded by ubiquitous RNAses. There is a need in the art for providing an efficient method for mRNA administration (e.g., for vaccination), which allows eliciting an adaptive immune response, wherein the administration is not severely impaired by early degradation of the antigen or by an inefficient translation of the mRNA due to inefficient release of the mRNA in the cell. Furthermore, there is a need to decrease the dose of mRNA vaccines to decrease potential safety concerns and to make the vaccines affordable for the third world.

There are many challenges associated with the delivery of nucleic acids to affect a desired response in a biological system. Nucleic acid based therapeutics, such as vaccines, have enormous potential, but there remains a need for more effective delivery of nucleic acids to appropriate sites within a cell, tissue, or organism in order to realize this potential. However, three problems currently face the use of oligonucleotides in therapeutic contexts. First, free RNAs are susceptible to nuclease digestion in plasma. Second, free RNAs have limited ability to gain access to the intracellular compartment where the relevant translation machinery resides. Third, only a small fraction of internalized oligonucleotide is released into the cytoplasm to become bioactive. Lipid nanoparticles (LNP) formed from the Ionizable Lipids of the Invention (as defined herein) combined with other lipid components, such as neutral lipids, steroids, PEG, PEGylated lipids, and oligonucleotides have been used to block degradation of the RNAs in plasma and facilitate the cellular uptake of the oligonucleotides. They may if correctly designed release therapeutic levels of oligonucleotide into the cytoplasm.

Localized delivery results in the systemic presence of RNAs resulting in unwanted side effects and reduction in efficacy. Vaccines are typically administered via intramuscular (IM) injection, and LNP requirements for delivery to dendritic cells via the IM route are different than intravenous (IV) delivery to hepatocytes. Hepatocyte targeting is due to the LNP associating with ApoE that targets LNP uptake to hepatocyte LDL receptors while ApoE may not have the same role in IM administration. A second targeting mechanism for LNPs is their net charge. Negatively charged LNPs target the spleen upon IV administration while positively charged LNPs target the lungs and near neutral LNPs target the liver. No published study has evaluated the influence of LNP charge in IM administration.

There remains a need for improved ionizable lipids and lipid nanoparticles for the delivery of oligonucleotides.

The Ionizable Lipids of the Invention (as defined herein) included in the lipid nanoparticles provide optimal drug: lipid ratios, protect the nucleic acid from degradation, and clearance in serum, are suitable for systemic or local delivery, and provide intracellular delivery of the nucleic acid. In addition, Ionizable Lipids of the Invention included in the lipid-nucleic acid particles are well-tolerated and provide an adequate therapeutic index, such that patient treatment at an effective dose of the nucleic acid is not associated with unacceptable toxicity and/or risk to the patient. The present invention provides these and related advantages.

III. SUMMARY OF THE INVENTION

The instant invention provides the surprising and unexpected discovery of Ionizable Lipids of the Invention (as defined below) for use in lipid nanoparticles (LNP) that provide an increase in potency of nucleic acid delivery (e.g., mRNA) for use in, for example, vaccine candidates that greatly facilitate the ability to meet three criteria for a successful mRNA vaccine—(1) lasting protection, (2) large volumes manufactured per year, and (3) a worldwide population with access and willingness to be vaccinated. Increased potency afforded by the Ionizable Lipids of the Invention reduces the required dose and adverse reactions while maintaining efficacy and increasing the ability to vaccinate globally by reducing cost and increasing manufacturing capacity. In certain embodiments, increased potency at these same doses increases protection.

The inventors have surprising and unexpectedly discovered a new class of ionizable lipids that can be used in LNPs that increase potency—meaning mRNA expression, immunogenicity and protection (e.g., when used in delivery of a vaccine) through the design of the lipid nanoparticle by two means:

1) improved ionizable lipid design and performance, and
2) production of more efficient lipid nanoparticles through control of LNP assembly.

In certain embodiments, the measure of potency increase is the reduction in dose the LNPs of the invention will achieve to obtain the same level of protection against viral challenge as a standard LNP representing those used in previous clinical trials.

In certain embodiments, the present invention encompasses a novel approach to the design of the ionizable lipid focusing on three structural features that are known to control delivery efficiency: (1) ionization in the endosomal pH range, (2) net charge at physiological pH, and (3) lipid tail conformation related to branching and saturation/unsaturation.

The invention also encompasses in silico analysis of candidates for synthesis, which is capable of eliminating undesirable candidates based on inappropriate predicted properties. The invention encompasses novel synthetic methods to make ionizable lipids. In other embodiments, the novel methods adhere to the design strategy by characterizing molecular ionization of the Ionizable Lipids of the Invention using NMR of water-soluble analogs and by measuring zeta potentials of LNPs over a pH range (3-10). In certain embodiments, the approach to candidate evaluation and elucidating structure-function relationships (SFRs) is comprehensive, including, but not limited to, in vitro and in vivo evaluation of translation and toxicity, in vitro assessment of cell uptake, endosomal release and innate immune sensor activation, in vivo characterization of distribution and cell trafficking, immunogenicity, and the use of current and evolving rodent and non-rodent animal models in viral challenge studies.

In certain embodiments, increased in vivo expression (e.g., >5×) of mRNA LNPs due to increased mixing concentration of the lipids and mRNA is achieved during assembly. In certain embodiments, key technical difficulties and high costs associated with systematically examining these parameters is overcome. By generalizing this finding to an array of ionizable lipids, the instant invention could transform the industrial production of more potent LNPs.

In certain embodiments, the invention encompasses the design and synthesis of potent ionizable lipids for intramuscular delivery and focused administration to a desired cell, tissue, or organ of mRNA vaccines In another embodiment, the invention encompasses ionizable lipids that increase potency and reduce dose (e.g., by at least 2×, 3×, 4×, 5×, 10×, 20×, 50×, or 100×) compared to previous delivery methods, while maintaining similar expression, immunogenicity and protection against viral challenge.

In another embodiment, the invention encompasses optimization of ionization properties of multivalent headgroups of the Ionizable Lipids of the Invention that produce both a positively charged LNP at neutral pH to limit systemic dissemination and increase endosomal ionization that increases vaccine potency, a highly branched and degradable lipid tails that can further increase potency through endosomal release, and the charge and structure of the ionizable lipid can influence LNP adjuvanticity.

In certain embodiments, the LNPs of the invention increase potency to limit adverse events, reduce manufacturing cost, and increase worldwide capacity to vaccinate.

In other embodiments, the invention encompasses the design and synthesis of ionizable lipids and LNPs for assessments of physicochemical and biological properties to identify more potent systems and underlying structure-function relationship (SFRs).

In another embodiment, the invention encompasses a method of significantly accelerating design of Ionizable Lipids of the Invention by the prediction of the pKa of ionizable lipids using software including ACDLabs Percepta.

In other embodiments, the predicted aqueous pKas for lipids are all significantly higher than that measured by TNS. In certain embodiments, a drop in pKa (e.g., 1-3 point drop) from an aqueous environment to the LNP environment has not been previously acknowledged in the LNP literature but is known for basic amino acids in lipid membranes. Without being bound by theory, a reasonable explanation can be found due to the higher solvation energy of protons in the lipid phase compared to the aqueous phase and electrostatic repulsion of protons from the cationic LNP, which can combine to reduce pKa by 1-3 points from aqueous to lipid phases. In certain embodiments, this capability is exploited in order to select specific headgroups and carbon spacers by examining pKa tables of potential candidates and selecting only those with appropriate pKa values. The majority of candidates can be accurately eliminated in this manner, generating enormous savings in synthesis and testing time and expense.

In certain embodiments, the invention encompasses optimized Ionizable Lipids of the Invention used in a lipid nanoparticle (LNP) formulation. Exemplary LNPs comprise an Ionizable Lipid of the Invention, a second lipid, a steroid, a polymer conjugated lipid, and a therapeutic agent, or a pharmaceutically acceptable salt thereof, encapsulated within or associated with the LNP.

In certain embodiments, the inventors have unexpectedly discovered that characteristics of the optimized formulations of the Ionizable Lipids of the Invention provide important improvements for LNP properties related to delivery of the therapeutic agent (e.g., increased stability and enhanced delivery).

In certain embodiments, the Ionizable Lipids of the Invention included in the lipid nanoparticles are used to deliver nucleic acids such as small interfering, antisense, micro- and/or messenger RNA.

Accordingly, in one embodiment is provided a LNP comprising:

i) an Ionizable Lipid of the Invention;

ii) a second lipid, for example, a neutral or zwitterionic lipid;

iii) a steroid;

iv) a polymer conjugated lipid; and v) a therapeutic agent (e.g., DNA or RNA), or a pharmaceutically acceptable salt thereof, encapsulated within or associated with the lipid nanoparticle.

Another embodiment provides an LNP comprising:

i) from 0.1 to 75 mol percent of an Ionizable Lipid of the Invention having an effective LNP pKa greater than 5.5;

ii) from 0 to 50 mol percent of a neutral or zwitterionic lipid;

iii) from 0 to 50 mol percent of an anionic lipid;

iv) from 10 to 55 mol percent of a steroid;

v) from 0.1 to 10 mol percent of a polymer conjugated lipid; and vi) a therapeutic agent, or a pharmaceutically acceptable salt thereof, encapsulated within or associated with the lipid nanoparticle, wherein the mol percent is determined based on total mol of lipids present in the lipid nanoparticle.

Another embodiment provides a lipid nanoparticle comprising:

i) an Ionizable Lipid of the Invention having an effective pKa;

ii) a neutral lipid;

iii) a steroid;

iv) a polymer conjugated lipid; and v) a therapeutic agent, or a pharmaceutically acceptable salt or prodrug thereof, encapsulated within or associated with the lipid nanoparticle.

In other embodiments, the invention encompasses pharmaceutical compositions comprising the Ionizable Lipids of the Invention for use in lipid nanoparticles and methods for use of the same for treatment of various diseases or conditions, such as those caused by infectious entities, cancer, and/or insufficiency of a protein, are also provided.

In other embodiments, the present invention provides a method for the targeted administration (e.g., to a particular tissue or organ) of a therapeutic agent to a patient in need thereof, the method comprising administering the Ionizable Lipids of the Invention or pharmaceutical composition comprising the same, to the subject.

In certain specific embodiments, the inventions encompass a compound of the formula V:

Formula V

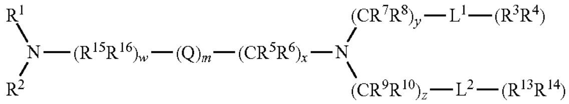

wherein each $R^1$ and each $R^2$ is independently selected from the group consisting of H, an optionally substituted $C_1$-$C_{22}$ alkyl, optionally substituted $C_2$-$C_{22}$ alkenyl, optionally substituted $C_2$-$C_{22}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C^6$ heteroaryl, optionally substituted $C_4$-$C_8$ aryloxy, optionally substituted $C_7$-$C_{10}$ arylalkyl; optionally substituted $C_5$-$C_{10}$ heteroarylalkyl group, optionally substituted amine; or $R^1$ and $R^2$ can together form a 3-7 membered heterocycloalkyl or heteroaryl ring, wherein each $R^3$, $R^4$, $R^{13}$ and $R^{14}$ is independently selected from the group consisting of an optionally substituted $C_1$-$C_{22}$ alkyl, optionally substituted $C_2$-$C_{22}$ alkenyl, optionally substituted $C_2$-$C_{22}$ alkynyl;

wherein each $R^5$, $R^6$, $R^7$, $R^8$, $R^9$, $R^{10}$, $R^{15}$, and $R^{16}$ is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl;

wherein each of w, x, y, and z is independently an integer from 0-10;

wherein each Q is independently an atom selected from O, NH, $NR^1$, and S;

wherein each of m is an integer from 0 to 8, preferably 0, 1, or 2; and wherein each of $L^1$ and $L^2$ is independently selected from the group consisting of —C(═O)—; OC(═O)—; —OC(═O)O—; —C(═O)O—; —C(═O)O($CR^5R^6R^7$); —NH—C(═O)—; —C(═O)NH—; —SO—; —$SO_2$—; —$SO_3$—; —$NSO_2$—; —$SO_2$N—; —NH(($C_1$-$C_8$)alkyl); —N(($C_1$-$C_8$)alkyl)$_2$; —NH(($C_6$)aryl); —N(($C_6$)aryl)$_2$; —NHC(═O)NH—; —NHC(═O)O—; —OC(═O)NH—; —NHC(═O)$NR^1$—; —NHC(═O)O—; —OC(═O)$NR^1$—; —C(═O)$R^1$—; —CO(($C_1$-$C_8$)alkyl); —CO(($C_6$)aryl); —$CO_2$(($C_1$-$C_8$)alkyl); —$CO_2$(($C_6$)aryl); —$SO_2$(($C_1$-$C_8$)alkyl); and —$SO_2$(($C_6$)aryl).

A compound of Formula III:

Formula III

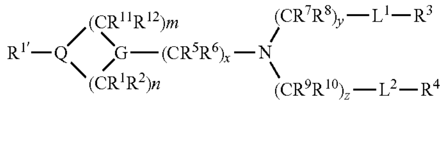

wherein each $R^{1'}$, $R^1$, $R^2$, $R^{11}$, and $R^{12}$ is independently selected from the group consisting of H, an optionally substituted $C_1$-$C_{22}$ alkyl, optionally substituted $C_2$-$C_{22}$ alkenyl, optionally substituted $C_2$-$C_{22}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C_6$ heteroaryl, optionally substituted $C_4$-$C_8$ aryloxy, optionally substituted $C_7$-$C_{10}$ arylalkyl; optionally substituted $C_5$-$C_{10}$ heteroarylalkyl group, optionally substituted amine; or $R^1$ and $R^2$ can together form cycloalkyl or heterocycloalkyl ring, wherein if Q is S or O the $R^1$ attached to the S or O is an electron pair;

wherein each $R^3$ and $R^4$ is independently selected from the group consisting of an optionally substituted $C_1$-$C_{22}$ alkyl, optionally substituted $C_2$-$C_{22}$ alkenyl, optionally substituted $C_2$-$C_{22}$ alkynyl;

wherein each $R^5$, $R^6$, $R^7$, $R^8$, $R^9$, and $R^{10}$ is independently selected from the group consisting of H, OH, halo, phenyl, benzyl, optionally substituted $C_1$-C22 alkyl, optionally substituted $C_2$-$C_{22}$alkenyl, optionally substituted $C_2$-$C_{22}$ alkynyl, wherein each of x, y, and z is independently an integer from 0-10;

wherein G and Q are each independently an atom selected from CH, 0, N, and S;

wherein each of m and n is an integer from 0-8; and wherein each of $L^1$ and $L^2$ is independently selected from the group consisting of —C(═O)—; OC(═O)—; —OC(═O)O—; —C(═O)O—; —C(═O)O($CR^1R^2R^3$); —NH—C(═O)—; —C(═O)NH—; —SO—; —$SO_2$—; —$SO_3$—; —$NSO_2$—; —$SO_2$N—; —NH(($C_1$-$C_8$)alkyl); —N(($C_1$-$C_8$)alkyl)$_2$; —NH(($C_6$)aryl); —N(($C_6$)aryl)$_2$; —NHC(═O)NH—; —NHC(═O)O—; —OC(═O)NH—; —NHC(═O)$NR^1$—; —NHC(═O)O—; —OC(═O)$NR^1$—; —C(═O)$R^1$—; —CO(($C_1$-$C_8$)alkyl); —CO(($C_6$)aryl); —$CO_2$(($C_1$-$C_8$)alkyl); —$CO_2$(($C_6$)aryl); —$SO_2$(($C_1$-$C_8$)alkyl); and —$SO_2$(($C_6$)aryl).

In certain preferred embodiments, the compound has the following structure:

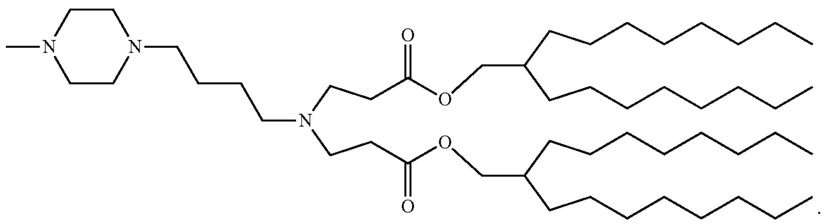 [SMILES: CCCCCCCCC(CCCCCCCC)COC(=O)CCN(CCCCN1CCN(C)CC1)CCC(=O)OCC(CCCCCCCC)CCCCCCCC]

In certain preferred embodiments, the compound has the following structure:

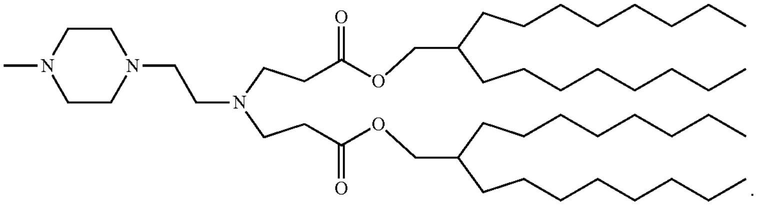 [SMILES: CCCCCCCCC(CCCCCCCC)COC(=O)CCN(CCC(=O)OCC(CCCCCCCC)CCCCCCCC)CCN1CCN(C)CC1]

In certain preferred embodiments, the compound has the following structure:

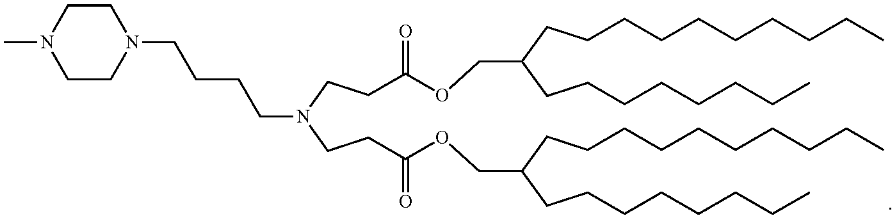 [SMILES: CCCCCCCCCCC(CCCCCCCC)COC(=O)CCN(CCCCN1CCN(C)CC1)CCC(=O)OCC(CCCCCCCC)CCCCCCCCCC]

In certain preferred embodiments, the compound has the following structure:
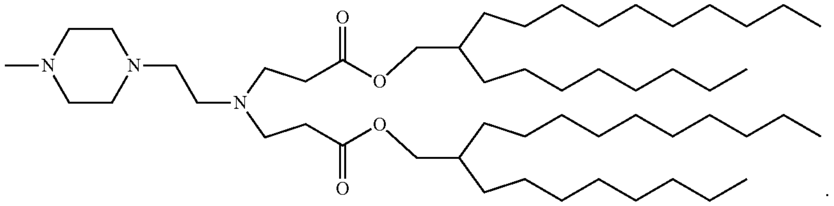 [SMILES: CCCCCCCCCCC(CCCCCCCC)COC(=O)CCN(CCC(=O)OCC(CCCCCCCC)CCCCCCCCCC)CCN1CCN(C)CC1]
In certain preferred embodiments, the compound has the following structure:
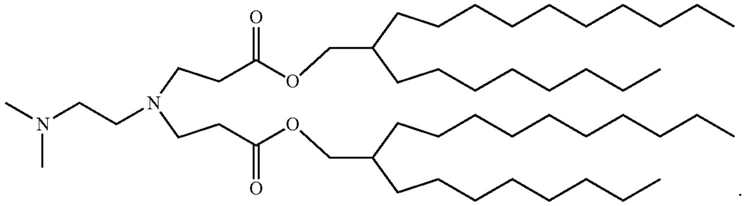 [SMILES: CCCCCCCCCCC(CCCCCCCC)COC(=O)CCN(CCC(=O)OCC(CCCCCCCC)CCCCCCCCCC)CCN(C)C]
In certain preferred embodiments, the compound has the following structure:
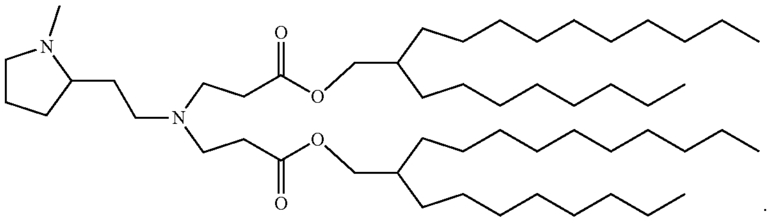 [SMILES: CCCCCCCCCCC(CCCCCCCC)COC(=O)CCN(CCC(=O)OCC(CCCCCCCC)CCCCCCCCCC)CCC1CCCN1C]
In certain preferred embodiments, the compound has the following structure:
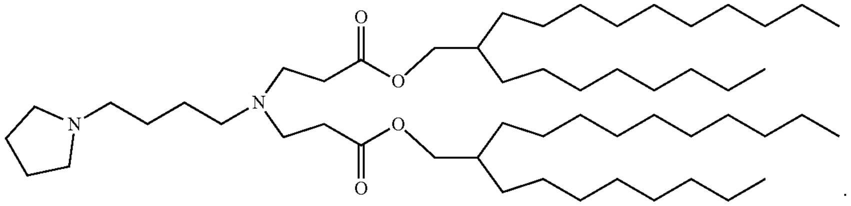 [SMILES: CCCCCCCCCCC(CCCCCCCC)COC(=O)CCN(CCCCN1CCCC1)CCC(=O)OCC(CCCCCCCC)CCCCCCCCCC]

In certain preferred embodiments, the compound has the following structure:

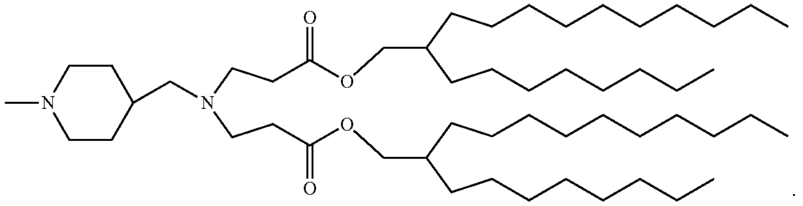 [SMILES: CCCCCCCCCCC(CCCCCCCC)COC(=O)CCN(CCC(=O)OCC(CCCCCCCC)CCCCCCCCCC)CC1CCN(C)CC1]

In certain preferred embodiments, the compound has the following structure:

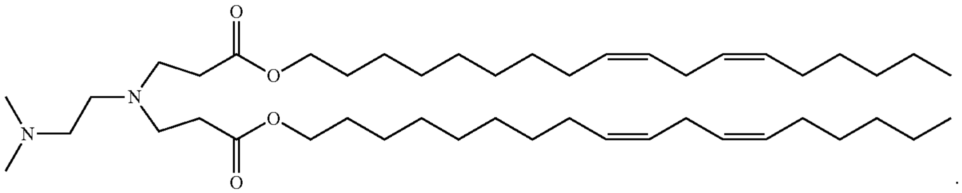 [SMILES: CCCCC/C=C\C/C=C\CCCCCCCCOC(=O)CCN(CCC(=O)OCCCCCCCC/C=C\C/C=C\CCCCC)CCN(C)C]

In certain preferred embodiments, the compound has the following structure:

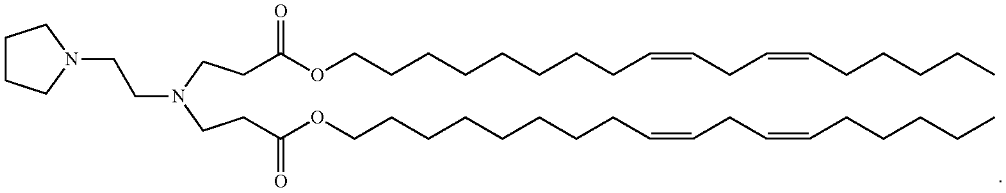 [SMILES: CCCCC/C=C\C/C=C\CCCCCCCCOC(=O)CCN(CCC(=O)OCCCCCCCC/C=C\C/C=C\CCCCC)CCN1CCCC1]

In certain preferred embodiments, the compound has the following structure:

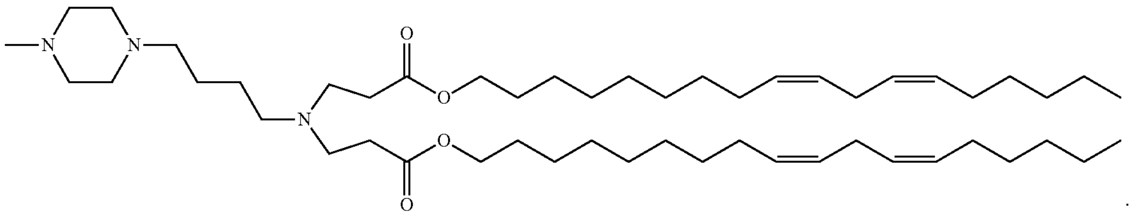 [SMILES: CCCCC/C=C\C/C=C\CCCCCCCCOC(=O)CCN(CCCCN1CCN(C)CC1)CCC(=O)OCCCCCCCC/C=C\C/C=C\CCCCC]

In other embodiments, the invention encompasses a lipid nanoparticle comprising:

i) a compound encompassed by the structures of Formula I, II, III, IV, V, VI, or VII;

ii) a second lipid, for example, a neutral or zwitterionic lipid;

iii) a steroid;

iv) a polymer conjugated lipid; and v) a therapeutic agent, for example, mRNA, or a pharmaceutically acceptable salt thereof, encapsulated within or associated with the lipid nanoparticle.

In other embodiments, the invention encompasses a lipid nanoparticle comprising:

i) a compound encompassed by the structures of Formula I, II, III, IV, V, VI, or VII;

ii) a second lipid, for example, a neutral or zwitterionic lipid;

iii) a steroid;

iv) a polymer conjugated lipid; and v) a therapeutic agent, or a pharmaceutically acceptable salt thereof, encapsulated within or associated with the lipid nanoparticle.

In other embodiments, the invention encompasses a method of targeted delivery a nucleic acid to a subject comprising administering to said subject a lipid nanoparticle comprising:

i) a compound encompassed by the structures of Formula I, II, III, IV, V, VI, or VII;

ii) a second lipid, for example, a neutral or zwitterionic lipid;

iii) a steroid;

iv) a polymer conjugated lipid; and v) a therapeutic agent, for example, mRNA or siRNA, or a pharmaceutically acceptable salt thereof, encapsulated within or associated with the lipid nanoparticle.

In other embodiments, the invention encompasses a method of targeted delivery a nucleic acid to a subject comprising administering to said subject a lipid nanoparticle comprising:

i) a compound encompassed by the structures of Formula I, II, III, IV, V, VI, or VII;

ii) a second lipid, for example, a neutral lipid;

iii) a steroid;

iv) a polymer conjugated lipid; and v) a therapeutic agent, or a pharmaceutically acceptable salt thereof, encapsulated within or associated with the lipid nanoparticle.

In other embodiments, the invention encompasses a lipid nanoparticle comprising:

i) an Ionizable Lipid of the Invention encompassed by the structures of Formula I, II, III, IV, V, VI, or VII;

ii) a second lipid, for example, a neutral or zwitterionic lipid;

iii) a steroid;

iv) a polymer conjugated lipid; and v) a therapeutic agent, or a pharmaceutically acceptable salt thereof, encapsulated within or associated with the lipid nanoparticle.

In other embodiments, the invention encompasses a lipid nanoparticle comprising:

i) a compound of structure:

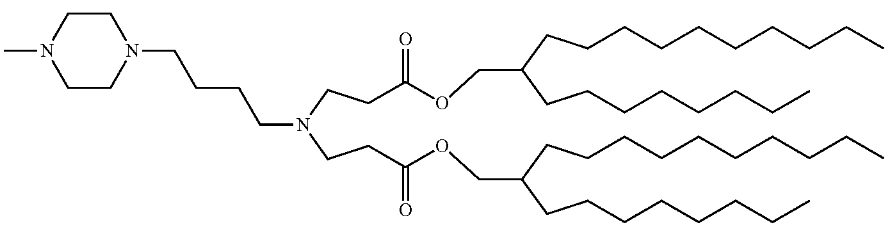 [SMILES: CCCCCCCCCCC(CCCCCCCC)COC(=O)CCN(CCCCN1CCN(C)CC1)CCC(=O)OCC(CCCCCCCC)CCCCCCCCCC]

ii) a second lipid, for example, a neutral or zwitterionic lipid;
iii) a steroid;
iv) a polymer conjugated lipid; and
v) a therapeutic agent, or a pharmaceutically acceptable salt thereof, encapsulated within or associated with the lipid nanoparticle.

In other embodiments, the invention encompasses a method of delivering a nucleic acid to a subject comprising administering to said subject a lipid nanoparticle comprising:
i) an Ionizable Lipid of the Invention encompassed by the structures of Formula I, II, III, IV, V, VI, or VII;
ii) a second lipid, for example, a neutral or zwitterionic lipid;
iii) a steroid;
iv) a polymer conjugated lipid; and
v) a therapeutic agent, or a pharmaceutically acceptable salt thereof, encapsulated within or associated with the lipid nanoparticle.

In other embodiments, the invention encompasses a method of delivering a nucleic acid to a subject comprising administering to said subject a lipid nanoparticle comprising:
i) an Ionizable Lipid of the Invention encompassed by the structures of Formula I, II, III, IV, V, VI, or VII, for example, a compound of formula;

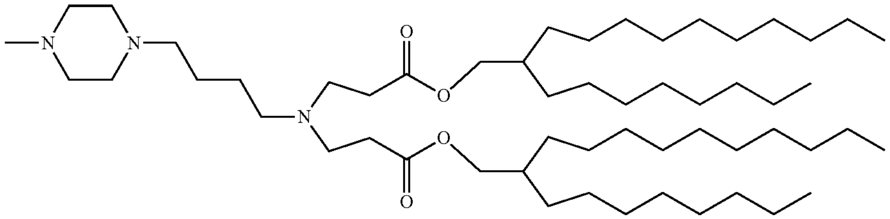 [SMILES: CCCCCCCCCCC(CCCCCCCC)COC(=O)CCN(CCCCN1CCN(C)CC1)CCC(=O)OCC(CCCCCCCC)CCCCCCCCCC]

ii) a second lipid, for example, a neutral or zwitterionic lipid;
iii) a steroid;
iv) a polymer conjugated lipid; and
v) a therapeutic agent, or a pharmaceutically acceptable salt thereof, encapsulated within or associated with the lipid nanoparticle.

In other embodiments, the invention encompasses a method of delivering a therapeutic agent comprising a therapeutic protein, a vaccine, a gene editing RNA to a subject comprising administering to said subject a lipid nanoparticle comprising:
i) an Ionizable Lipid of the Invention encompassed by the structures of Formula I, II, III, IV, V, VI, or VII, for example, a compound of structure:

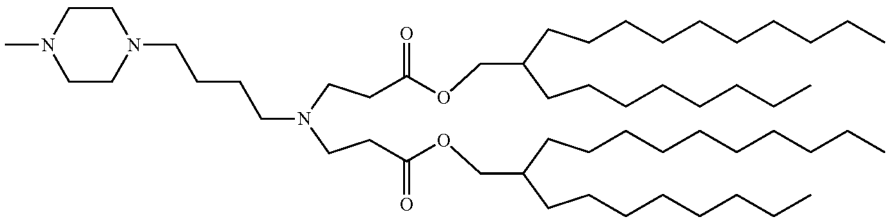 [SMILES: CCCCCCCCCCC(CCCCCCCC)COC(=O)CCN(CCCCN1CCN(C)CC1)CCC(=O)OCC(CCCCCCCC)CCCCCCCCCC]

ii) a second lipid, for example, a neutral or zwitterionic lipid;
iii) a steroid;
iv) a polymer conjugated lipid; and
v) a therapeutic agent, or a pharmaceutically acceptable salt thereof, encapsulated within or associated with the lipid nanoparticle.

IV. BRIEF DESCRIPTION OF THE DRAWINGS

FIG. 1 illustrates an exemplary approach to enhancing and improving mRNA potency and delivery using the Ionizable Lipids of the Invention included in Lipid Nanoparticles.

FIG. 2A illustrates a graph of the aqueous phase pKa of a custom-synthesized water-soluble head group of MC3 titrated from pH 7 to ph 12 and the chemical shift if the dimethylamine protons measured to fit the Henderson-Hasselbach equation (HH) to obtain a pKa of 9.45 similar to the 9.4 predicted by ACDLabs Percepta. FIG. 2B illustrates a graph of the zeta potential of 5 for Azane Diyl Diester (ADDE) LNPs and 2 LNPs made with MC3 and KC2 standards was measured from pH 3 to pH 10. FIG. 2C illustrates LNP pKas measured using traditional TNS method fit to HH.

FIG. 3A illustrates Firefly Luciferase Assay for mRNA Delivery Efficiency. FIG. 3B illustrates in vivo Translation of mRNA Fluc at 4 hours post-injection in BALB/c mice. FIG. 3C illustrates cryoTEM images of empty LNPs.

FIG. 4 illustrates robust binding antibody responses exhibited by exemplary first generation ADDE ionizable lipids of the invention. FIG. 4A illustrates SARS-CoV-2 S-specific IgG by ELISA. FIG. 4B illustrates neutralizing antibodies against VSVDG-RFP SARS-CoV-2 pseudovirus.

Figure 31A:
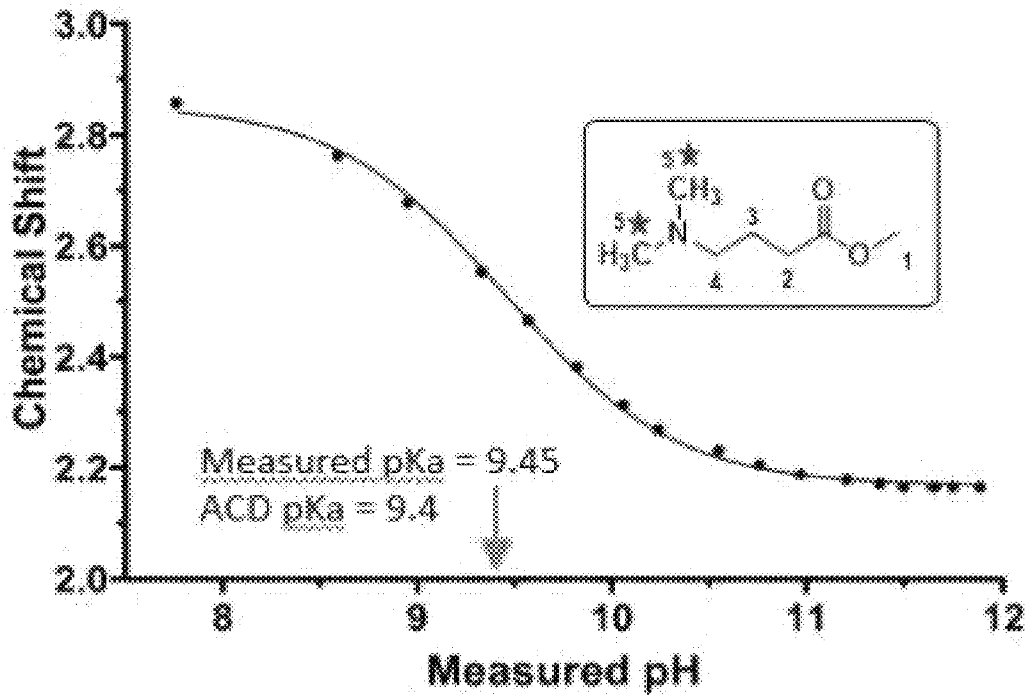
Figure 31B:
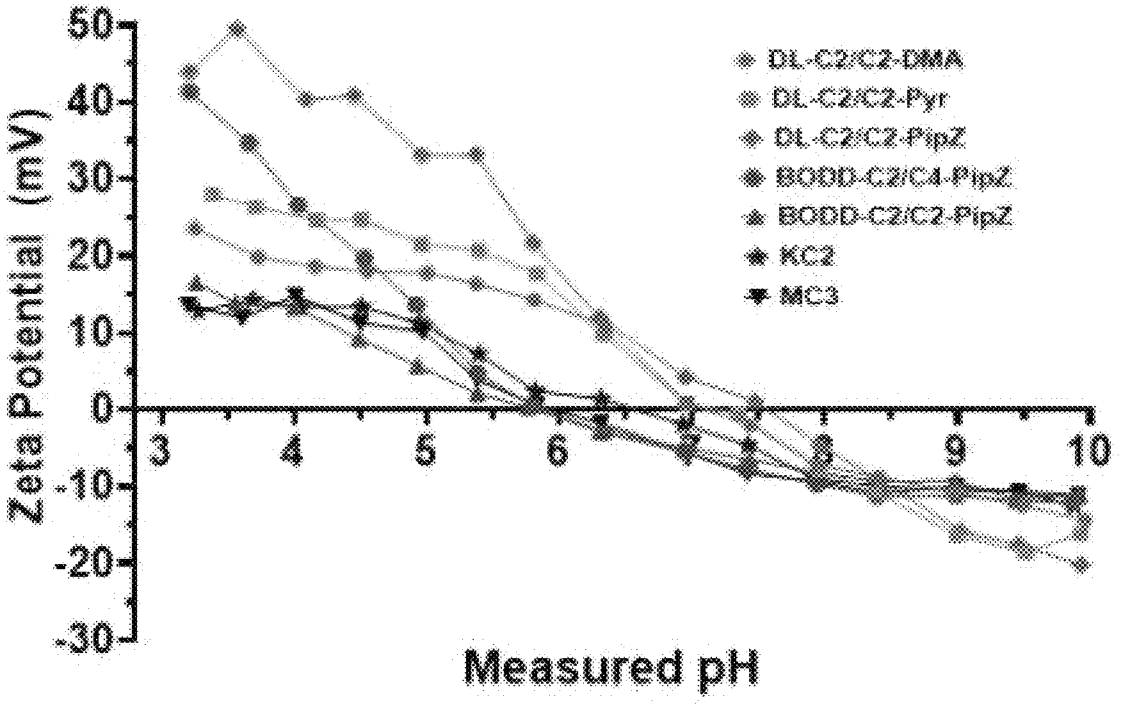
Figure 31C:
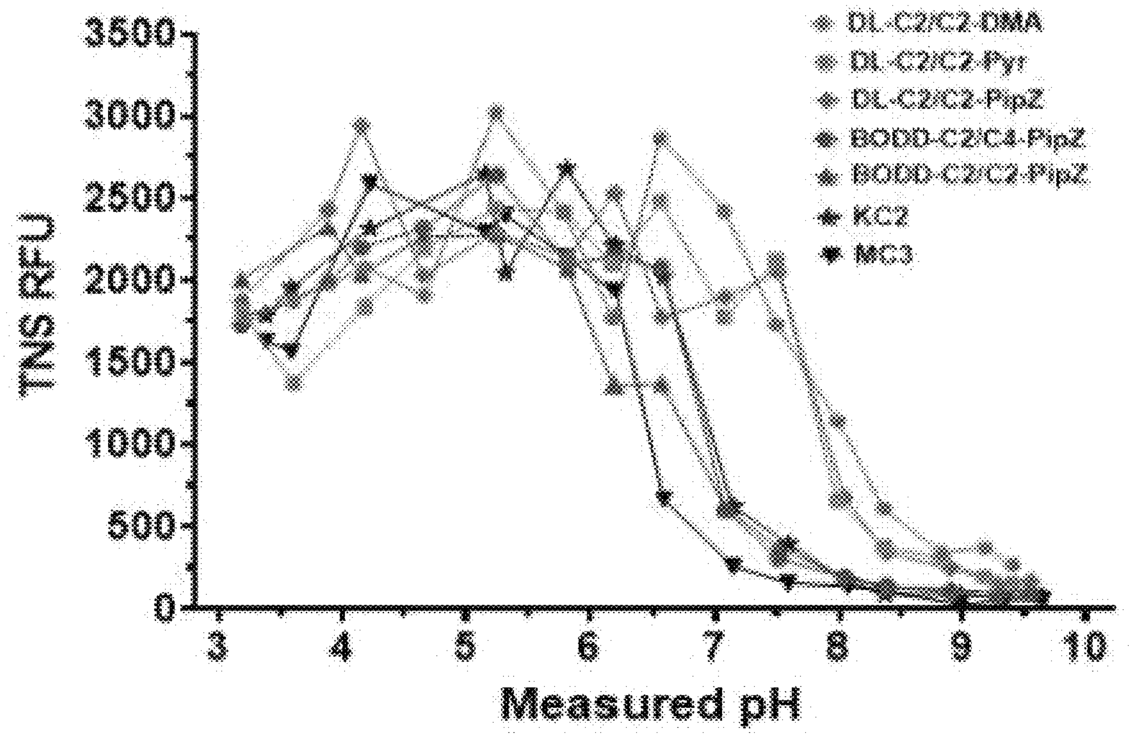

FIG. 31 illustrates graphs of molecular and LNP characterization of ionization and charge. FIG. 31A illustrates the aqueous phase pKa of a custom-synthesized water-soluble headgroup of MC3 titrated from pH 7 to pH 12 and the chemical shift of the DMA protons measured to fit the Henderson-Hasselbach (HH) equation. FIG. 31B illustrates the zeta potential of 5 ADDE LNPs and 2 LNPs made with MC3 and KC2 standards measured from pH 3 to pH 10. FIG. 31C illustrates LNP pKa's measured using traditional fluorescence enhancement of TNS due to binding to LNP fit to the HH equation.

Figure 32A:
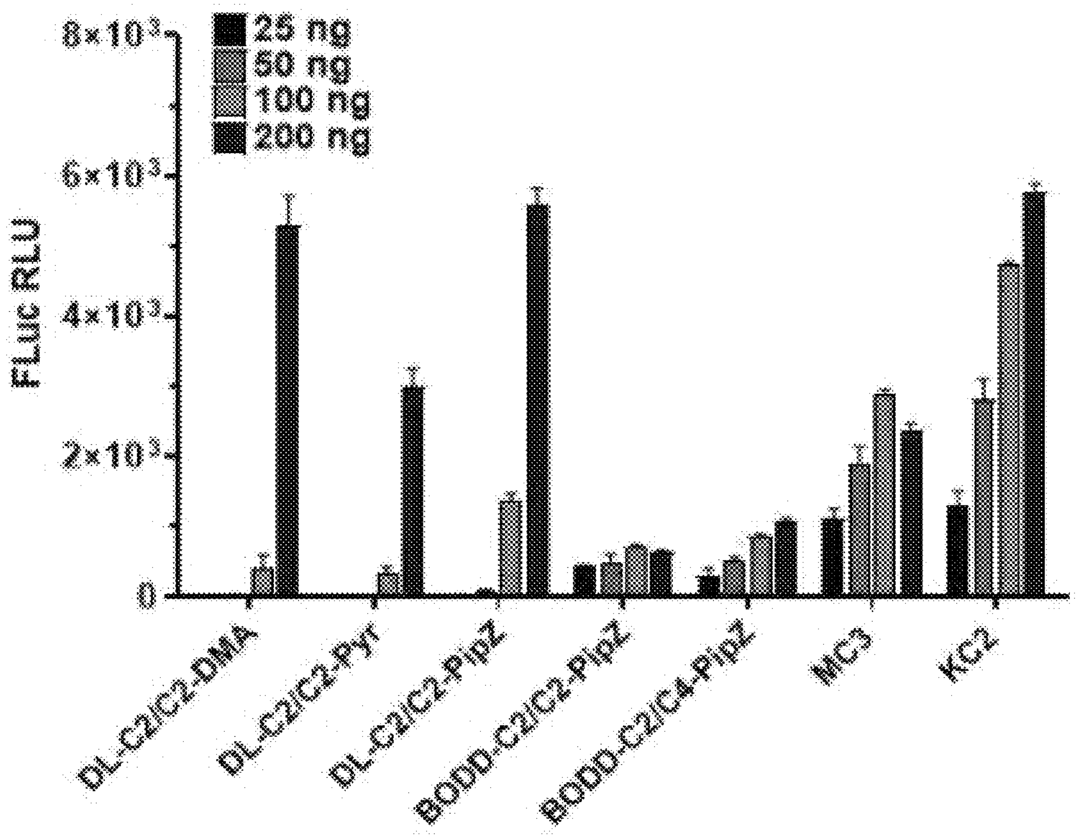
Figure 32B:
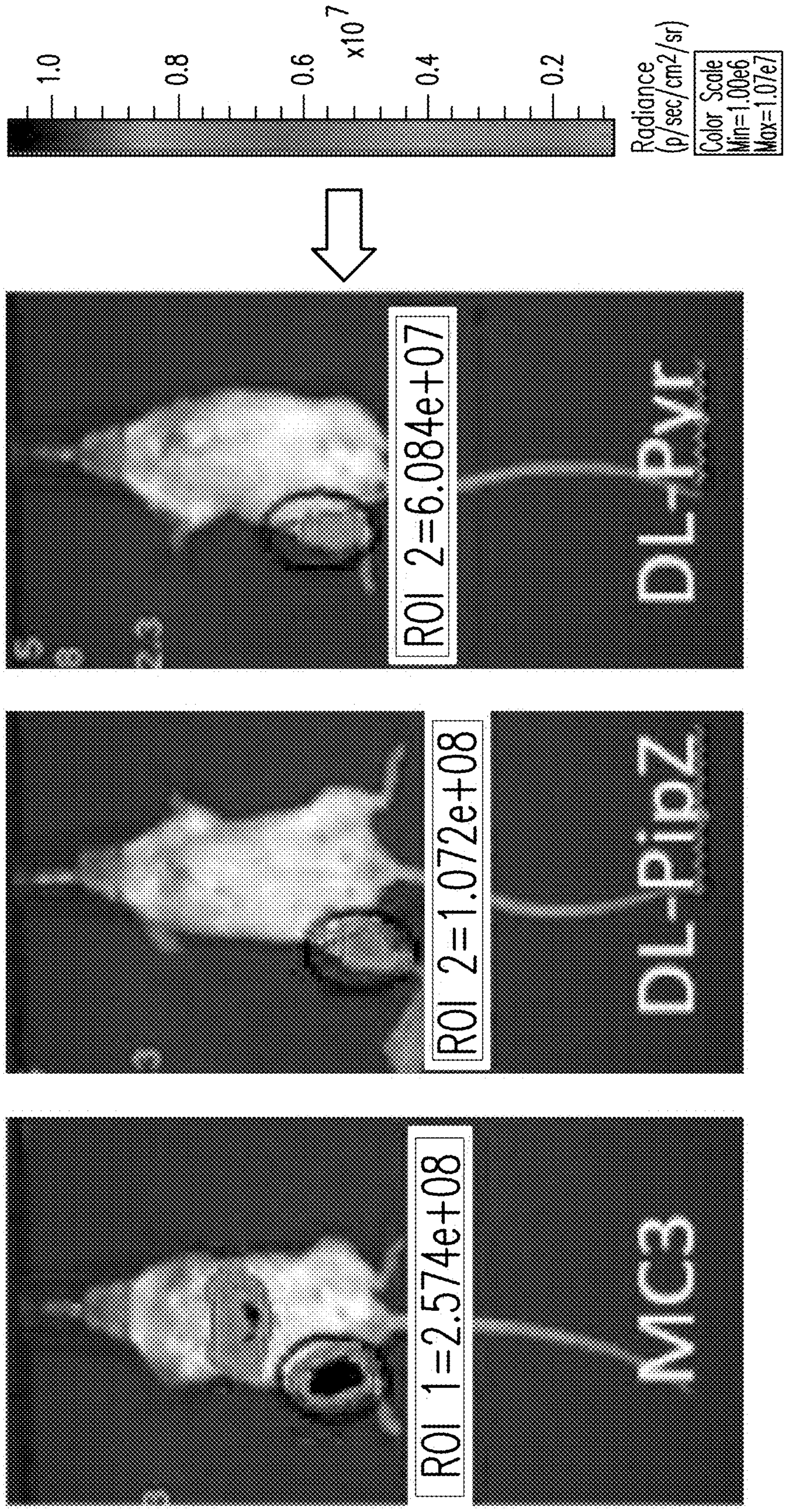
Figure 32C:
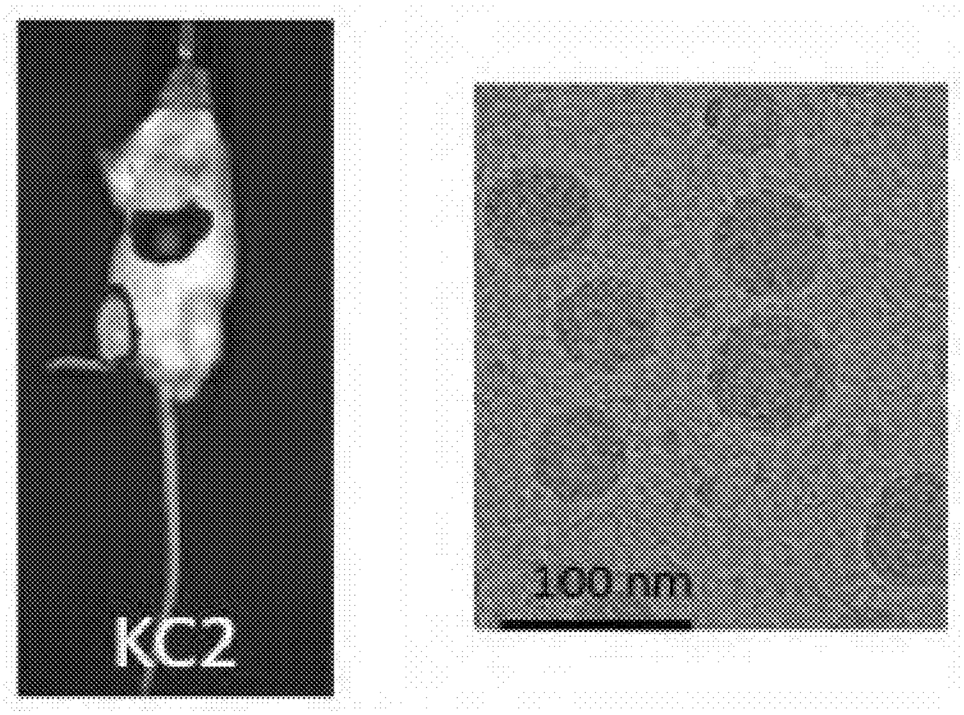

FIG. 32 illustrates luciferase reported expression in vitro and in vivo. FIG. 32A illustrates Fluc mRNA delivered in 5 ADDE LNPs and MC3 and KC2 LNPs to HEK 293 cells in serum containing media at doses from 25-200 ng per well containing 12 k cells. FIG. 32B illustrates 2.5 μg of Fluc mRNA delivered by IM injections in BALB/c mice (MC3 and KC2 containing LNPs display off target systemic expression in liver whiled DL-ADDE LNPs target expression to muscle and draining lymph nodes (see ex vivo). FIG. 32C illustrates KC2 containing LNPs imaged using CryoTEM showing spherical LNPs with diameters corresponding to that measured by DLS number size of 65 nm.

Figure 33A:
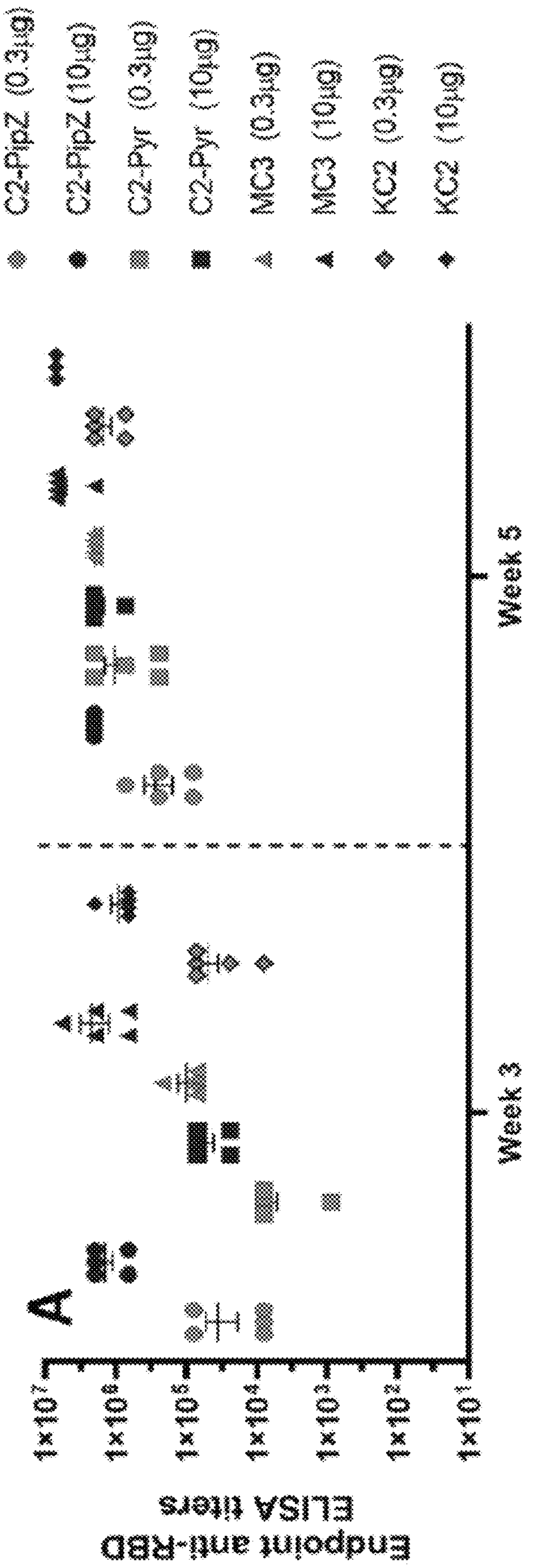
Figure 33B:
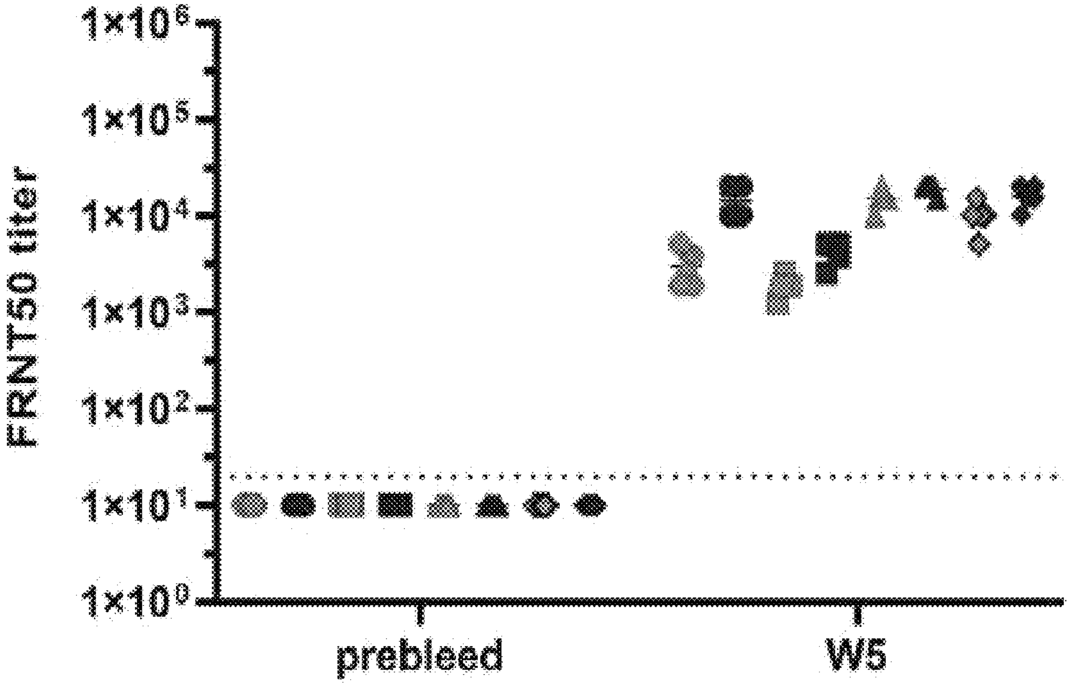

FIG. 33A illustrates ADDE ionizable lipids eliciting robust binding antibody responses in BALB/c mice (n=5/group) immunized at weeks 0 and 3 with 0.3 mg (green) and 10 mg (blue) of S-2P mRNA-encoded immunogen in 4 different LNPs and assessed for SARS-CoV-2 S-specific IgG by ELISA. FIG. 33B illustrates neutralizing antibodies against VSVΔG-RFP SARS-CoV-2 pseudovirus.

Figure 34:
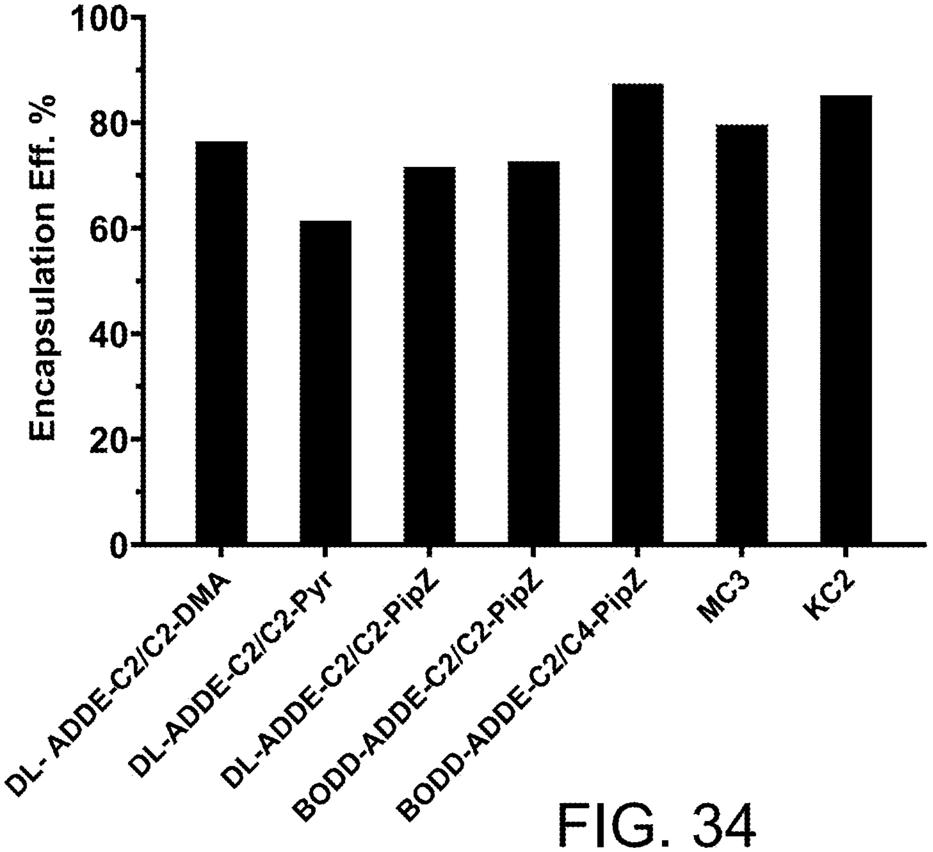

FIG. 34 illustrates a graph of Ribogreen Assay for mRNA Encapsulation Efficiency as exemplified in Example 8A.

Figure 35:
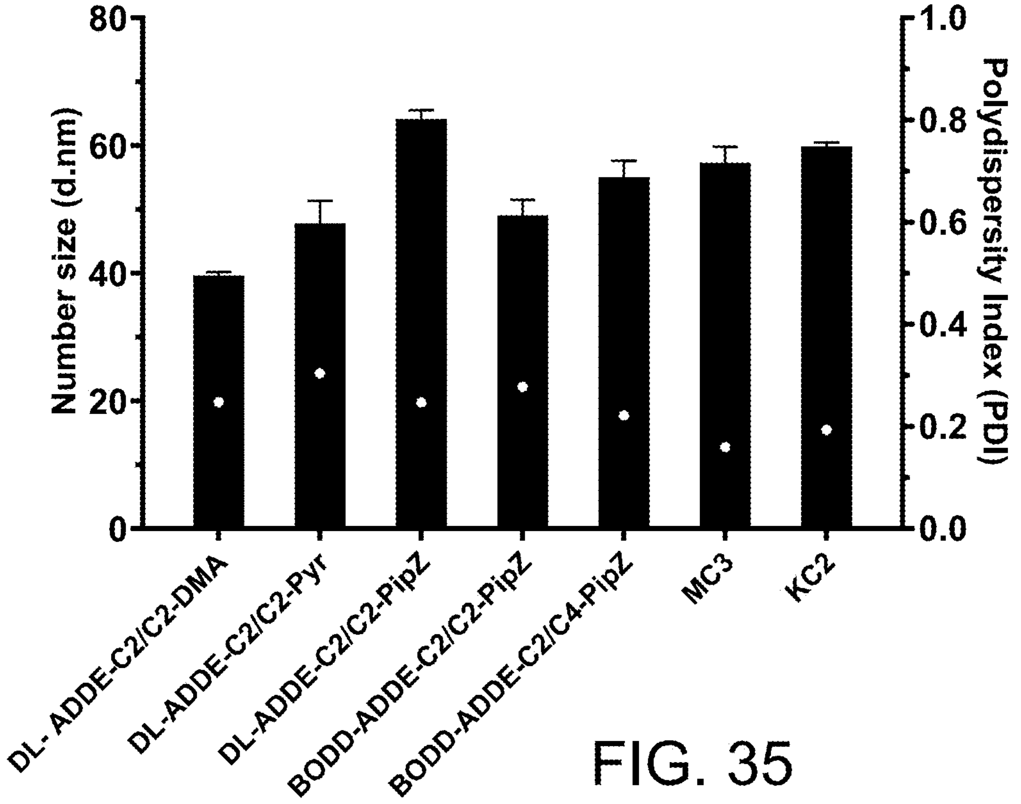

FIG. 35 illustrates a graph of Dynamic Light Scattering for LNP Size (white dots are PDI right y axis) as exemplified in Example 8B.

Figure 36:
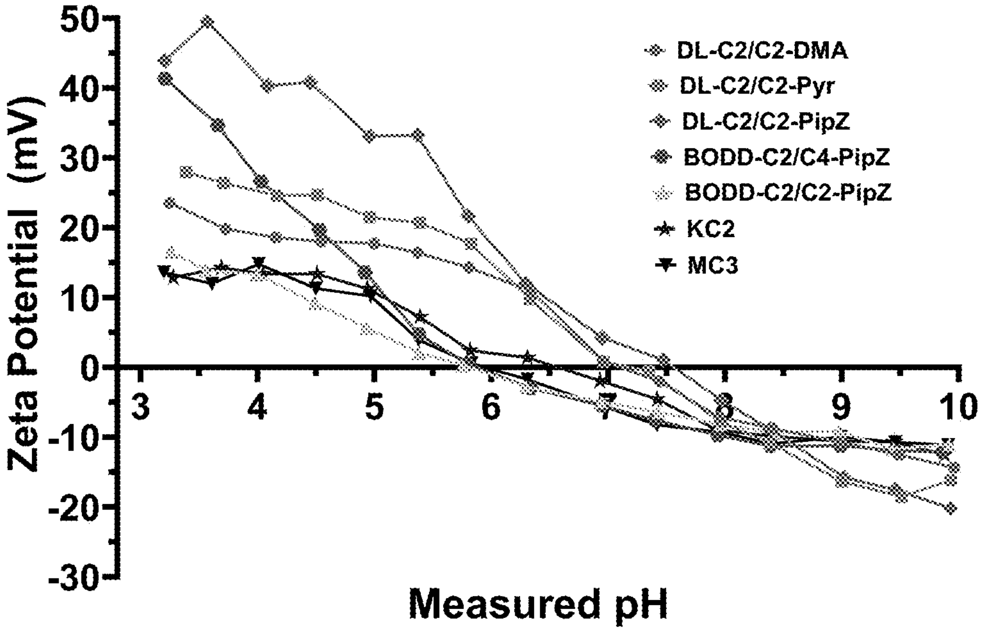

FIG. 36 illustrates a graph of Zeta Potential for LNP charge, pKa and Pi as exemplified in Example 8C.

Figure 37:
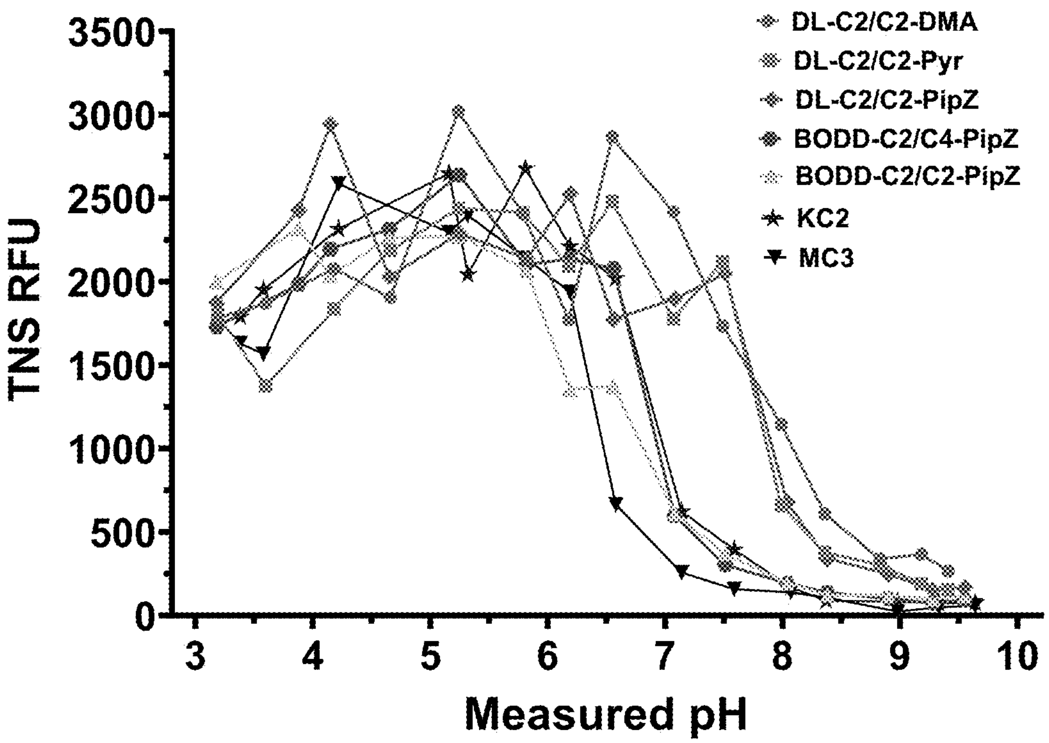

FIG. 37 illustrates a graph of TNS Assay for LNP pKa as exemplified in Example 8D.

Figure 38:
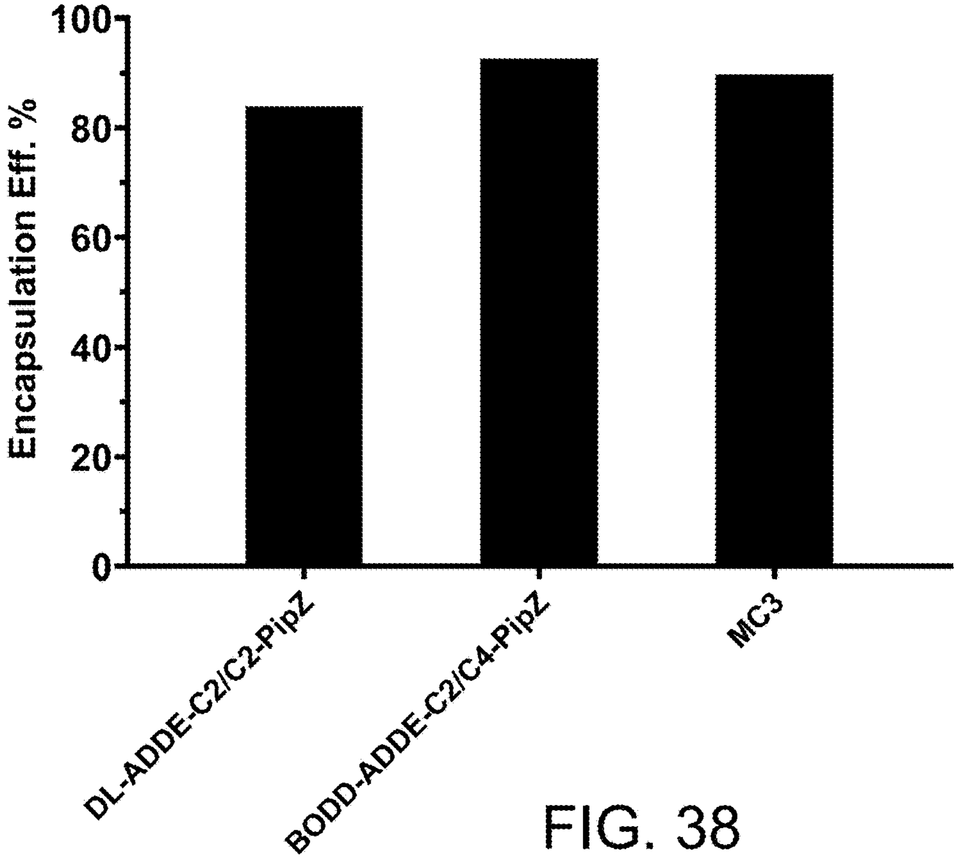

FIG. 38 illustrates a graph of Ribogreen Assay for mRNA Encapsulation Efficiency as exemplified in Example 9A.

Figure 39:
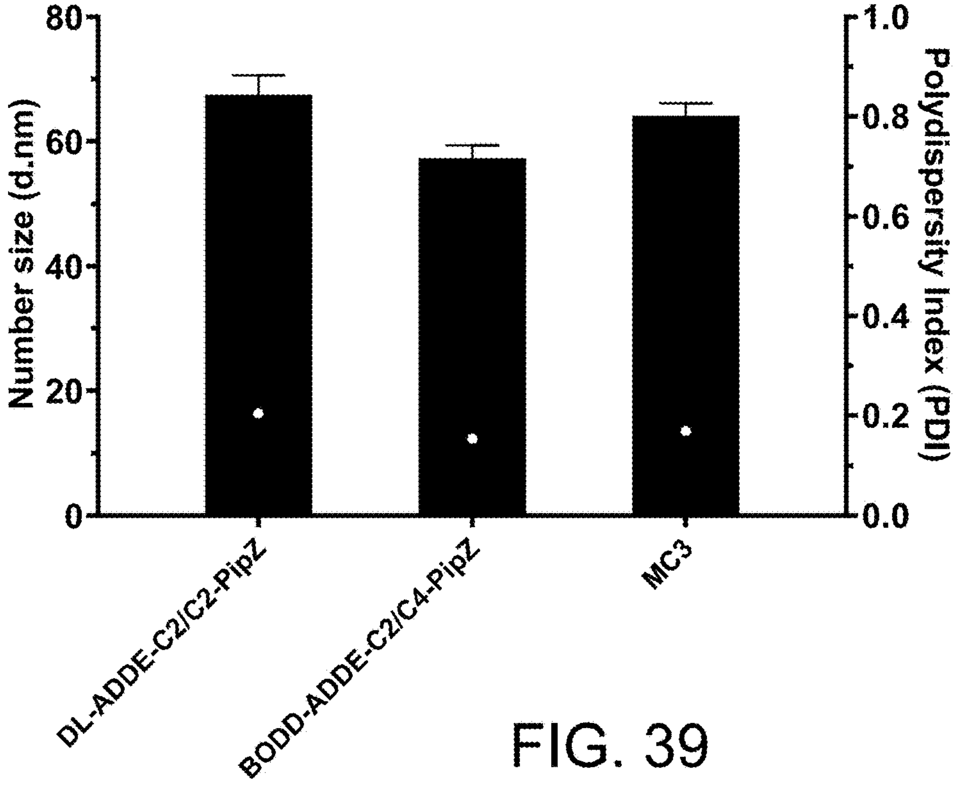
Figure 40A:
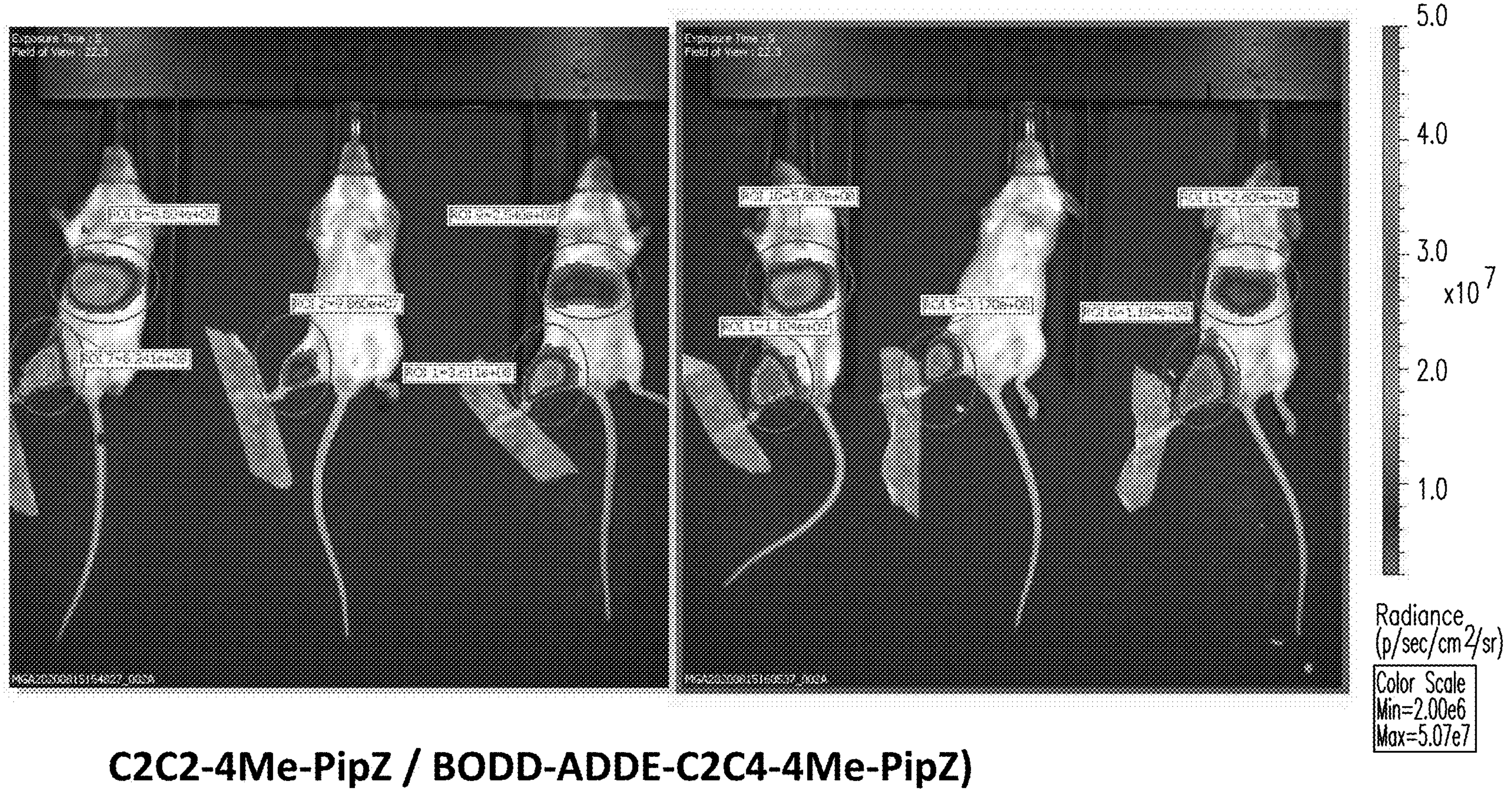
Figure 40B:
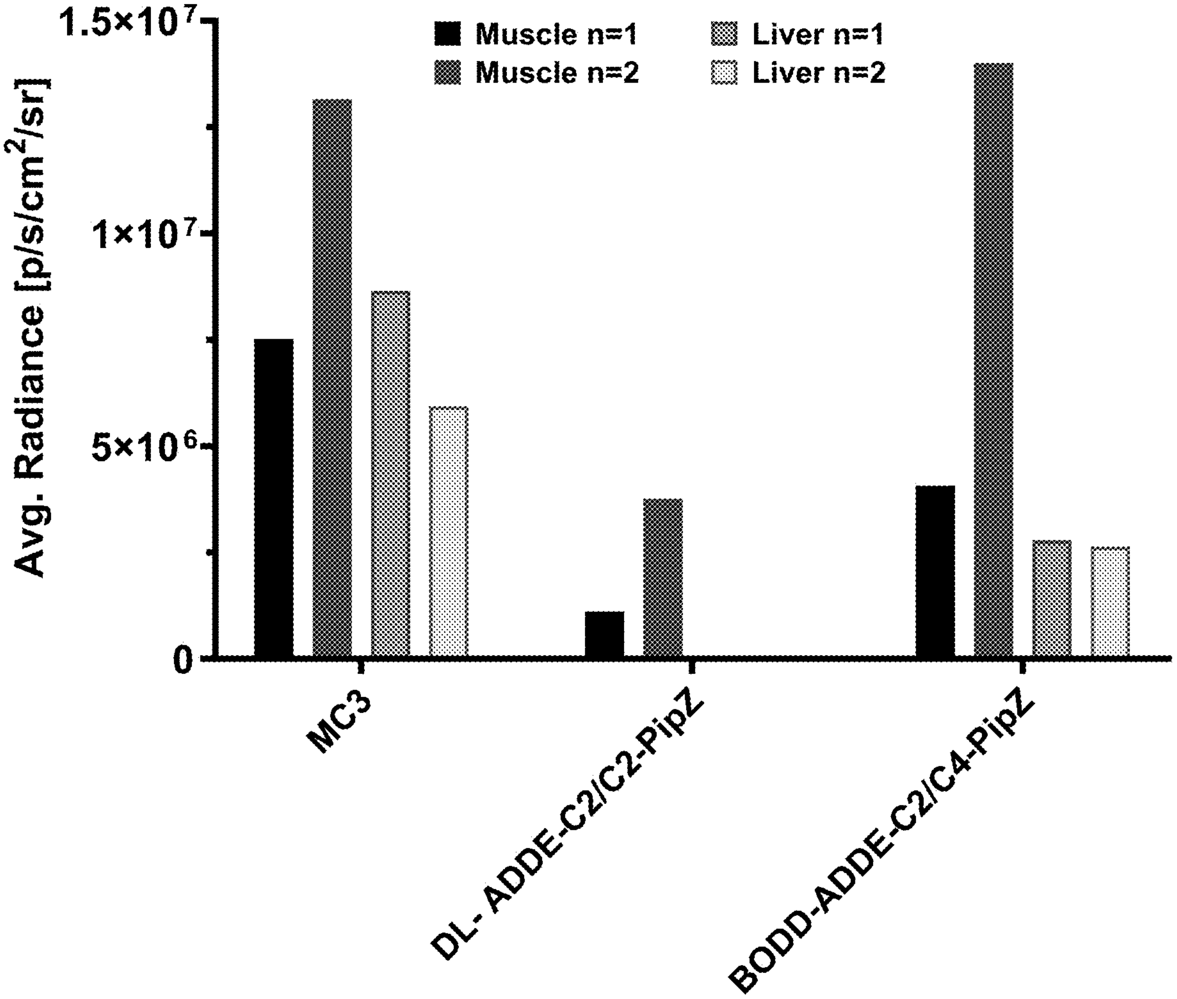
Figure 40C:
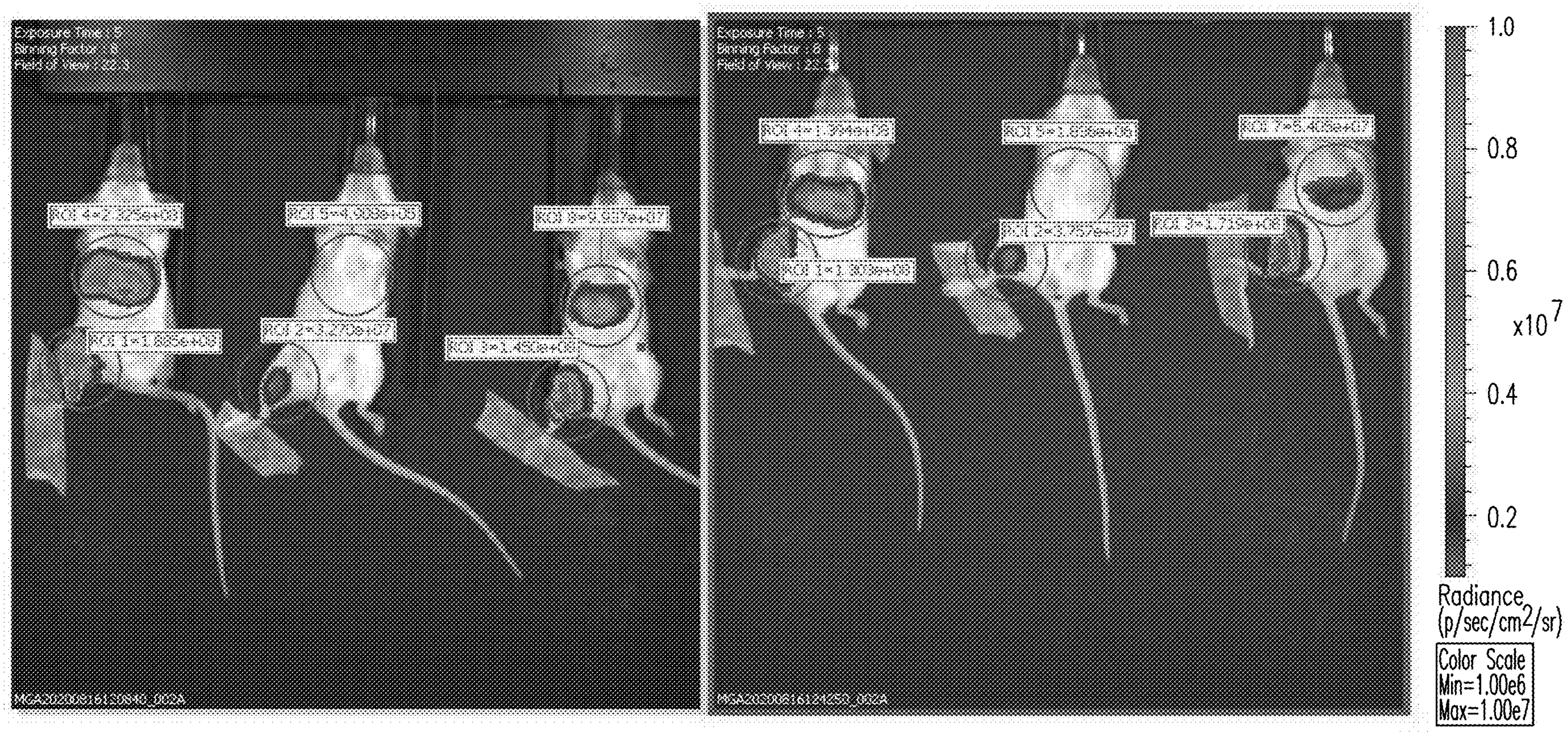
Figure 40D:
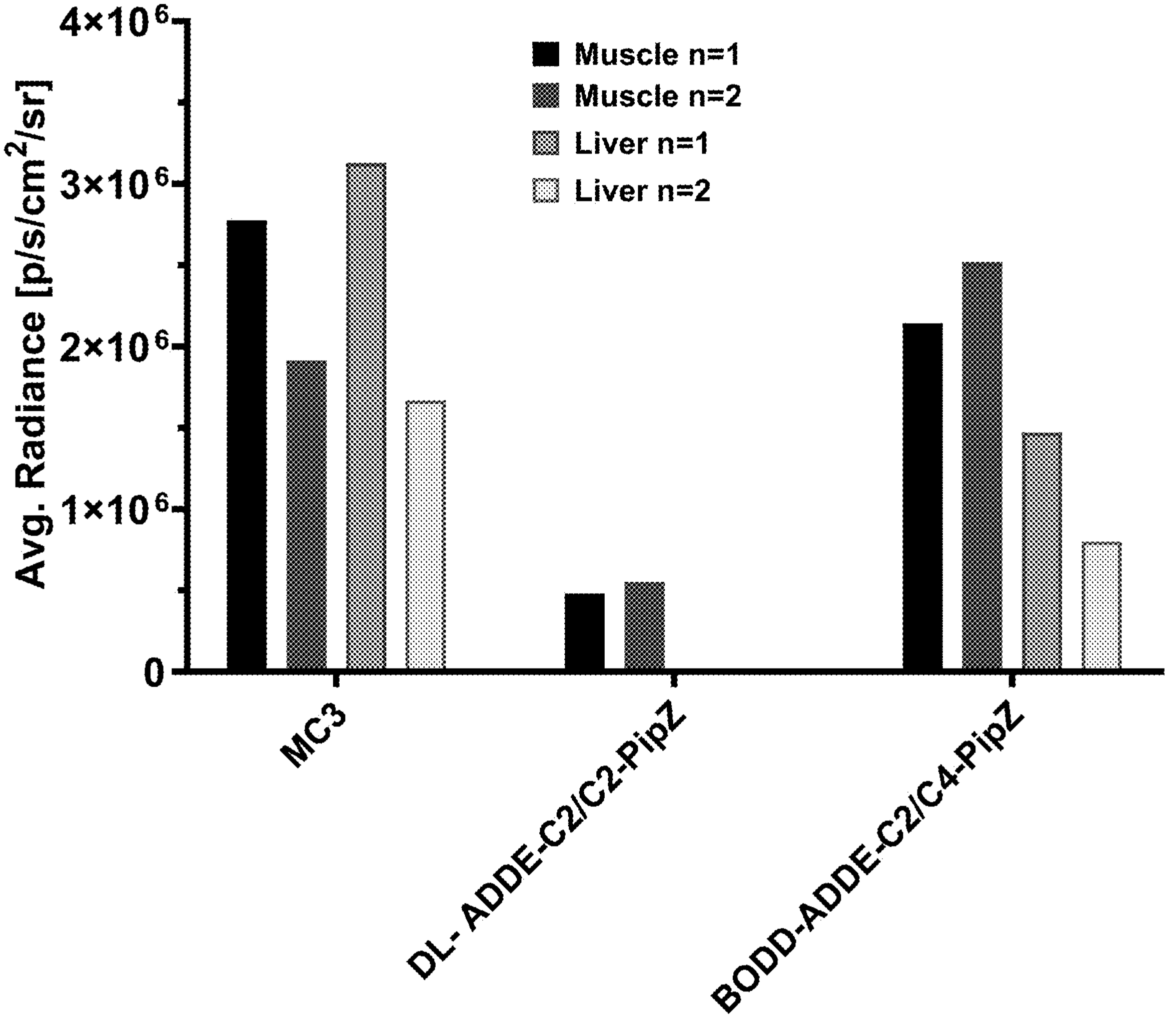
Figure 40E:
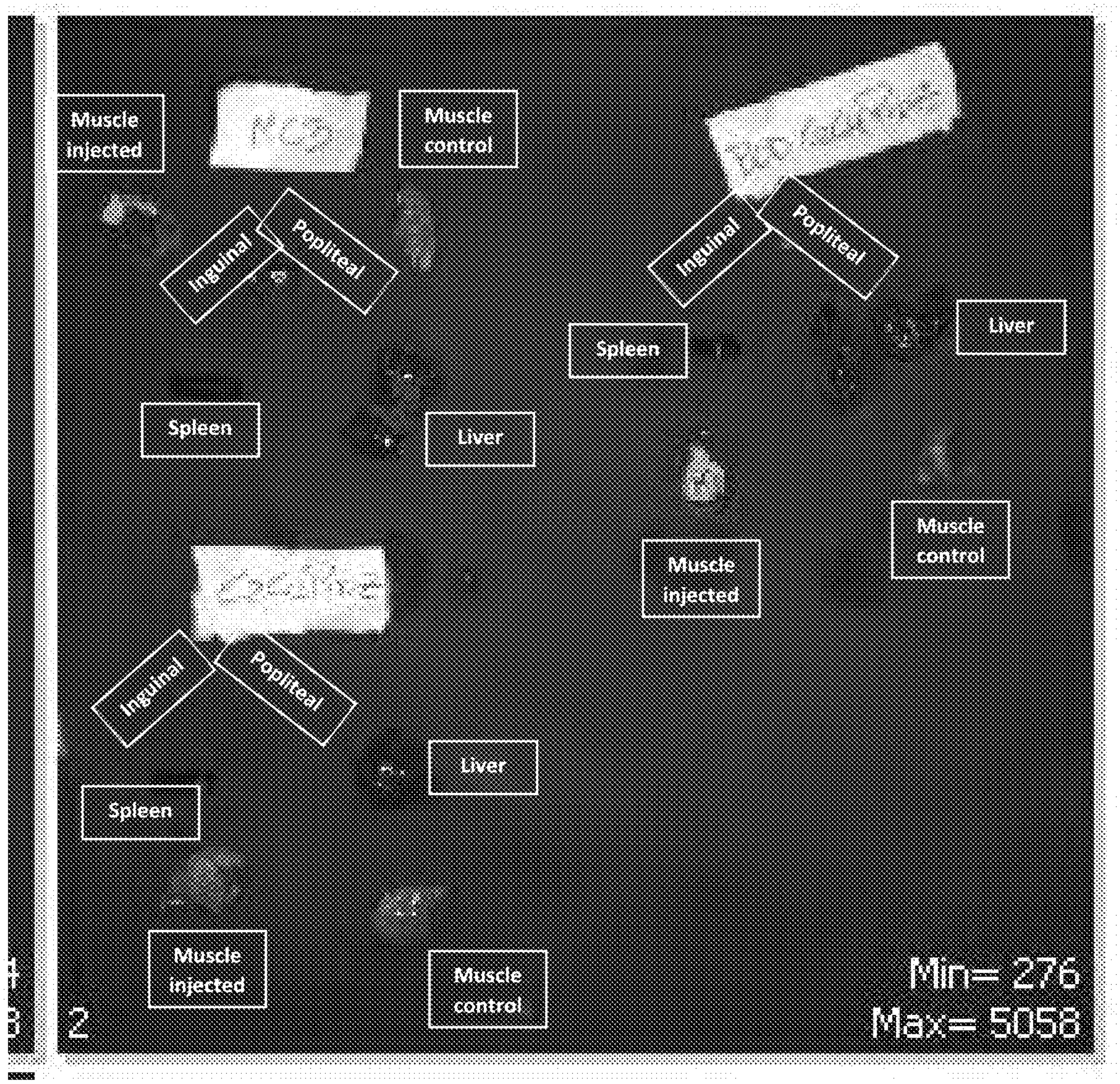
Figure 40F:
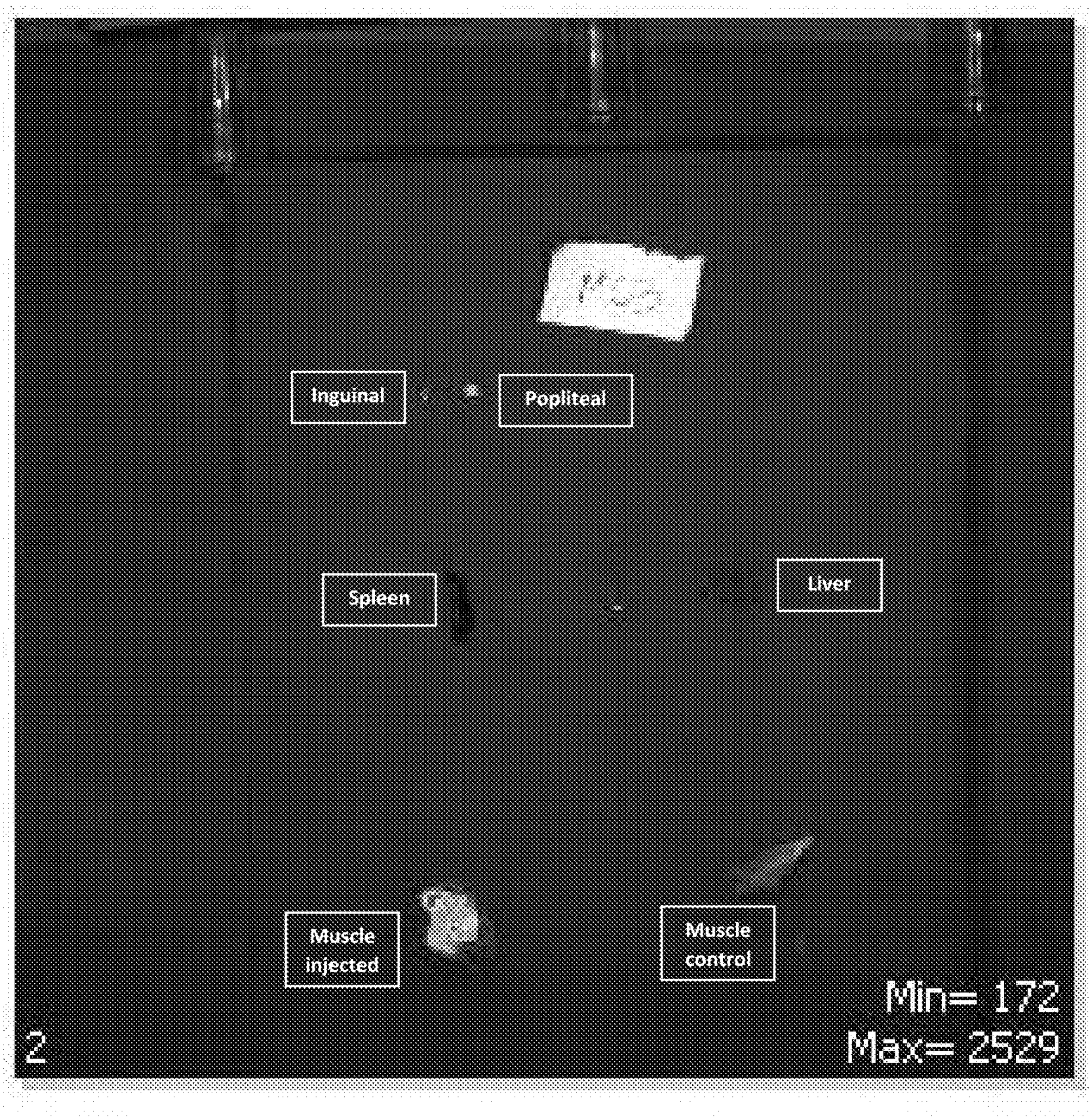
Figure 40G:
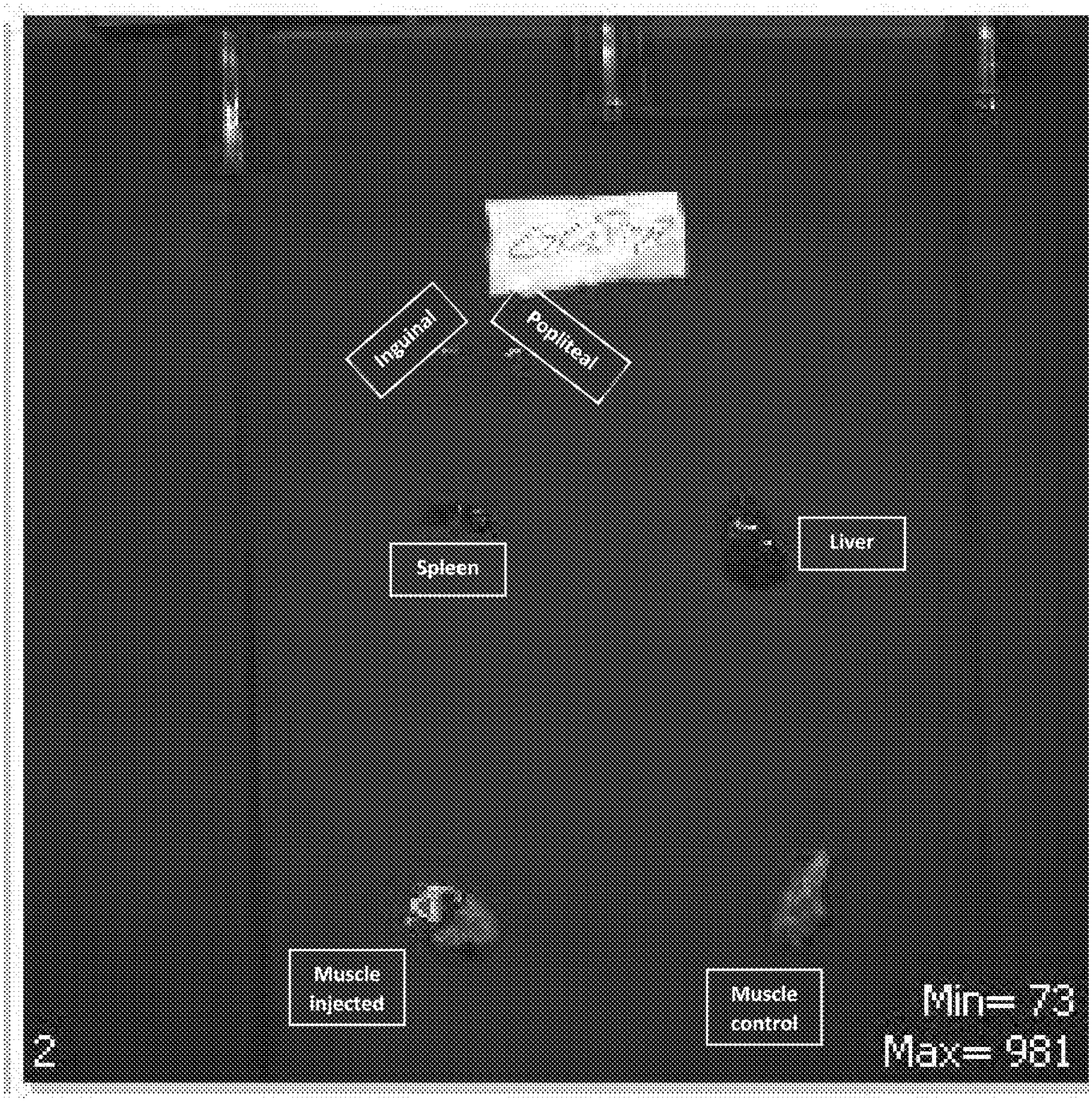
Figure 40H:
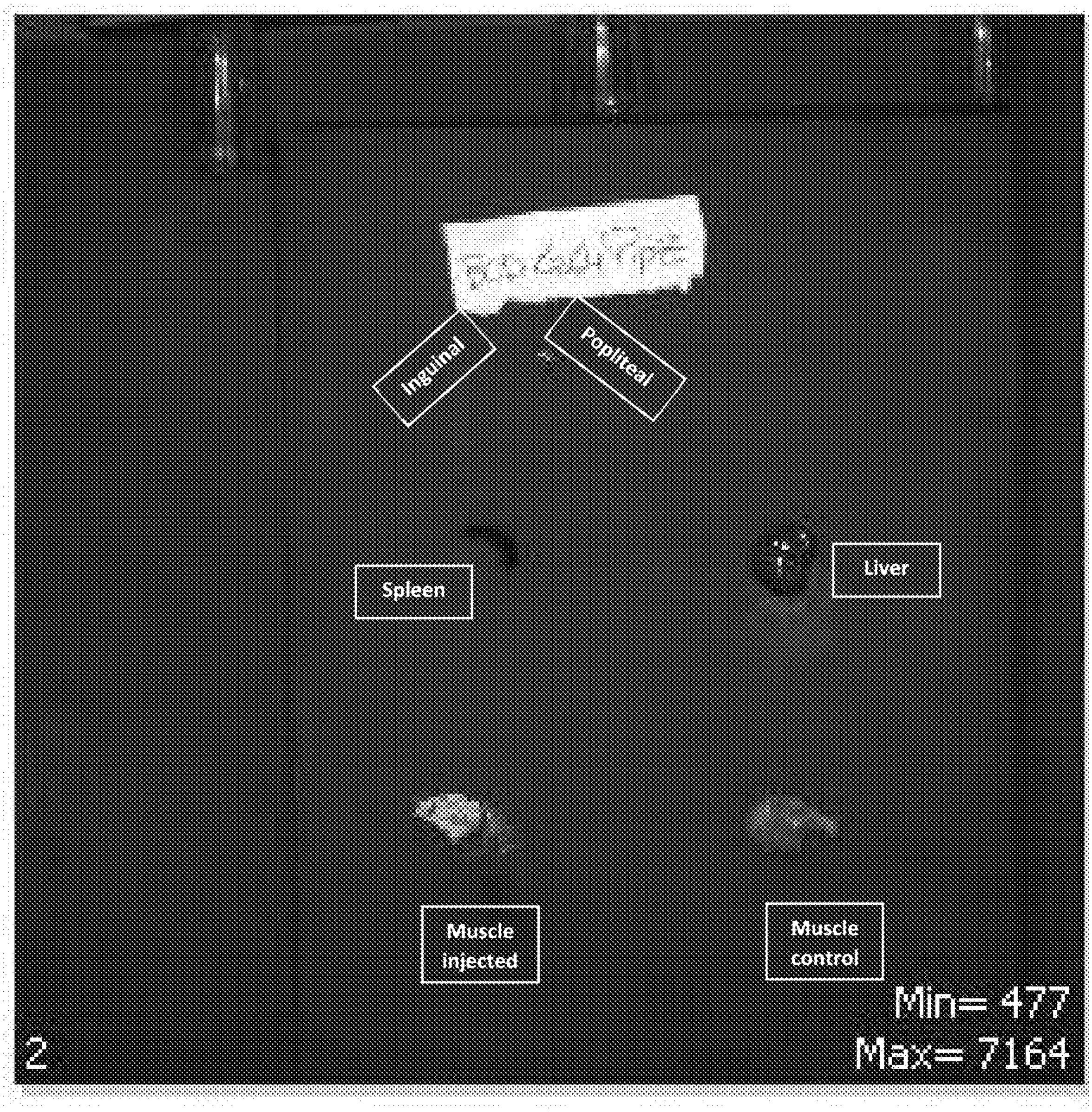

FIG. 39 illustrates a graph of Dynamic Light Scattering for LNP Size (white dots are PDI right y axis) as exemplified in Example 9B.

FIG. 40 illustrates in vivo vivo Firefly Luciferase expression in IM administration of 5 ug of encapsulated mRNA in mice in intramuscular (I.M.) injections. FIG. 40A illustrates 4 hour in-vivo imaging (left group 1, right group 2) from left to right (MC3/DL-ADDE-C2C2-4Me-PipZ/BODD-ADDE-C2C4-4Me-PipZ). FIG. 40B illustrates the presence in muscle and liver illustrating systemic distribution and local concentration of from left to right (MC3/DL-ADDE-C2C2-4Me-PipZ/BODD-ADDE-C2C4-4Me-PipZ) after intramuscular administration. FIG. 40C illustrates 24 hour in-vivo imaging (left group 1, right group 2) from left to right (MC3/DL-ADDE-C2C2-4Me-PipZ/BODD-ADDE-C2C4-4Me-PipZ). FIG. 40D illustrates the presence in muscle and liver illustrating systemic distribution and local concentration of from left to right (MC3/DL-ADDE-C2C2-4Me-PipZ/BODD-ADDE-C2C4-4Me-PipZ) after intramuscular administration. FIG. 40E illustrates the distribution of samples of MC3/DL-ADDE-C2C2-4Me-PipZ/BODD-ADDE-C2C4-4Me-PipZ after intramuscular administration. FIG. 40F illustrates the distribution of samples of MC3 after intramuscular administration. FIG. 40G illustrates the distribution of samples of DL-ADDE-C2C2-4Me-PipZ after intramuscular administration. FIG. 40H illustrates the distribution of samples of BODD-ADDE-C2C4-4Me-PipZ after intramuscular administration.

Figure 41:
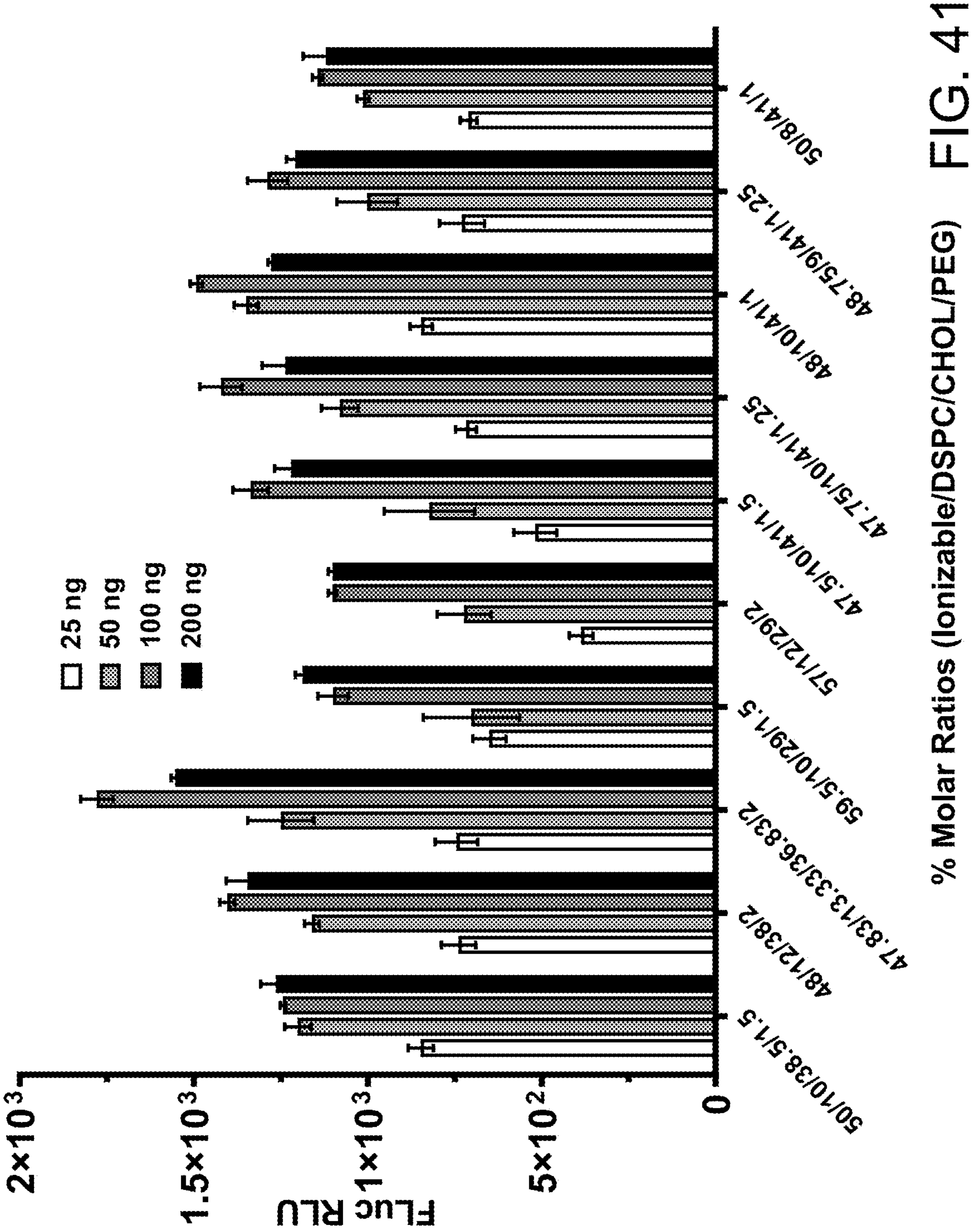

FIG. 41 illustrates a graph of Firefly Luciferase Assay for mRNA Delivery Efficiency as exemplified in Example 10A.

Figure 42:
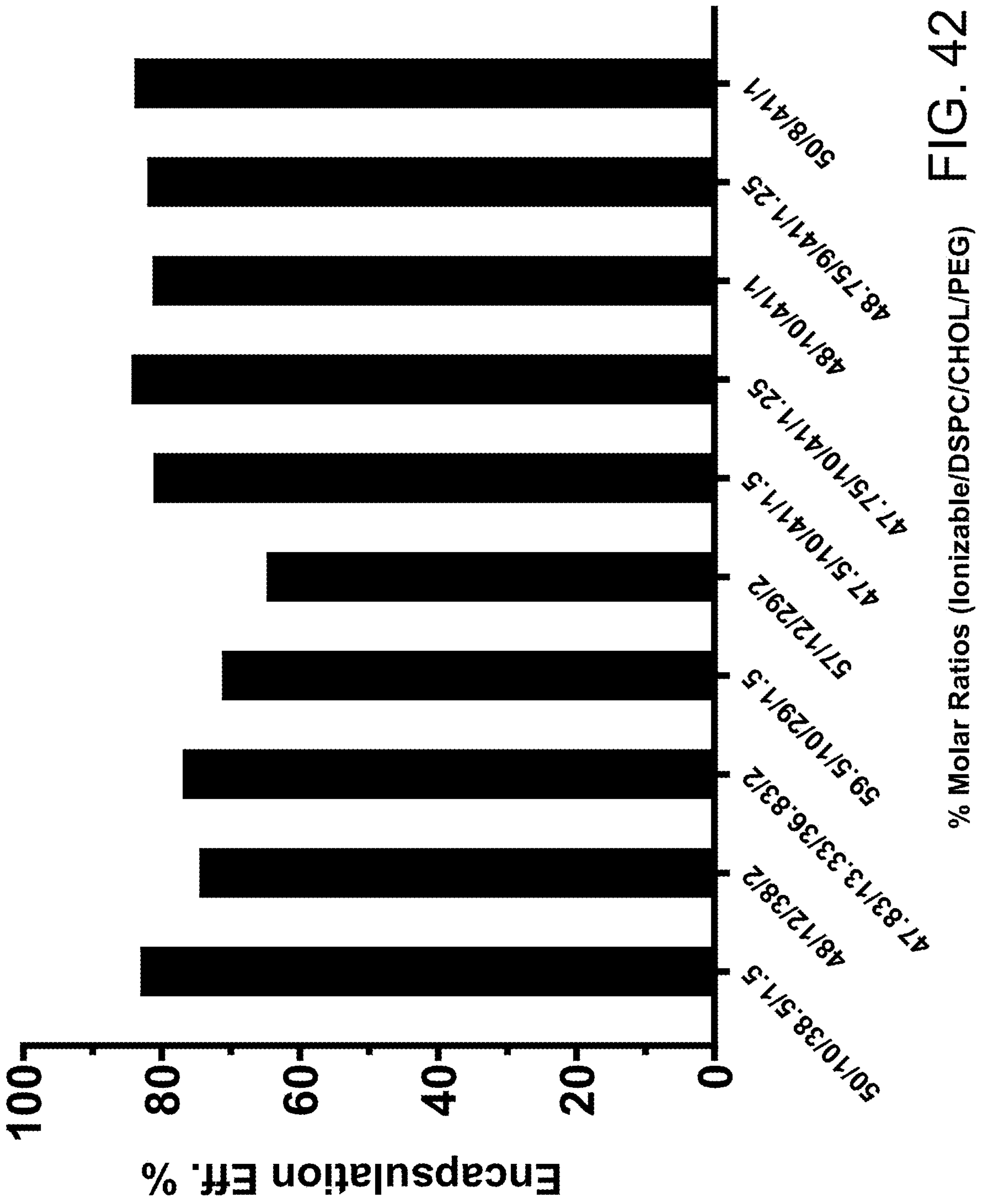

FIG. 42 illustrates a graph of Ribogreen Assay for mRNA Encapsulation Efficiency as exemplified in Example 10B.

Figure 43:
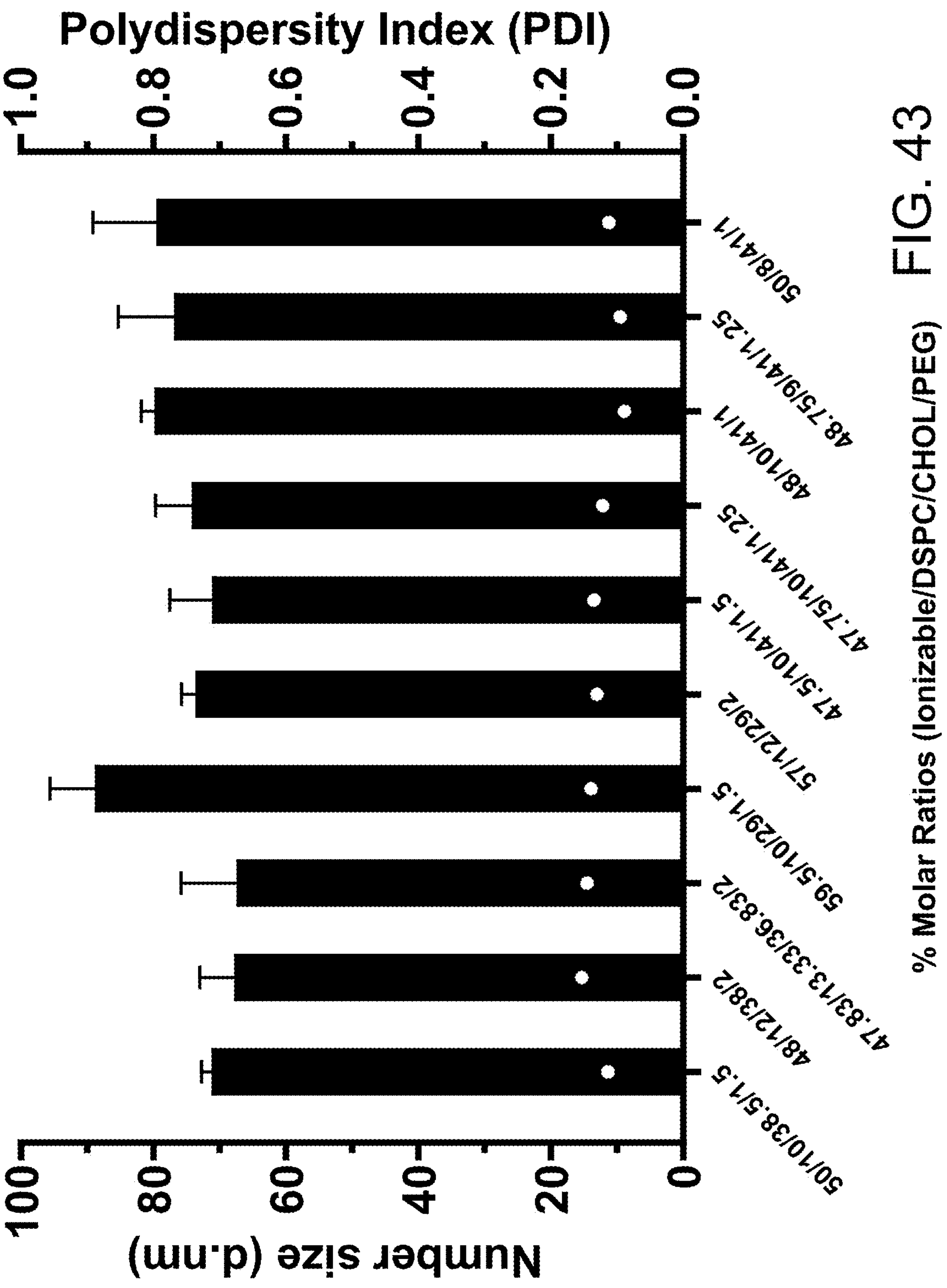

FIG. 43 illustrates a graph of Dynamic Light Scattering for LNP Size (white dots are PDI right y axis) as exemplified in Example 10C.

Figure 44:
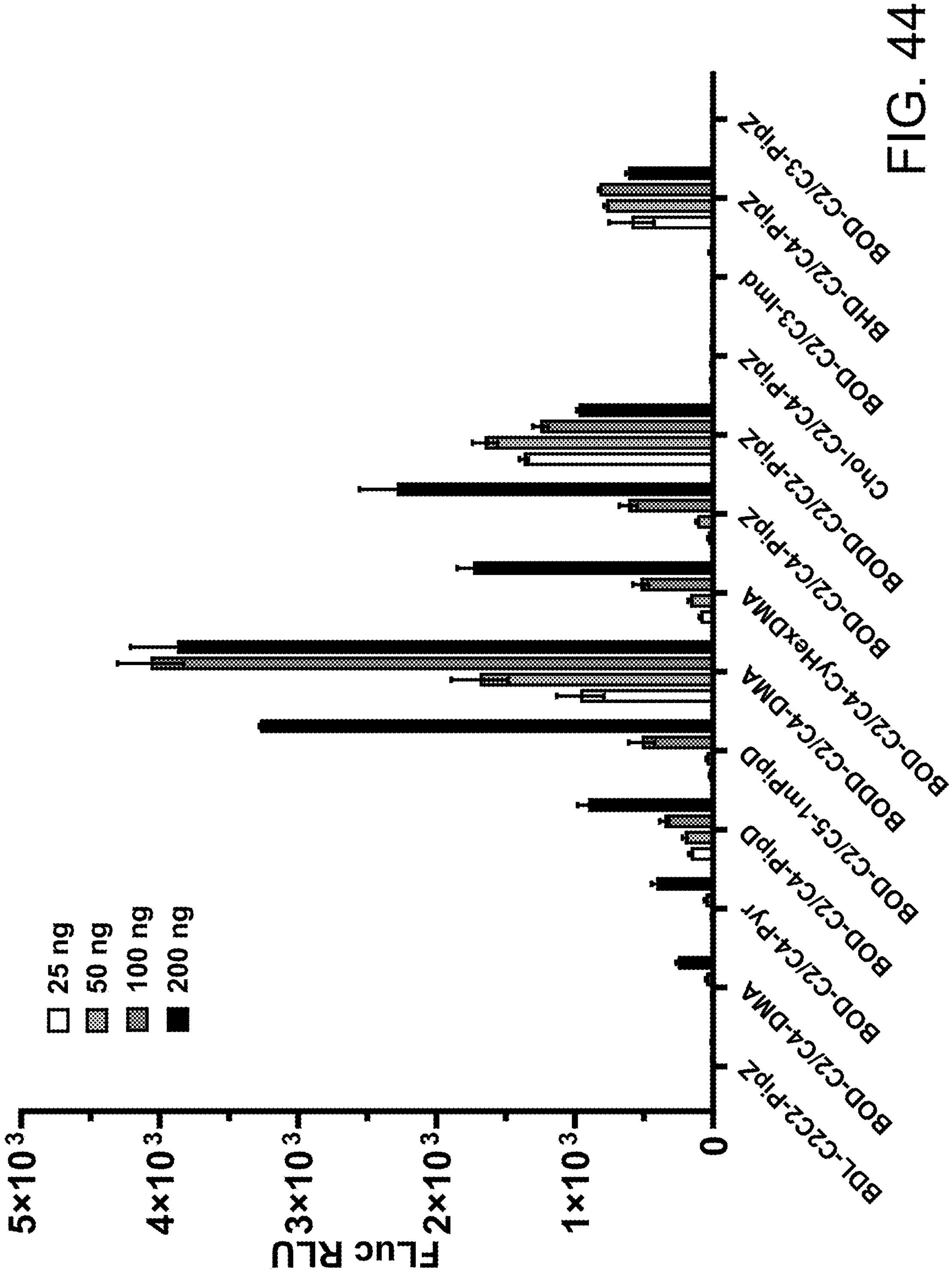

FIG. 44 illustrates a graph of Firefly Luciferase Assay for mRNA Delivery Efficiency as exemplified in Example 11A.

Figure 45:
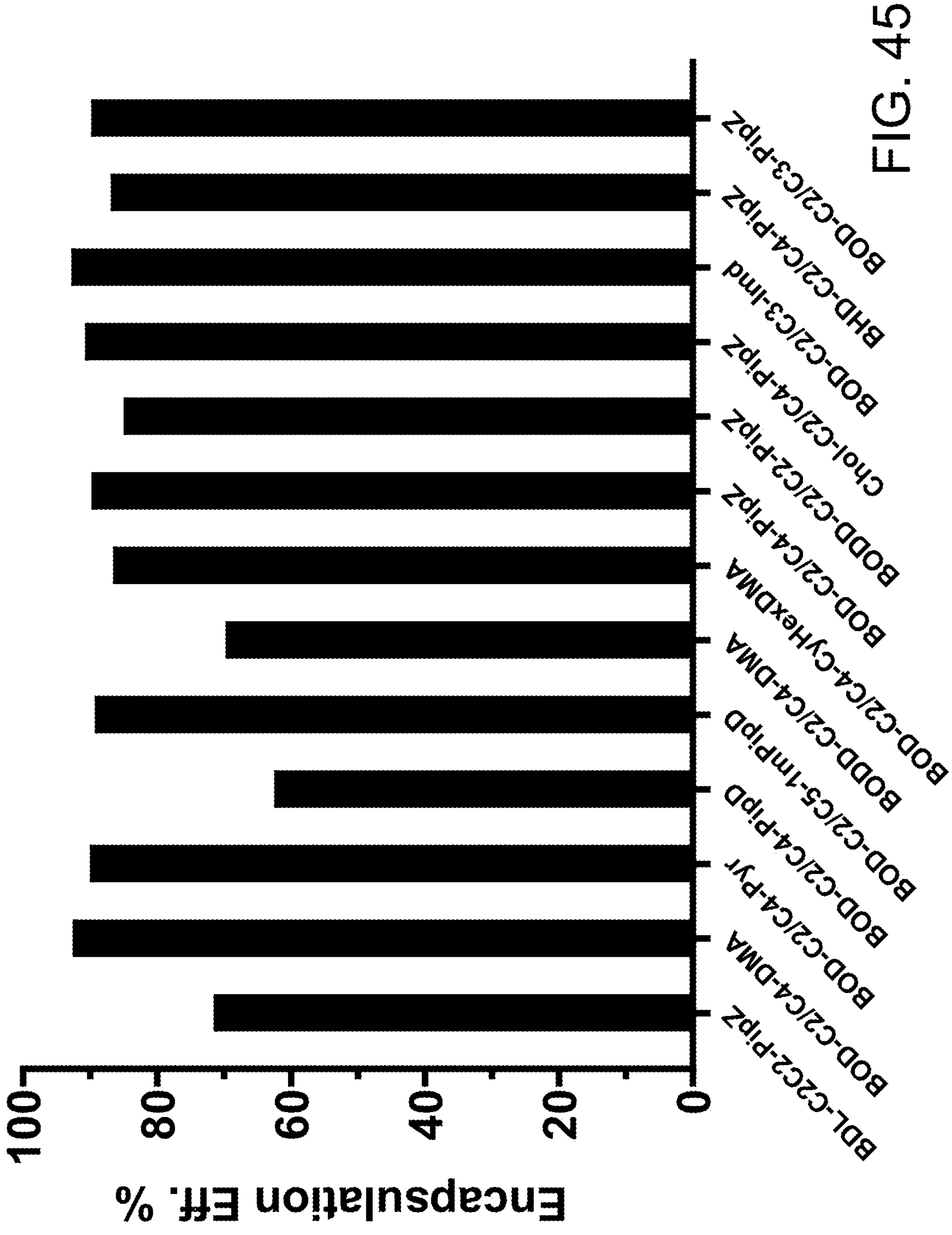

FIG. 45 illustrates a graph of Ribogreen Assay for mRNA Encapsulation Efficiency as exemplified in Example 11B.

Figure 46:
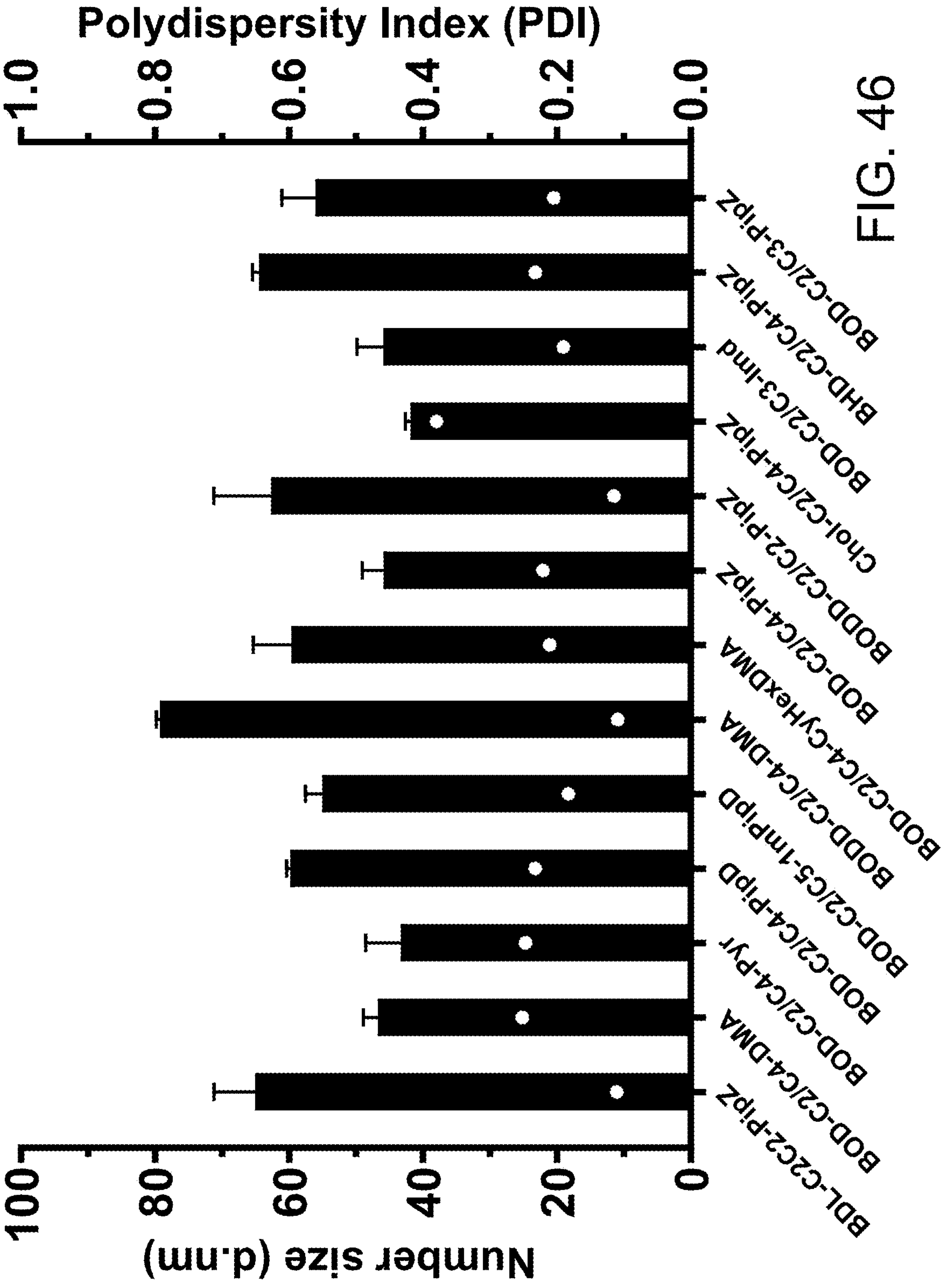

FIG. 46 illustrates a graph of Dynamic Light Scattering for LNP Size (white dots are PDI right y axis) as exemplified in Example 11C.

Figure 47:
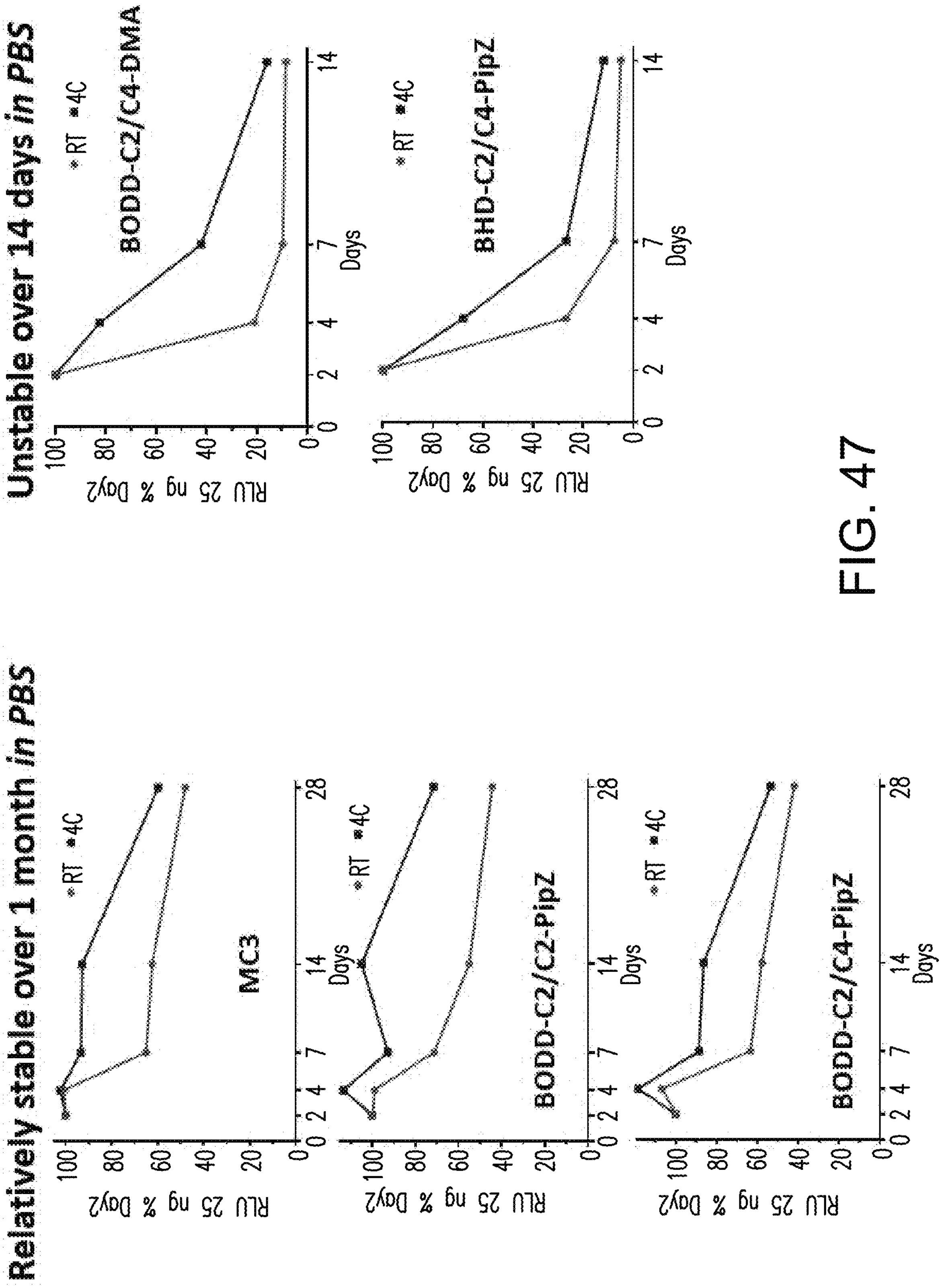

FIG. 47 illustrates graphs of Stability Assay based on in vitro potency using Firefly Luciferase Assays as exemplified in Example 12B.

Figure 48:
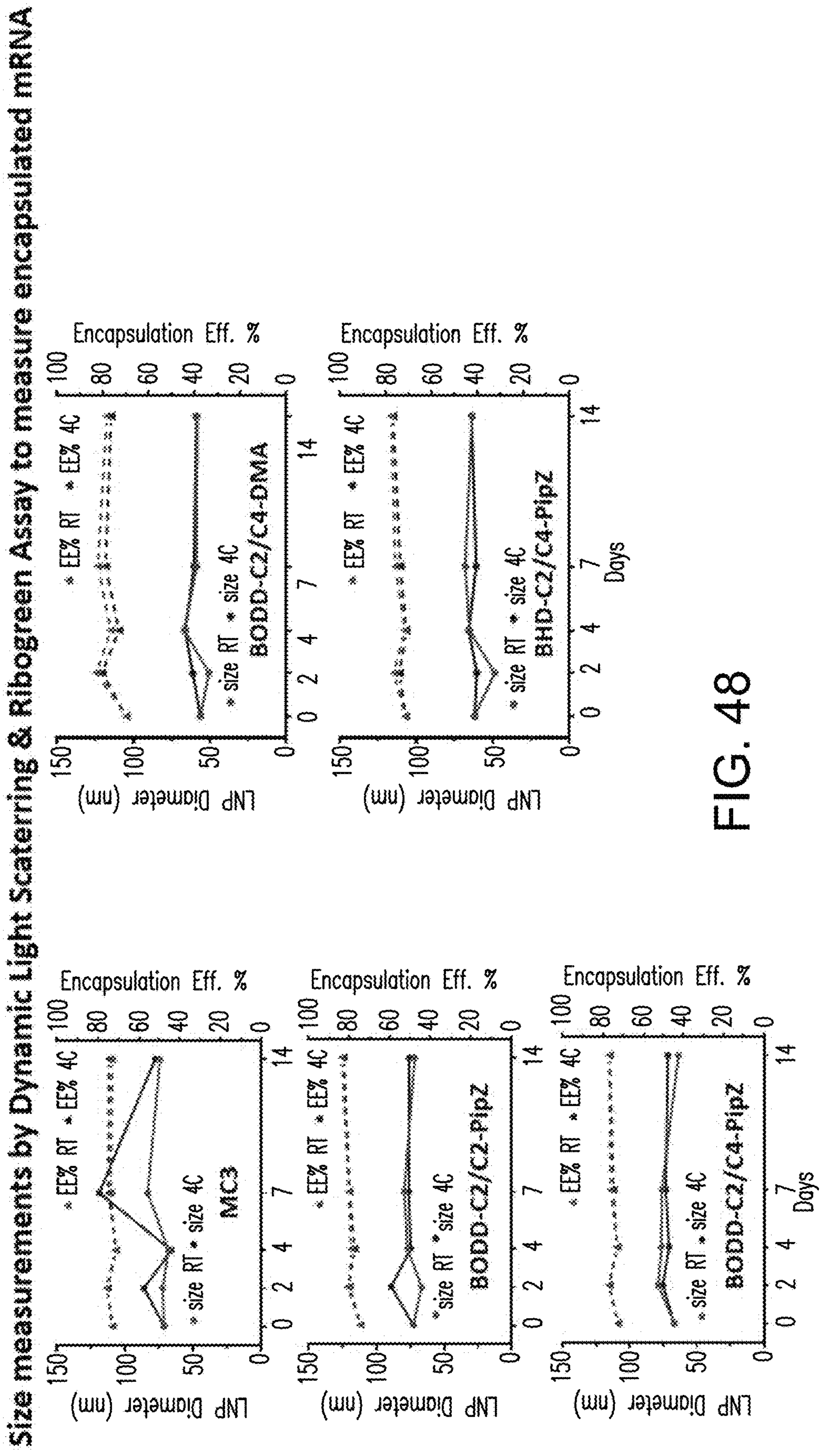

FIG. 48 illustrates a graph of Dynamic Light Scattering for LNP Size (white dots are PDI right y axis) as exemplified in Example 12C.

Figure 49:
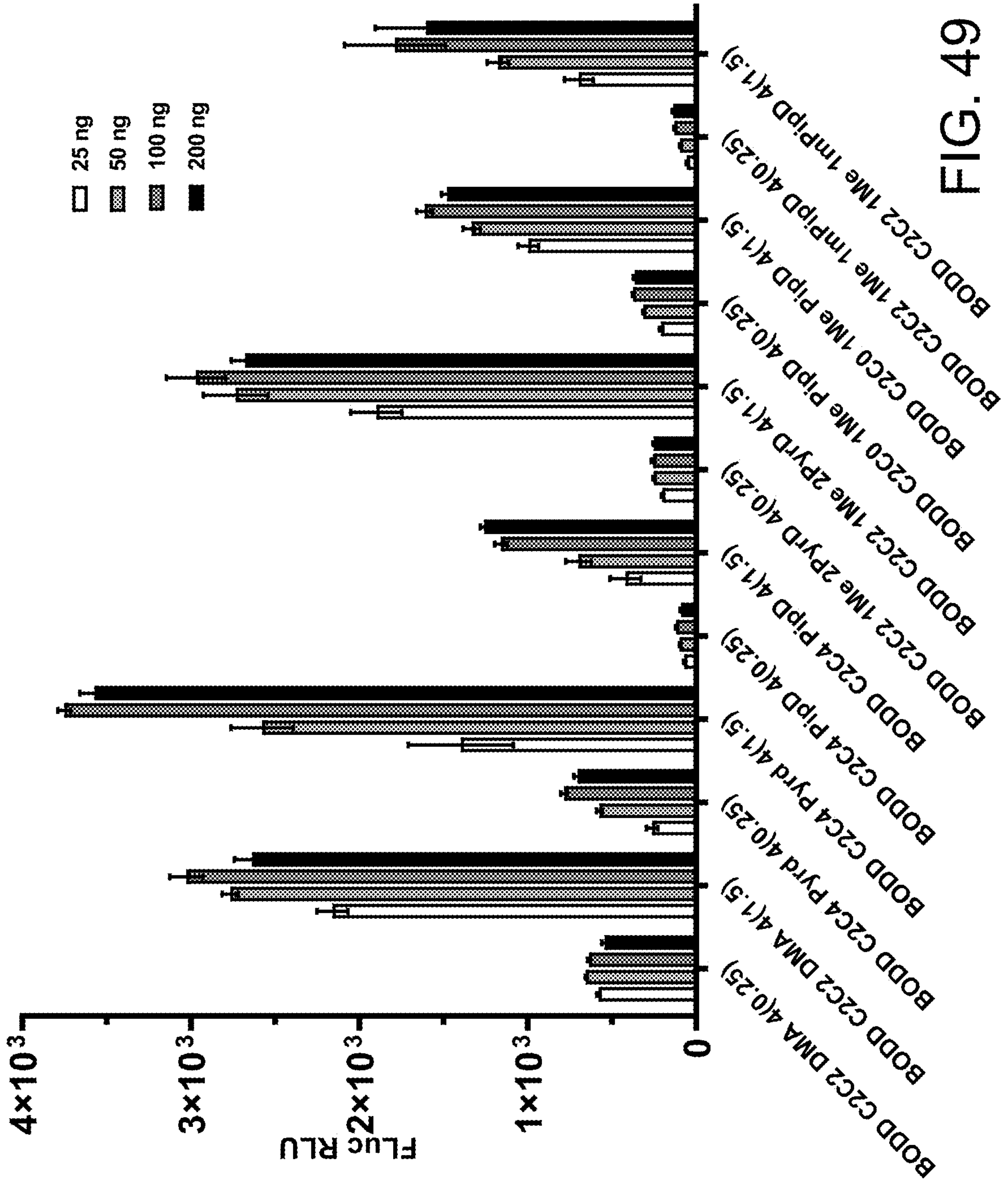

FIG. 49 illustrates a graph of Firefly Luciferase Assay for mRNA Delivery Efficiency as exemplified in Example 13A.

Figure 50:
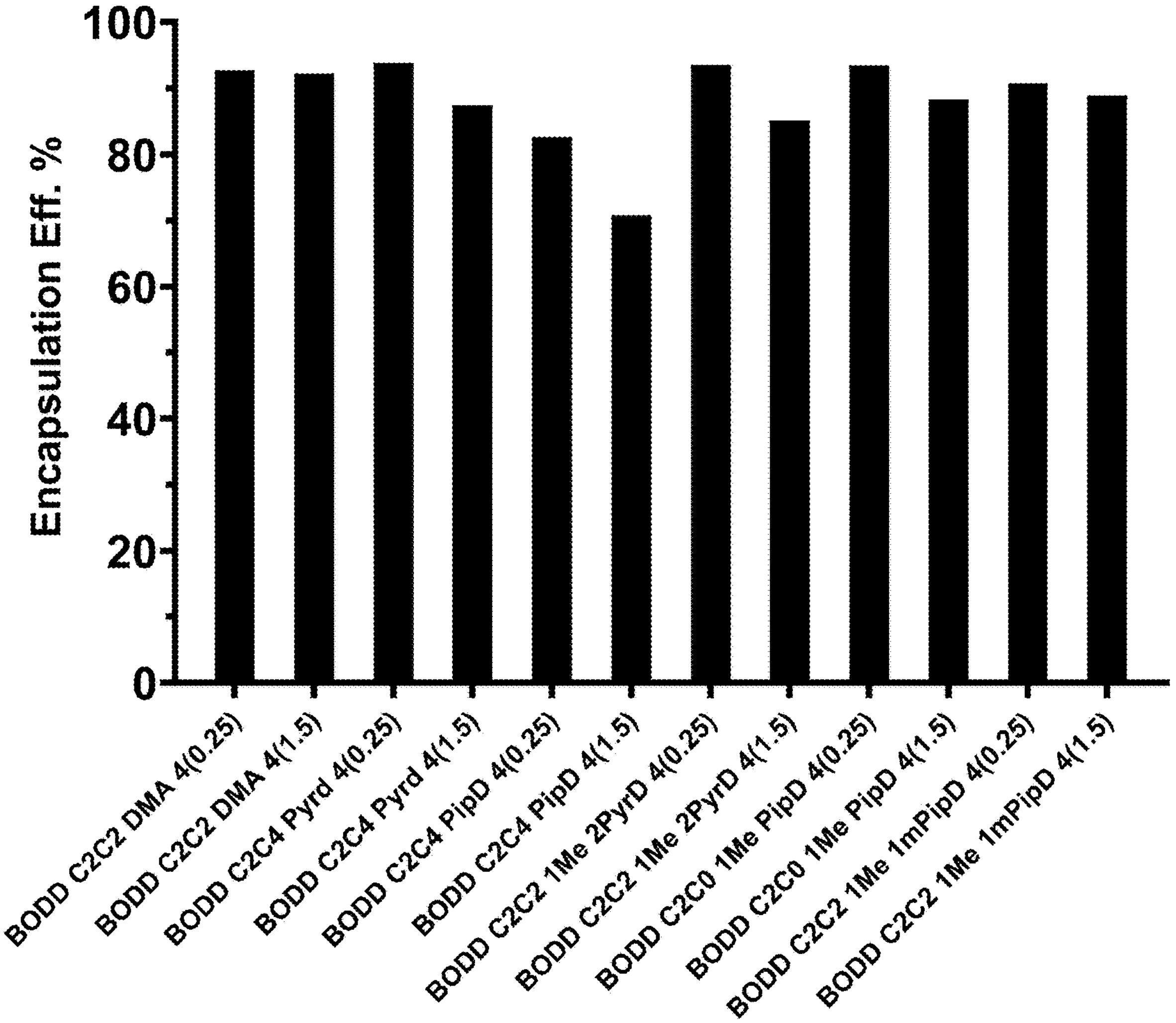

FIG. 50 illustrates a graph of Ribogreen Assay for mRNA Encapsulation Efficiency as exemplified in Example 13B.

Figure 51:
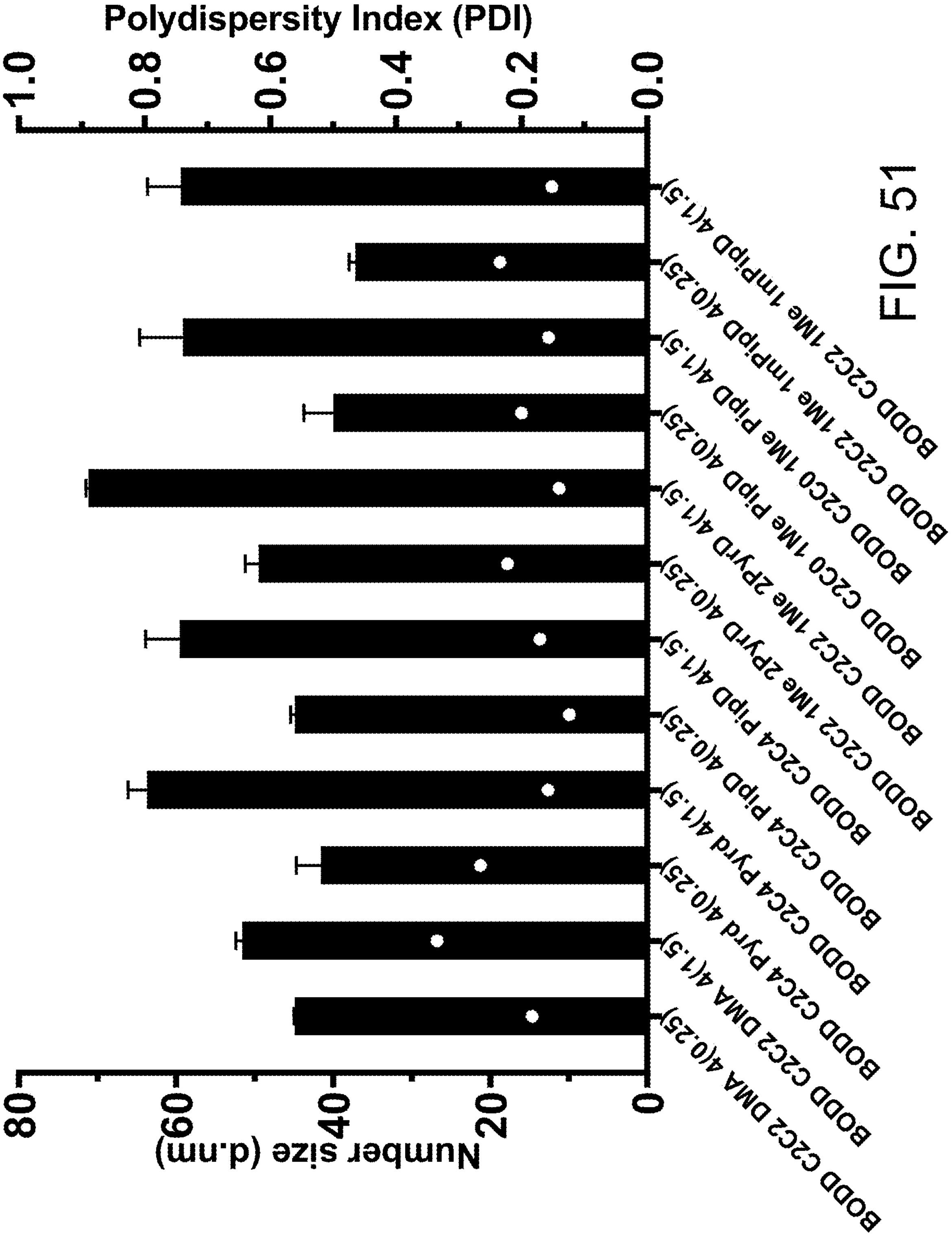

FIG. 51 illustrates a graph of Dynamic Light Scattering for LNP Size (white dots are PDI right y axis) as exemplified in Example 13C.

Figure 52:
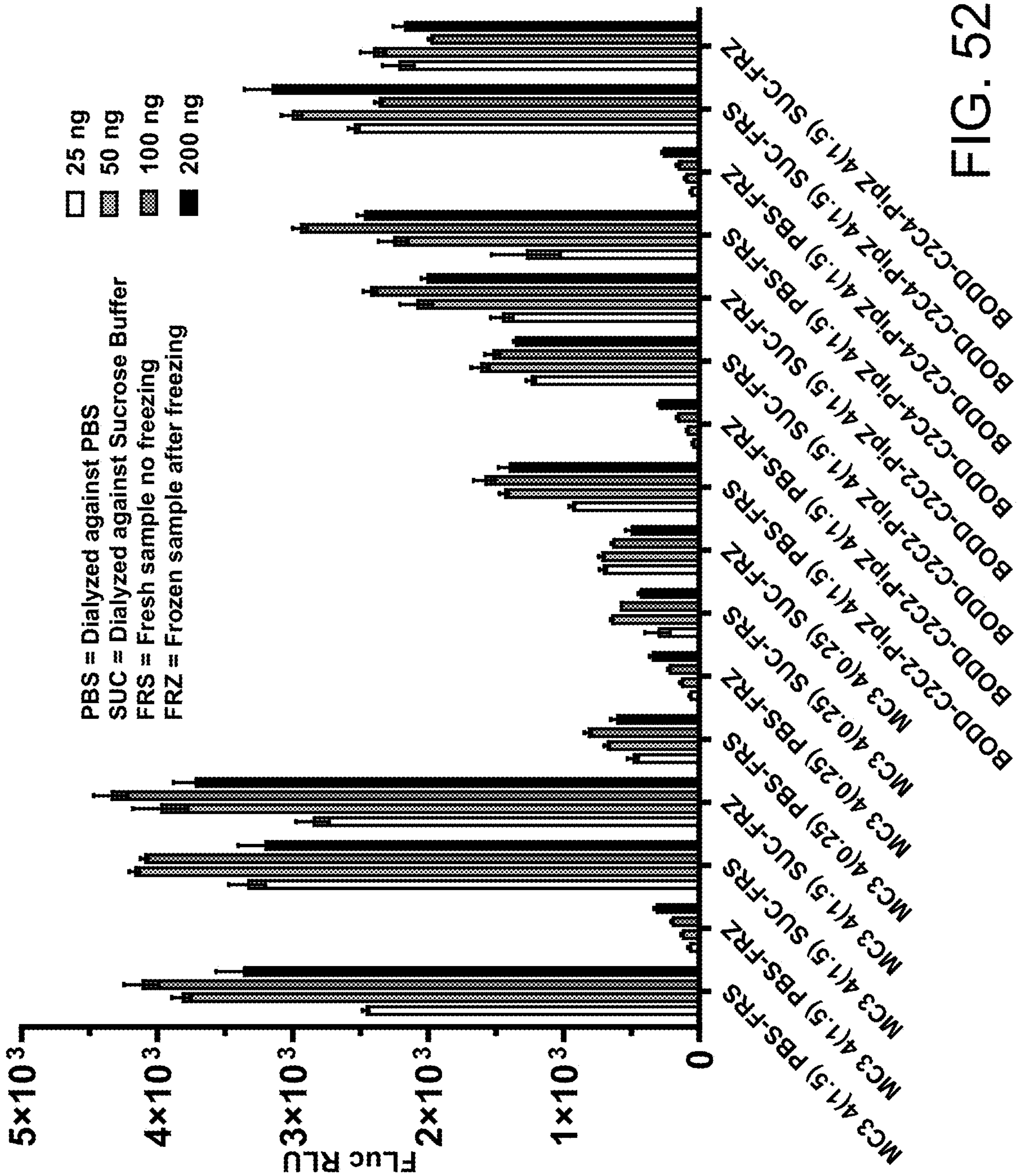

FIG. 52 illustrates a graph of Firefly Luciferase Assay for mRNA Delivery Efficiency as exemplified in Example 14A.

Figure 53:
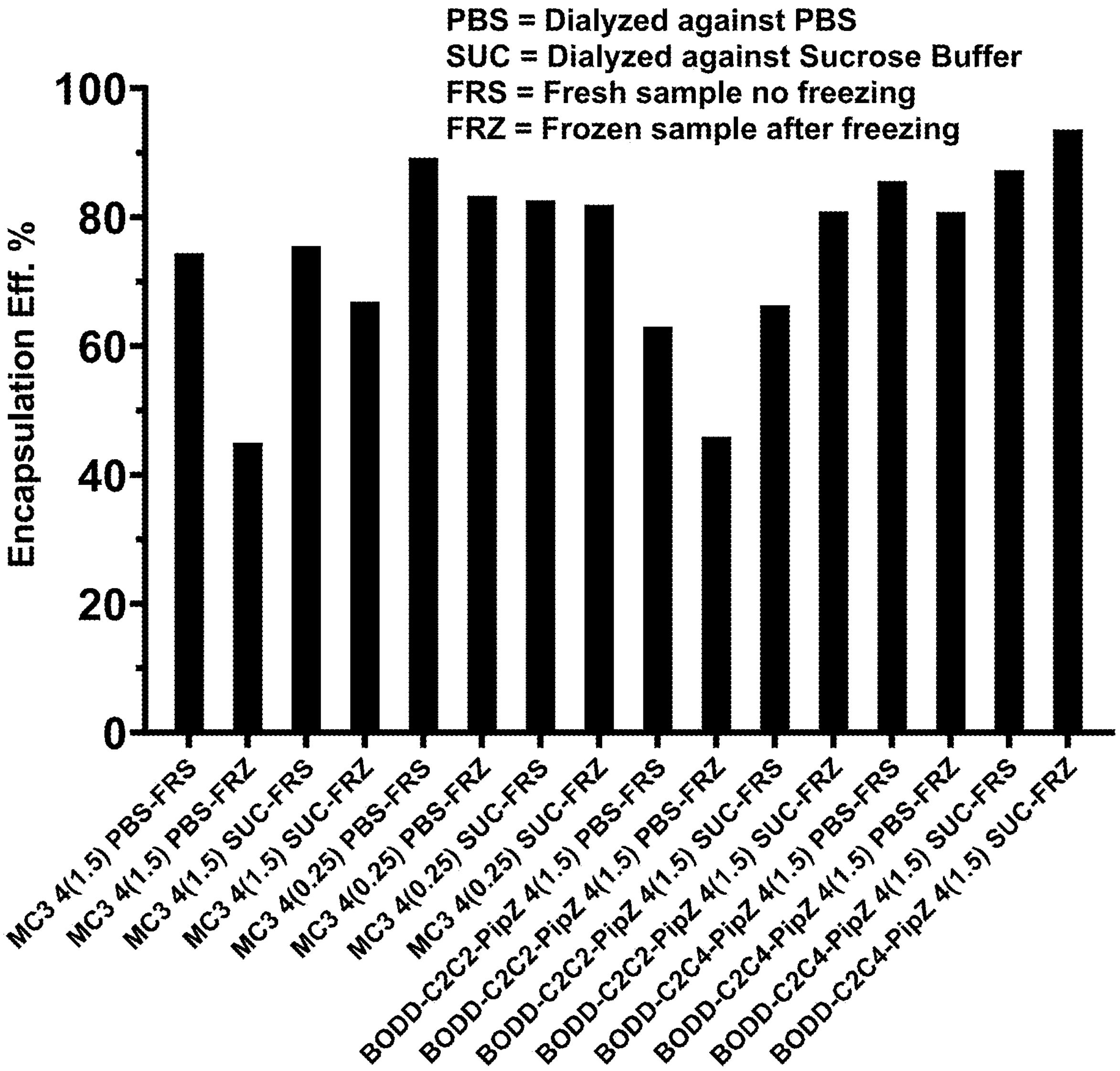

FIG. 53 illustrates a graph of Ribogreen Assay for mRNA Encapsulation Efficiency as exemplified in Example 14B.

Figure 54:
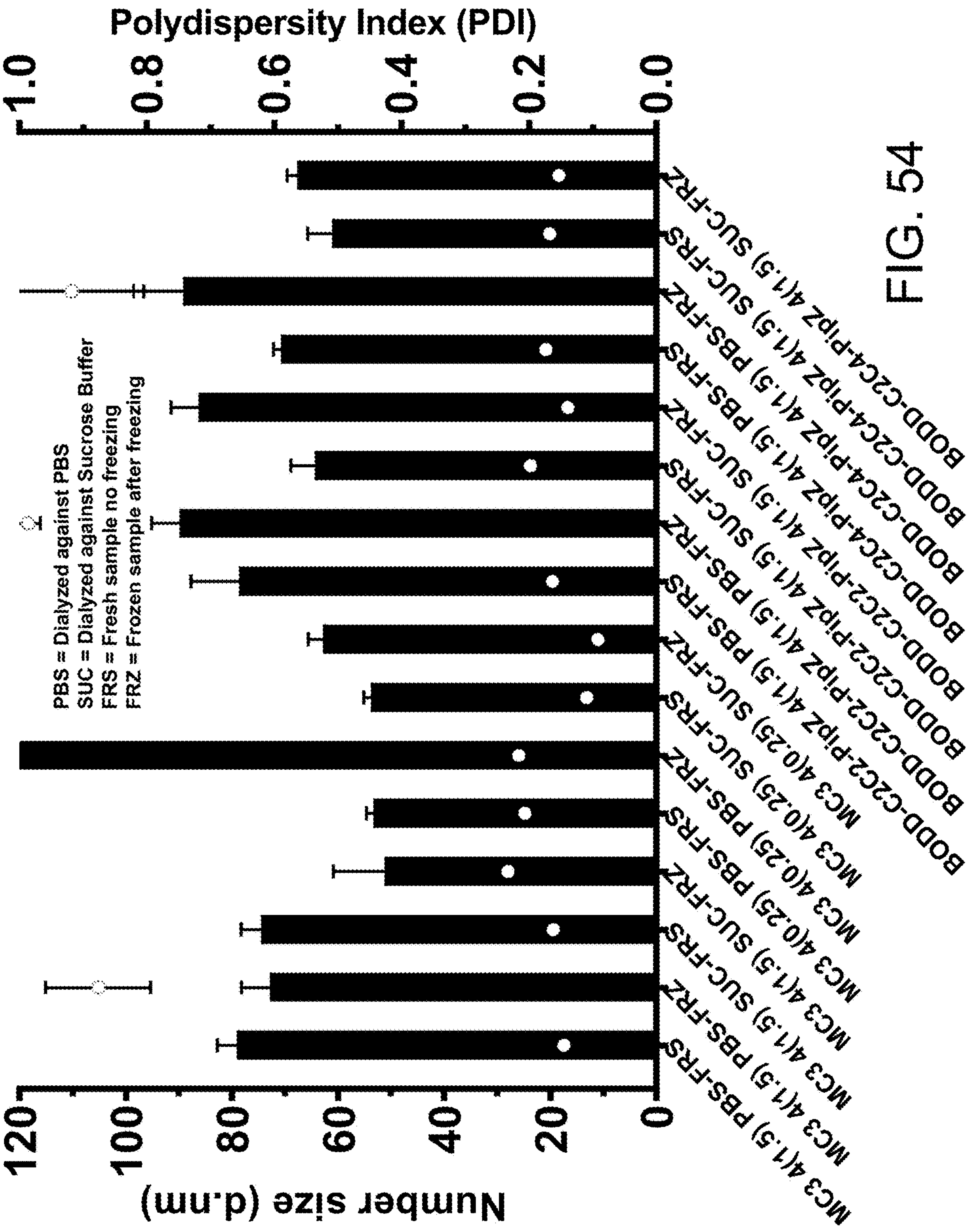

FIG. 54 illustrates a graph of Dynamic Light Scattering for LNP Size (white dots are PDI right y axis) as exemplified in Example 14C.

Figure 55:
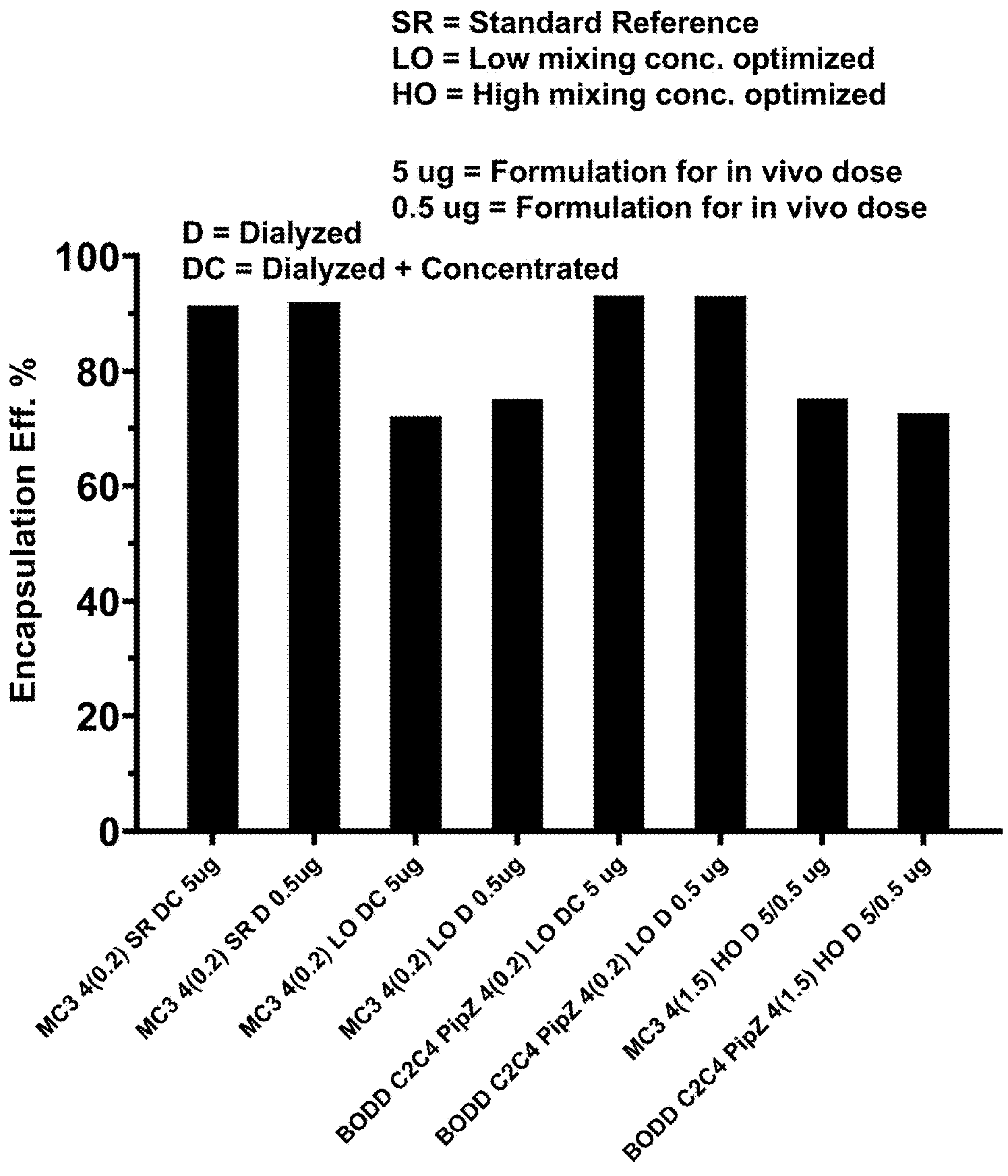

FIG. 55 illustrates a graph of Ribogreen Assay for mRNA Encapsulation Efficiency as exemplified 6 in Example 15A.

Figure 56:
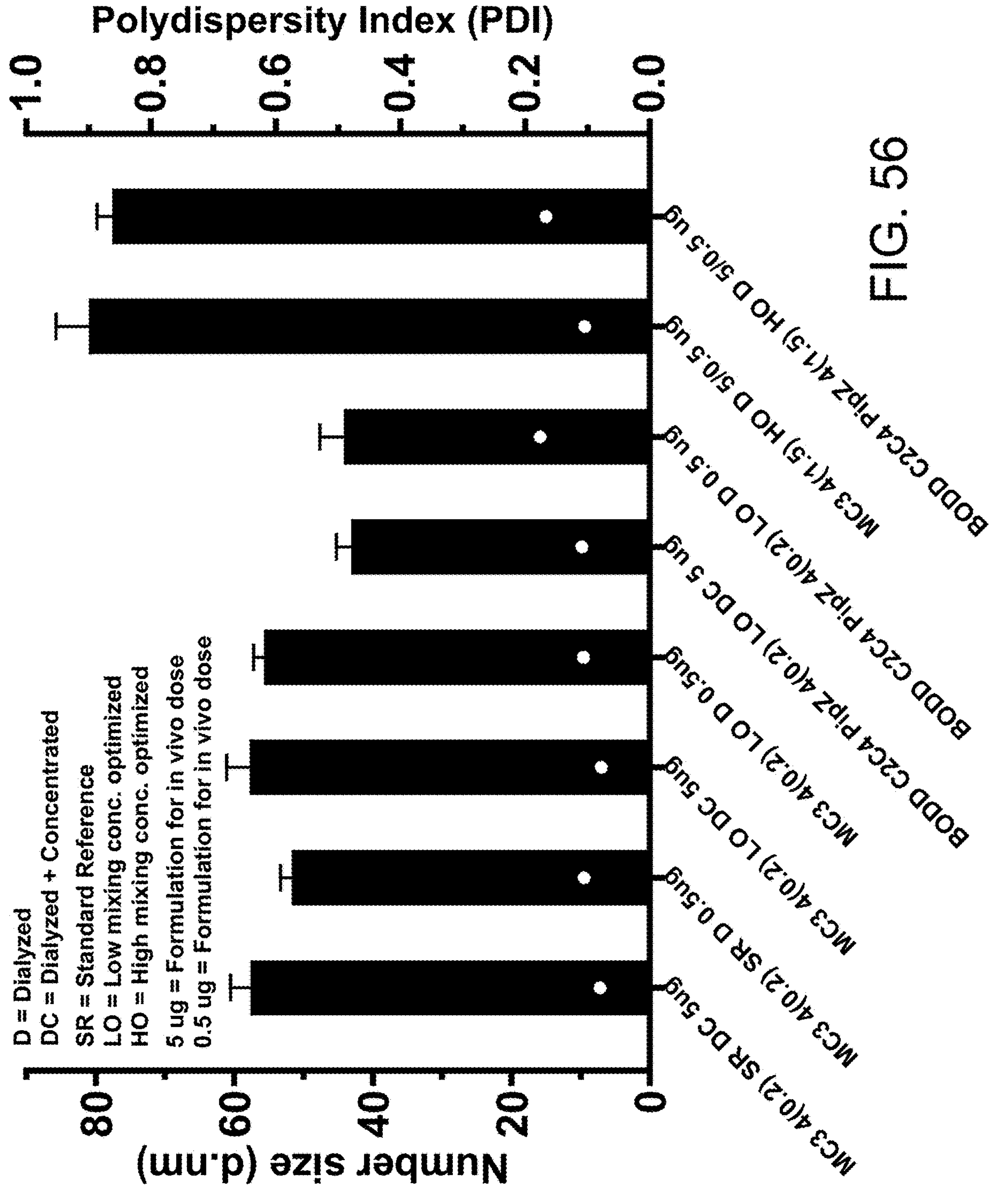
Figure 57A:
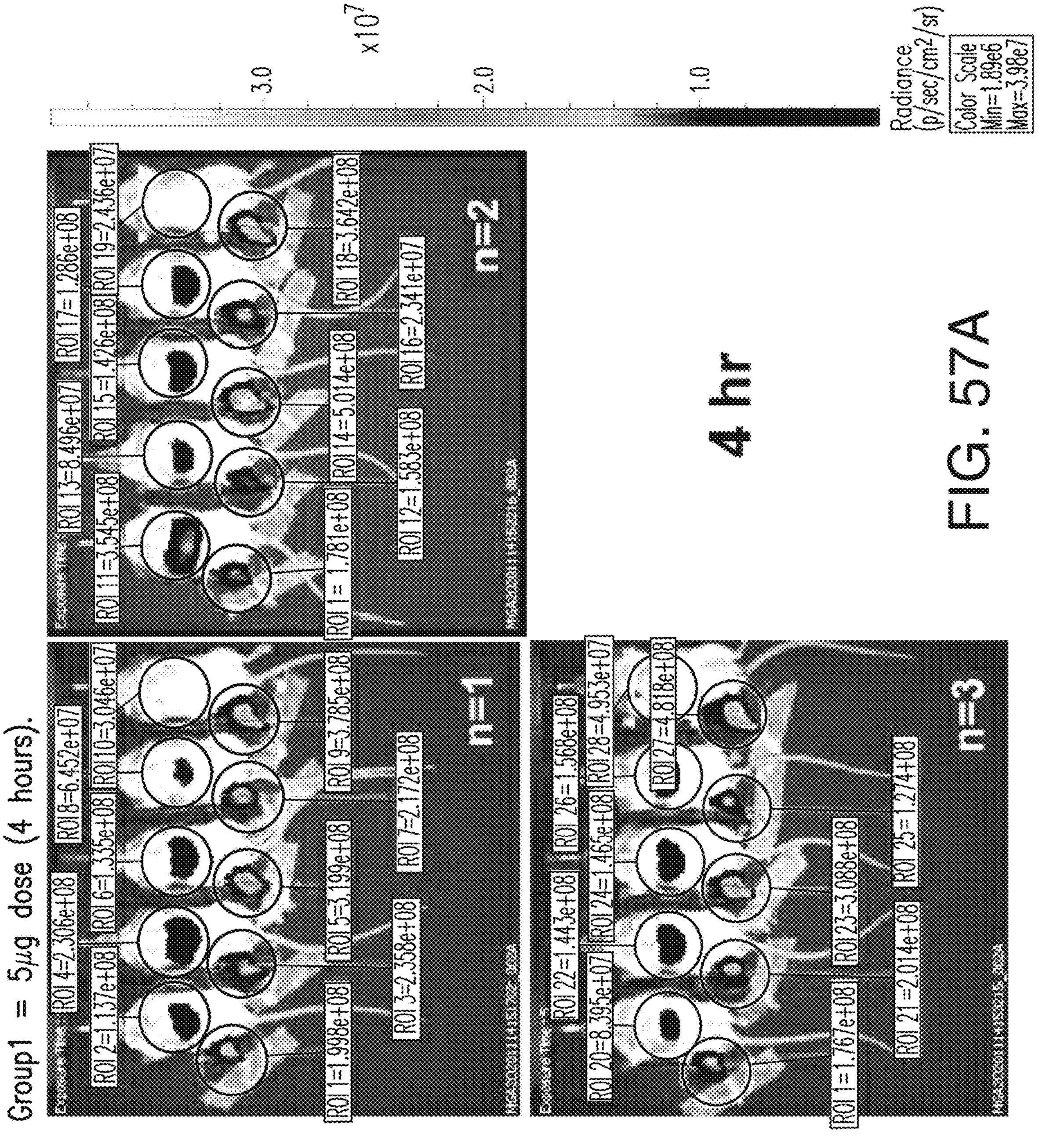
Figure 57A:
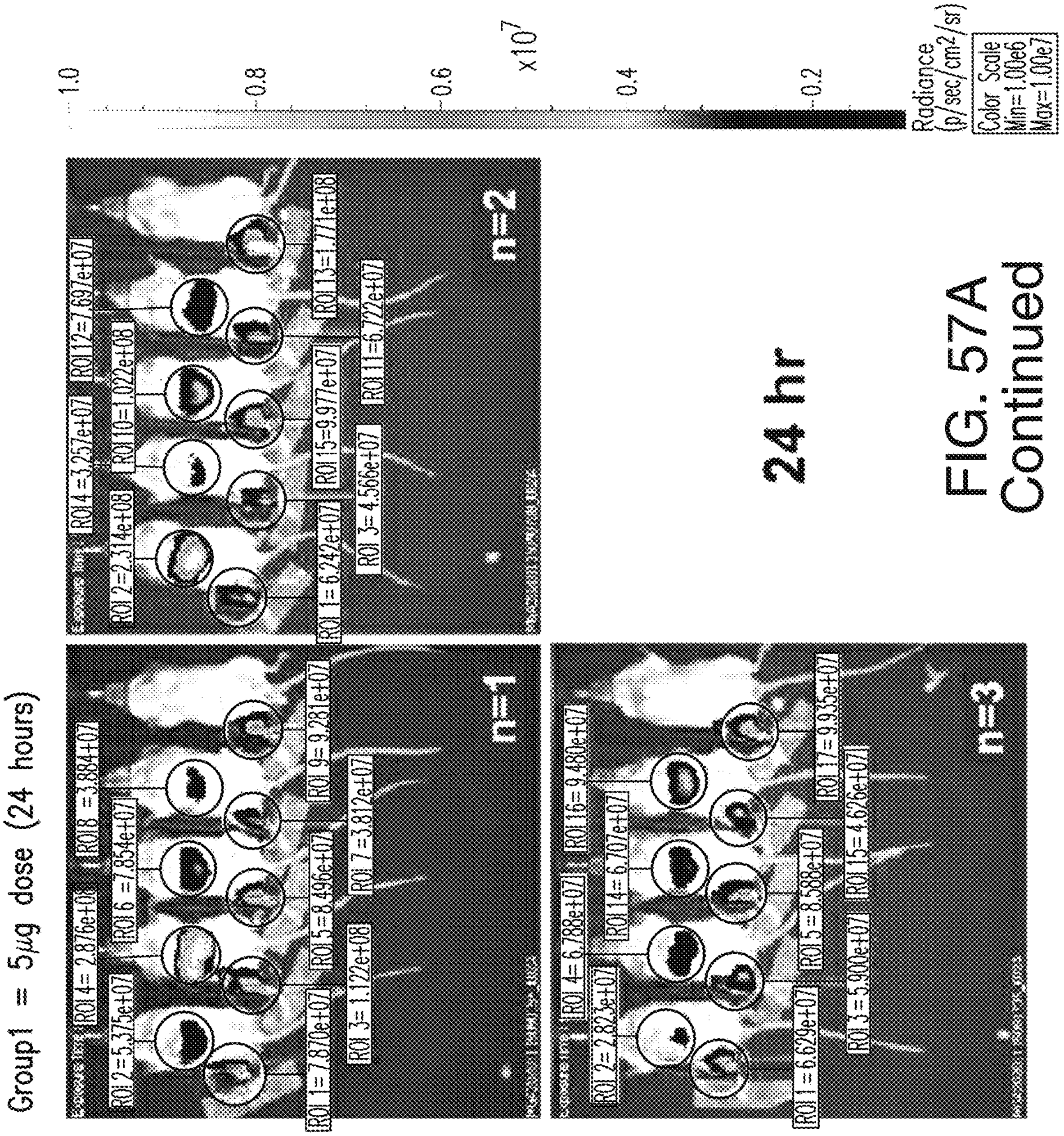
Figure 57B:
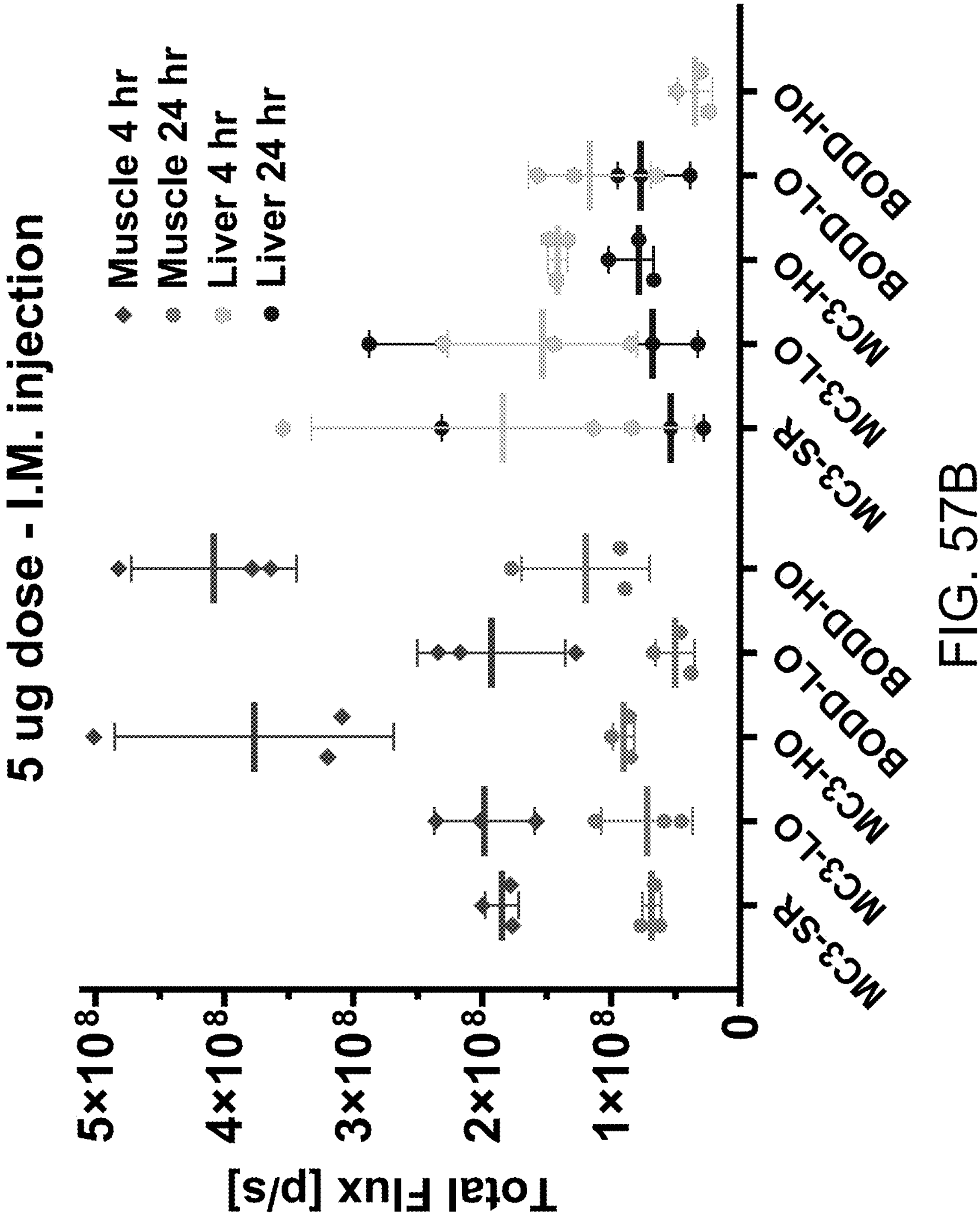
Figure 57C:
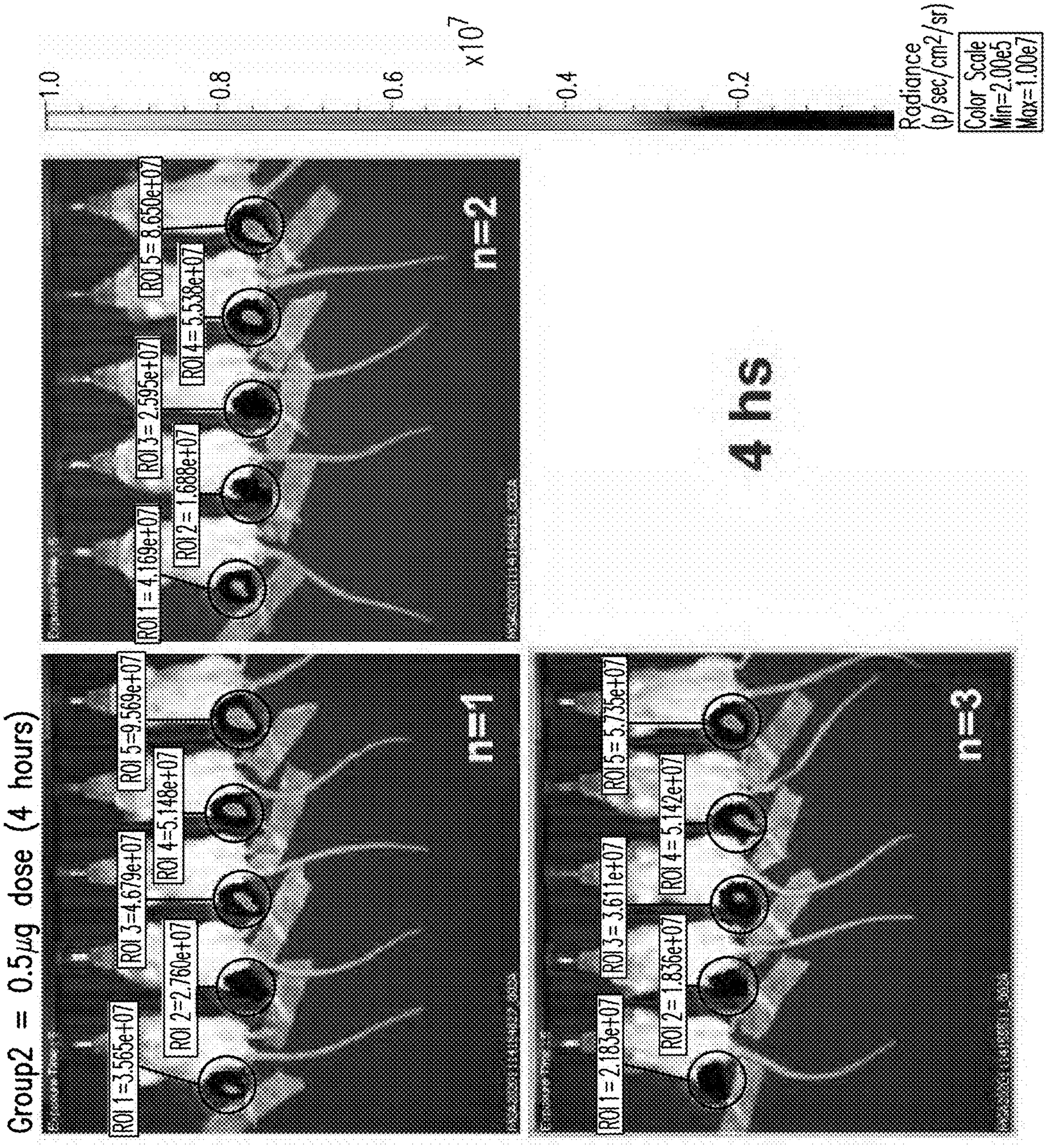
Figure 57C:
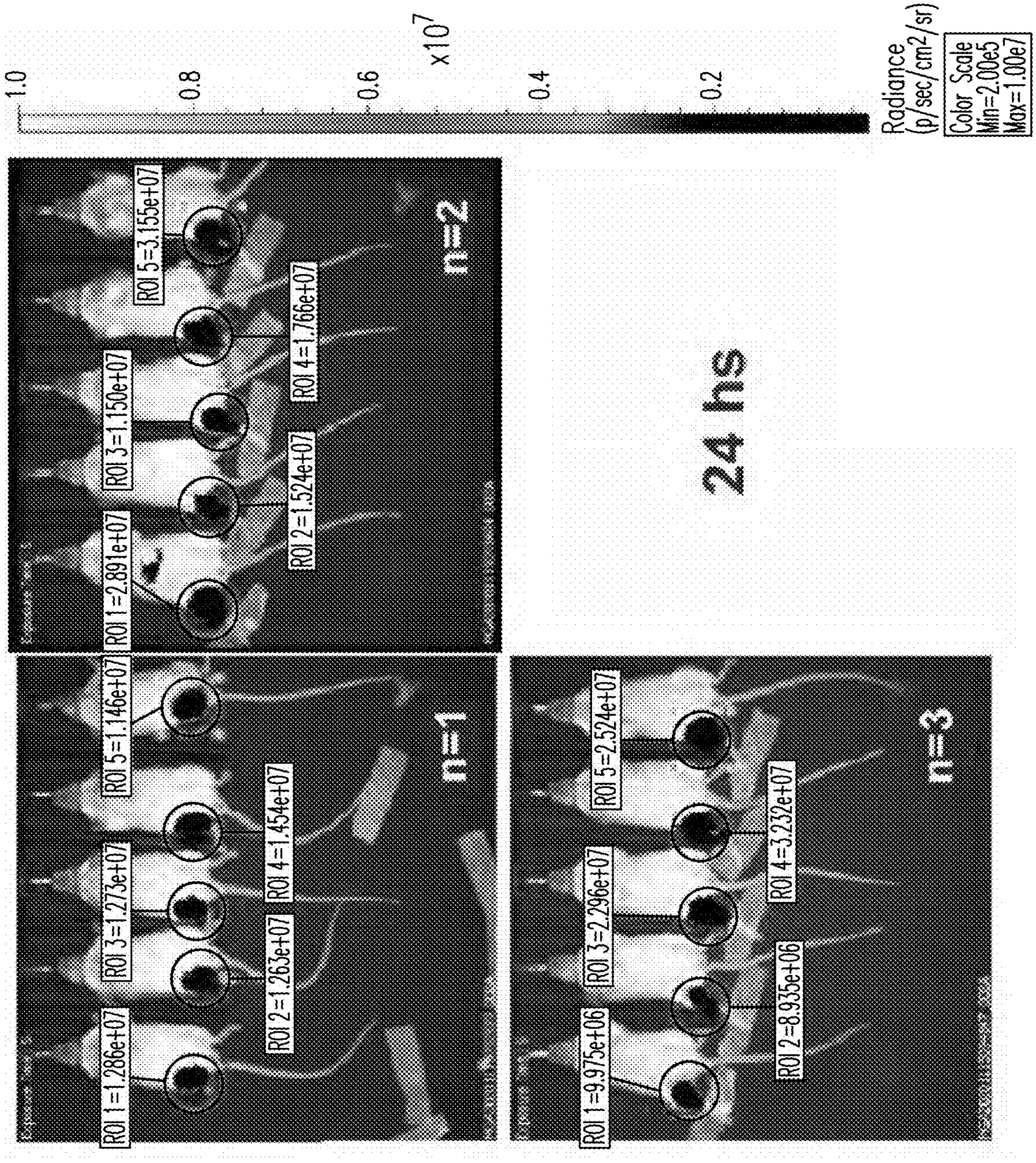
Figure 57D:
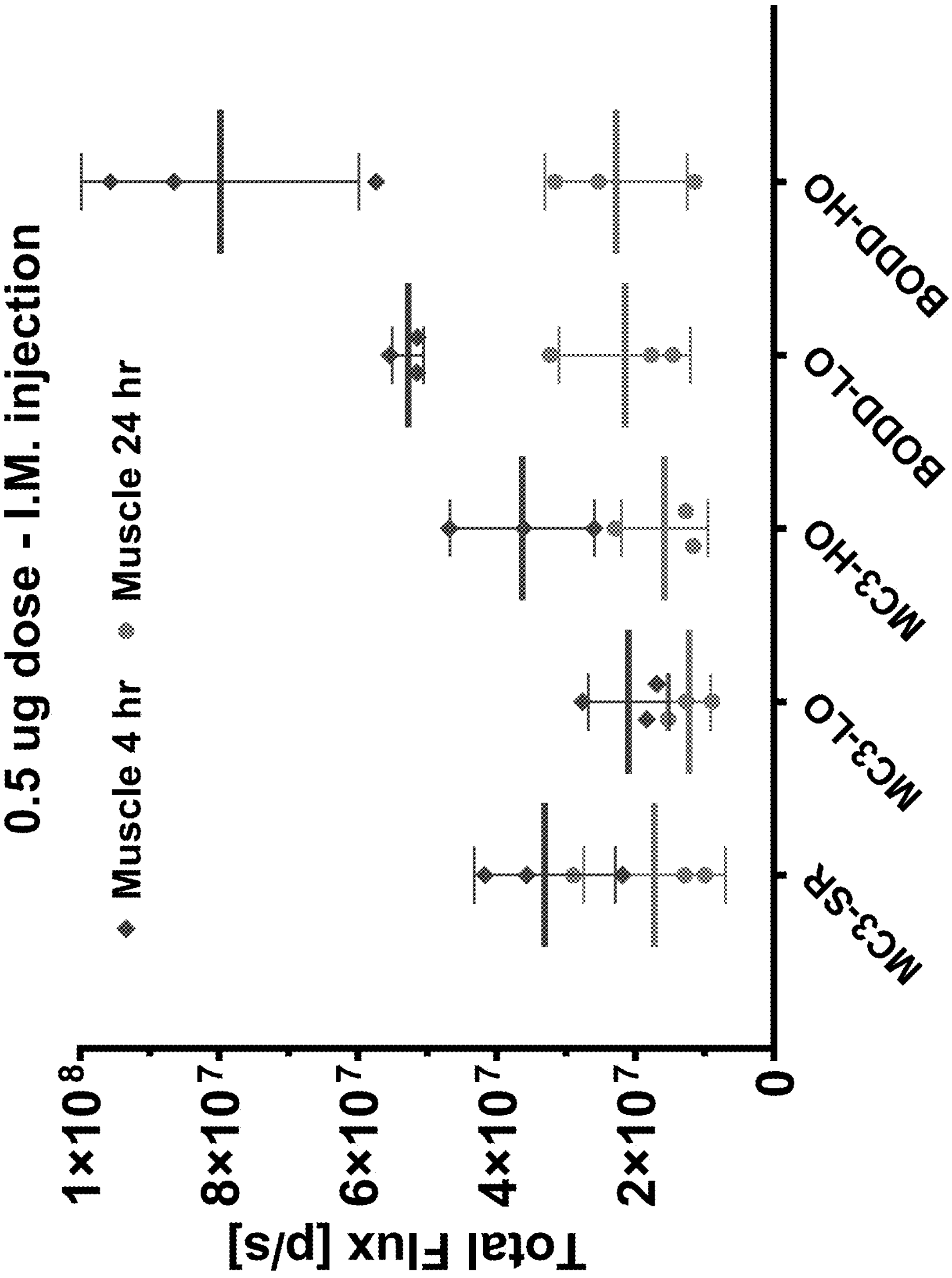
Figure 57E:
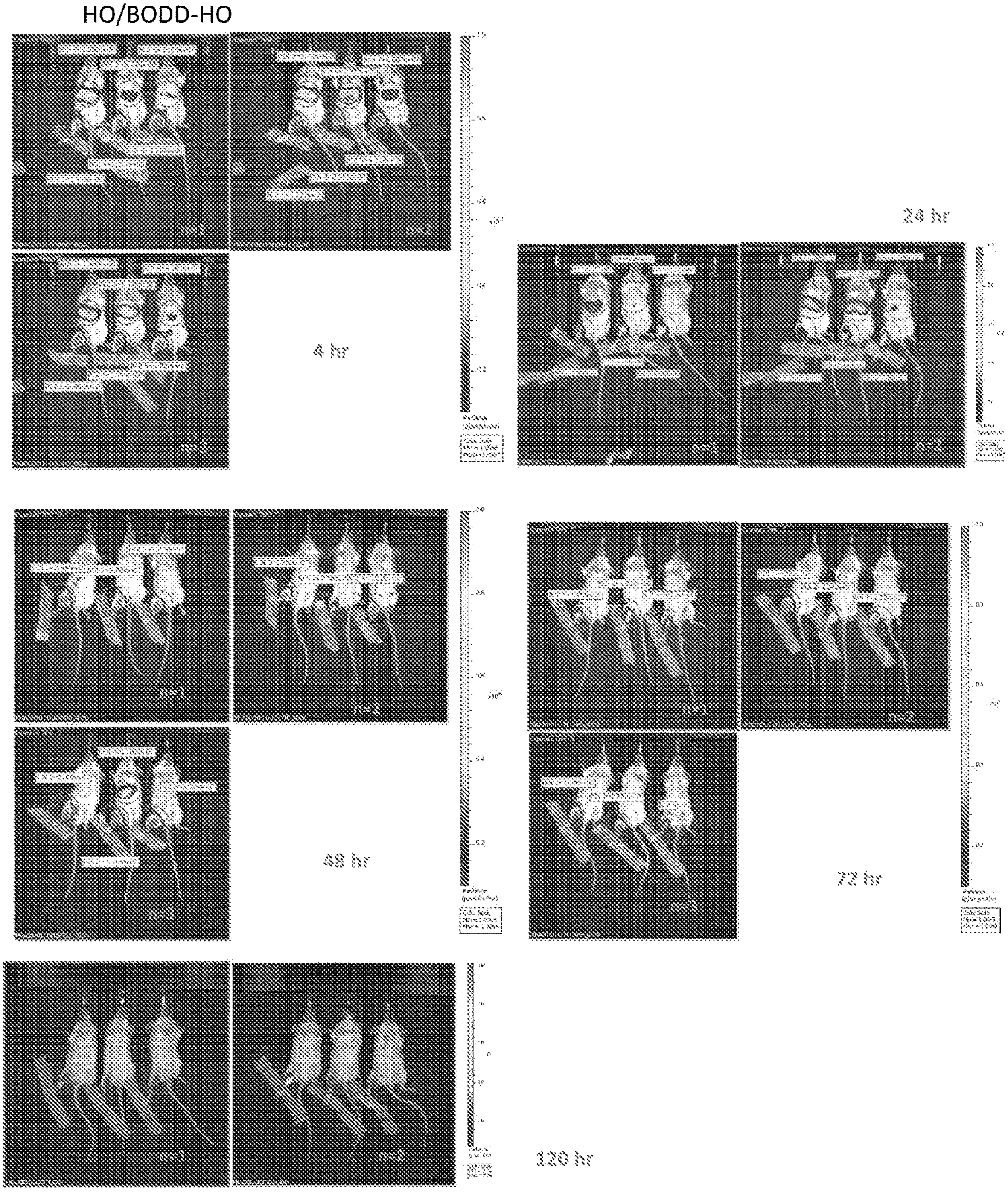
Figure 57F:
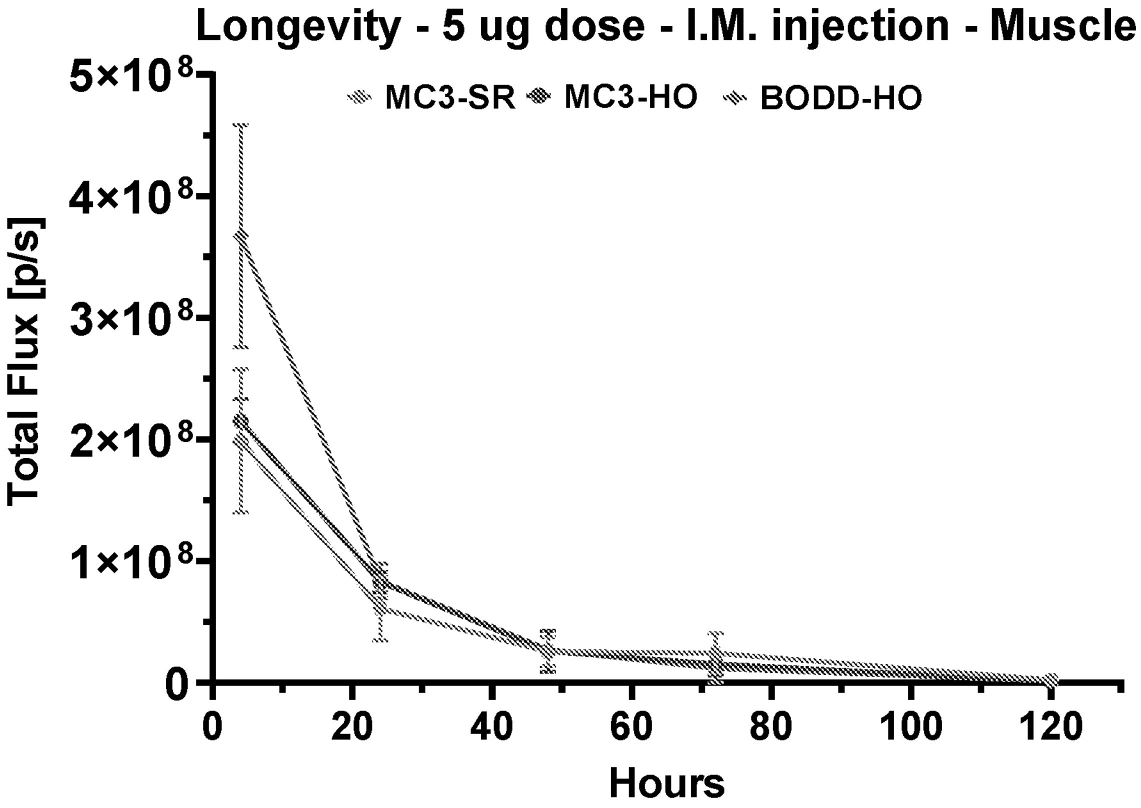
Figure 57H:
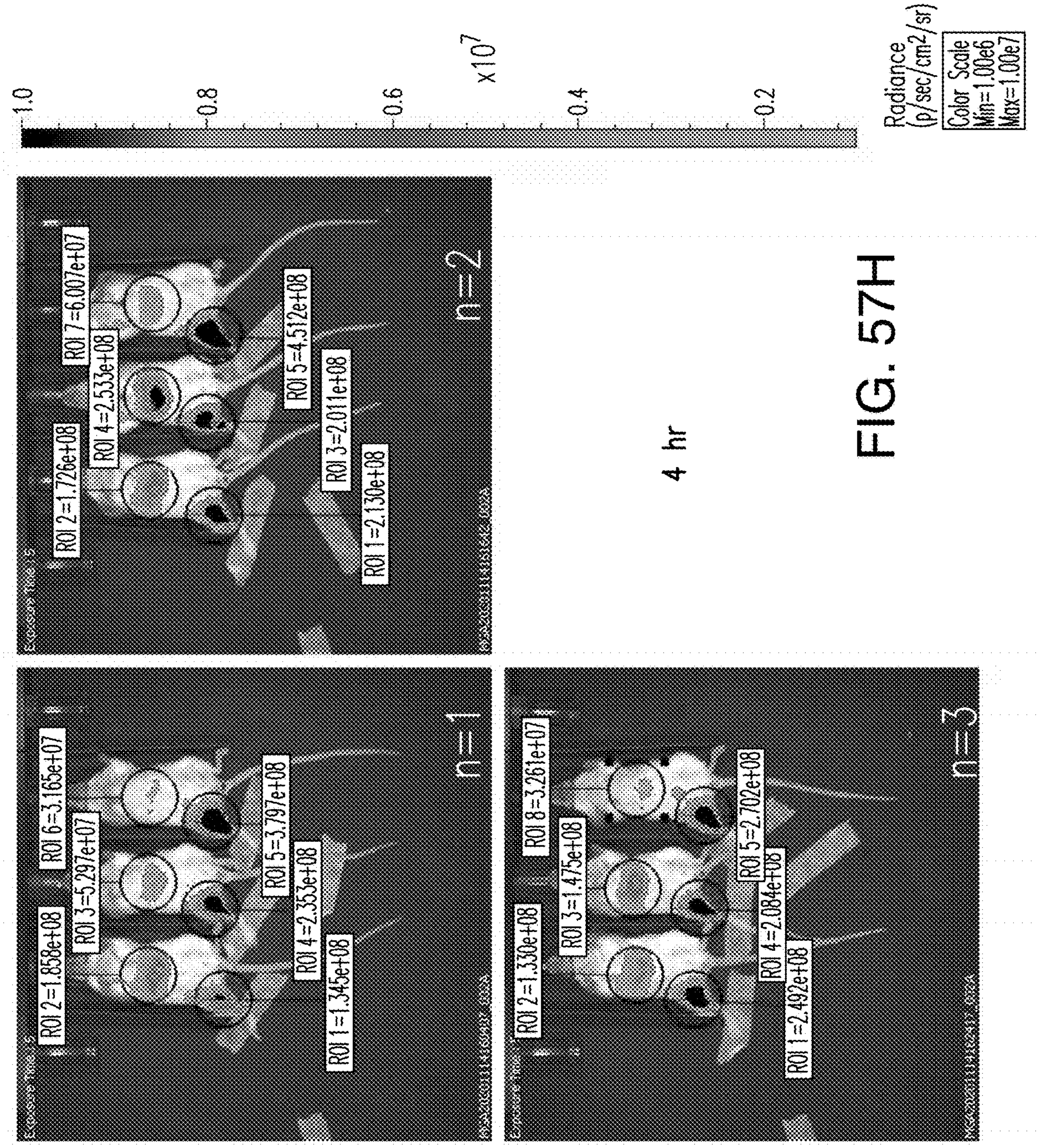
Figure 57H:
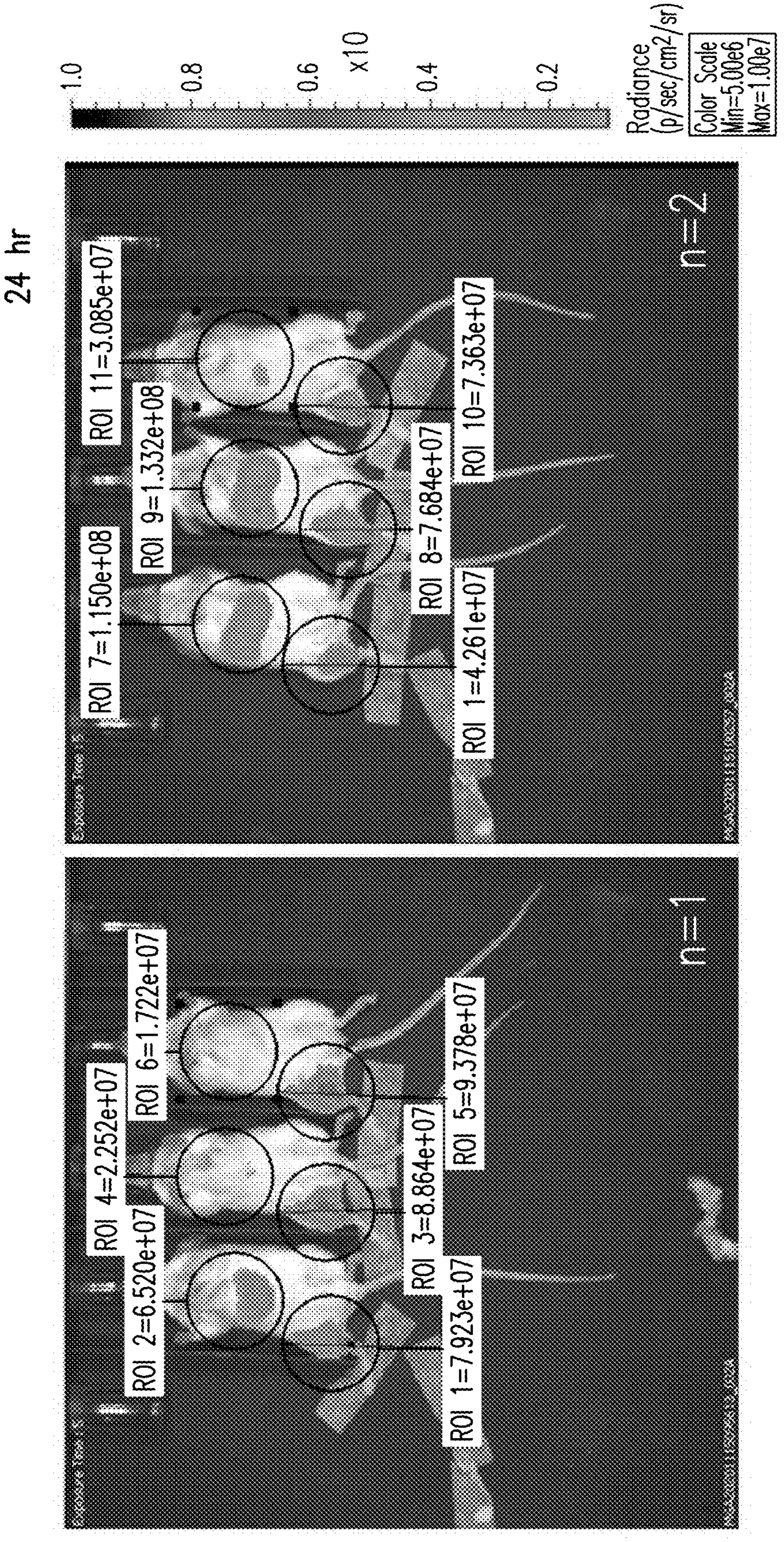
Figure 57H:
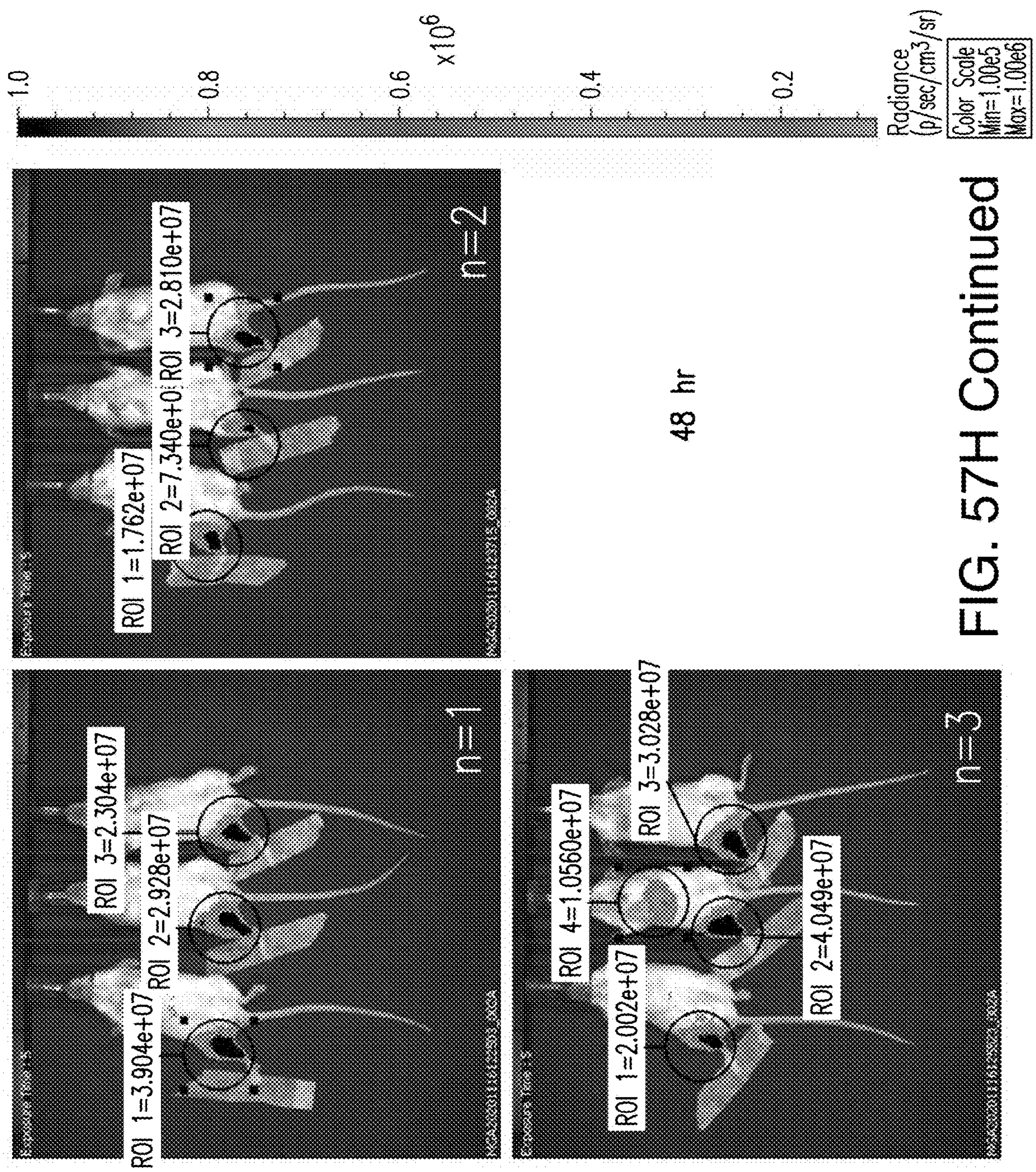
Figure 57H:
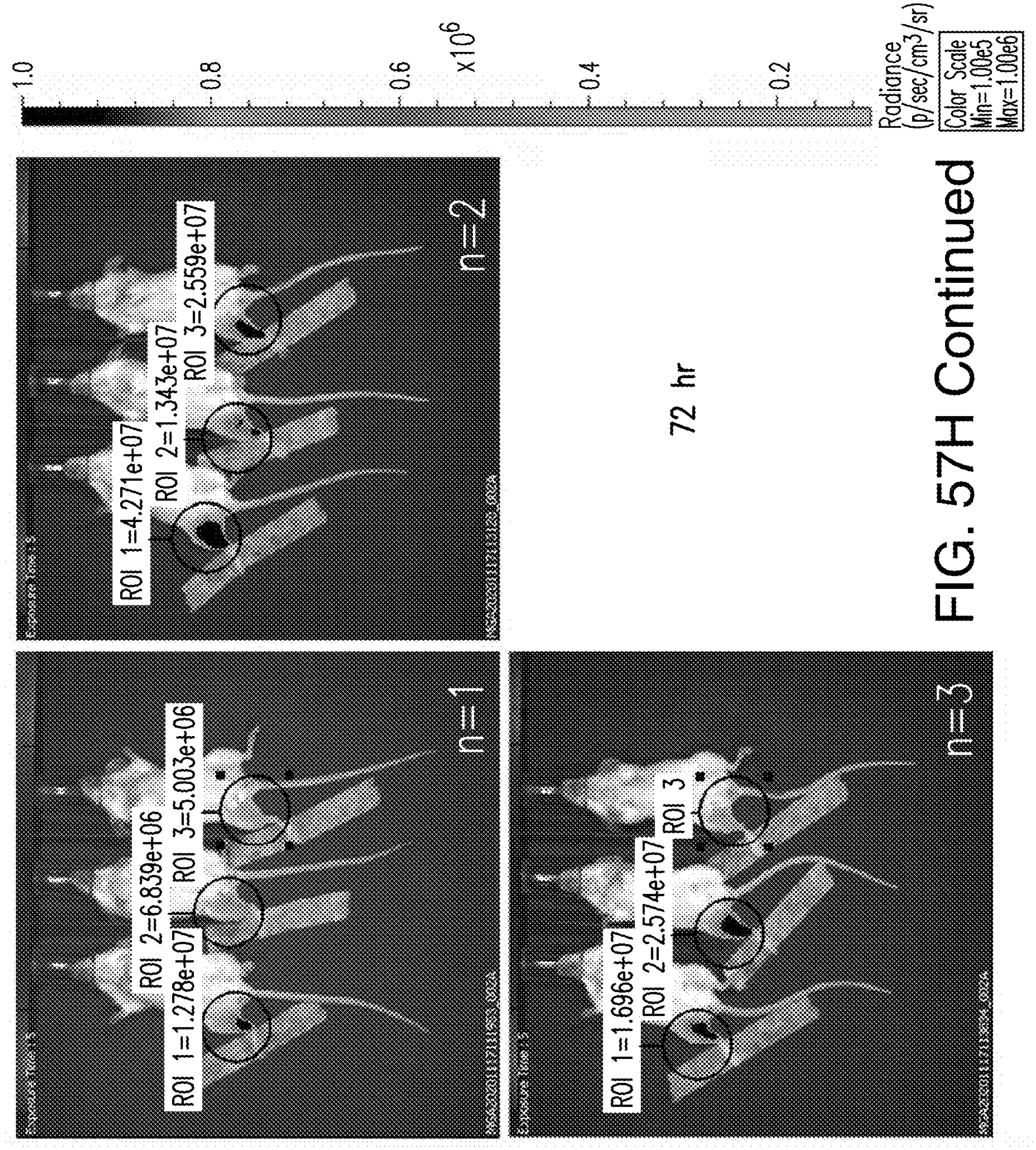
Figure 57H:
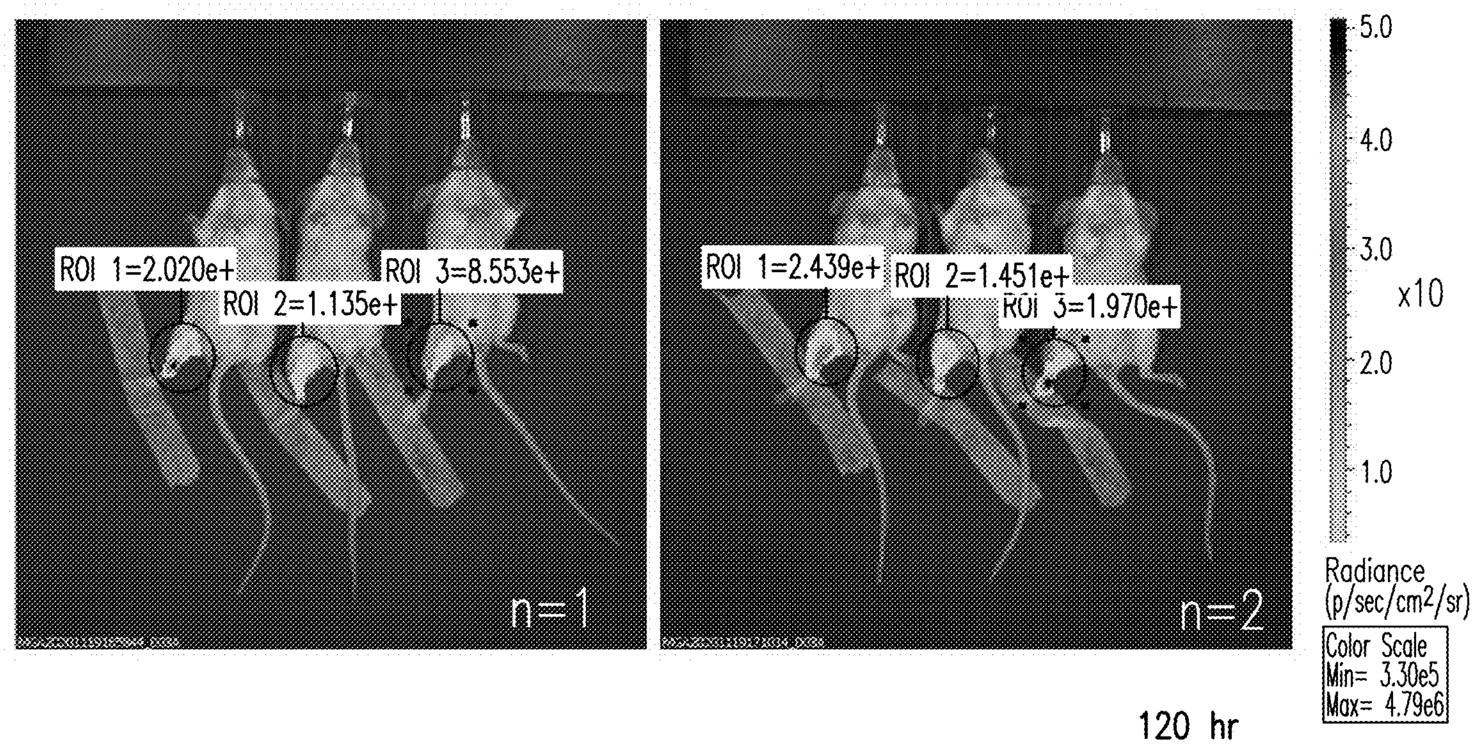
Figure 57I:
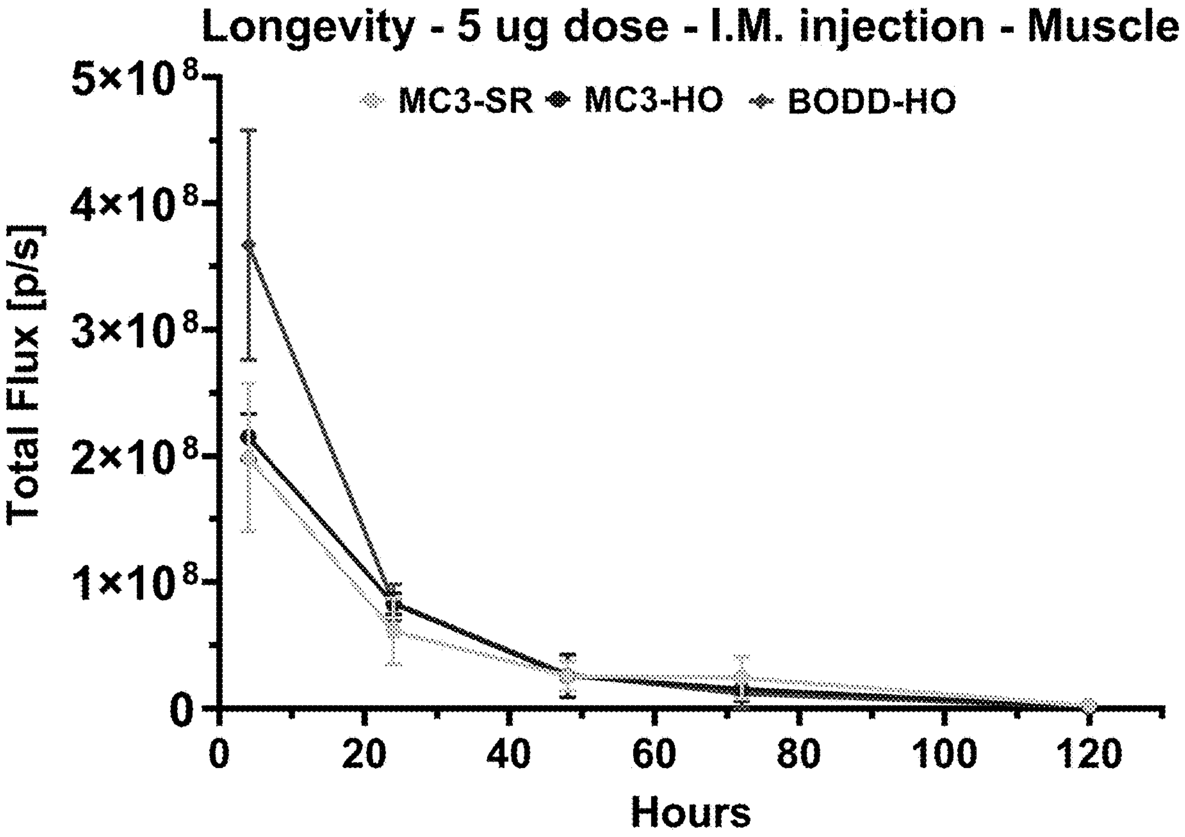

FIG. 56 illustrates a graph of Dynamic Light Scattering for LNP Size (white dots are PDI right y axis) as exemplified in Example 15B FIGS. 57A-57I illustrate exemplary ionizable lipid formulation BODD C2C4 PipZ at high 1.5 mg/ml mRNA mixing concentration for Rapid Microfluidic Mixing showing high delivery efficiency and potency in vivo versus reference lipid MC3 at standard mixing concentration 0.2 mg/ml.

Figure 58A:
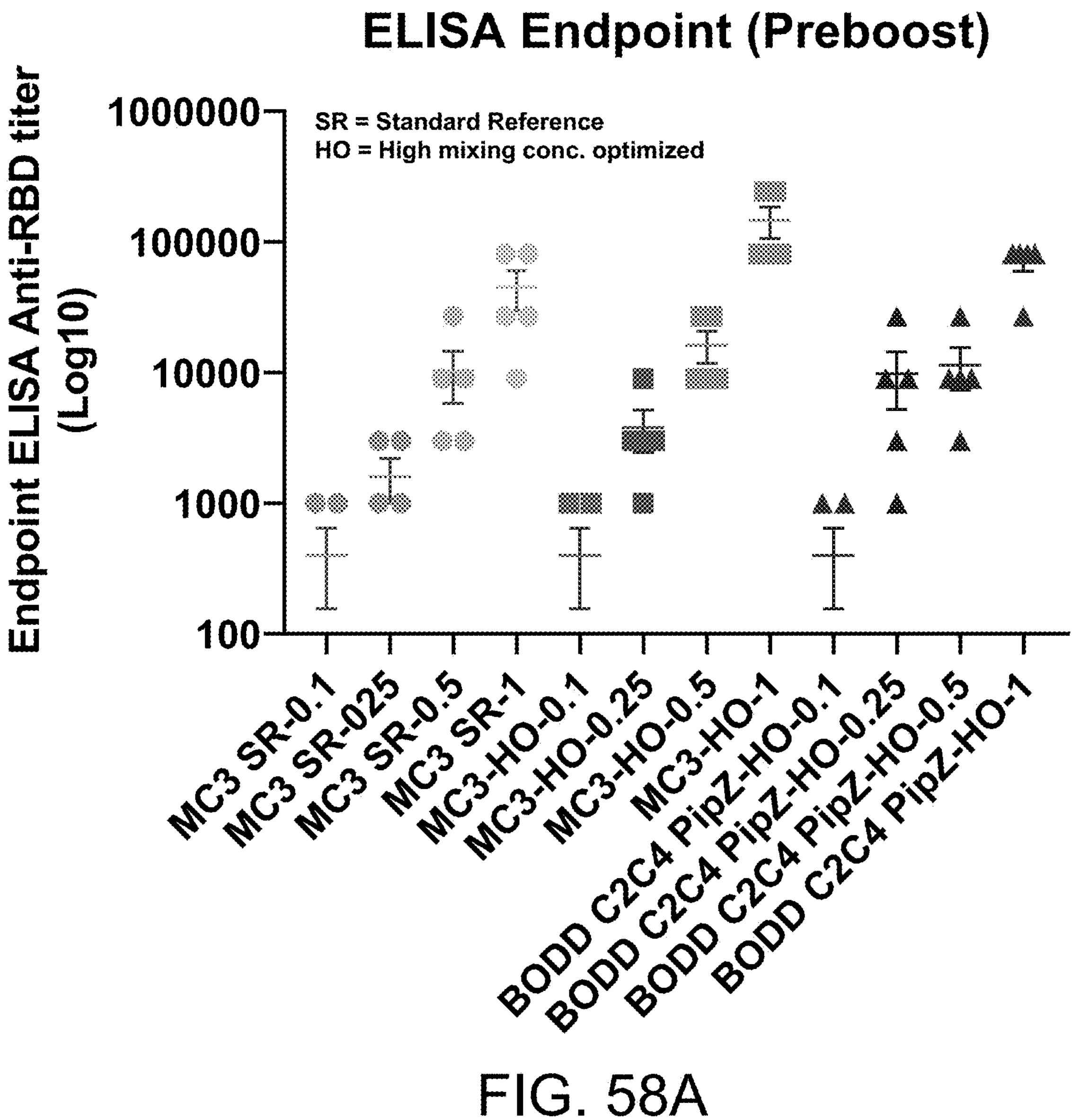
Figure 58B:
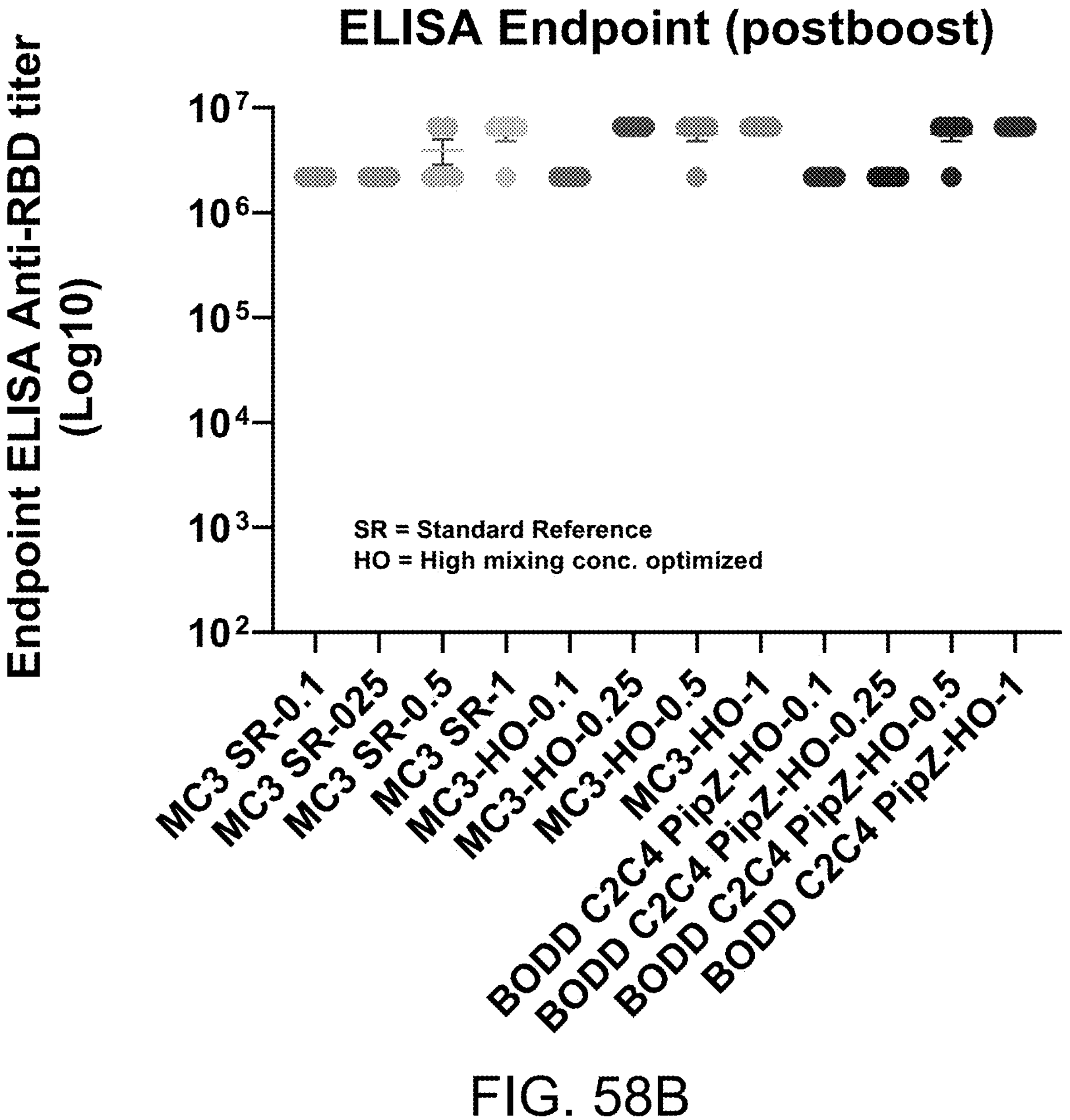

FIG. 58 illustrates In vivo immunogenicity Endpoint ELISA Anti-RBD titers as exemplified in Example 16A—FIG. 58A (PREBOOST), FIG. 58B (POSTBOOST).

Figure 59:
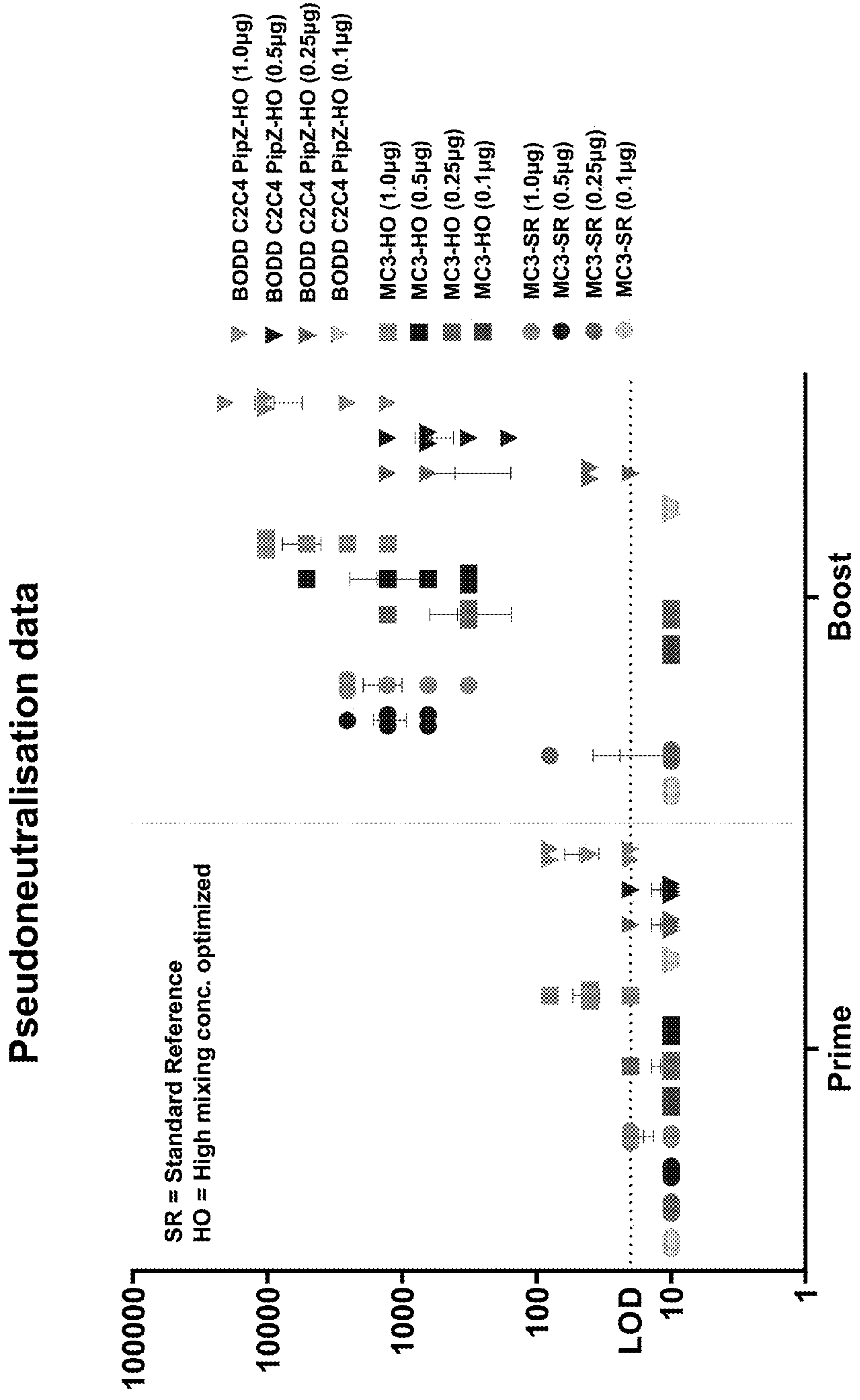

FIG. 59 illustrates In vivo immunogenicity FRNT50 titer for Psuedoneutralisation assay as exemplified in Example 16B.

Figure 60A:
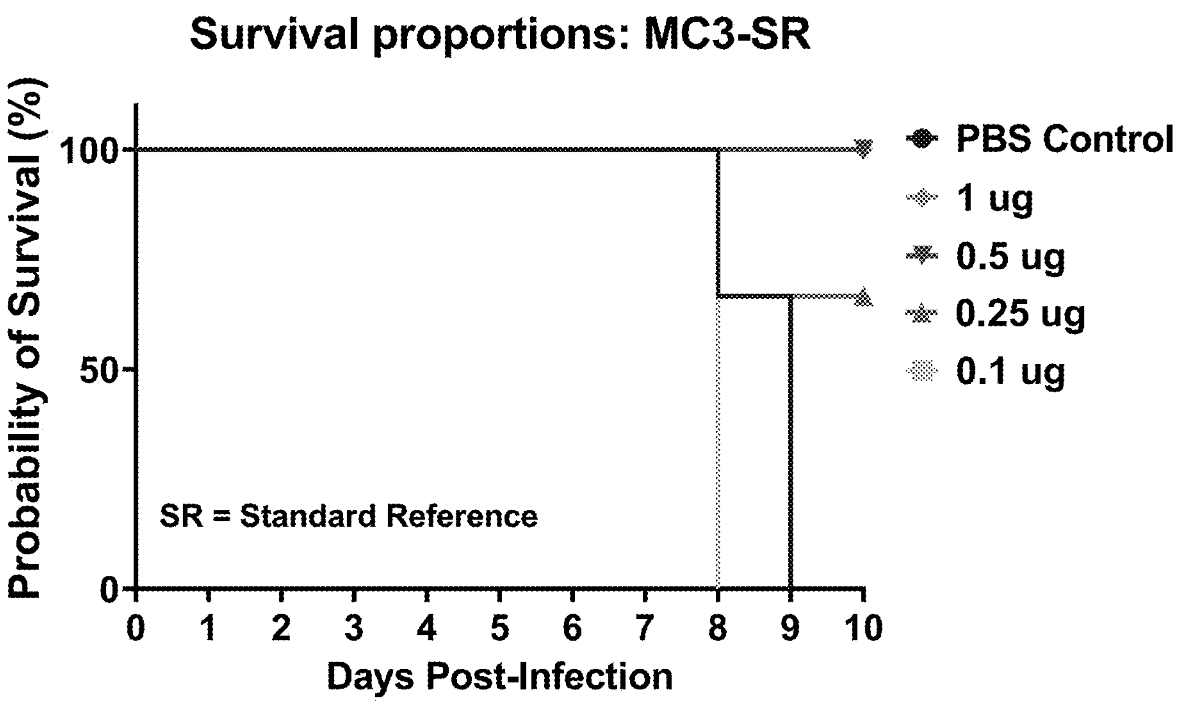
Figure 60B:
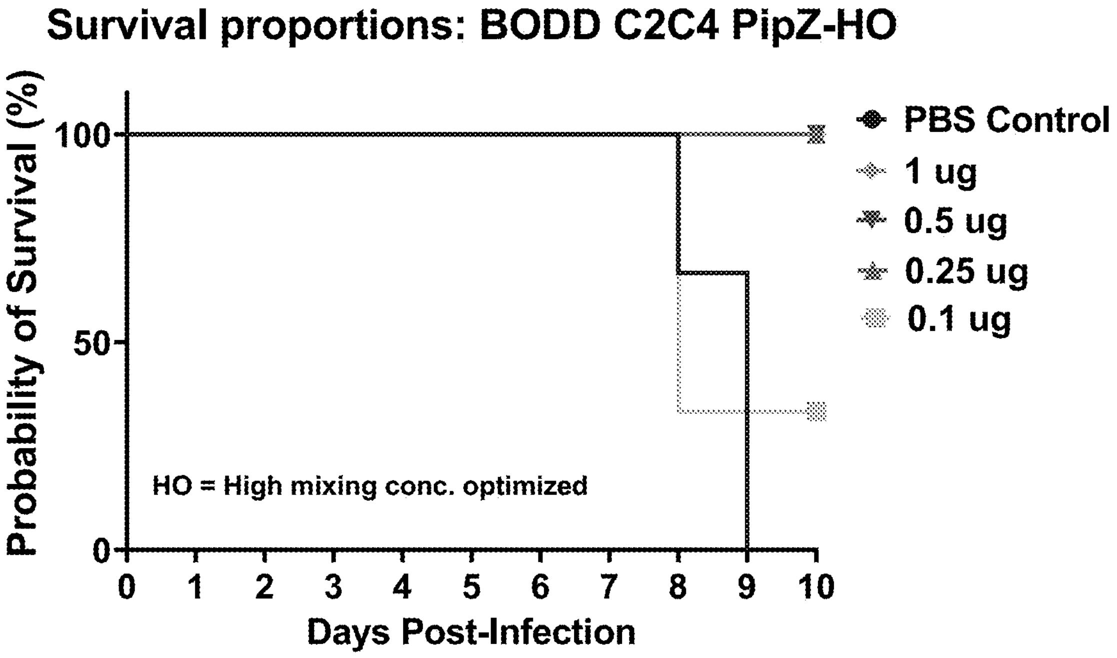
Figure 61A:
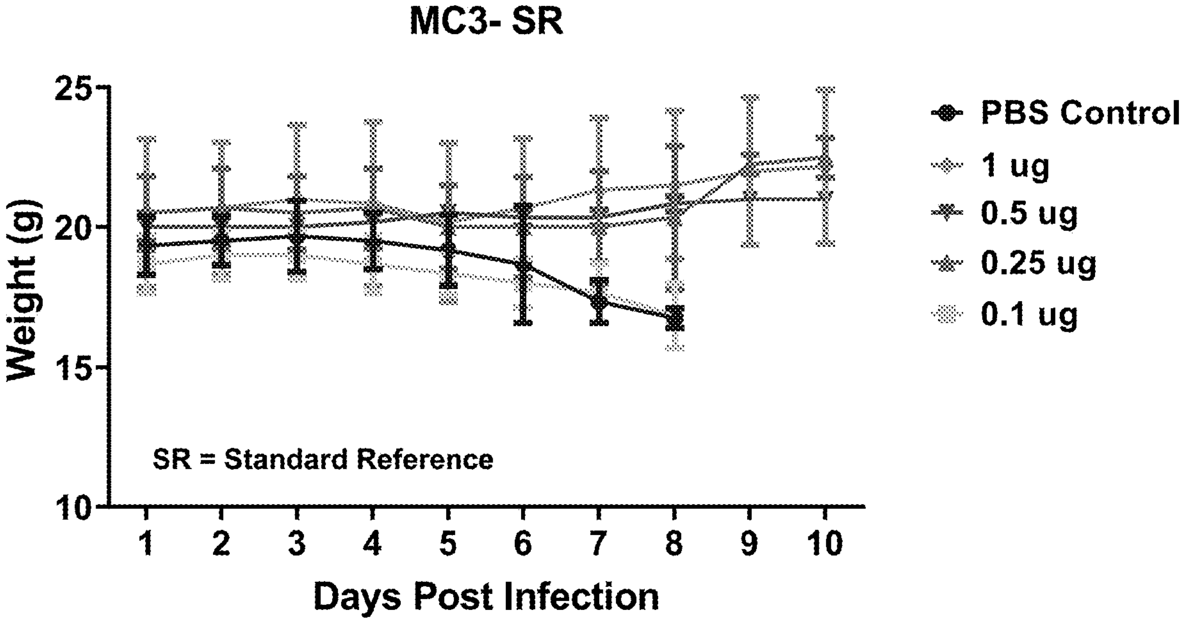
Figure 61B:
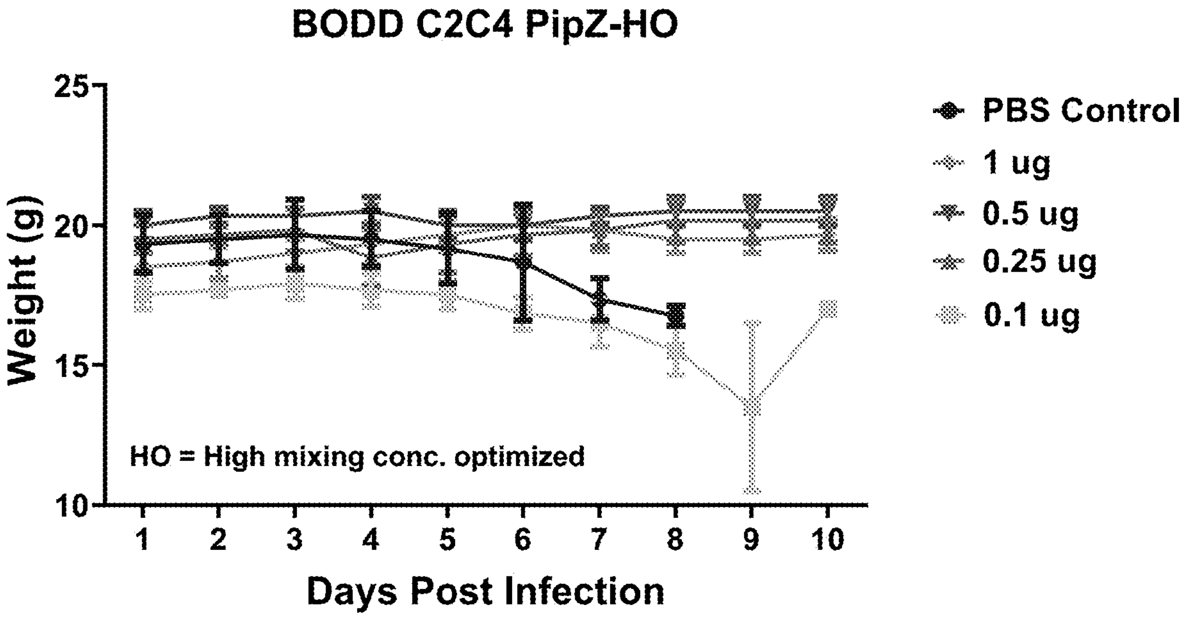
Figure 61C:
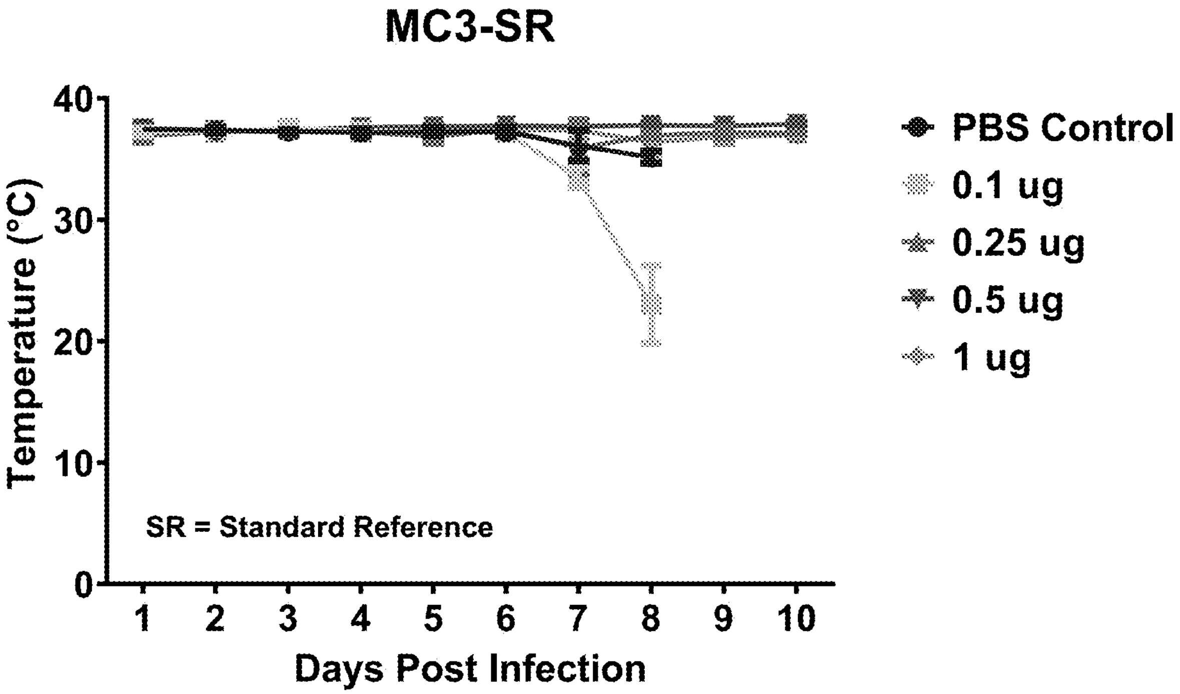
Figure 61D:
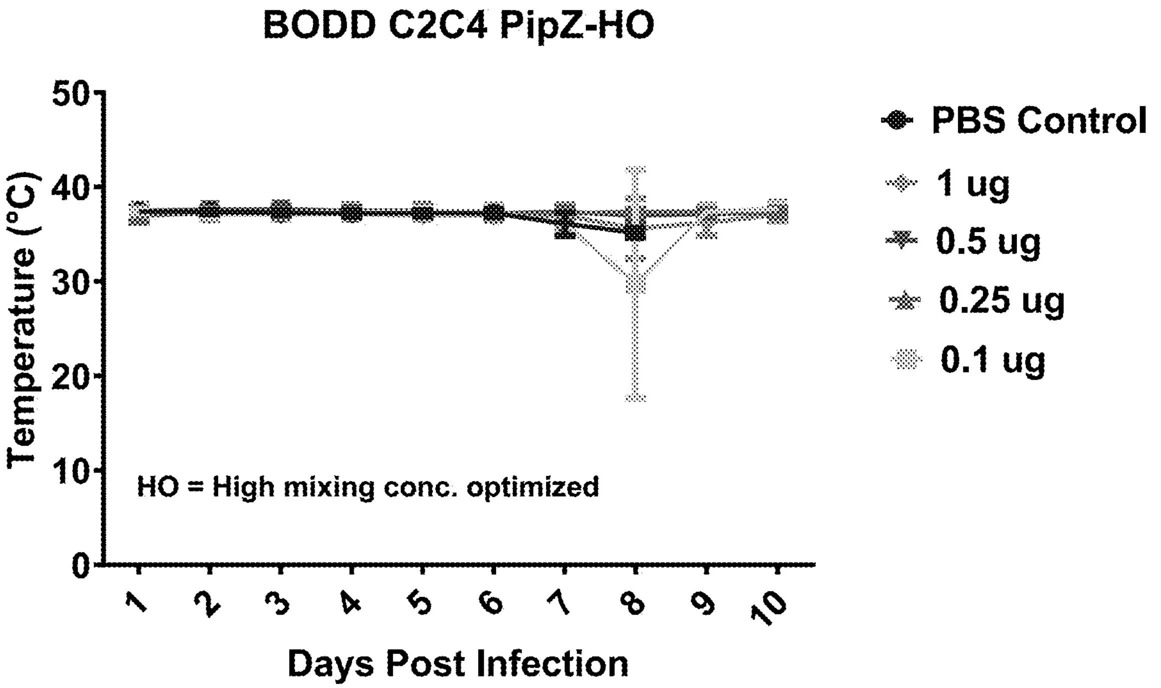

FIG. 60 illustrates In vivo protection against viral challenge—Survival proportion, Weight and Temperature in Challenge model as exemplified in Example 17A; FIG. 60A (SURVIVAL PROPORTIONS: MC3-SR); FIG. 60B (SURVIVAL PROPORTIONS: BODD C2C4 PipZ-HO)

FIG. 61A-61D illustrate In vivo weight and temperature in Challenge model as exemplified in Example 17B.

Figure 62:
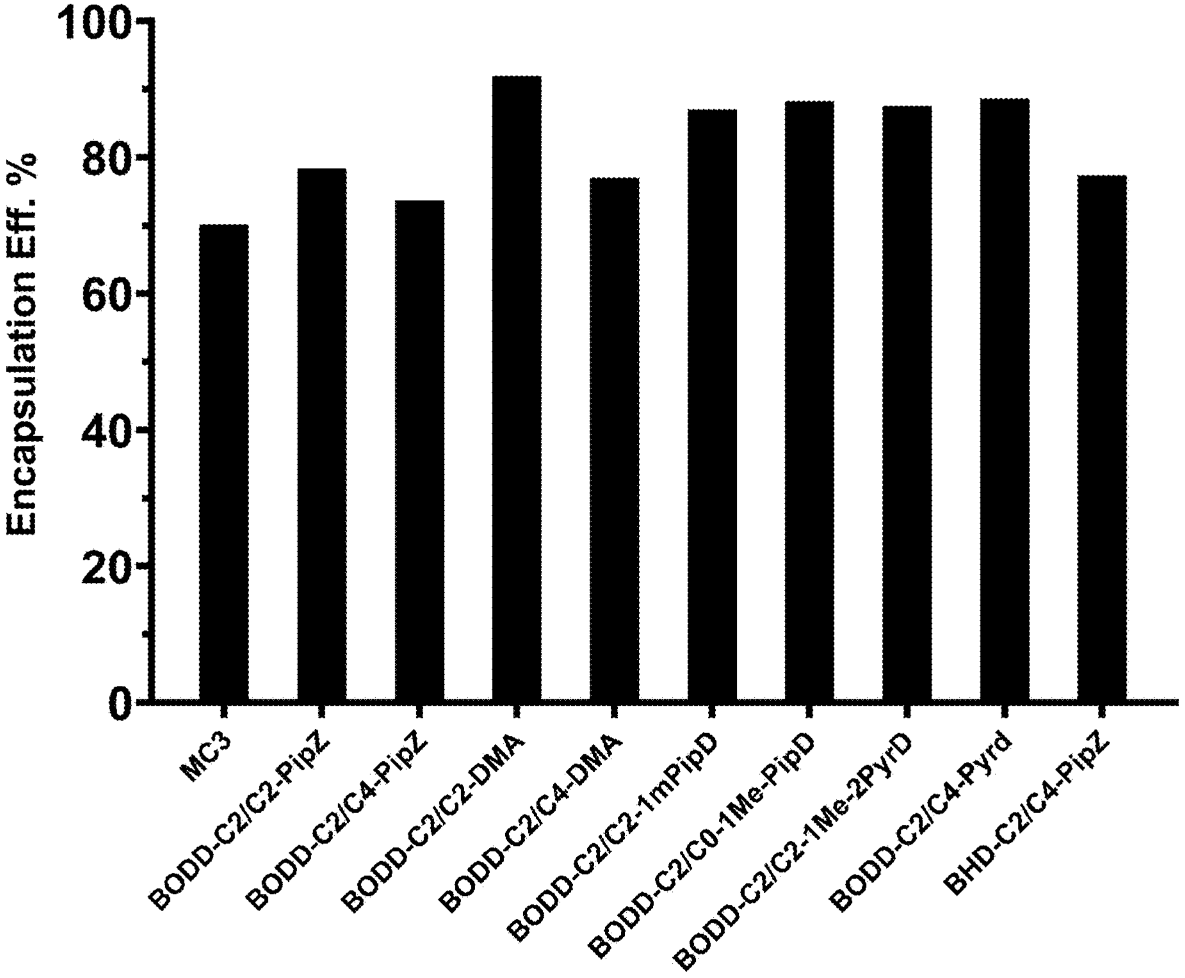

FIG. 62 illustrates a graph of Ribogreen Assay for mRNA Encapsulation Efficiency as exemplified in Example 18A.

Figure 63:
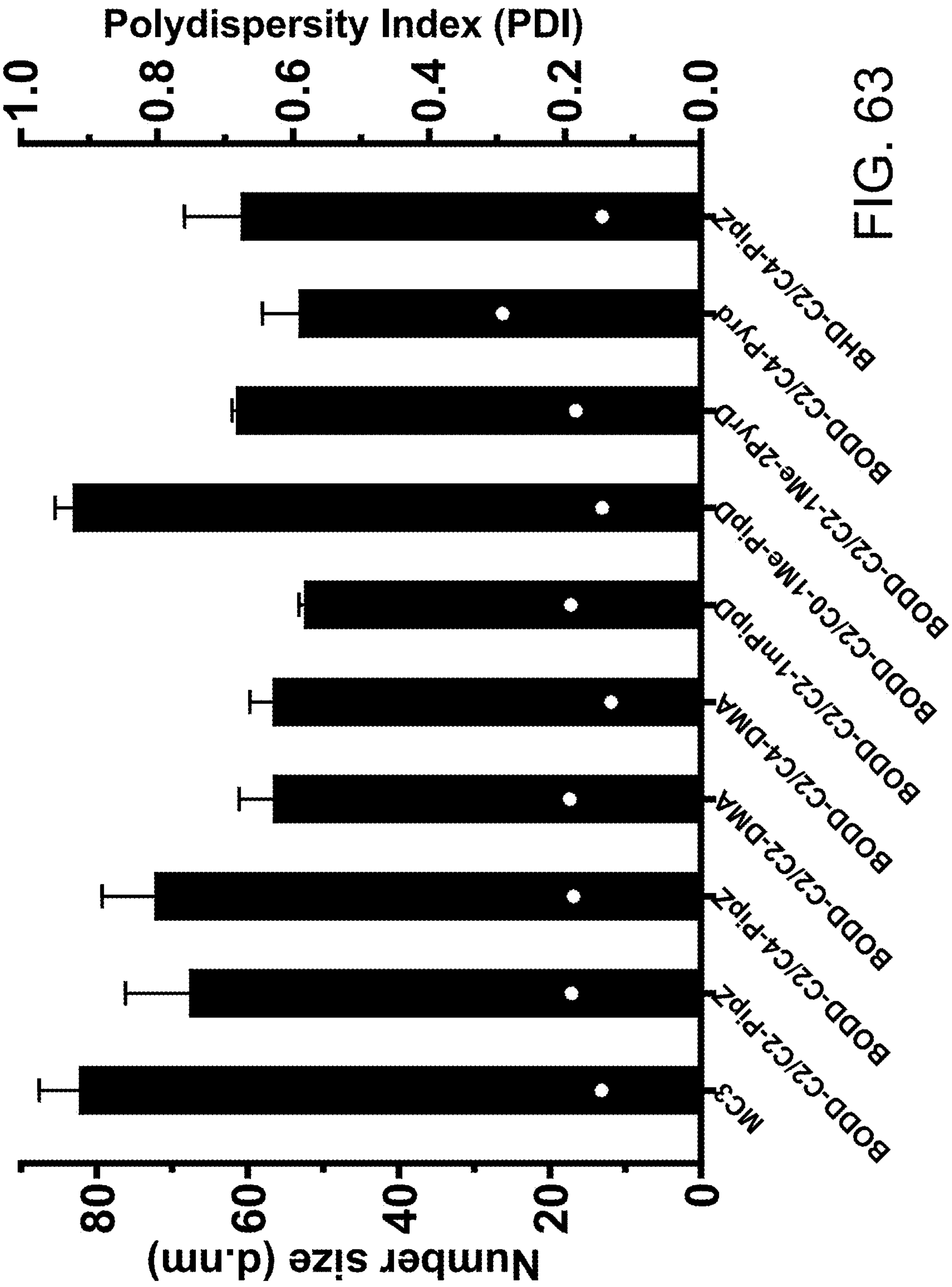

FIG. 63 illustrates a graph of Dynamic Light Scattering for LNP Size (white dots are PDI right y axis) as exemplified in Example 18B.

Figure 64A:
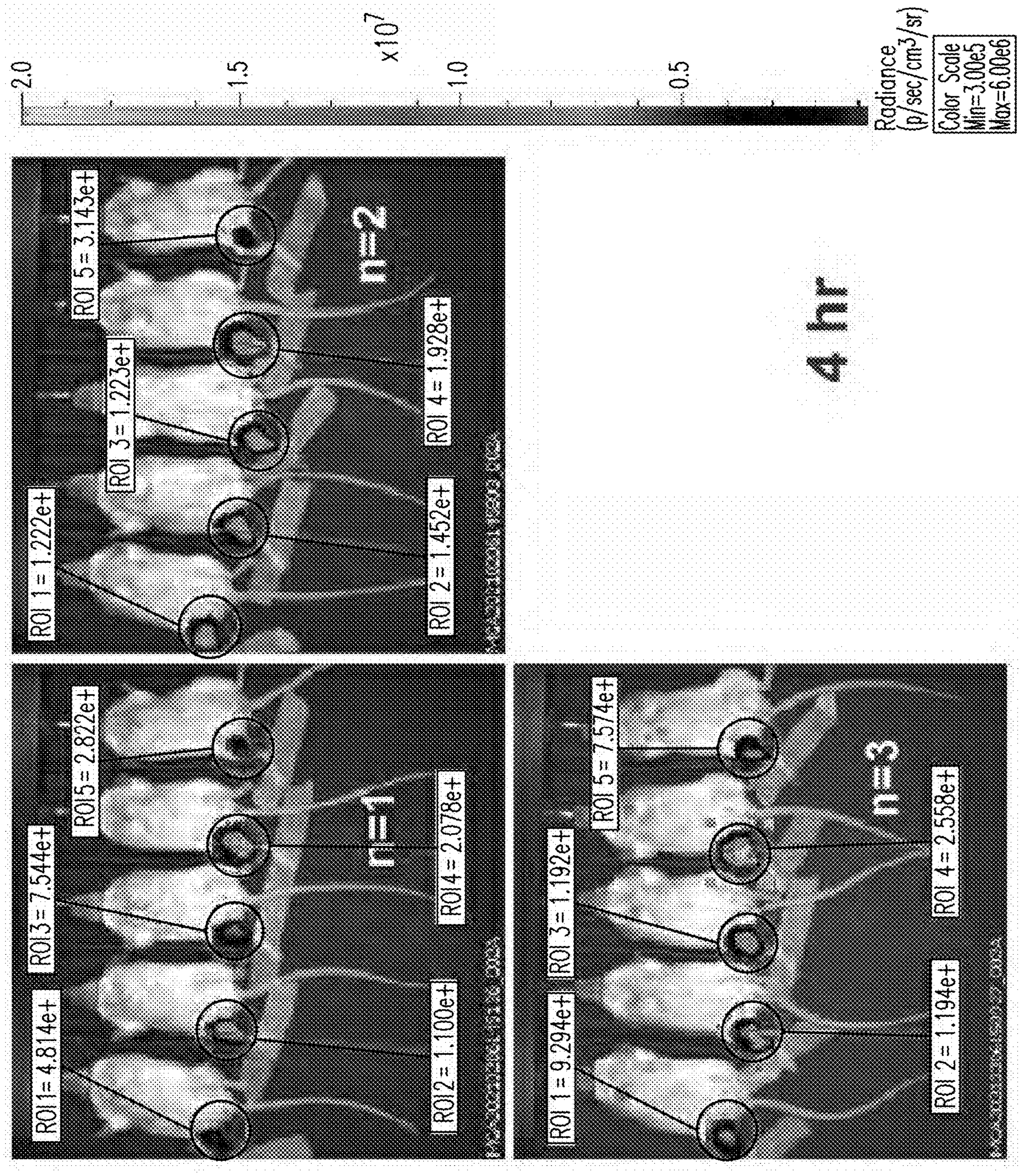
Figure 64A:
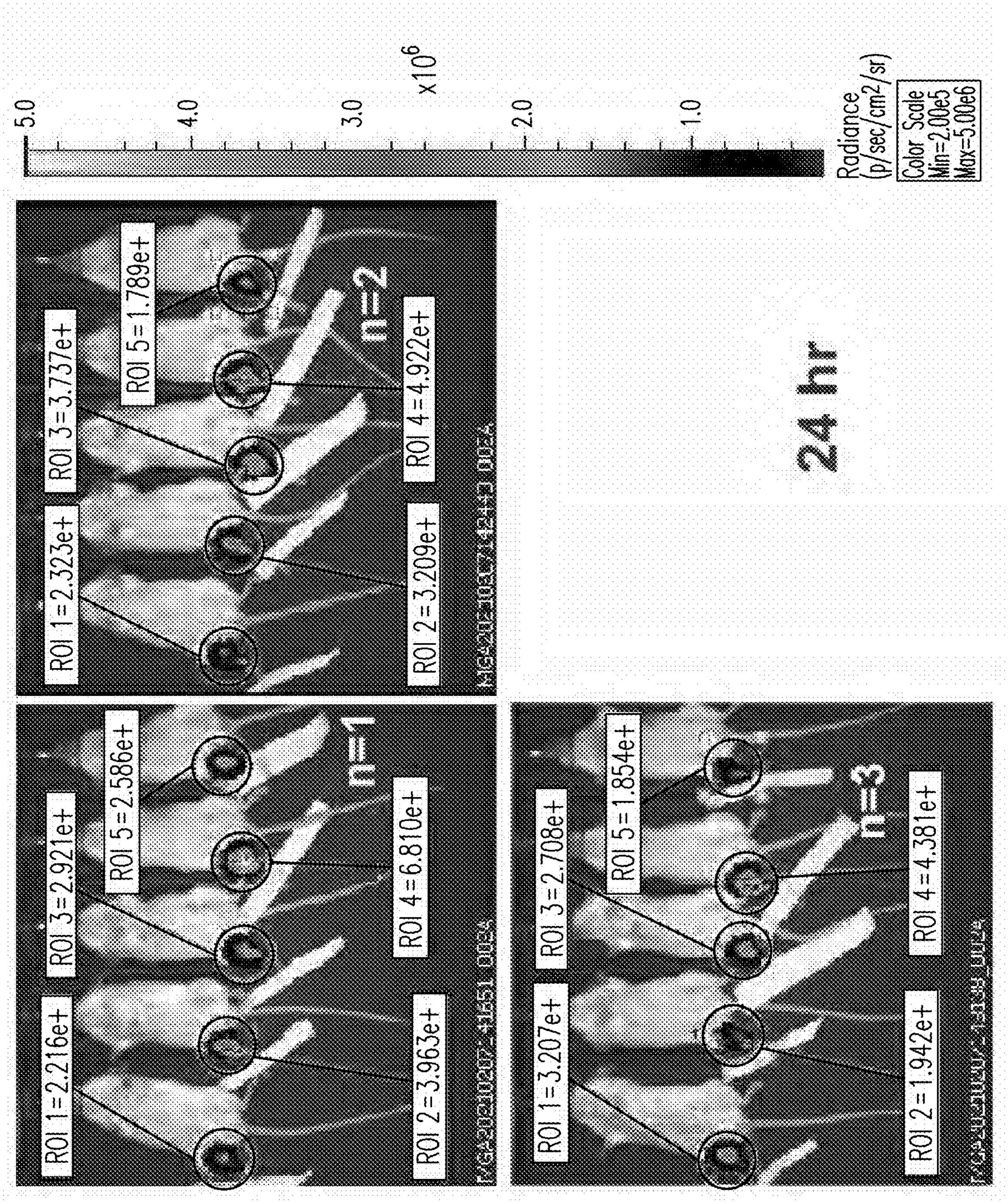
Figure 64B:
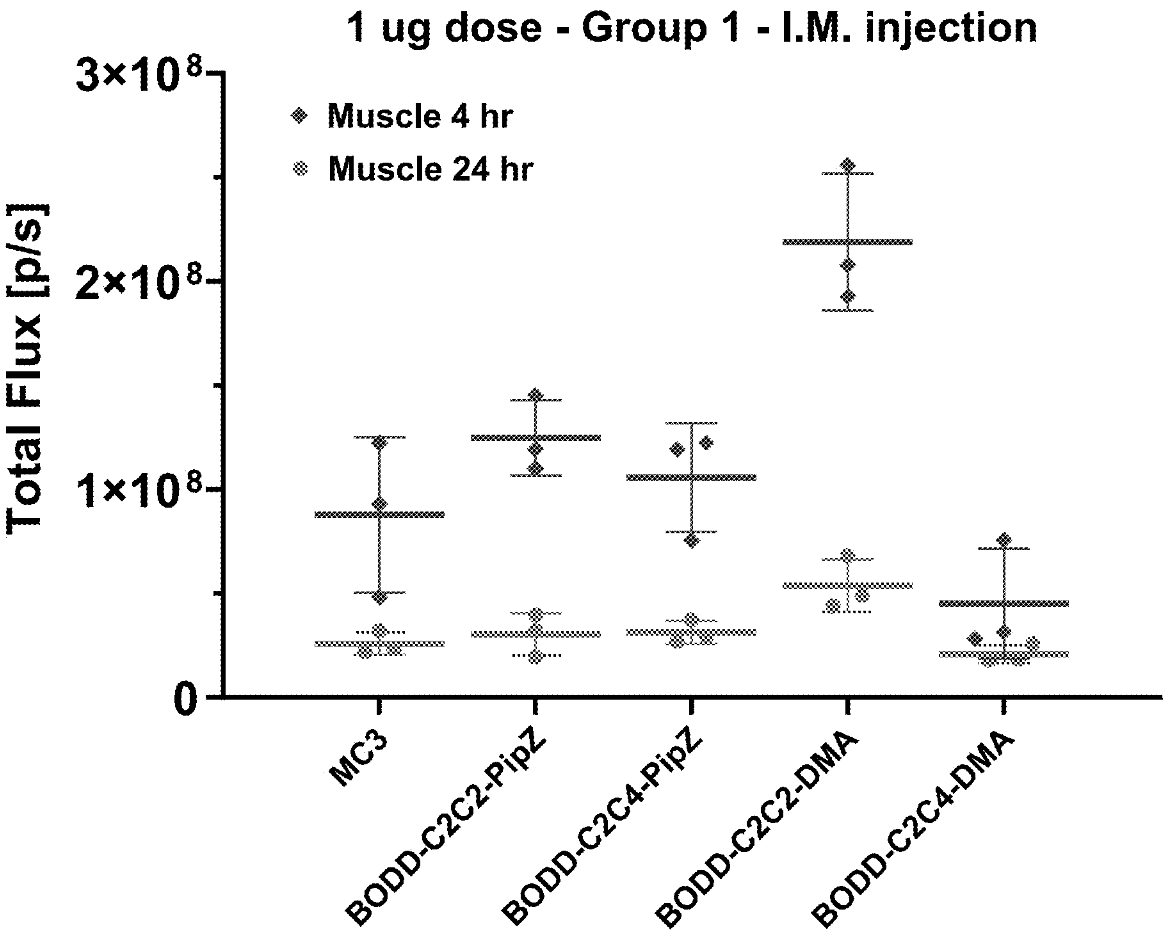
Figure 64C:
Figure 64C:
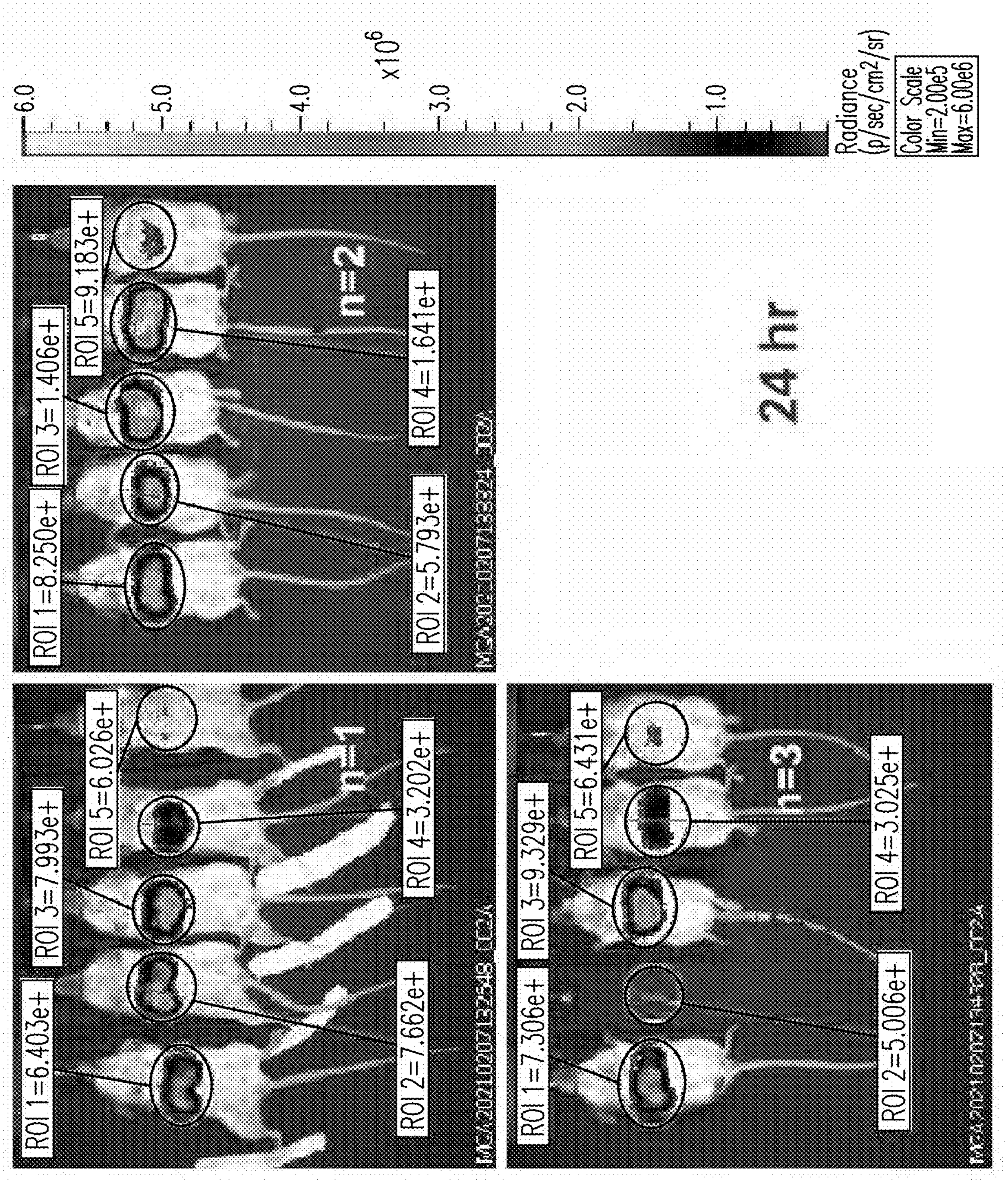
Figure 64D:
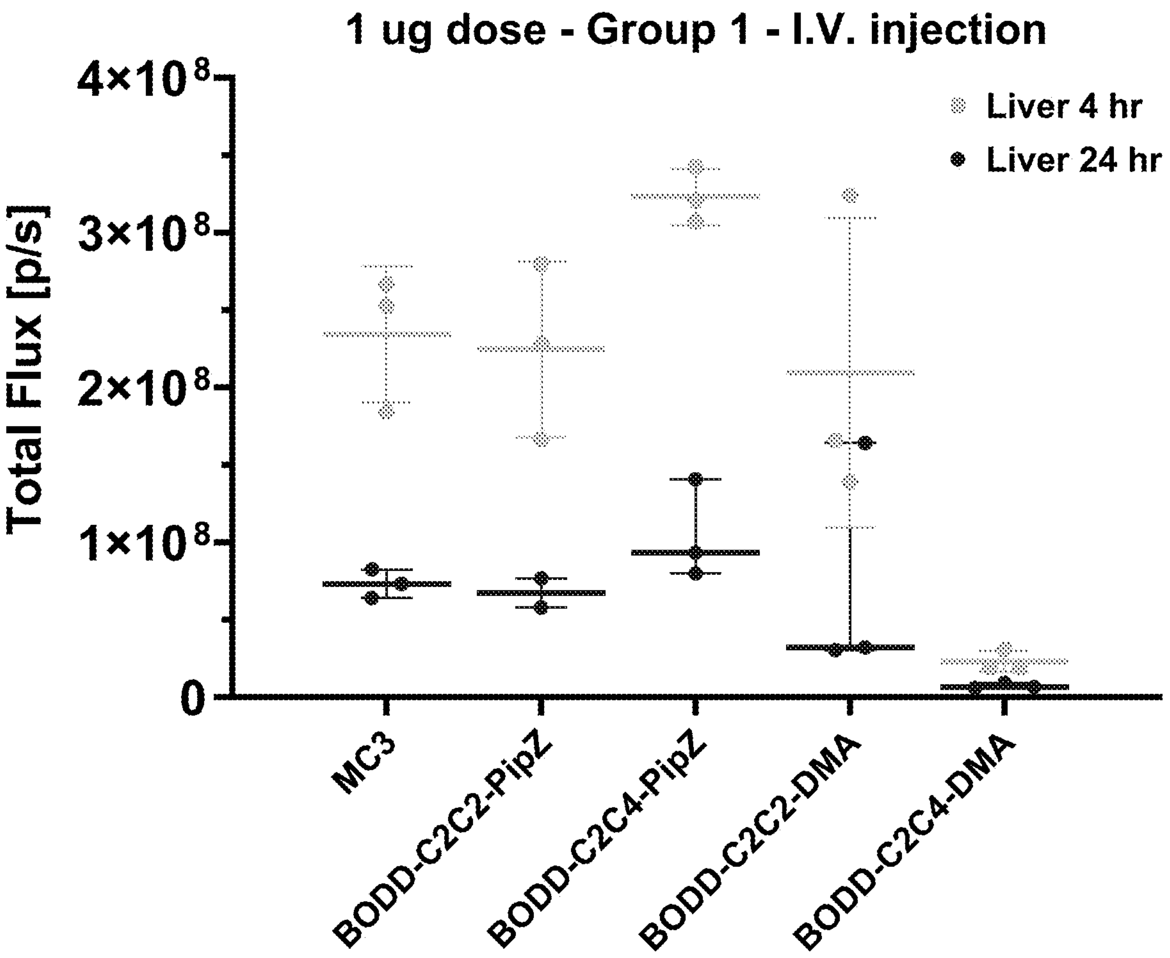
Figure 64E:
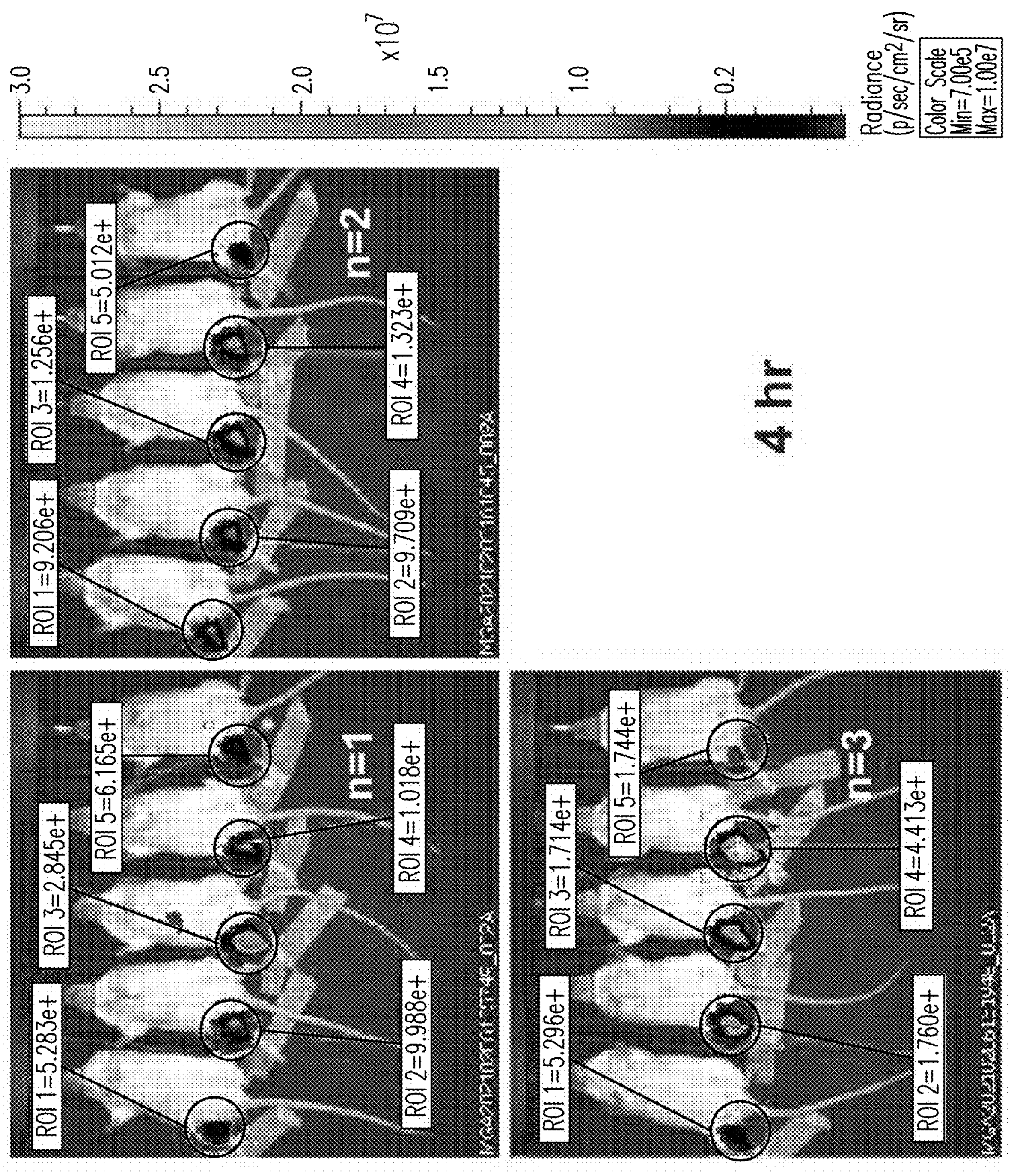
Figure 64E:
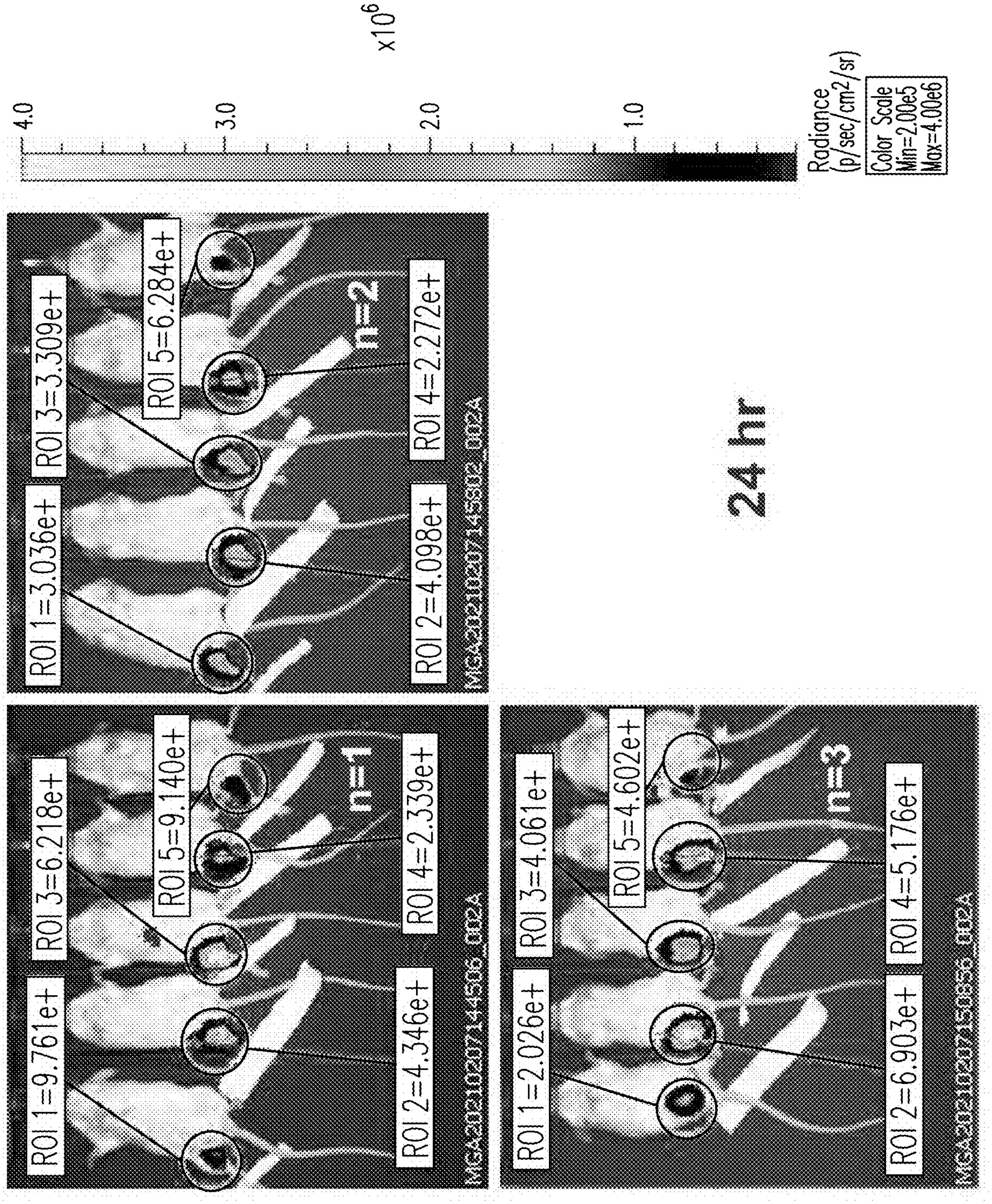
Figure 64F:
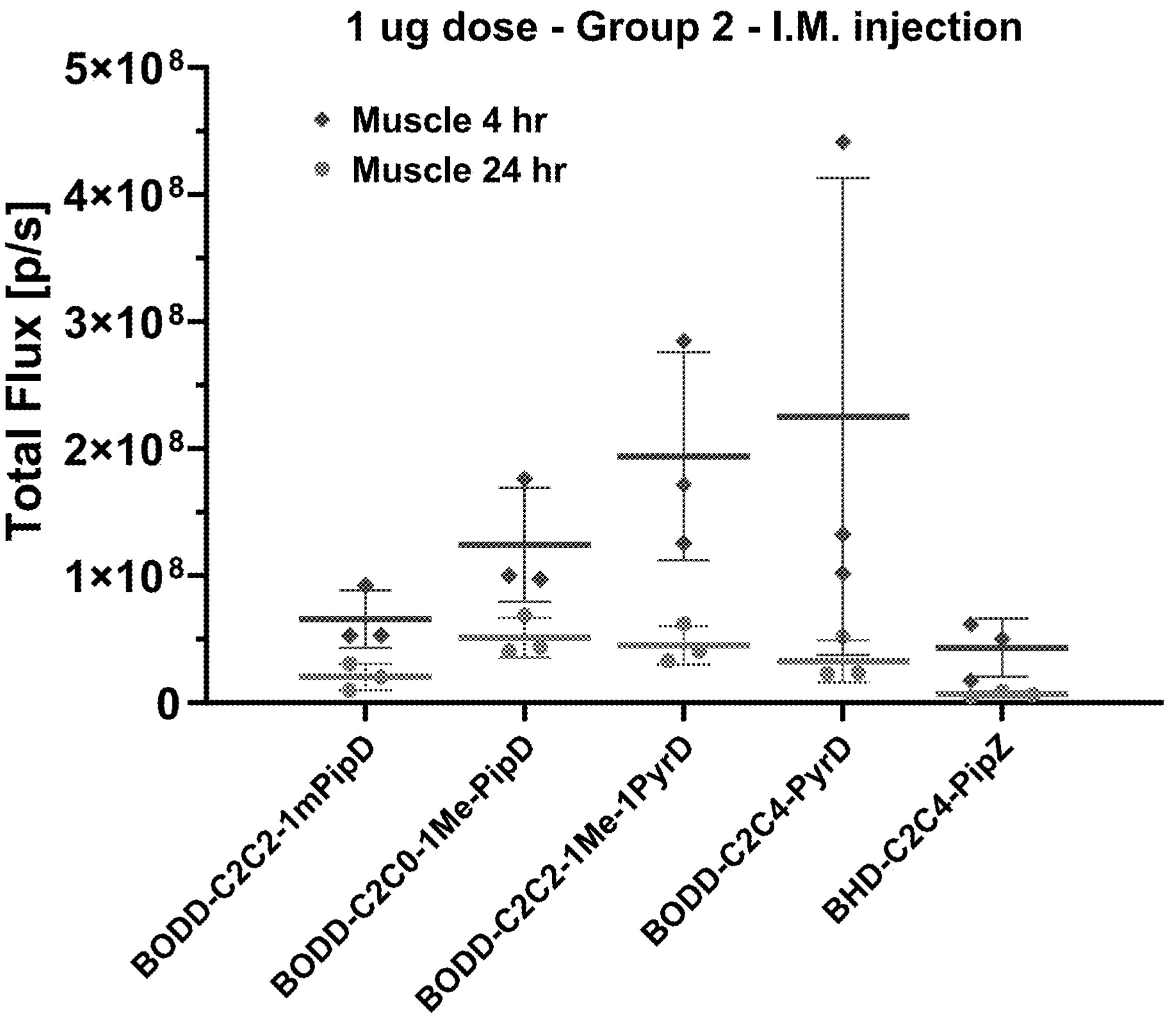
Figure 64G:
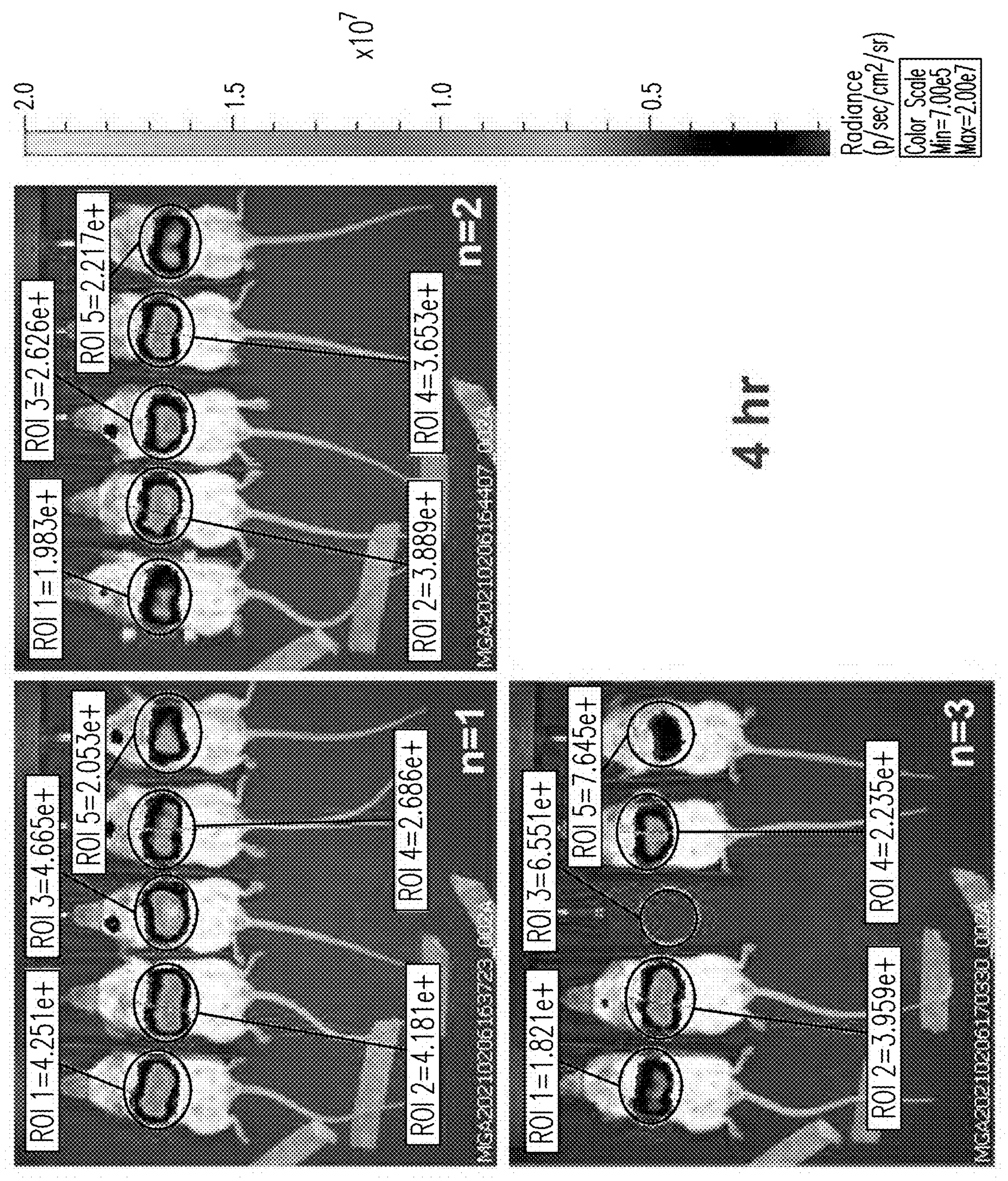
Figure 64G:
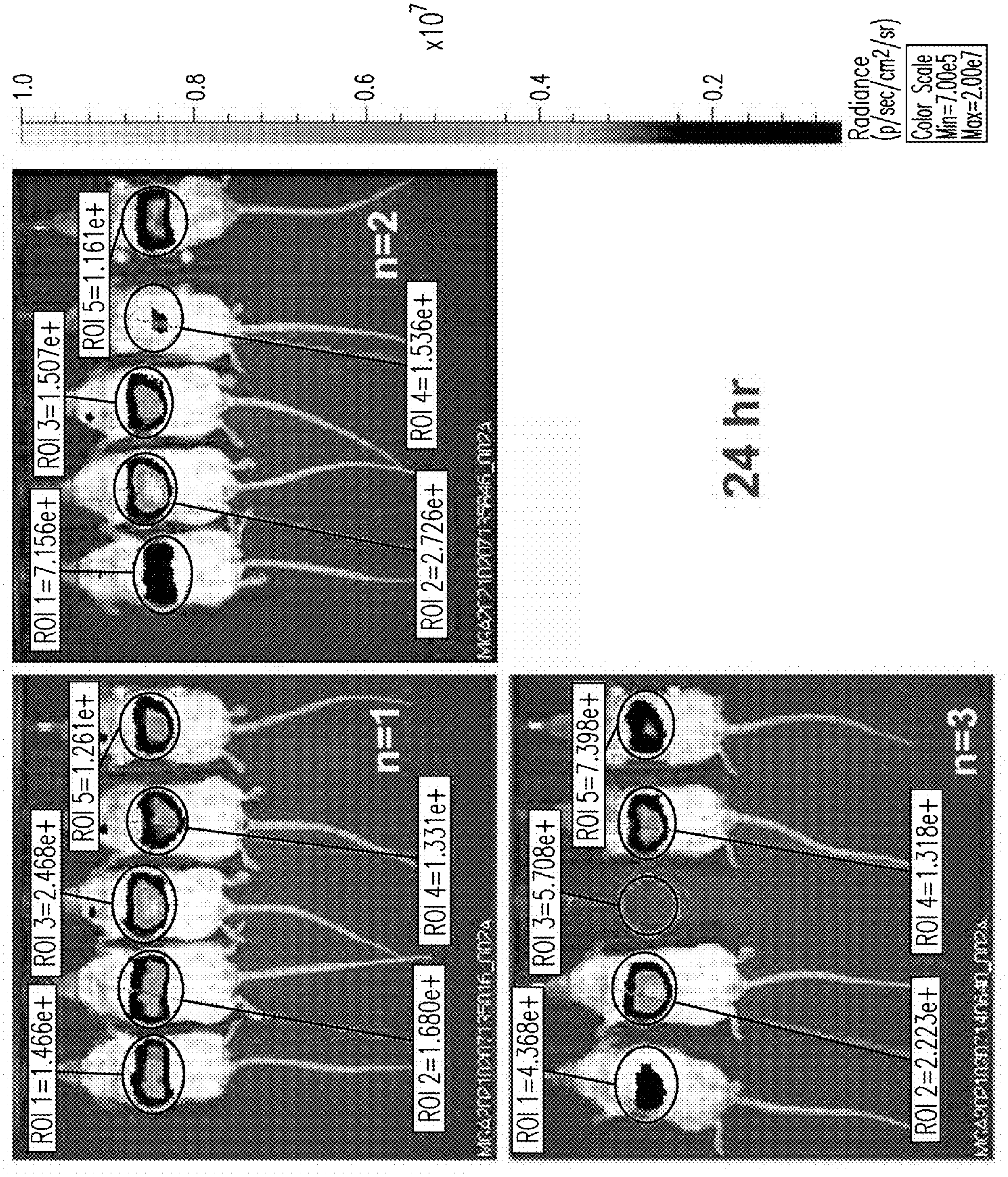
Figure 64H:
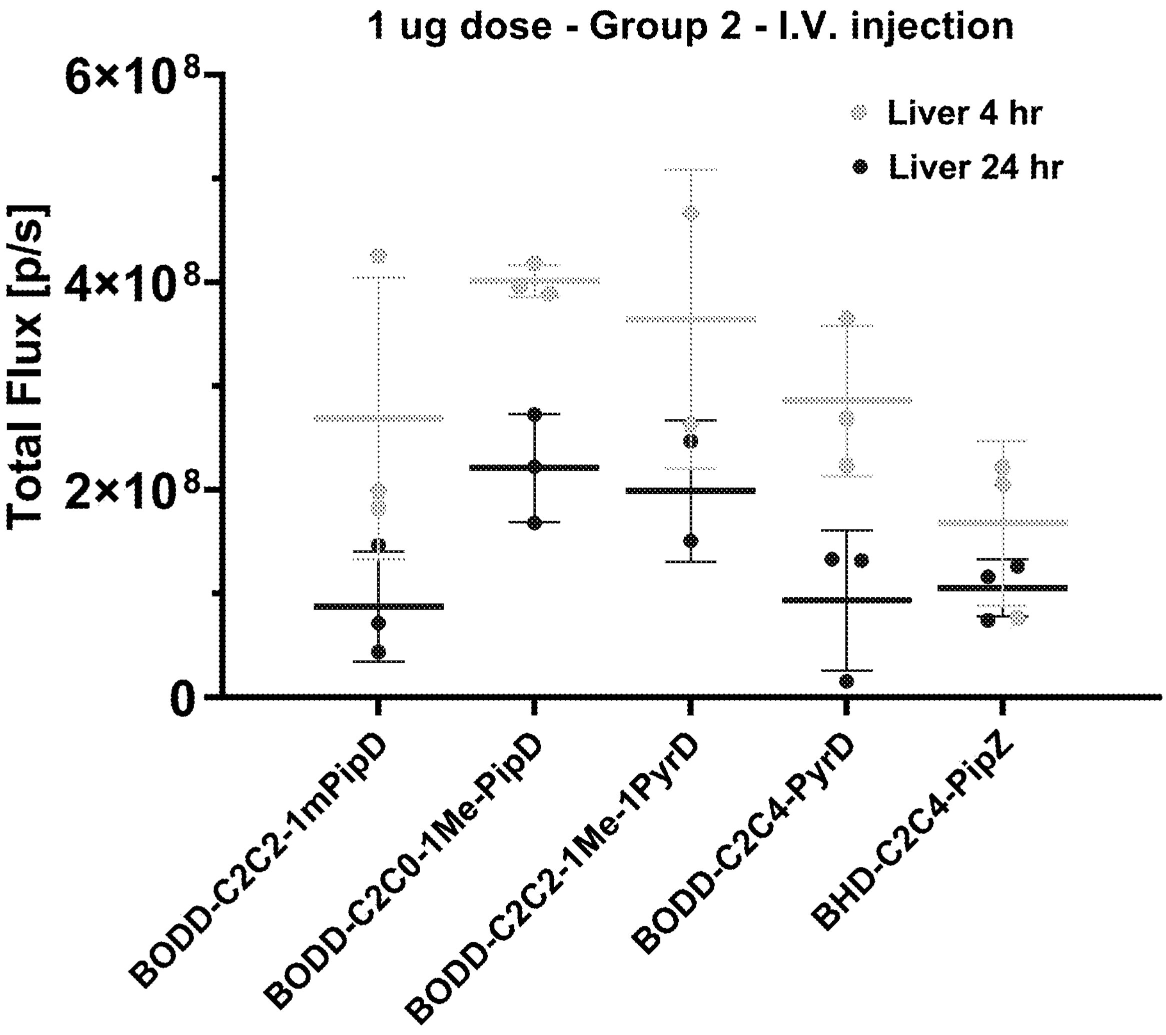
Figure 64I:
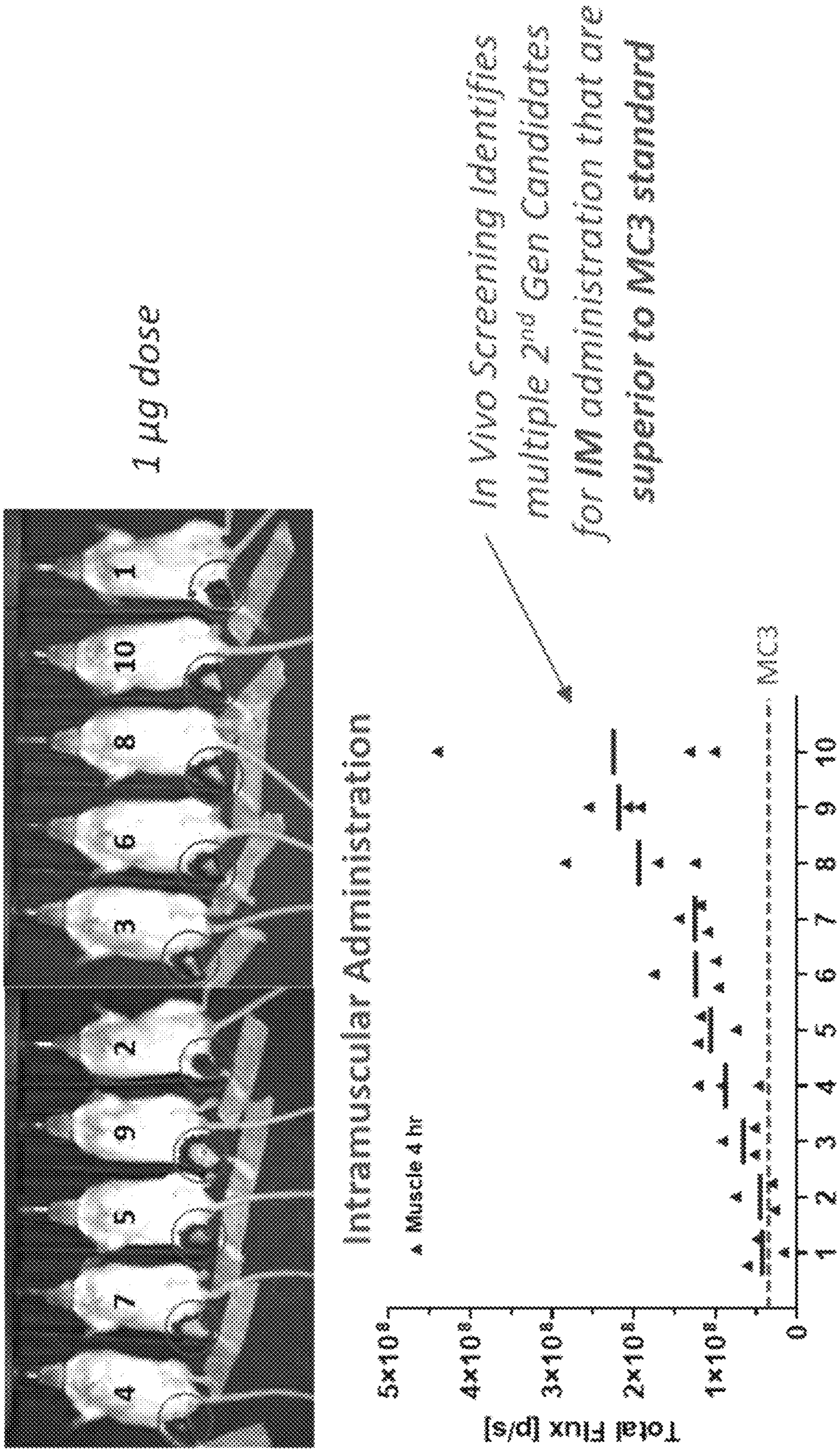
Figure 64J:
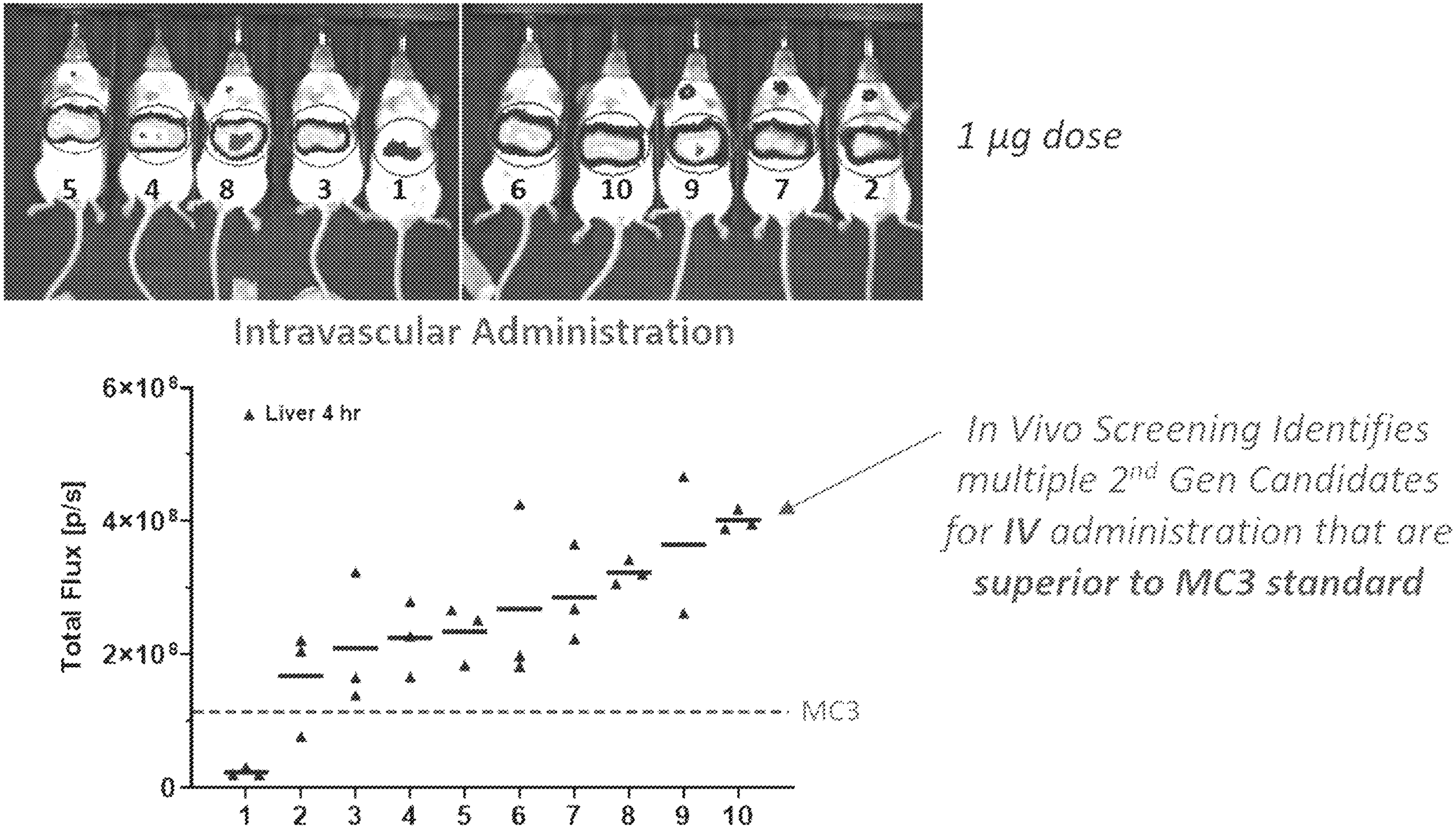

FIG. 64A-64H illustrate In vivo Firefly Luciferase expression in IM administration as exemplified in Example 18C. FIG. 64I-J illustrate in vivo screening of multiple $2^{nd}$ generation Ionizable Lipids of the Invention for IM (FIG. 64I) and IV (FIG. 64J) administration that are superior to an MC3 standard.

Figure 65:
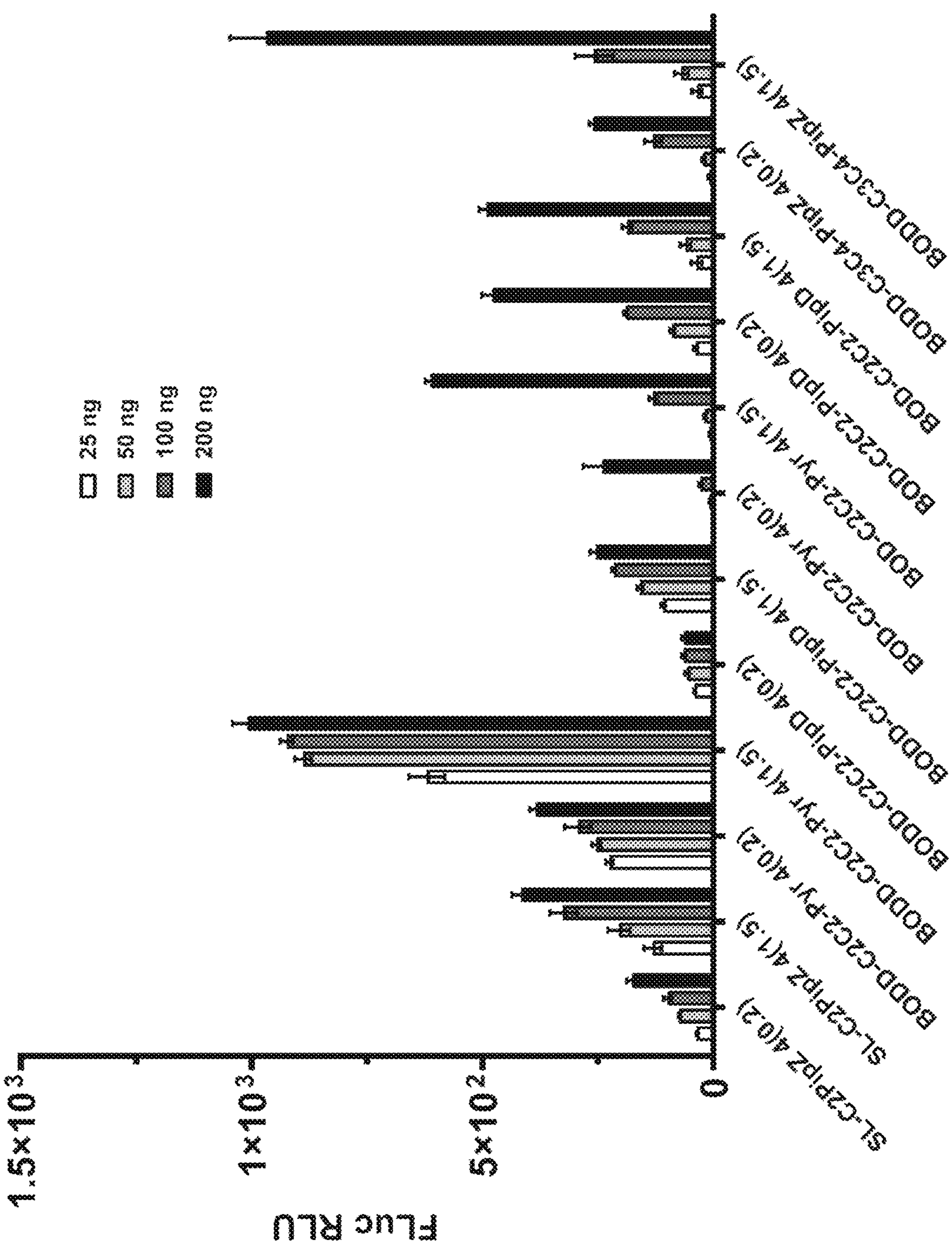
Figure 66:
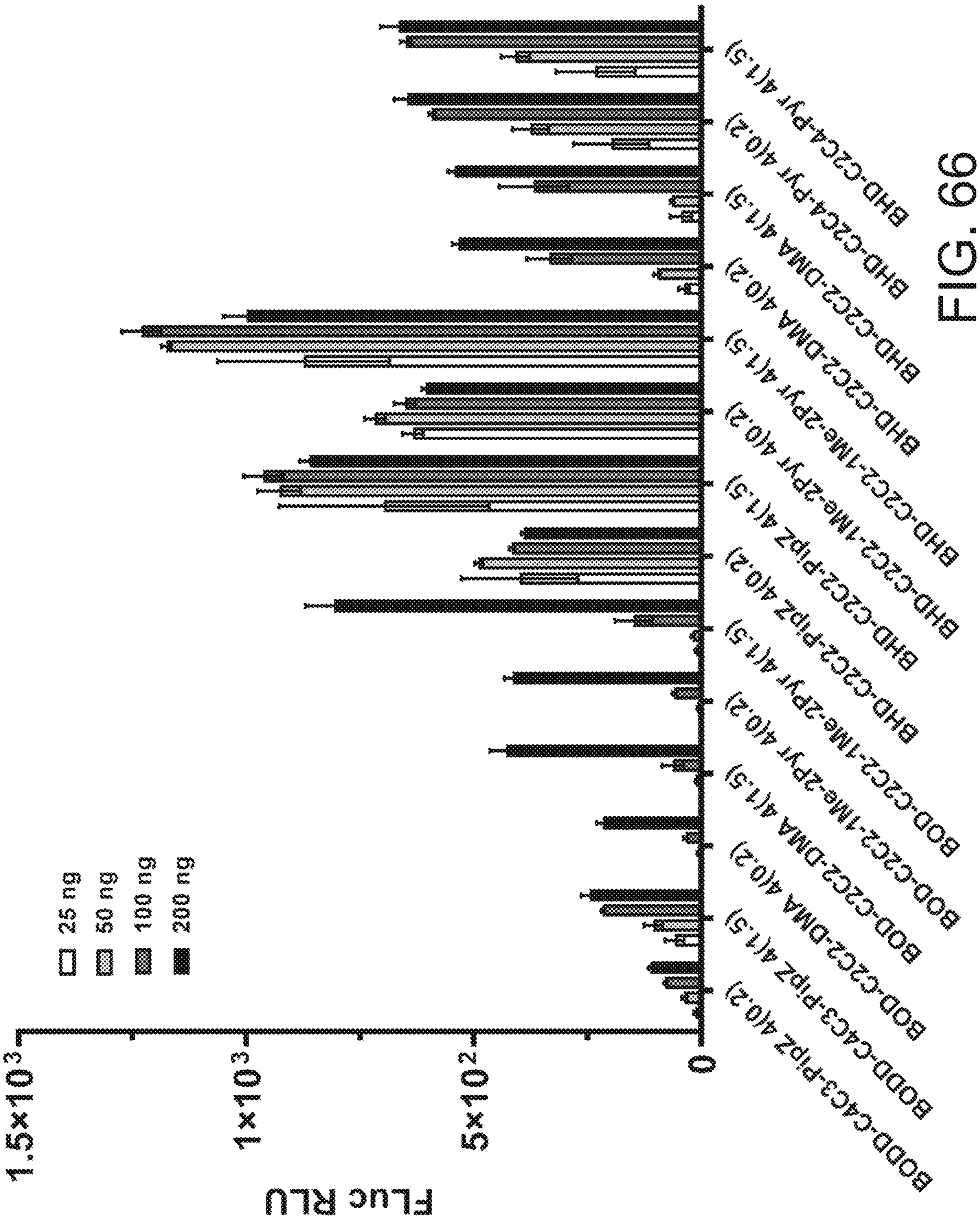

FIG. 65 and FIG. 66 illustrates Firefly Luciferase Assay for mRNA Delivery Efficiency as exemplified in Example 19A.

Figure 67:
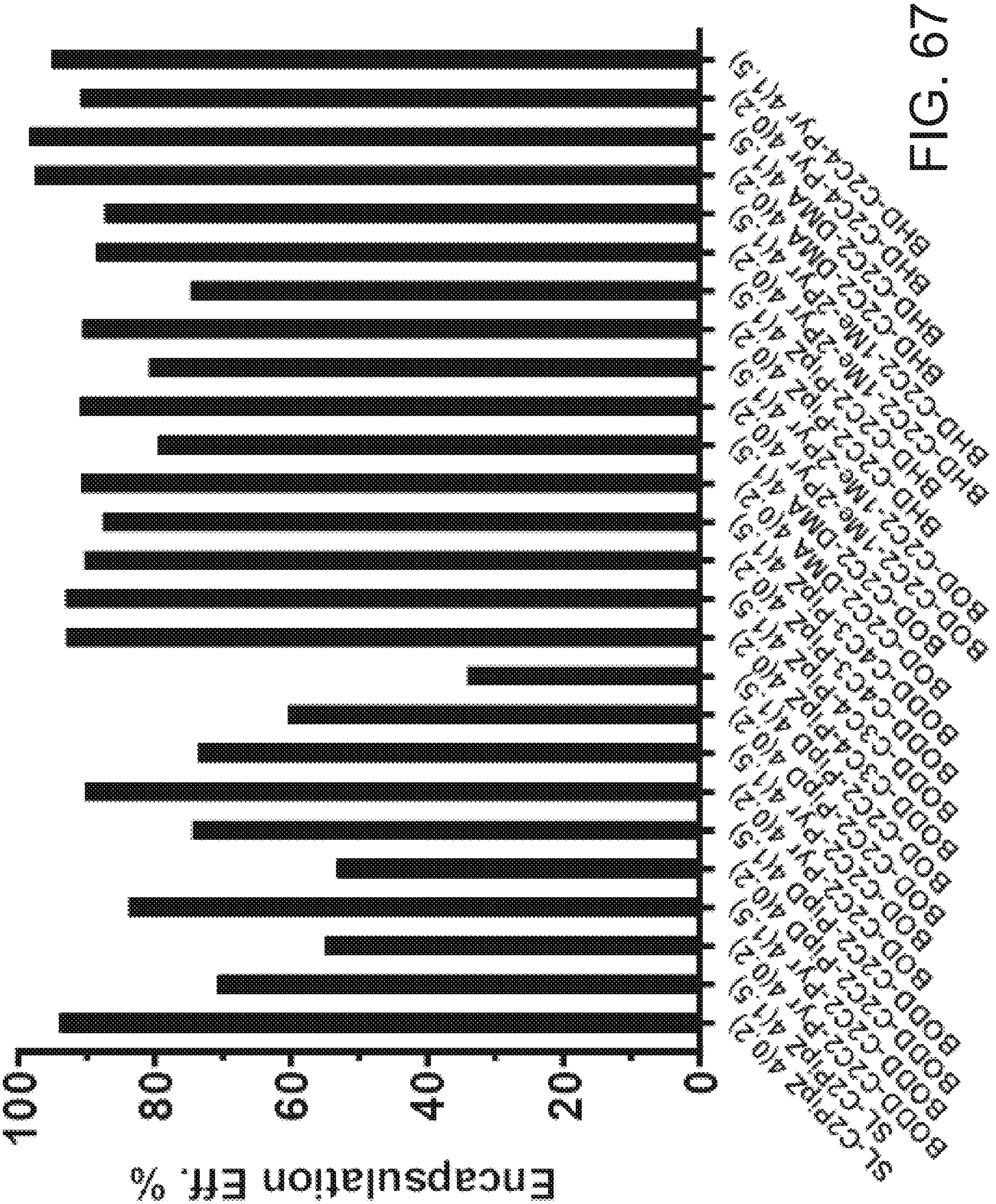

FIG. 67 illustrates a graph of Ribogreen Assay for mRNA Encapsulation Efficiency as exemplified in Example 19B.

Figure 68:
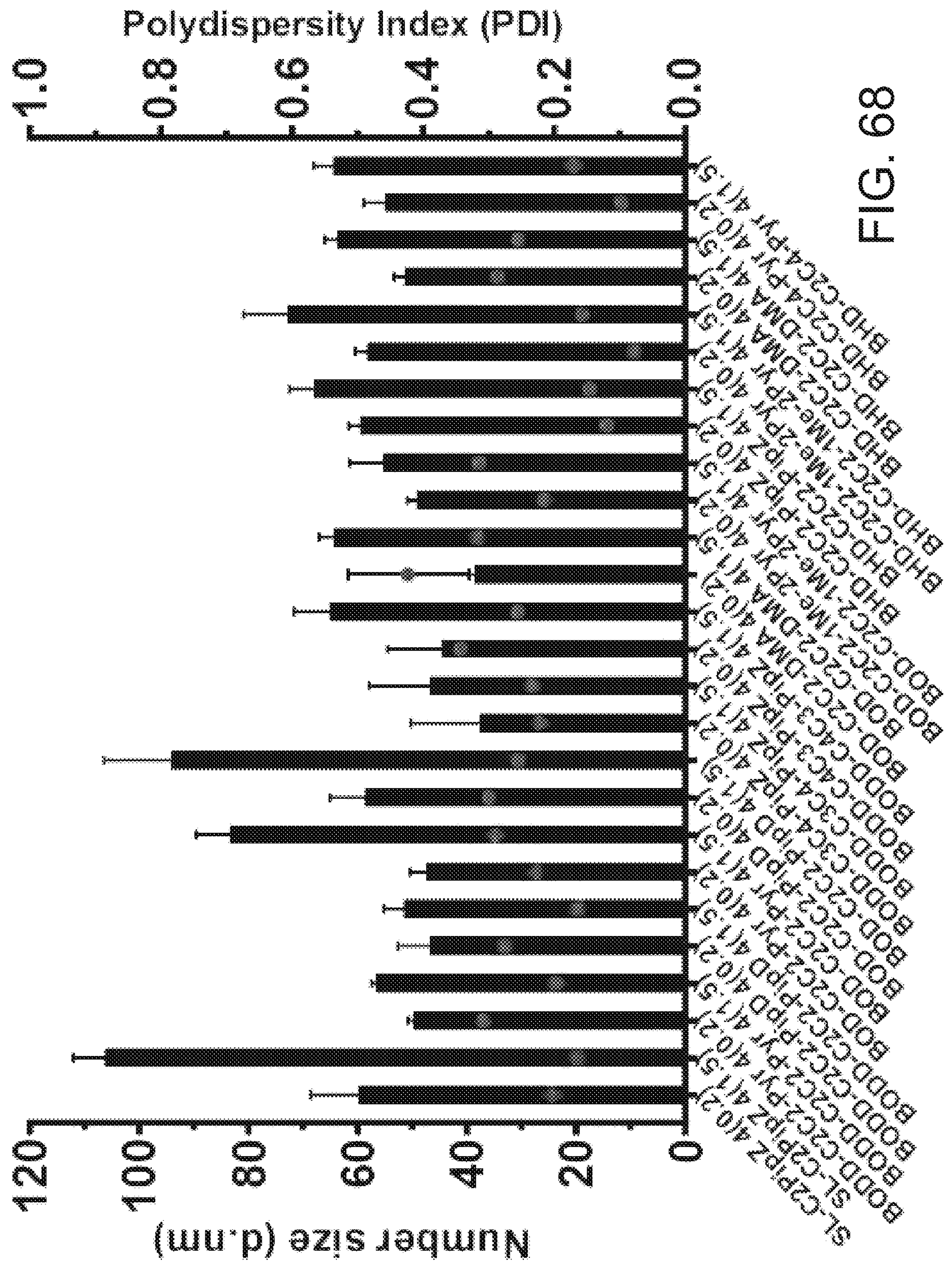

FIG. 68 illustrates a graph of Dynamic Light Scattering for LNP Size (white dots are PDI right y axis) as exemplified in Example 19C.

Figure 69:
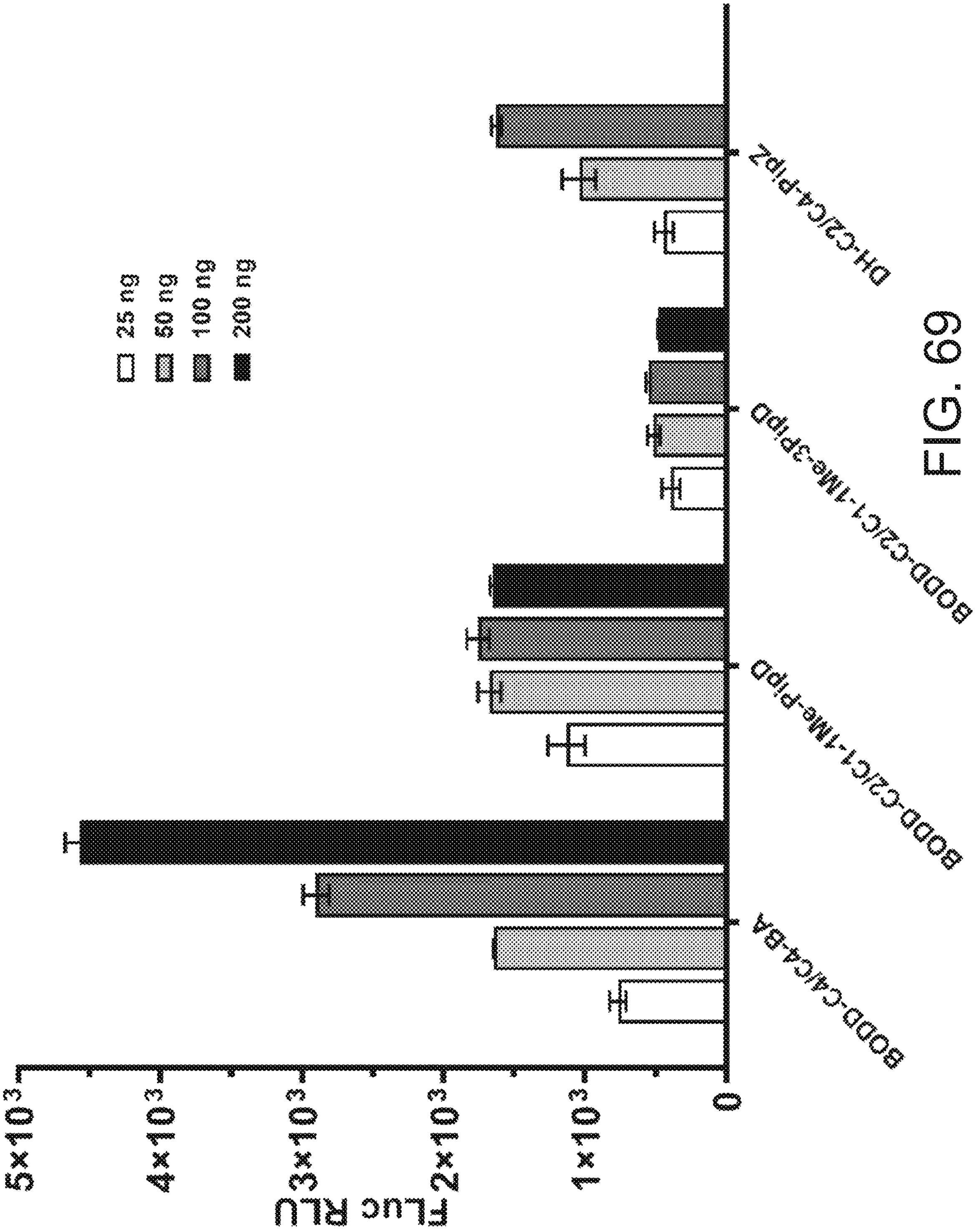

FIG. 69 illustrates Firefly Luciferase Assay for mRNA Delivery Efficiency as exemplified in Example 20A.

Figure 70:
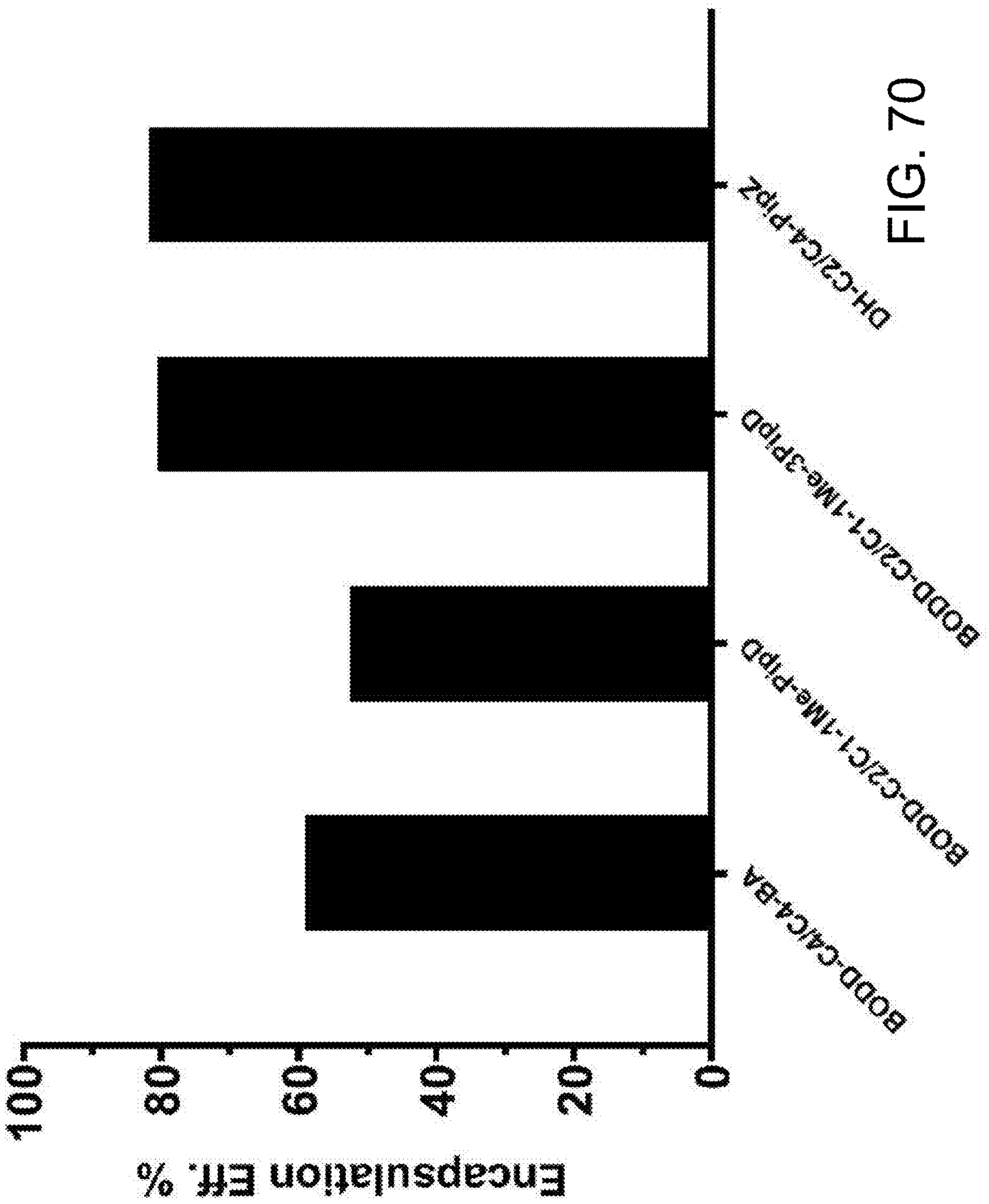

FIG. 70 illustrates a graph of Ribogreen Assay for mRNA Encapsulation Efficiency as exemplified in Example 20B.

Figure 71:
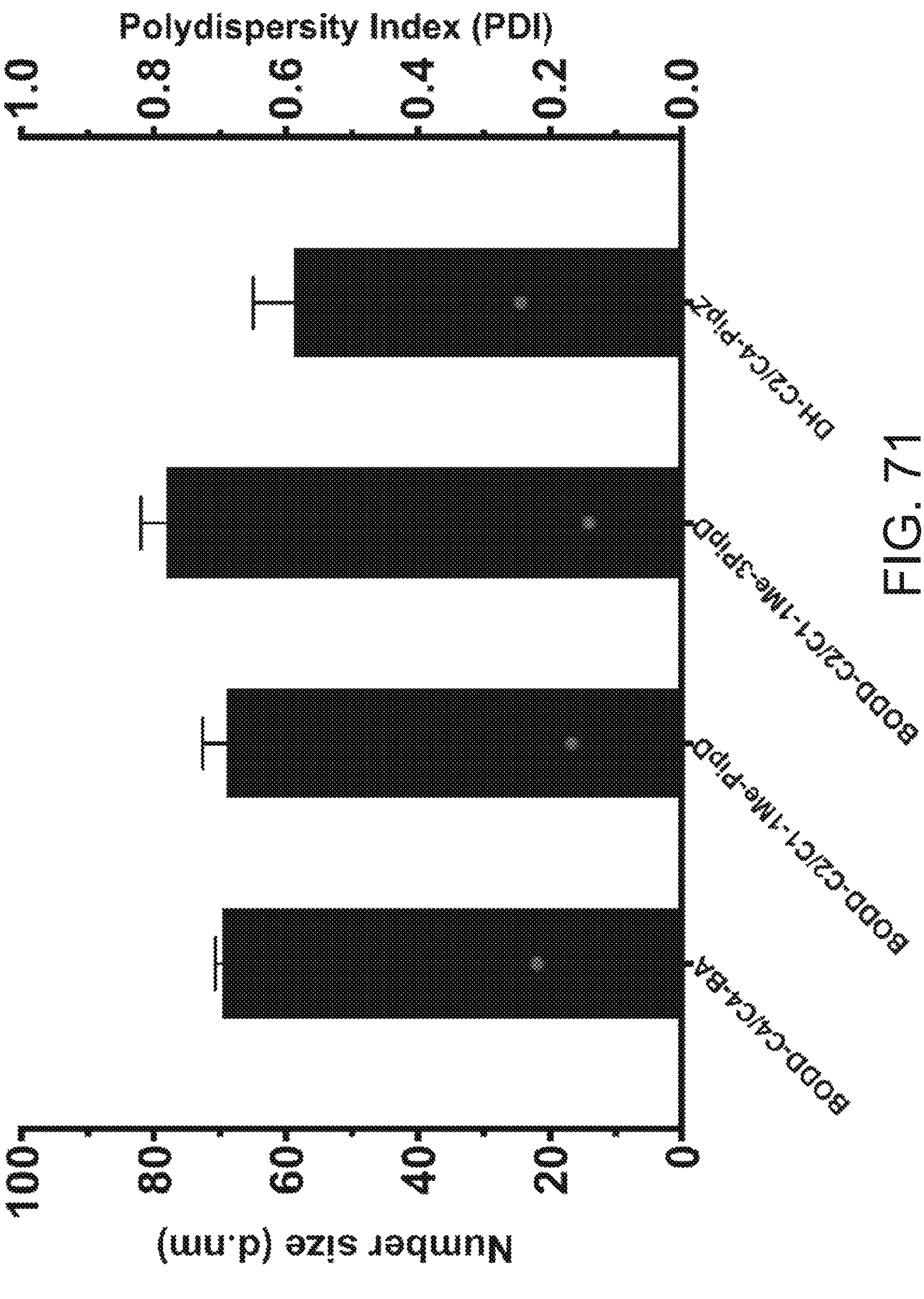

FIG. 71 illustrates a graph of Dynamic Light Scattering for LNP Size (white dots are PDI right y axis) as exemplified in Example 20C.

Figure 72:
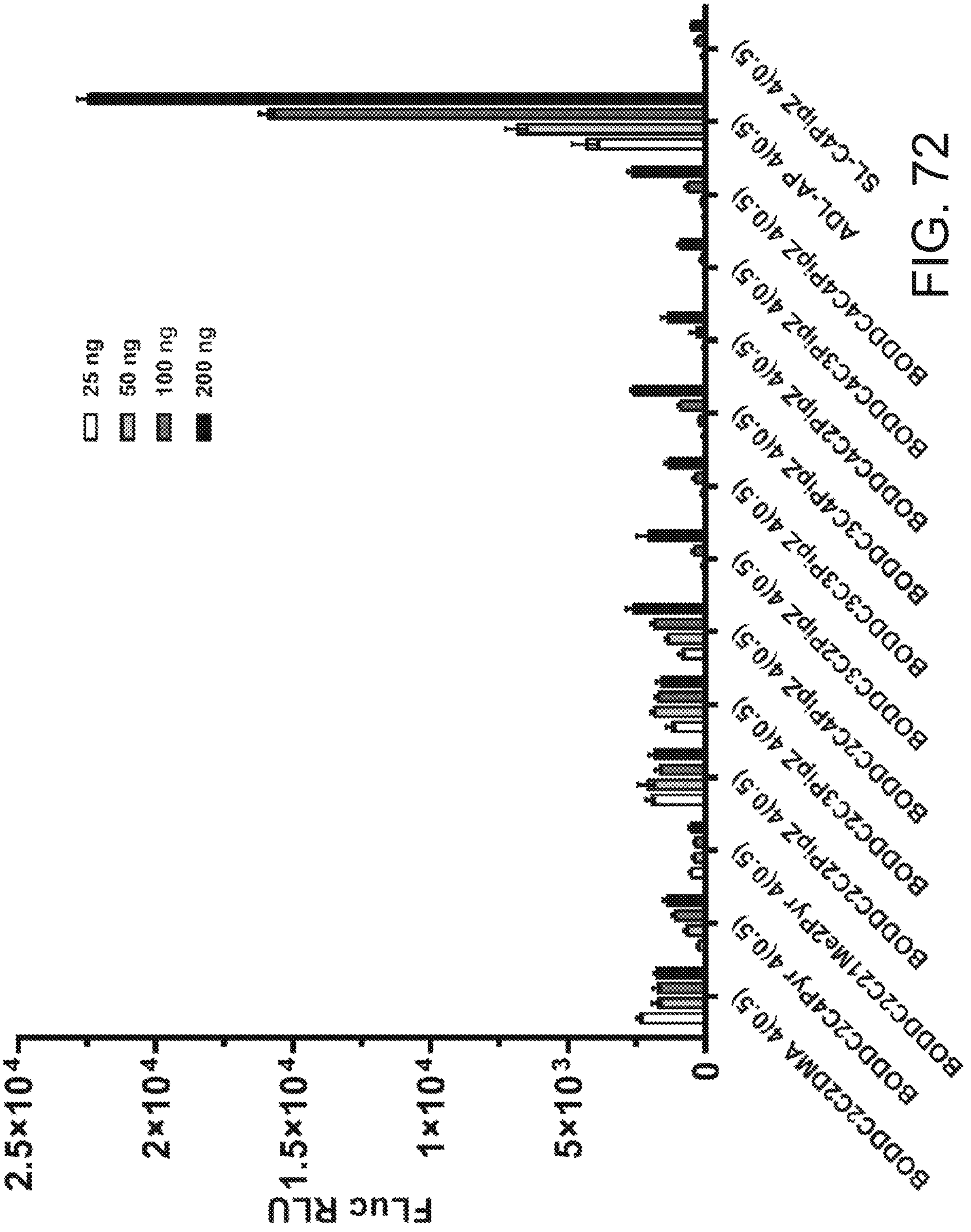

FIG. 72 illustrates Firefly Luciferase Assay for mRNA Delivery Efficiency as exemplified in Example 21A.

Figure 73:
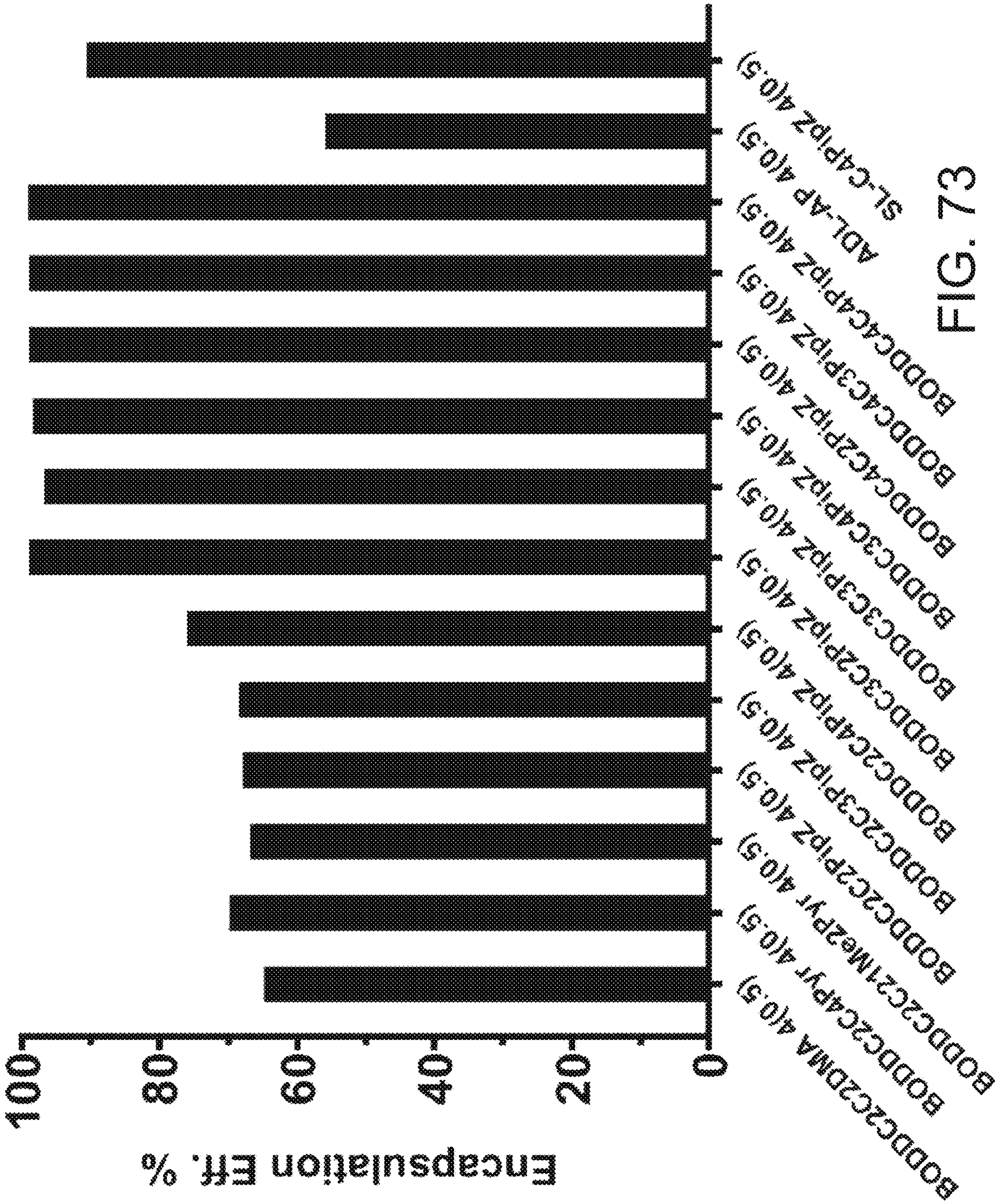

FIG. 73 illustrates a graph of Ribogreen Assay for mRNA Encapsulation Efficiency as exemplified in Example 21B.

Figure 74:
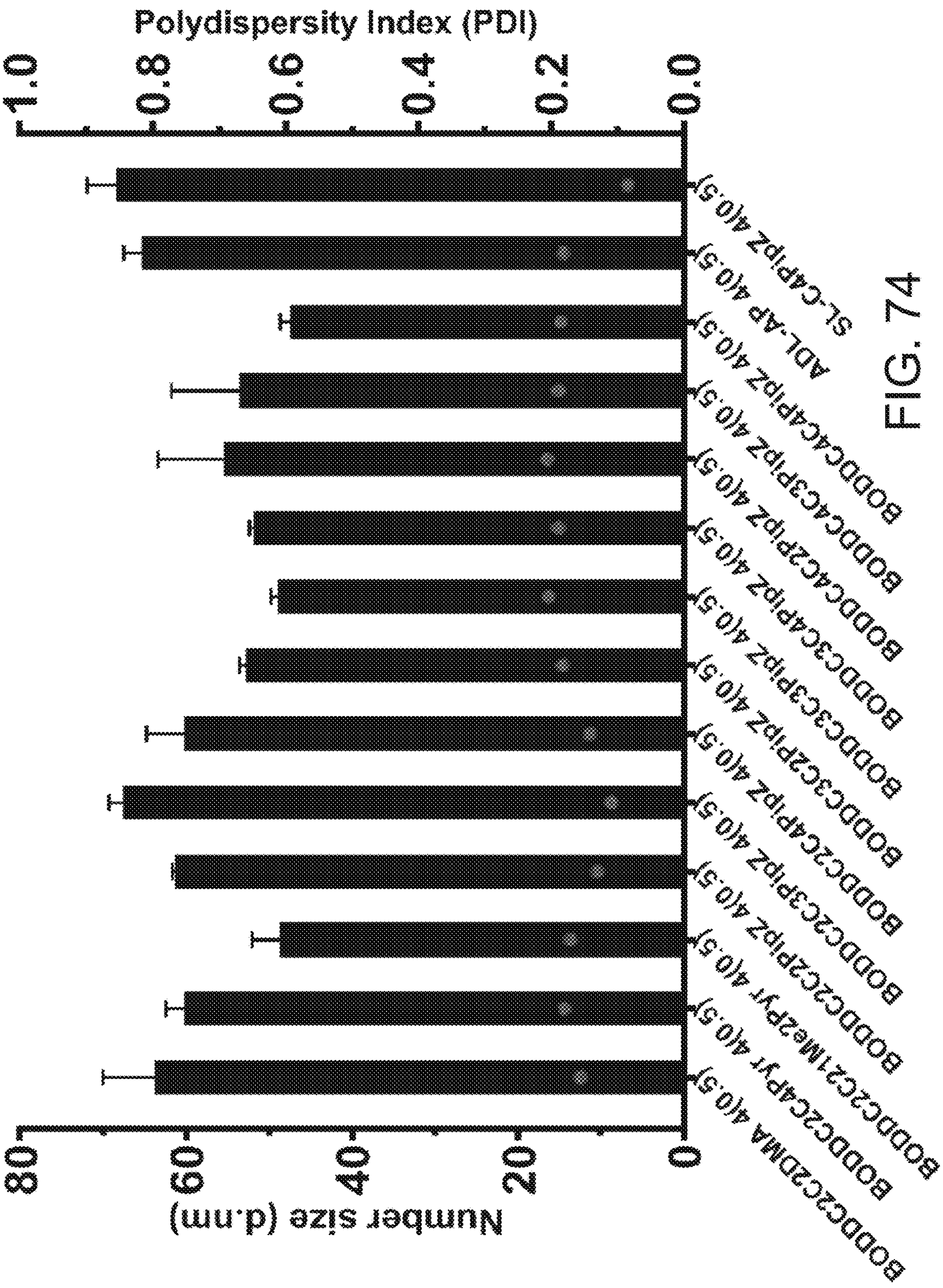

FIG. 74 illustrates a graph of Dynamic Light Scattering for LNP Size (white dots are PDI right y axis) as exemplified in Example 21C.

Figure 75:
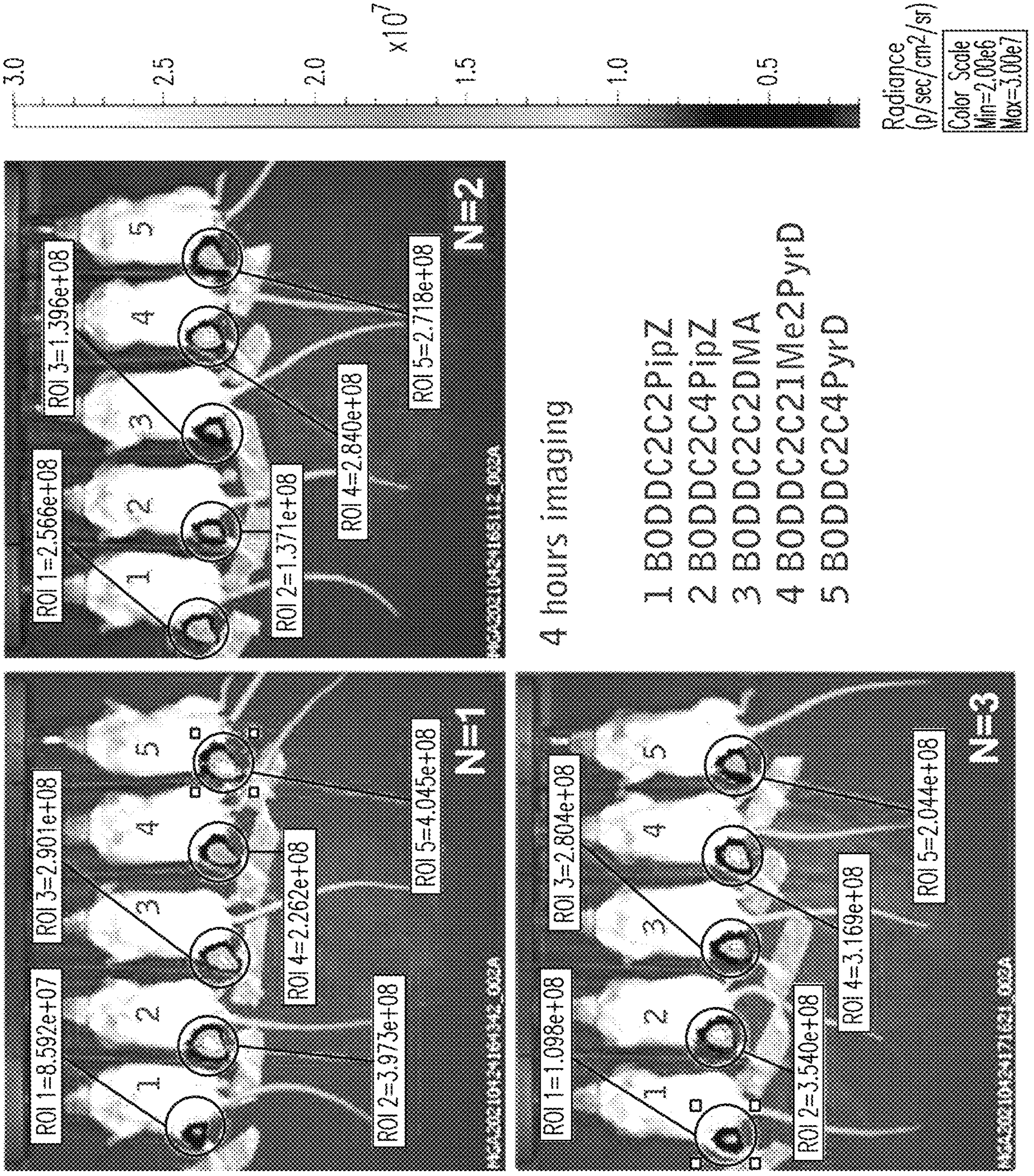
Figure 76:
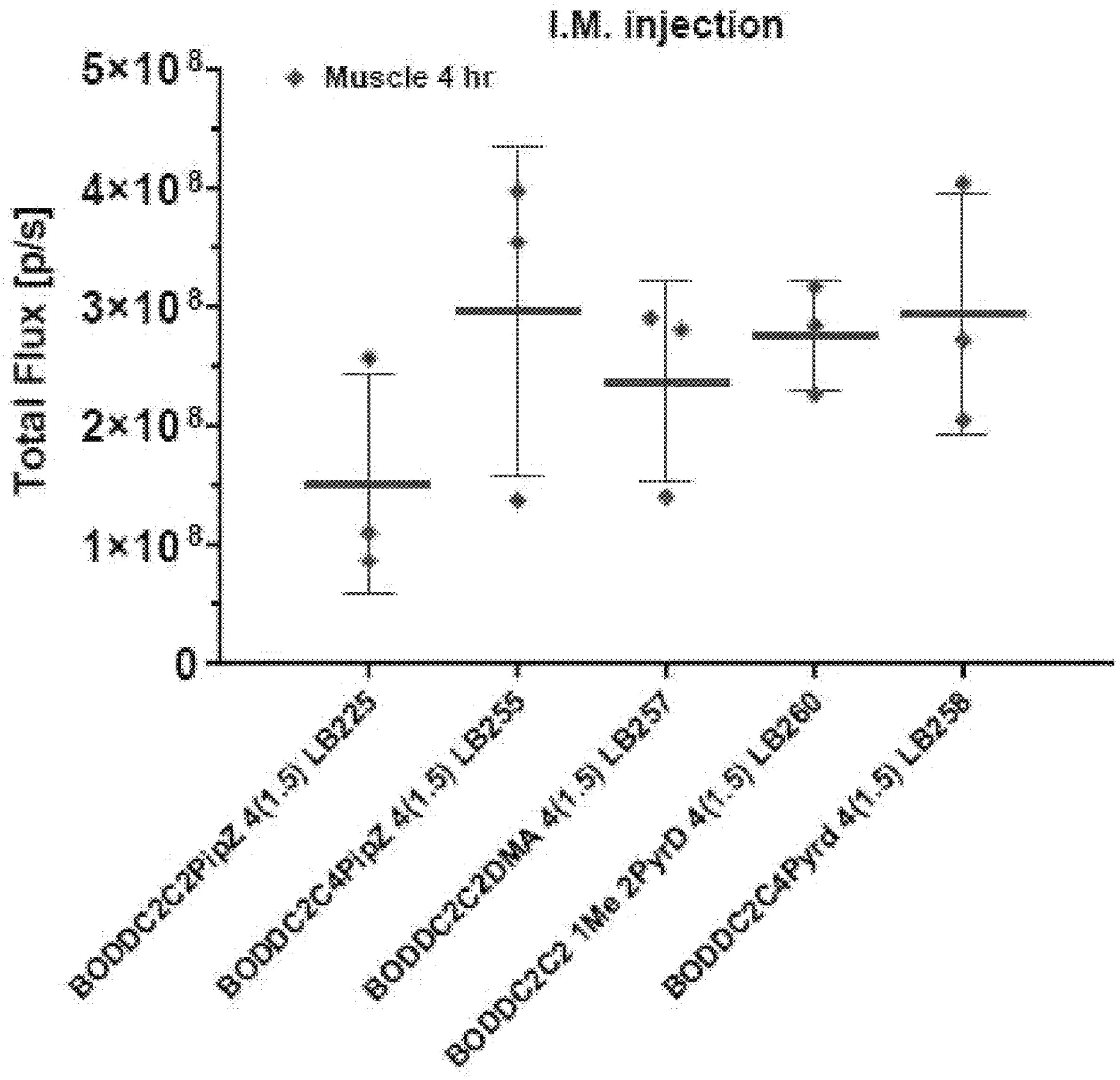

FIG. 75 and FIG. 76 illustrates the results of In vivo Firefly Luciferase expression of the Injection site in IM administration as exemplified in Example 22A.

Figure 77:
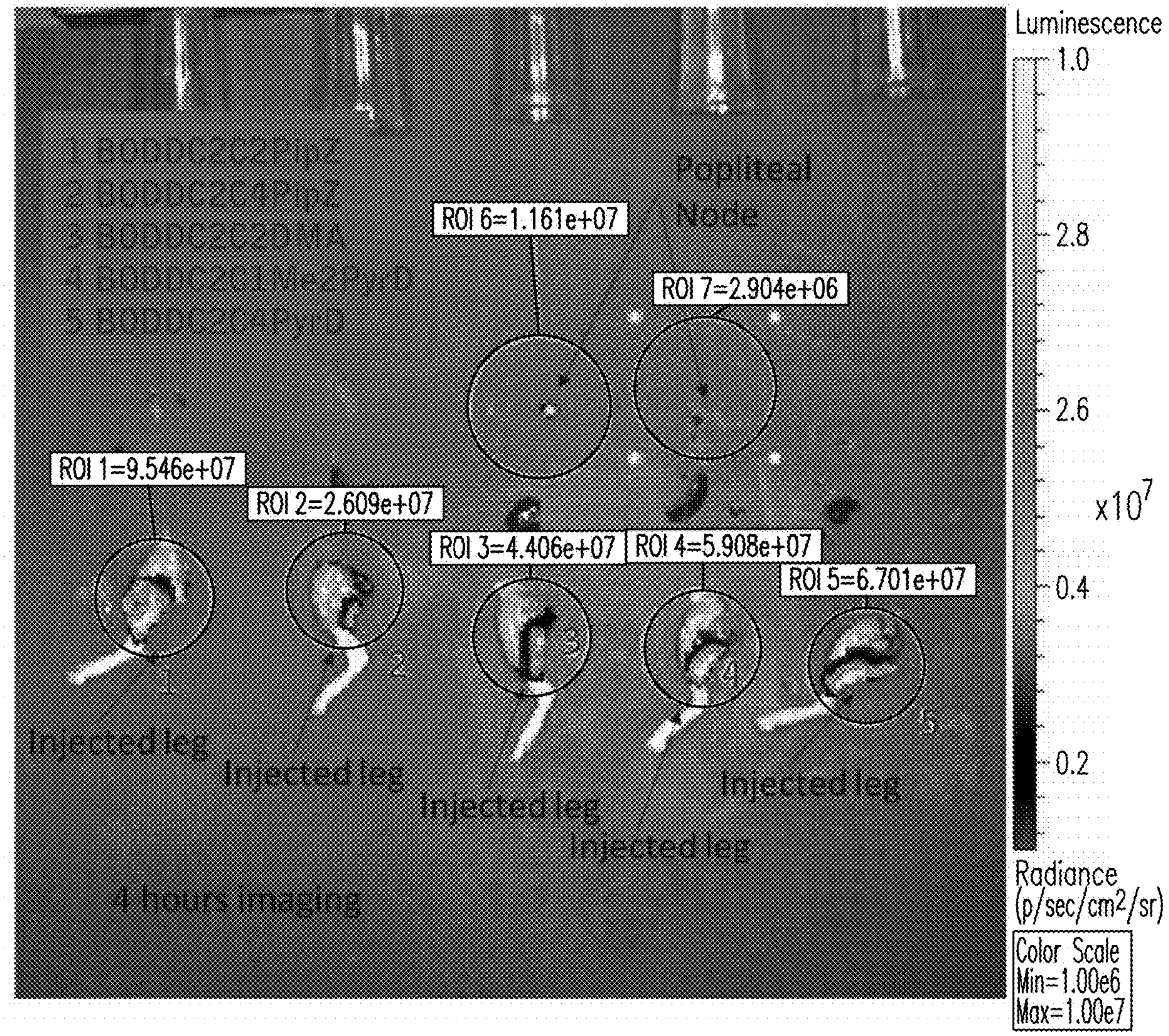
Figure 78:
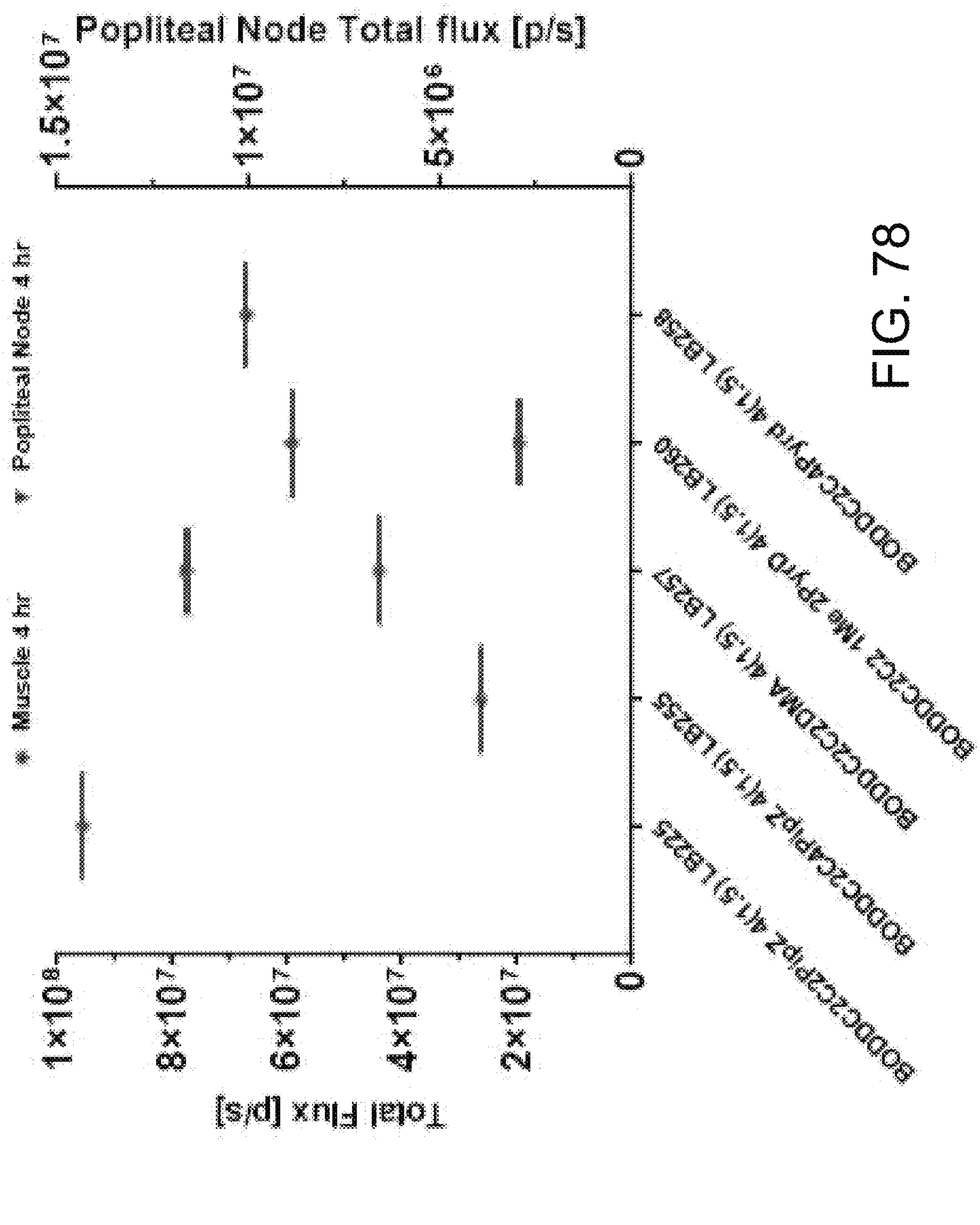

FIGS. 77 and 78 illustrates the results of Ex vivo Firefly Luciferase expression of the Injection site in IM administration as exemplified in Example 22B.

Figure 79:
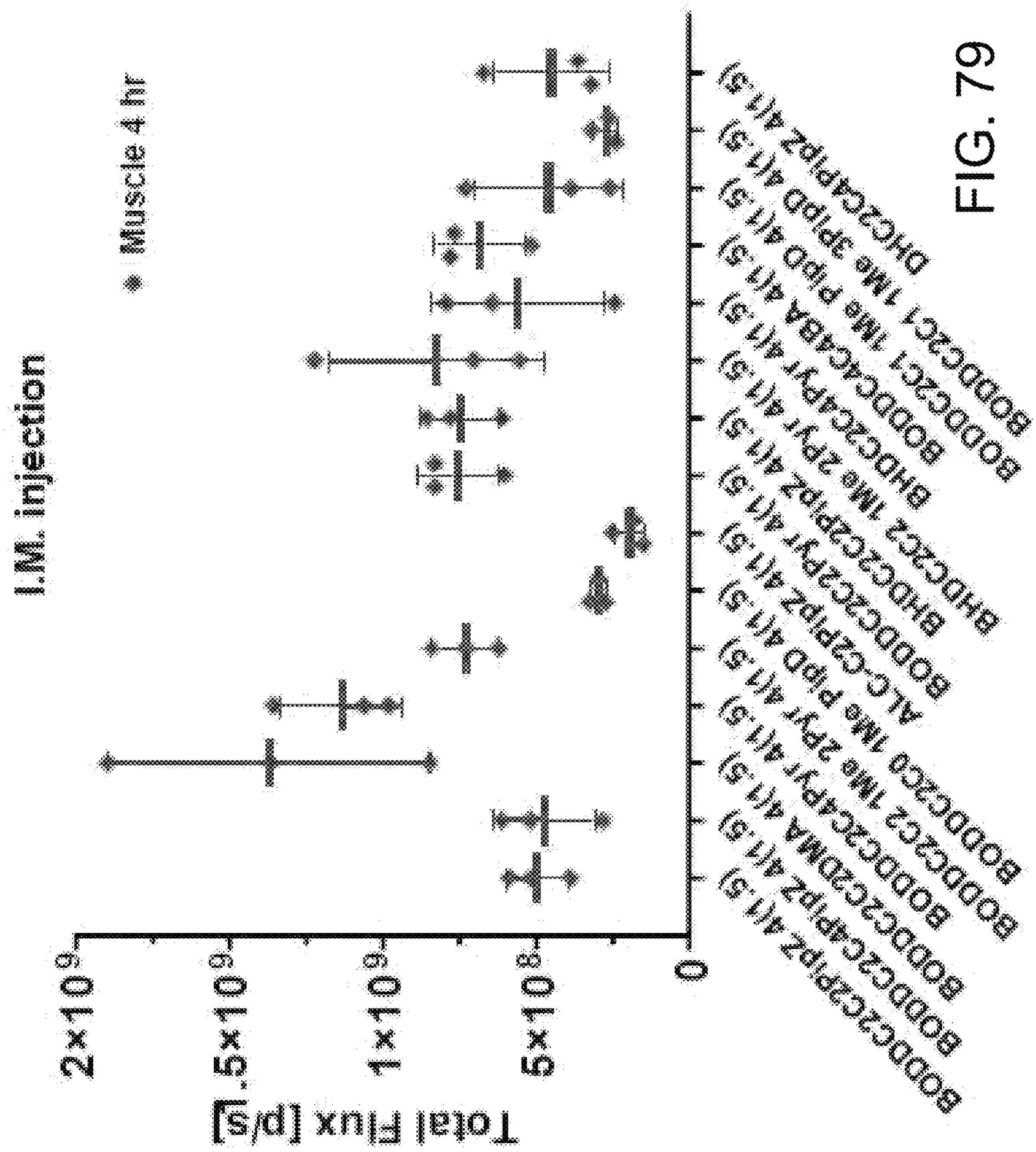
Figure 80:
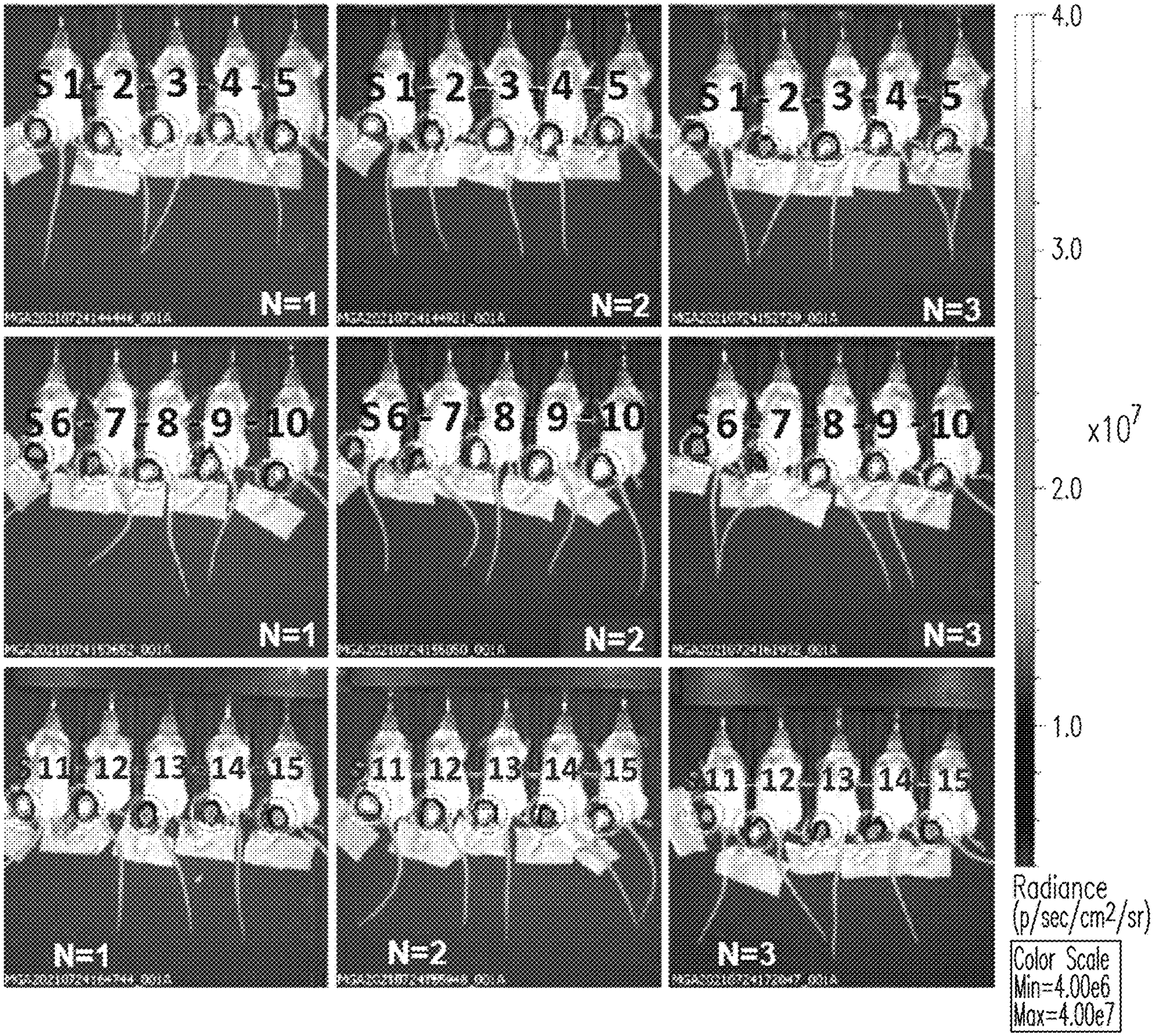

FIG. 79 and FIG. 80 illustrates the results of in vivo Firefly Luciferase expression of the Injection site in IM administration as exemplified in Example 23A.

Figure 81:
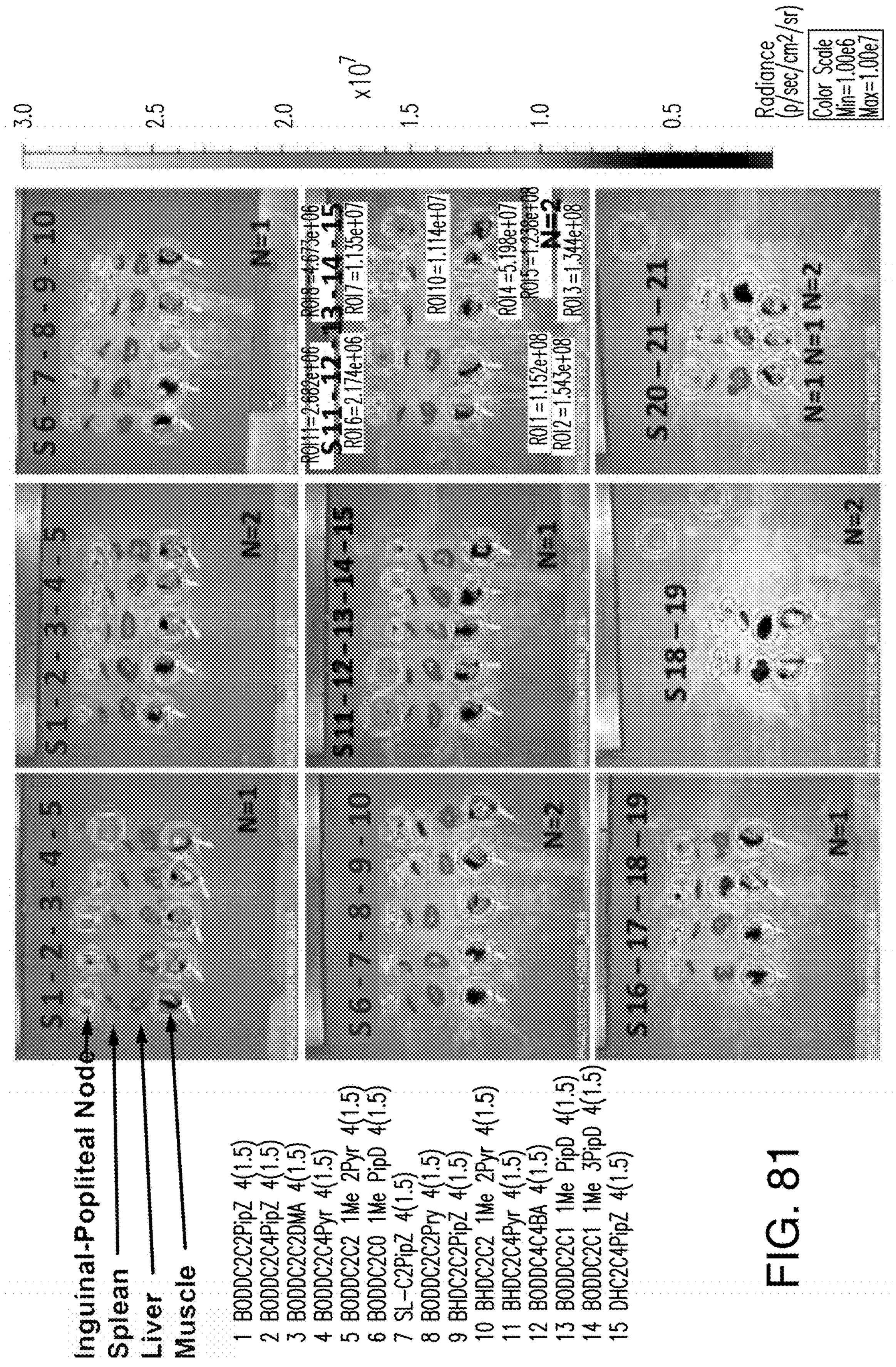
Figure 82:
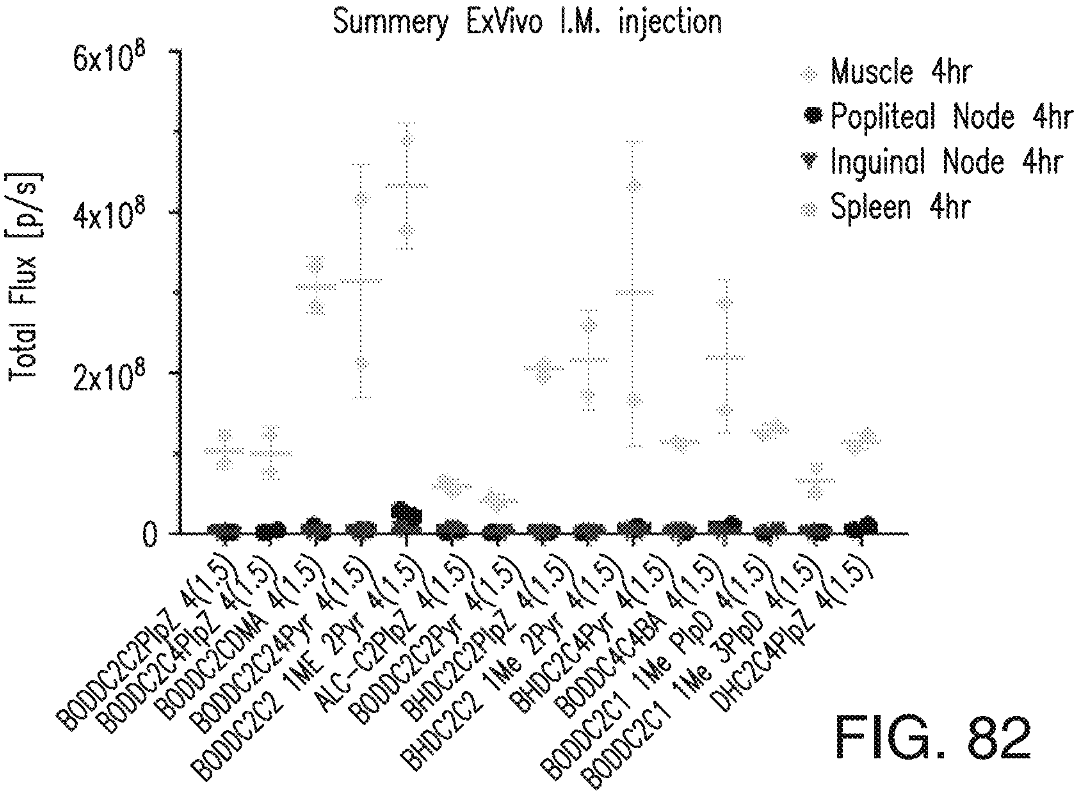
Figure 83:
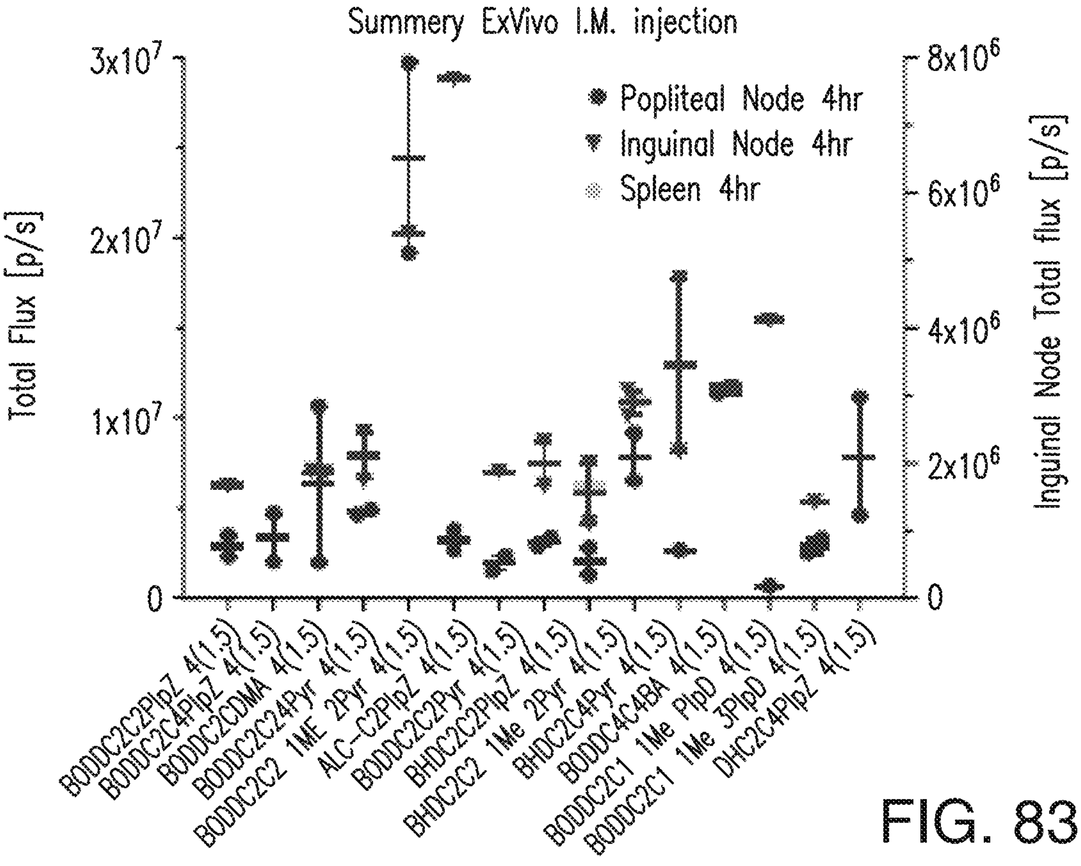

FIG. 81, FIG. 82, and FIG. 83 illustrates the results of ex vivo Firefly Luciferase expression of the Injection site in IM administration as exemplified in Example 23B.

FIG. 84A-FIG. 84F illustrates the results of multiprotic C24 ionizable lipid produces multistage protonation in the LNP and greater protonation in the endosomal pH range than the MC3 LNP and comparative data between MC3 LNP and C24 LNP.

Figure 85A:
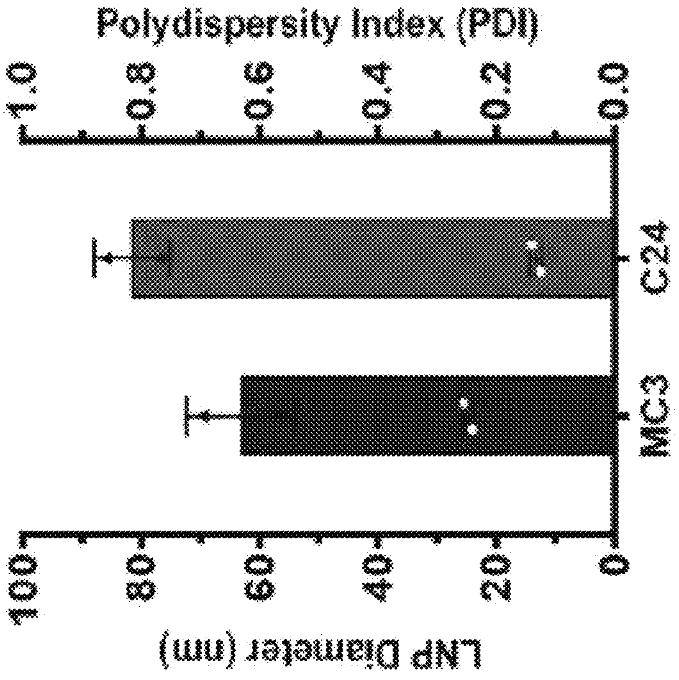
Figure 85B:
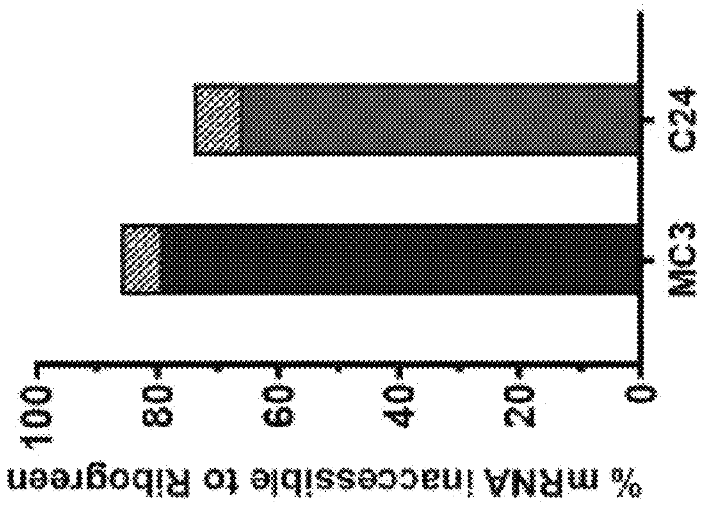
Figure 85C:
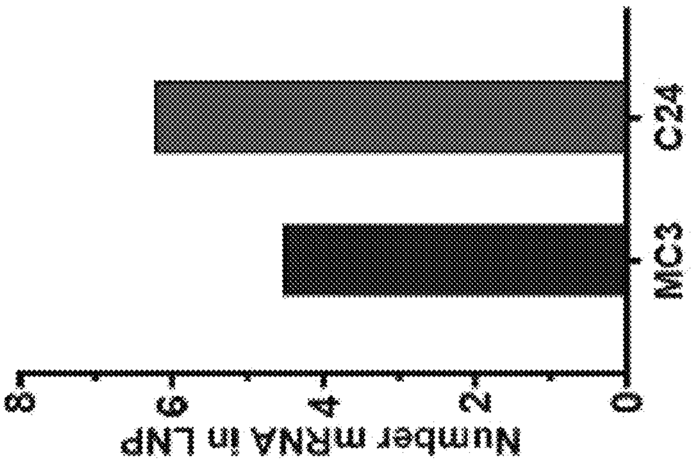
Figure 85E:
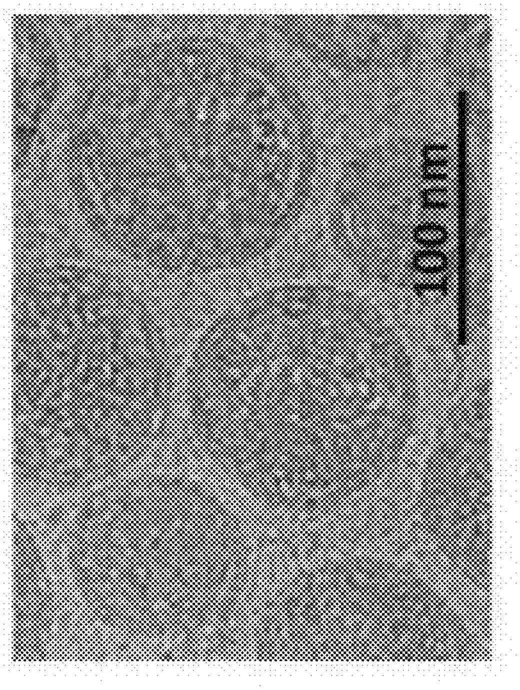

FIG. 85A-85C illustrates the effects of structural properties of C24 and MC3 lipid nanoparticles. FIG. 85A-85C illustrates empty LNPs.

FIG. 86A-FIG. 86F illustrates the results of luciferase expression after intramuscular (IM) administration in Balb/c mice shows significantly higher on-target and lower off-target mRNA expression with the C24 LNP than for MC3.

FIG. 87A-FIG. 87E illustrates the results of C24 LNPs generate 10 fold higher binding and pseudoneutralizing antibody titers than MC3 LNPs in immunogenicity studies with Balb/c mice.

FIG. 88A-FIG. 88I illustrates C24 LNPs, which are protective against lethal SARS-CoV-2 challenge at low doses of the S2P immunogen and completely eliminate lung infection. FIG. 88B-FIG. 88I illustrate comparative data for MC3 and C24 LNPs.

Figure 89A:
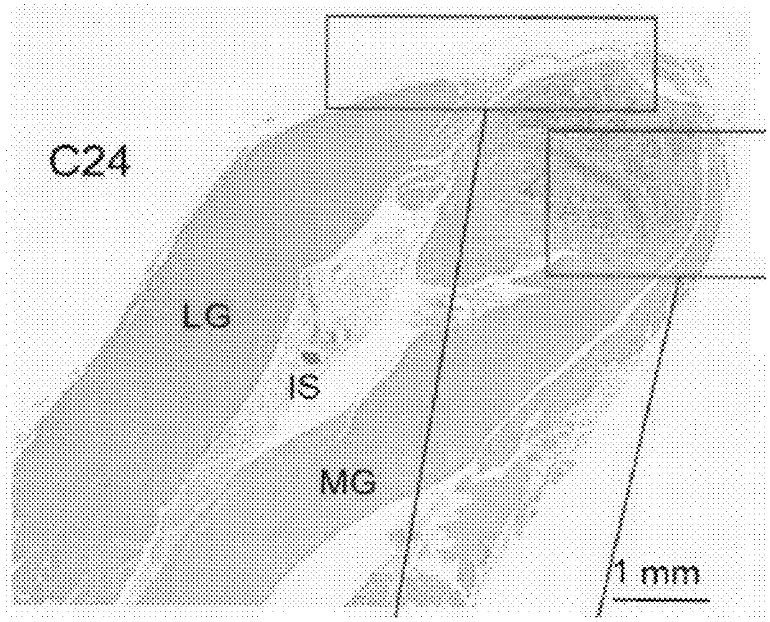
Figure 89B:
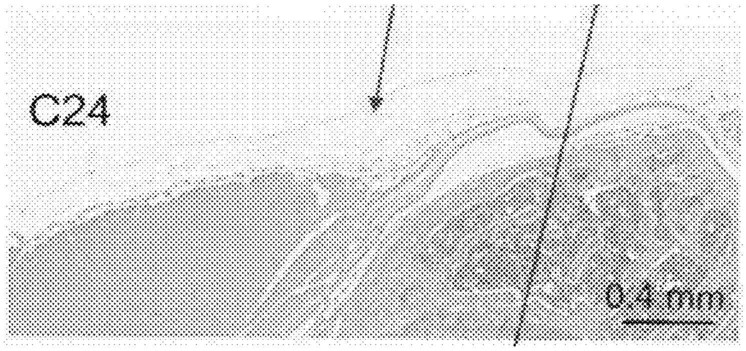
Figure 89C:
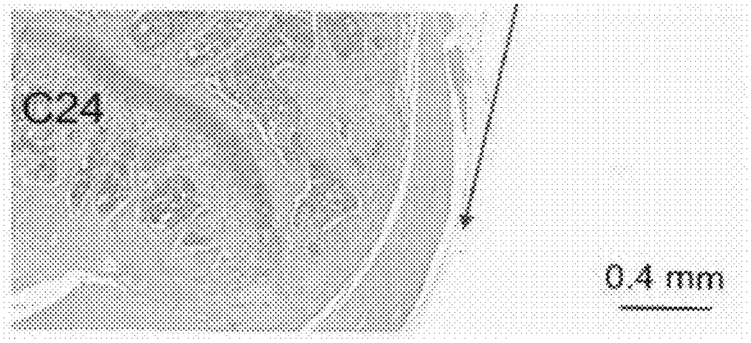

FIG. 89A-FIG. 891 illustrates local injection site inflammation is lower for C24 than MC3 mRNA LNPs.

FIG. 90A-FIG. 90F illustrates the bioactivity and mRNA integrity of C24 and MC3 LNPs, which are stable at 4° C. but decline at higher temperatures over 2 weeks.

Figure 91:
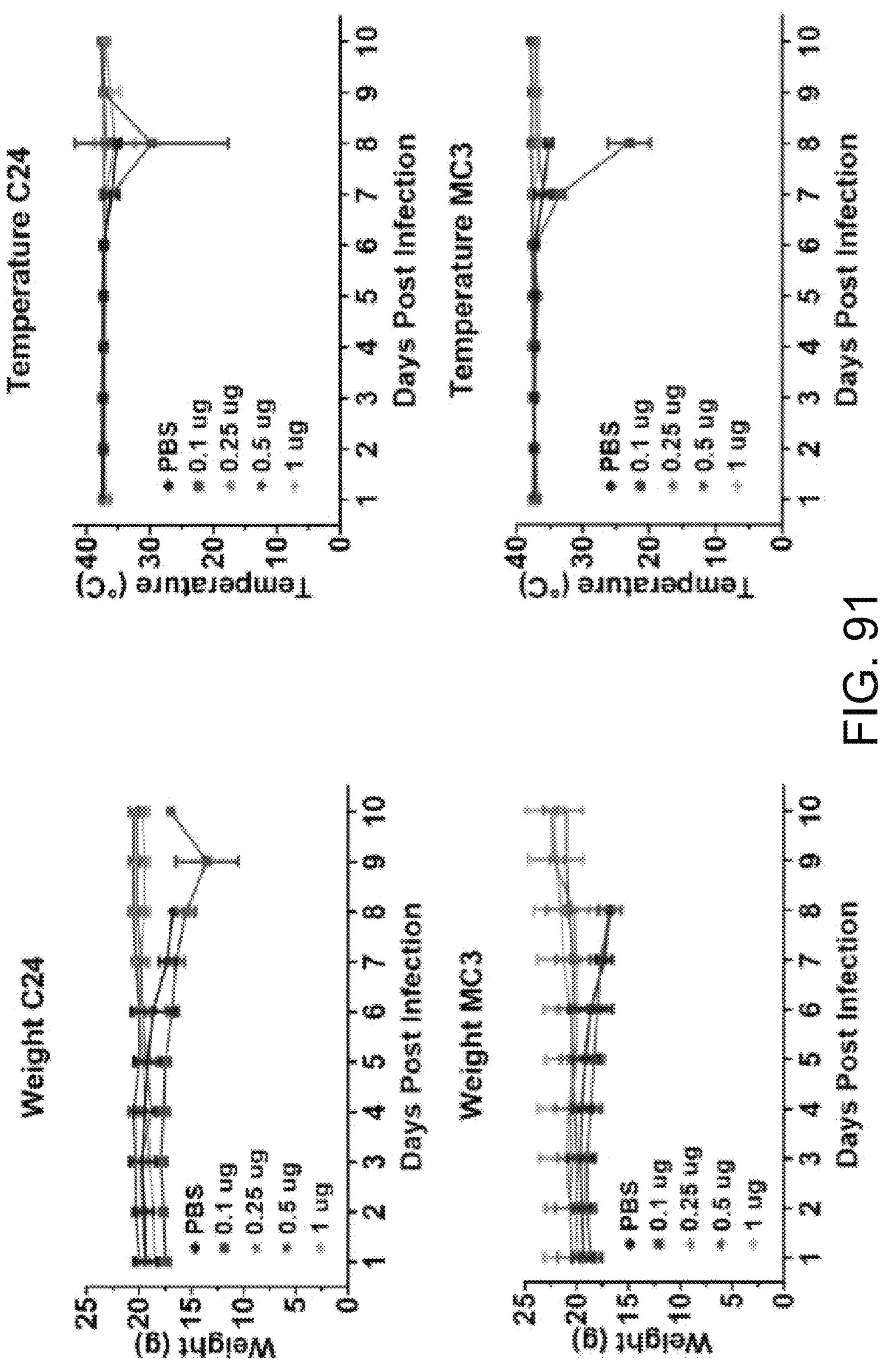

FIG. 91 illustrates weight and temperature effects in K18-hACE2 mice subject to lethal challenge on Day 0 after a Prime-Boost vaccination with C24 and MC3 LNPs containing the mRNA-encoded S2P immunogen at doses ranging from 0.1 to 1.0 μg.

Figure 92A:
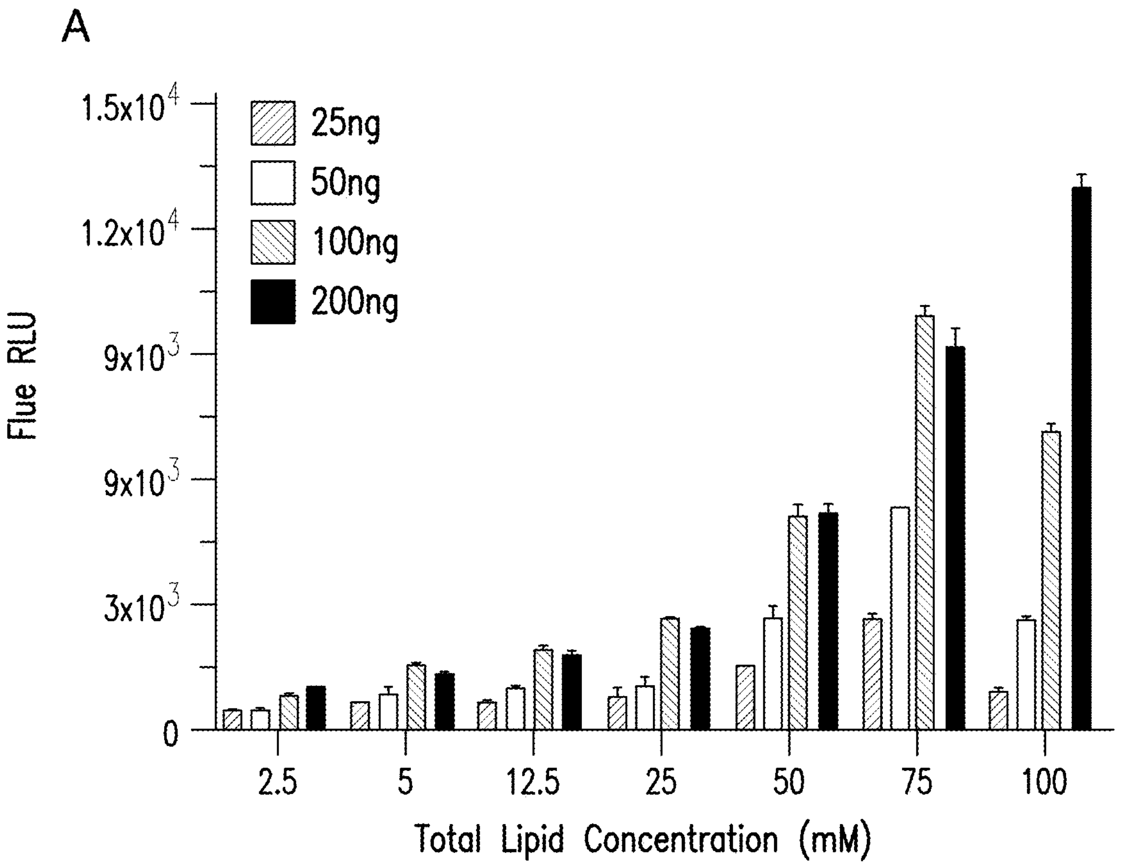
Figure 92B:
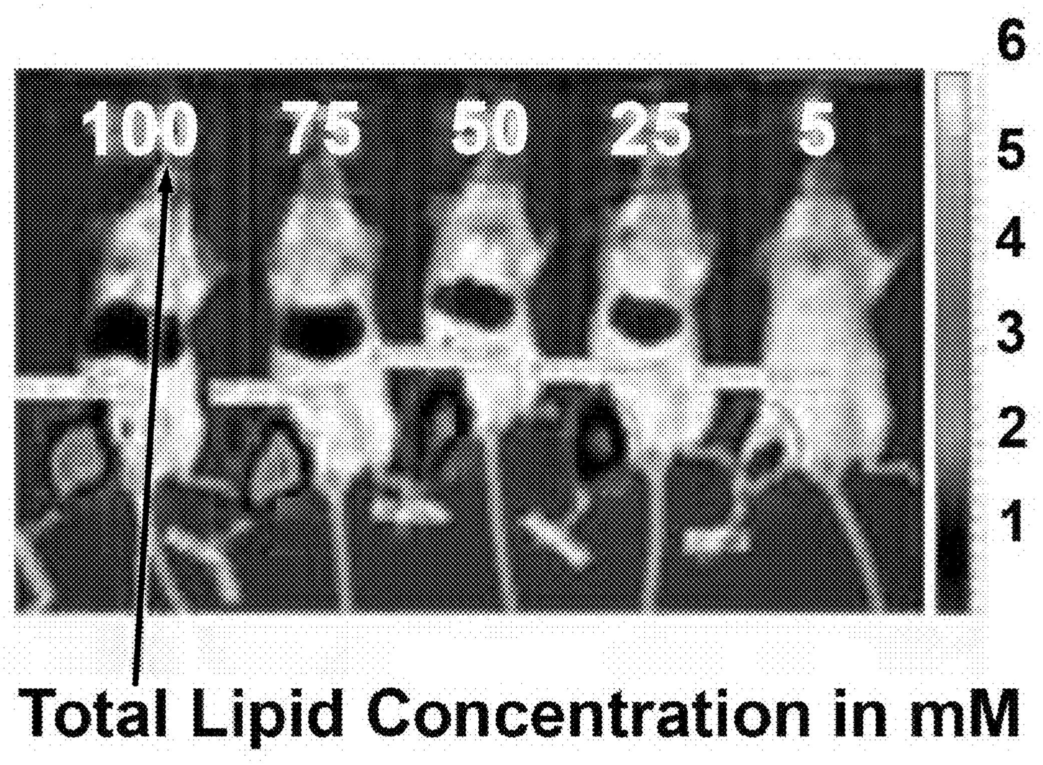
Figure 92C:
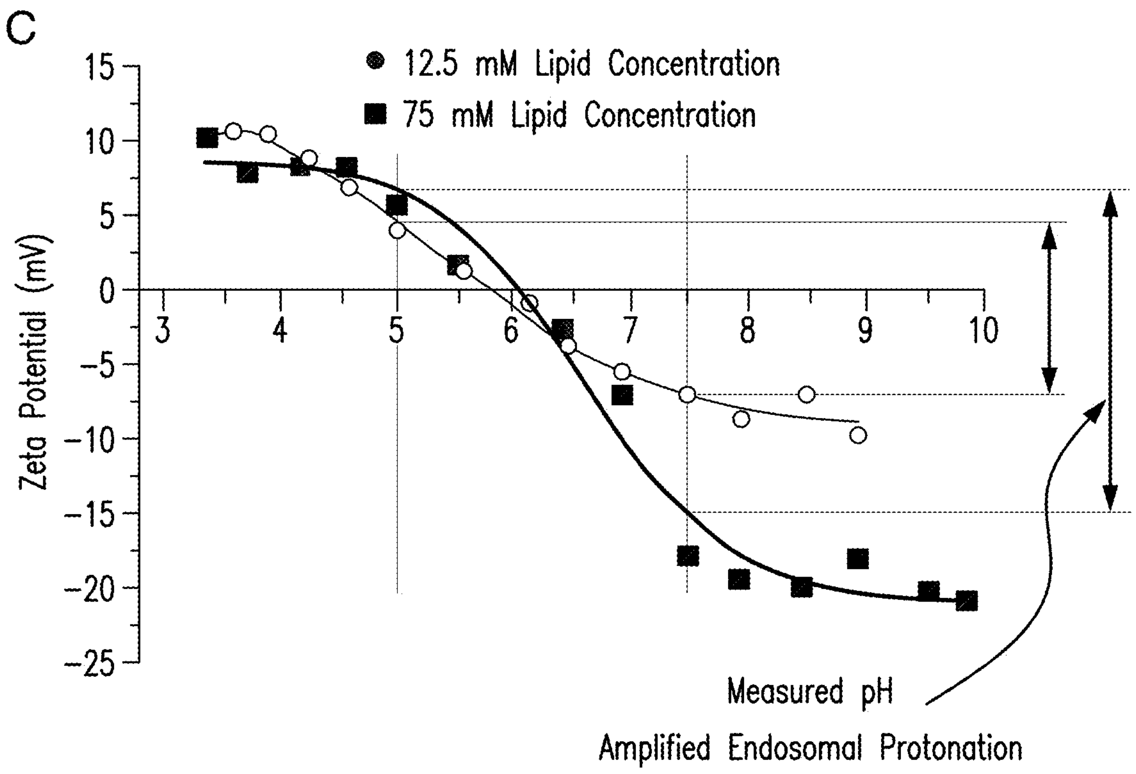

FIG. 92 illustrates LNP potency and endosomal protonation increase when the concentrations of lipids and mRNA are increased during microfluidic mixing. FIG. 92A) KC2 LNPs assembled at higher concentrations produced higher Fluc expression in vitro at the same doses of 25-200 ng per well containing 12 k HEK293 cells. FIG. 92B) LNPs produced at higher mixing concentrations (total lipid concentration in mM at mixing is shown above the animal), and diluted to a constant 5 μg dose in 50 μL for IM injection, are more potent (color bar is Radiance in 107 p/sec/cm2/sr). FIG. 92C) Zeta potential measurements reveal a greater increase in protonation when pH drops from 7.4 to 5 for the LNP prepared by high concentration mixing, suggesting greater endosomal release.

Figure 93:
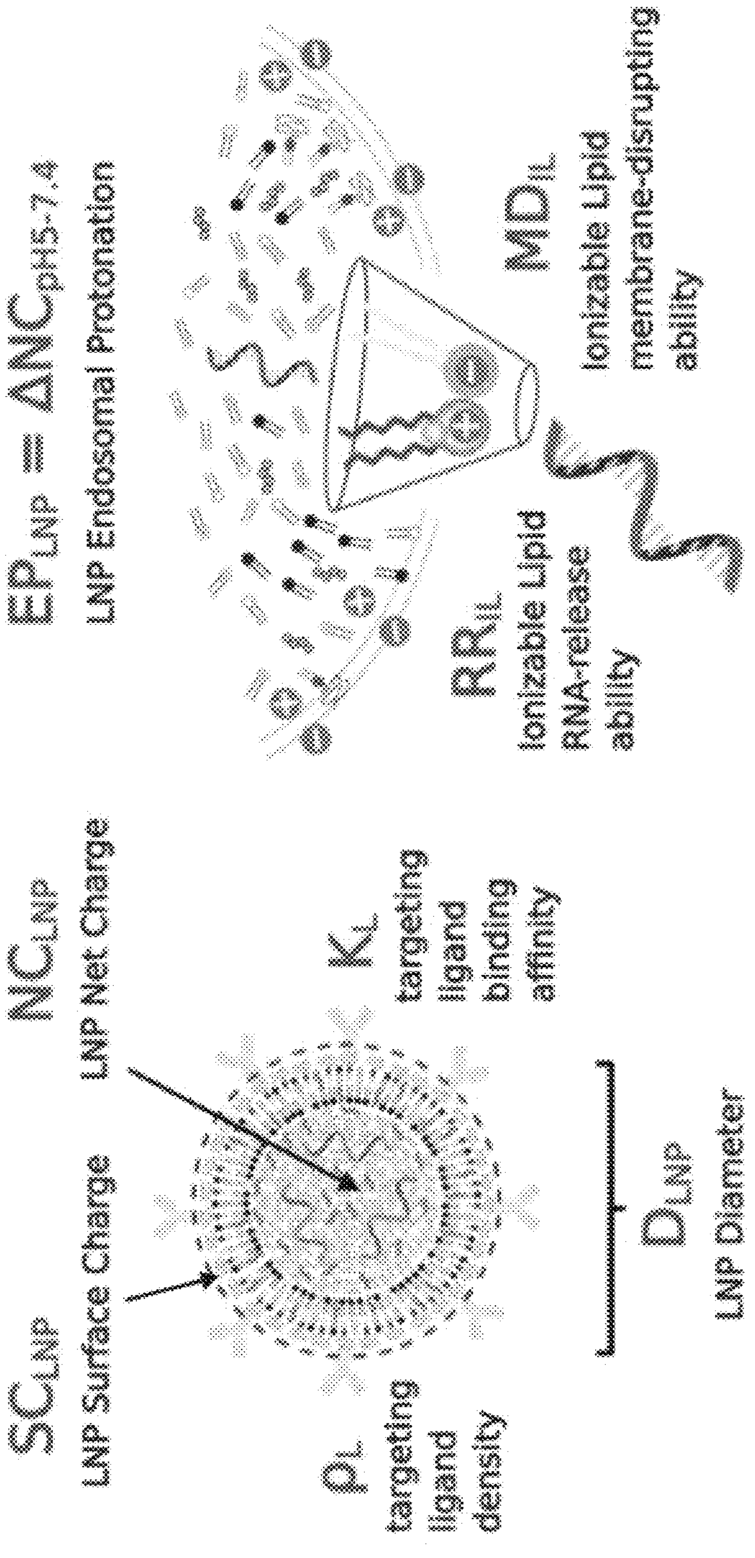

FIG. 93 illustrates determinants of LNP performance that will be measured, modeled and related to delivery efficiency, targeting, toxicity and reactogenicity in vitro and in animal models.

Figure 94:
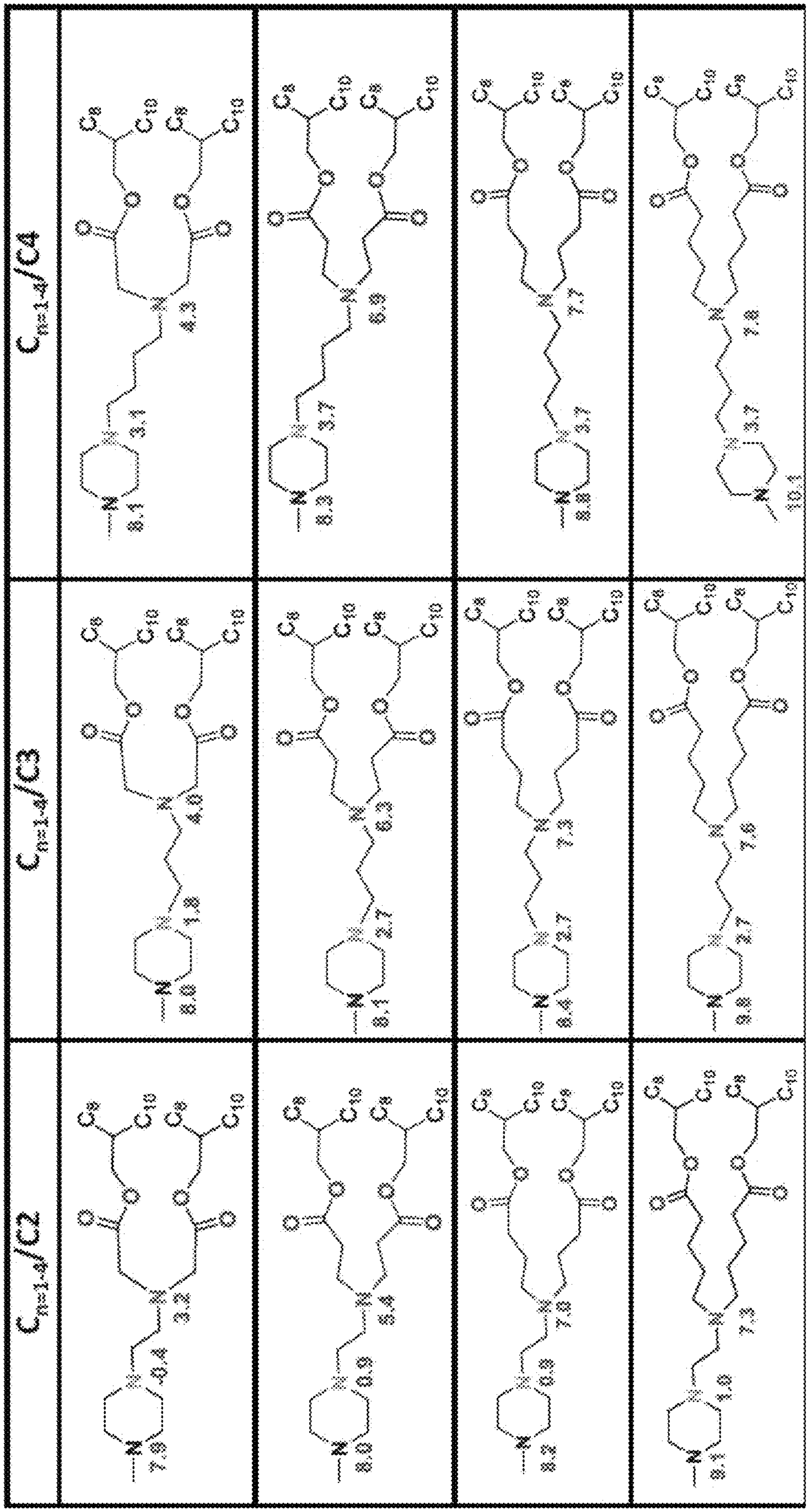

FIG. 94 illustrates exemplary BODD PipZ types of ionizable lipids. 12 members of this family were synthesized with different carbon spacers to generate ionizable lipids with molecular macro-ionization constants (shown on the Ns above) that span a 2 point range to characterize resulting LNP charge and endosomal protonation and relate these features to delivery efficiency and targeting.

Figure 95:
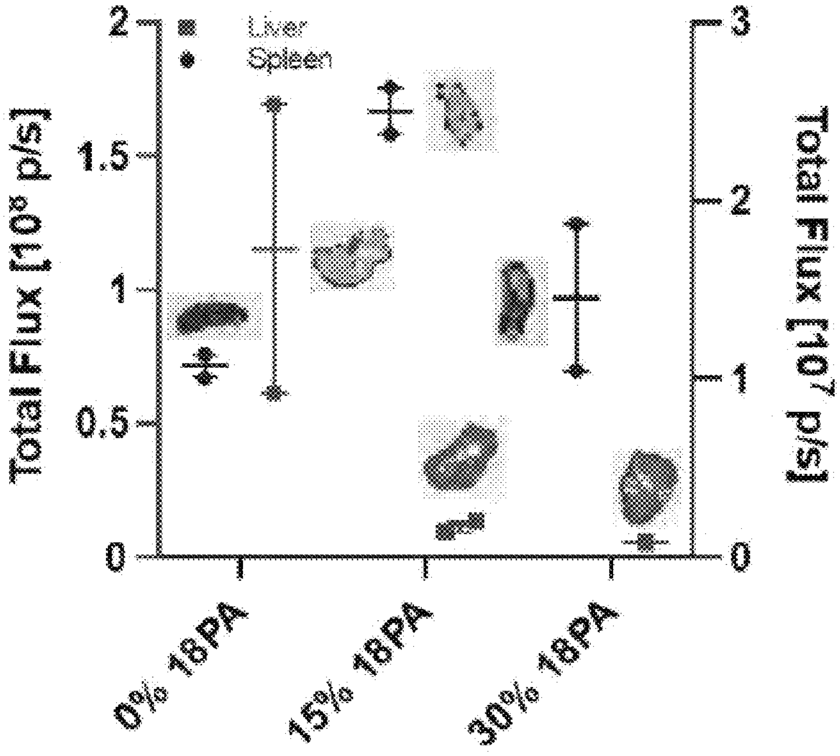

FIG. 95 illustrates negatively charged LNP reduces liver expression and increases expression in spleen. The anionic lipid 18-1PA was added to the lipid mix prior to mRNA LNP assembly at 15% and 30% of total lipids. Adding 18-1PA at 15% total lipids reduced liver expression of FLuc and increased spleen expression 2.5× upon IV administration.

Figure 96:
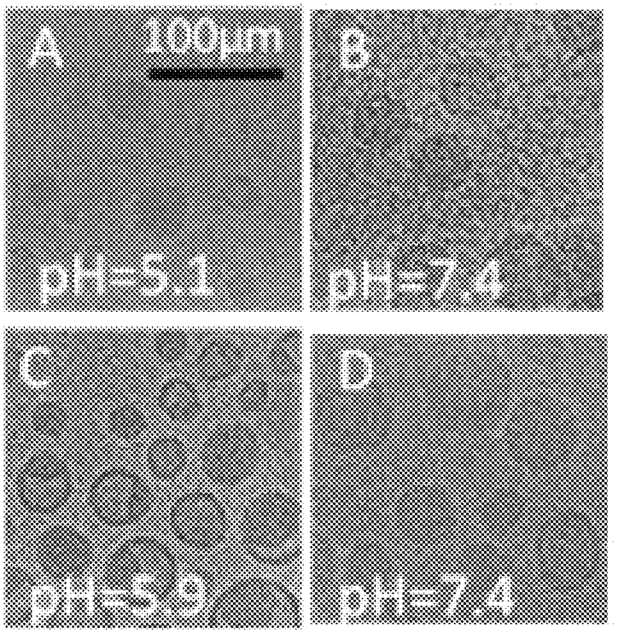

FIG. 96 illustrates assembly of Fluc LNPs at standard concentration (0.2 mg/ml mRNA in A,B) and high concentration (1.5 mg/ml mRNA in C,D) was imaged after ejection in ethanol/water at 1:2 v/v (A,C) or after dialysis in PBS to pH 7.4 (B, D). High potency mRNA LNPs produced at high mixing concentrations displayed greater levels of fused structures immediately upon mixing (C vs A) which were transformed to more homogeneous LNPs after dialysis.

V. DETAILED DESCRIPTION OF THE INVENTION

V.1. Definitions

Unless defined otherwise, or unless the specific context requires otherwise, all technical terms used herein have the same meaning as is commonly understood by a person skilled in the relevant technical field.

Percentages in the context of numbers should be understood as relative to the total number of the respective items. In other cases, and unless the context dictates otherwise, percentages should be understood as percentages by weight (wt.-%) or percentages by mole (mol.-%).

The singular forms "a", "an" and "the" should be understood as to include plural references unless the context clearly dictates otherwise. The expressions "an embodiment," "a specific embodiment," "one embodiment" and the like mean that a particular feature, property or characteristic, or a particular group or combination of features, properties or characteristics, as referred to in combination with the respective expression, is present in at least one of the embodiments of the invention. The occurrence of these expressions in various places throughout this description do not necessarily refer to the same embodiment. Moreover, the particular features, properties or characteristics may be combined in any suitable manner in one or more embodiments.

As used herein, the "adaptive immune system" is composed of highly specialized, systemic cells and processes that eliminate or prevent pathogenic growth and replication. The adaptive immune response provides the vertebrate immune system with the ability to recognize and remember specific pathogens (e.g., to generate immunity), and to mount stronger attacks each time the pathogen is encountered. The system is highly adaptable because of somatic hypermutation (a process of increased frequency of somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of that cell will then inherit genes encoding the same receptor specificity, including the Memory B cells and Memory T cells that are the keys to long-lived specific immunity. Immune network theory is a theory of how the adaptive immune system works, that is based on interactions between the variable regions of the receptors of T cells, B cells and of molecules made by T cells and B cells that have variable regions. As used herein, the term "adaptive immune response" is typically understood to be antigen-specific. Antigen specificity allows for the generation of responses that are tailored to specific antigens, pathogens or pathogen-infected cells. The ability to mount these tailored responses is maintained in the body by "memory cells." Should a pathogen infect the body more than once, these specific memory cells are used to quickly eliminate it. In this context, the first step of an adaptive immune response is the activation of naive antigen-specific T cells or different immune cells able to induce an antigen-specific immune response by antigen-presenting cells. This occurs in the lymphoid tissues and organs through which naive T cells are constantly passing. Cell types that can serve as antigen-presenting cells are, inter alia, dendritic cells, macrophages, and B cells. Each of these cells has a distinct function in eliciting immune responses. Dendritic cells take up antigens by phagocytosis and macropinocytosis and are stimulated by contact with for example a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. Presenting the antigen on MHC molecules leads to activation of T cells, which induces their proliferation and differentiation into armed effector T cells. The most important function of effector T cells is the killing of infected cells by CD8+ cytotoxic T cells and the activation of macrophages by Th1 cells, which together make up cell-mediated immunity, and the activation of B cells by both Th2 and Th1 cells to produce different classes of antibody, thus driving the humoral immune response. T cells recognize an antigen by their T cell receptors which do not recognize and bind antigen directly, but instead recognize short peptide fragments e.g. of pathogen-derived protein antigens, which are bound to MHC molecules on the surfaces of other cells.

As used herein, the term "adjuvant or an adjuvant component" in the broadest sense is typically a (e.g., pharmacological or immunological) agent or composition that may modify, e.g. enhance, the efficacy of other agents, such as a drug or vaccine. Conventionally, the term refers in the context of the invention to a compound or composition that serves as a carrier or auxiliary substance for immunogens and/or other pharmaceutically active compounds. It is to be interpreted in a broad sense and refers to a broad spectrum of substances that are able to increase the immunogenicity of antigens incorporated into or co-administered with an adjuvant in question. In the context of the invention an adjuvant will preferably enhance the specific immunogenic effect of the active agents of the present invention. Typically, "adjuvant" or "adjuvant component" has the same meaning and can be used mutually. Adjuvants may be divided, e.g., into immuno potentiators, antigenic delivery systems or even combinations thereof. As used herein, the term "adjuvant" is typically understood not to comprise agents which confer immunity by themselves. An adjuvant assists the immune system unspecifically to enhance the antigen-specific immune response by e.g. promoting presentation of an antigen to the immune system or induction of an unspecific innate immune response. Furthermore, an adjuvant may preferably e.g. modulate the antigen-specific immune response by e.g. shifting the dominating Th2-based antigen specific response to a more Th1-based antigen specific response or vice versa. Accordingly, an adjuvant may favourably modulate cytokine expression/secretion, antigen presentation, type of immune response etc.

As used herein, the term "alkyl group" means a saturated, monovalent unbranched or branched (substituted or unsubstituted) hydrocarbon chain. Examples of alkyl groups include, but are not limited to, $(C_1-C_{22})$alkyl groups, such as methyl, ethyl, propyl, isopropyl, 2-methyl-1-propyl, 2 methyl 2-propyl, 2-methyl-1-butyl, 3-methyl-1-butyl, 2 methyl-3-butyl, 2,2 dimethyl 1-propyl, 2-methyl-1-pentyl, 3 methyl-1-pentyl, 4 methyl-1-pentyl, 2-methyl-2-pentyl, 3-methyl-2-pentyl, 4 methyl 2 pentyl, 2,2 dimethyl 1 butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, octyl, decyl, dodecyl, etc. An alkyl group can be unsubstituted or substituted with one or two suitable substituents.

As used herein, the term an "alkenyl group" means a monovalent unbranched or branched hydrocarbon chain having one or more double bonds therein. The double bond of an alkenyl group can be unconjugated or conjugated to another unsaturated group. Suitable alkenyl groups include, but are not limited to $(C_2-C_{22})$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

As used herein, the term "alkoxy group" means an —O-alkyl group, wherein alkyl is as defined above. An alkoxy group can be unsubstituted or substituted with one or two suitable substituents. Preferably, the alkyl chain of an alkyloxy group is from 1 to 6 carbon atoms in length, referred to herein as "$(C_1-C_{22})$alkoxy".

As used herein, the term "alkoxycarbonyl" group means a monovalent group of the formula —C(O)-alkoxy. Preferably, the hydrocarbon chain of an alkoxycarbonyl group is from 1 to 22 carbon atoms in length.

As used herein, the term an "alkynyl group" means monovalent unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_6)$alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

As used herein, in the context of the present invention "antigen" refers typically to a substance which may be recognized by the immune system, preferably by the adaptive immune system, and is capable of triggering an antigen-specific immune response (e.g., by formation of antibodies and/or antigen-specific T cells as part of an adaptive immune response). Typically, an antigen may be or may comprise a peptide or protein which may be presented by the MHC to T-cells. In the sense of the present invention an antigen may be the product of translation of a provided nucleic acid molecule, preferably an mRNA as defined herein. In this context, also fragments, variants and derivatives of peptides and proteins comprising at least one epitope are understood as antigen.

As used herein, the term "antigen-providing mRNA" in the context of the invention may typically be an mRNA, having at least one open reading frame that can be translated by a cell or an organism provided with that mRNA. The product of this translation is a peptide or protein that may act as an antigen, preferably as an immunogen. The product may also be a fusion protein composed of more than one immunogen (e.g., a fusion protein that consists of two or more epitopes, peptides or proteins derived from the same or different virus-proteins), wherein the epitopes, peptides or proteins may be linked by linker sequences.

As used herein, the term "artificial mRNA (sequence)" may typically be understood to be an mRNA molecule, that does not occur naturally. In other words, an artificial mRNA molecule may be understood as a non-natural mRNA molecule. Such mRNA molecule may be non-natural due to its individual sequence (which does not occur naturally) and/or due to other modifications, for example, structural modifications of nucleotides which do not occur naturally. Typically, artificial mRNA molecules may be designed and/or generated by genetic engineering methods to correspond to a desired artificial sequence of nucleotides (heterologous sequence). In this context an artificial sequence is usually a sequence that may not occur naturally, i.e. it differs from the wild type sequence by at least one nucleotide. The term "wild type" may be understood as a sequence occurring in nature. Further, the term "artificial nucleic acid molecule" is not restricted to mean "one single molecule" but is, typically, understood to comprise an ensemble of identical molecules. Accordingly, it may relate to a plurality of identical molecules contained in an aliquot.

As used herein, the term an "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. Preferably, the aryl group is a monocyclic ring, wherein the ring comprises 6 carbon atoms, referred to herein as "$(C_6)$aryl".

As used herein, the term "aryloxy group" means an —O-aryl group, wherein aryl is as defined above. An aryloxy group can be unsubstituted or substituted with one or two suitable substituents. Preferably, the aryl ring of an aryloxy group is a monocyclic ring, wherein the ring comprises 6 carbon atoms, referred to herein as "$(C_6)$aryloxy".

As used herein, the term "B cell epitopes" are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form. Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

As used herein, the term "benzyl" means —$CH_2$-phenyl.

As used herein, the term "Bi-/multicistronic mRNA" is mRNA that typically may have two (bicistronic) or more (multicistronic) open reading frames (ORF) (coding regions or coding sequences). An open reading frame in this context is a sequence of several nucleotide triplets (codons) that can be translated into a peptide or protein. Translation of such an mRNA yields two (bicistronic) or more (multicistronic) distinct translation products (provided the ORFs are not identical). For expression in eukaryotes such mRNAs may for example comprise an internal ribosomal entry site (IRES) sequence.

As used herein, the term "CAP analogue" refers to a non-polymerizable di-nucleotide that has CAP functionality in that it facilitates translation or localization, and/or prevents degradation of the RNA molecule when incorporated at the 5'-end of the RNA molecule. Non-polymerizable means that the CAP analogue will be incorporated only at the 5'-terminus because it does not have a 5' triphosphate and therefore cannot be extended in the 3'-direction by a template-dependent RNA polymerase. In certain embodiments, the 5'-cap analogue utilizes Trilink Biotechnologies Clean-Cap Technology—https://www.trilinkbiotech.com/cleancap. As used herein, the term "CAP analogues" include, but are not limited to, a chemical structure selected from the group consisting of m7GpppG, m7GpppA, m7GpppC; unmethylated CAP analogues (e.g., GpppG); dimethylated CAP analogue (e.g., m2,7GpppG), trimethylated CAP analogue (e.g., m2,2,7GpppG), dimethylated symmetrical CAP analogues (e.g., m7Gpppm7G), or anti reverse CAP analogues (e.g., ARCA; m7,2'OmeGpppG, m7,2'dGpppG, m7,3'OmeGpppG, m7,3'dGpppG and their tetraphosphate derivatives) (Stepinski et al., 2001. RNA 7(10):1486-95). Further CAP analogues have been described previously (U.S. Pat. No. 7,074,596, WO2008/016473, WO2008/157688, WO2009/149253, WO2011/015347, and WO2013/059475), which are incorporated herein in their entirety. The synthesis of N7-(4-chlorophenoxyethyl) substituted dinucleotide CAP analogues has been described recently (Kore et al. (2013) Bioorg. Med. Chem. 21(15): 4570-4), which is incorporated herein in their entirety. As used herein, the term "5'-CAP structure" is typically a modified nucleotide (CAP analogue), particularly a guanine nucleotide, added to the 5'-end of an mRNA molecule. Preferably, the 5'-CAP is added using a 5'-5'-triphosphate linkage (also named m7GpppN). Further examples of 5'-CAP structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. These modified 5'-CAP structures may be used in the context of the present invention to modify the mRNA sequence of the inventive composition. Further modified 5'-CAP structures which may be used in the context of the present invention are CAP1 (additional methylation of the ribose of the adjacent nucleotide of m7GpppN), CAP2 (additional methylation of the ribose of the 2nd nucleotide downstream of the m7GpppN), CAP3 (additional methylation of the ribose of the 3rd nucleotide downstream of the m7GpppN), CAP4 (additional methylation of the ribose of the 4th nucleotide downstream of the m7GpppN), ARCA (anti-reverse CAP analogue), modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine. In the context of the present invention, a 5'-CAP structure may also be formed in chemical RNA synthesis or RNA in vitro transcription (co-transcriptional capping) using cCAP analogues, or a CAP structure may be formed in vitro using capping enzymes (e.g., commercially available capping kits).

As used herein, a "carbamoyl" group means the radical —$C(O)N(R')_2$, wherein R' is chosen from the group consisting of hydrogen, alkyl, and aryl.

As used herein, a "carbonyl" group is a divalent group of the formula —C═(O)—.

As used herein, the term "carrier" in the context of the invention may typically be a compound that facilitates transport and/or complexation of another compound. Said carrier may form a complex with said other compound. A polymeric carrier is a carrier that is formed of a polymer.

Unless a different meaning is clear from the specific context, the term "cationic" means that the respective structure bears a positive charge, either permanently, or not permanently but in response to certain conditions such as pH. Thus, the term "cationic" covers both "permanently cationic" and "cationisable". As used herein, "permanently cationic" means that the respective compound, or group or atom, is positively charged at any pH value or hydrogen ion activity of its environment. Typically, the positive charge is results from the presence of a quaternary nitrogen atom. Where a compound carries a plurality of such positive charges, it may be referred to as permanently polycationic, which is a subcategory of permanently cationic.

As used herein, the term "Cellular immunity/cellular immune response" relates typically to the activation of macrophages, natural killer cells (NK), antigen-specific cytotoxic T-lymphocytes, and the release of various cytokines in response to an antigen. In a more general way, cellular immunity is not related to antibodies but to the activation of cells of the immune system. A cellular immune response is characterized e.g., by activating antigen-specific cytotoxic T-lymphocytes that are able to induce apoptosis in body cells displaying epitopes of an antigen on their surface, such as virus-infected cells, cells with intracellular bacteria, and cancer cells displaying tumor antigens; activating macrophages and natural killer cells, enabling them to destroy pathogens; and stimulating cells to secrete a variety of cytokines that influence the function of other cells involved in adaptive immune responses and innate immune responses.

In the context of the invention, a "composition" refers to any type of composition in which the specified ingredients may be incorporated, optionally along with any further constituents, usually with at least one pharmaceutically acceptable carrier or excipient. Thus, the composition may be a dry composition such as a powder or granules, or a solid unit such as a lyophilised form or a tablet. Alternatively, the composition may be in liquid form, and each constituent may be independently incorporated in dissolved or dispersed (e.g. suspended or emulsified) form. In one of the preferred embodiments, the composition is formulated as a sterile solid composition, such as a powder or lyophilised form for reconstitution with an aqueous liquid carrier. Such formulation is also preferred for those versions of the composition which comprise a nucleic acid cargo as described in further detail below.

As used herein, a "compound" means a chemical substance (e.g., an Ionizable Lipid of the Invention), which is a material consisting of molecules having essentially the same chemical structure and properties. For a small molecular compound, the molecules are typically identical with respect to their atomic composition and structural configuration. For a macromolecular or polymeric compound, the molecules of a compound are highly similar but not all of them are necessarily identical. For example, a segment of a polymer that is designated to consist of 50 monomeric units may also contain individual molecules with e.g. 48 or 53 monomeric units.

Unless the context indicates or requires otherwise, the words "comprise", "comprises" and "comprising" and similar expressions are to be construed in an open and inclusive sense, as "including, but not limited to" in this description and in the claims.

As used herein, the term "cycloalkyl group" means a monocyclic or polycyclic saturated ring comprising carbon and hydrogen atoms and having no carbon-carbon multiple bonds. Examples of cycloalkyl groups include, but are not limited to, $(C_3-C_7)$cycloalkyl groups, such as cyclopropyl, cyclobutyl, cyclopentyl, cyclohexyl, and cycloheptyl, and saturated cyclic and bicyclic terpenes. A cycloalkyl group can be unsubstituted or substituted by one or two suitable substituents. Preferably, the cycloalkyl group is a monocyclic ring or bicyclic ring.

As used herein, the term "derivative of a peptide or protein" is typically understood to be a molecule that is derived from another molecule, such as said peptide or protein. A "derivative" of a peptide or protein also encompasses fusions comprising a peptide or protein used in the present invention. For example, the fusion comprises a label, such as, for example, an epitope, e.g., a FLAG epitope or a V5 epitope. For example, the epitope is a FLAG epitope. Such a tag is useful for, for example, purifying the fusion protein.

As used herein, the term "epitope (also called "antigen determinant"): refers to T cell epitopes or parts of the proteins in the context of the invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule.

As used herein, the term "fragments" of proteins or peptides in the context of the present invention may, typically, comprise a sequence of a protein or peptide as defined herein, which is, with regard to its amino acid sequence (or its encoded nucleic acid molecule), N-terminally and/or C-terminally truncated compared to the amino acid sequence of the original (native) protein (or its encoded nucleic acid molecule). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide. In this context a fragment of a protein may typically comprise an amino acid sequence having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with an amino acid sequence of the respective naturally occurring fill-length protein.

As used herein, the term "fragments of proteins or peptides" in the context of the present invention may furthermore comprise a sequence of a protein or peptide as defined herein, which has a length of for example at least 5 amino acids, preferably a length of at least 6 amino acids, preferably at least 7 amino acids, more preferably at least 8 amino acids, even more preferably at least 9 amino acids; even more preferably at least 10 amino acids; even more preferably at least 11 amino acids; even more preferably at least 12 amino acids; even more preferably at least 13 amino acids; even more preferably at least 14 amino acids; even more preferably at least 15 amino acids; even more preferably at least 16 amino acids; even more preferably at least 17 amino acids; even more preferably at least 18 amino acids; even more preferably at least 19 amino acids; even more preferably at least 20 amino acids; even more preferably at least 25 amino acids; even more preferably at least 30 amino acids; even more preferably at least 35 amino acids; even more preferably at least 50 amino acids; or most preferably at least 100 amino acids. For example such fragment may have a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form. Fragments of proteins or peptides may comprise at least one epitope of those proteins or peptides. Furthermore also domains of a protein, like the extracellular domain, the intracellular domain or the transmembrane domain and shortened or truncated versions of a protein may be understood to comprise a fragment of a protein.

As used herein, the term "full-length protein" as used herein typically refers to a protein that substantially comprises the entire amino acid sequence of the naturally occurring protein. Nevertheless, substitutions of amino acids e.g. due to mutation in the protein are also encompassed in the term full-length protein.

As used herein, "halogen" means fluorine, chlorine, bromine, or iodine. Accordingly, the meaning of the terms "halo" and "Hal" encompass fluoro, chloro, bromo, and iodo.

As used herein, the term an "heteroaryl group" means a monocyclic- or polycyclic aromatic ring comprising carbon atoms, hydrogen atoms, and one or more heteroatoms, preferably 1 to 3 heteroatoms, independently selected from nitrogen, oxygen, and sulfur. Illustrative examples of heteroaryl groups include, but are not limited to, pyridinyl, pyridazinyl, pyrimidinyl, pyrazyl, triazinyl, pyrrolyl, pyrazolyl, imidazolyl, (1,2,3)- and (1,2,4)-triazolyl, pyrazinyl, pyrimidinyl, tetrazolyl, furyl, thiophenyl, isoxazolyl, thiazolyl, furyl, phenyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms, referred to herein as "($C_2$-$C_5$)heteroaryl".

As used herein, the term "heterocycloalkyl group" means a monocyclic or polycyclic ring comprising carbon and hydrogen atoms and at least one heteroatom, preferably, 1 to 3 heteroatoms selected from nitrogen, oxygen, and sulfur, and having no unsaturation. Examples of heterocycloalkyl groups include pyrrolidinyl, pyrrolidino, piperidinyl, piperidino, piperazinyl, piperazino, morpholinyl, morpholino, thiomorpholinyl, dioxolanyl, thiomorpholino, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 3 to 6 carbon atoms and from 1 to 3 heteroatoms, referred to herein as ($C_1$-$C_6$)heterocycloalkyl.

As used herein, the terms "heterocyclic radical" or "heterocyclic ring" mean a heterocycloalkyl group or a heteroaryl group.

As used herein, the term "humoral immunity" refers typically to antibody production and the accessory processes that may accompany it. A humoral immune response may be typically characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

As used herein, the term "hydrate" means a compound of the invention or a salt thereof, that further includes a stoichiometric or non-stoichiometric amount of water bound by non-covalent intermolecular forces. The term hydrate includes solvates, which are stoichiometric or non-stoichiometric amounts of a solvent bound by non-covalent intermolecular forces. Preferred solvents are volatile, non-toxic, and/or acceptable for administration to humans in trace amounts.

As used herein, the term "hydrocarbyl" group means a monovalent group selected from ($C_1$-$C_{22}$)alkyl, ($C_2$-$C_{22}$) alkenyl, and ($C_2$-$C_5$)alkynyl, optionally substituted with one or two suitable substituents. Preferably, the hydrocarbon chain of a hydrocarbyl group is from 1 to 22 carbon atoms in length, referred to herein in certain instances as "($C_1$-$C_{22}$)hydrocarbyl".

As used herein, the term "identity of a sequence" means the percentage to which two sequences are identical, e.g. nucleic acid sequences or amino acid sequences as defined herein, preferably the amino acid sequences encoded by a nucleic acid sequence of the polymeric carrier as defined herein or the amino acid sequences themselves, the sequences can be aligned in order to be subsequently compared to one another. Therefore, e.g. a position of a first sequence may be compared with the corresponding position of the second sequence. If a position in the first sequence is occupied by the same component (residue) as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

As used herein, the term "immune system" may protect organisms from infection. If a pathogen breaks through a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts contains so called humoral and cellular components.

As used herein, the term "an immune response" may typically either be a specific reaction of the adaptive immune system to a particular antigen (so called specific or adaptive immune response) or an unspecific reaction of the innate immune system (so called unspecific or innate immune response). The invention relates to the core to specific reactions (adaptive immune responses) of the adaptive immune system. Particularly, it relates to adaptive immune responses to infections by viruses like e.g. Influenza viruses. However, this specific response can be supported by an additional unspecific reaction (innate immune response). Therefore, the invention also relates to a compound for simultaneous stimulation of the innate and the adaptive immune system to evoke an efficient adaptive immune response.

As used herein, the term "immunostimulatory RNA (isRNA)" in the context of the invention may typically be an RNA that is able to induce an innate immune response itself. It usually does not have an open reading frame and thus does not provide a peptide-antigen or immunogen but elicits an innate immune response e.g. by binding to a specific kind of Toll-like-receptor (TLR) or other suitable receptors. However, of course also mRNAs having an open reading frame and coding for a peptide/protein (e.g. an antigenic function) may induce an innate immune response.

As used herein, the term "influenza pandemic or pandemic flu" can occur when a non-human (novel) influenza virus gains the ability for efficient and sustained human-to-human transmission and then spreads globally. Influenza viruses that have the potential to cause a pandemic are referred to as "influenza viruses with pandemic potential" or "pandemic influenza virus". Examples of influenza viruses with pandemic potential include avian influenza A (H5N1) and avian influenza A (H7N9), which are two different "bird flu" viruses. These are non-human viruses (i.e., they are novel among humans and circulate in birds in parts of the world) so there is little to no immunity against these viruses among people. Human infections with these viruses have occurred rarely, but if either of these viruses was to change in such a way that it was able to infect humans easily and spread easily from person to person, an influenza pandemic could result.

As used herein, the term "innate immune system" also known as non-specific immune system, comprises the cells and mechanisms that defend the host from infection by other organisms in a non-specific manner. This means that the cells of the innate system recognize and respond to pathogens in a generic way, but unlike the adaptive immune system, it does not confer long-lasting or protective immunity to the host. The innate immune system may be e.g. activated by ligands of pathogen-associated molecular patterns (PAMP) receptors, e.g. Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent. Typically a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system through a process known as antigen presentation; and/or acting as a physical and chemical barrier to infectious agents.

As used herein, the term "ionizable" (e.g., as used in the term 'an Ionizable Lipid of the Invention') means that a compound, or group or atom, is charged at a certain pH and uncharged at another pH of its environment. Also in non-aqueous environments where no pH value can be determined, a ionizable compound, group or atom is positively charged at a high hydrogen ion concentration and negatively or uncharged at a low concentration or activity of hydrogen ions. It depends on the individual properties of the ionizable or polyionizable compound, in particular the pKa of the respective ionizable group or atom, at which pH or hydrogen ion concentration it is charged or uncharged. In diluted aqueous environments, the fraction of ionizable compounds, groups or atoms bearing a charge may be estimated using the so-called Henderson-Hasselbalch equation, which is well-known to a person skilled in the art. For example, in some embodiments, if a compound or moiety is ionizable, it is preferred that it is positively charged at a pH value of about 1 to 9, preferably 4 to 9, 5 to 8 or even 6 to 8, more preferably of a pH value of or below 9, of or below 8, of or below 7, most preferably at physiological pH values, e.g. about 7.3 to 7.4, i.e. under physiological conditions, particularly under physiological salt conditions of the cell in vivo. In other embodiments, the ionizable compound or moiety is predominantly neutral at physiological pH values, e.g. about 7.0-7.4, but becomes positively charged at lower pH values. In some embodiments, the preferred range of pKa for the cationisable compound or moiety is about 5 to about 7.

As used herein, the phrase "Ionizable Lipids of the Invention" means compounds disclosed herein including the ionizable lipid nanoparticle compounds disclosed herein. Particular compounds of the invention are compounds of formulas I, II, III, IV, V, VI, VII, VIII, or IX and pharmaceutically acceptable salts, hydrates, enantiomers, diastereomer, racemates or mixtures of stereoisomers thereof. Thus, "Ionizable Lipids of the invention" collectively means compound of formulas I, II, III, IV, V, VI, VII, VIII, or IX and pharmaceutically acceptable salts, hydrates, enantiomers, diastereomer, racemates or mixtures of stereoisomers thereof. The Ionizable Lipids of the invention are identified herein by their chemical structure and/or chemical name. Where a compound is referred to by both a chemical structure and a chemical name, and the chemical structure and chemical name conflict, the chemical structure is to be accorded more weight. The term "Ionizable Lipid of the Invention" typically refers to a molecule capable of being charged, which is, for example, positively charged (cationic) at a pH value of typically about 1 to 9. In some embodiments, the cationic component/compound is preferably charged at a pH value of or below 9 (e.g. 5 to 9), of or below 8 (e.g. 5 to 8), of or below 7 (e.g. 5 to 7), most preferably at physiological pH values, e.g. about 7.3 to 7.4, and endosomal pH values, e.g. about 7 to 5. Accordingly, a cationic peptide, protein, polysaccharide, lipid or polymer according to one embodiment of the present invention is, in certain embodiments, positively charged under physiological conditions, particularly under physiological salt conditions of the cell in vivo. In another preferred embodiment, the lipid nanoparticle, the cationic peptide, protein, polysaccharide, lipid or polymer according to the present invention is uncharged, has a neutral charge or is respectively electrically neutral under physiological conditions, particularly under physiological salt conditions of the cell in vivo. A cationic peptide or protein preferably contains a larger number of cationic amino acids, e.g. a larger number of Arg, His, Lys or Orn than other amino acid residues (in particular more cationic amino acids than anionic amino acid residues like Asp or Glu) or contains blocks predominantly formed by cationic amino acid residues. The expression "cationic" may also refer to "polycationic" components/compounds. The cationic component/compound may also refer to a cationic lipid capable of being positively charged. Exemplary cationic lipids include one or more amine group(s) which bear the positive charge. Preferred cationic lipids are ionizable such that they can exist in a positively charged or neutral form depending on pH. The ionization of the cationic lipid affects the surface charge of a lipid nanoparticle (LNP) under different pH conditions. This charge state can influence plasma protein absorption, blood clearance and tissue distribution (Semple, S. C., et al., Adv. Drug Deliv Rev 32:3-17 (1998)) as well as the ability to form non-bilayer structures (Hafez, I. M., et al., Gene Ther 8:1188-1196 (2001)) critical to the intracellular delivery of nucleic acids. As described elsewhere, the pKa of formulated cationic lipids is correlated with the effectiveness of LNPs for delivery of nucleic acids (see Jayaraman et al, Angewandte Chemie, International Edition (2012), 51(34), 8529-8533; Semple et al, Nature Biotechnology 28, 172-176 (2010)). In some embodiments of the present invention, the preferred range of pKa is about 5 to about 7. In preferred embodiments, the Ionizable Lipids of the Invention have a neutral charge with a slight positive or negative charge near pH 7. The Ionizable Lipids of the Invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the Ionizable Lipids of the Invention, encompass all of the corresponding compounds' enantiomers and stereoisomers, that is, both the stereomerically pure form (e.g., geometrically pure, enantiomerically pure, or diastereomerically pure) and enantiomeric and stereoisomeric mixtures. An Ionizable Lipids of the Invention is considered optically active or enantiomerically enriched (i.e., substantially the R-form or substantially the S-form) with respect to a chiral center when the compound is about 90% ee (enantiomeric excess) or greater, preferably, equal to or greater than 95% ee with respect to a particular chiral center. An Ionizable Lipids of the Invention is considered to be in enantiomerically-enriched form when the compound has an enantiomeric excess of greater than about 1% ee, preferably greater than about 5% ee, more preferably, greater than about 10% ee with respect to a particular chiral center. An Ionizable Lipids of the Invention is considered diastereomerically pure with respect to multiple chiral centers when the compound is about 90% de (diastereomeric excess) or greater, preferably, equal to or greater than 95% de with respect to a particular chiral center. An Ionizable Lipids of the Invention is considered to be in diastereomerically-enriched form when the compound has an diastereomeric excess of greater than about 1% de, preferably greater than about 5% de, more preferably, greater than about 10% de with respect to a particular chiral center. As used herein, a racemic mixture means about 50% of one enantiomer and about 50% of is corresponding enantiomer relative to all chiral centers in the molecule. Thus, the invention encompasses all enantiomerically-pure, enantiomerically-enriched, diastereomerically pure, diastereomerically enriched, and racemic mixtures of compounds of Formulas I through V. Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well-known asymmetric synthetic methods. The Ionizable Lipids of the Invention are defined herein by their chemical structures and/or chemical names. Where a compound is referred to by both a chemical structure and a chemical name, and the chemical structure and chemical name conflict, the chemical structure is determinative of the compound's identity. When administered to a patient, e.g., to an animal for veterinary use or for improvement of livestock, or to a human for clinical use, the Ionizable Lipids of the Invention are administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the Ionizable Lipids of the Invention are purified. As used herein, "purified" means that when isolated, the isolate contains at least 95%, preferably at least 98%, of a single hydroxy compound of the invention by weight of the isolate.

As used herein, the term "jet injection", as used herein, refers to a needle-free injection method, wherein a fluid containing at least one inventive mRNA sequence and, optionally, further suitable excipients is forced through an orifice, thus generating an ultra-fine liquid stream of high pressure that is capable of penetrating mammalian skin and, depending on the injection settings, subcutaneous tissue or muscle tissue. In principle, the liquid stream forms a hole in the skin, through which the liquid stream is pushed into the target tissue. Preferably, jet injection is used for intradermal, subcutaneous or intramuscular injection of the mRNA sequence according to the invention. In a preferred embodiment, jet injection is used for intramuscular injection of the mRNA sequence according to the invention. In a further preferred embodiment, jet injection is used for intradermal injection of the mRNA sequence according to the invention.

As used herein the term "lipidoid compound," also simply referred to as lipidoid, is a lipid-like compound, i.e. an amphiphilic compound with lipid-like physical properties.

In the context of the present invention the term lipid is considered to encompass lipidoids.

As used herein, the term "microneedle injection" refers to microscopic applicators used to deliver vaccines or other drugs across various barriers: while transdermal application is the most popular use of microneedles, intraocular and intracochlear microneedle drug delivery systems are emerging. Microneedles are constructed through various methods usually involving photolithographic processes or micromolding. These methods involve etching microscopic structure into resin or silicon in order to cast microneedles. Microneedles are made from a variety of material ranging from silicon, titanium, stainless steel, and polymers. Some microneedles are made of a drug to be delivered to the body but are shaped into a needle so they will penetrate the skin. The microneedles range in size, shape, and function but are all used as an alternative to other delivery methods like the conventional hypodermic needle or other injection apparatus.

As used herein, the term "monocistronic mRNA" may typically be an mRNA, that comprises only one open reading frame (coding sequence or coding region). An open reading frame in this context is a sequence of several nucleotide triplets (codons) that can be translated into a peptide or protein.

As used herein, the term "nucleic acid" means any DNA- or RNA-molecule. The term may be used for a polynucleotide and/or oligonucleotide. Wherever herein reference is made to a nucleic acid or nucleic acid sequence encoding a particular protein and/or peptide, said nucleic acid or nucleic acid sequence, respectively, preferably also comprises regulatory sequences allowing in a suitable host, e.g. a human being, its expression, i.e. transcription and/or translation of the nucleic acid sequence encoding the particular protein or peptide.

As used herein, the term "nucleoside modification" in the context of the present invention the term nucleoside modification refers to mRNA molecules or compounds comprising nucleosides, which are not usually part of mRNA, preferably non-natural nucleosides. In particular, the term preferably refers to mRNA nucleosides other than adenine, guanine, cytosine, uracil and in some cases thymine.

As used herein, the term "peptide" is an oligomer or polymer of at least two amino acid monomers. Usually the monomers are linked by peptide bonds. The term "peptide" does not limit the length of the polymer chain of amino acids. In some embodiments of the present invention a peptide may for example contain less than 50 monomer units. Longer peptides are also called polypeptides, typically having 50 to 600 monomeric units, more specifically 50 to 300 monomeric units.

As described herein "nucleoside" is defined as a compound containing a five-carbon sugar molecule (a pentose or ribose) or derivative thereof, and an organic base, purine or pyrimidine, or a derivative thereof. As described herein, "nucleotide" is defined as a nucleoside consisting of a phosphate group. In some embodiments, the chemical modifications can include an amino group, a thiol group, an alkyl group, or a halo group. In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In some embodiments, modified nucleosides include 5-aza-cytidine, pseudoisocytidme, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine. In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2, 6-diaminopurine, 7-deaza-8-aza-2, 6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine. In some embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

The phrase "pharmaceutically acceptable salt(s)," as used herein includes, but is not limited to, salts of acidic or basic groups that may be present in the compounds of the invention. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds of the invention that include an amino moiety also can form pharmaceutically acceptable salts with various amino acids, in addition to the acids mentioned above. Compounds of the invention that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein, the term "pharmaceutically effective amount" in the context of the invention is typically understood to be an amount that is sufficient to induce an immune response.

As used herein, the term "phenyl" means —$C_6H_5$. A phenyl group can be unsubstituted or substituted with one or two suitable substituents, wherein the substituent replaces an H of the phenyl group. As used herein, "Ph," represents a phenyl group or a substituted phenyl group.

As used herein, the prefix "poly-" refers to a plurality of atoms or groups having the respective property in a compound. If put in parenthesis, the presence of a plurality is optional. For example, (poly)cationic means cationic and/or polycationic. However, the absence of the prefix should not be interpreted such as to exclude a plurality. For example, a polycationic compound is also a cationic compound and may be referred to as such.

As used herein, the term "poly-A-tail" also called "3'-poly(A) tail or poly(A) sequence" is typically a long sequence of adenosine nucleotides of up to about 400 adenosine nucleotides, e.g. from about 25 to about 400, preferably from about 50 to about 400, more preferably from about 50 to about 300, even more preferably from about 50 to about 250, most preferably from about 60 to about 250 adenosine nucleotides, added to the 3'-end of a RNA. Moreover, poly(A) sequences, or poly(A) tails may be generated in vitro by enzymatic polyadenylation of the RNA, e.g. using Poly(A)polymerases derived from *E. coli* or yeast.

As used herein, the term "polyadenylation" is typically understood to be the addition of a poly(A) sequence to a nucleic acid molecule, such as an RNA molecule, e.g. to a premature mRNA. Polyadenylation may be induced by a so called polyadenylation signal. This signal is preferably located within a stretch of nucleotides at the 3'-end of a nucleic acid molecule, such as an RNA molecule, to be polyadenylated. A polyadenylation signal typically comprises a hexamer consisting of adenine and uracil/thymine nucleotides, preferably the hexamer sequence AAUAAA. Other sequences, preferably hexamer sequences, are also conceivable. Polyadenylation typically occurs during processing of a pre-mRNA (also called premature-mRNA). Typically, RNA maturation (from pre-mRNA to mature mRNA) comprises the step of polyadenylation.

As used herein, the term "Poly (C) sequence" is typically a long sequence of cytosine nucleotides, typically about 10 to about 200 cytosine nucleotides, preferably about 10 to about 100 cytosine nucleotides, more preferably about 10 to about 70 cytosine nucleotides or even more preferably about 20 to about 50 or even about 20 to about 30 cytosine nucleotides. A poly(C) sequence may preferably be located 3' of the coding region comprised by a nucleic acid.

As used herein, the term "protein" typically consists of one or more peptides and/or polypeptides folded into a 3-dimensional form, facilitating a biological function.

As used herein, the terms "Pyr" "Pyrd" and "PyrD" are used interchangeably and refer to a pyridine or pyridyl substituent.

As used herein, RNA encompasses messenger RNA and modified messenger RNA, as well as coding (cRNA) and noncoding RNA (ncRNA) including housekeeping ncRNAs (transfer RNA (i.e., tRNA) and ribosomalRNA (i.e, rRNA)) and regulatory ncRNAs, which are further classified according to their size including long ncRNAs (lncRNA) having at least 200 nucleotides and small ncRNAs have fewer than 200 nucleotides including micro RNA (miRNA), small nucleolar RNA (snoRNA), small nuclear RNA (snRNA), small-interfering RNA (siRNA), and PIWI-interacting RNA (piRNA).

As used herein, the terms "RNA in vitro transcription" or "in vitro transcription" relate to a process wherein RNA is synthesized in a cell-free system (in vitro). DNA, particularly plasmid DNA, is used as template for the generation of RNA transcripts. RNA may be obtained by DNA-dependent in vitro transcription of an appropriate DNA template, which according to the present invention is preferably a linearized plasmid DNA template. The promoter for controlling in vitro transcription can be any promoter for any DNA-dependent RNA polymerase. Particular examples of DNA-dependent RNA polymerases are the T7, T3, and SP6 RNA polymerases. A DNA template for in vitro RNA transcription may be obtained by cloning of a nucleic acid, in particular cDNA corresponding to the respective RNA to be in vitro transcribed, and introducing it into an appropriate vector for in vitro transcription, for example into plasmid DNA. In a preferred embodiment of the present invention the DNA template is linearized with a suitable restriction enzyme before it is transcribed in vitro. The cDNA may be obtained by reverse transcription of mRNA or chemical synthesis. Moreover, the DNA template for in vitro RNA synthesis may also be obtained by gene synthesis. As used herein, the methods for in vitro transcription are known in the art (see, e.g., Geall et al. (2013) Semin. Immunol. 25(2): 152-159; Brunelle et al. (2013) Methods Enzymol. 530:101-14). Reagents used in said method typically include:

1) a linearized DNA template with a promoter sequence that has a high binding affinity for its respective RNA polymerase such as bacteriophage-encoded RNA polymerases;
2) ribonucleoside triphosphates (NTPs) for the four bases (adenine, cytosine, guanine and uracil);
3) optionally a CAP analogue as defined above (e.g. m7G(5')ppp(5')G (m7G) or 10.1126/scitranslmed.aav5701): RNAs were capped using the m7G capping kit with 2'-O-methyltransferase (ScriptCap, CELLSCRIPT) to obtain cap1);
4) a DNA-dependent RNA polymerase capable of binding to the promoter sequence within the linearized DNA template (e.g. T7, T3 or SP6 RNA polymerase);
5) optionally a ribonuclease (RNase) inhibitor to inactivate any contaminating RNase;
6) optionally a pyrophosphatase to degrade pyrophosphate, which may inhibit transcription;
7) $MgCl_2$, which supplies Mg2+ ions as a co-factor for the polymerase;
8) a buffer to maintain a suitable pH value, which can also contain antioxidants (e.g. DTT), and/or polyamines such as spermidine at optimal concentrations.

As used herein, the term "stabilized nucleic acid, preferably mRNA" typically, exhibits a modification increasing resistance to in vivo degradation (e.g. degradation by an exo- or endo-nuclease) and/or ex vivo degradation (e.g. by the manufacturing process prior to vaccine administration, e.g. in the course of the preparation of the vaccine solution to be administered). Stabilization of RNA can, e.g., be achieved by providing a 5'-CAP-Structure, a Poly-A-Tail, or any other UTR-modification. It can also be achieved by chemical modification or modification of the G/C-content of the nucleic acid. Various other methods are known in the art and conceivable in the context of the invention.

As used herein, a composition that "substantially" comprises a compound means that the composition contains more than about 80% by weight, more preferably more than about 90% by weight, even more preferably more than about 95% by weight, and most preferably more than about 97% by weight of the compound.

As used herein, a reaction that is "substantially complete" means that the reaction contains more than about 80% by weight of the desired product, more preferably more than about 90% by weight of the desired product, even more preferably more than about 95% by weight of the desired product, and most preferably more than about 97% by weight of the desired product.

As used herein, a composition that is "substantially free" of a compound means that the composition contains less than about 20% by weight, more preferably less than about 10% by weight, even more preferably less than about 5% by weight, and most preferably less than about 3% by weight of the compound.

As used herein, a "substituted" or "substituent" each means a group that does not nullify the synthetic or pharmaceutical utility of the compounds of the invention or the intermediates useful for preparing them. Examples of suitable substituents include, but are not limited to: —$NH_2$; CN; halo, heterocycloalkyl; heterocycloaryl; ($C_1$-$C_{22}$)alkyl; ($C_2$-$C_{22}$)alkenyl; ($C_2$-$C_{22}$)alkynyl; ($C_6$)aryl; ($C_2$-$C_5$)heteroaryl; ($C_3$-$C_7$)cycloalkyl; ($C_1$-$C_8$)alkoxy; ($C_6$)aryloxy; —CN; —OH; oxo; halo, —$CO_2H$; —$NH_2$; —NH(($C_1$-$C_{22}$)alkyl); —N(($C_1$-$C_{22}$)alkyl)$_2$; —NH(($C_6$)aryl); —N(($C_6$)aryl)$_2$; —CHO; —CO(($C_1$-$C_{22}$)alkyl); —CO(($C_6$)aryl); —$CO_2$(($C_1$-$C_{22}$)alkyl); —$CO_2$(($C_6$)aryl); —$SO_2$(($C_1$-$C_{22}$)alkyl); and —$SO_2$(($C_6$)aryl) or any of the groups identified herein that can act as a suitable substituent. One of skill in the art can readily choose a suitable substituent based on the stability and pharmacological and synthetic activity of the compound of the invention.

As used herein, the term "5'-terminal oligopyrimidine tract (TOP)" is typically a stretch of pyrimidine nucleotides located at the 5'-terminal region of a nucleic acid molecule, such as the 5'-terminal region of certain mRNA molecules or the 5'-terminal region of a functional entity, e.g. the transcribed region, of certain genes. The sequence starts with a cytidine, which usually corresponds to the transcriptional start site, and is followed by a stretch of usually about 3 to 30 pyrimidine nucleotides. For example, the TOP may comprise 3, 4, 5, 6, 7, 8, 9, 10, 11, 12, 13, 14, 15, 16, 17, 18, 19, 20, 21, 22, 23, 24, 25, 26, 27, 28, 29, 30 or even more nucleotides. The pyrimidine stretch and thus the 5'-TOP ends one nucleotide 5' to the first purine nucleotide located downstream of the TOP. Messenger RNA that contains a 5'-terminal oligopyrimidine tract is often referred to as TOP mRNA. Accordingly, genes that provide such messenger RNAs are referred to as TOP genes. TOP sequences have, for example, been found in genes and mRNAs encoding peptide elongation factors and ribosomal proteins.

As used herein, the term "TOP motif" is a nucleic acid sequence which corresponds to a 5'-TOP as defined above. Thus, a TOP motif in the context of the present invention is preferably a stretch of pyrimidine nucleotides having a length of 3-30 nucleotides. Preferably, the TOP motif consists of at least 3 pyrimidine nucleotides, preferably at least 4 pyrimidine nucleotides, preferably at least 5 pyrimidine nucleotides, more preferably at least 6 nucleotides, more preferably at least 7 nucleotides, most preferably at least 8 pyrimidine nucleotides, wherein the stretch of pyrimidine nucleotides preferably starts at its 5'-end with a cytosine nucleotide. In TOP genes and TOP mRNAs, the TOP motif preferably starts at its 5'-end with the transcriptional start site and ends one nucleotide 5' to the first purine residue in said gene or mRNA. A TOP motif in the sense of the present invention is preferably located at the 5'-end of a sequence which represents a 5'-UTR or at the 5'-end of a sequence which codes for a 5'-UTR. Thus, preferably, a stretch of 3 or more pyrimidine nucleotides is called "TOP motif" in the sense of the present invention if this stretch is located at the 5'end of a respective sequence, such as the inventive mRNA, the 5'-UTR element of the inventive mRNA, or the nucleic acid sequence which is derived from the 5'-UTR of a TOP gene as described herein. In other words, a stretch of 3 or more pyrimidine nucleotides which is not located at the 5'-end of a 5'-UTR or a 5'-UTR element but anywhere within a 5'-UTR or a 5'-UTR element is preferably not referred to as "TOP motif".

As used herein, the term "TOP genes" are typically characterized by the presence of a 5'-terminal oligopyrimidine tract. Furthermore, most TOP genes are characterized by a growth-associated translational regulation. However, also TOP genes with a tissue specific translational regulation are known. As defined above, the 5'-UTR of a TOP gene corresponds to the sequence of a 5'-UTR of a mature mRNA derived from a TOP gene, which preferably extends from the nucleotide located 3' to the 5'-CAP to the nucleotide located 5' to the start codon. A 5'-UTR of a TOP gene typically does not comprise any start codons, preferably no upstream AUGs (uAUGs) or upstream open reading frames (uORFs). Therein, upstream AUGs and upstream open reading frames are typically understood to be AUGs and open reading frames that occur 5' of the start codon (AUG) of the open reading frame that should be translated. The 5'-UTRs of TOP genes are generally rather short. The lengths of 5'-UTRs of TOP genes may vary between 20 nucleotides up to 500 nucleotides, and are typically less than about 200 nucleotides, preferably less than about 150 nucleotides, more preferably less than about 100 nucleotides. Exemplary 5'-UTRs of TOP genes in the sense of the present invention are the nucleic acid sequences extending from the nucleotide at position 5 to the nucleotide located immediately 5' to the start codon (e.g. the ATG) in the sequences according to SEQ ID NOs: 1-1363, SEQ ID NO: 1395, SEQ ID NO: 1421 and SEQ ID NO: 1422 of international patent application WO2013/143700 or homologs or variants thereof, whose disclosure is incorporated herewith by reference. In this context a particularly preferred fragment of a 5'-UTR of a TOP gene is a 5'-UTR of a TOP gene lacking the 5'-TOP motif. The term "5'-UTR of a TOP gene" preferably refers to the 5'-UTR of a naturally occurring TOP gene.

As used herein, the "3'-untranslated region (3'-UTR)" is typically the part of an mRNA which is located between the protein coding region (i.e. the open reading frame) and the poly(A) sequence of the mRNA. A 3'-UTR of the mRNA is not translated into an amino acid sequence. The 3'-UTR sequence is generally encoded by the gene which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5'-Capping, splicing the pre-mature mRNA to excise optional introns and modifications of the 3'-end, such as polyadenylation of the 3'-end of the pre-mature mRNA and optional endo- or exonuclease cleavages etc. In the context of the present invention, a 3'-UTR corresponds to the sequence of a mature mRNA which is located 3' to the stop codon of the protein coding region, preferably immediately 3' to the stop codon of the protein coding region, and which extends to the 5'-side of the poly(A) sequence, preferably to the nucleotide immediately 5' to the poly(A) sequence. The term “corresponds to” means that the 3'-UTR sequence may be an RNA sequence, such as in the mRNA sequence used for defining the 3'-UTR sequence, or a DNA sequence which corresponds to such RNA sequence. In the context of the present invention, the term “a 3'-UTR of a gene”, such as “a 3'-UTR of an albumin gene”, is the sequence which corresponds to the 3'-UTR of the mature mRNA derived from this gene, i.e. the mRNA obtained by transcription of the gene and maturation of the pre-mature mRNA. The term “3'-UTR of a gene” encompasses the DNA sequence and the RNA sequence of the 3'-UTR.

As used herein, the term “5'-untranslated region (5'-UTR)” is typically understood to be a particular section of messenger RNA (mRNA). It is located 5' of the open reading frame of the mRNA. Typically, the 5'-UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites or a 5'-Terminal Oligopyrimidine Tract. The 5'-UTR may be posttranscriptionally modified, for example by addition of a 5'-CAP. In the context of the present invention, a 5'-UTR corresponds to the sequence of a mature mRNA which is located between the 5'-CAP and the start codon. Preferably, the 5'-UTR corresponds to the sequence which extends from a nucleotide located 3' to the 5'-CAP, preferably from the nucleotide located immediately 3' to the 5'-CAP, to a nucleotide located 5' to the start codon of the protein coding region, preferably to the nucleotide located immediately 5' to the start codon of the protein coding region. The nucleotide located immediately 3' to the 5'-CAP of a mature mRNA typically corresponds to the transcriptional start site. The term “corresponds to” means that the 5'-UTR sequence may be an RNA sequence, such as in the mRNA sequence used for defining the 5'-UTR sequence, or a DNA sequence which corresponds to such RNA sequence. In the context of the present invention, the term “a 5'-UTR of a gene”, such as “a 5'-UTR of a TOP gene”, is the sequence which corresponds to the 5'-UTR of the mature mRNA derived from this gene, i.e. the mRNA obtained by transcription of the gene and maturation of the pre-mature mRNA. The term “5'-UTR of a gene” encompasses the DNA sequence and the RNA sequence of the 5'-UTR.

As used herein, the term “vaccine” is typically understood to be a prophylactic or therapeutic material providing at least one antigen or antigenic function. The antigen or antigenic function may stimulate the body’s adaptive immune system to provide an adaptive immune response. As used herein, the term “vaccine for pandemic influenza/flu or pandemic influenza/flu vaccine” refers to a vaccine directed against a pandemic influenza virus is called herein as a vaccine for pandemic influenza/flu or pandemic influenza/flu vaccine. As used herein, the term “vaccine for seasonal influenza/flu or seasonal influenza/flu vaccine” refers to a vaccine directed against the seasonal occurring influenza viruses in a flu season is termed herein “vaccine for seasonal influenza/flu or seasonal influenza/flu vaccine”.

As used herein, the term “variants” of proteins or peptides as defined in the context of the present invention may be generated, having an amino acid sequence which differs from the original sequence in one or more mutation(s), such as one or more substituted, inserted and/or deleted amino acid(s). Preferably, these fragments and/or variants have the same biological function or specific activity compared to the full-length native protein, e.g. its specific antigenic property. “Variants” of proteins or peptides as defined in the context of the present invention may comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

As used herein, the term “variant” of a protein or peptide may have at least 70%, 75%, 80%, 85%, 90%, 95%, 98% or 99% amino acid identity over a stretch of 10, 20, 30, 50, 75 or 100 amino acids of such protein or peptide. Furthermore, variants of proteins or peptides as defined herein, which may be encoded by a nucleic acid molecule, may also comprise those sequences, wherein nucleotides of the encoding nucleic acid sequence are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

As used herein, the term “vehicle” means an agent, e.g. a carrier, that may typically be used within a pharmaceutical composition or vaccine for facilitating administering of the components of the pharmaceutical composition or vaccine to an individual.

V.2. Exemplary Ionizable Lipids of the Invention

The inventors have discovered a new class of ionizable lipids, the Ionizable Lipids of the Invention, that were synthesized including two or more ionizable amine head groups, two or more degradable linker groups, and two or more saturated or unsaturated or branched alkyl tails.

In its broadest embodiment, the Ionizable Lipids of the Invention have a structure of Formula I:

Head-Spacer-Linker-Spacer-Tail

Formula I wherein the pKa can be adjusted to effectuate targeted delivery to a specific tissue or organ of the body.

In certain embodiments, exemplary tail groups, head groups, and linker groups are each independently selected from the substituents identified in the respective category in Table 1 below. The substituent R groups depicted in the tables below include any of the substituent R groups as enabled and defined herein.

TABLE 1
| Tails |
|---|
| 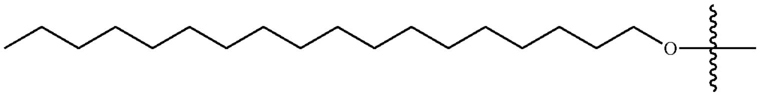 [SMILES: *OCCCCCCCCCCCCCCCCCC] |
| 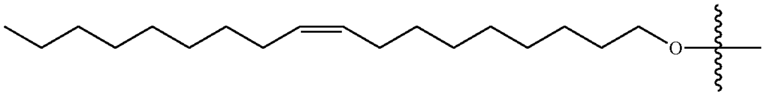 [SMILES: *OCCCCCCCC/C=C\CCCCCCCC] |
| 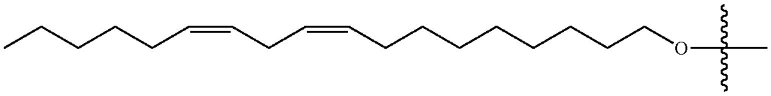 [SMILES: *OCCCCCCCC/C=C\C/C=C\CCCCC] |
| 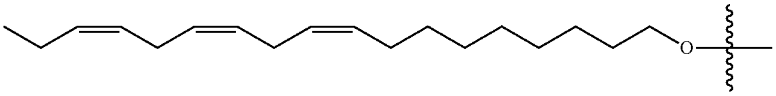 |
| 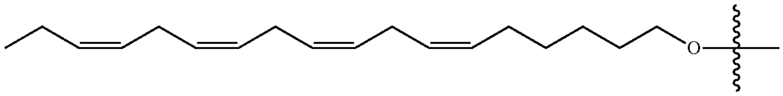 [SMILES: *OCCCCC/C=C\C/C=C\C/C=C\C/C=C\CC] |
| 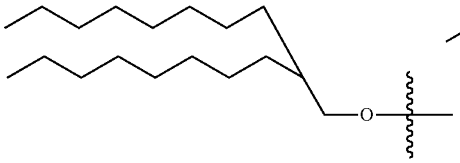 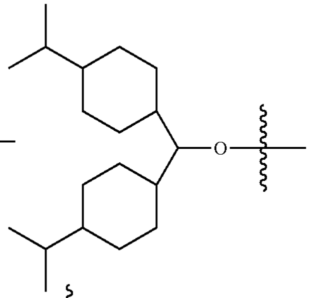 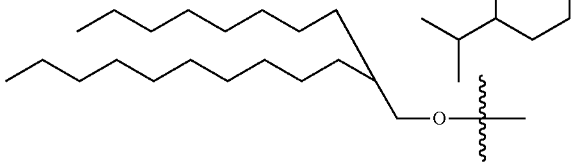 |
| 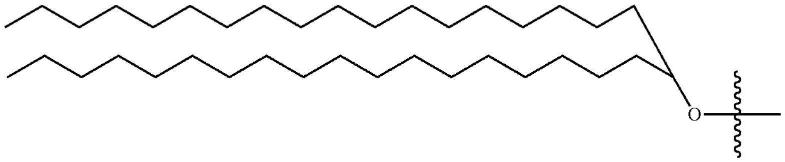 [SMILES: *OC(CCCCCCCCCCCCCCCCCC)CCCCCCCCCCCCCCCCCC] |
| 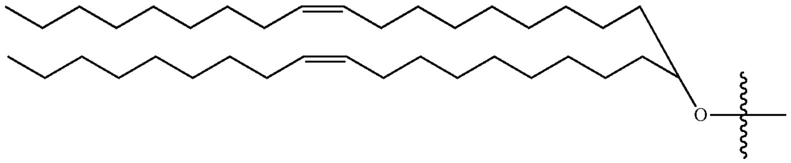 [SMILES: *OC(CCCCCCCC/C=C\CCCCCCCC)CCCCCCCC/C=C\CCCCCCCC] |
| 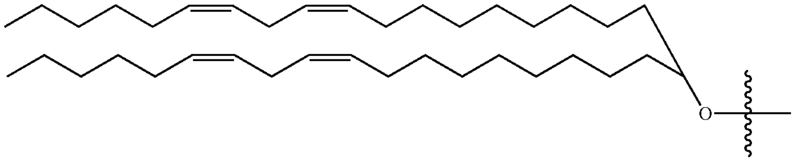 [SMILES: *OC(CCCCCCCC/C=C\C/C=C\CCCCC)CCCCCCCC/C=C\C/C=C\CCCCC] |

TABLE 1-continued
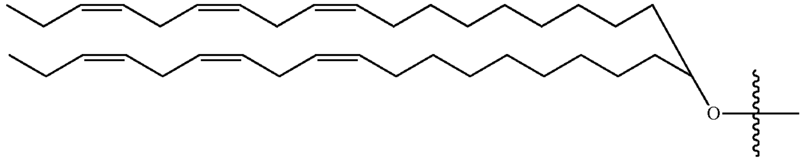 [SMILES: *OC(CCCCCCCC/C=C\C/C=C\C/C=C\CC)CCCCCCCC/C=C\C/C=C\C/C=C\CC]
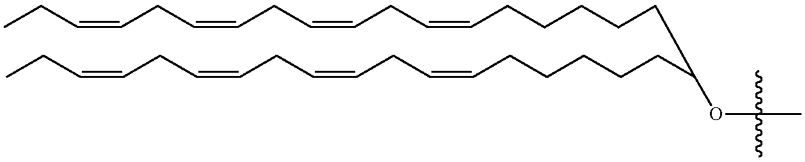 [SMILES: *OC(CCCCC/C=C\C/C=C\C/C=C\C/C=C\CC)CCCCC/C=C\C/C=C\C/C=C\C/C=C\CC]
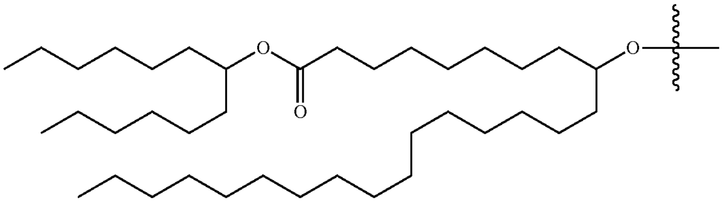 [SMILES: *OC(CCCCCCCCCCCCCCCC)CCCCCCCC(=O)OC(CCCCCC)CCCCCC]
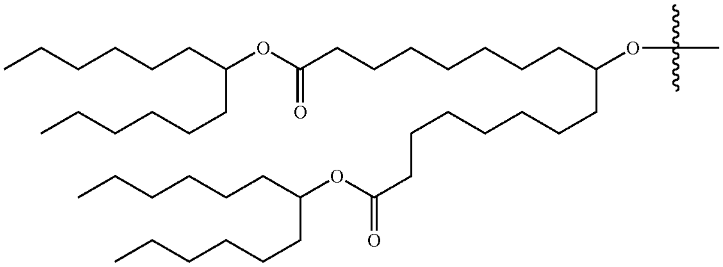 [SMILES: *OC(CCCCCCCC(=O)OC(CCCCCC)CCCCCC)CCCCCCCC(=O)OC(CCCCCC)CCCCCC]
Head
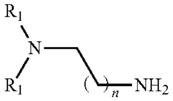
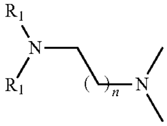
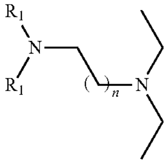
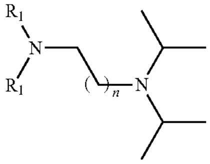
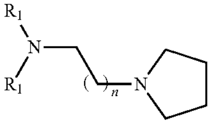

TABLE 1-continued
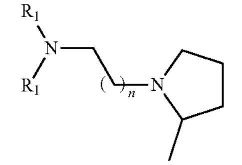
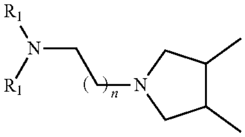
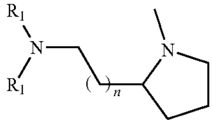
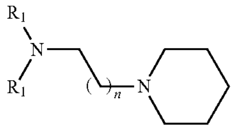
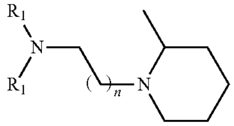
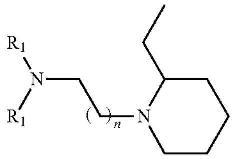
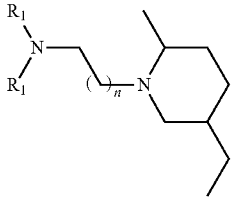
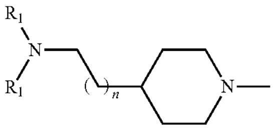
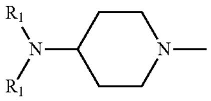
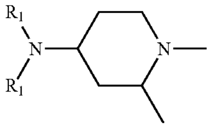
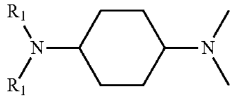

TABLE 1-continued
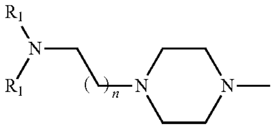
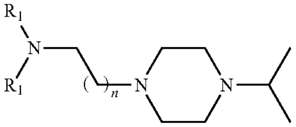
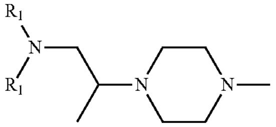
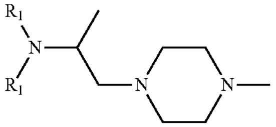
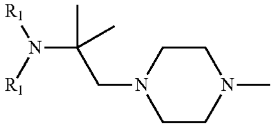
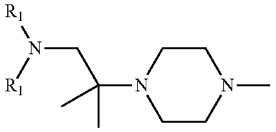
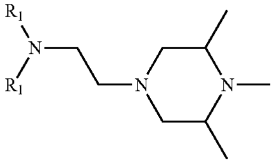
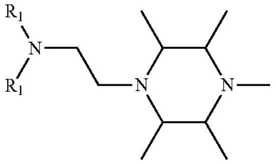
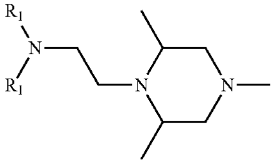
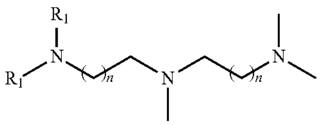

TABLE 1-continued
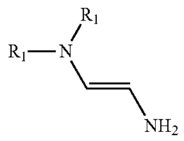
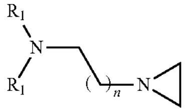
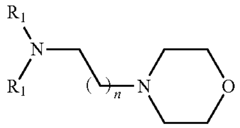
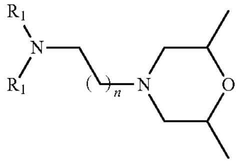
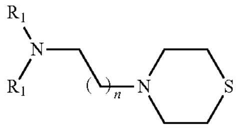
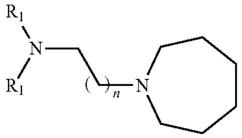
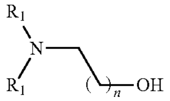
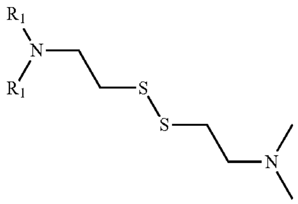
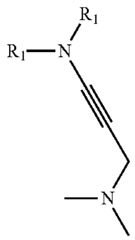
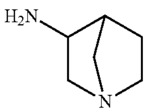

TABLE 1-continued
| Linkers | |
|---|---|
| L | —O(C═O)—, —(C═O)O— |
| L1 | —NH(C═O)— |
| L2 | —N(O═S═O)— |
| | 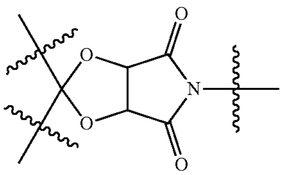 [SMILES: *N1C(=O)C2OC(*)(*)OC2C1=O] |
| L3 | Dioxolo, pyrrolidine-dione |
| L4 | 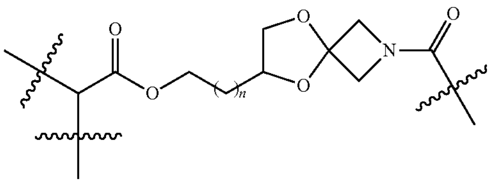 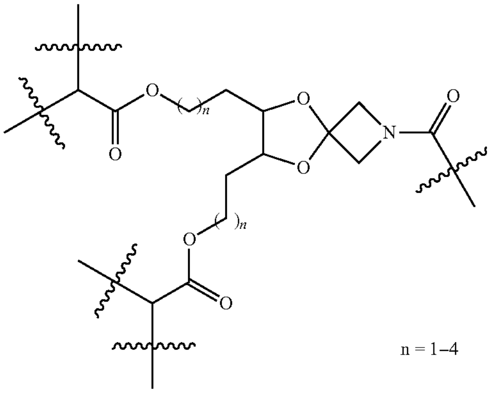 n = 1–4 |
| L5 | 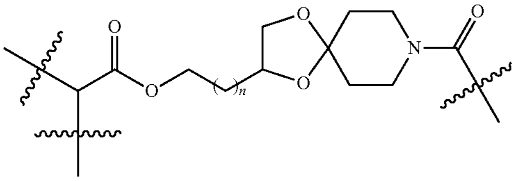 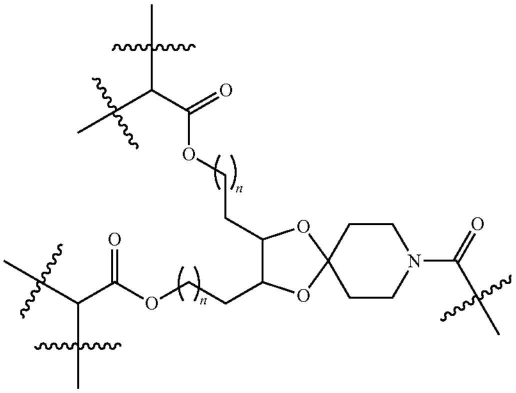 n = 1–4 |

TABLE 1a
| Exemplary Head Groups |
| --- |
| 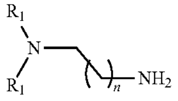 |
| 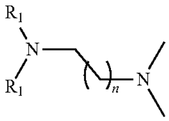 |
| 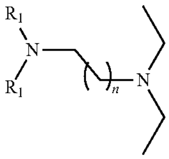 |
| 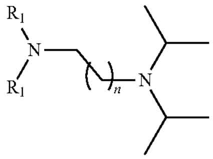 |
| 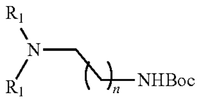 |
| 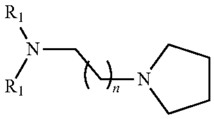 |
| 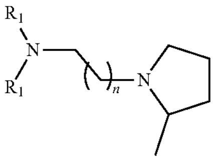 |
| 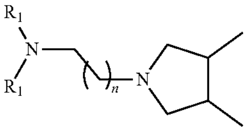 |
| 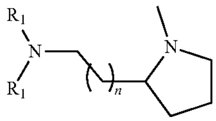 |
| 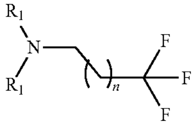 |
| 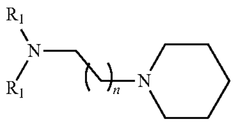 |
TABLE 1a-continued
| Exemplary Head Groups |
| --- |
| 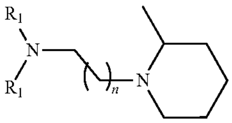 |
| 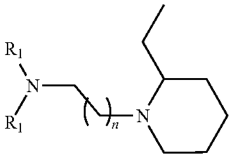 |
| 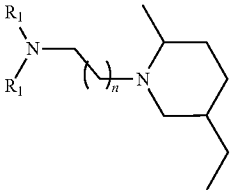 |
| 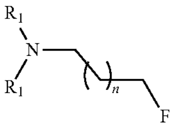 |
| 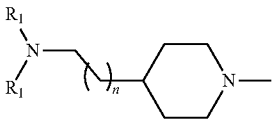 |
| 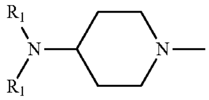 |
| 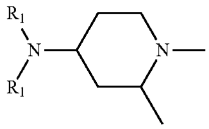 |
| 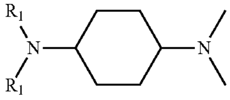 |
| 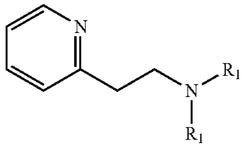 |
| 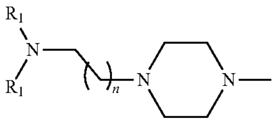 |
| 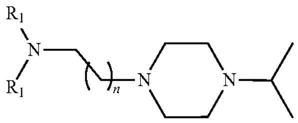 |

TABLE 1a-continued
Exemplary Head Groups
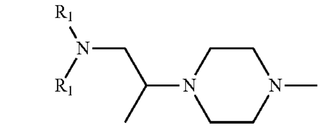
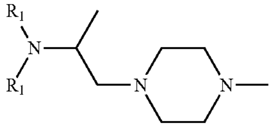
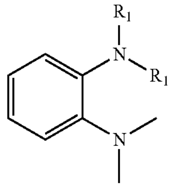
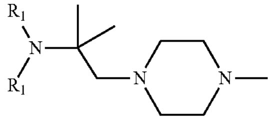
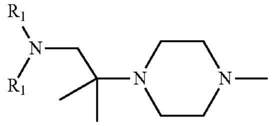
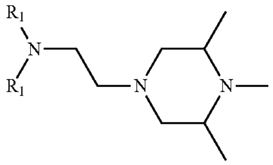
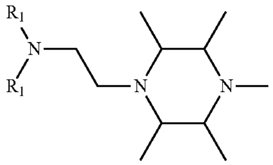
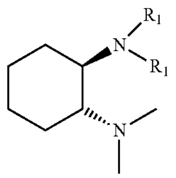
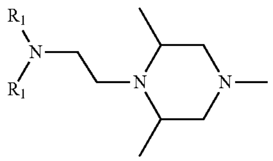
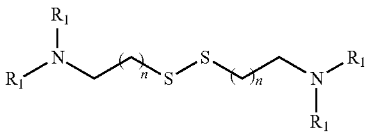
TABLE 1a-continued
Exemplary Head Groups
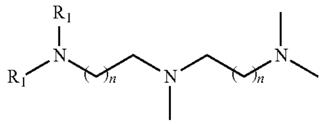
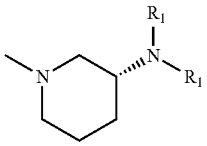
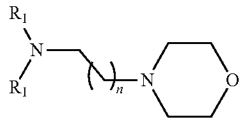
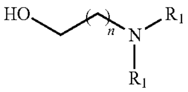
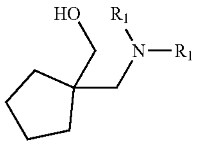
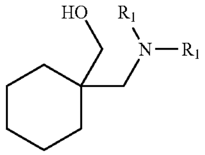
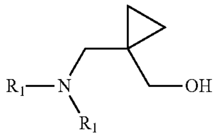
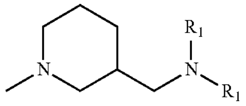
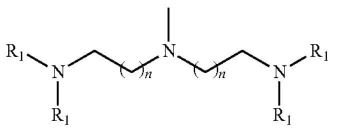
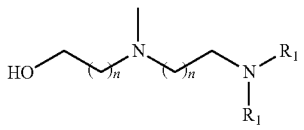
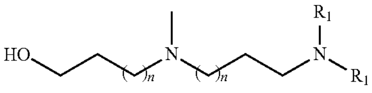

TABLE 1a-continued
| Exemplary Head Groups |
| --- |
| 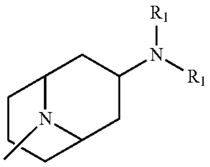 |
| 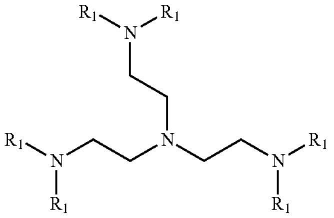 |
| 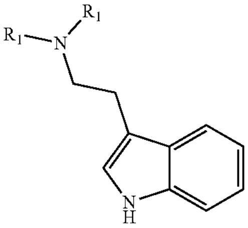 |
| 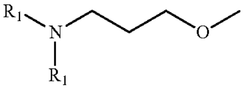 |
| 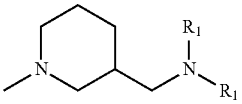 n = 1-6 |
TABLE 1c
| Exemplary Tail Groups | | | |
| --- | --- | --- | --- |
| Degradation | —$C_x/C_y$ | Abbreviation | $R_{TAIL}$ n = 0-7 |
| Primary | ($C_6/C_4$) | BBO | 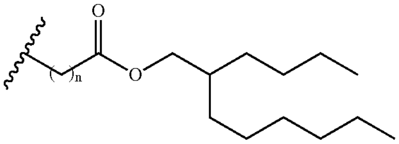 |
| Primary | ($C_{10}/C_8$) | BODD | 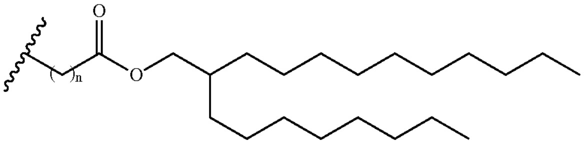 |
| Primary | ($C_{12}/C_{10}$) | BDTD | 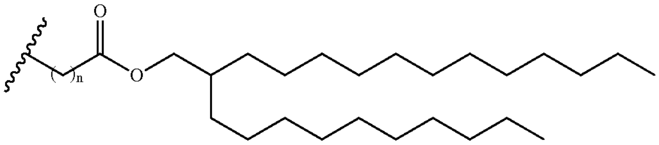 |
| Primary | ($C_{14}/C_{12}$) | BDHD | 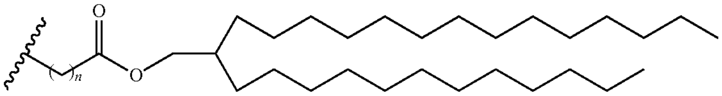 |
| Primary | ($C_8/C_8$) | BOD | 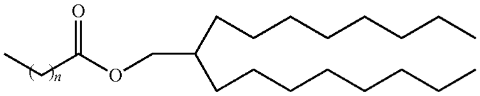 |
| Primay | ($C_{10}/C_{10}$) | DH | 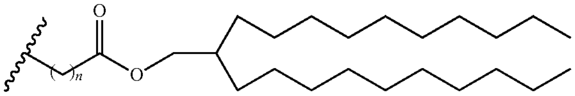 |
| Primary | $C_{18}$ | DL | 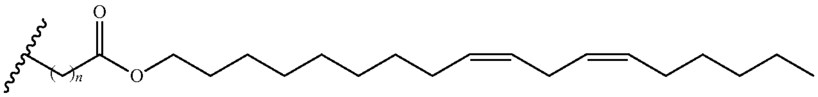 |

TABLE 1c-continued
| Exemplary Tail Groups | | | |
|---|---|---|---|
| Degradation | —$C_x$/$C_y$ | Abbre-viation | $R_{TAIL}$ n = 0-7 |
| Primary | $C_8$ Cis Geraniol | BDOD | 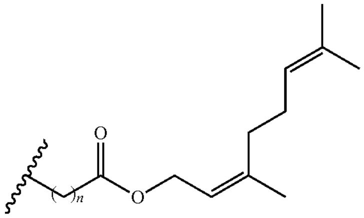 |
| Primary | $C_8$ Trans-Geraniol | Trans-BDOD | 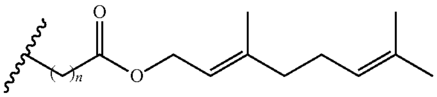 |
| Primary | $C_8$ Cis-2-Octenol | DOAD | 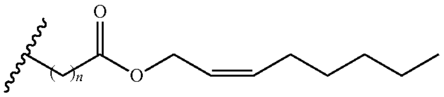 |
| Primary | $C_8$ Dimethyl Octanol | BDOA | 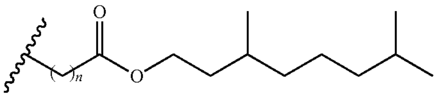 |
| Secondary | ($C_8$/$C_8$) | BHD | 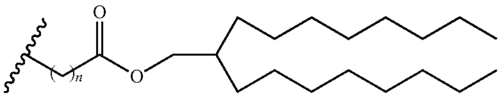 |
| Secondary | ($C_{18}$/$C_{18}$) | BDL | 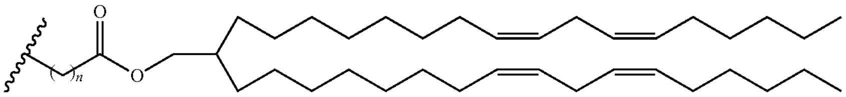 |
| Secondary | (Chol/Chol) | BChol | 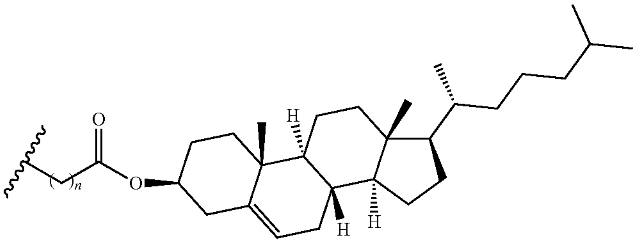 |
| Primary | R1 Tails | | 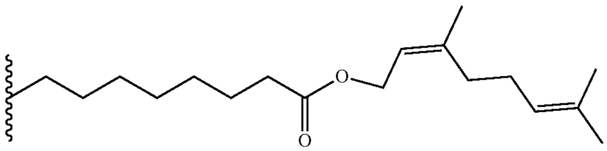 [SMILES: *CCCCCCCC(=O)OC/C=C(/C)CCC=C(C)C] 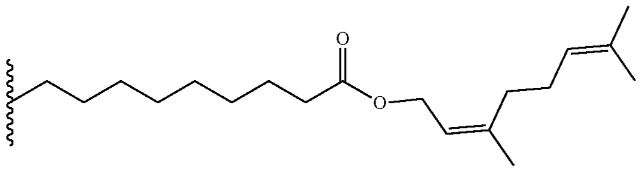 [SMILES: *CCCCCCCCC(=O)OC/C=C(/C)CCC=C(C)C] 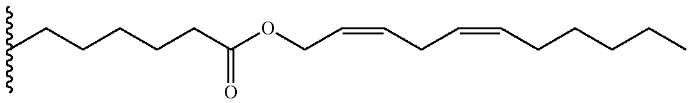 [SMILES: *CCCCCC(=O)OC/C=C\C/C=C\CCCCC] |

TABLE 1c-continued

| Exemplary Tail Groups | | | |
| --- | --- | --- | --- |
| Degradation | —$C_x$/$C_y$ | Abbre-viation | $R_{TAIL}$ n = 0-7 |
| | | | 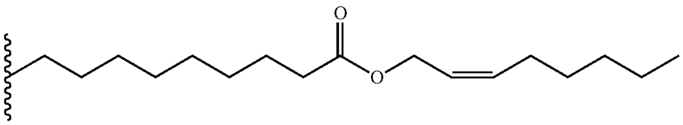 [SMILES: *CCCCCCCCC(=O)OC/C=C\CCCCC] |
| | | | 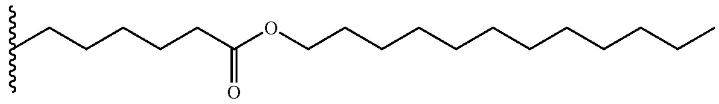 [SMILES: *CCCCCC(=O)OCCCCCCCCCCCC] |
| | | | 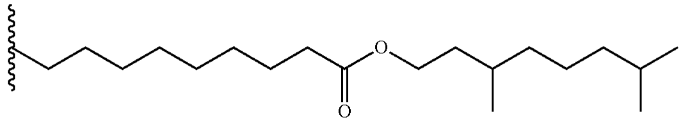 [SMILES: *CCCCCCCCC(=O)OCCC(C)CCCC(C)C] |
| | | | 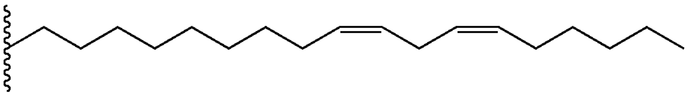 [SMILES: *CCCCCCCC/C=C\C/C=C\CCCCC] |
| | | | 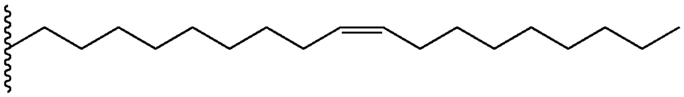 [SMILES: *CCCCCCCC/C=C\CCCCCCCC] |
| | | | 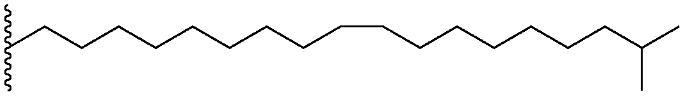 [SMILES: *CCCCCCCCCCCCCCCCC(C)C] |

In certain embodiments, the spacer is optional and is a substituted or unsubstituted $C_1$-$C_{22}$ alkyl group. In preferred embodiments, each spacer is independently a substituted or unsubstituted $C_1$ carbon, a substituted or unsubstituted $C_2$ carbon, a substituted or unsubstituted $C_3$ carbon, a substituted or unsubstituted C4 carbon, a substituted or unsubstituted $C_5$ carbon, a substituted or unsubstituted $C_6$ carbon, a substituted or unsubstituted C7 carbon, a substituted or unsubstituted $C_8$ carbon, a substituted or unsubstituted C9 carbon, a substituted or unsubstituted $C_{10}$ carbon, a substituted or unsubstituted C11 carbon, a substituted or unsubstituted $C_{12}$ carbon, a substituted or unsubstituted $C_{13}$ carbon, a substituted or unsubstituted $C_{14}$ carbon, a substituted or unsubstituted Cis carbon, a substituted or unsubstituted $C_{16}$ carbon, a substituted or unsubstituted $C_{17}$ carbon, a substituted or unsubstituted Cis carbon, a substituted or unsubstituted $C_{19}$ carbon, a substituted or unsubstituted $C_{20}$ carbon, a substituted or unsubstituted $C_{21}$ carbon, or a substituted or unsubstituted $C_{22}$ carbon.

In certain embodiments, the Ionizable Lipids of the Invention include candidate headgroup structures for DL=DiLinoleic Acid, ADDE=Azane Diyl DiEthyl, Cx/Cy=carbon spacers, DMA=DiMethylAmine, Pyr=Pyridine, PipZ=PiperaZine, PipD=PiperiDine, DIPA=DiIsopropylamine, DM=DiMethyl, BOD=BisOctylDecyl headgroups and Percepta predictions of pKa.

In certain embodiments exemplary, non-limited headgroups for each of Dimethyl Amine (Table 2), Piperdine (Table 3), Pyrrolidine (Table 4), and Piperazine (Table 5) are illustrated below. In certain embodiments, the pKas of the two amines can be tuned to achieve specific values to facilitate delivery to a specific tissue or organ. Percepta predictions for pKa are shown in black for the classic algorithm and in red for the Galas algorithm. Distancing the amines from each other brings the two pKas closer due to reduced electrostatic repulsion between the charged sites. Distancing the internal amine from the ester bond raises its pKa since the proton-binding free electron pair of the amine is further removed from the electron withdrawing ester. Choosing headgroup structures with appropriate pKas are expected to achieve both a slight positive charge or neutral LNP for IM localization and strong increasing positive charge below pH 7 for endolysosomal release capacity.

TABLE 2
Dimethyl Amine head Groups with $C_1$-$C_7$ Spacer Between the Head Group and Linker (pKas from ACD software are shown on the nitrogen atoms)
| C2 spacer for Linker | C3 spacer for Linker |
|---|---|
| 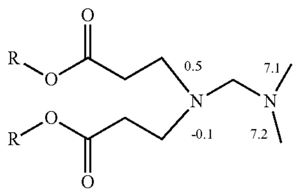 | 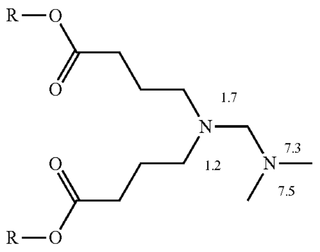 |
| 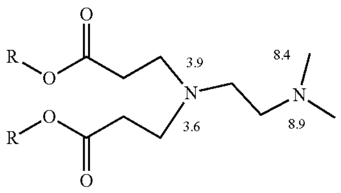 | 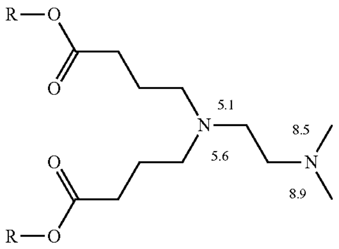 |
| 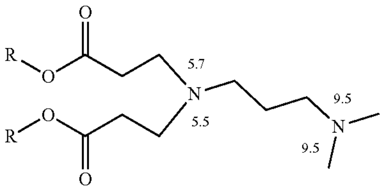 | 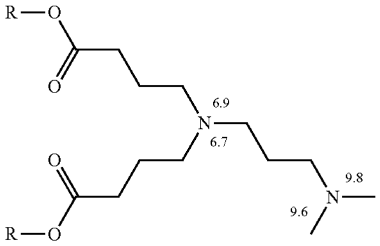 |
| 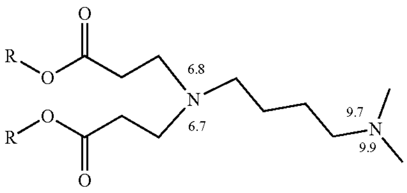 | 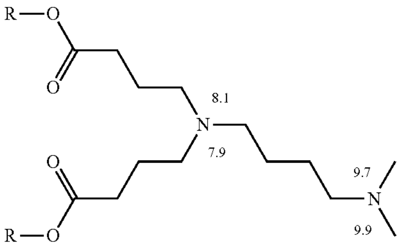 |
| 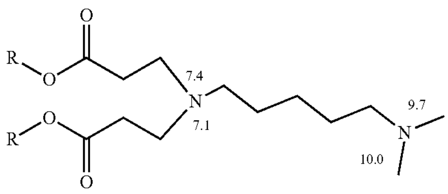 | 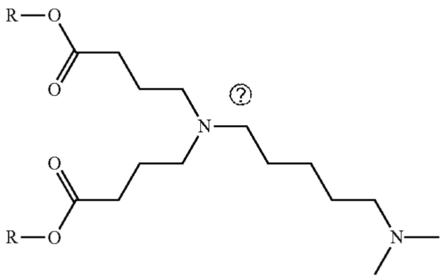 |

TABLE 2-continued
| Dimethyl Amine head Groups with $C_1$-$C_7$ Spacer Between the Head Group and Linker (pKas from ACD software are shown on the nitrogen atoms) | |
|---|---|
| 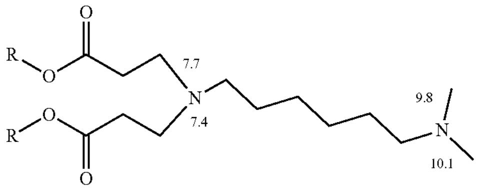 R **Linear chains** saturated, unsaturated, cyclic **Branched chains** saturated, unsaturated, cyclic | 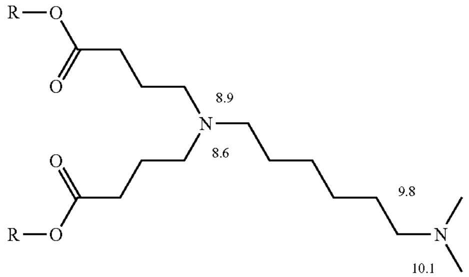 |
| C4 spacer for Linker | C5 spacer for Linker |
| 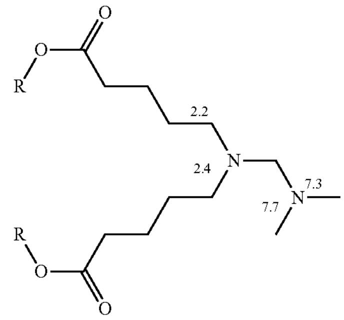 | 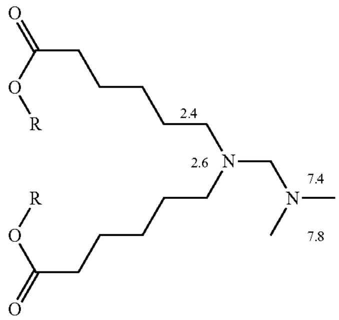 |
| 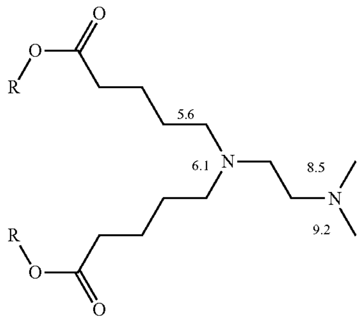 | 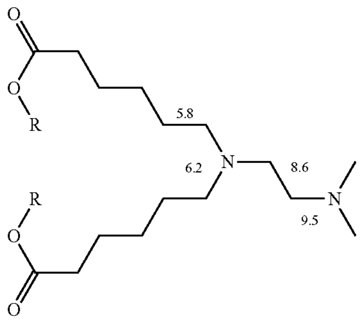 |
| 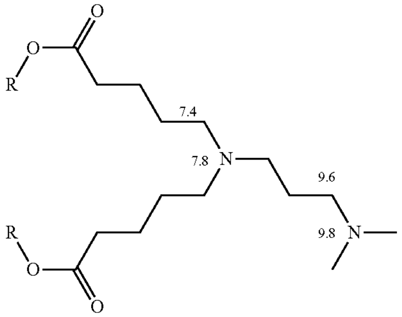 | 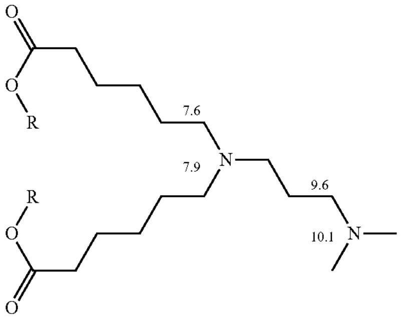 |

TABLE 2-continued
| Dimethyl Amine head Groups with $C_1$-$C_7$ Spacer Between the Head Group and Linker (pKas from ACD software are shown on the nitrogen atoms) | |
|---|---|
| 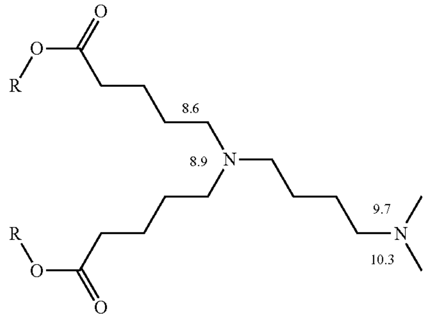 | 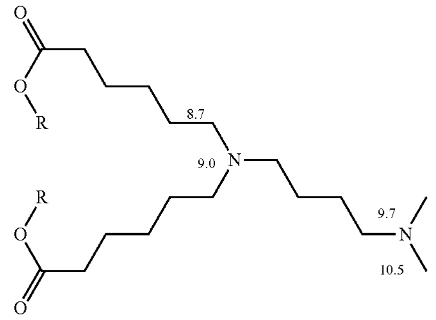 |
| 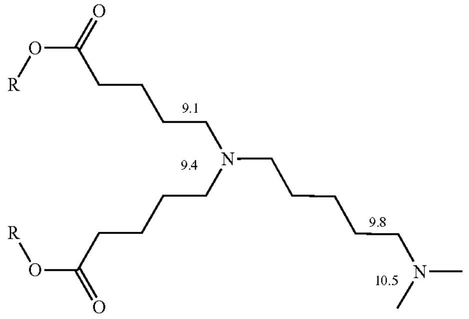 | 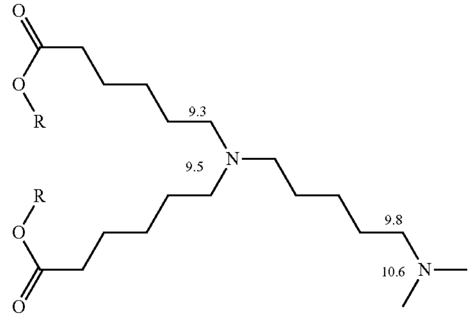 |
| 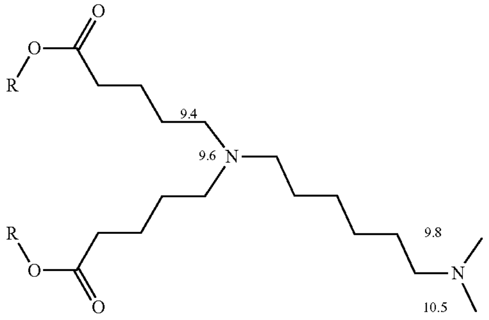 | 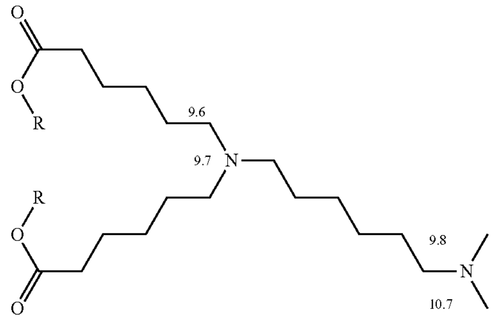 |
| C6 spacer for Linker | C7 spacer for Linker |
| 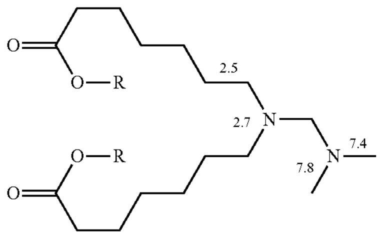 | 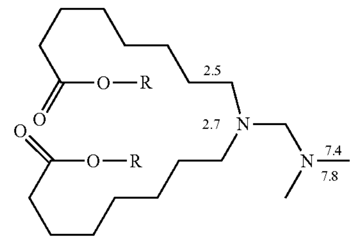 |
| 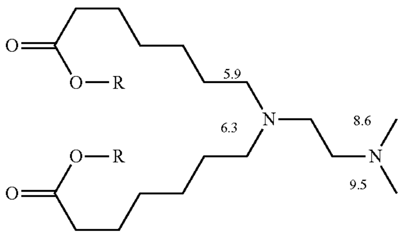 | 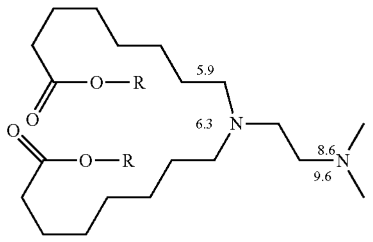 |

TABLE 2-continued
| Dimethyl Amine head Groups with $C_1$-$C_7$ Spacer Between the Head Group and Linker (pKas from ACD software are shown on the nitrogen atoms) | |
|---|---|
| 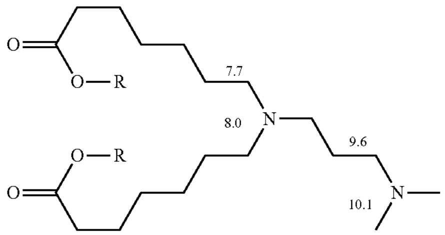 | 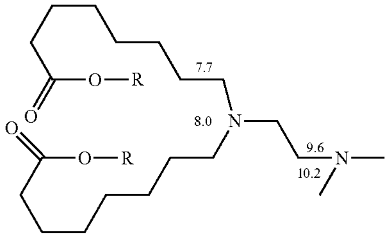 |
| 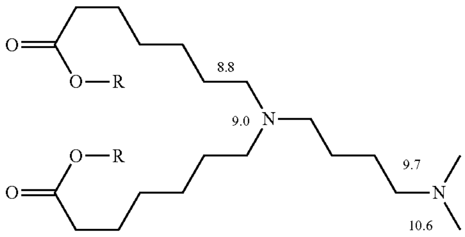 | 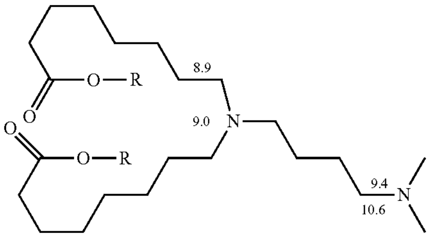 |
| 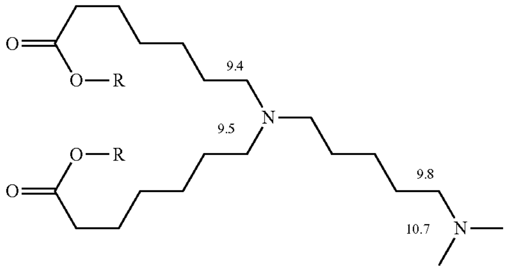 | 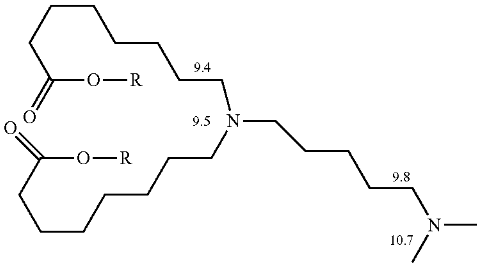 |
| 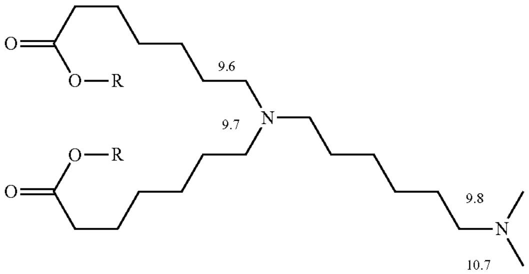 | 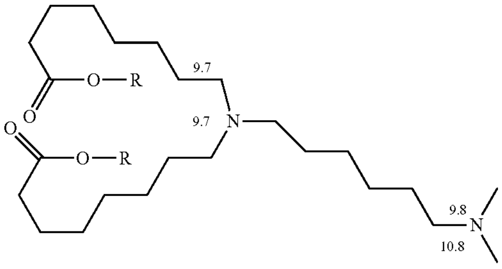 |
TABLE 3
| Piperidine head Groups with $C_1$-$C_7$ Spacer Between the Head Group and Linker (pKas from the ACD software are shown on the nitrogen atoms) | |
|---|---|
| C1 spacer for Linker | C2 spacer for Linker |
| 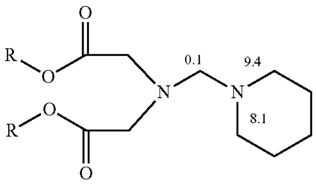 | 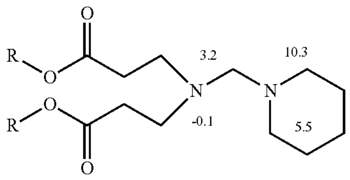 |

TABLE 3-continued
| Piperidine head Groups with $C_1$-$C_7$ Spacer Between the Head Group and Linker (pKas from the ACD software are shown on the nitrogen atoms) | |
|---|---|
| 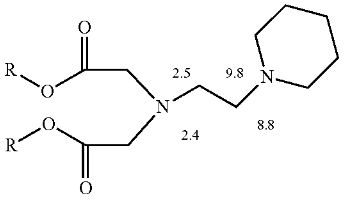 | 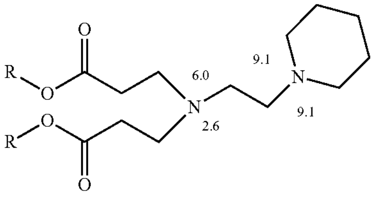 * |
| 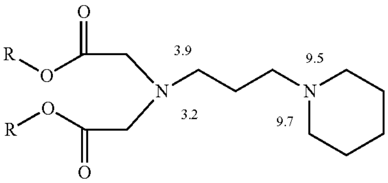 | 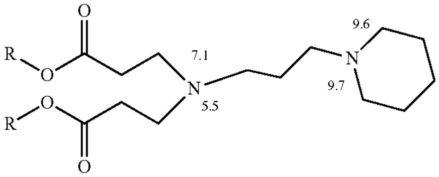 * |
| 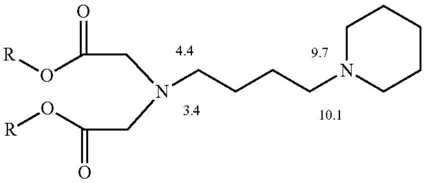 | 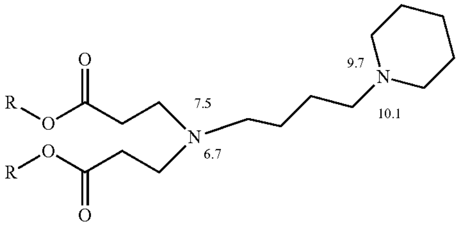 * |
| 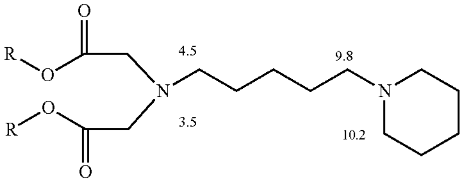 | 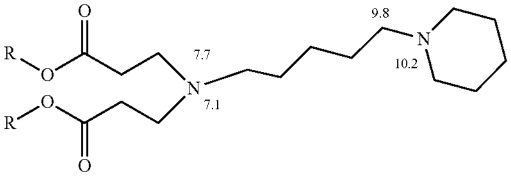 |
| 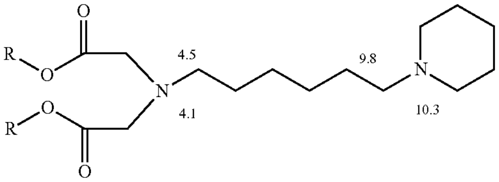 | 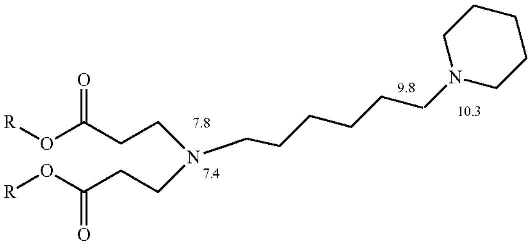 |
| C3 spacer for Linker | C4 spacer for Linker |
|---|---|
| 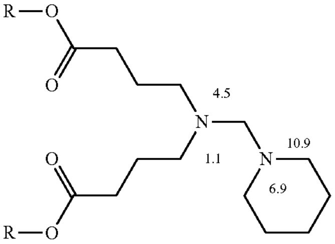 | 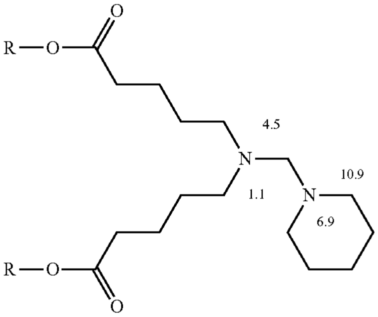 |

TABLE 3-continued
Piperidine head Groups with $C_1$-$C_7$ Spacer Between the Head Group and Linker (pKas from the ACD software are shown on the nitrogen atoms)
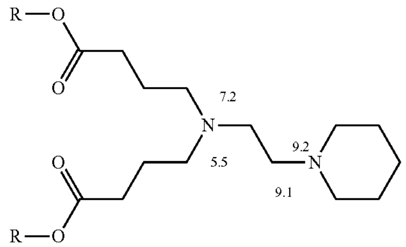
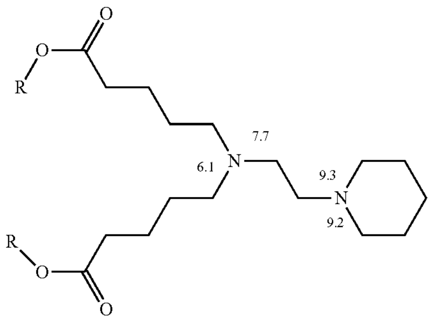
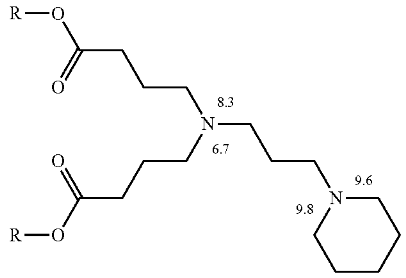
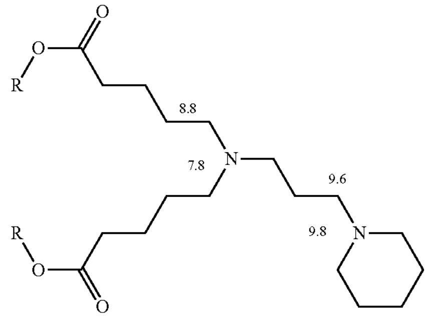
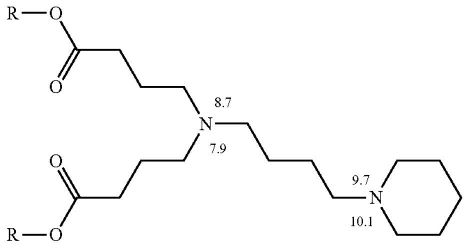
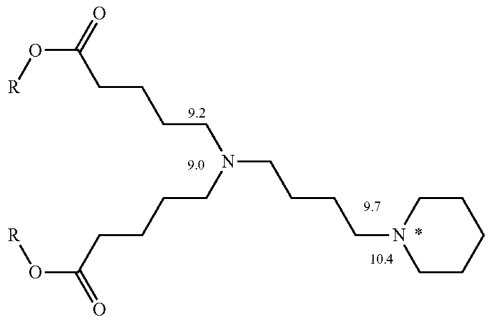
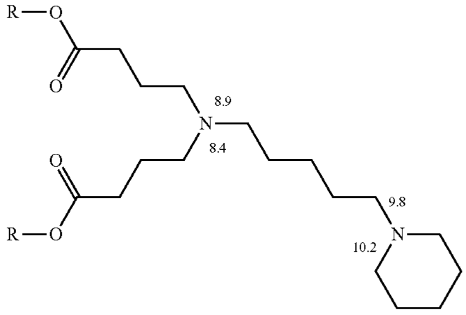
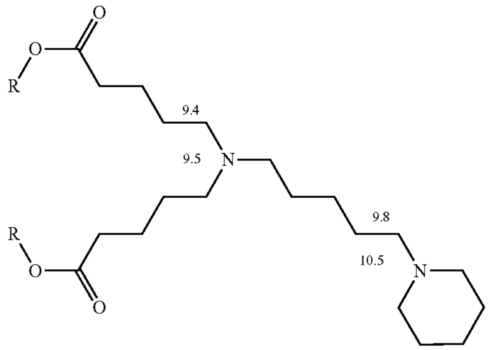

TABLE 3-continued
| Piperidine head Groups with $C_1$-$C_7$ Spacer Between the Head Group and Linker (pKas from the ACD software are shown on the nitrogen atoms) | |
|---|---|
| 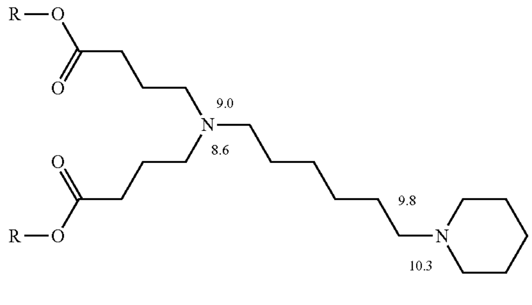 | 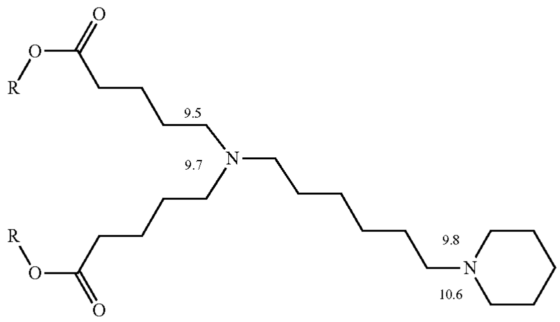 |
| C5 spacer for Linker | C6 spacer for Linker |
| 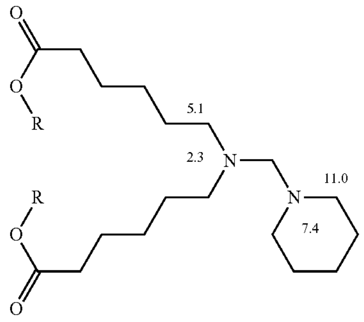 | 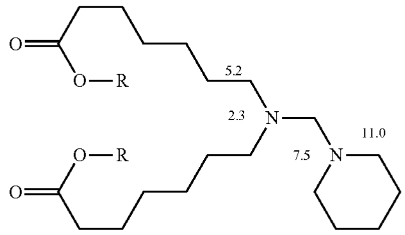 |
| 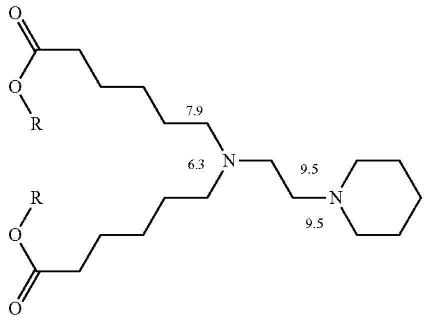 | 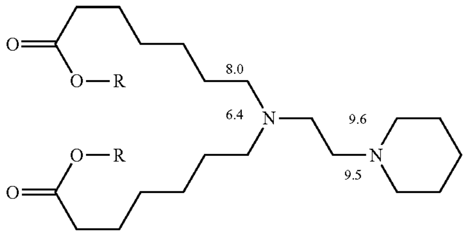 |
| 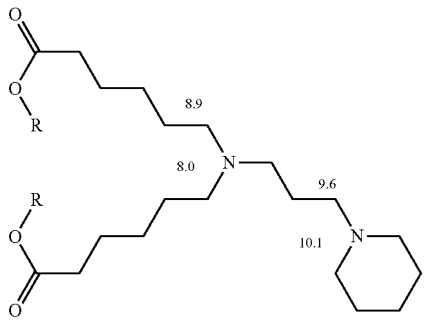 | 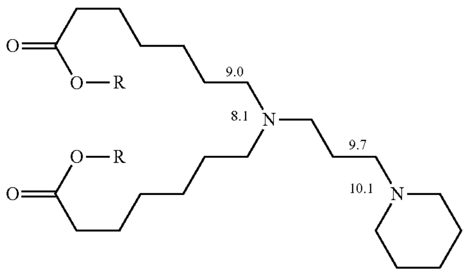 |

TABLE 3-continued
| Piperidine head Groups with $C_1$-$C_7$ Spacer Between the Head Group and Linker (pKas from the ACD software are shown on the nitrogen atoms) | |
|---|---|
| 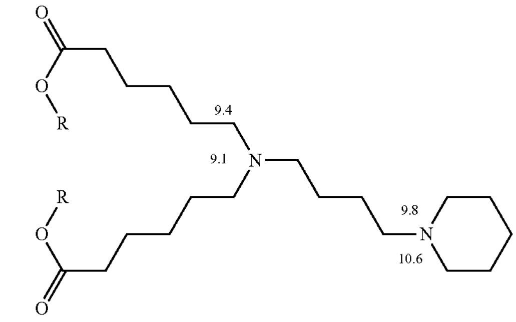 | 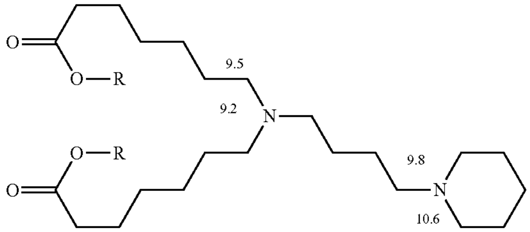 |
| 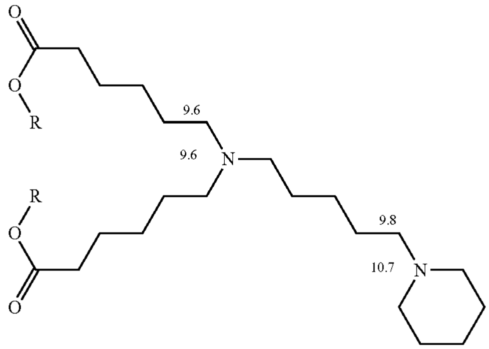 | 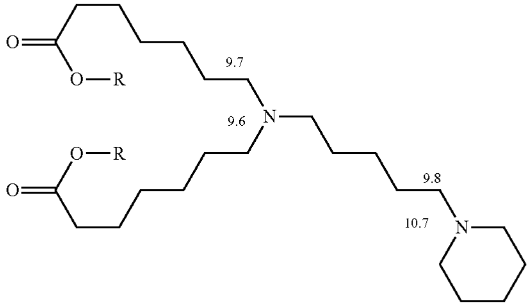 |
| 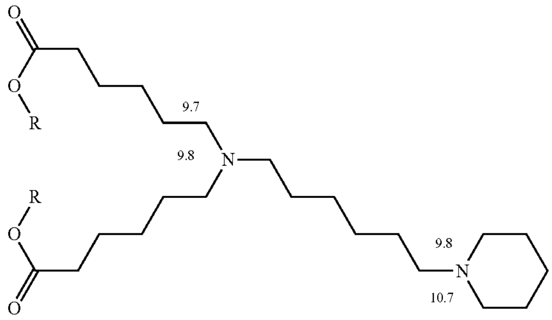 | 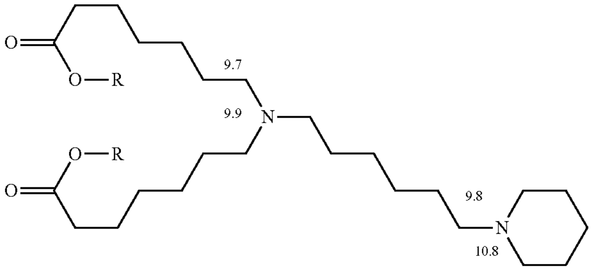 |
| | C7 spacer for Linker |
| | 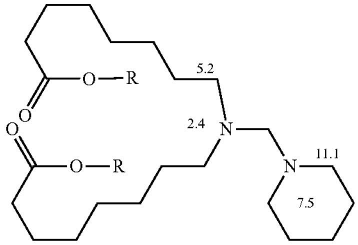 |
| | 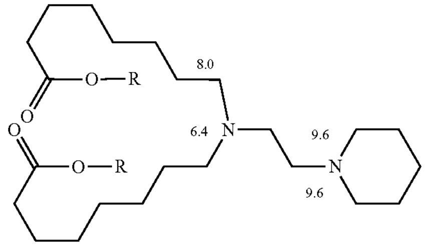 |

TABLE 3-continued
| Piperidine head Groups with $C_1$-$C_7$ Spacer Between the Head Group and Linker (pKas from the ACD software are shown on the nitrogen atoms) |
|---|
| 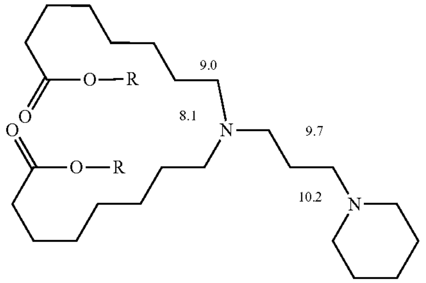 |
| 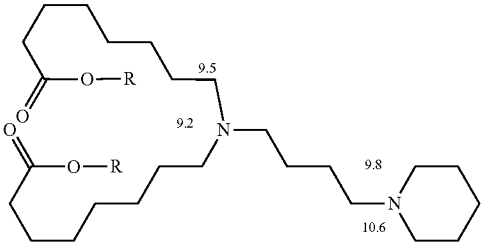 |
| 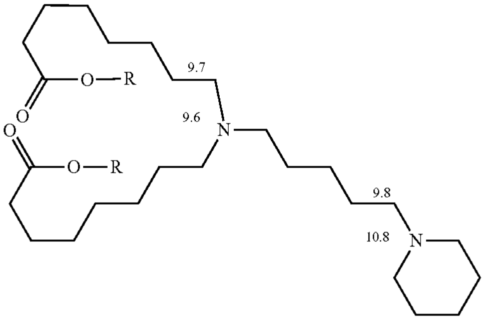 |
| 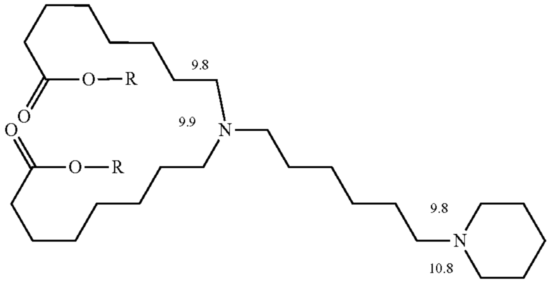 |
TABLE 4
| Pyrrolidine head Groups with $C_1$-$C_7$ Spacer Between the Head Group and Linker (pKas from the ACD software are shown on the nitrogen atoms) | |
|---|---|
| C2 spacer for Linker | C3 spacer for Linker |
| 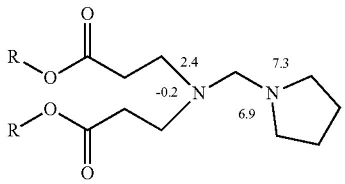 | 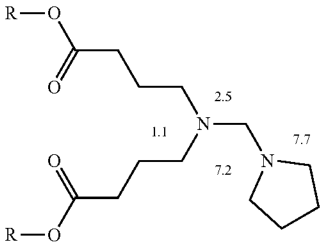 |

TABLE 4-continued
Pyrrolidine head Groups with $C_1$-$C_7$ Spacer Between the Head Group and Linker (pKas from the ACD software are shown on the nitrogen atoms)
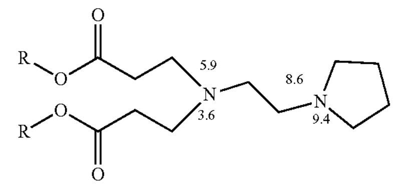
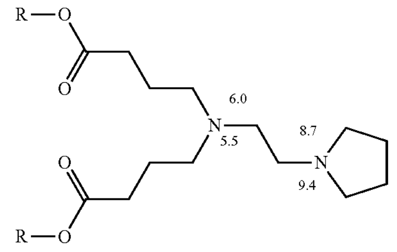
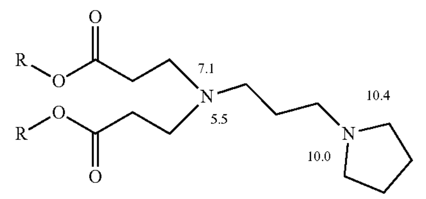
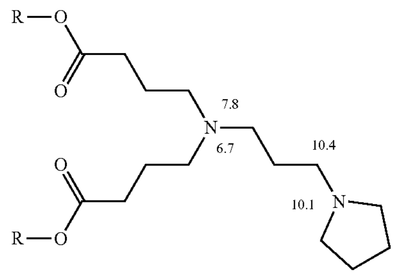
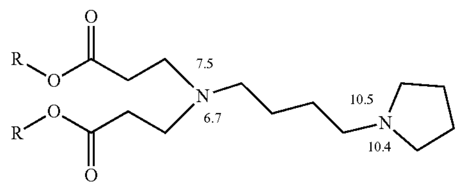
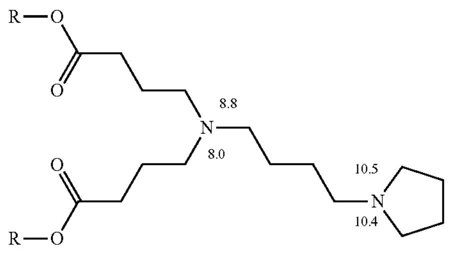
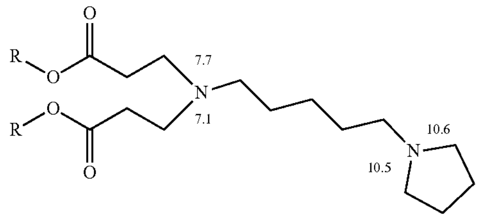
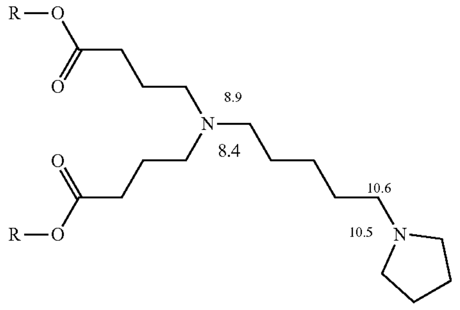

TABLE 4-continued
| Pyrrolidine head Groups with $C_1$-$C_7$ Spacer Between the Head Group and Linker (pKas from the ACD software are shown on the nitrogen atoms) | |
|---|---|
| 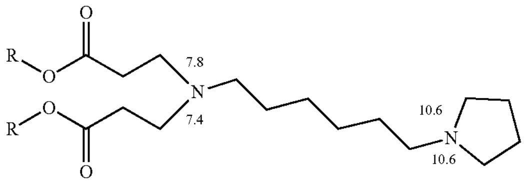 R **Linear chains** saturated, unsaturated, cyclic **Branched chains** saturated, unsaturated, cyclic | 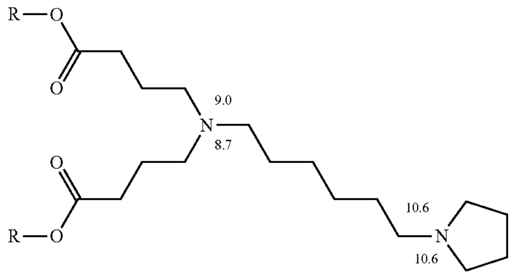 |
| C4 spacer for Linker | C5 spacer for Linker |
| 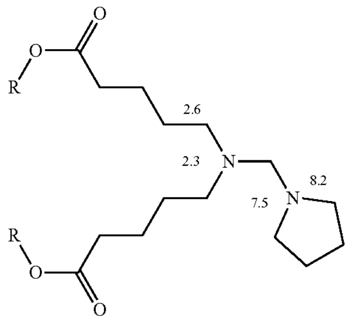 | 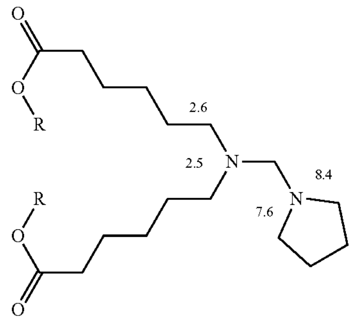 |
| 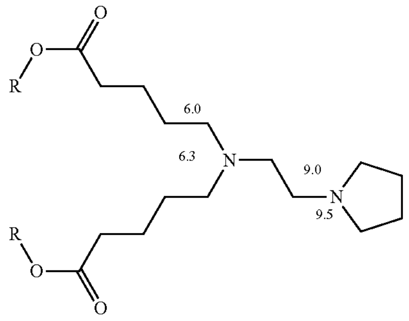 | 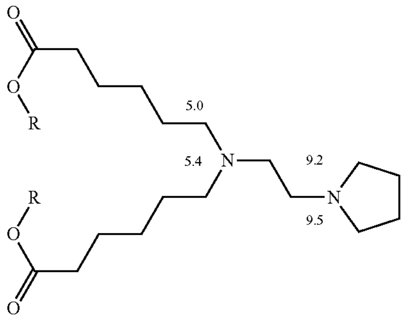 |
| 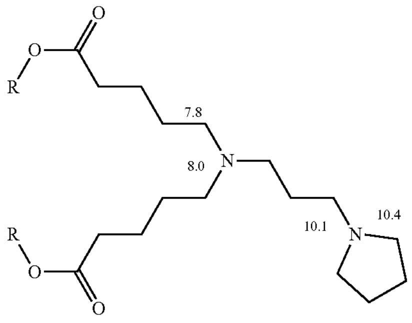 | 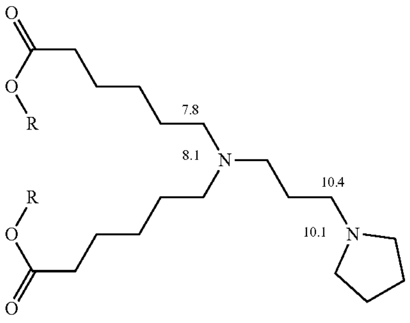 |

TABLE 4-continued
| Pyrrolidine head Groups with $C_1$-$C_7$ Spacer Between the Head Group and Linker (pKas from the ACD software are shown on the nitrogen atoms) | |
|---|---|
| 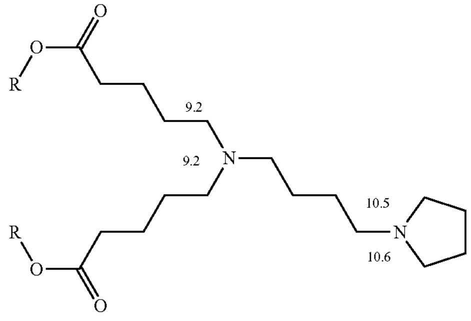 | 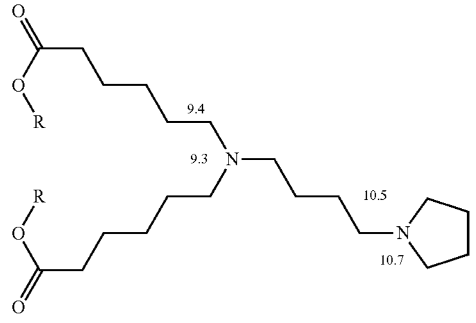 |
| 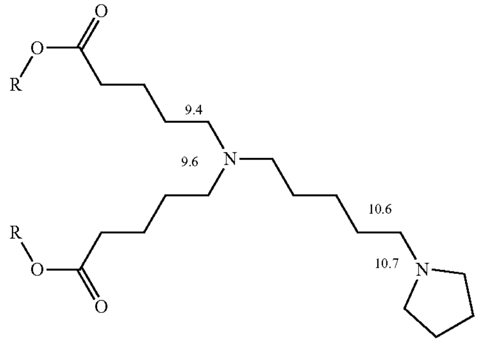 | 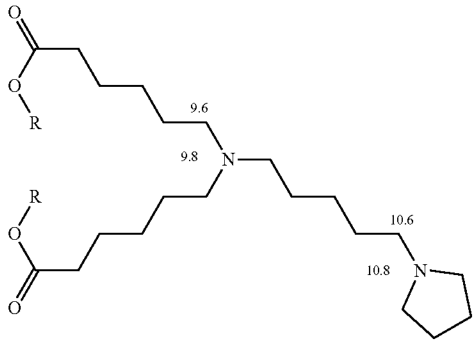 |
| 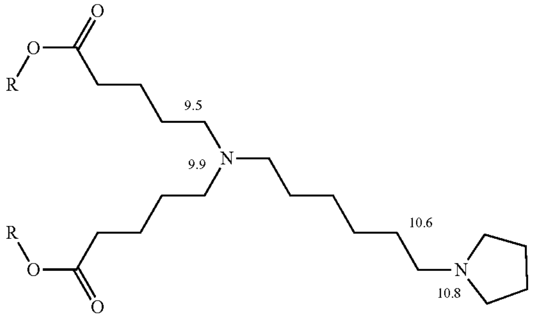 | 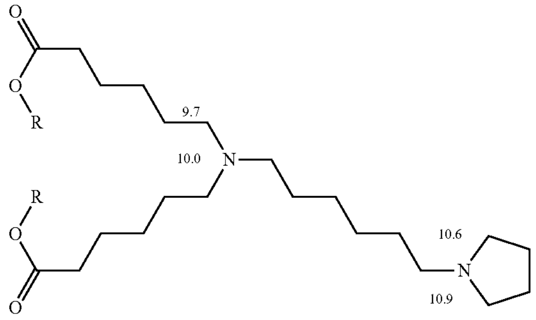 |
| C6 spacer for Linker | C7 spacer for Linker |
| 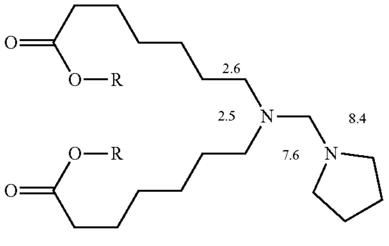 | 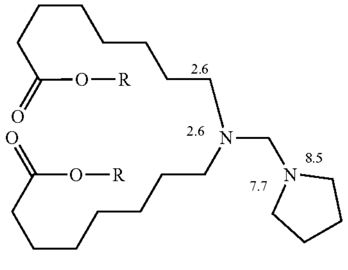 |
| 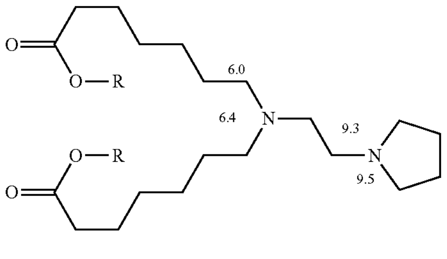 | 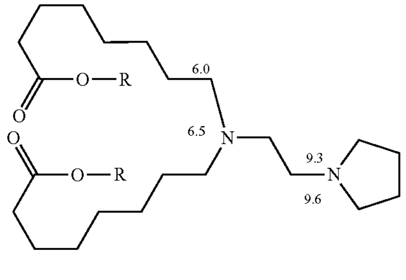 |

TABLE 4-continued
Pyrrolidine head Groups with $C_1$-$C_7$ Spacer Between the Head Group and Linker (pKas from the ACD software are shown on the nitrogen atoms)
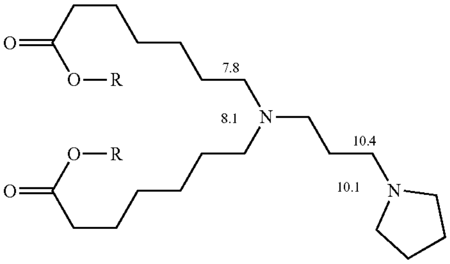
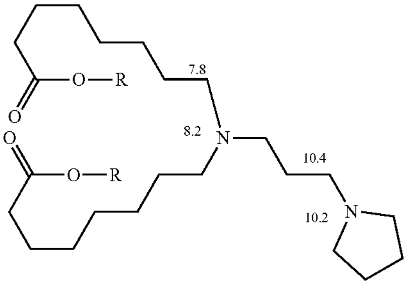
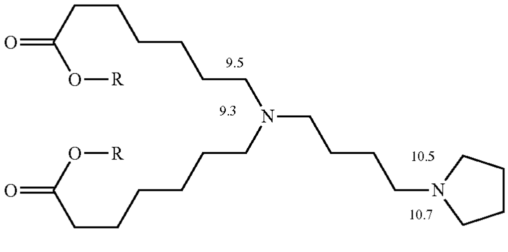
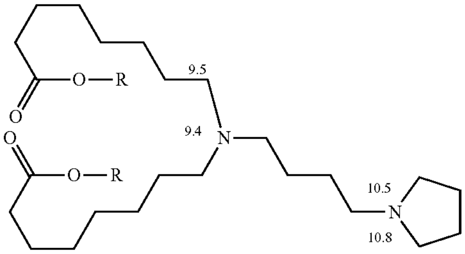
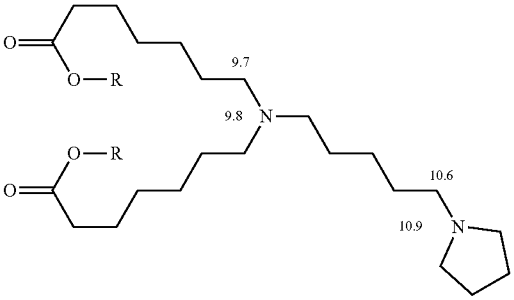
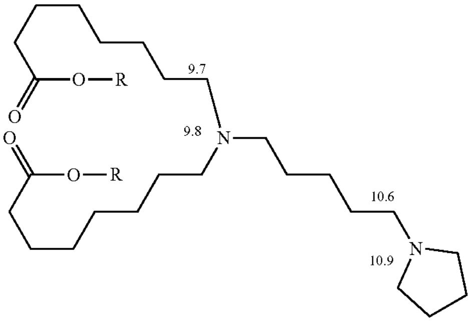
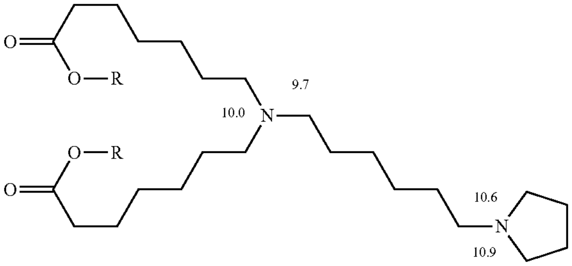
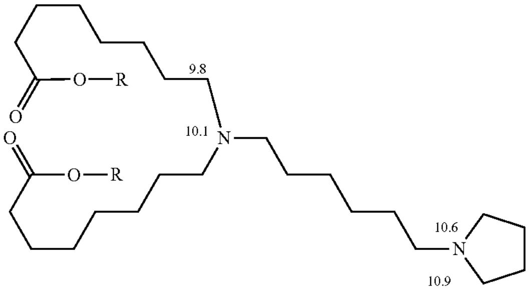

TABLE 5
| Piperazine head Groups with $C_1$-$C_7$ Spacer Between the Head Group and Linker (pKas from the ACD software are shown on the nitrogen atoms) | |
|---|---|
| C2 spacer for Linker | C3 spacer for Linker |
| 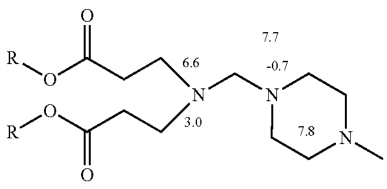 | 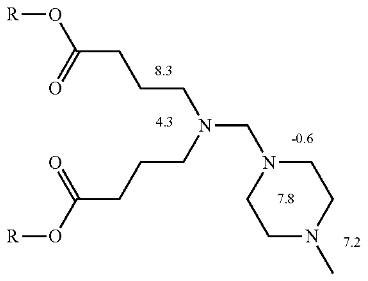 |
| 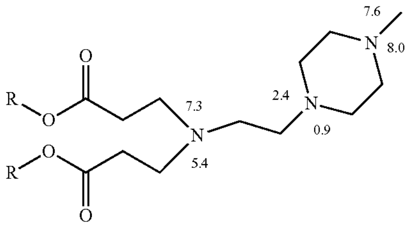 | 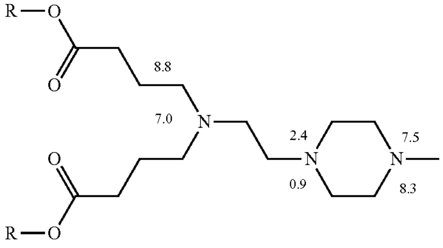 |
| 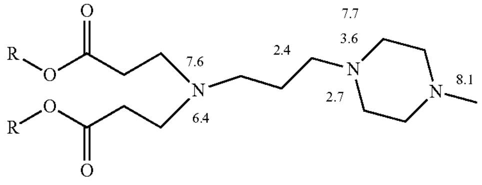 | 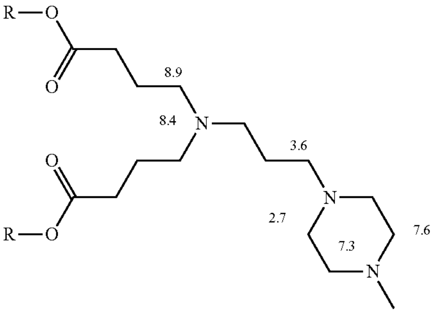 |
| 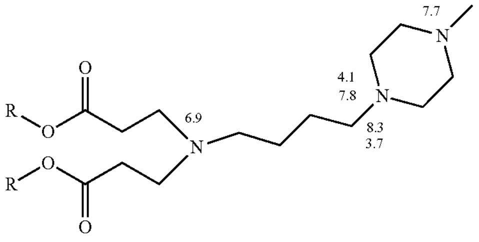 | 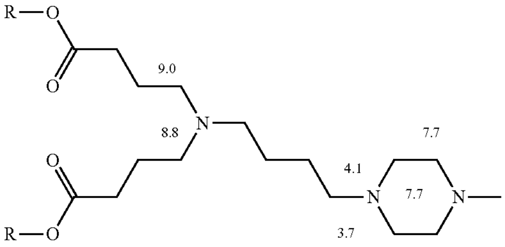 |
| 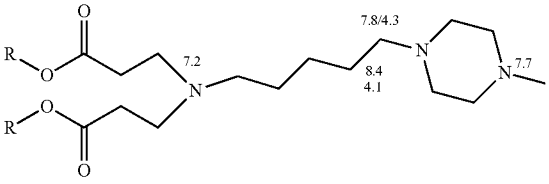 | 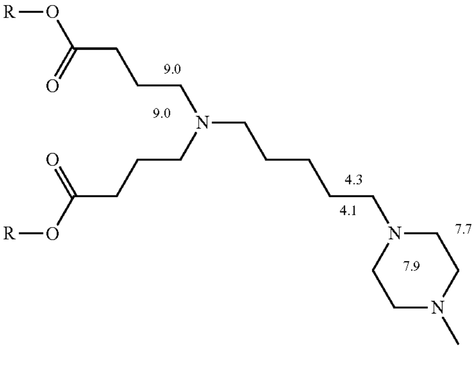 |

TABLE 5-continued
| Piperazine head Groups with $C_1$-$C_7$ Spacer Between the Head Group and Linker (pKas from the ACD software are shown on the nitrogen atoms) | |
|---|---|
| 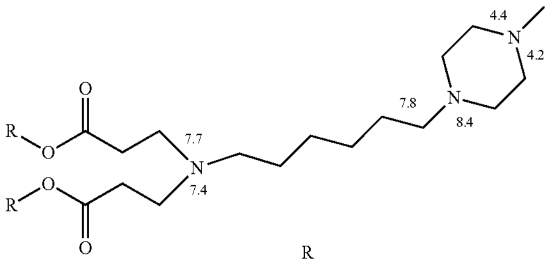 R<br>**Linear chains**<br>saturated, unsaturated, cyclic<br>**Branched chains**<br>saturated, unsaturated, cyclic | 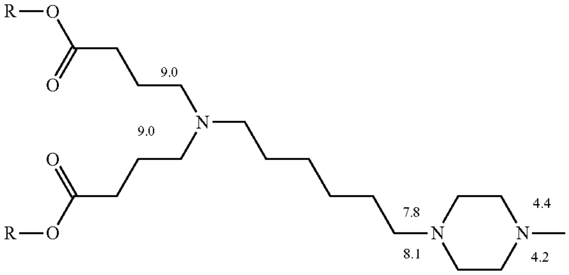 |
| C4 spacer for Linker | C5 spacer for Linker |
| 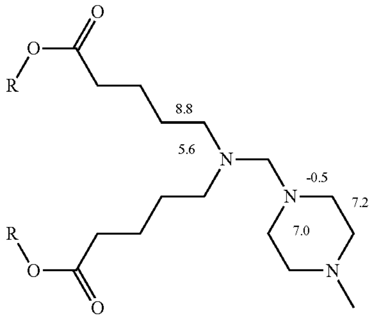 | 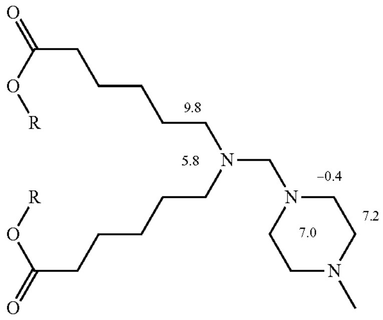 |
| 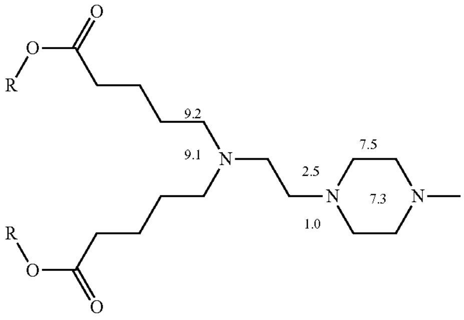 | 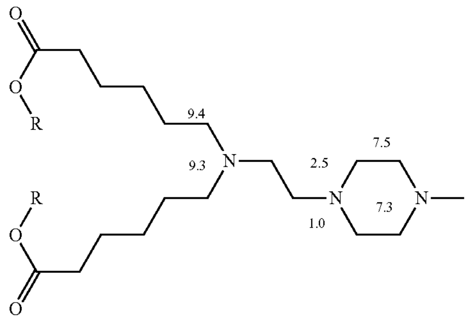 |
| 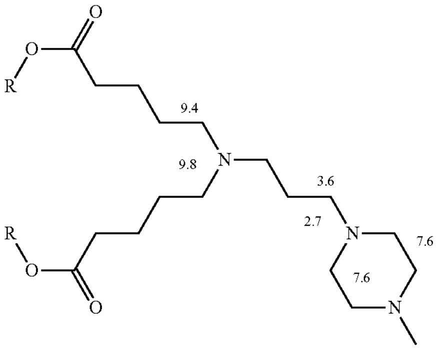 | 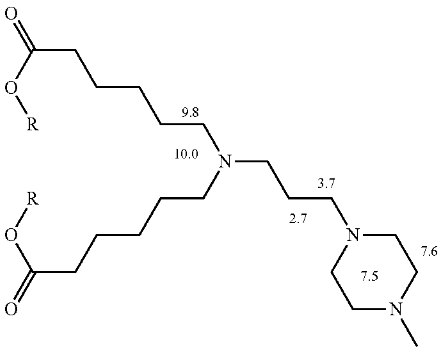 |

TABLE 5-continued
| Piperazine head Groups with $C_1$-$C_7$ Spacer Between the Head Group and Linker (pKas from the ACD software are shown on the nitrogen atoms) | |
|---|---|
| 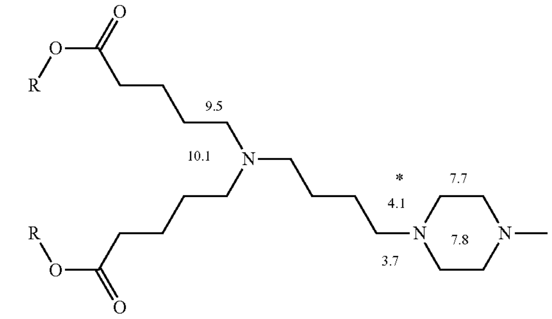 | 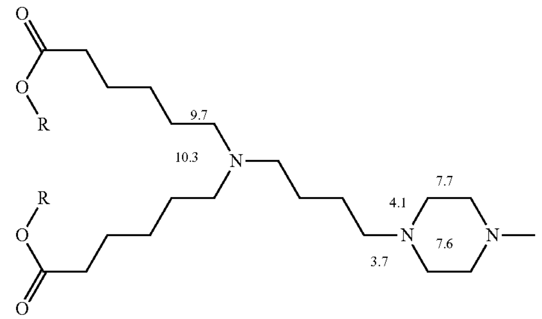 |
| 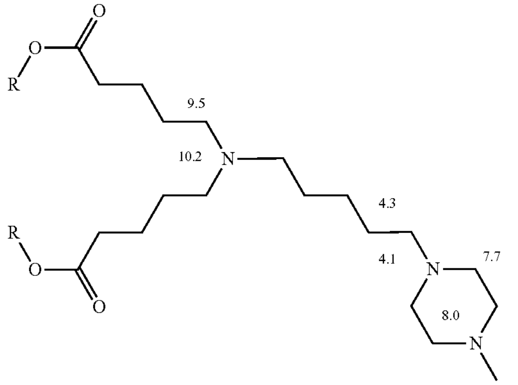 | 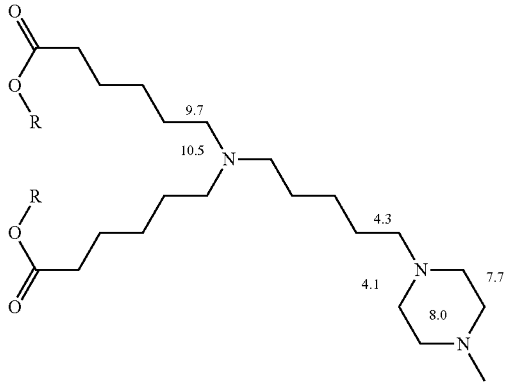 |
| 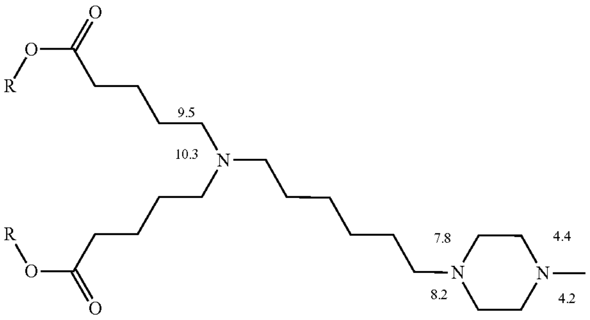 | 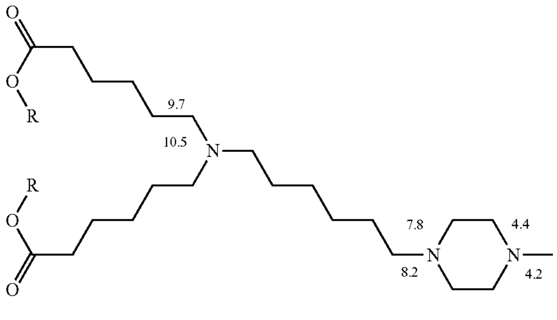 |
| C6 spacer for Linker | C7 spacer for Linker |
| 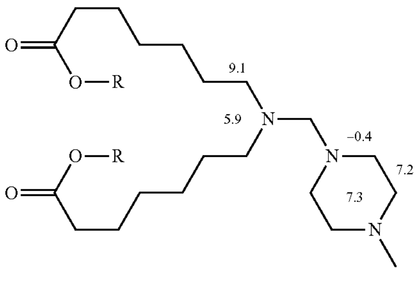 | 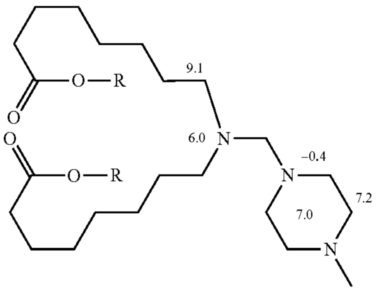 |

TABLE 5-continued
Piperazine head Groups with $C_1$-$C_7$ Spacer Between the Head Group and Linker (pKas from the ACD software are shown on the nitrogen atoms)
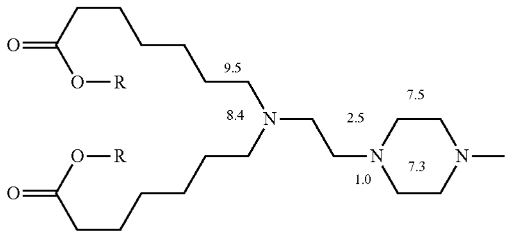
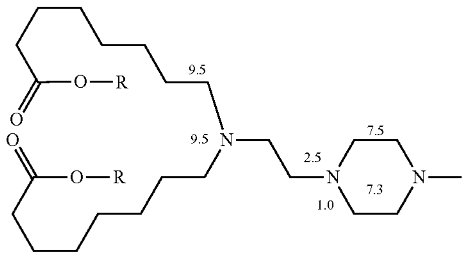
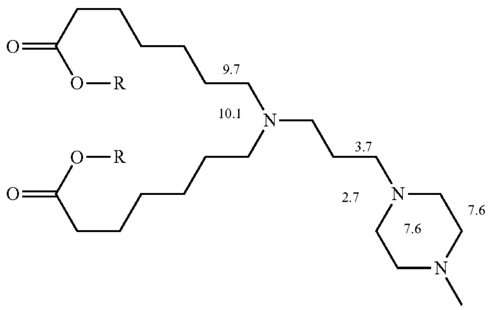
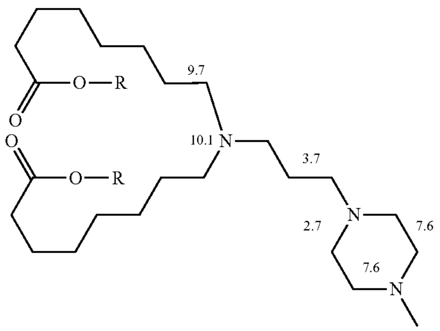
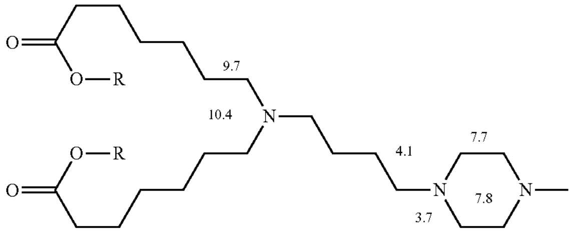
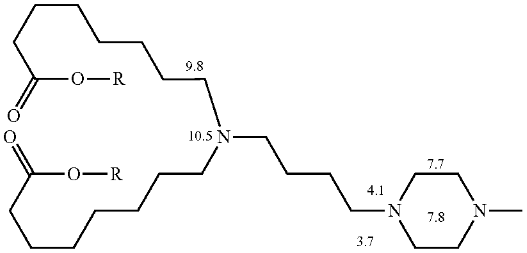
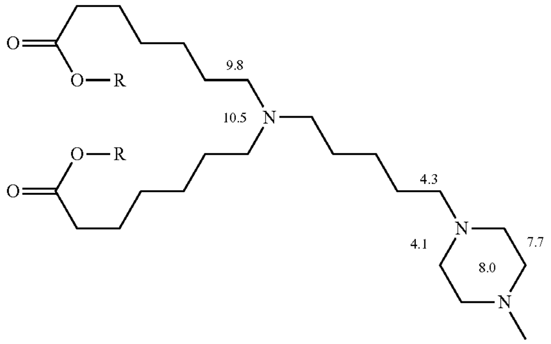
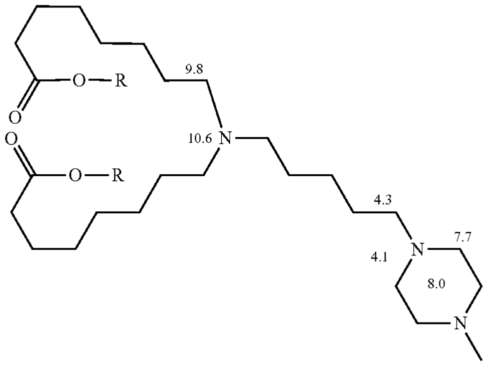
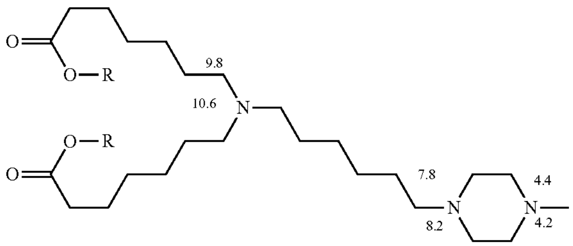
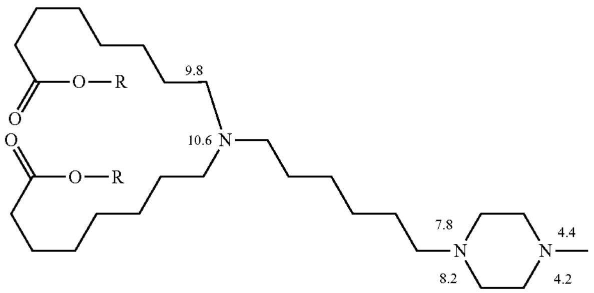

In certain embodiments, additional bivalent headgroups can be chosen along with Dimethylamine, Pyrrolidine, and Piperazine illustrated in Tables 2, 4, and 5, where carbon spacers can be changed to produce specific molecular pKas. In addition to specific ionization properties, some headgroups may have increased immune-adjuvanticity.
TABLE 6
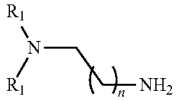
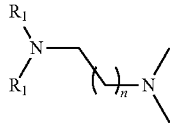
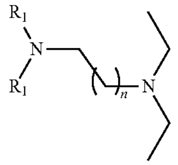
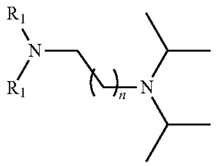
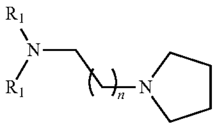
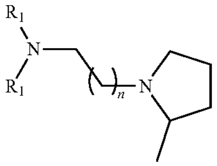
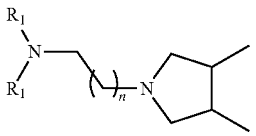
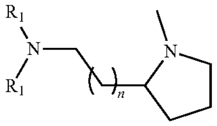
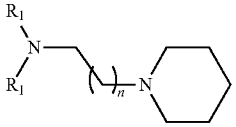
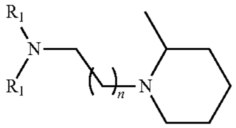
TABLE 6-continued
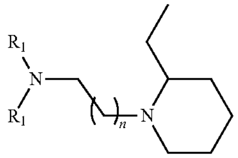
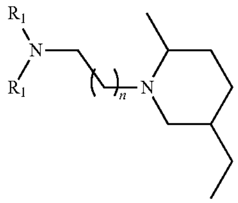
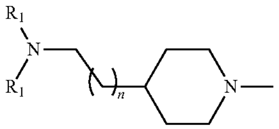
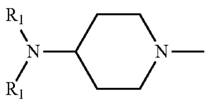
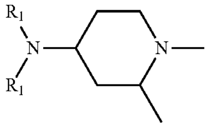
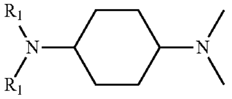
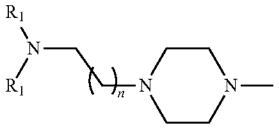
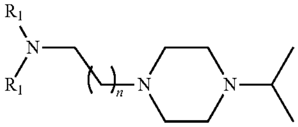
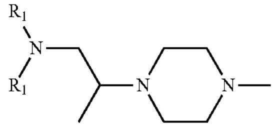
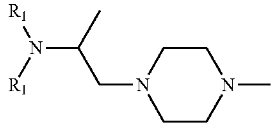
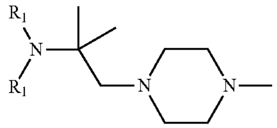

TABLE 6-continued
| |
|---|
| 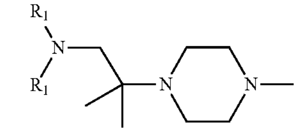 |
| 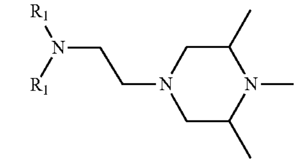 |
| 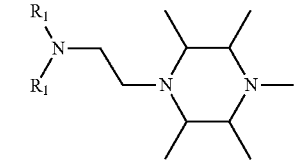 |
| 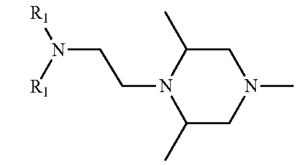 |
| 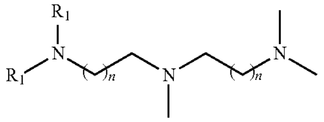 |
| 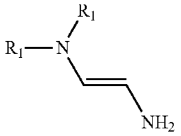 |
| 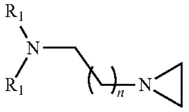 |
| 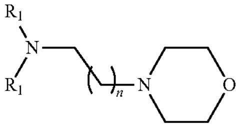 |
TABLE 6-continued
| |
|---|
| 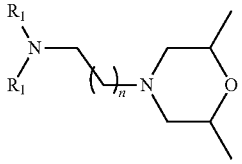 |
| 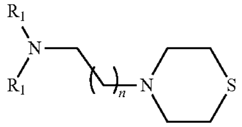 |
| 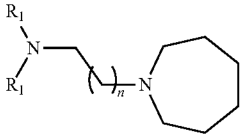 |
| 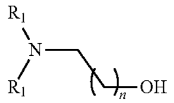 |
| 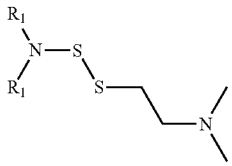 |
| 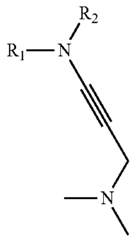 |
| 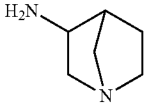 |
In certain embodiments, the Ionizable Lipids of the Invention include one or more linker groups, preferably 2, 3, 4, 5, 6, 7, 8, 9, or 10 linker groups.
Exemplary linkers are illustrated in Tables 7A-7E below.
TABLE 7A
| Linker | Two Linkers |
|---|---|
| L—O(C═O)—, —(C═O)O— | 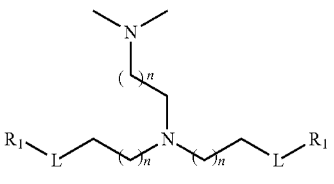 n = 1-6 |

TABLE 7A-continued
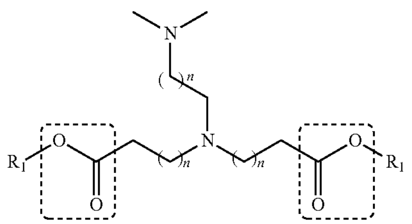
n = 1-6
| Linker | Four Linkers |
|---|---|
| L—O(C═O)—, —(C═O)O— | 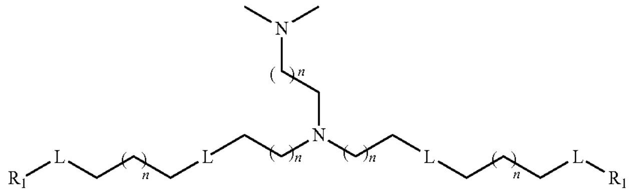 n = 1-6 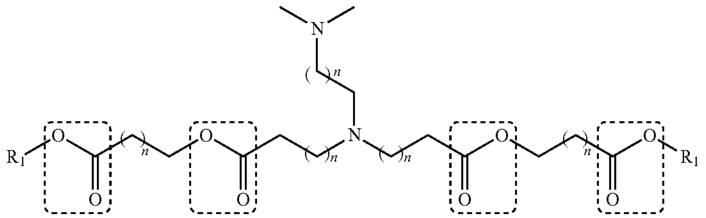 n = 1-6 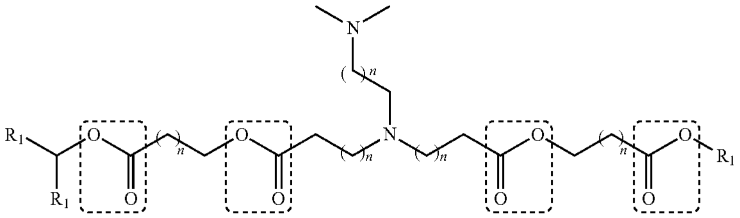 n = 1-6 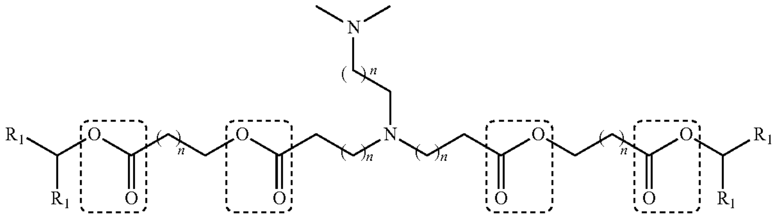 n = 1-6 |

TABLE 7A-continued
| Linker | Six Linkers |
|---|---|
| L—O(C═O)—,<br>—(C═O)O— | 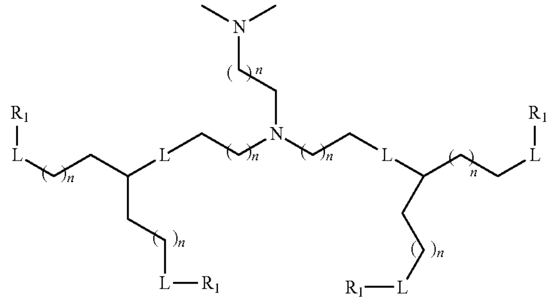<br>n = 1-6 |
| | 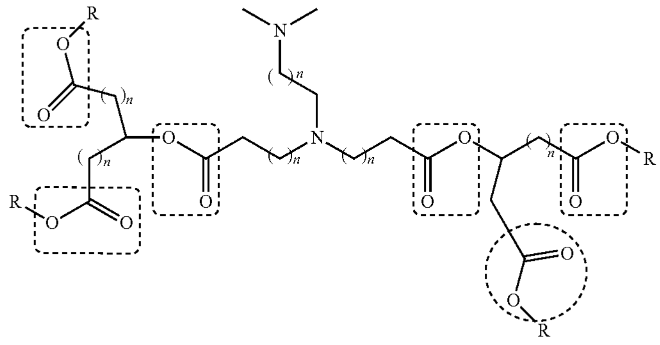<br>n = 1-6 |
| | 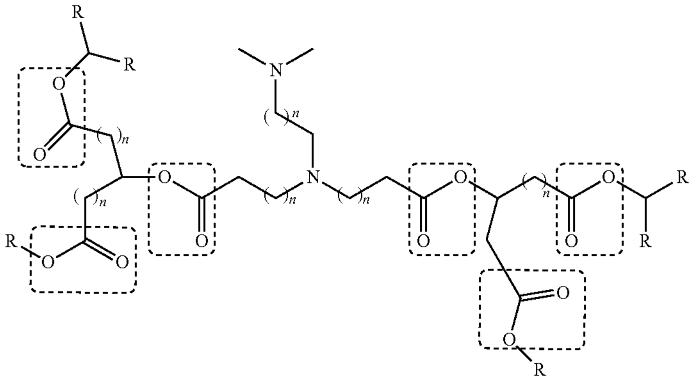<br>n = 1-6 |
| | 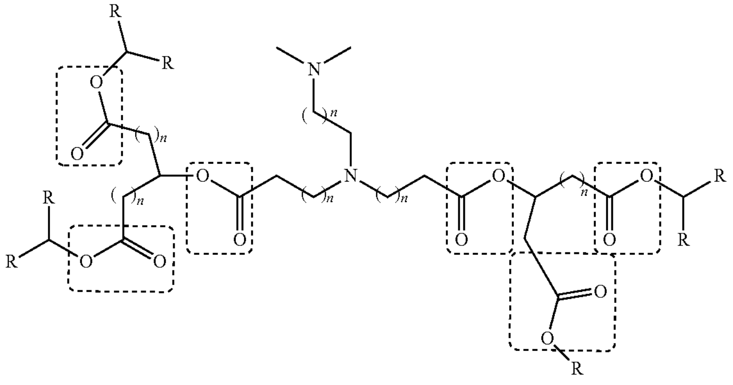<br>n = 1-6 |

TABLE 7B
| Linker | Two Linkers | Two Linkers |
| --- | --- | --- |
| L1 = —NH(C=O)— | 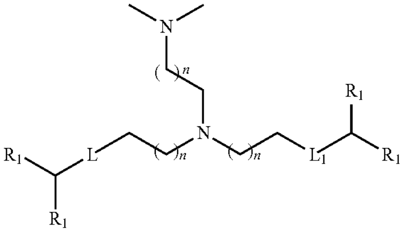 n = 1-6 | 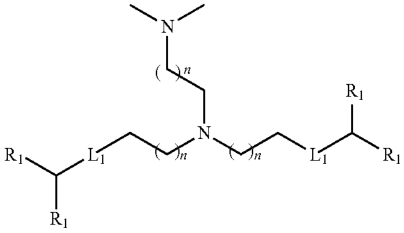 n = 1-6 |
| | 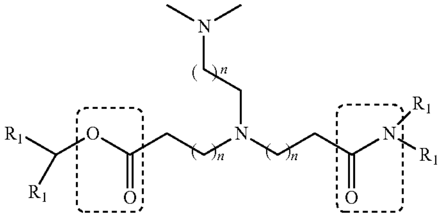 n = 1-6<br>Combination of —C(=O)O— and NH(C=O)— linkers | 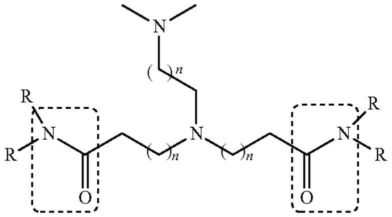 n = 1-6<br>Two symmetric NH(C=O)— linkers |
TABLE 7C
| Linker | | |
| --- | --- | --- |
| L2 = —N(O=S=O)— | 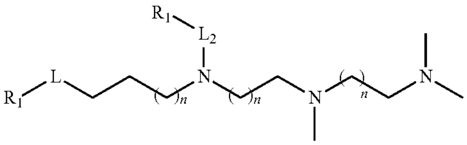 n = 1-6 | 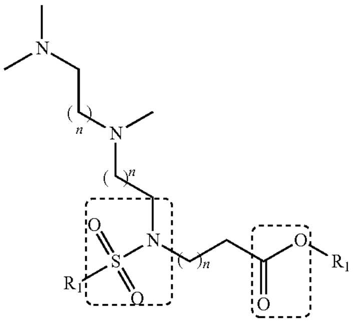 n = 1-6<br>Combination of —C(=O)O— and —N(O=S=O)— linkers |

TABLE 7D
| Linker | | |
|---|---|---|
| L3 = Dioxolo-pyrrolidine-dione | 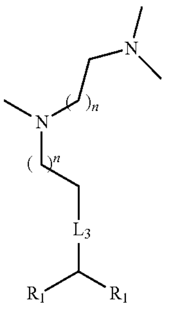 n = 1-6 | 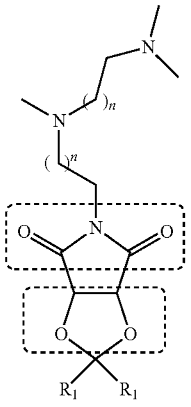 n = 1-6 Dioxolo-pyrrolidine-dione linker |
TABLE 7E
| Illustrative Mixed Linker Moieties |
|---|
| 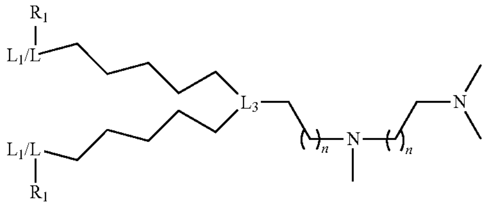 n = 1-6 |
| 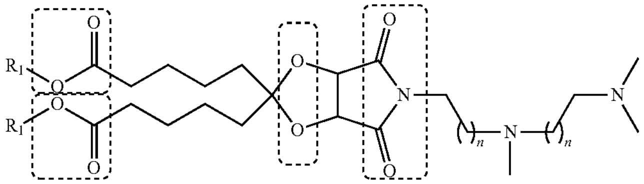 n = 1-6 |
| 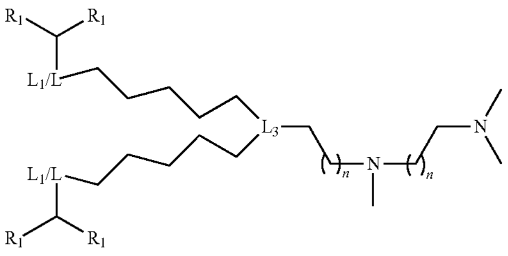 n = 1-6 |
| 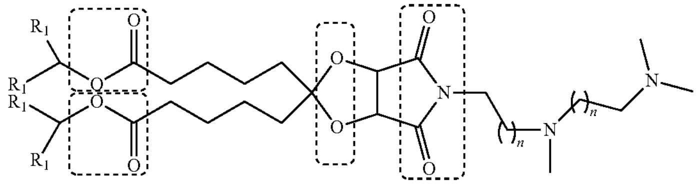 n = 1-6 |

TABLE 7E-continued
| Illustrative Mixed Linker Moieties |
| --- |
| 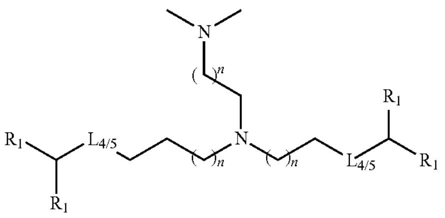 |
| n = 1-6 |
| 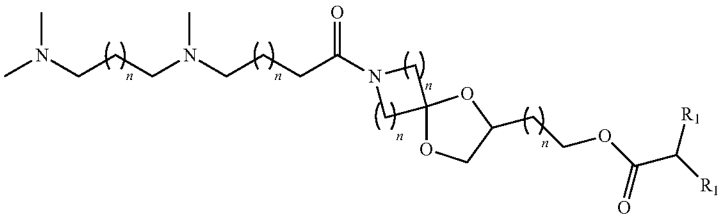 |
| n = 1-6 |
| 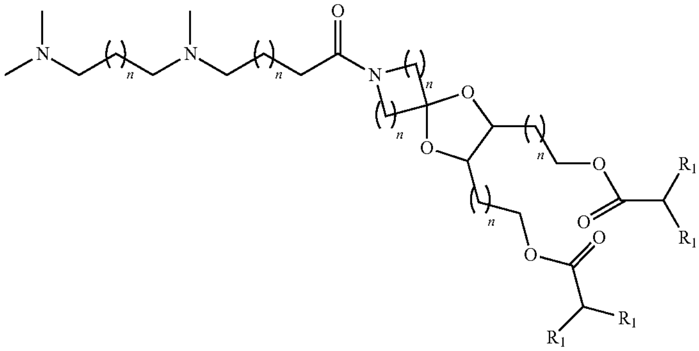 |
| n = 1-6 |
| 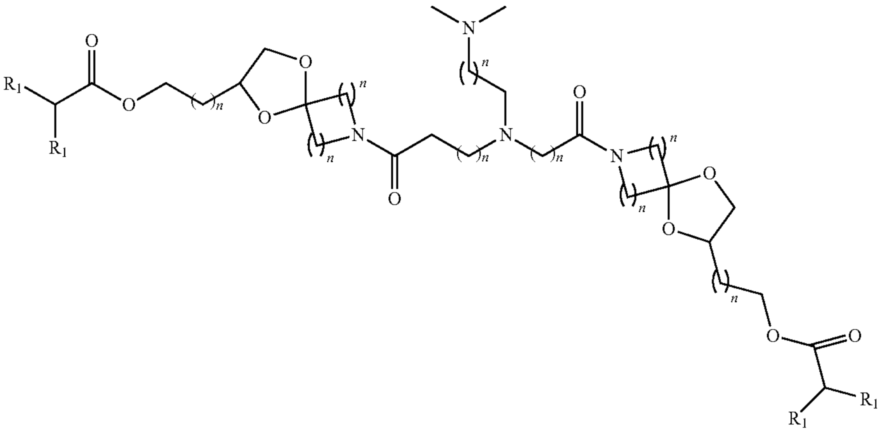 |
| n = 1-6 |

TABLE 7E-continued

| Illustrative Mixed Linker Moieties |
| --- |
| 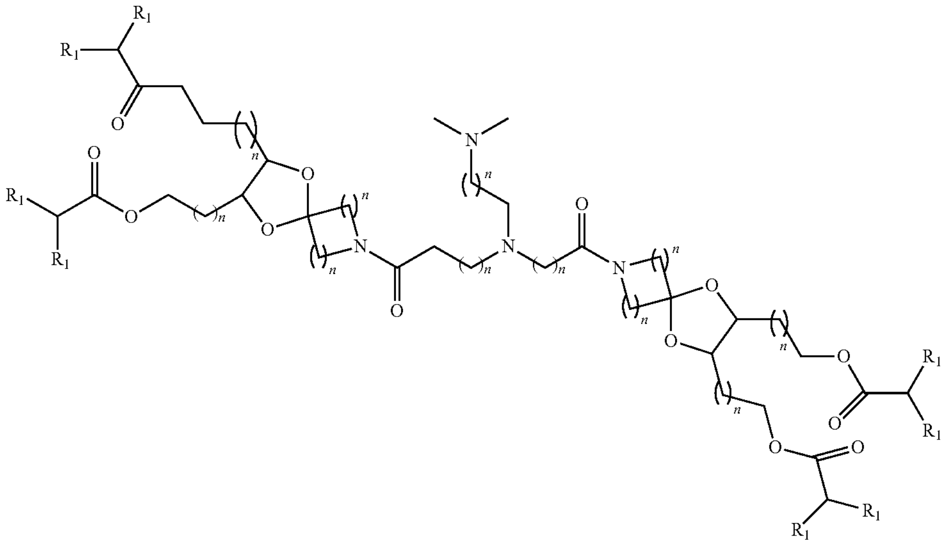 |
| n = 1-6 |

In certain embodiments, the shape of the alkyl tails of the Ionizable Lipid of the Invention is preferably cone-shaped and diverge in order to promote endolysosomal release by creating nonbilayer inverted hexagonal or other structures. Exemplary alkyl tails are illustrated in Table 8A, 8B, and 8C. In certain embodiments, this can be achieved by adding saturated bonds or branching. In other embodiments, adding ester bonds can increase tolerability through more rapid degradation.

TABLE 8A

| Degradable linkers-2 |
| --- |
| 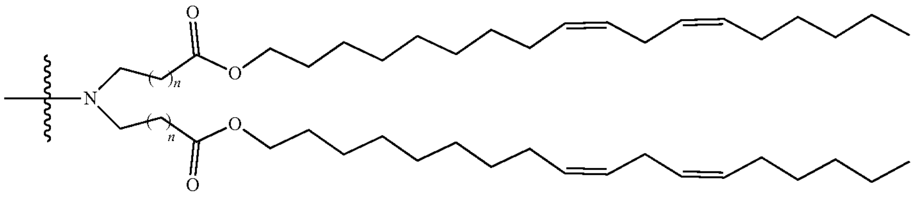 |

TABLE 8A-continued
Degradable linkers-4
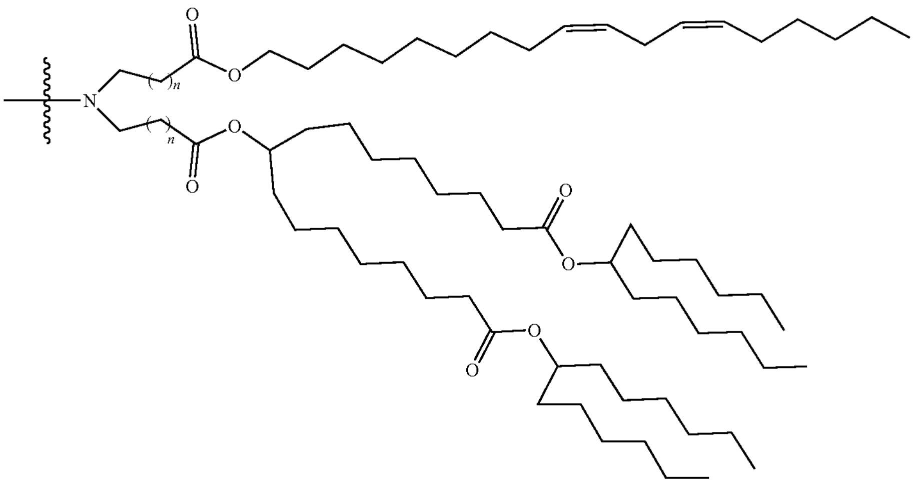
Degradable linkers-6
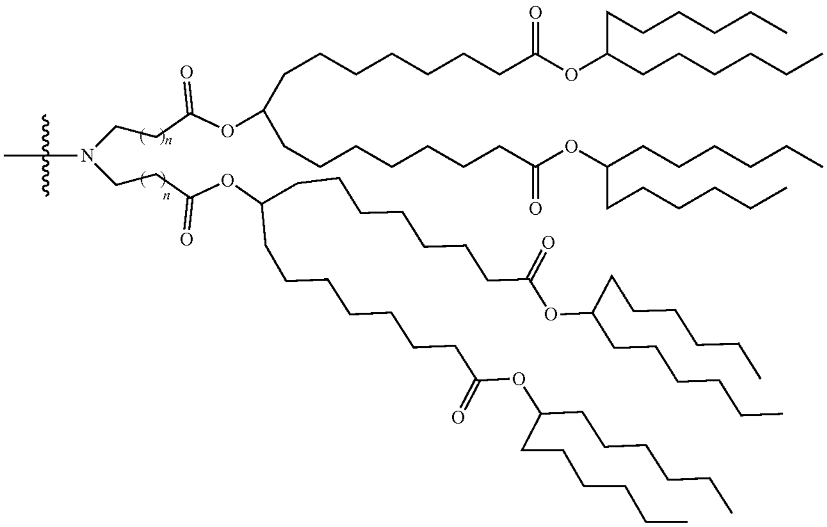
n = 1-5
TABLE 8B
Linear tails
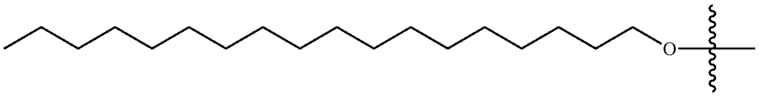 [SMILES: *OCCCCCCCCCCCCCCCCCC]
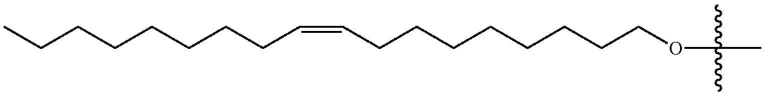 [SMILES: *OCCCCCCCC/C=C\CCCCCCCC]
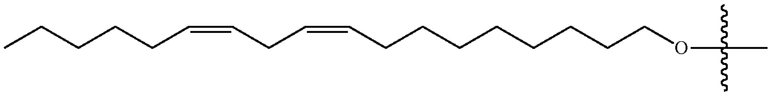 [SMILES: *OCCCCCCCC/C=C\C/C=C\CCCCC]

TABLE 8B-continued
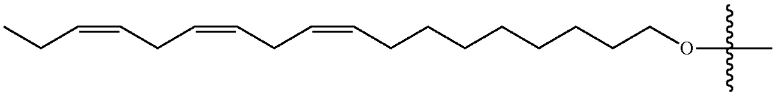 [SMILES: *OCCCCCCCC/C=C\C/C=C\C/C=C\CC]
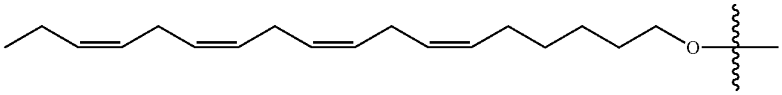 [SMILES: *OCCCCC/C=C\C/C=C\C/C=C\C/C=C\CC]
Bilayer tails
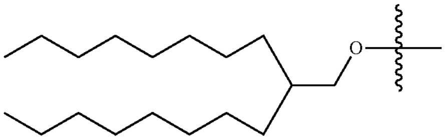
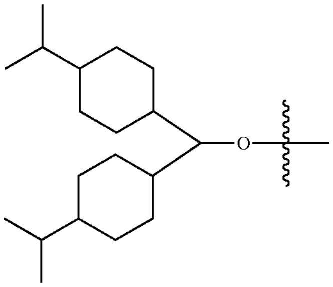
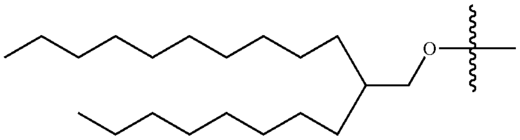
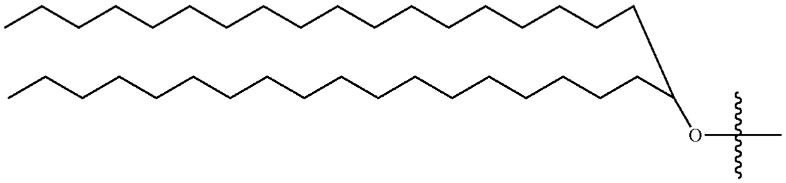 [SMILES: *OC(CCCCCCCCCCCCCCCCCC)CCCCCCCCCCCCCCCCCC]
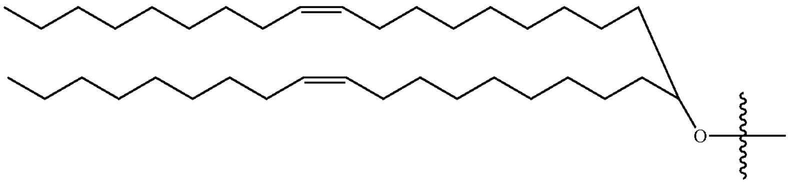 [SMILES: *OC(CCCCCCCC/C=C\CCCCCCCC)CCCCCCCC/C=C\CCCCCCCC]
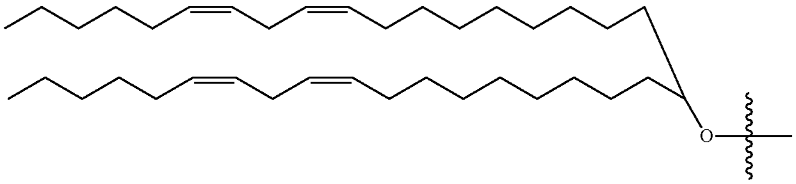 [SMILES: *OC(CCCCCCCC/C=C\C/C=C\CCCCC)CCCCCCCC/C=C\C/C=C\CCCCC]
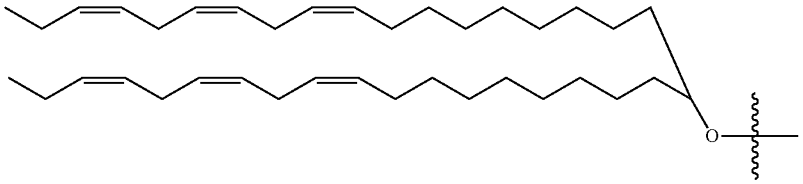 [SMILES: *OC(CCCCCCCC/C=C\C/C=C\C/C=C\CC)CCCCCCCC/C=C\C/C=C\C/C=C\CC]
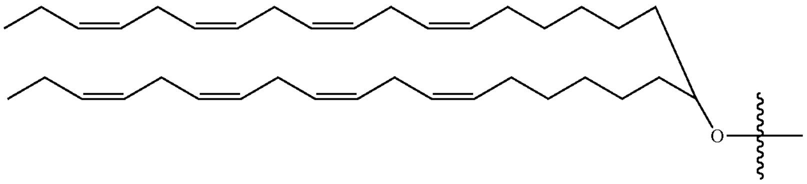 [SMILES: *OC(CCCCC/C=C\C/C=C\C/C=C\C/C=C\CC)CCCCC/C=C\C/C=C\C/C=C\C/C=C\CC]

TABLE 8B-continued
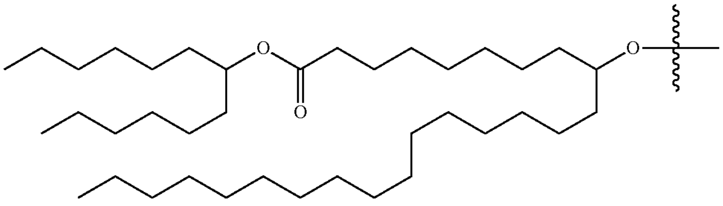 [SMILES: *OC(CCCCCCCCCCCCCCCC)CCCCCCCC(=O)OC(CCCCCC)CCCCCC]
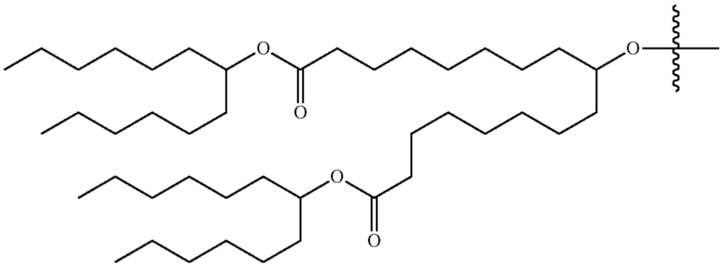 [SMILES: *OC(CCCCCCCC(=O)OC(CCCCCC)CCCCCC)CCCCCCCC(=O)OC(CCCCCC)CCCCCC]
TABLE 8C
Linear tails
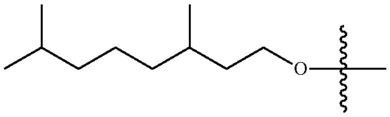 [SMILES: *OCCC(C)CCCC(C)C]
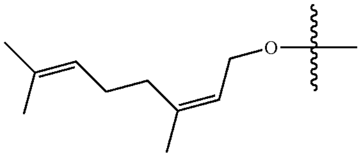 [SMILES: *OC/C=C(/C)CCC=C(C)C]
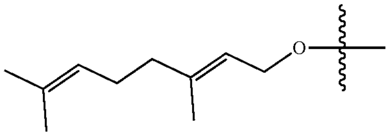 [SMILES: *OC/C=C(\C)CCC=C(C)C]
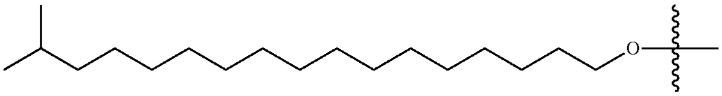 [SMILES: *OCCCCCCCCCCCCCCCC(C)C]
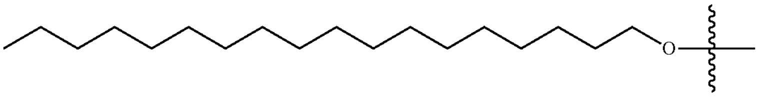 [SMILES: *OCCCCCCCCCCCCCCCCCC]
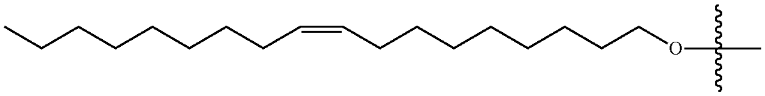 [SMILES: *OCCCCCCCC/C=C\CCCCCCCC]
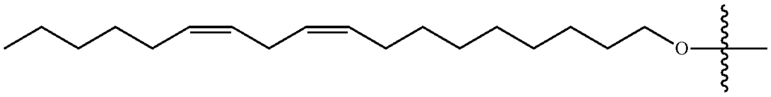 [SMILES: *OCCCCCCCC/C=C\C/C=C\CCCCC]

TABLE 8C-continued
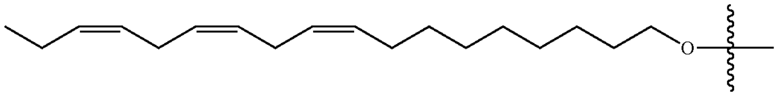 [SMILES: *OCCCCCCCC/C=C\C/C=C\C/C=C\CC]
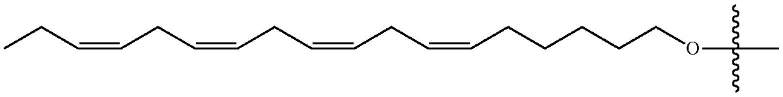
Bilayer tails
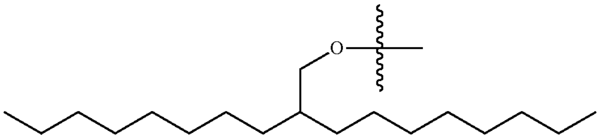 [SMILES: *OCC(CCCCCCCC)CCCCCCCC]
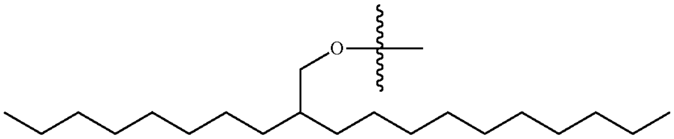 [SMILES: *OCC(CCCCCCCC)CCCCCCCCCC]
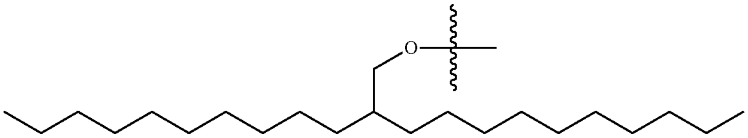 [SMILES: *OCC(CCCCCCCCCC)CCCCCCCCCC]
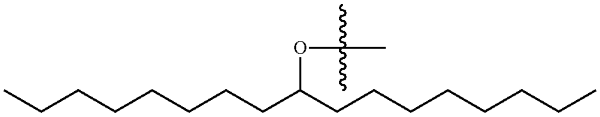 [SMILES: *OC(CCCCCCCC)CCCCCCCC]
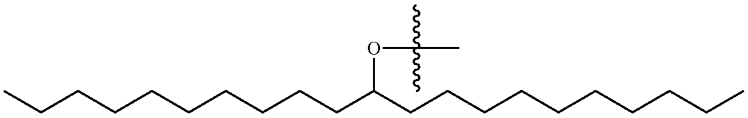 [SMILES: *OC(CCCCCCCCCC)CCCCCCCCCC]
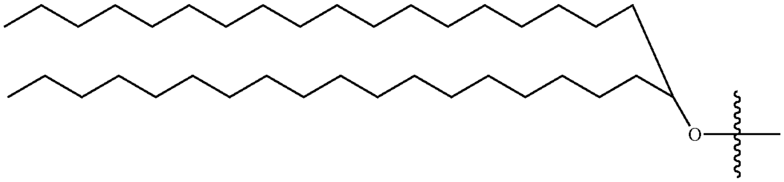 [SMILES: *OC(CCCCCCCCCCCCCCCCCC)CCCCCCCCCCCCCCCCCC]
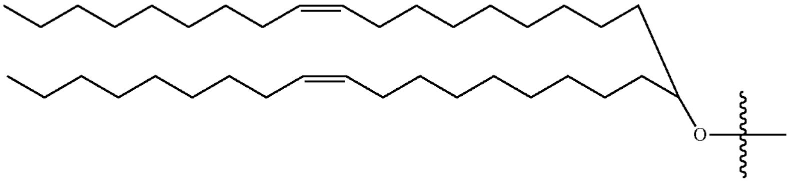
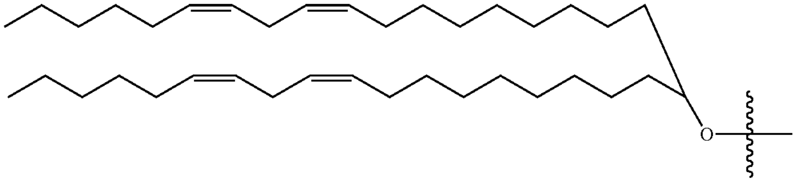 [SMILES: *OC(CCCCCCCC/C=C\C/C=C\CCCCC)CCCCCCCC/C=C\C/C=C\CCCCC]

TABLE 8C-continued

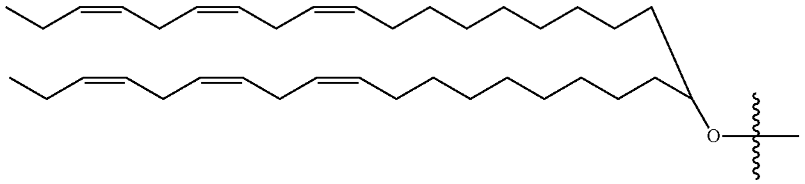 [SMILES: *OC(CCCCCCCC/C=C\C/C=C\C/C=C\CC)CCCCCCCC/C=C\C/C=C\C/C=C\CC]

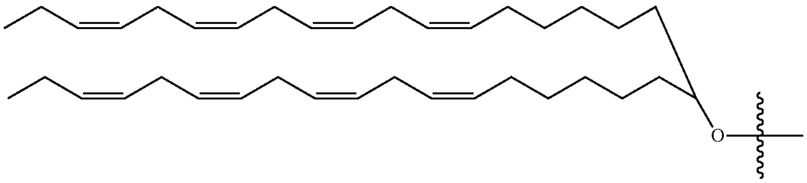 [SMILES: *OC(CCCCC/C=C\C/C=C\C/C=C\C/C=C\CC)CCCCC/C=C\C/C=C\C/C=C\C/C=C\CC]

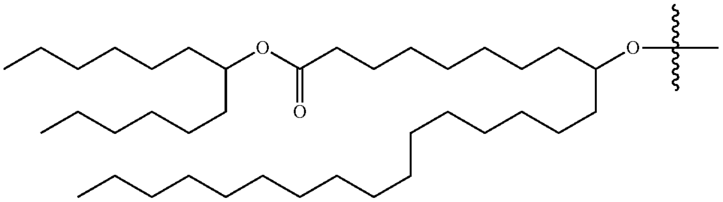 [SMILES: *OC(CCCCCCCCCCCCCCCC)CCCCCCCC(=O)OC(CCCCCC)CCCCCC]

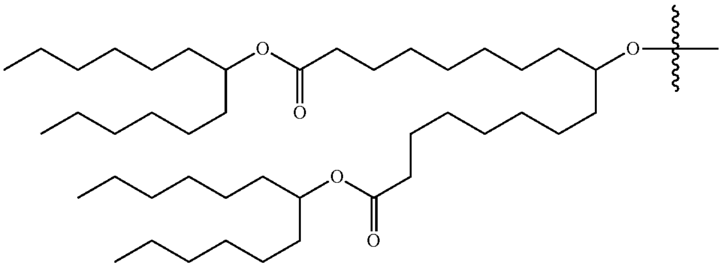 [SMILES: *OC(CCCCCCCC(=O)OC(CCCCCC)CCCCCC)CCCCCCCC(=O)OC(CCCCCC)CCCCCC]

Exemplary non-limiting examples of Ionizable Lipids of the Invention with Dimethylamine, Pyrrolidine, and Piperazine headgroups, ester linker, C4 spacers, and alkyl/alkylene tails are illustrated in Table 9 and can have pKas that permit a positively charged LNP at pH 7.4 for IM localization and a second internal amine with a pKa near 6.5 which can further ionize during endosomal acidification and provide release.

TABLE 9

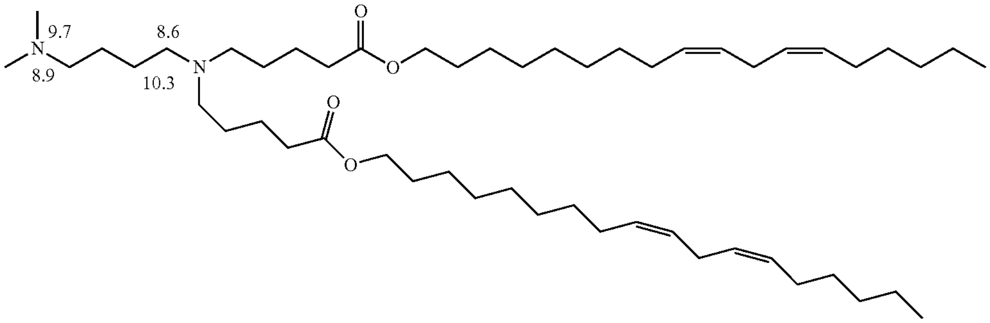 [SMILES: CCCCC/C=C\C/C=C\CCCCCCCCOC(=O)CCCCN(CCCCC(=O)OCCCCCCCC/C=C\C/C=C\CCCCC)CCCCN(C)C]

TABLE 9-continued

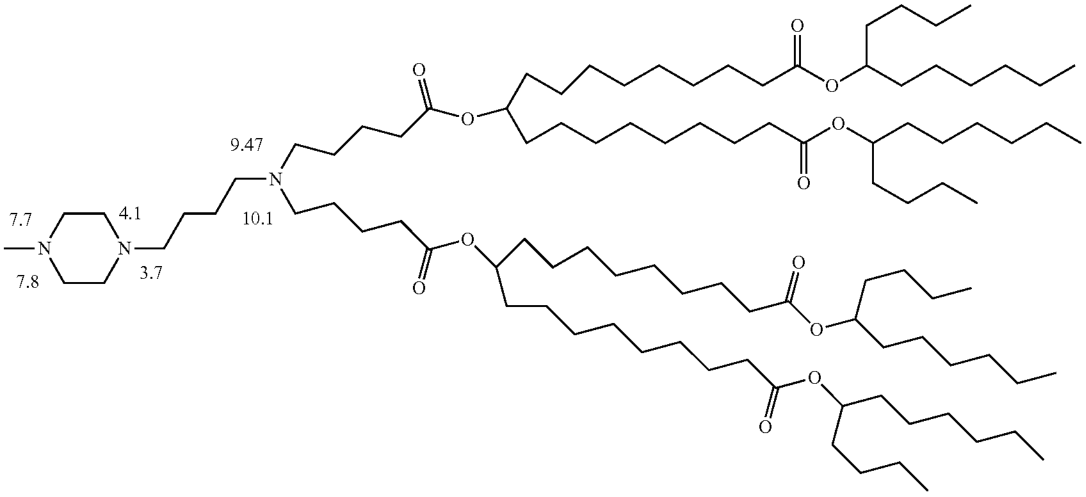 [SMILES: CCCCCCC(CCCC)OC(=O)CCCCCCCCC(CCCCCCCCC(=O)OC(CCCC)CCCCCC)OC(=O)CCCCN(CCCCC(=O)OC(CCCCCCCCC(=O)OC(CCCC)CCCCCC)CCCCCCCCC(=O)OC(CCCC)CCCCCC)CCCCN1CCN(C)CC1]

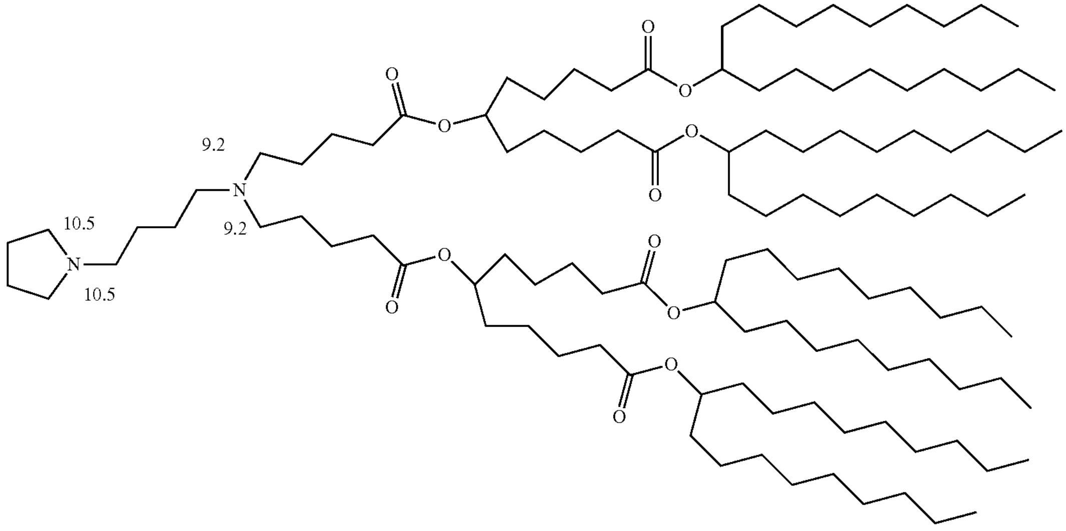 [SMILES: CCCCCCCCCC(CCCCCCCCC)OC(=O)CCCCC(CCCCC(=O)OC(CCCCCCCCC)CCCCCCCCC)OC(=O)CCCCN(CCCCC(=O)OC(CCCCC(=O)OC(CCCCCCCCC)CCCCCCCCC)CCCCC(=O)OC(CCCCCCCCC)CCCCCCCCC)CCCCN1CCCC1]

In another embodiment, the invention encompasses Ionizable Lipids of the Invention of Formula II:

Formula II

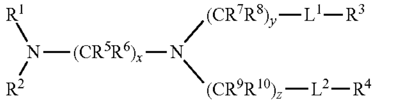

wherein each $R^1$ and $R^2$ is independently selected from the group consisting of H, an optionally substituted $C_1$-$C_{22}$ alkyl, optionally substituted $C_2$-$C_{22}$ alkenyl, optionally substituted $C_2$-$C_{22}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C_6$ heteroaryl, optionally substituted $C_4$-$C_8$ aryloxy, optionally substituted $C_7$-$C_{10}$ arylalkyl or optionally substituted $C_5$-$C_{10}$ heteroarylalkyl group, or $R^1$ and $R^2$ can together form a 3-7 membered heterocycle or heteroaryl ring;

wherein each $R^3$ and $R^4$ is independently selected from the group consisting of an optionally substituted $C_1$-$C_{22}$ alkyl, optionally substituted $C_2$-$C_{22}$ alkenyl, optionally substituted $C_2$-$C_{22}$ alkynyl, or wherein in $R^1$ and $R^2$ together comprise a 3-7 membered heterocycle or heteroaromatic ring;

wherein each $R^5$, $R^6$, $R^7$, $R^8$, $R^9$, and $R^{10}$ is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each of x, y, and z is independently an integer from 0-10; and wherein each of $L^1$ and $L^2$ is independently selected from the group consisting of —C(═O)—; OC(═O)—; —OC(═O)O—; —C(═O)O—; —C(═O)O$(CR^5R^6R^7)_m$; —NH—C(═O)—; —C(═O)NH—; —SO—; —$SO_2$—; —$SO_3$—; —$NSO_2$—; —$SO_2$N—; —NH(($C_1$-$C_8$)alkyl); —N(($C_1$-$C_8$)alkyl)$_2$; —NH(($C_6$)aryl); —N(($C_6$)aryl)$_2$; —NHC(═O)NH—; —NHC(═O)O—; —OC(═O)NH—; —NHC(═O)$NR^1$—; —NHC(═O)O—; —OC(═O)$NR^1$—; dioxolopyrrolidine-dione; —C(═O)$R^1$—; —CO(($C_1$-$C_{22}$)alkyl); —CO(($C_6$)aryl); —$CO_2$(($C_1$-$C_{22}$)alkyl); —$CO_2$(($C_6$)aryl); —$SO_2$(($C_1$-$C_{22}$)alkyl); and —$SO_2$(($C_6$)aryl).

The Ionizable Lipids of the Invention can optionally include carbon spacers between the first nitrogen and the second nitrogen (i.e., $CR^5R^6$ in Formula II above) and between second nitrogen and the ester linker (i.e., $CR^7R^8$ and $CR^9R^{10}$ in Formula II above). In certain embodiments, tails are symmetric including, for example, DiLinoleic Acid (DL) and the branched BisOctylDecyl (BOD).

In certain embodiments, $R^1$ is H.

In certain embodiments, $R^1$ is substituted or unsubstituted $C_1$-$C_{22}$ alkyl.

In certain embodiments, $R^1$ is substituted or unsubstituted $C_2$-$C_{22}$ alkenyl.

In certain embodiments, $R^1$ is substituted or unsubstituted $C_2$-$C_{22}$ alkynyl.

In certain embodiments, $R^1$ is substituted or unsubstituted $C_3$-$C_6$ cycloalkyl.

In certain embodiments, $R^1$ is substituted or unsubstituted $C_4$-$C_6$ heterocycloalkyl.

In certain embodiments, $R^1$ is substituted or unsubstituted $C_4$-$C_6$ alkylcycloalkyl.

In certain embodiments, $R^1$ is substituted or unsubstituted $C_4$-$C_6$ aryl.

In certain embodiments, $R^1$ is substituted or unsubstituted $C_3$-$C_6$ heteroaryl.

In certain embodiments, $R^1$ is substituted or unsubstituted $C_4$-$C_8$ aryloxy.

In certain embodiments, $R^1$ is substituted or unsubstituted $C_7$-$C_{10}$ arylalkyl.

In certain embodiments, $R^1$ is substituted or unsubstituted $C_5$-$C_{10}$ heteroarylalkyl group.

In certain embodiments, $R^2$ is H.

In certain embodiments, $R^2$ is substituted or unsubstituted $C_1$-$C_{22}$ alkyl.

In certain embodiments, $R^2$ is substituted or unsubstituted $C_2$-$C_{22}$ alkenyl In certain embodiments, $R^2$ is substituted or unsubstituted $C_2$-$C_{22}$ alkynyl In certain embodiments, $R^2$ is substituted or unsubstituted $C_3$-$C_6$ cycloalkyl.

In certain embodiments, $R^2$ is substituted or unsubstituted $C_4$-$C_6$ heterocycloalkyl.

In certain embodiments, $R^2$ is substituted or unsubstituted $C_4$-$C_6$ alkylcycloalkyl.

In certain embodiments, $R^2$ is substituted or unsubstituted $C_4$-$C_6$ aryl.

In certain embodiments, $R^2$ is substituted or unsubstituted $C_3$-$C_6$ heteroaryl.

In certain embodiments, $R^2$ is substituted or unsubstituted $C_4$-$C_8$ aryloxy.

In certain embodiments, $R^2$ is substituted or unsubstituted $C_7$-$C_{10}$ arylalkyl.

In certain embodiments, $R^2$ is substituted or unsubstituted $C_5$-$C_{10}$ heteroarylalkyl group.

In certain embodiments, $R^3$ is substituted or unsubstituted $C_1$-$C_{22}$ alkyl.

In certain embodiments, $R^3$ is substituted or unsubstituted $C_2$-$C_{22}$ alkenyl.

In certain embodiments, $R^3$ is substituted or unsubstituted $C_2$-$C_{22}$ alkynyl.

In a preferred embodiment, $R^3$ is substituted or unsubstituted —C(═O)O—$C_1$-$C_{22}$ alkyl.

In a preferred embodiment, $R^3$ is substituted or unsubstituted —C(═O)O—$C_1$-$C_{22}$ alkenyl.

In a preferred embodiment, $R^3$ is substituted or unsubstituted —C(═O)O—$C_1$-$C_{22}$ alkynyl.

In certain embodiments, $R^4$ is substituted or unsubstituted $C_1$-$C_{22}$ alkyl.

In certain embodiments, $R^4$ is substituted or unsubstituted $C_2$-$C_{22}$ alkenyl.

In certain embodiments, $R^4$ is substituted or unsubstituted $C_2$-$C_{22}$ alkynyl.

In a preferred embodiment, $R^4$ is substituted or unsubstituted —C(═O)O—$C_1$-$C_{22}$ alkyl.

In a preferred embodiment, $R^4$ is substituted or unsubstituted —C(═O)O—$C_1$-$C_{22}$ alkenyl.

In a preferred embodiment, $R^4$ is substituted or unsubstituted —C(═O)O—$C_1$-$C_{22}$ alkynyl.

In certain preferred embodiments, the substitution on $R^3$ and/or $R^4$ includes a terminal dioxolane group.

In certain embodiments, $R^5$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^5$ is H.

In certain embodiments, $R^5$ is OH.

In certain embodiments, $R^5$ is halo.

In certain embodiments, $R^5$ is phenyl.

In certain embodiments, $R^5$ is benzyl.

In certain embodiments, $R^5$ is substituted or unsubstituted $C_1$-$C_{22}$ alkyl.

In certain embodiments, $R^5$ is substituted or unsubstituted $C_2$-$C_{22}$ alkenyl.

In certain embodiments, $R^5$ is substituted or unsubstituted $C_2$-$C_{22}$ alkynyl.

In certain embodiments, $R^6$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^6$ is H.

In certain embodiments, $R^6$ is OH.

In certain embodiments, $R^6$ is halo.

In certain embodiments, $R^6$ is phenyl.

In certain embodiments, $R^6$ is benzyl.

In certain embodiments, $R^6$ is substituted or unsubstituted $C_1$-$C_{22}$ alkyl.

In certain embodiments, $R^6$ is substituted or unsubstituted $C_2$-$C_{22}$ alkenyl.

In certain embodiments, $R^6$ is substituted or unsubstituted $C_2$-$C_{22}$ alkynyl.

In certain embodiments, $R^7$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^7$ is H.

In certain embodiments, $R^7$ is OH.

In certain embodiments, $R^7$ is halo.

In certain embodiments, $R^7$ is phenyl.

In certain embodiments, $R^7$ is benzyl.

In certain embodiments, $R^7$ is substituted or unsubstituted $C_1$-$C_{22}$ alkyl.

In certain embodiments, $R^7$ is substituted or unsubstituted $C_2$-$C_{22}$ alkenyl.

In certain embodiments, $R^7$ is substituted or unsubstituted $C_2$-$C_{22}$ alkynyl.

In certain embodiments, $R^8$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^8$ is H.

In certain embodiments, $R^8$ is OH.

In certain embodiments, $R^8$ is halo.

In certain embodiments, $R^8$ is phenyl.

In certain embodiments, $R^8$ is benzyl.

In certain embodiments, $R^8$ is substituted or unsubstituted $C_1$-$C_{22}$ alkyl.

In certain embodiments, $R^8$ is substituted or unsubstituted $C_2$-$C_{22}$ alkenyl.

In certain embodiments, $R^8$ is substituted or unsubstituted $C_2$-$C_{22}$ alkynyl.

In certain embodiments, $R^9$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^9$ is H.

In certain embodiments, $R^9$ is OH.

In certain embodiments, $R^9$ is halo.

In certain embodiments, $R^9$ is phenyl.

In certain embodiments, $R^9$ is benzyl.

In certain embodiments, $R^9$ is substituted or unsubstituted $C_1$-$C_{22}$ alkyl.

In certain embodiments, $R^9$ is substituted or unsubstituted $C_2$-$C_{22}$ alkenyl.

In certain embodiments, $R^9$ is substituted or unsubstituted $C_2$-$C_{22}$ alkynyl.

In certain embodiments, $R^{10}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{10}$ is H.

In certain embodiments, $R^{10}$ is OH.

In certain embodiments, $R^{10}$ is halo.

In certain embodiments, $R^{10}$ is phenyl.

In certain embodiments, $R^{10}$ is benzyl.

In certain embodiments, $R^{10}$ is substituted or unsubstituted $C_1$-$C_{22}$ alkyl.

In certain embodiments, $R^{10}$ is substituted or unsubstituted $C_2$-$C_{22}$ alkenyl.

In certain embodiments, $R^{10}$ is substituted or unsubstituted $C_2$-$C_{22}$ alkynyl.

In certain embodiments, x is 0.

In certain embodiments, x is 1.

In certain embodiments, x is 2.

In certain embodiments, x is 3.

In certain embodiments, x is 4.

In certain embodiments, x is 5.

In certain embodiments, x is 6.

In certain embodiments, x is 7.

In certain embodiments, x is 8.

In certain embodiments, x is 9.

In certain embodiments, x is 10.

In certain embodiments, x is 11.

In certain embodiments, x is 12.

In certain embodiments, x is 13.

In certain embodiments, x is 14.

In certain embodiments, x is 15.

In certain embodiments, x is 16.

In certain embodiments, x is 17.

In certain embodiments, x is 18.

In certain embodiments, x is 19.

In certain embodiments, x is 20.

In certain embodiments, y is 0.

In certain embodiments, y is 1.

In certain embodiments, y is 2.

In certain embodiments, y is 3.

In certain embodiments, y is 4.

In certain embodiments, y is 5.

In certain embodiments, y is 6.

In certain embodiments, y is 7.

In certain embodiments, y is 8.

In certain embodiments, y is 9.

In certain embodiments, y is 10.

In certain embodiments, y is 11.

In certain embodiments, y is 12.

In certain embodiments, y is 13.

In certain embodiments, y is 14.

In certain embodiments, y is 15.

In certain embodiments, y is 16.

In certain embodiments, y is 17.

In certain embodiments, y is 18.

In certain embodiments, y is 19.

In certain embodiments, y is 20.

In certain embodiments, z is 0.

In certain embodiments, z is 1.

In certain embodiments, z is 2.

In certain embodiments, z is 3.

In certain embodiments, z is 4.

In certain embodiments, z is 5.

In certain embodiments, z is 6.

In certain embodiments, z is 7.

In certain embodiments, z is 8.

In certain embodiments, z is 9.

In certain embodiments, z is 10.

In certain embodiments, z is 11.

In certain embodiments, z is 12.

In certain embodiments, z is 13.

In certain embodiments, z is 14.

In certain embodiments, z is 15.

In certain embodiments, z is 16.

In certain embodiments, z is 17.

In certain embodiments, z is 18.

In certain embodiments, z is 19.

In certain embodiments, z is 20.

In certain embodiments $L^1$ is a bond.

In certain embodiments, $L^1$ is —C(═O)—.

In certain embodiments, $L^1$ is —OC(═O)O—.

In certain embodiments, $L^1$ is —NH—C(═O)—.

In certain embodiments, $L^1$ is —SO—.

In certain embodiments, $L^1$ is —$SO_2$—.

In certain embodiments, $L^1$ is OC(═O).

In certain embodiments, $L^1$ is —C(═O)O—.

In certain embodiments, $L^1$ is —C(═O)NH—.

In certain embodiments, $L^1$ is —$SO_3$—.

In certain embodiments, $L^1$ is —$NSO_2$—.

In certain embodiments, $L^1$ is —$SO_2$N.

In certain embodiments, $L^1$ is —NH(($C_1$-$C_{22}$)alkyl).

In certain embodiments, $L^1$ is —N(($C_1$-$C_8$)alkyl)$_2$.

In certain embodiments, $L^1$ is —NH(($C_6$)aryl).

In certain embodiments, $L^1$ is —N(($C_6$)aryl)$_2$.

In certain embodiments, $L^1$ is dioxolopyrrolidine-dione.

In certain embodiments, $L^1$ is —C(═O)$R^1$—.

In certain embodiments, $L^1$ is —CO(($C_1$-$C_{22}$)alkyl).

In certain embodiments, $L^1$ is —CO(($C_6$)aryl).

In certain embodiments, $L^1$ is —$CO_2$(($C_1$-$C_{22}$)alkyl).

In certain embodiments, $L^1$ is —$CO_2$(($C_6$)aryl).

In certain embodiments, $L^1$ is —$SO_2$(($C_1$-$C_{22}$)alkyl).

In certain embodiments, $L^1$ is —$SO_2$(($C_6$)aryl).

In certain embodiments $L^2$ is a bond.

In certain embodiments, $L^2$ is —C(═O)—.

In certain embodiments, $L^2$ is —OC(═O)O—.

In certain embodiments, $L^2$ is —OC(═O)O($CR^1R^2R^3$).

In certain embodiments, $L^2$ is —NH—C(═O)—.

In certain embodiments, $L^2$ is —SO—.

In certain embodiments, $L^2$ is —$SO_2$—.

In certain embodiments, $L^2$ is OC(═O).

In certain embodiments, $L^2$ is —C(═O)O—.

In certain embodiments, $L^2$ is —C(═O)NH—.

In certain embodiments, $L^2$ is —$SO_3$—.

In certain embodiments, $L^2$ is —$NSO_2$—.

In certain embodiments, $L^2$ is —$SO_2N$.

In certain embodiments, $L^2$ is —NH(($C_1$-$C_{22}$)alkyl).

In certain embodiments, $L^2$ is —N(($C_1$-$C_8$)alkyl)$_2$.

In certain embodiments, $L^2$ is —NH(($C_6$)aryl).

In certain embodiments, $L^2$ is —N(($C_6$)aryl)$_2$.

In certain embodiments, $L^2$ is dioxolopyrrolidine-dione.

In certain embodiments, $L^2$ is —C(=O)$R^1$—.

In certain embodiments, $L^2$ is —CO(($C_1$-$C_{22}$)alkyl).

In certain embodiments, $L^2$ is —CO(($C_6$)aryl).

In certain embodiments, $L^2$ is —$CO_2$(($C_1$-$C_{22}$)alkyl).

In certain embodiments, $L^2$ is —$CO_2$(($C_6$)aryl).

In certain embodiments, $L^2$ is —$SO_2$(($C_1$-$C_{22}$)alkyl).

In certain embodiments, $L^2$ is —$SO_2$(($C_6$)aryl).

In another embodiment, the invention encompasses Ionizable Lipids of the Invention of Formula III:

Formula III

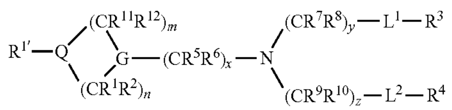

wherein each $R^{1'}$, $R^1$, $R^2$, $R^{11}$, and $R^{12}$ is independently selected from the group consisting of H, an optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C_6$ heteroaryl, optionally substituted $C_4$-$C_8$ aryloxy, optionally substituted $C_7$-$C_{10}$ arylalkyl; optionally substituted $C_5$-$C_{10}$ heteroarylalkyl group, optionally substituted amine; or $R^1$ and $R^2$ can together form cycloalkyl or heterocycloalkyl ring, wherein if Q is S or O the $R^1$ attached to the S or O is an electron pair;

wherein each $R^3$ and $R^4$ is independently selected from the group consisting of an optionally substituted $C_1$-$C_{22}$ alkyl, optionally substituted $C_2$-$C_{22}$ alkenyl, optionally substituted $C_2$-$C_{22}$ alkynyl;

wherein each $R^5$, $R^6$, $R^7$, $R^8$, $R^9$, and $R^{10}$ is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each of x, y, and z is independently an integer from 0-20;

wherein G and Q are each independently an atom selected from CH, 0, N, and S;

wherein each of m and n is an integer from 0-4; and wherein each of $L^1$ and $L^2$ is independently selected from the group consisting of —C(=O)—; OC(=O)—; —OC(=O)O—; —C(=O)O—; —C(=O)O($CR^5R^6R^7$)$_m$; —NH—C(=O)—; —C(=O)NH—; —SO—; —$SO_2$—; —$SO_3$—; —$NSO_2$—; —$SO_2N$—; —NH(($C_1$-$C_8$)alkyl); —N(($C_1$-$C_8$)alkyl)$_2$; —NH(($C_6$)aryl); —N(($C_6$)aryl)$_2$; —NHC(=O)NH—; —NHC(=O)O—; —OC(=O)NH—; —NHC(=O)$NR^1$—; —NHC(=O)O—; —OC(=O)$NR^1$—; —C(=O)$R^1$—; —CO(($C_1$-$C_8$)alkyl); —CO(($C_6$)aryl); —$CO_2$(($C_1$-$C_8$)alkyl); —$CO_2$(($C_6$)aryl); —$SO_2$(($C_1$-$C_8$)alkyl); —$SO_2$(($C_6$)aryl); and a disulfide bond.

In certain embodiments, $R^1$ is H.

In certain embodiments, $R^1$ is substituted or unsubstituted $C_1$-$C_{22}$ alkyl.

In certain embodiments, $R^1$ is substituted or unsubstituted $C_2$-$C_{22}$ alkenyl.

In certain embodiments, $R^1$ is substituted or unsubstituted $C_2$-$C_{22}$ alkynyl.

In certain embodiments, $R^1$ is substituted or unsubstituted $C_3$-$C_6$ cycloalkyl.

In certain embodiments, $R^1$ is substituted or unsubstituted $C_4$-$C_6$ heterocycloalkyl.

In certain embodiments, $R^1$ is substituted or unsubstituted $C_4$-$C_6$ alkylcycloalkyl.

In certain embodiments, $R^1$ is substituted or unsubstituted $C_4$-$C_6$ aryl.

In certain embodiments, $R^1$ is substituted or unsubstituted $C_3$-$C_6$ heteroaryl.

In certain embodiments, $R^1$ is substituted or unsubstituted $C_4$-$C_8$ aryloxy.

In certain embodiments, $R^1$ is substituted or unsubstituted $C_7$-$C_{10}$ arylalkyl.

In certain embodiments, $R^1$ is substituted or unsubstituted $C_5$-$C_{10}$ heteroarylalkyl group.

In certain embodiments, $R^2$ is H.

In certain embodiments, $R^2$ is substituted or unsubstituted $C_1$-$C_{22}$ alkyl.

In certain embodiments, $R^2$ is substituted or unsubstituted $C_2$-$C_{22}$ alkenyl In certain embodiments, $R^2$ is substituted or unsubstituted $C_2$-$C_{22}$ alkynyl In certain embodiments, $R^2$ is substituted or unsubstituted $C_3$-$C_6$ cycloalkyl.

In certain embodiments, $R^2$ is substituted or unsubstituted $C_4$-$C_6$ heterocycloalkyl.

In certain embodiments, $R^2$ is substituted or unsubstituted $C_4$-$C_6$ alkylcycloalkyl.

In certain embodiments, $R^2$ is substituted or unsubstituted $C_4$-$C_6$ aryl.

In certain embodiments, $R^2$ is substituted or unsubstituted $C_3$-$C_6$ heteroaryl.

In certain embodiments, $R^2$ is substituted or unsubstituted $C_4$-$C_8$ aryloxy.

In certain embodiments, $R^2$ is substituted or unsubstituted $C_7$-$C_{10}$ arylalkyl.

In certain embodiments, $R^2$ is substituted or unsubstituted $C_5$-$C_{10}$ heteroarylalkyl group.

In certain embodiments, $R^3$ is substituted or unsubstituted $C_1$-$C_{22}$ alkyl.

In certain embodiments, $R^3$ is substituted or unsubstituted $C_2$-$C_{22}$ alkenyl.

In certain embodiments, $R^3$ is substituted or unsubstituted $C_2$-$C_{22}$ alkynyl.

In a preferred embodiment, $R^3$ is substituted or unsubstituted —C(=O)O—$C_1$-$C_{22}$ alkyl.

In a preferred embodiment, $R^3$ is substituted or unsubstituted —C(=O)O—$C_1$-$C_{22}$ alkenyl.

In a preferred embodiment, $R^3$ is substituted or unsubstituted —C(=O)O—$C_1$-$C_{22}$ alkynyl.

In certain embodiments, $R^4$ is substituted or unsubstituted $C_1$-$C_{22}$ alkyl.

In certain embodiments, $R^4$ is substituted or unsubstituted $C_2$-$C_{22}$ alkenyl.

In certain embodiments, $R^4$ is substituted or unsubstituted $C_2$-$C_{22}$ alkynyl.

In a preferred embodiment, $R^4$ is substituted or unsubstituted —C(=O)O—$C_1$-$C_{22}$ alkyl.

In a preferred embodiment, $R^4$ is substituted or unsubstituted —C(=O)O—$C_1$-$C_{22}$ alkenyl.

In a preferred embodiment, $R^4$ is substituted or unsubstituted —C(=O)O—$C_1$-$C_{22}$ alkynyl.

In certain embodiments, $R^5$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^5$ is H.

In certain embodiments, $R^5$ is OH.

In certain embodiments, $R^5$ is halo.

In certain embodiments, $R^5$ is phenyl.

In certain embodiments, $R^5$ is benzyl.

In certain embodiments, $R^5$ is substituted or unsubstituted $C_1$-$C_{22}$ alkyl.

In certain embodiments, $R^5$ is substituted or unsubstituted $C_2$-$C_{22}$ alkenyl.

In certain embodiments, $R^5$ is substituted or unsubstituted $C_2$-$C_{22}$ alkynyl.

In certain embodiments, $R^6$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^6$ is H.

In certain embodiments, $R^6$ is OH.

In certain embodiments, $R^6$ is halo.

In certain embodiments, $R^6$ is phenyl.

In certain embodiments, $R^6$ is benzyl.

In certain embodiments, $R^6$ is substituted or unsubstituted $C_1$-$C_{22}$ alkyl.

In certain embodiments, $R^6$ is substituted or unsubstituted $C_2$-$C_{22}$ alkenyl.

In certain embodiments, $R^6$ is substituted or unsubstituted $C_2$-$C_{22}$ alkynyl.

In certain embodiments, $R^7$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^7$ is H.

In certain embodiments, $R^7$ is OH.

In certain embodiments, $R^7$ is halo.

In certain embodiments, $R^7$ is phenyl.

In certain embodiments, $R^7$ is benzyl.

In certain embodiments, $R^7$ is substituted or unsubstituted $C_1$-$C_{22}$ alkyl.

In certain embodiments, $R^7$ is substituted or unsubstituted $C_2$-$C_{22}$ alkenyl.

In certain embodiments, $R^7$ is substituted or unsubstituted $C_2$-$C_{22}$ alkynyl.

In certain embodiments, $R^8$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^8$ is H.

In certain embodiments, $R^8$ is OH.

In certain embodiments, $R^8$ is halo.

In certain embodiments, $R^8$ is phenyl.

In certain embodiments, $R^8$ is benzyl.

In certain embodiments, $R^8$ is substituted or unsubstituted $C_1$-$C_{22}$ alkyl.

In certain embodiments, $R^8$ is substituted or unsubstituted $C_2$-$C_{22}$ alkenyl.

In certain embodiments, $R^8$ is substituted or unsubstituted $C_2$-$C_{22}$ alkynyl.

In certain embodiments, $R^9$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^9$ is H.

In certain embodiments, $R^9$ is OH.

In certain embodiments, $R^9$ is halo.

In certain embodiments, $R^9$ is phenyl.

In certain embodiments, $R^9$ is benzyl.

In certain embodiments, $R^9$ is substituted or unsubstituted $C_1$-$C_{22}$ alkyl.

In certain embodiments, $R^9$ is substituted or unsubstituted $C_2$-$C_{22}$ alkenyl.

In certain embodiments, $R^9$ is substituted or unsubstituted $C_2$-$C_{22}$ alkynyl.

In certain embodiments, $R^{10}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{10}$ is H.

In certain embodiments, $R^{10}$ is OH.

In certain embodiments, $R^{10}$ is halo.

In certain embodiments, $R^{10}$ is phenyl.

In certain embodiments, $R^{10}$ is benzyl.

In certain embodiments, $R^{10}$ is substituted or unsubstituted $C_1$-$C_{22}$ alkyl.

In certain embodiments, $R^{10}$ is substituted or unsubstituted $C_2$-$C_{22}$ alkenyl.

In certain embodiments, $R^{10}$ is substituted or unsubstituted $C_2$-$C_{22}$ alkynyl.

In certain embodiments, x is 0.

In certain embodiments, x is 1.

In certain embodiments, x is 2.

In certain embodiments, x is 3.

In certain embodiments, x is 4.

In certain embodiments, x is 5.

In certain embodiments, x is 6.

In certain embodiments, x is 7.

In certain embodiments, x is 8.

In certain embodiments, x is 9.

In certain embodiments, x is 10.

In certain embodiments, x is 11.

In certain embodiments, x is 12.

In certain embodiments, x is 13.

In certain embodiments, x is 14.

In certain embodiments, x is 15.

In certain embodiments, x is 16.

In certain embodiments, x is 17.

In certain embodiments, x is 18.

In certain embodiments, x is 19.

In certain embodiments, x is 20.

In certain embodiments, y is 0.

In certain embodiments, y is 1.

In certain embodiments, y is 2.

In certain embodiments, y is 3.

In certain embodiments, y is 4.

In certain embodiments, y is 5.

In certain embodiments, y is 6.

In certain embodiments, y is 7.

In certain embodiments, y is 8.

In certain embodiments, y is 9.

In certain embodiments, y is 10.

In certain embodiments, y is 11.

In certain embodiments, y is 12.

In certain embodiments, y is 13.

In certain embodiments, y is 14.

In certain embodiments, y is 15.

In certain embodiments, y is 16.

In certain embodiments, y is 17.

In certain embodiments, y is 18.

In certain embodiments, y is 19.

In certain embodiments, y is 20.

In certain embodiments, z is 0.

In certain embodiments, z is 1.

In certain embodiments, z is 2.

In certain embodiments, z is 3.

In certain embodiments, z is 4.

In certain embodiments, z is 5.

In certain embodiments, z is 6.

In certain embodiments, z is 7.

In certain embodiments, z is 8.

In certain embodiments, z is 9.

In certain embodiments, z is 10.

In certain embodiments, z is 11.

In certain embodiments, z is 12.

In certain embodiments, z is 13.

In certain embodiments, z is 14.

In certain embodiments, z is 15.

In certain embodiments, z is 16.

In certain embodiments, z is 17.

In certain embodiments, z is 18.

In certain embodiments, z is 19.

In certain embodiments, z is 20.

In certain embodiments $L^1$ is a bond.

In certain embodiments, $L^1$ is —C(=O)—.

In certain embodiments, $L^1$ is —OC(=O)O—.

In certain embodiments, $L^1$ is —NH—C(=O)—.

In certain embodiments, $L^1$ is —SO—.

In certain embodiments, $L^1$ is —$SO_2$—.

In certain embodiments, $L^1$ is OC(=O).

In certain embodiments, $L^1$ is —C(=O)O—.

In certain embodiments, $L^1$ is —C(=O)NH—.

In certain embodiments, $L^1$ is —$SO_3$—.

In certain embodiments, $L^1$ is —$NSO_2$—.

In certain embodiments, $L^1$ is —$SO_2N$.

In certain embodiments, $L^1$ is —NH(($C_1$-$C_{22}$)alkyl).

In certain embodiments, $L^1$ is —N(($C_1$-$C_8$)alkyl)$_2$.

In certain embodiments, $L^1$ is —NH(($C_6$)aryl).

In certain embodiments, $L^1$ is —N(($C_6$)aryl)$_2$.

In certain embodiments, $L^1$ is dioxolopyrrolidine-dione.

In certain embodiments, $L^1$ is —C(=O)$R^1$—.

In certain embodiments, $L^1$ is —CO(($C_1$-$C_{22}$)alkyl).

In certain embodiments, $L^1$ is —CO(($C_6$)aryl).

In certain embodiments, $L^1$ is —$CO_2$(($C_1$-$C_{22}$)alkyl).

In certain embodiments, $L^1$ is —$CO_2$(($C_6$)aryl).

In certain embodiments, $L^1$ is —C(=O)O($R^1R^2R^3$)

In certain embodiments, $L^1$ is —$SO_2$(($C_1$-$C_{22}$)alkyl).

In certain embodiments, $L^1$ is —$SO_2$(($C_6$)aryl).

In certain embodiments $L^2$ is a bond.

In certain embodiments, $L^2$ is —C(=O)—.

In certain embodiments, $L^2$ is —OC(=O)O—.

In certain embodiments, $L^2$ is —NH—C(=O)—.

In certain embodiments, $L^2$ is —SO—.

In certain embodiments, $L^2$ is —$SO_2$—.

In certain embodiments, $L^2$ is OC(=O).

In certain embodiments, $L^2$ is —C(=O)O—.

In certain embodiments, $L^2$ is —C(=O)NH—.

In certain embodiments, $L^2$ is —$SO_3$—.

In certain embodiments, $L^2$ is —$NSO_2$—.

In certain embodiments, $L^2$ is —$SO_2N$.

In certain embodiments, $L^2$ is —NH(($C_1$-$C_{22}$)alkyl).

In certain embodiments, $L^2$ is —N(($C_1$-$C_8$)alkyl)$_2$.

In certain embodiments, $L^2$ is —NH(($C_6$)aryl).

In certain embodiments, $L^2$ is —N(($C_6$)aryl)$_2$.

In certain embodiments, $L^2$ is dioxolopyrrolidine-dione.

In certain embodiments, $L^2$ is —C(=O)$R^1$—.

In certain embodiments, $L^2$ is —CO(($C_1$-$C_{22}$)alkyl).

In certain embodiments, $L^2$ is —CO(($C_6$)aryl).

In certain embodiments, $L^2$ is —$CO_2$(($C_1$-$C_{22}$)alkyl).

In certain embodiments, $L^2$ is —$CO_2$(($C_6$)aryl).

In certain embodiments, $L^2$ is —$SO_2$(($C_1$-$C_{22}$)alkyl).

In certain embodiments, $L^2$ is —$SO_2$(($C_6$)aryl).

In certain embodiments, Q is CH.

In certain embodiments, Q is O.

In certain embodiments, Q is S.

In certain embodiments, Q is N.

In certain embodiments, G is CH.

In certain embodiments, G is O.

In certain embodiments, G is S.

In certain embodiments, G is N.

In another embodiment, the invention encompasses Ionizable Lipids of the Invention of Formula IV:

Formula IV

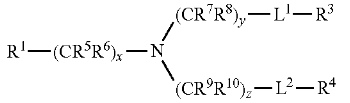

wherein $R^1$ is selected from the group consisting of H, an optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C_6$ heteroaryl, optionally substituted $C_4$-$C_8$ aryloxy, optionally substituted $C_7$-$C_{10}$ arylalkyl, and optionally substituted $C_5$-$C_{10}$ heteroarylalkyl group;

wherein each $R^3$ and $R^4$ is independently selected from the group consisting of an optionally substituted $C_1$-$C_{22}$ alkyl, optionally substituted $C_2$-$C_{22}$ alkenyl, optionally substituted $C_2$-$C_{22}$ alkynyl;

wherein each $R^5$, $R^6$, $R^7$, $R^8$, $R^9$, and $R^{10}$ is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each of x, y, and z is independently an integer from 0-10; and wherein each of $L^1$ and $L^2$ is independently selected from the group consisting of —C(=O)—; OC(=O)—; —OC(=O)O—; —C(=O)O—; —C(=O)O($CR^5R^6R^7$); —NH—C(=O)—; —C(=O)NH—; —SO—; —$SO_2$—; —$SO_3$—; —$NSO_2$—; —$SO_2N$—; —NH(($C_1$-$C_8$)alkyl); —N(($C_1$-$C_8$)alkyl)$_2$; —NH(($C_6$)aryl); —N(($C_6$)aryl)$_2$; —NHC(=O)NH—; —NHC(=O)O—; —OC(=O)NH—; —NHC(=O)N$R^1$—; —NHC(=O)O—; —OC(=O)N$R^1$—; —C(=O)$R^1$—; —CO(($C_1$-$C_8$)alkyl); —CO(($C_6$)aryl); —$CO_2$(($C_1$-$C_8$)alkyl); —$CO_2$(($C_6$)aryl); —$SO_2$(($C_1$-$C_8$)alkyl); and —$SO_2$(($C_6$)aryl).

In certain embodiments, $R^1$ is H.

In certain embodiments, $R^1$ is substituted or unsubstituted $C_1$-$C_{22}$ alkyl.

In certain embodiments, $R^1$ is substituted or unsubstituted $C_2$-$C_{22}$ alkenyl.

In certain embodiments, $R^1$ is substituted or unsubstituted $C_2$-$C_{22}$ alkynyl.

In certain embodiments, $R^1$ is substituted or unsubstituted $C_3$-$C_6$ cycloalkyl.

In certain embodiments, $R^1$ is substituted or unsubstituted $C_4$-$C_6$ heterocycloalkyl.

In certain embodiments, $R^1$ is substituted or unsubstituted $C_4$-$C_6$ alkylcycloalkyl.

In certain embodiments, $R^1$ is substituted or unsubstituted $C_4$-$C_6$ aryl.

In certain embodiments, $R^1$ is substituted or unsubstituted $C_3$-$C_6$ heteroaryl.

In certain embodiments, $R^1$ is substituted or unsubstituted $C_4$-$C_8$ aryloxy.

In certain embodiments, $R^1$ is substituted or unsubstituted $C_7$-$C_{10}$ arylalkyl.

In certain embodiments, $R^1$ is substituted or unsubstituted $C_5$-$C_{10}$ heteroarylalkyl group.

In certain embodiments, $R^3$ is substituted or unsubstituted $C_1$-$C_{22}$ alkyl.

In certain embodiments, $R^3$ is substituted or unsubstituted $C_2$-$C_{22}$ alkenyl.

In certain embodiments, $R^3$ is substituted or unsubstituted $C_2$-$C_{22}$ alkynyl.

In a preferred embodiment, $R^3$ is substituted or unsubstituted —C(=O)O—$C_1$-$C_{22}$ alkyl.

In a preferred embodiment, $R^3$ is substituted or unsubstituted —C(=O)O—$C_1$-$C_{22}$ alkenyl.

In a preferred embodiment, $R^3$ is substituted or unsubstituted —C(=O)O—$C_1$-$C_{22}$ alkynyl.

In certain embodiments, $R^4$ is substituted or unsubstituted $C_1$-$C_{22}$ alkyl.

In certain embodiments, $R^4$ is substituted or unsubstituted $C_2$-$C_{22}$ alkenyl.

In certain embodiments, $R^4$ is substituted or unsubstituted $C_2$-$C_{22}$ alkynyl.

In a preferred embodiment, $R^4$ is substituted or unsubstituted —C(=O)O—$C_1$-$C_{22}$ alkyl.

In a preferred embodiment, $R^4$ is substituted or unsubstituted —C(=O)O—$C_1$-$C_{22}$ alkenyl.

In a preferred embodiment, $R^4$ is substituted or unsubstituted —C(=O)O—$C_1$-$C_{22}$ alkynyl.

In certain embodiments, $R^5$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^5$ is H.

In certain embodiments, $R^5$ is OH.

In certain embodiments, $R^5$ is halo.

In certain embodiments, $R^5$ is phenyl.

In certain embodiments, $R^5$ is benzyl.

In certain embodiments, $R^5$ is substituted or unsubstituted $C_1$-$C_{22}$ alkyl.

In certain embodiments, $R^5$ is substituted or unsubstituted $C_2$-$C_{22}$ alkenyl.

In certain embodiments, $R^5$ is substituted or unsubstituted $C_2$-$C_{22}$ alkynyl.

In certain embodiments, $R^6$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^6$ is H.

In certain embodiments, $R^6$ is OH.

In certain embodiments, $R^6$ is halo.

In certain embodiments, $R^6$ is phenyl.

In certain embodiments, $R^6$ is benzyl.

In certain embodiments, $R^6$ is substituted or unsubstituted $C_1$-$C_{22}$ alkyl.

In certain embodiments, $R^6$ is substituted or unsubstituted $C_2$-$C_{22}$ alkenyl.

In certain embodiments, $R^6$ is substituted or unsubstituted $C_2$-$C_{22}$ alkynyl.

In certain embodiments, $R^7$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^7$ is H.

In certain embodiments, $R^7$ is OH.

In certain embodiments, $R^7$ is halo.

In certain embodiments, $R^7$ is phenyl.

In certain embodiments, $R^7$ is benzyl.

In certain embodiments, $R^7$ is substituted or unsubstituted $C_1$-$C_{22}$ alkyl.

In certain embodiments, $R^7$ is substituted or unsubstituted $C_2$-$C_{22}$ alkenyl.

In certain embodiments, $R^7$ is substituted or unsubstituted $C_2$-$C_{22}$ alkynyl.

In certain embodiments, $R^8$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^8$ is H.

In certain embodiments, $R^8$ is OH.

In certain embodiments, $R^8$ is halo.

In certain embodiments, $R^8$ is phenyl.

In certain embodiments, $R^8$ is benzyl.

In certain embodiments, $R^8$ is substituted or unsubstituted $C_1$-$C_{22}$ alkyl.

In certain embodiments, $R^8$ is substituted or unsubstituted $C_2$-$C_{22}$ alkenyl.

In certain embodiments, $R^8$ is substituted or unsubstituted $C_2$-$C_{22}$ alkynyl.

In certain embodiments, $R^9$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^9$ is H.

In certain embodiments, $R^9$ is OH.

In certain embodiments, $R^9$ is halo.

In certain embodiments, $R^9$ is phenyl.

In certain embodiments, $R^9$ is benzyl.

In certain embodiments, $R^9$ is substituted or unsubstituted $C_1$-$C_{22}$ alkyl.

In certain embodiments, $R^9$ is substituted or unsubstituted $C_2$-$C_{22}$ alkenyl.

In certain embodiments, $R^9$ is substituted or unsubstituted $C_2$-$C_{22}$ alkynyl.

In certain embodiments, $R^{10}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{10}$ is H.

In certain embodiments, $R^{10}$ is OH.

In certain embodiments, $R^{10}$ is halo.

In certain embodiments, $R^{10}$ is phenyl.

In certain embodiments, $R^{10}$ is benzyl.

In certain embodiments, $R^{10}$ is substituted or unsubstituted $C_1$-$C_{22}$ alkyl.

In certain embodiments, $R^{10}$ is substituted or unsubstituted $C_2$-$C_{22}$ alkenyl.

In certain embodiments, $R^{10}$ is substituted or unsubstituted $C_2$-$C_{22}$ alkynyl.

In certain embodiments, x is 0.

In certain embodiments, x is 1.

In certain embodiments, x is 2.

In certain embodiments, x is 3.

In certain embodiments, x is 4.

In certain embodiments, x is 5.

In certain embodiments, x is 6.

In certain embodiments, x is 7.
In certain embodiments, x is 8.
In certain embodiments, x is 9.
In certain embodiments, x is 10.
In certain embodiments, x is 11.
In certain embodiments, x is 12.
In certain embodiments, x is 13.
In certain embodiments, x is 14.
In certain embodiments, x is 15.
In certain embodiments, x is 16.
In certain embodiments, x is 17.
In certain embodiments, x is 18.
In certain embodiments, x is 19.
In certain embodiments, x is 20.
In certain embodiments, y is 0.
In certain embodiments, y is 1.
In certain embodiments, y is 2.
In certain embodiments, y is 3.
In certain embodiments, y is 4.
In certain embodiments, y is 5.
In certain embodiments, y is 6.
In certain embodiments, y is 7.
In certain embodiments, y is 8.
In certain embodiments, y is 9.
In certain embodiments, y is 10.
In certain embodiments, y is 11.
In certain embodiments, y is 12.
In certain embodiments, y is 13.
In certain embodiments, y is 14.
In certain embodiments, y is 15.
In certain embodiments, y is 16.
In certain embodiments, y is 17.
In certain embodiments, y is 18.
In certain embodiments, y is 19.
In certain embodiments, y is 20.
In certain embodiments, z is 0.
In certain embodiments, z is 1.
In certain embodiments, z is 2.
In certain embodiments, z is 3.
In certain embodiments, z is 4.
In certain embodiments, z is 5.
In certain embodiments, z is 6.
In certain embodiments, z is 7.
In certain embodiments, z is 8.
In certain embodiments, z is 9.
In certain embodiments, z is 10.
In certain embodiments, z is 11.
In certain embodiments, z is 12.
In certain embodiments, z is 13.
In certain embodiments, z is 14.
In certain embodiments, z is 15.
In certain embodiments, z is 16.
In certain embodiments, z is 17.
In certain embodiments, z is 18.
In certain embodiments, z is 19.
In certain embodiments, z is 20.
In certain embodiments $L^1$ is a bond.
In certain embodiments, $L^1$ is —C(═O)—.
In certain embodiments, $L^1$ is —OC(═O)O—.
In certain embodiments, $L^1$ is —NH—C(═O)—.
In certain embodiments, $L^1$ is —SO—.
In certain embodiments, $L^1$ is —$SO_2$—.
In certain embodiments, $L^1$ is OC(═O).
In certain embodiments, $L^1$ is —C(═O)O—.
In certain embodiments, $L^1$ is —C(═O)NH—.
In certain embodiments, $L^1$ is —$SO_3$—.
In certain embodiments, $L^1$ is —$NSO_2$—.
In certain embodiments, $L^1$ is —$SO_2N$.
In certain embodiments, $L^1$ is —NH(($C_1$-$C_{22}$)alkyl).
In certain embodiments, $L^1$ is —N(($C_1$-$C_8$)alkyl)$_2$.
In certain embodiments, $L^1$ is —NH(($C_6$)aryl).
In certain embodiments, $L^1$ is —N(($C_6$)aryl)$_2$.
In certain embodiments, $L^1$ is dioxolopyrrolidine-dione.
In certain embodiments, $L^1$ is —C(═O)$R^1$—.
In certain embodiments, $L^1$ is —CO(($C_1$-$C_{22}$)alkyl).
In certain embodiments, $L^1$ is —CO(($C_6$)aryl).
In certain embodiments, $L^1$ is —$CO_2$(($C_1$-$C_{22}$)alkyl).
In certain embodiments, $L^1$ is —$CO_2$(($C_6$)aryl).
In certain embodiments, $L^1$ is —C(═O)O($CR^1R^2R^3$)
In certain embodiments, $L^1$ is —$SO_2$(($C_1$-$C_{22}$)alkyl).
In certain embodiments, $L^1$ is —$SO_2$(($C_6$)aryl).
In certain embodiments $L^2$ is a bond.
In certain embodiments, $L^2$ is —C(═O)—.
In certain embodiments, $L^2$ is —OC(═O)O—.
In certain embodiments, $L^2$ is —NH—C(═O)—.
In certain embodiments, $L^2$ is —SO—.
In certain embodiments, $L^2$ is —$SO_2$—.
In certain embodiments, $L^2$ is OC(═O).
In certain embodiments, $L^2$ is —C(═O)O—.
In certain embodiments, $L^2$ is —C(═O)NH—.
In certain embodiments, $L^2$ is —$SO_3$—.
In certain embodiments, $L^2$ is —$NSO_2$—.
In certain embodiments, $L^2$ is —$SO_2N$.
In certain embodiments, $L^2$ is —NH(($C_1$-$C_{22}$)alkyl).
In certain embodiments, $L^2$ is —N(($C_1$-$C_8$)alkyl)$_2$.
In certain embodiments, $L^2$ is —NH(($C_6$)aryl).
In certain embodiments, $L^2$ is —N(($C_6$)aryl)$_2$.
In certain embodiments, $L^2$ is dioxolopyrrolidine-dione.
In certain embodiments, $L^2$ is —C(═O)$R^1$—.
In certain embodiments, $L^2$ is —CO(($C_1$-$C_{22}$)alkyl).
In certain embodiments, $L^2$ is —CO(($C_6$)aryl).
In certain embodiments, $L^2$ is —$CO_2$(($C_1$-$C_{22}$)alkyl).
In certain embodiments, $L^2$ is —$CO_2$(($C_6$)aryl).
In certain embodiments, $L^2$ is —$SO_2$(($C_1$-$C_{22}$)alkyl).
In certain embodiments, $L^2$ is —$SO_2$(($C_6$)aryl).

In another embodiment, the invention encompasses Ionizable Lipids of the Invention of Formula V:

Formula V

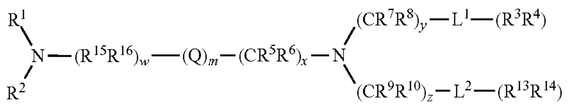

wherein each $R^1$ and each $R^2$ is independently selected from the group consisting of H, an optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C_6$ heteroaryl, optionally substituted $C_4$-$C_8$ aryloxy, optionally substituted $C_7$-$C_{10}$ arylalkyl; optionally substituted $C_5$-$C_{10}$ heteroarylalkyl group, optionally substituted amine; or $R^1$ and $R^2$ can together form a 3-7 membered heterocycle or heteroaryl ring;

wherein each $R^3$, $R^4$, $R^3$, and $R^{14}$ is independently selected from the group consisting of an optionally substituted $C_1$-$C_{22}$ alkyl, optionally substituted $C_2$-$C_{22}$ alkenyl, optionally substituted $C_2$-$C_{22}$ alkynyl;

wherein each $R^5$, $R^6$, $R^7$, $R^8$, $R^9$, $R^{10}$, $R^{15}$, and $R^{16}$ is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each of w, x, y, and z is independently an integer from 0-10;

wherein each Q is independently an atom selected from 0, NH, S, or a disulfide bond;

wherein each of m is an integer from 0-4, preferably 0, 1, or 2; and wherein each of $L^1$ and $L^2$ is independently selected from the group consisting of —C(═O)—; OC(═O)—; —OC(═O)O—; —C(═O)O—; —C(═O)O($CR^6R^7)_m$; —NH—C(═O)—; —C(═O)NH—; —SO—; —$SO_2$—; —$SO_3$—; —$NSO_2$—; —$SO_2$N—; —NH(($C_1$-$C_8$)alkyl); —N(($C_1$-$C_8$)alkyl)$_2$; —NH(($C_6$)aryl); —N(($C_6$)aryl)$_2$; —NHC(═O)NH—; —NHC(═O)O—; —OC(═O)NH—; —NHC(═O)$NR^1$—; —NHC(═O)O—; —OC(═O)$NR^1$—; —C(═O)$R^1$—; —CO(($C_1$-$C_8$)alkyl); —CO(($C_6$)aryl); —$CO_2$(($C_1$-$C_8$)alkyl); —$CO_2$(($C_6$)aryl); —$SO_2$(($C_1$-$C_8$)alkyl); and —$SO_2$(($C_6$)aryl).

In certain embodiments, $R^1$ is H.

In certain embodiments, $R^1$ is substituted or unsubstituted $C_1$-$C_{22}$ alkyl.

In certain embodiments, $R^1$ is substituted or unsubstituted $C_2$-$C_{22}$ alkenyl.

In certain embodiments, $R^1$ is substituted or unsubstituted $C_2$-$C_{22}$ alkynyl.

In certain embodiments, $R^1$ is substituted or unsubstituted $C_3$-$C_6$ cycloalkyl.

In certain embodiments, $R^1$ is substituted or unsubstituted $C_4$-$C_6$ heterocycloalkyl.

In certain embodiments, $R^1$ is substituted or unsubstituted $C_4$-$C_6$ alkylcycloalkyl.

In certain embodiments, $R^1$ is substituted or unsubstituted $C_4$-$C_6$ aryl.

In certain embodiments, $R^1$ is substituted or unsubstituted $C_3$-$C_6$ heteroaryl.

In certain embodiments, $R^1$ is substituted or unsubstituted $C_4$-$C_8$ aryloxy.

In certain embodiments, $R^1$ is substituted or unsubstituted $C_7$-$C_{10}$ arylalkyl.

In certain embodiments, $R^1$ is substituted or unsubstituted $C_5$-$C_{10}$ heteroarylalkyl group.

In certain embodiments, $R^2$ is H.

In certain embodiments, $R^2$ is substituted or unsubstituted $C_1$-$C_{22}$ alkyl.

In certain embodiments, $R^2$ is substituted or unsubstituted $C_2$-$C_{22}$ alkenyl In certain embodiments, $R^2$ is substituted or unsubstituted $C_2$-$C_{22}$ alkynyl In certain embodiments, $R^2$ is substituted or unsubstituted $C_3$-$C_6$ cycloalkyl.

In certain embodiments, $R^2$ is substituted or unsubstituted $C_4$-$C_6$ heterocycloalkyl.

In certain embodiments, $R^2$ is substituted or unsubstituted $C_4$-$C_6$ alkylcycloalkyl.

In certain embodiments, $R^2$ is substituted or unsubstituted $C_4$-$C_6$ aryl.

In certain embodiments, $R^2$ is substituted or unsubstituted $C_3$-$C_6$ heteroaryl.

In certain embodiments, $R^2$ is substituted or unsubstituted $C_4$-$C_8$ aryloxy.

In certain embodiments, $R^2$ is substituted or unsubstituted $C_7$-$C_{10}$ arylalkyl.

In certain embodiments, $R^2$ is substituted or unsubstituted $C_5$-$C_{10}$ heteroarylalkyl group.

In certain embodiments, $R^3$ is substituted or unsubstituted $C_1$-$C_{22}$ alkyl.

In certain embodiments, $R^3$ is substituted or unsubstituted $C_2$-$C_{22}$ alkenyl.

In certain embodiments, $R^3$ is substituted or unsubstituted $C_2$-$C_{22}$ alkynyl.

In a preferred embodiment, $R^3$ is substituted or unsubstituted —C(═O)O—$C_1$-$C_{22}$ alkyl.

In a preferred embodiment, $R^3$ is substituted or unsubstituted —C(═O)O—$C_1$-$C_{22}$ alkenyl.

In a preferred embodiment, $R^3$ is substituted or unsubstituted —C(═O)O—$C_1$-$C_{22}$ alkynyl.

In certain embodiments, $R^4$ is substituted or unsubstituted $C_1$-$C_{22}$ alkyl.

In certain embodiments, $R^4$ is substituted or unsubstituted $C_2$-$C_{22}$ alkenyl.

In certain embodiments, $R^4$ is substituted or unsubstituted $C_2$-$C_{22}$ alkynyl.

In a preferred embodiment, $R^4$ is substituted or unsubstituted —C(═O)O—$C_1$-$C_{22}$ alkyl.

In a preferred embodiment, $R^4$ is substituted or unsubstituted —C(═O)O—$C_1$-$C_{22}$ alkenyl.

In a preferred embodiment, $R^4$ is substituted or unsubstituted —C(═O)O—$C_1$-$C_{22}$ alkynyl.

In certain embodiments, each $R^5$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^5$ is H.

In certain embodiments, $R^5$ is OH.

In certain embodiments, $R^5$ is halo.

In certain embodiments, $R^5$ is phenyl.

In certain embodiments, $R^5$ is benzyl.

In certain embodiments, $R^5$ is substituted or unsubstituted $C_1$-$C_{22}$ alkyl.

In certain embodiments, $R^5$ is substituted or unsubstituted $C_2$-$C_{22}$ alkenyl.

In certain embodiments, $R^5$ is substituted or unsubstituted $C_2$-$C_{22}$ alkynyl.

In certain embodiments, each $R^6$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^6$ is H.

In certain embodiments, $R^6$ is OH.

In certain embodiments, $R^6$ is halo.

In certain embodiments, $R^6$ is phenyl.

In certain embodiments, $R^6$ is benzyl.

In certain embodiments, $R^6$ is substituted or unsubstituted $C_1$-$C_{22}$ alkyl.

In certain embodiments, $R^6$ is substituted or unsubstituted $C_2$-$C_{22}$ alkenyl.

In certain embodiments, $R^6$ is substituted or unsubstituted $C_2$-$C_{22}$ alkynyl.

In certain embodiments, $R^7$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^7$ is H.

In certain embodiments, $R^7$ is OH.

In certain embodiments, $R^7$ is halo.

In certain embodiments, $R^7$ is phenyl.

In certain embodiments, $R^7$ is benzyl.

In certain embodiments, $R^7$ is substituted or unsubstituted $C_1$-$C_{22}$ alkyl.

In certain embodiments, $R^7$ is substituted or unsubstituted $C_2$-$C_{22}$ alkenyl.

In certain embodiments, $R^7$ is substituted or unsubstituted $C_2$-$C_{22}$ alkynyl.

In certain embodiments, $R^8$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^8$ is H.

In certain embodiments, $R^8$ is OH.

In certain embodiments, $R^8$ is halo.

In certain embodiments, $R^8$ is phenyl.

In certain embodiments, $R^8$ is benzyl.

In certain embodiments, $R^8$ is substituted or unsubstituted $C_1$-$C_{22}$ alkyl.

In certain embodiments, $R^8$ is substituted or unsubstituted $C_2$-$C_{22}$ alkenyl.

In certain embodiments, $R^8$ is substituted or unsubstituted $C_2$-$C_{22}$ alkynyl.

In certain embodiments, $R^9$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^9$ is H.

In certain embodiments, $R^9$ is OH.

In certain embodiments, $R^9$ is halo.

In certain embodiments, $R^9$ is phenyl.

In certain embodiments, $R^9$ is benzyl.

In certain embodiments, $R^9$ is substituted or unsubstituted $C_1$-$C_{22}$ alkyl.

In certain embodiments, $R^9$ is substituted or unsubstituted $C_2$-$C_{22}$ alkenyl.

In certain embodiments, $R^9$ is substituted or unsubstituted $C_2$-$C_{22}$ alkynyl.

In certain embodiments, $R^{10}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{10}$ is H.

In certain embodiments, $R^{10}$ is OH.

In certain embodiments, $R^{10}$ is halo.

In certain embodiments, $R^{10}$ is phenyl.

In certain embodiments, $R^{10}$ is benzyl.

In certain embodiments, $R^{10}$ is substituted or unsubstituted $C_1$-$C_{22}$ alkyl.

In certain embodiments, $R^{10}$ is substituted or unsubstituted $C_2$-$C_{22}$ alkenyl.

In certain embodiments, $R^{10}$ is substituted or unsubstituted $C_2$-$C_{22}$ alkynyl.

In certain embodiments, w is 0.

In certain embodiments, w is 1.

In certain embodiments, w is 2.

In certain embodiments, w is 3.

In certain embodiments, w is 4.

In certain embodiments, w is 5.

In certain embodiments, w is 6.

In certain embodiments, w is 7.

In certain embodiments, w is 8.

In certain embodiments, w is 9.

In certain embodiments, w is 10.

In certain embodiments, w is 11.

In certain embodiments, w is 12.

In certain embodiments, w is 13.

In certain embodiments, w is 14.

In certain embodiments, w is 15.

In certain embodiments, w is 16.

In certain embodiments, w is 17.

In certain embodiments, w is 18.

In certain embodiments, w is 19.

In certain embodiments, w is 20.

In certain embodiments, x is 0.

In certain embodiments, x is 1.

In certain embodiments, x is 2.

In certain embodiments, x is 3.

In certain embodiments, x is 4.

In certain embodiments, x is 5.

In certain embodiments, x is 6.

In certain embodiments, x is 7.

In certain embodiments, x is 8.

In certain embodiments, x is 9.

In certain embodiments, x is 10.

In certain embodiments, x is 11.

In certain embodiments, x is 12.

In certain embodiments, x is 13.

In certain embodiments, x is 14.

In certain embodiments, x is 15.

In certain embodiments, x is 16.

In certain embodiments, x is 17.

In certain embodiments, x is 18.

In certain embodiments, x is 19.

In certain embodiments, x is 20.

In certain embodiments, y is 0.

In certain embodiments, y is 1.

In certain embodiments, y is 2.

In certain embodiments, y is 3.

In certain embodiments, y is 4.

In certain embodiments, y is 5.

In certain embodiments, y is 6.

In certain embodiments, y is 7.

In certain embodiments, y is 8.

In certain embodiments, y is 9.

In certain embodiments, y is 10.

In certain embodiments, y is 11.

In certain embodiments, y is 12.

In certain embodiments, y is 13.

In certain embodiments, y is 14.

In certain embodiments, y is 15.

In certain embodiments, y is 16.

In certain embodiments, y is 17.

In certain embodiments, y is 18.

In certain embodiments, y is 19.

In certain embodiments, y is 20.

In certain embodiments, z is 0.

In certain embodiments, z is 1.

In certain embodiments, z is 2.

In certain embodiments, z is 3.

In certain embodiments, z is 4.

In certain embodiments, z is 5.

In certain embodiments, z is 6.

In certain embodiments, z is 7.

In certain embodiments, z is 8.

In certain embodiments, z is 9.

In certain embodiments, z is 10.

In certain embodiments, z is 11.

In certain embodiments, z is 12.

In certain embodiments, z is 13.

In certain embodiments, z is 14.

In certain embodiments, z is 15.

In certain embodiments, z is 16.

In certain embodiments, z is 17.

In certain embodiments, z is 18.

In certain embodiments, z is 19.

In certain embodiments, z is 20.

In certain embodiments $L^1$ is a bond.

In certain embodiments, $L^1$ is —C(═O)—.
In certain embodiments, $L^1$ is —OC(═O)O—.
In certain embodiments, $L^1$ is —NH—C(═O)—.
In certain embodiments, $L^1$ is —SO—.
In certain embodiments, $L^1$ is —$SO_2$—.
In certain embodiments, $L^1$ is OC(═O).
In certain embodiments, $L^1$ is —C(═O)O—.
In certain embodiments, $L^1$ is —C(═O)NH—.
In certain embodiments, $L^1$ is —$SO_3$—.
In certain embodiments, $L^1$ is —$NSO_2$—.
In certain embodiments, $L^1$ is —$SO_2$N.
In certain embodiments, $L^1$ is —NH(($C_1$-$C_{22}$)alkyl).
In certain embodiments, $L^1$ is —N(($C_1$-$C_8$)alkyl)$_2$.
In certain embodiments, $L^1$ is —NH(($C_6$)aryl).
In certain embodiments, $L^1$ is —N(($C_6$)aryl)$_2$.
In certain embodiments, $L^1$ is dioxolopyrrolidine-dione.
In certain embodiments, $L^1$ is —C(═O)$R^1$—.
In certain embodiments, $L^1$ is —CO(($C_1$-$C_{22}$)alkyl).

In certain embodiments, m is 5.
In certain embodiments, m is 6.
In certain embodiments, m is 7.
In certain embodiments, m is 8.
In certain embodiments, m is 9.
In certain embodiments, m is 10.
In certain embodiments, m is 11.
In certain embodiments, m is 12.
In certain embodiments, m is 13.
In certain embodiments, m is 14.
In certain embodiments, m is 15.
In certain embodiments, m is 16.
In certain embodiments, m is 17.
In certain embodiments, m is 18.
In certain embodiments, m is 19.
In certain embodiments, m is 20.

In another embodiment, the invention encompasses Ionizable Lipids of the Invention of Formula VI:

Formula VI

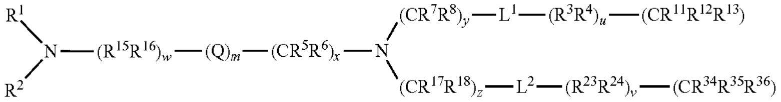

In certain embodiments, $L^1$ is —CO(($C_6$)aryl).
In certain embodiments, $L^1$ is —$CO_2$(($C_1$-$C_{22}$)alkyl).
In certain embodiments, $L^1$ is —$CO_2$(($C_6$)aryl).
In certain embodiments, $L^1$ is —C(═O)O($CR^1R^2R^3$)
In certain embodiments, $L^1$ is —$SO_2$(($C_1$-$C_{22}$)alkyl).
In certain embodiments, $L^1$ is —$SO_2$(($C_6$)aryl).
In certain embodiments $L^2$ is a bond.
In certain embodiments, $L^2$ is —C(═O)—.
In certain embodiments, $L^2$ is —OC(═O)O—.
In certain embodiments, $L^2$ is —NH—C(═O)—.
In certain embodiments, $L^2$ is —SO—.
In certain embodiments, $L^2$ is —$SO_2$—.
In certain embodiments, $L^2$ is OC(═O).
In certain embodiments, $L^2$ is —C(═O)O—.
In certain embodiments, $L^2$ is —C(═O)NH—.
In certain embodiments, $L^2$ is —$SO_3$—.
In certain embodiments, $L^2$ is —$NSO_2$—.
In certain embodiments, $L^2$ is —$SO_2$N.
In certain embodiments, $L^2$ is —NH(($C_1$-$C_{22}$)alkyl).
In certain embodiments, $L^2$ is —N(($C_1$-$C_8$)alkyl)$_2$.
In certain embodiments, $L^2$ is —NH(($C_6$)aryl).
In certain embodiments, $L^2$ is —N(($C_6$)aryl)$_2$.
In certain embodiments, $L^2$ is dioxolopyrrolidine-dione.
In certain embodiments, $L^2$ is —C(═O)$R^1$—.
In certain embodiments, $L^2$ is —CO(($C_1$-$C_{22}$)alkyl).
In certain embodiments, $L^2$ is —CO(($C_6$)aryl).
In certain embodiments, $L^2$ is —$CO_2$(($C_1$-$C_{22}$)alkyl).
In certain embodiments, $L^2$ is —$CO_2$(($C_6$)aryl).
In certain embodiments, $L^2$ is —$SO_2$(($C_1$-$C_{22}$)alkyl).
In certain embodiments, $L^2$ is —$SO_2$(($C_6$)aryl).
In certain embodiments, Q is CH.
In certain embodiments, Q is O.
In certain embodiments, Q is S.
In certain embodiments, Q is NH.
In certain embodiments, Q is a disulfide bond.
In certain embodiments, m is 0.
In certain embodiments, m is 1.
In certain embodiments, m is 2.
In certain embodiments, m is 3.
In certain embodiments, m is 4.

wherein each $R^1$ and each $R^2$ is independently selected from the group consisting of H, an optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C_6$ heteroaryl, optionally substituted $C_4$-$C_8$ aryloxy, optionally substituted $C_7$-$C_{10}$ arylalkyl; optionally substituted $C_5$-$C_{10}$ heteroarylalkyl group, optionally substituted amine; or $R^1$ and $R^2$ can together form a 3-7 membered heterocycle or heteroaryl ring;

wherein each $R^3$, $R^4$, $R^{23}$ and $R^{24}$ is independently selected from the group consisting of an optionally substituted $C_1$-$C_{22}$ alkyl, optionally substituted $C_2$-$C_{22}$ alkenyl, optionally substituted $C_2$-$C_{22}$ alkynyl;

wherein each $R^5$, $R^6$, $R^7$, $R^8$, $R^{11}$, $R^{12}$, $R^{13}$, $R^{17}$, $R^{18}$, $R^{34}$, $R^{35}$, $R^{36}$ is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each of u, v, w, x, y, and z is independently an integer from 0-20;

wherein each Q is independently an atom selected from 0, NH, S, or a disulfide bond;

wherein each of m is an integer from 0-4, preferably 0, 1, or 2; and wherein each of $L^1$ and $L^2$ is independently selected from the group consisting of —C(═O)—; OC(═O)—; —OC(═O)O—; —C(═O)O—; —C(═O)O($CR^6R^7$)$_m$; —NH—C(═O)—; —C(═O)NH—; —SO—; —$SO_2$—; —$SO_3$—; —$NSO_2$—; —$SO_2$N—; —NH(($C_1$-$C_8$)alkyl); —N(($C_1$-$C_8$)alkyl)$_2$; —NH(($C_6$)aryl); —N(($C_6$)aryl)$_2$; —NHC(═O)NH—; —NHC(═O)O—; —OC(═O)NH—; —NHC(═O)N$R^1$—; —NHC(═O)O—; —OC(═O)N$R^1$—; —C(═O)$R^1$—; —CO(($C_1$-$C_8$)alkyl); —CO(($C_6$)aryl); —$CO_2$(($C_1$-$C_8$)alkyl); —$CO_2$(($C_6$)aryl); —$SO_2$(($C_1$-$C_8$)alkyl); and —$SO_2$(($C_6$)aryl).

In certain embodiments, $R^1$ is H.

In certain embodiments, $R^1$ is substituted or unsubstituted $C_1$-$C_{22}$ alkyl.

In certain embodiments, $R^1$ is substituted or unsubstituted $C_2$-$C_{22}$ alkenyl.

In certain embodiments, $R^1$ is substituted or unsubstituted $C_2$-$C_{22}$ alkynyl.

In certain embodiments, $R^1$ is substituted or unsubstituted $C_3$-$C_6$ cycloalkyl.

In certain embodiments, $R^1$ is substituted or unsubstituted $C_4$-$C_6$ heterocycloalkyl.

In certain embodiments, $R^1$ is substituted or unsubstituted $C_4$-$C_6$ alkylcycloalkyl.

In certain embodiments, $R^1$ is substituted or unsubstituted $C_4$-$C_6$ aryl.

In certain embodiments, $R^1$ is substituted or unsubstituted $C_3$-$C_6$ heteroaryl.

In certain embodiments, $R^1$ is substituted or unsubstituted $C_4$-$C_8$ aryloxy.

In certain embodiments, $R^1$ is substituted or unsubstituted $C_7$-$C_{10}$ arylalkyl.

In certain embodiments, $R^1$ is substituted or unsubstituted $C_5$-$C_{10}$ heteroarylalkyl group.

In certain embodiments, $R^2$ is H.

In certain embodiments, $R^2$ is substituted or unsubstituted $C_1$-$C_{22}$ alkyl.

In certain embodiments, $R^2$ is substituted or unsubstituted $C_2$-$C_{22}$ alkenyl In certain embodiments, $R^2$ is substituted or unsubstituted $C_2$-$C_{22}$ alkynyl In certain embodiments, $R^2$ is substituted or unsubstituted $C_3$-$C_6$ cycloalkyl.

In certain embodiments, $R^2$ is substituted or unsubstituted $C_4$-$C_6$ heterocycloalkyl.

In certain embodiments, $R^2$ is substituted or unsubstituted $C_4$-$C_6$ alkylcycloalkyl.

In certain embodiments, $R^2$ is substituted or unsubstituted $C_4$-$C_6$ aryl.

In certain embodiments, $R^2$ is substituted or unsubstituted $C_3$-$C_6$ heteroaryl.

In certain embodiments, $R^2$ is substituted or unsubstituted $C_4$-$C_8$ aryloxy.

In certain embodiments, $R^2$ is substituted or unsubstituted $C_7$-$C_{10}$ arylalkyl.

In certain embodiments, $R^2$ is substituted or unsubstituted $C_5$-$C_{10}$ heteroarylalkyl group.

In certain embodiments, $R^3$ is substituted or unsubstituted $C_1$-$C_{22}$ alkyl.

In certain embodiments, $R^3$ is substituted or unsubstituted $C_2$-$C_{22}$ alkenyl.

In certain embodiments, $R^3$ is substituted or unsubstituted $C_2$-$C_{22}$ alkynyl.

In a preferred embodiment, $R^3$ is substituted or unsubstituted —C(═O)O—$C_1$-$C_{22}$ alkyl.

In a preferred embodiment, $R^3$ is substituted or unsubstituted —C(═O)O—$C_1$-$C_{22}$ alkenyl.

In a preferred embodiment, $R^3$ is substituted or unsubstituted —C(═O)O—$C_1$-$C_{22}$ alkynyl.

In certain embodiments, $R^4$ is substituted or unsubstituted $C_1$-$C_{22}$ alkyl.

In certain embodiments, $R^4$ is substituted or unsubstituted $C_2$-$C_{22}$ alkenyl.

In certain embodiments, $R^4$ is substituted or unsubstituted $C_2$-$C_{22}$ alkynyl.

In a preferred embodiment, $R^4$ is substituted or unsubstituted —C(═O)O—$C_1$-$C_{22}$ alkyl.

In a preferred embodiment, $R^4$ is substituted or unsubstituted —C(═O)O—$C_1$-$C_{22}$ alkenyl.

In a preferred embodiment, $R^4$ is substituted or unsubstituted —C(═O)O—$C_1$-$C_{22}$ alkynyl.

In certain embodiments, each $R^5$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^5$ is H.

In certain embodiments, $R^5$ is OH.

In certain embodiments, $R^5$ is halo.

In certain embodiments, $R^5$ is phenyl.

In certain embodiments, $R^5$ is benzyl.

In certain embodiments, $R^5$ is substituted or unsubstituted $C_1$-$C_{22}$ alkyl.

In certain embodiments, $R^5$ is substituted or unsubstituted $C_2$-$C_{22}$ alkenyl.

In certain embodiments, $R^5$ is substituted or unsubstituted $C_2$-$C_{22}$ alkynyl.

In certain embodiments, each $R^6$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^6$ is H.

In certain embodiments, $R^6$ is OH.

In certain embodiments, $R^6$ is halo.

In certain embodiments, $R^6$ is phenyl.

In certain embodiments, $R^6$ is benzyl.

In certain embodiments, $R^6$ is substituted or unsubstituted $C_1$-$C_{22}$ alkyl.

In certain embodiments, $R^6$ is substituted or unsubstituted $C_2$-$C_{22}$ alkenyl.

In certain embodiments, $R^6$ is substituted or unsubstituted $C_2$-$C_{22}$ alkynyl.

In certain embodiments, $R^7$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^7$ is H.

In certain embodiments, $R^7$ is OH.

In certain embodiments, $R^7$ is halo.

In certain embodiments, $R^7$ is phenyl.

In certain embodiments, $R^7$ is benzyl.

In certain embodiments, $R^7$ is substituted or unsubstituted $C_1$-$C_{22}$ alkyl.

In certain embodiments, $R^7$ is substituted or unsubstituted $C_2$-$C_{22}$ alkenyl.

In certain embodiments, $R^7$ is substituted or unsubstituted $C_2$-$C_{22}$ alkynyl.

In certain embodiments, $R^8$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^8$ is H.

In certain embodiments, $R^8$ is OH.

In certain embodiments, $R^8$ is halo.

In certain embodiments, $R^8$ is phenyl.

In certain embodiments, $R^8$ is benzyl.

In certain embodiments, $R^8$ is substituted or unsubstituted $C_1$-$C_{22}$ alkyl.

In certain embodiments, $R^8$ is substituted or unsubstituted $C_2$-$C_{22}$ alkenyl.

In certain embodiments, $R^8$ is substituted or unsubstituted $C_2$-$C_{22}$ alkynyl.

In certain embodiments, $R^9$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^9$ is H.

In certain embodiments, $R^9$ is OH.

In certain embodiments, $R^9$ is halo.

In certain embodiments, $R^9$ is phenyl.

In certain embodiments, $R^9$ is benzyl.

In certain embodiments, $R^9$ is substituted or unsubstituted $C_1$-$C_{22}$ alkyl.

In certain embodiments, $R^9$ is substituted or unsubstituted $C_2$-$C_{22}$ alkenyl.

In certain embodiments, $R^9$ is substituted or unsubstituted $C_2$-$C_{22}$ alkynyl.

In certain embodiments, $R^{10}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{10}$ is H.

In certain embodiments, $R^{10}$ is OH.

In certain embodiments, $R^{10}$ is halo.

In certain embodiments, $R^{10}$ is phenyl.

In certain embodiments, $R^{10}$ is benzyl.

In certain embodiments, $R^{10}$ is substituted or unsubstituted $C_1$-$C_{22}$ alkyl.

In certain embodiments, $R^{10}$ is substituted or unsubstituted $C_2$-$C_{22}$ alkenyl.

In certain embodiments, $R^{10}$ is substituted or unsubstituted $C_2$-$C_{22}$ alkynyl.

In certain embodiments, $R^{11}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{11}$ is H.

In certain embodiments, $R^{11}$ is OH.

In certain embodiments, $R^{11}$ is halo.

In certain embodiments, $R^{11}$ is phenyl.

In certain embodiments, $R^{11}$ is benzyl.

In certain embodiments, $R^{11}$ is substituted or unsubstituted $C_1$-$C_{22}$ alkyl.

In certain embodiments, $R^{11}$ is substituted or unsubstituted $C_2$-$C_{22}$ alkenyl.

In certain embodiments, $R^{11}$ is substituted or unsubstituted $C_2$-$C_{22}$ alkynyl.

In certain embodiments, $R^{12}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{12}$ is H.

In certain embodiments, $R^{12}$ is OH.

In certain embodiments, $R^{12}$ is halo.

In certain embodiments, $R^{12}$ is phenyl.

In certain embodiments, $R^{12}$ is benzyl.

In certain embodiments, $R^{12}$ is substituted or unsubstituted $C_1$-$C_{22}$ alkyl.

In certain embodiments, $R^{12}$ is substituted or unsubstituted $C_2$-$C_{22}$ alkenyl.

In certain embodiments, $R^{12}$ is substituted or unsubstituted $C_2$-$C_{22}$ alkynyl.

In certain embodiments, $R^{13}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{13}$ is H.

In certain embodiments, $R^{13}$ is OH.

In certain embodiments, $R^{13}$ is halo.

In certain embodiments, $R^{13}$ is phenyl.

In certain embodiments, $R^{13}$ is benzyl.

In certain embodiments, $R^{13}$ is substituted or unsubstituted $C_1$-$C_{22}$ alkyl.

In certain embodiments, $R^{13}$ is substituted or unsubstituted $C_2$-$C_{22}$ alkenyl.

In certain embodiments, $R^{13}$ is substituted or unsubstituted $C_2$-$C_{22}$ alkynyl.

In certain embodiments, $R^{14}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{14}$ is H.

In certain embodiments, $R^{14}$ is OH.

In certain embodiments, $R^{14}$ is halo.

In certain embodiments, $R^{14}$ is phenyl.

In certain embodiments, $R^{14}$ is benzyl.

In certain embodiments, $R^{14}$ is substituted or unsubstituted $C_1$-$C_{22}$ alkyl.

In certain embodiments, $R^{14}$ is substituted or unsubstituted $C_2$-$C_{22}$ alkenyl.

In certain embodiments, $R^{14}$ is substituted or unsubstituted $C_2$-$C_{22}$ alkynyl.

In certain embodiments, $R^{15}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{15}$ is H.

In certain embodiments, $R^{15}$ is OH.

In certain embodiments, $R^{15}$ is halo.

In certain embodiments, $R^{15}$ is phenyl.

In certain embodiments, $R^{15}$ is benzyl.

In certain embodiments, $R^{15}$ is substituted or unsubstituted $C_1$-$C_{22}$ alkyl.

In certain embodiments, $R^{15}$ is substituted or unsubstituted $C_2$-$C_{22}$ alkenyl.

In certain embodiments, $R^{15}$ is substituted or unsubstituted $C_2$-$C_{22}$ alkynyl.

In certain embodiments, $R^{16}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{16}$ is H.

In certain embodiments, $R^{16}$ is OH.

In certain embodiments, $R^{16}$ is halo.

In certain embodiments, $R^{16}$ is phenyl.

In certain embodiments, $R^{16}$ is benzyl.

In certain embodiments, $R^{16}$ is substituted or unsubstituted $C_1$-$C_{22}$ alkyl.

In certain embodiments, $R^{16}$ is substituted or unsubstituted $C_2$-$C_{22}$ alkenyl.

In certain embodiments, $R^{16}$ is substituted or unsubstituted $C_2$-$C_{22}$ alkynyl.

In certain embodiments, u is 0.

In certain embodiments, u is 1.

In certain embodiments, u is 2.

In certain embodiments, u is 3.

In certain embodiments, u is 4.

In certain embodiments, u is 5.

In certain embodiments, u is 6.

In certain embodiments, u is 7.

In certain embodiments, u is 8.

In certain embodiments, u is 9.

In certain embodiments, u is 10.

In certain embodiments, u is 11.

In certain embodiments, u is 12.

In certain embodiments, u is 13.

In certain embodiments, u is 14.
In certain embodiments, u is 15.
In certain embodiments, u is 16.
In certain embodiments, u is 17.
In certain embodiments, u is 18.
In certain embodiments, u is 19.
In certain embodiments, u is 20.
In certain embodiments, v is 0.
In certain embodiments, v is 1.
In certain embodiments, v is 2.
In certain embodiments, v is 3.
In certain embodiments, v is 4.
In certain embodiments, v is 5.
In certain embodiments, v is 6.
In certain embodiments, v is 7.
In certain embodiments, v is 8.
In certain embodiments, v is 9.
In certain embodiments, v is 10.
In certain embodiments, v is 11.
In certain embodiments, v is 12.
In certain embodiments, v is 13.
In certain embodiments, v is 14.
In certain embodiments, v is 15.
In certain embodiments, v is 16.
In certain embodiments, v is 17.
In certain embodiments, v is 18.
In certain embodiments, v is 19.
In certain embodiments, v is 20.
In certain embodiments, w is 0.
In certain embodiments, w is 1.
In certain embodiments, w is 2.
In certain embodiments, w is 3.
In certain embodiments, w is 4.
In certain embodiments, w is 5.
In certain embodiments, w is 6.
In certain embodiments, w is 7.
In certain embodiments, w is 8.
In certain embodiments, w is 9.
In certain embodiments, w is 10.
In certain embodiments, w is 11.
In certain embodiments, w is 12.
In certain embodiments, w is 13.
In certain embodiments, w is 14.
In certain embodiments, w is 15.
In certain embodiments, w is 16.
In certain embodiments, w is 17.
In certain embodiments, w is 18.
In certain embodiments, w is 19.
In certain embodiments, w is 20.
In certain embodiments, x is 0.
In certain embodiments, x is 1.
In certain embodiments, x is 2.
In certain embodiments, x is 3.
In certain embodiments, x is 4.
In certain embodiments, x is 5.
In certain embodiments, x is 6.
In certain embodiments, x is 7.
In certain embodiments, x is 8.
In certain embodiments, x is 9.
In certain embodiments, x is 10.
In certain embodiments, x is 11.
In certain embodiments, x is 12.
In certain embodiments, x is 13.
In certain embodiments, x is 14.
In certain embodiments, x is 15.
In certain embodiments, x is 16.
In certain embodiments, x is 17.
In certain embodiments, x is 18.
In certain embodiments, x is 19.
In certain embodiments, x is 20.
In certain embodiments, y is 0.
In certain embodiments, y is 1.
In certain embodiments, y is 2.
In certain embodiments, y is 3.
In certain embodiments, y is 4.
In certain embodiments, y is 5.
In certain embodiments, y is 6.
In certain embodiments, y is 7.
In certain embodiments, y is 8.
In certain embodiments, y is 9.
In certain embodiments, y is 10.
In certain embodiments, y is 11.
In certain embodiments, y is 12.
In certain embodiments, y is 13.
In certain embodiments, y is 14.
In certain embodiments, y is 15.
In certain embodiments, y is 16.
In certain embodiments, y is 17.
In certain embodiments, y is 18.
In certain embodiments, y is 19.
In certain embodiments, y is 20.
In certain embodiments, z is 0.
In certain embodiments, z is 1.
In certain embodiments, z is 2.
In certain embodiments, z is 3.
In certain embodiments, z is 4.
In certain embodiments, z is 5.
In certain embodiments, z is 6.
In certain embodiments, z is 7.
In certain embodiments, z is 8.
In certain embodiments, z is 9.
In certain embodiments, z is 10.
In certain embodiments, z is 11.
In certain embodiments, z is 12.
In certain embodiments, z is 13.
In certain embodiments, z is 14.
In certain embodiments, z is 15.
In certain embodiments, z is 16.
In certain embodiments, z is 17.
In certain embodiments, z is 18.
In certain embodiments, z is 19.
In certain embodiments, z is 20.
In certain embodiments $L^1$ is a bond.
In certain embodiments, $L^1$ is —C(═O)—.
In certain embodiments, $L^1$ is —OC(═O)O—.
In certain embodiments, $L^1$ is —NH—C(═O)—.
In certain embodiments, $L^1$ is —SO—.
In certain embodiments, $L^1$ is —$SO_2$—.
In certain embodiments, $L^1$ is OC(═O).
In certain embodiments, $L^1$ is —C(═O)O—.
In certain embodiments, $L^1$ is —C(═O)NH—.
In certain embodiments, $L^1$ is —$SO_3$—.
In certain embodiments, $L^1$ is —$NSO_2$—.
In certain embodiments, $L^1$ is —$SO_2N$.
In certain embodiments, $L^1$ is —NH(($C_1$-$C_{22}$)alkyl).
In certain embodiments, $L^1$ is —N(($C_1$-$C_8$)alkyl)$_2$.
In certain embodiments, $L^1$ is —NH(($C_6$)aryl).
In certain embodiments, $L^1$ is —N(($C_6$)aryl)$_2$.
In certain embodiments, $L^1$ is dioxolopyrrolidine-dione.
In certain embodiments, $L^1$ is —C(═O)$R^1$—.
In certain embodiments, $L^1$ is —CO(($C_1$-$C_{22}$)alkyl).
In certain embodiments, $L^1$ is —CO(($C_6$)aryl).
In certain embodiments, $L^1$ is —$CO_2$(($C_1$-$C_{22}$)alkyl).
In certain embodiments, $L^1$ is —$CO_2$(($C_6$)aryl).

In certain embodiments, $L^1$ is —C(=O)O($CR^1R^2R^3$)

In certain embodiments, $L^1$ is —$SO_2$(($C_1$-$C_{22}$)alkyl).

In certain embodiments, $L^1$ is —$SO_2$(($C_6$)aryl).

In certain embodiments $L^2$ is a bond.

In certain embodiments, $L^2$ is —C(=O)—.

In certain embodiments, $L^2$ is —OC(=O)O—.

In certain embodiments, $L^2$ is —NH—C(=O)—.

In certain embodiments, $L^2$ is —SO—.

In certain embodiments, $L^2$ is —$SO_2$—.

In certain embodiments, $L^2$ is OC(=O).

In certain embodiments, $L^2$ is —C(=O)O—.

In certain embodiments, $L^2$ is —C(=O)NH—.

In certain embodiments, $L^2$ is —$SO_3$—.

In certain embodiments, $L^2$ is —$NSO_2$—.

In certain embodiments, $L^2$ is —$SO_2$N.

In certain embodiments, $L^2$ is —NH(($C_1$-$C_{22}$)alkyl).

In certain embodiments, $L^2$ is —N(($C_1$-$C_8$)alkyl)$_2$.

In certain embodiments, $L^2$ is —NH(($C_6$)aryl).

In certain embodiments, $L^2$ is —N(($C_6$)aryl)$_2$.

In certain embodiments, $L^2$ is dioxolopyrrolidine-dione.

In certain embodiments, $L^2$ is —C(=O)$R^1$—.

In certain embodiments, $L^2$ is —CO(($C_1$-$C_{22}$)alkyl).

In certain embodiments, $L^2$ is —CO(($C_6$)aryl).

In certain embodiments, $L^2$ is —$CO_2$(($C_1$-$C_{22}$)alkyl).

In certain embodiments, $L^2$ is —$CO_2$(($C_6$)aryl).

In certain embodiments, $L^2$ is —$SO_2$(($C_1$-$C_{22}$)alkyl).

In certain embodiments, $L^2$ is —$SO_2$(($C_6$)aryl).

In certain embodiments, Q is CH.

In certain embodiments, Q is O.

In certain embodiments, Q is S.

In certain embodiments, Q is NH.

In certain embodiments, Q is a disulfide bond.

In certain embodiments, m is 0.

In certain embodiments, m is 1.

In certain embodiments, m is 2.

In certain embodiments, m is 3.

In certain embodiments, m is 4.

In certain embodiments, m is 5.

In certain embodiments, m is 6.

In certain embodiments, m is 7.

In certain embodiments, m is 8.

In certain embodiments, m is 9.

In certain embodiments, m is 10.

In certain embodiments, m is 11.

In certain embodiments, m is 12.

In certain embodiments, m is 13.

In certain embodiments, m is 14.

In certain embodiments, m is 15.

In certain embodiments, m is 16.

In certain embodiments, m is 17.

In certain embodiments, m is 18.

In certain embodiments, m is 19.

In certain embodiments, m is 20.

In another embodiment, the invention encompasses Ionizable Lipids of the Invention of Formula VII:

Formula VII

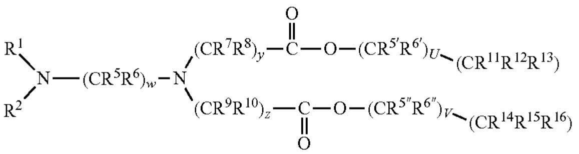

wherein each $R^1$ and each $R^2$ is independently selected from the group consisting of H, an optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C_6$ heteroaryl, optionally substituted $C_4$-$C_8$ aryloxy, optionally substituted $C_7$-$C_{10}$ arylalkyl; optionally substituted $C_5$-$C_{10}$ heteroarylalkyl group, optionally substituted amine; or $R^1$ and $R^2$ can together form a 3-7 membered heterocycloalkyl or heteroaryl ring;

wherein each $R^5$, $R^6$, $R^{5'}$, $R^{6'}$, $R^{5''}$, and $R^{6''}$ is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each $R^5$, $R^6$, $R^7$, $R^8$, $R^9$, $R^{10}$, $R^{11}$, $R^{12}$, $R^{13}$, $R^{14}$, $R^{15}$, and $R^{16}$ is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each of u, v, w, y, and z is independently an integer from 0-20;

wherein each Q is independently an atom selected from 0, NH, S, or a disulfide bond; and wherein each of $L^1$ and $L^2$ is independently selected from the group consisting of —C(=O)—; OC(=O)—; —OC(=O)O—; —C(=O)O—; —C(=O)O($CR^5R^6R^7$)$_m$; —NH—C(=O)—; —C(=O)NH—; —SO—; —$SO_2$—; —$SO_3$—; —$NSO_2$—; —$SO_2$N—; —NH(($C_1$-$C_8$)alkyl); —N(($C_1$-$C_8$)alkyl)$_2$; —NH(($C_6$)aryl); —N(($C_6$)aryl)$_2$; —NHC(=O)NH—; —NHC(=O)O—; —OC(=O)NH—; —NHC(=O)$NR^1$—; —NHC(=O)O—; —OC(=O)$NR^1$—; —C(=O)$R^1$—; —CO(($C_1$-$C_8$)alkyl); —CO(($C_6$)aryl); —$CO_2$(($C_1$-$C_8$)alkyl); —$CO_2$(($C_6$)aryl); —$SO_2$(($C_1$-$C_8$)alkyl); and —$SO_2$(($C_6$)aryl).

In certain embodiments, $R^1$ is H.

In certain embodiments, $R^1$ is substituted or unsubstituted $C_1$-$C_{22}$ alkyl.

In certain embodiments, $R^1$ is substituted or unsubstituted $C_2$-$C_{22}$ alkenyl.

In certain embodiments, $R^1$ is substituted or unsubstituted $C_2$-$C_{22}$ alkynyl.

In certain embodiments, $R^1$ is substituted or unsubstituted $C_3$-$C_6$ cycloalkyl.

In certain embodiments, $R^1$ is substituted or unsubstituted $C_4$-$C_6$ heterocycloalkyl.

In certain embodiments, $R^1$ is substituted or unsubstituted $C_4$-$C_6$ alkylcycloalkyl.

In certain embodiments, $R^1$ is substituted or unsubstituted $C_4$-$C_6$ aryl.

In certain embodiments, $R^1$ is substituted or unsubstituted $C_3$-$C_6$ heteroaryl.

In certain embodiments, $R^1$ is substituted or unsubstituted $C_4$-$C_8$ aryloxy.

In certain embodiments, $R^1$ is substituted or unsubstituted $C_7$-$C_{10}$ arylalkyl.

In certain embodiments, $R^1$ is substituted or unsubstituted $C_5$-$C_{10}$ heteroarylalkyl group.

In certain embodiments, $R^2$ is H.

In certain embodiments, $R^2$ is substituted or unsubstituted $C_1$-$C_{22}$ alkyl.

In certain embodiments, $R^2$ is substituted or unsubstituted $C_2$-$C_{22}$ alkenyl In certain embodiments, $R^2$ is substituted or unsubstituted $C_2$-$C_{22}$ alkynyl In certain embodiments, $R^2$ is substituted or unsubstituted $C_3$-$C_6$ cycloalkyl.

In certain embodiments, $R^2$ is substituted or unsubstituted $C_4$-$C_6$ heterocycloalkyl.

In certain embodiments, $R^2$ is substituted or unsubstituted $C_4$-$C_6$ alkylcycloalkyl.

In certain embodiments, $R^2$ is substituted or unsubstituted $C_4$-$C_6$ aryl.

In certain embodiments, $R^2$ is substituted or unsubstituted $C_3$-$C_6$ heteroaryl.

In certain embodiments, $R^2$ is substituted or unsubstituted $C_4$-$C_8$ aryloxy.

In certain embodiments, $R^2$ is substituted or unsubstituted $C_7$-$C_{10}$ arylalkyl.

In certain embodiments, $R^2$ is substituted or unsubstituted $C_5$-$C_{10}$ heteroarylalkyl group.

In certain embodiments, each $R^5$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^5$ is H.

In certain embodiments, $R^5$ is OH.

In certain embodiments, $R^5$ is halo.

In certain embodiments, $R^5$ is phenyl.

In certain embodiments, $R^5$ is benzyl.

In certain embodiments, $R^5$ is substituted or unsubstituted $C_1$-$C_{22}$ alkyl.

In certain embodiments, $R^5$ is substituted or unsubstituted $C_2$-$C_{22}$ alkenyl.

In certain embodiments, $R^5$ is substituted or unsubstituted $C_2$-$C_{22}$ alkynyl.

In certain embodiments, each $R^6$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^6$ is H.

In certain embodiments, $R^6$ is OH.

In certain embodiments, $R^6$ is halo.

In certain embodiments, $R^6$ is phenyl.

In certain embodiments, $R^6$ is benzyl.

In certain embodiments, $R^6$ is substituted or unsubstituted $C_1$-$C_{22}$ alkyl.

In certain embodiments, $R^6$ is substituted or unsubstituted $C_2$-$C_{22}$ alkenyl.

In certain embodiments, $R^6$ is substituted or unsubstituted $C_2$-$C_{22}$ alkynyl.

In certain embodiments, $R^7$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^7$ is H.

In certain embodiments, $R^7$ is OH.

In certain embodiments, $R^7$ is halo.

In certain embodiments, $R^7$ is phenyl.

In certain embodiments, $R^7$ is benzyl.

In certain embodiments, $R^7$ is substituted or unsubstituted $C_1$-$C_{22}$ alkyl.

In certain embodiments, $R^7$ is substituted or unsubstituted $C_2$-$C_{22}$ alkenyl.

In certain embodiments, $R^7$ is substituted or unsubstituted $C_2$-$C_{22}$ alkynyl.

In certain embodiments, $R^8$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^8$ is H.

In certain embodiments, $R^8$ is OH.

In certain embodiments, $R^8$ is halo.

In certain embodiments, $R^8$ is phenyl.

In certain embodiments, $R^8$ is benzyl.

In certain embodiments, $R^8$ is substituted or unsubstituted $C_1$-$C_{22}$ alkyl.

In certain embodiments, $R^8$ is substituted or unsubstituted $C_2$-$C_{22}$ alkenyl.

In certain embodiments, $R^8$ is substituted or unsubstituted $C_2$-$C_{22}$ alkynyl.

In certain embodiments, $R^9$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^9$ is H.

In certain embodiments, $R^9$ is OH.

In certain embodiments, $R^9$ is halo.

In certain embodiments, $R^9$ is phenyl.

In certain embodiments, $R^9$ is benzyl.

In certain embodiments, $R^9$ is substituted or unsubstituted $C_1$-$C_{22}$ alkyl.

In certain embodiments, $R^9$ is substituted or unsubstituted $C_2$-$C_{22}$ alkenyl.

In certain embodiments, $R^9$ is substituted or unsubstituted $C_2$-$C_{22}$ alkynyl.

In certain embodiments, $R^{10}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{10}$ is H.

In certain embodiments, $R^{10}$ is OH.

In certain embodiments, $R^{10}$ is halo.

In certain embodiments, $R^{10}$ is phenyl.

In certain embodiments, $R^{10}$ is benzyl.

In certain embodiments, $R^{10}$ is substituted or unsubstituted $C_1$-$C_{22}$ alkyl.

In certain embodiments, $R^{10}$ is substituted or unsubstituted $C_2$-$C_{22}$ alkenyl.

In certain embodiments, $R^{10}$ is substituted or unsubstituted $C_2$-$C_{22}$ alkynyl.

In certain embodiments, $R^{11}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{11}$ is H.

In certain embodiments, $R^{11}$ is OH.

In certain embodiments, $R^{11}$ is halo.

In certain embodiments, $R^{11}$ is phenyl.

In certain embodiments, $R^{11}$ is benzyl.

In certain embodiments, $R^{11}$ is substituted or unsubstituted $C_1$-$C_{22}$ alkyl.

In certain embodiments, $R^{11}$ is substituted or unsubstituted $C_2$-$C_{22}$ alkenyl.

In certain embodiments, $R^{11}$ is substituted or unsubstituted $C_2$-$C_{22}$ alkynyl.

In certain embodiments, $R^{11}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{12}$ is H.

In certain embodiments, $R^{12}$ is OH.

In certain embodiments, $R^{12}$ is halo.

In certain embodiments, $R^{12}$ is phenyl.

In certain embodiments, $R^{12}$ is benzyl.

In certain embodiments, $R^{12}$ is substituted or unsubstituted $C_1$-$C_{22}$ alkyl.

In certain embodiments, $R^{12}$ is substituted or unsubstituted $C_2$-$C_{22}$ alkenyl.

In certain embodiments, $R^{12}$ is substituted or unsubstituted $C_2$-$C_{22}$ alkynyl.

In certain embodiments, $R^{13}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{13}$ is H.

In certain embodiments, $R^{13}$ is OH.

In certain embodiments, $R^{13}$ is halo.

In certain embodiments, $R^{13}$ is phenyl.

In certain embodiments, $R^{13}$ is benzyl.

In certain embodiments, $R^{13}$ is substituted or unsubstituted $C_1$-$C_{22}$ alkyl.

In certain embodiments, $R^3$ is substituted or unsubstituted $C_2$-$C_{22}$ alkenyl.

In certain embodiments, $R^{13}$ is substituted or unsubstituted $C_2$-$C_{22}$ alkynyl.

In certain embodiments, $R^{14}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{14}$ is H.

In certain embodiments, $R^{14}$ is OH.

In certain embodiments, $R^{14}$ is halo.

In certain embodiments, $R^{14}$ is phenyl.

In certain embodiments, $R^{14}$ is benzyl.

In certain embodiments, $R^{14}$ is substituted or unsubstituted $C_1$-$C_{22}$ alkyl.

In certain embodiments, $R^{14}$ is substituted or unsubstituted $C_2$-$C_{22}$ alkenyl.

In certain embodiments, $R^{14}$ is substituted or unsubstituted $C_2$-$C_{22}$ alkynyl.

In certain embodiments, $R^{15}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{15}$ is H.

In certain embodiments, $R^{15}$ is OH.

In certain embodiments, $R^{15}$ is halo.

In certain embodiments, $R^{15}$ is phenyl.

In certain embodiments, $R^{15}$ is benzyl.

In certain embodiments, $R^{15}$ is substituted or unsubstituted $C_1$-$C_{22}$ alkyl.

In certain embodiments, $R^{15}$ is substituted or unsubstituted $C_2$-$C_{22}$ alkenyl.

In certain embodiments, $R^{15}$ is substituted or unsubstituted $C_2$-$C_{22}$ alkynyl.

In certain embodiments, $R^{16}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{16}$ is H.

In certain embodiments, $R^{16}$ is OH.

In certain embodiments, $R^{16}$ is halo.

In certain embodiments, $R^{16}$ is phenyl.

In certain embodiments, $R^{16}$ is benzyl.

In certain embodiments, $R^{16}$ is substituted or unsubstituted $C_1$-$C_{22}$ alkyl.

In certain embodiments, $R^{16}$ is substituted or unsubstituted $C_2$-$C_{22}$ alkenyl.

In certain embodiments, $R^{16}$ is substituted or unsubstituted $C_2$-$C_{22}$ alkynyl.

In certain embodiments, u is 0.

In certain embodiments, u is 1.

In certain embodiments, u is 2.

In certain embodiments, u is 3.

In certain embodiments, u is 4.

In certain embodiments, u is 5.

In certain embodiments, u is 6.

In certain embodiments, u is 7.

In certain embodiments, u is 8.

In certain embodiments, u is 9.

In certain embodiments, u is 10.

In certain embodiments, u is 11.

In certain embodiments, u is 12.

In certain embodiments, u is 13.

In certain embodiments, u is 14.

In certain embodiments, u is 15.

In certain embodiments, u is 16.

In certain embodiments, u is 17.

In certain embodiments, u is 18.

In certain embodiments, u is 19.

In certain embodiments, u is 20.

In certain embodiments, v is 0.

In certain embodiments, v is 1.

In certain embodiments, v is 2.

In certain embodiments, v is 3.

In certain embodiments, v is 4.

In certain embodiments, v is 5.

In certain embodiments, v is 6.

In certain embodiments, v is 7.

In certain embodiments, v is 8.

In certain embodiments, v is 9.

In certain embodiments, v is 10.

In certain embodiments, v is 11.

In certain embodiments, v is 12.

In certain embodiments, v is 13.

In certain embodiments, v is 14.

In certain embodiments, v is 15.

In certain embodiments, v is 16.

In certain embodiments, v is 17.

In certain embodiments, v is 18.

In certain embodiments, v is 19.

In certain embodiments, v is 20.

In certain embodiments, w is 0.

In certain embodiments, w is 1.

In certain embodiments, w is 2.

In certain embodiments, w is 3.

In certain embodiments, w is 4.

In certain embodiments, w is 5.

In certain embodiments, w is 6.

In certain embodiments, w is 7.

In certain embodiments, w is 8.

In certain embodiments, w is 9.

In certain embodiments, w is 10.

In certain embodiments, w is 11.

In certain embodiments, w is 12.

In certain embodiments, w is 13.

In certain embodiments, w is 14.

In certain embodiments, w is 15.

In certain embodiments, w is 16.

In certain embodiments, w is 17.

In certain embodiments, w is 18.

In certain embodiments, w is 19.

In certain embodiments, w is 20.

In certain embodiments, y is 0.

In certain embodiments, y is 1.

In certain embodiments, y is 2.

In certain embodiments, y is 3.

In certain embodiments, y is 4.

In certain embodiments, y is 5.

In certain embodiments, y is 6.

In certain embodiments, y is 7.
In certain embodiments, y is 8.
In certain embodiments, y is 9.
In certain embodiments, y is 10.
In certain embodiments, y is 11.
In certain embodiments, y is 12.
In certain embodiments, y is 13.
In certain embodiments, y is 14.
In certain embodiments, y is 15.
In certain embodiments, y is 16.
In certain embodiments, y is 17.
In certain embodiments, y is 18.
In certain embodiments, y is 19.
In certain embodiments, y is 20.
In certain embodiments, z is 0.
In certain embodiments, z is 1.
In certain embodiments, z is 2.
In certain embodiments, z is 3.
In certain embodiments, z is 4.
In certain embodiments, z is 5.
In certain embodiments, z is 6.
In certain embodiments, z is 7.
In certain embodiments, z is 8.
In certain embodiments, z is 9.
In certain embodiments, z is 10.
In certain embodiments, z is 11.
In certain embodiments, z is 12.
In certain embodiments, z is 13.
In certain embodiments, z is 14.
In certain embodiments, z is 15.
In certain embodiments, z is 16.
In certain embodiments, z is 17.
In certain embodiments, z is 18.
In certain embodiments, z is 19.
In certain embodiments, z is 20.
In certain embodiments $L^1$ is a bond.
In certain embodiments, $L^1$ is —C(═O)—.
In certain embodiments, $L^1$ is —OC(═O)O—.
In certain embodiments, $L^1$ is —NH—C(═O)—.
In certain embodiments, $L^1$ is —SO—.
In certain embodiments, $L^1$ is —$SO_2$—.
In certain embodiments, $L^1$ is OC(═O).
In certain embodiments, $L^1$ is —C(═O)O—.
In certain embodiments, $L^1$ is —C(═O)NH—.
In certain embodiments, $L^1$ is —$SO_3$—.
In certain embodiments, $L^1$ is —$NSO_2$—.
In certain embodiments, $L^1$ is —$SO_2N$.
In certain embodiments, $L^1$ is —NH(($C_1$-$C_{22}$)alkyl).
In certain embodiments, $L^1$ is —N(($C_1$-$C_8$)alkyl)$_2$.
In certain embodiments, $L^1$ is —NH(($C_6$)aryl).
In certain embodiments, $L^1$ is —N(($C_6$)aryl)$_2$.
In certain embodiments, $L^1$ is dioxolopyrrolidine-dione.
In certain embodiments, $L^1$ is —C(═O)$R^1$—.
In certain embodiments, $L^1$ is —CO(($C_1$-$C_{22}$)alkyl).
In certain embodiments, $L^1$ is —CO(($C_6$)aryl).
In certain embodiments, $L^1$ is —$CO_2$(($C_1$-$C_{22}$)alkyl).
In certain embodiments, $L^1$ is —$CO_2$(($C_6$)aryl).
In certain embodiments, $L^1$ is —$SO_2$(($C_1$-$C_{22}$)alkyl).
In certain embodiments, $L^1$ is —$SO_2$(($C_6$)aryl).
In certain embodiments $L^2$ is a bond.
In certain embodiments, $L^2$ is —C(═O)—.
In certain embodiments, $L^2$ is —OC(═O)O—.
In certain embodiments, $L^2$ is —NH—C(═O)—.
In certain embodiments, $L^2$ is —SO—.
In certain embodiments, $L^2$ is —$SO_2$—.
In certain embodiments, $L^2$ is OC(═O).
In certain embodiments, $L^2$ is —C(═O)O—.
In certain embodiments, $L^2$ is —C(═O)NH—.
In certain embodiments, $L^2$ is —$SO_3$—.
In certain embodiments, $L^2$ is —$NSO_2$—.
In certain embodiments, $L^2$ is —$SO_2N$.
In certain embodiments, $L^2$ is —NH(($C_1$-$C_{22}$)alkyl).
In certain embodiments, $L^2$ is —N(($C_1$-$C_8$)alkyl)$_2$.
In certain embodiments, $L^2$ is —NH(($C_6$)aryl).
In certain embodiments, $L^2$ is —N(($C_6$)aryl)$_2$.
In certain embodiments, $L^2$ is dioxolopyrrolidine-dione.
In certain embodiments, $L^2$ is —C(═O)$R^1$—.
In certain embodiments, $L^2$ is —CO(($C_1$-$C_{22}$)alkyl).
In certain embodiments, $L^2$ is —CO(($C_6$)aryl).
In certain embodiments, $L^2$ is —$CO_2$(($C_1$-$C_{22}$)alkyl).
In certain embodiments, $L^2$ is —$CO_2$(($C_6$)aryl).
In certain embodiments, $L^2$ is —$CO_2$($CR^1R^2R^3$).
In certain embodiments, $L^2$ is —$SO_2$(($C_1$-$C_{22}$)alkyl).
In certain embodiments, $L^2$ is —$SO_2$(($C_6$)aryl).
In certain embodiments, Q is CH.
In certain embodiments, Q is O.
In certain embodiments, Q is S.
In certain embodiments, Q is NH.
In certain embodiments, Q is a disulfide bond.
In certain embodiments, m is 0.
In certain embodiments, m is 1.
In certain embodiments, m is 2.
In certain embodiments, m is 3.
In certain embodiments, m is 4.
In certain embodiments, m is 5.
In certain embodiments, m is 6.
In certain embodiments, m is 7.
In certain embodiments, m is 8.
In certain embodiments, m is 9.
In certain embodiments, m is 10.
In certain embodiments, m is 11.
In certain embodiments, m is 12.
In certain embodiments, m is 13.
In certain embodiments, m is 14.
In certain embodiments, m is 15.
In certain embodiments, m is 16.
In certain embodiments, m is 17.
In certain embodiments, m is 18.
In certain embodiments, m is 19.
In certain embodiments, m is 20.

In another embodiment, the invention encompasses Ionizable Lipids of the Invention of Formula VIII:

Formula VIII

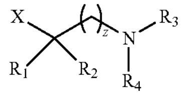

wherein $R_1$ and $R_2$ are each independently selected from the group consisting of H, an optionally substituted $C_1$-$C_{22}$ alkyl, optionally substituted $C_2$-$C_{22}$ alkenyl, optionally substituted $C_2$-$C_{22}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C_6$ heteroaryl, optionally substituted $C_4$-$C_8$ aryloxy, optionally substituted $C_7$-$C_{10}$ arylalkyl or optionally substituted $C_5$-$C_{10}$ heteroarylalkyl group;

$R_3$ and $R_4$ are each independently optionally substituted $C_{10}$-$C_{22}$ alkyl, optionally substituted $C_{10}$-$C_{22}$ alkenyl, optionally substituted $C_{10}$-$C_{22}$ alkynyl, or $R^1$ and $R^2$ can together form a 3-7 membered heterocycle or heteroaryl ring X is OH, or $NR_1R_2$; and Z is an integer from 0 to 5.

In certain embodiments, the ionizable lipid of Formula VIII is selected from the group consisting of:

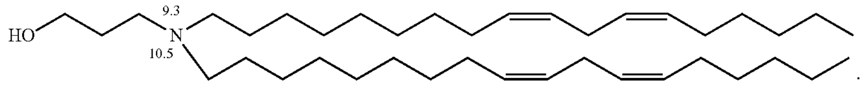

In certain embodiments, the ionizable lipid of Formula VIII is selected from the group consisting of:

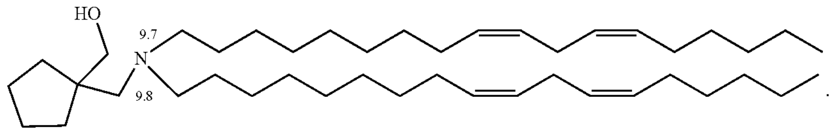 [SMILES: CCCCC/C=C\C/C=C\CCCCCCCCN(CCCCCCCC/C=C\C/C=C\CCCCC)CC1(CO)CCCC1]

In certain embodiments, the ionizable lipid of Formula VIII is selected from the group consisting of:

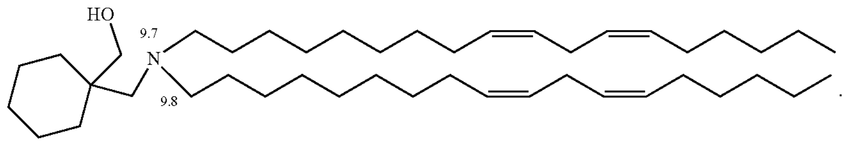 [SMILES: CCCCC/C=C\C/C=C\CCCCCCCCN(CCCCCCCC/C=C\C/C=C\CCCCC)CC1(CO)CCCCC1]

In certain embodiments, the ionizable lipid of Formula VIII is selected from the group consisting of:

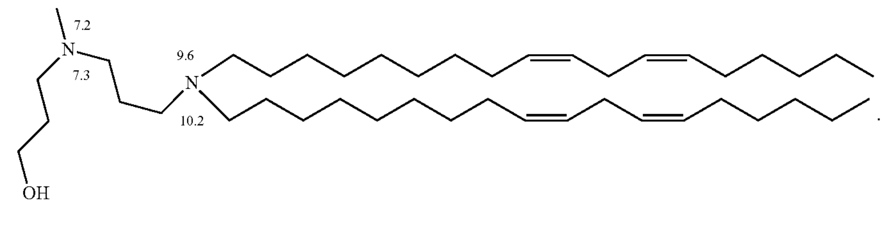 [SMILES: CCCCC/C=C\C/C=C\CCCCCCCCN(CCCCCCCC/C=C\C/C=C\CCCCC)CCCN(C)CCCO]

In certain embodiments, the ionizable lipid of Formula VIII is selected from the group consisting of:

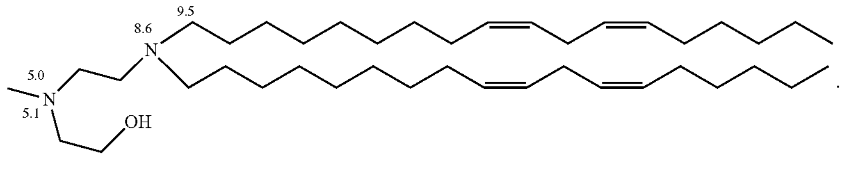

In certain embodiments, the ionizable lipid of Formula VIII is selected from the group consisting of:

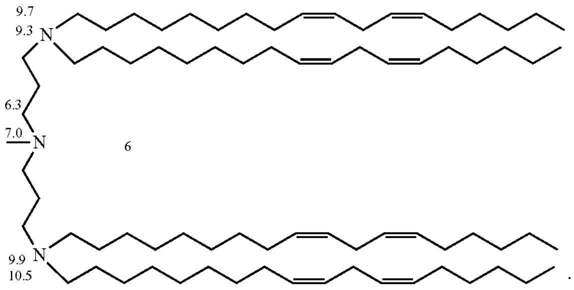 [SMILES: CCCCC/C=C\C/C=C\CCCCCCCCN(CCCCCCCC/C=C\C/C=C\CCCCC)CCCN(C)CCCN(CCCCCCCC/C=C\C/C=C\CCCCC)CCCCCCCC/C=C\C/C=C\CCCCC]

6

In certain embodiments, the ionizable lipid of Formula VIII is selected from the group consisting of:

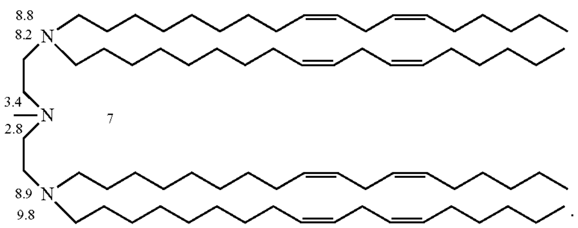 [SMILES: CCCCC/C=C\C/C=C\CCCCCCCCN(CCCCCCCC/C=C\C/C=C\CCCCC)CCN(C)CCN(CCCCCCCC/C=C\C/C=C\CCCCC)CCCCCCCC/C=C\C/C=C\CCCCC]

7

In certain embodiments, the ionizable lipid of Formula VIII is selected from the group consisting of:

wherein each $R^5$, $R^6$, $R^{5'}$, $R^{6'}$, $R^{5''}$, and $R^{6''}$ is independently selected from the group consisting of H, OH, halo, phenyl, benzyl, optionally substituted $C_1$-$C_{22}$ alkyl, optionally substituted $C_2$-$C_{22}$ alkenyl, optionally substituted $C_2$-$C_{22}$ alkynyl, wherein each $R^5$, $R^6$, $R^7$, $R^8$, $R^9$, $R^{10}$, $R^{11}$, $R^{12}$, $R^3$, $R^{14}$, $R^5$, and $R^{16}$ is independently selected from the group consisting of H, OH, halo, phenyl, benzyl, optionally substituted $C_1$-$C_{22}$alkyl, optionally substituted $C_2$-$C_{22}$ alkenyl, optionally substituted $C_2$-$C_{22}$ alkynyl, wherein each of u, v, w, y, and z is independently an integer from 0-20;

wherein X is O, S, or N; and wherein each of $L^1$ and $L^2$ is independently selected from the group consisting of —C(═O)—; OC(═O)—; —OC(═O)O—; —C(═O)O—; —C(═O)O$(CR^5R^6R^7)_m$; —NH—C(═O)—; —C(═O)NH—; —SO—; —$SO_2$—; —$SO_3$—; —$NSO_2$—; —$SO_2$N—; —NH(($C_1$-$C_8$)alkyl); —N(($C_1$-$C_8$)alkyl$)_2$; —NH(($C_6$)aryl); —N(($C_6$)aryl$)_2$; —NHC(═O)NH—; —NHC(═O)O—; —OC(═O)NH—; —NHC(═O)$NR^1$—; —NHC(═O)O—; —OC(═O)$NR^1$—; —C(═O)$R^1$—; —CO(($C_1$-$C_8$)alkyl); —CO(($C_6$)aryl); —$CO_2$(($C_1$-$C_8$)alkyl); —$CO_2$(($C_6$)aryl); —$SO_2$(($C_1$-$C_8$)alkyl); and —$SO_2$(($C_6$)aryl).

In certain embodiments, $R^1$ is H.

In certain embodiments, $R^1$ is substituted or unsubstituted $C_1$-$C_{22}$ alkyl.

In certain embodiments, $R^1$ is substituted or unsubstituted $C_2$-$C_{22}$ alkenyl.

In certain embodiments, $R^1$ is substituted or unsubstituted $C_2$-$C_{22}$ alkynyl.

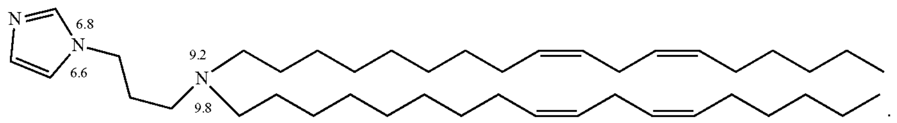 [SMILES: CCCCC/C=C\C/C=C\CCCCCCCCN(CCCCCCCC/C=C\C/C=C\CCCCC)CCCn1ccnc1]

In another embodiment, the invention encompasses Ionizable Lipids of the Invention of Formula IX:

Formula IX

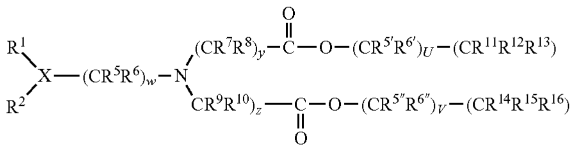

wherein each $R^1$ and each $R^2$ is independently selected from the group consisting of H, an electron pair, an optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C_6$ heteroaryl, optionally substituted $C_4$-$C_8$ aryloxy, optionally substituted $C_7$-$C_{10}$ arylalkyl; optionally substituted $C_5$-$C_{10}$ heteroarylalkyl group, optionally substituted amine; or $R^1$ and $R^2$ can together form a 3-7 membered heterocycle or heteroaryl ring;

In certain embodiments, $R^1$ is substituted or unsubstituted $C_3$-$C_6$ cycloalkyl.

In certain embodiments, $R^1$ is substituted or unsubstituted $C_4$-$C_6$ heterocycloalkyl.

In certain embodiments, $R^1$ is substituted or unsubstituted $C_4$-$C_6$ alkylcycloalkyl.

In certain embodiments, $R^1$ is substituted or unsubstituted $C_4$-$C_6$ aryl.

In certain embodiments, $R^1$ is substituted or unsubstituted $C_3$-$C_6$ heteroaryl.

In certain embodiments, $R^1$ is substituted or unsubstituted $C_4$-$C_8$ aryloxy.

In certain embodiments, $R^1$ is substituted or unsubstituted $C_7$-$C_{10}$ arylalkyl.

In certain embodiments, $R^1$ is substituted or unsubstituted $C_5$-$C_{10}$ heteroarylalkyl group.

In certain embodiments, $R^2$ is H.

In certain embodiments, $R^2$ is substituted or unsubstituted $C_1$-$C_{22}$ alkyl.

In certain embodiments, $R^2$ is substituted or unsubstituted $C_2$-$C_{22}$ alkenyl In certain embodiments, $R^2$ is substituted or unsubstituted $C_2$-$C_{22}$ alkynyl In certain embodiments, $R^2$ is substituted or unsubstituted $C_3$-$C_6$ cycloalkyl.

In certain embodiments, $R^2$ is substituted or unsubstituted $C_4$-$C_6$ heterocycloalkyl.

In certain embodiments, $R^2$ is substituted or unsubstituted $C_4$-$C_6$ alkylcycloalkyl.

In certain embodiments, $R^2$ is substituted or unsubstituted $C_4$-$C_6$ aryl.

In certain embodiments, $R^2$ is substituted or unsubstituted $C_3$-$C_6$ heteroaryl.

In certain embodiments, $R^2$ is substituted or unsubstituted $C_4$-$C_8$ aryloxy.

In certain embodiments, $R^2$ is substituted or unsubstituted $C_7$-$C_{10}$ arylalkyl.

In certain embodiments, $R^2$ is substituted or unsubstituted $C_5$-$C_{10}$ heteroarylalkyl group.

In certain embodiments, each $R^5$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^5$ is H.

In certain embodiments, $R^5$ is OH.

In certain embodiments, $R^5$ is halo.

In certain embodiments, $R^5$ is phenyl.

In certain embodiments, $R^5$ is benzyl.

In certain embodiments, $R^5$ is substituted or unsubstituted $C_1$-$C_{22}$ alkyl.

In certain embodiments, $R^5$ is substituted or unsubstituted $C_2$-$C_{22}$ alkenyl.

In certain embodiments, $R^5$ is substituted or unsubstituted $C_2$-$C_{22}$ alkynyl.

In certain embodiments, each $R^6$ is independently H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^6$ is H.

In certain embodiments, $R^6$ is OH.

In certain embodiments, $R^6$ is halo.

In certain embodiments, $R^6$ is phenyl.

In certain embodiments, $R^6$ is benzyl.

In certain embodiments, $R^6$ is substituted or unsubstituted $C_1$-$C_{22}$ alkyl.

In certain embodiments, $R^6$ is substituted or unsubstituted $C_2$-$C_{22}$ alkenyl.

In certain embodiments, $R^6$ is substituted or unsubstituted $C_2$-$C_{22}$ alkynyl.

In certain embodiments, $R^7$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^7$ is H.

In certain embodiments, $R^7$ is OH.

In certain embodiments, $R^7$ is halo.

In certain embodiments, $R^7$ is phenyl.

In certain embodiments, $R^7$ is benzyl.

In certain embodiments, $R^7$ is substituted or unsubstituted $C_1$-$C_{22}$ alkyl.

In certain embodiments, $R^7$ is substituted or unsubstituted $C_2$-$C_{22}$ alkenyl.

In certain embodiments, $R^7$ is substituted or unsubstituted $C_2$-$C_{22}$ alkynyl.

In certain embodiments, $R^8$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^8$ is H.

In certain embodiments, $R^8$ is OH.

In certain embodiments, $R^8$ is halo.

In certain embodiments, $R^8$ is phenyl.

In certain embodiments, $R^8$ is benzyl.

In certain embodiments, $R^8$ is substituted or unsubstituted $C_1$-$C_{22}$ alkyl.

In certain embodiments, $R^8$ is substituted or unsubstituted $C_2$-$C_{22}$ alkenyl.

In certain embodiments, $R^8$ is substituted or unsubstituted $C_2$-$C_{22}$ alkynyl.

In certain embodiments, $R^9$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^9$ is H.

In certain embodiments, $R^9$ is OH.

In certain embodiments, $R^9$ is halo.

In certain embodiments, $R^9$ is phenyl.

In certain embodiments, $R^9$ is benzyl.

In certain embodiments, $R^9$ is substituted or unsubstituted $C_1$-$C_{22}$ alkyl.

In certain embodiments, $R^9$ is substituted or unsubstituted $C_2$-$C_{22}$ alkenyl.

In certain embodiments, $R^9$ is substituted or unsubstituted $C_2$-$C_{22}$ alkynyl.

In certain embodiments, $R^{10}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{10}$ is H.

In certain embodiments, $R^{10}$ is OH.

In certain embodiments, $R^{10}$ is halo.

In certain embodiments, $R^{10}$ is phenyl.

In certain embodiments, $R^{10}$ is benzyl.

In certain embodiments, $R^{10}$ is substituted or unsubstituted $C_1$-$C_{22}$ alkyl.

In certain embodiments, $R^{10}$ is substituted or unsubstituted $C_2$-$C_{22}$ alkenyl.

In certain embodiments, $R^{10}$ is substituted or unsubstituted $C_2$-$C_{22}$ alkynyl.

In certain embodiments, $R^{11}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{11}$ is H.

In certain embodiments, $R^{11}$ is OH.

In certain embodiments, $R^{11}$ is halo.

In certain embodiments, $R^{11}$ is phenyl.

In certain embodiments, $R^{11}$ is benzyl.

In certain embodiments, $R^{11}$ is substituted or unsubstituted $C_1$-$C_{22}$ alkyl.

In certain embodiments, $R^{11}$ is substituted or unsubstituted $C_2$-$C_{22}$ alkenyl.

In certain embodiments, $R^{11}$ is substituted or unsubstituted $C_2$-$C_{22}$ alkynyl.

In certain embodiments, $R^{11}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{12}$ is H.

In certain embodiments, $R^{12}$ is OH.

In certain embodiments, $R^{12}$ is halo.

In certain embodiments, $R^{12}$ is phenyl.

In certain embodiments, $R^2$ is benzyl.

In certain embodiments, $R^{12}$ is substituted or unsubstituted $C_1$-$C_{22}$ alkyl.

In certain embodiments, $R^{12}$ is substituted or unsubstituted $C_2$-$C_{22}$ alkenyl.

In certain embodiments, $R^{12}$ is substituted or unsubstituted $C_2$-$C_{22}$ alkynyl.

In certain embodiments, $R^{13}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{13}$ is H.

In certain embodiments, $R^{13}$ is OH.

In certain embodiments, $R^{13}$ is halo.

In certain embodiments, $R^{13}$ is phenyl.

In certain embodiments, $R^{13}$ is benzyl.

In certain embodiments, $R^{13}$ is substituted or unsubstituted $C_1$-$C_{22}$ alkyl.

In certain embodiments, $R^{13}$ is substituted or unsubstituted $C_2$-$C_{22}$ alkenyl.

In certain embodiments, $R^{13}$ is substituted or unsubstituted $C_2$-$C_{22}$ alkynyl.

In certain embodiments, $R^{14}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{14}$ is H.

In certain embodiments, $R^{14}$ is OH.

In certain embodiments, $R^{14}$ is halo.

In certain embodiments, $R^{14}$ is phenyl.

In certain embodiments, $R^{14}$ is benzyl.

In certain embodiments, $R^{14}$ is substituted or unsubstituted $C_1$-$C_{22}$ alkyl.

In certain embodiments, $R^{14}$ is substituted or unsubstituted $C_2$-$C_{22}$ alkenyl.

In certain embodiments, $R^{14}$ is substituted or unsubstituted $C_2$-$C_{22}$ alkynyl.

In certain embodiments, $R^{15}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{15}$ is H.

In certain embodiments, $R^{15}$ is OH.

In certain embodiments, $R^{15}$ is halo.

In certain embodiments, $R^{15}$ is phenyl.

In certain embodiments, $R^{15}$ is benzyl.

In certain embodiments, $R^{15}$ is substituted or unsubstituted $C_1$-$C_{22}$ alkyl.

In certain embodiments, $R^{15}$ is substituted or unsubstituted $C_2$-$C_{22}$ alkenyl.

In certain embodiments, $R^{15}$ is substituted or unsubstituted $C_2$-$C_{22}$ alkynyl.

In certain embodiments, $R^{16}$ is H, OH, halo, phenyl, benzyl, substituted or unsubstituted $C_1$-$C_{22}$ alkyl, substituted or unsubstituted $C_2$-$C_{22}$ alkenyl; or substituted or unsubstituted $C_2$-$C_{22}$ alkynyl.

In certain embodiments, $R^{16}$ is H.

In certain embodiments, $R^{16}$ is OH.

In certain embodiments, $R^{16}$ is halo.

In certain embodiments, $R^{16}$ is phenyl.

In certain embodiments, $R^{16}$ is benzyl.

In certain embodiments, $R^{16}$ is substituted or unsubstituted $C_1$-$C_{22}$ alkyl.

In certain embodiments, $R^{16}$ is substituted or unsubstituted $C_2$-$C_{22}$ alkenyl.

In certain embodiments, $R^{16}$ is substituted or unsubstituted $C_2$-$C_{22}$ alkynyl.

In certain embodiments, u is 0.

In certain embodiments, u is 1.

In certain embodiments, u is 2.

In certain embodiments, u is 3.

In certain embodiments, u is 4.

In certain embodiments, u is 5.

In certain embodiments, u is 6.

In certain embodiments, u is 7.

In certain embodiments, u is 8.

In certain embodiments, u is 9.

In certain embodiments, u is 10.

In certain embodiments, u is 11.

In certain embodiments, u is 12.

In certain embodiments, u is 13.

In certain embodiments, u is 14.

In certain embodiments, u is 15.

In certain embodiments, u is 16.

In certain embodiments, u is 17.

In certain embodiments, u is 18.

In certain embodiments, u is 19.

In certain embodiments, u is 20.

In certain embodiments, v is 0.

In certain embodiments, v is 1.

In certain embodiments, v is 2.

In certain embodiments, v is 3.

In certain embodiments, v is 4.

In certain embodiments, v is 5.

In certain embodiments, v is 6.

In certain embodiments, v is 7.

In certain embodiments, v is 8.

In certain embodiments, v is 9.

In certain embodiments, v is 10.

In certain embodiments, v is 11.

In certain embodiments, v is 12.

In certain embodiments, v is 13.

In certain embodiments, v is 14.

In certain embodiments, v is 15.

In certain embodiments, v is 16.

In certain embodiments, v is 17.

In certain embodiments, v is 18.

In certain embodiments, v is 19.

In certain embodiments, v is 20.

In certain embodiments, w is 0.

In certain embodiments, w is 1.

In certain embodiments, w is 2.

In certain embodiments, w is 3.

In certain embodiments, w is 4.

In certain embodiments, w is 5.

In certain embodiments, w is 6.

In certain embodiments, w is 7.

In certain embodiments, w is 8.

In certain embodiments, w is 9.

In certain embodiments, w is 10.

In certain embodiments, w is 11.

In certain embodiments, w is 12.

In certain embodiments, w is 13.

In certain embodiments, w is 14.

In certain embodiments, w is 15.

In certain embodiments, w is 16.

In certain embodiments, w is 17.

In certain embodiments, w is 18.

In certain embodiments, w is 19.

In certain embodiments, w is 20.

In certain embodiments, y is 0.

In certain embodiments, y is 1.

In certain embodiments, y is 2.

In certain embodiments, y is 3.

In certain embodiments, y is 4.

In certain embodiments, y is 5.

In certain embodiments, y is 6.

In certain embodiments, y is 7.

In certain embodiments, y is 8.

In certain embodiments, y is 9.

In certain embodiments, y is 10.

In certain embodiments, y is 11.

In certain embodiments, y is 12.

In certain embodiments, y is 13.

In certain embodiments, y is 14.

In certain embodiments, y is 15.

In certain embodiments, y is 16.

In certain embodiments, y is 17.

In certain embodiments, y is 18.

In certain embodiments, y is 19.

In certain embodiments, y is 20.

In certain embodiments, z is 0.

In certain embodiments, z is 1.

In certain embodiments, z is 2.

In certain embodiments, z is 3.

In certain embodiments, z is 4.

In certain embodiments, z is 5.

In certain embodiments, z is 6.

In certain embodiments, z is 7.

In certain embodiments, z is 8.

In certain embodiments, z is 9.

In certain embodiments, z is 10.

In certain embodiments, z is 11.

In certain embodiments, z is 12.

In certain embodiments, z is 13.

In certain embodiments, z is 14.

In certain embodiments, z is 15.

In certain embodiments, z is 16.

In certain embodiments, z is 17.

In certain embodiments, z is 18.

In certain embodiments, z is 19.

In certain embodiments, z is 20.

In certain embodiments $L^1$ is a bond.

In certain embodiments, $L^1$ is —C(═O)—.

In certain embodiments, $L^1$ is —OC(═O)O—.

In certain embodiments, $L^1$ is —NH—C(═O)—.

In certain embodiments, $L^1$ is —SO—.

In certain embodiments, $L^1$ is —$SO_2$—.

In certain embodiments, $L^1$ is OC(═O).

In certain embodiments, $L^1$ is —C(═O)O—.

In certain embodiments, $L^1$ is —C(═O)NH—.

In certain embodiments, $L^1$ is —$SO_3$—.

In certain embodiments, $L^1$ is —$NSO_2$—.

In certain embodiments, $L^1$ is —$SO_2N$.

In certain embodiments, $L^1$ is —NH(($C_1$-$C_{22}$)alkyl).

In certain embodiments, $L^1$ is —N(($C_1$-$C_8$)alkyl)$_2$.

In certain embodiments, $L^1$ is —NH(($C_6$)aryl).

In certain embodiments, $L^1$ is —N(($C_6$)aryl)$_2$.

In certain embodiments, $L^1$ is dioxolopyrrolidine-dione.

In certain embodiments, $L^1$ is —C(═O)$R^1$—.

In certain embodiments, $L^1$ is —CO(($C_1$-$C_{22}$)alkyl).

In certain embodiments, $L^1$ is —CO(($C_6$)aryl).

In certain embodiments, $L^1$ is —$CO_2$(($C_1$-$C_{22}$)alkyl).

In certain embodiments, $L^1$ is —$CO_2$(($C_6$)aryl).

In certain embodiments, $L^1$ is —$SO_2$(($C_1$-$C_{22}$)alkyl).

In certain embodiments, $L^1$ is —$SO_2$(($C_6$)aryl).

In certain embodiments $L^2$ is a bond.

In certain embodiments, $L^2$ is —C(═O)—.

In certain embodiments, $L^2$ is —OC(═O)O—.

In certain embodiments, $L^2$ is —NH—C(═O)—.

In certain embodiments, $L^2$ is —SO—.

In certain embodiments, $L^2$ is —$SO_2$—.

In certain embodiments, $L^2$ is OC(═O).

In certain embodiments, $L^2$ is —C(═O)O—.

In certain embodiments, $L^2$ is —C(═O)NH—.

In certain embodiments, $L^2$ is —$SO_3$—.

In certain embodiments, $L^2$ is —$NSO_2$—.

In certain embodiments, $L^2$ is —$SO_2N$.

In certain embodiments, $L^2$ is —NH(($C_1$-$C_{22}$)alkyl).

In certain embodiments, $L^2$ is —N(($C_1$-$C_8$)alkyl)$_2$.

In certain embodiments, $L^2$ is —NH(($C_6$)aryl).

In certain embodiments, $L^2$ is —N(($C_6$)aryl)$_2$.

In certain embodiments, $L^2$ is dioxolopyrrolidine-dione.

In certain embodiments, $L^2$ is —C(═O)$R^1$—.

In certain embodiments, $L^2$ is —CO(($C_1$-$C_{22}$)alkyl).

In certain embodiments, $L^2$ is —CO(($C_6$)aryl).

In certain embodiments, $L^2$ is —$CO_2$(($C_1$-$C_{22}$)alkyl).

In certain embodiments, $L^2$ is —$CO_2$(($C_6$)aryl).

In certain embodiments, $L^2$ is —$CO_2$($CR^1R^2R^3$).

In certain embodiments, $L^2$ is —$SO_2$(($C_1$-$C_{22}$)alkyl).

In certain embodiments, $L^2$ is —$SO_2$(($C_6$)aryl).

In certain embodiments, Q is CH.

In certain embodiments, X is O.

In certain embodiments, X is S.

In certain embodiments, X is N.

In certain embodiments, m is 0.

In certain embodiments, m is 1.

In certain embodiments, m is 2.

In certain embodiments, m is 3.

In certain embodiments, m is 4.

In certain embodiments, m is 5.

In certain embodiments, m is 6.

In certain embodiments, m is 7.

In certain embodiments, m is 8.

In certain embodiments, m is 9.

In certain embodiments, m is 10.

In certain embodiments, m is 11.

In certain embodiments, m is 12.

In certain embodiments, m is 13.

In certain embodiments, m is 14.

In certain embodiments, m is 15.

In certain embodiments, m is 16.

In certain embodiments, m is 17.

In certain embodiments, m is 18.

In certain embodiments, m is 19.

In certain embodiments, m is 20.

V.3. Illustrative Ionizable Lipids of the Invention

Illustrative, non-limiting examples of Ionizable Lipids of the Invention are illustrated in Table 10 (the column with the heading "Method" refers to the method of synthesizing the particular compound as set for below in section V.4. Methods Of Making The Ionizable Lipids Of The Invention).

TABLE 10
| No | Lipid structure | pKa-Classic | pKa-Galas | Method |
|---|---|---|---|---|
| 1. | 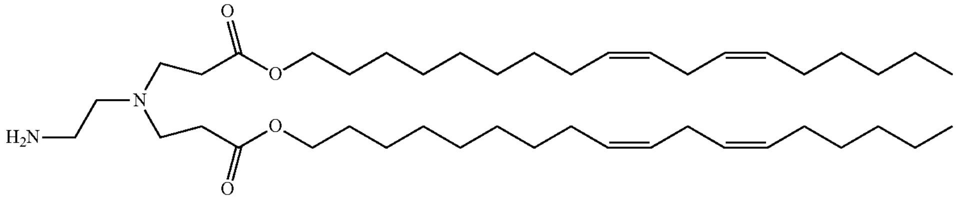 [SMILES: CCCCC/C=C\C/C=C\CCCCCCCCOC(=O)CCN(CCN)CCC(=O)OCCCCCCCC/C=C\C/C=C\CCCCC] | 9.48, 5.15 | 9.55 3.63 | A |
| 2. | 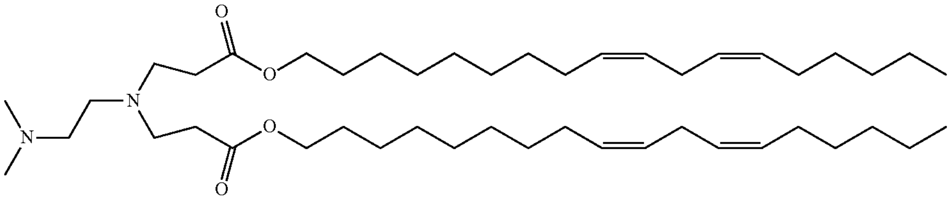 [SMILES: CCCCC/C=C\C/C=C\CCCCCCCCOC(=O)CCN(CCC(=O)OCCCCCCCC/C=C\C/C=C\CCCCC)CCN(C)C] | 8.43, 3.9 | 8.85 3.63 | A |
| 3. | 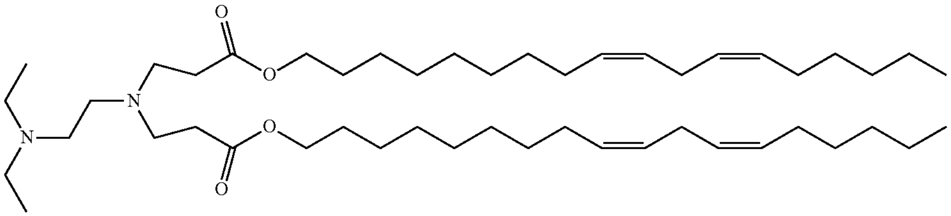 [SMILES: CCCCC/C=C\C/C=C\CCCCCCCCOC(=O)CCN(CCC(=O)OCCCCCCCC/C=C\C/C=C\CCCCC)CCN(CC)CC] | 8.61, 3.91 | 9.45 3.63 | A |
| 4. | 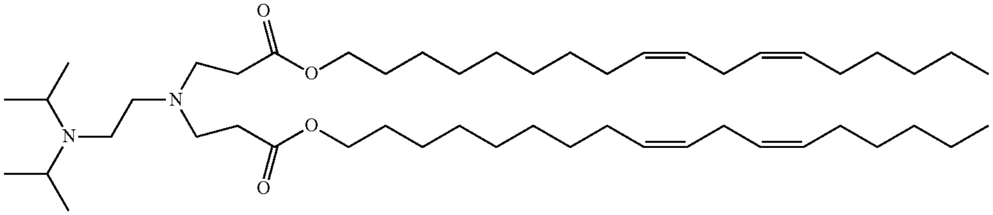 [SMILES: CCCCC/C=C\C/C=C\CCCCCCCCOC(=O)CCN(CCC(=O)OCCCCCCCC/C=C\C/C=C\CCCCC)CCN(C(C)C)C(C)C] | 10.33, 3.92 | 9.65 3.63 | A |

TABLE 10-continued
| No | Lipid structure | pKa-Classic | pKa-Galas | Method |
| --- | --- | --- | --- | --- |
| 5. | 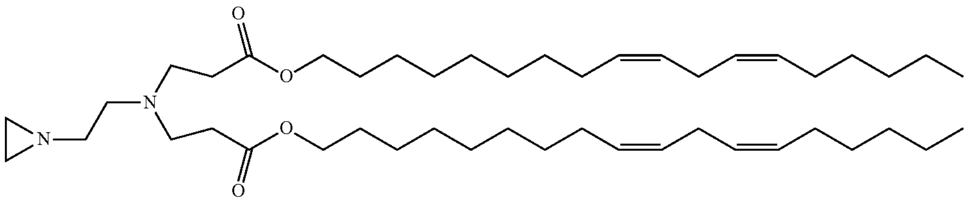 [SMILES: CCCCC/C=C\C/C=C\CCCCCCCCOC(=O)CCN(CCC(=O)OCCCCCCCC/C=C\C/C=C\CCCCC)CCN1CC1] | 7.53<br>3.81 | 6.87<br>3.54 | A |
| 6. | 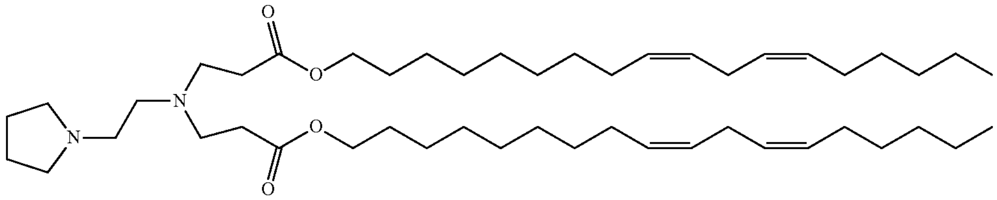 [SMILES: CCCCC/C=C\C/C=C\CCCCCCCCOC(=O)CCN(CCC(=O)OCCCCCCCC/C=C\C/C=C\CCCCC)CCN1CCCC1] | 8.61<br>5.93 | 9.35<br>3.63 | A |
| 7. | 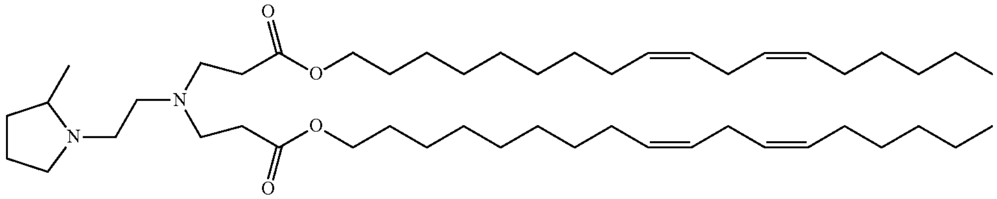 [SMILES: CCCCC/C=C\C/C=C\CCCCCCCCOC(=O)CCN(CCC(=O)OCCCCCCCC/C=C\C/C=C\CCCCC)CCN1CCCC1C] | 8.67<br>5.99 | 9.35<br>3.63 | A |
| 8. | 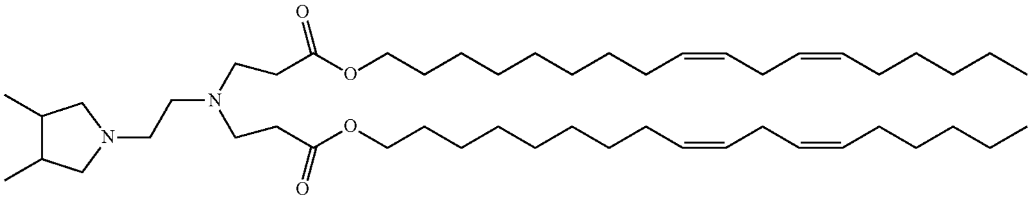 [SMILES: CCCCC/C=C\C/C=C\CCCCCCCCOC(=O)CCN(CCC(=O)OCCCCCCCC/C=C\C/C=C\CCCCC)CCN1CC(C)C(C)C1] | 8.69<br>5.99 | 9.35<br>3.63 | A |
| 9. | 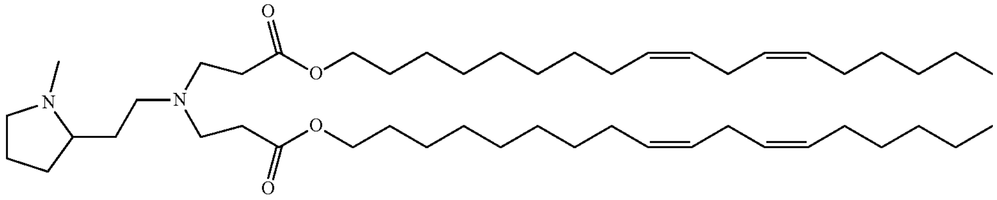 [SMILES: CCCCC/C=C\C/C=C\CCCCCCCCOC(=O)CCN(CCC(=O)OCCCCCCCC/C=C\C/C=C\CCCCC)CCC1CCCN1C] | 10.38<br>7.17 | 10.04<br>5.45 | A |

TABLE 10-continued
| No | Lipid structure | pKa-Classic | pKa-Galas | Method |
|---|---|---|---|---|
| 10. | 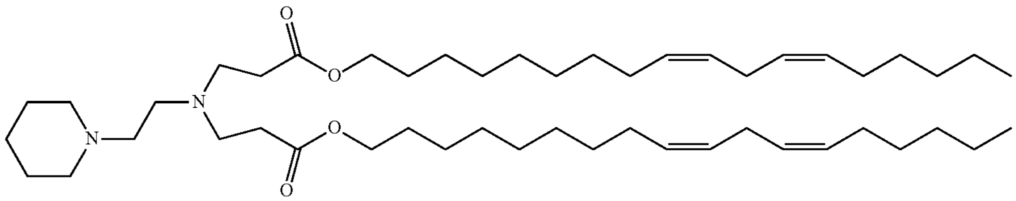 [SMILES: CCCCC/C=C\C/C=C\CCCCCCCCOC(=O)CCN(CCC(=O)OCCCCCCCC/C=C\C/C=C\CCCCC)CCN1CCCCC1] | 9.1<br>5.99 | 9.05<br>3.63 | A |
| 11. | 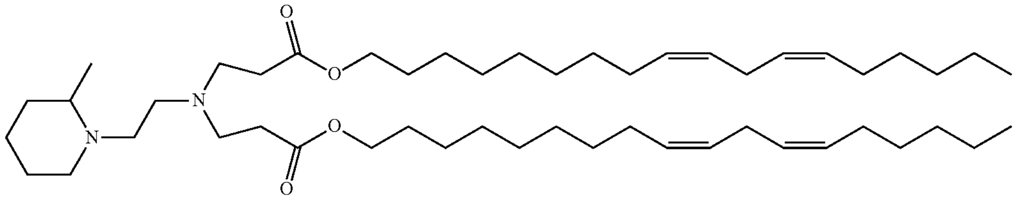 [SMILES: CCCCC/C=C\C/C=C\CCCCCCCCOC(=O)CCN(CCC(=O)OCCCCCCCC/C=C\C/C=C\CCCCC)CCN1CCCCC1C] | 9.4<br>5.99 | 9.45<br>3.63 | A |
| 12. | 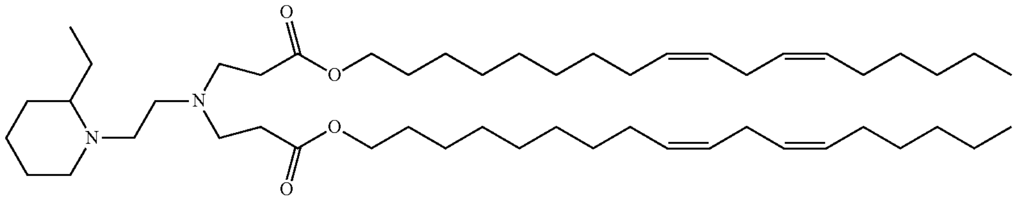 [SMILES: CCCCC/C=C\C/C=C\CCCCCCCCOC(=O)CCN(CCC(=O)OCCCCCCCC/C=C\C/C=C\CCCCC)CCN1CCCCC1CC] | 9.37<br>5.99 | 9.45<br>3.63 | A |
| 13. | 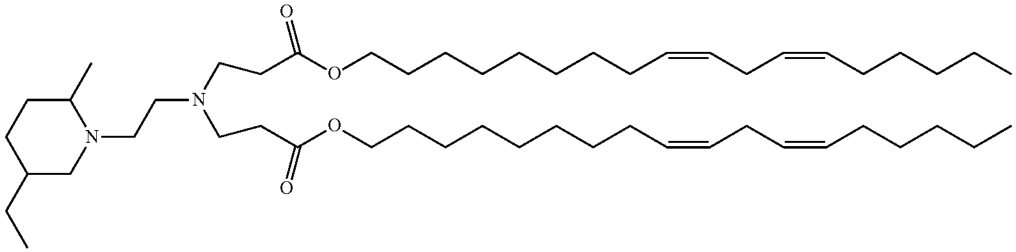 [SMILES: CCCCC/C=C\C/C=C\CCCCCCCCOC(=O)CCN(CCC(=O)OCCCCCCCC/C=C\C/C=C\CCCCC)CCN1CC(CC)CCC1C] | 9.44<br>5.99 | 9.45<br>3.63 | A |

TABLE 10-continued
| No | Lipid structure | pKa-Classic | pKa-Galas | Method |
|---|---|---|---|---|
| 14. | 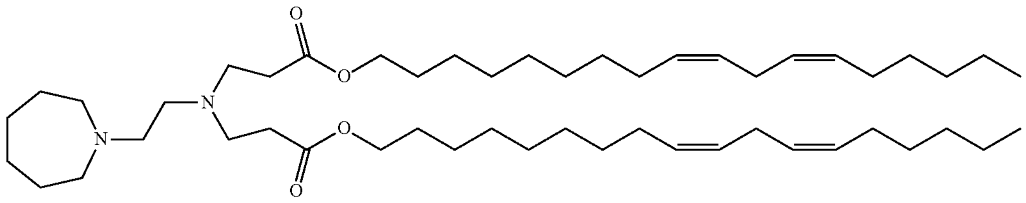 [SMILES: CCCCC/C=C\C/C=C\CCCCCCCCOC(=O)CCN(CCC(=O)OCCCCCCCC/C=C\C/C=C\CCCCC)CCN1CCCCCC1] | 8.59<br>5.91 | 9.05<br>3.63 | A |
| 15. | 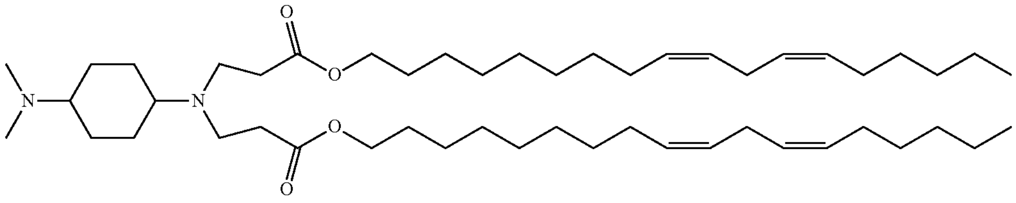 [SMILES: CCCCC/C=C\C/C=C\CCCCCCCCOC(=O)CCN(CCC(=O)OCCCCCCCC/C=C\C/C=C\CCCCC)C1CCC(N(C)C)CC1] | 10.67<br>6.32 | 9.86<br>6.38 | A |
| 16. | 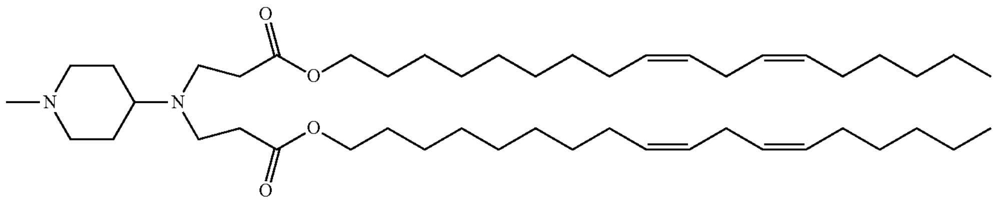 [SMILES: CCCCC/C=C\C/C=C\CCCCCCCCOC(=O)CCN(CCC(=O)OCCCCCCCC/C=C\C/C=C\CCCCC)C1CCN(C)CC1] | 8.86<br>3.32 | 9.71<br>4.7 | A |
| 17. | 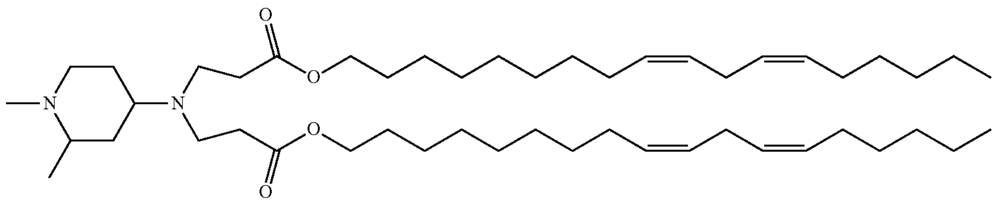 [SMILES: CCCCC/C=C\C/C=C\CCCCCCCCOC(=O)CCN(CCC(=O)OCCCCCCCC/C=C\C/C=C\CCCCC)C1CCN(C)C(C)C1] | 9.34<br>3.33 | 9.71<br>4.7 | A |
| 18. | 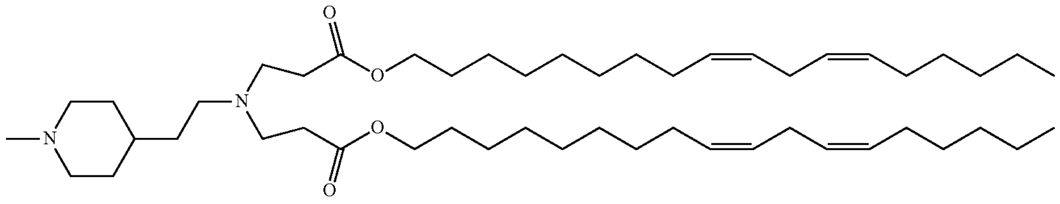 [SMILES: CCCCC/C=C\C/C=C\CCCCCCCCOC(=O)CCN(CCC(=O)OCCCCCCCC/C=C\C/C=C\CCCCC)CCN1CCN(C)CC1] | 9.49<br>7.54 | 9.87<br>6.93 | A |

TABLE 10-continued
| No | Lipid structure | pKa-Classic | pKa-Galas | Method |
|---|---|---|---|---|
| 19. | 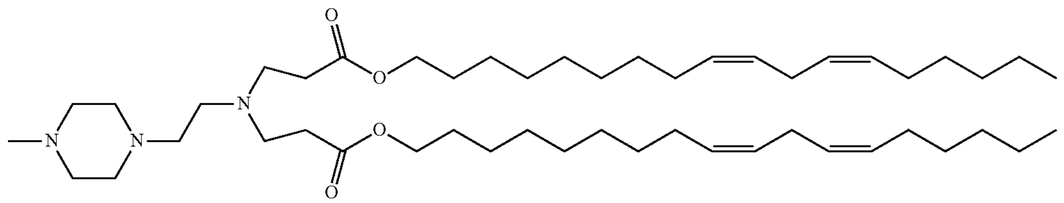 | 7.63<br>7.33<br>2.38 | 7.97<br>5.4<br>0.85 | A |
| 20. | 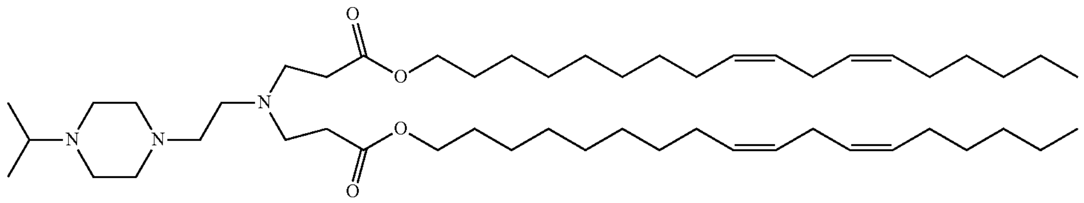 [SMILES: CCCCC/C=C\C/C=C\CCCCCCCCOC(=O)CCN(CCC(=O)OCCCCCCCC/C=C\C/C=C\CCCCC)CCN1CCN(C(C)C)CC1] | 8.04<br>7.33<br>2.33 | 8.37<br>5.42<br>0.86 | A |
| 21. | 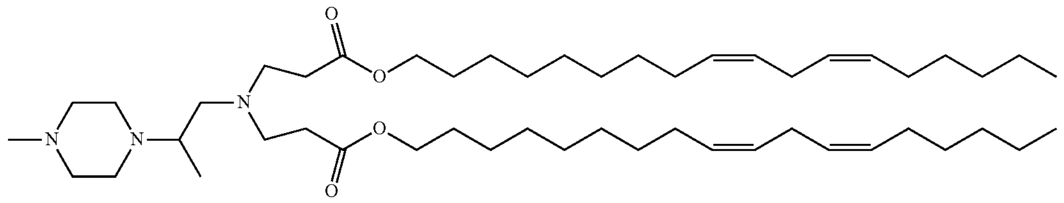 [SMILES: CCCCC/C=C\C/C=C\CCCCCCCCOC(=O)CCN(CCC(=O)OCCCCCCCC/C=C\C/C=C\CCCCC)CC(C)N1CCN(C)CC1] | 7.68<br>7.26<br>2.46 | 7.97<br>5.4<br>0.85 | A |
| 22. | 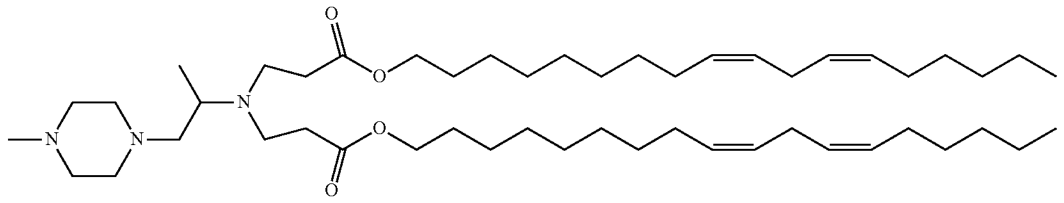 [SMILES: CCCCC/C=C\C/C=C\CCCCCCCCOC(=O)CCN(CCC(=O)OCCCCCCCC/C=C\C/C=C\CCCCC)C(C)CN1CCN(C)CC1] | 7.63<br>7.41<br>2.72 | 7.97<br>5.4<br>0.85 | A |
| 23. | 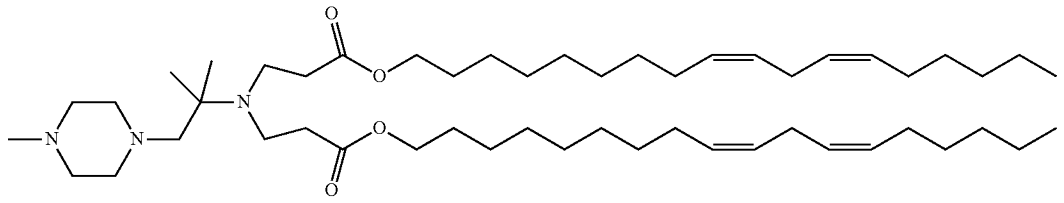 [SMILES: CCCCC/C=C\C/C=C\CCCCCCCCOC(=O)CCN(CCC(=O)OCCCCCCCC/C=C\C/C=C\CCCCC)C(C)(C)CN1CCN(C)CC1] | 8.88<br>7.49<br>2.66 | 7.97<br>5.4<br>0.85 | A |

TABLE 10-continued
| No | Lipid structure | pKa-Classic | pKa-Galas | Method |
|---|---|---|---|---|
| 24. | 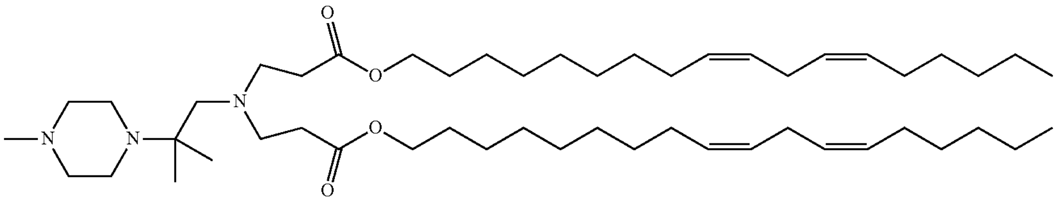 [SMILES: CCCCC/C=C\C/C=C\CCCCCCCCOC(=O)CCN(CCC(=O)OCCCCCCCC/C=C\C/C=C\CCCCC)CC(C)(C)N1CCN(C)CC1] | 8.97<br>7.5<br>2.54 | 7.97<br>5.4<br>0.85 | A |
| 25. | 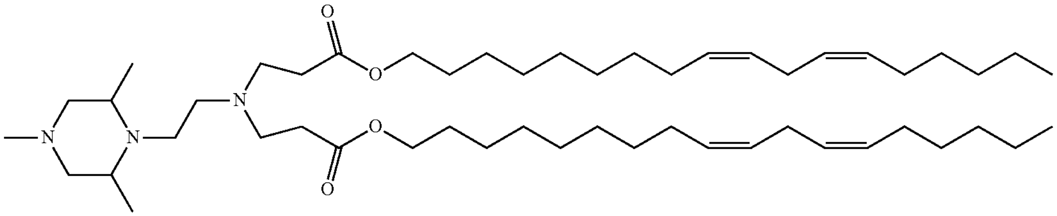 [SMILES: CCCCC/C=C\C/C=C\CCCCCCCCOC(=O)CCN(CCC(=O)OCCCCCCCC/C=C\C/C=C\CCCCC)CCN1C(C)CN(C)CC1C] | 8.46<br>7.33<br>2.5 | 7.97<br>5.4<br>0.85 | A |
| 26. | 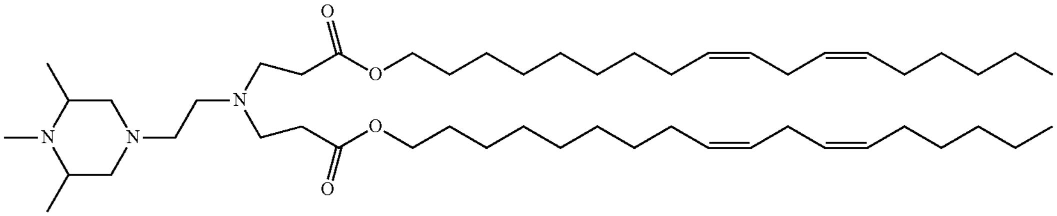 [SMILES: CCCCC/C=C\C/C=C\CCCCCCCCOC(=O)CCN(CCC(=O)OCCCCCCCC/C=C\C/C=C\CCCCC)CCN1CC(C)N(C)C(C)C1] | 8.61<br>7.33<br>2.45 | 7.97<br>5.4<br>0.85 | A |
| 27. | 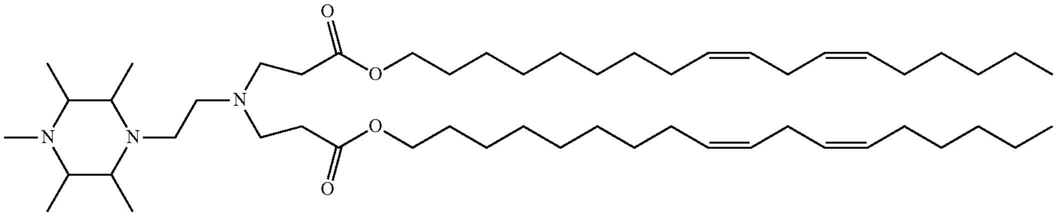 [SMILES: CCCCC/C=C\C/C=C\CCCCCCCCOC(=O)CCN(CCC(=O)OCCCCCCCC/C=C\C/C=C\CCCCC)CCN1C(C)C(C)N(C)C(C)C1C] | 8.67<br>7.33<br>2.58 | 7.97<br>5.4<br>0.85 | A |

TABLE 10-continued
| No | Lipid structure | pKa-Classic | pKa-Galas | Method |
|---|---|---|---|---|
| 28. | 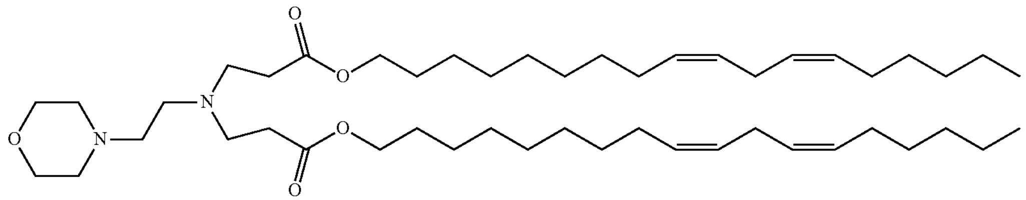 [SMILES: CCCCC/C=C\C/C=C\CCCCCCCCOC(=O)CCN(CCC(=O)OCCCCCCCC/C=C\C/C=C\CCCCC)CCN1CCOCC1] | 7.42<br>5.46 | 6.39<br>3.27 | A |
| 29. | 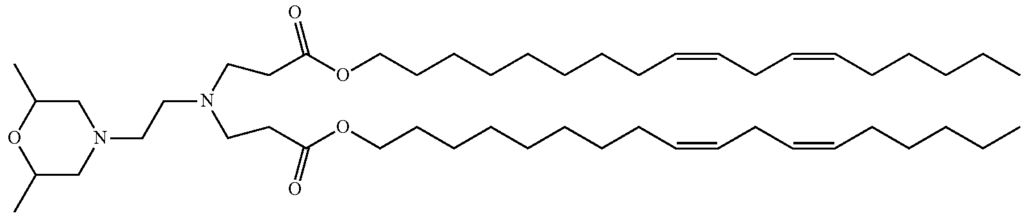 [SMILES: CCCCC/C=C\C/C=C\CCCCCCCCOC(=O)CCN(CCC(=O)OCCCCCCCC/C=C\C/C=C\CCCCC)CCN1CC(C)OC(C)C1] | 7.45<br>5.49 | 6.39<br>3.27 | A |
| 30. | 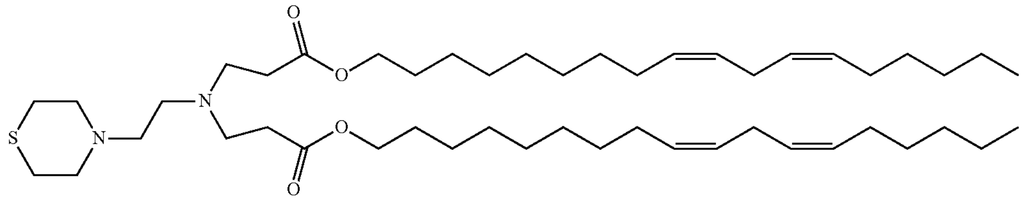 [SMILES: CCCCC/C=C\C/C=C\CCCCCCCCOC(=O)CCN(CCC(=O)OCCCCCCCC/C=C\C/C=C\CCCCC)CCN1CCSCC1] | 7.45<br>3.86 | 7.57<br>3.49 | A |
| 31. | 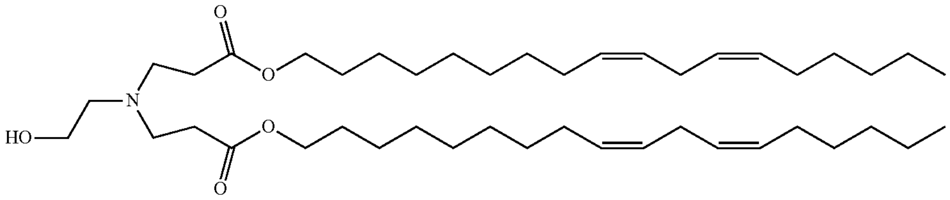 [SMILES: CCCCC/C=C\C/C=C\CCCCCCCCOC(=O)CCN(CCO)CCC(=O)OCCCCCCCC/C=C\C/C=C\CCCCC] | 6.9 | 6.4 | A |

TABLE 10-continued
| No | Lipid structure | pKa-Classic | pKa-Galas | Method |
|---|---|---|---|---|
| 32. | 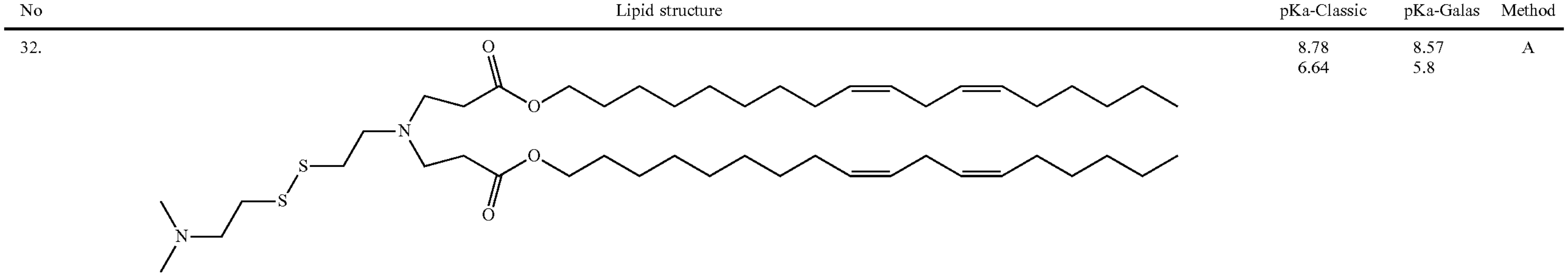 | 8.78<br>6.64 | 8.57<br>5.8 | A |
| 33. | 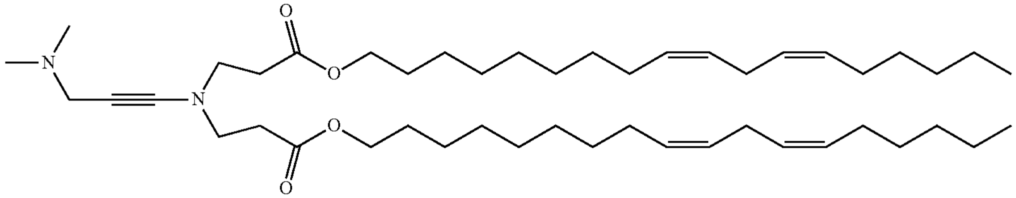 [SMILES: CCCCC/C=C\C/C=C\CCCCCCCCOC(=O)CCN(C#CCN(C)C)CCC(=O)OCCCCCCCC/C=C\C/C=C\CCCCC] | 5.05<br>3.12 | 7.84<br>5.32 | A |
| 34. | 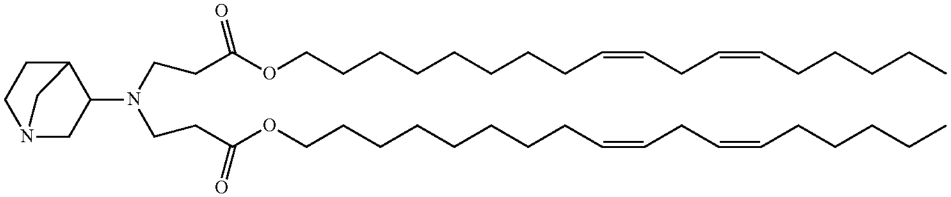 [SMILES: CCCCC/C=C\C/C=C\CCCCCCCCOC(=O)CCN(CCC(=O)OCCCCCCCC/C=C\C/C=C\CCCCC)C1CN2CCC1C2] | 10.18<br>3.98 | 9.35<br>3.63 | A |
| 35. | 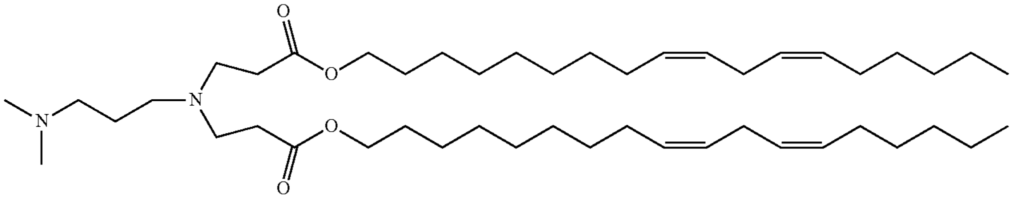 [SMILES: CCCCC/C=C\C/C=C\CCCCCCCCOC(=O)CCN(CCCN(C)C)CCC(=O)OCCCCCCCC/C=C\C/C=C\CCCCC] | 9.54<br>5.69 | 9.54<br>5.45 | A |

TABLE 10-continued
| No | Lipid structure | pKa-Classic | pKa-Galas | Method |
|---|---|---|---|---|
| 36. | 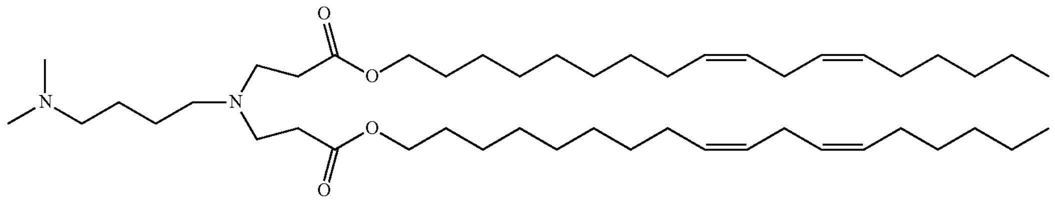 [SMILES: CCCCC/C=C\C/C=C\CCCCCCCCOC(=O)CCN(CCCCN(C)C)CCC(=O)OCCCCCCCC/C=C\C/C=C\CCCCC] | 9.69<br>6.84 | 9.89<br>6.66 | A |
| 37. | 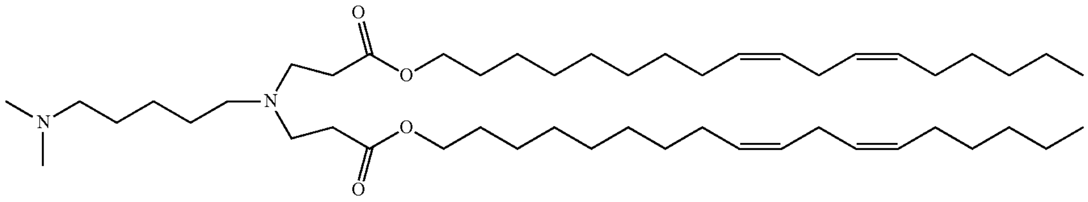 [SMILES: CCCCC/C=C\C/C=C\CCCCCCCCOC(=O)CCN(CCCCCN(C)C)CCC(=O)OCCCCCCCC/C=C\C/C=C\CCCCC] | 9.74<br>7.42 | 10.02<br>7.12 | A |
| 38. | 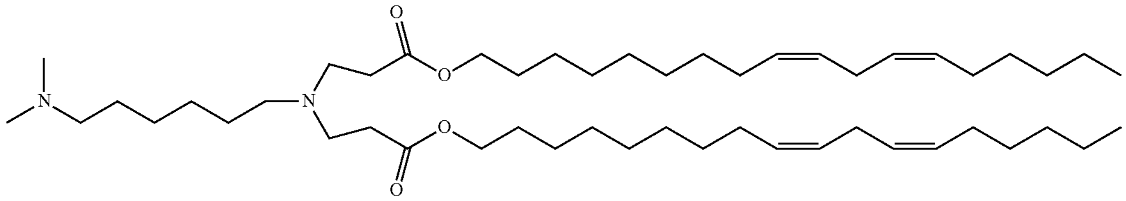 [SMILES: CCCCC/C=C\C/C=C\CCCCCCCCOC(=O)CCN(CCCCCCN(C)C)CCC(=O)OCCCCCCCC/C=C\C/C=C\CCCCC] | 9.76<br>7.65 | 10.07<br>7.36 | A |
| 39. | 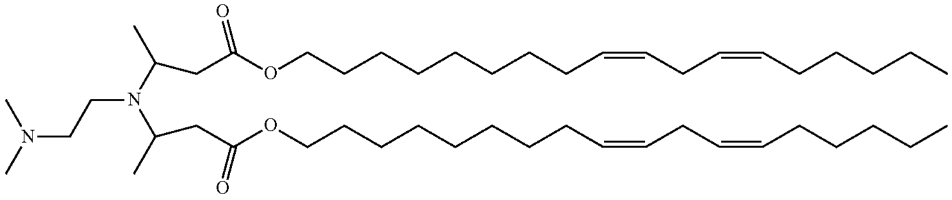 [SMILES: CCCCC/C=C\C/C=C\CCCCCCCCOC(=O)CC(C)N(CCN(C)C)C(C)CC(=O)OCCCCCCCC/C=C\C/C=C\CCCCC] | 8.44<br>5.77 | 8.85<br>3.63 | A |
| 40. | 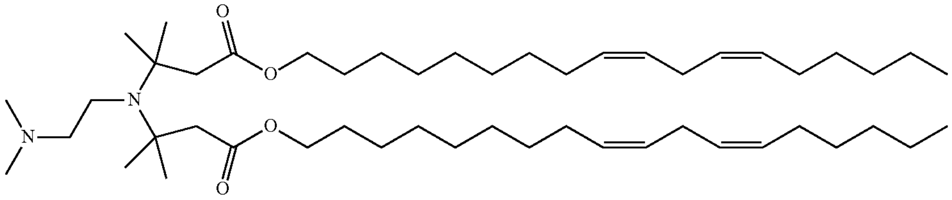 [SMILES: CCCCC/C=C\C/C=C\CCCCCCCCOC(=O)CC(C)(C)N(CCN(C)C)C(C)(C)CC(=O)OCCCCCCCC/C=C\C/C=C\CCCCC] | 8.57<br>5.78 | 8.85<br>3.63 | A |

TABLE 10-continued
| No | Lipid structure | pKa-Classic | pKa-Galas | Method |
|---|---|---|---|---|
| 41. | 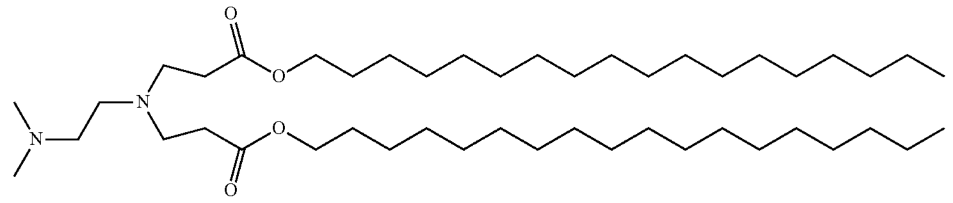 [SMILES: CCCCCCCCCCCCCCCCCCOC(=O)CCN(CCC(=O)OCCCCCCCCCCCCCCCCCC)CCN(C)C] | 8.43<br>3.9 | 8.85<br>3.63 | A |
| 42. | 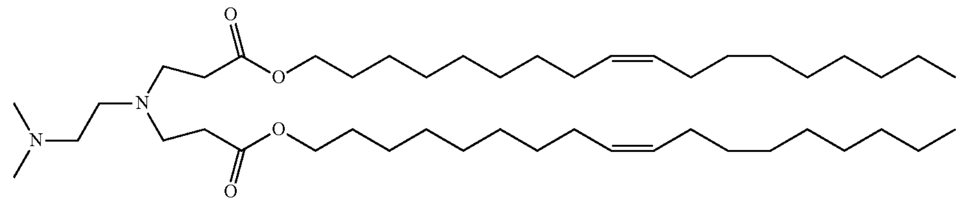 [SMILES: CCCCCCCC/C=C\CCCCCCCCOC(=O)CCN(CCC(=O)OCCCCCCCC/C=C\CCCCCCCC)CCN(C)C] | 8.43<br>3.9 | 8.85<br>3.63 | A |
| 43. | 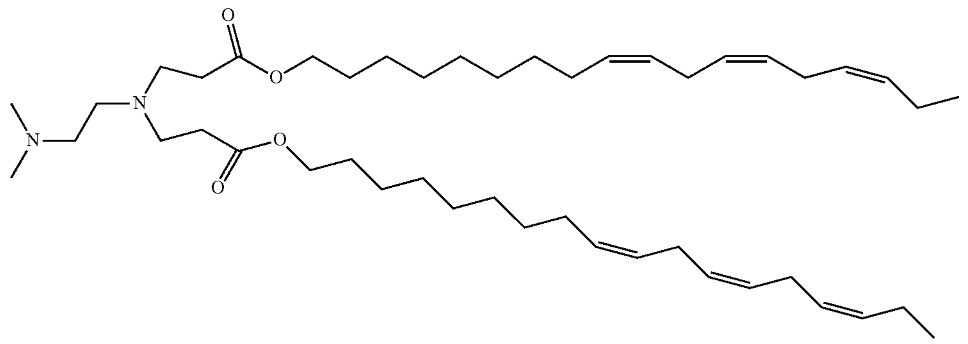 [SMILES: CC/C=C\C/C=C\C/C=C\CCCCCCCCOC(=O)CCN(CCC(=O)OCCCCCCCC/C=C\C/C=C\C/C=C\CC)CCN(C)C] | 8.43<br>3.9 | 8.85<br>3.63 | A |
| 44. | 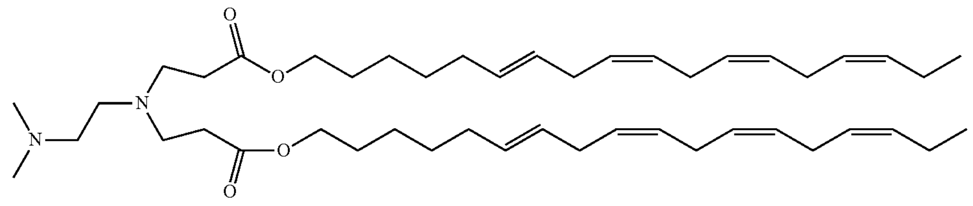 [SMILES: CC/C=C\C/C=C\C/C=C\C/C=C/CCCCCOC(=O)CCN(CCC(=O)OCCCCC/C=C/C/C=C\C/C=C\C/C=C\CC)CCN(C)C] | 8.43<br>3.9 | 8.85<br>3.63 | A |

TABLE 10-continued
| No | Lipid structure | pKa-Classic | pKa-Galas | Method |
|---|---|---|---|---|
| 45. | 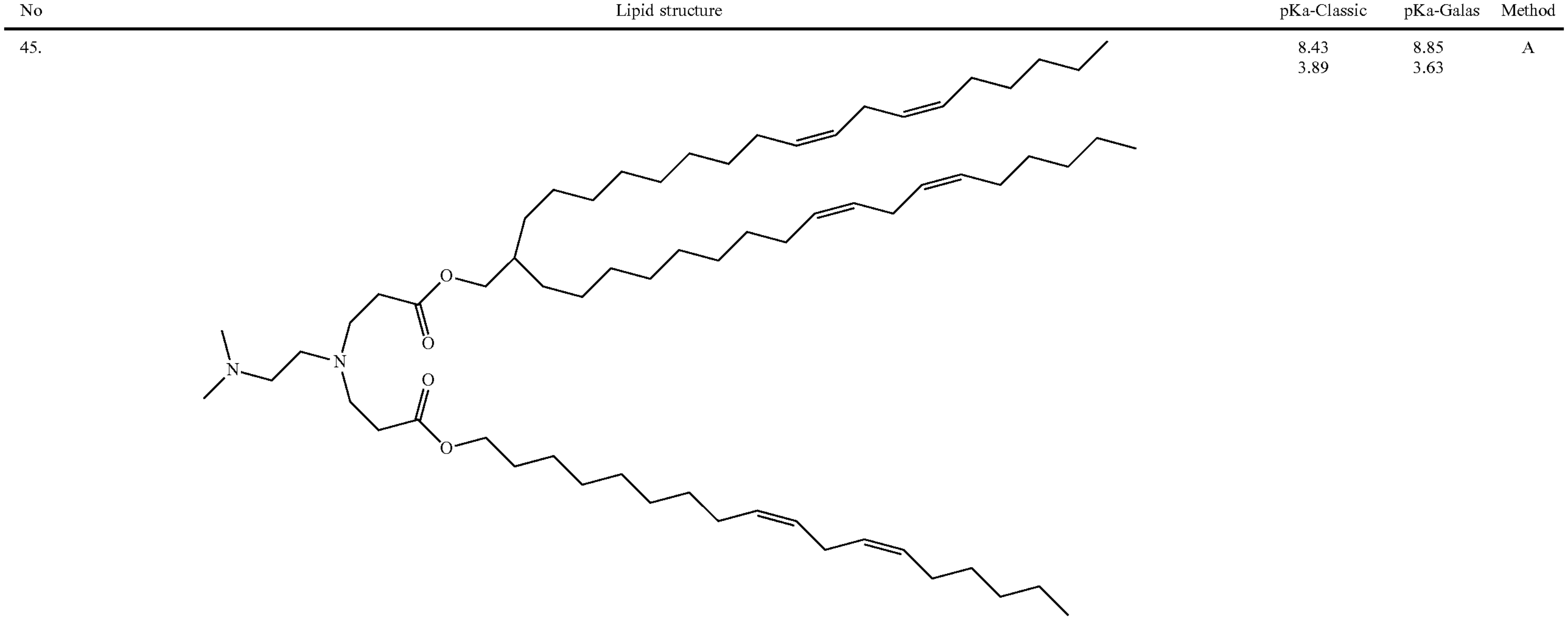 | 8.43<br>3.89 | 8.85<br>3.63 | A |

TABLE 10-continued
| No | Lipid structure | pKa-Classic | pKa-Galas | Method |
|---|---|---|---|---|
| 46. | 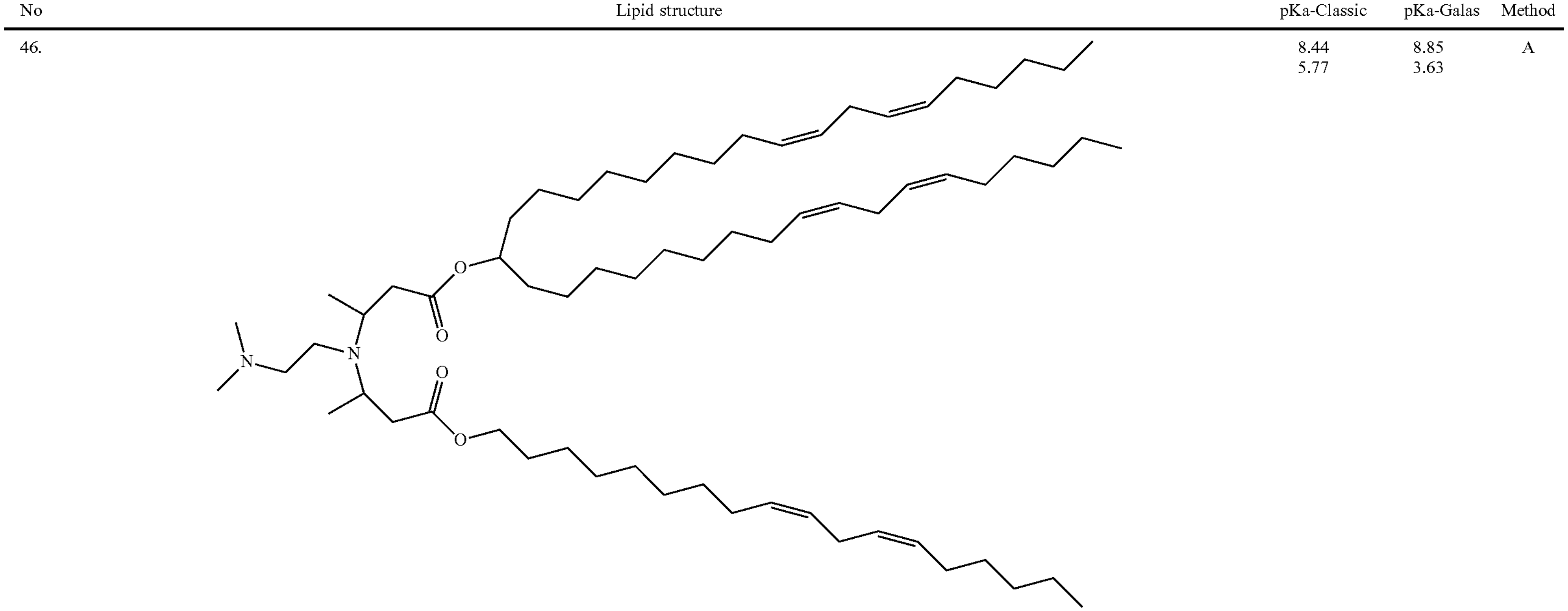 | 8.44<br>5.77 | 8.85<br>3.63 | A |

TABLE 10-continued
| No | Lipid structure | pKa-Classic | pKa-Galas | Method |
|---|---|---|---|---|
| 47. | 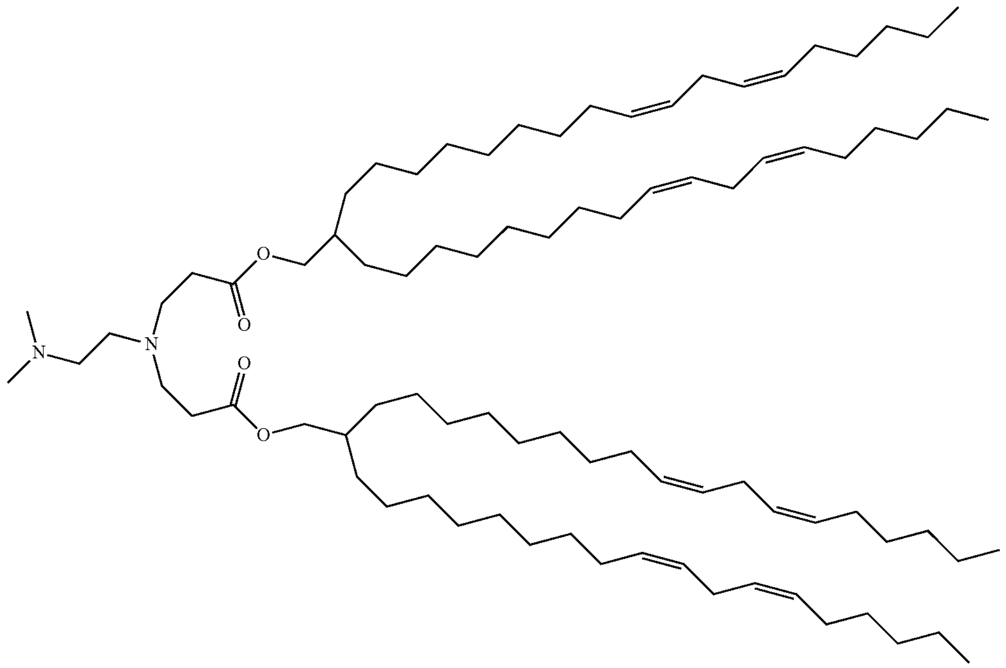 [SMILES: CCCCC/C=C\C/C=C\CCCCCCCCC(CCCCCCCC/C=C\C/C=C\CCCCC)COC(=O)CCN(CCC(=O)OCC(CCCCCCCC/C=C\C/C=C\CCCCC)CCCCCCCC/C=C\C/C=C\CCCCC)CCN(C)C] | 8.43<br>3.88 | 8.85<br>3.63 | A |
| 48. | 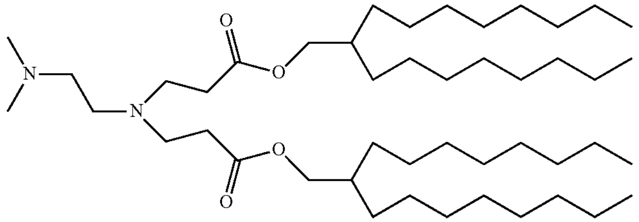 [SMILES: CCCCCCCCC(CCCCCCCC)COC(=O)CCN(CCC(=O)OCC(CCCCCCCC)CCCCCCCC)CCN(C)C] | 8.43<br>3.88 | 8.85<br>3.63 | A |

TABLE 10-continued
| No | Lipid structure | pKa-Classic | pKa-Galas | Method |
|---|---|---|---|---|
| 49. | 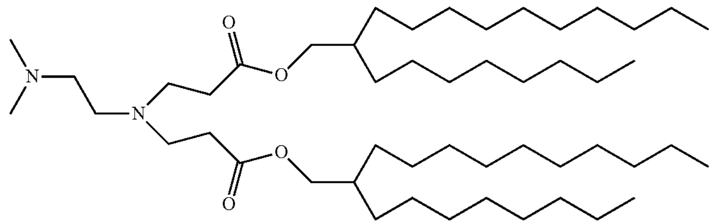 [SMILES: CCCCCCCCCCC(CCCCCCCC)COC(=O)CCN(CCC(=O)OCC(CCCCCCCC)CCCCCCCCCC)CCN(C)C] | 8.43<br>3.88 | 8.85<br>3.63 | A |
| 50. | 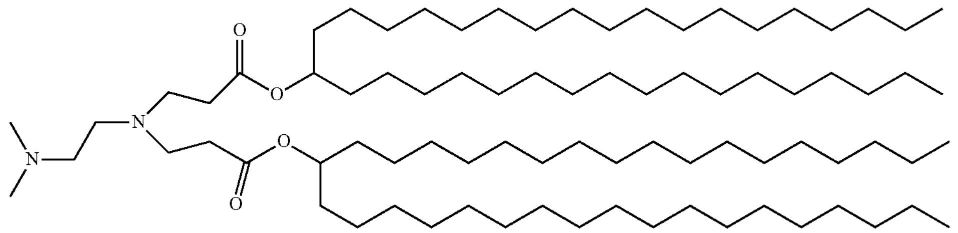 [SMILES: CCCCCCCCCCCCCCCCCCC(CCCCCCCCCCCCCCCCC)OC(=O)CCN(CCC(=O)OC(CCCCCCCCCCCCCCCCC)CCCCCCCCCCCCCCCCCC)CCN(C)C] | 8.43<br>3.86 | 8.85<br>3.63 | A |
| 51. | 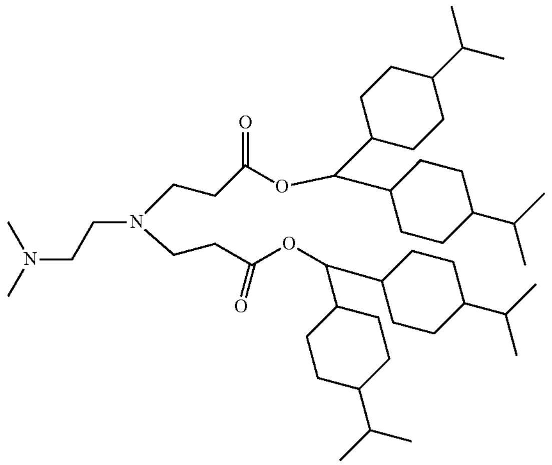 [SMILES: CC(C)C1CCC(C(OC(=O)CCN(CCC(=O)OC(C2CCC(C(C)C)CC2)C2CCC(C(C)C)CC2)CCN(C)C)C2CCC(C(C)C)CC2)CC1] | 8.43<br>3.83 | 8.85<br>3.63 | A |

TABLE 10-continued
| No | Lipid structure | pKa-Classic | pKa-Galas | Method |
| --- | --- | --- | --- | --- |
| 52. | 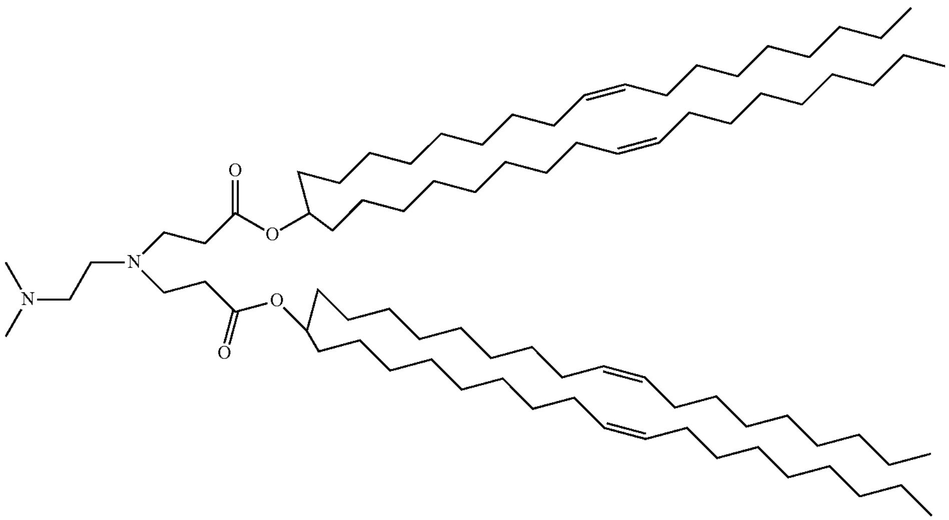 [SMILES: CCCCCCCC/C=C\CCCCCCCCC(CCCCCCCC/C=C\CCCCCCCC)OC(=O)CCN(CCC(=O)OC(CCCCCCCC/C=C\CCCCCCCC)CCCCCCCC/C=C\CCCCCCCC)CCN(C)C] | 8.43<br>3.86 | 8.85<br>3.63 | A |
| 53. | 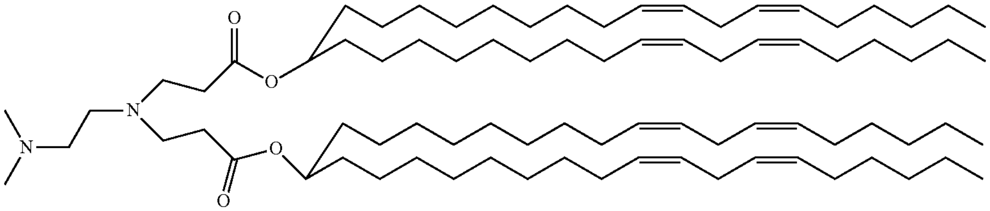 [SMILES: CCCCC/C=C\C/C=C\CCCCCCCCC(CCCCCCCC/C=C\C/C=C\CCCCC)OC(=O)CCN(CCC(=O)OC(CCCCCCCC/C=C\C/C=C\CCCCC)CCCCCCCC/C=C\C/C=C\CCCCC)CCN(C)C] | 8.43<br>3.86 | 8.85<br>3.63 | A |
| 54. | 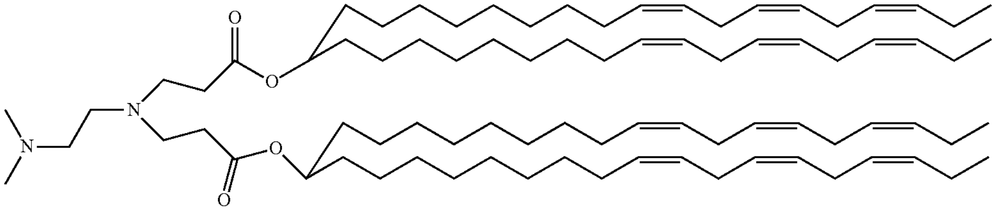 [SMILES: CC/C=C\C/C=C\C/C=C\CCCCCCCCC(CCCCCCCC/C=C\C/C=C\C/C=C\CC)OC(=O)CCN(CCC(=O)OC(CCCCCCCC/C=C\C/C=C\C/C=C\CC)CCCCCCCC/C=C\C/C=C\C/C=C\CC)CCN(C)C] | 8.43<br>3.86 | 8.85<br>3.63 | A |

TABLE 10-continued
| No | Lipid structure | pKa-Classic | pKa-Galas | Method |
|---|---|---|---|---|
| 55. | 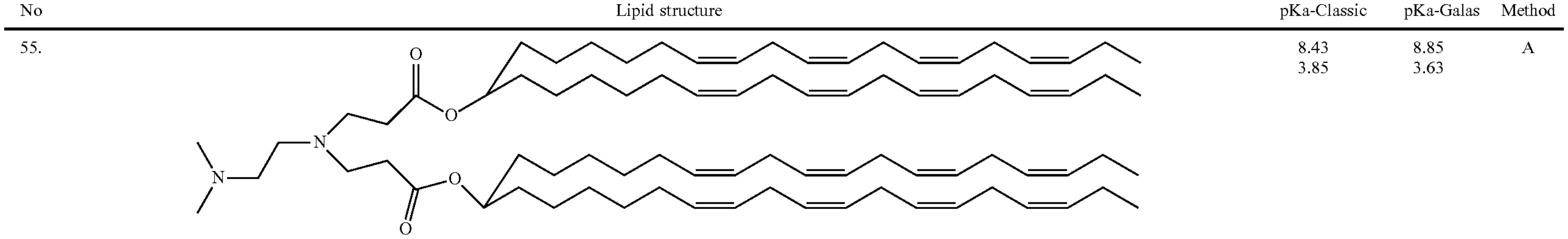 | 8.43<br>3.85 | 8.85<br>3.63 | A |
| 56. | 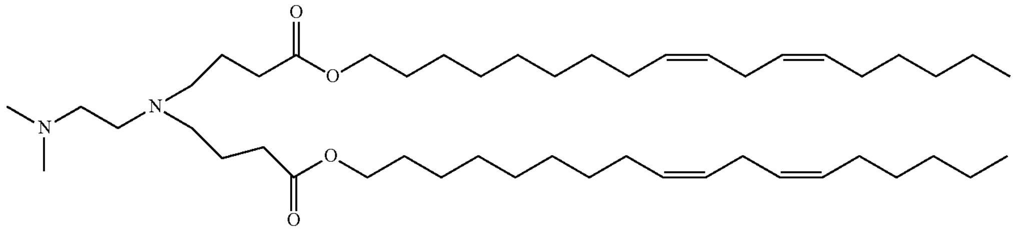 [SMILES: CCCCC/C=C\C/C=C\CCCCCCCCOC(=O)CCCN(CCCC(=O)OCCCCCCCC/C=C\C/C=C\CCCCC)CCN(C)C] | 8.51<br>5.13 | 8.94<br>5.45 | B |
| 57. | 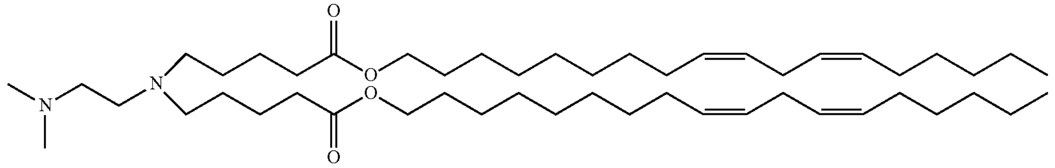 [SMILES: CCCCC/C=C\C/C=C\CCCCCCCCOC(=O)CCCCN(CCCCC(=O)OCCCCCCCC/C=C\C/C=C\CCCCC)CCN(C)C] | 8.54<br>5.62 | 9.23<br>6.08 | B |
| 58. | 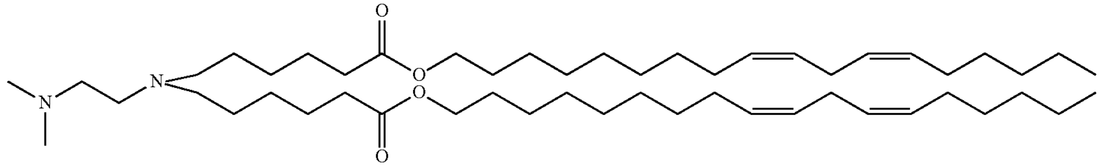 [SMILES: CCCCC/C=C\C/C=C\CCCCCCCCOC(=O)CCCCCN(CCCCCC(=O)OCCCCCCCC/C=C\C/C=C\CCCCC)CCN(C)C] | 8.56<br>5.82 | 9.45<br>6.22 | B |
| 59. | 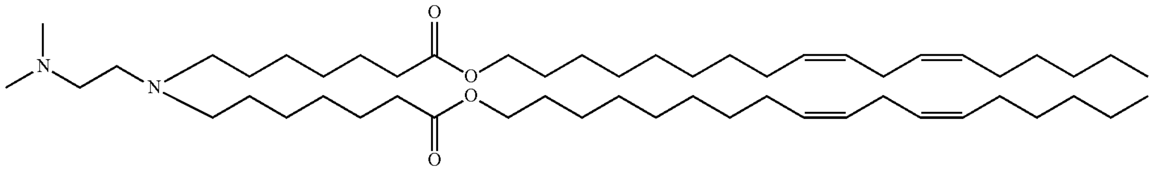 [SMILES: CCCCC/C=C\C/C=C\CCCCCCCCOC(=O)CCCCCCN(CCCCCCC(=O)OCCCCCCCC/C=C\C/C=C\CCCCC)CCN(C)C] | 8.57<br>5.88 | 9.54<br>6.26 | B |

TABLE 10-continued
| No | Lipid structure | pKa-Classic | pKa-Galas | Method |
|---|---|---|---|---|
| 60. | 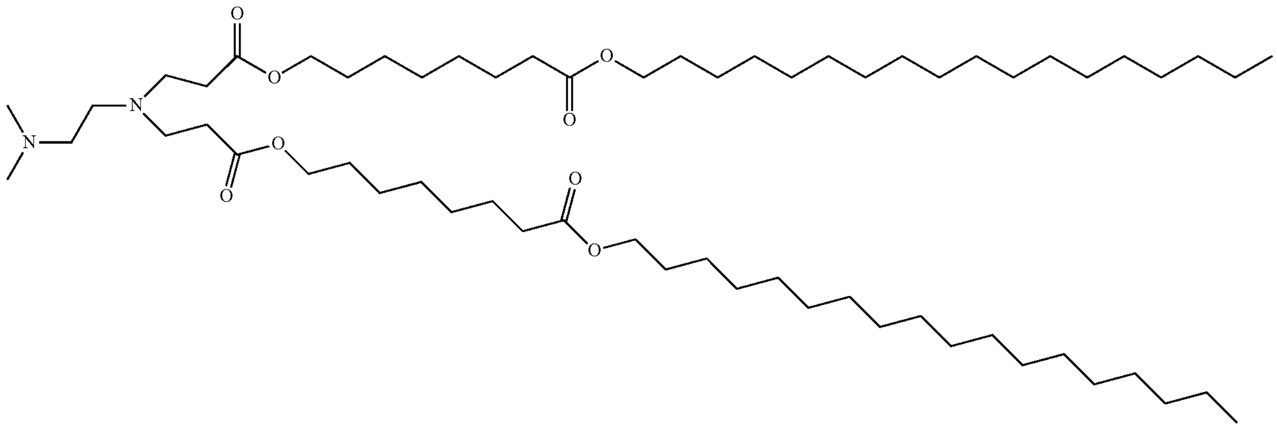 [SMILES: CCCCCCCCCCCCCCCCCCOC(=O)CCCCCCCOC(=O)CCN(CCC(=O)OCCCCCCCC(=O)OCCCCCCCCCCCCCCCCCC)CCN(C)C] | 8.43<br>3.9 | 8.85<br>3.63 | C-1 |
| 61. | 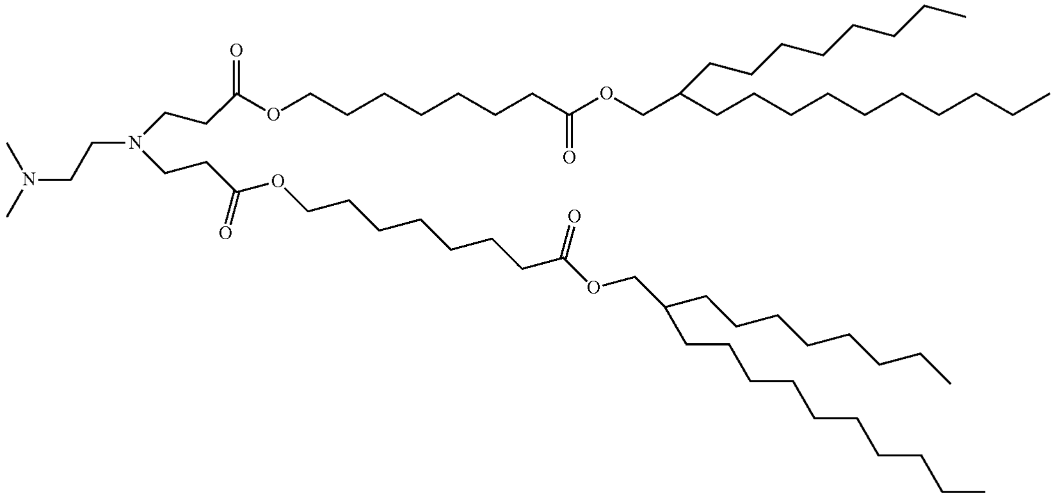 [SMILES: CCCCCCCCCCC(CCCCCCCC)COC(=O)CCCCCCCOC(=O)CCN(CCC(=O)OCCCCCCCC(=O)OCC(CCCCCCCC)CCCCCCCCCC)CCN(C)C] | 8.43<br>3.9 | 8.85<br>3.63 | C-1 |

TABLE 10-continued
| No | Lipid structure | pKa-Classic | pKa-Galas | Method |
| --- | --- | --- | --- | --- |
| 62. | 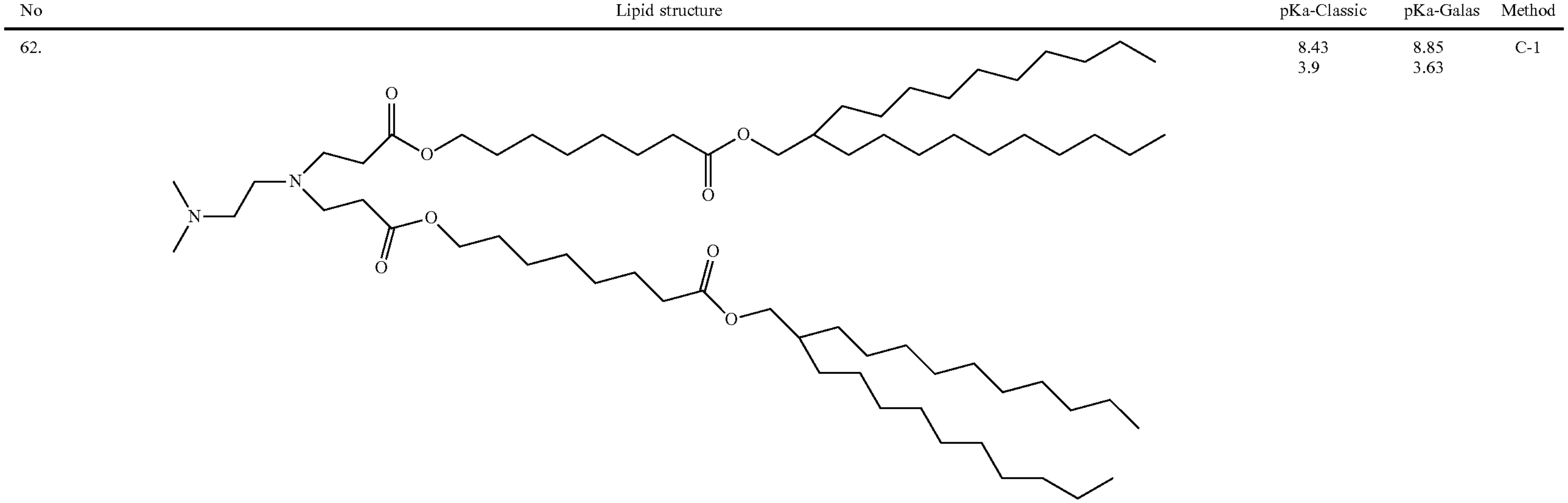 | 8.43<br>3.9 | 8.85<br>3.63 | C-1 |
| 63. | 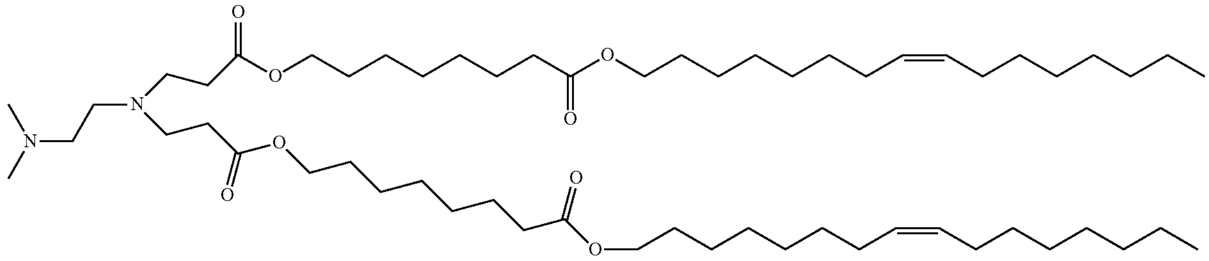 [SMILES: CCCCCCC/C=C\CCCCCCCOC(=O)CCCCCCCOC(=O)CCN(CCC(=O)OCCCCCCCC(=O)OCCCCCCC/C=C\CCCCCCC)CCN(C)C] | 8.43<br>3.9 | 8.85<br>3.63 | C-1 |

TABLE 10-continued
| No | Lipid structure | pKa-Classic | pKa-Galas | Method |
|---|---|---|---|---|
| 64. | 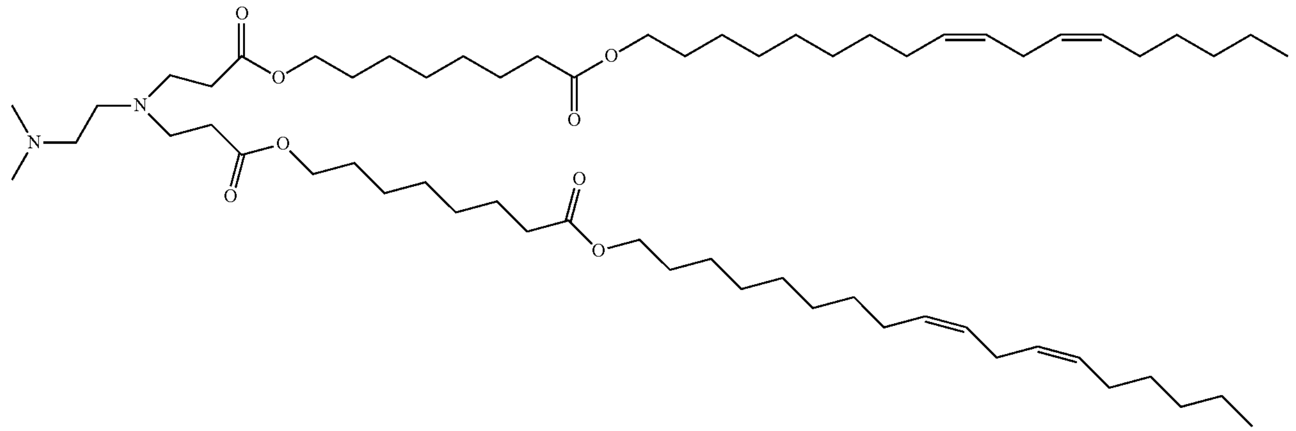 [SMILES: CCCCC/C=C\C/C=C\CCCCCCCCOC(=O)CCCCCCCOC(=O)CCN(CCC(=O)OCCCCCCCC(=O)OCCCCCCCC/C=C\C/C=C\CCCCC)CCN(C)C] | 8.43<br>3.9 | 8.85<br>3.63 | C-1 |
| 65. | 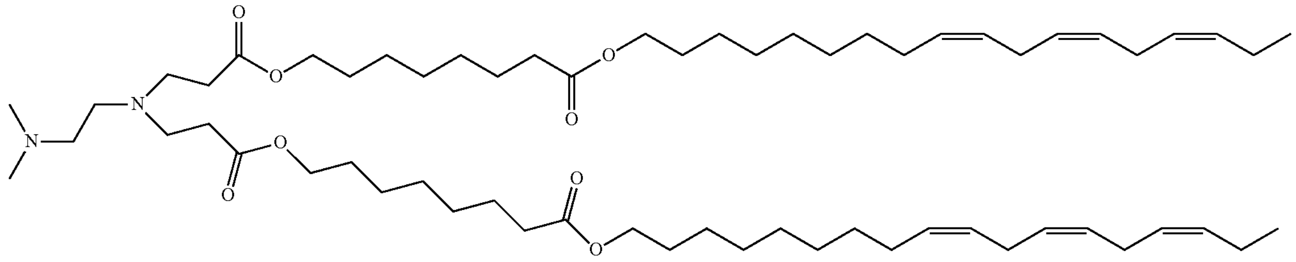 [SMILES: CC/C=C\C/C=C\C/C=C\CCCCCCCCOC(=O)CCCCCCCOC(=O)CCN(CCC(=O)OCCCCCCCC(=O)OCCCCCCCC/C=C\C/C=C\C/C=C\CC)CCN(C)C] | 8.43<br>3.9 | 8.85<br>3.63 | C-1 |
| 66. | 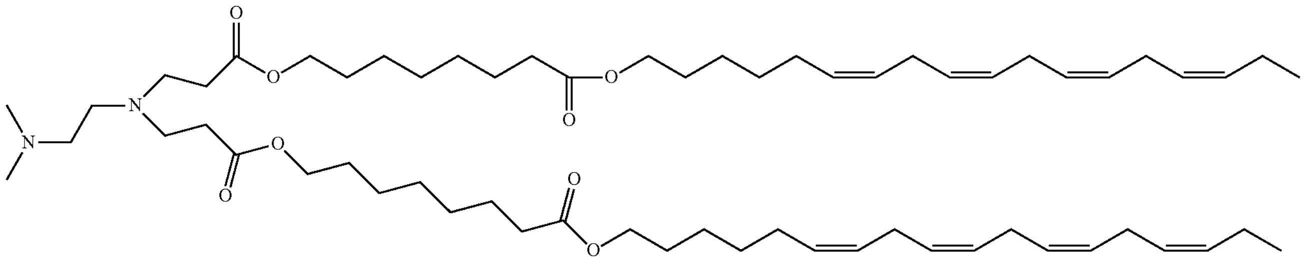 [SMILES: CC/C=C\C/C=C\C/C=C\C/C=C\CCCCCOC(=O)CCCCCCCOC(=O)CCN(CCC(=O)OCCCCCCCC(=O)OCCCCC/C=C\C/C=C\C/C=C\C/C=C\CC)CCN(C)C] | 8.43<br>3.9 | 8.85<br>3.63 | C-1 |

TABLE 10-continued
| No | Lipid structure | pKa-Classic | pKa-Galas | Method |
| --- | --- | --- | --- | --- |
| 67. | 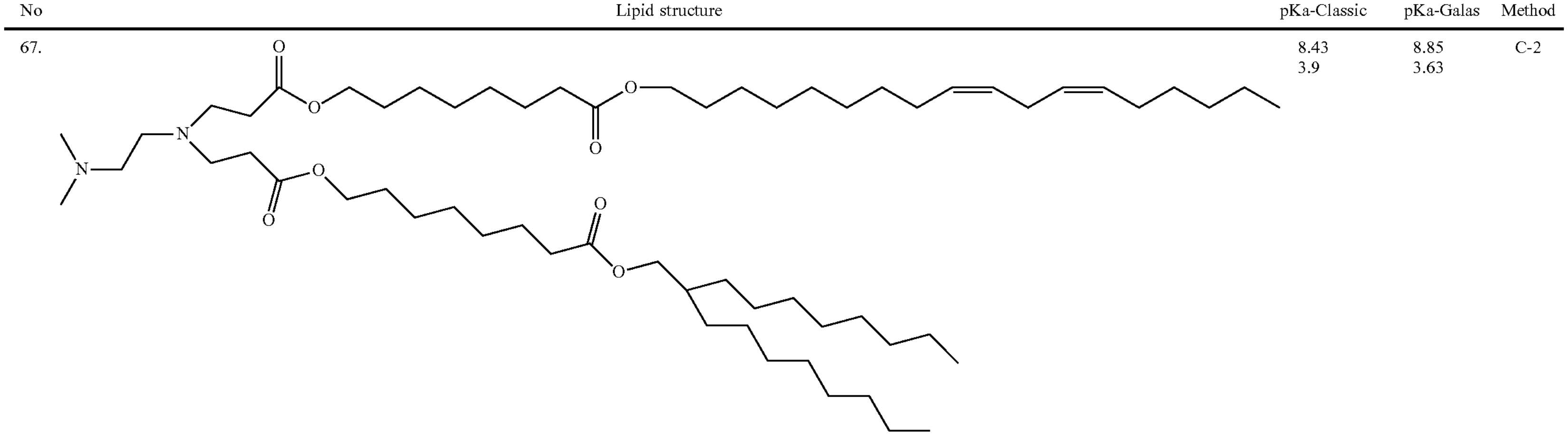 | 8.43<br>3.9 | 8.85<br>3.63 | C-2 |
| 68. | 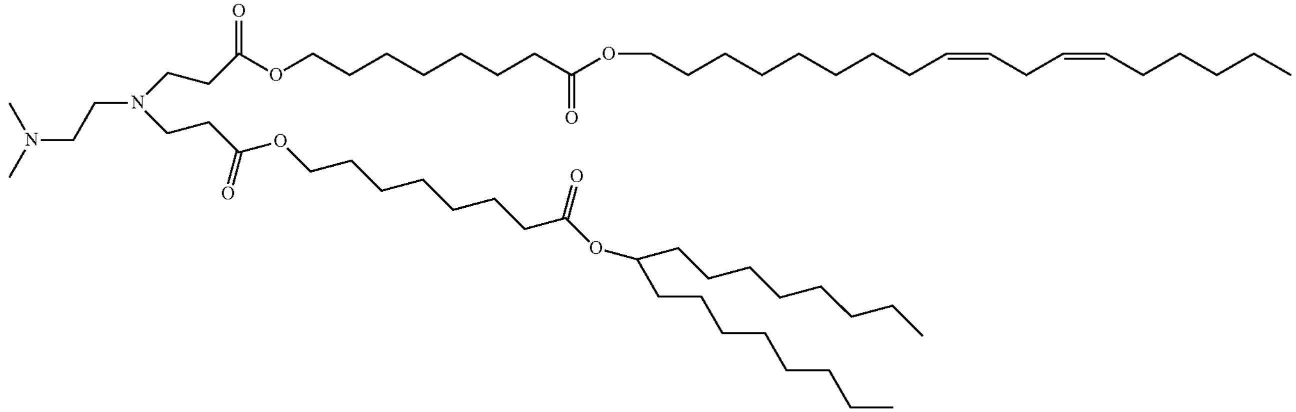 [SMILES: CCCCC/C=C\C/C=C\CCCCCCCCOC(=O)CCCCCCCOC(=O)CCN(CCC(=O)OCCCCCCCC(=O)OC(CCCCCCCC)CCCCCCCC)CCN(C)C] | 8.43<br>3.9 | 8.85<br>3.63 | C-2 |

TABLE 10-continued
| No | Lipid structure | pKa-Classic | pKa-Galas | Method |
|---|---|---|---|---|
| 69. | 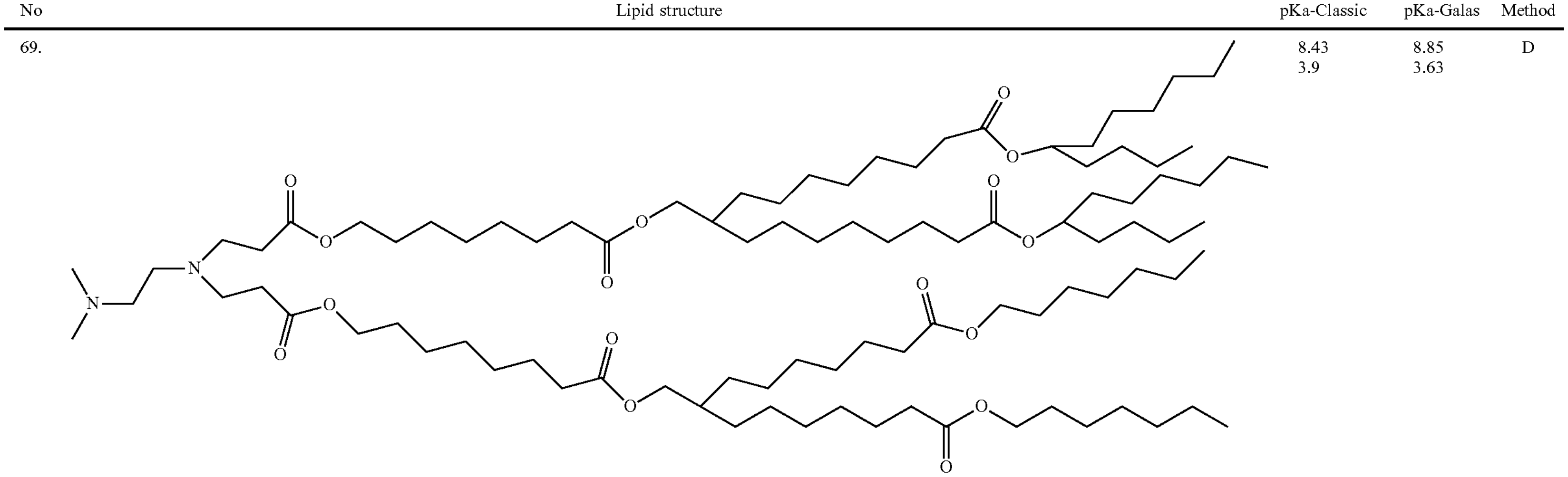 | 8.43<br>3.9 | 8.85<br>3.63 | D |
| 70. | 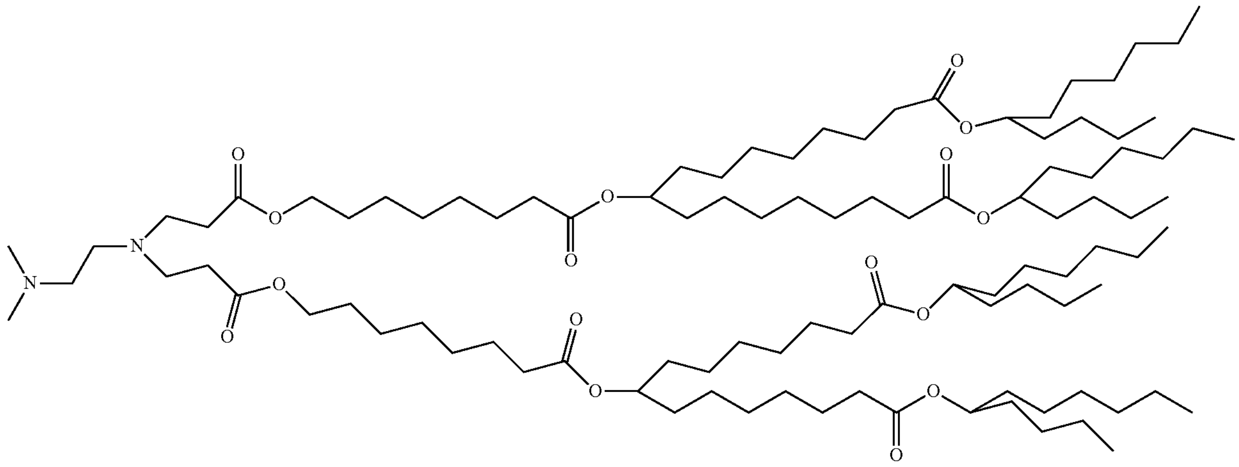 [SMILES: CCCCCCC(CCCC)OC(=O)CCCCCCCC(CCCCCCCC(=O)OC(CCCC)CCCCCC)OC(=O)CCCCCCCOC(=O)CCN(CCC(=O)OCCCCCCCC(=O)OC(CCCCCCC(=O)OC(CCCC)CCCCCC)CCCCCCC(=O)OC(CCCC)CCCCCC)CCN(C)C] | 8.43<br>3.9 | 8.85<br>3.63 | D |

TABLE 10-continued
| No | Lipid structure | pKa-Classic | pKa-Galas | Method |
|---|---|---|---|---|
| 71. | 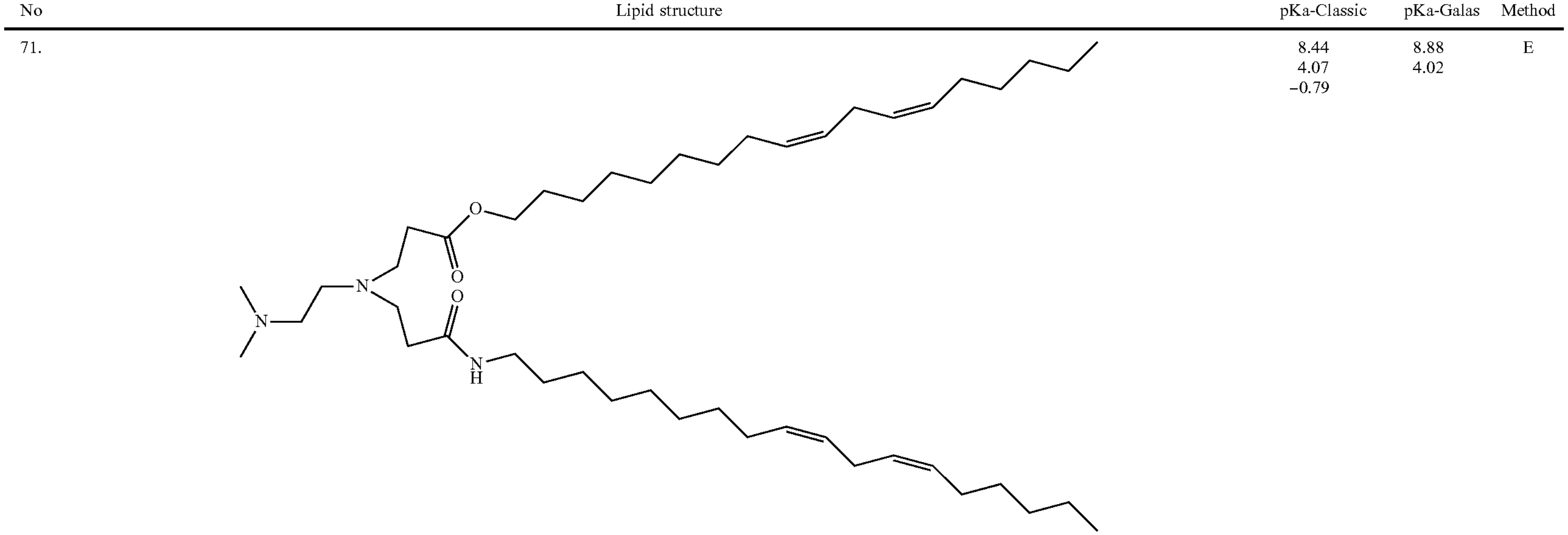 | 8.44<br>4.07<br>−0.79 | 8.88<br>4.02 | E |
| 72. | 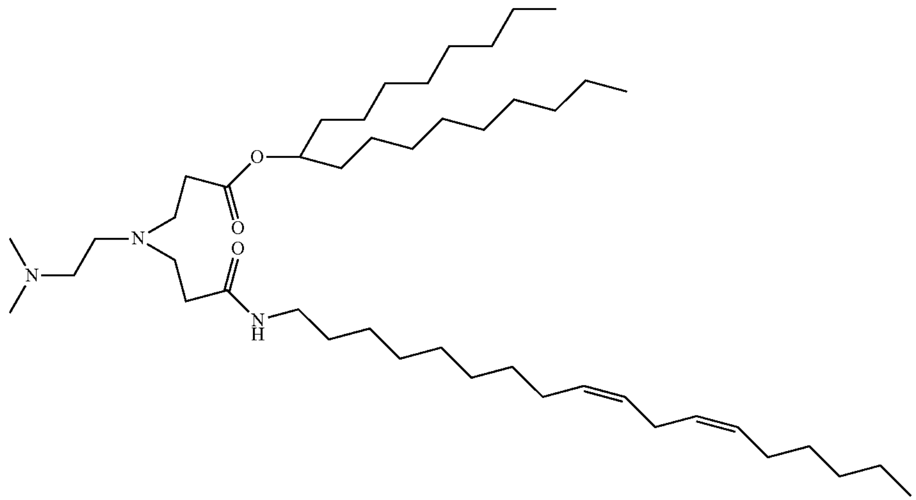 [SMILES: CCCCC/C=C\C/C=C\CCCCCCCCNC(=O)CCN(CCC(=O)OC(CCCCCCCC)CCCCCCCCC)CCN(C)C] | 8.44<br>4.05<br>−0.79 | 8.88<br>4.02 | E |

TABLE 10-continued
| No | Lipid structure | pKa-Classic | pKa-Galas | Method |
|---|---|---|---|---|
| 73. | 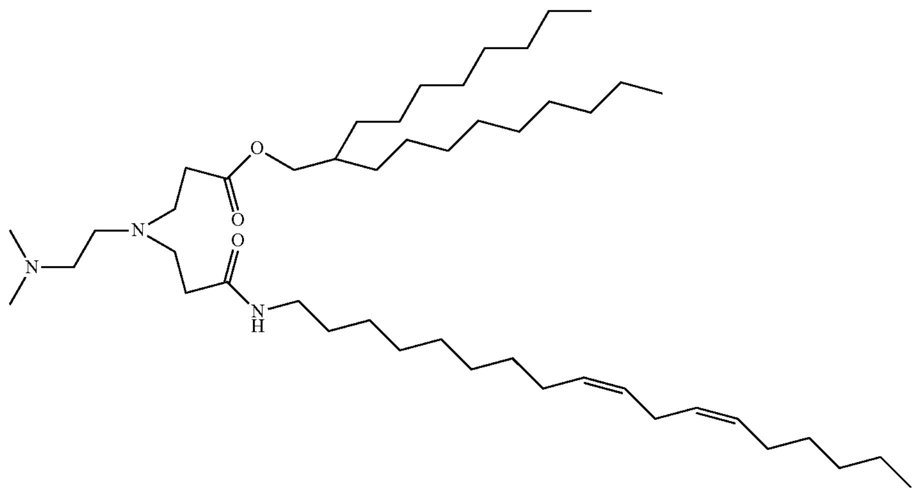 [SMILES: CCCCC/C=C\C/C=C\CCCCCCCCNC(=O)CCN(CCC(=O)OCC(CCCCCCCC)CCCCCCCCC)CCN(C)C] | 8.44<br>4.07<br>−0.79 | 8.88<br>4.02 | E |

TABLE 10-continued
| No | Lipid structure | pKa-Classic | pKa-Galas | Method |
|---|---|---|---|---|
| 74. | 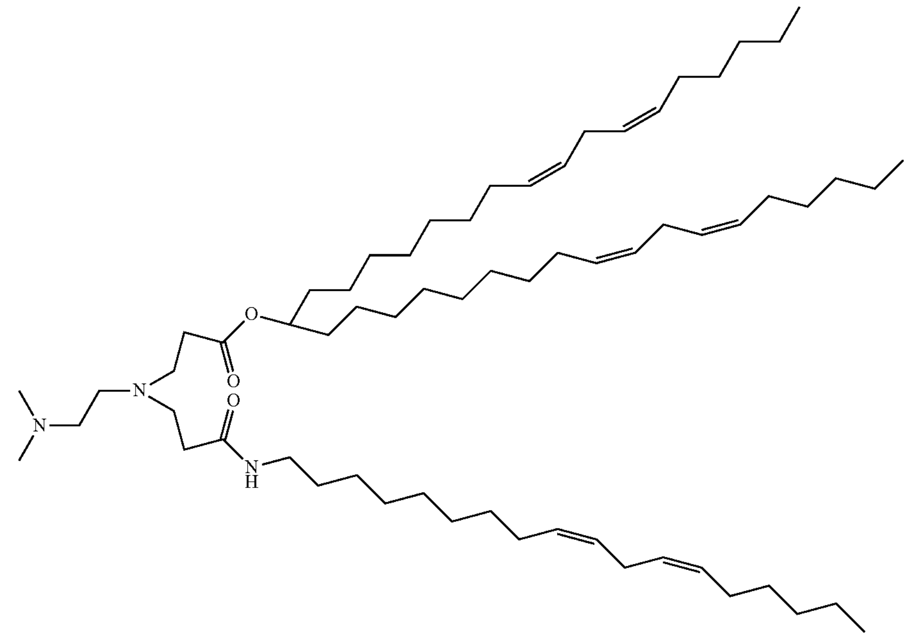 [SMILES: CCCCC/C=C\C/C=C\CCCCCCCCNC(=O)CCN(CCC(=O)OC(CCCCCCC/C=C\C/C=C\CCCCC)CCCCCCCC/C=C\C/C=C\CCCCC)CCN(C)C] | 8.44<br>4.05<br>−0.79 | 8.88<br>4.02 | E |
| 75. | 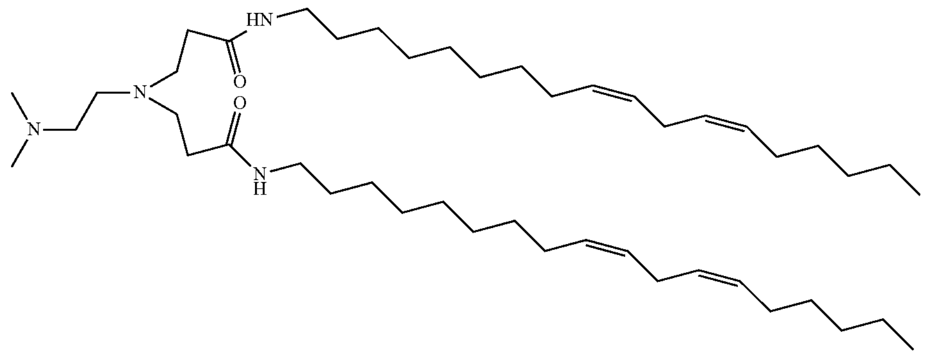 [SMILES: CCCCC/C=C\C/C=C\CCCCCCCCNC(=O)CCN(CCC(=O)NCCCCCCCC/C=C\C/C=C\CCCCC)CCN(C)C] | 8.46<br>4.25<br>−0.49 | 8.9<br>4.12 | F |

TABLE 10-continued
| No | Lipid structure | pKa-Classic | pKa-Galas | Method |
|---|---|---|---|---|
| 76. | 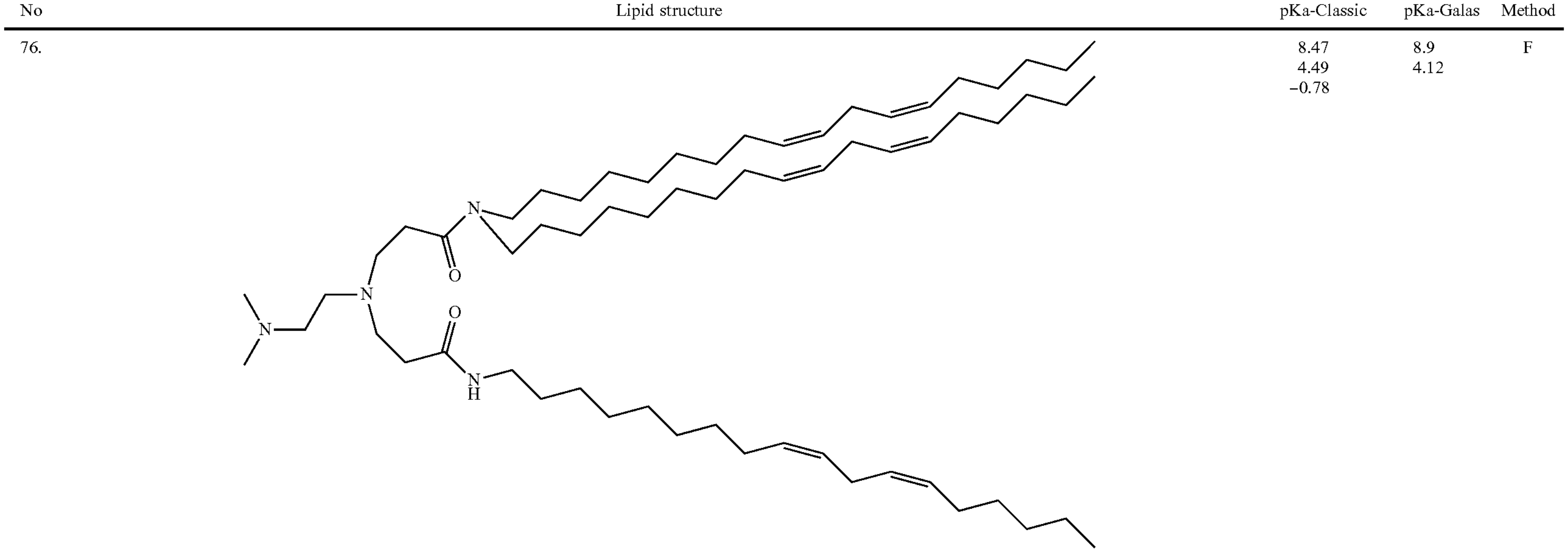 | 8.47<br>4.49<br>−0.78 | 8.9<br>4.12 | F |
| 77. | 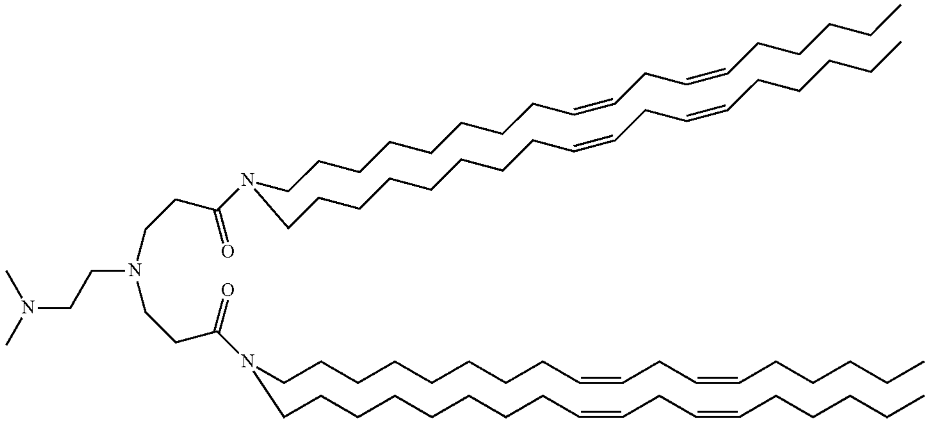 [SMILES: CCCCC/C=C\C/C=C\CCCCCCCCN(CCCCCCCC/C=C\C/C=C\CCCCC)C(=O)CCN(CCC(=O)N(CCCCCCCC/C=C\C/C=C\CCCCC)CCCCCCCC/C=C\C/C=C\CCCCC)CCN(C)C] | 8.49<br>4.73<br>−0.48 | 8.9<br>4.12 | F |

TABLE 10-continued
| No | Lipid structure | pKa-Classic | pKa-Galas | Method |
|---|---|---|---|---|
| 78. | 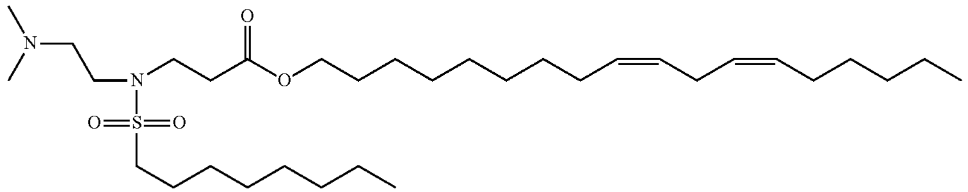 [SMILES: CCCCC/C=C\C/C=C\CCCCCCCCOC(=O)CCN(CCN(C)C)S(=O)(=O)CCCCCCCC] | 8.64<br>−12.54 | 7.93 | G |
| 79. | 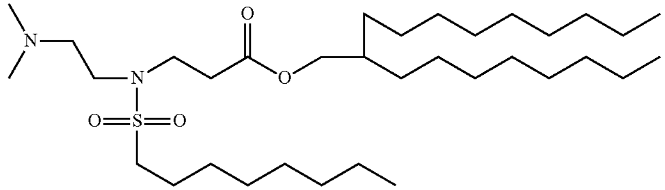 [SMILES: CCCCCCCCCC(CCCCCCCC)COC(=O)CCN(CCN(C)C)S(=O)(=O)CCCCCCCC] | 8.64<br>−12.55 | 7.93 | G |
| 80. | 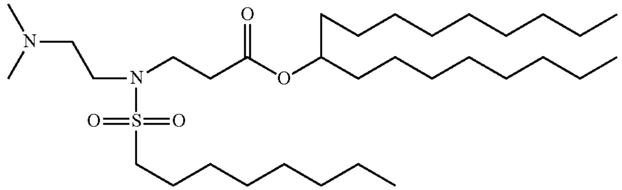 [SMILES: CCCCCCCCCC(CCCCCCCC)OC(=O)CCN(CCN(C)C)S(=O)(=O)CCCCCCCC] | 8.64<br>−12.57 | 7.93 | G |
| 81. | 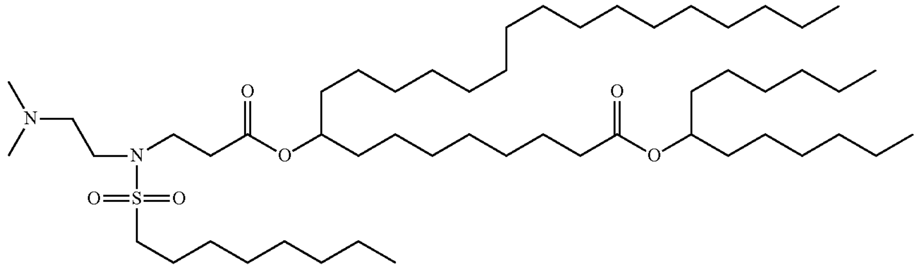 [SMILES: CCCCCCCCCCCCCCCCC(CCCCCCCC(=O)OC(CCCCCC)CCCCCC)OC(=O)CCN(CCN(C)C)S(=O)(=O)CCCCCCCC] | 8.64<br>−12.57 | 7.93 | G |

TABLE 10-continued
| No | Lipid structure | pKa-Classic | pKa-Galas | Method |
|---|---|---|---|---|
| 82. | 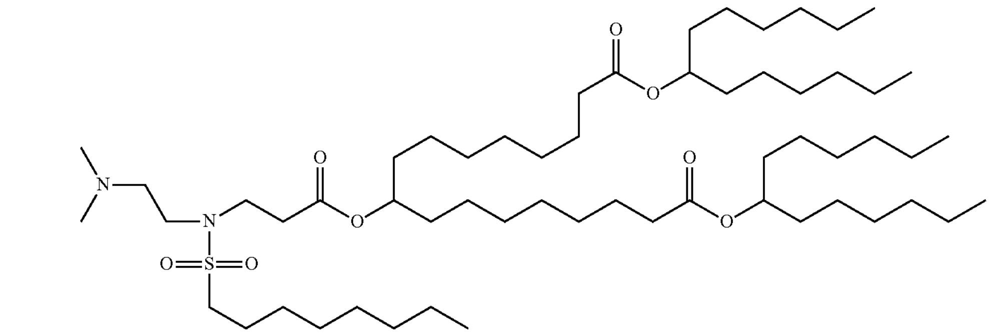 [SMILES: CCCCCCCCS(=O)(=O)N(CCC(=O)OC(CCCCCCCC(=O)OC(CCCCCC)CCCCCC)CCCCCCCC(=O)OC(CCCCCC)CCCCCC)CCN(C)C] | 8.64<br>−12.57 | 7.93 | G |
| 83. | 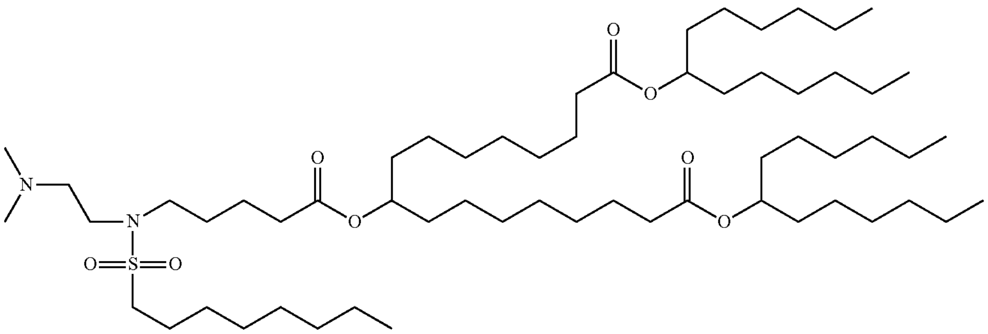 [SMILES: CCCCCCCCS(=O)(=O)N(CCCCC(=O)OC(CCCCCCCC(=O)OC(CCCCCC)CCCCCC)CCCCCCCC(=O)OC(CCCCCC)CCCCCC)CCN(C)C] | 8.68<br>−11.39 | 7.99 | G |
| 84. | 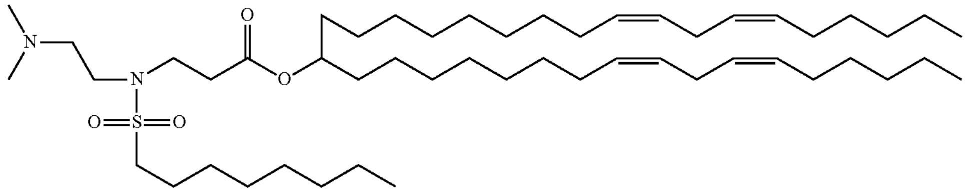 [SMILES: CCCCC/C=C\C/C=C\CCCCCCCCC(CCCCCCC/C=C\C/C=C\CCCCC)OC(=O)CCN(CCN(C)C)S(=O)(=O)CCCCCCCC] | 8.64<br>−12.57 | 7.93 | G |
| 85. | 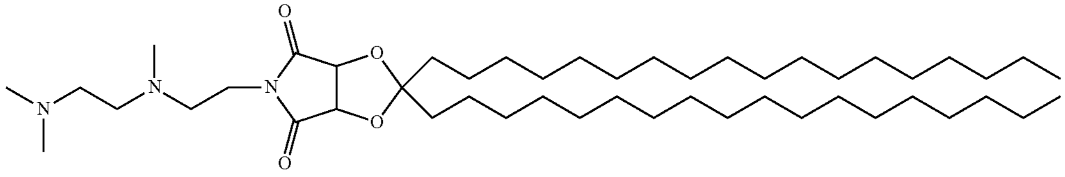 [SMILES: CCCCCCCCCCCCCCCCCCC1(CCCCCCCCCCCCCCCCCC)OC2C(=O)N(CCN(C)CCN(C)C)C(=O)C2O1] | 8.5<br>4.97<br>−2.17 | 8.93<br>3.85 | H |

TABLE 10-continued
| No | Lipid structure | pKa-Classic | pKa-Galas | Method |
|---|---|---|---|---|
| 86. | 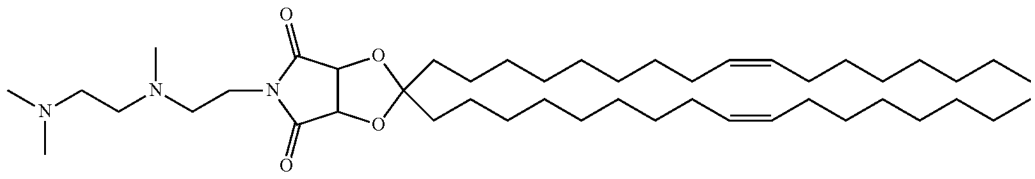 [SMILES: CCCCCCC/C=C\CCCCCCCCC1(CCCCCCCC/C=C\CCCCCCC)OC2C(=O)N(CCN(C)CCN(C)C)C(=O)C2O1] | 8.5<br>4.97<br>−2.17 | 8.93<br>3.85 | H |
| 87. | 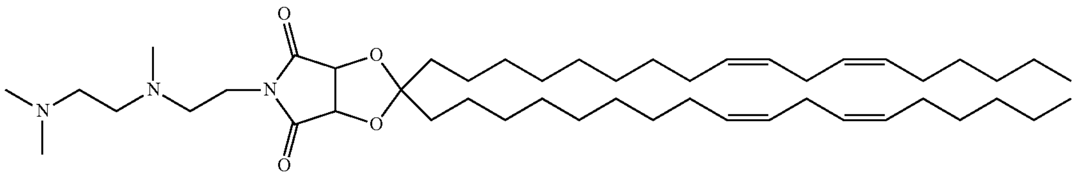 [SMILES: CCCCC/C=C\C/C=C\CCCCCCCCC1(CCCCCCCC/C=C\C/C=C\CCCCC)OC2C(=O)N(CCN(C)CCN(C)C)C(=O)C2O1] | 8.5<br>4.97<br>−2.17 | 8.93<br>3.85 | H |
| 88. | 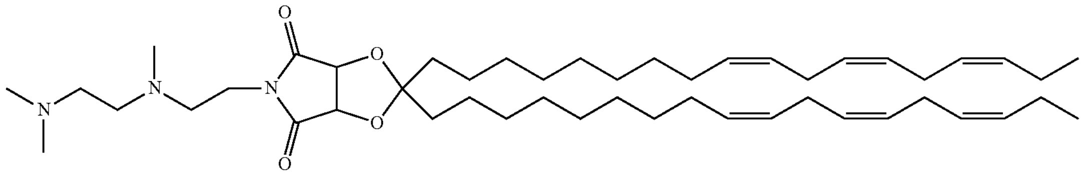 [SMILES: CC/C=C\C/C=C\C/C=C\CCCCCCCCC1(CCCCCCCC/C=C\C/C=C\C/C=C\CC)OC2C(=O)N(CCN(C)CCN(C)C)C(=O)C2O1] | 8.5<br>4.97<br>−2.17 | 8.93<br>3.85 | H |
| 89. | 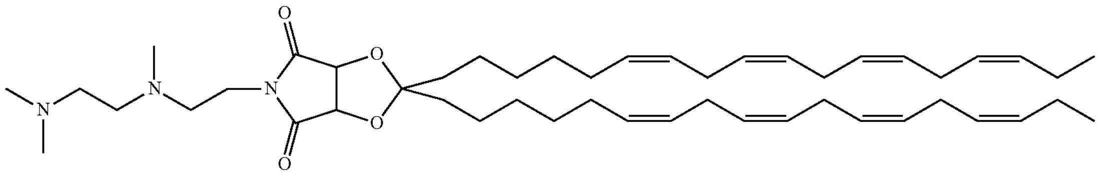 [SMILES: CC/C=C\C/C=C\C/C=C\C/C=C\CCCCCC1(CCCCC/C=C\C/C=C\C/C=C\C/C=C\CC)OC2C(=O)N(CCN(C)CCN(C)C)C(=O)C2O1] | 8.5<br>4.97<br>−2.17 | 8.93<br>3.85 | H |
| 90. | 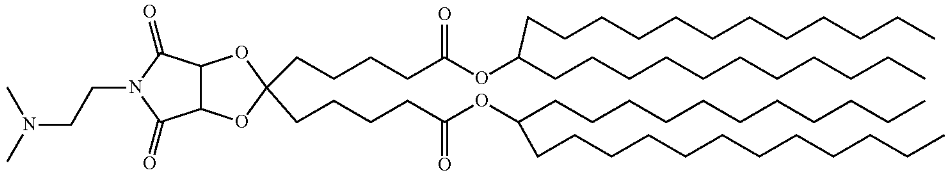 [SMILES: CCCCCCCCCCCCC(CCCCCCCCCCC)OC(=O)CCCCC1(CCCCC(=O)OC(CCCCCCCCCCC)CCCCCCCCCCCC)OC2C(=O)N(CCN(C)C)C(=O)C2O1] | 8.84<br>−2.81 | 7.56 | H |

TABLE 10-continued
| No | Lipid structure | pKa-Classic | pKa-Galas | Method |
|---|---|---|---|---|
| 91. | 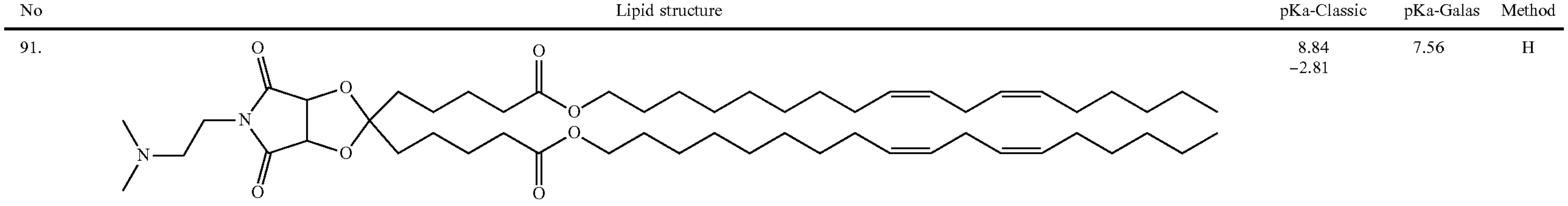 | 8.84<br>−2.81 | 7.56 | H |
| 92. | 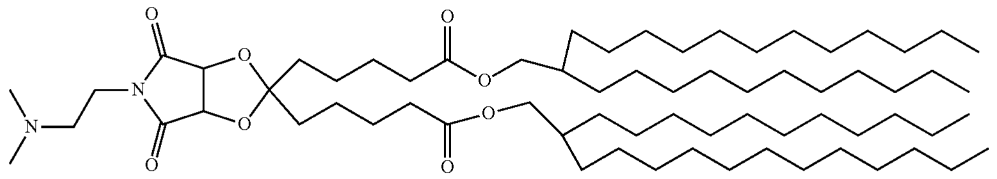 [SMILES: CCCCCCCCCCCCC(CCCCCCCCCCC)COC(=O)CCCCC1(CCCCC(=O)OCC(CCCCCCCCCCC)CCCCCCCCCCCC)OC2C(=O)N(CCN(C)C)C(=O)C2O1] | 8.84<br>−2.81 | 7.56 | H |
| 93. | 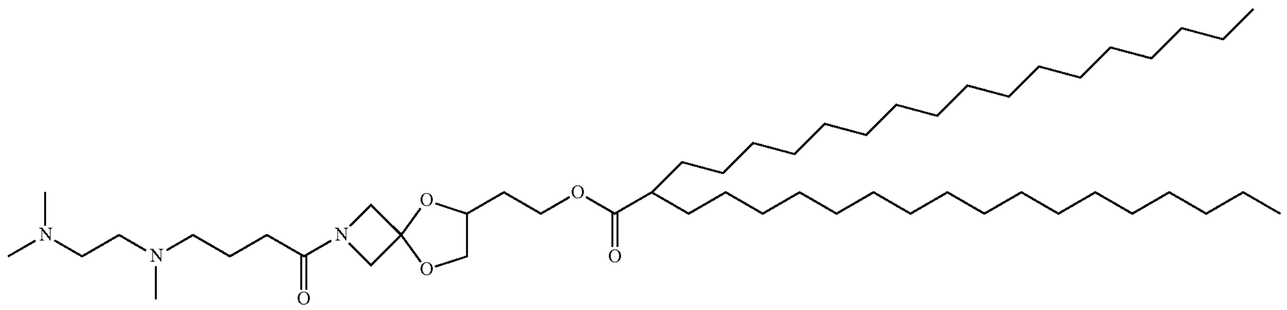 [SMILES: CCCCCCCCCCCCCCCCCC(CCCCCCCCCCCCCCCCC)C(=O)OCCC1COC2(CN(C(=O)CCCN(C)CCN(C)C)C2)O1] | 8.54<br>5.64<br>−0.23 | 8.98<br>5.8 | I |
| 94. | 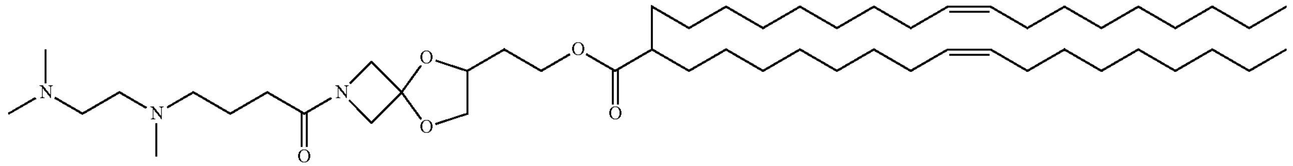 [SMILES: CCCCCCCC/C=C\CCCCCCCCC(CCCCCCC/C=C\CCCCCCCC)C(=O)OCCC1COC2(CN(C(=O)CCCN(C)CCN(C)C)C2)O1] | 8.54<br>5.64<br>−0.23 | 8.98<br>5.8 | I |
| 95. | 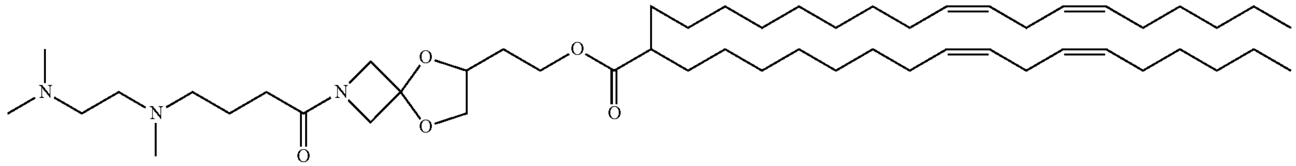 [SMILES: CCCCC/C=C\C/C=C\CCCCCCCCC(CCCCCCC/C=C\C/C=C\CCCCC)C(=O)OCCC1COC2(CN(C(=O)CCCN(C)CCN(C)C)C2)O1] | 8.54<br>5.64<br>−0.23 | 8.98<br>5.8 | I |

TABLE 10-continued
| No | Lipid structure | pKa-Classic | pKa-Galas | Method |
|---|---|---|---|---|
| 96. | 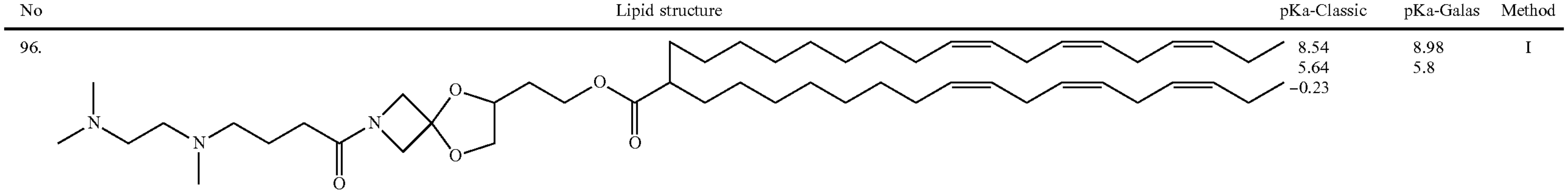 | 8.54<br>5.64<br>−0.23 | 8.98<br>5.8 | I |
| 97. | 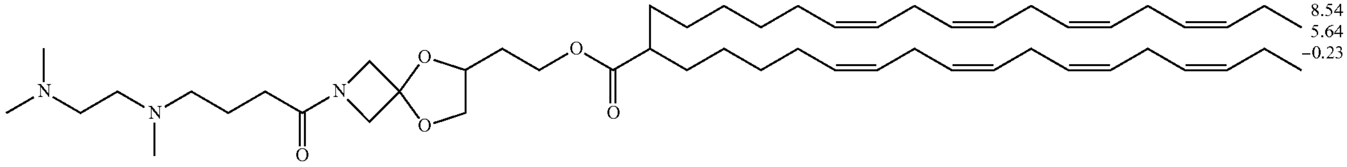 | 8.54<br>5.64<br>−0.23 | 8.98<br>5.8 | I |
| 98. | 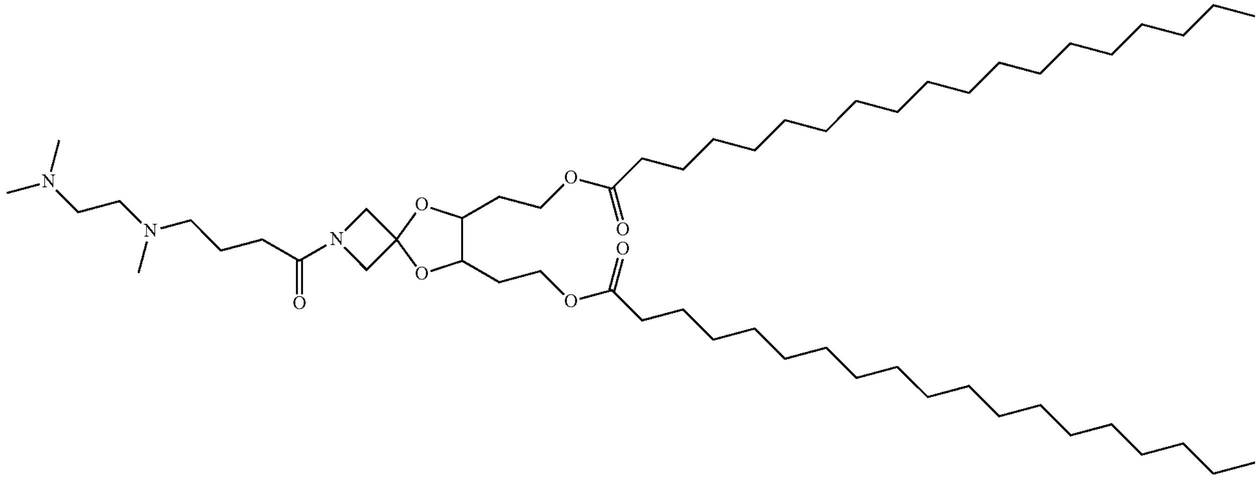 [SMILES: CCCCCCCCCCCCCCCCCCC(=O)OCCC1OC2(CN(C(=O)CCCN(C)CCN(C)C)C2)OC1CCOC(=O)CCCCCCCCCCCCCCCCCC] | 8.54<br>5.64<br>−0.34 | 8.98<br>5.8 | I |

TABLE 10-continued
| No | Lipid structure | pKa-Classic | pKa-Galas | Method |
|---|---|---|---|---|
| 99. | 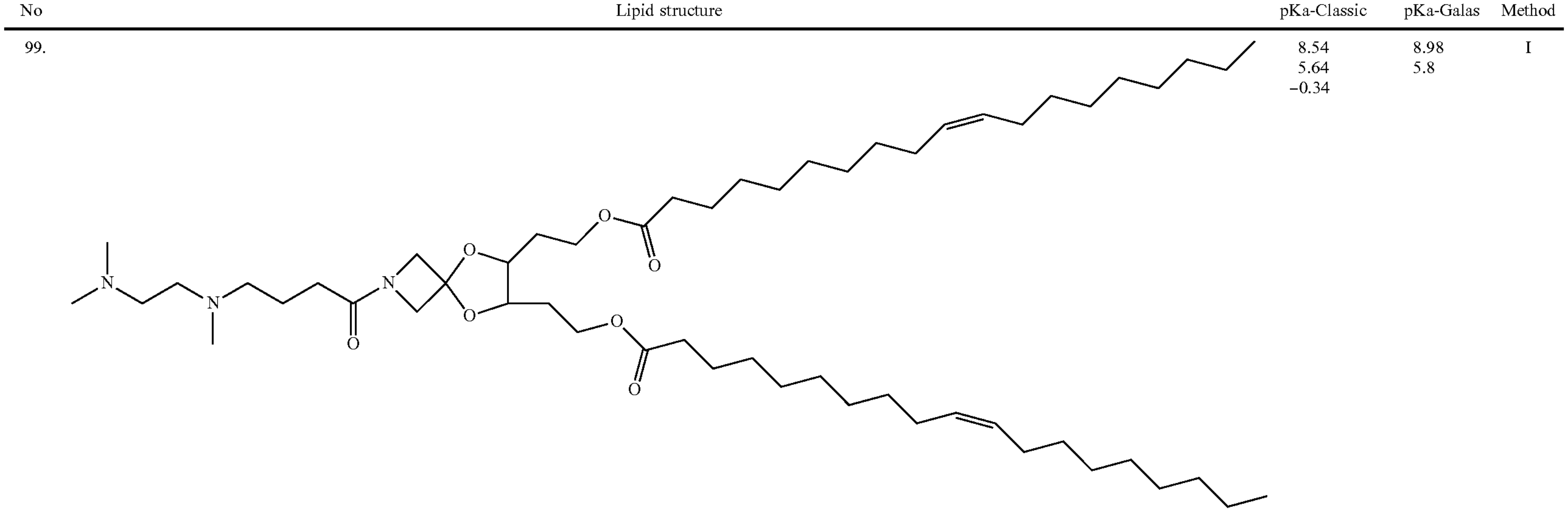 | 8.54<br>5.64<br>−0.34 | 8.98<br>5.8 | I |
| 100. | 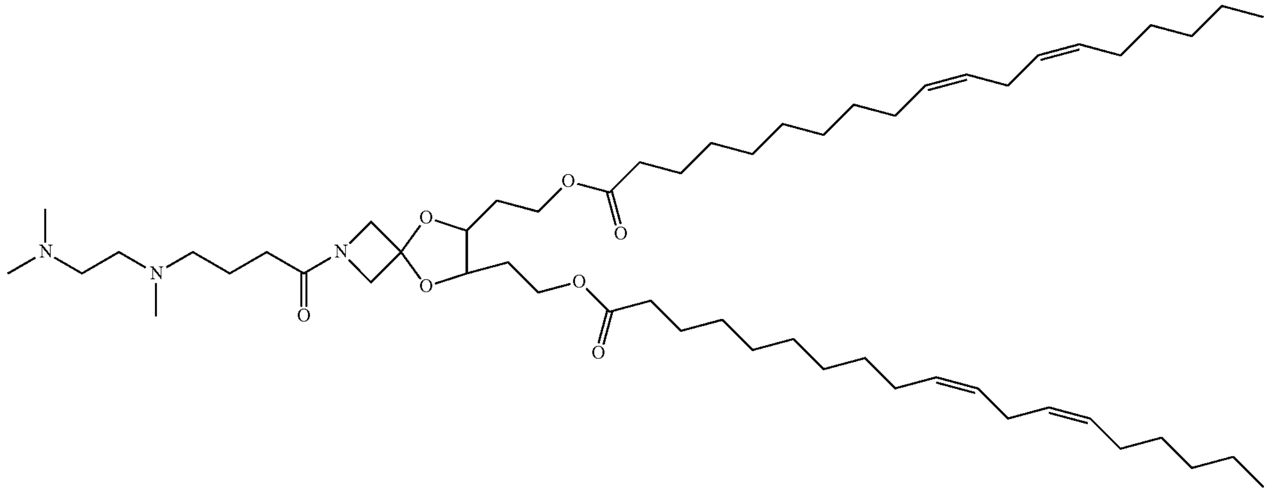 [SMILES: CCCCC/C=C\C/C=C\CCCCCCCCC(=O)OCCC1OC2(CN(C(=O)CCCN(C)CCN(C)C)C2)OC1CCOC(=O)CCCCCCCC/C=C\C/C=C\CCCCC] | 8.54<br>5.64<br>−0.34 | 8.98<br>5.8 | I |

TABLE 10-continued
| No | Lipid structure | pKa-Classic | pKa-Galas | Method |
|---|---|---|---|---|
| 101. | 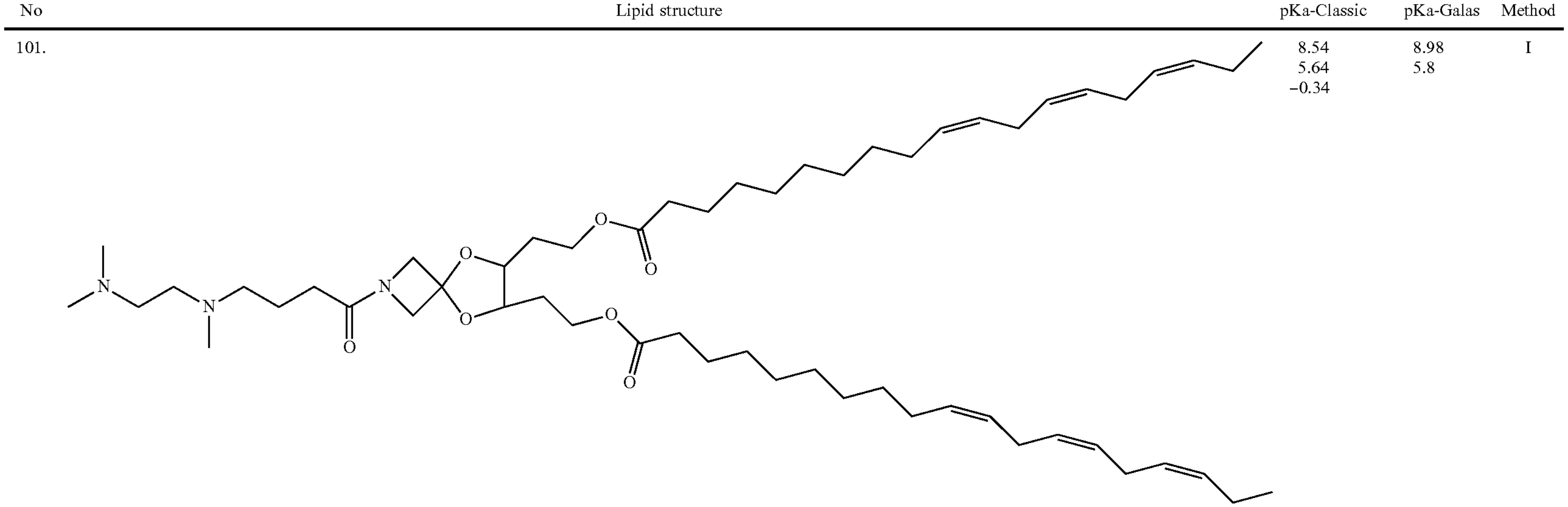 | 8.54<br>5.64<br>−0.34 | 8.98<br>5.8 | I |
| 102. | 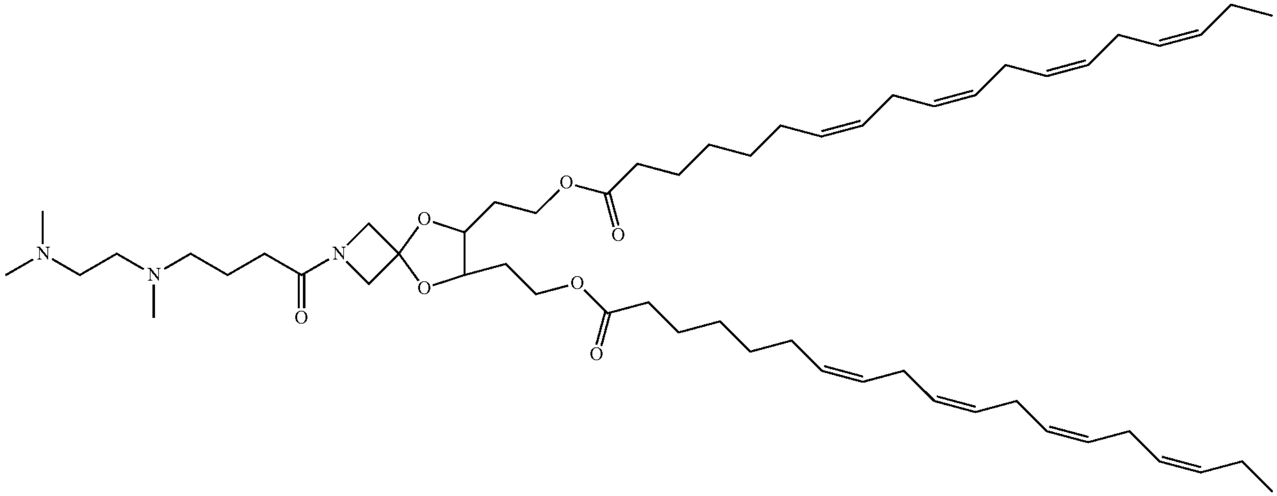 [SMILES: CC/C=C\C/C=C\C/C=C\C/C=C\CCCCCC(=O)OCCC1OC2(CN(C(=O)CCCN(C)CCN(C)C)C2)OC1CCOC(=O)CCCCC/C=C\C/C=C\C/C=C\C/C=C\CC] | 8.54<br>5.64<br>−0.34 | 8.98<br>5.8 | I |

TABLE 10-continued
| No | Lipid structure | pKa-Classic | pKa-Galas | Method |
|---|---|---|---|---|
| 103. | 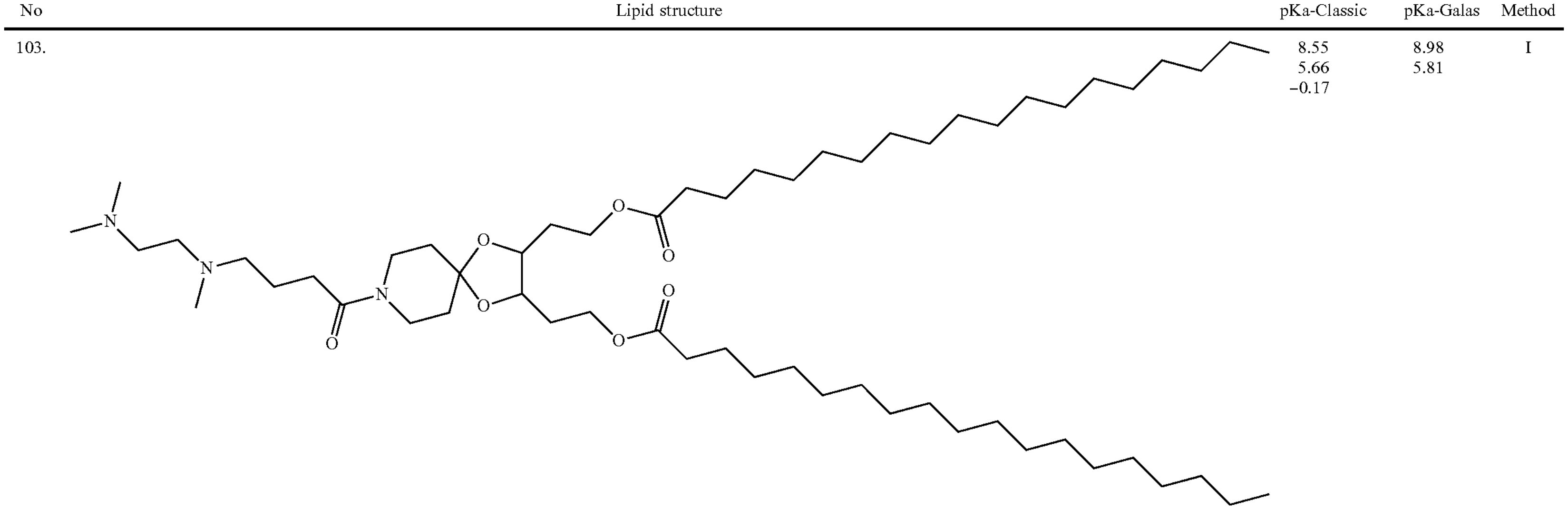 | 8.55<br>5.66<br>−0.17 | 8.98<br>5.81 | I |
| 104. | 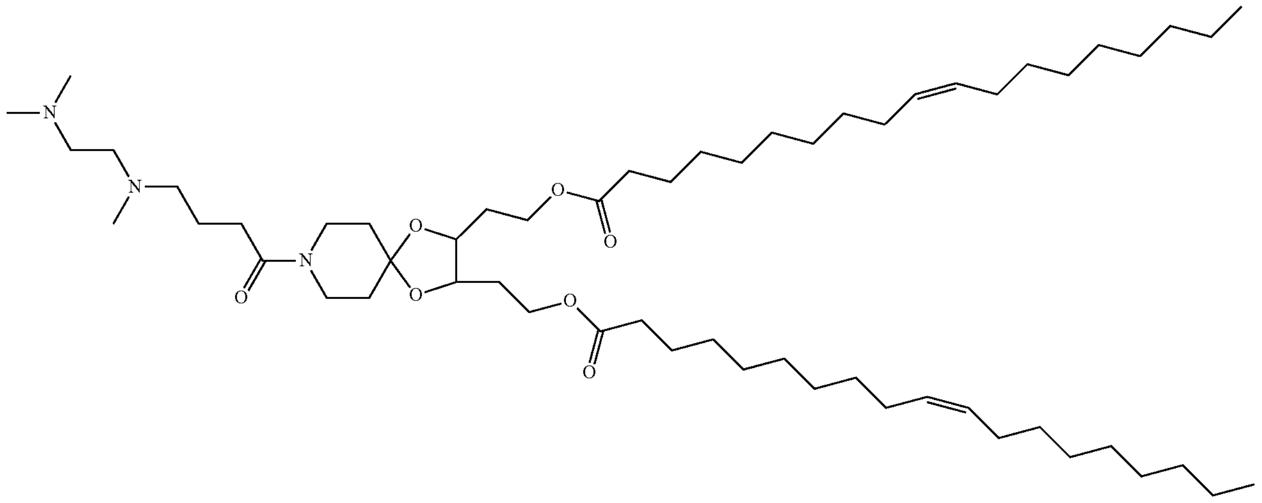 [SMILES: CCCCCCCC/C=C\CCCCCCCCC(=O)OCCC1OC2(CCN(C(=O)CCCN(C)CCN(C)C)CC2)OC1CCOC(=O)CCCCCCCC/C=C\CCCCCCCC] | 8.55<br>5.66<br>−0.17 | 8.98<br>5.81 | I |

TABLE 10-continued
| No | Lipid structure | pKa-Classic | pKa-Galas | Method |
|---|---|---|---|---|
| 105. | 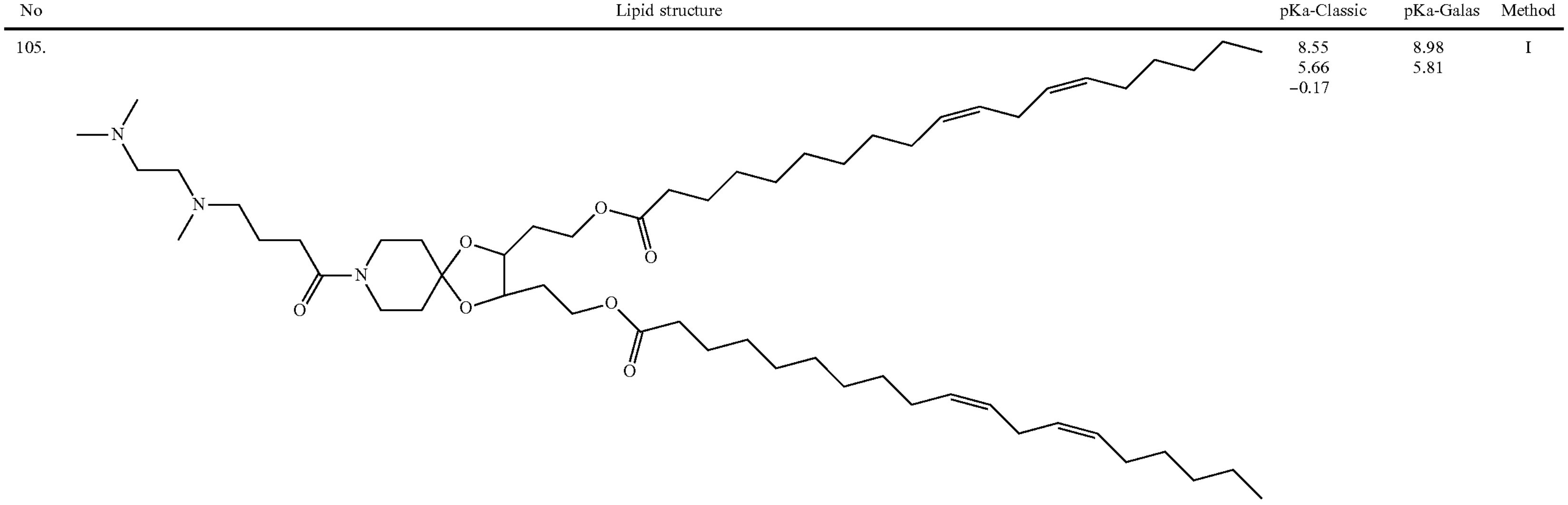 | 8.55<br>5.66<br>−0.17 | 8.98<br>5.81 | I |
| 106. | 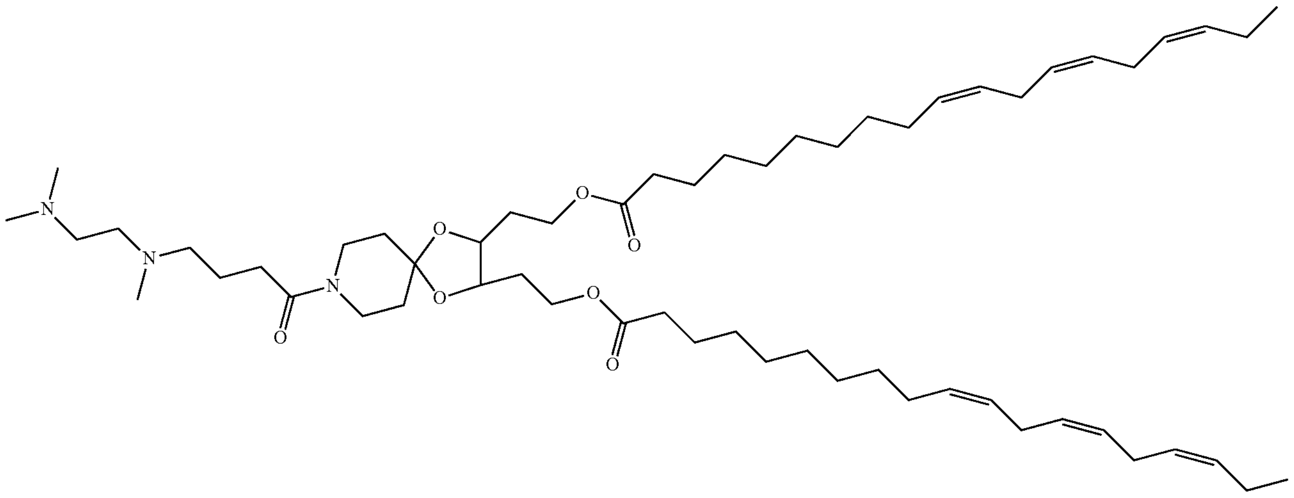 [SMILES: CC/C=C\C/C=C\C/C=C\CCCCCCCCC(=O)OCCC1OC2(CCN(C(=O)CCCN(C)CCN(C)C)CC2)OC1CCOC(=O)CCCCCCCC/C=C\C/C=C\C/C=C\CC] | 8.55<br>5.66<br>−0.17 | 8.98<br>5.81 | I |

TABLE 10-continued
| No | Lipid structure | pKa-Classic | pKa-Galas | Method |
|---|---|---|---|---|
| 107. | 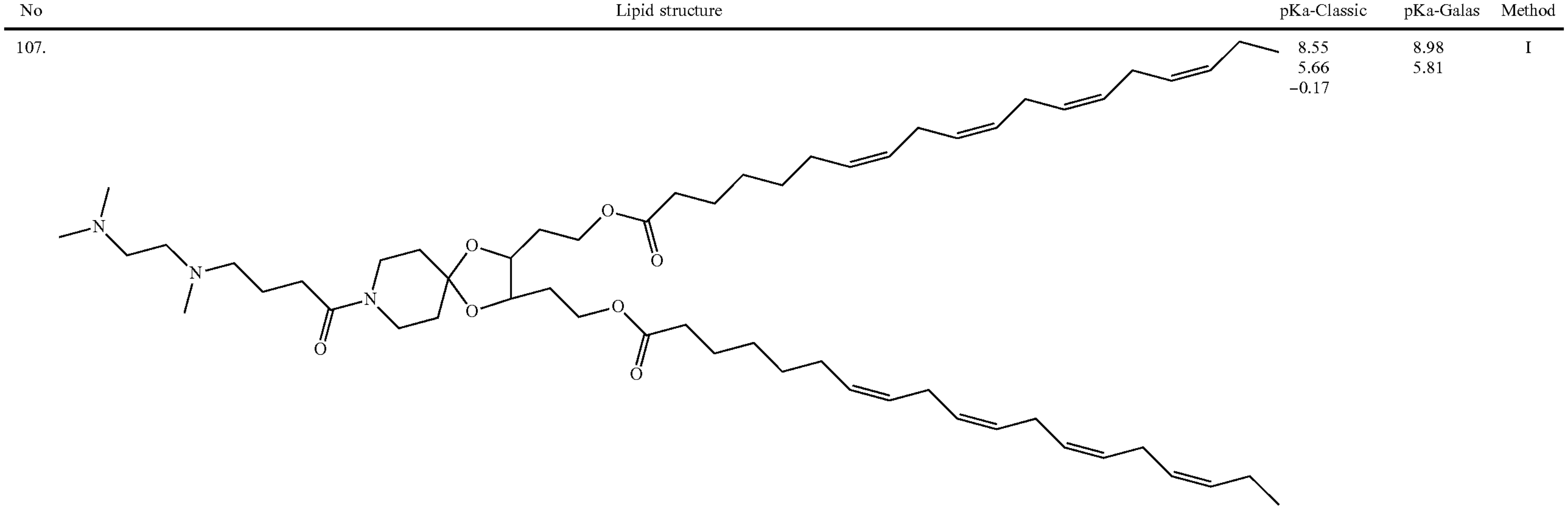 | 8.55<br>5.66<br>−0.17 | 8.98<br>5.81 | I |
| 108. | 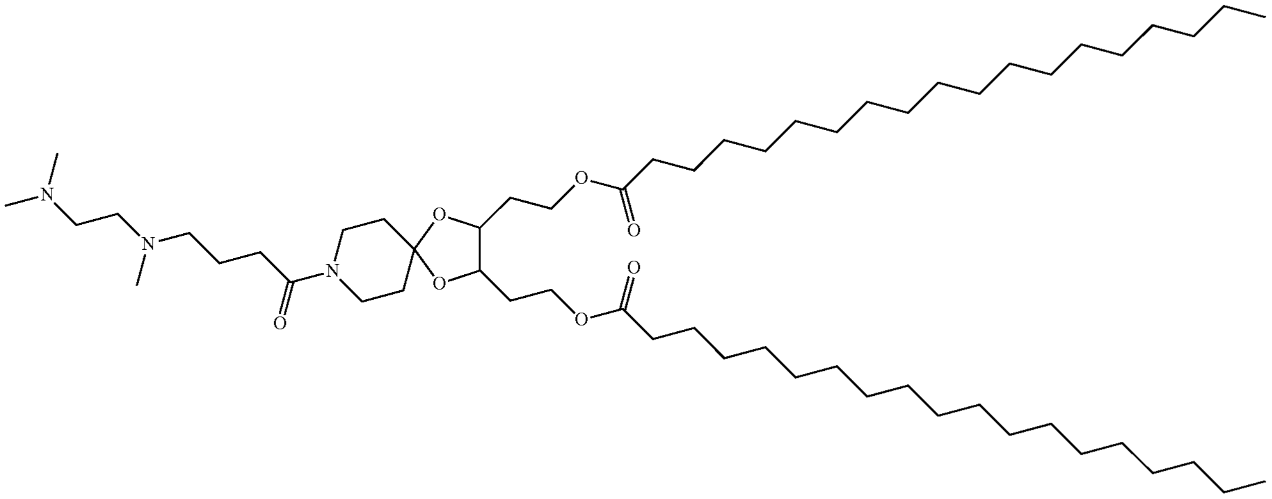 [SMILES: CCCCCCCCCCCCCCCCCCC(=O)OCCC1OC2(CCN(C(=O)CCCN(C)CCN(C)C)CC2)OC1CCOC(=O)CCCCCCCCCCCCCCCCCC] | 8.55<br>5.66<br>−0.17 | 8.98<br>5.81 | I |

TABLE 10-continued
| No | Lipid structure | pKa-Classic | pKa-Galas | Method |
|---|---|---|---|---|
| 109. | 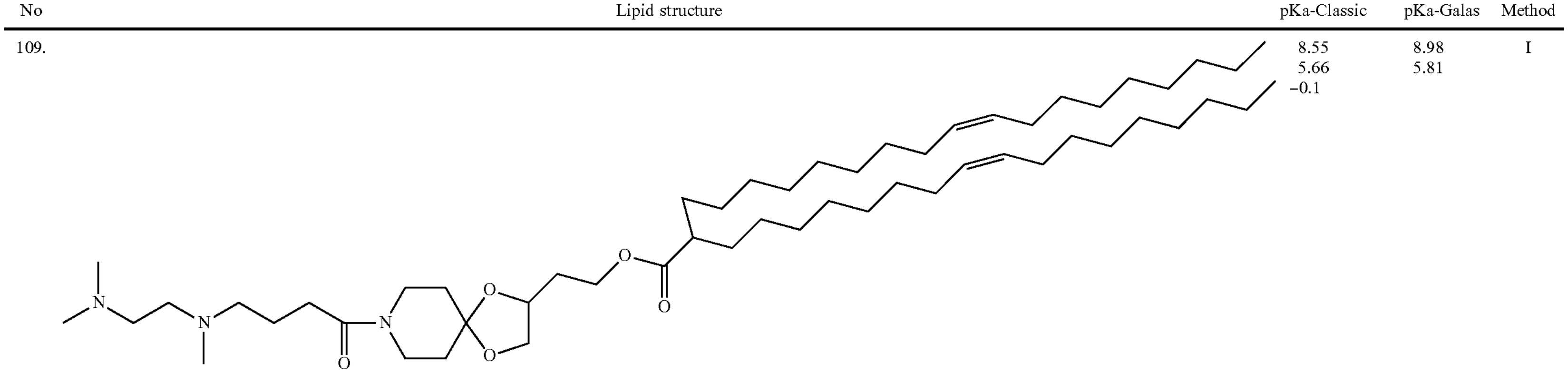 | 8.55<br>5.66<br>−0.1 | 8.98<br>5.81 | I |
| 110. | 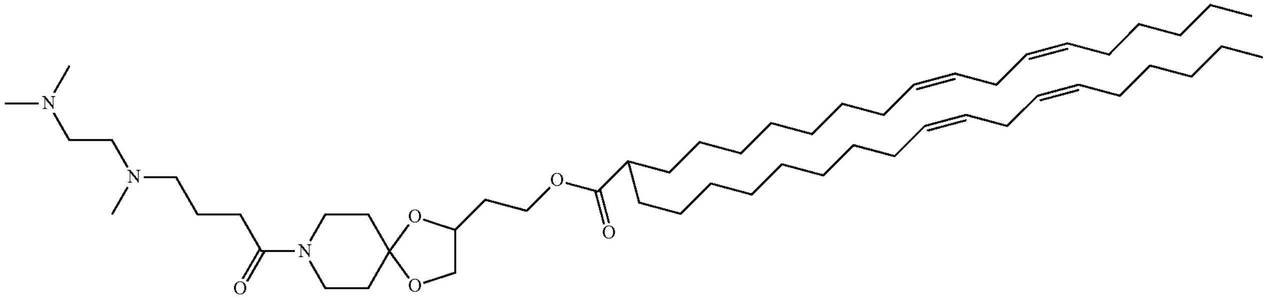 [SMILES: CCCCC/C=C\C/C=C\CCCCCCCCC(CCCCCCC/C=C\C/C=C\CCCCC)C(=O)OCCC1COC2(CCN(C(=O)CCCN(C)CCN(C)C)CC2)O1] | 8.55<br>5.66<br>−0.1 | 8.98<br>5.81 | I |

TABLE 10-continued
| No | Lipid structure | pKa-Classic | pKa-Galas | Method |
| --- | --- | --- | --- | --- |
| 111. | 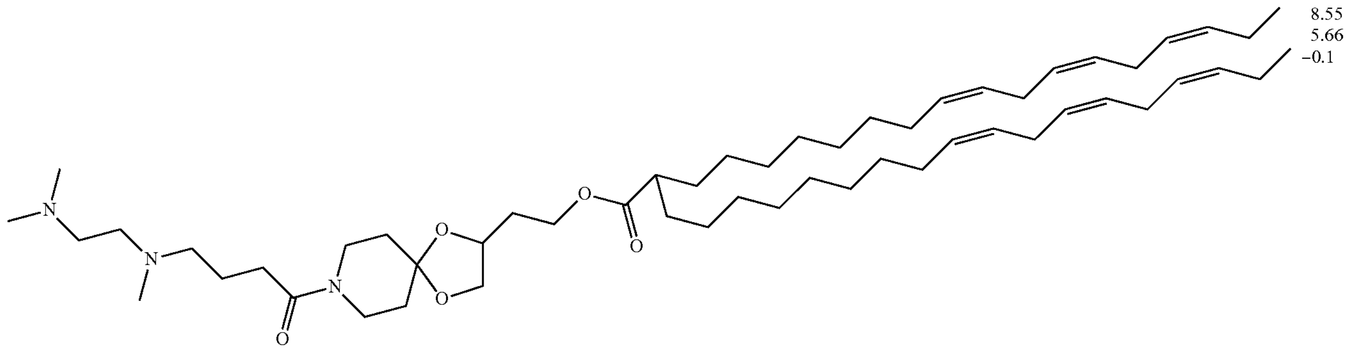 | 8.55<br>5.66<br>−0.1 | 8.98<br>5.81 | I |
| 112. | 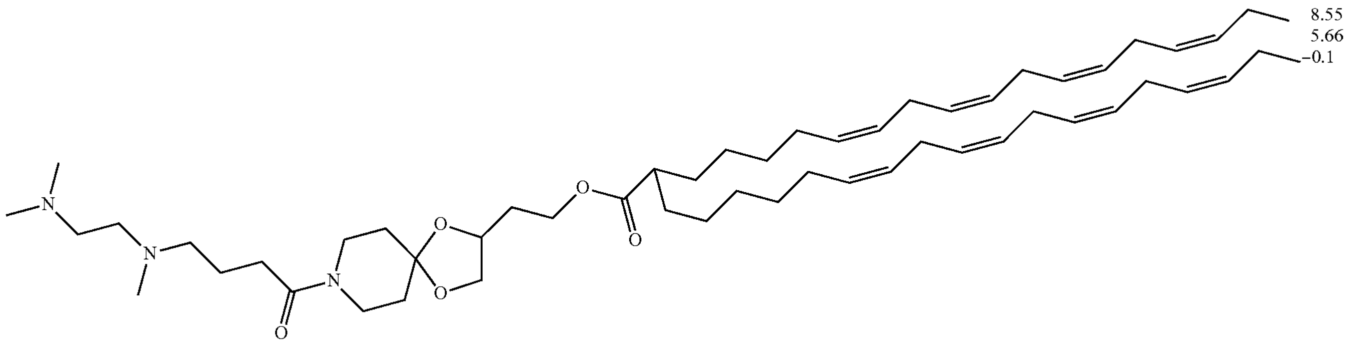 | 8.55<br>5.66<br>−0.1 | 8.98<br>5.81 | I |

In another embodiment of the invention, adjusting the pKa of the Ionizable Lipids of the Invention can direct the administration of the lipid nanoparticle-nucleic acid complex (LNP-NA) to a particular tissue or organ. The inventors surprisingly found that the design of the Ionizable Lipids of the Invention can be significantly accelerated using the prediction of the pKa of ionizable lipids using software, for example, ACDLabs Percepta. The inventors found that the predicted aqueous pKas for ionizable lipids are all significantly higher than that measured by TNS. In certain embodiments, a drop in pKa from an aqueous environment to the LNP environment has not been previously acknowledged in the literature. Without being bound by theory, a reasonable explanation can be found due to the higher solvation energy of protons in the lipid phase compared with the aqueous phase and electrostatic repulsion of protons from the Ionizable Lipids of the Invention in the LNP, which can combine to reduce pKa by 1-3 points from aqueous to lipid phases. In certain embodiments, this predictive capability can be used in order to select specific headgroups and carbon spacers by examining pKa tables of potential candidates and selecting only those with appropriate pKa values. Candidates can be accurately eliminated in this manner, generating enormous savings in synthesis and testing time and expense.

In certain embodiments, the pKa of the Ionizable Lipids of the Invention included in the LNP is measured by fluorescent enhancement of an anionic lipophilic dye TNS binding to the LNP containing the ionizable lipid. Prior studies have shown that the TNS pKa needs to be near 6.5 for efficient delivery to liver upon IV administration. The pKa in the aqueous phase can be predicted by software such ACDLabs Percepta, resulting in pKas that are higher than the TNS pKa. Given the importance of the LNP pKa in determining their efficiency, we developed new methods (zeta potential, $^1$H NMR, modeling) to link the intrinsic pKa of the ionizable lipid to LNP ionization properties, in order to rationally design effective systems for mRNA delivery.

TABLE 11a pKa of Known Ionizable Lipids

| Lipid | Structure |
|---|---|
| MC3[1] | 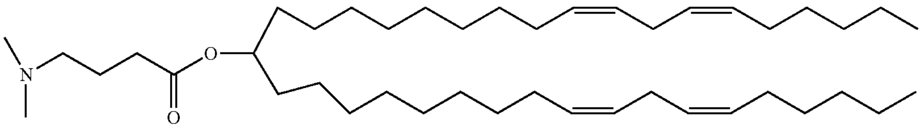 [SMILES: CCCCC/C=C\C/C=C\CCCCCCCCC(CCCCCCCC/C=C\C/C=C\CCCCC)OC(=O)CCCN(C)C] |
| KC2[1] | 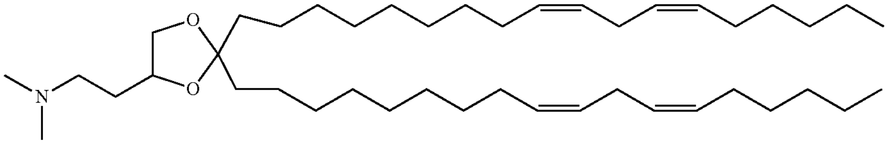 [SMILES: CCCCC/C=C\C/C=C\CCCCCCCCC1(CCCCCCCC/C=C\C/C=C\CCCCC)OCC(CCN(C)C)O1] |
| DLinDMA[2] | 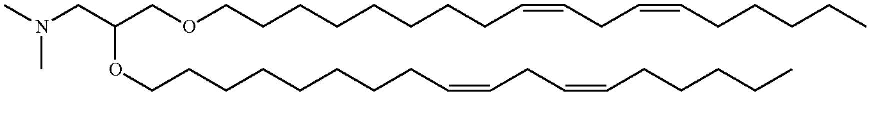 [SMILES: CCCCC/C=C\C/C=C\CCCCCCCCOCC(CN(C)C)OCCCCCCCC/C=C\C/C=C\CCCCC] |
| DODMA[3] | 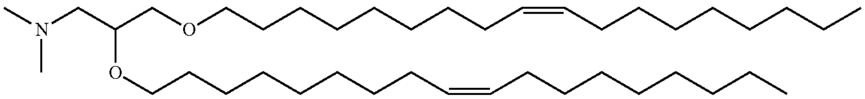 [SMILES: CCCCCCCC/C=C\CCCCCCCCOCC(CN(C)C)OCCCCCCCC/C=C\CCCCCCCC] |
| DODAP[4] | 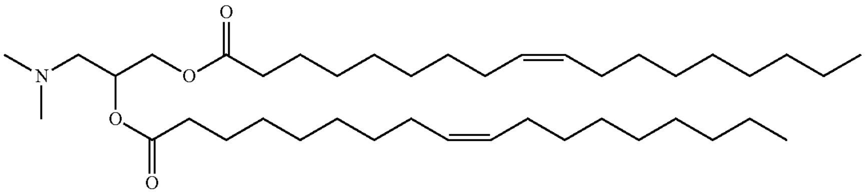 [SMILES: CCCCCCCC/C=C\CCCCCCCC(=O)OCC(CN(C)C)OC(=O)CCCCCCC/C=C\CCCCCCCC] |
| Moderna Lipid 5[5] | 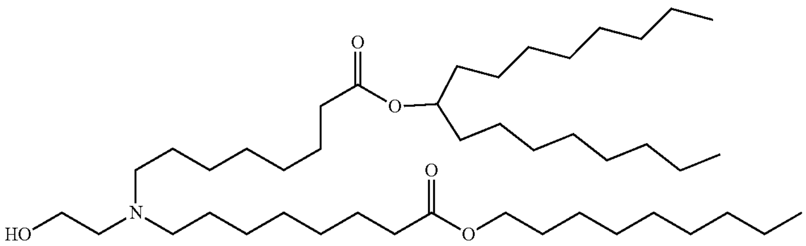 [SMILES: CCCCCCCCCOC(=O)CCCCCCCN(CCO)CCCCCCCC(=O)OC(CCCCCCCC)CCCCCCCC] |

TABLE 11a-continued
pKa of Known Ionizable Lipids
Moderna Lipid H[6]
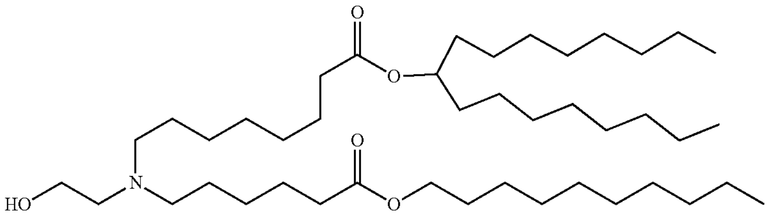 [SMILES: CCCCCCCCCCOC(=O)CCCCCN(CCO)CCCCCCCC(=O)OC(CCCCCCCC)CCCCCCCC]
Acuitas Compound 10[7]
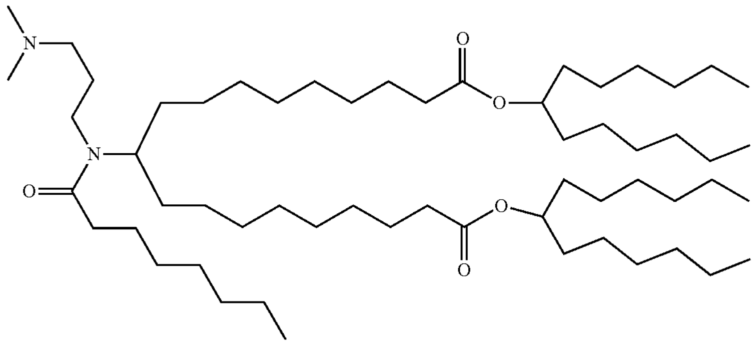 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]
Acuitas Compound 15[7]
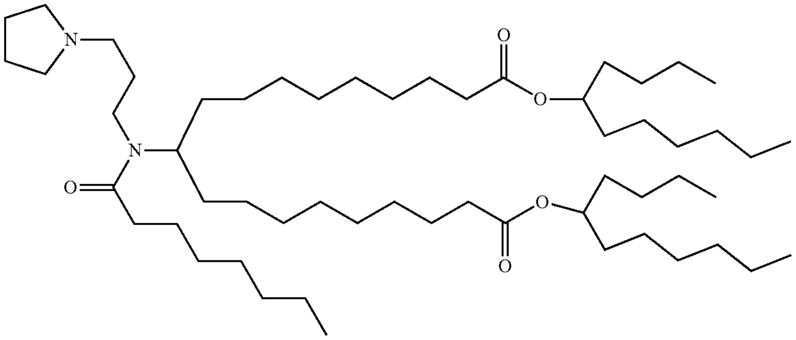 [SMILES: CCCCCCCC(=O)N(CCCN1CCCC1)C(CCCCCCCCC(=O)OC(CCCC)CCCCCC)CCCCCCCCC(=O)OC(CCCC)CCCCCC]
Acutias Compound-0315
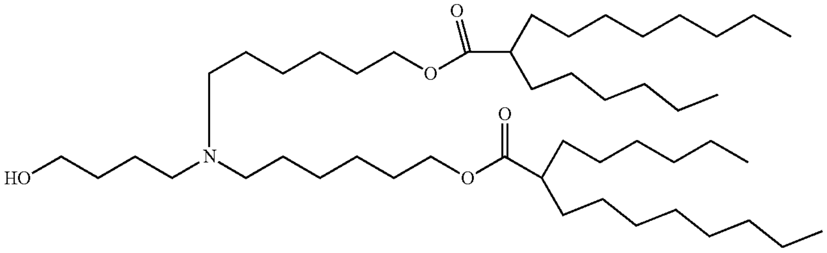 [SMILES: CCCCCCCCC(CCCCCC)C(=O)OCCCCCCN(CCCCO)CCCCCCOC(=O)C(CCCCCC)CCCCCCCC]
| Lipid | pKa ACD-Galas | pKa, ACD-Classic | pKa, TNS | ΔpKa = Classic-Galas | ΔpKa = Classic-TNS |
|---|---|---|---|---|---|
| MC3[1] | 9.1 | 9.4 | 6.44 | 2.66 | 2.96 |
| KC2[1] | 9.0 | 9.3 | 6.68 | 2.32 | 2.62 |
| DLinDMA[2] | 8.4 | 8.6 | 6.8 | 1.6 | 1.8 |
| DODMA[3] | 8.4 | 8.6 | 7.0 | 1.4 | 1.6 |
| DODAP[4] | 7.6 | 8.0 | 5.8 | 1.8 | 2.2 |
| Moderna Lipid 5[5] | 9.9 | 8.9 | 6.56 | 3.34 | 2.34 |
| Moderna Lipid H[6] | 9.8 | 8.9 | 6.68 | 3.12 | 2.22 |
| Acuitas Compound 10[7] | 9.2 | 9.4 | 6.16 | 3.04 | 3.24 |
| Acuitas Compound 15[7] | 9.7 | 10.3 | 6.32 | 3.38 | 3.98 |
| Acuitas Compound-0315 | 10.5 | 9.6 | | | |

TABLE 11b
Ionizable Lipids with Internal pKas (including Exemplary Ionizable Lipids of the Invention and known Lipids)
| No. | Lipid Name | Exemplary Ionizable Lipids with pKas |
|---|---|---|
| 1 | DL-ADDE-C2/C2 DMA | 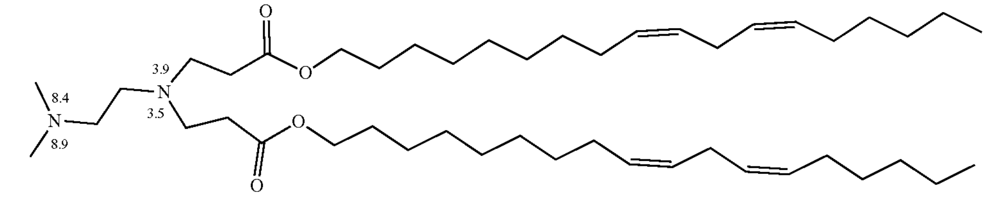 [SMILES: CCCCC/C=C\C/C=C\CCCCCCCCOC(=O)CCN(CCC(=O)OCCCCCCCC/C=C\C/C=C\CCCCC)CCN(C)C] |
| 2 | DL-ADDE-C2/C3-DMA | 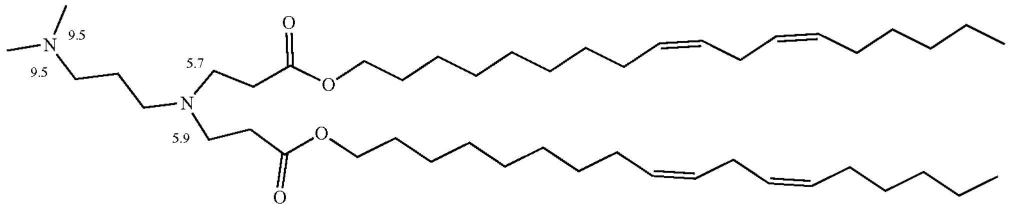 [SMILES: CCCCC/C=C\C/C=C\CCCCCCCCOC(=O)CCN(CCCN(C)C)CCC(=O)OCCCCCCCC/C=C\C/C=C\CCCCC] |
| 3 | DL-ADDE-C2/C4-DMA | 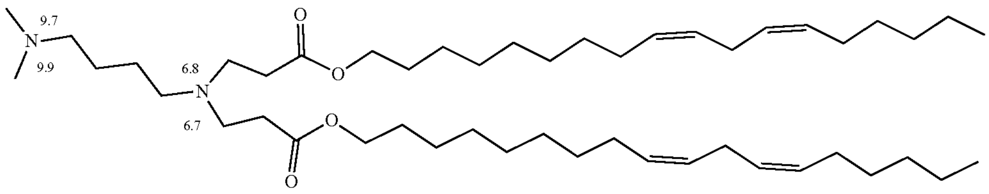 [SMILES: CCCCC/C=C\C/C=C\CCCCCCCCOC(=O)CCN(CCCCN(C)C)CCC(=O)OCCCCCCCC/C=C\C/C=C\CCCCC] |
| 4 | DL-ADDE-C4/C4-DMA | 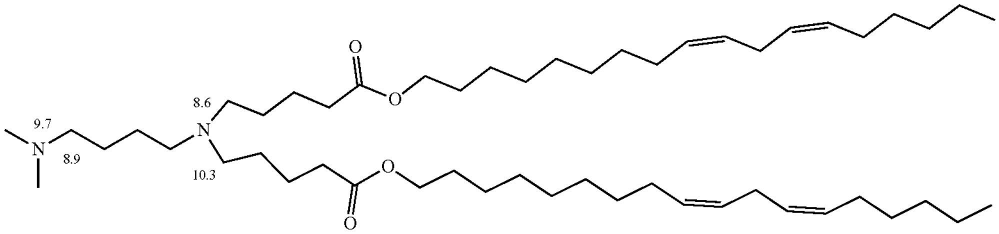 [SMILES: CCCCC/C=C\C/C=C\CCCCCCCCOC(=O)CCCCN(CCCCC(=O)OCCCCCCCC/C=C\C/C=C\CCCCC)CCCCN(C)C] |
| 5 | DL-ADDE-C2/C3-DME-DMA | 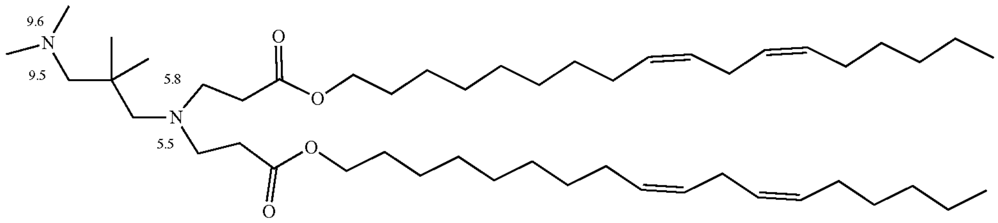 [SMILES: CCCCC/C=C\C/C=C\CCCCCCCCOC(=O)CCN(CCC(=O)OCCCCCCCC/C=C\C/C=C\CCCCC)CC(C)(C)CN(C)C] |
| 6 | DL-ADDE-C2/C2-Pyr | 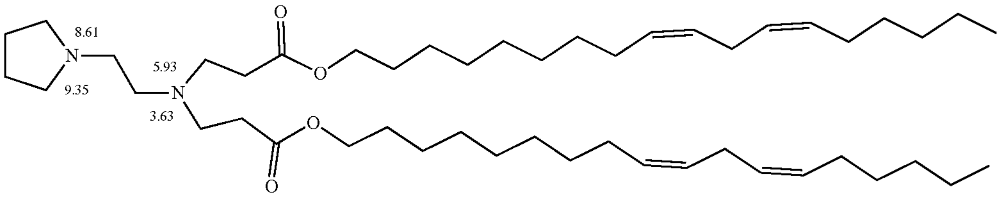 [SMILES: CCCCC/C=C\C/C=C\CCCCCCCCOC(=O)CCN(CCC(=O)OCCCCCCCC/C=C\C/C=C\CCCCC)CCN1CCCC1] |
| 7 | DL-ADDE-C2/C3-DMe-DMA | 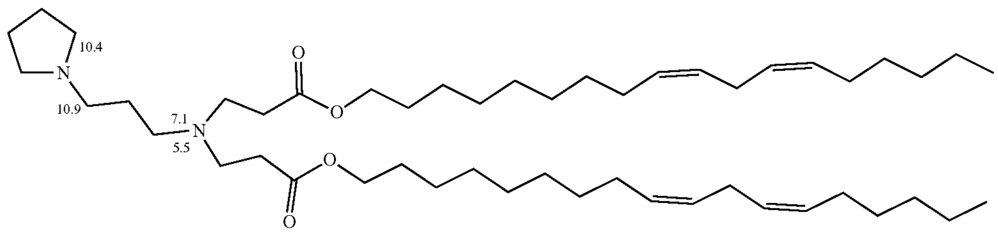 [SMILES: CCCCC/C=C\C/C=C\CCCCCCCCOC(=O)CCN(CCCN1CCCC1)CCC(=O)OCCCCCCCC/C=C\C/C=C\CCCCC] |

TABLE 11b-continued
| Ionizable Lipids with Internal pKas (including Exemplary Ionizable Lipids of the Invention and known Lipids) | | |
|---|---|---|
| No. | Lipid Name | Exemplary Ionizable Lipids with pKas |
| 8 | DL-ADDE-C2/C4-Pyr | 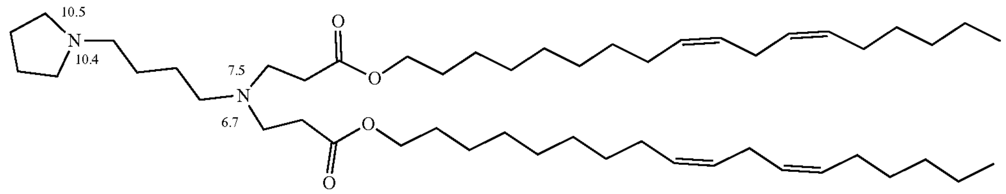 [SMILES: CCCCC/C=C\C/C=C\CCCCCCCCOC(=O)CCN(CCCCN1CCCC1)CCC(=O)OCCCCCCCC/C=C\C/C=C\CCCCC] |
| 9 | DL-ADDE-C4/C4-Pyr | 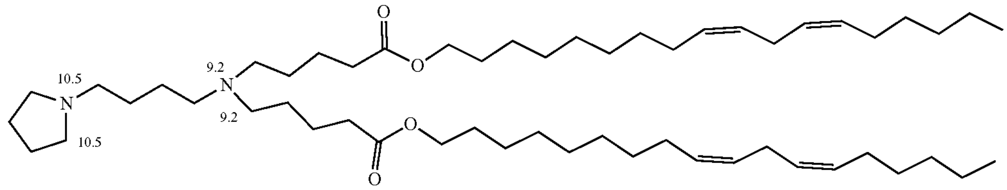 [SMILES: CCCCC/C=C\C/C=C\CCCCCCCCOC(=O)CCCCN(CCCCC(=O)OCCCCCCCC/C=C\C/C=C\CCCCC)CCCCN1CCCC1] |
| 10 | DL-ADDE-C2/C2-4Me-PipZ | 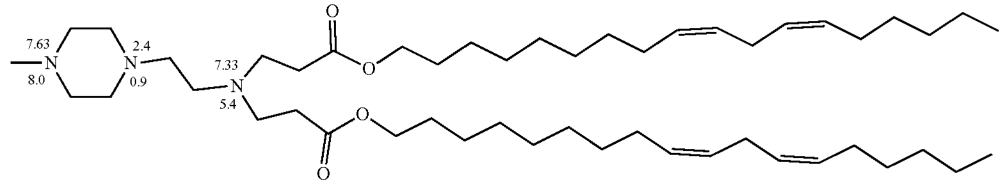 [SMILES: CCCCC/C=C\C/C=C\CCCCCCCCOC(=O)CCN(CCC(=O)OCCCCCCCC/C=C\C/C=C\CCCCC)CCN1CCN(C)CC1] |
| 11 | DL-ADDE-C2/C3-4Me-PipZ | 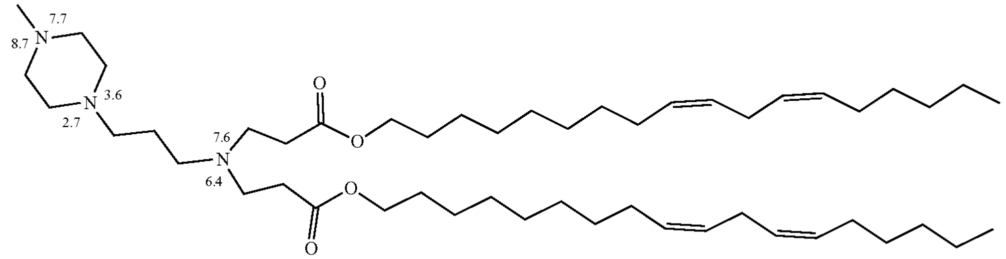 [SMILES: CCCCC/C=C\C/C=C\CCCCCCCCOC(=O)CCN(CCCN1CCN(C)CC1)CCC(=O)OCCCCCCCC/C=C\C/C=C\CCCCC] |
| 12 | DL-ADDE-C2/C4-4Me-PipZ | 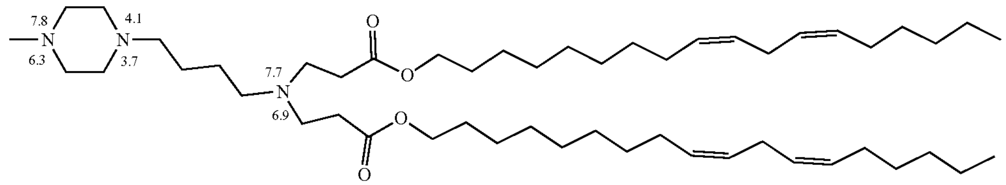 [SMILES: CCCCC/C=C\C/C=C\CCCCCCCCOC(=O)CCN(CCCCN1CCN(C)CC1)CCC(=O)OCCCCCCCC/C=C\C/C=C\CCCCC] |
| 13 | DL-ADDE-C4/C4-4Me-PipZ | 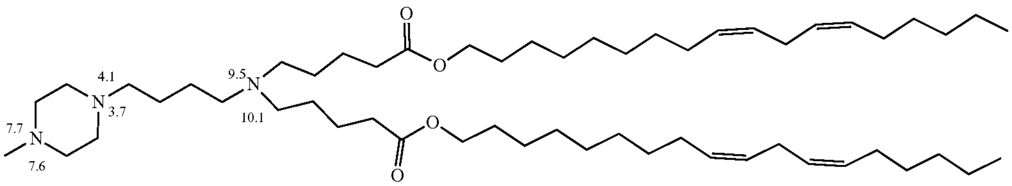 [SMILES: CCCCC/C=C\C/C=C\CCCCCCCCOC(=O)CCCCN(CCCCC(=O)OCCCCCCCC/C=C\C/C=C\CCCCC)CCCCN1CCN(C)CC1] |
| 14 | DL-ADDE-C2/C2-PipD | 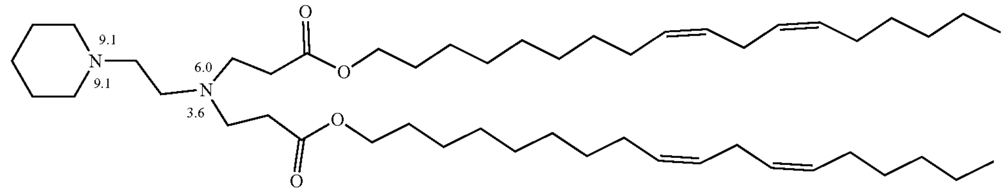 [SMILES: CCCCC/C=C\C/C=C\CCCCCCCCOC(=O)CCN(CCC(=O)OCCCCCCCC/C=C\C/C=C\CCCCC)CCN1CCCCC1] |

TABLE 11b-continued
Ionizable Lipids with Internal pKas (including Exemplary Ionizable Lipids of the Invention and known Lipids)
| No. | Lipid Name | Exemplary Ionizable Lipids with pKas |
| --- | --- | --- |
| 15 | DL-ADDE-C2/C3-PipD | 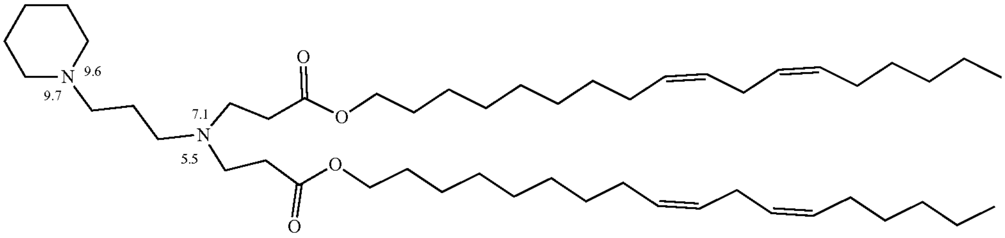 [SMILES: CCCCC/C=C\C/C=C\CCCCCCCCOC(=O)CCN(CCCN1CCCCC1)CCC(=O)OCCCCCCCC/C=C\C/C=C\CCCCC] |
| 16 | DL-ADDE-C2/C4-PipD | 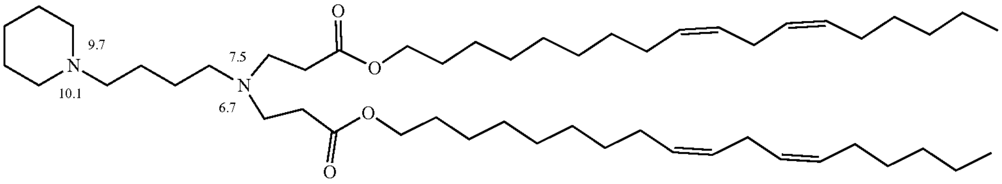 [SMILES: CCCCC/C=C\C/C=C\CCCCCCCCOC(=O)CCN(CCCCN1CCCCC1)CCC(=O)OCCCCCCCC/C=C\C/C=C\CCCCC] |
| 17 | DL-ADDE-C4/C4-PipD | 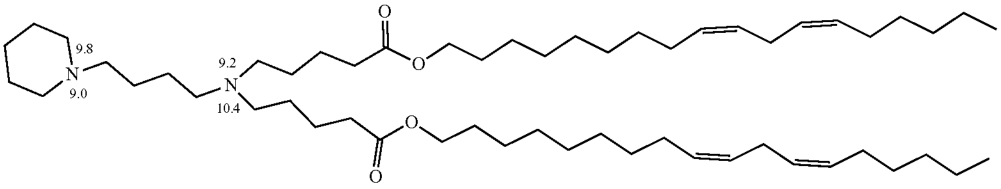 [SMILES: CCCCC/C=C\C/C=C\CCCCCCCCOC(=O)CCCCN(CCCCC(=O)OCCCCCCCC/C=C\C/C=C\CCCCC)CCCCN1CCCCC1] |
| 18 | DL-ADDE-C2/C2-EM | 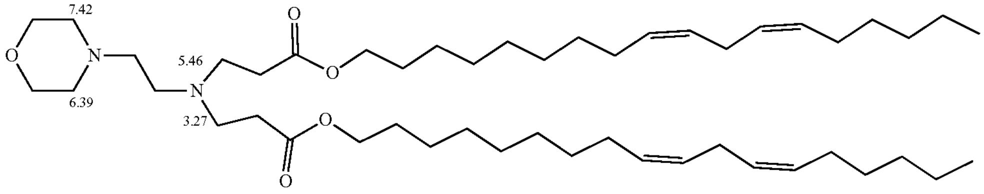 [SMILES: CCCCC/C=C\C/C=C\CCCCCCCCOC(=O)CCN(CCC(=O)OCCCCCCCC/C=C\C/C=C\CCCCC)CCN1CCOCC1] |
| 19 | DL-ADDE-C2/C2-DeBoc | 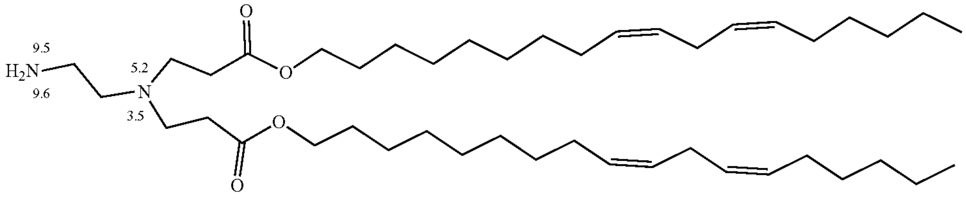 [SMILES: CCCCC/C=C\C/C=C\CCCCCCCCOC(=O)CCN(CCN)CCC(=O)OCCCCCCCC/C=C\C/C=C\CCCCC] |
| 20 | DL-ADDE-C2/C2-DIA | 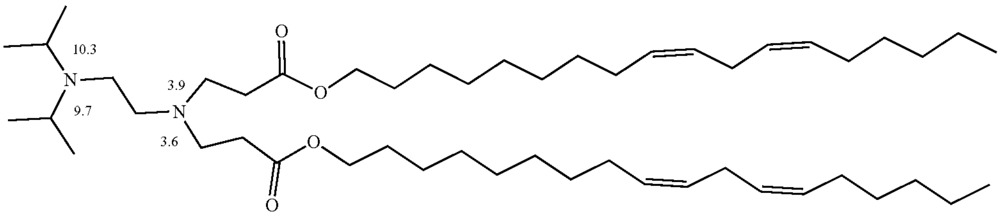 [SMILES: CCCCC/C=C\C/C=C\CCCCCCCCOC(=O)CCN(CCC(=O)OCCCCCCCC/C=C\C/C=C\CCCCC)CCN(C(C)C)C(C)C] |
| 21 | DL-ADDE-C2/C2-1Me-PipD | 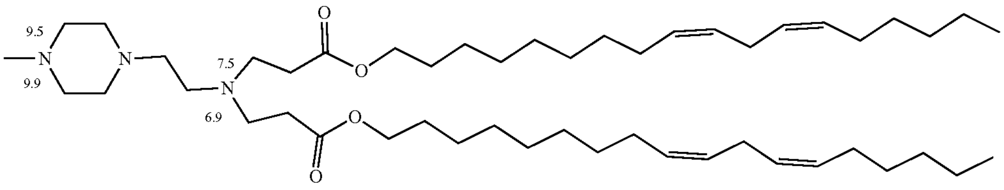 [SMILES: CCCCC/C=C\C/C=C\CCCCCCCCOC(=O)CCN(CCC(=O)OCCCCCCCC/C=C\C/C=C\CCCCC)CCN1CCN(C)CC1] |

TABLE 11b-continued
Ionizable Lipids with Internal pKas (including Exemplary Ionizable Lipids of the Invention and known Lipids)
| No. | Lipid Name | Exemplary Ionizable Lipids with pKas |
|---|---|---|
| 22 | DL-ADDE-IP | 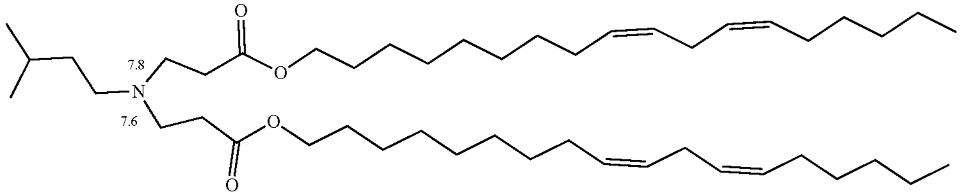 [SMILES: CCCCC/C=C\C/C=C\CCCCCCCCOC(=O)CCN(CCC(=O)OCCCCCCCC/C=C\C/C=C\CCCCC)CCC(C)C] |
| 23 | DL-ADDE-EA | 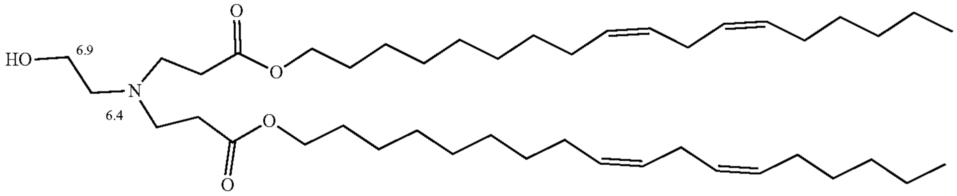 [SMILES: CCCCC/C=C\C/C=C\CCCCCCCCOC(=O)CCN(CCO)CCC(=O)OCCCCCCCC/C=C\C/C=C\CCCCC] |
| 24 | DL-ADDE-PA | 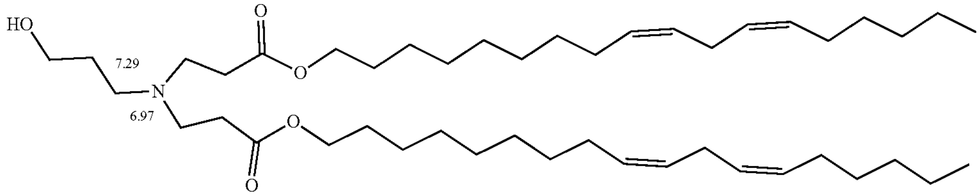 [SMILES: CCCCC/C=C\C/C=C\CCCCCCCCOC(=O)CCN(CCCO)CCC(=O)OCCCCCCCC/C=C\C/C=C\CCCCC] |
| 25 | DL-ADDE-C2/C2-Amine (Boc) | 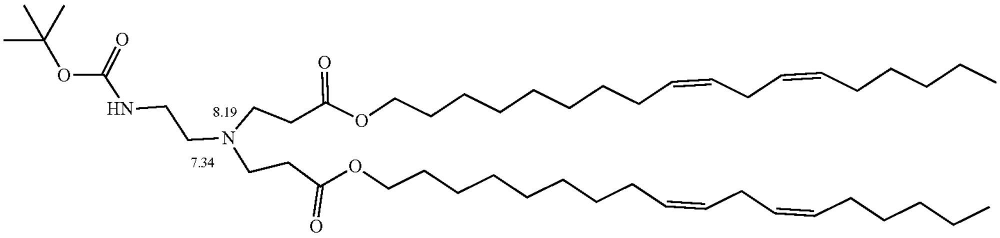 [SMILES: CCCCC/C=C\C/C=C\CCCCCCCCOC(=O)CCN(CCNC(=O)OC(C)(C)C)CCC(=O)OCCCCCCCC/C=C\C/C=C\CCCCC] |
| 26 | BOD-C2/C4-DMA | 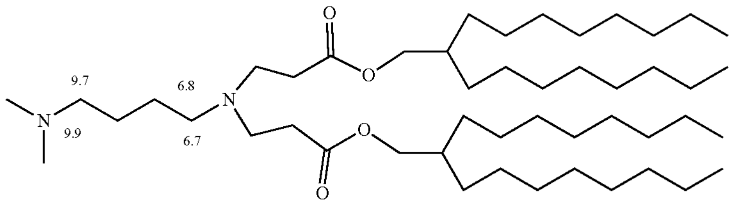 [SMILES: CCCCCCCCC(CCCCCCCC)COC(=O)CCN(CCCCN(C)C)CCC(=O)OCC(CCCCCCCC)CCCCCCCC] |
| 27 | BOD-C2/C4-PyrD | 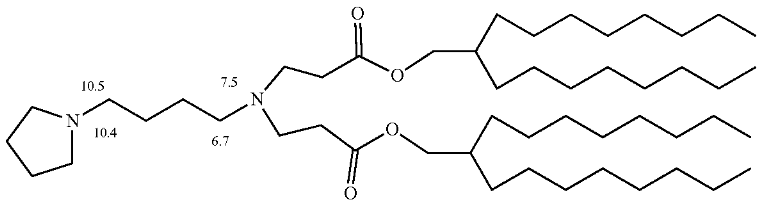 [SMILES: CCCCCCCCC(CCCCCCCC)COC(=O)CCN(CCCCN1CCCC1)CCC(=O)OCC(CCCCCCCC)CCCCCCCC] |
| 28 | BOD-C2/C4-PipD | 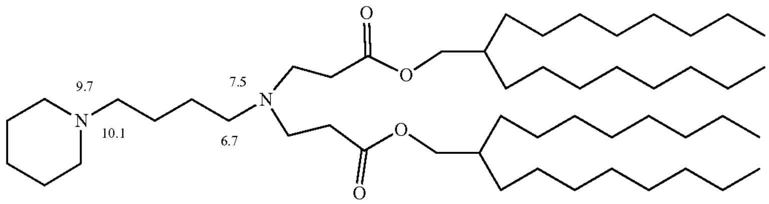 [SMILES: CCCCCCCCC(CCCCCCCC)COC(=O)CCN(CCCCN1CCCCC1)CCC(=O)OCC(CCCCCCCC)CCCCCCCC] |

TABLE 11b-continued
Ionizable Lipids with Internal pKas (including Exemplary Ionizable Lipids of the Invention and known Lipids)
| No. | Lipid Name | Exemplary Ionizable Lipids with pKas |
|---|---|---|
| 29 | BOD-C2/C2-4Me-PipZ | 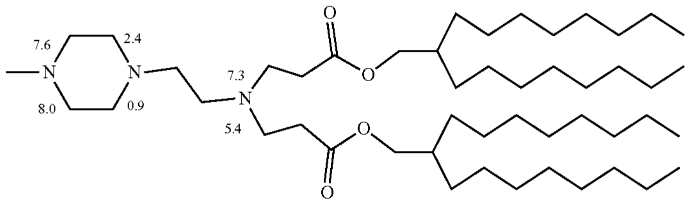 [SMILES: CCCCCCCCC(CCCCCCCC)COC(=O)CCN(CCC(=O)OCC(CCCCCCCC)CCCCCCCC)CCN1CCN(C)CC1] |
| 30 | BOD-C2/C3-4Me-PipZ | 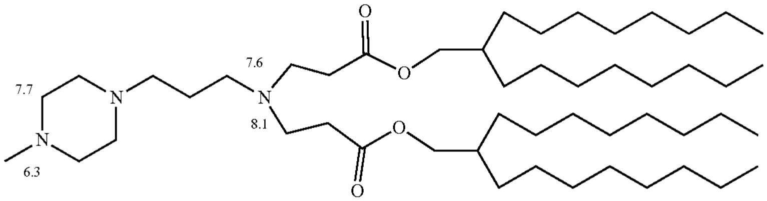 [SMILES: CCCCCCCCC(CCCCCCCC)COC(=O)CCN(CCCN1CCN(C)CC1)CCC(=O)OCC(CCCCCCCC)CCCCCCCC] |
| 31 | BOD-C2/C4-4Me-PipZ | 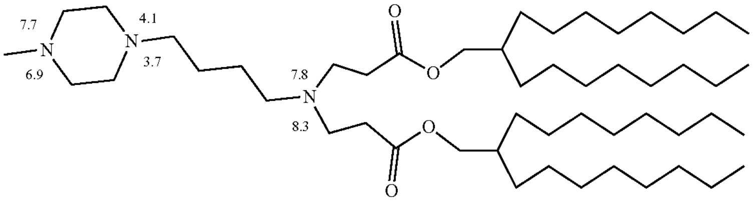 [SMILES: CCCCCCCCC(CCCCCCCC)COC(=O)CCN(CCCCN1CCN(C)CC1)CCC(=O)OCC(CCCCCCCC)CCCCCCCC] |
| 32 | BOD-C2/C2-1mPipD | 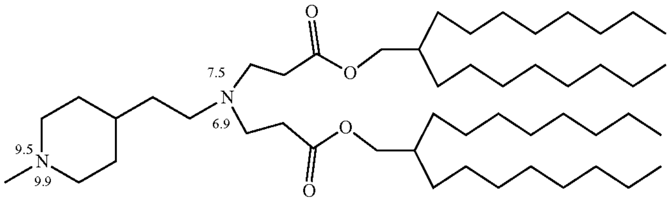 [SMILES: CCCCCCCCC(CCCCCCCC)COC(=O)CCN(CCC(=O)OCC(CCCCCCCC)CCCCCCCC)CCC1CCN(C)CC1] |
| 33 | BOD-C2/C4-CyHexDMA | 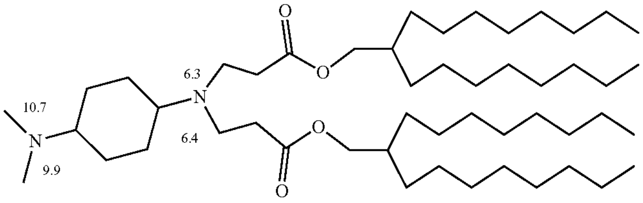 [SMILES: CCCCCCCCC(CCCCCCCC)COC(=O)CCN(CCC(=O)OCC(CCCCCCCC)CCCCCCCC)C1CCC(N(C)C)CC1] |
| 34 | BOD-C2/C3-Imd | 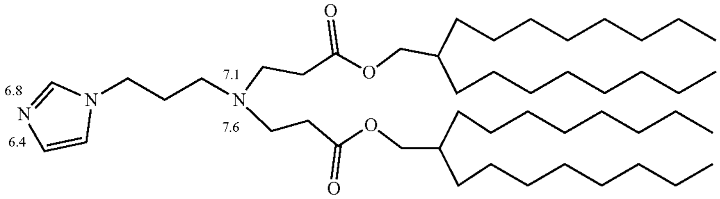 [SMILES: CCCCCCCCC(CCCCCCCC)COC(=O)CCN(CCCn1ccnc1)CCC(=O)OCC(CCCCCCCC)CCCCCCCC] |
| 35 | BODD-C2/C2-DMA | 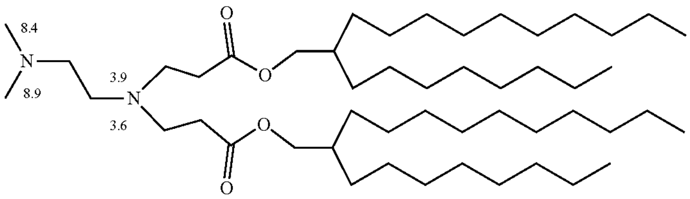 [SMILES: CCCCCCCCCCC(CCCCCCCC)COC(=O)CCN(CCC(=O)OCC(CCCCCCCC)CCCCCCCCCC)CCN(C)C] |

TABLE 11b-continued
Ionizable Lipids with Internal pKas (including Exemplary Ionizable Lipids of the Invention and known Lipids)
| No. | Lipid Name | Exemplary Ionizable Lipids with pKas |
|---|---|---|
| 36 | BODD-C2/C4-DMA | 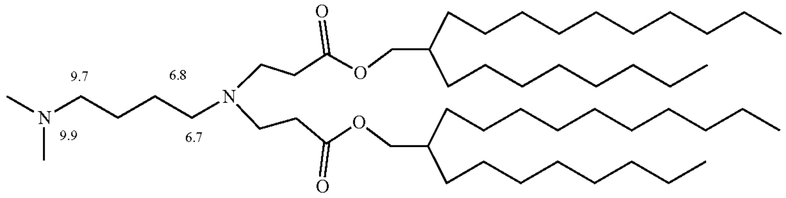 [SMILES: CCCCCCCCCCC(CCCCCCCC)COC(=O)CCN(CCCCN(C)C)CCC(=O)OCC(CCCCCCCC)CCCCCCCCCC] |
| 37 | BODD-C2/C2-PipZ | 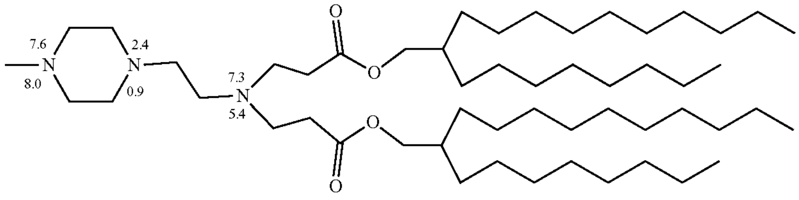 [SMILES: CCCCCCCCCCC(CCCCCCCC)COC(=O)CCN(CCC(=O)OCC(CCCCCCCC)CCCCCCCCCC)CCN1CCN(C)CC1] |
| 38 | BODD-C2/C4-PipZ | 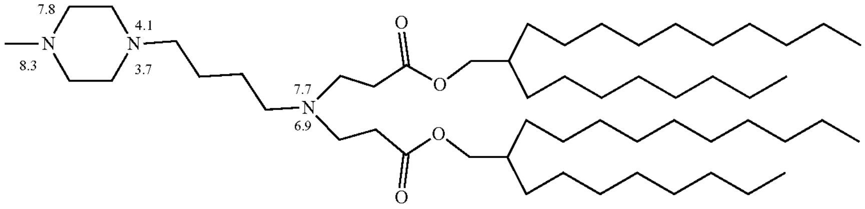 [SMILES: CCCCCCCCCCC(CCCCCCCC)COC(=O)CCN(CCCCN1CCN(C)CC1)CCC(=O)OCC(CCCCCCCC)CCCCCCCCCC] |
| 39 | BODD-C2/C4-Pyrd | 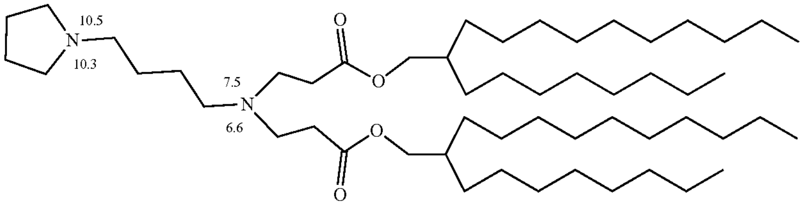 [SMILES: CCCCCCCCCCC(CCCCCCCC)COC(=O)CCN(CCCCN1CCCC1)CCC(=O)OCC(CCCCCCCC)CCCCCCCCCC] |
| 40 | BODD-C2/C4-PipD | 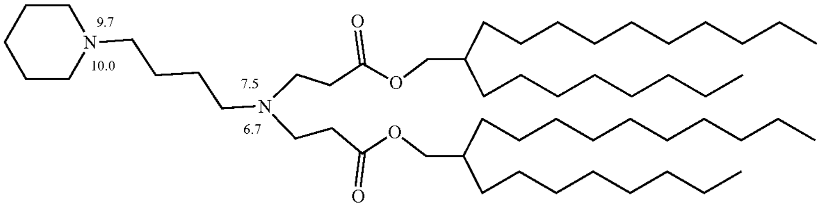 [SMILES: CCCCCCCCCCC(CCCCCCCC)COC(=O)CCN(CCCCN1CCCCC1)CCC(=O)OCC(CCCCCCCC)CCCCCCCCCC] |
| 41 | BODD-C2/C2-1Me-2PyrD | 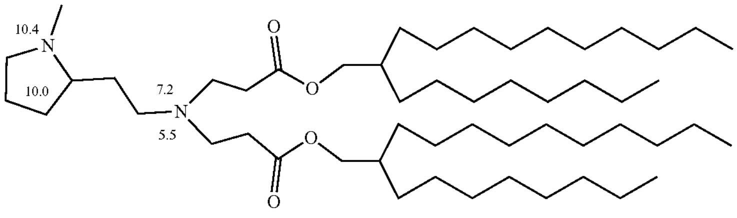 [SMILES: CCCCCCCCCCC(CCCCCCCC)COC(=O)CCN(CCC(=O)OCC(CCCCCCCC)CCCCCCCCCC)CCC1CCCN1C] |
| 42 | BODD-C2C0-1Me-PipD | 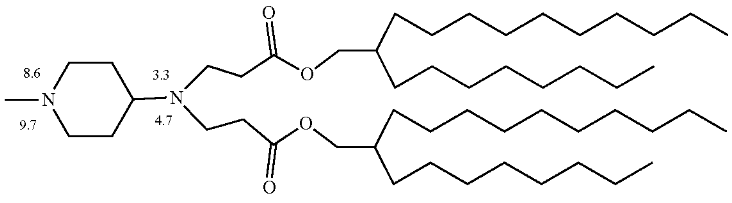 [SMILES: CCCCCCCCCCC(CCCCCCCC)COC(=O)CCN(CCC(=O)OCC(CCCCCCCC)CCCCCCCCCC)C1CCN(C)CC1] |

TABLE 11b-continued
Ionizable Lipids with Internal pKas (including Exemplary Ionizable Lipids of the Invention and known Lipids)
| No. | Lipid Name | Exemplary Ionizable Lipids with pKas |
|---|---|---|
| 43 | BODD-C2C2-1Me-PipD | 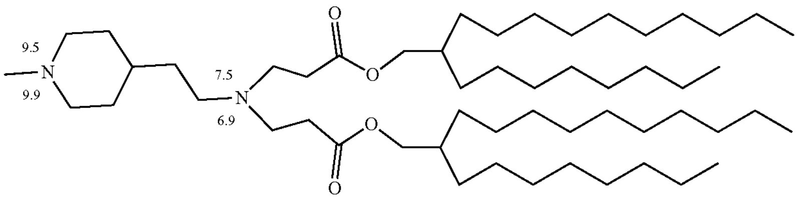 [SMILES: CCCCCCCCCCC(CCCCCCCC)COC(=O)CCN(CCC(=O)OCC(CCCCCCCC)CCCCCCCCCC)CCC1CCN(C)CC1] |
| 44 | BDL-C2C2-PipZ | 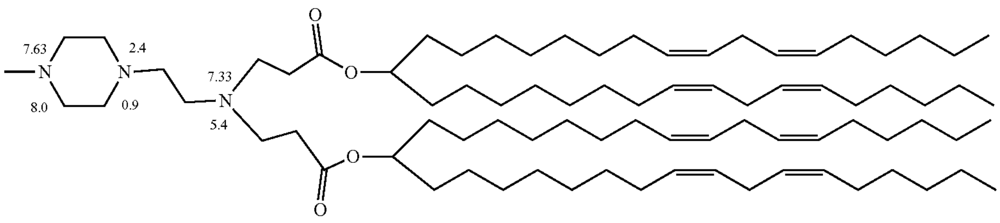 |
| 45 | BHD-C2/C4-PipZ | 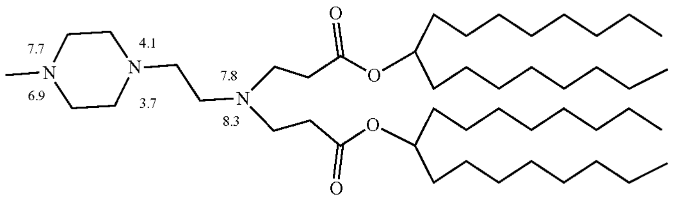 [SMILES: CCCCCCCCC(CCCCCCCC)OC(=O)CCN(CCC(=O)OC(CCCCCCCC)CCCCCCCC)CCN1CCN(C)CC1] |
| 46 | BChol-C2/C4-PipZ | 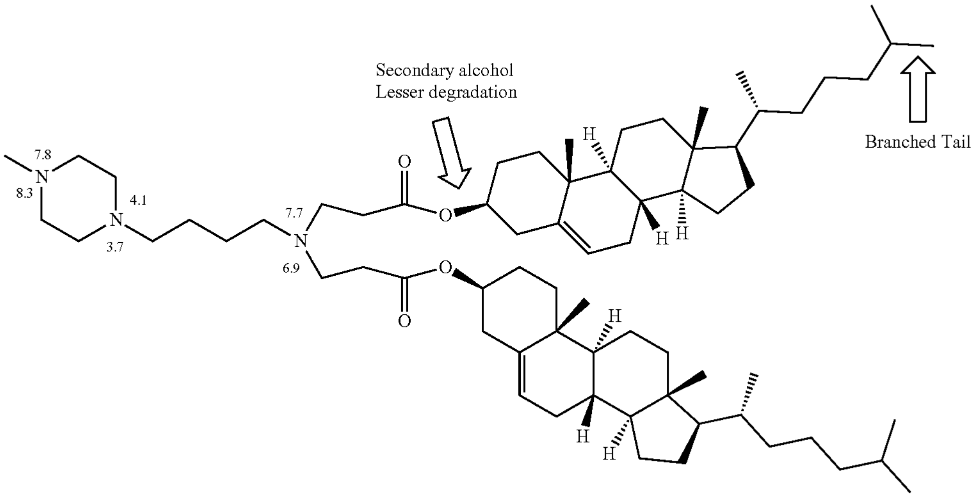 [SMILES: CC(C)CCC[C@@H](C)[C@H]1CC[C@H]2[C@@H]3CC=C4C[C@@H](OC(=O)CCN(CCCCN5CCN(C)CC5)CCC(=O)O[C@H]5CC[C@@]6(C)C(=CC[C@H]7[C@@H]8CC[C@H]([C@H](C)CCCC(C)C)[C@@]8(C)CC[C@@H]76)C5)CC[C@]4(C)[C@H]3CC[C@]12C] |
| 47 | L-Amide-AE | 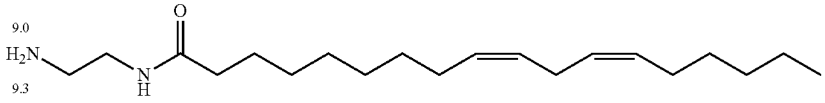 [SMILES: CCCCC/C=C\C/C=C\CCCCCCCC(=O)NCCN] |
| 48 | L-Amide-DMA | 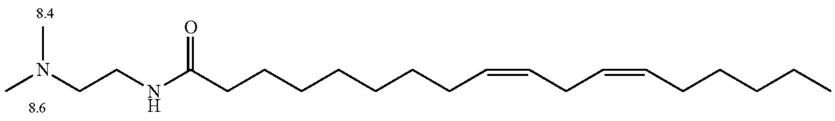 |
| 49 | L-Amide-AEDS | 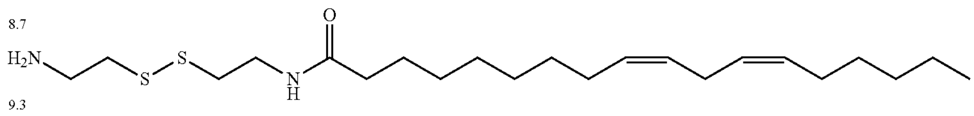 |

TABLE 11b-continued

| Ionizable Lipids with Internal pKas (including Exemplary Ionizable Lipids of the Invention and known Lipids) | | |
|---|---|---|
| No. | Lipid Name | Exemplary Ionizable Lipids with pKas |
| 50 | DSDMA | 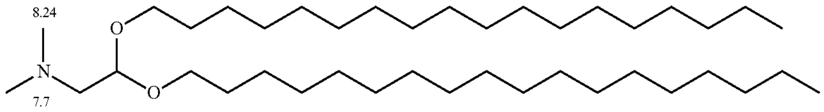 [SMILES: CCCCCCCCCCCCCCCCCCOC(CN(C)C)OCCCCCCCCCCCCCCCCCC] |
| 51 | MC3-Synthesized | 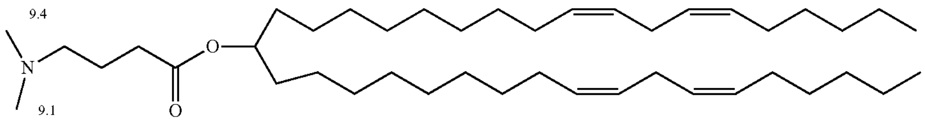 [SMILES: CCCCC/C=C\C/C=C\CCCCCCCCC(CCCCCCCC/C=C\C/C=C\CCCCC)OC(=O)CCCN(C)C] |
| 52 | SM-102 | 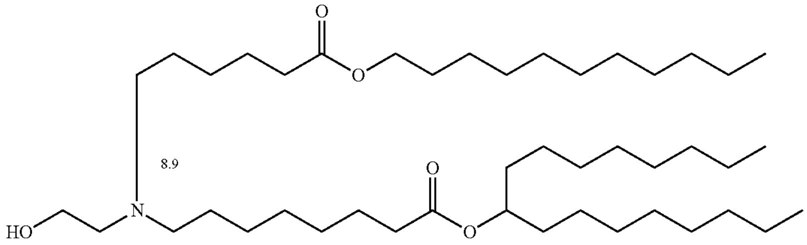 [SMILES: CCCCCCCCCCCOC(=O)CCCCCN(CCO)CCCCCCCC(=O)OC(CCCCCCCC)CCCCCCCC] |
| 53 | ALC-0315 | 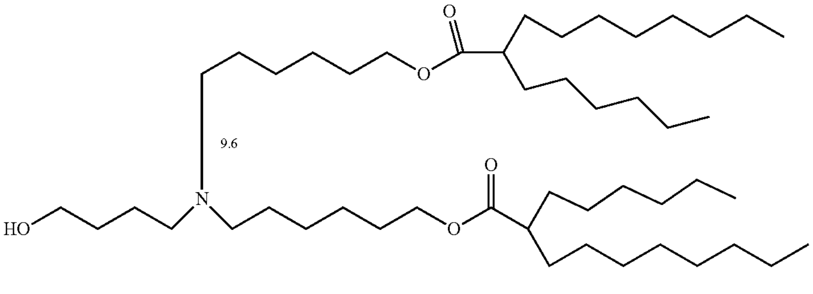 [SMILES: CCCCCCCCC(CCCCCC)C(=O)OCCCCCCN(CCCCO)CCCCCCOC(=O)C(CCCCCC)CCCCCCCC] |
| 54 | ALC-C2PipZ | 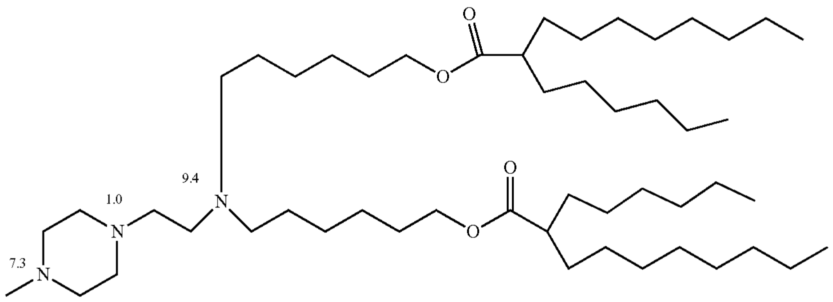 [SMILES: CCCCCCCCC(CCCCCC)C(=O)OCCCCCCN(CCCCCCOC(=O)C(CCCCCC)CCCCCCCC)CCN1CCN(C)CC1] |

In certain embodiments, the invention encompasses a new class of ionizable lipids (the Ionizable Lipids of the Invention) synthesized bearing two ionizable amines and two degradable ester linkers to linoleic acid tails or branched tails. DL=DiLinoleic Acid, ADDE=Azane Diyl DiEthyl, Cx/Cy=carbon spacers, DMA=DiMethylAmine, Pyr=Pyridine, PipZ=PiperaZine, PipD=PiperiDine, DIPA=DiIsopropylamine, DM=DiMethyl, BOD=BisOctylDecyl. Most ADDE ionizable lipids successfully transfected HEK 293 cells in vitro, with the exception of 4 listed below that were not active, possibly due to the bulkiness of their headgroups and restricted conformations.

TABLE 12
| pKA of Illustrative Ionizable Lipids of the Invention | |
|---|---|
| Lipid | Structure |
| DL-ADDE-C2/C2-DMA | 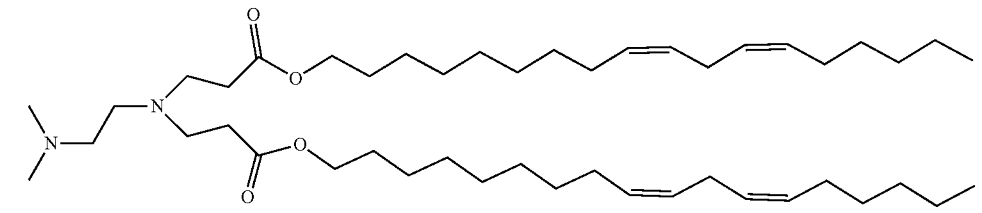 [SMILES: CCCCC/C=C\C/C=C\CCCCCCCCOC(=O)CCN(CCC(=O)OCCCCCCCC/C=C\C/C=C\CCCCC)CCN(C)C] |
| DL-ADDE-C2/C3-DMA | 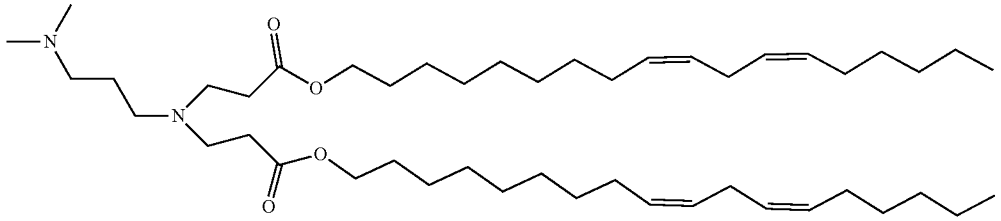 [SMILES: CCCCC/C=C\C/C=C\CCCCCCCCOC(=O)CCN(CCCN(C)C)CCC(=O)OCCCCCCCC/C=C\C/C=C\CCCCC] |
| DL-ADDE-C2/C4-DMA | 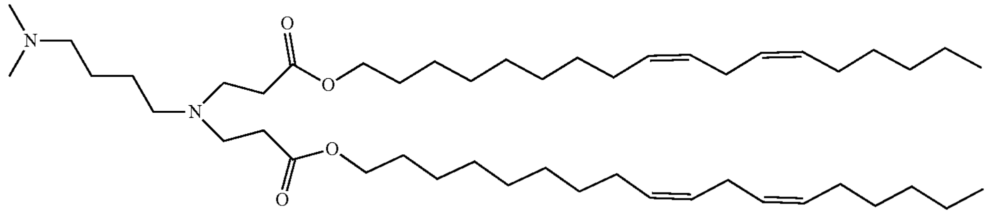 [SMILES: CCCCC/C=C\C/C=C\CCCCCCCCOC(=O)CCN(CCCCN(C)C)CCC(=O)OCCCCCCCC/C=C\C/C=C\CCCCC] |
| DL-ADDE-C4/C4-DMA | 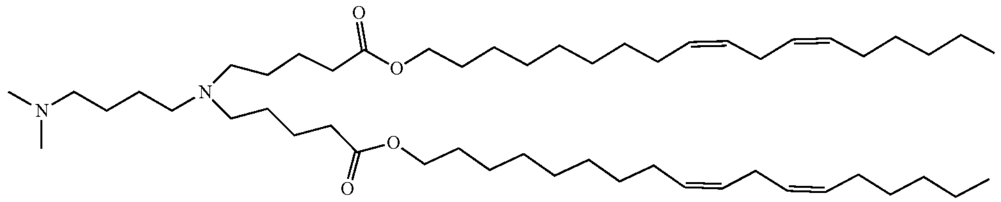 [SMILES: CCCCC/C=C\C/C=C\CCCCCCCCOC(=O)CCCCN(CCCCC(=O)OCCCCCCCC/C=C\C/C=C\CCCCC)CCCCN(C)C] |
| DL-ADDE-C2/C2-Pyr | 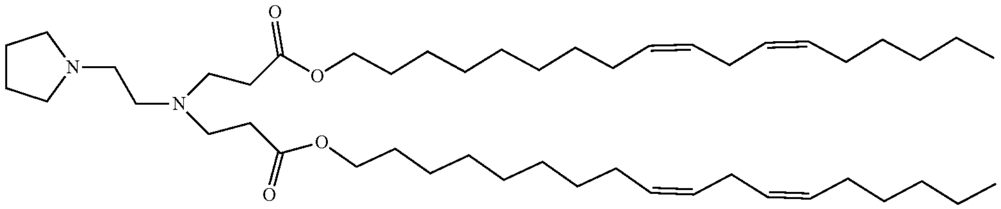 [SMILES: CCCCC/C=C\C/C=C\CCCCCCCCOC(=O)CCN(CCC(=O)OCCCCCCCC/C=C\C/C=C\CCCCC)CCN1CCCC1] |
| DL-ADDE-C2/C3-Pyr | 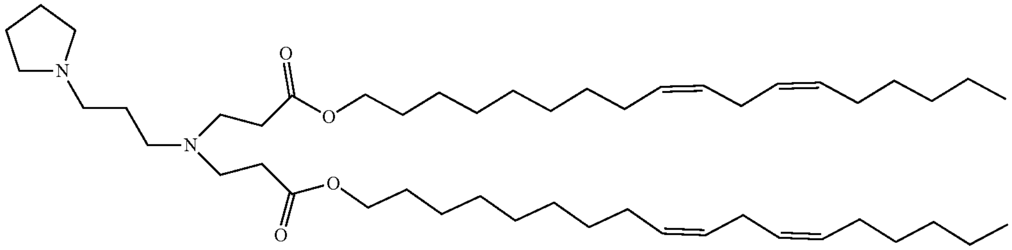 [SMILES: CCCCC/C=C\C/C=C\CCCCCCCCOC(=O)CCN(CCCN1CCCC1)CCC(=O)OCCCCCCCC/C=C\C/C=C\CCCCC] |

TABLE 12-continued
| pKA of Illustrative Ionizable Lipids of the Invention | |
|---|---|
| DL-ADDE-C2/C4-Pyr | 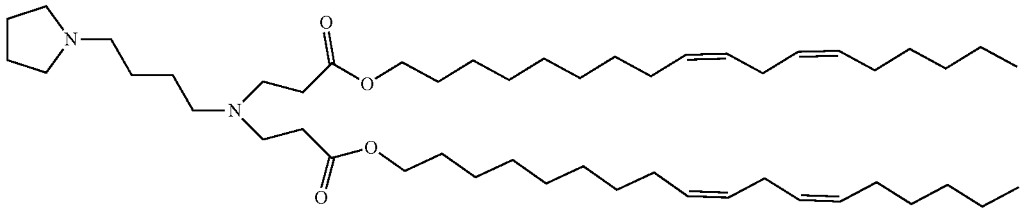 [SMILES: CCCCC/C=C\C/C=C\CCCCCCCCOC(=O)CCN(CCCCN1CCCC1)CCC(=O)OCCCCCCCC/C=C\C/C=C\CCCCC] |
| DL-ADDE-C4/C4-Pyr | 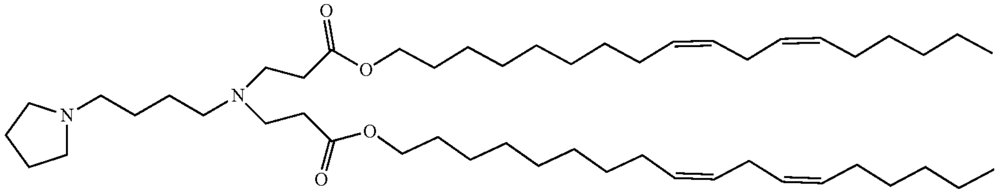 [SMILES: CCCCC/C=C\C/C=C\CCCCCCCCOC(=O)CCN(CCCCN1CCCC1)CCC(=O)OCCCCCCCC/C=C\C/C=C\CCCCC] |
| DL-ADDE-C2/C2-PipD | 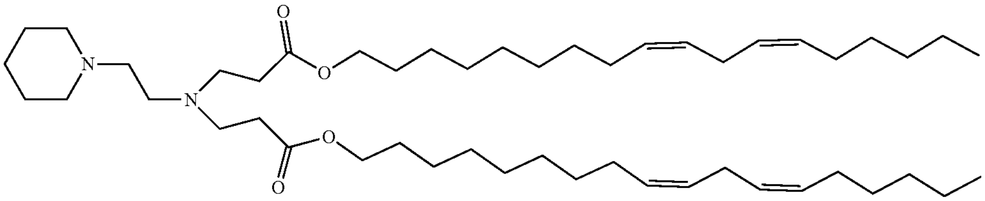 [SMILES: CCCCC/C=C\C/C=C\CCCCCCCCOC(=O)CCN(CCC(=O)OCCCCCCCC/C=C\C/C=C\CCCCC)CCN1CCCCC1] |
| DL-ADDE-C2/C3-PipD | 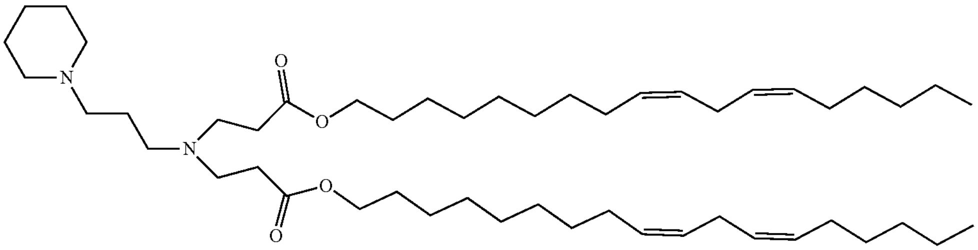 [SMILES: CCCCC/C=C\C/C=C\CCCCCCCCOC(=O)CCN(CCCN1CCCCC1)CCC(=O)OCCCCCCCC/C=C\C/C=C\CCCCC] |
| DL-ADDE-C2/C4-PipD | 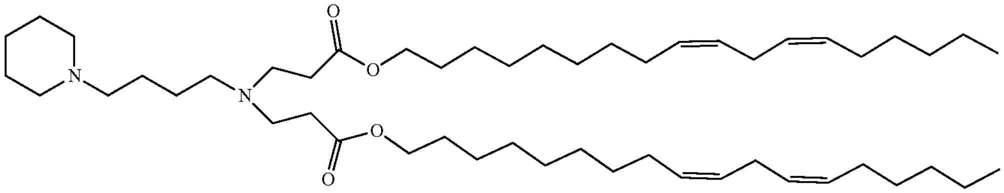 [SMILES: CCCCC/C=C\C/C=C\CCCCCCCCOC(=O)CCN(CCCCN1CCCCC1)CCC(=O)OCCCCCCCC/C=C\C/C=C\CCCCC] |
| DL-ADDE-C4/C4-PipD | 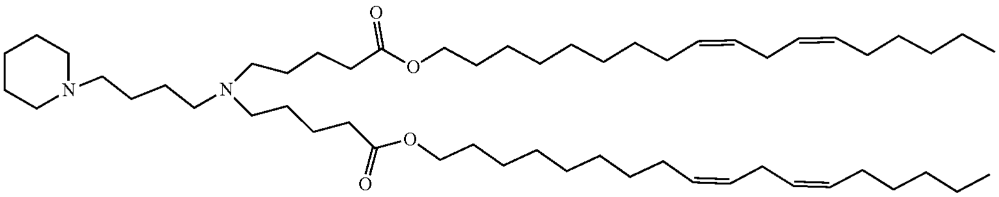 [SMILES: CCCCC/C=C\C/C=C\CCCCCCCCOC(=O)CCCCN(CCCCC(=O)OCCCCCCCC/C=C\C/C=C\CCCCC)CCCCN1CCCCC1] |
| DL-ADDE-C2/C2-4Me-PipZ | 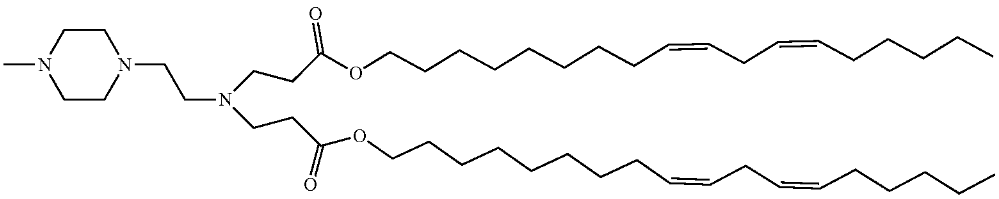 [SMILES: CCCCC/C=C\C/C=C\CCCCCCCCOC(=O)CCN(CCC(=O)OCCCCCCCC/C=C\C/C=C\CCCCC)CCN1CCN(C)CC1] |

TABLE 12-continued
| pKA of Illustrative Ionizable Lipids of the Invention | |
|---|---|
| DL-ADDE-C2/C3-4Me-PipZ | 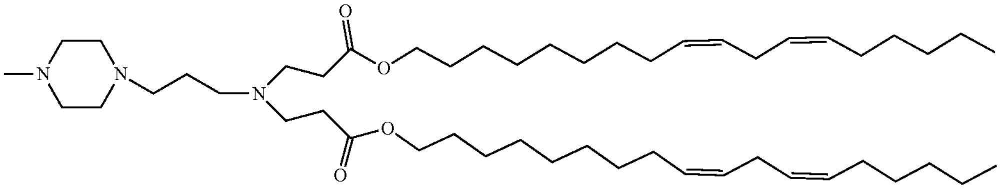 [SMILES: CCCCC/C=C\C/C=C\CCCCCCCCOC(=O)CCN(CCCN1CCN(C)CC1)CCC(=O)OCCCCCCCC/C=C\C/C=C\CCCCC] |
| DL-ADDE-C2/C4-4Me-PipZ | 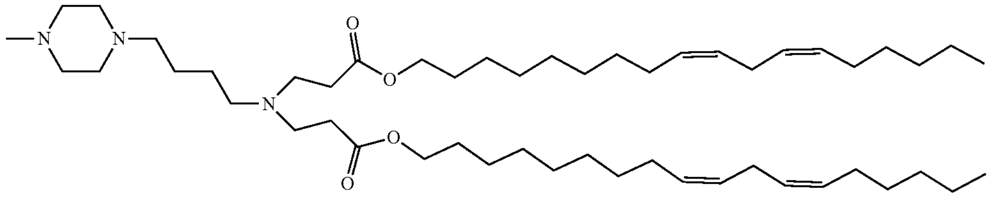 [SMILES: CCCCC/C=C\C/C=C\CCCCCCCCOC(=O)CCN(CCCCN1CCN(C)CC1)CCC(=O)OCCCCCCCC/C=C\C/C=C\CCCCC] |
| DL-ADDE-C4/C4-4Me-PipZ | 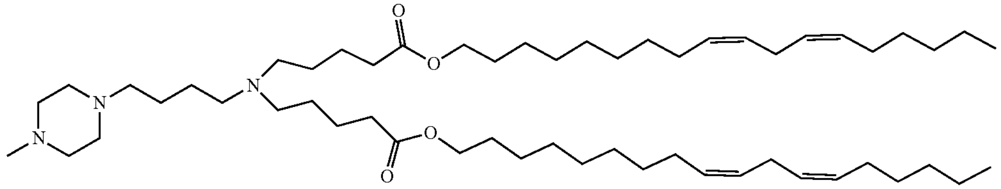 [SMILES: CCCCC/C=C\C/C=C\CCCCCCCCOC(=O)CCCCN(CCCCC(=O)OCCCCCCCC/C=C\C/C=C\CCCCC)CCCCN1CCN(C)CC1] |
| DL-ADDE-C2/C2-DIPA | 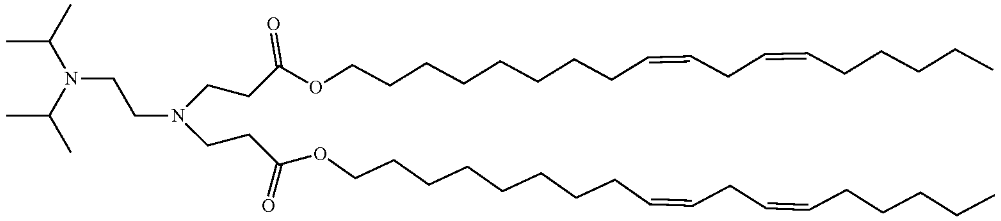 [SMILES: CCCCC/C=C\C/C=C\CCCCCCCCOC(=O)CCN(CCC(=O)OCCCCCCCC/C=C\C/C=C\CCCCC)CCN(C(C)C)C(C)C] |
| DL-ADDE-C2/C2-BocA | 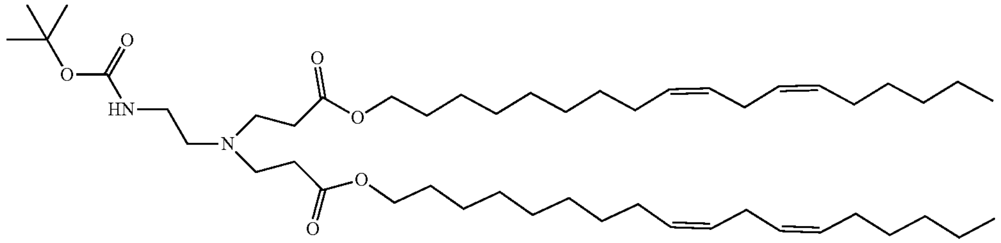 [SMILES: CCCCC/C=C\C/C=C\CCCCCCCCOC(=O)CCN(CCNC(=O)OC(C)(C)C)CCC(=O)OCCCCCCCC/C=C\C/C=C\CCCCC] |
| DL-ADDE-C2/C2-DeBocA | 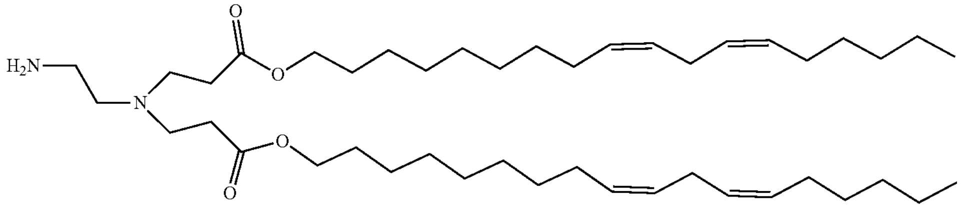 [SMILES: CCCCC/C=C\C/C=C\CCCCCCCCOC(=O)CCN(CCN)CCC(=O)OCCCCCCCC/C=C\C/C=C\CCCCC] |
| DL-ADDE-C2/C3-DM-DMA | 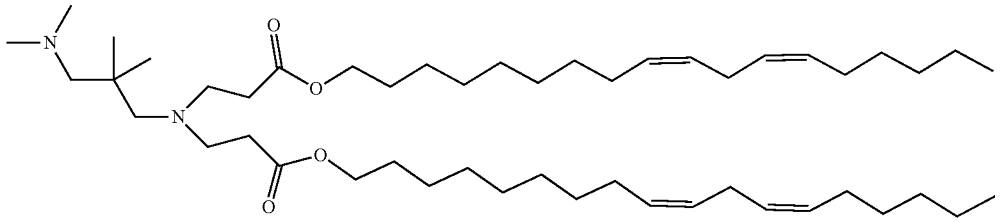 [SMILES: CCCCC/C=C\C/C=C\CCCCCCCCOC(=O)CCN(CCC(=O)OCCCCCCCC/C=C\C/C=C\CCCCC)CC(C)(C)CN(C)C] |

TABLE 12-continued
| pKA of Illustrative Ionizable Lipids of the Invention | |
|---|---|
| DL-C2C2-1Me-PipD | 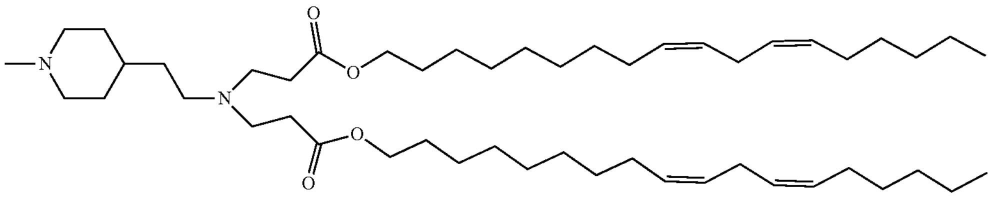 |
| BOD-ADDE-C2/C2-DMA | 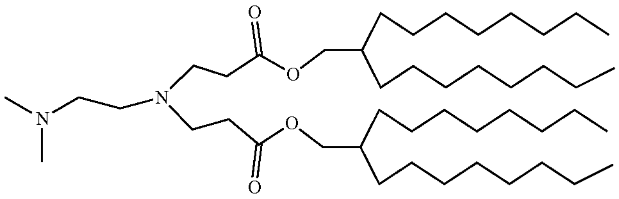 [SMILES: CCCCCCCCC(CCCCCCCC)COC(=O)CCN(CCC(=O)OCC(CCCCCCCC)CCCCCCCC)CCN(C)C] |
| BOD-ADDE-C2/C4-DMA | 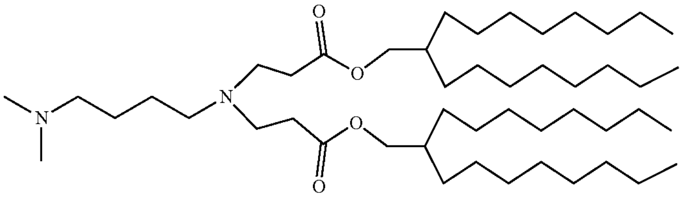 [SMILES: CCCCCCCCC(CCCCCCCC)COC(=O)CCN(CCCCN(C)C)CCC(=O)OCC(CCCCCCCC)CCCCCCCC] |
| BOD-ADDE-C2/C2-Pyr | 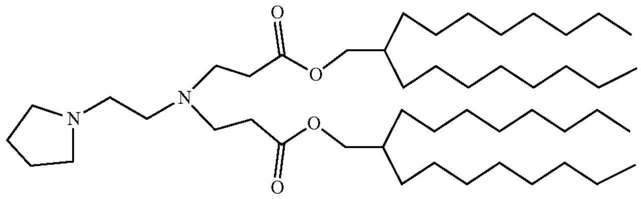 [SMILES: CCCCCCCCC(CCCCCCCC)COC(=O)CCN(CCC(=O)OCC(CCCCCCCC)CCCCCCCC)CCN1CCCC1] |
| BOD-ADDE-C2/C4-Pyr | 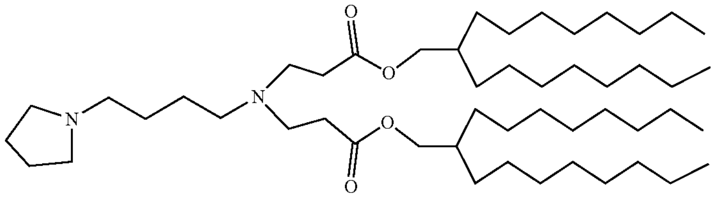 [SMILES: CCCCCCCCC(CCCCCCCC)COC(=O)CCN(CCCCN1CCCC1)CCC(=O)OCC(CCCCCCCC)CCCCCCCC] |
| BOD-ADDE-C2/C2-PipD | 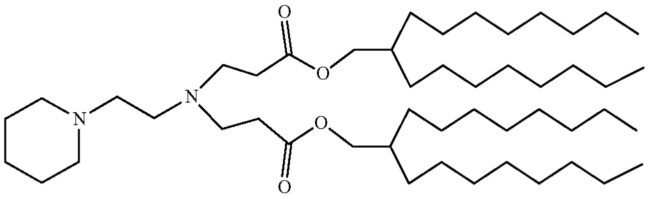 [SMILES: CCCCCCCCC(CCCCCCCC)COC(=O)CCN(CCC(=O)OCC(CCCCCCCC)CCCCCCCC)CCN1CCCCC1] |
| BOD-ADDE-C2/C4-PipD | 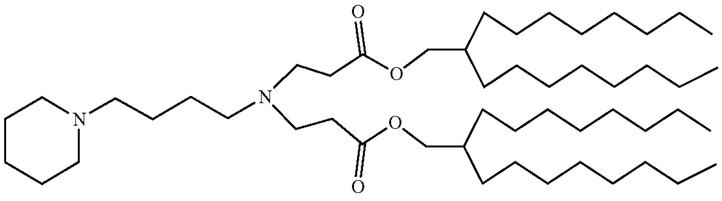 [SMILES: CCCCCCCCC(CCCCCCCC)COC(=O)CCN(CCCCN1CCCCC1)CCC(=O)OCC(CCCCCCCC)CCCCCCCC] |

TABLE 12-continued
| pKA of Illustrative Ionizable Lipids of the Invention | |
|---|---|
| BOD-ADDE-C2/C2-4Me-PipZ | 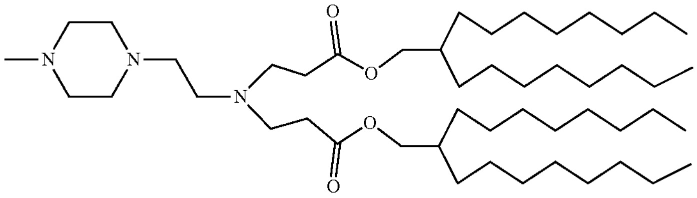 [SMILES: CCCCCCCCC(CCCCCCCC)COC(=O)CCN(CCC(=O)OCC(CCCCCCCC)CCCCCCCC)CCN1CCN(C)CC1] |
| BOD-ADDE-C2/C3-4Me-PipZ | 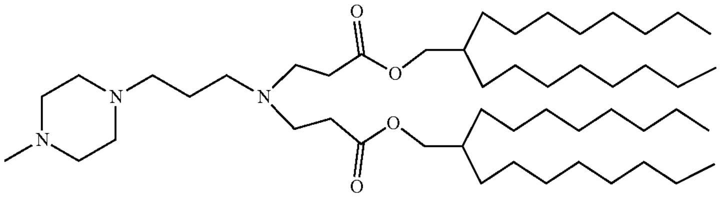 [SMILES: CCCCCCCCC(CCCCCCCC)COC(=O)CCN(CCCN1CCN(C)CC1)CCC(=O)OCC(CCCCCCCC)CCCCCCCC] |
| BOD-ADDE-C2/C4-4Me-PipZ | 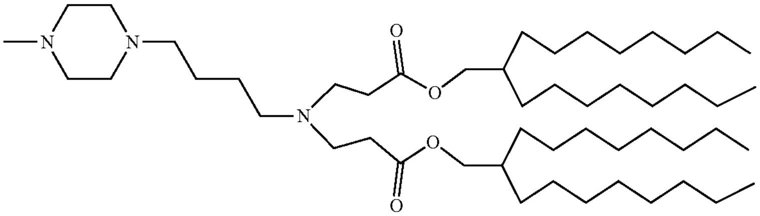 [SMILES: CCCCCCCCC(CCCCCCCC)COC(=O)CCN(CCCCN1CCN(C)CC1)CCC(=O)OCC(CCCCCCCC)CCCCCCCC] |
| BOD-ADDE-C2/C2-1Me-PipD | 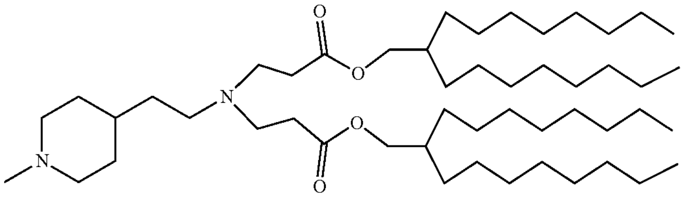 [SMILES: CCCCCCCCC(CCCCCCCC)COC(=O)CCN(CCC(=O)OCC(CCCCCCCC)CCCCCCCC)CCC1CCN(C)CC1] |
| BOD-ADDE-C2/C4-CyHexDMA | 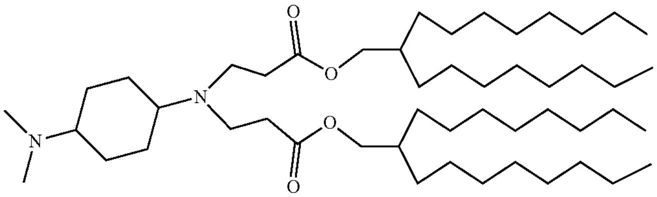 [SMILES: CCCCCCCCC(CCCCCCCC)COC(=O)CCN(CCC(=O)OCC(CCCCCCCC)CCCCCCCC)C1CCC(N(C)C)CC1] |
| BOD-ADDE-C2/C3-Imd | 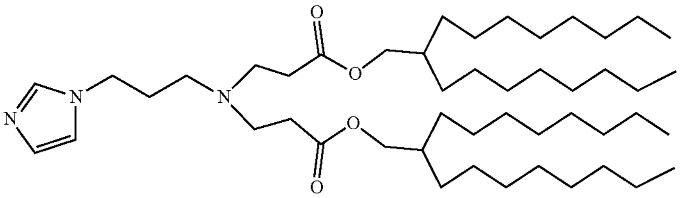 [SMILES: CCCCCCCCC(CCCCCCCC)COC(=O)CCN(CCCn1ccnc1)CCC(=O)OCC(CCCCCCCC)CCCCCCCC] |
| BODD-ADDE-C2/C2-DMA | 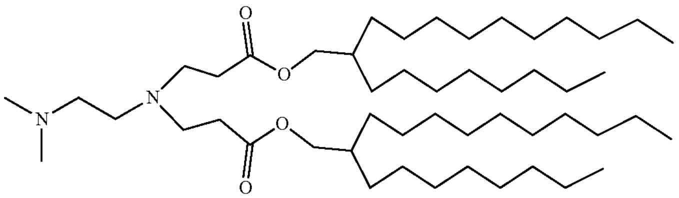 [SMILES: CCCCCCCCCCC(CCCCCCCC)COC(=O)CCN(CCC(=O)OCC(CCCCCCCC)CCCCCCCCCC)CCN(C)C] |

TABLE 12-continued
| pKA of Illustrative Ionizable Lipids of the Invention | |
|---|---|
| BODD-ADDE-C2/C4-DMA | 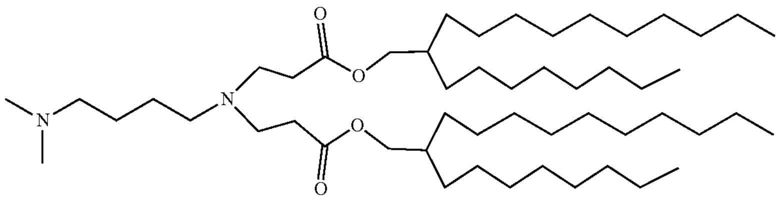 [SMILES: CCCCCCCCCCC(CCCCCCCC)COC(=O)CCN(CCCCN(C)C)CCC(=O)OCC(CCCCCCCC)CCCCCCCCCC] |
| BODD-ADDE-C2/C2-Pyr | 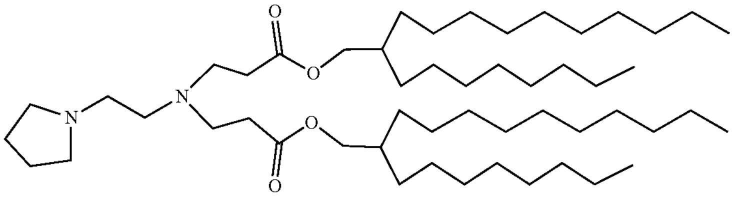 [SMILES: CCCCCCCCCCC(CCCCCCCC)COC(=O)CCN(CCC(=O)OCC(CCCCCCCC)CCCCCCCCCC)CCN1CCCC1] |
| BODD-ADDE-C2/C4-Pyr | 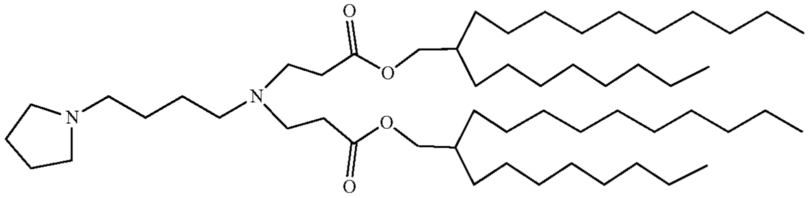 [SMILES: CCCCCCCCCCC(CCCCCCCC)COC(=O)CCN(CCCCN1CCCC1)CCC(=O)OCC(CCCCCCCC)CCCCCCCCCC] |
| BODD-ADDE-C2/C2-PipD | 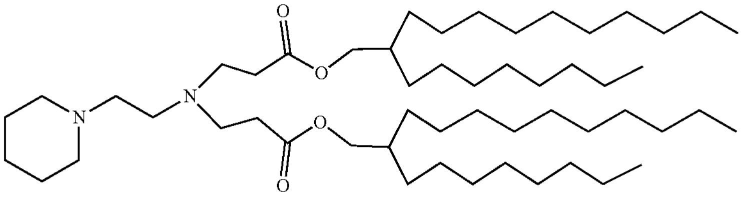 [SMILES: CCCCCCCCCCC(CCCCCCCC)COC(=O)CCN(CCC(=O)OCC(CCCCCCCC)CCCCCCCCCC)CCN1CCCCC1] |
| BODD-ADDE-C2/C4-PipD | 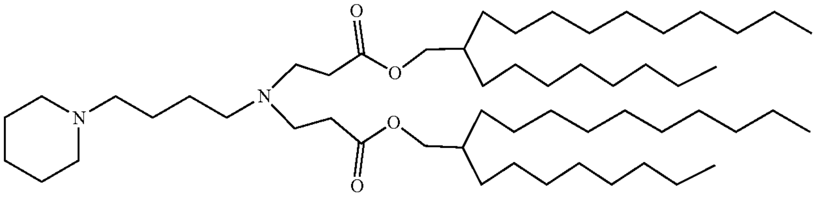 [SMILES: CCCCCCCCCCC(CCCCCCCC)COC(=O)CCN(CCCCN1CCCCC1)CCC(=O)OCC(CCCCCCCC)CCCCCCCCCC] |
| BODD-ADDE-C2/C2-4Me-PipZ | 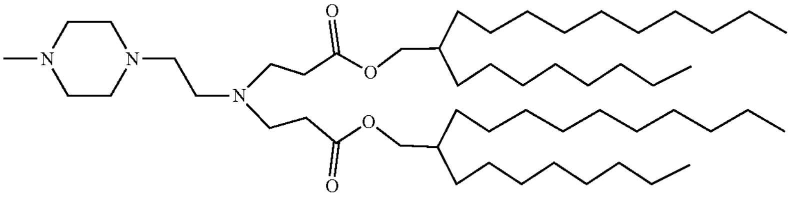 [SMILES: CCCCCCCCCCC(CCCCCCCC)COC(=O)CCN(CCC(=O)OCC(CCCCCCCC)CCCCCCCCCC)CCN1CCN(C)CC1] |
| BOD-ADDE-C2/C4-4Me-PipZ | 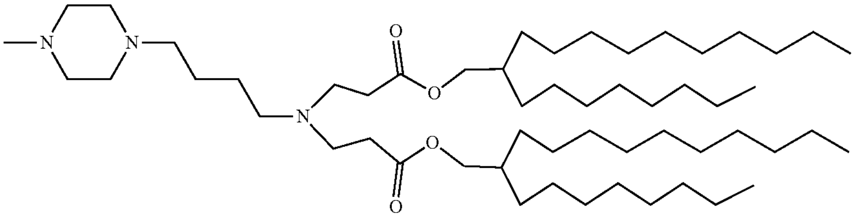 [SMILES: CCCCCCCCCCC(CCCCCCCC)COC(=O)CCN(CCCCN1CCN(C)CC1)CCC(=O)OCC(CCCCCCCC)CCCCCCCCCC] |

TABLE 12-continued
| pKA of Illustrative Ionizable Lipids of the Invention | |
|---|---|
| BODD-ADDE-C2C2-1MePipD | 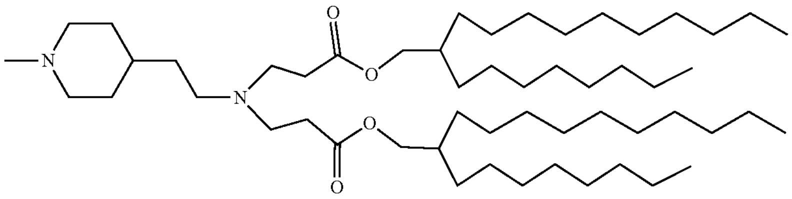 [SMILES: CCCCCCCCCCC(CCCCCCCC)COC(=O)CCN(CCC(=O)OCC(CCCCCCCC)CCCCCCCCCC)CCC1CCN(C)CC1] |
| BODD-ADDE-C2C0-1Me-PipD | 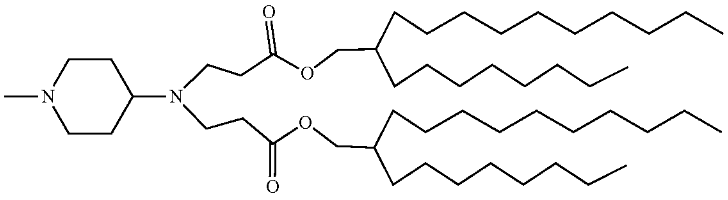 [SMILES: CCCCCCCCCCC(CCCCCCCC)COC(=O)CCN(CCC(=O)OCC(CCCCCCCC)CCCCCCCCCC)C1CCN(C)CC1] |
| BODD-ADDE-C2C2-1Me-2Pyr | 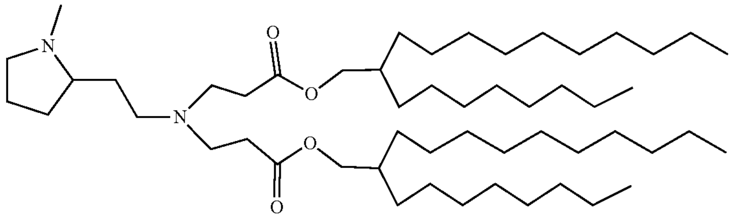 [SMILES: CCCCCCCCCCC(CCCCCCCC)COC(=O)CCN(CCC(=O)OCC(CCCCCCCC)CCCCCCCCCC)CCC1CCCN1C] |
| BHD-ADDE-C2/C2-DMA | 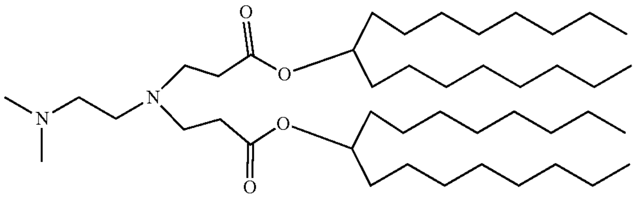 [SMILES: CCCCCCCCC(CCCCCCCC)OC(=O)CCN(CCC(=O)OC(CCCCCCCC)CCCCCCCC)CCN(C)C] |
| BHD-ADDE-C2/C4-DMA | 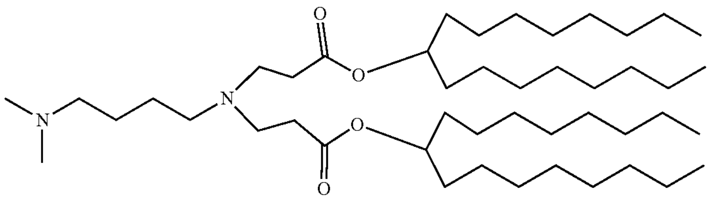 [SMILES: CCCCCCCCC(CCCCCCCC)OC(=O)CCN(CCCCN(C)C)CCC(=O)OC(CCCCCCCC)CCCCCCCC] |
| BHD-ADDE-C2/C2-Pyr | 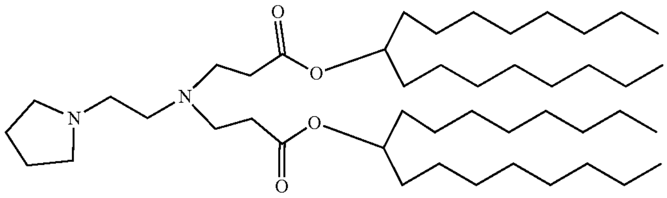 [SMILES: CCCCCCCCC(CCCCCCCC)OC(=O)CCN(CCC(=O)OC(CCCCCCCC)CCCCCCCC)CCN1CCCC1] |
| BHD-ADDE-C2/C4-Pyr | 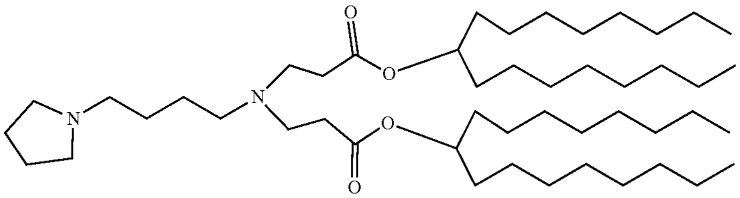 [SMILES: CCCCCCCCC(CCCCCCCC)OC(=O)CCN(CCCCN1CCCC1)CCC(=O)OC(CCCCCCCC)CCCCCCCC] |

TABLE 12-continued
| pKA of Illustrative Ionizable Lipids of the Invention | |
|---|---|
| BHD-ADDE-C2/C2-PipD | 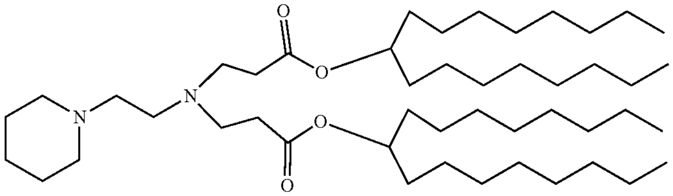 [SMILES: CCCCCCCCC(CCCCCCCC)OC(=O)CCN(CCC(=O)OC(CCCCCCCC)CCCCCCCC)CCN1CCCCC1] |
| BHD-ADDE-C2/C2-PipZ | 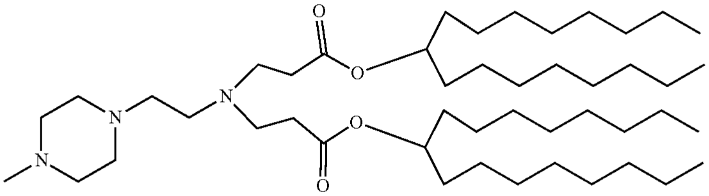 [SMILES: CCCCCCCCC(CCCCCCCC)OC(=O)CCN(CCC(=O)OC(CCCCCCCC)CCCCCCCC)CCN1CCN(C)CC1] |
| BHD-ADDE-C2/C4-PipZ | 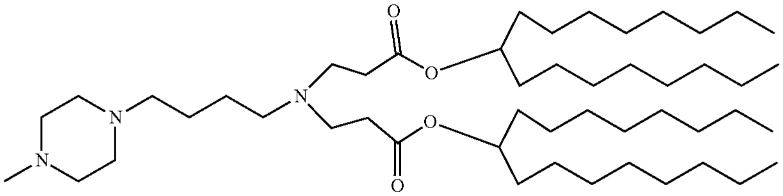 [SMILES: CCCCCCCCC(CCCCCCCC)OC(=O)CCN(CCCCN1CCN(C)CC1)CCC(=O)OC(CCCCCCCC)CCCCCCCC] |
| BHD-ADDE-C2/C4-PipD | 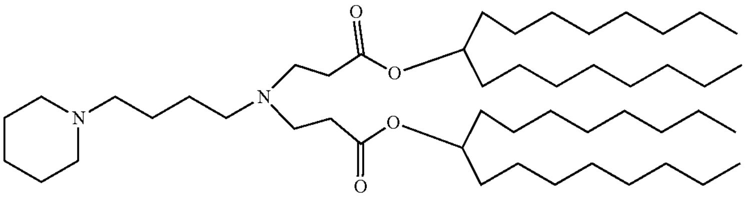 [SMILES: CCCCCCCCC(CCCCCCCC)OC(=O)CCN(CCCCN1CCCCC1)CCC(=O)OC(CCCCCCCC)CCCCCCCC] |
| BDL-ADDE-C2/C2-PipZ | 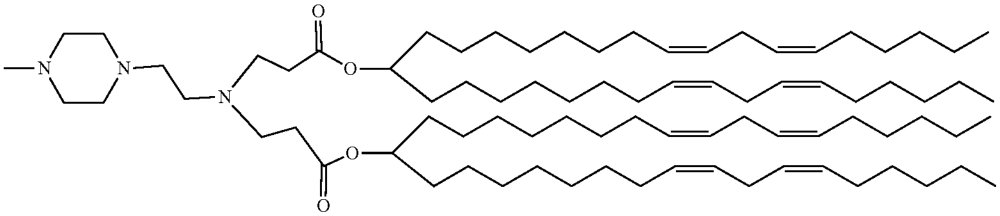 |
| BChol-ADDE-C2/C4-PipZ | 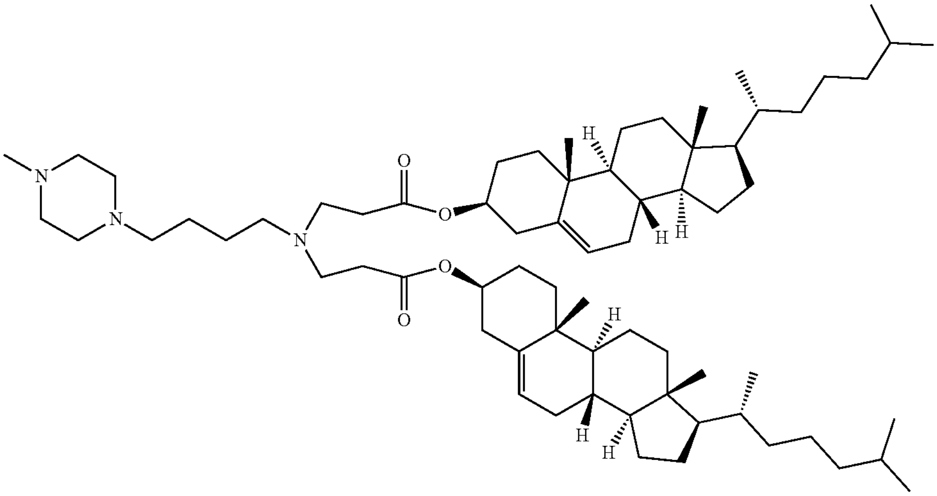 [SMILES: CC(C)CCC[C@@H](C)[C@H]1CC[C@H]2[C@@H]3CC=C4C[C@@H](OC(=O)CCN(CCCCN5CCN(C)CC5)CCC(=O)O[C@H]5CC[C@@]6(C)C(=CC[C@H]7[C@@H]8CC[C@H]([C@H](C)CCCC(C)C)[C@@]8(C)CC[C@@H]76)C5)CC[C@]4(C)[C@H]3CC[C@]12C] |

TABLE 12-continued pKA of Illustrative Ionizable Lipids of the Invention

| | pKa, ACD-Galas | pKa, ACD-Classic | Transfection +/− |
|---|---|---|---|
| DL-ADDE-C2/C2-DMA | 8.9, 3.6 | 8.4, 3.9 | + |
| DL-ADDE-C2/C3-DMA | 9.5, 5.5 | 9.5, 5.7 | + |
| DL-ADDE-C2/C4-DMA | 9.9, 6.7 | 9.7, 6.8 | + |
| DL-ADDE-C4/C4-DMA | 10.3, 8.9 | 9.7, 8.6 | + |
| DL-ADDE-C2/C2-Pyr | 9.4, 3.6 | 8.6, 5.9 | + |
| DL-ADDE-C2/C3-Pyr | 10.0, 5.5 | 10.4, 7.1 | + |
| DL-ADDE-C2/C4-Pyr | 10.4, 6.7 | 10.5, 7.5 | |
| DL-ADDE-C4/C4-Pyr | 10.6, 9.2 | 10.5, 9.2 | |
| DL-ADDE-C2/C2-PipD | 9.1, 3.6 | 9.1, 6.0 | + |
| DL-ADDE-C2/C3-PipD | 9.7, 5.5 | 9.6, 7.1 | |
| DL-ADDE-C2/C4-PipD | 10.1, 6.7 | 9.7, 7.5 | |
| DL-ADDE-C4/C4-PipD | 10.4, 9.0 | 9.8, 9.2 | + |
| DL-ADDE-C2/C2-4Me-PipZ | 8.0, 5.4, 0.8 | 7.6, 7.3, 2.4 | + |
| DL-ADDE-C2/C3-4Me-PipZ | 8.1, 6.4, 2.7 | 7.7, 7.6, 3.6 | + |
| DL-ADDE-C2/C4-4Me-PipZ | 8.3, 6.9, 3.7 | 7.8, 7.7, 4.1 | + |
| DL-ADDE-C4/C4-4Me-PipZ | 10.1, 7.8, 3.7 | 9.5, 7.7, 4.1 | + |
| DL-ADDE-C2/C2-DIPA | 9.7, 3.6 | 10.3, 3.9 | − |
| DL-ADDE-C2/C2-BocA | 10.8, 7.3 | 12.7, 8.2 | − |
| DL-ADDE-C2/C2-DeBocA | 9.6, 3.6 | 9.5, 5.2 | − |
| DL-ADDE-C2/C3-DM-DMA | 9.5, 5.5 | 9.6, 5.8 | − |
| DL-C2C2-1Me-PipD | 9.9, 5.9 | 9.5, 7.5 | |
| BOD-ADDE-C2/C2-DMA | 8.9, 3.6 | 8.4, 3.9 | |
| BOD-ADDE-C2/C4-DMA | 9.9, 6.7 | 9.7, 6.8 | |
| BOD-ADDE-C2/C2-Pyr | 9.5, 3.6 | 8.6, 5.9 | |
| BOD-ADDE-C2/C4-Pyr | 10.4, 6.7 | 10.5, 7.5 | |
| BOD-ADDE-C2/C2-PipD | 9.1, 3.6 | 9.1, 6.0 | |
| BOD-ADDE-C2/C4-PipD | 10.1, 6.7 | 9.7, 7.5 | |
| BOD-ADDE-C2/C2-4Me-PipZ | 8.0, 5.4, 0.85 | 7.6, 7.3, 2.4 | |
| BOD-ADDE-C2/C3-4Me-PipZ | 8.1, 6.3, 2.7 | 7.7, 7.6, 3.6 | |
| BOD-ADDE-C2/C4-4Me-PipZ | 8.3, 6.9, 3.7 | 7.8, 7.7, 4.1 | |
| BOD-ADDE-C2/C2-1Me-PipD | 9.9, 6.9 | 9.5, 7.5 | |
| BOD-ADDE-C2/C4-CyHexDMA | 9.9, 6.4 | 10.7, 6.3 | |
| BOD-ADDE-C2/C3-Imd | 7.6, 6.4 | 7.1, 6.8 | |
| BODD-ADDE-C2/C2-DMA | 8.9, 3.6 | 8.4, 3.9 | |
| BODD-ADDE-C2/C4-DMA | 9.9, 6.7 | 9.7, 6.8 | |
| BODD-ADDE-C2/C2-Pyr | 9.4, 3.6 | 8.6, 5.9 | |
| BODD-ADDE-C2/C4-Pyr | 10.4, 6.7 | 10.5, 7.5 | |
| BODD-ADDE-C2/C2-PipD | 9.1, 3.6 | 9.1, 6.0 | |
| BODD-ADDE-C2/C4-PipD | 10.1, 6.7 | 9.7, 7.5 | |
| BODD-ADDE-C2/C2-4Me-PipZ | 8.0, 5.4, 0.85 | 7.6, 7.3, 2.4 | + |
| BOD-ADDE-C2/C4-4-Me-PipZ | 8.3, 6.9, 3.7 | 7.8, 7.7, 4.1 | + |
| BODD-ADDE-C2C2-1MePipD | 9.9, 6.9 | 9.5, 7.5 | |
| BODD-ADDE-C2C0-1Me-PipD | 9.7, 4.7 | 8.9, 3.3 | |
| BODD-ADDE-C2C2-1Me-2Pyr | 10.0, 5.5 | 10.4, 7.2 | |
| BHD-ADDE-C2/C2-DMA | 8.9, 3.6 | 8.4, 3.9 | |
| BHD-ADDE-C2/C4-DMA | 9.9, 6.7 | 9.7, 6.8 | |
| BHD-ADDE-C2/C2-Pyr | 9.4, 3.6 | 8.6, 5.9 | |
| BHD-ADDE-C2/C4-Pyr | 10.4, 6.7 | 10.5, 7.5 | |
| BHD-ADDE-C2/C2-PipD | 9.1, 3.6 | 9.1, 6.0 | |
| BHD-ADDE-C2/C2-PipZ | 8.0, 5.4, 0.85 | 7.6, 7.3, 2.4 | |
| BHD-ADDE-C2/C4-PipZ | 8.3, 6.9, 3.7 | 7.8, 7.7, 4.1 | |
| BHD-ADDE-C2/C4-PipD | 10.1, 6.7 | 9.7, 7.5 | |
| BHD-ADDE-C2/C2-PipZ | 8.0, 5.4, 0.85 | 7.6, 7.3, 2.4 | |
| BChol-ADDE-C2/C4-PipZ | 8.3, 6.9, 3.7 | 7.8, 7.7, 4.1 | |

In certain embodiments, additional ionizable lipids were synthesized bearing one ionizable amine and two linoleic acid tails linked to headgroups such as Isopentylamine (IP), Ethylalcohol (EA), Propyl alcohol (PA) via degradable esters as illustrated in Table 13A.

TABLE 13A

| Lipid | Structure | pKa(ACD)-Galas | pKa(ACD)-Classic | Transfection +/− |
|---|---|---|---|---|
| DL-ADDE-IP | 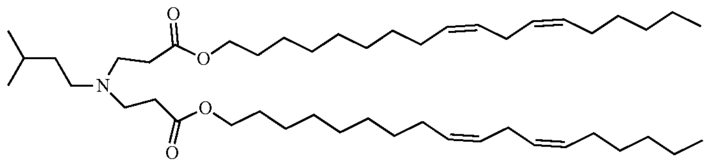 [SMILES: CCCCC/C=C\C/C=C\CCCCCCCCOC(=O)CCN(CCC(=O)OCCCCCCCC/C=C\C/C=C\CCCCC)CCC(C)C] | 7.6 | 7.8 | − |
| DL-ADDE-EA | 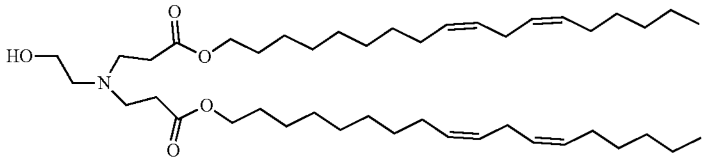 [SMILES: CCCCC/C=C\C/C=C\CCCCCCCCOC(=O)CCN(CCO)CCC(=O)OCCCCCCCC/C=C\C/C=C\CCCCC] | 6.4 | 6.9 | − |
| DL-ADDE-PA | 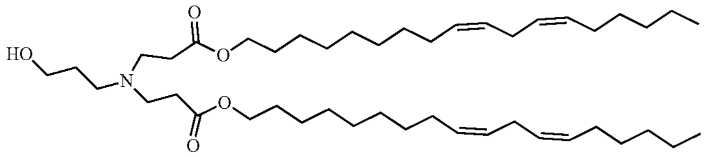 [SMILES: CCCCC/C=C\C/C=C\CCCCCCCCOC(=O)CCN(CCCO)CCC(=O)OCCCCCCCC/C=C\C/C=C\CCCCC] | 7.0 | 7.3 | − |

In certain embodiments, a second class of lipids contains one ionizable groups (DMA) and two different linkers: degradable ester and non-degradable OctaSulfonAmido (OSA). Additionally, these lipids contain either a linear (Linoyl) or branched tail (Octadecanyl) as illustrated in Table 13B.

TABLE 13B

| Lipid | Structure | pKa(ACD)-Galas | pKa(ACD)-Classic | Transfection +/− |
|---|---|---|---|---|
| L-OSA-C2/C4-DMA | 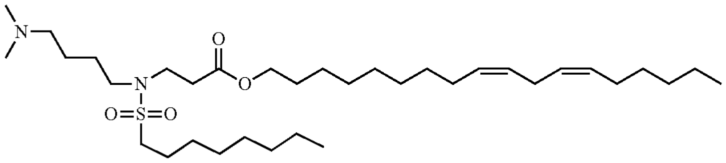 [SMILES: CCCCC/C=C\C/C=C\CCCCCCCCOC(=O)CCN(CCCCN(C)C)S(=O)(=O)CCCCCCCC] | 9.9 | 9.6 | untested |
| OD-OSA-C2/C4-DMA | 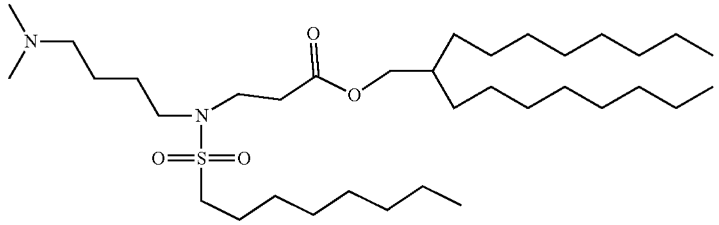 [SMILES: CCCCCCCCC(CCCCCCCC)COC(=O)CCN(CCCCN(C)C)S(=O)(=O)CCCCCCCC] | 9.9 | 9.6 | untested |

In certain embodiments, a third class of ionizable lipids with one ionizable amine and one linoleic acid (L) tail both linked to the headgroup such as (Aminoethane (AE), Dimethylamine, and Aminoethyldisulfonyl (AEDS)) via non degradable amides as illustrated in Table 13C.

TABLE 13C

| Lipid | Structure | pKa(ACD)-Galas | pKa(ACD)-Classic | Transfection +/− |
|---|---|---|---|---|
| L-Amide-AE | 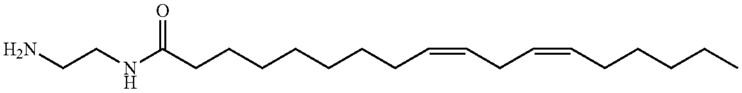 [SMILES: CCCCC/C=C\C/C=C\CCCCCCCC(=O)NCCN] | 9.3 | 9.0 | − |
| L-Amide-DMA | 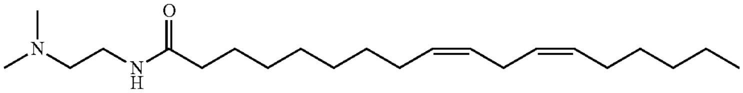 [SMILES: CCCCC/C=C\C/C=C\CCCCCCCC(=O)NCCN(C)C] | 8.6 | 8.4 | − |
| L-Amide-AEDS | 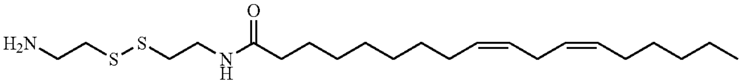 [SMILES: CCCCC/C=C\C/C=C\CCCCCCCC(=O)NCCSSCCN] | 9.3 | 8,7 | − |

In certain embodiments, exemplary Ionizable Lipids of the Invention including alkyl lipids are illustrated with predicted pKa from ACD Classic and ACD Galas including the Method of synthesis are illustrated in Table 13D.

TABLE 13D

| Entry | Abbreviation | Lipids | Method |
|---|---|---|---|
| 1. | BOD-C2/C2-DMA | 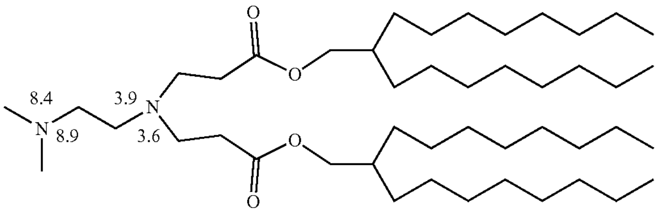 [SMILES: CCCCCCCCC(CCCCCCCC)COC(=O)CCN(CCC(=O)OCC(CCCCCCCC)CCCCCCCC)CCN(C)C] | 9 |
| 2. | BOD-C2/C4-DMA | 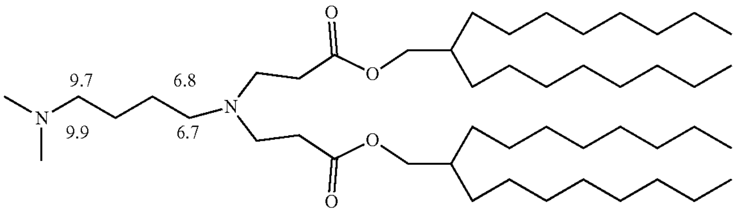 [SMILES: CCCCCCCCC(CCCCCCCC)COC(=O)CCN(CCCCN(C)C)CCC(=O)OCC(CCCCCCCC)CCCCCCCC] | 9 |
| 3. | BOD-C2/C2-Pyr | 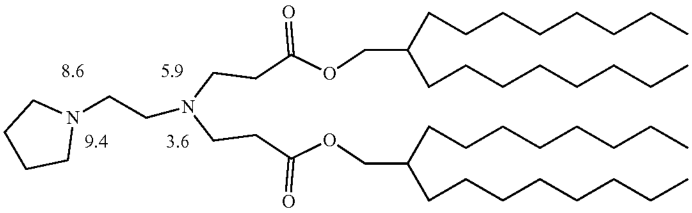 [SMILES: CCCCCCCCC(CCCCCCCC)COC(=O)CCN(CCC(=O)OCC(CCCCCCCC)CCCCCCCC)CCN1CCCC1] | 9 |
| 4. | BOD-C2/C4-Pyr | 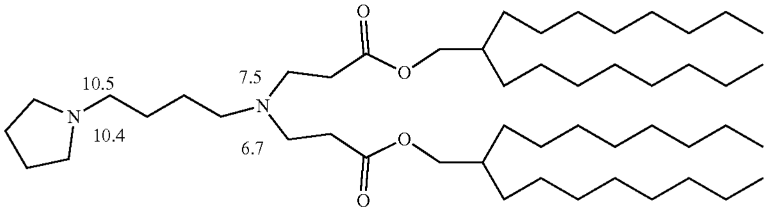 [SMILES: CCCCCCCCC(CCCCCCCC)COC(=O)CCN(CCCCN1CCCC1)CCC(=O)OCC(CCCCCCCC)CCCCCCCC] | 9 |

TABLE 13D-continued
| Entry | Abbreviation | Lipids | Method |
|---|---|---|---|
| 5. | BOD-C2/C2-1Me-2Pyr | 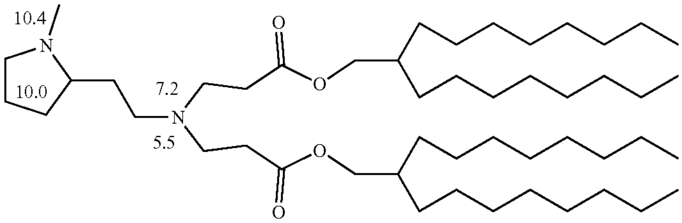 [SMILES: CCCCCCCCC(CCCCCCCC)COC(=O)CCN(CCC(=O)OCC(CCCCCCCC)CCCCCCCC)CCC1CCCN1C] | 9 |
| 6. | BOD-C2/C0-1Me-PipD | 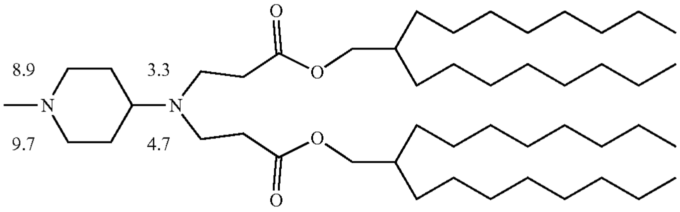 [SMILES: CCCCCCCCC(CCCCCCCC)COC(=O)CCN(CCC(=O)OCC(CCCCCCCC)CCCCCCCC)C1CCN(C)CC1] | 9 |
| 7. | BOD-C2/C2-1Me-PipD | 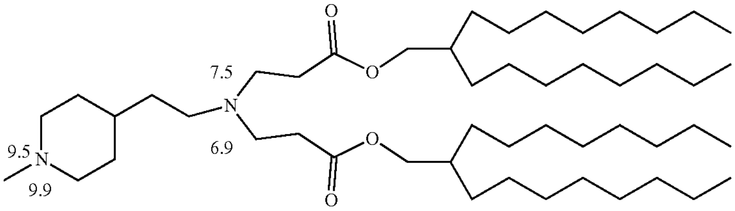 [SMILES: CCCCCCCCC(CCCCCCCC)COC(=O)CCN(CCC(=O)OCC(CCCCCCCC)CCCCCCCC)CCC1CCN(C)CC1] | 9 |
| 8. | BOD-C2/C2-PipD | 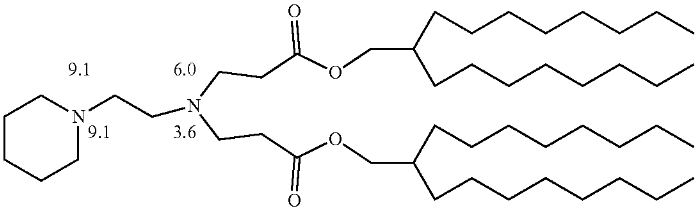 [SMILES: CCCCCCCCC(CCCCCCCC)COC(=O)CCN(CCC(=O)OCC(CCCCCCCC)CCCCCCCC)CCN1CCCCC1] | 9 |
| 9. | BOD-C2/C4-PipD | 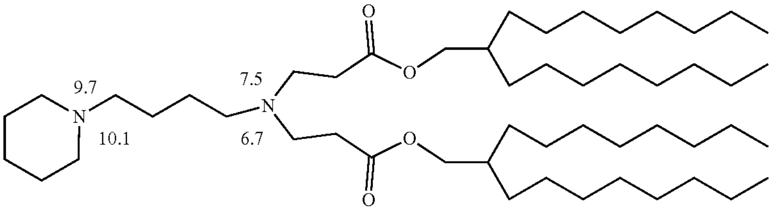 [SMILES: CCCCCCCCC(CCCCCCCC)COC(=O)CCN(CCCCN1CCCCC1)CCC(=O)OCC(CCCCCCCC)CCCCCCCC] | 9 |
| 10. | BOD-C2/C2-PipZ | 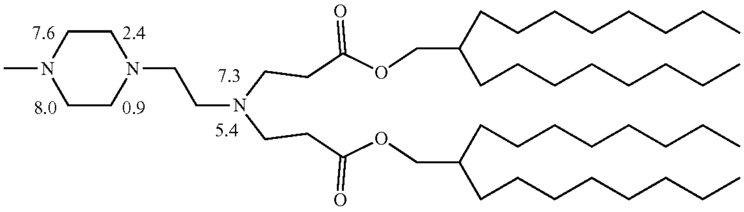 [SMILES: CCCCCCCCC(CCCCCCCC)COC(=O)CCN(CCC(=O)OCC(CCCCCCCC)CCCCCCCC)CCN1CCN(C)CC1] | 9 |
| 11. | BOD-C2/C3-PipZ | 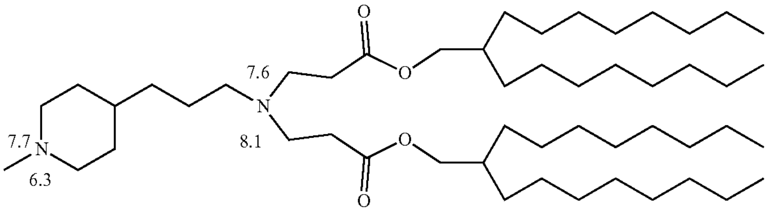 [SMILES: CCCCCCCCC(CCCCCCCC)COC(=O)CCN(CCCC1CCN(C)CC1)CCC(=O)OCC(CCCCCCCC)CCCCCCCC] | 9 |

TABLE 13D-continued
| Entry | Abbreviation | Lipids | Method |
|---|---|---|---|
| 12. | BOD-C2/C4-PipZ | 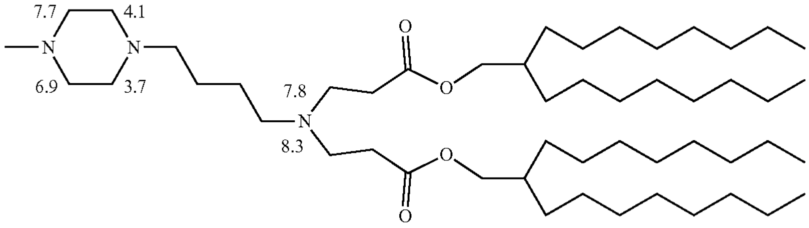 [SMILES: CCCCCCCCC(CCCCCCCC)COC(=O)CCN(CCCCN1CCN(C)CC1)CCC(=O)OCC(CCCCCCCC)CCCCCCCC] | 9 |
| 13. | BOD-C2/C3-Img | 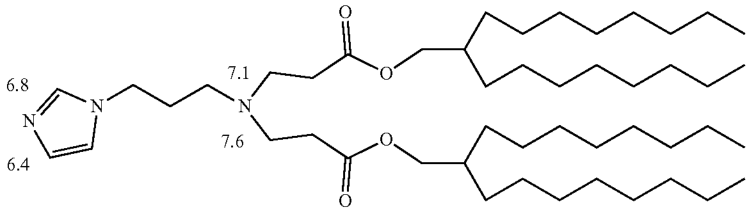 [SMILES: CCCCCCCCC(CCCCCCCC)COC(=O)CCN(CCCn1ccnc1)CCC(=O)OCC(CCCCCCCC)CCCCCCCC] | 9 |
| 14. | BOD-C2/C4-CyHexDMA | 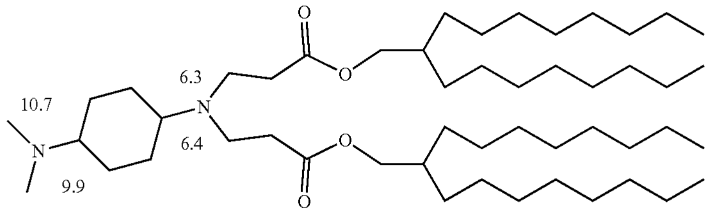 [SMILES: CCCCCCCCC(CCCCCCCC)COC(=O)CCN(CCC(=O)OCC(CCCCCCCC)CCCCCCCC)C1CCC(N(C)C)CC1] | 9 |
| 15. | BODD-C2/C2-DMA | 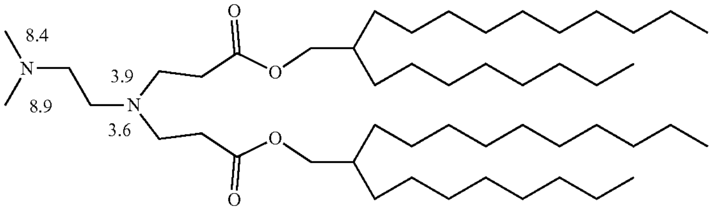 [SMILES: CCCCCCCCCCC(CCCCCCCC)COC(=O)CCN(CCC(=O)OCC(CCCCCCCC)CCCCCCCCCC)CCN(C)C] | 9 |
| 16. | BODD-C2/C4-DMA | 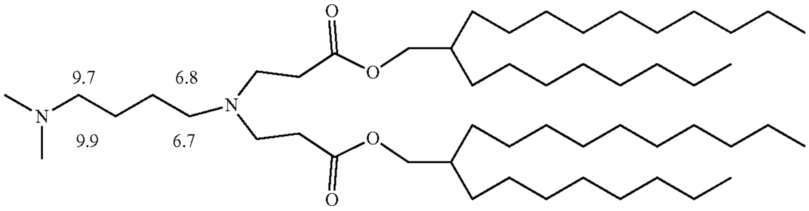 [SMILES: CCCCCCCCCCC(CCCCCCCC)COC(=O)CCN(CCCCN(C)C)CCC(=O)OCC(CCCCCCCC)CCCCCCCCCC] | 9 |
| 17. | BODD-C2/C2-Pyr | 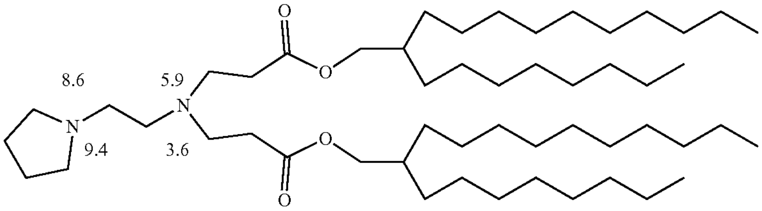 [SMILES: CCCCCCCCCCC(CCCCCCCC)COC(=O)CCN(CCC(=O)OCC(CCCCCCCC)CCCCCCCCCC)CCN1CCCC1] | 9 |
| 18. | BODD-C2/C4-Pyr | 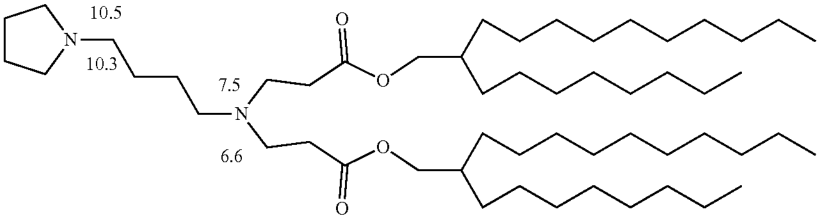 [SMILES: CCCCCCCCCCC(CCCCCCCC)COC(=O)CCN(CCCCN1CCCC1)CCC(=O)OCC(CCCCCCCC)CCCCCCCCCC] | 9 |

TABLE 13D-continued
| Entry | Abbreviation | Lipids | Method |
|---|---|---|---|
| 19. | BODD-C2/C2-1Me-2Pyr | 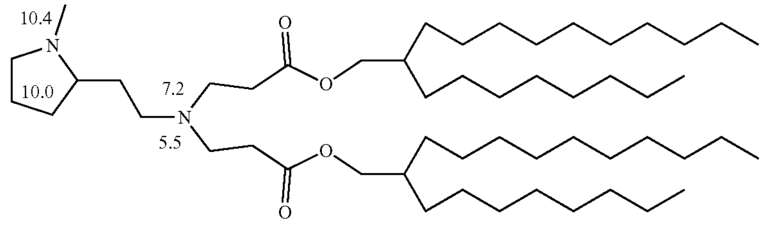 [SMILES: CCCCCCCCCCC(CCCCCCCC)COC(=O)CCN(CCC(=O)OCC(CCCCCCCC)CCCCCCCCCC)CCC1CCCN1C] | 9 |
| 20. | BODD-C2/C0-1Me-PipD | 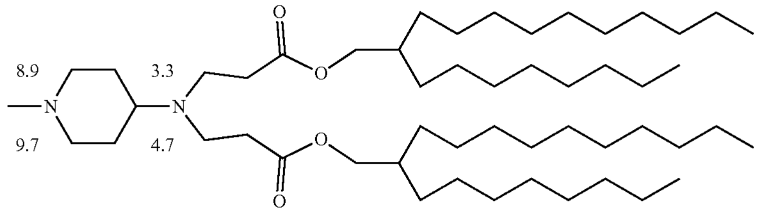 [SMILES: CCCCCCCCCCC(CCCCCCCC)COC(=O)CCN(CCC(=O)OCC(CCCCCCCC)CCCCCCCCCC)C1CCN(C)CC1] | 9 |
| 21 | BODD-C2C1-1Me-PipD | 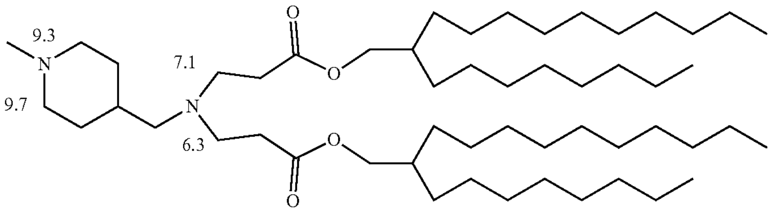 [SMILES: CCCCCCCCCCC(CCCCCCCC)COC(=O)CCN(CCC(=O)OCC(CCCCCCCC)CCCCCCCCCC)CC1CCN(C)CC1] | 9 |
| 22 | BODD-C2/C0-1Me-3PipD | 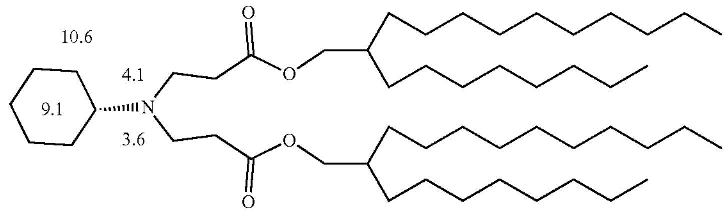 | 9 |
| 23. | BODD-C2/C1-1Me-3PipD | 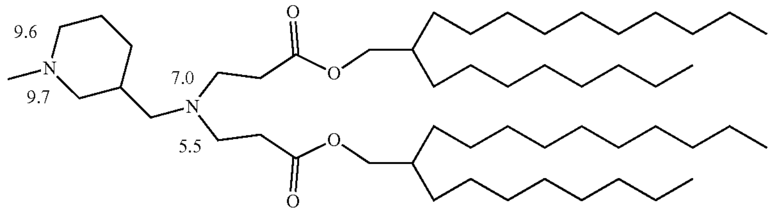 [SMILES: CCCCCCCCCCC(CCCCCCCC)COC(=O)CCN(CCC(=O)OCC(CCCCCCCC)CCCCCCCCCC)CC1CCCN(C)C1] | 9 |
| 24. | BODD-C2/C2-1Me-PipD | 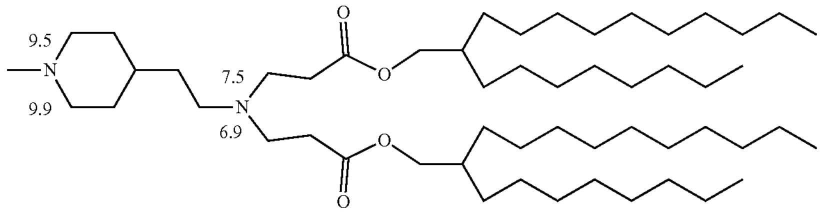 [SMILES: CCCCCCCCCCC(CCCCCCCC)COC(=O)CCN(CCC(=O)OCC(CCCCCCCC)CCCCCCCCCC)CCC1CCN(C)CC1] | 9 |
| 25. | BODD-C2/C2-PipD | 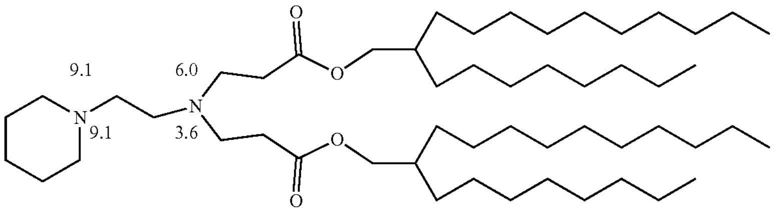 [SMILES: CCCCCCCCCCC(CCCCCCCC)COC(=O)CCN(CCC(=O)OCC(CCCCCCCC)CCCCCCCCCC)CCN1CCCCC1] | 9 |

TABLE 13D-continued
| Entry | Abbreviation | Lipids | Method |
| --- | --- | --- | --- |
| 26. | BODD-C2/C4-PipD | 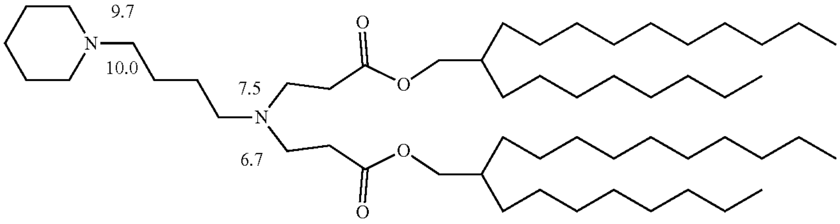 [SMILES: CCCCCCCCCCC(CCCCCCCC)COC(=O)CCN(CCCCN1CCCCC1)CCC(=O)OCC(CCCCCCCC)CCCCCCCCCC] | 9 |
| 27. | BODD-C1/C2-PipZ | 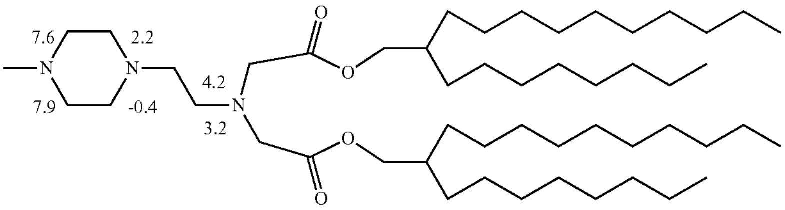 [SMILES: CCCCCCCCCCC(CCCCCCCC)COC(=O)CN(CCN1CCN(C)CC1)CC(=O)OCC(CCCCCCCC)CCCCCCCCCC] | 10 |
| 28. | BODD-C1/C3-PipZ | 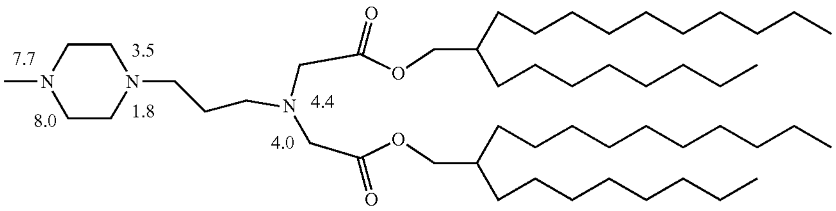 [SMILES: CCCCCCCCCCC(CCCCCCCC)COC(=O)CN(CCCN1CCN(C)CC1)CC(=O)OCC(CCCCCCCC)CCCCCCCCCC] | 10 |
| 29. | BODD-C1/C4-PipZ | 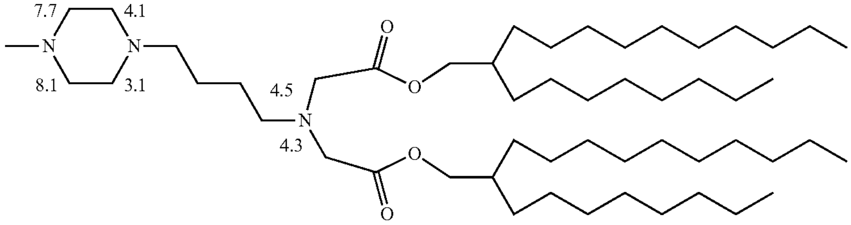 [SMILES: CCCCCCCCCCC(CCCCCCCC)COC(=O)CN(CCCCN1CCN(C)CC1)CC(=O)OCC(CCCCCCCC)CCCCCCCCCC] | 10 |
| 30. | BODD-C2/C2-PipZ | 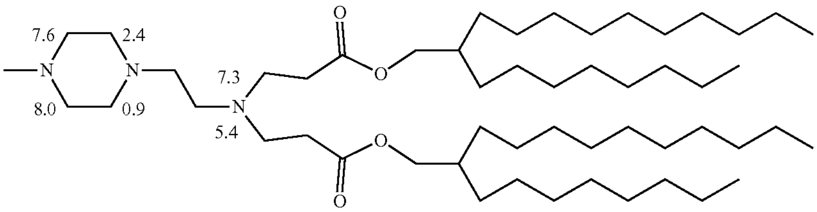 [SMILES: CCCCCCCCCCC(CCCCCCCC)COC(=O)CCN(CCC(=O)OCC(CCCCCCCC)CCCCCCCCCC)CCN1CCN(C)CC1] | 9 |
| 31. | BODD-C2/C3-PipZ | 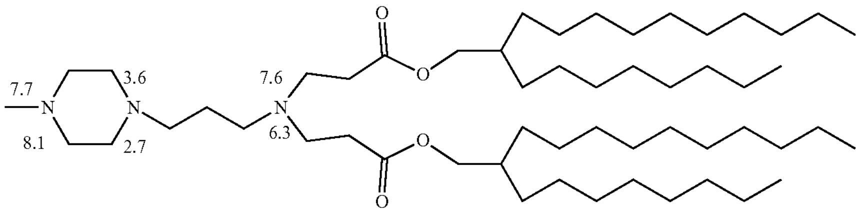 [SMILES: CCCCCCCCCCC(CCCCCCCC)COC(=O)CCN(CCCN1CCN(C)CC1)CCC(=O)OCC(CCCCCCCC)CCCCCCCCCC] | 9 |
| 32. | BODD-C2/C4-PipZ | 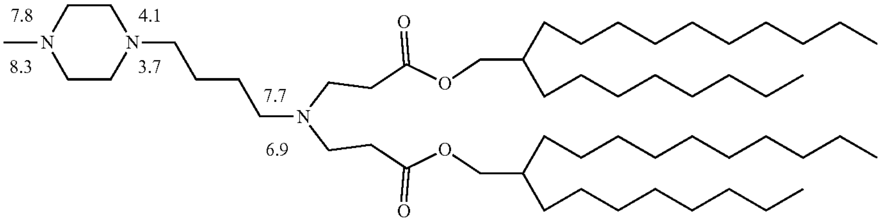 [SMILES: CCCCCCCCCCC(CCCCCCCC)COC(=O)CCN(CCCCN1CCN(C)CC1)CCC(=O)OCC(CCCCCCCC)CCCCCCCCCC] | 9 |

TABLE 13D-continued
| Entry | Abbreviation | Lipids | Method |
|---|---|---|---|
| 33. | BODD-C3/C2-PipZ | 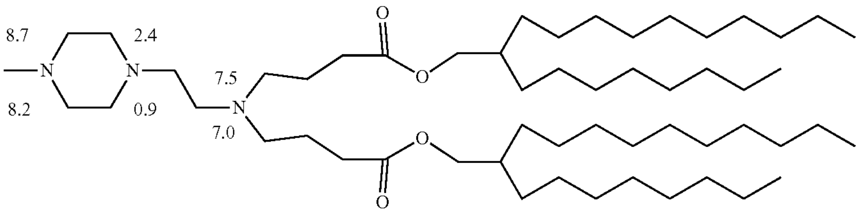 [SMILES: CCCCCCCCCCC(CCCCCCCC)COC(=O)CCCN(CCCC(=O)OCC(CCCCCCCC)CCCCCCCCCC)CCN1CCN(C)CC1] | 10 |
| 34. | BODD-C3/C3-PipZ | 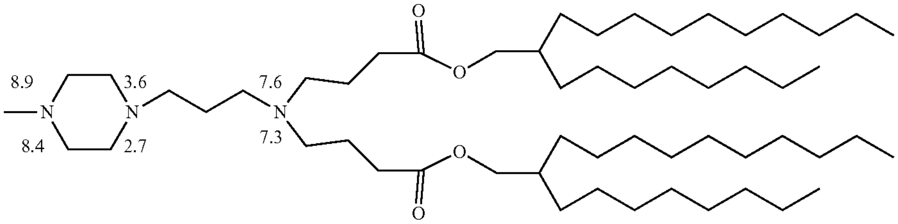 [SMILES: CCCCCCCCCCC(CCCCCCCC)COC(=O)CCCN(CCCC(=O)OCC(CCCCCCCC)CCCCCCCCCC)CCCN1CCN(C)CC1] | 10 |
| 35. | BODD-C3/C4-PipZ | 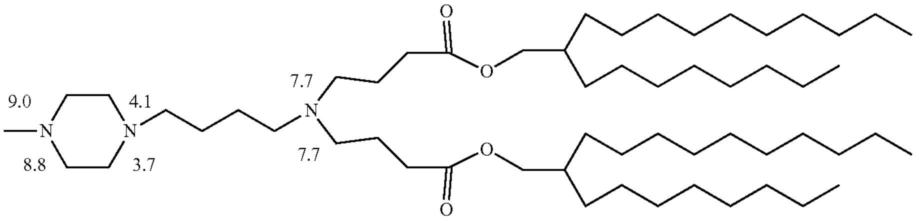 [SMILES: CCCCCCCCCCC(CCCCCCCC)COC(=O)CCCN(CCCCN1CCN(C)CC1)CCCC(=O)OCC(CCCCCCCC)CCCCCCCCCC] | 10 |
| 36. | BODD-C4/C2-PipZ | 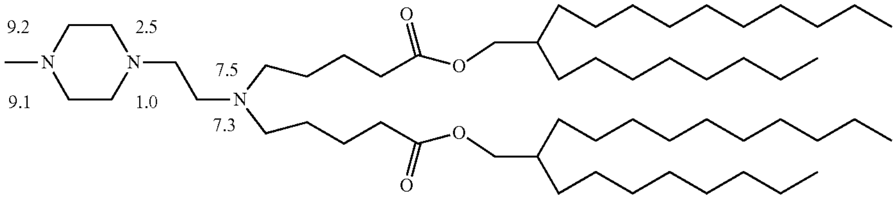 [SMILES: CCCCCCCCCCC(CCCCCCCC)COC(=O)CCCCN(CCCCC(=O)OCC(CCCCCCCC)CCCCCCCCCC)CCN1CCN(C)CC1] | 10 |
| 37. | BODD-C4/C3-PipZ | 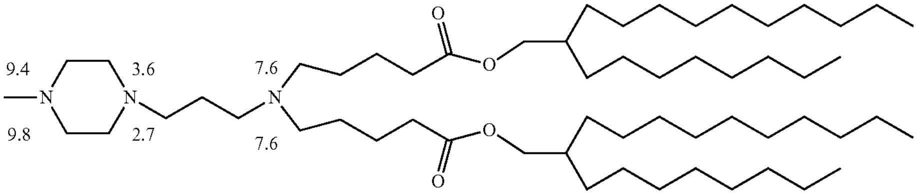 [SMILES: CCCCCCCCCCC(CCCCCCCC)COC(=O)CCCCN(CCCCC(=O)OCC(CCCCCCCC)CCCCCCCCCC)CCCN1CCN(C)CC1] | 10 |
| 38. | BODD-C4/C4-PipZ | 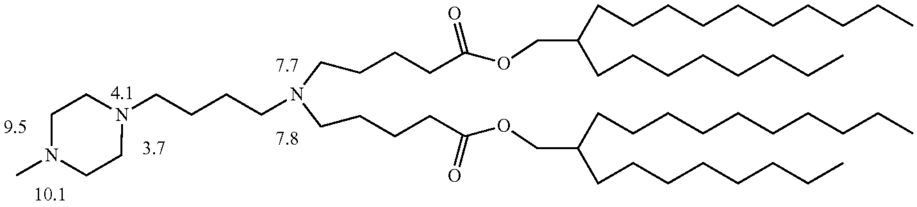 [SMILES: CCCCCCCCCCC(CCCCCCCC)COC(=O)CCCCN(CCCCC(=O)OCC(CCCCCCCC)CCCCCCCCCC)CCCCN1CCN(C)CC1] | 10 |
| 39. | BODD-C2/C0-9Me-9ABN | 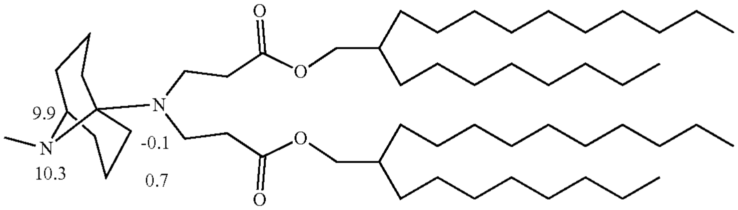 [SMILES: CCCCCCCCCCC(CCCCCCCC)COC(=O)CCN(CCC(=O)OCC(CCCCCCCC)CCCCCCCCCC)C12CCCC(CCC1)N2C] | 9 |

TABLE 13D-continued
| Entry | Abbreviation | Lipids | Method |
|---|---|---|---|
| 40. | BODD-C2/C0-CyHexyl-2DMA | 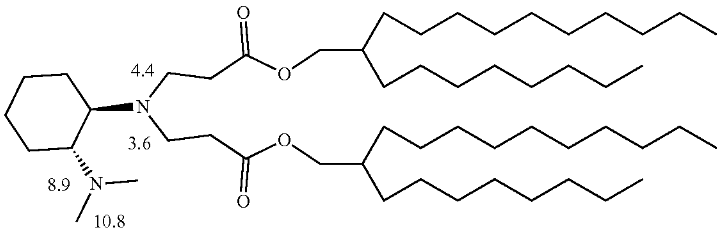 [SMILES: CCCCCCCCCCC(CCCCCCCC)COC(=O)CCN(CCC(=O)OCC(CCCCCCCC)CCCCCCCCCC)[C@@H]1CCCC[C@H]1N(C)C] | 9 |
| 41. | BODD-C4/C4-BA | 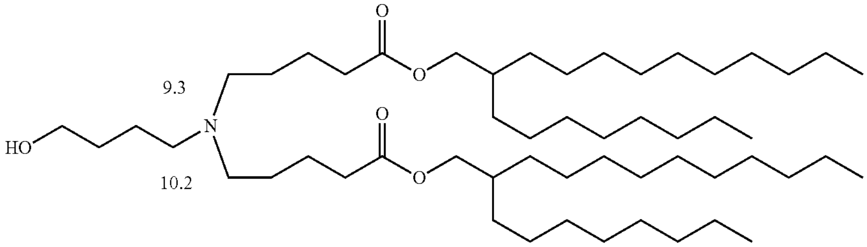 [SMILES: CCCCCCCCCCC(CCCCCCCC)COC(=O)CCCCN(CCCCO)CCCCC(=O)OCC(CCCCCCCC)CCCCCCCCCC] | 10 |
| 42. | BBO-C2/C4-PipZ | 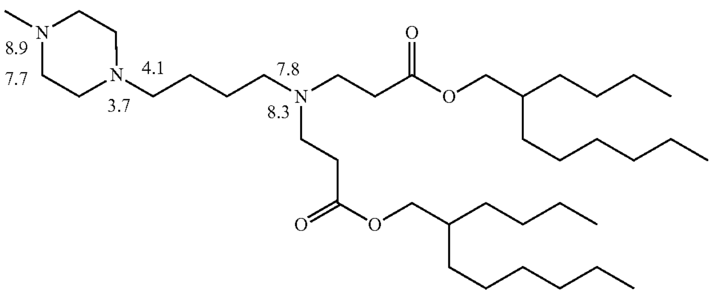 [SMILES: CCCCCCC(CCCC)COC(=O)CCN(CCCCN1CCN(C)CC1)CCC(=O)OCC(CCCC)CCCCCC] | 9 |
| 43. | BDTD-C2/C4-PipZ | 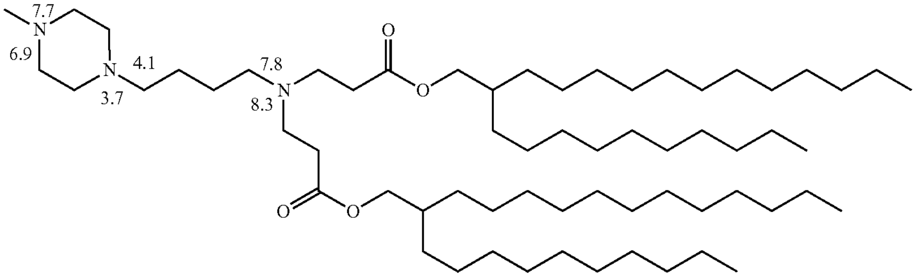 [SMILES: CCCCCCCCCCCCC(CCCCCCCCCC)COC(=O)CCN(CCCCN1CCN(C)CC1)CCC(=O)OCC(CCCCCCCCCC)CCCCCCCCCCCC] | 9 |
| 44. | BDHD-C2/C4-PipZ | 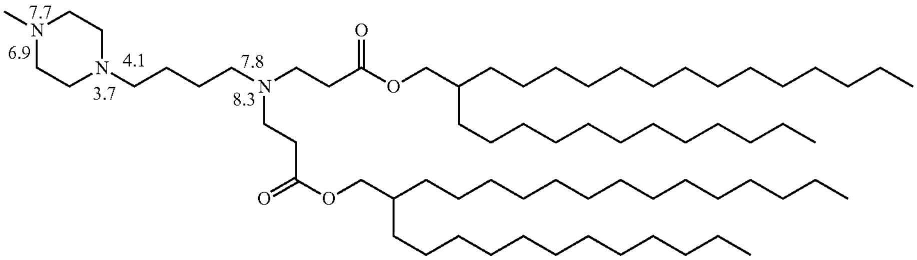 [SMILES: CCCCCCCCCCCCCCC(CCCCCCCCCCCC)COC(=O)CCN(CCCCN1CCN(C)CC1)CCC(=O)OCC(CCCCCCCCCCCC)CCCCCCCCCCCCCC] | 9 |
| 45. | BHD-C2/C2-DMA | 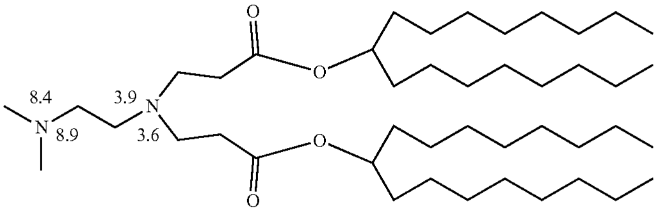 [SMILES: CCCCCCCCC(CCCCCCCC)OC(=O)CCN(CCC(=O)OC(CCCCCCCC)CCCCCCCC)CCN(C)C] | 9 |

TABLE 13D-continued
| Entry | Abbreviation | Lipids | Method |
|---|---|---|---|
| 46. | BHD-C2/C2-1Me-2Pyr | 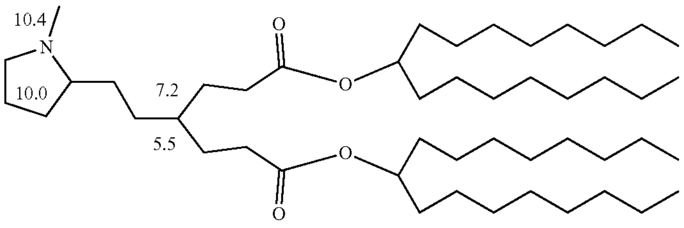 [SMILES: CCCCCCCCC(CCCCCCCC)OC(=O)CCC(CCC(=O)OC(CCCCCCCC)CCCCCCCC)CCC1CCCN1C] | 9 |
| 47. | BHD-C2/C4-Pyr | 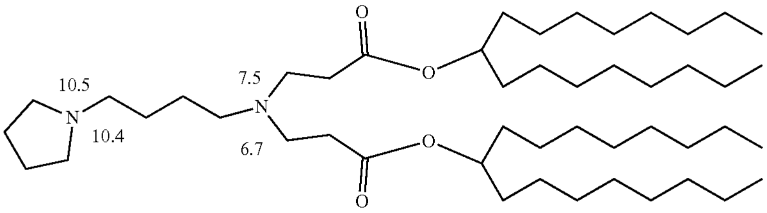 [SMILES: CCCCCCCCC(CCCCCCCC)OC(=O)CCN(CCCCN1CCCC1)CCC(=O)OC(CCCCCCCC)CCCCCCCC] | 9 |
| 48. | BHD-C2/C0-1Me-PipD | 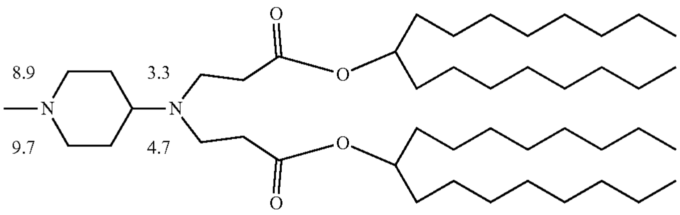 [SMILES: CCCCCCCCC(CCCCCCCC)OC(=O)CCN(CCC(=O)OC(CCCCCCCC)CCCCCCCC)C1CCN(C)CC1] | 9 |
| 49. | BHD-C2/C2-PipZ | 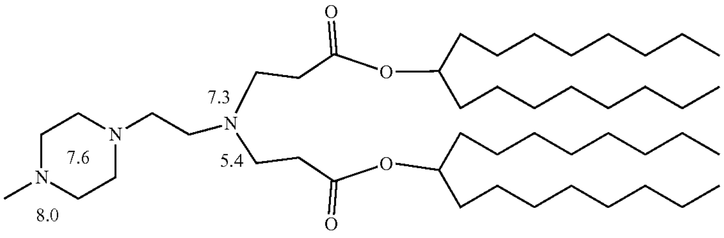 [SMILES: CCCCCCCCC(CCCCCCCC)OC(=O)CCN(CCC(=O)OC(CCCCCCCC)CCCCCCCC)CCN1CCN(C)CC1] | 9 |
| 50. | BHD-C2/C4-PipZ | 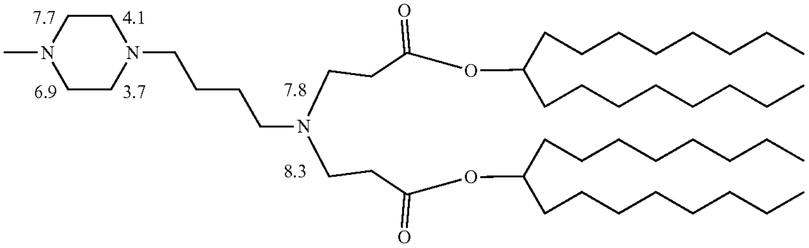 [SMILES: CCCCCCCCC(CCCCCCCC)OC(=O)CCN(CCCCN1CCN(C)CC1)CCC(=O)OC(CCCCCCCC)CCCCCCCC] | 9 |
| 51. | DH-C2/C4-PipZ | 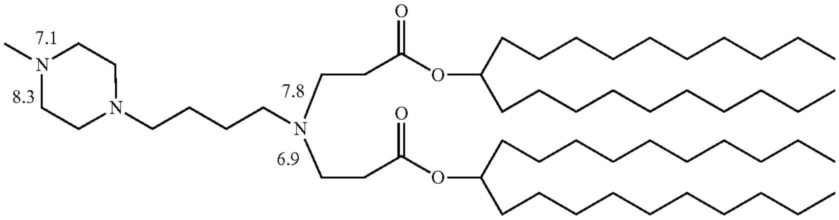 [SMILES: CCCCCCCCCCC(CCCCCCCCCC)OC(=O)CCN(CCCCN1CCN(C)CC1)CCC(=O)OC(CCCCCCCCCC)CCCCCCCCCC] | 9 |

TABLE 13D-continued
| Entry | Abbreviation | Lipids | Method |
|---|---|---|---|
| 52. | BChol-C2/C4-PipZ | 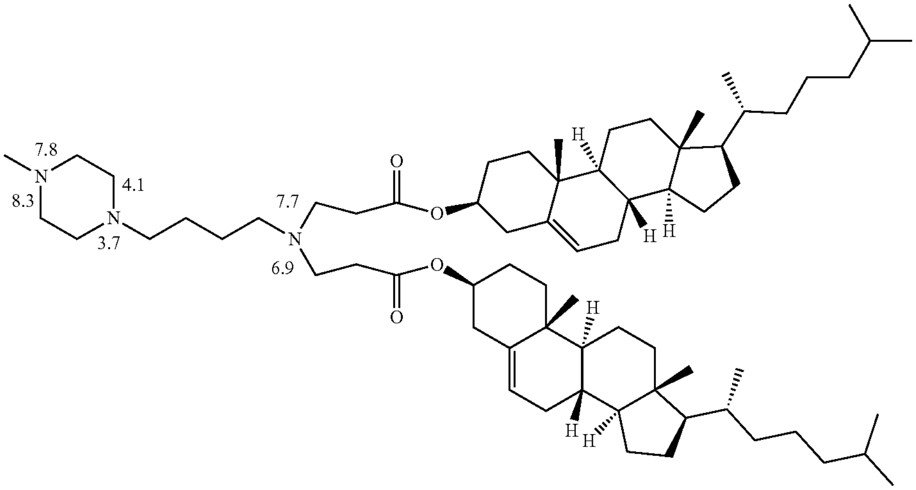 [SMILES: CC(C)CCC[C@@H](C)[C@H]1CC[C@H]2[C@@H]3CC=C4C[C@@H](OC(=O)CCN(CCCCN5CCN(C)CC5)CCC(=O)O[C@H]5CC[C@@]6(C)C(=CC[C@H]7[C@@H]8CC[C@H]([C@H](C)CCCC(C)C)[C@@]8(C)CC[C@@H]76)C5)CC[C@]4(C)[C@H]3CC[C@]12C] | 9 |
| 53. | BDOD-C2/C2-PipZ | 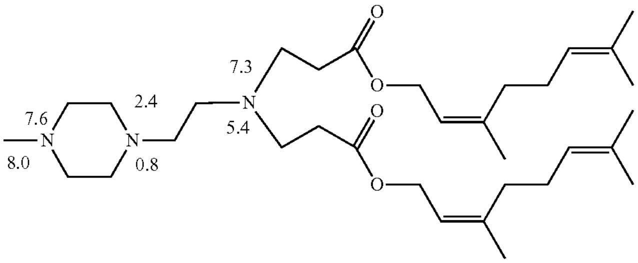 [SMILES: CC(C)=CCC/C(C)=C\COC(=O)CCN(CCC(=O)OC/C=C(/C)CCC=C(C)C)CCN1CCN(C)CC1] | 9 |
| 54. | BDOD-C2/C4-PipZ | 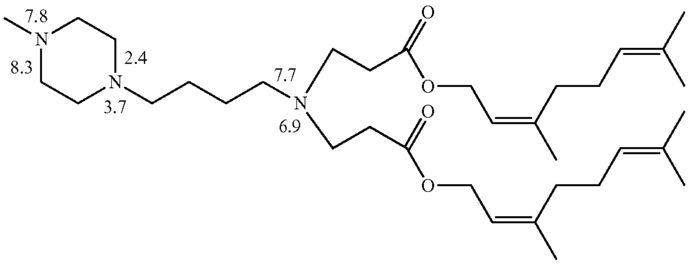 [SMILES: CC(C)=CCC/C(C)=C\COC(=O)CCN(CCCCN1CCN(C)CC1)CCC(=O)OC/C=C(/C)CCC=C(C)C] | 9 |
| 55. | TODD-TMTP | 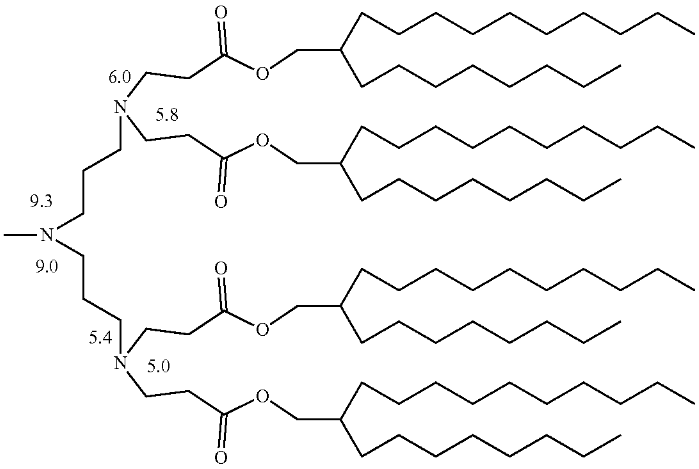 [SMILES: CCCCCCCCCCC(CCCCCCCC)COC(=O)CCN(CCCN(C)CCCN(CCC(=O)OCC(CCCCCCCC)CCCCCCCCCC)CCC(=O)OCC(CCCCCCCC)CCCCCCCCCC)CCC(=O)OCC(CCCCCCCC)CCCCCCCCCC] | 9 |

TABLE 13D-continued
| Entry | Abbreviation | Lipids | Method |
|---|---|---|---|
| 56. | TODD-DS-C2/C4-ME | 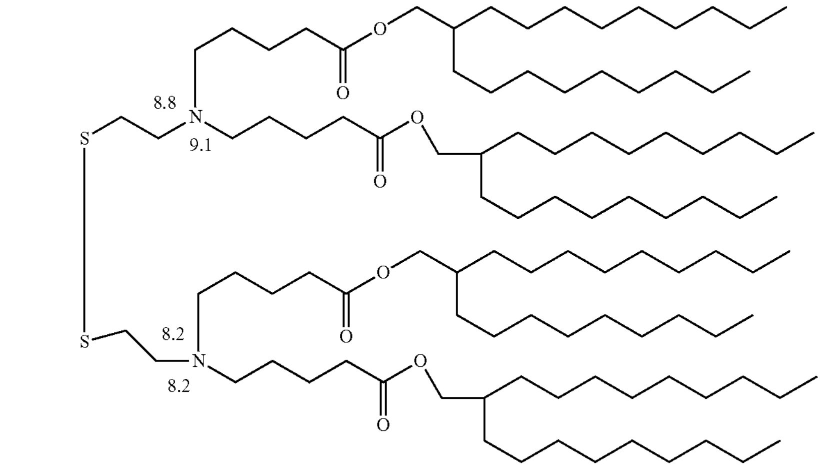 [SMILES: CCCCCCCCCC(CCCCCCCCC)COC(=O)CCCCN(CCCCC(=O)OCC(CCCCCCCCC)CCCCCCCCC)CCSSCCN(CCCCC(=O)OCC(CCCCCCCCC)CCCCCCCCC)CCCCC(=O)OCC(CCCCCCCCC)CCCCCCCCC] | 10 |
| 57. | M-DS-C2/C4-ME | 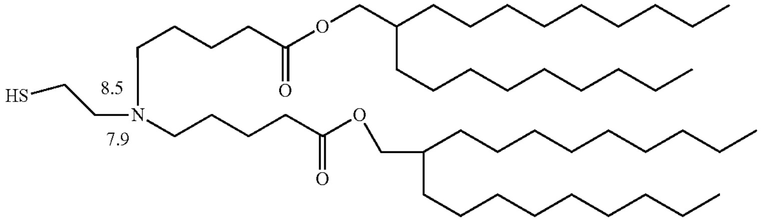 [SMILES: CCCCCCCCCC(CCCCCCCCC)COC(=O)CCCCN(CCS)CCCCC(=O)OCC(CCCCCCCCC)CCCCCCCCC] | 10 |
| 58. | ADL-AP | 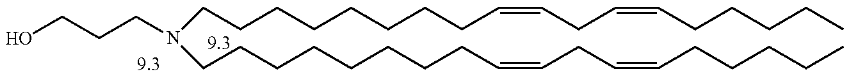 | 11 |
| 59. | ADL-C2-DMA | 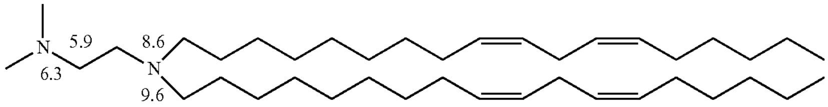 [SMILES: CCCCC/C=C\C/C=C\CCCCCCCCN(CCCCCCCC/C=C\C/C=C\CCCCC)CCN(C)C] | 11 |
| 60. | ADL-C4-DMA | 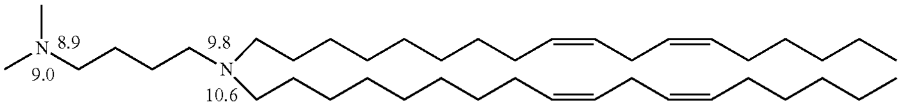 [SMILES: CCCCC/C=C\C/C=C\CCCCCCCCN(CCCCCCCC/C=C\C/C=C\CCCCC)CCCCN(C)C] | 11 |
| 61. | ADL-C2-1Me-Pyr | 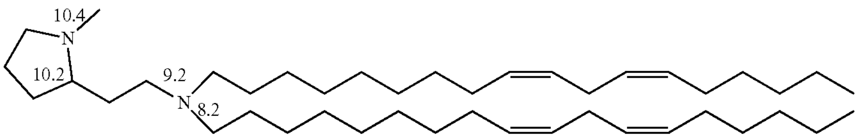 [SMILES: CCCCC/C=C\C/C=C\CCCCCCCCN(CCCCCCCC/C=C\C/C=C\CCCCC)CCC1CCCN1C] | 11 |
| 62. | ADL-C2-PipZ | 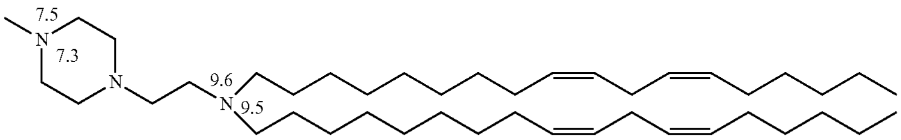 [SMILES: CCCCC/C=C\C/C=C\CCCCCCCCN(CCCCCCCC/C=C\C/C=C\CCCCC)CCN1CCN(C)CC1] | 11 |
| 63. | ADL-C4-PipZ | 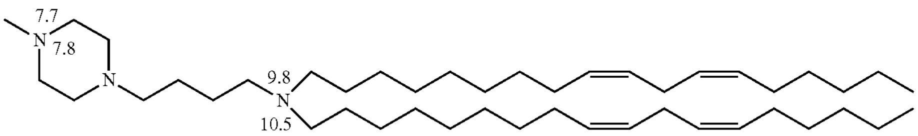 [SMILES: CCCCC/C=C\C/C=C\CCCCCCCCN(CCCCCCCC/C=C\C/C=C\CCCCC)CCCCN1CCN(C)CC1] | 11 |

TABLE 13D-continued
| Entry | Abbreviation | Lipids | Method |
|---|---|---|---|
| 64. | ADL-C2C2-EMAE | 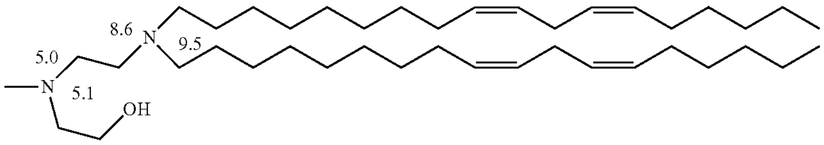 [SMILES: CCCCC/C=C\C/C=C\CCCCCCCCN(CCCCCCCC/C=C\C/C=C\CCCCC)CCN(C)CCO] | 11 |
| 65. | ADL-C3C3-PMAP | 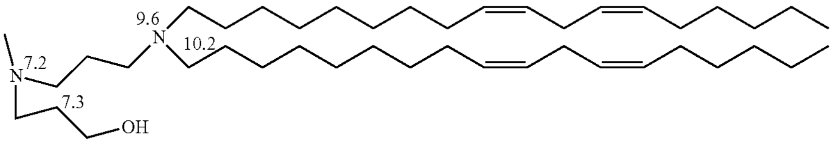 [SMILES: CCCCC/C=C\C/C=C\CCCCCCCCN(CCCCCCCC/C=C\C/C=C\CCCCC)CCCN(C)CCCO] | 11 |
| 66. | ADL-C2C2-CPAE | 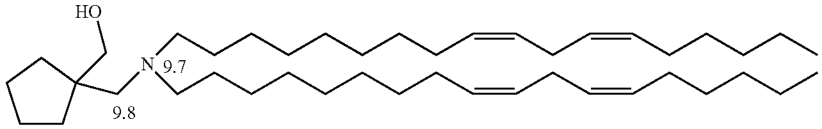 [SMILES: CCCCC/C=C\C/C=C\CCCCCCCCN(CCCCCCCC/C=C\C/C=C\CCCCC)CC1(CO)CCCC1] | 11 |
| 67. | ADL-C2C2-CHAE | 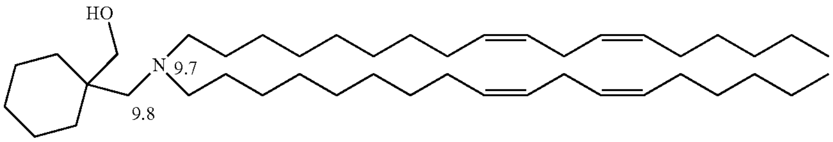 [SMILES: CCCCC/C=C\C/C=C\CCCCCCCCN(CCCCCCCC/C=C\C/C=C\CCCCC)CC1(CO)CCCCC1] | 11 |
| 68. | DS-BADL-ET | 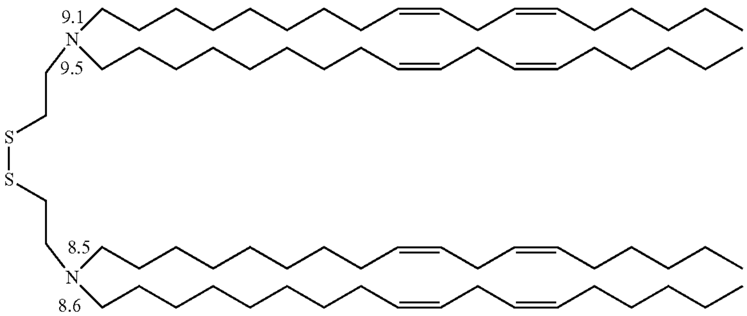 [SMILES: CCCCC/C=C\C/C=C\CCCCCCCCN(CCCCCCCC/C=C\C/C=C\CCCCC)CCSSCCN(CCCCCCCC/C=C\C/C=C\CCCCC)CCCCCCCC/C=C\C/C=C\CCCCC] | 11 |
| 69. | DS-BADL-AEP | 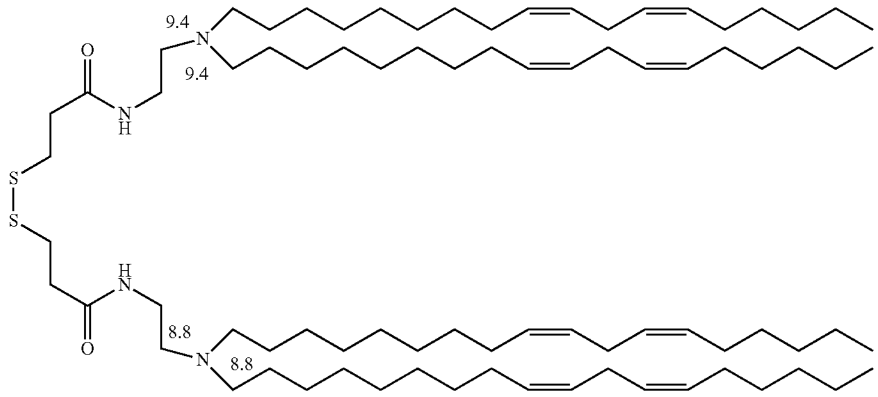 [SMILES: CCCCC/C=C\C/C=C\CCCCCCCCN(CCCCCCCC/C=C\C/C=C\CCCCC)CCNC(=O)CCSSCCC(=O)NCCN(CCCCCCCC/C=C\C/C=C\CCCCC)CCCCCCCC/C=C\C/C=C\CCCCC] | 11 |

TABLE 13D-continued
| Entry | Abbreviation | Lipids | Method |
|---|---|---|---|
| 70. | TADL-TMTP | 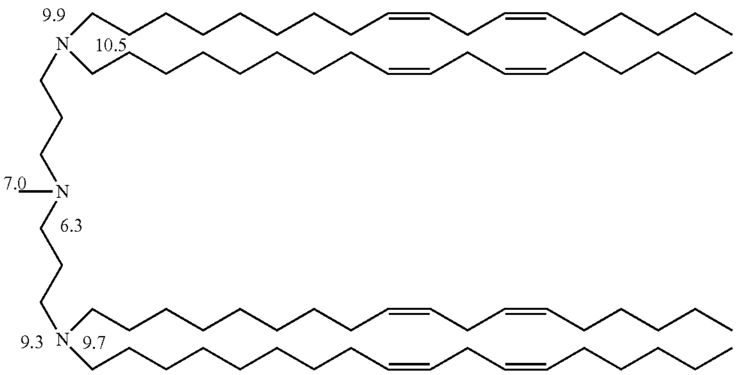 [SMILES: CCCCC/C=C\C/C=C\CCCCCCCCN(CCCCCCCC/C=C\C/C=C\CCCCC)CCCN(C)CCCN(CCCCCCCC/C=C\C/C=C\CCCCC)CCCCCCCC/C=C\C/C=C\CCCCC] | 11 |
| 71. | TADL-TMTE | 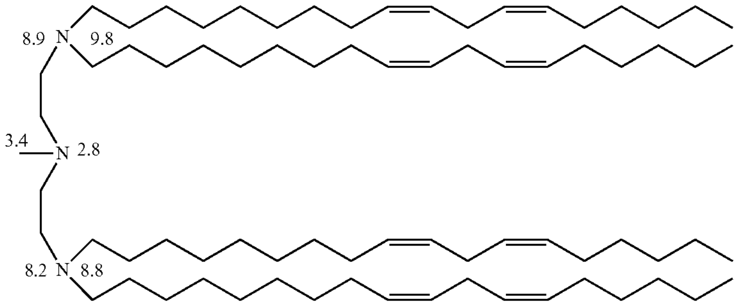 [SMILES: CCCCC/C=C\C/C=C\CCCCCCCCN(CCCCCCCC/C=C\C/C=C\CCCCC)CCN(C)CCN(CCCCCCCC/C=C\C/C=C\CCCCC)CCCCCCCC/C=C\C/C=C\CCCCC] | 11 |
| 72. | ADL-C3-Imd | 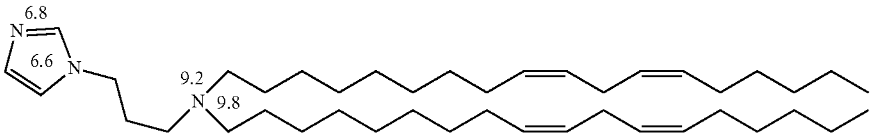 [SMILES: CCCCC/C=C\C/C=C\CCCCCCCCN(CCCCCCCC/C=C\C/C=C\CCCCC)CCCn1ccnc1] | 11 |
| 73. | BDMOHx-AP | 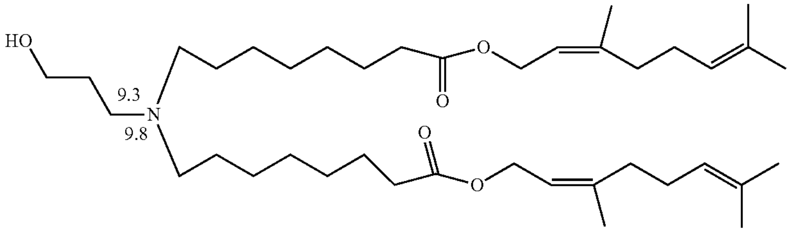 [SMILES: CC(C)=CCC/C(C)=C\COC(=O)CCCCCCCN(CCCO)CCCCCCCC(=O)OC/C=C(/C)CCC=C(C)C] | 11 |
| 74. | BDMOH-AP | 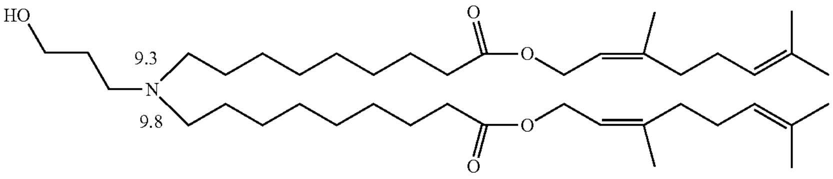 [SMILES: CC(C)=CCC/C(C)=C\COC(=O)CCCCCCCCN(CCCO)CCCCCCCCC(=O)OC/C=C(/C)CCC=C(C)C] | 11 |
| 75. | 2,4-CisOD-AP | 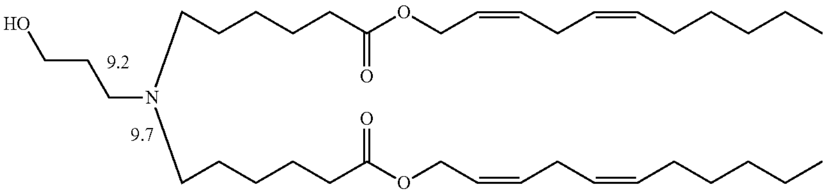 [SMILES: CCCCC/C=C\C/C=C\COC(=O)CCCCCN(CCCO)CCCCCC(=O)OC/C=C\C/C=C\CCCCC] | 11 |

TABLE 13D-continued
| Entry | Abbreviation | Lipids | Method |
|---|---|---|---|
| 76. | 4-CisOD-AP | 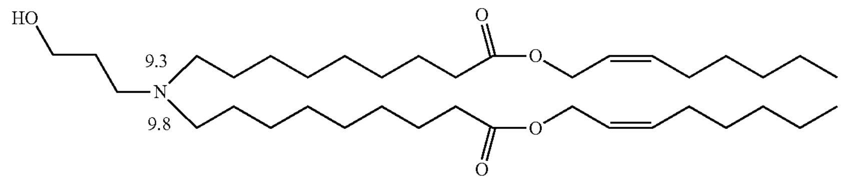 [SMILES: CCCCC/C=C\COC(=O)CCCCCCCCN(CCCO)CCCCCCCCC(=O)OC/C=C\CCCCC] | 11 |
| 77. | OD-AP | 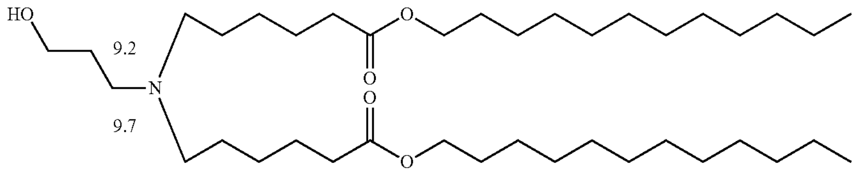 [SMILES: CCCCCCCCCCCCOC(=O)CCCCCN(CCCO)CCCCCC(=O)OCCCCCCCCCCCC] | 11 |
| 78. | 3,7DM-AP | 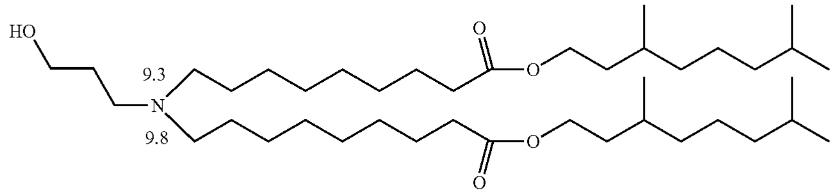 [SMILES: CC(C)CCCC(C)CCOC(=O)CCCCCCCCN(CCCO)CCCCCCCCC(=O)OCCC(C)CCCC(C)C] | 11 |
| 79. | MC3-ADL-AP | 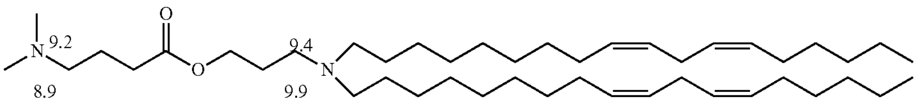 [SMILES: CCCCC/C=C\C/C=C\CCCCCCCCN(CCCCCCCC/C=C\C/C=C\CCCCC)CCCOC(=O)CCCN(C)C] | 11 |
| 80. | PipZ-C4-USL | 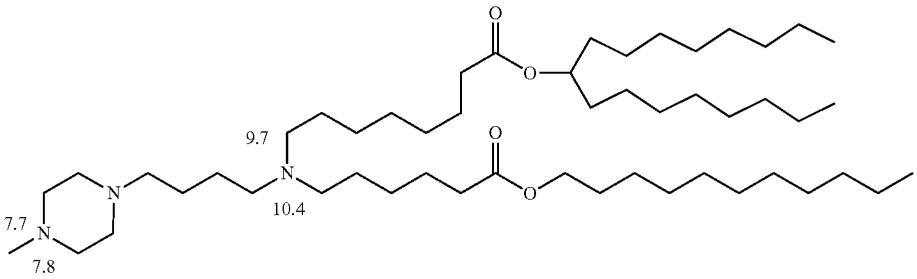 [SMILES: CCCCCCCCCCCOC(=O)CCCCCN(CCCCCCCC(=O)OC(CCCCCCCC)CCCCCCCC)CCCCN1CCN(C)CC1] | 12 |
| 81. | PipZ-C4-ODUD | 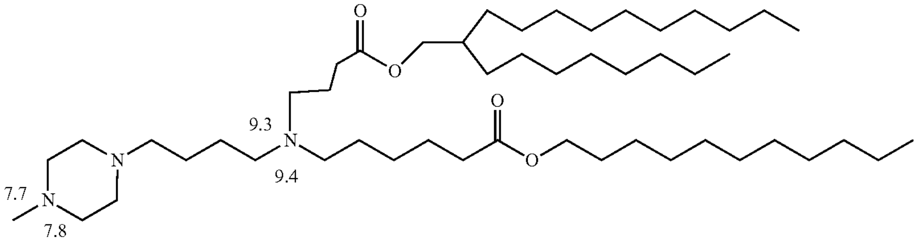 [SMILES: CCCCCCCCCCCOC(=O)CCCCCN(CCCCN1CCN(C)CC1)CCCC(=O)OCC(CCCCCCCC)CCCCCCCCCC] | 12 |
| 82. | PipZ-C4-C25-OHUD | 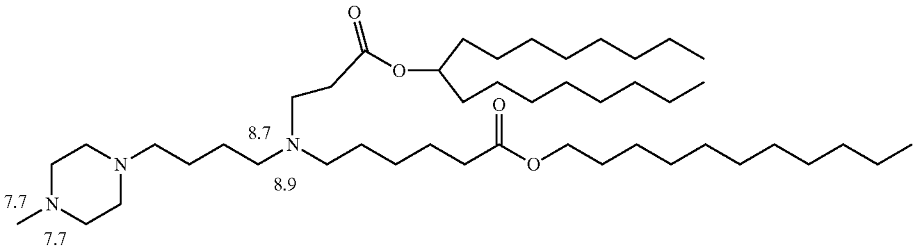 [SMILES: CCCCCCCCCCCOC(=O)CCCCCN(CCCCN1CCN(C)CC1)CCC(=O)OC(CCCCCCCC)CCCCCCCC] | 12 |

TABLE 13D-continued
| Entry | Abbreviation | Lipids | Method |
| --- | --- | --- | --- |
| 83. | PipZ-C4-C23-DDUD | 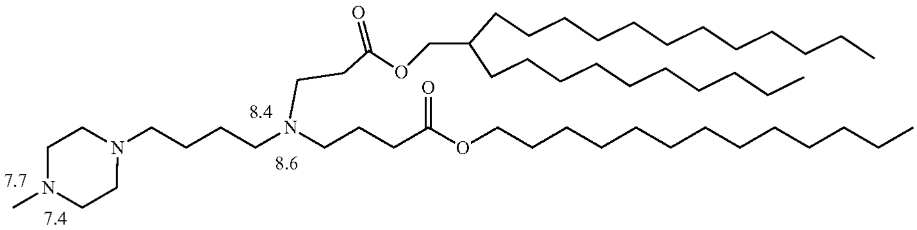 [SMILES: CCCCCCCCCCCCCOC(=O)CCCN(CCCCN1CCN(C)CC1)CCC(=O)OCC(CCCCCCCCCC)CCCCCCCCCCCC] | 12 |
| 84. | PipZ-C4-C23OHUD | 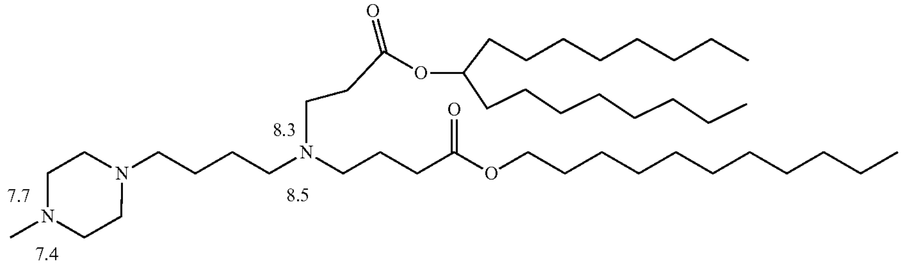 [SMILES: CCCCCCCCCCCOC(=O)CCCN(CCCCN1CCN(C)CC1)CCC(=O)OC(CCCCCCCC)CCCCCCCC] | 12 |
| 85. | PipZ-C3-C23DDUD | 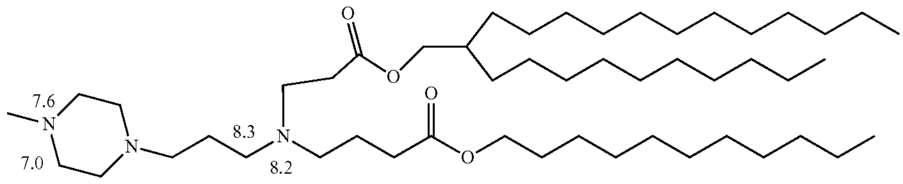 [SMILES: CCCCCCCCCCCCC(CCCCCCCCCC)COC(=O)CCN(CCCC(=O)OCCCCCCCCCCC)CCCN1CCN(C)CC1] | 12 |
| 86. | PipZ-C2-C23DUD | 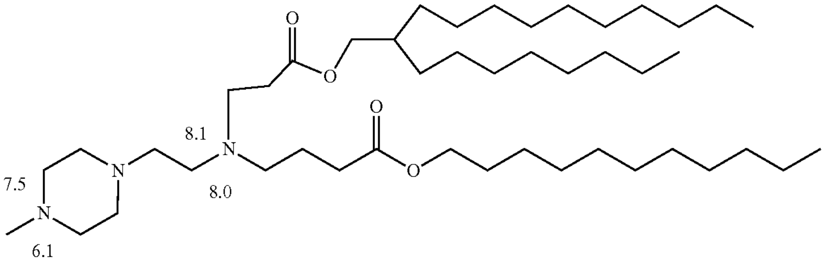 [SMILES: CCCCCCCCCCCOC(=O)CCCN(CCC(=O)OCC(CCCCCCCC)CCCCCCCCCC)CCN1CCN(C)CC1] | 12 |
| 87. | MC3-SM102 DMAC3-USL | 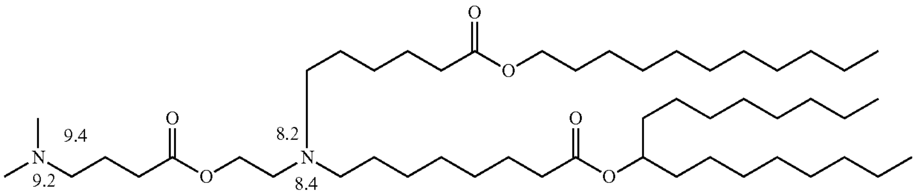 [SMILES: CCCCCCCCCCCOC(=O)CCCCCN(CCCCCCCC(=O)OC(CCCCCCCC)CCCCCCCC)CCOC(=O)CCCN(C)C] | 12 |
| 88. | MC2-UnSym | 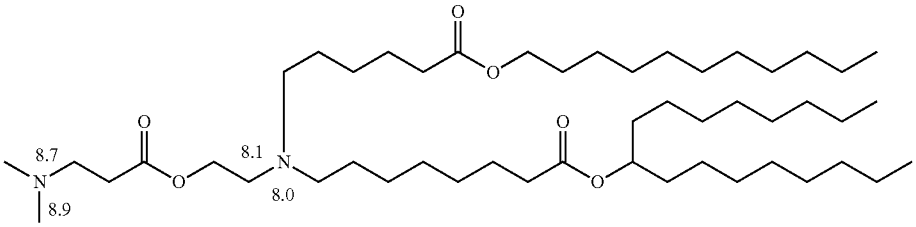 [SMILES: CCCCCCCCCCCOC(=O)CCCCCN(CCCCCCCC(=O)OC(CCCCCCCC)CCCCCCCC)CCOC(=O)CCN(C)C] | 12 |

TABLE 13D-continued
| Entry | Abbreviation | Lipids | Method |
|---|---|---|---|
| 89. | PipZ-C2-UnSym | 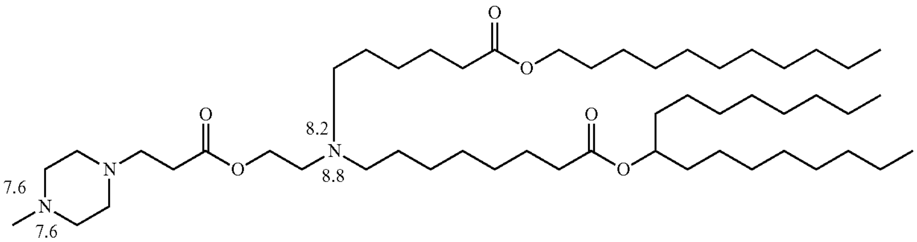 [SMILES: CCCCCCCCCCCOC(=O)CCCCCN(CCCCCCCC(=O)OC(CCCCCCCC)CCCCCCCC)CCOC(=O)CCN1CCN(C)CC1] | 12 |
| 90. | 1Me-Pip-C3-UnSym | 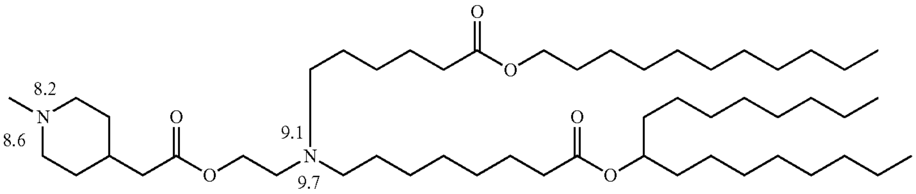 [SMILES: CCCCCCCCCCCOC(=O)CCCCCN(CCCCCCCC(=O)OC(CCCCCCCC)CCCCCCCC)CCOC(=O)CC1CCN(C)CC1] | 12 |
| 91. | 1Me-pyr-C3-UnSym | 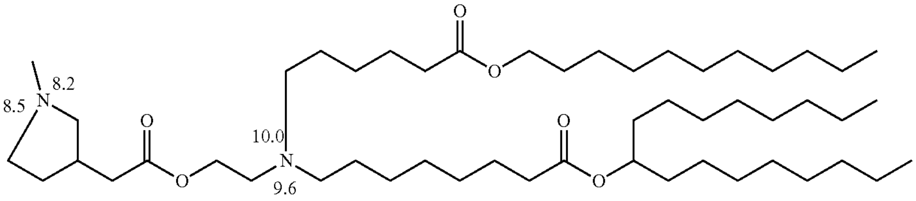 [SMILES: CCCCCCCCCCCOC(=O)CCCCCN(CCCCCCCC(=O)OC(CCCCCCCC)CCCCCCCC)CCOC(=O)CC1CCN(C)C1] | 12 |
| 92. | AP-C2-BUnSym | 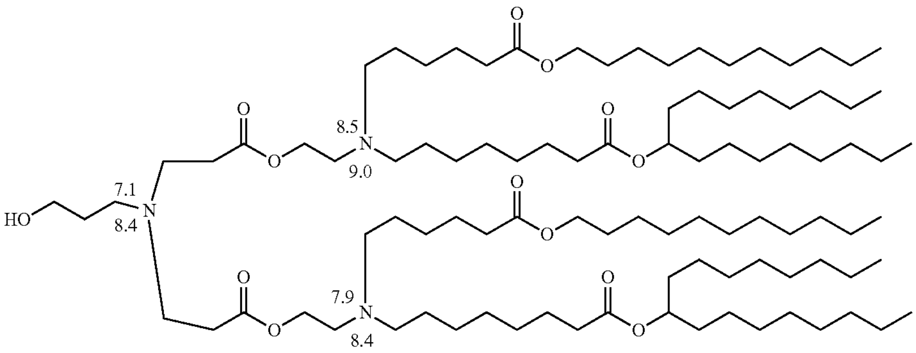 [SMILES: CCCCCCCCCCCOC(=O)CCCCCN(CCCCCCCC(=O)OC(CCCCCCCC)CCCCCCCC)CCOC(=O)CCN(CCCO)CCC(=O)OCCN(CCCCCCCC(=O)OC(CCCCCCCC)CCCCCCCC)CCCCCC(=O)OCCCCCCCCCCC] | 12 |
| 93. | AP-C4-BUnSym | 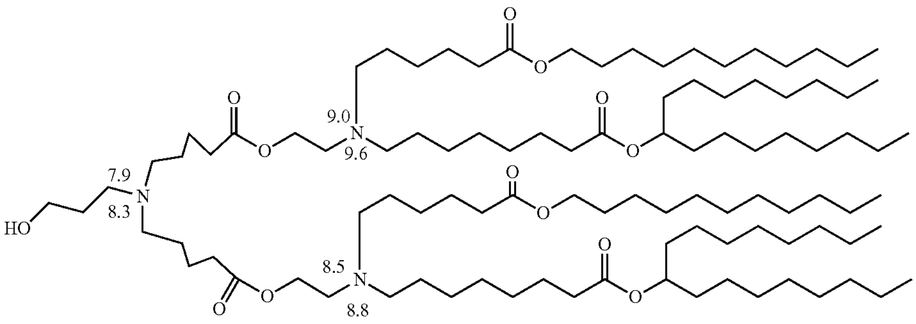 [SMILES: CCCCCCCCCCCOC(=O)CCCCCN(CCCCCCCC(=O)OC(CCCCCCCC)CCCCCCCC)CCOC(=O)CCCCN(CCCO)CCCCC(=O)OCCN(CCCCCCCC(=O)OC(CCCCCCCC)CCCCCCCC)CCCCCC(=O)OCCCCCCCCCCC] | 12 |

TABLE 13D-continued
| Entry | Abbreviation | Lipids | Method |
|---|---|---|---|
| 94. | PipZ-C4C2-BUnSym | 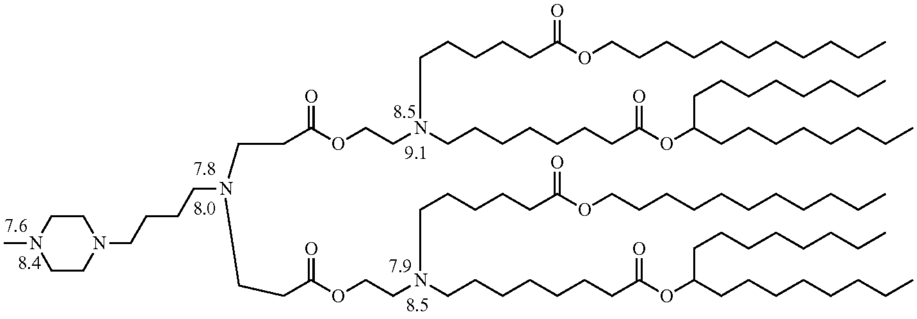 [SMILES: CCCCCCCCCCCOC(=O)CCCCCN(CCCCCCCC(=O)OC(CCCCCCCC)CCCCCCCC)CCOC(=O)CCN(CCCCN1CCN(C)CC1)CCC(=O)OCCN(CCCCCCCC(=O)OC(CCCCCCCC)CCCCCCCC)CCCCCC(=O)OCCCCCCCCCCC] | 12 |
| 95. | ALC-C4PipZ SL-C4PipZ | 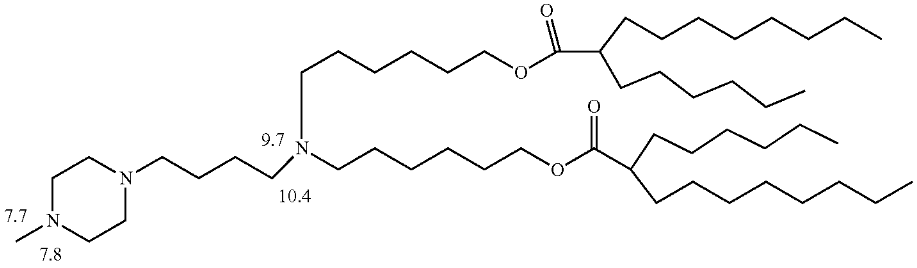 [SMILES: CCCCCCCCC(CCCCCC)C(=O)OCCCCCCN(CCCCCCOC(=O)C(CCCCCC)CCCCCCCC)CCCCN1CCN(C)CC1] | 13 |
| 96. | ALC-C2PipZ SL-C2PipZ | 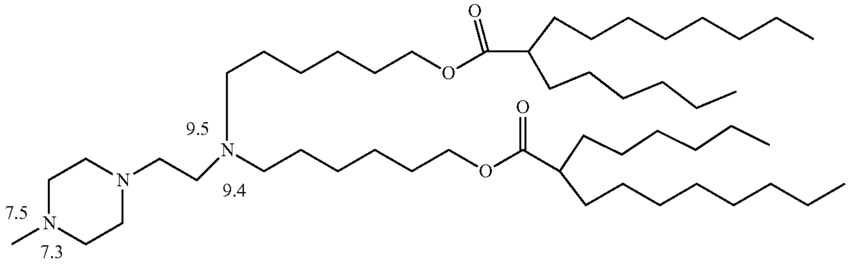 [SMILES: CCCCCCCCC(CCCCCC)C(=O)OCCCCCCN(CCCCCCOC(=O)C(CCCCCC)CCCCCCCC)CCN1CCN(C)CC1] | 13 |
| 97. | PipZ-C4/C5-Sym | 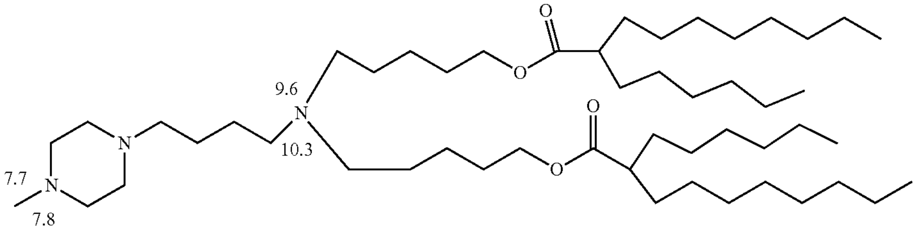 [SMILES: CCCCCCCCC(CCCCCC)C(=O)OCCCCCN(CCCCCOC(=O)C(CCCCCC)CCCCCCCC)CCCCN1CCN(C)CC1] | 13 |
| 98. | PipZ-C4/C4-Sym | 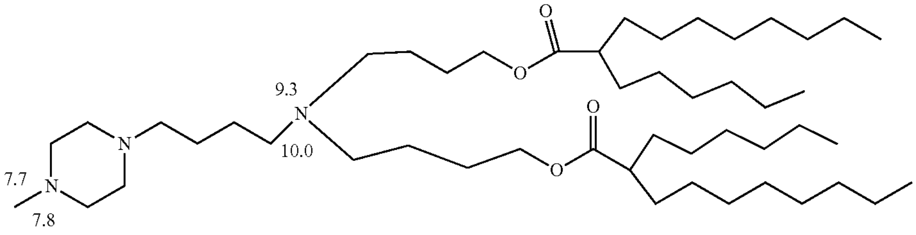 [SMILES: CCCCCCCCC(CCCCCC)C(=O)OCCCCN(CCCCOC(=O)C(CCCCCC)CCCCCCCC)CCCCN1CCN(C)CC1] | 13 |

TABLE 13D-continued
| Entry | Abbreviation | Lipids | Method |
| --- | --- | --- | --- |
| 99. | PipZ-C3/C3-Sym | 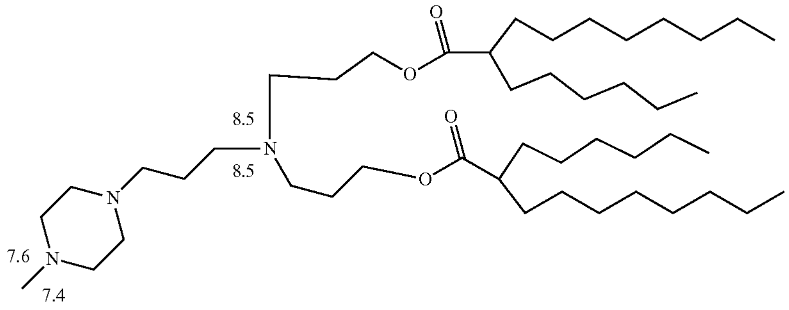 [SMILES: CCCCCCCCC(CCCCCC)C(=O)OCCCN(CCCOC(=O)C(CCCCCC)CCCCCCCC)CCCN1CCN(C)CC1] | 13 |
| 100. | PipZ-C2/C3-Sym | 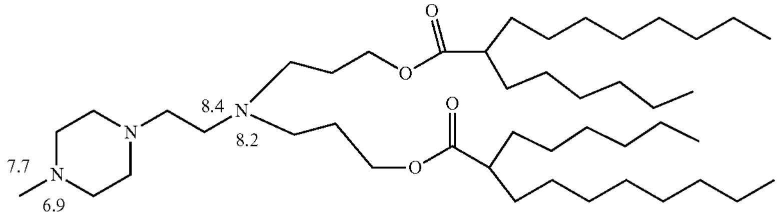 [SMILES: CCCCCCCCC(CCCCCC)C(=O)OCCCN(CCCOC(=O)C(CCCCCC)CCCCCCCC)CCN1CCN(C)CC1] | 13 |
| 101. | PipZ-C4/C3-Sym | 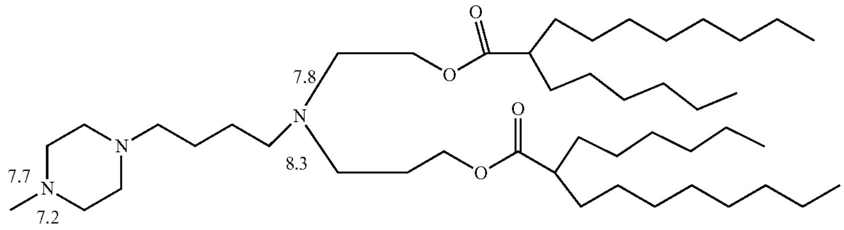 [SMILES: CCCCCCCCC(CCCCCC)C(=O)OCCCN(CCCCN1CCN(C)CC1)CCOC(=O)C(CCCCCC)CCCCCCCC] | 13 |
| 102. | PipZ-C4-C6-BSym | 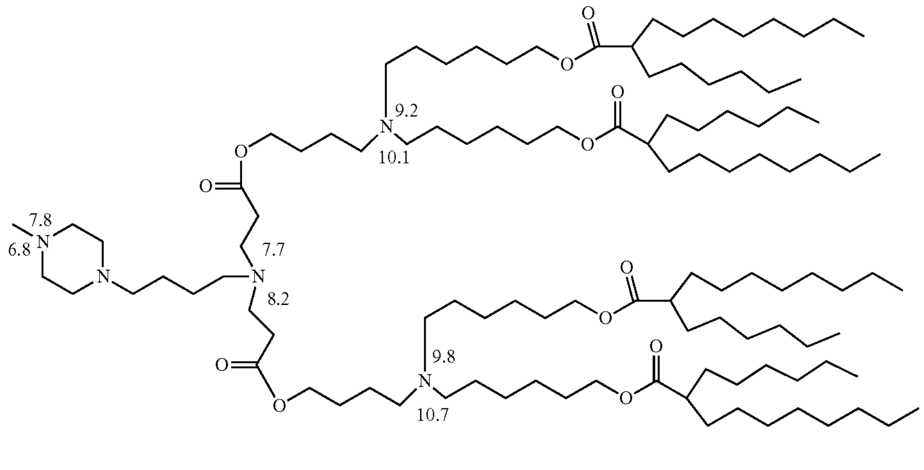 [SMILES: CCCCCCCCC(CCCCCC)C(=O)OCCCCCCN(CCCCCCOC(=O)C(CCCCCC)CCCCCCCC)CCCCOC(=O)CCN(CCCCN1CCN(C)CC1)CCC(=O)OCCCCN(CCCCCCOC(=O)C(CCCCCC)CCCCCCCC)CCCCCCOC(=O)C(CCCCCC)CCCCCCCC] | 13 |

TABLE 13D-continued
| Entry | Abbreviation | Lipids | Method |
|---|---|---|---|
| 103. | BA-C4/C6-BSym | 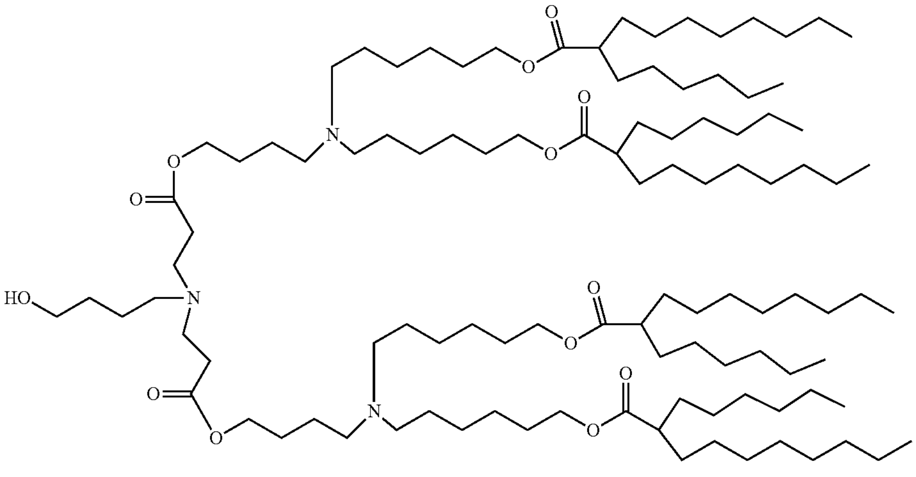 [SMILES: CCCCCCCCC(CCCCCC)C(=O)OCCCCCCN(CCCCCCOC(=O)C(CCCCCC)CCCCCCCC)CCCCOC(=O)CCN(CCCCO)CCC(=O)OCCCCN(CCCCCCOC(=O)C(CCCCCC)CCCCCCCC)CCCCCCOC(=O)C(CCCCCC)CCCCCCCC] | 13 |
| 104. | ALC-C2/C3-MC3 SL-C2/C3-DMAC3 | 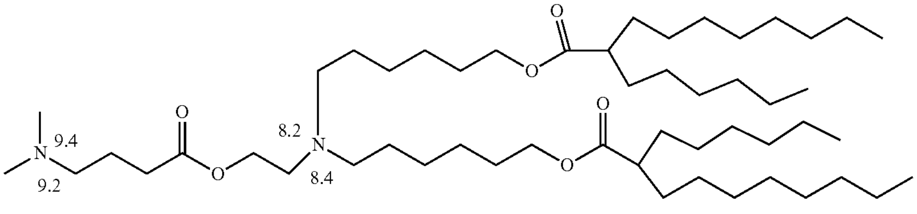 [SMILES: CCCCCCCCC(CCCCCC)C(=O)OCCCCCCN(CCCCCCOC(=O)C(CCCCCC)CCCCCCCC)CCOC(=O)CCCN(C)C] | 13 |
| 105. | ALC-C3/C3-MC3 SL-C3/C3-DMAC3 | 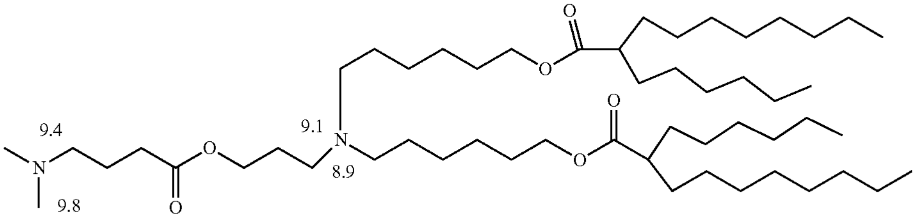 [SMILES: CCCCCCCCC(CCCCCC)C(=O)OCCCCCCN(CCCCCCOC(=O)C(CCCCCC)CCCCCCCC)CCCOC(=O)CCCN(C)C] | 13 |
| 106. | MC3-ALC0315 DMAC3-SL | 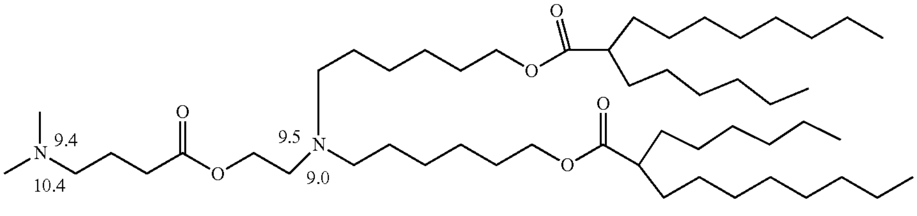 [SMILES: CCCCCCCCC(CCCCCC)C(=O)OCCCCCCN(CCCCCCOC(=O)C(CCCCCC)CCCCCCCC)CCOC(=O)CCCN(C)C] | 13 |
| 107. | ADTD-C2/C4-PipZ | 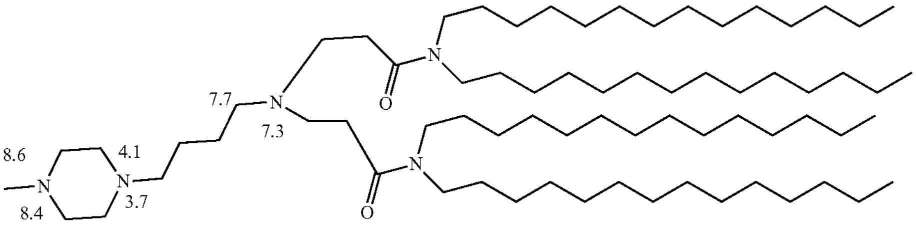 [SMILES: CCCCCCCCCCCCCCN(CCCCCCCCCCCCCC)C(=O)CCN(CCCCN1CCN(C)CC1)CCC(=O)N(CCCCCCCCCCCCCC)CCCCCCCCCCCCCC] | 14 |
| 108. | ADTD-C2/C4-DMA | 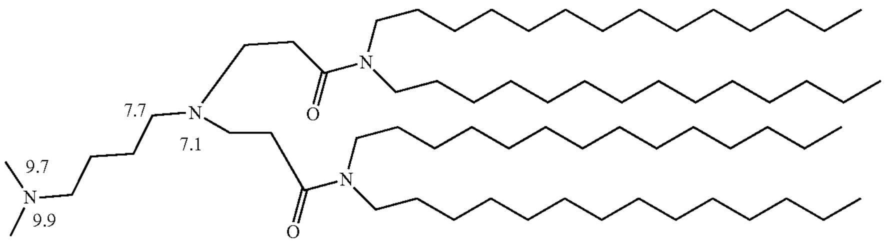 [SMILES: CCCCCCCCCCCCCCN(CCCCCCCCCCCCCC)C(=O)CCN(CCCCN(C)C)CCC(=O)N(CCCCCCCCCCCCCC)CCCCCCCCCCCCCC] | 14 |

TABLE 13D-continued
| Entry | Abbreviation | Lipids | Method |
|---|---|---|---|
| 109. | PipZ-C4-A-Amide | 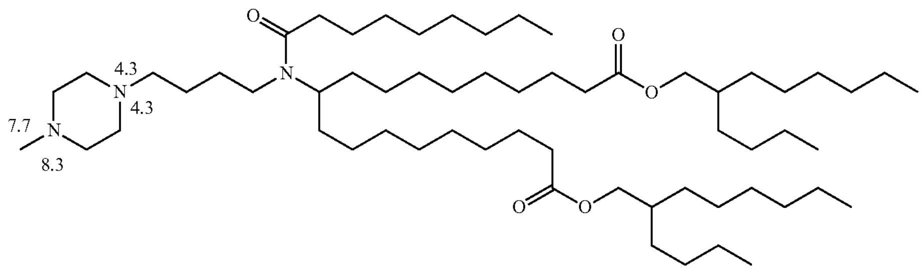 [SMILES: CCCCCCCCC(=O)N(CCCCN1CCN(C)CC1)C(CCCCCCCCC(=O)OCC(CCCC)CCCCCC)CCCCCCCCC(=O)OCC(CCCC)CCCCCC] | 15 |
| 110. | PipZ-C4-A9-Sulfonamide | 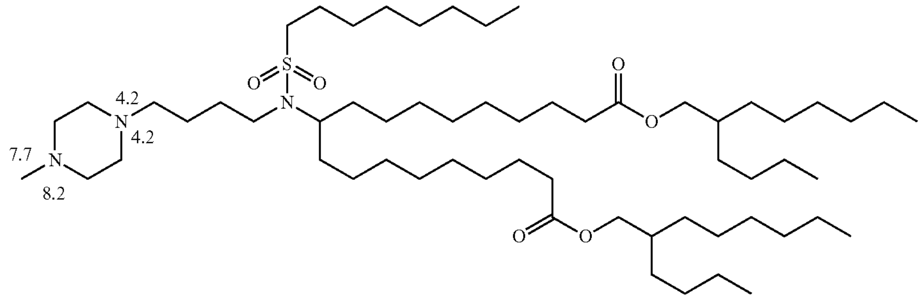 [SMILES: CCCCCCCCS(=O)(=O)N(CCCCN1CCN(C)CC1)C(CCCCCCCCC(=O)OCC(CCCC)CCCCCC)CCCCCCCCC(=O)OCC(CCCC)CCCCCC] | 15 |
| 111. | PipZ-C4-A9-PolyAmide | 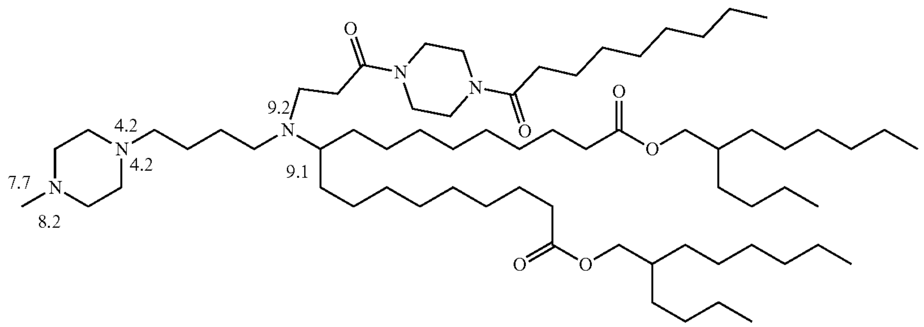 [SMILES: CCCCCCCCC(=O)N1CCN(C(=O)CCN(CCCCN2CCN(C)CC2)C(CCCCCCCCC(=O)OCC(CCCC)CCCCCC)CCCCCCCCC(=O)OCC(CCCC)CCCCCC)CC1] | 15 |
| 112. | OH-C2-C24-PipZ | 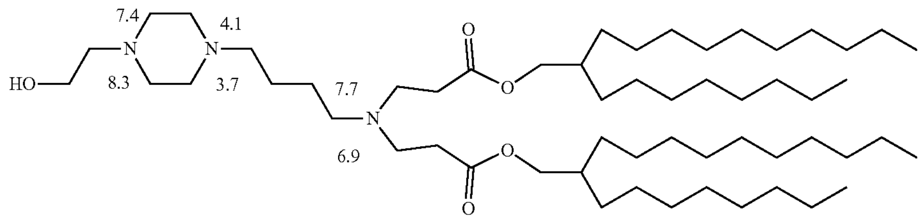 [SMILES: CCCCCCCCCCC(CCCCCCCC)COC(=O)CCN(CCCCN1CCN(CCO)CC1)CCC(=O)OCC(CCCCCCCC)CCCCCCCCCC] | 16 |
| 113. | OH-C4-C24-PipZ | 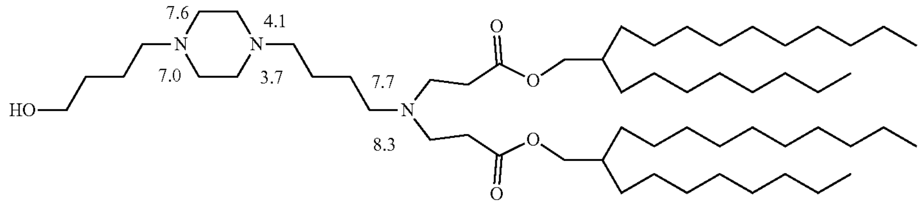 [SMILES: CCCCCCCCCCC(CCCCCCCC)COC(=O)CCN(CCCCN1CCN(CCCCO)CC1)CCC(=O)OCC(CCCCCCCC)CCCCCCCCCC] | 16 |
| 114. | PipZ-C24-ODD | 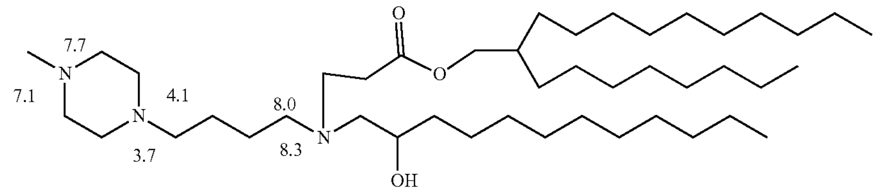 [SMILES: CCCCCCCCCCC(O)CN(CCCCN1CCN(C)CC1)CCC(=O)OCC(CCCCCCCC)CCCCCCCCCC] | 16 |

TABLE 13D-continued
| Entry | Abbreviation | Lipids | Method |
|---|---|---|---|
| 115. | PipZ-C24-DL | 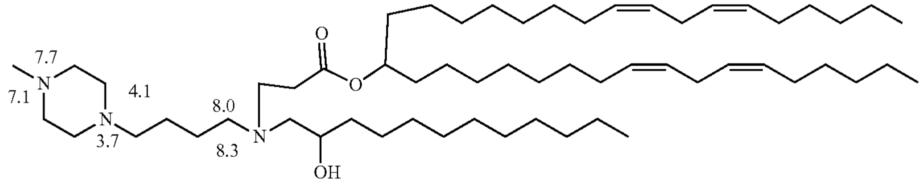 [SMILES: CCCCC/C=C\C/C=C\CCCCCCCC(CCCCCCC/C=C\C/C=C\CCCCC)OC(=O)CCN(CCCCN1CCN(C)CC1)CC(O)CCCCCCCCCC] | 16 |
| 116. | PipZ-C24-4-ODD | 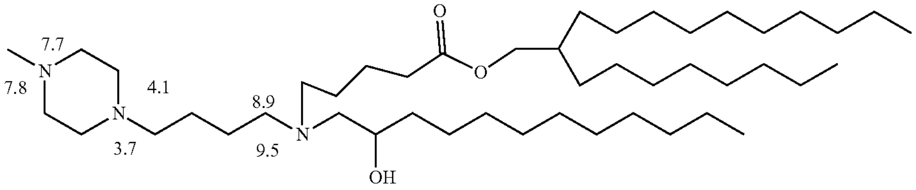 [SMILES: CCCCCCCCCCC(O)CN(CCCCC(=O)OCC(CCCCCCCC)CCCCCCCCCC)CCCCN1CCN(C)CC1] | 16 |
| 117. | PipZ-C24-5-ODD | 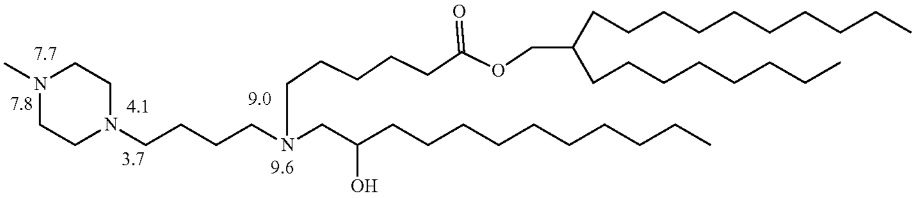 [SMILES: CCCCCCCCCCC(O)CN(CCCCCC(=O)OCC(CCCCCCCC)CCCCCCCCCC)CCCCN1CCN(C)CC1] | 16 |
| 118. | DA-C6-C4-Azirine | 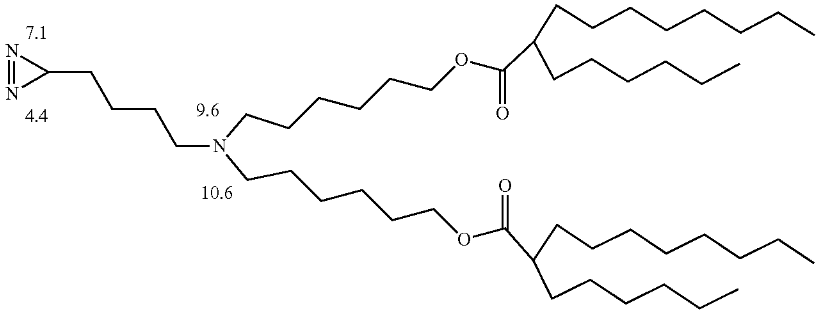 [SMILES: CCCCCCCCC(CCCCCC)C(=O)OCCCCCCN(CCCCCCOC(=O)C(CCCCCC)CCCCCCCC)CCCCC1N=N1] | 16 |
| 119. | DA-C4-C4-Azirine | 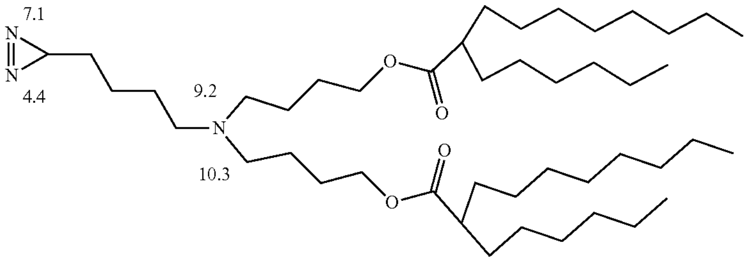 [SMILES: CCCCCCCCC(CCCCCC)C(=O)OCCCCN(CCCCOC(=O)C(CCCCCC)CCCCCCCC)CCCCC1N=N1] | 16 |
| 120. | CF3-C6-C4-Azane | 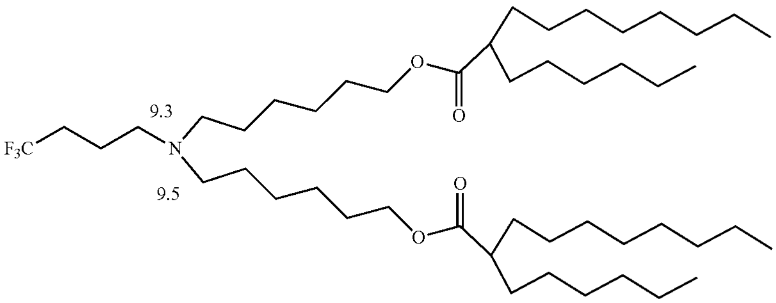 [SMILES: CCCCCCCCC(CCCCCC)C(=O)OCCCCCCN(CCCCCCOC(=O)C(CCCCCC)CCCCCCCC)CCCC(F)(F)F] | 16 |

V.4. Illustrative Methods of Making the Ionizable Lipids of the Invention

The Ionizable Lipids of the Invention can be synthesized by various routes using commercially available reagents. The below methods provide illustrative techniques to make the Ionizable Lipids of the Invention.

General Reaction Scheme 1

Method A

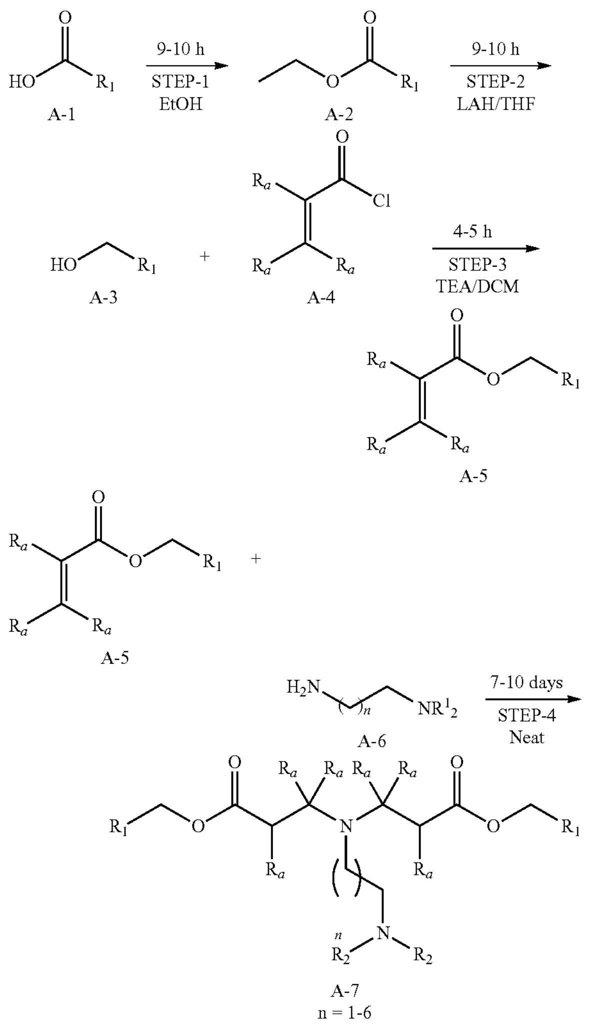

Illustrative embodiments of the Ionizable Lipids of the Invention with two degradable esters (e.g., compound A-7) can be prepared according to general reaction Scheme 1 ("Method A"), wherein $R^1$ is a saturated or unsaturated $C_1$-$C_{18}$ alkyl with linear chains or saturated/unsaturated chains and bilayer tails (symmetric and unsymmetrical), n is an integer from 1 to 6. Referring to the General Reaction Scheme 1, compounds of structure A-1 can be purchased from commercial sources or prepared according to the methods familiar to one of the ordinary skill in the art. A mixture of A-1 in solvent ethanol is treated with catalytic amount of sulfuric acid to give the ester A-2, then A-2 is treated with LAH (e.g., lithium aluminium hydride) in anhydrous THF for 9-10 h to obtain alcohol derivative A-3. The purified A-3 is reacted with acryloyl chloride derivatives (where Ra=$CH_3$, $C_2H_5$ and/or isopropyl groups) A-4, a base (e.g., triethyl amine) in dichloromethane for 4-5 hours to get substituted acylation products A-5. A mixture of the acylated product and head groups (R1) N,N-dimethyl-diamine A-6 is heated at a temperature and time sufficient to produce A-7 after any necessarily workup and or purification step.

General Reaction Scheme 2

Method B

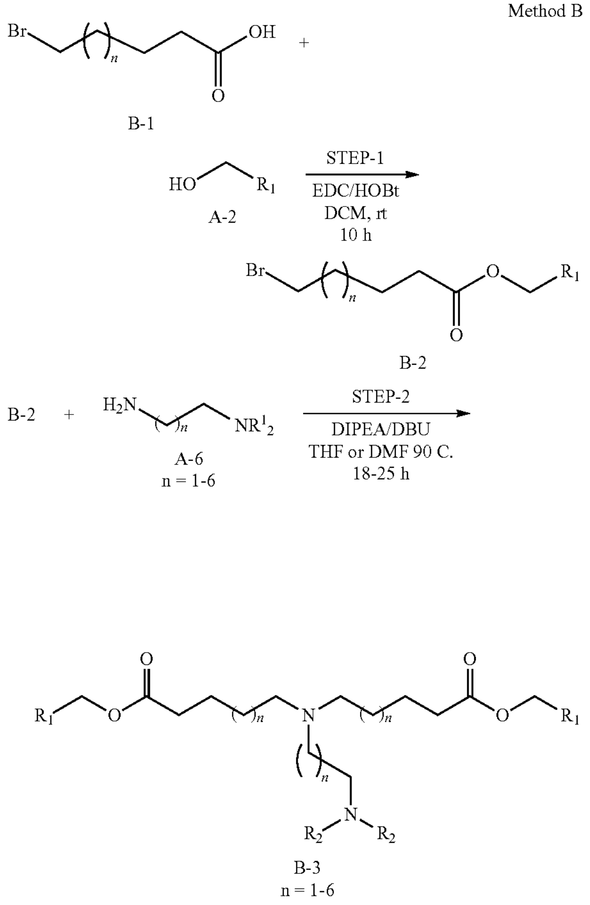

Illustrative embodiments of the Ionizable Lipids of the Invention with carbon spacers increased between the linker and internal amine (e.g., compound B-3) can be prepared according to general reaction Scheme 2 ("Method B"), wherein $R^1$ is a saturated or unsaturated $C_1$-$C_{18}$ alkyl with linear chains or saturated/unsaturated with bilayer tails (symmetric and unsymmetrical), n is an integer from 1 to 6. Referring to the General Reaction Scheme 2, compounds of structure A-2 are prepared according to the methods familiar to one of the ordinary skill in art. A mixture of B-1 and A-2 in methylene dichloride as the solvent is treated with a catalytic amount of N-(3-dimethylaminopropyl)-N'-ethyl-carbodiimide hydrochloride (EDC·HCl), hydroxybenzotriazole (HOBt) with a base such as triethyl amine to give the ester derivative B-2, then the mixture of B-2 and A-6 is treated with base (e.g., N,N-diisopropylethyl amine or 1,8-diazabicyclo[5.4.0]undec-7-ene) in anhydrous THF heated at a temperature and time sufficient 2-5 days to produce B-3 after any necessarily workup and or purification step.

General Reaction Scheme 3

Method C

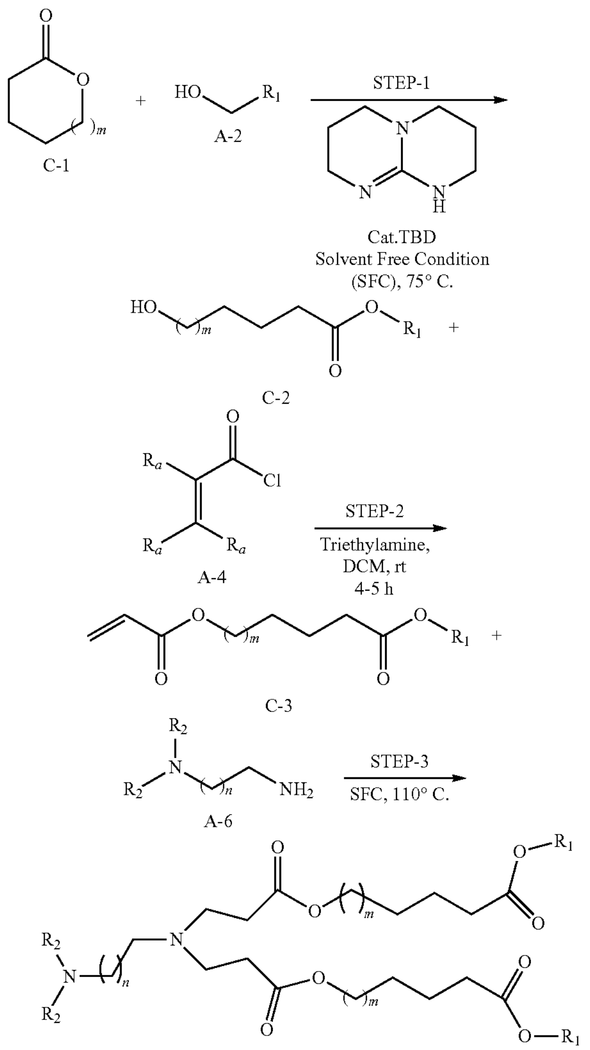

C-1 A-2 C-2 A-4 C-3 A-6 C-4

Illustrative embodiments of the Ionizable Lipids of the Invention (symmetrical with 4 ester groups) (e.g., compound C-4) can be prepared according to general reaction Scheme 3 (“Method C”), wherein $R^1$ is a saturated or unsaturated $C_1$-$C_{18}$ alkyl with linear chains or saturated/unsaturated with bilayer tails (symmetric and unsymmetrical), where m is an integer from −1 to 2, n is an integer from 1 to 6. Referring to the General Reaction Scheme 3, compounds of structure A-2 are prepared according to the methods familiar to one of the ordinary skill in the art. A mixture of C-1 and A-2 are treated with solvent free conditions in Schlenk tube purged with nitrogen gas (maintained under anhydrous conditions) with a catalytic amount of the organocatalyst 1,5,7-triazabicyclo[4.4.0]dec-5-ene (TBD) heated at a temperature to afford ester derivative C-2. The purified C-2 is mixed with acryloyl chloride A-4 using methylene chloride as a solvent in the presence of triethylamine. Then the reaction is allowed to stir at room temperature until the consumption of starting materials to obtain C-3. A mixture of the acylated product and head groups C-3 and N,N-dimethyldiamine A-6 is heated at a temperature and time sufficient to produce C-4 after any necessarily workup and or purification step.

General Reaction Scheme 4

Method-C1

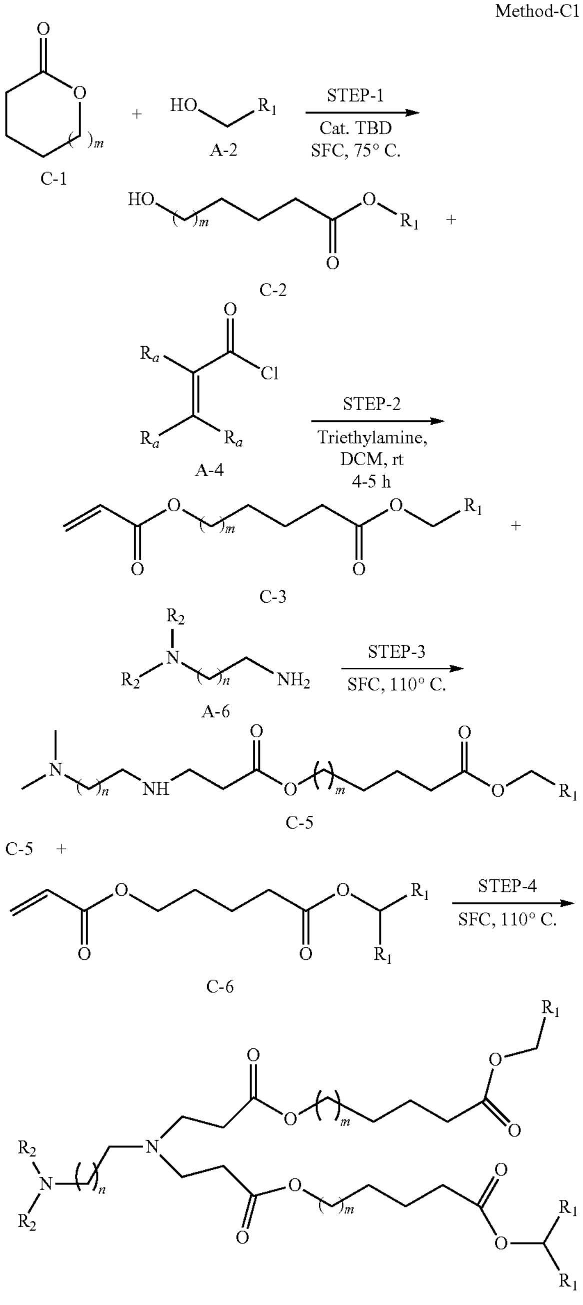

C-1 A-2 C-2 A-4 C-3 A-6 C-5 C-5 + C-6 C-7

Illustrative embodiments of the Ionizable Lipids of the Invention (unsymmetrical with 4 ester groups) (e.g., compound C-7) can be prepared according to general reaction Scheme 4 (“Method-C1”), wherein $R^1$ is a saturated or unsaturated $C_1$-$C_{18}$ is alkyl with linear chains or saturated/unsaturated with bilayer tails (symmetric and unsymmetrical), where m is an integer from −1 to 2, n is an integer from 1 to 6. Referring to the General Reaction Scheme 4, compounds of structure A-2 are prepared according to the methods familiar to one of the ordinary skill in the art. A mixture of C-1 and A-2 are treated with solvent free conditions in a Schlenk tube purged with nitrogen gas (maintained under anhydrous conditions) with a catalytic amount of the organocatalyst 1,5,7-triazabicyclo[4.4.0]dec-5-ene (TBD) heated at a temperature to afford ester derivative C-2. The purified C-2 is mixed with acryloyl chloride A-4 using methylene chloride as a solvent in the presence of triethylamine. The reaction is allowed to stir at room temperature until the consumption of stating materials to obtain C-3. A mixture of the acylated C-3 product and head groups N,N-dimethyldiamine A-6 in equal amounts are reacted with heating at a temperature and time sufficient to produce C-5. Further purified C-5 is treated with C-6 (bilayered tail) in the same equivalents and heated at a temperature and time sufficient to produce C-7 after any necessarily workup and or purification step.

General Reaction Scheme 5

Method D

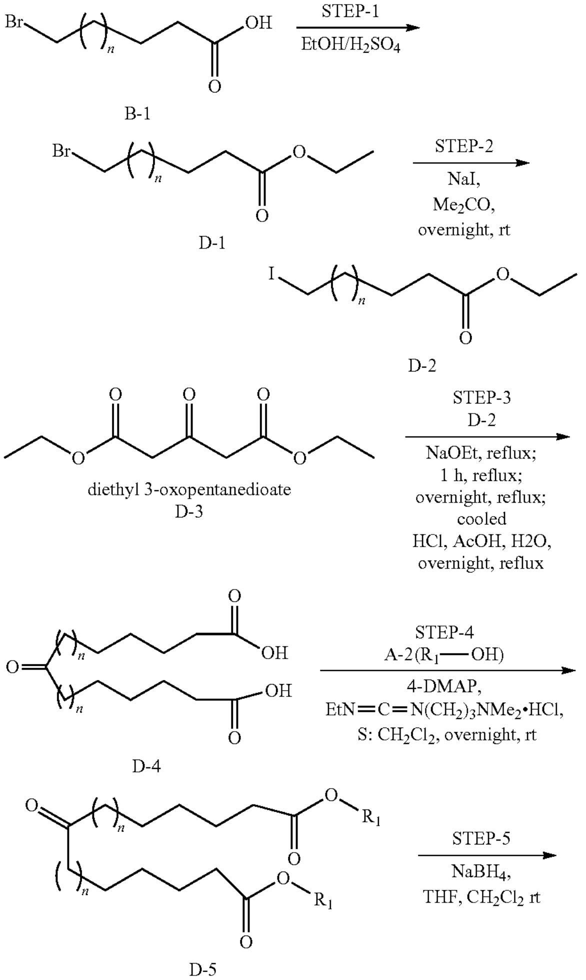

B-1
D-1
D-2
diethyl 3-oxopentanedioate
D-3
D-4
D-5

-continued

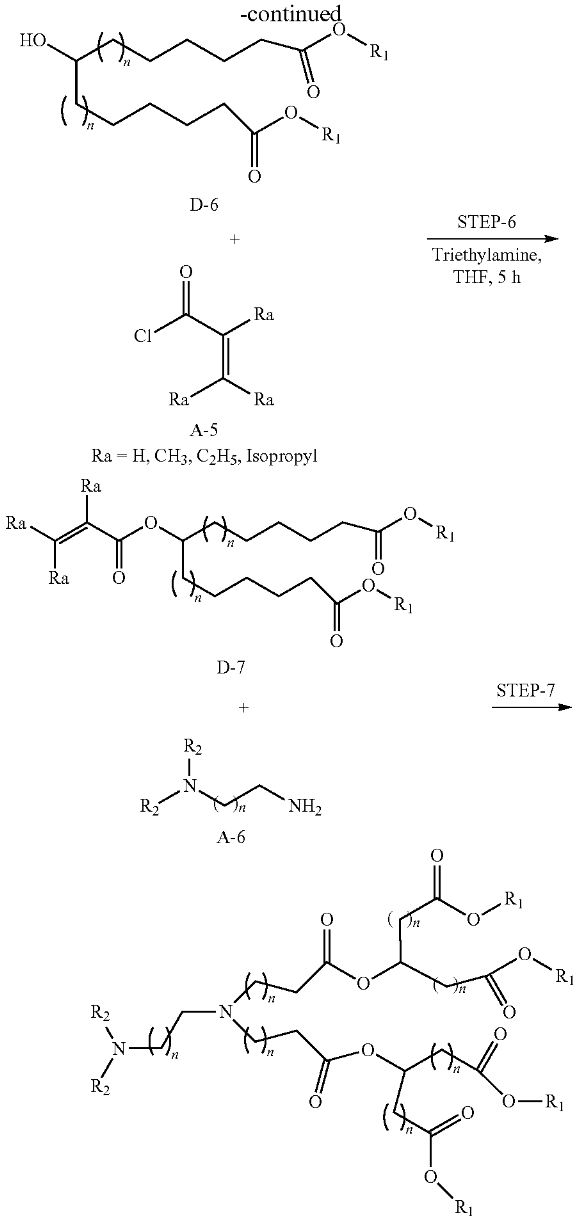

D-6
A-5
D-7
A-6
D-8

Illustrative embodiments of the Ionizable Lipids of the Invention with six degradable esters (e.g., compound D-8) can be prepared according to general reaction Scheme 5 ("Method D"), wherein $R^1$ is a saturated or unsaturated $C_1$-$C_{18}$ alkyl with linear chains or saturated/unsaturated with bilayer tails (symmetric and unsymmetrical), n is an integer from 1 to 6, $R^2$ is alkyl, cyclic, heterocyclic substituents and $R^4$ is ester derivative with an alkyl chain. Referring to the General Reaction Scheme 5, compounds of structure B-1, A-1, A-2, A-5 and A-6 can be purchased from commercial sources or prepared according to the methods familiar to one of the ordinary skill in the art. Esterification of B-1 in presence of ethanol using a catalytic amount of sulfuric acid obtained D-1. Further, the alkyl bromide is converted to the corresponding alkyl iodide D-2 with a solution of sodium iodide in acetone by the classic Finkelstein reaction. A mixture of D-2 and D-3 is reacted with sodium ethoxide (NaOEt) in ethanol at reflux, followed by acidification to low pH to obtain D-4. In Step 4, esterification was done in the presence of N-(3-dimethylaminopropyl)-N'-ethylcarbodiimide hydrochloride (EDC·HCl) and a catalytic amount of 4-dimethylaminopyridine (4-DMAP) in methylene dichloride for overnight to obtain D-5. Further D-5 is reduced to the corresponding alcohol in the presence of sodium borohydride ($NaBH_4$) to get D-6. Purified D-6 is reacted with acryloyl chloride derivatives (where Ra=$CH_3$, $C_2H_5$ and/or isopropyl groups) A-5 in the presence of a base (e.g., triethylamine) in tetrahydrofuran solvent for 4-5 hours to get the substituted acylation products D-7. A mixture of the acylated product D-7 and head groups (R1) N,N-dimethyldiamine A-6 is heated at a temperature and time sufficient to produce D-8 after any necessarily workup and or purification step.

General Reaction Scheme 6

Method-E, F and G

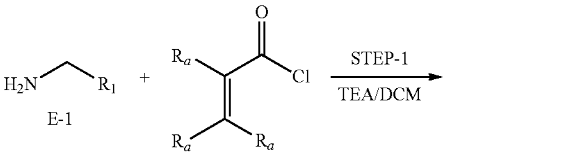

E-1

A-4

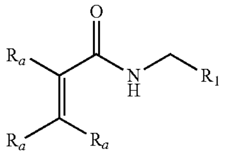

E-2

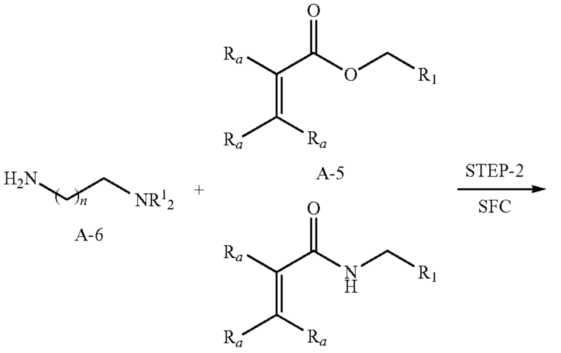

A-6

A-5

E-2

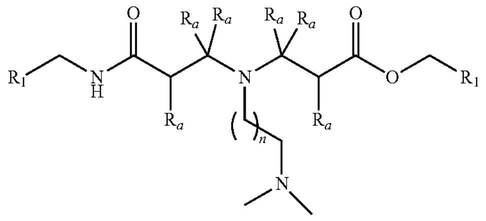

E-3
n = 1-6

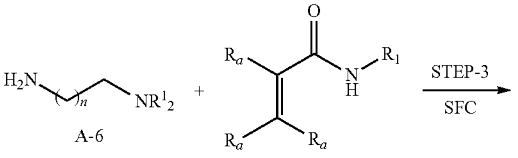

A-6

E-2

-continued

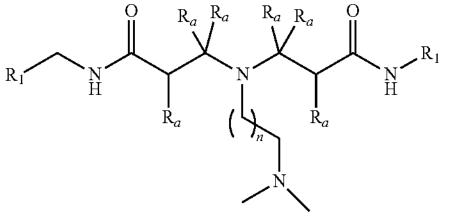

F
n = 1-6

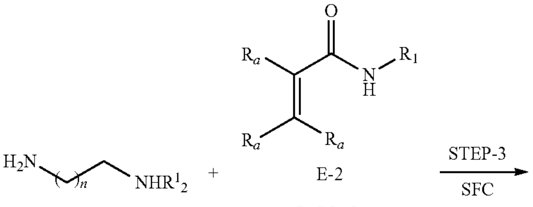

A-6

E-2

$R_bSO_2Cl$

E-4
$R_b$ = Alkyl
($C_n$, n = 1-18),
Cyclo alkyl

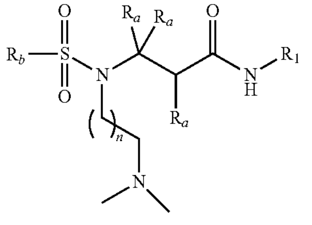

G
n = 1-6

Illustrative embodiments of the Ionizable Lipids of the Invention with degradable and non-degradable esters (e.g., compounds E, F and G) can be prepared according to general reaction Scheme 6 ("Method E"), wherein $R^1$ is a saturated or unsaturated $C_1$-$C_{18}$ alkyl with linear chains or saturated/unsaturated with bilayer tails (symmetric and unsymmetrical), n is an integer from 1 to 6, $R^2$ is alkyl, cyclic, heterocyclic substituents. Referring to the General Reaction Scheme 6, compounds of structure E-1, A-4, E-2, A-5 and A-6 can be purchased from commercial sources or prepared according to the methods familiar to one of the ordinary skill in the art. E-1 is reacted with acryloyl chloride A-4 in methylene chloride in the presence of the reagent triethylamine to obtain E-2. In Step-2, A-6 is reacted with A-5 to obtain the monoalkylated product in situ. Further addition of A-5 dropwise under solvent free conditions is followed by heating for a time sufficient to produce E-3 after any necessarily workup and or purification step. In step 3, A-6 is reacted with 2 equivalents of acryloylamide under a nitrogen atmosphere under solvent free conditions followed by heating at a temperature and time sufficient to produce compound F after any necessarily workup and or purification step. In Step 4 A-6 is reacted with one equivalent of E-2 to obtain mono alkylated product and it further reacted with alkyl sulfonyl chloride to get nondegradable linkers derivatives G after any necessarily workup and or purification step.

General Reaction Scheme 7

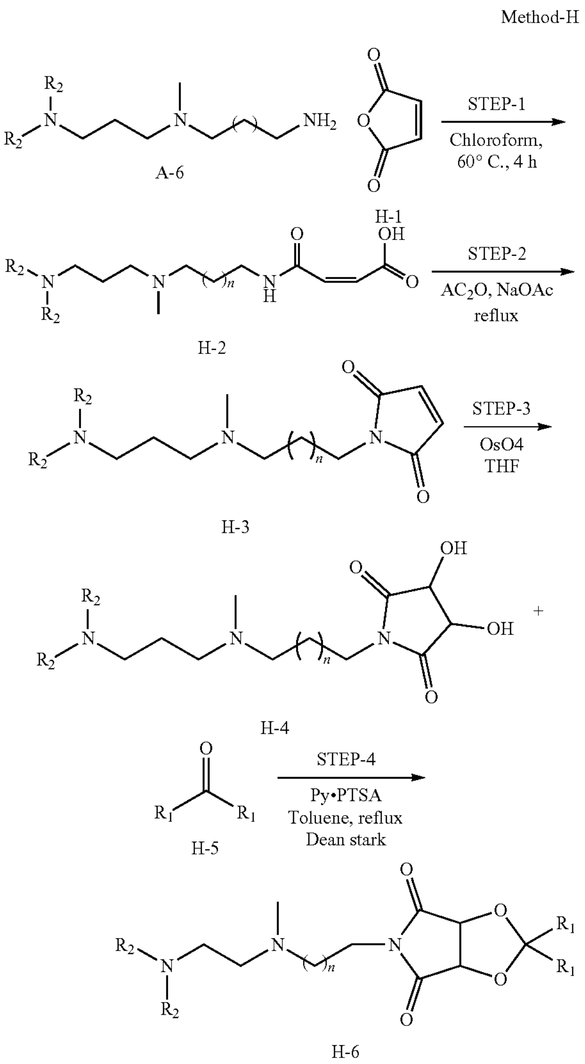

Illustrative embodiments of the Ionizable Lipids of the Invention with spiro dioxolane derivatives (e.g., compound H) is prepared according to general reaction Scheme 7 ("Method H"), wherein $R^1$ is a saturated or unsaturated $C_1$-$C_{18}$ alkyl with linear chains or saturated/unsaturated with bilayer tails (symmetric and unsymmetrical), n is an integer from 1 to 6, $R^2$ is alkyl, cyclic, heterocyclic substituents. Referring to the General Reaction Scheme 5, compounds of structure A-6, H-1, H-5 and necessary catalysts can be purchased from commercial sources or prepared according to the methods familiar to one of the ordinary skill in the art. Maleic anhydride reacts with 3-(dimethylamino)-1-propylamine (DMAPA) to yield 3-(N,N-dimethylamino)propyl maleamic acid H-2. The reaction was carried out in chloroform by addition of the amine to maleic anhydride at room temperature and subsequent heating to 60° C. After purification, H-2 is reacted with sodium acetate in acetic anhydride and heated at a temperature and time sufficient to produce G-3 after any necessarily workup and or purification step. In step 3, a hydroxylation reaction is performed using osmium tetroxide in anhydrous THF overnight to obtain HA. A mixture of H-4 and H-5 are dissolved in toluene solvent and the round bottom flask is equipped with Dean-Stark apparatus and the reaction is subsequently heated to reflux for 8 h and the obtained water in the Dean-Stark apparatus is collected in a separate flask as the reaction continues until the consumption of starting materials to obtain H-6 after any necessarily workup and or purification step.

General Reaction Scheme 8

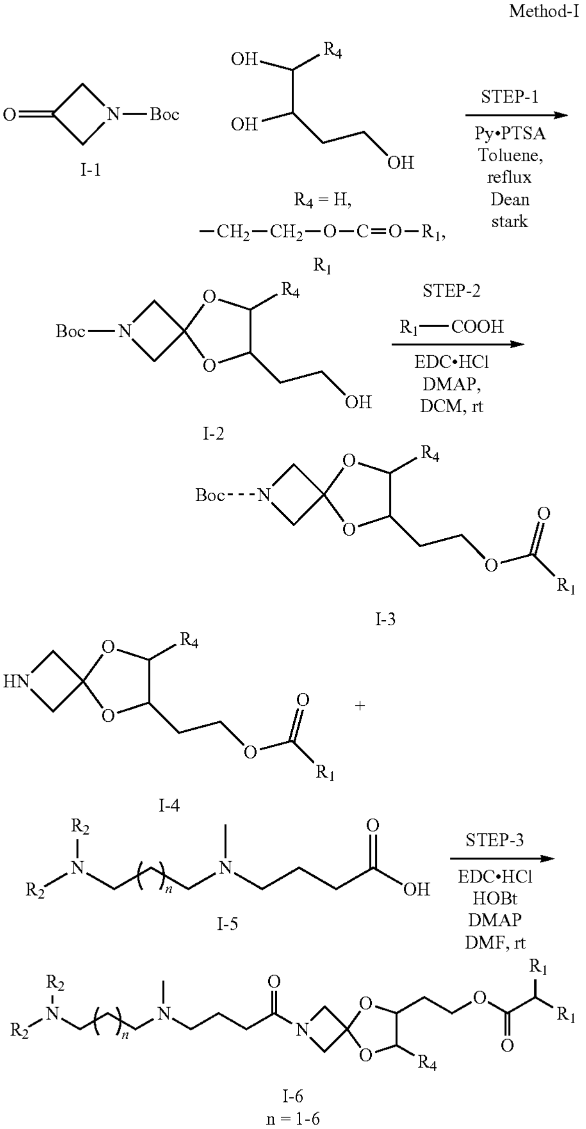

Illustrative embodiments of the Ionizable Lipids of the Invention with spiro dioxolane derivatives (e.g., compound I) is prepared according to general reaction Scheme 8 ("Method I"), wherein $R^1$ is a saturated or unsaturated $C_1$-$C_{18}$ alkyl with linear chains or saturated/unsaturated with bilayer tails (symmetric and unsymmetrical), n is an integer from 1 to 6, $R^2$ is alkyl, cyclic, heterocyclic substituents. Referring to the General Reaction Scheme 8, compounds of structure I-1, I-5 and necessary catalysts can be purchased from commercial sources or prepared according to the methods familiar to one of the ordinary skill in the art. A mixture of I-1, 1,2,5-pentanetriol and pyridinium p-toluenesulfonate in toluene is refluxed under nitrogen overnight with a Dean-Stark apparatus to remove water and the reaction is allowed to reflux until complete consumption of reactants to obtain I-2. Esterification was done in step 2, I-2 was reacted with different alkyl saturated/unsaturated linear or bilayer acids with reagents like EDC·HCl and 4-DMAP in methylene dichloride for overnight to obtain I-3. Deprotection of the amine affords the I-4 derivative. In step 3, I-4 and I-5 are reacted in the presence of EDC·HCl, HOBt and DMAP or triethylamine. All these mixtures are dissolved in dimethylformamide and allowed to stir at room temperature until the consumption of starting materials to obtain I-6 after any necessarily workup and or purification step.

General Reaction Scheme 9

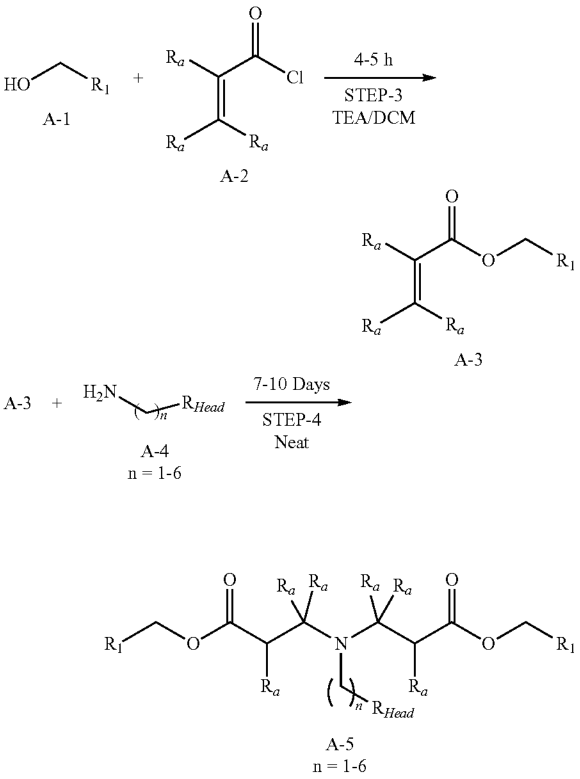

Illustrative embodiments of a lipid with two degradable esters (e.g., compound A-5) can be prepared according to general reaction Scheme 9, wherein $R_1$ is a saturated or unsaturated $C_1$-$C_{18}$ alkyl with linear chains or saturated/unsaturated with bilayer tails (symmetric and unsymmetrical), n is an integer from 1 to 6. Referring to the General Reaction Scheme 9, compounds of structure A-1 are purchased from commercial sources and/or prepared according to the methods familiar to one of the ordinary skill in art. A-1 is reacted with A-2 acryloyl chloride derivatives (where Ra=$CH_3$, $C_2H_5$ and/or isopropyl groups) with catalytic amount of base (e.g., triethyl amine) in methylene chloride solvent for 4-5 hours to get substituted acylation products A-3. A mixture of the acylated product and head groups (R1) N,N-dimethyldiamine and or primary amines substituents such as N-alkyl, acyclic, cyclic, heterocyclic, aromatic amines) A-4 is heated at a temperature and time sufficient to produce A-5 after any necessary workup and or purification step.

General Reaction Scheme 10

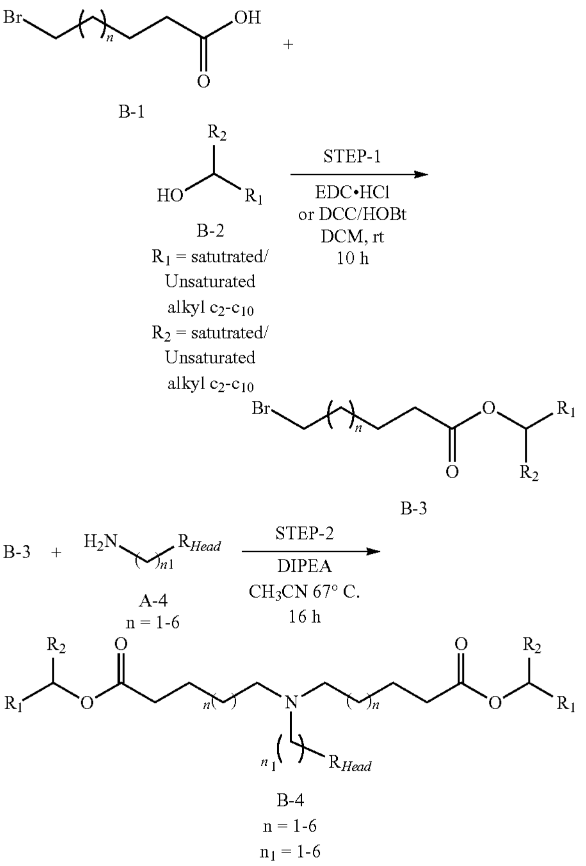

Illustrative embodiments of the lipids with carbon spacers increased between the linker and internal amine (e.g., compound B-2) can be prepared according to general reaction Scheme 10, wherein $R_1$ and $R_2$ is a saturated or unsaturated $C_1$-$C_{18}$ alkyl with linear chains or saturated/unsaturated with bilayer tails (symmetric and unsymmetrical), n is an integer from 1 to 6. Referring to the General Reaction Scheme 10, compounds of structure B-2 are prepared according to the methods familiar to one of the ordinary skill in art. Mixtures of B-1 and B-2 in methylene dichloride as the solvent is treated with stoichiometric amounts of N-(3-dimethylaminopropyl)-N'-ethylcarbodiimide hydrochloride(EDC·HCl) or DCC Dicyclohexyl carbodimide, hydroxybenzotriazole (HOBt) with a base such as triethyl amine to give the ester derivative B-3, then the mixture of B-3 and A-4 is treated with base (e.g., N,N-diisopropylethyl amine) in anhydrous acetonitrile solvent heated at a 67° C. temperature for 16 h, to produce B-4 after any necessarily workup and or purification.

General Reaction Scheme 11

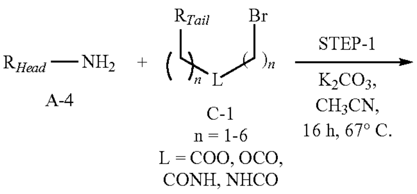

-continued

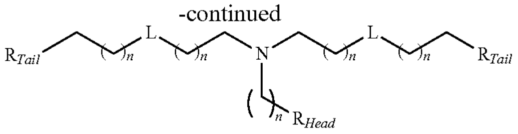

C-2
n = 1-8

Illustrative embodiments of the lipid with degradable/non degradable (e.g., compound C-2) can be prepared according to general reaction Scheme 11, wherein R Tail is a saturated or unsaturated $C_1$-$C_{18}$ alkyl with linear chains or saturated/unsaturated with bilayer tails (symmetric and unsymmetrical), n is an integer from 1 to 8. Referring to the General Reaction Scheme 11, compounds of structure A-4 purchased from commercial sources and or prepared according to the methods familiar to one of the ordinary skill in art. A-4 is reacted with C-1 with catalytic amount of base (e.g., potassium carbonate, N,N-diisopropyl ethylamine, potassium iodide) in acetonitrile solvent for 16 hours at 67° C. temperature to produce C-2 after any necessarily workup and or purification step.

General Reaction Scheme 12

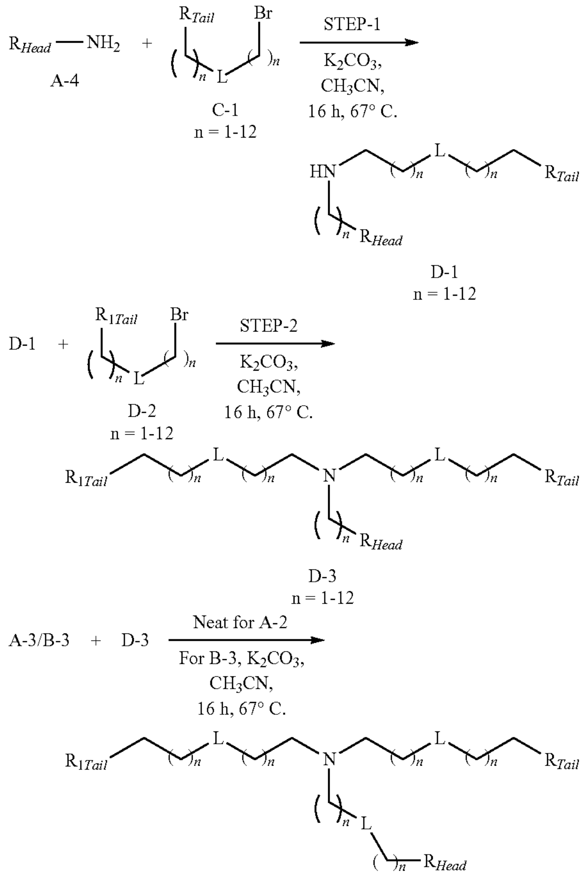

A-4

C-1
n = 1-12

D-1
n = 1-12

D-2
n = 1-12

D-3
n = 1-12

A-3/B-3 + D-3

D-4/D-5
n = 1-12
L = COO, OCO, CONH, NHCO

Illustrative embodiments of the lipid with degradable/non degradable (e.g., compound D-4) can be prepared according to general reaction Scheme 12, wherein R Tail is a saturated or unsaturated $C_1$-$C_{18}$ alkyl with linear chains or saturated/unsaturated with bilayer tails (symmetric and unsymmetrical), n is an integer from 1 to 12. Referring to the General Reaction Scheme 12, Compounds of structure A-4 purchased from commercial sources and or prepared according to the methods familiar to one of the ordinary skill in art. Excess equivalents of A-4 is reacted with one equivalents of C-1 with catalytic amount of base (e.g., potassium carbonate, N,N-diisopropyl ethylamine, potassium iodide) in acetonitrile solvent for 16 hours at 67° C. temperature to produce D-1 after any necessarily workup and or purification step. Then D-1 is reacted with D-2 same as step-1 to produce D-3. React A-3 with D-3 under solvent free condition to produce D-4 for procedure follow scheme-1. Moreover, N, N-alkylation is done by reacting with B-3 and D-3 in the same procedure as in general reaction scheme 10.

General Reaction Scheme 13

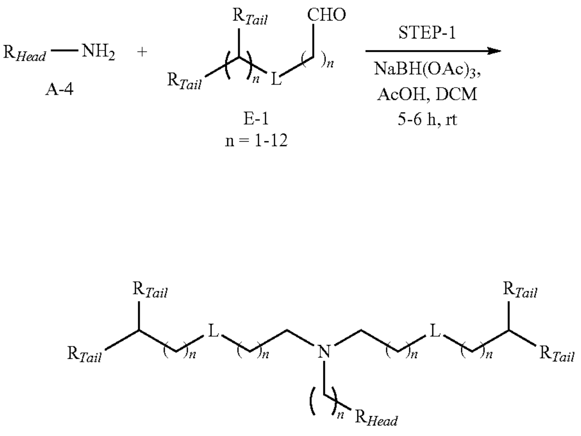

A-4

E-1
n = 1-12

E-2
n = 1-12
L = COO, OCO, CONH, NHCO

Illustrative embodiments of the lipid with degradable/non degradable (e.g., compound E-2) can be prepared according to general reaction Scheme 13, wherein R Tail is a saturated or unsaturated $C_1$-$C_{18}$ alkyl with linear chains or saturated/unsaturated with bilayer tails (symmetric and unsymmetrical), n is an integer from 1 to 12. Referring to the General Reaction Scheme 13, compounds of structure A-4 and E-1 purchased from commercial sources and or prepared according to the methods familiar to one of the ordinary skill in art. Excess equivalents of E-1 is reacted with one equivalents of A-4 with stoichiometric amount of sodium triacetoxyborohydride in methylene chloride solvent for 4-5 hours at room temperature to produce E-2 after any necessarily workup and or purification step.

General Reaction Scheme 14

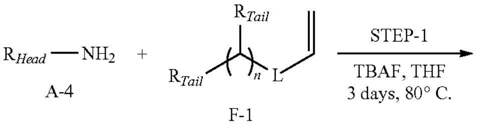

A-4

F-1
n = 1-14
L = CONH

-continued

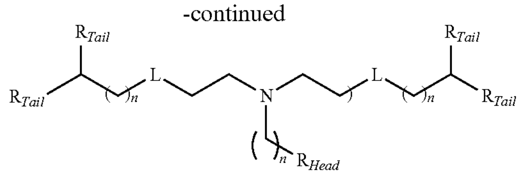

F-2
n = 1-14

Illustrative embodiments of the lipid with degradable/non degradable (e.g., compound F-2) can be prepared according to general reaction Scheme 14, wherein R Tail is a saturated or unsaturated $C_1$-$C_{18}$ alkyl with linear chains or saturated/unsaturated with bilayer tails (symmetric and unsymmetrical), n is an integer from 1 to 14. Referring to the General Reaction Scheme 14, compounds of structures A-4 and F-1 purchased from commercial sources and or prepared according to the methods familiar to one of the ordinary skill in art. Excess equivalents of F-1 is reacted with one equivalents of A-4 with catalytic amount of tetra butyl ammonium fluoride in tetrahydrofuran solvent for 3 days at 80° C. to produce F-2 after any necessarily workup and or purification step.

General Reaction Scheme 15

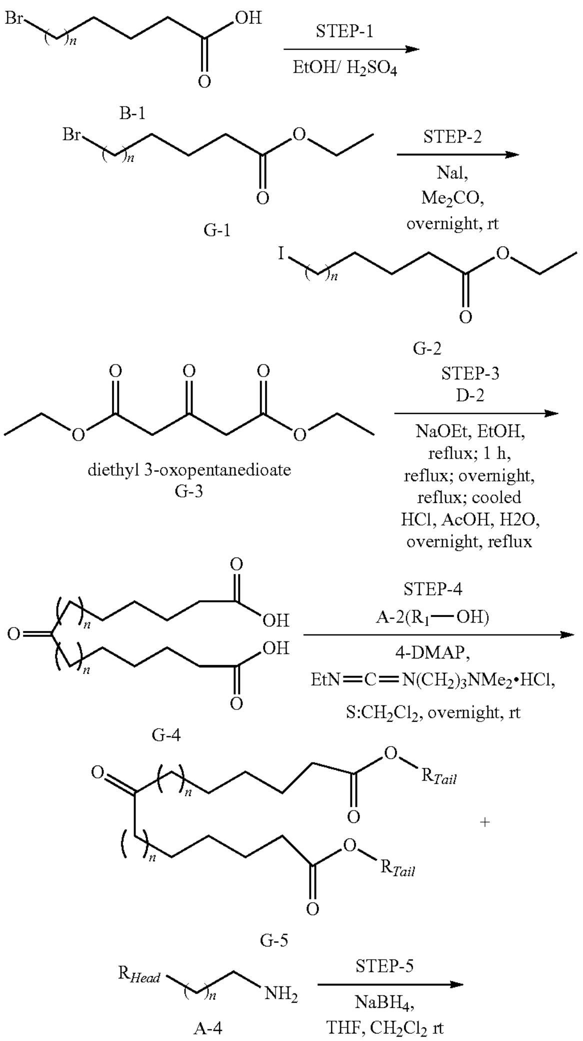

-continued

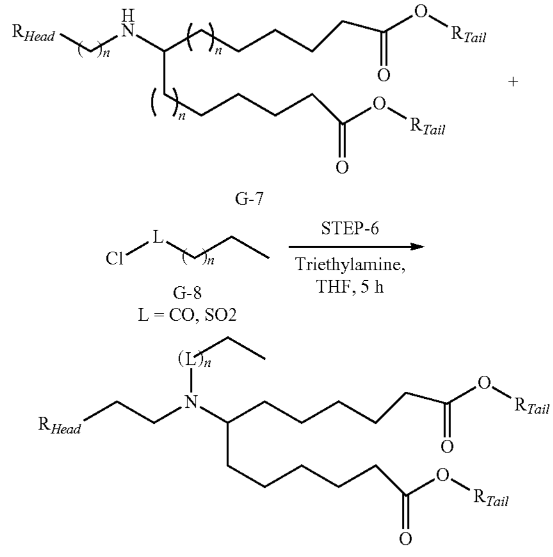

Illustrative embodiments of the lipid with six degradable esters (e.g., compound D-8) can be prepared according to general reaction Scheme 15, wherein RTail is a saturated or unsaturated $C_1$-$C_{18}$ alkyl with linear chains or saturated/unsaturated with bilayer tails (symmetric and unsymmetrical), n is an integer from 1 to 8, RHead is alkyl, cyclic, heterocyclic substituents. Referring to the General Reaction Scheme 7, compounds of structure B-1 and A-4 can be purchased from commercial sources or prepared according to the methods familiar to one of the ordinary skill in the art. Esterification of B-1 in presence of ethanol using a catalytic amount of sulfuric acid obtained G-1. Further, the alkyl bromide is converted to the corresponding alkyl iodide G-2 with a solution of sodium iodide in acetone by the classic Finkelstein reaction. A mixture of G-2 and G-3 is reacted with sodium ethoxide (NaOEt) in ethanol at reflux, followed by acidification to low pH to obtain GA. In Step 4, Fischer esterification was done in the presence of N-(3-dimethylaminopropyl)-N'-ethylcarbodiimide hydrochloride (EDC·HCl) and a catalytic amount of 4-dimethylaminopyridine (4-DMAP) in methylene dichloride for overnight to obtain G-5. Further G-5 is reduced to the corresponding reductive amination in the presence of sodium borohydride (NaBH4) to get G-6. Purified G-6 is reacted with acyl or sulfonyl chloride derivatives G-8 in the presence of a base (e.g., triethylamine) in tetrahydrofuran solvent for 4-5 hours to get the substituted acylation products G-9 at a temperature and time sufficient to produce D-8 after any necessarily workup and or purification step.

General Reaction Scheme 16

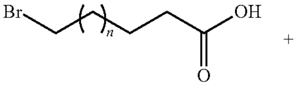

B-1

-continued

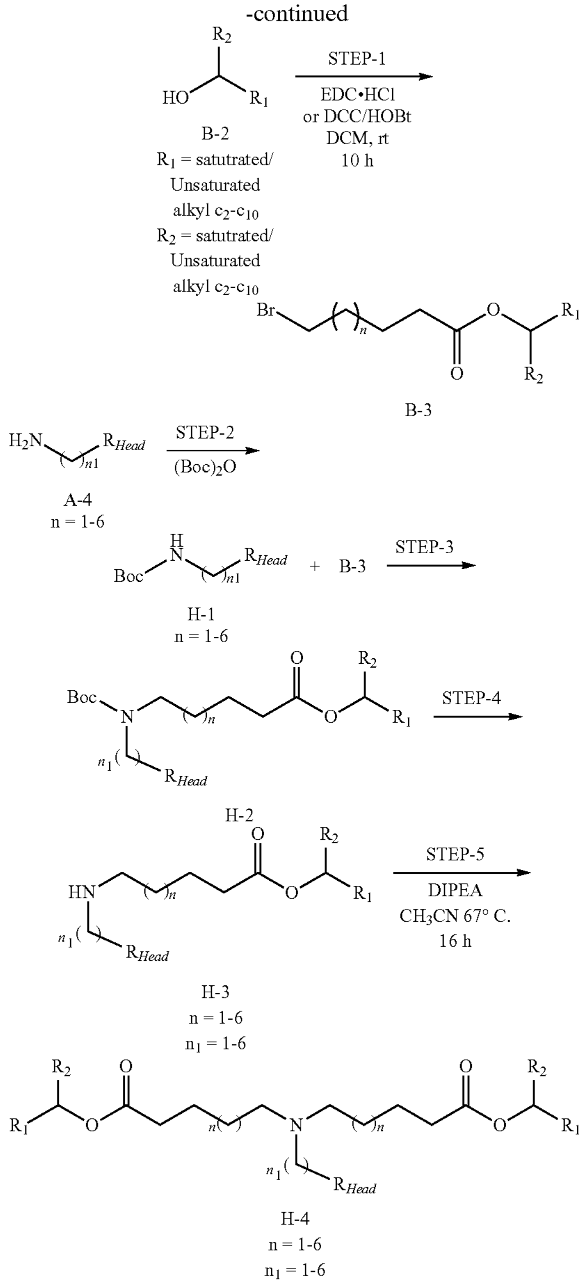

B-2

$R_1$ = satutrated/ Unsaturated alkyl $c_2$-$c_{10}$ $R_2$ = satutrated/ Unsaturated alkyl $c_2$-$c_{10}$

B-3

A-4 n = 1-6

H-1 n = 1-6

H-2

H-3 n = 1-6

$n_1$ = 1-6

H-4 n = 1-6

$n_1$ = 1-6

Illustrative embodiments of the lipids with carbon spacers increased between the linker and internal amine (e.g., compound H-4) can be prepared according to general reaction Scheme 16, wherein R1 and R2 is a saturated or unsaturated $C_1$-$C_{18}$ alkyl with linear chains or saturated/unsaturated with bilayer tails (symmetric and unsymmetrical), n and n1 are integer's from 1 to 6. Referring to the General Reaction Scheme 16, compounds of structure HA are prepared according to the methods familiar to one of the ordinary skill in art. Mixtures of B-1 and B-2 in methylene dichloride as the solvent is treated with stoichiometric amounts of N-(3-dimethylaminopropyl)-N-ethylcarbodiimide hydrochloride (EDC·HCl) or DCC Dicyclohexyl carbodimide, hydroxybenzotriazole (HOBt) with a base such as triethyl amine to give the ester derivative B-3. On the other hand, protection of amine H-1 was done according to previous methods to produce H-1, then the mixture of B-3 and H-1 is treated with base (e.g., N,N-diisopropylethyl amine) in anhydrous acetonitrile solvent heated at a 67 C temperature for 16 h, to produce H-3, then deprotection is done in presence of acid media then followed by N-alkyation to produce H-4 after any necessarily workup and or purification.

V.5. Targeted Delivery of the LNPs Including the Ionizable Lipids of the Invention In certain embodiments, it was surprisingly found that the Ionizable Lipids of the Invention when used in vaccines for intramuscular (IM) injection, the LNP requirements for delivery to dendritic cells via the IM route are different than intravenous (IV) delivery to hepatocytes. In certain embodiments, hepatocyte targeting is due to the LNP associating with ApoE that targets LNP uptake to hepatocyte LDL receptors while ApoE may not have the same role in IM administration. In certain embodiments, a second targeting mechanism for LNPs is their net charge. In certain embodiments, negatively charged LNPs target the spleen upon IV administration while positively charged LNPs target the lungs and near neutral LNPs target the liver. The inventors have surprisingly discovered, however, a significant charge effect based on the finding that previously known LNPs rapidly disseminate and express systemically upon IM administration, while the Ionizable Lipids of the Invention utilized in LNP can be tuned to have a slight positive charge or be near neutral at physiological pH and do not disseminate and are expressed locally in muscle and draining lymph nodes to generate a robust immune response through targeted delivery. In certain embodiments, localization of expression can increase potency and reduce systemic adverse events by avoiding off-target expression.

In certain embodiments, protonation of the Ionizable Lipids of the Invention and branched lipid tails promote endosomal release, and LNP charge influences targeting. In other embodiments, the Ionizable Lipids of the Invention influence LNP structure on its adjuvanticity. In certain embodiments, an asymmetric ionizable lipid LNP acted as a strong Th2-biased adjuvant when delivered with protein subunit antigens.

In certain embodiments, the variety of these LNP driven adjuvant effects motivates the identification of structure function relationships (SFRs) controlling these properties which may involve the cyclic vs linear nature of the head-groups.

Without being bound by theory, the invention encompasses Ionizable Lipids of the Invention and potent LNPs, for example, for use in mRNA vaccines, based on the understanding of SFRs connecting LNP ionization, charge and structure to delivery efficiency, targeting, and adjuvanticity for intramuscular administration with potential application to other sites of delivery.

In certain embodiments, pKas were obtained from ACD-Labs Percepta for the ionizable lipid, and by zeta potential and TNS for LNPs containing the ionizable lipids. In other embodiments, LNP isoelectric pI was obtained from the zeta potential, and LNP diameter is number-average from DLS. Average mRNA copies per LNP was calculated using a molecular volume model and the DLS diameter and is proportional to LNP volume.

In certain embodiments, the invention encompasses Ionizable Lipids of the Invention encompassed by the structure of Formula I:

Head-Spacer-Linker-Spacer-Tail    Formula I wherein the pKa can be adjusted to effectuate targeted delivery to a specific tissue or organ of the body. One of ordinary skill will recognize that the Ionizable Lipids of the Invention of Formulas I-IX and specific embodiments thereof can be used for targeted delivery of LNPs.

In certain embodiments, the Ionizable Lipids of the Invention can be tuned to have a slight positive charge or be near neutral at physiological pH, so they do not systemically disseminate and are expressed locally, for example, in muscle and draining lymph nodes to generate a robust immune response through targeted delivery. In certain embodiments, localization of expression can increase potency and reduce systemic adverse events by avoiding off-target expression.

In certain embodiments, protonation and utilization of branched lipid tails in the Ionizable Lipids of the Invention for use in LNPs promote endosomal release, and LNP charge influencing targeting—a third SFR is the influence of LNP structure on its adjuvanticity. In certain embodiments, asymmetric Ionizable Lipids of the Invention in the LNP act as a strong Th2-biased adjuvant when delivered with protein subunit antigens and the LNP mRNA vaccines drive a Tfh-biased response that stimulates the proliferation of Tfh and germinal center B cells and a potent long-lived neutralizing antibody response.

In certain embodiments, the Ionizable Lipids of the Invention are designed with three structural features that are known to control delivery efficiency—ionization in the endosomal pH range, net charge at physiological pH, and lipid tail conformation related to branching and saturation/unsaturation. In certain embodiments, the approach to candidate evaluation and elucidating structure-function relationships (SFRs) includes in vitro and in vivo evaluation of translation and toxicity, in vitro assessment of cell uptake, endosomal release and innate immune sensor activation, in vivo characterization of distribution and cell trafficking, immunogenicity, and the use of current and evolving rodent and non-rodent animal models in viral challenge studies.

In certain embodiments, the Ionizable Lipids of the Invention possess increased in vivo expression (>5×) of mRNA LNPs due to increased mixing concentration of the lipids and mRNA during assembly.

In certain embodiments, the targeted delivery of LNPs including the Ionizable Lipids of the Invention involves: 1) Optimization of ionization properties of multivalent headgroups that can produce both a slightly positive or near neutral LNP at physiological pH to limit systemic dissemination and increase endosomal ionization that increases vaccine potency. In other embodiments, the targeted delivery of LNPs including Ionizable Lipids of the Invention involves highly branched and degradable lipid tails that can further increase potency through endosomal release. In other embodiments, the targeted delivery of LNPs including Ionizable Lipids of the Invention involves the charge and structure of the Ionizable Lipids of the Invention can influence LNP adjuvanticity.

In certain embodiments, the LNP potency is increased to limit adverse events, reduce manufacturing cost, and increase ability to vaccinate large population groups.

In certain embodiments, the invention encompasses a LNP delivery system that is superior to the current LNPs with protection at lower dose, lower reactogenicity, lower systemic distribution and greater stability in storage than the current LNPs in vaccines. In certain embodiments, first generation C24 LNPs were superior to MC3, the standard reference LNP in the field, in terms of all of these properties, and exceeded the published neutralizing titers of the vaccine in their preclinical study. In certain embodiments, head-to-head comparisons with the disclosed vaccines formulations using our latest second generation LNPs that are improvements over C24. In certain embodiments, the invention encompasses mechanisms-of-action to identify cell types and cell reactions involved in the vaccine response. In certain embodiments, by combining charge-mediated targeting to eliminate off-target liver expression and increase spleen targeting, with ligand-mediated targeting for specific cell uptake in T cells, we will precisely target delivery to splenic T cells. In certain embodiments, the systematic screening of a diverse and unique library of highly potent ionizable lipids allows identification of several other achievable cell-specific targets that will be optimized through charge- and ligand-mediated targeting combined with formulation and manufacturing process parameters.

In certain embodiments, the invention encompasses using 3 mRNA-encoded reporters, luciferase, mCherry and Cre-recombinase and one mRNA-encoded immunogen, the S2P SARS-Cov-2 immunogen. In certain embodiments, these constructs are sufficient to develop general principles and models of expression, targeting and toxicity of mRNA lipid nanoparticles. In certain embodiments, substitution of other RNA sequences, whether small (siRNA) or large (self-amplifying RNA, multivalent vaccines, gene-editing designs) will require relatively minor or moderate modifications to LNP formulations and manufacturing.

In certain embodiments, the invention encompasses methods to identify LNP features that predict the targeting performance attributes and provide methods to measure them. In certain embodiments, the improved manufacturing processes permit the identification of appropriate in process controls (IPCs) to ensure consistent manufacturing of high potency LNPs. In certain embodiments, the methods could be implemented on various systems requiring targeted delivery of a therapeutic or prophylactic agent.

In certain embodiments, the invention encompasses a novel library of ionizable lipids with systematic changes in structure and theoretical ionization properties. In certain embodiments, a series of project modules described herein allows the acquisition of the data sets that will permit the predictive models to relate performance determining properties of the LNPs to molecular, formulation and manufacturing parameters (multiple models for each arrow on the three far left boxes below).

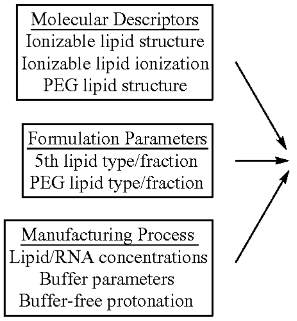

-continued

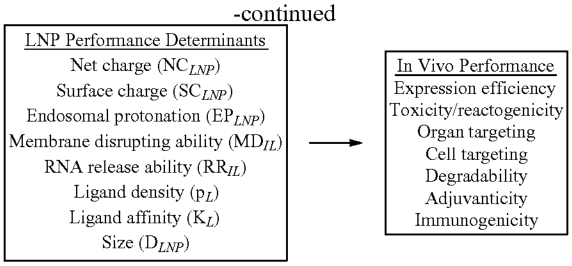

In certain embodiments, some of the models are statistical involving machine learning approaches while some will be mechanistic. In certain embodiments, the performance of LNPs that have been characterized for features currently understood to influence performance (in middle box above and predicted as described above). In certain embodiments, the measured in vitro and in vivo performance include expression efficiency, organ- and cell-targeting, toxicity, degradability and immunogenicity (far right box above).

In certain embodiments, in vitro cell culture based characterization and in vivo characterization of performance in animal models predict LNP performance from LNP characteristics (arrow from central box to far right box above).

In certain embodiments, the determinants of mRNA-LNP expression and targeting in vivo include, but are not limited to LNP net charge (NCLNP), surface charge (SCLNP), endosomal protonation (EPLNP), size (DLNP), ionizable lipid membrane-disrupting ability (MDIL), ionizable lipid RNA-release ability (RRIL), targeting ligand density (ρL) and binding affinity (KL). In certain embodiments, these parameters are in turn determined by ionizable lipid ionization and structural properties as well as by formulation parameters (e.g., lipid types and mole ratios), manufacturing processes (e.g., concentrations, buffer, pH, solvent ratios, flow rates) and ligand conjugation. In certain embodiments, the models predict NCLNP, SCLNP, EPLNP, DLNP, MDIL, RRIL, ρL and KL from ionizable lipid properties, formulation parameters and manufacturing process parameters and a model to predict mRNA stability in LNPs.

In one embodiment, LNP net charge (NCLNP), surface charge (SCLNP), and endosomal protonation (EPLNP) prediction are derived from ionizable lipid structure and ionization properties. In one embodiment, the invention encompasses a method to theoretically predict LNP ionization properties from the molecular ionization constants of monoprotic ionizable lipids and extended to multiprotic ionizable lipids that have greater potential to control both endosomal protonation and net charge of the LNP.

In one embodiment, the structure of lipid tails is important for the delivery, release and expression efficiency of mRNA LNPs and is thought to be due to their endosomal membrane disrupting and RNA release abilities.

In certain embodiments, the invention encompasses methods to assess mRNA cleavage during storage in LNPs. In one embodiment, the ionizable lipid influences the rate of cleavage through the pH dependence of the kinetics of this reaction.

In one embodiment, LNP net charge (NCLNP), surface charge (SCLNP), endosomal protonation (EPLNP), size (DLNP), ionizable lipid membrane disrupting ability (MDIL) and RNA release ability (RRIL) prediction is obtained from LNP formulation. In one embodiment, LNP charge can be modified by changing formulation ratios, adding a 5th lipid and by designing specific ionization properties into the ionizable lipid. In one embodiment, different PEG lipid structures can also influence expression and targeting.

In one embodiment, methods of preparing the lipid solutions and mRNA solutions prior to mixing and self-assembly form LNPs that are more efficient delivery vehicles according to reporter expression in vitro and in vivo. In one embodiment, these novel solutions have higher concentrations of the lipids and mRNA during self-assembly and also specific methods for protonating the ionizable lipid. In one embodiment, a statistical machine learning model will relate manufacturing parameters to LNP characteristics.

In one embodiment, conjugated targeting ligands directly to intact LNPs show large increases in cell-specific targeting.

In other embodiments, for certain LNPs, ApoE adsorption is necessary for the cellular uptake of LNPs. In certain embodiments, decreased activity of LNPs with higher PEG-lipid content in hepatocytes resulted in reduced association of ApoE with LNPs. In certain embodiments, LNPs with 5% PEG-lipid have a lower binding affinity with ApoE compared to LNPs with 1.5% PEG-lipid. In certain embodiments, by introducing unique targeting ligands to the highly PEGylated LNPs, ApoE-mediated cellular uptake can be blocked and selective delivery of LNPs can be achieved.

In certain embodiments, mannose-conjugated nanoparticles have been investigated in various targeted delivery studies, and these nanoparticles have been proven to be safe. To introduce mannose moieties on the surface of LNPs, mannose-PEG lipid is used.

V.6. Lipid Nanoparticles Containing Ionizable Lipids of the Invention

In certain embodiments, the invention encompasses Lipid Nanoparticles including one or more Ionizable Lipids of the Invention. In certain embodiments, the LNPs include a second lipid. In certain embodiments, the LNP's include a steroid. In other embodiments, the LNP's include a pegylated lipid. In other embodiments, the LNP's include a nucleic acid, preferably mRNA.

As used herein the term "lipid nanoparticle," also referred to as LNP, refers to a particle having at least one dimension on the order of nanometers (e.g., 1-1,000 nm) which includes Ionizable Lipid of the Invention, for example an Ionizable Lipid of the Invention encompassed by Formula (I), (II), (III), (IV), (V), (VI), (VII), (VIII), or (IX) or a pharmaceutically acceptable salt thereof. In some embodiments, such lipid nanoparticles comprise, for example an Ionizable Lipid of the Invention encompassed by Formula (I), (II), (III), (IV), (V), (VI), (VII), (VIII), or (IX) and one or more excipients selected from neutral lipids, charged lipids, steroids and polymer conjugated lipids (e.g., a pegylated lipid). In some embodiments, the nucleic acid, preferably mRNA, or a portion thereof, is encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells e.g. an adverse immune response. In some embodiments, the mRNA or a portion thereof is associated with the lipid nanoparticles.

In the context of the present invention, lipid nanoparticles are not restricted to any particular morphology, and should be interpreted as to include any morphology generated when an Ionizable Lipid of the Invention encompassed by Formula (I), (II), (III) (IV), (V), (VI), (VII), (VIII), or (IX) and optionally one or more further lipids are combined, e.g. in an aqueous environment and/or in the presence of a nucleic acid compound. For example, a liposome, a lipid complex, a lipoplex and the like are within the scope of a lipid nanoparticle.

In various embodiments, the lipid nanoparticles have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In certain embodiments, the mRNA, when present in the lipid nanoparticles, is resistant in aqueous solution to degradation with a nuclease. As used herein, the mean diameter may be represented by the number-weighted average as determined by dynamic light scattering.

An LNP may comprise any Ionizable Lipid of the Invention encompassed by Formula (I), (II), (III) (IV), (V), (VI), (VII), (VIII), and (IX) capable of forming a particle to which the one or more nucleic acid molecules are attached, or in which the one or more nucleic acid molecules are encapsulated. The term "lipid" refers to a group of organic compounds that are derivatives of fatty acids (e.g., esters) and are generally characterized by being insoluble in water but soluble in many organic solvents. Lipids are usually divided in at least three classes: (1) "simple lipids" which include fats and oils as well as waxes; (2) "compound lipids" which include phospholipids and glycolipids; and (3) "derived lipids" such as steroids.

In one embodiment, the mRNA-comprising LNP comprises one or more Ionizable Lipids of the Invention encompassed by Formula (I), (II), (III) (IV), (V), (VI), (VII), (VIII), or (IX) as defined herein, and one or more stabilizing lipids. Stabilizing lipids include neutral lipids and pegylated lipids.

As mentioned, the LNP comprises for example an Ionizable Lipid of the Invention encompassed by Formula (I), (II), (III) (IV), (V), (VI), (VII), (VIII), or (IX). In certain embodiments, the Ionizable Lipids of the Invention are preferably cationisable, (i.e., it becomes protonated as the pH is lowered below the pKa of the ionizable group of the lipid), but is progressively more neutral at higher pH values. In certain embodiments, when positively charged, the lipid is then able to associate with negatively charged nucleic acids. In certain embodiments, the Ionizable Lipid of the Invention comprises a zwitterionic lipid that assumes a positive charge on pH decrease. The LNP may comprise any lipid capable of forming a particle to which the one or more nucleic acid molecules are attached, or in which the one or more nucleic acid molecules are encapsulated.

In certain embodiments, the LNP may comprise a further cationic or cationisable lipid, (i.e., any of a number of lipid species which carry a net positive charge at a selective pH) such as physiological pH. Examples of such lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3dioleoyloxy)propyl)-N,N,N-trimethylammonium chloride (DOTAP); 3-(N—(N',N'dimethylaminoethane)-carbamoyl) cholesterol (DC-Chol), N-(1-(2,3-dioleoyloxy)propyl)N-2-(sperminecarboxamido)ethyl)-N,N-dimethylammonium trifluoracetate (DOSPA), dioctadecylamidoglycyl carboxyspermine (DOGS), 1,2-dioleoyl-3-dimethylammonium propane (DODAP), N,N-dimethyl-2,3-dioleoyloxy) propylamine (DODMA), and N-(1,2dimyristyloxyprop-3-yl)-N,N-dimethyl-N-hydroxyethyl ammonium bromide (DMRIE).

Additionally, a number of commercial preparations of lipids are available which can be used in the present invention. These include, for example, LIPOFECTIN® (commercially available cationic liposomes comprising DOTMA and 1,2-dioleoyl-sn-3phosphoethanolamine (DOPE), from GIBCO/BRL, Grand Island, N.Y.); LIPOFECTAMINE® (commercially available cationic liposomes comprising N-(1-(2,3dioleyloxy)propyl)-N-(2-(sperminecarboxamido) ethyl)-N,N-dimethylammonium trifluoroacetate (DOSPA) and (DOPE), from GIBCO/BRL); and TRANSFECTAM® (commercially available cationic lipids comprising dioctadecylamidoglycyl carboxyspermine (DOGS) in ethanol from Promega Corp., Madison, Wis.). The following lipids are cationic and have a positive charge at below physiological pH: DODAP, DODMA, DMDMA, 1,2-dilinoleyloxy-N,N-dimethylaminopropane (DLinDMA), 1,2-dilinolenyloxy-N,N-dimethylaminopropane (DLenDMA).

In further embodiment, the further lipid is an amino lipid. Suitable amino lipids useful in the invention include those described in WO2012/016184, incorporated herein by reference in its entirety. Representative amino lipids include, but are not limited to, 1,2-dilinoleyoxy-3-(dimethylamino) acetoxypropane (DLin-DAC), 1,2-dilinoleyoxy-3morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,Ndilinoleylamino)-1,2-propanediol (DLinAP), 3-(N,N-dioleylamino)-1,2-propanediol (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA).

In certain embodiments, the LNP comprises one or more additional lipids which stabilize the formation of particles during their formation.

Suitable stabilizing lipids include neutral lipids and anionic lipids. The term "neutral lipid" refers to any one of a number of lipid species that exist in either an uncharged or neutral zwitterionic form at physiological pH. Representative neutral lipids include diacylphosphatidylcholines, diacylphosphatidylethanolamines, ceramides, sphingomyelins, dihydro sphingomyelins, cephalins, and cerebrosides.

Exemplary neutral lipids include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-lcarboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoylphosphatidyethanol amine (SOPE), and 1,2- dielaidoyl-sn-glycero-3-phophoethanolamine (transDOPE). In one embodiment, the neutral lipid is 1,2-distearoyl-sn-glycero-3phosphocholine (DSPC).

In some embodiments, the LNPs comprise a neutral lipid selected from DSPC, DPPC, DMPC, DOPC, POPC, DOPE and SM. In various embodiments, the molar ratio of the Ionizable Lipid of the Invention (e.g., lipid encompassed by the structure of Formula (I), (II) (III), (IV), (V), (VI), or (VII)) to the neutral lipid ranges from about 2:1 to about 8:1. In certain embodiments, the molar ration is 2:1, 2.5:1, 3:1, 3.5:1, 4:1; 4.5:1, 5:1, 5.5:1, 6:1, 6.5:1, 7:1; 7.5:1; 8:1; 8.5:1, 9:1, 9.5:1; 10:1; 11:1; 15:1; 20:1; 30:1; 50:1, and all molar ratios included within these ranges.

In various embodiments, the LNPs further comprise a steroid or steroid analogue.

In certain embodiments, the steroid or steroid analogue is cholesterol. In some of these embodiments, the molar ratio of the Ionizable Lipids of the Invention (e.g., lipids encompassed by the structure of Formula (I), (II), (III), (IV), (V), (VI), or (VII)) to steroid ranges from about 5:1 to 1:1. In certain embodiments, the molar ration is 2:1, 2.5:1, 3:1, 3.5:1, 4:1; 4.5:1, 5:1, 5.5:1, 6:1, 6.5:1, 7:1; 7.5:1; 8:1; 8.5:1, 9:1, 9.5:1; 10:1; 11:1; 15:1; 20:1; 30:1; 50:1, and all molar ratios included within these ranges.

The term "anionic lipid" refers to any lipid that is negatively charged at physiological pH. These lipids include phosphatidylglycerol, cardiolipin, diacylphosphatidylserine, diacylphosphatidic acid, Ndodecanoylphosphatidylethanolamines, N-succinylphosphatidylethanolamines, Nglutarylphosphatidylethanolamines, lysylphosphatidylglycerols, palmitoyloleyolphosphatidylglycerol (POPG), and other anionic modifying groups joined to neutral lipids.

In certain embodiments, the LNP comprises glycolipids (e.g., monosialoganglioside GM1).

In some embodiments, the LNPs comprise a polymer conjugated lipid. The term "polymer conjugated lipid" refers to a molecule comprising both a lipid portion and a polymer portion. An example of a polymer conjugated lipid is a pegylated lipid. The term "pegylated lipid" refers to a molecule comprising both a lipid portion and a polyethylene glycol portion. Pegylated lipids are known in the art and include 1-(monomethoxy-polyethyleneglycol)-2,3-dimyristoylglycerol (PEG-s-DMG) and the like.

In certain embodiments, the LNP comprises an additional, stabilizing-lipid which is a polyethylene glycol-lipid (pegylated lipid). Suitable polyethylene glycollipids include PEG-modified phosphatidylethanolamine, PEG-modified phosphatidic acid, PEG-modified ceramides (e.g., PEG-CerC14 or PEG-CerC20), PEG-modified dialkylamines, PEG-modified diacylglycerols, PEG-modified dialkylglycerols. Representative polyethylene glycol-lipids include PEG-c-DOMG, PEG-c-DMA, and PEG-s-DMG. In one embodiment, the polyethylene glycol-lipid is N-[(methoxy poly(ethylene glycol)2000)carbamyl]-1,2-dimyristyloxlpropyl-3-amine (PEG-c-DMA). In one embodiment, the polyethylene glycol-lipid is PEG-c-DOMG). In other embodiments, the LNPs comprise a pegylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-O-(2',3'-di(tetradecanoyloxy)propyl-1-O-(ω-methoxy(polyethoxy)ethyl)butanedioate (PEG-S-DMG), a pegylated ceramide (PEG-cer), or a PEG dialkoxypropylcarbamate such as o-methoxy (polyethoxy)ethyl-N-(2,3di(tetradecanoxy)propyl)carbamate or 2,3-di(tetradecanoxy)propyl-N-(ω-methoxy(polyethoxy)ethyl)carbamate. In various embodiments, the molar ratio of the cationic lipid to the pegylated lipid ranges from about 400:1 to about 10:1.

As mentioned, the mRNA comprising lipid nanoparticle may comprise a pegylated lipid having the following structure:

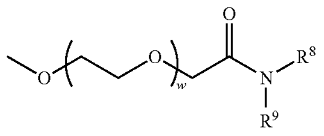

or a pharmaceutically acceptable salt, tautomer or stereoisomer thereof, wherein:

$R^8$ and $R^9$ are each independently a straight or branched, saturated or unsaturated alkyl chain containing from 10 to 30 carbon atoms, wherein the alkyl chain is optionally interrupted by one or more ester bonds; and w has mean value ranging from 30 to 60.

In some of the foregoing embodiments of the pegylated lipid, $R^8$ and $R^9$ are not both n-octadecyl when w is 42. In some other embodiments, $R^8$ and $R^9$ are each independently a straight or branched, saturated or unsaturated alkyl chain containing from 10 to 18 carbon atoms. In some embodiments, $R^8$ and $R^9$ are each independently a straight or branched, saturated or unsaturated alkyl chain containing from 12 to 16 carbon atoms. In some embodiments, $R^8$ and $R^9$ are each independently a straight or branched, saturated or unsaturated alkyl chain containing 12 carbon atoms. In some embodiments, $R^8$ and $R^9$ are each independently a straight or branched, saturated or unsaturated alkyl chain containing 14 carbon atoms. In other embodiments, $R^8$ and $R^9$ are each independently a straight or branched, saturated or unsaturated alkyl chain containing 16 carbon atoms. In still more embodiments, $R^8$ and $R^9$ are each independently a straight or branched, saturated or unsaturated alkyl chain containing 18 carbon atoms. In still other embodiments, $R^8$ is a straight or branched, saturated or unsaturated alkyl chain containing 12 carbon atoms and $R^9$ is a straight or branched, saturated or unsaturated alkyl chain containing 14 carbon atoms.

In various embodiments, w spans a range that is selected such that the PEG portion has an average molecular weight of about 400 to about 6000 g/mol. In some embodiments, the average w is about 50.

In certain embodiments, the PEG lipid is present in the LNP in an amount from about 1 to about 10 mole percent, relative to the total lipid content of the nanoparticle. In one embodiment, the PEG lipid is present in the LNP in an amount from about 1 to about 5 mole percent. In one embodiment, the PEG lipid is present in the LNP in about 1 mole percent or about 1.5 mole percent.

In certain embodiments, the LNP comprises one or more targeting moieties which are capable of targeting the LNP to a cell or cell population. For example, in one embodiment, the targeting moiety is a ligand which directs the LNP to a receptor found on a cell surface.

In certain embodiments, the LNP comprises one or more internalization domains. For example, in one embodiment, the LNP comprises one or more domains which bind to a cell to induce the internalization of the LNP. For example, in one embodiment, the one or more internalization domains bind to a receptor found on a cell surface to induce receptor-mediated uptake of the LNP. In certain embodiments, the LNP is capable of binding a biomolecule in vivo, where the LNP-bound biomolecule can then be recognized by a cell-surface receptor to induce internalization. For example, in one embodiment, the LNP binds systemic ApoE, which leads to the uptake of the LNP and associated cargo.

Other exemplary LNPs and their manufacture are described in the art, for example in U.S. Patent Application Publication No. US20120276209, Semple et al., 2010, Nat Biotechnol., 28(2):172-176; Akinc et al., 2010, Mol Ther., 18(7): 1357-1364; Basha et al., 2011, Mol Ther, 19(12): 2186-2200; Leung et al., 2012, J Phys Chem C Nanomater Interfaces, 116(34): 18440-18450; Lee et al., 2012, Int J Cancer., 131(5): E781-90; Belliveau et al., 2012, Mol Ther nucleic Acids, 1: e37; Jayaraman et al., 2012, Angew Chem Int Ed Engl., 51(34): 8529-8533; Mui et al., 2013, Mol Ther Nucleic Acids. 2, e139; Maier et al., 2013, Mol Ther., 21(8): 1570-1578; and Tam et al., 2013, Nanomedicine, 9(5): 665-74, each of which are incorporated by reference in their entirety.

In preferred embodiments, the lipid nanoparticles have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. As mentioned, the mean diameter may correspond to the number-weighted average as determined by dynamic light scattering.

In another preferred embodiment of the invention the lipid nanoparticles have a hydrodynamic diameter in the range from about 50 nm to about 300 nm, or from about 60 nm to about 250 nm, from about 60 nm to about 150 nm, or from about 60 nm to about 120 nm, respectively.

In certain embodiments, the mRNA, when present in the lipid nanoparticles, is resistant in aqueous solution to degradation with a nuclease.

The total amount of mRNA in the lipid nanoparticles varies and may be defined depending on the mRNA to total lipid w/w ratio. In certain embodiments, the nanoparticle ratio is from 2 to 10. In one embodiment of the invention, the mRNA to total lipid ratio is less than 0.06 w/w, preferably between 0.03 and 0.04 w/w.

In some embodiments, the LNPs comprise an Ionizable Lipid of the Invention of encompassed by any of the structures of Formula (I), (II), (III), (IV), (V), (VI), or (VII); a mRNA compound as defined above, a neutral lipid, a steroid and a pegylated lipid.

In certain embodiments, the LNP comprises one or more targeting moieties which are capable of targeting the LNP to a cell or cell population. For example, in one embodiment, the targeting moiety is a ligand which directs the LNP to a receptor found on a cell surface.

In certain embodiments, the LNP comprises one or more internalization domains. For example, in one embodiment, the LNP comprises one or more domains which bind to a cell to induce the internalization of the LNP. For example, in one embodiment, the one or more internalization domains bind to a receptor found on a cell surface to induce receptor-mediated uptake of the LNP. In certain embodiments, the LNP is capable of binding a biomolecule in vivo, where the LNP-bound biomolecule can then be recognized by a cell-surface receptor to induce internalization. For example, in one embodiment, the LNP binds systemic ApoE, which leads to the uptake of the LNP and associated cargo.

In particular the invention relates to the following non-limiting specific embodiments.

In a preferred embodiment, the invention relates to a mRNA comprising lipid nanoparticle comprising a Ionizable Lipid of the Invention according to formula (I), (II), (II), (IV), (V), (VI), or (VII) as defined above and a mRNA compound comprising a mRNA sequence encoding at least one antigenic peptide or protein, and DSPC, cholesterol and a PEG lipid at a ratio of about 50:10:38.5:1.

In a specific preferred embodiment the invention relates to a mRNA comprising lipid nanoparticle, comprising a Ionizable Lipid of the Invention, a PEG-lipid, a mRNA compound comprising a mRNA sequence encoding at least one antigenic peptide or protein, a steroid and a neutral lipid, wherein preferably, at a ratio of about 50:10:38.5:1.5 that encapsulates unmodified, 1-methylpseudouridine modified or codon-optimized mRNA. Preferably the antigenic peptide or protein is derived from pathogenic antigens, tumor antigens, allergenic antigens or autoimmune self-antigens or a fragment or variant thereof.

In certain embodiments, the invention encompasses a 50-100 nm diameter LNP including the Ionizable Lipids of the Invention composed of the nucleic acid and 4 lipids: an Ionizable Lipids of the Invention with an amine group (50%), a second lipid (e.g., 1,2-distearoyl-sn-glycero-3-phosphocholine (DSPC)) (10%), a steroid (e.g., cholesterol) (38.5%), and a pegylated lipid (e.g., 1,2-dimyristoyl-rac-glycero-3-methoxypolyethylene glycol-2000 (DMG-PEG2000)) (1.5%) (mole ratios in parentheses).

In certain embodiments, the amount of the Ionizable Lipid of the Invention included in the LNP is 1, 1.1, 1.2, 1.3, 1.4, 1.5, 1.6, 1.7, 1.8, 1.9, 2, 2.1, 2.2, 2.3, 2.4. 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4. 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.10, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4. 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16, 16.1, 16.2, 16.3, 16.4. 16.5, 16.6, 16.7, 16.8, 16.9, 17, 17.1, 17.2, 17.3, 17.4, 17.5, 17.6, 17.7, 17.8, 17.9, 18, 18.1, 18.2, 18.3, 18.4, 18.5, 18.6, 18.7, 18.8, 18.9, 19, 19.1, 19.2, 19.3, 19.4, 19.5, 19.6, 19.7, 19.8, 19.9, 20, 21.1, 21.2, 21.3, 21.4, 21.5, 21.6, 21.7, 21.8, 21.9, 30, 31, 31.1, 31.2, 31.3, 31.4, 31.5, 31.6, 31.7, 31.8, 31.9, 32, 32.1, 32.2, 32.3, 32.4. 32.5, 32.6, 32.7, 32.8, 32.9, 33, 33.1, 33.2, 33.3, 33.4, 33.5, 33.6, 33.7, 33.8, 33.9, 34, 34.1, 34.2, 34.3, 34.4, 34.5, 34.6, 34.7, 34.8, 34.9, 35, 35.1, 35.2, 35.3, 35.4, 35.5, 35.6, 35.7, 35.8, 35.9, 36, 36.1, 36.2, 36.3, 36.4. 36.5, 36.6, 36.7, 36.8, 36.9, 37, 37.1, 37.2, 37.3, 37.4, 37.5, 37.6, 37.7, 37.8, 37.9, 38, 38.1, 38.2, 38.3, 38.4, 38.5, 38.6, 38.7, 38.8, 38.9, 39, 39.1, 39.2, 39.3, 39.4, 39.5, 39.6, 39.7, 39.8, 39.9, 40, 40.1, 40.2, 40.3, 40.4, 40.5, 40.6, 40.7, 40.8, 40.9, 41, 41.1, 41.2, 41.3, 41.4, 41.5, 41.6, 41.7, 41.8, 41.9, 42, 42.1, 42.2, 42.3, 42.4. 42.5, 42.6, 42.7, 42.8, 42.9, 43, 43.1, 43.2, 43.3, 43.4, 43.5, 43.6, 43.7, 43.8, 43.9, 44, 44.1, 44.2, 44.3, 44.4, 44.5, 44.6, 44.7, 44.8, 44.9, 45, 45.1, 45.2, 45.3, 45.4, 45.5, 45.6, 45.7, 45.8, 45.9, 46, 46.1, 46.2, 46.3, 46.4. 46.5, 46.6, 46.7, 46.8, 46.9, 47, 47.1, 47.2, 47.3, 47.4, 47.5, 47.6, 47.7, 47.8, 47.9, 48, 48.1, 48.2, 48.3, 48.4, 48.5, 48.6, 48.7, 48.8, 48.9, 49, 49.1, 49.2, 49.3, 49.4, 49.5, 49.6, 49.7, 49.8, 49.9, 50, 55, 60, 65, 70, or 75 molar percent.

In certain embodiments, the amount of the second lipid included in the LNP is 1, 1.1, 1.2, 1.3, 1.4, 1.5, 1.6, 1.7, 1.8, 1.9, 2, 2.1, 2.2, 2.3, 2.4. 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4. 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.10, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4. 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16, 16.1, 16.2, 16.3, 16.4. 16.5, 16.6, 16.7, 16.8, 16.9, 17, 17.1, 17.2, 17.3, 17.4, 17.5, 17.6, 17.7, 17.8, 17.9, 18, 18.1, 18.2, 18.3, 18.4, 18.5, 18.6, 18.7, 18.8, 18.9, 19, 19.1, 19.2, 19.3, 19.4, 19.5, 19.6, 19.7, 19.8, 19.9, 20, 21.1, 21.2, 21.3, 21.4, 21.5, 21.6, 21.7, 21.8, 21.9, 30, 31, 31.1, 31.2, 31.3, 31.4, 31.5, 31.6, 31.7, 31.8, 31.9, 32, 32.1, 32.2, 32.3, 32.4. 32.5, 32.6, 32.7, 32.8, 32.9, 33, 33.1, 33.2, 33.3, 33.4, 33.5, 33.6, 33.7, 33.8, 33.9, 34, 34.1, 34.2, 34.3, 34.4, 34.5, 34.6, 34.7, 34.8, 34.9, 35, 35.1, 35.2, 35.3, 35.4, 35.5, 35.6, 35.7, 35.8, 35.9, 36, 36.1, 36.2, 36.3, 36.4. 36.5, 36.6, 36.7, 36.8, 36.9, 37, 37.1, 37.2, 37.3, 37.4, 37.5, 37.6, 37.7, 37.8, 37.9, 38, 38.1, 38.2, 38.3, 38.4, 38.5, 38.6, 38.7, 38.8, 38.9, 39, 39.1, 39.2, 39.3, 39.4, 39.5, 39.6, 39.7, 39.8, 39.9, or 40 mole percent.

In certain embodiments, the amount of the steroid included in the LNP is 1, 1.1, 1.2, 1.3, 1.4, 1.5, 1.6, 1.7, 1.8, 1.9, 2, 2.1, 2.2, 2.3, 2.4. 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4. 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.10, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4. 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16, 16.1, 16.2, 16.3, 16.4. 16.5, 16.6, 16.7, 16.8, 16.9, 17, 17.1, 17.2, 17.3, 17.4, 17.5, 17.6, 17.7, 17.8, 17.9, 18, 18.1, 18.2, 18.3, 18.4, 18.5, 18.6, 18.7, 18.8, 18.9, 19, 19.1, 19.2, 19.3, 19.4, 19.5, 19.6, 19.7, 19.8, 19.9, 20, 21.1, 21.2, 21.3, 21.4, 21.5, 21.6, 21.7, 21.8, 21.9, 30, 31, 31.1, 31.2, 31.3, 31.4, 31.5, 31.6, 31.7, 31.8, 31.9, 32, 32.1, 32.2, 32.3, 32.4. 32.5, 32.6, 32.7, 32.8, 32.9, 33, 33.1, 33.2, 33.3, 33.4, 33.5, 33.6, 33.7, 33.8, 33.9, 34, 34.1, 34.2, 34.3, 34.4, 34.5, 34.6, 34.7, 34.8, 34.9, 35, 35.1, 35.2, 35.3, 35.4, 35.5, 35.6, 35.7, 35.8, 35.9, 36, 36.1, 36.2, 36.3, 36.4. 36.5, 36.6, 36.7, 36.8, 36.9, 37, 37.1, 37.2, 37.3, 37.4, 37.5, 37.6, 37.7, 37.8, 37.9, 38, 38.1, 38.2, 38.3, 38.4, 38.5, 38.6, 38.7, 38.8, 38.9, 39, 39.1, 39.2, 39.3, 39.4, 39.5, 39.6, 39.7, 39.8, 39.9, 40, 40.1, 40.2, 40.3, 40.4, 40.5, 40.6, 40.7, 40.8, 40.9, 41, 41.1, 41.2, 41.3, 41.4, 41.5, 41.6, 41.7, 41.8, 41.9, 42, 42.1, 42.2, 42.3, 42.4. 42.5, 42.6, 42.7, 42.8, 42.9, 43, 43.1, 43.2, 43.3, 43.4, 43.5, 43.6, 43.7, 43.8, 43.9, 44, 44.1, 44.2, 44.3, 44.4, 44.5, 44.6, 44.7, 44.8, 44.9, 45, 45.1, 45.2, 45.3, 45.4, 45.5, 45.6, 45.7, 45.8, 45.9, 46, 46.1, 46.2, 46.3, 46.4. 46.5, 46.6, 46.7, 46.8, 46.9, 47, 47.1, 47.2, 47.3, 47.4, 47.5, 47.6, 47.7, 47.8, 47.9, 48, 48.1, 48.2, 48.3, 48.4, 48.5, 48.6, 48.7, 48.8, 48.9, 49, 49.1, 49.2, 49.3, 49.4, 49.5, 49.6, 49.7, 49.8, 49.9, 50, 55, 60, 65, 70, or 75 mole percent.

In certain embodiments, the amount of the pegylated lipid included in the LNP is 1, 1.1, 1.2, 1.3, 1.4, 1.5, 1.6, 1.7, 1.8, 1.9, 2, 2.1, 2.2, 2.3, 2.4. 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4. 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.10, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4. 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16, 16.1, 16.2, 16.3, 16.4. 16.5, 16.6, 16.7, 16.8, 16.9, 17, 17.1, 17.2, 17.3, 17.4, 17.5, 17.6, 17.7, 17.8, 17.9, 18, 18.1, 18.2, 18.3, 18.4, 18.5, 18.6, 18.7, 18.8, 18.9, 19, 19.1, 19.2, 19.3, 19.4, 19.5, 19.6, 19.7, 19.8, 19.9, or 20 mole percent.

In certain embodiments, the hydrophilic DMG-PEG forms the shell of the LNP. The amount of nucleic acid is represented by the NP mole ratio of the amine on the ionizable lipid to the phosphate groups on the nucleic acid backbone and is typically 3-6. In certain embodiments, the pKa of the LNP to be in the 6-7 range corresponding to the pH in the early endosome. A link between the pKa of the ionizable lipid in the LNP and gene silencing efficiency showed an LNP pKa in the range 6-7 produced more silencing for the ionizable lipid DLinDMA and was associated with promoting lipid structures that could disrupt the membrane of the endosome. The pKa of the LNP was measured using the pH-dependence of fluorescence enhancement of the anionic dye TNS. In certain embodiments, the pKa-dependent endosomal release mechanism was described as an ion-pairing event between the cationic protonated ionizable lipid and anionic endosomal phospholipids where a divergent cone-shape lipid tail of the ionizable lipid facilitates membrane rupture.

In particular preferred embodiments, the lipid nanoparticle includes a mRNA included in the lipid nanoparticle, wherein preferably the antigenic peptide or protein is derived from hemagglutinin (HA), neuraminidase (NA), nucleoprotein (NP), matrix protein 1 (M1), matrix protein 2 (M2), non-structural protein 1 (NS1), non-structural protein 2 (NS2), nuclear export protein (NEP), polymerase acidic protein (PA), polymerase basic protein PB1, PB1-F2, or polymerase basic protein 2 (PB2) of an influenza virus or a fragment or variant thereof. More preferably the antigenic peptide or protein is derived from hemagglutinin (HA) or neuraminidase (NA) of an influenza virus or a fragment or variant thereof. Even more preferably the antigenic peptide or protein is at least one full-length protein of hemagglutinin (HA) and/or at least one full-length protein of neuraminidase (NA) of an influenza virus or a variant thereof. In a further preferred embodiment the influenza virus is selected from an influenza A, B or C virus. In a particularly preferred embodiment the influenza A virus is selected from an influenza virus characterized by a hemagglutinin (HA) selected from the group consisting of H1, H2, H3, H4, H5, H6, H7, H8, H9, H10, H11, H12, H13, H14, H15, H16, H17 and H18 and/or the influenza A virus is selected from an influenza virus characterized by a neuraminidase (NA) selected from the group consisting of N1, N2, N3, N4, N5, N6, N7, N8, N9, N10, and N11. Preferably, the influenza A virus is selected from the group consisting of H1N1, H1N2, H2N2, H3N1, H3N2, H3N8, H5N1, H5N2, H5N3, H5N8, H5N9, H7N1, H7N2, H7N3, H7N4, H7N7, H7N9, H9N2, and H10N7, preferably from H1N1, H3N2, H5N1. Most preferably, the mRNA sequence comprises at least one coding region encoding at least one antigenic peptide or protein derived from hemagglutinin (HA) of an influenza virus or a fragment or variant thereof and at least one antigenic peptide or protein derived from neuraminidase (NA) of an influenza virus or a fragment or variant thereof. In a specifically preferred embodiment the mRNA sequence comprises at least one coding region encoding at least one antigenic peptide or protein derived from hemagglutinin (HA) and/or at least one antigenic peptide or protein derived from neuraminidase (NA) of an influenza A virus selected from the group consisting of H1N1, H1N2, H2N2, H3N1, H3N2, H3N8, H5N1, H5N2, H5N3, H5N8, H5N9, H7N1, H7N2, H7N3, H7N4, H7N7, H7N9, H9N2, and H10N7, preferably from H1N1, H3N2, H5N1 or a fragment or variant thereof.

V.7. Methods of Making the LNPs of the Invention

The invention further relates to a method of preparing lipid nanoparticles comprising the steps of:

(i) combining (a) an Ionizable Lipid of the Invention as defined above or a pharmaceutically acceptable salt, tautomer, prodrug or stereoisomer thereof, (b) a PEG lipid;

(c) at least one mRNA compound comprising an mRNA sequence encoding at least one antigenic peptide or protein; and (d) optionally a steroid; and (e) optionally a neutral lipid;

(ii) solubilizing the Ionizable lipid and/or the PEG lipid and optionally the neutral lipid and/or the steroid or a steroid derivative in ethanol;

(iii) mixing the ethanolic lipid solution with an aqueous solution comprising the mRNA polynucleotide (iv) removing the ethanol to form lipid nanoparticles encapsulating or associating with the mRNA polynucleotide; and optionally;

(v) pH adjustment through dilution, dialysis, or filtration;

(vi) separating or purifying the lipid nanoparticles.

The ethanol may be removed by any suitable method which does not negatively affect the lipids or the forming lipid nanoparticles. In one embodiment of the invention the ethanol is removed by dialysis. In an alternative embodiment the ethanol is removed by diafiltration.

Separation and optimal purification of the lipid nanoparticles might also be performed by any suitable method. Preferably the lipid nanoparticles are filtrated, more preferably the lipid nanoparticles are separated or purified by filtration through a sterile filter.

V.8. Pharmaceutical Compositions of the Invention

The invention also encompasses pharmaceutical compositions and/or vaccines comprising an Ionizable Lipid of the Invention and a nucleic acid.

In a preferred embodiment, the pharmaceutical composition or the vaccine according to the invention comprising mRNA comprises lipid nanoparticles, which have a molar ratio of approximately 50:10:38.5:1.5, preferably 47.5:10:40.8:1.7 or more preferably 47.4:10:40.9:1.7 (i.e., proportion (mol %) of Ionizable Lipid of the Invention, DSPC, cholesterol and PEG-lipid; solubilized in ethanol). In another embodiment, the molar ratio is 48:12:38:2.

The invention further relates to a pharmaceutical composition comprising at least one lipid nanoparticle according to the present invention. In certain embodiments, the lipid nanoparticle comprises an mRNA compound comprising a sequence encoding at least one antigenic peptide or protein as defined herein.

In one embodiment of the invention the mRNA sequence encodes one antigenic peptide or protein. In an alternative embodiment of the invention the mRNA sequence encodes more than one antigenic peptide or protein.

In one embodiment of the invention, the pharmaceutical composition comprises a lipid nanoparticle according to the invention, wherein the lipid nanoparticle comprises more than one mRNA compounds, which each comprise a different mRNA sequence encoding an antigenic peptide or protein.

In an alternative embodiment of the invention the pharmaceutical composition comprises a second lipid nanoparticle, wherein the mRNA compound comprised by the second lipid nanoparticle is different from the mRNA compound comprised by the first lipid nanoparticle.

In a further aspect, the present invention concerns a composition comprising mRNA comprising lipid nanoparticles wherein the mRNA comprises an mRNA sequence comprising at least one coding region as defined herein and a pharmaceutically acceptable carrier. The composition according to the invention is preferably provided as a pharmaceutical composition or as a vaccine.

According to a preferred embodiment, the pharmaceutical composition or the vaccine according to the invention comprises mRNA comprising lipid nanoparticles comprising at least one mRNA comprising at least one mRNA sequence as defined above, wherein the at least one coding region of the at least one mRNA sequence encodes at least one antigenic peptide or protein preferably derived from a protein of an influenza virus or Rabies virus, preferably any one of the hemagglutinin (HA) or neuraminidase (NA) proteins or glycoproteins, or a fragment or variant of any one of these proteins.

Preferably, the pharmaceutical composition or the vaccine according to the invention comprises mRNA comprising lipid nanoparticles comprising at least one mRNA comprising at least one mRNA sequence as defined above, wherein the at least one coding sequence of the at least one mRNA sequence comprises or consists of a nucleic acid sequence encoding at least one antigenic peptide or protein preferably derived from a protein of an influenza virus, preferably any one of the hemagglutinin (HA) or neuraminidase (NA) proteins, or a fragment or variant thereof, wherein the protein derived from a protein of an influenza virus preferably comprises or consists of any one of the amino acid sequences or a fragment or variant of any one of these sequences. Alternatively, the antigenic peptide or protein is derived from a Rabies virus, preferably from glycoprotein of a Rabies virus, or a fragment or variant of any one of these sequences.

Preferably, the pharmaceutical composition or the vaccine according to the invention comprises mRNA comprising lipid nanoparticles comprising at least one mRNA comprising at least one mRNA sequence as defined above, wherein the at least one coding sequence of the mRNA sequence comprises or consists of a nucleic acid sequence encoding at least one antigenic peptide or protein derived from a protein of an influenza virus or Rabies virus, or a fragment or variant thereof, wherein the antigenic peptide or protein derived from a protein of an influenza virus or Rabies virus.

The pharmaceutical composition or vaccine according to the invention may thus comprise mRNA comprising lipid nanoparticles comprising at least one mRNA comprising at least one mRNA sequence comprising at least one coding region, encoding at least one antigenic peptide or protein, preferably derived from a protein of an influenza virus or Rabies virus or a fragment or variant thereof, wherein the at least one coding region of the at least one mRNA sequence encodes one specific antigenic peptide or protein e.g. derived from a protein of an influenza virus defined herein or a fragment or a variant thereof.

Alternatively, the pharmaceutical composition or vaccine of the present invention may comprise mRNA comprising lipid nanoparticles comprising at least one mRNA compound comprising at least one mRNA sequence according to the invention, wherein the at least one mRNA sequence encodes at least two, three, four, five, six, seven, eight, nine, ten, eleven or twelve distinct antigenic peptides or proteins e.g. derived from a protein of an influenza virus as defined herein or a fragment or variant thereof.

In this context it is particularly preferred that the at least one mRNA compound comprised in the pharmaceutical composition or vaccine is a bi- or multicistronic mRNA, which encodes the at least two, three, four, five, six, seven, eight, nine, ten, eleven or twelve distinct antigenic peptides or proteins e.g. derived from a protein of an influenza virus. Mixtures between these embodiments are also envisaged, such as compositions comprising more than one mRNA sequence, wherein at least one mRNA sequence may be monocistronic, while at least one other mRNA sequence may be bi- or multicistronic.

The pharmaceutical composition or vaccine according to the present invention, preferably the at least one coding sequence of the mRNA sequence comprised therein, may thus comprise any combination of the nucleic acid sequences as defined herein.

Preferably, the pharmaceutical composition or vaccine comprises mRNA comprising lipid nanoparticle comprising a plurality or more than one of the mRNA sequences according to the invention, wherein each mRNA sequence comprises at least one coding region encoding at least one antigenic peptide or protein derived from a protein of an influenza virus or a fragment or variant thereof.

In a particularly preferred embodiment the composition comprises at least 2, 3, 4, 5, 6, 7, 6, 9, 10, 11, 12, 13, 14, 15, 16, 17, 18, 19, 20, 25, 30, 35, 40, 45, 50, 60, 70, 80, or 100 different mRNA sequences each encoding at least one antigenic peptide or protein, for example, derived from a protein of an influenza virus or a fragment or variant thereof as defined above, for example, derived from hemagglutinin (HA) or neuraminidase (NA) of an influenza virus or a fragment or variant thereof.

In another embodiment the composition comprises 4 different mRNA sequences each encoding at least one antigenic peptide or protein preferably derived from a protein of an influenza virus or a fragment or variant thereof as defined above, for example, derived from hemagglutinin (HA) or neuraminidase (NA) of an influenza virus or a fragment or variant thereof.

In this context it is particularly preferred that each mRNA sequence encodes at least one different antigenic peptide or protein derived from proteins of the same pathogen, e.g. influenza virus, wherein it is particularly preferred that the antigenic peptide or protein is derived from different proteins of the same pathogen, e.g. influenza virus. Preferably the composition comprises at least two mRNA sequences, wherein at least one mRNA sequence encodes at least one antigenic peptide or protein derived from hemagglutinin (HA) of the influenza virus and at least one mRNA sequence encodes at least one antigenic peptide or protein derived from neuraminidase (NA) of the same influenza virus.

In another preferred embodiment each mRNA sequence encodes at least one different antigenic peptide or protein derived from proteins of different pathogens, e.g. influenza viruses. Preferably each mRNA sequence encodes at least one antigenic peptide or protein derived from hemagglutinin (HA) and/or neuraminidase (NA) of different influenza viruses.

Preferably, the pharmaceutical composition or vaccine according to the invention comprises a plurality of mRNA sequences each encoding at least one antigenic peptide or protein derived from hemagglutinin (HA) and/or neuraminidase (NA) of an influenza virus, wherein at least one antigenic peptide or protein derived from hemagglutinin (HA) and/or neuraminidase (NA) of 2, 3, 4, 5, 6, 7, 6, 9, 10, 11, 12, 13, 14, 15, 16, 17, 18, 19, 20, 25, 30, 35, 40, 45, 50, 60, 70, 80, or 100 different influenza viruses are encoded by the plurality of mRNA sequences.

In this context it is particularly preferred that the pharmaceutical composition or vaccine comprises at least one mRNA comprising lipid nanoparticle comprising a mRNA compound comprising a mRNA sequence encoding at least one antigenic peptide or protein derived from a protein of influenza A virus H1, preferably hemagglutinin (HA) and/or neuraminidase (NA), at least one mRNA sequence encoding at least one antigenic peptide or protein derived from a protein of influenza A virus H3, preferably hemagglutinin (HA) and/or neuraminidase (NA), at least one mRNA sequence encoding at least one antigenic peptide or protein derived from a protein of influenza A virus H5, preferably hemagglutinin (HA) and/or neuraminidase (NA), and optionally at least one mRNA sequence encoding at least one antigenic peptide or protein derived from a protein of influenza A virus H7, preferably hemagglutinin (HA) and/or neuraminidase (NA), and/or optionally at least one mRNA sequence encoding at least one antigenic peptide or protein derived from a protein of influenza A virus H9, preferably hemagglutinin (HA) and/or neuraminidase (NA).

Preferably, the pharmaceutical composition or vaccine comprises at least one mRNA comprising lipid nanoparticle comprising a mRNA compound comprising a mRNA sequence encoding at least one antigenic peptide or protein derived from hemagglutinin (HA) and/or at least one mRNA sequence encoding at least one antigenic peptide or protein derived from neuraminidase (NA) of influenza A virus H1, at least one mRNA sequence encoding at least one antigenic peptide or protein derived from hemagglutinin (HA) and/or at least one mRNA sequence encoding at least one antigenic peptide or protein derived from neuraminidase (NA) of influenza A virus H3, at least one mRNA sequence encoding at least one antigenic peptide or protein derived from hemagglutinin (HA) and/or at least one mRNA sequence encoding at least one antigenic peptide or protein derived from neuraminidase (NA) of influenza A virus H5, and optionally at least one mRNA sequence encoding at least one antigenic peptide or protein derived from preferably hemagglutinin (HA) and/or at least one mRNA sequence encoding at least one antigenic peptide or protein derived from neuraminidase (NA) of influenza A virus H7, and/or optionally at least one mRNA sequence encoding at least one antigenic peptide or protein derived from, preferably hemagglutinin (HA) and/or at least one mRNA sequence encoding at least one antigenic peptide or protein derived from neuraminidase (NA) of influenza A virus H9.

In a specific embodiment the pharmaceutical composition or vaccine comprises at least one mRNA comprising lipid nanoparticle comprising an mRNA compound comprising a mRNA sequence encoding at least one antigenic peptide or protein derived from hemagglutinin (HA) and/or at least one mRNA sequence encoding at least one antigenic peptide or protein derived from neuraminidase (NA) of influenza A virus H1N1, at least one mRNA sequence encoding at least one antigenic peptide or protein derived from hemagglutinin (HA) and/or at least one mRNA sequence encoding at least one antigenic peptide or protein derived from neuraminidase (NA) of influenza A virus H3N2, at least one mRNA sequence encoding at least one antigenic peptide or protein derived from hemagglutinin (HA) and/or at least one mRNA sequence encoding at least one antigenic peptide or protein derived from neuraminidase (NA) of influenza A virus H5N1.

Additionally, the pharmaceutical composition or vaccine preferably further comprises at least one mRNA comprising lipid nanoparticle comprising a mRNA compound comprising a mRNA sequence encoding at least one antigenic peptide or protein derived from hemagglutinin (HA) and/or at least one mRNA sequence encoding at least one antigenic peptide or protein derived from neuraminidase (NA) of at least one influenza B virus, encapsulated or associated with mRNA comprising lipid nanoparticles according to the invention.

V.9. Nucleic Acids for Use in the LNPs of the Invention

The present invention is based on the surprising finding that a nucleic acid (e.g., m-RNA) encoding at least one antigenic peptide or protein included in lipid nanoparticles (LNPs) induces very efficiently antigen-specific immune responses against the encoded antigenic peptide or protein at a low dosage and dosing regimen, which do not require frequent administration.

Another advantages of the inventive mRNA encoding at least one antigenic peptide or protein comprised in lipid nanoparticles (LNPs) are: induction of a strong humoral immune response; induction of b-cell memory; faster onset of immune protection; longevity of the induced immune responses; induction of broad cellular t-cell responses; induction of a (local and transient) pro-inflammatory environment; no induction of systemic cytokine or chemokine response; well tolerability, no side-effects, non-toxic; advantageous stability characteristics; formulation compatible with many different antigens: larger antigen cocktails feasible based on the same (production) technology; no vector immunity, i.e. technology can be used to vaccinate the same subject multiple times against multiple (different) antigens; speed, adaptability, simplicity and scalability of production.

In particular, the invention relates to lipid nanoparticles and uses thereof. In certain embodiments, the lipid nanoparticles comprise at least:

(i) an Ionizable Lipid of the Invention and/or a PEG-lipid; and (ii) an mRNA compound comprising an mRNA sequence encoding an antigenic peptide or protein.

In certain embodiments, the lipid nanoparticle comprising mRNA may comprise further compounds, such as one or more neutral lipids, steroids and combinations of said compounds. Suitable compounds will be described in detail below.

In certain embodiments, the mRNA compound comprising an mRNA sequence encoding an antigenic peptide or protein may be a mRNA molecule. In one embodiment of the invention, the mRNA compound is a natural and non-modified mRNA. Within the context of the present invention, natural and non-modified mRNA encompasses mRNA generated in vitro, without chemical modifications or changes in the sequence.

In an alternative embodiment of the invention, the mRNA compound comprises an artificial mRNA. In the context of the present invention artificial mRNA encompasses mRNA with chemical modifications, sequence modifications or non-natural sequences.

In a preferred embodiment of the invention, the mRNA compound does not comprise nucleoside modifications, in particular no base modifications. In a further embodiment, the mRNA compound does not comprise 1-methylpseudouridine modifications. In one preferred embodiment, the mRNA comprises only the naturally existing nucleosides. In a further preferred embodiment, the mRNA compound does not comprise any chemical modification and optionally comprises sequence modifications. In a further preferred embodiment of the invention the mRNA compound only comprises the naturally existing nucleosides adenine, uracil, guanine and cytosine.

According to certain embodiments of the present invention, the mRNA sequence is mono-, bi-, or multicistronic, preferably as defined herein. The coding sequences in a bi- or multicistronic mRNA preferably encode distinct peptides or proteins as defined herein or a fragment or variant thereof. Preferably, the coding sequences encoding two or more peptides or proteins may be separated in the bi- or multicistronic mRNA by at least one IRES (internal ribosomal entry site) sequence, as defined below. Thus, the term "encoding two or more peptides or proteins" may mean, without being limited thereto, that the bi- or even multicistronic mRNA, may encode e.g. at least two, three, four, five, six or more (preferably different) peptides or proteins or their fragments or variants within the definitions provided herein. More preferably, without being limited thereto, the bi- or even multicistronic mRNA, may encode, for example, at least two, three, four, five, six or more (preferably different) peptides or proteins as defined herein or their fragments or variants as defined herein.

In this context, a so-called IRES (internal ribosomal entry site) sequence as defined above can function as a sole ribosome binding site, but it can also serve to provide a bi- or even multicistronic mRNA as defined above, which encodes several peptides or proteins which are to be translated by the ribosomes independently of one another. Examples of IRES sequences, which can be used according to the invention, are those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukoma virus (MLV), simian immunodeficiency viruses (SIV) or cricket paralysis viruses (CrPV). The TEV, tobacco etch virus 5' UTR we use is an IRES.

According to a further embodiment the at least one coding region of the mRNA sequence according to the invention may encode at least two, three, four, five, six, seven, eight and more peptides or proteins (or fragments and derivatives thereof) as defined herein linked with or without an amino acid linker sequence, wherein said linker sequence can comprise rigid linkers, flexible linkers, cleavable linkers (e.g., self-cleaving peptides) or a combination thereof. Therein, the peptides or proteins may be identical or different or a combination thereof. Particular peptide or protein combinations can be encoded by said mRNA encoding at least two peptides or proteins as explained herein (also referred to herein as "multi-antigen-constructs/mRNA").

In a particular aspect of the invention, the lipid nanoparticles comprise an mRNA compound, comprising an mRNA sequence encoding an antigenic peptide or protein, or a fragment, variant or derivative thereof.

These antigenic peptides or proteins may be derived from pathogenic antigens, tumor antigens, allergenic antigens or autoimmune self-antigens, preferably as defined herein. In the context of the present invention, antigenic peptides or proteins preferably exclude luciferases.

V.9.1. Pathogenic Antigens

Such pathogenic antigens are derived from pathogenic organisms, in particular bacterial, viral or protozoological (multicellular) pathogenic organisms, which evoke an immunological reaction by subject, in particular a mammalian subject, more particularly a human. More specifically, pathogenic antigens are preferably surface antigens, e.g. proteins (or fragments of proteins, e.g. the exterior portion of a surface antigen) located at the surface of the virus or the bacterial or protozoological organism.

Pathogenic antigens are peptide or protein antigens preferably derived from a pathogen associated with infectious disease which are preferably selected from antigens derived from the pathogens *Acinetobacter baumannii, Anaplasma* genus, *Anaplasma phagocytophilum, Ancylostoma braziliense, Ancylostoma duodenale, Arcanobacterium haemolyticum, Ascaris lumbricoides, Aspergillus* genus, Astroviridae, *Babesia* genus, *Bacillus anthracis, Bacillus cereus, Bartonella henselae*, BK virus, *Blastocystis hominis, Blastomyces dermatitidis, Bordetella pertussis, Borrelia burgdorferi, Borrelia* genus, *Borrelia* spp, *Brucella* genus, *Brugia malayi*, Bunyaviridae family, *Burkholderia cepacia* and other *Burkholderia* species, *Burkholderia mallei, Burkholderia pseudomallei*, Caliciviridae family, *Campylobacter* genus, *Candida albicans, Candida* spp, *Chlamydia trachomatis, Chlamydophila pneumoniae, Chlamydophila psittaci*, CD prion, *Clonorchis sinensis, Clostridium botulinum, Clostridium difficile, Clostridium perfringens, Clostridium perfringens, Clostridium* spp, *Clostridium tetani, Coccidioides* spp, coronaviruses, *Corynebacterium diphtheriae, Coxiella burnetii*, Crimean-Congo hemorrhagic fever virus, *Cryptococcus neoformans, Cryptosporidium* genus, Cytomegalovirus (CMV), Dengue viruses (DEN-1, DEN-2, DEN-3 and DEN-4), *Dientamoeba fragilis*, Ebolavirus (EBOV), *Echinococcus* genus, *Ehrlichia chaffeensis, Ehrlichia ewingii, Ehrlichia genus, Entamoeba histolytica, Enterococcus* genus, *Enterovirus* genus, Enteroviruses, mainly Coxsackie A virus and *Enterovirus* 71 (EV71), *Epidermophyton* spp, Epstein-Barr Virus (EBV), *Escherichia coli* O157:H7, 0111 and 0104:H4, *Fasciola hepatica* and *Fasciola gigantica*, FFI prion, Filarioidea superfamily, Flaviviruses, *Francisella tularensis, Fusobacterium genus, Geotrichum candidum, Giardia intestinalis, Gnathostoma* spp, GSS prion, Guanarito virus, *Haemophilus ducreyi, Haemophilus influenzae, Helicobacter pylori*, Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Japanese encephalitis virus, JC virus, Junin virus, Kingella kingae, *Klebsiella granulomatis*, Kuru prion, Lassa virus, *Legionella pneumophila, Leishmania* genus, Leptospira genus, *Listeria monocytogenes*, Lymphocytic choriomeningitis virus (LCMV), Machupo virus, *Malassezia* spp, Marburg virus, Measles virus, *Metagonimus* yokagawai, Microsporidia phylum, Molluscum contagiosum virus (MCV), Mumps virus, *Mycobacterium leprae* and *Mycobacterium* lepromatosis, *Mycobacterium tuberculosis, Mycobacterium ulcerans, Mycoplasma pneumoniae, Naegleria fowleri, Necator americanus, Neisseria gonorrhoeae, Neisseria meningitidis, Nocardia asteroides, Nocardia* spp, *Onchocerca volvulus*, Orientia tsutsugamushi, Orthomyxoviridae family (Influenza), *Paracoccidioides brasiliensis, Paragonimus* spp, *Paragonimus westermani*, Parvovirus B19, *Pasteurella* genus, *Plasmodium* genus, *Pneumocystis jirovecii*, Poliovirus, Rabies virus, Respiratory syncytial virus (RSV), Rhinovirus, rhinoviruses, *Rickettsia akari, Rickettsia genus, Rickettsia prowazekii, Rickettsia rickettsii, Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii, Staphylococcus* genus, *Staphylococcus* genus, *Streptococcus agalactiae, Streptococcus pneumoniae, Streptococcus pyogenes, Strongyloides stercoralis, Taenia* genus, *Taenia solium*, Tick-borne encephalitis virus (TBEV), *Toxocara canis* or *Toxocara cati, Toxoplasma gondii, Treponema pallidum, Trichinella spiralis, Trichomonas vaginalis, Trichophyton* spp, *Trichuris trichiura, Trypanosoma brucei, Trypanosoma cruzi, Ureaplasma urealyticum*, Varicella zoster virus (VZV), Varicella zoster virus (VZV), Variola major or Variola minor, vCJD prion, Venezuelan equine encephalitis virus, *Vibrio cholerae*, West Nile virus, Western equine encephalitis virus, *Wuchereria bancrofti*, Yellow fever virus, *Yersinia enterocolitica, Yersinia pestis*, and *Yersinia pseudotuberculosis.*

In this context particularly preferred are antigens from the pathogens selected from Influenza virus, SARS-COV-2, respiratory syncytial virus (RSV), Herpes simplex virus (HSV), human Papilloma virus (HPV), Human immunodeficiency virus (HIV), *Plasmodium, Clostridium difficile, Staphylococcus aureus*, Dengue virus, *Chlamydia trachomatis, Brucella*, Cytomegalovirus (CMV), Hepatitis B virus (HBV), *Mycobacterium tuberculosis*, Rabies virus, Crimean-Congo Hemorrhagic Fever virus and Yellow Fever Virus.

Furthermore, the pathogenic antigen (antigen derived from a pathogen associated with infectious disease) may be preferably selected from the following antigens: Outer membrane protein A OmpA, biofilm associated protein Bap, transport protein MucK (*Acinetobacter baumannii, Acinetobacter* infections)); variable surface glycoprotein VSG, microtubule-associated protein MAPP15, trans-sialidase TSA (*Trypanosoma brucei*, African sleeping sickness (African trypanosomiasis)); HIV p24 antigen, HIV envelope proteins (Gp120, Gp41, Gp160), polyprotein GAG, negative factor protein Nef, trans-activator of transcription Tat (HIV (Human immunodeficiency virus), AIDS (Acquired immunodeficiency syndrome)); galactose-inhibitable adherence protein GIAP, 29 kDa antigen Eh29, Gal/GalNAc lectin, protein CRT, 125 kDa immunodominant antigen, protein M17, adhesin ADH112, protein STIRP (*Entamoeba histolytica*, Amoebiasis); Major surface proteins 1-5 (MSP1a, MSP1b, MSP2, MSP3, MSP4, MSP5), type IV secretion system proteins (VirB2, VirB7, VirB11, VirD4) (*Anaplasma* genus, Anaplasmosis); protective Antigen PA, edema factor EF, lethal factor LF, the S-layer homology proteins SLH (*Bacillus anthracis*, Anthrax); acranolysin, phospholipase D, collagen-binding protein CbpA (*Arcanobacterium hae-

*molyticum, Arcanobacterium haemolyticum* infection); nucleocapsid protein NP, glycoprotein precursor GPC, glycoprotein GPI, glycoprotein GP2 (Junin virus, Argentine hemorrhagic fever); chitin-protein layer proteins, 14 kDa surface antigen A14, major sperm protein MSP, MSP polymerization-organizing protein MPOP, MSP fiber protein 2 MFP2, MSP polymerization-activating kinase MPAK, ABA-1-like protein ALB, protein ABA-1, cuticulin CUT-1 (*Ascaris lumbricoides*, Ascariasis); 41 kDa allergen Asp v13, allergen Asp f3, major conidial surface protein rodlet A, protease Pepip, GPI-anchored protein Gellp, GPI-anchored protein Crflp (*Aspergillus* genus, Aspergillosis); family VP26 protein, VP29 protein (Astroviridae, Astrovirus infection); Rhoptry-associated protein 1 RAP-1, merozoite surface antigens MSA-1, MSA-2 (a1, a2, b, c), 12D3, 11C5, 21B4, P29, variant erythrocyte surface antigen VESA1, Apical Membrane Antigen 1 AMA-1 (*Babesia* genus, Babesiosis); hemolysin, enterotoxin C, PXO1-51, glycolate oxidase, ABC-transporter, penicillin-binding protein, zinc transporter family protein, pseudouridine synthase Rsu, plasmid replication protein RepX, oligoendopeptidase F, prophage membrane protein, protein HemK, flagellar antigen H, 28.5-kDa cell surface antigen (*Bacillus cereus, Bacillus cereus* infection); large T antigen LT, small T antigen, capsid protein VP1, capsid protein VP2 (BK virus, BK virus infection); 29 kDa-protein, caspase-3-like antigens, glycoproteins (*Blastocystis hominis, Blastocystis hominis* infection); yeast surface adhesin WI-1 (*Blastomyces dermatitidis*, Blastomycosis); nucleoprotein N, polymerase L, matrix protein Z, glycoprotein GP (Machupo virus, Bolivian hemorrhagic fever); outer surface protein A OspA, outer surface protein OspB, outer surface protein OspC, decorin binding protein A DbpA, decorin binding protein B DbpB, flagellar filament 41 kDa core protein Fla, basic membrane protein A precursor BmpA (Immunodominant antigen P39), outer surface 22 kDa lipoprotein precursor (antigen IPLA7), variable surface lipoprotein vlsE (*Borrelia* genus, *Borrelia* infection); Botulinum neurotoxins BoNT/A1, BoNT/A2, BoNT/A3, BoNT/B, BoNT/C, BoNT/D, BoNT/E, BoNT/F, BoNT/G, recombinant botulinum toxin F He domain FHc (*Clostridium botulinum*, Botulism (and Infant botulism)); nucleocapsid, glycoprotein precursor (Sabia virus, Brazilian hemorrhagic fever); copper/Zinc superoxide dismutase SodC, bacterioferritin Bfr, 50S ribosomal protein RplL, OmpA-like transmembrane domain-containing protein Omp31, immunogenic 39-kDa protein M5 P39, zinc ABC transporter periplasmic zinc-binding protein znuA, periplasmic immunogenic protein Bp26, 30S ribosomal protein S12 RpsL, glyceraldehyde-3-phosphate dehydrogenase Gap, 25 kDa outer-membrane immunogenic protein precursor Omp25, invasion protein B lalB, trigger factor Tig, molecular chaperone DnaK, putative peptidyl-prolyl cis-trans isomerase SurA, lipoprotein Omp19, outer membrane protein MotY Omp16, conserved outer membrane protein D15, malate dehydrogenase Mdh, component of the Type-IV secretion system (T4SS) VirJ, lipoprotein of unknown function BAB1_0187 (*Brucella* genus, Brucellosis); members of the ABC transporter family (LoiC, OppA, and PotF), putative lipoprotein releasing system transmembrane protein LolC/E, flagellin FliC, *Burkholderia* intracellular motility A BimA, bacterial Elongation factor-Tu EF-Tu, 17 kDa OmpA-like protein, boaA coding protein, boaB coding protein (*Burkholderia cepacia* and other *Burkholderia* species, *Burkholderia* infection); mycolyl-transferase Ag85A, heat-shock protein Hsp65, protein TB10.4, 19 kDa antigen, protein PstS3, heat-shock protein Hsp70 (*Mycobacterium ulcerans*, Buruli ulcer); norovirus major and minor viral capsid proteins VP1 and VP2, genome polyprotein, Sapoviurus capsid protein VP1, protein Vp3, geome polyprotein (Caliciviridae family, Calicivirus infection (Norovirus and Sapovirus)); major outer membrane protein PorA, flagellin FlaA, surface antigen CjaA, fibronectin binding protein CadF, aspartate/glutamate-binding ABC transporter protein PeblA, protein FspAI, protein FspA2 (*Campylobacter* genus, Campylobacteriosis); glycolytic enzyme enolase, secreted aspartyl proteinases SAP1-10, glycophosphatidylinositol (GPI)-linked cell wall protein, protein Hyrl, complement receptor 3-related protein CR3-RP, adhesin Als3p, heat shock protein 90 kDa hsp90, cell surface hydrophobicity protein CSH (usually *Candida albicans* and other *Candida* species, Candidiasis); 17-kDa antigen, protein P26, trimeric autotransporter adhesins TAAs, *Bartonella* adhesin A BadA, variably expressed outer-membrane proteins Vomps, protein Pap3, protein HbpA, envelope-associated protease HtrA, protein OMP89, protein GroEL, protein LalB, protein OMP43, dihydrolipoamide succinyltransferase SucB (*Bartonella henselae*, Cat-scratch disease); amastigote surface protein-2, amastigote-specific surface protein SSP4, cruzipain, trans-sialidase TS, trypomastigote surface glycoprotein TSA-1, complement regulatory protein CRP-10, protein G4, protein G2, paraxonemal rod protein PAR2, paraflagellar rod component Par1, mucin-Associated Surface Proteins MPSP (*Trypanosoma cruzi*, Chagas Disease (American trypanosomiasis)); envelope glycoproteins (gB, gC, gE, gH, gI, gK, gL) (Varicella zoster virus (VZV), Chickenpox); major outer membrane protein MOMP, probable outer membrane protein PMPC, outer membrane complex protein B OmcB, heat shock proteins Hsp60 HSP10, protein *IncA*, proteins from the type III secretion system, ribonucleotide reductase small chain protein NrdB, plasmid protein Pgp3, chlamydial outer protein N CopN, antigen CT521, antigen CT425, antigen CT043, antigen TC0052, antigen TC0189, antigen TC0582, antigen TC0660, antigen TC0726, antigen TC0816, antigen TC0828 (*Chlamydia trachomatis, Chlamydia*); low calcium response protein E LCrE, chlamydial outer protein N CopN, serine/threonine-protein kinase PknD, acyl-carrier-protein S-malonyltransferase FabD, single-stranded DNA-binding protein Ssb, major outer membrane protein MOMP, outer membrane protein 2 Omp2, polymorphic membrane protein family (Pmp1, Pmp2, Pmp3, Pmp4, Pmp5, Pmp6, Pmp7, Pmp8, Pmp9, Pmp10, Pmp11, Pmp12, Pmp13, Pmp14, Pmp15, Pmp16, Pmp17, Pmp18, Pmp19, Pmp20, Pmp21) (*Chlamydophila pneumoniae, Chlamydophila pneumoniae* infection); cholera toxin B CTB, toxin coregulated pilin A TcpA, toxin coregulated pilin TcpF, toxin co-regulated pilus biosynthesis ptrotein F TcpF, cholera enterotoxin subunit A, cholera enterotoxin subunit B, Heat-stable enterotoxin ST, mannose-sensitive hemagglutinin MSHA, outer membrane protein U Porin ompU, Poring B protein, polymorphic membrane protein-D (*Vibrio cholerae*, Cholera); propionyl-CoA carboxylase PCC, 14-3-3 protein, prohibitin, cysteine proteases, glutathione transferases, gelsolin, cathepsin L proteinase CatL, Tegumental Protein 20.8 kDa TP20.8, tegumental protein 31.8 kDa TP31.8, lysophosphatidic acid phosphatase LPAP, (*Clonorchis sinensis*, Clonorchiasis); surface layer proteins SLPs, glutamate dehydrogenase antigen GDH, toxin A, toxin B, cysteine protease Cwp84, cysteine protease Cwp13, cysteine protease Cwp19, Cell Wall Protein CwpV, flagellar protein FliC, flagellar protein FliD, Zmp-1, CdeM, CdeC (*Clostridium difficile, Clostridium difficile* infection); rhinoviruses: capsid proteins VP1, VP2, VP3, VP4; coronaviruses: sprike proteins S, envelope proteins E, membrane proteins M, nucleocapsid proteins N (usually rhinoviruses and coronaviruses, Common cold (Acute viral rhinopharyngitis; Acute coryza)); prion protein Prp (CJD prion, Creutzfeldt-Jakob disease (CJD)); envelope protein Gc, envelope protein Gn, nucleocapsid proteins (Crimean-Congo hemorrhagic fever virus, Crimean-Congo hemorrhagic fever (CCHF)); virulence-associated DEAD-box RNA helicase VAD1, galactoxylomannan-protein GalXM, glucuronoxylomannan GXM, mannoprotein MP (*Cryptococcus neoformans*, Cryptococcosis); acidic ribosomal protein P2 CpP2, mucin antigens MucI, Muc2, Muc3 Muc4, Muc5, Muc6, Muc7, surface adherence protein CP20, surface adherence protein CP23, surface protein CP12, surface protein CP21, surface protein CP40, surface protein CP60, surface protein CP15, surface-associated glycopeptides gp40, surface-associated glycopeptides gp15, oocyst wall protein AB, profilin PRF, apyrase (*Cryptosporidium* genus, Cryptosporidiosis); fatty acid and retinol binding protein-1 FAR-1, tissue inhibitor of metalloproteinase TIMP (TMP), cysteine proteinase ACEY-1, cysteine proteinase ACCP-1, surface antigen Ac-16, secreted protein 2 ASP-2, metalloprotease 1 MTP-1, aspartyl protease inhibitor API-1, surface-associated antigen SAA-1, adult-specific secreted factor Xa serine protease inhibitor anticoagulant AP, cathepsin D-like aspartic protease ARR-1 (usually *Ancylostoma braziliense*; multiple other parasites, Cutaneous larva migrans (CLM)); cathepsin L-like proteases, 53/25-kDa antigen, 8 kDa family members, cysticercus protein with a marginal trypsin-like activity TsAg5, oncosphere protein TSOL18, oncosphere protein TSOL45-1A, lactate dehydrogenase A LDHA, lactate dehydrogenase B LDHB (*Taenia solium*, Cysticercosis); pp65 antigen, membrane protein pp15, capsid-proximal tegument protein pp150, protein M45, DNA polymerase UL54, helicase UL105, glycoprotein gM, glycoprotein gN, glcoprotein H, glycoprotein B gB, protein UL83, protein UL94, protein UL99 (Cytomegalovirus (CMV), Cytomegalovirus infection); capsid protein C, premembrane protein prM, membrane protein M, envelope protein E (domain I, domain IL, domain II), protein NS1, protein NS2A, protein NS2B, protein NS3, protein NS4A, protein 2K, protein NS4B, protein NS5 (Dengue viruses (DEN-1, DEN-2, DEN-3 and DEN-4)-Flaviviruses, Dengue fever); 39 kDa protein (*Dientamoeba fragilis*, Dientamoebiasis); diphtheria toxin precursor Tox, diphtheria toxin DT, pilin-specific sortase SrtA, shaft pilin protein SpaA, tip pilin protein SpaC, minor pilin protein SpaB, surface-associated protein DIP1281 (*Corynebacterium diphtheriae*, Diphtheria); glycoprotein GP, nucleoprotein NP, minor matrix protein VP24, major matrix protein VP40, transcription activator VP30, polymerase cofactor VP35, RNA polymerase L (Ebolavirus (EBOV), Ebola hemorrhagic fever); prion protein (vCOD prion, Variant Creutzfeldt-Jakob disease (vCOD, nvCOD)); UvrABC system protein B, protein Flp1, protein Flp2, protein Flp3, protein TadA, hemoglobin receptor HgbA, outer membrane protein TdhA, protein CpsRA, regulator CpxR, protein SapA, 18 kDa antigen, outer membrane protein NcaA, protein LspA, protein LspAl, protein LspA2, protein LspB, outer membrane component DsrA, lectin DltA, lipoprotein Hip, major outer membrane protein OMP, outer membrane protein OmpA2 (*Haemophilus ducreyi*, Chancroid); aspartyl protease 1 Pep1, phospholipase B PLB, alpha-mannosidase 1 AMN1, glucanosyltransferase GEL1, urease URE, peroxisomal matrix protein Pmpl, proline-rich antigen Pra, humal T-cell reactive protein TcrP (*Coccidioides immitis* and *Coccidioides* posadasii, Coccidioidomycosis); allergen Tri r 2, heat shock protein 60 Hsp60, fungal actin Act, antigen Tri r2, antigen Tri r4, antigen Tri t1, protein IV, glycerol-3-phosphate dehydrogenase Gpdl, osmosensor HwSholA, osmosensor HwSholB, histidine kinase HwHhk7B, allergen *Mala* s 1, allergen *Mala* s 11, thioredoxin Trx *Mala* s 13, allergen *Mala* f, allergen *Mala* s (usually *Trichophyton* spp, *Epidermophyton* spp., *Malassezia* spp., *Hortaea werneckii*, Dermatophytosis); protein EG95, protein EG10, protein EG18, protein EgA31, protein EM18, antigen EPC1, antigen B, antigen 5, protein P29, protein 14-3-3, 8-kDa protein, myophilin, heat shock protein 20 HSP20, glycoprotein GP-89, fatty acid binding protein FAPB (*Echinococcus* genus, Echinococcosis); major surface protein 2 MSP2, major surface protein 4 MSP4, MSP variant SGV1, MSP variant SGV2, outer membrane protein OMP, outer membrane protein 19 OMP-19, major antigenic protein MAP1, major antigenic protein MAP1-2, major antigenic protein MAPiB, major antigenic protein MAP1-3, Erum2510 coding protein, protein GroEL, protein GroES, 30-kDA major outer membrane proteins, GE 100-kDa protein, GE 130-kDa protein, GE 160-kDa protein (*Ehrlichia* genus, Ehrlichiosis); secreted antigen SagA, sagA-like proteins SalA and SalB, collagen adhesin Scm, surface proteins Fmsl (EbpA(fm), Fms5 (EbpB(fm), Fms9 (EpbC(fm) and Fms10, protein EbpC(fm), 96 kDa immunoprotective glycoprotein G1 (*Enterococcus* genus, *Enterococcus* infection); genome polyprotein, polymerase 3D, viral capsid protein VP1, viral capsid protein VP2, viral capsid protein VP3, viral capsid protein VP4, protease 2A, protease 3C (*Enterovirus* genus, *Enterovirus* infection); outer membrane proteins OM, 60 kDa outer membrane protein, cell surface antigen OmpA, cell surface antigen OmpB (sca5), 134 kDa outer membrane protein, 31 kDa outer membrane protein, 29.5 kDa outer membrane protein, cell surface protein SCA4, cell surface protein Adrl (RP827), cell surface protein Adr2 (RP828), cell surface protein SCA1, Invasion protein invA, cell division protein fts, secretion proteins sec 0family, virulence proteins virB, tlyA, tlyC, parvulin-like protein Pip, preprotein translocase SecA, 120-kDa surface protein antigen SPA, 138 kD complex antigen, major 100-kD protein (protein I), intracytoplasmic protein D, protective surface protein antigen SPA (*Rickettsia prowazekii*, Epidemic typhus); Epstein-Barr nuclear antigens (EBNA-1, EBNA-2, EBNA-3A, EBNA-3B, EBNA-3C, EBNA-leader protein (EBNA-LP)), latent membrane proteins (LMP-1, LMP-2A, LMP-2B), early antigen EBV-EA, membrane antigen EBV-MA, viral capsid antigen EBV-VCA, alkaline nuclease EBV-AN, glycoprotein H, glycoprotein gp350, glycoprotein gp110, glycoprotein gp42, glycoprotein gHgL, glycoprotein gB (Epstein-Barr Virus (EBV), Epstein-Barr Virus Infectious Mononucleosis); capsid protein VP2, capsid protein VP1, major protein NS1 (Parvovirus B19, Erythema infectiosum (Fifth disease)); pp65 antigen, glycoprotein 105, major capsid protein, envelope glycoprotein H, protein U51 (Human herpesvirus 6 (HHV-6) and Human herpesvirus 7 (HHV-7), Exanthem subitum); thioredoxin-glutathione reductase TGR, cathepsins L1 and L2, Kunitz-type protein KTM, leucine aminopeptidase LAP, cysteine proteinase Fas2, saposin-like protein-2 SAP-2, thioredoxin peroxidases TPx, Prx-1, Prx-2, cathepsin I cysteine proteinase CL3, protease cathepsin L CL1, phosphoglycerate kinase PGK, 27-kDa secretory protein, 60 kDa protein HSP35alpha, glutathione transferase GST, 28.5 kDa tegumental antigen 28.5 kDa TA, cathepsin B3 protease CatB3, Type I cystatin stefin-1, cathepsin L5, cathepsin Llg and cathepsin B, fatty acid binding protein FABP, leucine aminopeptidases LAP (*Fasciola hepatica* and *Fasciola gigantica*, Fasciolosis); prion protein (FFI prion, Fatal familial insomnia (FFI)); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, Thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, secreted larval acidic proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, Cox-2 (Filarioidea superfamily, Filariasis); phospholipase C PLC, heat-labile enterotoxin B, Iota toxin component Ib, protein CPE1281, pyruvate ferredoxin oxidoreductase, elongation factor G EF-G, perfringolysin O Pfo, glyceraldehyde-3-phosphate dehydrogenase GapC, Fructose-bisphosphate aldolase Alf2, *Clostridium perfringens* enterotoxin CPE, alpha toxin AT, alpha toxoid ATd, epsilon-toxoid ETd, protein HP, large cytotoxin TpeL, endo-beta-N-acetylglucosaminidase Naglu, phosphoglyceromutase Pgm (*Clostridium perfringens*, Food poisoning by *Clostridium perfringens*); leukotoxin IktA, adhesion FadA, outer membrane protein RadD, high-molecular weight arginine-binding protein (*Fusobacterium* genus, *Fusobacterium* infection); phospholipase C PLC, heat-labile enterotoxin B, Iota toxin component Ib, protein CPE1281, pyruvate ferredoxin oxidoreductase, elongation factor G EF-G, perfringolysin O Pfo, glyceraldehyde-3-phosphate dehydrogenase GapC, fructose-bisphosphate aldolase Alf2, *Clostridium perfringens* enterotoxin CPE, alpha toxin AT, alpha toxoid ATd, epsilon-toxoid ETd, protein HP, large cytotoxin TpeL, endo-beta-N-acetylglucosaminidase Naglu, phosphoglyceromutase Pgm (usually *Clostridium perfringens*; other *Clostridium* species, Gas gangrene (Clostridial myonecrosis)); lipase A, lipase B, peroxidase DecI (*Geotrichum candidum*, Geotrichosis); prion protein (GSS prion, Gerstmann-Striussler-Scheinker syndrome (GSS)); cyst wall proteins CWP1, CWP2, CWP3, variant surface protein VSP, VSP1, VSP2, VSP3, VSP4, VSP5, VSP6, 56 kDa antigen, pyruvate ferredoxin oxidoreductase PFOR, alcohol dehydrogenase E ADHE, alpha-giardin, alpha8-giardin, alpha1-guiardin, beta-giardin, cystein proteases, glutathione-S-transferase GST, arginine deiminase ADI, fructose-1,6-bisphosphat aldolase FBA, Giardia trophozoite antigens GTA (GTA1, GTA2), ornithine carboxyl transferase OCT, striated fiber-asseblin-like protein SALP, uridine phosphoryl-like protein UPL, alpha-tubulin, beta-tubulin (*Giardia intestinalis*, Giardiasis); members of the ABC transporter family (LolC, OppA, and PotF), putative lipoprotein releasing system transmembrane protein LolC/E, flagellin FliC, *Burkholderia* intracellular motility A BimA, bacterial Elongation factor-Tu EF-Tu, 17 kDa OmpA-like protein, boaA coding protein (*Burkholderia mallei*, Glanders); cyclophilin CyP, 24 kDa third-stage larvae protien GS24, excretion-secretion products ESPs (40, 80, 120 and 208 kDa) (*Gnathostoma spinigerum* and *Gnathostoma hispidum*, Gnathostomiasis); pilin proteins, minor pilin-associated subunit pilC, major pilin subunit and variants pilE, pilS, phase variation protein porA, Porin B PorB, protein TraD, Neisserial outer membrane antigen H.8, 70 kDa antigen, major outer membrane protein PI, outer membrane proteins PIA and PIB, W antigen, surface protein A NspA, transferrin binding protein TbpA, transferrin binding protein TbpB, PBP2, mtrR coding protein, ponA coding protein, membrane permease FbpBC, FbpABC protein system, LbpAB proteins, outer membrane protein Opa, outer membrane transporter FetA, iron-repressed regulator MpeR (*Neisseria gonorrhoeae*, Gonorrhea); outer membrane protein A OmpA, outer membrane protein C OmpC, outer membrane protein K17 OmpK17 (*Klebsiella granulomatis*, Granuloma inguinale (Donovanosis)); fibronectin-binding protein Sfb, fibronectin/fibrinogen-binding protein FBP54, fibronectin-binding protein FbaA, M protein type 1 Emm1, M protein type 6 Emm6, immunoglobulin-binding protein 35 Sib35, Surface protein R28 Spr28, superoxide dismutase SOD, C5a peptidase ScpA, antigen I/II AgI/II, adhesin AspA, G-related alpha2-macroglobulin-binding protein GRAB, surface fibrillar protein M5 (*Streptococcus pyogenes*, Group A streptococcal infection); C protein P3 antigen, arginine deiminase proteins, adhesin BibA, 105 kDA protein BPS, surface antigens c, surface antigens R, surface antigens X, trypsin-resistant protein R1, trypsin-resistant protein R3, trypsin-resistant protein R4, surface immunogenic protein Sip, surface protein Rib, Leucine-rich repeats protein LrrG, serine-rich repeat protein Srr-2, C protein alpha-antigen Bca, Beta antigen Bag, surface antigen Epsilon, alpha-like protein ALP1, alpha-like protein ALP5 surface antigen delta, alpha-like protein ALP2, alpha-like protein ALP3, alpha-like protein ALP4, Cbeta protein Bac (*Streptococcus agalactiae*, Group B streptococcal infection); transferrin-binding protein 2 Tbp2, phosphatase P4, outer membrane protein P6, peptidoglycan-associated lipoprotein Pal, protein D, protein E, adherence and penetration protein Hap, outer membrane protein 26 Omp26, outer membrane protein P5 (Fimbrin), outer membrane protein D15, outer membrane protein OmpP2, 5'-nucleotidase NucA, outer membrane protein P1, outer membrane protein P2, outer membrane lipoprotein Pcp, Lipoprotein E, outer membrane protein P4, fuculokinase FucK, [Cu,Zn]-superoxide dismutase SodC, protease HtrA, protein 0145, alpha-galactosylceramide (*Haemophilus influenzae, Haemophilus influenzae* infection); polymerase 3D, viral capsid protein VP1, viral capsid protein VP2, viral capsid protein VP3, viral capsid protein VP4, protease 2A, protease 3C (Enteroviruses, mainly Coxsackie A virus and *Enterovirus* 71 (EV71), Hand, foot and mouth disease (HFMD)); RNA polymerase L, protein L, glycoprotein Gn, glycoprotein Gc, nucleocapsid protein S, envelope glycoprotein G1, nucleoprotein NP, protein N, polyprotein M (Sin Nombre virus, Hantavirus, Hantavirus Pulmonary Syndrome (HPS)); heat shock protein HspA, heat shock protein HspB, citrate synthase GltA, protein UreB, heat shock protein Hsp60, neutrophil-activating protein NAP, catalase KatA, vacuolating cytotoxin VacA, urease alpha UreA, urease beta Ureb, protein Cpn10, protein groES, heat shock protein Hsp10, protein MopB, cytotoxicity-associated 10 kDa protein CAG, 36 kDa antigen, beta-lactamase HcpA, Beta-lactamase HcpB (*Helicobacter pylori, Helicobacter pylori* infection); integral membrane proteins, aggregation-prone proteins, 0-antigen, toxin-antigens Stx2B, toxin-antigen StxlB, adhesion-antigen fragment Int28, protein EspA, protein EspB, Intimin, protein Tir, protein IntC300, protein Eae (*Escherichia coli* O157:H7, 0111 and 0104:H4, Hemolytic-uremic syndrome (HUS)); RNA polymerase L, protein L, glycoprotein Gn, glycoprotein Gc, nucleocapsid protein S, envelope glycoprotein G1, nucleoprotein NP, protein N, polyprotein M (Bunyaviridae family, Hemorrhagic fever with renal syndrome (HFRS)); glycoprotein G, matrix protein M, nucleoprotein N, fusion protein F, polymerase L, protein W, proteinC, phosphoprotein p, non-structural protein V (Henipavirus (Hendra virus Nipah virus), Henipavirus infections); polyprotein, glycoproten Gp2, hepatitis A surface antigen HBAg, protein 2A, virus protein VP1, virus protein VP2, virus protein VP3, virus protein VP4, protein P1B, protein P2A, protein P3AB, protein P3D (Hepatitis A Virus, Hepatitis A); hepatitis B surface antigen HBsAg, Hepatitis B core antigen HbcAg, polymerase, protein Hbx, preS2 middle surface protein, surface protein L, large S protein, virus protein VP1, virus protein VP2, virus protein VP3, virus protein VP4 (Hepatitis B Virus (HBV), Hepatitis B); envelope glycoprotein E1 gp32 gp35, envelope glycoprotein E2 NS1 gp68 gp70, capsid protein C, core protein Core, polyprotein, virus protein VP1, virus protein VP2, virus protein VP3, virus protein VP4, antigen G, protein NS3, protein NS5A, (Hepatitis C Virus, Hepatitis C); virus protein VP1, virus protein VP2, virus protein VP3, virus protein VP4, large hepatitis delta antigen, small hepatitis delta antigen (Hepatitis D Virus, Hepatitis D); virus protein VP1, virus protein VP2, virus protein VP3, virus protein VP4, capsid protein E2 (Hepatitis E Virus, Hepatitis E); glycoprotein L UL1, uracil-DNA glycosylase UL2, protein UL3, protein UL4, DNA replication protein UL5, portal protein UL6, virion maturation protein UL7, DNA helicase UL8, replication origin-binding protein UL9, glycoprotein M UL10, protein UL11, alkaline exonuclease UL12, serine-threonine protein kinase UL13, tegument protein UL14, terminase UL15, tegument protein UL16, protein UL17, capsid protein VP23 UL18, major capsid protein VP5 UL19, membrane protein UL20, tegument protein UL21, Glycoprotein H (UL22), Thymidine Kinase UL23, protein UL24, protein UL25, capsid protein P40 (UL26, VP24, VP22A), glycoprotein B (UL27), ICP18.5 protein (UL28), major DNA-binding protein ICP8 (UL29), DNA polymerase UL30, nuclear matrix protein UL31, envelope glycoprotein UL32, protein UL33, inner nuclear membrane protein UL34, capsid protein VP26 (UL35), large tegument protein UL36, capsid assembly protein UL37, VP19C protein (UL38), ribonucleotide reductase (Large subunit) UL39, ribonucleotide reductase (Small subunit) UL40, tegument protein/virion host shutoff VHS protein (UL41), DNA polymerase processivity factor UL42, membrane protein UL43, glycoprotein C (UL44), membrane protein UL45, tegument proteins VP11/12 (UL46), tegument protein VP13/14 (UL47), virion maturation protein VP16 (UL48, Alpha-TIF), envelope protein UL49, dUTP diphosphatase UL50, tegument protein UL51, DNA helicase/primase complex protein UL52, glycoprotein K (UL53), transcriptional regulation protein IE63 (ICP27, UL54), protein UL55, protein UL56, viral replication protein ICP22 (IE68, US1), protein US2, serine/threonine-protein kinase US3, glycoprotein G (US4), glycoprotein J (US5), glycoprotein D (US6), glycoprotein I (US7), glycoprotein E (US8), tegument protein US9, capsid/tegument protein US10, Vmw21 protein (US11), ICP47 protein (IE12, US12), major transcriptional activator ICP4 (IE175, RS1), E3 ubiquitin ligase ICPO (IE110), latency-related protein 1 LRP1, latency-related protein 2 LRP2, neurovirulence factor RL 1 (ICP34.5), latency-associated transcript LAT (Herpes simplex virus 1 and 2 (HSV-1 and HSV-2), Herpes simplex); heat shock protein Hsp60, cell surface protein HIC, dipeptidyl peptidase type IV DppIV, M antigen, 70 kDa protein, 17 kDa histone-like protein (*Histoplasma capsulatum*, Histoplasmosis); fatty acid and retinol binding protein-1 FAR-1, tissue inhibitor of metalloproteinase TIMP (TMP), cysteine proteinase ACEY-1, cysteine proteinase ACCP-1, surface antigen Ac-16, secreted protein 2 ASP-2, metalloprotease 1 MTP-1, aspartyl protease inhibitor API-1, surface-associated antigen SAA-1, surface-associated antigen SAA-2, adult-specific secreted factor Xa, serine protease inhibitor anticoagulant AP, cathepsin D-like aspartic protease ARR-1, glutathione S-transferase GST, aspartic protease APR-1, acetylcholinesterase AChE (*Ancylostoma duodenale* and *Necator americanus*, Hookworm infection); protein NS1, protein NP1, protein VPI, protein VP2, protein VP3 (Human bocavirus (HBoV), Human bocavirus infection); major surface protein 2 MSP2, major surface protein 4 MSP4, MSP variant SGV1, MSP variant SGV2, outer membrane protein OMP, outer membrane protein 19 OMP-19, major antigenic protein MAP1, major antigenic protein MAP1-2, major antigenic protein MAPIB, major antigenic protein MAP1-3, Erum2510 coding protein, protein GroEL, protein GroES, 30-kDA major outer membrane proteins, GE 100-kDa protein, GE 130-kDa protein, GE 160-kDa protein (*Ehrlichia ewingii, Human ewingii* ehrlichiosis); major surface proteins 1-5 (MSP1a, MSP1b, MSP2, MSP3, MSP4, MSP5), type IV secreotion system proteins VirB2, VirB7, VirB11, VirD4 (*Anaplasma phagocytophilum*, Human granulocytic anaplasmosis (HGA)); protein NS1, small hydrophobic protein NS2, SH protein, fusion protein F, glycoprotein G, matrix protein M, matrix protein M2-1, matrix protein M2-2, phosphoprotein P, nucleoprotein N, polymerase L (Human metapneumovirus (hMPV), Human metapneumovirus infection); major surface protein 2 MSP2, major surface protein 4 MSP4, MSP variant SGV1, MSP variant SGV2, outer membrane protein OMP, outer membrane protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein (*Ehrlichia chaffeensis*, Human monocytic ehrlichiosis); replication protein E1, regulatory protein E2, protein E3, protein E4, protein E5, protein E6, protein E7, protein E8, major capsid protein L1, minor capsid protein L2 (Human papillomavirus (HPV), Human papillomavirus (HPV) infection); fusion protein F, hemagglutinin-neuramidase HN, glycoprotein G, matrix protein M, phosphoprotein P, nucleoprotein N, polymerase L (Human parainfluenza viruses (HPIV), Human parainfluenza virus infection); Hemagglutinin (HA), Neuraminidase (NA), Nucleoprotein (NP), M1 protein, M2 protein, NS1 protein, NS2 protein (NEP protein: nuclear export protein), PA protein, PB1 protein (polymerase basic 1 protein), PB1-F2 protein and PB2 protein (Orthomyxoviridae family, Influenza virus (flu)); genome polyprotein, protein E, protein M, capsid protein C (Japanese encephalitis virus, Japanese encephalitis); RTX toxin, type IV pili, major pilus subunit PilA, regulatory transcription factors PilS and PilR, protein sigma54, outer membrane proteins (Kingella kingae, Kingella kingae infection); prion protein (Kuru prion, Kuru); nucleoprotein N, polymerase L, matrix protein Z, glycoprotein GP (Lassa virus, Lassa fever); peptidoglycan-associated lipoprotein PAL, 60 kDa chaperonin Cpn60 (groEL, HspB), type IV pilin PilE, outer membrane protein MIP, major outer membrane protein MompS, zinc metalloproteinase MSP (*Legionella pneumophila*, Legionellosis (Legionnaires' disease, Pontiac fever)); P4 nuclease, protein WD, ribonucleotide reductase M2, surface membrane glycoprotein Pg46, cysteine proteinase CP, glucose-regulated protein 78 GRP-78, stage-specific S antigen-like protein A2, ATPase F1, beta-tubulin, heat shock protein 70 Hsp70, KMP-11, glycoprotein GP63, protein BT1, nucleoside hydrolase NH, cell surface protein B1, ribosomal protein P1-like protein P1, sterol 24-c-methyltransferase SMT, LACK protein, histone H1, SPB1 protein, thiol specific antioxidant TSA, protein antigen STIl, signal peptidase SP, histone H2B, surface antigen PSA-2, cystein proteinase b Cpb (*Leishmania* genus, Leishmaniasis); major membrane protein I, serine-rich antigen-45 kDa, 10 kDa caperonin GroES, HSP kDa antigen, amino-oxononanoate synthase AONS, protein recombinase A RecA, Acetyl-/propionyl-coenzyme A carboxylase alpha, alanine racemase, 60 kDa chaperonin 2, ESAT-6-like protein EcxB (L-ESAT-6), protein Lsr2, protein ML0276, Heparin-binding hemagglutinin HBHA, heat-shock protein 65 Hsp65, mycPI or ML0041 coding protein, htrA2 or ML0176 coding protein, htrA4 or ML2659 coding protein, gcp or ML0379 coding protein, clpC or ML0235 coding protein (*Mycobacterium leprae* and *Mycobacterium* lepromatosis, Leprosy); outer membrane protein LipL32, membrane protein LIC10258, membrane protein LP30, membrane protein LIC12238, Ompa-like protein Lsa66, surface protein LigA, surface protein LigB, major outer membrane protein OmpL1, outer membrane protein LipL41, protein LigAni, surface protein LcpA, adhesion protein LipL53, outer membrane protein UpL32, surface protein Lsa63, flagellin FlaB1, membran lipoprotein LipL21, membrane protein pL40, leptospiral surface adhesin Lsa27, outer membrane protein OmpL36, outer membrane protein OmpL37, outer membrane protein OmpL47, outer membrane protein OmpL54, acyltransferase LpxA (Leptospira genus, Leptospirosis); listeriolysin O precursor My (LLO), invasion-associated protein Iap (P60), Listeriolysin regulatory protein PrfA, Zinc metalloproteinase Mpl, Phosphatidylinositol-specific phospholipase C PLC (PicA, PlcB), O-acetyltransferase Oat, ABC-transporter permease Im.G_1771, adhesion protein LAP, LAP receptor Hsp60, adhesin LapB, haemolysin listeriolysin O LLO, protein ActA, Internalin A InlA, protein InlB (*Listeria monocytogenes*, Listeriosis); outer surface protein A OspA, outer surface protein OspB, outer surface protein OspC, decorin binding protein A DbpA, decorin binding protein B DbpB, flagellar filament 41 kDa core protein Fla, basic membrane protein A BmpA (Immunodominant antigen P39), outer surface 22 kDa lipoprotein precursor (antigen IPLA7), variable surface lipoprotein vlsE (usually *Borrelia burgdorferi* and other *Borrelia* species, Lyme disease (Lyme borreliosis)); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, Secreted Larval Acidic Proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, protein Cox-2 (*Wuchereria bancrofti* and *Brugia malayi*, Lymphatic filariasis (Elephantiasis)); glycoprotein GP, matrix protein Z, polymerase L, nucleoprotein N (Lymphocytic choriomeningitis virus (LCMV), Lymphocytic choriomeningitis); thrombospondin-related anonymous protein TRAP, SSP2 Sporozoite surface protein 2, apical membrane antigen 1 AMA1, rhoptry membrane antigen RMA1, acidic basic repeat antigen ABRA, cell-traversal protein PF, protein Pvs25, merozoite surface protein 1 MSP-1, merozoite surface protein 2 MSP-2, ring-infected erythrocyte surface antigen RESALiver stage antigen 3 LSA-3, protein Eba-175, serine repeat antigen 5 SERA-5, circumsporozoite protein CS, merozoite surface protein 3 MSP3, merozoite surface protein 8 MSP8, enolase PF10, hepatocyte erythrocyte protein 17 kDa HEP17, erythrocyte membrane protein 1 EMP1, protein Kbetamerozoite surface protein 4/5 MSP 4/5, heat shock protein Hsp90, glutamate-rich protein GLURP, merozoite surface protein 4 MSP-4, protein STARP, circumsporozoite protein-related antigen precursor CRA (*Plasmodium* genus, Malaria); nucleoprotein N, membrane-associated protein VP24, minor nucleoprotein VP30, polymerase cofactor VP35, polymerase L, matrix protein VP40, envelope glycoprotein GP (Marburg virus, Marburg hemorrhagic fever (MHF)); protein C, matrix protein M, phosphoprotein P, non-structural protein V, hemagglutinin glycoprotein H, polymerase L, nucleoprotein N, fusion protein F (Measles virus, Measles); members of the ABC transporter family (LolC, OppA, and PotF), putative lipoprotein releasing system transmembrane protein LolC/E, flagellin FliC, *Burkholderia* intracellular motility A BimA, bacterial Elongation factor-Tu EF-Tu, 17 kDa OmpA-like protein, boaA coding protein, boaB coding protein (*Burkholderia pseudomallei*, Melioidosis (Whitmore's disease)); pilin proteins, minor pilin-associated subunit pilC, major pilin subunit and variants pilE, pilS, phase variation protein porA, Porin B PorB, protein TraD, Neisserial outer membrane antigen H.8, 70 kDa antigen, major outer membrane protein PI, outer membrane proteins PIA and PIB, W antigen, surface protein A NspA, transferrin binding protein TbpA, transferrin binding protein TbpB, PBP2, mtrR coding protein, ponA coding protein, membrane permease FbpBC, FbpABC protein system, LbpAB proteins, outer membrane protein Opa, outer membrane transporter FetA, iron-repressed regulator MpeR, factor H-binding protein fHbp, adhesin NadA, protein NhbA, repressor FarR (*Neisseria meningitidis*, Meningococcal disease); 66 kDa protein, 22 kDa protein (usually *Metagonimus yokagawai*, Metagonimiasis); polar tube proteins (34, 75, and 170 kDa in Glugea, 35, 55 and 150 kDa in Encephalitozoon), kinesin-related protein, RNA polymerase II largest subunit, similar to integral membrane protein YIPA, anti-silencing protein 1, heat shock transcription factor HSF, protein kinase, thymidine kinase, NOP-2 like nucleolar protein (Microsporidia phylum, Microsporidiosis); CASP8 and FADD-like apoptosis regulator, Glutathione peroxidase GPX1, RNA helicase NPH-II NPH2, Poly(A) polymerase catalytic subunit PAPL, Major envelope protein P43K, early transcription factor 70 kDa subunit VETFS, early transcription factor 82 kDa subunit VETFL, metalloendopeptidase Gi-type, nucleoside triphosphatase I NPH1, replication protein A28-like MC134L, RNA polymease 7 kDa subunit RPO7 (Molluscum contagiosum virus (MCV), Molluscum contagiosum (MC)); matrix protein M, phosphoprotein PN, small hydrophobic protein SH, nucleoprotein N, protein V, fusion glycoprotein F, hemagglutinin-neuraminidase HN, RNA polymerase L (Mumps virus, Mumps); Outer membrane proteins OM, cell surface antigen OmpA, cell surface antigen OmpB (sca5), cell surface protein SCA4, cell surface protein SCA1, intracytoplasmic protein D, crystalline surface layer protein SLP, protective surface protein antigen SPA (*Rickettsia typhi*, Murine typhus (Endemic typhus)); adhesin P1, adhesion P30, protein p116, protein P40, cytoskeletal protein HNMW1, cytoskeletal protein HMW2, cytoskeletal protein HMW3, MPN152 coding protein, MPN426 coding protein, MPN456 coding protein, MPN-500 coding protein (*Mycoplasma pneumoniae, Mycoplasma* pneumonia); NocA, Iron dependent regulatory protein, VapA, VapD, VapF, VapG, caseinolytic protease, filament tip-associated 43-kDa protein, protein P24, protein P61, 15-kDa protein, 56-kDa protein (usually *Nocardia asteroides* and other *Nocardia* species, Nocardiosis); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, Thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, Secreted Larval Acidic Proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, Cox-2 (*Onchocerca volvulus*, Onchocerciasis (River blindness)); 43 kDa secreted glycoprotein, glycoprotein gp0, glycoprotein gp75, antigen Pb27, antigen Pb40, heat shock protein Hsp65, heat shock protein Hsp70, heat shock protein Hsp90, protein P10, triosephosphate isomerase TPI, N-acetyl-glucosamine-binding lectin Paracoccin, 28 kDa protein Pb28 (*Paracoccidioides brasiliensis*, Paracoccidioidomycosis (South American blastomycosis)); 28-kDa cruzipain-like cystein protease Pw28CCP (usually *Paragonimus westermani* and other *Paragonimus* species, Paragonimiasis); outer membrane protein OmpH, outer membrane protein Omp28, protein PM1539, protein PM0355, protein PM1417, repair protein MutL, protein BcbC, prtein PM0305, formate dehydrogenase-N, protein PM0698, protein PM1422, DNA gyrase, lipoprotein PlpE, adhesive protein Cp39, heme aquisition system receptor HasR, 39 kDa capsular protein, iron-regulated OMP IROMP, outer membrane protein OmpA87, fimbrial protein Ptf, fimbrial subunit protein PtfA, transferrin binding protein Tbpl, esterase enzyme MesA, *Pasteurella multocida* toxin PMT, adhesive protein Cp39 (*Pasteurella* genus, Pasteurellosis); "filamentous hemagglutinin FhaB, adenylate cyclase CyaA, pertussis toxin subunit 4 precursor PtxD, pertactin precursor Prn, toxin subunit 1 PtxA, protein Cpn60, protein brkA, pertussis toxin subunit 2 precursor PtxB, pertussis toxin subunit 3 precursor PtxC, pertussis toxin subunit 5 precursor PtxE, pertactin Prn, protein Fim2, protein Fim3; "(*Bordetella pertussis*, Pertussis (Whooping cough)); "F1 capsule antigen, virulence-associated V antigen, secreted effector protein LcrV, V antigen, outer membrane protease Pla, secreted effector protein YopD, putative secreted protein-tyrosine phosphatase YopH, needle complex major subunit YscF, protein kinase YopO, putative autotransporter protein YapF, inner membrane ABC-transporter YbtQ (Irp7), putative sugar binding protein YP00612, heat shock protein 90 HtpG, putative sulfatase protein YdeN, outer-membrane lipoprotein carrier protein LolA, secretion chaperone YerA, putative lipoprotein YP00420, hemolysin activator protein HpmB, pesticin/yersiniabactin outer membrane receptor Psn, secreted effector protein YopE, secreted effector protein YopF, secreted effector protein YopK, outer membrane protein YopN, outer membrane protein YopM, Coagulase/fibrinolysin precursor Pla; "(*Yersinia pestis*, Plague); protein PhpA, surface adhesin PsaA, pneumolysin Ply, ATP-dependent protease Clp, lipoate-protein ligase LplA, cell wall surface anchored protein psrP, sortase SrtA, glutamyl-tRNA synthetase GltX, choline binding protein A CbpA, pneumococcal surface protein A PspA, pneumococcal surface protein C PspC, 6-phosphogluconate dehydrogenase Gnd, iron-binding protein PiaA, Murein hydrolase LytB, proteon LytC, protease A1 (*Streptococcus pneumoniae*, Pneumococcal infection); major surface protein B, kexin-like protease KEX1, protein A12, 55 kDa antigen P55, major surface glycoprotein Msg (*Pneumocystis jirovecii, Pneumocystis* pneumonia (PCP)); genome polyprotein, polymerase 3D, viral capsid protein VP1, viral capsid protein VP2, viral capsid protein VP3, viral capsid protein VP4, protease 2A, protease 3C (Poliovirus, Poliomyelitis); protein Nfa1, exendin-3, secretory lipase, cathepsin B-like protease, cysteine protease, cathepsin, peroxiredoxin, protein Cry1Ac (usually *Naegleria fowleri*, Primary amoebic meningoencephalitis (PAM)); agnoprotein, large T antigen, small T antigen, major capsid protein VP1, minor capsid protein Vp2 (JC virus, Progressive multifocal leukoencephalopathy); low calcium response protein E LCrE, chlamydial outer protein N CopN, serine/threonine-protein kinase PknD, acyl-carrier-protein S-malonyltransferase FabD, single-stranded DNA-binding protein Ssb, major outer membrane protein MOMP, outer membrane protein 2 Omp2, polymorphic membrane protein family (Pmpl, Pmp2, Pmp3, Pmp4, Pmp5, Pmp6, Pmp7, Pmp8, Pmp9, Pmp10, Pmp11, Pmp12, Pmp13, Pmp14, Pmp15, Pmp16, Pmp17, Pmp18, Pmp19, Pmp20, Pmp21) (*Chlamydophila psittaci*, Psittacosis); outer membrane protein P1, heat shock protein B HspB, peptide ABC transporter, GTP-binding protein, protein IcmB, ribonuclease R, phosphatas SixA, protein DsbD, outer membrane protein TolC, DNA-binding protein PhoB, ATPase DotB, heat shock protein B HspB, membrane protein Com1, 28 kDa protein, DNA-3-methyladenine glycosidase I, pouter membrane protein OmpH, outer membrane protein AdaA, glycine cleavage system T-protein (*Coxiella burnetii*, Q fever); nucleoprotein N, large structural protein L, phophoprotein P, matrix protein M, glycoprotein G (Rabies virus, Rabies); fusionprotein F, nucleoprotein N, matrix protein M, matrix protein M2-1, matrix protein M2-2, phophoprotein P, small hydrophobic protein SH, major surface glycoprotein G, polymerase L, non-structural protein 1 NS1, non-structural protein 2 NS2 (Respiratory syncytial virus (RSV), Respiratory syncytial virus infection); genome polyprotein, polymerase 3D, viral capsid protein VP1, viral capsid protein VP2, viral capsid protein VP3, viral capsid protein VP4, protease 2A, protease 3C (Rhinovirus, Rhinovirus infection); outer membrane proteins OM, cell surface antigen OmpA, cell surface antigen OmpB (sca5), cell surface protein SCA4, cell surface protein SCA1, protein PS120, intracytoplasmic protein D, protective surface protein antigen SPA (*Rickettsia* genus, Rickettsial infection); outer membrane proteins OM, cell surface antigen OmpA, cell surface antigen OmpB (sca5), cell surface protein SCA4, cell surface protein SCA1, intracytoplasmic protein D (*Rickettsia akari*, Rickettsialpox); envelope glycoprotein GP, polymerase L, nucleoprotein N, non-structural protein NSS (Rift Valley fever virus, Rift Valley fever (RVF)); outer membrane proteins OM, cell surface antigen OmpA, cell surface antigen OmpB (sca5), cell surface protein SCA4, cell surface protein SCA1, intracytoplasmic protein D (*Rickettsia rickettsii*, Rocky mountain spotted fever (RMSF)); non-structural protein 6 NS6, non-structural protein 2 NS2, intermediate capsid protein VP6, inner capsid protein VP2, non-structural protein 3 NS3, RNA-directed RNA polymerase L, protein VP3, non-structural protein 1 NS1, non-structural protein 5 NS5, outer capsid glycoprotein VP7, non-structural glycoprotein 4 NS4, outer capsid protein VP4; (Rotavirus, Rotavirus infection); polyprotein P200, glycoprotein E1, glycoprotein E2, protein NS2, capsid protein C (Rubella virus, Rubella); chaperonin GroEL (MopA), inositol phosphate phosphatase SopB, heat shock protein HslU, chaperone protein DnaJ, protein TviB, protein IroN, flagellin FliC, invasion protein SipC, glycoprotein gp43, outer membrane protein LamB, outer membrane protein PagC, outer membrane protein TolC, outer membrane protein NmpC, outer membrane protein FadL, transport protein SadA, transferase WgaP, effector proteins SifA, SteC, SseL, SseJ and SseF (*Salmonella* genus, *Salmonellosis*); "protein 14, non-structural protein NS7b, non-structural protein NS8a, protein 9b, protein 3a, nucleoprotein N, non-structural protein NS3b, non-structural protein NS6, protein 7a, non-structural protein NS8b, membrane protein M, envelope small membrane protein EsM, replicase polyprotein 1a, spike glycoprotein S, replicase polyprotein lab; SARS coronavirus, SARS (Severe Acute Respiratory Syndrome)); serin protease, Atypical *Sarcoptes* Antigen 1 ASA1, glutathione S-transferases GST, cystein protease, serine protease, apolipoprotein (*Sarcoptes scabiei*, Scabies); glutathione S-transferases GST, paramyosin, hemoglbinase SM32, major egg antigen, 14 kDa fatty acid-binding protein Sm14, major larval surface antigen P37, 22.6 kDa tegumental antigen, calpain CANP, triphospate isomerase Tim, surface protein 9B, outer capsid protein VP2, 23 kDa integral membrane protein Sm23, Cu/Zn-superoxide dismutase, glycoprotein Gp, myosin (*Schistosoma* genus, Schistosomiasis (Bilharziosis)); 60 kDa chaperonin, 56 kDa type-specific antigen, pyruvate phosphate dikinase, 4-hydroxybenzoate octaprenyltransferase (Orientia tsutsugamushi, Scrub typhus); dehydrogenase GuaB, invasion protein Spa32, invasin IpaA, invasin IpaB, invasin IpaC, invasin IpaD, invasin IpaH, invasin IpaJ (*Shigella* genus, Shigellosis (Bacillary dysentery)); protein P53, virion protein US10 homolog, transcriptional regulator IE63, transcriptional transactivator IE62, protease P33, alpha trans-inducing factor 74 kDa protein, deoxyuridine 5'-triphosphate nucleotidohydrolase, transcriptional transactivator IE4, membrane protein UL43 homolog, nuclear phosphoprotein UL3 homolog, nuclear protein UL4 homolog, replication origin-binding protein, membrane protein 2, phosphoprotein 32, protein 57, DNA polymerase processivity factor, portal protein 54, DNA primase, tegument protein UL14 homolog, tegument protein UL21 homolog, tegument protein UL55 homolog, tripartite terminase subunit UL33 homolog, tripartite terminase subunit UL15 homolog, capsid-binding protein 44, virion-packaging protein 43 (Varicella zoster virus (VZV), Shingles (Herpes zoster)); truncated 3-beta hydroxy-5-ene steroid dehydrogenase homolog, virion membrane protein A13, protein A19, protein A31, truncated protein A35 homolog, protein A37.5 homolog, protein A47, protein A49, protein A51, semaphorin-like protein A43, serine proteinase inhibitor 1, serine proteinase inhibitor 2, serine proteinase inhibitor 3, protein A6, protein B15, protein C1, protein C5, protein C6, protein F7, protein F8, protein F9, protein F11, protein F14, protein F15, protein F16 (Variola major or Variola minor, Smallpox (Variola)); adhesin/glycoprotein gp70, proteases (*Sporothrix schenckii*, Sporotrichosis); heme-iron binding protein IsdB, collagen adhesin Cna, clumping factor A ClfA, protein MecA, fibronectin-binding protein A FnbA, enterotoxin type A EntA, enterotoxin type B EntB, enterotoxin type C EntC1, enterotoxin type C EntC2, enterotoxin type D EntD, enterotoxin type E EntE, Toxic shock syndrome toxin-1 TSST-1, Staphylokinase, Penicillin binding protein 2a PBP2a (MecA), secretory antigen SssA (*Staphylococcus* genus, Staphylococcal food poisoning); heme-iron binding protein IsdB, collagen adhesin Cna, clumping factor A ClfA, protein MecA, fibronectin-binding protein A FnbA, enterotoxin type A EntA, enterotoxin type B EntB, enterotoxin type C EntC1, enterotoxin type C EntC2, enterotoxin type D EntD, enterotoxin type E EntE, Toxic shock syndrome toxin-1 TSST-1, Staphylokinase, Penicillin binding protein 2a PBP2a (MecA), secretory antigen SssA (*Staphylococcus* genus e.g. *aureus*, Staphylococcal infection); antigen Ss-IR, antigen NIE, strongylastacin, Na+-K+ ATPase Sseat-6, tropomysin SsTmy-1, protein LEC-5, 41 kDa aantigen P5, 41-kDa larval protein, 31-kDa larval protein, 28-kDa larval protein (*Strongyloides stercoralis*, Strongyloidiasis); glycerophosphodiester phosphodiesterase GlpQ (Gpd), outer membrane protein TmpB, protein Tp92, antigen TpF1, repeat protein Tpr, repeat protein F TprF, repeat protein G TprG, repeat protein I TprI, repeat protein J TprJ, repeat protein K TprK, treponemal membrane protein A TmpA, lipoprotein, 15 kDa Tpp15, 47 kDa membrane antigen, miniferritin TpF1, adhesin Tp0751, lipoprotein TP0136, protein TpN17, protein TpN47, outer membrane protein TP0136, outer membrane protein TP0155, outer membrane protein TP0326, outer membrane protein TP0483, outer membrane protein TP0956 (*Treponema pallidum*, Syphilis); Cathepsin L-like proteases, 53/25-kDa antigen, 8 kDa family members, cysticercus protein with a marginal trypsin-like activity TsAg5, oncosphere protein TSOL18, oncosphere protein TSOL45-1A, lactate dehydrogenase A LDHA, lactate dehydrogenase B LDHB (*Taenia* genus, Taeniasis); tetanus toxin TetX, tetanus toxin C TTC, 140 kDa S layer protein, flavoprotein beta-subunit CT3, phospholipase (lecithinase), phosphocarrier protein HPr (*Clostridium tetani*, Tetanus (Lockjaw)); genome polyprotein, protein E, protein M, capsid protein C (Tick-borne encephalitis virus (TBEV), Tick-borne encephalitis); 58-kDa antigen, 68-kDa antigens, *Toxocara* larvae excretory-secretory antigen TES, 32-kDa glycoprotein, glycoprotein TES-70, glycoprotein GP31, excretory-secretory antigen TcES-57, perienteric fluid antigen Pe, soluble extract antigens Ex, excretory/secretory larval antigens ES, antigen TES-120, polyprotein allergen TBA-1, cathepsin L-like cysteine protease c-cpl-1, 26-kDa protein (*Toxocara canis* or *Toxocara cati*, Toxocariasis (Ocular Larva Migrans (OLM) and Visceral Larva Migrans (VLM))); microneme proteins (MIC1, MIC2, MIC3, MIC4, MIC5, MIC6, MIC7, MIC8), rhoptry protein Rop2, rhoptry proteins (Rop1, Rop2, Rop3, Rop4, Rop5, Rop6, Rop7, Rop16, Rjop17), protein SRi, surface antigen P22, major antigen p24, major surface antigen p30, dense granule proteins (GRA1, GRA2, GRA3, GRA4, GRA5, GRA6, GRA7, GRA8, GRA9, GRA10), 28 kDa antigen, surface antigen SAG1, SAG2 related antigen, nucleoside-triphosphatase 1, nucleoside-triphosphatase 2, protein Stt3, HesB-like domain-containing protein, rhomboid-like protease 5, toxomepsin 1 (*Toxoplasma gondii*, Toxoplasmosis); 43 kDa secreted glycoprotein, 53 kDa secreted glycoprotein, paramyosin, antigen Ts21, antigen Ts87, antigen p46000, TSL-1 antigens, caveolin-1 CAV-1, 49 kDa newborn larva antigen, prosaposin homologue, serine protease, serine proteinase inhibitor, 45-kDa glycoprotein Gp45 (*Trichinella spiralis*, Trichinellosis); Myb-like transcriptional factors (Myb1, Myb2, Myb3), adhesion protein AP23, adhesion protein AP33, adhesin protein AP33-3, adhesins AP51, adhesin AP65, adhesion protein AP65-1, alpha-actinin, kinesin-associated protein, teneurin, 62 kDa proteinase, subtilisin-like serine protease SUB1, cysteine proteinase gene 3 CP3, alpha-enolase Enol, cysteine proteinase CP30, heat shock proteins (Hsp70, Hsp60), immunogenic protein P270, (*Trichomonas vaginalis*, Trichomoniasis); beta-tubulin, 47-kDa protein, secretory leucocyte-like proteinase-1 SLP-1, 50-kDa protein TT50, 17 kDa antigen, 43/47 kDa protein (*Trichuris trichiura*, Trichuriasis (Whipworm infection)); protein ESAT-6 (EsxA), 10 kDa filtrate antigen EsxB, secreted antigen 85-B FBPB, fibronectin-binding protein A FbpA (Ag85A), serine protease PepA, PPE family protein PPE18, fibronectin-binding protein D FbpD, immunogenic protein MPT64, secreted protein MPT51, catalase-peroxidase-peroxynitritase T KATG, periplasmic phosphate-binding lipoprotein PSTS3 (PBP-3, Phos-1), iron-regulated heparin binding hemagglutinin Hbha, PPE family protein PPE14, PPE family protein PPE68, protein Mtb72F, protein Apa, immunogenic protein MPT63, periplasmic phosphate-binding lipoprotein PSTS1 (PBP-1), molecular chaperone DnaK, cell surface lipoprotein Mpt83, lipoprotein P23, phosphate transport system permease protein pstA, 14 kDa antigen, fibronectin-binding protein C FbpCI, Alanine dehydrogenase TB43, Glutamine synthetase 1, ESX-1 protein, protein CFP10, TB10.4 protein, protein MPT83, protein MTB12, protein MTB8, Rpf-like proteins, protein MTB32, protein MTB39, crystallin, heat-shock protein HSP65, protein PST-S(usually *Mycobacterium tuberculosis*, Tuberculosis); outer membrane protein FobA, outer membrane protein FobB, intracellular growth locus IglC1, intracellular growth locus IglC2, aminotransferase Wbt1, chaperonin GroEL, 17 kDa major membrane protein TUL4, lipoprotein LpnA, chitinase family 18 protein, isocitrate dehydrogenase, Nif3 family protein, type IV pili glycosylation protein, outer membrane protein tolC, FAD binding family protein, type IV pilin multimeric outer membrane protein, two component sensor protein KdpD, chaperone protein DnaK, protein ToIQ (*Francisella tularensis*, Tularemia); "MB antigen, urease, protein GyrA, protein GyrB, protein ParC, protein ParE, lipid associated membrane proteins LAMP, thymidine kinase TK, phospholipase PL-A1, phospholipase PL-A2, phospholipase PL-C, surface-expressed 96-kDa antigen; "(*Ureaplasma urealyticum, Ureaplasma urealyticum* infection); non-structural polyprotein, structural polyprotein, capsid protein CP, protein E1, protein E2, protein E3, protease P1, protease P2, protease P3 (Venezuelan equine encephalitis virus, Venezuelan equine encephalitis); glycoprotein GP, matrix protein Z, polymerase L, nucleoprotein N (Guanarito virus, Venezuelan hemorrhagic fever); polyprotein, protein E, protein M, capsid protein C, protease NS3, protein NS1, protein NS2A, protein AS2B, protein NS4A, protein NS4B, protein NS5 (West Nile virus, West Nile Fever); capsid protein CP, protein E1, protein E2, protein E3, protease P2 (Western equine encephalitis virus, Western equine encephalitis); genome polyprotein, protein E, protein M, capsid protein C, protease NS3, protein NS1, protein NS2A, protein AS2B, protein NS4A, protein NS4B, protein NS5 (Yellow fever virus, Yellow fever); putative Yop targeting protein YobB, effector protein YopD, effector protein YopE, protein YopH, effector protein YopJ, protein translocation protein YopK, effector protein YopT, protein YpkA, flagellar biosyntheses protein FlhA, peptidase M48, potassium efflux system KefA, transcriptional regulatoer RovA, adhesin Ifp, translocator portein LcrV, protein PcrV, invasin Inv, outer membrane protein OmpF-like porin, adhesin YadA, protein kinase C, phospholipase C1, protein PsaA, mannosyltransferase-like protein WbyK, protein YscU, antigen YPMa (*Yersinia pseudotuberculosis, Yersinia pseudotuberculosis* infection); effector protein YopB, 60 kDa chaperonin, protein WbcP, tyrosin-protein phosphatase YopH, protein YopQ, enterotoxin, Galactoside permease, reductaase NrdE, protein YasN, Invasin Inv, adhesin YadA, outer membrane porin F OmpF, protein UspAI, protein EibA, protein Hia, cell surface protein Ail, chaperone SycD, protein LcrD, protein LcrG, protein LcrV, protein SycE, protein YopE, regulator protein TyeA, protein YopM, protein YopN, protein YopO, protein YopT, protein YopD, protease ClpP, protein MyfA, protein FilA, and protein PsaA (*Yersinia enterocolitica*, Yersiniosis).

The brackets in the preceding section indicate the particular pathogen or the family of pathogens of which the antigen(s) is/are derived and the infectious disease with which the pathogen is associated.

In a particularly preferred embodiment of the first aspect of the invention the mRNA compound comprises a mRNA sequence comprises a coding region, encoding at least one antigenic peptide or protein derived from hemagglutinin (HA), neuraminidase (NA), nucleoprotein (NP), matrix protein 1 (M1), matrix protein 2 (M2), non-structural protein 1 (NS1), non-structural protein 2 (NS2), nuclear export protein (NEP), polymerase acidic protein (PA), polymerase basic protein PB1, PB1-F2, or polymerase basic protein 2 (PB2) of an influenza virus or a fragment or variant thereof.

In this context, the amino acid sequence of the at least one antigenic peptide or protein may be selected from any peptide or protein derived from hemagglutinin (HA), neuraminidase (NA), nucleoprotein (NP), matrix protein 1 (M1), matrix protein 2 (M2), non-structural protein 1 (NS1), non-structural protein 2 (NS2), nuclear export protein (NEP), polymerase acidic protein (PA), polymerase basic protein PB1, PB1-F2, or polymerase basic protein 2 (PB2) of an influenza virus or a fragment or variant or from any synthetically engineered influenza virus peptide or protein.

In a preferred embodiment of the invention the coding region encodes at least one antigenic peptide or protein derived from hemagglutinin (HA) and/or neuraminidase (NA) of an influenza virus or a fragment or variant thereof. In this context the hemagglutinin (HA) and the neuraminidase (NA) may be chosen from the same influenza virus or from different influenza viruses.

In this context it is particularly preferred that the at least one coding region encodes at least one full-length protein of hemagglutinin (HA), neuraminidase (NA), nucleoprotein (NP), matrix protein 1 (M1), matrix protein 2 (M2), non-structural protein 1 (NS1), non-structural protein 2 (NS2), nuclear export protein (NEP), polymerase acidic protein (PA), polymerase basic protein PB1, PB1-F2, or polymerase basic protein 2 (PB2) of an influenza virus or a variant thereof.

In particularly preferred embodiments the at least one coding region encodes at least one full-length protein of hemagglutinin (HA), and/or at least one full-length protein of neuraminidase (NA) of an influenza virus or a variant thereof.

The term "full-length protein" as used herein typically refers to a protein that substantially comprises the entire amino acid sequence of the naturally occurring protein.

In specific embodiments the influenza virus peptide or protein is derived from an influenza A, B or C virus (strain).

In specific embodiments the virus peptide or protein is derived from a coronavirus, for example, SARS-CoV-1, SARS-CoV-2, MERS, etc. (strain).

The influenza A virus may be selected from influenza A viruses characterized by a hemagglutinin (HA) selected from the group consisting of H1, H2, H3, H4, H5, H6, H7, H8, H9, H10, H11, H12, H13, H14, H15, H16, H17 and H18. Preferably the influenza A virus is selected from an influenza virus characterized by a hemagglutinin (HA) selected from the group consisting of H1, H3, H5 or H9.

Furthermore, particularly preferred are influenza A viruses characterized by a neuraminidase (NA) selected from the group consisting of N1, N2, N3, N4, N5, N6, N7, N8, N9, N10, and N11. Most preferably the influenza A virus is characterized by a neuraminidase (NA) selected from the group consisting of N1, N2, and N8.

In particularly preferred embodiments the influenza A virus is selected from the group consisting of H1N1, H1N2, H2N2, H3N1, H3N2, H3N8, H5N1, H5N2, H5N3, H5N8, H5N9, H7N1, H7N2, H7N3, H7N4, H7N7, H7N9, H9N2, H10N8, and H10N7, preferably from H1N1, H3N2, H5N1, and H5N8.

In this context it is particularly preferred that the at least one coding region of the inventive mRNA sequence encodes at least one antigenic peptide or protein derived from hemagglutinin (HA) and/or at least one antigenic peptide or protein derived from neuraminidase (NA) of an influenza A virus selected from the group consisting of H1N1, H1N2, H2N2, H3N1, H3N2, H3N8, H5N1, H5N2, H5N3, H5N8, H5N9, H7N1, H7N2, H7N3, H7N4, H7N7, H7N9, H9N2, H10N8 and H10N7, preferably from H1N1, H3N2, H5N1, H5N8 or a fragment or variant thereof.

In the context of the present invention a fragment of a protein or a variant thereof encoded by the at least one coding region of the mRNA sequence according to the invention may typically comprise an amino acid sequence having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with an amino acid sequence of the respective naturally occurring full-length protein or a variant thereof.

In specific embodiments the antigenic peptide or protein is derived from a hemagglutinin (HA) protein of an influenza A virus.

Furthermore, in this context the coding region encoding at least one antigenic peptide or protein derived from hemagglutinin (HA) and/or neuraminidase (NA) of an influenza virus or a fragment, variant or derivative thereof, may be selected from any nucleic acid sequence comprising a coding region encoding hemagglutinin (HA) or neuraminidase (NA) derived from any influenza virus isolate or a fragment or variant thereof.

In a particularly preferred embodiment of the first aspect of the invention the mRNA compound comprising an mRNA sequence comprises a coding region, encoding at least one antigenic peptide or protein derived from glycoprotein G of a Rabies virus or a fragment or variant thereof.

In this context, the amino acid sequence of the at least one antigenic peptide or protein may be selected from any peptide or protein derived from a glycoprotein of a Rabies virus or a fragment or variant or from any synthetically engineered Rabies virus peptide or protein.

In a preferred embodiment of the present invention the coding region encodes at least one antigenic peptide or protein derived from a glycoprotein of a Rabies virus or a fragment or variant thereof.

In this context it is particularly preferred that the at least one coding region encodes at least one full-length protein of a glycoprotein of a Rabies virus or a variant thereof.

As used herein, the term "full-length protein" preferably relates to the full-length sequence of protein indicated in the sequence listing of the present invention.

In this context it is further preferred that the at least one coding sequence of the mRNA sequence of the present invention encodes at least one antigenic peptide or protein which is derived from a glycoprotein of a Rabies virus, or a fragment or variant thereof.

Each glycoprotein of a Rabies virus is identified by the database accession number of the corresponding protein (see sequence listing numeric identifier <223> which indicates the Protein or Nucleic Acid Accession No. (GenBank)). If the respective Protein or Nucleic Acid Accession No. (GenBank) is searched further on in the sequence listing, the next SEQ ID NO: which show said Protein or Nucleic Acid Accession No. (GenBank) under numeric identifier <223> corresponding to the nucleic acid sequence of the wild type mRNA encoding said protein.

Furthermore, in this context the coding region encoding at least one antigenic peptide or protein derived from glycoprotein of a Rabies virus or a fragment, variant or derivative thereof, may be selected from any nucleic acid sequence comprising a coding region encoding glycoprotein derived from any Rabies virus isolate or a fragment or variant thereof.

Ebolaviruses and the genetically-related Marburgviruses are human pathogens that cause severe diseases. Ebolaviruses and Marburgviruses are filoviruses, which are enveloped viruses featuring a negative-stranded RNA genome. The family of Filoviridae comprises three genera: Ebolavirus, Marburgvirus and Cuevavirus. The genus of Cuevaviruses as well as Marburgviruses include only one species, i.e. Lloviu cuevavirus (Lloviu virus—LLOV) and Marburg marburgvirus, respectively, which is subdivided in Marburg virus (MARV) and Ravn virus (RAVV). The genus of Ebolaviruses comprises five known species, i.e. Bundibugyo ebolavirus (Bundibugyo virus—BDBV), Reston ebolavirus (Reston virus—RESTV), Sudan ebolavirus (Sudan virus—SUDV), Tai Forest ebolavirus (Tai Forest virus—TAFV) (=Côte d'Ivoire ebolavirus), and Zaire ebolavirus (Ebola virus—EBOV). While Cuevaviruses have been isolated from bats and their potential as a pathogen in humans remains unknown, both Ebolaviruses and Marburgviruses are human pathogens that cause Ebolavirus disease (EVD) and Marburgvirus disease, respectively, characterised by haemorrhagic fever and an extremely high mortality rate. In the context of the present invention, any virus, virus member, virus strain, virus type, virus sub-type, virus isolate, virus variant, or virus serotype or genetic reassortant of a virus belonging to or being related to or being derived from viruses of the families and genera listed above are considered to be a "Ebola virus".

In a particularly preferred embodiment of the first aspect of the invention the mRNA compound comprising an mRNA sequence comprises a coding region, encoding at least one antigenic peptide or protein derived from the glycoprotein (GP) and/or the matrix protein 40 (VP40) and/or the nucleoprotein (NP) of a virus of the genus Ebolavirus or Marburgvirus or a fragment, variant or derivative thereof.

In this context, the amino acid sequence of the at least one antigenic peptide or protein may be selected from any peptide or protein derived from glycoprotein (GP) and/or the matrix protein 40 (VP40) and/or the nucleoprotein (NP) a glycoprotein of an Ebola virus or a fragment or variant or from any synthetically engineered Ebola virus peptide or protein.

In a preferred embodiment of the present invention the coding region encodes at least one antigenic peptide or protein derived from a glycoprotein of an Ebola virus or a fragment or variant thereof. In this context it is particularly preferred that the at least one coding region encodes at least one full-length protein of a glycoprotein of an Ebola virus or a variant thereof.

In particularly preferred embodiments the mRNA sequence comprises at least one coding region encoding glycoprotein of a Ebola virus. In particularly preferred embodiments the mRNA sequence comprises at least one coding region encoding VP40 of a Ebola virus. In particularly preferred embodiments the mRNA sequence comprises at least one coding region encoding NP of a Ebola virus.

In particularly preferred embodiments the mRNA sequence comprises at least one coding region encoding an antigenic peptide or protein of an Ebola virus comprising an RNA sequence selected from the following RNA sequences:

mRNA encoding GP protein of Ebola virus: SEQ ID NOs: 37-39 of the patent application WO2016097065, or fragments or variants of these sequences. In this context, SEQ ID NOs: 37-39 of WO2016097065 and the disclosure relating to SEQ ID NOs: 37-39 of WO2016097065 are incorporated herein by reference.

mRNA encoding VP40 of Ebola virus: SEQ ID NOs: 40-42 of the patent application WO2016097065, or fragments or variants of these sequences. In this context, SEQ ID NOs: 40-42 of WO2016097065 and the disclosure relating to SEQ ID NOs: 40-42 of WO2016097065 are incorporated herein by reference.

mRNA encoding NP of Ebola virus: SEQ ID NOs: 43-44 of the patent application WO2016097065, or fragments or variants of these sequences. In this context, SEQ ID NOs: 43-44 of WO2016097065 and the disclosure relating to SEQ ID NOs: 43-44 of WO2016097065 are incorporated herein by reference.

V.9.3. Tumor Antigens

Preferably, the at least one coding sequence of the mRNA compound comprising an mRNA sequence according to the invention encodes a tumor antigen, preferably as defined herein, or a fragment or variant thereof, wherein the tumor antigen is preferably selected from the group consisting of 1A01_HLA-A/m; 1A02; 5T4; ACRBP; AFP; AKAP4; alpha-actinin-_4/m; alpha-methylacyl-coenzyme_A_racemase; ANDR; ART-4; ARTC1/m; AURKB; B2MG; B3GN5; B4GN1; B7H4; BAGE-1; BASI; BCL-2; bcr/abl; beta-catenin/m; BING-4; BIRC7; BRCA1/m; BY55; calreticulin; CAMEL; CASP-8/m; CASPA; cathepsin_B; cathepsin_L; CD1A; CD1B; CD1C; CD1D; CD1E; CD20; CD22; CD276; CD33; CD3E; CD3Z; CD44_Isoform_1; CD44_Isoform_6; CD4; CD52; CD55; CD56; CD80; CD86; CD8A; CDC27/m; CDE30; CDK4/m; CDKN2A/m; CEA; CEAM6; CH3L2; CLCA2; CML28; CML66; COA-1/m; coactosin-like_protein; collagen_XXIII; COX-2; CP1B1; CSAG2; CT45A1; CT55; CT-_9/BRD6; CTAG2_Isoform_LAGE-1A; CTAG2_Isoform_LAGE-1B; CTCFL; Cten; cyclin_B1; cyclin_D1; cyp-B; DAM-10; DEPIA; E7; EF1A2; EFTUD2/m; EGFR; EGLN3; ELF2/m; EMMPRIN; EpCam; EphA2; EphA3; ErbB3; ERBB4; ERG; ETV6; EWS; EZH2; FABP7; FCGR3A_Version_1; FCGR3A_Version_2; FGF5; FGFR2; fibronectin; FOS; FOXP3; FUT1; G250; GAGE-1; GAGE-2; GAGE-3; GAGE-4; GAGE-5; GAGE-6; GAGE7b; GAGE-8_(GAGE-2D); GASR; GnT-V; GPC3; GPNMB/m; GRM3; HAGE; hepsin; Her2/neu; HLA-A2/m; homeobox_NKX3.1; HOM-TES-85; HPG1; HS71A; HS71B; HST-2; hTERT; iCE; IF2B3; IL10; IL-13Ra2; IL2-RA; IL2-RB; IL2-RG; IL-5; IMP3; ITA5; ITB1; ITB6; kallikrein-2; kallikrein-4; KI20A; KIAA0205; KIF2C; KK-LC-1; LDLR; LGMN; LIRB2; LY6K; MAGA5; MAGA8; MAGAB; MAGE-A10; MAGE-A12; MAGE-A1; MAGE-A2; MAGE-A3; MAGE-A4; MAGE-A6; MAGE-A9; MAGE-B10; MAGE-B16; MAGE-B17; MAGE-Bi; MAGE-B2; MAGE-B3; MAGE-B4; MAGE-B5; MAGE-B6; MAGE-C1; MAGE-C2; MAGE-C3; MAGE-D1; MAGE-D2; MAGE-D4; MAGE-_E1; MAGE-E1_(MAGE1); MAGE-E2; MAGE-F1; MAGE-H1; MAGEL2; mammaglobin_A; MART-1/melan-A; MART-2; MC1_R; M-CSF; mesothelin; MITF; MMP1_1; MMP7; MUC-1; MUM-1/m; MUM-2/m; MYCN; MYO1A; MYO1B; MYO1C; MYO1D; MYO1E; MYO1F; MYO1G; MYO1H; NA17; NA88-A; Neo-PAP; NFYC/m; NGEP; NPM; NRCAM; NSE; NUF2; NY-ESO-1; OA1; OGT; OS-9; osteocalcin; osteopontin; p53; PAGE-4; PAI-1; PAI-2; PAP; PATE; PAX3; PAX5; PD1L1; PDCD1; PDEF; PECA1; PGCB; PGFRB; Pim-1_-Kinase; Pin-1; PLAC1; PMEL; PML; POTEF; POTE; PRAME; PRDX5/m; PRM2; prostein; proteinase-3; PSA; PSB9; PSCA; PSGR; PSM; PTPRC; RAB8A; RAGE-1; RARA; RASH; RASK; RASN; RGS5; RHAMM/CD168; RHOC; RSSA; RU1; RU2; RUNX1; S-100; SAGE; SART-_1; SART-2; SART-3; SEPR; SERPINB5; SIA7F; SIA8A; SIAT9; SIRT2/m; SOX10; SP17; SPNXA; SPXN3; SSX-1; SSX-2; SSX3; SSX-4; ST1A1; STAG2; STAMP-1; STEAP-1; Survivin-2B; survivin; SYCP1; SYT-SSX-1; SYT-SSX-2; TARP; TCRg; TF2AA; TGFB1; TGFR2; TGM-4; TIE2; TKTL1; TPI/m; TRGV11; TRGV9; TRPC1; TRP-p8; TSG10; TSPY1; TVC_(TRGV3); TX101; tyrosinase; TYRP1; TYRP2; UPA; VEGFR1; WT1; and XAGE1.

Further antigens useful for the present invention are shown herein below (gene names followed by bracket with protein accession NOs):

1A01_HLA-A/m (UniProtKB: P30443); 1A02 (UniProtKB: P01892); 5T4 (UniProtKB: Q13641); ACRBP (UniProtKB: Q8NEB7); AFP (UniProtKB: P02771); AKAP4 (UniProtKB: Q5JQC9); alpha-actinin-_4/m (UniProtKB: B4DSX0); alpha-actinin-4/m (UniProtKB: B4E337); alpha-actinin-_4/m (UniProtKB: 043707); alpha-methylacyl-coenzyme A_racemase (UniProtKB: A0A024RE16); alpha-methylacyl-coenzyme A_racemase (UniProtKB: A8KAC3); ANDR (UniProtKB: P10275); ART-4 (UniProtKB: Q9ULX3); ARTCi/m (UniProtKB: P52961); AURKB (UniProtKB: Q96GD4); B2MG (UniProtKB: P61769); B3GN5 (UniProtKB: Q9BYG0); B4GN1 (UniProtKB: Q00973); B7H4 (UniProtKB: Q7Z7D3); BAGE-1 (UniProtKB: Q13072); BASI (UniProtKB: P35613); BCL-2 (UniProtKB: A9QXG9); bcr/abl (UniProtKB: A9UEZ4); bcr/abl (UniProtKB: A9UEZ7); bcr/abl (UniProtKB: A9UEZ8); bcr/abl (UniProtKB: A9UEZ9); bcr/abl (UniProtKB: A9UF00); bcr/abl (UniProtKB: A9UF01); bcr/abl (UniProtKB: A9UF03); bcr/abl (UniProtKB: A9UF04); bcr/abl (UniProtKB: A9UF05); bcr/abl (UniProtKB: A9UF06); bcr/abl (UniProtKB: A9UF08); beta-catenin/m (UniProtKB: P35222); beta-catenin/m (UniProtKB: Q8WYA6); BING-4 (UniProtKB: 015213); BIRC7 (UniProtKB: Q96CA5); BRCA1/m (UniProtKB: A0A024R1V0); BRCA1/m (UniProtKB: A0A024R1V7); BRCA1/m (UniProtKB: A0A024RIZ8); BRCA1/m (UniProtKB: A0A068BFX7); BRCA1/m (UniProtKB: C6YB45); BRCA1/m (UniProtKB: C6YB47); BRCA1/m (UniProtKB: G3XAC3); BY55 (UniProtKB: 095971); calreticulin (UniProtKB: B4DHR1); calreticulin (UniProtKB: B4E2Y9); calreticulin (UniProtKB: P27797); calreticulin (UniProtKB: Q96L12); CAMEL (UniProtKB: 095987); CASP-8/m (UniProtKB: Q14790); CASPA (UniProtKB: Q92851-4); cathepsin_B (UniProtKB: A0A024R374); cathepsin_B (UniProtKB: P07858); cathepsin_L (UniProtKB: A0A024R276); cathepsin_L (UniProtKB: P07711); cathepsin_L (UniProtKB: Q9HBQ7); CD1A (UniProtKB: P06126); CD1B (UniProtKB: P29016); CD1C (UniProtKB: P29017); CD1D (UniProtKB: P15813); CD1E (UniProtKB: P15812); CD20 (UniProtKB: P11836); CD22 (UniProtKB: 060926); CD22 (UniProtKB: P20273); CD22 (UniProtKB: QOEAF5); CD276 (UniProtKB:

Q5ZPR3); CD33 (UniProtKB: B4DF51); CD33 (UniProtKB: P20138); CD33 (UniProtKB: Q546G0); CD3E (UniProtKB: P07766); CD3Z (UniProtKB: P20963); CD44_Isoform_1 (UniProtKB: P16070); CD44_Isoform_6 (UniProtKB: P16070-6); CD4 (UniProtKB: P01730); CD52 (UniProtKB: P31358); CD52 (UniProtKB: Q6IBD0); CD52 (UniProtKB: V9HWN9); CD55 (UniProtKB: B1AP15); CD55 (UniProtKB: D3DT85); CD55 (UniProtKB: D3DT86); CD55 (UniProtKB: P08174); CD56 (UniProtKB: P13591); CD80 (UniProtKB: AONOP2); CD80 (UniProtKB: P33681); CD86 (UniProtKB: P42081); CD8A (UniProtKB: P01732); CDC27/m (UniProtKB: G5EA36); CDC27/m (UniProtKB: P30260); CDE30 (UniProtKB: P28908); CDK4/m (UniProtKB: A0A024RBB6); CDK4/m (UniProtKB: P11802); CDK4/m (UniProtKB: Q6LC83); CDK4/m (UniProtKB: Q96BE9); CDKN2A/m (UniProtKB: D1LYX3); CDKN2A/m (UniProtKB: G3XAG3); CDKN2A/m (UniProtKB: K7PML8); CDKN2A/m (UniProtKB: L8E941); CDKN2A/m (UniProtKB: Q8N726); CEA (RefSeq: NP_004354); CEAM6 (UniProtKB: P40199); CH3L2 (UniProtKB: Q15782); CLCA2 (UniProtKB: Q9UQC9); CML28 (UniProtKB: Q9NQT4); CML66 (UniProtKB: Q96RS6); COA-1/m (UniProtKB: Q5T124); coactosin-like_protein (UniProtKB: Q14019); collagen_XXIII (UniProtKB: L8EAS4); collagen_XXIII (UniProtKB: Q86Y22); COX-2 (UniProtKB: Q6ZYK7); CP1B1 (UniProtKB: Q16678); CSAG2 (UniProtKB: Q9Y5P2-2); CSAG2 (UniProtKB: Q9Y5P2); CT45A1 (UniProtKB: Q5HYN5); CT55 (UniProtKB: Q8WUE5); CT-_9/BRD6 (UniProtKB: Q58F21); CTAG2_Isoform_LAGE-1A (UniProtKB: 075638-2); CTAG2_Isoform_LAGE-1B (UniProtKB: 075638); CTCFL (UniProtKB: Q8NI51); Cten (UniProtKB: Q8IZW8); cyclin_B1 (UniProtKB: P14635); cyclin_D1 (UniProtKB: P24385); cyp-B (UniProtKB: P23284); DAM-10 (UniProtKB: P43366); DEPlA (UniProtKB: Q5TB30); E7 (UniProtKB: P03129); E7 (UniProtKB: P06788); E7 (UniProtKB: P17387); E7 (UniProtKB: P06429); E7 (UniProtKB: P27230); E7 (UniProtKB: P24837); E7 (UniProtKB: P21736); E7 (UniProtKB: P26558); E7 (UniProtKB: P36831); E7 (UniProtKB: P36833); E7 (UniProtKB: Q9QCZ1); E7 (UniProtKB: Q81965); E7 (UniProtKB: Q80956); EF1A2 (UniProtKB: Q05639); EFTUD2/m (UniProtKB: Q15029); EGFR (UniProtKB: A0A0B4J1Y5); EGFR (UniProtKB: E7BSV0); EGFR (UniProtKB: LOR6G1); EGFR (UniProtKB: P00533-2); EGFR (UniProtKB: P00533); EGFR (UniProtKB: Q147T7); EGFR (UniProtKB: Q504U8); EGFR (UniProtKB: Q8NDU8); EGLN3 (UniProtKB: Q9H6Z9); ELF2/m (UniProtKB: B7Z720); EMMPRIN (UniProtKB: Q54A51); EpCam (UniProtKB: P16422); EphA2 (UniProtKB: P29317); EphA3 (UniProtKB: P29320); EphA3 (UniProtKB: Q6P4R6); ErbB3 (UniProtKB: B3KWG5); ErbB3 (UniProtKB: B4DGQ7); ERBB4 (UniProtKB: Q15303); ERG (UniProtKB: P11308); ETV6 (UniProtKB: P41212); EWS (UniProtKB: Q01844); EZH2 (UniProtKB: F2YMM1); EZH2 (UniProtKB: G3XAL2); EZH2 (UniProtKB: LOR855); EZH2 (UniProtKB: Q15910); EZH2 (UniProtKB: S4S3R8); FABP7 (UniProtKB: 015540); FCGR3A_Version_1 (UniProtKB: P08637); FCGR3A_Version_2 (CCDS: CCDS1232.1); FGF5 (UniProtKB: P12034); FGF5 (UniProtKB: Q60518); FGFR2 (UniProtKB: P21802); fibronectin (UniProtKB: A0A024R5I6); fibronectin (UniProtKB: A0A024RB01); fibronectin (UniProtKB: A0A024RDT9); fibronectin (UniProtKB: A0A024RDV5); fibronectin (UniProtKB: A6NH44); fibronectin (UniProtKB: A8K6A5); fibronectin (UniProtKB: B2R627); fibronectin (UniProtKB: B3KXM5); fibronectin (UniProtKB: B4DIC5); fibronectin (UniProtKB: B4DN21); fibronectin (UniProtKB: B4DS98); fibronectin (UniProtKB: B4DTH2); fibronectin (UniProtKB: B4DTK1); fibronectin (UniProtKB: B4DU16); fibronectin (UniProtKB: B7Z3W5); fibronectin (UniProtKB: B7Z939); fibronectin (UniProtKB: G5E9X3); fibronectin (UniProtKB: Q9H382); FOS (UniProtKB: P01100); FOXP3 (UniProtKB: Q9BZS1); FUT1 (UniProtKB: P19526); G250 (UniProtKB: Q16790); GAGE-1 (Genbank: AAA82744); GAGE-2 (UniProtKB: Q6NT46); GAGE-3 (UniProtKB: Q13067); GAGE-4 (UniProtKB: Q13068); GAGE-5 (UniProtKB: Q13069); GAGE-6 (UniProtKB: Q13070); GAGE7b (UniProtKB: 076087); GAGE-8_(GAGE-2D) (UniProtKB: Q9UEU5); GASR (UniProtKB: P32239); GnT-V (UniProtKB: Q09328); GPC3 (UniProtKB: I6QTG3); GPC3 (UniProtKB: P51654); GPC3 (UniProtKB: Q8IYG2); GPNMB/m (UniProtKB: A0A024RA55); GPNMB/m (UniProtKB: Q14956); GPNMB/m (UniProtKB: Q8IXJ5); GPNMB/m (UniProtKB: Q96F58); GRM3 (UniProtKB: Q14832); HAGE (UniProtKB: Q9NXZ2); hepsin (UniProtKB: B2ZDQ2); hepsin (UniProtKB: P05981); Her2/neu (UniProtKB: B4DTR1); Her2/neu (UniProtKB: L8E8G2); Her2/neu (UniProtKB: P04626); Her2/neu (UniProtKB: Q9UK79); HLA-A2/m (UniProtKB: Q95387); HLA-A2/m (UniProtKB: Q9MYF8); homeobox_NKX3.1 (UniProtKB: Q99801); HOM-TES-85 (UniProtKB: B2RBQ6); HOM-TES-85 (UniProtKB: Q9P127); HPG1 (Pubmed: 12543784); HS71A (UniProtKB: PODMV8); HS71B (UniProtKB: PODMV9); HST-2 (UniProtKB: P10767); hTERT (UniProtKB: 094807); iCE (UniProtKB: 000748); IF2B3 (UniProtKB: 000425); I10 (UniProtKB: P22301); IL-13Ra2 (UniProtKB: Q14627); 1L2-RA (UniProtKB: P01589); IL2-RB (UniProtKB: P14784); IL2-RG (UniProtKB: P31785); IL-5 (UniProtKB: P05113); IMP3 (UniProtKB: Q9NV31); ITA5 (UniProtKB: P08648); ITB1 (UniProtKB: P05556); ITB6 (UniProtKB: P18564); kallikrein-2 (UniProtKB: A0A024R4J4); kallikrein-2 (UniProtKB: A0A024R4N3); kallikrein-2 (UniProtKB: BOAZU9); kallikrein-2 (UniProtKB: B4DU77); kallikrein-2 (UniProtKB: P20151); kallikrein-2 (UniProtKB: Q6T774); kallikrein-2 (UniProtKB: Q6T775); kallikrein-4 (UniProtKB: A0A0C4DFQ5); kallikrein-4 (UniProtKB: Q5BQA0); kallikrein-4 (UniProtKB: Q96PTO); kallikrein-4 (UniProtKB: Q96PT1); kallikrein-4 (UniProtKB: Q9Y5K2); KI20A (UniProtKB: 095235); KIAA0205 (UniProtKB: Q92604); KIF2C (UniProtKB: Q99661); KK-LC-1 (UniProtKB: Q5H943); LDLR (UniProtKB: P01130); LGMN (UniProtKB: Q99538); LIRB2 (UniProtKB: Q8N423); LY6K (UniProtKB: Q17RY6); MAGA5 (UniProtKB: P43359); MAGA8 (UniProtKB: P43361); MAGAB (UniProtKB: P43364); MAGE-A10 (UniProtKB: A0A024RC14); MAGE-A12 (UniProtKB: P43365); MAGE-A1 (UniProtKB: P43355); MAGE-A2 (UniProtKB: P43356); MAGE-A3 (UniProtKB: P43357); MAGE-A4 (UniProtKB: A0A024RC12); MAGE-A4 (UniProtKB: P43358); MAGE-A4 (UniProtKB:

Q1RN33); MAGE-A6 (UniProtKB: A8K072); MAGE-A6 (UniProtKB: P43360); MAGE-A6 (UniProtKB: Q6FHI5); MAGE-A9 (UniProtKB: P43362); MAGE-B10 (UniProtKB: Q96LZ2); MAGE-B16 (UniProtKB: A2A368); MAGE-B17 (UniProtKB: A8MXT2); MAGE-B1 (UniProtKB: Q96TG1); MAGE-B2 (UniProtKB: 015479); MAGE-B3 (UniProtKB: 015480); MAGE-B4 (UniProtKB: 015481); MAGE-B5 (UniProtKB: Q9BZ81); MAGE-B6 (UniProtKB: Q8N7X4); MAGE-C1 (UniProtKB: 060732); MAGE-C2 (UniProtKB: Q9UBF1); MAGE-C3 (UniProtKB: Q8TD91); MAGE-D1 (UniProtKB: Q9Y5V3); MAGE-D2 (UniProtKB: Q9UNF1); MAGE-D4 (UniProtKB: Q96JG8); MAGE-E1 (UniProtKB: Q6IAI7); MAGE-E1_(MAGEl) (UniProtKB: Q9HCI5); MAGE-E2 (UniProtKB: Q8TD90); MAGE-F1 (UniProtKB: Q9HAY2); MAGE-H1 (UniProtKB: Q9H213); MAGEL2 (UniProtKB: Q9UJ55); mammaglobin_A (UniProtKB: Q13296); mammaglobin_A (UniProtKB: Q6NX70); MART-1/melan-A (UniProtKB: Q16655); MART-2 (UniProtKB: Q5VTY9); MC1_R (UniProtKB: Q01726); MC1_R (UniProtKB: Q1JUL4); MC1_R (UniProtKB: Q1JUL6); MC1_R (UniProtKB: QIJUL8); MC1_R (UniProtKB: Q1JUL9); MC1_R (UniProtKB: Q1JUM0); MC1_R (UniProtKB: Q1JUM2); MC1_R (UniProtKB: Q1JUM3); MC1_R (UniProtKB: Q1JUM4); MC1_R (UniProtKB: Q1JUM5); MC1_R (UniProtKB: Q6UR92); MC1_R (UniProtKB: Q6UR94); MC1_R (UniProtKB: Q6UR95); MC1_R (UniProtKB: Q6UR96); MC1_R (UniProtKB: Q6UR97); MC1_R (UniProtKB: Q6UR98); MC1_R (UniProtKB: Q6UR99); MC1_R (UniProtKB: Q6URA0); MC1_R (UniProtKB: Q86YW1); MC1_R (UniProtKB: V9Q5S2); MC1_R (UniProtKB: V9Q671); MC1_R (UniProtKB: V9Q783); MC1_R (UniProtKB: V9Q7F1); MC1_R (UniProtKB: V9Q8N1); MC1_R (UniProtKB: V9Q977); MC1_R (UniProtKB: V9Q9P5); MC1_R (UniProtKB: V9Q9R8); MC1_R (UniProtKB: V9QAE0); MC1_R (UniProtKB: V9QAR2); MC1_R (UniProtKB: V9QAW3); MC1_R (UniProtKB: V9QB02); MC1_R (UniProtKB: V9QB58); MC1_R (UniProtKB: V9QBY6); MC1_R (UniProtKB: V9QC17); MC1_R (UniProtKB: V9QC66); MC1_R (UniProtKB: V9QCQ4); MC1_R (UniProtKB: V9QDF4); MC1_R (UniProtKB: V9QDN7); MC1_R (UniProtKB: V9QDQ6); M-CSF (UniProtKB: P09603); mesothelin (UniProtKB: Q13421); MITF (UniProtKB: 075030-8); MITF (UniProtKB: 075030-9); MITF (UniProtKB: 075030); MMP1_1 (UniProtKB: B3KQS8); MMP7 (UniProtKB: P09237); MUC-1 (Genbank: AAA60019); MUM-1/m (RefSeq: NP_116242); MUM-2/m (UniProtKB: Q9Y5R8); MYCN (UniProtKB: P04198); MYO1A (UniProtKB: Q9UBC5); MYO1B (UniProtKB: 043795); MYO1C (UniProtKB: 000159); MYO1D (UniProtKB: 094832); MYO1E (UniProtKB: Q12965); MYO1F (UniProtKB: 000160); MYO1G (UniProtKB: BOI1T2); MYO1H (RefSeq: NP_001094891); NA17 (UniProtKB: Q3V5L5); NA88-A (Pubmed: 10790436); Neo-PAP (UniProtKB: Q9BWT3); NFYC/m (UniProtKB: Q13952); NGEP (UniProtKB: Q6IWH7); NPM (UniProtKB: P06748); NRCAM (UniProtKB: Q92823); NSE (UniProtKB: P09104); NUF2 (UniProtKB: Q9BZD4); NY-ESO-1 (UniProtKB: P78358); OA1 (UniProtKB: P51810); OGT (UniProtKB: 015294); OS-9 (UniProtKB: B4DH11); OS-9 (UniProtKB: B4E321); OS-9 (UniProtKB: B7Z8E7); OS-9 (UniProtKB: Q13438); osteocalcin (UniProtKB: P02818); osteopontin (UniProtKB: A0A024RDE2); osteopontin (UniProtKB: A0A024RDE6); osteopontin (UniProtKB: A0A024RDJ0); osteopontin (UniProtKB: B7Z351); osteopontin (UniProtKB: F2YQ21); osteopontin (UniProtKB: P10451); p53 (UniProtKB: P04637); PAGE-4 (UniProtKB: 060829); PAI-1 (UniProtKB: P05121); PAI-2 (UniProtKB: P05120); PAP (UniProtKB: Q06141); PAP (UniProtKB: Q53S56); PATE (UniProtKB: Q8WXA2); PAX3 (UniProtKB: P23760); PAX5 (UniProtKB: Q02548); PD1L1 (UniProtKB: Q9NZQ7); PDCD1 (UniProtKB: Q15116); PDEF (UniProtKB: 095238); PECA1 (UniProtKB: P16284); PGCB (UniProtKB: Q96GW7); PGFRB (UniProtKB: P09619); Pim-1_-Kinase (UniProtKB: A0A024RD25); Pin-1 (UniProtKB: 015428); Pin-1 (UniProtKB: Q13526); Pin-1 (UniProtKB: Q49AR7); PLAC1 (UniProtKB: Q9HBJ0); PMEL (UniProtKB: P40967); PML (UniProtKB: P29590); POTEF (UniProtKB: A5A3E0); POTE (UniProtKB: Q86YR6); PRAME (UniProtKB: A0A024R1E6); PRAME (UniProtKB: P78395); PRDX5/m (UniProtKB: P30044); PRM2 (UniProtKB: P04554); prostein (UniProtKB: Q96JT2); proteinase-3 (UniProtKB: D6CHE9); proteinase-3 (UniProtKB: P24158); PSA (UniProtKB: P55786); PSB9 (UniProtKB: P28065); PSCA (UniProtKB: D3DWI6); PSCA (UniProtKB: 043653); PSGR (UniProtKB: Q9H255); PSM (UniProtKB: Q04609); PTPRC (RefSeq: NP_002829); RAB8A (UniProtKB: P61006); RAGE-1 (UniProtKB: Q9UQ07); RARA (UniProtKB: P10276); RASH (UniProtKB: P01112); RASK (UniProtKB: P01116); RASN (UniProtKB: PO1111); RGS5 (UniProtKB: 015539); RHAMM/CD168 (UniProtKB: 075330); RHOC (UniProtKB: P08134); RSSA (UniProtKB: P08865); RU1 (UniProtKB: Q9UHJ3); RU2 (UniProtKB: Q9UHG0); RUNX1 (UniProtKB: Q01196); S-100 (UniProtKB: V9HW39); SAGE (UniProtKB: Q9NXZ1); SART-_1 (UniProtKB: 043290); SART-2 (UniProtKB: Q9UL01); SART-3 (UniProtKB: Q15020); SEPR (UniProtKB: Q12884); SERPINB5 (UniProtKB: P36952); SIA7F (UniProtKB: Q969X2); SIA8A (UniProtKB: Q92185); SIAT9 (UniProtKB: Q9UNP4); SIRT2/m (UniProtKB: A0A024ROG8); SIRT2/m (UniProtKB: Q8IXJ6); SOX10 (UniProtKB: P56693); SP17 (UniProtKB: Q15506); SPNXA (UniProtKB: Q9NS26); SPXN3 (UniProtKB: Q5MJ09); SSX-1 (UniProtKB: Q16384); SSX-2 (UniProtKB: Q16385); SSX3 (UniProtKB: Q99909); SSX-4 (UniProtKB: 060224); ST1A1 (UniProtKB: P50225); STAG2 (UniProtKB: Q8N3U4-2); STAMP-1 (UniProtKB: Q8NFT2); STEAP-1 (UniProtKB: A0A024RA63); STEAP-1 (UniProtKB: Q9UHE8); Survivin-2B (UniProtKB: 015392-2); survivin (UniProtKB: 015392); SYCP1 (UniProtKB: A0A024ROI2); SYCP1 (UniProtKB: B7ZLS9); SYCP1 (UniProtKB: Q15431); SYCP1 (UniProtKB: Q3MHC4); SYT-SSX-1 (UniProtKB: A4PIV7); SYT-SSX-1 (UniProtKB: A4PIV8); SYT-SSX-2 (UniProtKB: A4PIV9); SYT-SSX-2 (UniProtKB: A4PIW0); TARP (UniProtKB: Q0VGM3); TCRg (UniProtKB: A2JGV3); TF2AA (UniProtKB: P52655); TGFB1 (UniProtKB: P01137); TGFR2 (UniProtKB: P37173); TGM-4 (UniProtKB: B2R7D1); TIE2 (UniProtKB: Q02763); TKTL1 (UniProtKB: P51854); TPI/m (UniProtKB: P60174); TRGV11 (UniProtKB: Q99601); TRGV9 (UniProtKB: A4D1X2); TRGV9 (UniProtKB:

Q99603); TRGV9 (UniProtKB: Q99604); TRPC1 (UniProtKB: P48995); TRP-p8 (UniProtKB: Q7Z2W7); TSG10 (UniProtKB: Q9BZW7); TSPY1 (UniProtKB: Q01534); TVC_(TRGV3) (Genbank: M13231.1); TX101 (UniProtKB: Q9BY14-2); tyrosinase (UniProtKB: A0A024DBG7); tyrosinase (UniProtKB: L8B082); tyrosinase (UniProtKB: L8B086); tyrosinase (UniProtKB: L8B0B9); tyrosinase (UniProtKB: 075767); tyrosinase (UniProtKB: P14679); tyrosinase (UniProtKB: U3M8NO); tyrosinase (UniProtKB: U3M9D5); tyrosinase (UniProtKB: U3M9J2); TYRP1 (UniProtKB: P17643); TYRP2 (UniProtKB: P40126); UPA (UniProtKB: Q96NZ9); VEGFR1 (UniProtKB: B5A924); WT1 (UniProtKB: A0A0H5AUY0); WT1 (UniProtKB: P19544); WT1 (UniProtKB: Q06250); XAGE1 (UniProtKB: Q9HD64).

V.9.4. Checkpoint Inhibitors

Negative regulatory T cell surface molecules were discovered, which are upregulated in activated T cells in order to dampen their activity, thus reducing the effectiveness of said activated T cells in the killing of tumor cells. These inhibitory molecules were termed negative co-stimulatory molecules due to their homology to the T cell co-stimulatory molecule CD28. These proteins, also referred to as immune checkpoint proteins, function in multiple pathways including the attenuation of early activation signals, competition for positive costimulation and direct inhibition of antigen presenting cells (Bour-Jordan et al., 2011. Immunol Rev. 241(1):180-205).

In the context of the present invention, a checkpoint modulator is typically a molecule, such as a protein (e.g. an antibody), a dominant negative receptor, a decoy receptor, or a ligand or a fragment or variant thereof, which modulates the function of an immune checkpoint protein, e.g. it inhibits or reduces the activity of checkpoint inhibitors (or inhibitory checkpoint molecules) or it stimulates or enhances the activity of checkpoint stimulators (or stimulatory checkpoint molecules). Therefore, checkpoint modulators as defined herein, influence the activity of checkpoint molecules.

In this context, inhibitory checkpoint molecules are defined as checkpoint inhibitors and can be used synonymously. In addition, stimulatory checkpoint molecules are defined as checkpoint stimulators and can be used synonymously.

Preferably, the checkpoint modulator is selected from agonistic antibodies, antagonistic antibodies, ligands, dominant negative receptors, and decoy receptors or combinations thereof.

Methods for generating and using mRNA-encoded antibodies are known in the art (e.g. WO2008/083949 or PCT/EP2017/060226).

Preferred inhibitory checkpoint molecules that may be inhibited by a checkpoint modulator in the context of the invention are PD-1, PD-L1, CTLA-4, PD-L2, LAG3, TIM3/HAVCR2, 2B4, A2aR, B7H3, B7H4, BTLA, CD30, CD160, CD155, GAL9, HVEM, IDO1, IDO2, KIR, LAIR1 and VISTA.

Preferred stimulatory checkpoint molecules that may be stimulated by a checkpoint modulator in the context of the invention are CD2, CD27, CD28, CD40, CD137, CD226, CD276, GITR, ICOS, OX40 and CD70.

According to a preferred embodiment, the pharmaceutical composition or vaccine comprising RNAs of the invention is for use as described herein, wherein the use comprises—as an additional pharmaceutically active ingredient—a checkpoint modulator selected from the group consisting of the checkpoint modulator is selected from the group consisting of a PD-1 inhibitor, a PD-L1 inhibitor, a PD-L2 inhibitor, a CTLA-4 inhibitor, a LAG3 inhibitor, a TIM3 inhibitor, a TIGIT-inhibitor, an OX40 stimulator, a 4-1BB stimulator, a CD40L stimulator, a CD28 stimulator and a GITR stimulator.

According to a preferred embodiment, the checkpoint modulator as used herein targets a member of the PD-1 pathway. Members of the PD-1 pathway are typically proteins, which are associated with PD-1 signaling. On the one hand, this group comprises proteins, which induce PD-1 signaling upstream of PD-1 as e.g. the ligands of PD-1, PD-L1 and PD-L2, and the signal transduction receptor PD-1. On the other hand, this group comprises signal transduction proteins downstream of PD-1 receptor. Particularly preferred as members of the PD-1 pathway in the context of the present invention are PD-1, PD-L1 and PD-L2.

In the context of the present invention, a PD-1 pathway antagonist (or PD-1 inhibitor) is preferably defined herein as a compound capable to impair the PD-1 pathway signaling, preferably signaling mediated by the PD-1 receptor. Therefore, the PD-1 pathway antagonist may be any antagonist directed against any member of the PD-1 pathway capable of antagonizing PD-1 pathway signaling.

In a preferred embodiment, the checkpoint modulator used herein is a PD-1 inhibitor or a PD-L1 inhibitor, wherein the PD-1 inhibitor is preferably an antagonistic antibody directed against PD-1 and the PD-L1 inhibitor is preferably an antagonistic antibody directed against PD-L1.

In this context, the antagonist may be an antagonistic antibody as defined herein, targeting any member of the PD-1 pathway, preferably an antagonistic antibody directed against PD-1 receptor, PD-L1 or PD-L2. Such an antagonistic antibody may also be encoded by a nucleic acid. Also, the PD-1 pathway antagonist may be a fragment of the PD-1 receptor blocking the activity of PD1 ligands. B7-1 or fragments thereof may act as PD1-antagonizing ligands as well. Additionally, a PD-1 pathway antagonist may be a protein comprising (or a nucleic acid coding for) an amino acid sequence capable of binding to PD-1 but preventing PD-1 signaling, e.g. by inhibiting PD-1 and B7-H1 or B7-DL interaction (WO 2014/127917; WO2012062218).

Particularly preferred are the anti-PD1 antibodies Nivolumab (MDX-1106/BMS-936558/ONO-4538), (Brahmer et al., 2010. J Clin Oncol. 28(19):3167-75; PMID: 20516446); Pidilizumab (CT-011), (Berger et al., 2008. Clin Cancer Res. 14(10):3044-51; PMID: 18483370); Pembrolizumab (MK-3475, SCH 900475); AMP-224, and MEDI0680 (AMP-514).

Particularly preferred are also the anti-PD-L1 antibodies MDX-1105/BMS-936559 (Brahmer et al. 2012. N Engl J Med. 366(26):2455-65; PMID: 22658128); atezolizumab (MPDL3280A/RG7446); durvalumab (MEDI4736); and avelumab (MSB0010718).

According to another embodiment, the checkpoint modulator used herein is an OX40 stimulator. OX40 is a member of the TNFR-superfamily of receptors, and is expressed on the surface of antigen-activated mammalian CD4+ and CD8+T lymphocytes. OX40 ligand (OX40L, also known as gp34, ACT-4-L, and CD252) is a protein that specifically interacts with the OX40 receptor. The term OX40L includes the entire OX40 ligand, soluble OX40 ligand, and fusion proteins comprising a functionally active portion of OX40 ligand covalently linked to a second moiety, e.g., a protein domain. Also included within the definition of OX40L are variants which vary in amino acid sequence from naturally occurring OX40L, but which retain the ability to specifically bind to the OX40 receptor. Further included within the definition of OX40L are variants thereof, which enhance the biological activity of OX40. An OX40 agonist is a molecule which induces or enhances the biological activity of OX40, e.g. signal transduction mediated by OX40. An OX40 agonist is preferably defined herein as a binding molecule capable of specific binding to OX40. Therefore, the OX40 agonist may be any agonist binding to OX40 and capable of stimulating OX40 signaling. In this context, the OX40 agonist may be an agonistic antibody binding to OX40.

OX40 agonists and anti-0X40 monoclonal antibodies are described in WO1995/021251, WO1995/012673 and WO1995/21915. Particularly preferred is the anti-0X40 antibody 9B12, a murine anti-0X40 monoclonal antibody directed against the extracellular domain of human OX40 (Weinberg et al., 2006. J. Immunother. 29(6):575-585).

In another embodiment, the checkpoint modulator as used herein is an antagonistic antibody is selected from the group consisting of anti-CTLA4, anti-PD1, anti-PD-L1, anti-Vista, anti-Tim-3, anti-TIGIT, anti-LAG-3, and anti-BTLA.

Preferably, an anti-CTLA4 antibody that may be used as a checkpoint modulator is directed against Cytotoxic T lymphocyte antigen-4 (CTLA-4). CTLA-4 is mainly expressed within the intracellular compartment of T cells. After a potent or long-lasting stimulus to a naïve T cell via the T cell receptor (TCR), CTLA-4 is transported to the cell surface and concentrated at the immunological synapse. CTLA-4 then competes with CD28 for CD80/CD86 and down-modulates TCR signaling via effects on Akt signaling. Thus CTLA-4 functions physiologically as a signal dampener (Weber, J. 2010. Semin. Oncol. 37(5):430-9).

In preferred embodiments, the pharmaceutical composition or vaccine comprising RNAs of the invention is for use as described herein, wherein the use comprises—as an additional pharmaceutically active ingredient—a CTLA4 antagonist, which is preferably an antagonistic antibody directed against CTLA4 (anti-CTLA4 antibody). The term 'CTLA4 antagonist' as used herein comprises any compound, such as an antibody, that antagonizes the physiological function of CTLA4. In the context of the present invention, the term 'anti-CTLA4 antibody' may refer to an antagonistic antibody directed against CTLA4 (or a functional fragment or variant of said antibody) or to a nucleic acid, preferably an RNA, encoding said antagonistic antibody (or a functional fragment thereof). A functional fragment or variant of an anti-CTLA4 antibody preferably acts as a CTLA4 antagonist. More preferably, the term 'anti-CTLA4 antibody' refers to a monoclonal antibody directed against CTLA4 (or a functional fragment or variant of such an antibody) or to a nucleic acid encoding a monoclonal antibody directed against CTLA4 (or a functional fragment or variant of such an antibody). The term 'anti-CTLA4 antibody' as used herein may refer to the heavy or light antibody chain, respectively, or also refer to both antibody chains (heavy and light chain), or to a fragment or variant of any one of these chains. Preferably, the fragment or variant of an anti-CTLA4 antibody as used herein is a functional fragment or variant, preferably as described herein.

Particularly preferred are the anti-CTLA-4 antibodies ipilimumab (Yervoy®), tremelimumab, and AGEN-1884. Further preferred anti-CTLA4 antibodies as used herein comprise BMS 734016; BMS-734016; BMS734016; MDX 010; MDX 101; MDX-010; MDX-101; MDX-CTLA-4; MDX-CTLA4; MDX010; Winglore; and Yervoy, or a functional fragment or variant of any one of these antibodies.

According to a further embodiment, the checkpoint modulator as used herein is at least one antibody described in Table 1 or a fragment or variant thereof

V.5. Combination Cancer Therapy

More preferably, the subject receiving the pharmaceutical composition or vaccine comprising RNAs of the invention, the combination thereof or the pharmaceutical composition or vaccine comprising said RNA(s) is a patient suffering from a tumor or cancer disease as described herein and who received or receives chemotherapy (e.g. first-line or second-line chemotherapy), radiotherapy, chemoradiation (combination of chemotherapy and radiotherapy), kinase inhibitors, antibody therapy and/or checkpoint modulators (e.g., CTLA4 inhibitors, PD1 pathway inhibitors), or a patient, who has achieved partial response or stable disease after having received one or more of the treatments specified above. More preferably, the subject is a patient suffering from a tumor or cancer disease as described herein and who received or receives a compound conventionally used in any of these diseases as described herein, more preferably a patient who receives or received a checkpoint modulator.

The following compounds are preferred compounds which preferably are used in standard therapies and can be applied in combination with the pharmaceutical compositions or vaccines comprising RNAs of the invention: Cetuximab (Erbitux), paclitaxel albumin bound (Abraxane), (gimeracil+oteracil+tegafur) (TS-1), Docetaxel (Docetaxel, Doxel, Taxotere, Docetaxel An, Docel, Nanoxel M, Tautax, Docetaxel-AS, Docetaxel-M, Qvidadotax, Relidoce, Taxelo, Oncodocel, Doxotel, Pacancer, Docetrust, Dodetax, Dodabur, Soulaxcin, Taxedol, Docefim, Docetaxel, Ribodocel, Critidoc, Asodoc, Chemodoc, Docelibbs, Docenat, Dincilezan, Dostradixinol, Docefrez, Camitotic, Oncotaxel, Somatixel, Belotaxel, Qvidadotax, Taxceus, Cetadocure, Docetaxel CT, Tevaxter, Docirena, Eurotere, Axtere, Celotax, Taxanit, Drobanos, Cetado, Doxocad, Taxceus, Egidox, Tedocad, Docecad, Docelex, Docetax, Docetaxel, Docetere, Dotax, Taxuba, Monotaxel, Taceedo, Detaxl, Docet, Docetaxel, Ferdotax, Wintaxel), (tegafur+uracil) (Uft, Uft E, Tefudex, Unitoral, Luporal, Tagracil), Fluorouracil (5-FU), (gimeracil+oteracil+tegafur) ODT (TS-1 Combination OD), bleomycin sulfate (Tecnomicina, Cinaleo, Bleomycin, Bloicin-S, Bonar, Bleocin, Bleomycin Sulfate, Bleo, Bleocel, Bleotex, Oncobleo, Bleonco, Bleosol, Lyoble, Bleomycin Sulfate, Blenamax, Bleomycin, Blenoxane, Bleomicina, Bleomycine Bellon, Bleoprim), carboplatin (Carboplatin, Platamine CS, Carbaccord, Carboplatina, Carboplatino, Paraplatin, Carbosin, Tecnocarb, Carbomerck, Paract, Carboplatine CTRS, Carboplatine Intsel Chimos, Carboplatin, Carbokem, Carbotinol, Fauldcarbo, Evocarb, Citoplatina, Platin), ciprofloxacin (Hypoflox, Ufexil), ciprofloxacin hydrochloride (Ciprofloxacin Pharma, Prodin, Ciproxin), cisplatin (Cisplatin, Stritin, Ifapla, Accocit, Unistin, Cancertin, Cisplan, Citoplax, Nuoxin, Placis, Cisplatino, Displanor, Randa, Cispla, Fauldcispla, Briplatin, Platinex, Platinol, Platinex, Riboplatin, Cisplatine, Platistine CS, Platosin, Accocit, Cisplatino) cyclophosphamide (Endoxan, Cyclophosphamide), doxifluridine (Doxifluridine, May Vladimir), doxorubicin (Doxorubicin Hydrochloride, Adriamycin RDF, Doxorubicin, Doxorubicin PFS), epirubicin, hydrochloride (Brecila, Cloridrato De Epirrubicina, Epirubicin, Farmorubicina, Nuovodox, Adnexa, 4-Eppedo, Favicin), fluorouracil (Agicil, Fluorouracil, Fauldfluor, Oncourcil, Flocil, 5 Flucel), folic acid+methotrexate (Truxofol), human adenovirus type 5 (recombinant) (Oncorine), hydroxyurea (Oxyrea, Durea, Myelostat, Riborea, Unidrea, Ondrea, Hydran, Leukocel, Hydroxyurea, Hydrea), ifosfamide (Holoxan, Ifosfamide EG), levamisole (Zirsol), methotrexate Methotrexate (Tratoben, Methotrexate, Fresexate, Neometho, Fauldmetro, Methotrexate Sodium, Methocel, Hytas, Methaccord, Methofill, Metotrexato, Traxacord, Plastomet, Tevatrex, Metrex, Caditrex, Carditrex, Vibzi, Imutrex, Biotrexate, Methorex, Mexate, Neotrexate, Oncotrex, Remtrex, Trixilem, Hi-Trex, Metorex, Trex, Unitrexate, Ebetrexac, Fauldexato, Lantarel, Maxtrex, Miantrex CS, Rheumatrex, Folex, Folex PFS, Abitrexate, Tevametho, Trexall, Emthexate, Abitrexate, Meadow), mitomycin (Mitomycin C, Mitomycin, Mitonco, Lyomit), nedaplatin (Jiebaishu, Aoxianda, Aqupla), nimesulide (Nimulid), nimotuzumab (Biomab EGFR, Laedemab), nitrofurantoin (Furatsilin), ofloxacin (Entof), paclitaxel (Paclitaxel, Taxol), peplomycin sulfate (Pepleo), picibanil (Picibanil), pirarubicin (Pirarubicin Hydrochloride, Therarubicin, Pinorubin), sodium glycididazole (CMNa), tegafur (Utefos, Icarus, Futraful, Tegafur Gimeracil Oteracil Potassium), temoporfin (Foscan), topotecan hydrochloride (Topotecan), ubenimex (Ubenimex), vinblastine sulfate (Vinblastine, Vblastin), vincristine sulfate (Vincristine, Vincristine Sulfate, Vincristin, Sutivin, vindesine sulfate (Eldisine), carboplatin (Carboplatine Qualimed, Carboplatine, Carboplatino, Carboplatin), cisplatin (Cisplatin), docetaxel (Kamdocon, Naltoxater, Docetaxel), fluorouracil (Fluorouracil, Fluorouracile, Fluorouracil), methotrexate (Methotrexate Sodium, Mexate, Mexate Aq, Biometrox, Medsatrexate, Otaxem), vincristine sulfate (Oncovin), fluorouracil, sunitinib malate, acitretin, fibrin sealant, cetuximab, cetuximab, erlotinib, cisplatin; docetaxel; fluorouracil, undisclosed anti-cancer drug, gefitinib, pravastatin sodium, sirolimus, undisclosed chemotherapy, cisplatin; docetaxel; fluorouracil, sirolimus, fluorouracil; undisclosed taxane, methyl aminolevulinate hydrochloride, cisplatin; docetaxel; fluorouracil, erlotinib hydrochloride, cetuximab, imiquimod, undisclosed Chinese herbal medicine, aspirin; enalapril maleate, undisclosed chemotherapy, cetuximab, (gimeracil+oteracil+tegafur); carboplatin; cisplatin, cisplatin; fluorouracil; nimotuzumab, carboplatin; paclitaxel albumin bound, cisplatin; nedaplatin, bleomycin, nedaplatin, cisplatin; paclitaxel, paclitaxel albumin bound, (gimeracil+oteracil+tegafur), bleomycin; undisclosed chemotherapy, apatinib; docetaxel, undisclosed immunomodulatory supplement, BCM-95, aminolevulinic acid hydrochloride, nedaplatin, cisplatin; palifermin, cetuximab, gefitinib, bevacizumab, belagenpumatucel-L, cisplatin; tirapazamine, cisplatin; tirapazamine, cisplatin; gemcitabine; paclitaxel; topotecan; vinorelbine, cisplatin; fluorouracil, panitumumab, carboplatin; docetaxel; gemcitabine hydrochloride; vinorelbine tartrate, amifostine; fluorouracil, cisplatin; fluorouracil, carboplatin; paclitaxel, tirapazamine, cisplatin; epoetin alfa, figitumumab, melphalan; tumor necrosis factor alf, cisplatin, cisplatin; fluorouracil, cisplatin; undisclosed chemotherapy, docetaxel, contusugene ladenovec, cisplatin; fluorouracil; paclitaxel, docetaxel, human papillomavirus [serotypes 16, 18] (bivalent) vaccine, isotretinoin, cisplatin; fluorouracil, misonidazole, paclitaxel, palifermin, endostatin, pilocarpine, cisplatin; docetaxel; filgrastim; fluorouracil; paclitaxel, cisplatin; docetaxel; filgrastim; fluorouracil; paclitaxel, cisplatin; irinotecan hydrochloride, cisplatin; gemcitabine, cisplatin; epirubicin; fluorouracil; undisclosed chemotherapy, methyl aminolevulinate hydrochloride, carboplatin; paclitaxel, carbogen; carbon dioxide; niacinamide, cisplatin; fluorouracil, talimogene laherparepvec, epoetin alfa, cisplatin; fluorouracil; panitumumab, cisplatin; fluorouracil, cisplatin; fluorouracil, aldesleukin, cisplatin; fluorouracil, cisplatin; paclitaxel, cisplatin; fluorouracil, fluorouracil; leucovorin; lobaplatin, cisplatin, cisplatin; ethyl mercaptan; ifosfamide; mesna; mitolactol, doxorubicin; levamisole, (tegafur+uracil), cisplatin; fluorouracil, cisplatin; vinorelbine, carboplatin; cisplatin; gemcitabine hydrochloride, *Corynebacterium parvum*; doxorubicin, capecitabine; cisplatin; fluorouracil; paclitaxel, fluorouracil; leucovorin; methotrexate, rAd-p53, cetuximab; cisplatin; docetaxel, PV-10, methyl aminolevulinate hydrochloride, cisplatin; fluorouracil, paclitaxel; topotecan hydrochloride, carboplatin; cisplatin; paclitaxel, cisplatin; topotecan hydrochloride, cisplatin; etoposide, docetaxel; fluorouracil, aspirin, cisplatin; gemcitabine, *Lactobacillus brevis* CD2, cisplatin; docetaxel, fosbretabulin tromethamine, panitumumab, fluorouracil, paclitaxel, carboplatin; cisplatin; docetaxel; fluorouracil, fluorouracil, erlotinib hydrochloride, cisplatin; undisclosed chemotherapy; vinorelbine, (gimeracil+oteracil+tegafur); carboplatin, cetuximab, contusugene ladenovec, cetuximab, methyl aminolevulinate hydrochloride, cyclophosphamide, (gimeracil+oteracil+tegafur); cisplatin, paclitaxel albumin bound, carboplatin; paclitaxel, cisplatin; gemcitabine, capecitabine; cisplatin, docetaxel, Z-100, cisplatin; ifosfamide; paclitaxel, nimotuzumab, irinotecan hydrochloride, celecoxib; methotrexate, Nutrison, carboplatin; cisplatin; fluorouracil; paclitaxel, cisplatin; paclitaxel, cisplatin; docetaxel; vinorelbine, paclitaxel, (gimeracil+oteracil+tegafur); cisplatin, carboplatin; paclitaxel, methyl aminolevulinate hydrochloride, Aibin, cisplatin; fluorouracil, porfimer sodium, carboplatin; cisplatin; tocotrienol; vinorelbine, (gimeracil+oteracil+tegafur); cisplatin; paclitaxel, docetaxel, ipilimumab, cisplatin, VB-4847, celecoxib; thalidomide, cisplatin; epirubicin; fluorouracil, cisplatin; fluorouracil, fluorouracil, carboplatin; paclitaxel, cetuximab; cisplatin; docetaxel, autologous cytokine induced killer cells, cisplatin; docetaxel; fluorouracil, cisplatin; epirubicin; fluorouracil, tergenpumatucel-L, cetuximab; cisplatin; docetaxel, Elental, cisplatin; nimotuzumab; paclitaxel, eicosapentaenoic acid; undisclosed nutritional supplement, palbociclib, pembrolizumab (Keytruda), nimotuzumab, apatorsen and dacomitinib.

As used herein, the terms "tumor", "cancer" or "cancer disease" refer to a malignant disease, which is preferably selected from the group consisting of Adenocystic carcinoma (Adenoid cystic carcinoma), Adrenocortical carcinoma, AIDS-related cancers, AIDS-related lymphoma, Anal cancer, Appendix cancer, Astrocytoma, Basal cell carcinoma, Bile duct cancer, Bladder cancer, Bone cancer, Osteosarcoma/Malignant fibrous histiocytoma, Brainstem glioma, Brain tumor, cerebellar astrocytoma, cerebral astrocytoma/malignant glioma, ependymoma, medulloblastoma, supratentorial primitive neuroectodermal tumors, visual pathway and hypothalamic glioma, Breast cancer, Bronchial adenomas/carcinoids, Burkitt lymphoma, childhood Carcinoid tumor, gastrointestinal Carcinoid tumor, Carcinoma of unknown primary, primary Central nervous system lymphoma, childhood Cerebellar astrocytoma, childhood Cerebral astrocytoma/Malignant glioma, Cervical cancer, Childhood cancers, Chronic lymphocytic leukemia, Colon Cancer, Cutaneous T-cell lymphoma including Mycosis Fungoides and Sezary Syndrome, Desmoplastic small round cell tumor, Endometrial cancer, Ependymoma, Esophageal cancer, Ewing's sarcoma in the Ewing family of tumors, Childhood Extracranial germ cell tumor, Extragonadal Germ cell tumor, Extrahepatic bile duct cancer, Intraocular melanoma, Retinoblastoma, Gallbladder cancer, Gastric (Stomach) cancer, Gastrointestinal Carcinoid Tumor, Gastrointestinal stromal tumor (GIST), extracranial, extragonadal, or ovarian Germ cell tumor, Gestational trophoblastic tumor, Glioma of the brain stem, Childhood Cerebral Astrocytoma, Childhood Visual Pathway and Hypothalamic Glioma, Gastric carcinoid, Hairy cell leukemia, Head and neck cancer, Heart cancer, Hepatocellular (liver) cancer, Hodgkin lymphoma, Human Papilloma Virus (HPV)-related cancer, Hypopharyngeal cancer, childhood Hypothalamic and visual pathway glioma, Intraocular Melanoma, Islet Cell Carcinoma (Endocrine Pancreas), Kaposi sarcoma, Kidney cancer (renal cell cancer), Laryngeal Cancer, Lip and Oral Cavity Cancer, Liposarcoma, Liver Cancer, Non-Small Cell Lung Cancer, Small Cell Lung Cancer, Lymphomas, AIDS-related Lymphoma, Burkitt Lymphoma, Hodgkin Lymphoma, Non-Hodgkin Lymphomas, Primary Central Nervous System Lymphoma, Malignant Fibrous Histiocytoma of Bone/Osteosarcoma, Childhood Medulloblastoma, Melanoma, Intraocular (Eye) Melanoma, Merkel Cell Carcinoma, Adult Malignant Mesothelioma, Childhood Mesothelioma, Head or Neck Cancer, Mouth Cancer, Childhood Multiple Endocrine Neoplasia Syndrome, Multiple Myeloma/Plasma Cell Neoplasm, Multiple Myeloma (Cancer of the Bone-Marrow), Nasal cavity and paranasal sinus cancer, Nasopharyngeal carcinoma, Neuroblastoma, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, islet cell Pancreatic cancer, Paranasal sinus and nasal cavity cancer, Parathyroid cancer, Penile cancer, Pharyngeal cancer, Pheochromocytoma, Pineal astrocytoma, Pineal germinoma, childhood Pineoblastoma and supratentorial primitive neuroectodermal tumors, Pituitary adenoma, Plasma cell neoplasia/plasmocytoma/Multiple myeloma, Pleuropulmonary blastoma, Primary central nervous system lymphoma, Prostate cancer, Rectal cancer, Renal cell carcinoma (kidney cancer), Cancer of the Renal pelvis and ureter, Retinoblastoma, childhood Rhabdomyosarcoma, Salivary gland cancer, Sarcoma of the Ewing family of tumors, Kaposi Sarcoma, soft tissue Sarcoma, uterine Sarcoma, Skin cancer (nonmelanoma), Skin cancer (melanoma), Merkel cell Skin carcinoma, Small intestine cancer, Squamous cell carcinoma, metastatic Squamous neck cancer with occult primary, soft tissue sarcoma (STS), childhood Supratentorial primitive neuroectodermal tumor, Testicular cancer (seminoma and non-seminoma), Throat cancer, childhood Thymoma, Thymoma and Thymic carcinoma, Thyroid cancer, childhood Thyroid cancer, Transitional cell cancer of the renal pelvis and ureter, gestational Trophoblastic tumor, Urethral cancer, endometrial Uterine cancer, Uterine sarcoma, Vaginal cancer, childhood Visual pathway and hypothalamic glioma, Vulvar cancer, and childhood Wilms tumor (kidney cancer).

V.9.Allergenic Antigens

Antigens associated with allergy or allergic disease (allergens or allergenic antigens) are preferably derived from a source selected from the list consisting of:

*Acarus* spp (Aca s 1, Aca s 10, Aca s 10.0101, Aca s 13, Aca s 13.0101, Aca s 2, Aca s 3, Aca s 7, Aca s 8), *Acanthocybium* spp (Aca so 1), *Acanthocheilonema* spp (Aca v 3, Aca v 3.0101), *Acetes* spp (Ace ja 1), *Actinidia* spp (Act a 1, Act c 1, Act c 10, Act c 10.0101, Act c 2, Act c 4, Act c 5, Act c 5.0101, Act c 8, Act c 8.0101, Act c Chitinase, Act d 1, Act d 1.0101, Act d 10, Act d 10.0101, Act d 10.0201, Act d 11, Act d 11.0101, Act d 2, Act d 2.0101, Act d 3, Act d 3.0101, Act d 3.02, Act d 4, Act d 4.0101, Act d 5, Act d 5.0101, Act d 6, Act d 6.0101, Act d 7, Act d 7.0101, Act d 8, Act d 8.0101, Act d 9, Act d 9.0101, Act d Chitinase, Act e 1, Act e 5), *Acyrthosiphon* spp (Acy pi 7, Acy pi 7.0101, Acy pi 7.0102), *Adenia* spp (Ade v RIP), *Aedes* spp (Aed a 1, Aed a 1.0101, Aed a 2, Aed a 2.0101, Aed a 3, Aed a 3.0101, Aed a 4, Aed a 7, Aed a 7.0101, Aed a 7.0102, Aed a 7.0103, Aed a 7.0104, Aed a 7.0105, Aed a 7.0106, Aed a 7.0107, Aed a 7.0108, Aed a 7.0109, Aed a 7.0110, Aed a 7.0111, Aed al 1, Aed al 3, Aed al 37 kD, Aed v 37 kD, Aed v 63 kD), *Aegilops* spp (Aeg ta 28, Aeg ta alpha_Gliadin, Aeg um 28, Aeg un 28), *Aethaloperca* spp (Aet ro 1), *Agropyron* spp (Agr c 7), *Agrostis* spp (Agr ca 1, Agr ca 5, Agr g 1, Agr g 4, Agr s 5), *Agrobacterium* spp (Agr sp CP4 EPSPS), *Ailuropoda* spp (Ail me Phosvitin, Ail me TCTP), *Aix* spp (Aix ga 1, Aix sp 1), *Aleuroglyphus* spp (Ale o 1, Ale o 10, Ale o 10.0101, Ale o 10.0102, Ale o 13, Ale o 14, Ale o 2, Ale o 20, Ale o 3, Ale o 5, Ale o 7, Ale o 8, Ale o 9), *Allium* spp (All a 3, All a Alliin lyase, All c 3, All c 30 kD, All c 4, All c Alliin lyase, All p Alliin lyase, All s Alliin lyase), *Alnus* spp (Aln g 1, Aln g 1.0101, Aln g 1/Bet v 1/Cor a 1 TPC7, Aln g 1/Bet v 1/Cor a 1 TPC9, Aln g 2, Aln g 4, Aln g 4.0101), *Alopochen* spp (Alo ae 1), *Alopecurus* spp (Alo p 1, Alo p 5), *Alternaria* spp (Alt a 1, Alt a 1.0101, Alt a 1.0102, Alt a 10, Alt a 10.0101, Alt a 12, Alt a 12.0101, Alt a 13, Alt a 13.0101, Alt a 2, Alt a 3, Alt a 3.0101, Alt a 4, Alt a 4.0101, Alt a 5, Alt a 5.0101, Alt a 6, Alt a 6.0101, Alt a 7, Alt a 7.0101, Alt a 70 kD, Alt a 8, Alt a 8.0101, Alt a 9, Alt a MnSOD, Alt a NTF2, Alt a TCTP, Alt ar 1, Alt arg 1, Alt b 1, Alt bl 1, Alt br 1, Alt c 1, Alt ca 1, Alt ce 1, Alt ch 1, Alt ci 1, Alt co 1, Alt cr 1, Alt ct 1, Alt cu 1, Alt cy 1, Alt d 1, Alt du 1, Alt e 1, Alt et 1, Alt eu 1, Alt ga 1, Alt gr 1, Alt j 1, Alt I 1, Alt lo 1, Alt m 1, Alt me 1, Alt mi 1, Alt mo 1, Alt o 1, Alt p 1, Alt ph 1, Alt po 1, Alt ps 1, Alt r 1, Alt s 1, Alt se 1, Alt sm 1, Alt so 1, Alt su 1, Alt t 1, Alt te 1, Alt to 1), *Amaranthus* spp (Ama r 2, Ama r 2.0101, Ama v 2, Ama v 2.0101, Ama v 2.0201), *Ambrosia* spp (Amb a 1, Amb a 1.0101, Amb a 1.0201, Amb a 1.0202, Amb a 1.0301, Amb a 1.0302, Amb a 1.0303, Amb a 1.0304, Amb a 1.0305, Amb a 1.0401, Amb a 1.0402, Amb a 1.0501, Amb a 1.0502, Amb a 10, Amb a 10.0101, Amb a 3, Amb a 3.0101, Amb a 4, Amb a 4.0101, Amb a 5, Amb a 5.0101, Amb a 6, Amb a 6.0101, Amb a 7, Amb a 7.0101, Amb a 8, Amb a 8.0101, Amb a 8.0102, Amb a 9, Amb a 9.0101, Amb a 9.0102, Amb a CPI, Amb p 1, Amb p 5, Amb p 5.0101, Amb p 5.0201, Amb t 5, Amb t 5.0101, Amb t 8), *Ammothea* spp (Amm h 7, Amm h 7.0101), *Anadara* spp (Ana br 1), *Ananas* spp (Ana c 1, Ana c 1.0101, Ana c 2, Ana c 2.0101, Ana c 2.0101 (MUXF3)), *Anas* spp (Ana ca 1), *Anarhichas* spp (Ana I 1), *Anacardium* spp (Ana o 1, Ana o 1.0101, Ana o 1.0102, Ana o 2, Ana o 2.0101, Ana o 3, Ana o 3.0101), *Anas* spp (Ana p 1, Ana p 2, Ana p 3), *Anguilla* spp (Ang a 1, Ang j 1), *Anisakis* spp (Ani s 1, Ani s 1.0101, Ani s 10, Ani s 10.0101, Ani s 11, Ani s 11.0101, Ani s 12, Ani s 12.0101, Ani s 2, Ani s 2.0101, Ani s 24 kD, Ani s 3, Ani s 3.0101, Ani s 4, Ani s 4.0101, Ani s 5, Ani s 5.0101, Ani s 6, Ani s 6.0101, Ani s 7, Ani s 7.0101, Ani s 8, Ani s 8.0101, Ani s 9, Ani s 9.0101, Ani s CCOS3, Ani s Cytochrome B, Ani s FBPP, Ani s NADHDS4L, Ani s NARaS, Ani s PEPB, Ani s Troponin), *Annona* spp (Ann c Chitinase), *Anopheles* spp (Ano da 17, Ano da 17.0101, Ano da 27, Ano da 27.0101, Ano da 7, Ano da 7.0101, Ano g 7, Ano g 7.0101), *Anser* spp (Ans a 1, Ans a 2, Ans a 3, Ans in 1), *Anthoxanthum* spp (Ant o 1, Ant o 1.0101, Ant o 12, Ant o 13, Ant o 2, Ant o 4, Ant o 5, Ant o 6, Ant o 7), *Apis* spp (Api c 1, Api c 1.0101, Api c 10, Api c 2, Api c 4, Api d 1, Api d 1.0101, Api d 4, Api fl 4), *Apium* spp (Api g 1, Api g 1.0101, Api g 1.0201, Api g 2, Api g 2.0101, Api g 3, Api g 3.0101, Api g 4, Api g 4.0101, Api g 5, Api g 5.0101, Api g 6, Api g 6.0101), *Apis* spp (Api m 1, Api m 1.0101, Api m 10, Api m 10.0101, Api m 11, Api m 11.0101, Api m 11.0201, Api m 13 kD, Api m 2, Api m 2.0101, Api m 3, Api m 3.0101, Api m 4, Api m 4.0101, Api m 5, Api m 5.0101, Api m 6, Api m 6.0101, Api m 7, Api m 7.0101, Api m 8, Api m 8.0101, Api m 9, Api m 9.0101, Api m A1-A2, Api m A1-A2-A3, Api m Apalbumin 1, Api m Apalbumin 2, Api me 1, Api me 4), *Arachis* spp (Ara d 2, Ara d 6, Ara f 3, Ara f 4, Ara h 1, Ara h 1.0101, Ara h 10, Ara h 10.0101, Ara h 10.0102, Ara h 11, Ara h 11.0101, Ara h 2, Ara h 2.0101, Ara h 2.0102, Ara h 2.0201, Ara h 2.0202, Ara h 3, Ara h 3.0101, Ara h 4, Ara h 4.0101, Ara h 5, Ara h 5.0101, Ara h 6, Ara h 6.0101, Ara h 7, Ara h 7.0101, Ara h 7.0201, Ara h 7.0202, Ara h 8, Ara h 8.0101, Ara h 8.0201, Ara h 9, Ara h 9.0101, Ara h 9.0201, Ara h Agglutinin, Ara h Oleosin 18 kD, Ara i 2, Ara i 6), *Arabidopsis* spp (Ara t 3, Ara t 8, Ara t GLP), *Archosargus* spp (Arc pr 1), *Archaeopotamobius* spp (Arc s 8, Arc s 8.0101), *Aequipecten* spp (Arg i 1), *Argas* spp (Arg r 1, Arg r 1.0101), *Ariopsis* spp (Ari fe 1), *Armoracia* spp (Arm r HRP), *Arrhenatherum* spp (Arr e 1, Arr e 5), *Artemisia* spp (Art a 1, Art ap 1), *Artemia* spp (Art fr 1, Art fr 1.0101, Art fr 5, Art fr 5.0101), *Arthrobacter* spp (Art gl CO), *Achorion* spp (Art gy 7), *Artocarpus* spp (Art h 17 kD, Art h 4), *Arthrospira* spp (Art pl beta Phycocyanin), *Artemisia* spp (Art v 1, Art v 1.0101, Art v 1.0102, Art v 1.0103, Art v 1.0104, Art v 1.0105, Art v 1.0106, Art v 1.0107, Art v 2, Art v 2.0101, Art v 3, Art v 3.0101, Art v 3.0201, Art v 3.0202, Art v 3.0301, Art v 4, Art v 4.0101, Art v 4.0201, Art v 47 kD, Art v 5, Art v 5.0101, Art v 6, Art v 6.0101, Art v 60 kD), *Arthroderma* spp (Art va 4), *Ascaris* spp (Asc 1 3, Asc 1 3.0101, Asc 1 3.0102, Asc 134 kD, Asc s 1, Asc s 1.0101, Asc s 3, Asc s 3.0101, Asc s GST), *Aspergillus* spp (Asp aw Glucoamylase, Asp c 22, Asp f 1, Asp f 1.0101, Asp f 10, Asp f 10.0101, Asp f 11, Asp f 11.0101, Asp f 12, Asp f 12.0101, Asp f 13, Asp f 13.0101, Asp f 15, Asp f 15.0101, Asp f 16, Asp f 16.0101, Asp f 17, Asp f 17.0101, Asp f 18, Asp f 18.0101, Asp f 2, Asp f 2.0101, Asp f 22, Asp f 22.0101, Asp f 23, Asp f 23.0101, Asp f 27, Asp f 27.0101, Asp f 28, Asp f 28.0101, Asp f 29, Asp f 29.0101, Asp f 3, Asp f 3.0101, Asp f 34, Asp f 34.0101, Asp f 4, Asp f 4.0101, Asp f 5, Asp f 5.0101, Asp f 56 kD, Asp f 6, Asp f 6.0101, Asp f 7, Asp f 7.0101, Asp f 8, Asp f 8.0101, Asp f 99, Asp f 9.0101, Asp f AfCalAp, Asp f AT_V, Asp f Catalase, Asp f Chitosanase, Asp f CP, Asp f DPPV, Asp f FDH, Asp f gamma_Actin, Asp f Glucosidase, Asp f GPI, Asp f GST, Asp f GT, Asp f IAO, Asp f IPMI, Asp f LPL1, Asp f LPL3, Asp f Mannosidase, Asp f MDH, Asp f PL, Asp f PUP, Asp f RPS3, Asp f SXR, Asp fl 13, Asp fl 13.0101, Asp fl 18, Asp fl 2, Asp fl 21, Asp fl 3, Asp fl 4, Asp fl 7, Asp fl 8, Asp fl 9, Asp me Seaprose, Asp n 14, Asp n 14.0101, Asp n 18, Asp n 18.0101, Asp n 25, Asp n 25.0101, Asp n 30, Asp n Glucoamylase, Asp n Hemicellulase, Asp n Pectinase, Asp o 13, Asp o 13.0101, Asp o 21, Asp o 21.0101, Asp o 3, Asp o 4, Asp o 7, Asp o 8, Asp o Lactase, Asp o Lipase, Asp oc 13, Asp r 1, Asp sa AP, Asp sp Glucoamylase, Asp sp Glucoseoxidase, Asp sp PL, Asp sp PME, Asp sy 13, Asp v 13, Asp v 13.0101, Asp v Catalase A, Asp v Enolase, Asp v GAPDH, Asp v MDH, Asp v SXR), *Asparagus* spp (Aspa o 1, Aspa o 1.01, Aspa o 1.02, Aspa o 17 kD, Aspa o 4), *Aspergillus* spp (Aspe ni 2, Aspe ni 3, Aspe ni 4, Aspe ni 7, Aspe ni 8, Aspe ni 9), *Avena* spp (Ave s 1, Ave s 12, Ave s 13, Ave s 2, Ave s 4, Ave s 5, Ave s 7), *Babylonia* spp (Bab ja 1), *Bacillus* spp (Bac al Subtilisin, Bac cl Subtilisin, Bac I Subtilisin, Bac li aA, Bac li Subtilisin), *Bactrocera* spp (Bac ol 27, Bac ol 27.0101), *Bacillus* spp (Bac sp aA1, Bac sp aA3, Bac sp Decarboxylase, Bac st amyM, Bac su Subtilisin, Bac t CrylAb, Bac t Cry1Fa, Bac t Cry3Bbl, Bac t Cry9c), *Bagre* spp (Bag ma 1), *Balistes* spp (Bal ca 1), *Balanus* spp (Bal r 1, Bal r 1.0101), *Beauveria* spp (Bea b Aid, Bea b Enol, Bea b f2, Bea b Hex), *Bertholletia* spp (Ber e 1, Ber e 1.0101, Ber e 2, Ber e 2.0101), *Beryx* spp (Ber sp 1), *Betula* spp (Bet ab 1, Bet al 1, Bet ch 1, Bet co 1, Bet da 1, Bet gr 1, Bet hu 1, Bet le 1, Bet me 1, Bet n 1, Bet p 1, Bet pa 1, Bet po 1, Bet pu 1, Bet pu 2, Bet pu 4, Bet pu 6, Bet pu 7, Bet sc 1, Bet ut 1, Bet v 1, Bet v 1 B1-B1-B1, Bet v 1 fv Mal 4x, Bet v 1.0101, Bet v 1.0102, Bet v 1.0103, Bet v 1.0201, Bet v 1.0301, Bet v 1.0401, Bet v 1.0402, Bet v 1.0501, Bet v 1.0601, Bet v 1.0602, Bet v 1.0701, Bet v 1.0801, Bet v 1.0901, Bet v 1.1001, Bet v 1.1101, Bet v 1.1201, Bet v 1.1301, Bet v 1.1401, Bet v 1.1402, Bet v 1.1501, Bet v 1.1502, Bet v 1.1601, Bet v 1.1701, Bet v 1.1801, Bet v 1.1901, Bet v 1.2001, Bet v 1.2101, Bet v 1.2201, Bet v 1.2301, Bet v 1.2401, Bet v 1.2501, Bet v 1.2601, Bet v 1.2701, Bet v 1.2801, Bet v 1.2901, Bet v 1.3001, Bet v 1.3101, Bet v 2, Bet v 2.0101, Bet v 3, Bet v 3.0101, Bet v 4, Betv 4.0101, Bet v 6, Bet v 6.0101, Bet v 6.0102, Bet v 7, Bet v 7.0101, Bet v 8, Bet v Glucanase), *Beta* spp (Beta v 1, Beta v 1.0101, Beta v 2, Beta v 2.0101), *Blattella* spp (Bla g 1, Bla g 1.0101, Bla g 1.0102, Bla g 1.0103, Bla g 1.0201, Bla g 1.0202, Bla g 2, Bla g 2.0101, Bla g 2.0201, Bla g 36 kD, Bla g 4, Bla g 4.0101, Bla g 4.0201, Bla g 5, Bla g 5.0101, Bla g 5.0201, Bla g 6, Bla g 6.0101, Bla g 6.0201, Bla g 6.0301, Bla g 7, Bla g 7.0101, Bla g 8, Bla g 8.0101, Bla g 9, Bla g Enolase, Bla g GSTD1, Bla g RACK1, Bla g TPI, Bla g Trypsin, Bla g Vitellogenin), *Blatta* spp (Bla o 1, Bla o 7), *Blomia* spp (Blo t 1, Blo t 1.0101, Blo t 1.0201, Blo t 10, Blo t 10.0101, Blo t 10.0102, Blo t 11, Blo t 11.0101, Blo t 12, Blo t 12.0101, Blo t 12.0102, Blo t 13, Blo t 13.0101, Blo t 14, Blo t 15, Blo t 18, Blo t 19, Blo t 19.0101, Blo t 2, Blo t 2.0101, Blo t 2.0102, Blo t 2.0103, Blo t 20, Blo t 21, Blo t 21.0101, Blo t 3, Blo t 3.0101, Blo t 4, Blo t 4.0101, Blo t 5, Blo t 5.0101, Blo t 6, Blo t 6.0101, Blo t 7, Blo t 8, Blo t 9, Blo t HSP70), *Bombus* spp (Bom ar 4, Bom by 4, Bom p 1, Bom p 1.0101, Bom p 2, Bom p 3, Bom p 4, Bom p 4.0101, Bom t 1, Bom t 1.0101, Bom t 4, Bom t 4.0101), *Bombyx* spp (Bomb m 1, Bomb m 1.0101, Bomb m 7, Bomb m 7.0101, Bomb m 7.0102, Bomb m 7.0103, Bomb m 7.0104, Bomb m 7.0105, Bomb m 7.0106), *Boophilus* spp (Boo m 1, Boo m 7, Boo m 7.0101), *Bos* spp (Bos d 2, Bos d 2.0101, Bos d 2.0102, Bos d 2.0103, Bos d 3, Bos d 3.0101, Bos d 4, Bos d 4.0101, Bos d 5, Bos d 5.0101, Bos d 5.0102, Bos d 6, Bos d 6 (MDA), Bos d 6.0101, Bos d 7, Bos d 7.0101, Bos d 8, Bos d 8 alphaS1, Bos d 8 alphaS2, Bos d 8 beta, Bos d 8 kappa, Bos d alpha2I, Bos d alpha2I.0101, Bos d Chymosin, Bos d Fibrin, Bos d Gelatin, Bos d HG, Bos d Insulin, Bos d Lactoferrin, Bos d Lactoperoxidase, Bos d Myoglobin, Bos d OBP, Bos d OSCP, Bos d Phosvitin, Bos d PLA2, Bos d PRVB, Bos d Thrombin, Bos d TI, Bos gr ALA, Bos gr Myoglobin), *Bothrops* spp (Bot as 1, Bot at 1), *Bouteloua* spp (Bou g 1), *Biting* spp (Bov ov 1), *Brama* spp (Bra du 1), *Brassica* spp (Bra j 1, Bra j 1.0101, Bra n 1, Bra n 1.0101, Bra n 4, Bra n 7, Bra n 8, Bra n PG, Bran i 8, Bra o 3, Bra o 3.0101, Bra r 1, Bra r 1.0101, Bra r 2, Bra r 2.0101, Bra r 3, Bra r 4, Bra r 7), *Bromus* spp (Bro a 1, Bro a 4), *Brosme* spp (Bro br 1), *Bromus* spp (Bro i 1, Bro i 5, Bro i 7), *Brugia* spp (Bru m 3, Bru m 3.0101, Bru m Bm33), *Bubalus* spp (Bub b ALA, Bub b BLG, Bub b Casein, Bub b Casein alphaS1, Bub b Casein alphaS2, Bub b Casein beta, Bub b Casein kappa), *Caenorhabditis* spp (Cae b 3, Cae b 3.0101, Cae br 3, Cae br 3.0101, Cae e 3, Cae e 3.0101, Cae e 3.0102, Cae re 13, Cae re 13.0101), *Cajanus* spp (Caj c 1), *Caligus* spp (Cal cl 1, Cal cl 1.0101, Cal cl 1.0102), *Calamus* spp (Cal le 1), *Callinectes* spp (Cal s 2), *Camelus* spp (Cam d ALA, Cam d Casein, Cam d Casein alphaS1, Cam d Casein alphaS2, Cam d Casein beta, Cam d Casein kappa), *Camponotus* spp (Cam fl 7, Cam fl 7.0101), *Canis* spp (Can f 1, Can f 1.0101, Can f 2, Can f 2.0101, Can f 3, Can f 3.0101, Can f 4, Can f 4.0101, Can f 5, Can f 5.0101, Can f 6, Can f 6.0101, Can f Feld1-like, Can f Homs2-like, Can f Phosvitin, Can f TCTP), *Canthidermis* spp (Can ma 1), *Cancer* spp (Can mg 2, Can p 1), *Cannabis* spp (Can s 3), *Candida* spp (Cand a 1, Cand a 1.0101, Cand a 3, Cand a 3.0101, Cand a CAAP, Cand a CyP, Cand a Enolase, Cand a FPA, Cand a MnSOD, Cand a PGK, Cand b 2, Cand b 2.0101, Cand b FDH, Cand r Lipase), *Capsicum* spp (Cap a 1, Cap a 1.0101, Cap a 17 kD, Cap a 2, Cap a 2.0101, Cap a 30 kD, Cap a Glucanase, Cap ch 17 kD), *Caprella* spp (Cap e 1), *Capra* spp (Cap h ALA, Cap h BLG, Cap h Casein, Cap h Casein alphaS1, Cap h Casein alphaS2, Cap h Casein beta, Cap h Casein kappa, Cap h GSA), *Capitulum* spp (Cap m 1), *Carassius* spp (Car au 1), *Carpinus* spp (Car b 1, Car b 1.0101, Car b 1.0102, Car b 1.0103, Car b 1.0104, Car b 1.0105, Car b 1.0106, Car b 1.0107, Car b 1.0108, Car b 1.0109, Car b 1.0110, Car b 1.0111, Car b 1.0112, Car b 1.0113, Car b 1.0201, Car b 1.0301, Car b 1.0302, Car b 2, Car b 4), *Caranx* spp (Car cr 1), *Carya* spp (Car i 1, Car i 1.0101, Car i 2, Car i 4, Car i 4.0101), *Carcinus* spp (Car ma 2), *Caryota* spp (Car mi 2), *Carica* spp (Car p 1, Car p Chitinase, Car p Chymopapain, Car p Endoproteinase), *Castanea* spp (Cas c 24 kD, Cas s 1, Cas s 1.0101, Cas s 1.0102, Cas s 1.0103, Cas s 2, Cas s 5, Cas s 5.0101, Cas s 8, Cas s 8.0101, Cas s 9, Cas s 9.0101), *Catharanthus* spp (Cat r 1, Cat r 1.0101, Cat r 17 kD, Cat r 2), *Caulolatilus* spp (Cau ch 1), *Cavia* spp (Cav p 1, Cav p 1.0101, Cav p 2, Cav p 2.0101, Cav p 3, Cav p 3.0101, Cav p Gelatin, Cav p GSA), *Centropristis* spp (Cen s 1), *Cephalopholis* spp (Cep so 1), *Charybdis* spp (Cha f 1, Cha f 1.0101), *Chaetodipterus* spp (Cha fa 1), *Chamaecyparis* spp (Cha o 1, Cha o 1.0101, Cha o 2, Cha o 2.0101), *Chenopodium* spp (Che a 1, Che a 1.0101, Che a 2, Che a 2.0101, Che a 3, Che a 3.0101), *Chironomus* spp (Chi k 1, Chi k 10, Chi k 10.0101), *Chinchilla* spp (Chi 121 kD_a, Chi 121 kD_b), *Chionoecetes* spp (Chi o 1, Chi o 1.0101, Chi o 2, Chi o 4, Chi o 6, Chi o alpha_Actin, Chi o SERCA), *Chironomus* spp (Chi t 1, Chi t 1.0101, Chi t 1.0201, Chi t 2, Chi t 2.0101, Chi t 2.0102, Chi t 3, Chi t 3.0101, Chi t 4, Chi t 4.0101, Chi t 5, Chi t 5.0101, Chi t 6, Chi t 6.0101, Chi t 6.0201, Chi t 7, Chi t 7.0101, Chi t 8, Chi t 8.0101, Chi t 9, Chi t 9.0101), *Chlamys* spp (Chl n 1), *Chloephaga* spp (Chl pi 1), *Chortoglyphus* spp (Cho a 10), *Chrysomela* spp (Chr tr 7, Chr tr 7.0101), *Cicer* spp (Cic a 2S Albumin, Cic a Albumin), *Cichorium* spp (Cic i 1), *Cimex* spp (Cim I Nitrophorin), *Citrus* spp (Cit I 1, Cit 13, Cit I 3.0101), *Citrullus* spp (Cit la 2, Cit la MDH, Cit la TPI), *Citrus* spp (Cit r 3, Cit r 3.0101, Cit s 1, Cit s 1.0101, Cit s 2, Cit s 2.0101, Cit s 3, Cit s 3.0101, Cit s 3.0102, Cit s IFR), *Cladosporium* spp (Cla c 14, Cla c 14.0101, Cla c 9, Cla c 9.0101, Cla h 1, Cla h 10, Cla h 10.0101, Cla h 12, Cla h 12.0101, Cla h 2, Cla h 2.0101, Cla h 42 kD, Cla h 5, Cla h 5.0101, Cla h 6, Cla h 6.0101, Cla h 7, Cla h 7.0101, Cla h 8, Cla h 8 CSP, Cla h 8.0101, Cla h 9, Cla h 9.0101, Cla h abH, Cla h GST, Cla h HChl, Cla h HSP70, Cla h NTF2, Cla h TCTP), *Clostridium* spp (Clo hi Collagenase, Clo t Toxoid), *Clupea* spp (Clu h 1, Clu h 1.0101, Clu h 1.0201, Clu h 1.0301), *Cocos* spp (Coc n 2, Coc n 4, Coc n 5), *Coccidioides* spp (Coc po 8), *Coffea* spp (Cof a 1, Cof a 1.0101), *Columba* spp (Col I PSA), *Coprinus* spp (Cop c 1, Cop c 1.0101, Cop c 2, Cop c 2.0101, Cop c 3, Cop c 3.0101, Cop c 4, Cop c 5, Cop c 5.0101, Cop c 6, Cop c 7, Cop c 7.0101), *Corylus* spp (Cor a 1, Cor a 1.0101, Cor a 1.0102, Cor a 1.0103, Cor a 1.0104, Cor a 1.0201, Cor a 1.0301, Cor a 1.0401, Cor a 1.0402, Cor a 1.0403, Cor a 1.0404, Cor a 10, Cor a 10.0101, Cor a 11, Cor a 11.0101, Cor a 12, Cor a 12.0101, Cor a 13, Cor a 13.0101, Cor a 14, Cor a 14.0101, Cor a 2, Cor a 2.0101, Cor a 2.0102, Cor a 8, Cor a 8.0101, Cor a 9, Cor a 9.0101), *Corynebacterium* spp (Cor d Toxoid), *Corylus* spp (Cor he 1), *Coryphaena* spp (Cor hi 1), *Coriandrum* spp (Cor s 1, Cor s 11 kD, Cor s 2), *Cotoneaster* spp (Cot 13), *Crangon* spp (Cra c 1, Cra c 1.0101, Cra c 2, Cra c 2.0101, Cra c 4, Cra c 4.0101, Cra c 5, Cra c 5.0101, Cra c 6, Cra c 6.0101, Cra c 8, Cra c 8.0101), *Crassostrea* spp (Cra g 1), *Cricetus* spp (Cri c HSA), *Crivellia* spp (Cri pa 1), *Crocus* spp (Cro s 1, Cro s 1.0101, Cro s 2, Cro s 2.0101, Cro s 3, Cro s 3.01, Cro s 3.02), *Cryptomeria* spp (Cry j 1, Cry j 1.0101, Cry j 1.0102, Cry j 1.0103, Cry j 2, Cry j 2.0101, Cry j 2.0102, Cryj 3, Cryj 3.1, Cryj 3.2, Cryj 3.3, Cryj 3.4, Cryj 3.5, Cryj 3.6, Cryj 3.7, Cryj 3.8, Cryj 4, Cryj AP, Cry j Chitinase, Cry j CPA9, Cry j IFR, Cry j LTP, Cry j P1-P2), *Cryphonectria* spp (Cry p AP), *Ctenocephalides* spp (Cte f 1, Cte f 1.0101, Cte f 2, Cte f 2.0101, Cte f 3, Cte f 3.0101), *Ctenopharyngodon* spp (Cte id 1), *Cucumis* spp (Cuc m 1, Cuc m 1.0101, Cuc m 2, Cuc m 2.0101, Cuc m 3, Cuc m 3.0101, Cuc m Lec17, Cuc m MDH), *Cucurbita* spp (Cuc ma 18 kD, Cuc ma 2, Cuc p 2, Cuc p AscO), *Cucumis* spp (Cuc s 2), *Culicoides* spp (Cul n 1, Cul n 10, Cul n 11, Cul n 2, Cul n 3, Cul n 4, Cul n 5, Cul n 6, Cul n 7, Cul n 8, Cul n 9, Cul n HSP70), *Culex* spp (Cul q 28 kD, Cul q 35 kD, Cul q 7, Cul q 7.0101, Cul q 7.0102), *Culicoides* spp (Cul so 1), *Cuminum* spp (Cum c 1, Cum c 2), *Cupressus* spp (Cup a 1, Cup a 1.0101, Cup a 1.02, Cup a 2, Cup a 3, Cup a 4, Cup a 4.0101, Cup s 1, Cup s 1.0101, Cup s 1.0102, Cup s 1.0103, Cup s 1.0104, Cup s 1.0105, Cup s 3, Cup s 3.0101, Cup s 3.0102, Cup s 3.0103, Cup s 8), *Cochliobolus* spp (Cur I 1, Cur I 1.0101, Cur I 2, Cur I 2.0101, Cur I 3, Cur I 3.0101, Cur I 4, Cur I 4.0101, Cur I ADH, Cur I GST, Cur I MnSOD, Cur I Oryzin, Cur I Trx, Cur I ZPS1), *Cyanochen* spp (Cya cy 1), *Cynoscion* spp (Cyn ar 1), *Cynosurus* spp (Cyn cr 1, Cyn cr 5), *Cynodon* spp (Cyn d 1, Cyn d 1.0101, Cyn d 1.0102, Cyn d 1.0103, Cyn d 1.0104, Cyn d 1.0105, Cyn d 1.0106, Cyn d 1.0107, Cyn d 1.0201, Cyn d 1.0202, Cyn d 1.0203, Cyn d 1.0204, Cyn d 10, Cyn d 11, Cyn d 12, Cyn d 12.0101, Cyn d 13, Cyn d 15, Cyn d 15.0101, Cyn d 2, Cyn d 22, Cyn d 22.0101, Cyn d 23, Cyn d 23.0101, Cyn d 24, Cyn d 24.0101, Cyn d 4, Cyn d 5, Cyn d 6, Cyn d 7, Cyn d 7.0101), *Cynoscion* spp (Cyn ne 1), *Cynomys* spp (Cyn sp Lipocalin), *Cyprinus* spp (Cyp c 1, Cyp c 1.01, Cyp c 1.02), *Daboia* spp (Dab ru 1), *Dactylis* spp (Dac g 1, Dac g 1.01, Dac g 1.0101, Dac g 1.02, Dac g 12, Dac g 13, Dac g 2, Dac g 2.0101, Dac g 3, Dac g 3.0101, Dac g 4, Dac g 4.0101, Dac g 5, Dac g 5.0101, Dac g 7), *Dama* spp (Dam d CSA), *Danio* spp (Dan re 1, Dan re 2, Dan re alpha2I, Dan re CK), *Dasyatis* spp (Das ak 1, Das am 1, Das sa 1), *Daucus* spp (Dau c 1, Dau c 1.0101, Dau c 1.0102, Dau c 1.0103, Dau c 1.0104, Dau c 1.0105, Dau c 1.0201, Dau c 1.0301, Dau c 3, Dau c 4, Dau c 4.0101, Dau c CyP), *Decapterus* spp (Dec ru 1), *Dendronephthya* spp (Den n 1, Den n 1.0101), *Dermatophagoides* spp (Der f 1, Der f 1.0101, Der f 1.0102, Der f 1.0103, Der f 1.0104, Der f 1.0105, Der f 1.0106, Der f 1.0107, Der f 1.0108, Der f 1.0109, Der f 1.0110, Der f 10, Der f 10.0101, Der f 10.0102, Der f 11, Der f 11.0101, Der f 13, Der f 13.0101, Der f 14, Der f 14.0101, Der f 15, Der f 15.0101, Der f 16, Der f 16.0101, Der f 17, Der f 17.0101, Der f 18, Der f 18.0101, Der f 2, Der f 2.0101, Der f 2.0102, Der f 2.0103, Der f 2.0104, Der f 2.0105, Der f 2.0106, Der f 2.0107, Der f 2.0108, Der f 2.0109, Der f 2.0110, Der f 2.0111, Der f 2.0112, Der f 2.0113, Der f 2.0114, Der f 2.0115, Der f 2.0116, Der f 2.0117, Der f 20, Der f 21, Der f 22, Der f 22.0101, Der f 3, Der f 3.0101, Der f 4, Der f 5, Der f 6, Der f 6.0101, Der f 7, Der f 7.0101, Der f 8, Der f 9, Der f HSP70), *Dermanyssus* spp (Der g 10, Der g 10.0101), *Dermatophagoides* spp (Der m 1, Der m 1.0101, Der p 1, Der p 1.0101, Der p 1.0102, Der p 1.0103, Der p 1.0104, Der p 1.0105, Der p 1.0106, Der p 1.0107, Der p 1.0108, Der p 1.0109, Der p 1.0110, Der p 1.0111, Der p 1.0112, Der p 1.0113, Der p 1.0114, Der p 1.0115, Der p 1.0116, Der p 1.0117, Der p 1.0118, Der p 1.0119, Der p 1.0120, Der p 1.0121, Der p 1.0122, Der p 1.0123, Der p 1.0124, Der p 10, Der p 10.0101, Der p 10.0102, Der p 10.0103, Der p 11, Der p 11.0101, Der p 13, Der p 14, Der p 14.0101, Der p 15, Der p 18, Der p 2, Der p 2.0101, Der p 2.0102, Der p 2.0103, Der p 2.0104, Der p 2.0105, Der p 2.0106, Der p 2.0107, Der p 2.0108, Der p 2.0109, Der p 2.0110, Der p 2.0111, Der p 2.0112, Der p 2.0113, Der p 2.0114, Der p 2.0115, Der p 20, Der p 20.0101, Der p 21, Der p 21.0101, Der p 23, Der p 23.0101, Der p 3, Der p 3.0101, Der p 4, Der p 4.0101, Der p 5, Der p 5.0101, Der p 5.0102, Der p 6, Der p 6.0101, Der p 7, Der p 7.0101, Der p 8, Der p 8.0101, Der p 9, Der p 9.0101, Der p 9.0102, Der p P1-P2, Der p P2-P1, Der s 1, Der s 2, Der s 3), *Dianthus* spp (Dia c RIP), *Dicranopteris* spp (Dic I 2S Albumin), *Diospyros* spp (Dio k 17 kD, Dio k 4, Dio k IFR), *Dioscorea* spp (Dio p TSP), *Diplodus* spp (Dip ho 1), *Distichlis* spp (Dis s 1, Dis s 7), *Ditrema* spp (Dit te 1), *Dolichovespula* spp (Dol a 1, Dol a 2, Dol a 5, Dol a 5.0101), *Dolichos* spp (Dol b Agglutinin), *Dolichovespula* spp (Dol m 1, Dol m 1.0101, Dol m 1.02, Dol m 2, Dol m 2.0101, Dol m 5, Dol m 5.0101, Dol m 5.02), *Drosophila* spp (Dro an 7, Dro an 7.0101, Dro er 7, Dro er 7.0101, Dro er 7.0102, Dro gr 7, Dro gr 7.0101, Dro gr 7.0102, Dro m 7, Dro m 7.0101, Dro m 7.0102, Dro m 7.0103, Dro m 7.0104, Dro m 7.0105, Dro m 7.0106, Dro m 7.0107, Dro m 7.0108, Dro m 7.0109, Dro m 7.0110, Dro m 7.0111, Dro m 7.0112, Dro m 7.0113, Dro m 9, Dro m MnSOD, Dro mo 7, Dro mo 7.0101, Dro pp 7, Dro pp 7.0101, Dro se 7, Dro se 7.0101, Dro si 7, Dro si 7.0101, Dro si 7.0102, Dro vi 7, Dro vi 7.0101, Dro wi 7, Dro wi 7.0101, Dro y 7, Dro y 7.0101, Dro y 7.0102, Dro y 7.0103), *Echium* spp (Ech p Cytochrome C), *Elaeis* spp (Ela g 2, Ela g Bd31 kD), *Elops* spp (Elo sa 1), *Embellisia* spp (Emb a 1, Emb i 1, Emb nz 1, Emb t 1), *Engraulis* spp (Eng e 1), *Enteroctopus* spp (Ent d 1), *Epinephelus* spp (Epi bl 1, Epi co 1, Epi fl 1, Epi mc 1, Epi mo 1), *Epicoccum* spp (Epi p 1, Epi p 1.0101, Epi p 12 kD, Epi p GST), *Epinephelus* spp (Epi po 1, Epi un 1), *Equisetum* spp (Equ a 17 kD), *Equus* spp (Equ as 4, Equ as DSA, Equ bu 4, Equ c 1, Equ c 1.0101, Equ c 2, Equ c 2.0101, Equ c 2.0102, Equ c 3, Equ c 3.0101, Equ c 4, Equ c 4.0101, Equ c 5, Equ c 5.0101, Equ c ALA, Equ c BLG, Equ c Casein, Equ c Casein beta, Equ c Casein kappa, Equ c PRVB, Equ he 4, Equ z ZSA), *Erimacrus* spp (Eri i 1, Eri i 1.0101, Eri i 1.0102), *Eriocheir* spp (Eri s 1, Eri s 1.0101, Eri s 2), *Erwinia* spp (Erw ch Asparaginase), *Escherichia* spp (Esc c Asparaginase, Esc c beta GAL), *Esox* spp (Eso I 1), *Euphausia* spp (Eup p 1, Eup p 1.0101), *Euphasia* spp (Eup s 1, Eup s 1.0101), *Euroglyphus* spp (Eur m 1, Eur m 1.0101, Eur m 1.0102, Eur m 1.0103, Eur m 10, Eur m 14, Eur m 14.0101, Eur m 2, Eur m 2.0101, Eur m 2.0102, Eur m 3, Eur m 3.0101, Eur m 4, Eur m 4.0101), *Evynnis* spp (Evy j 1), *Fagopyrum* spp (Fag e 1, Fag e 1.0101, Fag e 10 kD, Fag e 19 kD, Fag e 2, Fag e 2.0101, Fag e TI), *Fagus* spp (Fag s 1, Fag s 1.0101, Fag s 2, Fag s 4), *Fagopyrum* spp (Fag t 1, Fag t 10 kD, Fag t 2, Fag t 2.0101), *Felis* spp (Fel d 1, Fel d 1.0101, Fel d 2, Fel d 2.0101, Fel d 3, Fel d 3.0101, Fel d 4, Fel d 4.0101, Fel d 5, Fel d 5.0101, Fel d 6, Fel d 6.0101, Fel d 7, Fel d 7.0101, Fel d 8, Fel d 8.0101, Fel d IgG), *Fenneropenaeus* spp (Fen c 1, Fen c 2, Fen me 1, Fen me 1.0101), *Festuca* spp (Fes e 1, Fes e 13, Fes e 4, Fes e 5, Fes e 7, Fes p 1, Fes p 13, Fes p 4, Fes p 4.0101, Fes p 5, Fes r 1, Fes r 5), *Ficus* spp (Fic c 17 kD, Fic c 4, Fic c Ficin), *Foeniculum* spp (Foe v 1, Foe v 2), *Forsythia* spp (For s 1), *Forcipomyia* spp (For t 1, For t 1.0101, For t 2, For t 2.0101, For t 7, For t FPA, For t Myosin, For t TPI), *Fragaria* spp (Fra a 1, Fra a 1.0101, Fra a 3, Fra a 3.0101, Fra a 3.0102, Fra a 3.0201, Fra a 3.0202, Fra a 3.0203, Fra a 3.0204, Fra a 3.0301, Fra a 4, Fra a 4.0101, Fra c 1), *Fraxinus* spp (Fra e 1, Fra e 1.0101, Fra e 1.0102, Fra e 1.0201, Fra e 12, Fra e 2, Fra e 3, Fra e 9), *Fragaria* spp (Fra v 1), *Fusarium* spp (Fus c 1, Fus c 1.0101, Fus c 2, Fus c 2.0101, Fus c 3, Fus s 1, Fus s 45 kD, Fus sp Lipase), *Gadus* spp (Gad c 1, Gad c 1.0101, Gad c APDH, Gad m 1, Gad m 1.0101, Gad m 1.0102, Gad m 1.0201, Gad m 1.0202, Gad m 45 kD, Gad m Gelatin, Gad ma 1), *Gallus* spp (Gal d 1, Gal d 1.0101, Gal d 2, Gal d 2.0101, Gal d 3, Gal d 3.0101, Gal d 4, Gal d 4.0101, Gal d 5, Gal d 5.0101, Gal d 6, Gal d 6.0101, Gal d Apo I, Gal d Apo VI, Gal d GPI, Gal d HG, Gal d IgY, Gal d L-PGDS, Gal d Ovomucin, Gal d Phosvitin, Gal d PRVB, Gal la 4), *Galleria* spp (Gal m 18 kD, Gal m 24 kD), *Gallus* spp (Gal so 4), *Gammarus* spp (Gam s TM), *Gelonium* spp (Gel m RIP), *Geothelphusa* spp (Geo de 1), *Glossina* spp (Glo m 5, Glo m 5.0101, Glo m 7, Glo m 7.0101, Glo m 7.0102, Glo m 7.0103), *Glycine* spp (Gly a Bd30K, Gly ar Bd30K, Gly ca Bd30K, Gly cl Bd30K, Gly cu Bd30K, Gly cy Bd30K), *Glycyphagus* spp (Gly d 10, Gly d 10.0101, Gly d 13, Gly d 2, Gly d 2.0101, Gly d 2.0201, Gly d 2.03, Gly d 2/Lep d 2 L1, Gly d 2/Lep d 2 L2, Gly d 2/Lep d 2 L3, Gly d 2/Lep d 2 L4, Gly d 2/Lep d 2 R1, Gly d 2/Lep d 2 R2, Gly d 2/Lep d 2 R3, Gly d 2/Lep d 2 R4, Gly d 2/Lep d 2 R5, Gly d 20, Gly d 3, Gly d 5, Gly d 5.01, Gly d 5.02, Gly d 7, Gly d 8), *Glycine* spp (Gly f Bd30K, Gly I Bd30K, Gly m 1, Gly m 1.0101, Gly m 1.0102, Gly m 2, Gly m 2.0101, Gly m 2S Albumin, Gly m 3, Gly m 3.0101, Gly m 3.0102, Gly m 39 kD, Gly m 4, Gly m 4.0101, Gly m 5, Gly m 5.0101, Gly m 5.0201, Gly m 5.0301, Gly m 5.0302, Gly m 50 kD, Gly m 6, Gly m 6.0101, Gly m 6.0201, Gly m 6.0301, Gly m 6.0401, Gly m 6.0501, Gly m 68 kD, Gly m Agglutinin, Gly m Bd28K, Gly m Bd30K, Gly m Bd60K, Gly m CPI, Gly m EAP, Gly m TI, Gly mi Bd30K, Gly s Bd30K, Gly t Bd30K, Gly to Bd30K), *Gossypium* spp (Gos h Vicilin), *Haemophilus* spp (Hae in P6), *Haemaphysalis* spp (Hae I 7, Hae I 7.0101, Hae q 7, Hae q 7.0101), *Haliotis* spp (Hal a 1, Hal d 1, Hal di 1, Hal di PM, Hal m 1, Hal m 1.0101, Hal r 1, Hal r 49 kD, Hal ru 1), *Harmonia* spp (Har a 1, Har a 1.0101, Har a 2, Har a 2.0101), *Harpegnathos* spp (Har sa 7, Har sa 7.0101, Har sa 7.0102), *Helianthus* spp (Hel a 1, Hel a 1.0101, Hel a 2, Hel a 2.0101, Hel a 2S Albumin, Hel a 3, Hel a 3.0101, Hel a 4), *Helix* spp (Hel ap 1, Hel as 1, Hel as 1.0101), *Heligmosomoides* spp (Hel p 3, Hel p 3.0101), *Helianthus* spp (Hel tu 1), *Hemanthias* spp (Hem le 1), *Hemifusus* spp (Hem t 1), *Heterodera* spp (Het g 3, Het g 3.0101), *Hevea* spp (Hev b 1, Hev b 1.0101, Hev b 10, Hev b 10.0101, Hev b 10.0102, Hev b 10.0103, Hev b 11, Hev b 11.0101, Hev b 11.0102, Hev b 12, Hev b 12.0101, Hev b 13, Hev b 13.0101, Hev b 14, Hev b 14.0101, Hev b 2, Hev b 2.0101, Hev b 3, Hev b 3.0101, Hev b 4, Hev b 4.0101, Hev b 5, Hev b 5.0101, Hev b 6, Hev b 6.01, Hev b 6.02, Hev b 6.0202, Hev b 6.03, Hev b 7, Hev b 7.01, Hev b 7.02, Hev b 7.D2, Hev b 7.S2, Hev b 8, Hev b 8.0101, Hev b 8.0102, Hev b 8.0201, Hev b 8.0202, Hev b 8.0203, Hev b 8.0204, Hev b 9, Hev b 9.0101, Hev b Citrate binding Protein, Hev b GAPDH, Hev b HSP80, Hev b IFR, Hev b Proteasome subunit, Hev b Rotamase, Hev b SPI, Hev b Trx, Hev b UDPGP), *Hexa-*

*grammos* spp (Hex ot 1), *Hippoglossus* spp (Hip h 1), *Hippoglossoides* spp (Hip pl 1), *Hippoglossus* spp (Hip st 1), *Hirudo* spp (Hir me Hirudin), *Holcus* spp (Hol I1, Hol 11.0101, Hol 11.0102, Hol 12, Hol 14, Hol 15, Hol I 5.0101, Hol I 5.0201), *Holocnemus* spp (Hol pl 9, Hol pl Hemocyanin), *Homarus* spp (Hom a 1, Hom a 1.0101, Hom a 1.0102, Hom a 1.0103, Hom a 3, Hom a 3.0101, Hom a 4, Hom a 6, Hom a 6.0101, Hom g 1, Hom g 2), *Homo* spp (Hom s 1, Hom s 1.0101, Hom s 2, Hom s 2.0101, Hom s 3, Hom s 3.0101, Hom s 4, Hom s 4.0101, Hom s 5, Hom s 5.0101, Hom s AAT, Hom s ACTH, Hom s Adalimumab, Hom s ALA, Hom s alpha_Actin, Hom s alpha-Galactosidase, Hom s APDH, Hom s Arylsulfatase B, Hom s Casein, Hom s CyP A, Hom s CyP B, Hom s CyP C, Hom s DSF70, Hom s DSG3, Hom s eIF6, Hom s Etanercept, Hom s Factor IX, Hom s Factor VII, Hom s Factor VIII, Hom s G-CSF, Hom s Glucocerebrosidase, Hom s Glucosidase, Hom s HLA-DR-alpha, Hom s HSA, Hom s Iduronidase, Hom s Idursulfase, Hom s IgA, Hom s Insulin, Hom s Lactoferrin, Hom s Laminin gamma_2, Hom s MnSOD, Hom s Oxytocin, Hom s P2, Hom s Phosvitin, Hom s Profilin, Hom s PSA, Hom s RP1, Hom s TCTP, Hom s TL, Hom s TPA, Hom s TPO, Hom s Transaldolase, Hom s Trx, Hom s Tubulin-alpha, Hom s/Mus m Basiliximab, Hom s/Mus m Cetuximab, Hom s/Mus m Cetuximab (Gal-Gal), Hom s/Mus m Infliximab, Hom s/Mus m Natalizumab, Hom s/Mus m Omalizumab, Hom s/Mus m Palivizumab, Hom s/Mus m Rituximab, Hom s/Mus m Tocilizumab, Hom s/Mus m Trastuzumab), *Hoplostethus* spp (Hop a 1), *Hordeum* spp (Hor v 1, Hor v 12, Hor v 12.0101, Hor v 13, Hor v 14, Hor v 15, Hor v 15.0101, Hor v 16, Hor v 16.0101, Hor v 17, Hor v 17.0101, Hor v 18 kD, Hor v 2, Hor v 21, Hor v 21.0101, Hor v 28, Hor v 33, Hor v 4, Hor v 5, Hor v 5.0101, Hor v BDAI, Hor v BTI), *Humicola* spp (Hum in Cellulase), *Humulus* spp (Hum j 1, Hum j 1.0101, Hum j 10 kD, Hum j 2), *Huso* spp (Hus h 1), *Hylocereus* spp (Hyl un LTP), *Hymenocephalus* spp (Hym st 1), *Hyperoglyphe* spp (Hyp by 1), *Hypophthalmichthys* spp (Hyp mo 1), *Hypophthalmichthy* spp (Hyp no 1), *Ictalurus* spp (Ict fu 1, Ict p 1), *Imperata* spp (Imp c 4, Imp c 5, Imp c VIIIel), *Ixodes* spp (Ixo r 2, Ixo sc 7, Ixo sc 7.0101), *Jasus* spp (Jas la 1, Jas la 1.0101, Jas la 1.0102), *Juglans* spp (Jug ca 1, Jug ca 2, Jug ci 1, Jug ci 2, Jug n 1, Jug n 1.0101, Jug n 2, Jug n 2.0101, Jug r 1, Jug r 1.0101, Jug r 2, Jug r 2.0101, Jug r 3, Jug r 3.0101, Jug r 4, Jug r 4.0101, Jug r 5), *Juniperus* spp (Jun a 1, Jun a 1.0101, Jun a 1.0102, Jun a 2, Jun a 2.0101, Jun a 3, Jun a 3.0101, Jun c 1, Jun o 1, Jun o 4, Jun o 4.0101, Jun r 3, Jun r 3.1, Jun r 3.2, Jun v 1, Jun v 1.0101, Jun v 1.0102, Jun v 3, Jun v 3.0101, Jun v 3.0102, Jun v 4), *Katsuwonus* spp (Kat p 1), *Kyphosus* spp (Kyp se 1), *Lachnolaimus* spp (Lac ma 1), *Lachesis* spp (Lac mu 1), *Lactuca* spp (Lac s 1, Lac s 1.0101), *Lagocephalus* spp (Lag la 1), *Larus* spp (Lar a 1, Lar a 2, Lar a 3), *Larimichthys* spp (Lar po 1), *Lates* spp (Lat c 1), *Lateolabrax* spp (Lat ja 1), *Lathyrus* spp (Lat oc Agglutinin), *Leiostomus* spp (Lei xa 1), *Lens* spp (Len c 1, Len c 1.0101, Len c 1.0102, Len c 1.0103, Len c 2, Len c 2.0101, Len c 3, Len c 3.0101, Len c Agglutinin), *Leopardus* spp (Leo p 1), *Lepidoglyphus* spp (Lep d 10, Lep d 10.0101, Lep d 12, Lep d 13, Lep d 13.0101, Lep d 2, Lep d 2.0101, Lep d 2.0102, Lep d 2.0201, Lep d 2.0202, Lep d 3, Lep d 39 kD, Lep d 5, Lep d 5.0101, Lep d 5.0102, Lep d 5.0103, Lep d 7, Lep d 7.0101, Lep d 8, Lep d alpha Tubulin), *Lepomis* spp (Lep gi 1), *Leptomelanosoma* spp (Lep i 1), *Lepomis* spp (Lep ma 1), *Lepisma* spp (Lep s 1, Lep s 1.0101, Lep s 1.0102), *Lepeophtheirus* spp (Lep sa 1, Lep sa 1.0101, Lep sa 1.0102, Lep sa 1.0103), *Leptailurus* spp (Lep se 1), *Lepidorhombus* spp (Lep w 1, Lep w 1.0101), *Lethocerus* spp (Let in 7, Let in 7.0101, Let in 7.0102), *Leuciscus* spp (Leu ce 1), *Lewia* spp (Lew in 1), *Ligustrum* spp (Lig v 1, Lig v 1.0101, Lig v 1.0102, Lig v 2), *Lilium* spp (Lil 12, Lil I PG), *Limanda* spp (Lim fe 1), *Limnonectes* spp (Lim m 1), *Limulus* spp (Lim p 1, Lim p 1.0101, Lim p 2, Lim p LPA), *Liposcelis* spp (Lip b 1, Lip b 1.0101), *Litchi* spp (Lit c 1, Lit c 1.0101, Lit c IFR, Lit c TPI), *Lithobates* spp (Lit ca 1), *Litopenaeus* spp (Lit se 1, Lit v 1, Lit v 1.0101, Lit v 2, Lit v 2.0101, Lit v 3, Lit v 3.0101, Lit v 4, Lit v 4.0101), *Filiaria* spp (Loa lo 3, Loa lo 3.0101), *Lobotes* spp (Lob su 1), *Locusta* spp (Loc m 7, Loc m 7.0101), *Loligo* spp (Lol b 1, Lol e 1), *Lolium* spp (Lol m 2, Lol m 5, Lol p 1, Lol p 1.0101, Lol p 1.0102, Lol p 1.0103, Lol p 10, Lol p 11, Lol p 11.0101, Lol p 12, Lol p 13, Lol p 2, Lol p 2.0101, Lol p 3, Lol p 3.0101, Lol p 4, Lol p 4.0101, Lol p 5, Lol p 5.0101, Lol p 5.0102, Lol p 7, Lol p CyP, Lol p FT, Lol p Legumin), *Lonomia* spp (Lon o 7, Lon o 7.0101), *Lophodytes* spp (Lop cu 1), *Lophonetta* spp (Lop sp 1), *Lupinus* spp (Lup a 1, Lup a alpha_Conglutin, Lup a delta_Conglutin, Lup a gamma_Conglutin, Lup an 1, Lup an 1.0101, Lup an alpha_Conglutin, Lup an delta_Conglutin, Lup an gamma_Conglutin, Lup 117 kD), *Lutjanus* spp (Lut a 1, Lut c 1, Lut cy 1, Lut gr 1, Lut gu 1, Lut jo 1), *Lutraria* spp (Lut p 1), *Lutjanus* spp (Lut pu 1, Lut sy 1), *Lycopersicon* spp (Lyc e 1, Lyc e 1.0101, Lyc e 11 S Globulin, Lyc e 2, Lyc e 2.0101, Lyc e 2.0102, Lyc e 3, Lyc e 3.0101, Lyc e 4, Lyc e 4.0101, Lyc e ARP60S, Lyc e Chitinase, Lyc e Glucanase, Lyc e Peroxidase, Lyc e PG, Lyc e PME, Lyc e PR23, Lyc e Vicilin), *Maconellicoccus* spp (Mac h 7, Mac h 7.0101), *Macruronus* spp (Mac ma 1, Mac n 1), *Macdura* spp (Mac po 17 kD), *Macrobrachium* spp (Mac ro 1, Mac ro 1.0101, Mac ro Hemocyanin), *Macropus* spp (Macr s Gelatin), *Malus* spp (Mal d 1, Mal d 1.0101, Mal d 1.0102, Mal d 1.0103, Mal d 1.0104, Mal d 1.0105, Mal d 1.0106, Mal d 1.0107, Mal d 1.0108, Mal d 1.0109, Mal d 1.0201, Mal d 1.0202, Mal d 1.0203, Mal d 1.0204, Mal d 1.0205, Mal d 1.0206, Mal d 1.0207, Mal d 1.0208, Mal d 1.0301, Mal d 1.0302, Mal d 1.0303, Mal d 1.0304, Mal d 1.0401, Mal d 1.0402, Mal d 1.0403, Mal d 2, Mal d 2.0101, Mal d 3, Mal d 3.0101, Mal d 3.0102, Mal d 3.0201, Mal d 3.0202, Mal d 3.0203, Mal d 4, Mal d 4.0101, Mal d 4.0102, Mal d 4.0201, Mal d 4.0202, Mal d 4.0301, Mal d 4.0302), *Malpighia* spp (Mal g 4, Mal g Hevein), *Malus* spp (Mal p 1), *Malassezia* spp (*Mala* f 2, *Mala* f 2.0101, *Mala* f 3, *Mala* f 3.0101, *Mala* f 4, *Mala* f 4.0101, *Mala* g 10, *Mala* s 1, *Mala* s 1.0101, *Mala* s 10, *Mala* s 10.0101, *Mala* s 11, *Mala* s 11.0101, *Mala* s 12, *Mala* s 12.0101, *Mala* s 13, *Mala* s 13.0101, *Mala* s 5, *Mala* s 5.0101, *Mala* s 6, *Mala* s 6.0101, *Mala* s 7, *Mala* s 7.0101, *Mala* s 8, *Mala* s 8.0101, *Mala* s 9, *Mala* s 9.0101), *Manihot* spp (Man e 5, Man e 5.0101, Man e FPA, Man e GAPDH), *Mangifera* spp (Man i 1, Man i 14 kD, Man i 2, Man i 3, Man i 3.01, Man i 3.02, Man i Chitinase), *Marsupenaeus* spp (Mar j 1, Mar j 1.0101, Mar j 2, Mar j 4), *Matricaria* spp (Mat c 17 kD), *Mecopoda* spp (Mec e 7), *Megalobrama* spp (Meg am 2, Meg am CK), *Megathura* spp (Meg c Hemocyanin), *Megalops* spp (Meg sp 1), *Melanogrammus* spp (Mel a 1), *Meleagris* spp (Mel g 1, Mel g 2, Mel g 3, Mel g PRVB, Mel g TSA), *Melicertus* spp (Mel I 1), *Menticirrhus* spp (Men am 1), *Mercurialis* spp (Mer a 1, Mer a 1.0101), *Merluccius* spp (Mer ap 1, Mer au 1, Mer bi 1, Mer ca 1, Mer ga 1, Mer hu 1), *Merlangius* spp (Mer me 1), *Merluccius* spp (Mer mr 1, Mer pa 1, Mer po 1, Mer pr 1, Mer se 1), *Meriones* spp (Mer un 23 kD), *Metarhizium* spp (Met a 30), *Metapenaeopsis* spp (Met ba 1), *Metapenaeus* spp (Met e 1, Met e 1.0101, Met e 2), *Metasequoia* spp (Met gl 2), *Metapenaeus* spp (Met j 1, Met j 2), *Metanephrops* spp (Met ja 1), *Metapenaeopsis* spp (Met la 1), *Metanephrops* spp (Met t 2), *Micromesistius* spp (Mic po 1), *Micropogonias* spp (Mic un 1), *Mimachlamys* spp (Mim n 1), *Momordica* spp (Mom c RIP), *Morus* spp (Mor a 17 kD, Mor a 4), *Morone* spp (Mor am 1), *Morus* spp (Mor n 3, Mor n 3.0101), *Morone* spp (Mor sa 1, Mor sc 1), *Mugil* spp (Mug c 1), *Muraenolepis* spp (Mur mi 1), *Musa* spp (Mus a 1, Mus a 1.0101, Mus a 2, Mus a 2.0101, Mus a 3, Mus a 3.0101, Mus a 4, Mus a 4.0101, Mus a 5, Mus a 5.0101, Mus a 5.0102), *Mus* spp (Mus m 1, Musm 1.0101, Mus m 1.0102, Mus m 2, Mus m Gelatin, Mus m IgG, Mus m MSA, Mus m Muromonab, Mus m Phosvitin), *Mustela* spp (Mus p 17 kD), *Musa* spp (Mus xp 1, Mus xp 2, Mus xp 5), *Mycteroperca* spp (Myc bo 1, Myc mi 1, Myc ph 1), *Myceliophthora* spp (Myc sp Laccase), *Myrmecia* spp (Myr p 1, Myr p 1.0101, Myr p 2, Myr p 2.0101, Myr p 2.0102, Myr p 3, Myr p 3.0101), *Mytilus* spp (Myt e 1, Myt g 1, Myt g PM), *Myzus* spp (Myz p 7, Myz p 7.0101), *Nemorhedus* spp (Nae go Hya), *Necator* spp (Nec a Calreticulin), *Nemipterus* spp (Nem vi 1), *Neosartorya* spp (Neo fi 1, Neo fi 22), *Neochen* spp (Neo ju 1), *Neoscona* spp (Neo n 7, Neo n 7.0101), *Nephelium* spp (Nep I GAPDH), *Nephrops* spp (Nep n 1, Nep n DF9), *Neptunea* spp (Nep po 1, Nep po 1.0101), *Nicotiana* spp (Nic t 8, Nic t Osmotin, Nic t Villin), *Nimbya* spp (Nim c 1, Nim s 1), *Nippostrongylus* spp (Nip b Agl), *Nycticebus* spp (Nyc c 1), *Octopus* spp (Oct f 1, Oct I 1, Oct v 1, Oct v 1.0101, Oct v PM), *Ocyurus* spp (Ocy ch 1), *Olea* spp (Ole e 1, Ole e 1.0101, Ole e 1.0102, Ole e 1.0103, Ole e 1.0104, Ole e 1.0105, Ole e 1.0106, Ole e 1.0107, Ole e 10, Ole e 10.0101, Ole e 11, Ole e 11.0101, Ole e 11.0102, Ole e 12, Ole e 13, Ole e 2, Ole e 2.0101, Ole e 3, Ole e 3.0101, Ole e 36 kD, Ole e 4, Ole e 4.0101, Ole e 5, Ole e 5.0101, Ole e 6, Ole e 6.0101, Ole e 7, Ole e 7.0101, Ole e 8, Ole e 8.0101, Ole e 9, Ole e 9.0101), *Ommastrephes* spp (Omm b 1, Omm b 1.0101), *Oncorhynchus* spp (Onc ke 1, Onc ke 18 kD, Onc ke alpha2I, Onc ke Vitellogenin, Onc m 1, Onc m 1.0101, Onc m 1.0201, Onc m alpha2I, Onc m Protamine, Onc m Vitellogenin, Onc ma 1, Onc ma FPA, Onc ma FSA, Onc ma TPI, Onc n 1), *Onchocerca* spp (Onc o 3, Onc o 3.0101), *Oncorhynchus* spp (Onc ts 1), *Onchocerca* spp (Onc v 3, Onc v 3.0101), *Oratosquilla* spp (Ora o 1, Ora o 1.0101), *Oreochromis* spp (Ore a 1, Ore mo 1, Ore mo 2, Ore mo FPA, Ore mo SCAF7145, Ore ni 1, Ore ni 18 kD, Ore ni 45 kD), *Ornithonyssus* spp (Orn sy 10, Orn sy 10.0101, Orn sy 10.0102), *Oryctolagus* spp (Ory c 1, Ory c 1.0101, Ory c 2, Ory c Casein, Ory c Phosvitin, Ory c RSA), *Oryza* spp (Ory s 1, Ory s 1.0101, Ory s 11, Ory s 12, Ory s 12.0101, Ory s 13, Ory s 14, Ory s 17 kD, Ory s 19 kD, Ory s2, Ory s23, Ory s 3, Ory s 7, Ory s aA_TI, Ory s GLP52, Ory s GLP63, Ory s Glyoxalase I, Ory s NRA), *Ostrya* spp (Ost c 1, Ost c 1.0101), *Ovis* spp (Ovi a ALA, Ovi a BLG, Ovi a Casein, Ovi a Casein alphaSI, Ovi a Casein alphaS2, Ovi a Casein beta, Ovi a Casein kappa, Ovi a Phosvitin, Ovi a SSA), *Pachycondyla* spp (Pac c 3), *Pagrus* spp (Pag m 1, Pag pa 1), *Pampus* spp (Pam ar 1, Pam c 1), *Pandalus* spp (Pan b 1, Pan b 1.0101), *Pangasius* spp (Pan bo 1), *Pandalus* spp (Pan e 1, Pan e 1.0101, Pan e 4), *Panulirus* spp (Pan h 1, Pan by 1), *Pangasius* spp (Pan by 18 kD, Pan by 45 kD), *Panulirus* spp (Pan j 1), *Panthera* spp (Pan I 1, Pan o 1, Pan p 1), *Panulirus* spp (Pan s 1, Pan s 1.0101), *Panthera* spp (Pan t 1), *Pan* spp (Pan tr TCTP), *Papaver* spp (Pap s 17 kD, Pap s 2, Pap s 34 kD), *Papilio* spp (Pap xu 7, Pap xu 7.0101, Pap xu 7.0102), *Paralichthys* spp (Par a 1), *Parasilurus* spp (Par as 1, Par c 1), *Paralithodes* spp (Par c 1.0101, Par c 1.0102, Par f 1), *Parthenium* spp (Par h 1), *Parietaria* spp (Par j 1, Par j 1.0101, Par j 1.0102, Par j 1.0103, Par j 1.0201, Par j 2, Par j 2.0101, Par j 2.0102, Par j 3, Par j 3.0101, Par j 3.0102, Par j 4, Par j 4.0101, Par j J1-J2), *Paralichthys* spp (Par le 1), *Parietaria* spp (Par m 1, Par o 1, Par o 1.0101), *Paralichthys* spp (Par ol 1, Par of alpha2I), *Parahucho* spp (Par pe Vitellogenin), *Passiflora* spp (Pas e Chitinase, Pas e Hevein), *Paspalum* spp (Pas n 1, Pas n 1.0101, Pas n 13), *Patinopecten* spp (Pat y 1), *Pediculus* spp (Ped h 7, Ped h 7.0101), *Penaeus* spp (Pen a 1, Pen a 1.0101, Pen a 1.0102, Pen a 1.0102 (103-117), Pen a 1.0102 (109-123), Pen a 1.0102 (1-15), Pen a 1.0102 (115-129), Pen a 1.0102 (121-135), Pen a 1.0102 (127-141), Pen a 1.0102 (13-27), Pen a 1.0102 (133-147), Pen a 1.0102 (139-153), Pen a 1.0102 (145-159)), *Farfantepenaeus* spp (Pen a 1.0102 (151-165)), *Penaeus* spp (Pen a 1.0102 (157-171), Pen a 1.0102 (163-177), Pen a 1.0102 (169-183), Pen a 1.0102 (175-189), Pen a 1.0102 (181-195), Pen a 1.0102 (187-201), Pen a 1.0102 (193-207), Pen a 1.0102 (19-33), Pen a 1.0102 (199-213), Pen a 1.0102 (205-219), Pen a 1.0102 (211-225), Pen a 1.0102 (217-231), Pen a 1.0102 (223-237), Pen a 1.0102 (229-243)), *Farfantepenaeus* spp (Pen a 1.0102 (235-249)), *Penaeus* spp (Pen a 1.0102 (241-255), Pen a 1.0102 (247-261), Pen a 1.0102 (253-267), Pen a 1.0102 (25-39), Pen a 1.0102 (259-273), Pen a 1.0102 (265-279), Pen a 1.0102 (270-284), Pen a 1.0102 (31-45), Pen a 1.0102 (37-51), Pen a 1.0102 (43-57), Pen a 1.0102 (49-63)), *Farfantepenaeus* spp (Pen a 1.0102 (55-69)), *Penaeus* spp (Pen a 1.0102 (61-75), Pen a 1.0102 (67-81), Pen a 1.0102 (7-21), Pen a 1.0102 (73-87), Pen a 1.0102 (79-93), Pen a 1.0102 (85-99), Pen a 1.0102 (91-105), Pen a 1.0102 (97-111), Pen a 1.0103), *Penicillium* spp (Pen b 13, Pen b 13.0101, Pen b 26, Pen b 26.0101, Pen c 1, Pen c 13, Pen c 13.0101, Pen c 18, Pen c 19, Pen c 19.0101, Pen c 2, Pen c 22, Pen c 22.0101, Pen c 24, Pen c 24.0101, Pen c 3, Pen c 3.0101, Pen c 30, Pen c 30.0101, Pen c 32, Pen c 32.0101, Pen c MnSOD, Pen ch 13, Pen ch 13.0101, Pen ch 18, Pen ch 18.0101, Pen ch 20, Pen ch 20.0101, Pen ch 31, Pen ch 31.0101, Pen ch 33, Pen ch 33.0101, Pen ch 35, Pen ch 35.0101, Pen ch MnSOD), *Penaeus* spp (Pen i 1, Pen i 1.0101, Pen m 1, Penm 1.0101, Penm 1.0102, Pen m 2, Pen m 2.0101, Pen m 3, Pen m 3.0101, Pen m 4, Pen m 4.0101, Pen m 6, Pen m 6.0101), *Penicillium* spp (Pen o 18, Pen o 18.0101), *Penaeus* spp (Pena o 1, Pena o 1.0101), *Periplaneta* spp (Per a 1, Per a 1.0101, Per a 1.0102, Per a 1.0103, Per a 1.0104, Per a 1.0105, Per a 1.0201, Per a 10, Per a 10.0101, Per a 2, Per a 3, Per a 3.0101, Per a 3.0201, Per a 3.0202, Per a 3.0203, Per a 4, Per a 5, Per a 6, Per a 6.0101, Per a 7, Per a 7.0101, Per a 7.0102, Per a 7.0103, Per a 9, Per a 9.0101, Per a Cathepsin, Per a FABP, Per a Trypsin, Per f 1, Per f 7, Per f 7.0101), *Perna* spp (Per v 1), *Persea* spp (Pers a 1, Pers a 1.0101, Pers a 4), *Petroselinum* spp (Pet c 1, Pet c 2, Pet c 3), *Phalaris* spp (Pha a 1, Pha a 1.0101, Pha a 5, Pha a 5.0101, Pha a 5.02, Pha a 5.03, Pha a 5.04), *Phaseolus* spp (Pha v 3, Pha v 3.0101, Pha v 3.0201, Pha v aAI, Pha v aAI.0101, Pha v Chitinase, Pha v PHA, Pha v Phaseolin), *Phleum* spp (Phl p 1, Phl p 1.0101, Phi p 1.0102, Phi p 11, Phi p 11.0101, Phi p 12, Phi p 12.0101, Phi p 12.0102, Phi p 12.0103, Phi p 13, Phl p 13.0101, PhI p 2, Phi p 2.0101, Phi p 3, Phi p 3.0101, PhI p 3.0102, Phi p 4, Phi p 4.0101, Phi p 4.0102, Phl p 4.0201, Phl p 4.0202, Phl p 4.0203, Phl p 4.0204, Phl p 5, Phl p 5.0101, Phl p 5.0102, Phl p 5.0103, Phl p 5.0104, Phl p 5.0105, Phl p 5.0106, Phl p 5.0107, Phl p 5.0108, Phl p 5.0109, Phl p 5.0201, Phl p 5.0202, Phl p 5.0203, Phl p 5.0204, Phl p 5.0205, Phl p 5.0206, Phl p 5.0207, Phl p 6, Phl p 6.0101, Phl p 6.0102, Phl p 7, Phl p 7.0101, Phl p P1-P2-P5-P6, Phl p P2-P6, Phl p P5-P1, Phl p P6-P2), *Phoenix* spp (Pho d 2, Pho d 2.0101, Pho d 40 kD, Pho d 90 kD), *Phodopus* spp (Pho s 21 kD), *Phoma* spp (Pho t 1), *Phragmites* spp (Phr a 1, Phr a 12, Phr a 13, Phr a 4, Phr a 5), *Phytolacca* spp (Phy a RIP), *Pimpinella* spp (Pim a 1, Pim a 2), *Pinna* spp (Pin a 1), *Piper* spp (Pip n 14 kD, Pip n 28 kD), *Pisum* spp (Pis s 1, Pis s 1.0101, Pis s 1.0102, Pis s 2, Pis s 2.0101, Pis s 5, Pis s Agglutinin, Pis s Albumin), *Pistacia* spp (Pis v 1, Pis v 1.0101, Pis v 2, Pis v 2.0101, Pis v 2.0201, Pis v 3, Pis v 3.0101, Pis v 4, Pis v 4.0101, Pis v 5, Pis v 5.0101), *Platanus* spp (Pla a 1, Pla a 1.0101, Pla a 2, Pla a 2.0101, Pla a 3, Pla a 3.0101, Pla a 8), *Platichthys* spp (Pla f 1), *Plantago* spp (Pla I 1, Pla I 1.0101, Pla I 1.0102, Pla I 1.0103, Pla I Cytochrome C), *Platanus* spp (Pla oc 1, Pla or 1, Pla or 1.0101, Pla or 2, Pla or 2.0101, Pla or 3, Pla or 3.0101, Pla or 4, Pla or CyP, Pla r 1), *Plectropomus* spp (Pie ar 1), *Pleospora* spp (Pie h 1), *Plectropomus* spp (Pie le 1), *Plodia* spp (Plo i 1, Plo i 1.0101, Plo i 2, Plo i 2.0101), *Poa* spp (Poa p 1, Poa p 1.0101, Poa p 10, Poa p 12, Poa p 13, Poa p 2, Poa p 4, Poa p 5, Poa p 5.0101, Poa p 6, Poa p 7), *Polistes* spp (Pol a 1, Pol a 1.0101, Pol a 2, Pol a 2.0101, Pol a 5, Pol a 5.0101, Pol d 1, Pol d 1.0101, Pol d 1.0102, Pol d 1.0103, Pol d 1.0104, Pol d 4, Pol d 4.0101, Pol d 5, Pol d 5.0101, Pol e 1, Pol e 1.0101, Pol e 2, Pol e 4, Pol e 4.0101, Pol e 5, Pol e 5.0101, Pol f 5, Pol f 5.0101, Pol g 1, Pol g 1.0101, Pol g 2, Pol g 4, Pol g 5, Pol g 5.0101, Pol he MLT, Pol m 5, Pol m 5.0101), *Polypedilum* spp (Pol n 1), *Pollicipes* spp (Pol po 1), *Pollachius* spp (Pol vi 1), *Polybia* spp (Poly p 1, Poly p 1.0101, Poly p 2, Poly p 5, Poly s 5, Poly s 5.0101), *Pomatomus* spp (Pom sa 1), *Pongo* spp (Pon ab HSA), *Pontastacus* spp (Pon 14, Pon I 4.0101, Pon I 7, Pon I 7.0101), *Portunus* spp (Por s 1, Por s 1.0101, Por s 1.0102, Por tr 1, Por tr 1.0101), *Protortonia* spp (Pro ca 38 kD), *Procumbarus* spp (Pro cl 1, Pro cl 1.0101, Pro cl 21 kD), *Prosopis* spp (Pro j 20 kD), *Prunus* spp (Pru ar 1, Pru ar 1.0101, Pru ar 3, Pru ar 3.0101, Pru av 1, Pru av 1.0101, Pru av 1.0201, Pru av 1.0202, Pru av 1.0203, Pru av 2, Pru av 2.0101, Pru av 3, Pru av 3.0101, Pru av 4, Pru av 4.0101, Pru c 1, Pru d 1, Pru d 2, Pru d 3, Pru d 3.0101, Pru d 4, Pru du 1, Pru du 2, Pru du 2S Albumin, Pru du 3, Pru du 3.0101, Pru du 4, Pru du 4.0101, Pru du 4.0102, Pru du 5, Pru du 5.0101, Pru du 6, Pru du 6.0101, Pru du 6.0201, Pru du Conglutin, Pru p 1, Pru p 1.0101, Pru p 2, Pru p 2.0101, Pru p 2.0201, Pru p 2.0301, Pru p 3, Pru p 3.0101, Pru p 3.0102, Pru p 4, Pru p 4.0101, Pru p 4.0201, Pru sa 3), *Psilocybe* spp (Psi c 1, Psi c 1.0101, Psi c 2, Psi c 2.0101), *Psoroptes* spp (Pso o 1, Pso o 10, Pso o 10.0101, Pso o 11, Pso o 13, Pso o 14, Pso o 2, Pso o 21, Pso o 3, Pso o 5, Pso o 7), *Puma* spp (Pum c 1), *Punica* spp (Pun g 3), *Pyrus* spp (Pyr c 1, Pyr c 1.0101, Pyr c 3, Pyr c 3.0101, Pyr c 4, Pyr c 4.0101, Pyr c 5, Pyr c 5.0101, Pyr py 2), *Quercus* spp (Que a 1, Que a 1.0101, Que a 1.0201, Que a 1.0301, Que a 1.0401, Que a 2, Que a 4), *Rachycentron* spp (Rac ca 1), *Rana* spp (Ran e 1, Ran e 1.0101, Ran e 2, Ran e 2.0101), *Ranina* spp (Ran ra 1), *Rangifer* spp (Ran t BLG), *Rattus* spp (Rat n 1, Rat n 1.0101, Rat n Casein, Rat n Gelatin, Rat n IgG, Rat n Phosvitin, Rat n RSA, Rat n Transferrin), *Rhizomucor* spp (Rhi m AP), *Rhizopus* spp (Rhi nv Lipase, Rhi o Lipase), *Rhomboplites* spp (Rho au 1), *Rhodotorula* spp (Rho m 1, Rho m 1.0101, Rho m 2, Rho m 2.0101), *Ricinus* spp (Ric c 1, Ric c 1.0101, Ric c 2, Ric c 3, Ric c 8, Ric c RIP), *Rivulus* spp (Riv ma 1), *Robinia* spp (Rob p 2, Rob p 4, Rob p Glucanase), *Rosa* spp (Ros r 3), *Roystonea* spp (Roy e 2), *Rubus* spp (Rub i 1, Rub i 1.0101, Rub i 3, Rub i 3.0101, Rub i Chitinase, Rub i CyP), *Saccharomyces* spp (Sac c Carboxypeptidase Y, Sac c CyP, Sac c Enolase, Sac c Glucosidase, Sac c Invertase, Sac c MnSOD, Sac c P2, Sac c Profilin), *Salvelinus* spp (Sal f 1), *Salsola* spp (Sal k 1, Sal k 1.0101, Sal k 1.0201, Sal k 1.0301, Sal k 1.0302, Sal k 2, Sal k 2.0101, Sal k 3, Sal k 3.0101, Sal k 4, Sal k 4.0101, Sal k 4.0201, Sal k 5, Sal k 5.0101), *Salvelinus* spp (Sal le Vitellogenin), *Salmo* spp (Sal s 1, Sal s 1.0101, Sal s 1.0201, Sal s 2, Sal s 2.0101, Sal s Gelatin), *Sambucus* spp (Sam n 1), *Sander* spp (San lu 1), *Saponaria* spp (Sap o RIP), *Sardinops* spp (Sar m 1), *Sarkidiornis* spp (Sar ml 1), *Sardina* spp (Sar p 1), *Sarcoptes* spp (Sar s 1, Sar s 14, Sar s 3, Sar s GST, Sar s PM), *Sardinops* spp (Sar sa 1, Sar sa 1.0101), *Schistosoma* spp (Sch j GST, Sch j PM, Sch j Sj22, Sch j Sj67, Sch ma Sm20, Sch ma Sm21, Sch ma Sm22, Sch ma Sm31), *Sciaenops* spp (Sci oc 1), *Scomber* spp (Sco a 1), *Scombermorus* spp (Sco ca 1), *Scomberomorus* spp (Sco g 1), *Scomber* spp (Sco j 1, Sco ma 1, Sco s 1), *Scolopendra* spp (Sco y 7, Sco y 7.0101), *Scylla* spp (Scy o 1, Scy o 1.0101, Scy o 2, Scy pa 1, Scy pa 2, Scy s 1, Scy s 1.0101, Scy s 2), *Sebastes* spp (Seb fa 1, Seb in 1, Seb m 1, Seb m 1.0101, Seb m 1.0201), *Secale* spp (Sec c 1, Sec c 12, Sec c 13, Sec c 2, Sec c 20, Sec c 20.0101, Sec c 20.0201, Sec c 28, Sec c 3, Sec c 4, Sec c 4.0101, Sec c 4.0201, Sec c 5, Sec c 5.0101, Sec c aA_TI, Sec c aA_TI.0101), *Senecio* spp (Sen j MDH, Sen j PL), *Sepia* spp (Sep e 1, Sep e 1.0101), *Sepioteuthis* spp (Sep I 1, Sep 1 1.0101), *Sepia* spp (Sep m 1), *Seriola* spp (Ser d 1, Ser la 1), *Sergestes* spp (Ser lu 1), *Seriola* spp (Ser q 1, Ser ri 1), *Sesamum* spp (Ses i 1, Ses i 1.0101, Ses i 2, Ses i 2.0101, Ses i 3, Ses i 3.0101, Ses i 4, Ses i 4.0101, Ses i 5, Ses i 5.0101, Ses i 6, Ses i 6.0101, Ses i 7, Ses i 7.0101, Ses i 8), *Shigella* spp (Shi bo GST, Shi dy GST), *Simulia* spp (Sim vi 1, Sim vi 2, Sim vi 3, Sim vi 4, Sim vi 70 kD), *Sinapis* spp (Sin a 1, Sin a 1.0101, Sin a 1.0104, Sin a 1.0105, Sin a 1.0106, Sin a 1.0107, Sin a 1.0108, Sin a 2, Sin a 2.0101, Sin a 3, Sin a 3.0101, Sin a 4, Sin a 4.0101), *Sinonovacula* spp (Sin c 1, Sin c 1.0101), *Solenopsis* spp (Sol g 2, Sol g 2.0101, Sol g 3, Sol g 3.0101, Sol g 4, Sol g 4.0101, Sol g 4.0201, Sol i 1, Sol i 1.0101, Sol i 2, Sol i 2.0101, Sol i 3, Sol i 3.0101, Sol i 4, Sol i 4.0101), *Solenocera* spp (Sol me 1), *Solenopsis* spp (Sol r 1, Sol r 2, Sol r 2.0101, Sol r 3, Sol r 3.0101, Sol s 2, Sol s 2.0101, Sol s 3, Sol s 3.0101, Sol s 4), *Solea* spp (Sol so 1, Sol so TPI), *Solanum* spp (Sola t 1, Sola t 1.0101, Sola t 2, Sola t 2.0101, Sola t 3, Sola t 3.0101, Sola t 3.0102, Sola t 4, Sola t 4.0101, Sola t 8, Sola t Glucanase), *Sorghum* spp (Sor b 1, Sor h 1, Sor h 1.0101, Sor h 12, Sor h 7), *Sparus* spp (Spa a 1), *Sphyrna* spp (Sph ti 1), *Spirulina* spp (Spi mx beta Phycocyanin), *Spinacia* spp (Spi o 2, Spi o RuBisCO), *Squilla* spp (Squ ac 1, Squ ac 1.0101, Squ o 1, Squ o 1.0101), *Staphylococcus* spp (Sta a FBP, Sta a SEA, Sta a SEB, Sta a SEC, Sta a SED, Sta a SEE, Sta a TSST), *Stachybotrys* spp (Sta c 3, Sta c 3.0101, Sta c Cellulase, Sta c Hemolysin, Sta c SchS34, Sta c Stachyrase A), *Stemphylium* spp (Ste b 1, Ste c 1, Ste v 1), *Stolephorus* spp (Sto i 1), *Struthio* spp (Str c 1, Str c 2, Str c 3), *Streptococcus* spp (Str dy Streptokinase), *Streptomyces* spp (Str g Pronase), *Streptococcus* spp (Str pn PspC), *Strongylocentrotus* spp (Str pu 18 kD, Str pu Vitellogenin), *Streptococcus* spp (Str py SPEA, Str py SPEC, Str py Streptokinase), *Strongyloides* spp (Str st 45 kD), *Streptomyces* spp (Str v PAT), *Styela* spp (Sty p 1), *Suidasia* spp (*Sui* m 1, *Sui* m 13, *Sui* m 2, *Sui* m 3, *Sui* m 5, *Sui* m 5.01, *Sui* m 5.02, *Sui* m 5.03, *Sui* m 6, *Sui* m 7, *Sui* m 8, *Sui* m 9), *Sus* spp (Sus s ACTH, Sus s ALA, Sus s Amylase, Sus s BLG, Sus s Casein, Sus s Casein alphaS1, Sus s Casein alphaS2, Sus s Casein beta, Sus s Casein kappa, Sus s Gelatin, Sus s HG, Sus s Insulin, Sus s Lipase, Sus s Pepsin, Sus s Phosvitin, Sus s PRVB, Sus s PSA, Sus s TCTP), *Syntelopodeuma* spp (Syn y 7, Syn y 7.0101), *Syringa* spp (Syr v 1, Syr v 1.0101, Syr v 1.0102, Syr v 1.0103, Syr v 2, Syr v 3, Syr v 3.0101), *Tabanus* spp (Tab y 1, Tab y 1.0101, Tab y 2, Tab y 2.0101, Tab y 5, Tab y 5.0101), *Tadorna* spp (Tad ra 1), *Talaromyces* spp (Tal st 22, Tal st 3, Tal st 8), *Taraxacum* spp (Tar o 18 kD), *Taxodium* spp (Tax d 2),

*Tegenaria* spp (Teg d Hemocyanin), *Teladorsagia* spp (Tel ci 3), *Thaumetopoea* spp (Tha p 1, Tha p 1.0101, Tha p 2, Tha p 2.0101), *Theragra* spp (The c 1), *Thermomyces* spp (The l Lipase, The sp Lipase, The sp Xylanase), *Thunnus* spp (Thu a 1, Thu a 1.0101, Thu a Collagen, Thu al 1, Thu at 1, Thu o 1, Thu o Collagen), *Thuja* spp (Thu oc 3, Thu p 1), *Thunnus* spp (Thu t 1, Thu to 1), *Thyrsites* spp (Thy at 1), *Thyrophygus* spp (Thy y 7, Thy y 7.0101), *Todarodes* spp (Tod p 1, Tod p 1.0101, Tod p 1.0102), *Toxoptera* spp (Tox c 7, Tox c 7.0101), *Toxocara* spp (Tox ca TES120, Tox ca TES26, Tox ca TES30), *Toxoplasma* spp (Tox g HSP70), *Trachypenaeus* spp (Tra c 1), *Trachinotus* spp (Tra ca 1), *Trachurus* spp (Tra j 1, Tra j Gelatin, Tra tr Gelatin), *Triticum* spp (Tri a 1, Tri a 10 kD, Tri a 12, Tri a 12.0101, Tri a 12.0102, Tri a 12.0103, Tri a 12.0104, Tri a 13, Tri a 14, Tri a 14.0101, Tri a 14.0201, Tri a 15, Tri a 15.0101, Tri a 18, Tri a 18.0101, Tri a 19, Tri a 19.0101, Tri a 2, Tri a 21, Tri a 21.0101, Tri a 23kd, Tri a 25, Tri a 25.0101, Tri a 26, Tri a 26.0101, Tri a 27, Tri a 27.0101, Tri a 28, Tri a 28.0101, Tri a 29, Tri a 29.0101, Tri a 29.0201, Tri a 3, Tri a 30, Tri a 30.0101, Tri a 31, Tri a 31.0101, Tri a 32, Tri a 32.0101, Tri a 33, Tri a 33.0101, Tri a 34, Tri a 34.0101, Tri a 35, Tri a 35.0101, Tri a 36, Tri a 36.0101, Tri a 37, Tri a 37.0101, Tri a 4, Tri a 4.0101, Tri a 4.0201, Tri a 5, Tri a 7, Tri a aA_SI, Tri a alpha_Gliadin, Tri a bA, Tri a Bd36K, Tri a beta Gliadin, Tri a Chitinase, Tri a CM16, Tri a DH, Tri a Endochitinase, Tri a gamma_Gliadin, Tri a Germin, Tri a Gliadin, Tri a GST, Tri a LMW Glu, Tri a LMW-GS B16, Tri a LMW-GS P42, Tri a LMW-GS P73, Tri a LTP2, Tri a omega2_Gliadin, Tri a Peroxidase, Tri a Peroxidase 1, Tri a SPI, Tri a TLP, Tri a Tritin, Tri a XI), *Tritirachium* spp (Tri al Proteinase K), *Tribolium* spp (Tri ca 17, Tri ca 17.0101, Tri ca 7, Tri ca 7.0101), *Trichostrongylus* spp (Tri co 3, Tri co 3.0101), *Trichophyton* spp (Tri eq 4), *Trigonella* spp (Tri fg 1, Tri fg 2, Tri fg 3, Tri fg 4), *Trichosanthes* spp (Tri k RIP), *Trichiurus* spp (Tri le 1), *Triticum* spp (Tri m Peroxidase), *Trichophyton* spp (Tri me 2, Tri me 4), *Trisetum* spp (Tri p 1, Tri p 5), *Trichinella* spp (Tri ps 3, Tri ps 3.0101), *Trichophyton* spp (Tri r 2, Tri r 2.0101, Tri r 4, Tri r 4.0101), *Trichoderma* spp (Tri rs Cellulase), *Triticum* spp (Tri s 14), *Trichophyton* spp (Tri sc 2, Tri sc 4, Tri so 2), *Trichinella* spp (Tri sp 3, Tri sp 3.0101, Tri sp 3.0102, Tri sp 3.0103, Tri sp 3.0104, Tri sp 3.0105, Tri sp 3.0106), *Trichophyton* spp (Tri t 1, Tri t 1.0101, Tri t 4, Tri t 4.0101), *Triticum* spp (Tri td 14, Tri td aA_TI), *Trichoderma* spp (Tri v Cellulase), *Trichophyton* spp (Tri ve 4), *Triatoma* spp (Tria p 1, Tria p 1.0101), *Triplochiton* spp (Trip s 1), *Turbo* spp (Tur c 1, Tur c PM), *Tyrophagus* spp (Tyr p 1, Tyr p 10, Tyr p 10.0101, Tyr p 10.0102, Tyr p 13, Tyr p 13.0101, Tyr p 2, Tyr p 2.0101, Tyr p 24, Tyr p 24.0101, Tyr p 3, Tyr p 3.0101, Tyr p 4, Tyr p 5, Tyr p 5.01, Tyr p 5.02, Tyr p 5.03, Tyr p 7, Tyr p alpha Tubulin), *Ulocladium* spp (Ulo a 1, Ulo at 1, Ulo b 1, Ulo c 1, Ulo co 1, Ulo cu 1, Ulo mu 1, Ulo ob 1, Ulo se 1, Ulo su 1, Ulo tu 1), *Uncia* spp (Unc u 1), *Urophycis* spp (Uro te 1), *Vaccinium* spp (Vac m 3), *Varroa* spp (Var j 13 kD), *Venerupis* spp (Ven ph 1, Ven ph 1.0101), *Vespula* spp (Ves f 1, Ves f 2, Ves f 5, Ves f 5.0101, Ves g 1, Ves g 2, Ves g 5, Ves g 5.0101, Ves m 1, Ves m 1.0101, Ves m 2, Ves m 2.0101, Ves m 5, Ves m 5.0101, Ves m MLT, Ves p 1, Ves p 2, Ves p 5, Ves p 5.0101, Ves s 1, Ves s 1.0101, Ves s 2, Ves s 5, Ves s 5.0101, Ves v 1, Ves v 1.0101, Ves v 2, Ves v 2.0101, Ves v 2.0201, Ves v 3, Ves v 3.0101, Ves v 5, Ves v 5.0101, Ves v 5-Pol a 5, Ves vi 5, Ves vi 5.0101), *Vespa* spp (Vesp c 1, Vesp c 1.0101, Vesp c 2, Vesp c 5, Vesp c 5.0101, Vesp c 5.0102, Vesp m 1, Vesp m 1.0101, Vesp m 5, Vesp m 5.0101, Vesp ma 1, Vesp ma 2, Vesp ma 5, Vesp ma MLT, Vesp v MLT), *Vigna* spp (Vig r 1, Vig r 1.0101, Vig r 17 kD, Vig r 5, Vig r 8S Globulin, Vig r Albumin, Vig r beta-Conglycinin), *Vitis* spp (Vit v 1, Vit v 1.0101, Vit v 4, Vit v 5, Vit v Glucanase, Vit v TLP), *Xiphias* spp (Xip g 1, Xip g 1.0101, Xip g 25 kD), *Zea* spp (*Zea* m 1, *Zea* m 1.0101, *Zea* m 11, *Zea* m 12, *Zea* m 12.0101, *Zea* m 12.0102, *Zea* m 12.0103, *Zea* m 12.0104, *Zea* m 12.0105, *Zea* m 13, *Zea* m 14, *Zea* m 14.0101, *Zea* m 14.0102, *Zea* m 2, *Zea* m 20S, *Zea* m 22, *Zea* m 25, *Zea* m 25.0101, *Zea* m 27 kD Zein, *Zea* m 3, *Zea* m 4, *Zea* m 5, *Zea* m 50 kD Zein, *Zea* m 7, *Zea* m Chitinase, *Zea* m G1, *Zea* m G2, *Zea* m PAO, *Zea* m Zm13), *Zeus* spp (Zeu fa 1), *Ziziphus* spp (Ziz m 1, Ziz m 1.0101), *Zoarces* spp (Zoa a ISP III), *Zygophyllum* spp (Zyg f 2).

In this context, the terms in brackets indicate the particular preferred allergenic antigens (allergens) from the particular source.

Most preferably the allergenic antigen is preferably derived from a source (e.g. a plant (e.g. grass or a tree), a natural product (e.g. milk, nuts etc.), a fungal source (e.g. *Aspergillus*) or a bacterial source or from an animal source or animal poison (e.g. cat, dog, venom of bees etc.), preferably selected from the list consisting of grass pollen (e.g. pollen of rye), tree pollen (e.g. pollen of hazel, birch, alder, ash), flower pollen, herb pollen (e.g. pollen of mugwort), dust mite (e.g. Der f 1, Der p 1, Eur m 1, Der m 1 Der f 2, Der p 2, Eur m 2, Tyr p 2, Lep d 2), mold (e.g. allergens of *Acremonium, Aspergillus, Cladosporium, Fusarium, Mucor, Penicillium, Rhizopus, Stachybotrys, Trichoderma*, or *Alternaria*), animals (e.g Fel d1, Fel d 2, Fel d3, or Fel d4 of cats), food (e.g. allergens of fish (e.g. bass, cod, flounder), seafood (e.g. crab, lobster, shrimps), egg, wheat, nuts (e.g. peanuts, almonds, cashews, walnuts), soya, milk, etc.) or insect venom (e.g. allergens from the venom of wasps, bees, hornets, ants, mosquitoes, or ticks).

Autoimmune Self-Antigens

Autoimmune self-antigens, i.e. antigens associated with autoimmune disease or autoantigens, may be associated with an autoimmune disease affecting at least one or more of the following organ systems: the circulatory system, the digestive system, the endocrine system, the excretory system, the immune system, the integumentary system, the muscular system, the nervous system, the reproductive system, the respiratory system, the skeletal system, preferably with the cardiovascular system, the neuroendocrine system, the musculoskeletal system or gastrointestinal system. Therein the circulatory system is the organ system which enables pumping and channeling blood to and from the body and lungs with heart, blood and blood vessels. The digestive system enables digestion and processing food with salivary glands, esophagus, stomach, liver, gallbladder, pancreas, intestines, colon, rectum and anus. The endocrine system enables communication within the body using hormones made by endocrine glands such as the hypothalamus, pituitary or pituitary gland, pineal body or pineal gland, thyroid gland, parathyroid gland and adrenal glands. The excretory system comprises kidneys, ureters, bladder and urethra and is involved in fluid balance, electrolyte balance and excretion of urine. The immune system comprises structures involved in the transfer of lymph between tissues and the blood stream, the lymph and the nodes and vessels which may be responsible for transport of cellular and humoral components of the immune system. It is responsible for defending against disease-causing agents and comprises among others leukocytes, tonsils, adenoids, thymus and spleen. The integumentary system comprises skin, hair and nails. The muscular system enables movement with muscles together with the skeletal system which comprises bones, cartilage, ligaments and tendons and provides structural support. The nervous system is responsible for collecting, transferring and processing information and comprises the brain, spinal cord and nerves. The reproductive system comprises the sex organs, such as ovaries, fallopian tubes, uterus, vagina, mammary glands, testes, vas deferens, seminal vesicles, prostate and penis. The respiratory system comprises the organs used for breathing, the pharynx, larynx, trachea, bronchi, lungs and diaphragm and acts together with the circulation system.

Autoimmune self-antigens (antigens associated with autoimmune disease or autoantigens) are selected from autoantigens associated with autoimmune diseases selected from Addison disease (autoimmune adrenalitis, Morbus Addison), alopecia areata, Addison's anemia (Morbus Biermer), autoimmune hemolytic anemia (AIHA), autoimmune hemolytic anemia (AIHA) of the cold type (cold hemagglutinine disease, cold autoimmune hemolytic anemia (AIHA) (cold agglutinin disease), (CHAD)), autoimmune hemolytic anemia (AIHA) of the warm type (warm AIHA, warm autoimmune haemolytic anemia (AIHA)), autoimmune hemolytic Donath-Landsteiner anemia (paroxysmal cold hemoglobinuria), antiphospholipid syndrome (APS), atherosclerosis, autoimmune arthritis, arteriitis temporalis, Takayasu arteriitis (Takayasu's disease, aortic arch disease), temporal arteriitis/giant cell arteriitis, autoimmune chronic gastritis, autoimmune infertility, autoimmune inner ear disease (AIED), Basedow's disease (Morbus Basedow), Bechterew's disease (Morbus Bechterew, ankylosing spondylitis, spondylitis ankylosans), Behcet's syndrome (Morbus Behcet), bowel disease including autoimmune inflammatory bowel disease (including colitis ulcerosa (Morbus Crohn, Crohn's disease), cardiomyopathy, particularly autoimmune cardiomyopathy, idiopathic dilated cardiomyopathy (DCM), celiac sprue dermatitis (gluten mediated enteropathia), chronic fatigue immune dysfunction syndrome (CFIDS), chronic inflammatory demyelinating polyneuropathy (CIDP), chronic polyarthritis, Churg-Strauss syndrome, cicatricial pemphigoid, Cogan syndrome, CREST syndrome (syndrome with Calcinosis cutis, Raynaud phenomenon, motility disorders of the esophagus, sklerodaktylia and teleangiectasia), Crohn's disease (Morbus Crohn, colitis ulcerosa), dermatitis herpetiformis during, dermatologic autoimmune diseases, dermatomyositis, Diabetes, Diabetes mellitus Type 1 (type I diabetes, insuline dependent Diabetes mellitus), Diabetes mellitus Type 2 (type II diabetes), essential mixed cryoglobulinemia, essential mixed cryoglobulinemia, fibromyalgia, fibromyositis, Goodpasture syndrome (anti-GBM mediated glomerulonephritis), graft versus host disease, Guillain-Barre syndrome (GBM, Polyradikuloneuritis), haematologic autoimmune diseases, Hashimoto thyroiditis, hemophilia, acquired hemophilia, hepatitis, autoimmune hepatitis, particularly autoimmune forms of chronic hepatitis, idiopathic pulmonary fibrosis (IPF), idiopathic thrombocytopenic purpura, Immuno-thrombocytopenic purpura (Morbus Werlhof; ITP), IgA nephropathy, infertility, autoimmune infertility, juvenile rheumatoid arthritis (Morbus Still, Still syndrome), Lambert-Eaton syndrome, lichen planus, lichen sclerosus, lupus erythematosus, systemic lupus erythematosus (SLE), lupus erythematosus (discoid form), Lyme arthritis (Lyme disease, *Borrelia* arthritis), Meniere's disease (Morbus Meniere); mixed connective tissue disease (MCTD), multiple sclerosis (MS, encephalomyelitis disseminate, Charcot's disease), Myasthenia gravis (myasthenia, MG), myosits, polymyositis, neural autoimmune diseases, neurodermitis, pemphigus vulgaris, bullous pemphigoid, scar forming pemphigoid; polyarteriitis nodosa (periarteiitis nodosa), polychondritis (panchondritis), polyglandular (autoimmune) syndrome (PGA syndrome, Schmidt's syndrome), Polymyalgia rheumatica, primary agammaglobulinemia, primary biliary cirrhosis PBC, primary autoimmune cholangitis), progressive systemic sclerosis (PSS), Psoriasis, Psoriasis vulgaris, Raynaud's phenomena, Reiter's syndrome (Morbus Reiter, urethral conjunctive synovial syndrome)), rheumatoid arthritis (RA, chronic polyarthritis, rheumatic disease of the joints, rheumatic fever), sarcoidosis (Morbus Boeck, Besnier-Boeck-Schaumann disease), stiff-man syndrome, Sclerodermia, Scleroderma, Sjögren's syndrome, sympathetic ophtalmia; Transient gluten intolerance, transplanted organ rejection, uveitis, autoimmune uveiitis, Vasculitis, Vitiligo, (leucoderma, piebold skin), and Wegner's disease (Morbus Wegner, Wegner's granulomatosis).

These and other proteins acting as autoimmune self-antigens are understood to be therapeutic, as they are meant to treat the subject, in particular a mammal, more particularly a human being, by vaccinating with a self-antigen which is expressed by the mammal, e.g. the human, itself and which triggers an undesired immune response, which is not raised in a healthy subject. Accordingly, such proteins acting as self-antigens are typically of mammalian, in particular human origin.

Particularly preferred in this context are autoimmune self-antigens (autoantigens) selected from:

- myelin basic protein (MBP), proteolipid protein (PLP), and myelin oligodendrocyte glycoprotein (MOG), in each case associated with multiple sclerosis (MS);
- CD44, preproinsulin, proinsulin, insulin, glutamic acid decaroxylase (GAD65), tyrosine phosphatase-like insulinoma antigen 2 (IA2), zinc transporter ((ZnT8), and heat shock protein 60 (HSP60), in each case associated with diabetes Typ I;
- interphotoreceptor retinoid-binding protein (IRBP) associated with autoimmune uveitis;
- acetylcholine receptor AchR, and insulin-like growth factor-1 receptor (IGF-1R), in each case associated with Myasthenia gravis;
- M-protein from beta-hemolytic streptocci (pseudo-autoantigen) associated with Rheumatic Fever;
- Macrophage migration inhibitory factor associated with Arthritis;
- Ro/La RNP complex, alpha- and beta-fodrin, islet cell autoantigen, poly(ADP)ribose polymerase (PARP), NuMA, NOR-90, Ro60 autoantigen, and p27 antigen, in each case associated with Sjögren's syndrome;
- Ro60 autoantigen, low-density lipoproteins, Sm antigens of the U-1 small nuclear ribonucleoprotein complex (B/B', D1, D2, D3, E, F, G), and RNP ribonucleoproteins, in each case associated with lupus erythematosus;
- oxLDL, beta(2)GPI, HSP60/65, and oxLDL/beta(2)GPI, in each case associated with Atherosclerosis;
- cardiac beta(1)-adrenergic receptor associated with idiopathic dilated cardiomyopathy (DCM);
- histidyl-tRNA synthetase (HisRS) associated with myositis;
- topoisomerase I associated with scleroderma disease.

Furthermore, in other embodiments said autoimmune self-antigen is associated with the respective autoimmune disease, like e.g. IL-17, heat shock proteins, and/or any idiotype pathogenic T cell or chemokine receptor which is expressed by immune cells involved in the autoimmune response in said autoimmune disease (such as any autoimmune diseases described herein).

Preferably, the at least one coding region of the mRNA compound comprising an mRNA sequence according to the invention comprises at least two, three, four, five, six, seven, eight or more nucleic acid sequences identical to or having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with any one of the nucleic acid sequences disclosed in the sequence listing (or respectively in Tables 1-5 or FIGS. 20-24 of PCT/EP2016/075843), or a fragment or variant of any one of said nucleic acid sequences.

Preferably, the mRNA sequence comprising at least one coding region as defined herein typically comprises a length of about 50 to about 20000, or 100 to about 20000 nucleotides, preferably of about 250 to about 20000 nucleotides, more preferably of about 500 to about 10000, even more preferably of about 500 to about 5000.

According to a further embodiment, the mRNA sequence according to the invention is an artificial mRNA sequence as defined herein.

According to a further embodiment, the mRNA compound comprising an mRNA sequence according to the invention is a modified mRNA sequence, preferably a modified mRNA sequence as described herein. In this context, a modification as defined herein preferably leads to a stabilization of the mRNA sequence according to the invention. More preferably, the invention thus provides a stabilized mRNA sequence comprising at least one coding region as defined herein.

According to one embodiment, the mRNA compound comprising an mRNA sequence of the present invention may thus be provided as a "stabilized mRNA sequence", that is to say as an mRNA that is essentially resistant to in vivo degradation (e.g. by an exo- or endo-nuclease). Such stabilization can be affected, for example, by a modified phosphate backbone of the mRNA of the present invention. A backbone modification in connection with the present invention is a modification in which phosphates of the backbone of the nucleotides contained in the mRNA are chemically modified. Nucleotides that may be preferably used in this connection contain e.g. a phosphorothioate-modified phosphate backbone, preferably at least one of the phosphate oxygens contained in the phosphate backbone being replaced by a sulfur atom. Stabilized mRNAs may further include, for example: non-ionic phosphate analogues, such as, for example, alkyl and aryl phosphonates, in which the charged phosphonate oxygen is replaced by an alkyl or aryl group, or phosphodiesters and alkylphosphotriesters, in which the charged oxygen residue is present in alkylated form. Such backbone modifications typically include, without implying any limitation, modifications from the group consisting of methylphosphonates, phosphoramidates and phosphorothioates (e.g. cytidine-5'-O-(1-thiophosphate)).

In the following, specific modifications are described, which are preferably capable of "stabilizing" the mRNA as defined herein.

V.9. Chemical Modifications

The term "mRNA modification" as used herein may refer to chemical modifications comprising backbone modifications as well as sugar modifications or base modifications.

In this context, a modified mRNA (sequence) as defined herein may contain nucleotide analogues/modifications, e.g. backbone modifications, sugar modifications or base modifications. A backbone modification in connection with the present invention is a modification, in which phosphates of the backbone of the nucleotides contained in an mRNA compound comprising an mRNA sequence as defined herein are chemically modified. A sugar modification in connection with the present invention is a chemical modification of the sugar of the nucleotides of the mRNA compound comprising an mRNA sequence as defined herein. Furthermore, a base modification in connection with the present invention is a chemical modification of the base moiety of the nucleotides of the mRNA compound comprising an mRNA sequence. In this context, nucleotide analogues or modifications are preferably selected from nucleotide analogues, which are applicable for transcription and/or translation.

The modified nucleosides and nucleotides, which may be incorporated into a modified mRNA compound comprising an mRNA sequence as described herein, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R═H, alkyl, cycloalkyl, aryl, aralkyl, heteroaryl or sugar); polyethyleneglycols (PEG), $—O(CH_2CH_2)nCH_2CH_2OR$; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g., NH2; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified mRNA can include nucleotides containing, for instance, arabinose as the sugar.

The phosphate backbone may further be modified in the modified nucleosides and nucleotides, which may be incorporated into a modified mRNA compound comprising an mRNA sequence as described herein. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

The modified nucleosides and nucleotides, which may be incorporated into a modified mRNA compound comprising an mRNA sequence as described herein can further be modified in the nucleobase moiety. Examples of nucleobases found in mRNA include, but are not limited to, adenine, guanine, cytosine and uracil.

For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogues/modifications are selected from base modifications, which are preferably selected from 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl-inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group. In specific embodiments, a modified nucleoside is 5'-O-(1-thiophosphate)-adenosine, 5'-O-(1-thiophosphate)-cytidine, 5'-O-(1-thiophosphate)-guanosine, 5'-O-(1-thiophosphate)-uridine or 5'-O-(1-thiophosphate)-pseudouridine.

In further specific embodiments, a modified mRNA may comprise nucleoside modifications selected from 6-aza-cytidine, 2-thio-cytidine, α-thio-cytidine, Pseudo-iso-cytidine, 5-aminoallyl-uridine, 5-iodo-uridine, N1-methyl-pseudouridine, 5,6-dihydrouridine, a-thio-uridine, 4-thio-uridine, 6-aza-uridine, 5-hydroxy-uridine, deoxy-thymidine, 5-methyl-uridine, Pyrrolo-cytidine, inosine, α-thio-guanosine, 6-methyl-guanosine, 5-methyl-cytidine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, α-thio-adenosine, 8-azido-adenosine, 7-deaza-adenosine.

In a very specific embodiment of the invention, the mRNA compound does not comprise a base modification as described above.

According to a further embodiment, a modified mRNA compound comprising an mRNA sequence as defined herein can contain a lipid modification. Such a lipid-modified mRNA typically comprises an mRNA as defined herein. Such a lipid-modified mRNA as defined herein typically further comprises at least one linker covalently linked with that mRNA, and at least one lipid covalently linked with the respective linker. Alternatively, the lipid-modified mRNA comprises at least one mRNA as defined herein and at least one (bifunctional) lipid covalently linked (without a linker) with that mRNA. According to a third alternative, the lipid-modified mRNA comprises an mRNA molecule as defined herein, at least one linker covalently linked with that mRNA, and at least one lipid covalently linked with the respective linker, and also at least one (bifunctional) lipid covalently linked (without a linker) with that mRNA. In this context, it is particularly preferred that the lipid modification is present at the terminal ends of a linear mRNA sequence.

According to another embodiment, the mRNA comprising lipid nanoparticles comprises an mRNA compound comprising an mRNA sequence, which may be modified, and thus stabilized, by modifying the guanosine/cytosine (G/C) content of the mRNA sequence, preferably of the at least one coding region of the mRNA compound comprising an mRNA sequence of the present invention.

In a particularly preferred embodiment of the present invention, the G/C content of the coding region of the mRNA compound comprising an mRNA sequence of the present invention is modified, particularly increased, compared to the G/C content of the coding region of the respective wild type mRNA, i.e. the unmodified mRNA. The amino acid sequence encoded by the mRNA is preferably not modified as compared to the amino acid sequence encoded by the respective wild type mRNA. This modification of the mRNA sequence of the present invention is based on the fact that the sequence of any mRNA region to be translated is important for efficient translation of that mRNA. Thus, the composition of the mRNA and the sequence of various nucleotides are important. In particular, sequences having an increased G (guanosine)/C (cytosine) content are more stable than sequences having an increased A (adenosine)/U (uracil) content. According to the invention, the codons of the mRNA are therefore varied compared to the respective wild type mRNA, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage). Depending on the amino acid to be encoded by the mRNA, there are various possibilities for modification of the mRNA sequence, compared to its wild type sequence. In the case of amino acids, which are encoded by codons, which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present. In contrast, codons which contain A and/or U nucleotides can be modified by substitution of other codons, which code for the same amino acids but contain no A and/or U. Examples of these are: the codons for Pro can be modified from CCU or CCA to CCC or CCG; the codons for Arg can be modified from CGU or CGA or AGA or AGG to CGC or CGG; the codons for Ala can be modified from GCU or GCA to GCC or GCG; the codons for Gly can be modified from GGU or GGA to GGC or GGG. In other cases, although A or U nucleotides cannot be eliminated from the codons, it is however possible to decrease the A and U content by using codons which contain a lower content of A and/or U nucleotides. Examples of these are: the codons for Phe can be modified from UUU to UUC; the codons for Leu can be modified from UUA, UUG, CUU or CUA to CUC or CUG; the codons for Ser can be modified from UCU or UCA or AGU to UCC, UCG or AGC; the codon for Tyr can be modified from UAU to UAC; the codon for Cys can be modified from UGU to UGC; the codon for His can be modified from CAU to CAC; the codon for Gin can be modified from CAA to CAG; the codons for Ile can be modified from AUU or AUA to AUC; the codons for Thr can be modified from ACU or ACA to ACC or ACG; the codon for Asn can be modified from AAU to AAC; the codon for Lys can be modified from AAA to AAG; the codons for Val can be modified from GUU or GUA to GUC or GUG; the codon for Asp can be modified from GAU to GAC; the codon for Glu can be modified from GAA to GAG; the stop codon UAA can be modified to UAG or UGA. In the case of the codons for Met (AUG) and Trp (UGG), on the other hand, there is no possibility of sequence modification. The substitutions listed above can be used either individually or in all possible combinations to increase the G/C content of the mRNA sequence of the present invention compared to its particular wild type mRNA (i.e. the original sequence). Thus, for example, all codons for Thr occurring in the wild type sequence can be modified to ACC (or ACG). Preferably, however, for example, combinations of the above substitution possibilities are used:

- substitution of all codons coding for Thr in the original sequence (wild type mRNA) to ACC (or ACG) and substitution of all codons originally coding for Ser to UCC (or UCG or AGC);
- substitution of all codons coding for Ile in the original sequence to AUC and
- substitution of all codons originally coding for Lys to AAG and
- substitution of all codons originally coding for Tyr to UAC;
- substitution of all codons coding for Val in the original sequence to GUC (or GUG) and
- substitution of all codons originally coding for Glu to GAG and
- substitution of all codons originally coding for Ala to GCC (or GCG) and
- substitution of all codons originally coding for Arg to CGC (or CGG);
- substitution of all codons coding for Val in the original sequence to GUC (or GUG) and
- substitution of all codons originally coding for Glu to GAG and
- substitution of all codons originally coding for Ala to GCC (or GCG) and
- substitution of all codons originally coding for Gly to GGC (or GGG) and
- substitution of all codons originally coding for Asn to AAC;
- substitution of all codons coding for Val in the original sequence to GUC (or GUG) and
- substitution of all codons originally coding for Phe to UUC and
- substitution of all codons originally coding for Cys to UGC and
- substitution of all codons originally coding for Leu to CUG (or CUC) and
- substitution of all codons originally coding for Gin to CAG and
- substitution of all codons originally coding for Pro to CCC (or CCG); etc.

Preferably, the G/C content of the coding region of the mRNA compound comprising an mRNA sequence of the present invention is increased by at least 7%, more preferably by at least 15%, particularly preferably by at least 20%, compared to the G/C content of the coding region of the wild type RNA, which codes for an antigen as defined herein or a fragment or variant thereof. According to a specific embodiment at least 5%, 10%, 20%, 30%, 40%, 50%, 60%, more preferably at least 70%, even more preferably at least 80% and most preferably at least 90%, 95% or even 100% of the substitutable codons in the region coding for a peptide or protein as defined herein or a fragment or variant thereof or the whole sequence of the wild type mRNA sequence are substituted, thereby increasing the GC/content of said sequence. In this context, it is particularly preferable to increase the G/C content of the mRNA sequence of the present invention, preferably of the at least one coding region of the mRNA sequence according to the invention, to the maximum (i.e., 100% of the substitutable codons) as compared to the wild type sequence. According to the invention, a further preferred modification of the mRNA sequence of the present invention is based on the finding that the translation efficiency is also determined by a different frequency in the occurrence of tRNAs in cells. Thus, if so-called "rare codons" are present in the mRNA sequence of the present invention to an increased extent, the corresponding modified mRNA sequence is translated to a significantly poorer degree than in the case where codons coding for relatively "frequent" tRNAs are present. According to the invention, in the modified mRNA sequence of the present invention, the region which codes for a peptide or protein as defined herein or a fragment or variant thereof is modified compared to the corresponding region of the wild type mRNA sequence such that at least one codon of the wild type sequence, which codes for a tRNA which is relatively rare in the cell, is exchanged for a codon, which codes for a tRNA which is relatively frequent in the cell and carries the same amino acid as the relatively rare tRNA. By this modification, the sequence of the mRNA of the present invention is modified such that codons for which frequently occurring tRNAs are available are inserted. In other words, according to the invention, by this modification all codons of the wild type sequence, which code for a tRNA which is relatively rare in the cell, can in each case be exchanged for a codon, which codes for a tRNA which is relatively frequent in the cell and which, in each case, carries the same amino acid as the relatively rare tRNA. Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons, which use for the particular amino acid the tRNA which occurs the most frequently, e.g. the Gly codon, which uses the tRNA, which occurs the most frequently in the (human) cell, are particularly preferred. According to the invention, it is particularly preferable to link the sequential G/C content which is increased, in particular maximized, in the modified mRNA sequence of the present invention, with the "frequent" codons without modifying the amino acid sequence of the protein encoded by the coding region of the mRNA sequence. This preferred embodiment allows provision of a particularly efficiently translated and stabilized (modified) mRNA sequence of the present invention. The determination of a modified mRNA sequence of the present invention as described above (increased G/C content; exchange of tRNAs) can be carried out using the computer program explained in WO02/098443—the disclosure content of which is included in its full scope in the present invention. Using this computer program, the nucleotide sequence of any desired mRNA sequence can be modified with the aid of the genetic code or the degenerative nature thereof such that a maximum G/C content results, in combination with the use of codons which code for tRNAs occurring as frequently as possible in the cell, the amino acid sequence coded by the modified mRNA sequence preferably not being modified compared to the non-modified sequence. Alternatively, it is also possible to modify only the G/C content or only the codon usage compared to the original sequence. The source code in Visual Basic 6.0 (development environment used: Microsoft Visual Studio Enterprise 6.0 with Servicepack 3) is also described in WO02/098443. In a further preferred embodiment of the present invention, the A/U content in the environment of the ribosome binding site of the mRNA sequence of the present invention is increased compared to the A/U content in the environment of the ribosome binding site of its respective wild type mRNA. This modification (an increased A/U content around the ribosome binding site) increases the efficiency of ribosome binding to the mRNA. An effective binding of the ribosomes to the ribosome binding site (Kozak sequence: SEQ ID NO: 224307 or SEQ ID NO: 224308, the AUG forms the start codon) in turn has the effect of an efficient translation of the mRNA. According to a further embodiment of the present invention, the mRNA sequence of the present invention may be modified with respect to potentially destabilizing sequence elements. Particularly, the coding region and/or the 5' and/or 3' untranslated region of this mRNA sequence may be modified compared to the respective wild type mRNA such that it contains no destabilizing sequence elements, the encoded amino acid sequence of the modified mRNA sequence preferably not being modified compared to its respective wild type mRNA. It is known that, for example in sequences of eukaryotic mRNAs, destabilizing sequence elements (DSE) occur, to which signal proteins bind and regulate enzymatic degradation of mRNA in vivo. For further stabilization of the modified mRNA sequence, optionally in the region which encodes at least one peptide or protein as defined herein or a fragment or variant thereof, one or more such modifications compared to the corresponding region of the wild type mRNA can therefore be carried out, so that no or substantially no destabilizing sequence elements are contained there. According to the invention, DSE present in the untranslated regions (3'- and/or 5'-UTR) can also be eliminated from the mRNA sequence of the present invention by such modifications. Such destabilizing sequences are e.g. AU-rich sequences (AURES), which occur in 3'-UTR sections of numerous unstable mRNAs (Caput et al., Proc. Natl. Acad. Sci. USA 1986, 83: 1670 to 1674). The mRNA sequence of the present invention is therefore preferably modified compared to the respective wild type mRNA such that the mRNA sequence of the present invention contains no such destabilizing sequences. This also applies to those sequence motifs which are recognized by possible endonucleases, e.g., the sequence GAACAAG, which is contained in the 3'-UTR segment of the gene encoding the transferrin receptor (Binder et al., EMBO J. 1994, 13: 1969 to 1980). These sequence motifs are also preferably removed in the mRNA sequence of the present invention.

According to a preferred embodiment, the present invention provides mRNA comprising lipid nanoparticles wherein the mRNA comprises an mRNA sequence as defined herein comprising at least one coding region, wherein the coding region comprises or consists of any one of the (modified) RNA sequences as disclosed in the sequence listing having numeric identifier <223> which starts with "derived and/or modified CDS sequence (opt1)", "derived and/or modified CDS sequence (opt2)", "derived and/or modified CDS sequence (opt3)", "derived and/or modified CDS sequence (opt4)", or "derived and/or modified CDS sequence (opt5)", or respectively "column C" of Tables 1-5 or FIGS. 20-24 of PCT/EP2016/075843 (incorporated herein by reference), or of a fragment or variant of any one of these sequences.

According to a particularly preferred embodiment, the present invention provides mRNA comprising lipid nanoparticles wherein the mRNA comprises an mRNA sequence as defined herein comprising at least one coding region encoding at least one antigenic peptide or protein derived from hemagglutinin (HA) of an influenza A virus, wherein the coding region comprises or consists of any one of the (modified) RNA sequences or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from hemagglutinin (HA) of an influenza B virus, wherein the coding region comprises or consists of any one of the (modified) RNA sequences, or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from neuraminidase (NA) of an influenza A virus, wherein the coding region comprises or consists of any one of the (modified) RNA sequences or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from neuraminidase (NA) of an influenza B virus, wherein the coding region comprises or consists of any one of the (modified) RNA sequences or a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from glycoprotein of a Rabies virus, wherein the coding region comprises or consists of any one of the (modified) RNA sequences or of a fragment or variant of any one of these sequences.

In a further preferred embodiment, the at least one coding region of the mRNA sequence according to the invention comprises or consists of an RNA sequence identical to or having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with any one of the (modified) RNA sequences or of a fragment or variant of any one of these sequences.

According to a particularly preferred embodiment, the at least one coding region of the mRNA sequence according to the invention comprises or consists of an RNA sequence having a sequence identity of at least 80% with any one of the (modified) RNA sequences or of a fragment or variant of any one of these sequences.

According to the invention, a further preferred modification of the mRNA compound comprising an mRNA sequence comprised in the mRNA of the mRNA comprising lipid nanoparticles of the present invention is based on the finding that codons encoding the same amino acid typically occur at different frequencies. According to the invention, in the modified mRNA compound comprising an mRNA sequence of the present invention, the coding coding region as defined herein is preferably modified compared to the corresponding coding region of the respective wild type mRNA such that the frequency of the codons encoding the same amino acid corresponds to the naturally occurring frequency of that codon according to the human codon usage.

For example, in the case of the amino acid alanine (Ala) present in an amino acid sequence encoded by the at least one coding region of the mRNA compound comprising an mRNA sequence according to the invention, the wild type coding region is preferably adapted in a way that the codon "GCC" is used with a frequency of 0.40, the codon "GCT" is used with a frequency of 0.28, the codon "GCA" is used with a frequency of 0.22 and the codon "GCG" is used with a frequency of 0.10 etc.

According to a preferred embodiment, the present invention provides mRNA comprising lipid nanoparticles wherein the mRNA comprises an mRNA sequence as defined herein comprising at least one coding region, wherein the coding region comprises or consists of any one of the (modified) RNA sequences, or of a fragment or variant of any one of these sequences.

According to a particularly preferred embodiment, the present invention provides mRNA comprising lipid nanoparticles wherein the mRNA comprises an mRNA sequence as defined herein comprising at least one coding region encoding at least one antigenic peptide or protein derived from hemagglutinin (HA) of an influenza A virus, wherein the coding region comprises or consists of any one of the (modified) RNA sequences, or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from hemagglutinin (HA) of an influenza B virus, wherein the coding region comprises or consists of any one of the (modified) RNA sequences, or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from neuraminidase (NA) of an influenza A virus, wherein the coding region comprises or consists of any one of the (modified) RNA sequences, or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from neuraminidase (NA) of an influenza B virus, wherein the coding region comprises or consists of any one of the (modified) RNA sequences or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from glycoprotein of a Rabies virus, wherein the coding region comprises or consists of any one of the (modified) RNA sequences or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from an Ebola virus, wherein the coding region comprises or consists of any one of the (modified) RNA sequences or fragments or variants of these sequences.

In a further preferred embodiment, the at least one coding region of the mRNA sequence according to the invention comprises or consists of an RNA sequence identical to or having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with any one of the (modified) RNA sequences or of a fragment or variant of any one of these sequences.

According to a particularly preferred embodiment, the at least one coding region of the mRNA sequence according to the invention comprises or consists of an RNA sequence having a sequence identity of at least 80% with any one of the (modified) RNA sequences or of a fragment or variant of any one of these sequences.

As described above it is preferred according to the invention, that all codons of the wild type sequence which code for a tRNA, which is relatively rare in the cell, are exchanged for a codon which codes for a tRNA, which is relatively frequent in the cell and which, in each case, carries the same amino acid as the relatively rare tRNA. Such an optimization procedure increases the codon adaptation index (CAI) and ultimately maximises the CAI. In the context of the invention, sequences with increased or maximized CAI are typically referred to as "codon-optimized" sequences and/or CAI increased and/or maximized sequences. According to a preferred embodiment, the mRNA compound comprising an mRNA sequence of the present invention comprises at least one coding region, wherein the coding region/sequence is codon-optimized as described herein. More preferably, the codon adaptation index (CAI) of the at least one coding sequence is at least 0.5, at least 0.8, at least 0.9 or at least 0.95. Most preferably, the codon adaptation index (CAI) of the at least one coding sequence is 1.

For example, in the case of the amino acid alanine (Ala) present in the amino acid sequence encoded by the at least one coding sequence of the RNA according to the invention, the wild type coding sequence is adapted in a way that the most frequent human codon "GCC" is always used for said amino acid, or for the amino acid Cysteine (Cys), the wild type sequence is adapted in a way that the most frequent human codon "TGC" is always used for said amino acid etc.

According to a preferred embodiment, the present invention provides mRNA comprising lipid nanoparticles wherein the mRNA comprises an mRNA sequence as defined herein comprising at least one coding region, wherein the coding region comprises or consists of any one of the (modified) RNA sequences or of a fragment or variant of any one of these sequences.

According to a particularly preferred embodiment, the present invention provides mRNA comprising lipid nanoparticles wherein the mRNA comprises an mRNA sequence as defined herein comprising at least one coding region encoding at least one antigenic peptide or protein derived from hemagglutinin (HA) of an influenza A virus, wherein the coding region comprises or consists of any one of the (modified) RNA sequences or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from hemagglutinin (HA) of an influenza B virus, wherein the coding region comprises or consists of any one of the (modified) RNA sequences or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from neuraminidase (NA) of an influenza A virus, wherein the coding region comprises or consists of any one of the (modified) RNA sequences or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from neuraminidase (NA) of an influenza B virus, wherein the coding region comprises or consists of any one of the (modified) RNA sequences or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from glycoprotein of a Rabies virus, wherein the coding region comprises or consists of any one of the (modified) RNA sequences or of a fragment or variant of any one of these sequences.

In a further preferred embodiment, the at least one coding region of the mRNA sequence according to the invention comprises or consists of an RNA sequence identical to or having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with any one of the (modified) RNA sequences or of a fragment or variant of any one of these sequences.

According to a particularly preferred embodiment, the at least one coding region of the mRNA sequence according to the invention comprises or consists of an RNA sequence having a sequence identity of at least 80% with any one of the (modified) RNA sequences or of a fragment or variant of any one of these sequences.

According to another embodiment, the mRNA compound comprising an mRNA sequence of the present invention may be modified by modifying, preferably increasing, the cytosine (C) content of the mRNA sequence, preferably of the coding region of the mRNA sequence.

In a particularly preferred embodiment of the present invention, the C content of the coding region of the mRNA sequence of the present invention is modified, preferably increased, compared to the C content of the coding region of the respective wild type mRNA, i.e. the unmodified mRNA. The amino acid sequence encoded by the at least one coding region of the mRNA sequence of the present invention is preferably not modified as compared to the amino acid sequence encoded by the respective wild type mRNA.

In a preferred embodiment of the present invention, the modified mRNA sequence is modified such that at least 10%, 20%, 30%, 40%, 50%, 60%, 70% or 80%, or at least 90% of the theoretically possible maximum cytosine-content or even a maximum cytosine-content is achieved.

In further preferred embodiments, at least 10%, 20%, 30%, 40%, 50%, 60%, 70%, 80%, 90% or even 100% of the codons of the target mRNA wild type sequence, which are "cytosine content optimizable" are replaced by codons having a higher cytosine-content than the ones present in the wild type sequence.

In a further preferred embodiment, some of the codons of the wild type coding sequence may additionally be modified such that a codon for a relatively rare tRNA in the cell is exchanged by a codon for a relatively frequent tRNA in the cell, provided that the substituted codon for a relatively frequent tRNA carries the same amino acid as the relatively rare tRNA of the original wild type codon. Preferably, all of the codons for a relatively rare tRNA are replaced by a codon for a relatively frequent tRNA in the cell, except codons encoding amino acids, which are exclusively encoded by codons not containing any cytosine, or except for glutamine (Gln), which is encoded by two codons each containing the same number of cytosines.

In a further preferred embodiment of the present invention, the modified target mRNA is modified such that at least 80%, or at least 90% of the theoretically possible maximum cytosine-content or even a maximum cytosine-content is achieved by means of codons, which code for relatively frequent tRNAs in the cell, wherein the amino acid sequence remains unchanged.

Due to the naturally occurring degeneracy of the genetic code, more than one codon may encode a particular amino acid. Accordingly, 18 out of 20 naturally occurring amino acids are encoded by more than one codon (with Tryp and Met being an exception), e.g. by 2 codons (e.g. Cys, Asp, Glu), by three codons (e.g. Ile), by 4 codons (e.g. Al, Gly, Pro) or by 6 codons (e.g. Leu, Arg, Ser). However, not all codons encoding the same amino acid are utilized with the same frequency under in vivo conditions. Depending on each single organism, a typical codon usage profile is established.

The term "cytosine content-optimizable codon" as used within the context of the present invention refers to codons, which exhibit a lower content of cytosines than other codons encoding the same amino acid. Accordingly, any wild type codon, which may be replaced by another codon encoding the same amino acid and exhibiting a higher number of cytosines within that codon, is considered to be cytosine-optimizable (C-optimizable). Any such substitution of a C-optimizable wild type codon by the specific C-optimized codon within a wild type coding region increases its overall C-content and reflects a C-enriched modified mRNA sequence. According to a preferred embodiment, the mRNA sequence of the present invention, preferably the at least one coding region of the mRNA sequence of the present invention comprises or consists of a C-maximized mRNA sequence containing C-optimized codons for all potentially C-optimizable codons. Accordingly, 100% or all of the theoretically replaceable C-optimizable codons are preferably replaced by C-optimized codons over the entire length of the coding region.

In this context, cytosine-content optimizable codons are codons, which contain a lower number of cytosines than other codons coding for the same amino acid.

Any of the codons GCG, GCA, GCU codes for the amino acid Ala, which may be exchanged by the codon GCC encoding the same amino acid, and/or the codon UGU that codes for Cys may be exchanged by the codon UGC encoding the same amino acid, and/or the codon GAU which codes for Asp may be exchanged by the codon GAC encoding the same amino acid, and/or the codon that UUU that codes for Phe may be exchanged for the codon UUC encoding the same amino acid, and/or any of the codons GGG, GGA, GGU that code Gly may be exchanged by the codon GGC encoding the same amino acid, and/or the codon CAU that codes for His may be exchanged by the codon CAC encoding the same amino acid, and/or any of the codons AUA, AUU that code for Ile may be exchanged by the codon AUC, and/or any of the codons UUG, UUA, CUG, CUA, CUU coding for Leu may be exchanged by the codon CUC encoding the same amino acid, and/or the codon AAU that codes for Asn may be exchanged by the codon AAC encoding the same amino acid, and/or any of the codons CCG, CCA, CCU coding for Pro may be exchanged by the codon CCC encoding the same amino acid, and/or any of the codons AGG, AGA, CGG, CGA, CGU coding for Arg may be exchanged by the codon CGC encoding the same amino acid, and/or any of the codons AGU, AGC, UCG, UCA, UCU coding for Ser may be exchanged by the codon UCC encoding the same amino acid, and/or any of the codons ACG, ACA, ACU coding for Thr may be exchanged by the codon ACC encoding the same amino acid, and/or any of the codons GUG, GUA, GUU coding for Val may be exchanged by the codon GUC encoding the same amino acid, and/or the codon UAU coding for Tyr may be exchanged by the codon UAC encoding the same amino acid.

In any of the above instances, the number of cytosines is increased by 1 per exchanged codon. Exchange of all non C-optimized codons (corresponding to C-optimizable codons) of the coding region results in a C-maximized coding sequence. In the context of the invention, at least 70%, preferably at least 80%, more preferably at least 90%, of the non C-optimized codons within the at least one coding region of the mRNA sequence according to the invention are replaced by C-optimized codons.

It may be preferred that for some amino acids the percentage of C-optimizable codons replaced by C-optimized codons is less than 70%, while for other amino acids the percentage of replaced codons is higher than 70% to meet the overall percentage of C-optimization of at least 70% of all C-optimizable wild type codons of the coding region.

Preferably, in a C-optimized mRNA sequence of the invention, at least 50% of the C-optimizable wild type codons for any given amino acid are replaced by C-optimized codons, e.g. any modified C-enriched mRNA sequence preferably contains at least 50% C-optimized codons at C-optimizable wild type codon positions encoding any one of the above mentioned amino acids Ala, Cys, Asp, Phe, Gly, His, Ile, Leu, Asn, Pro, Arg, Ser, Thr, Val and Tyr, preferably at least 60%.

In this context codons encoding amino acids, which are not cytosine content-optimizable and which are, however, encoded by at least two codons, may be used without any further selection process. However, the codon of the wild type sequence that codes for a relatively rare tRNA in the cell, e.g. a human cell, may be exchanged for a codon that codes for a relatively frequent tRNA in the cell, wherein both code for the same amino acid. Accordingly, the relatively rare codon GAA coding for Glu may be exchanged by the relative frequent codon GAG coding for the same amino acid, and/or the relatively rare codon AAA coding for Lys may be exchanged by the relative frequent codon AAG coding for the same amino acid, and/or the relatively rare codon CAA coding for Gin may be exchanged for the relative frequent codon CAG encoding the same amino acid.

In this context, the amino acids Met (AUG) and Trp (UGG), which are encoded by only one codon each, remain unchanged. Stop codons are not cytosine-content optimized, however, the relatively rare stop codons amber, ochre (UAA, UAG) may be exchanged by the relatively frequent stop codon opal (UGA).

The single substitutions listed above may be used individually as well as in all possible combinations in order to optimize the cytosine-content of the modified mRNA sequence compared to the wild type mRNA sequence.

Accordingly, the at least one coding sequence as defined herein may be changed compared to the coding region of the respective wild type mRNA in such a way that an amino acid encoded by at least two or more codons, of which one comprises one additional cytosine, such a codon may be exchanged by the C-optimized codon comprising one additional cytosine, wherein the amino acid is preferably unaltered compared to the wild type sequence.

According to a preferred embodiment, the present invention provides mRNA comprising lipid nanoparticles wherein the mRNA comprises an mRNA sequence as defined herein comprising at least one coding region, wherein the coding region comprises or consists of any one of the (modified) RNA sequences or of a fragment or variant of any one of these sequences.

According to a particularly preferred embodiment, the present invention provides mRNA comprising lipid nanoparticles wherein the mRNA comprises an mRNA sequence as defined herein comprising at least one coding region encoding at least one antigenic peptide or protein derived from hemagglutinin (HA) of an influenza A virus, wherein the coding region comprises or consists of any one of the (modified) RNA sequences or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from hemagglutinin (HA) of an influenza B virus, wherein the coding region comprises or consists of any one of the (modified) RNA sequences or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from neuraminidase (NA) of an influenza A virus, wherein the coding region comprises or consists of any one of the (modified) RNA sequences or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from neuraminidase (NA) of an influenza B virus, wherein the coding region comprises or consists of any one of the (modified) RNA sequences or of a fragment or variant of any one of these sequences.

According to a further particularly preferred embodiment, the present invention provides mRNA comprising lipid nanoparticles wherein the mRNA comprises an mRNA sequence as defined herein comprising at least one coding region encoding at least one antigenic peptide or protein derived from glycoprotein of a Rabies virus, wherein the coding region comprises or consists of any one of the (modified) RNA sequences or of a fragment or variant of any one of these sequences.

In a further preferred embodiment, the at least one coding region of the mRNA sequence according to the invention comprises or consists of an RNA sequence identical to or having a sequence identity of at least 5%, 10%, 20%, 30%, 40%, 50%, 60%, 70%, 80%, 85%, 86%, 87%, 88%, 89%, 90%, 91%, 92%, 93%, 94%, 95%, 96%, 97%, 98%, or 99%, preferably of at least 70%, more preferably of at least 80%, even more preferably at least 85%, even more preferably of at least 90% and most preferably of at least 95% or even 97%, with any one of the (modified) RNA sequences or of a fragment or variant of any one of these sequences.

According to a particularly preferred embodiment, the at least one coding region of the mRNA compound comprising an mRNA sequence according to the invention comprises or consists of an RNA sequence having a sequence identity of at least 80% with any one of the (modified) RNA sequences or of a fragment or variant of any one of these sequences.

According to a particularly preferred embodiment, the present invention provides mRNA comprising lipid nanoparticles wherein the mRNA comprises an mRNA sequence, comprising at least one coding region as defined herein, wherein the G/C content of the at least one coding region of the mRNA sequence is increased compared to the G/C content of the corresponding coding region of the corresponding wild type mRNA, and/or wherein the C content of the at least one coding region of the mRNA sequence is increased compared to the C content of the corresponding coding region of the corresponding wild type mRNA, and/or wherein the codons in the at least one coding region of the mRNA sequence are adapted to human codon usage, wherein the codon adaptation index (CAI) is preferably increased or maximised in the at least one coding region of the mRNA sequence, and wherein the amino acid sequence encoded by the mRNA sequence is preferably not being modified compared to the amino acid sequence encoded by the corresponding wild type mRNA.

According to another preferred embodiment of the invention, a modified mRNA sequence as defined herein, can be modified by the addition of a so-called “5'-CAP structure”, which preferably stabilizes the mRNA as described herein. A 5'-CAP is an entity, typically a modified nucleotide entity, which generally“caps” the 5'-end of a mature mRNA. A 5'-CAP may typically be formed by a modified nucleotide, particularly by a derivative of a guanine nucleotide. Preferably, the 5'-CAP is linked to the 5'-terminus via a 5'-5'-triphosphate linkage. A 5'-CAP may be methylated, e.g. m7GpppN, wherein N is the terminal 5' nucleotide of the nucleic acid carrying the 5'-CAP, typically the 5'-end of an mRNA. m7GpppN is the 5'-CAP structure, which naturally occurs in mRNA transcribed by polymerase II and is therefore preferably not considered as modification comprised in a modified mRNA in this context. Accordingly, a modified mRNA sequence of the present invention may comprise a m7GpppN as 5'-cap, but additionally the modified mRNA sequence typically comprises at least one further modification as defined herein.

Further examples of 5'-CAP structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. These modified 5'-CAP structures are regarded as at least one modification in this context.

Particularly preferred modified 5'-CAP structures are capI (methylation of the ribose of the adjacent nucleotide of m7G), cap2 (additional methylation of the ribose of the 2nd nucleotide downstream of the m7G), cap3 (additional methylation of the ribose of the 3rd nucleotide downstream of the m7G), cap4 (methylation of the ribose of the 4th nucleotide downstream of the m7G), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine. Accordingly, the RNA according to the invention preferably comprises a 5'-CAP structure.

According to a further preferred embodiment, the mRNA compound comprising an mRNA sequence of the present invention may contain a poly-A tail on the 3'-terminus of typically about 10 to 200 adenosine nucleotides, preferably about 10 to 100 adenosine nucleotides, more preferably about 40 to 80 adenosine nucleotides or even more preferably about 50 to 70 adenosine nucleotides.

Preferably, the poly(A) sequence in the mRNA compound comprising an mRNA sequence of the present invention is derived from a DNA template by RNA in vitro transcription. Alternatively, the poly(A) sequence may also be obtained in vitro by common methods of chemical-synthesis without being necessarily transcribed from a DNA-progenitor. Moreover, poly(A) sequences, or poly(A) tails may be generated by enzymatic polyadenylation of the RNA according to the present invention using commercially available polyadenylation kits and corresponding protocols known in the art.

Alternatively, the mRNA as described herein optionally comprises a polyadenylation signal, which is defined herein as a signal, which conveys polyadenylation to a (transcribed) RNA by specific protein factors (e.g. cleavage and polyadenylation specificity factor (CPSF), cleavage stimulation factor (CstF), cleavage factors I and II (CF I and CF II), poly(A) polymerase (PAP)). In this context, a consensus polyadenylation signal is preferred comprising the NN(U/T)ANA consensus sequence. In a particularly preferred aspect, the polyadenylation signal comprises one of the following sequences: AA(U/T)AAA or A(U/XU/T)AAA (wherein uridine is usually present in RNA and thymidine is usually present in DNA).

According to a further preferred embodiment, the mRNA compound comprising an mRNA sequence of the present invention may contain a poly(C) tail on the 3'-terminus of typically about 10 to 200 cytosine nucleotides, preferably about 10 to 100 cytosine nucleotides, more preferably about 20 to 70 cytosine nucleotides or even more preferably about 20 to 60 or even 10 to 40 cytosine nucleotides.

In one preferred embodiment the mRNA compound comprising an mRNA sequence comprises, preferably in 5'- to 3'-direction:

a) a 5'-CAP structure, preferably m7GpppAm(Cap1) and m7GpppA(Cap0);
b) at least one coding region encoding at least one antigenic peptide or protein,
c) optionally, a poly(A) sequence, preferably comprising from about 50 to about 250 adenosines, more preferably from about 75 to about 125 adenosines, and most preferably from about 85 to about 95 adenosines, and in certain embodiments 95 adenosines;
d) optionally, a poly(C) sequence, preferably comprising from about 10 to about 100 cytosines, more preferably from about 20 to about 50 cytosines, and most preferably from about 25 to about 35 adenos cytosines and in certain embodiments 30 cytosines.

In a more preferred embodiment the mRNA sequence comprises, preferably in 5'- to 3'-direction:

a) a 5'-CAP structure, preferably m7GpppAm(Cap1) and m7GpppA(Cap0);
b) at least one coding region encoding at least one antigenic peptide or protein derived from a protein of an influenza or rabies virus or a fragment or variant thereof,
c) optionally, a poly(A) sequence, preferably comprising from about 50 to about 250 adenosines, more preferably from about 75 to about 100 adenosines, and most preferably from about 85 to about 95 adenosines, and in certain embodiments 95 adenosines;
d) optionally, a poly(C) sequence, preferably comprising from about 10 to about 100 cytosines, more preferably from about 20 to about 50 cytosines, and most preferably from about 25 to about 35 adenos cytosines and in certain embodiments 30 cytosines.

In a particularly preferred embodiment the mRNA sequence comprises, preferably in 5'- to 3'-direction:

a) a 5'-CAP structure, preferably m7GpppAm(Cap1) and m7GpppA(Cap0);
b) at least one coding region encoding at least one antigenic peptide or protein derived from a protein of an influenza virus or a rabies virus or a fragment or variant thereof, preferably comprising or consisting of any one of the nucleic acid sequences as disclosed in the sequence listing having a numeric identifier <223> which starts with "derived and/or modified CDS sequence (wt)" or "derived and/or modified CDS sequence (opt1)", "derived and/or modified CDS sequence (opt2)", "derived and/or modified CDS sequence (opt3)", "derived and/or modified CDS sequence (opt4)", or "derived and/or modified CDS sequence (opt5)" or of a fragment or variant of any one of these sequences),
c) optionally, a poly(A) sequence, preferably comprising from about 50 to about 250 adenosines, more preferably from about 75 to about 100 adenosines, and most preferably from about 85 to about 105 adenosines, and in certain embodiments 97 to 101 adenosines;
d) optionally, a poly(C) sequence, preferably comprising from about 10 to about 100 cytosines, more preferably from about 20 to about 50 cytosines, and most preferably from about 25 to about 35 adenos cytosines and in certain embodiments 30 cytosines.

In a preferred embodiment, the mRNA compound comprising an mRNA sequence according to the invention comprises at least one 5'- or 3'-UTR element. In this context, an UTR element comprises or consists of a nucleic acid sequence, which is derived from the 5'-or 3'-UTR of any naturally occurring gene or which is derived from a fragment, a homolog or a variant of the 5'- or 3'-UTR of a gene. Preferably, the 5'- or 3'-UTR element used according to the present invention is heterologous to the at least one coding region of the mRNA sequence of the invention. Even if 5'- or 3'-UTR elements derived from naturally occurring genes are preferred, also synthetically engineered UTR elements may be used in the context of the present invention.

The term "3'-UTR element" typically refers to a nucleic acid sequence, which comprises or consists of a nucleic acid sequence that is derived from a 3'-UTR or from a variant of a 3'-UTR. A 3'-UTR element in the sense of the present invention may represent the 3'-UTR of an RNA, preferably an mRNA. Thus, in the sense of the present invention, preferably, a 3'-UTR element may be the 3'-UTR of an RNA, preferably of an mRNA, or it may be the transcription template for a 3'-UTR of an RNA. Thus, a 3'-UTR element preferably is a nucleic acid sequence which corresponds to the 3'-UTR of an RNA, preferably to the 3'-UTR of an mRNA, such as an mRNA obtained by transcription of a genetically engineered vector construct. Preferably, the 3'-UTR element fulfils the function of a 3'-UTR or encodes a sequence which fulfils the function of a 3'-UTR.

Preferably, the at least one 3'-UTR element comprises or consists of a nucleic acid sequence derived from the 3'-UTR of a chordate gene, preferably a vertebrate gene, more preferably a mammalian gene, most preferably a human gene, or from a variant of the 3'-UTR of a chordate gene, preferably a vertebrate gene, more preferably a mammalian gene, most preferably a human gene.

Preferably, the mRNA compound comprising an mRNA sequence of the present invention comprises a 3'-UTR element, which may be derivable from a gene that relates to an mRNA with an enhanced half-life (that provides a stable mRNA), for example a 3'-UTR element as defined and described below. Preferably, the 3'-UTR element is a nucleic acid sequence derived from a 3'-UTR of a gene, which preferably encodes a stable mRNA, or from a homolog, a fragment or a variant of said gene.

In a particularly preferred embodiment, the 3'-UTR element comprises or consists of a nucleic acid sequence, which is derived from a 3'-UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene, or from a variant of a 3'-UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene according to SEQ ID NOs: 1369-1390 of the patent application WO2013/143700, whose disclosure is incorporated herein by reference, or from a homolog, a fragment or a variant thereof. In a particularly preferred embodiment, the 3'-UTR element comprises or consists of a nucleic acid sequence which is derived from a 3'-UTR of an albumin gene, preferably a vertebrate albumin gene, more preferably a mammalian albumin gene.

The term "a nucleic acid sequence which is derived from the 3'-UTR of a [ . . . ] gene" preferably refers to a nucleic acid sequence which is based on the 3'-UTR sequence of a [ . . . ] gene or on a part thereof, such as on the 3'-UTR of an albumin gene, an α-globin gene, a β-globin gene, a tyrosine hydroxylase gene, a lipoxygenase gene, or a collagen alpha gene, such as a collagen alpha 1(I) gene, preferably of an albumin gene or on a part thereof. This term includes sequences corresponding to the entire 3'-UTR sequence, i.e. the full length 3'-UTR sequence of a gene, and sequences corresponding to a fragment of the 3'-UTR sequence of a gene, such as an albumin gene, α-globin gene, β-globin gene, tyrosine hydroxylase gene, lipoxygenase gene, or collagen alpha gene, such as a collagen alpha 1(I) gene, preferably of an albumin gene.

The term "a nucleic acid sequence which is derived from a variant of the 3'-UTR of a [ . . . ] gene" preferably refers to a nucleic acid sequence, which is based on a variant of the 3'-UTR sequence of a gene, such as on a variant of the 3'-UTR of an albumin gene, an α-globin gene, a β-globin gene, a tyrosine hydroxylase gene, a lipoxygenase gene, or a collagen alpha gene, such as a collagen alpha 1(I) gene, or on a part thereof as described above. This term includes sequences corresponding to the entire sequence of the variant of the 3'-UTR of a gene, i.e. the full length variant 3'-UTR sequence of a gene, and sequences corresponding to a fragment of the variant 3'-UTR sequence of a gene. A fragment in this context preferably consists of a continuous stretch of nucleotides corresponding to a continuous stretch of nucleotides in the full-length variant 3'-UTR, which represents at least 20%, preferably at least 30%, more preferably at least 40%, more preferably at least 50%, even more preferably at least 60%, even more preferably at least 70%, even more preferably at least 80%, and most preferably at least 90% of the full-length variant 3'-UTR. Such a fragment of a variant, in the sense of the present invention, is preferably a functional fragment of a variant as described herein.

According to a preferred embodiment, the mRNA compound comprising an mRNA sequence according to the invention comprises a 5'-CAP structure and/or at least one 3'-untranslated region element (3'-UTR element), preferably as defined herein. More preferably, the RNA further comprises a 5'-UTR element as defined herein.

In one preferred embodiment the mRNA compound comprising an mRNA sequence comprises, preferably in 5'- to 3'-direction:

a) a 5'-CAP structure, preferably m7GpppAm(Cap1) and m7GpppA(Cap0);
b) at least one coding region encoding at least one antigenic peptide or protein,
c) optionally a 3'-UTR element, preferably comprising or consisting of a nucleic acid sequence which is derived from an alpha globin gene, a homolog, a fragment or a variant thereof,
d) optionally, a poly(A) sequence, preferably comprising from about 50 to about 250 adenosines, more preferably from about 75 to about 100 adenosines, and most preferably from about 85 to about 105 adenosines, and in certain embodiments 97 to 101 adenosines;
e) optionally, a poly(C) sequence, preferably comprising from about 10 to about 100 cytosines, more preferably from about 20 to about 50 cytosines, and most preferably from about 25 to about 35 adenos cytosines and in certain embodiments 30 cytosines.

In a preferred embodiment the mRNA sequence comprises, preferably in 5'- to 3'-direction:

a) a 5'-CAP structure, preferably m7GpppAm(Cap1) and m7GpppA(Cap0);
b) at least one coding region encoding at least one antigenic peptide or protein, preferably derived from a protein of an influenza virus or a Rabies virus or a fragment or variant thereof, c) optionally a 3'-UTR element, preferably comprising or consisting of a nucleic acid sequence which is derived from an alpha globin gene, a homolog, a fragment or a variant thereof, d) optionally, a poly(A) sequence, preferably comprising from about 50 to about 250 adenosines, more preferably from about 75 to about 100 adenosines, and most preferably from about 85 to about 105 adenosines, and in certain embodiments 97 to 101 adenosines;

e) optionally, a poly(C) sequence, preferably comprising from about 10 to about 100 cytosines, more preferably from about 20 to about 50 cytosines, and most preferably from about 25 to about 35 adenos cytosines and in certain embodiments 30 cytosines.

In a particularly preferred embodiment the mRNA sequence comprises, preferably in 5'- to 3'-direction:

a) a 5'-CAP structure, preferably m7GpppAm(Cap1) and m7GpppA(Cap0);

b) at least one coding region encoding at least one antigenic peptide or protein preferably derived from a protein of an influenza virus or Rabies virus or a fragment or variant thereof, or of a fragment or variant of any one of these sequences, c) optionally a 3'-UTR element, preferably comprising or consisting of a nucleic acid sequence which is derived from an alpha globin gene, a homolog, a fragment or a variant thereof, d) optionally, a poly(A) sequence, preferably comprising from about 50 to about 250 adenosines, more preferably from about 75 to about 100 adenosines, and most preferably from about 85 to about 105 adenosines, and in certain embodiments 97 to 101 adenosines;

e) optionally, a poly(C) sequence, preferably comprising from about 10 to about 100 cytosines, more preferably from about 20 to about 50 cytosines, and most preferably from about 25 to about 35 adenos cytosines and in certain embodiments 30 cytosines.

In a particularly preferred embodiment, the at least one mRNA compound comprising an mRNA sequence comprises at least one 5'-untranslated region element (5'-UTR element). Preferably, the at least one 5'-UTR element comprises or consists of a nucleic acid sequence, which is derived from the 5'-UTR of a TOP gene or which is derived from a fragment, homolog or variant of the 5'-UTR of a TOP gene.

It is particularly preferred that the 5'-UTR element does not comprise a TOP motif or a 5'-TOP, as defined above.

In some embodiments, the nucleic acid sequence of the 5'-UTR element, which is derived from a 5'-UTR of a TOP gene, terminates at its 3'-end with a nucleotide located at position 1, 2, 3, 4, 5, 6, 7, 8, 9 or 10 upstream of the start codon (e.g. A(U/T)G) of the gene or mRNA it is derived from. Thus, the 5'-UTR element does not comprise any part of the protein coding region. Thus, preferably, the only protein coding part of the at least one mRNA sequence is provided by the coding region.

The nucleic acid sequence derived from the 5'-UTR of a TOP gene is preferably derived from a eukaryotic TOP gene, preferably a plant or animal TOP gene, more preferably a chordate TOP gene, even more preferably a vertebrate TOP gene, most preferably a mammalian TOP gene, such as a human TOP gene.

For example, the 5'-UTR element is preferably selected from 5'-UTR elements comprising or consisting of a nucleic acid sequence.

In a preferred embodiment, the 5'-UTR element of the mRNA compound comprising an mRNA sequence according to the invention comprises or consists of a nucleic acid sequence, which is derived from a nucleic acid sequence extending from nucleotide position 5 (i.e. the nucleotide that is located at position 5 in the sequence) to the nucleotide position immediately 5' to the start codon (located at the 3'-end of the sequences).

In a particularly preferred embodiment, the 5'-UTR element comprises or consists of a nucleic acid sequence, which is derived from a 5'-UTR of a TOP gene encoding a ribosomal protein or from a variant of a 5'-UTR of a TOP gene encoding a ribosomal protein. For example, the 5'-UTR element comprises or consists of a nucleic acid sequence, which is derived from a 5'-UTR of a nucleic acid sequence according to any of SEQ ID NOs: 67, 170, 193, 244, 259, 554, 650, 675, 700, 721, 913, 1016, 1063, 1120, 1138, and 1284-1360 of the patent application WO2013/143700, a corresponding RNA sequence, a homolog thereof, or a variant thereof as described herein, preferably lacking the 5'-TOP motif. As described above, the sequence extending from position 5 to the nucleotide immediately 5' to the ATG (which is located at the 3'-end of the sequences) corresponds to the 5'-UTR of said sequences.

Preferably, the 5'-UTR element comprises or consists of a nucleic acid sequence, which is derived from a 5'-UTR of a TOP gene encoding a ribosomal Large protein (RPL) or from a homolog or variant of a 5'-UTR of a TOP gene encoding a ribosomal Large protein (RPL). For example, the 5'-UTR element comprises or consists of a nucleic acid sequence, which is derived from a 5'-UTR of a nucleic acid sequence according to any of SEQ ID NOs: 67, 259, 1284-1318, 1344, 1346, 1348-1354, 1357, 1358, 1421 and 1422 of PCT patent application publication WO2013/143700 (incorporated herein by reference), a corresponding RNA sequence, a homolog thereof, or a variant thereof as described herein, preferably lacking the 5'-TOP motif.

In a particularly preferred embodiment, the 5'-UTR element comprises or consists of a nucleic acid sequence which is derived from the 5'-UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, or from a variant of the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, wherein preferably the 5'-UTR element does not comprise the 5'-TOP of said gene.

Accordingly, in a particularly preferred embodiment, the 5'-UTR element comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% corresponding to SEQ ID NO: 1368 of the patent application WO2013/143700) or preferably to a corresponding RNA sequence, or wherein the at least one 5'-UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, wherein, preferably, the fragment is as described above, i.e. being a continuous stretch of nucleotides representing at least 20% etc. of the full-length 5'-UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In some embodiments, the mRNA compound comprising an mRNA sequence according to the invention comprises a 5'-UTR element, which comprises or consists of a nucleic acid sequence, which is derived from the 5'-UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL 11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB, or from a homolog or variant thereof, wherein preferably the 5'-UTR element does not comprise a TOP motif or the 5'-TOP of said genes, and wherein optionally the 5'-UTR element starts at its 5'-end with a nucleotide located at position 1, 2, 3, 4, 5, 6, 7, 8, 9 or 10 downstream of the 5'-terminal oligopyrimidine tract (TOP) and wherein further optionally the 5'-UTR element which is derived from a 5'-UTR of a TOP gene terminates at its 3'-end with a nucleotide located at position 1, 2, 3, 4, 5, 6, 7, 8, 9 or 10 upstream of the start codon (A(U/T)G) of the gene it is derived from.

In further particularly preferred embodiments, the 5'-UTR element comprises or consists of a nucleic acid sequence, which is derived from the 5'-UTR of a ribosomal protein Large 32 gene (RPL32), a ribosomal protein Large 35 gene (RPL35), a ribosomal protein Large 21 gene (RPL21), an ATP synthase, H+ transporting, mitochondrial F1 complex, alpha subunit 1, cardiac muscle (ATP5A1) gene, an hydroxysteroid (17-beta) dehydrogenase 4 gene (HSD17B4), an androgen-induced 1 gene (AIG1), cytochrome c oxidase subunit VIc gene (COX6C), or a N-acylsphingosine amidohydrolase (acid ceramidase) 1 gene (ASAH1) or from a variant thereof, preferably from a vertebrate ribosomal protein Large 32 gene (RPL32), a vertebrate ribosomal protein Large 35 gene (RPL35), a vertebrate ribosomal protein Large 21 gene (RPL21), a vertebrate ATP synthase, H+ transporting, mitochondrial F1 complex, alpha subunit 1, cardiac muscle (ATP5A1) gene, a vertebrate hydroxysteroid (17-beta) dehydrogenase 4 gene (HSD17B4), a vertebrate androgen-induced 1 gene (AIG1), a vertebrate cytochrome c oxidase subunit VIc gene (COX6C), or a vertebrate N-acylsphingosine amidohydrolase (acid ceramidase) 1 gene (ASAH1) or from a variant thereof, more preferably from a mammalian ribosomal protein Large 32 gene (RPL32), a ribosomal protein Large 35 gene (RPL35), a ribosomal protein Large 21 gene (RPL21), a mammalian ATP synthase, H+ transporting, mitochondrial F1 complex, alpha subunit 1, cardiac muscle (ATP5A1) gene, a mammalian hydroxysteroid (17-beta) dehydrogenase 4 gene (HSD17B4), a mammalian androgen-induced 1 gene (AIG1), a mammalian cyto-chrome c oxidase subunit VIc gene (COX6C), or a mammalian N-acylsphingosine ami-dohydrolase (acid ceramidase) 1 gene (ASAH1) or from a variant thereof, most preferably from a human ribosomal protein Large 32 gene (RPL32), a human ribosomal protein Large 35 gene (RPL35), a human ribosomal protein Large 21 gene (RPL21), a human ATP synthase, H+ transporting, mitochondrial F1 complex, alpha subunit 1, cardiac muscle (ATP5A1) gene, a human hydroxysteroid (17-beta) dehydrogenase 4 gene (HSD17B4), a human androgen-induced 1 gene (AIG1), a human cytochrome c oxidase subunit VIc gene (COX6C), or a human N-acylsphingosine amidohydrolase (acid ceramidase) 1 gene (ASAH1) or from a variant thereof, wherein preferably the 5'-UTR element does not comprise the 5'-TOP of said gene.

Accordingly, in a particularly preferred embodiment, the 5'-UTR element comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO: 1368, or SEQ ID NOs: 1412-1420 of the patent application WO2013/143700, or a corresponding RNA sequence, or wherein the at least one 5'-UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO: 1368, or SEQ ID NOs: 1412-1420 of the patent application WO2013/143700, wherein, preferably, the fragment is as described above, i.e. being a continuous stretch of nucleotides representing at least 20% etc. of the full-length 5'-UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Accordingly, in a particularly preferred embodiment, the 5'-UTR element comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO: 1 (5'-UTR of ATP5A1 lacking the 5'-terminal oligopyrimidine tract: GCGGCTCGGC-CATGTCCCAGTACAGTCCG-GAGGCTGCGGCTGCAGAAGTACCGC CTGCGGAGTAACTGCAAAG; corresponding to SEQ ID NO: 224289 of the patent application WO2013/143700) or preferably to a corresponding RNA sequence (SEQ ID NO: 224290), or wherein the at least one 5'-UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID NO: 224289 or more preferably to a corresponding RNA sequence (SEQ ID NO: 224290), wherein, preferably, the fragment is as described above, i.e. being a continuous stretch of nucleotides representing at least 20% etc. of the full-length 5'-UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Preferably, the at least one 5'-UTR element and the at least one 3'-UTR element act synergistically to increase protein production from the at least one mRNA sequence as described above.

According to a preferred embodiment the mRNA compound comprising an mRNA sequence according to the invention comprises, preferably in 5'- to 3'-direction:

a) a 5'-CAP structure, preferably m7GpppN;
b) optionally a 5'-UTR element which preferably comprises or consists of a nucleic acid sequence which is derived from the 5'-UTR of a TOP gene, more preferably comprising or consisting of the corresponding RNA sequence of a nucleic acid sequence according to SEQ ID NO: 224287, as shown in SEQ ID NO: 224288, a homolog, a fragment or a variant thereof,
c) at least one coding region encoding at least one antigenic peptide or protein preferably derived from a protein of an influenza virus or a Rabies virus, or a fragment or variant thereof, preferably comprising or consisting of any one of the nucleic acid sequences as disclosed in the sequence listing having a numeric identifier <223> which starts with "derived and/or modified CDS sequence (wt)" or "derived and/or modified CDS sequence (opt1)", "derived and/or modified CDS sequence (opt2)", "derived and/or modified CDS sequence (opt3)", "derived and/or modified CDS sequence (opt4)", or "derived and/or modified CDS sequence (opt5)", or respectively "column B" or "column C" of Tables 1-5 or FIGS. 20-24 of PCT/EP2016/075843 (incorporated herein by reference), SEQ ID NOs: 32013-64024, or SEQ ID NOs: 64025-224084 or of a fragment or variant of any one of these sequences,
d) optionally a 3'-UTR element which preferably comprises or consists of a nucleic acid sequence which is derived from a gene providing a stable mRNA, preferably comprising or consisting of the corresponding RNA sequence of a nucleic acid sequence or a homolog, a fragment or a variant thereof,
e) optionally a poly(A) sequence preferably comprising from about 50 to about 250 adenosines, more preferably from about 75 to about 100 adenosines, and most preferably from about 85 to about 105 adenosines, and in certain embodiments 97 to 101 adenosines; and
f) optionally a poly(C) sequence, preferably comprising from about 10 to about 100 cytosines, more preferably from about 20 to about 50 cytosines, and most preferably from about 25 to about 35 adenos cytosines and in certain embodiments 30 cytosines.

Signal Peptides

According to another particularly preferred embodiment, the mRNA sequence according to the invention may additionally or alternatively encode a secretory signal peptide. Such signal peptides are sequences, which typically exhibit a length of about 15 to 30 amino acids and are preferably located at the N-terminus of the encoded peptide, without being limited thereto. Signal peptides as defined herein preferably allow the transport of the antigen, antigenic protein or antigenic peptide as encoded by the at least one mRNA sequence into a defined cellular compartment, preferably the cell surface, the endoplasmic reticulum (ER) or the endosomal-lysosomal compartment. Examples of secretory signal peptide sequences as defined herein include, without being limited thereto, signal sequences of classical or non-classical MHC-molecules (e.g. signal sequences of MHC I and II molecules, e.g. of the MHC class I molecule HLA-A*0201), signal sequences of cytokines or immunoglobulines as defined herein, signal sequences of the invariant chain of immunoglobulines or antibodies as defined herein, signal sequences of LampI, Tapasin, Erp57, Calretikulin, Calnexin, and further membrane associated proteins or of proteins associated with the endoplasmic reticulum (ER) or the endosomal-lysosomal compartment. Most preferably, signal sequences of MHC class I molecule HLA-A*0201 may be used according to the present invention. For example, a signal peptide derived from HLA-A is preferably used in order to promote secretion of the encoded antigen as defined herein or a fragment or variant thereof. More preferably, an HLA-A signal peptide is fused to an encoded antigen as defined herein or to a fragment or variant thereof.

Production of mRNA

The mRNA according to the present invention may be prepared using any method known in the art, including synthetic methods such as e.g. solid phase RNA synthesis, as well as in vitro methods, such as RNA in vitro transcription reactions, particularly as described in the examples.

As noted, the mRNA compound according to the invention in encapsulated in or associated with a lipid nanoparticle.

Adjuvants Of The Invention

Suitable adjuvants may furthermore be selected from nucleic acids having the formula GlXmGn, wherein: G is guanosine, uracil or an analogue of guanosine or uracil; X is guanosine, uracil, adenosine, thymidine, cytosine or an analogue of the above-mentioned nucleotides; I is an integer from 1 to 40, wherein when I=1 G is guanosine or an analogue thereof, when I>1 at least 50% of the nucleotides are guanosine or an analogue thereof, m is an integer and is at least 3; wherein when m=3 X is uracil or an analogue thereof, when m>3 at least 3 successive uracils or analogues of uracil occur; n is an integer from 1 to 40, wherein when n=1 G is guanosine or an analogue thereof, when n>1 at least 50% of the nucleotides are guanosine or an analogue thereof, or formula: (NuGlXmGnNv)a, wherein: G is guanosine (guanine), uridine (uracil) or an analogue of guanosine (guanine) or uridine (uracil), preferably guanosine (guanine) or an analogue thereof; X is guanosine (guanine), uridine (uracil), adenosine (adenine), thymidine (thymine), cytidine (cytosine), or an analogue of these nucleotides (nucleosides), preferably uridine (uracil) or an analogue thereof; N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides); a is an integer from 1 to 20, preferably from 1 to 15, most preferably from 1 to 10; I is an integer from 1 to 40, wherein when I=1, G is guanosine (guanine) or an analogue thereof, when I>1, at least 50% of these nucleotides (nucleosides) are guanosine (guanine) or an analogue thereof, m is an integer and is at least 3; wherein when m=3, X is uridine (uracil) or an analogue thereof, and when m>3, at least 3 successive uridines (uracils) or analogues of uridine (uracil) occur; n is an integer from 1 to 40, wherein when n=1, G is guanosine (guanine) or an analogue thereof, when n>1, at least 50% of these nucleotides (nucleosides) are guanosine (guanine) or an analogue thereof; u,v may be independently from each other an integer from 0 to 50, preferably wherein when u=0, v>1, or when v=0, u>1; wherein the nucleic acid molecule of formula (NuGIXmGnNv)a has a length of at least 50 nucleotides, preferably of at least 100 nucleotides, more preferably of at least 150 nucleotides, even more preferably of at least 200 nucleotides and most preferably of at least 250 nucleotides.

In certain embodiments, the Ionizable Lipids of the Invention have an adjuvant effect. In particular embodiments, the Ionizable Lipids of the Invention can also act as an adjuvant.

In some embodiments, adjuvants are for example: montanide ISA-51 (Seppic Inc., Fairfield, N.J., United States of America); QS-21 (Aquila Biopharmaceuticals. Inc., Framingham, Mass., United States of America); Arlacel A; oeleic acid; tetanus helper peptides (such as but not limited to QYIKANSKFIGITEL (SEQ ID NO: 2) and/or AQYIKANSKFIGITEL (SEQ ID NO: 3); GM-CSF; cyclophosamide; *bacillus* Calmette-Guerin (BCG); *Corynbacterium parvum*; levamisole, azimezone; isoprinisone; dinitrochlorobenezene (DNCB); keyhole limpet hemocyanin (KLH); Freunds adjuvant (complete and incomplete); mineral gels; aluminum hydroxide (Alum); lysolecithin; pluronic polyols; polyanions; peptides; oil emulsions; nucleic acids (such as but not limited to soluble-stranded RNAs; dsRNA) dinitrophenol; diphtheria toxin (DT); toll-like receptor (TLR; such as but not limited to TLR3, TLR4, TLR7, TLR8, and/or TLR9) agonists (including but not limited to endotoxins such as lipopolysaccharide (LPS); monophosphoryl lipid A (MPL); and/or polyinosinic-polycytidylic acid (poly-ICLC/HILTONOL®; Oncovir, Inc., Washington, D.C., United States of America); IMO-2055; glucopyranosyl lipid A (GLA); QS-21 (a saponin extracted from the bark of the *Quillaja saponaria* tree, also known as the soap bark tree or Soapbark); resiquimod (a TLR7/8 agonist); CDX-1401 (a fusion protein consisting of a fully human monoclonal antibody with specificity for the dendritic cell receptor DEC-205 linked to the NY-ESO-1 tumor antigen); Juvaris' Cationic Lipid-DNA Complex; Vaxfectin; and combinations thereof. In one embodiment, adjuvants using heterogeneous monophosphoryl Lipid A (MPL) derived from *Salmonella minnesota* R595 are used to induce Th-1 type immune responses to heterologous proteins in animal and human vaccines. Exemplary monophosphoryl Lipid A type adjuvants are shown below:

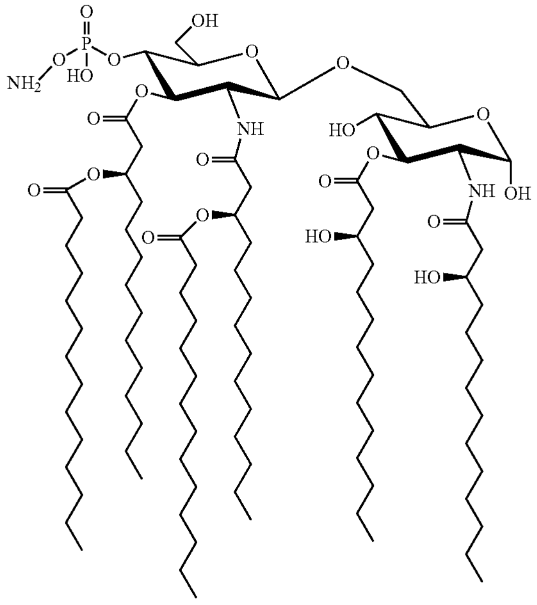

PHAD®

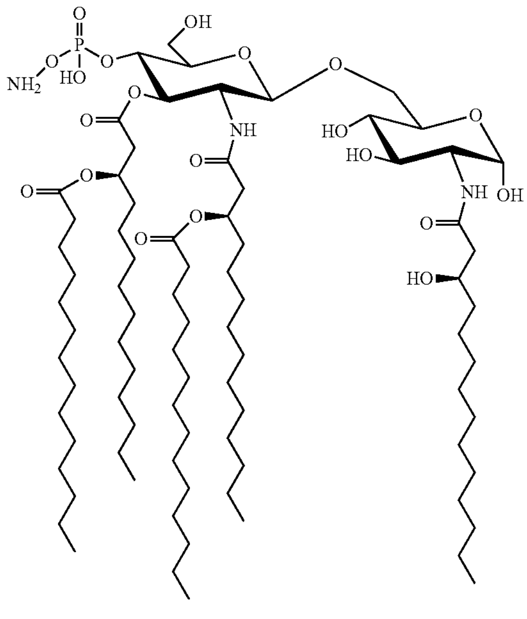

3D-PHAD®

-continued

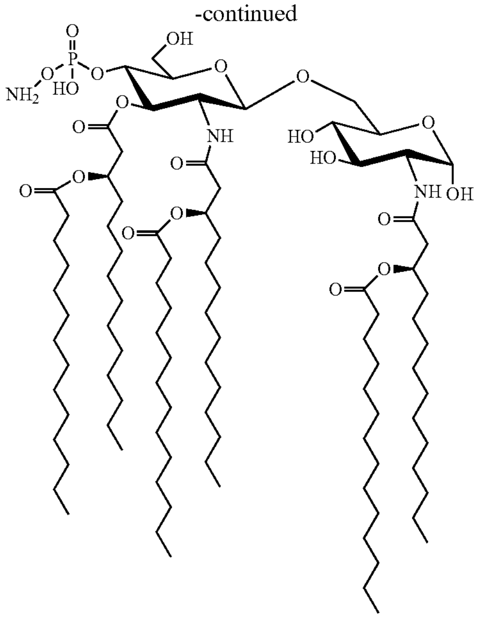

3D(6A)-PHAD®

Other suitable adjuvants may furthermore be selected from nucleic acids having the formula: CIXmCn, wherein: C is cytosine, uracil or an analogue of cytosine or uracil; X is guanosine, uracil, adenosine, thymidine, cytosine or an analogue of the above-mentioned nucleotides; I is an integer from 1 to 40, wherein when I=1 C is cytosine or an analogue thereof, when I>1 at least 50% of the nucleotides are cytosine or an analogue thereof; m is an integer and is at least 3; wherein when m=3 X is uracil or an analogue thereof, when m>3 at least 3 successive uracils or analogues of uracil occur; n is an integer from 1 to 40, wherein when n=1 C is cytosine or an analogue thereof, when n>1 at least 50% of the nucleotides are cytosine or an analogue thereof.

In this context the disclosure of WO2008/014979 and WO2009/095226 is also incorporated herein by reference.

In a further aspect, the present invention provides a vaccine, which is based on the mRNA comprising lipid nanoparticles according to the invention comprising at least one mRNA compound comprising a mRNA sequence comprising coding region as defined herein. The vaccine according to the invention is preferably a (pharmaceutical) composition as defined herein.

Accordingly, the vaccine according to the invention is based on the same components as the (pharmaceutical) composition described herein. Insofar, it may be referred to the description of the (pharmaceutical) composition as provided herein. Preferably, the vaccine according to the invention comprises at least one mRNA comprising lipid nanoparticles comprising at least one mRNA sequence as defined herein and a pharmaceutically acceptable carrier. In embodiments, where the vaccine comprises more than one mRNA sequence (such as a plurality of RNA sequences according to the invention, wherein each preferably encodes a distinct antigenic peptide or protein) encapsulated in mRNA comprising lipid nanoparticles, the vaccine may be provided in physically separate form and may be administered by separate administration steps. The vaccine according to the invention may correspond to the (pharmaceutical) composition as described herein, especially where the mRNA sequences are provided by one single composition. However, the inventive vaccine may also be provided physically separated. For instance, in embodiments, wherein the vaccine comprises more than one mRNA sequences/species encapsulated in mRNA comprising lipid nanoparticles as defined herein, these RNA species may be provided such that, for example, two, three, four, five or six separate compositions, which may contain at least one mRNA species/sequence each (e.g. three distinct mRNA species/sequences), each encoding distinct antigenic peptides or proteins, are provided, which may or may not be combined. Also, the inventive vaccine may be a combination of at least two distinct compositions, each composition comprising at least one mRNA encoding at least one of the antigenic peptides or proteins defined herein. Alternatively, the vaccine may be provided as a combination of at least one mRNA, preferably at least two, three, four, five, six or more mRNAs, each encoding one of the antigenic peptides or proteins defined herein. The vaccine may be combined to provide one single composition prior to its use or it may be used such that more than one administration is required to administer the distinct mRNA sequences/species encoding any of the antigenic peptides or proteins encapsulated in mRNA comprising lipid nanoparticles as defined herein. If the vaccine contains at least one mRNA comprising lipid nanoparticles, typically comprising at least two mRNA sequences, encoding the antigen combinations defined herein, it may e.g. be administered by one single administration (combining all mRNA species/sequences), by at least two separate administrations. Accordingly; any combination of mono-, bi- or multicistronic mRNAs encoding the at least one antigenic peptide or protein or any combination of antigens as defined herein (and optionally further antigens), provided as separate entities (containing one mRNA species) or as combined entity (containing more than one mRNA species), is understood as a vaccine according to the present invention. According to a particularly preferred embodiment of the inventive vaccine, the at least one antigen, preferably a combination as defined herein of at least two, three, four, five, six or more antigens encoded by the inventive composition as a whole, is provided as an individual (monocistronic) mRNA, which is administered separately.

As with the (pharmaceutical) composition according to the present invention, the entities of the vaccine may be provided in liquid and or in dry (e.g. lyophilized) form. They may contain further components, in particular further components allowing for its pharmaceutical use. The vaccine or the (pharmaceutical) composition may, e.g., additionally contain a pharmaceutically acceptable carrier and/or further auxiliary substances and additives and/or adjuvants.

The vaccine or (pharmaceutical) composition typically comprises a safe and effective amount of the mRNA compound according to the invention as defined herein, encoding an antigenic peptide or protein as defined herein or a fragment or variant thereof or a combination of antigens, encapsulate within and/or associated with the lipid nanoparticles. As used herein, "safe and effective amount" means an amount of the mRNA that is sufficient to significantly induce a positive modification of cancer or a disease or disorder related to cancer. At the same time, however, a "safe and effective amount" is small enough to avoid serious side-effects, that is to say to permit a sensible relationship between advantage and risk. The determination of these limits typically lies within the scope of sensible medical judgment. In relation to the vaccine or (pharmaceutical) composition of the present invention, the expression "safe and effective amount" preferably means an amount of the mRNA (and thus of the encoded antigen) that is suitable for stimulating the adaptive immune system in such a manner that no excessive or damaging immune reactions are achieved but, preferably, also no such immune reactions below a measurable level. Such a "safe and effective amount" of the mRNA of the (pharmaceutical) composition or vaccine as defined herein may furthermore be selected in dependence of the type of mRNA, e.g. monocistronic, bi- or even multicistronic mRNA, since a bi- or even multicistronic mRNA may lead to a significantly higher expression of the encoded antigen(s) than the use of an equal amount of a monocistronic mRNA. A "safe and effective amount" of the mRNA of the (pharmaceutical) composition or vaccine as defined above will furthermore vary in connection with the particular condition to be treated and also with the age and physical condition of the patient to be treated, the severity of the condition, the duration of the treatment, the nature of the accompanying therapy, of the particular pharmaceutically acceptable carrier used, and similar factors, within the knowledge and experience of the accompanying doctor. The vaccine or composition according to the invention can be used according to the invention for human and also for veterinary medical purposes, as a pharmaceutical composition or as a vaccine.

In a preferred embodiment, the mRNA comprising lipid nanoparticle of the (pharmaceutical) composition, vaccine or kit of parts according to the invention is provided in lyophilized form. Preferably, the lyophilized mRNA comprising lipid nanoparticles are reconstituted in a suitable buffer, advantageously based on an aqueous carrier, prior to administration, e.g. Ringer-Lactate solution, Ringer solution, a phosphate buffer solution. In a preferred embodiment, the (pharmaceutical) composition, the vaccine or the kit of parts according to the invention contains at least one, two, three, four, five, six or more mRNA compounds, which may be provided as a single species of lipid nanoparticles, or separately for each LNP species, optionally in lyophilized form (optionally together with at least one further additive) and which are preferably reconstituted separately in a suitable buffer (such as Ringer-Lactate solution) prior to their use so as to allow individual administration of each of the (monocistronic) mRNAs.

The vaccine or (pharmaceutical) composition according to the invention may typically contain a pharmaceutically acceptable carrier. The expression "pharmaceutically acceptable carrier" as used herein preferably includes the liquid or non-liquid basis of the inventive vaccine. If the inventive vaccine is provided in liquid form, the carrier will be water, typically pyrogen-free water; isotonic saline or buffered (aqueous) solutions, e.g phosphate, citrate etc. buffered solutions. Particularly for injection of the inventive vaccine, water or preferably a buffer, more preferably an aqueous buffer, may be used, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$)), $CaI_2$, $CaBr_2$, $CaCO_3$, $CaSO_4$, $Ca(OH)_2$. Furthermore, organic anions of the aforementioned cations may be contained in the buffer. According to a more preferred embodiment, the buffer suitable for injection purposes as defined above, may contain salts selected from sodium chloride (NaCl), calcium chloride ($CaCl_2$)) and optionally potassium chloride (KCl), wherein further anions may be present additional to the chlorides. $CaCl_2$) can also be replaced by another salt like KCl. Typically, the salts in the injection buffer are present in a concentration of at least 50 mM sodium chloride (NaCl), at least 3 mM potassium chloride (KCl) and at least 0.01 mM calcium chloride ($CaCl_2$)). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. in "in vivo" methods occurring liquids such as blood, lymph, cytosolic liquids, or other body liquids, or e.g. liquids, which may be used as reference media in "in vitro" methods, such as common buffers or liquids. Such common buffers or liquids are known to a skilled person.

However, one or more compatible solid or liquid fillers or diluents or encapsulating compounds may be used as well, which are suitable for administration to a person. The term "compatible" as used herein means that the constituents of the inventive vaccine are capable of being mixed with the mRNA according to the invention as defined herein, in such a manner that no interaction occurs, which would substantially reduce the pharmaceutical effectiveness of the inventive vaccine under typical use conditions. Pharmaceutically acceptable carriers, fillers and diluents must, of course, have sufficiently high purity and sufficiently low toxicity to make them suitable for administration to a person to be treated. Some examples of compounds which can be used as pharmaceutically acceptable carriers, fillers or constituents thereof are sugars, such as, for example, lactose, glucose, trehalose and sucrose; starches, such as, for example, corn starch or potato starch; dextrose; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from *theobroma*; polyols, such as, for example, polypropylene glycol, glycerol, sorbitol, mannitol and polyethylene glycol; alginic acid.

The choice of a pharmaceutically acceptable carrier is determined, in principle, by the manner, in which the pharmaceutical composition or vaccine according to the invention is administered. The composition or vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, composition or vaccines according to the present invention may be administered by an intradermal, subcutaneous, or intramuscular route, preferably by injection, which may be needle-free and/or needle injection. Compositions/vaccines are therefore preferably formulated in liquid or solid form. The suitable amount of the vaccine or composition according to the invention to be administered can be determined by routine experiments, e.g. by using animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to a physiologically tolerable pH, such as about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels and the like. If the inventive composition or vaccine is to be administered perorally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs and storability, which are not critical for the purposes of the present invention, and can be made without difficulty by a person skilled in the art.

The inventive vaccine or composition can additionally contain one or more auxiliary substances in order to further increase the immunogenicity. A synergistic action of the mRNA contained in the inventive composition and of an auxiliary substance, which may be optionally be co-formulated (or separately formulated) with the inventive vaccine or composition as described above, is preferably achieved thereby. Depending on the various types of auxiliary substances, various mechanisms may play a role in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response produced by the immune-stimulating adjuvant according to the invention to be enhanced and/or influenced in a targeted manner. Particularly preferred auxiliary substances are cytokines, such as monokines, lymphokines, interleukins or chemokines, that-additional to induction of the adaptive immune response by the encoded at least one antigen-promote the innate immune response, such as IL-1, IL-2, IL-3, IL-4, IL-5, IL-6, IL-7, IL-8, I1-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, INF-alpha, IFN-beta, INF-gamma, GM-CSF, G-CSF, M-CSF, LT-beta or TNF-alpha, growth factors, such as hGH. Preferably, such immunogenicity increasing agents or compounds are provided separately (not co-formulated with the inventive vaccine or composition) and administered individually.

Further additives which may be included in the inventive vaccine or composition are emulsifiers, such as, for example, Tween; wetting agents, such as, for example, sodium lauryl sulfate; colouring agents; taste-imparting agents, pharmaceutical carriers; tablet-forming agents; stabilizers; antioxidants; preservatives.

The inventive vaccine or composition can also additionally contain any further compound, which is known to be immune-stimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

Another class of compounds, which may be added to an inventive vaccine or composition in this context, may be CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, that is to say the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

According to another aspect of the present invention, the present invention also provides a kit, in particular a kit of parts, comprising the mRNA compound comprising mRNA sequence as defined herein and at least one lipid according to formula (I), (II), (III) or (IV) as defined above. In a further embodiment the kit comprises a lipid nanoparticle as defined above or the (pharmaceutical) composition comprising a lipid nanoparticle as defined above, and/or the vaccine according to the invention, optionally a liquid vehicle for solubilising and optionally technical instructions with information on the administration and dosage of the mRNA comprising lipid nanoparticles, the composition and/or the vaccine. The technical instructions may contain information about administration and dosage of the mRNA comprising lipid nanoparticles, the composition and/or the vaccine. Such kits, preferably kits of parts, may be applied e.g. for any of the above mentioned applications or uses, preferably for the use of the lipid nanoparticle according to the invention (for the preparation of an inventive medicament, preferably a vaccine) for the treatment or prophylaxis of influenza virus infections or diseases or disorders related thereto. The kits may also be applied for the use of the lipid nanoparticle, the composition or the vaccine as defined herein (for the preparation of an inventive vaccine) for the treatment or prophylaxis of influenza virus infections or diseases or disorders related thereto, wherein the lipid nanoparticle, the composition and/or the vaccine may be capable of inducing or enhancing an immune response in a mammal as defined above. Such kits may further be applied for the use of the lipid nanoparticle, the composition or the vaccine as defined herein (for the preparation of an inventive vaccine) for modulating, preferably for eliciting, e.g. to induce or enhance, an immune response in a mammal as defined above, and preferably for supporting treatment or prophylaxis of influenza virus infections or diseases or disorders related thereto. Kits of parts, as a special form of kits, may contain one or more identical or different compositions and/or one or more identical or different vaccines as described herein in different parts of the kit. Kits of parts may also contain an (e.g. one) composition, an (e.g. one) vaccine and/or the mRNA comprising lipid nanoparticles according to the invention in different parts of the kit, e.g. each part of the kit containing an mRNA comprising lipid nanoparticles as defined herein, preferably encoding a distinct antigen. Preferably, the kit or the kit of parts contains as a part a vehicle for solubilising the mRNA according to the invention, the vehicle optionally being Ringer-lactate solution. Any of the above kits may be used in a treatment or prophylaxis as defined above.

In another embodiment of this aspect, the kit according to the present invention may additionally contain at least one adjuvant. In a further embodiment, the kit according to the present invention may additionally contain at least one further pharmaceutically active component, preferably a therapeutic compound suitable for treatment and/or prophylaxis of cancer or a related disorder. Moreover, in another embodiment, the kit may additionally contain parts and/or devices necessary or suitable for the administration of the composition or the vaccine according to the invention, including needles, applicators, patches, injection-devices.

In a further aspect the invention relates to the use of the mRNA comprising lipid nanoparticles or the pharmaceutical composition as a medicament. In an alternative embodiment the present invention relates to the use of the pharmaceutical composition or the mRNA comprising lipid in the manufacture of a medicament. In particular said medicament is for therapeutically or prophylactically raising an immune response of a subject in need thereof.

In a preferred embodiment the medicament is for prevention or treatment of cancer or tumour diseases, infectious diseases, allergies, or autoimmune diseases or disorders related thereto.

In particular the medicament is for the treatment of a subject, preferably a vertebrate. In a preferred embodiment the subject is a mammal, preferably selected from the group comprising goat, cattle, swine, dog, cat, donkey, monkey, ape, a rodent such as a mouse, hamster, rabbit and, particularly, human.

In a particular preferred embodiment the medicament is a vaccine, preferably a tumor, influenza or rabies vaccine. In a specific embodiment the medicament is a rabies vaccine used in rabies treatment.

The medicament might be administered in any suitable way. Preferably the medicament is for parenteral administration, in particular injection.

The invention further relates to a method for eliciting or enhancing an immune response in a subject in need thereof, comprising administering to the subject a lipid nanoparticle as defined above or a pharmaceutical composition as defined above.

In a further aspect the invention relates to a method for prevention or treatment of cancer or tumour diseases, infectious diseases, allergies, or autoimmune diseases or disorders related thereto in a subject in need thereof, comprising administering to the subject a lipid nanoparticle as defined above or a pharmaceutical composition as defined above.

According to one aspect of the present invention, the mRNA comprising lipid nanoparticles, the (pharmaceutical) composition or the vaccine may be used according to the invention (for the preparation of a medicament) for the treatment or prophylaxis of cancer or tumour diseases, infectious diseases, allergies, or autoimmune diseases or disorders related thereto. In this context particularly preferred is the treatment or prophylaxis of Influenza virus or Rabies virus infections.

Furthermore, also included in the present inventions are methods of treating or preventing cancer or tumour diseases, infectious diseases, allergies, or autoimmune diseases or disorders related thereto, preferably as defined herein, by administering to a subject in need thereof a pharmaceutically effective amount of the mRNA comprising lipid nanoparticles, the (pharmaceutical) composition or the vaccine according to the invention. Such a method typically comprises an optional first step of preparing the mRNA comprising lipid nanoparticles, the composition or the vaccine of the present invention, and a second step, comprising administering (a pharmaceutically effective amount of) said composition or vaccine to a patient/subject in need thereof. A subject in need thereof will typically be a mammal. In the context of the present invention, the mammal is preferably selected from the group comprising, without being limited thereto, e.g. goat, cattle, swine, dog, cat, donkey, monkey, ape, a rodent such as a mouse, hamster, rabbit and, particularly, human. In some embodiments of the invention, the subject is a bird, preferably a chicken.

In this context, preferably included in the present invention are methods of treating or preventing influenza virus or Rabies virus infections or disorders related thereto.

The invention also relates to the use of the mRNA comprising lipid nanoparticles, the composition or the vaccine according to the invention, preferably for eliciting an immune response in a mammal, preferably for the treatment or prophylaxis of cancer or tumour diseases, infectious diseases, allergies, or autoimmune diseases or disorders related thereto, preferably of influenza virus or Rabies virus infections or a related condition as defined herein.

The present invention furthermore comprises the use of the mRNA comprising lipid nanoparticles, the (pharmaceutical) composition or the vaccine according to the invention as defined herein for modulating, preferably for inducing or enhancing, an immune response in a mammal as defined herein, more preferably for preventing and/or treating influenza virus infections, or of diseases or disorders related thereto. In this context, support of the treatment or prophylaxis of influenza virus infections may be any combination of a conventional influenza therapy method such as therapy with antivirals such as neuraminidase inhibitors (e.g. oseltamivir and zanamivir) and M2 protein inhibitors (e.g. adamantane derivatives), and a therapy using the RNA or the pharmaceutical composition as defined herein. Support of the treatment or prophylaxis of influenza virus infections may be also envisaged in any of the other embodiments defined herein. Accordingly, any use of the mRNA comprising lipid nanoparticles, the (pharmaceutical) composition or the vaccine according to the invention in co-therapy with any other approach, preferably one or more of the above therapeutic approaches, in particular in combination with antivirals is within the scope of the present invention.

For administration, preferably any of the administration routes may be used as defined herein. In particular, an administration route is used, which is suitable for treating or preventing an influenza virus infection as defined herein or diseases or disorders related thereto, by inducing or enhancing an adaptive immune response on the basis of an antigen encoded by the mRNA comprising lipid nanoparticles according to the invention. Administration of the composition and/or the vaccine according to the invention may then occur prior, concurrent and/or subsequent to administering another composition and/or vaccine as defined herein, which may—in addition—contain another mRNA comprising lipid nanoparticle or combination of mRNA comprising lipid nanoparticles encoding a different antigen or combination of antigens, wherein each antigen encoded by the mRNA sequence according to the invention is preferably suitable for the treatment or prophylaxis of influenza virus infections and diseases or disorders related thereto. In this context, a treatment as defined herein may also comprise the modulation of a disease associated to influenza virus infection and of diseases or disorders related thereto.

According to a preferred embodiment of this aspect of the invention, the (pharmaceutical) composition or the vaccine according to the invention is administered by injection. Any suitable injection technique known in the art may be employed. Preferably, the inventive composition is administered by injection, preferably by needle-less injection, for example by jet-injection.

In one embodiment, the inventive composition comprises at least one, two, three, four, five, six, seven, eight, nine, ten, eleven, twelve or more mRNAs as defined herein, each of which is preferably injected separately, preferably by needle-less injection. Alternatively, the inventive composition comprises at least one, two, three, four, five, six, seven, eight, nine, ten, eleven, twelve or more mRNAs, wherein the at least one, two, three, four, five, six, seven, eight, nine, ten, eleven, twelve or more mRNAs are administered, preferably by injection as defined herein, as a mixture.

In a further aspect the invention relates to a method of immunization of a subject against an antigen or a combination of antigens.

The immunization protocol for the immunization of a subject against an antigen or a combination of at least two, three, four, five, six, seven, eight, nine, ten, eleven, twelve or more antigens as defined herein typically comprises a series of single doses or dosages of the (pharmaceutical) composition or the vaccine according to the invention. A single dosage, as used herein, refers to the initial/first dose, a second dose or any further doses, respectively, which are preferably administered in order to “boost” the immune reaction. In this context, each single dosage preferably comprises the administration of the same antigen or the same combination of antigens as defined herein, wherein the interval between the administration of two single dosages can vary from at least one day, preferably 2, 3, 4, 5, 6 or 7 days, to at least one week, preferably 2, 3, 4, 5, 6, 7 or 8 weeks. The intervals between single dosages may be constant or vary over the course of the immunization protocol, e.g. the intervals may be shorter in the beginning and longer towards the end of the protocol. Depending on the total number of single dosages and the interval between single dosages, the immunization protocol may extend over a period of time, which preferably lasts at least one week, more preferably several weeks (e.g. 2, 3, 4, 5, 6, 7, 8, 9, 10, 11 or 12 weeks), even more preferably several months (e.g. 3, 4, 5, 6, 7, 8, 9, 10, 11, 12, 18 or 24 months). Each single dosage preferably encompasses the administration of an antigen, preferably of a combination of at least two, three, four, five, six, seven, eight, nine, ten, eleven, twelve or more antigens as defined herein and may therefore involve at least one, preferably 1, 2, 3, 4, 5, 6, 7, 8, 9, 10, 11 or 12 injections. In some cases, the composition or the vaccine according to the invention is administered as a single dosage typically in one injection. In the case, where the vaccine according to the invention comprises separate mRNA formulations encoding distinct antigens as defined herein, the minimum number of injections carried out during the administration of a single dosage corresponds to the number of separate components of the vaccine. In certain embodiments, the administration of a single dosage may encompass more than one injection for each component of the vaccine (e.g. a specific mRNA formulation comprising an mRNA encoding, for instance, one antigenic peptide or protein as defined herein). For example, parts of the total volume of an individual component of the vaccine may be injected into different body parts, thus involving more than one injection. In a more specific example, a single dosage of a vaccine comprising four separate mRNA formulations, each of which is administered in two different body parts, comprises eight injections. Typically, a single dosage comprises all injections required to administer all components of the vaccine, wherein a single component may be involved more than one injection as outlined above. In the case, where the administration of a single dosage of the vaccine according to the invention encompasses more than one injection, the injection are carried out essentially simultaneously or concurrently, i.e. typically in a time-staggered fashion within the time-frame that is required for the practitioner to carry out the single injection steps, one after the other. The administration of a single dosage therefore preferably extends over a time period of several minutes, e.g. 2, 3, 4, 5, 10, 15, 30 or 60 minutes.

Administration of the mRNA comprising lipid nanoparticles as defined herein, the (pharmaceutical) composition or the vaccine according to the invention may be carried out in a time staggered treatment. A time staggered treatment may be e.g. administration of the mRNA comprising lipid nanoparticles, the composition or the vaccine prior, concurrent and/or subsequent to a conventional therapy of influenza virus infections or diseases or disorders related thereto, e.g. by administration of the mRNA comprising lipid nanoparticles, the composition or the vaccine prior, concurrent and/or subsequent to a therapy or an administration of a therapeutic suitable for the treatment or prophylaxis of influenza virus infections or diseases or disorders related thereto. Such time staggered treatment may be carried out using e.g. a kit, preferably a kit of parts as defined herein.

Time staggered treatment may additionally or alternatively also comprise an administration of the mRNA comprising lipid nanoparticles as defined herein, the (pharmaceutical) composition or the vaccine according to the invention in a form, wherein the mRNA encoding an antigenic peptide or protein as defined herein or a fragment or variant thereof, preferably forming part of the composition or the vaccine, is administered parallel, prior or subsequent to another mRNA comprising lipid nanoparticles as defined above, preferably forming part of the same inventive composition or vaccine. Preferably, the administration (of all mRNA comprising lipid nanoparticles) occurs within an hour, more preferably within 30 minutes, even more preferably within 15, 10, 5, 4, 3, or 2 minutes or even within 1 minute. Such time staggered treatment may be carried out using e.g. a kit, preferably a kit of parts as defined herein.

In a preferred embodiment, the pharmaceutical composition or the vaccine of the present invention is administered repeatedly, wherein each administration preferably comprises individual administration of the at least one mRNA comprising lipid nanoparticles of the inventive composition or vaccine. At each time point of administration, the at least one mRNA may be administered more than once (e.g. 2 or 3 times). In a particularly preferred embodiment of the invention, at least two, three, four, five, six or more mRNA sequences (each encoding a distinct one of the antigens as defined herein) encapsulated or associated with mRNA comprising lipid nanoparticles as defined above, wherein the mRNA sequences are part of mRNA compounds of the same or different lipid nanoparticles, are administered at each time point, wherein each mRNA is administered twice by injection, distributed over the four limbs.

Additional Applications of the Ionizable Lipids of the Invention

Gene Editing

The invention also encompasses composition and methods for delivering a nucleic acid, preferably RNA, more preferably single guide RNA (sgRNA) and engineered CRISPR/CRISPR-associated (Cas) 9-based compositions for gene expression alterations, genomic manipulations, and gene involvement in genetic disorders. It has been found useful to correct or reduce the effects of mutations. In certain embodiments, the CRISPR/Cas9-based system contains the Cas9 protein and at least one guide RNA (the guide RNA provides the DNA targeting specificity of the system) and is delivered using an LNP comprising one or more Ionizable Lipids of the Invention.

In particular, the present disclosure describes Cas9 fusion proteins that integrate the CRISPR/Cas9-based DNA sequence targeting function with additional activity, thus allowing for altered gene expression and/or epigenetic context. This system can also be used to correct or mitigate the effects of genomic manipulation and genetic mutations.

The present disclosure also provides certain compositions and methods for delivering a wide variety of gRNAs that target the CRISPR/CRISPR-associated (Cas) 9-based system and one or more endogenous genes comprising an LNP comprising one or more Ionizable Lipids of the Invention. Cotransfection of a wide variety of sgRNAs targeting a single promoter allows synergistic activation, however, cotransfection of a wide variety of plasmids may vary in each cell due to copy number differences resulting in an expression level. Furthermore, gene activation following transfection is transient due to dilution of plasmid DNA over time. Furthermore, many cell types are not readily transfected and transient gene expression may not be sufficient to elicit a therapeutic effect.

This LNP compositions comprising one or more Ionizable Lipids of the Invention is capable of controlling both the magnitude and timing of CRISPR/Cas9-dependent gene regulation. Furthermore, the LNP compositions comprising one or more Ionizable Lipids of the Invention provides strong and persistent gene expression levels that facilitate therapeutic use of the CRISPR/Cas9 system in primary cells. Finally, the LNP compositions comprising one or more Ionizable Lipids of the Invention can be used to simultaneously edit a wide variety of genes (eg, for the simultaneous knockout of several oncogenes).

The present invention is further directed to a method of correcting a mutant gene in a cell. The method comprises the step of administering to a cell containing the DNA targeting system, the isolated polynucleotide and an LNP comprising an Ionizable Lipid of the Invention. The correction of the mutated gene can include homology-directed repair. The method can further include the step of administering the donor DNA to the cells. The mutated gene can include a premature stop codon and a frameshift mutation that results in a truncated gene product. Modification of the mutated gene can include nuclease-mediated heterologous end joining. Modification of the mutated gene can include deletion of the premature stop codon, disruption of the splice acceptor site, deletion of one or more exons, or disruption of the splice donor sequence. Deletion of one or more exons can result in correction of the reading frame.

In certain embodiments, the present invention is directed to a method of treating a subject carrying a mutant dystrophin gene in need thereof. The method comprises the step of administering to the subject the DNA targeting system, the isolated polynucleotide or a vector. In certain embodiments, the subject animal can be afflicted with Duchenne muscular dystrophy.

The present invention is directed to a method of correcting a mutant dystrophin gene in a cell. The method comprises the step of administering the DNA targeting system, the isolated polynucleotide, the vector, or the cell to a cell containing a mutant dystrophin gene. The mutant dystrophin gene can include an immature stop codon, a reading frame disrupted by a genetic defect, an abnormal splice acceptor site, or an abnormal splice donor site, where the target region is the immature stop codon, the disruption. Located upstream or downstream of the defined reading frame, aberrant splice acceptor site or aberrant splice donor site. Modification of the mutant dystrophin gene can include homology-directed repair. The method can further include the step of administering donor DNA to the cells. The mutated dystrophin gene can include a premature stop codon and a frameshift mutation that results in a truncated gene product. Modifications of the mutant dystrophin gene can include nuclease-mediated heterologous end joining. Modifications of the mutant dystrophin gene can include deletion of premature stop codons, modification of disrupted reading frames, or modulation of splicing by disruption of splice acceptor sites or disruption of splice donor sequences. Modifications of the mutant dystrophin gene can include deletion of exons 45-55 or exon 51.

The present invention is directed to a kit comprising the fusion protein, the DNA targeting system, the isolated polynucleotide, the vector or the cell.

The present invention is directed to a method of modulating mammalian gene expression in a cell. The method comprises contacting the cell with a polynucleotide encoding a DNA targeting system. A DNA targeting system comprises a fusion protein and at least one guide RNA (gRNA) included in a LNP comprising a Ionizable Lipid of the Invention.

The DNA targeting system can include 1 to 10 different gRNAs. Different gRNAs can bind to different regions within the target gene. The target region can be separated by at least one nucleotide. Target regions can be separated by about 15 to about 700 base pairs. Each of the different gRNAs can bind at least one different target gene. The different target genes can be located on the same chromosome. Different target genes can be located on different chromosomes. The at least one target region may be in a non-open chromatin region, an open chromatin region, a target gene promoter region, a target gene enhancer region, a target gene transcription region, or a region upstream of a transcription start site of a target gene. The at least one target region can be located from about 1 to about 1000 base pairs upstream of the transcription start site of the target gene. The at least one target region can be located from about 1 to about 600 base pairs upstream of the transcription start site of the target gene. Gene expression can be induced. The DNA targeting system consists of 2 different gRNAs, 3 different gRNAs, 4 different gRNAs, 5 different gRNAs, 6 different gRNAs, 7 different gRNAs, 8 different gRNAs, 9 different gRNAs, or 10 different gRNAs. Can be included. The at least one guide RNA can target the promoter region of a gene selected from the group consisting of ASCL1, BRN2, MYT1L, NANOG, VEGFA, TERT, IL1B, IL1R2, IL1RN, HBG1, HBG2 and MYOD1. At least one target region can be within an intron or exon of the target gene.

The present invention is directed to compositions that induce mammalian gene expression in cells. The composition comprises the fusion protein and at least one guide RNA (gRNA) included in a LNP comprising a Ionizable Lipid of the Invention.

The present invention is directed to compositions that induce mammalian gene expression in cells. The composition comprises an isolated polynucleotide sequence encoding the fusion protein and at least one guide RNA (gRNA). The at least one guide RNA can target the promoter region of a gene selected from the group consisting of ASCL1, BRN2, MYT1L, NANOG, VEGFA, TERT, IL1B, IL1R2, IL1RN, HBG1, HBG2 and MYOD1.

The present invention is directed to cells containing the above compositions that induce mammalian gene expression in the cells.

The present invention is directed to the composition for inducing mammalian gene expression in cells, or a kit containing the cells containing the composition for inducing mammalian gene expression in cells.

The present invention is directed to a kit for inducing mammalian gene expression in cells. The kit comprises the composition for inducing mammalian gene expression in a cell or the cell containing the composition for inducing mammalian gene expression in a cell.

Protein Replacement Therapy

In some embodiments, the methods, composition and kits as disclosed herein can be tailored for use in methods for protein replacement therapy in vivo. In some examples, a synthetic modified RNA encoding a protein of interest can be delivered to a tissue and/or organ for in vivo protein expression in a method for treatment of a variety of different diseases where protein expression is desirable. In some examples, a disease can be a loss-of-function disease as disclosed herein, e.g., without limitation muscular dystrophy, cystic fibrosis and other diseases where the level of protein expression of a particular protein is inadequate and/or gene expression results in a non-functional protein.

Additionally, a method for in vivo delivery of synthetic modified RNA using a LNP comprising an Ionizable Lipid of the Invention for in vivo protein expression as disclosed herein can be used to create an animal model platform, which can be used to study whole-organ and systemic pathophysiology. In some examples, the methods as disclosed herein provide an in vivo system, using both small- and large-animal models, such as primates and porcine models, for testing and/or the development of therapeutics for clinical use in human patients.

In some examples, the methods and compositions and kits as disclosed herein for in vivo protein expression using synthetic modified RNAs included in a LNP comprising an Ionizable Lipid of the Invention can be for the development and treatment of a disease or disorder. In some examples, a disease or disorder is a genetic and/or acquired disorder that is the result of insufficient expression of a particular protein or expression of a malfunctioning version of a protein. In some examples, the disease or disorder is an acquired disorder, for example, cardiovascular disease or disorder as disclosed herein.

In another example, the methods and compositions and kits as disclosed herein for in vivo protein expression using synthetic modified RNAs included in a LNP comprising an Ionizable Lipid of the Invention can be used in regenerative medicine strategies as well. For example, in some examples, a composition comprising at least one synthetic modified RNA encoding a protein of interest can also comprise a population of cells of interest. Stated another way, in some examples, the present disclosure provides methods for regenerative cell therapy comprising administering to the subject a combination of at least one synthetic modified RNAs with a population of cells of interest. In some examples, a cell population is a stem cell population, and in some examples a stem cell population is a population of cardiac precursor cells or cardiac progenitor cells. In some examples a stem cell is an Isl1+ stem cell population, or is a vascular progenitor cell population. Such cell populations are well known in the art, and include, but are not limited to the cell populations disclosed in International Patent Applications, WO/2008/054819, WO2010/144678, WO2010/042856, and U.S. Patent Applications 2010/0166714, US2011/0033430, US2010/021713 and US2011/0003327, each of which is incorporated herein by reference.

Cell Programming and Cell Therapy

In another embodiment the invention encompasses, he invention disclosed herein relates to an allogeneic cell therapy for the stimulation of the host immune system in humans without GVH toxicity, and whereby said allogeneic cells are subsequently rejected by the host immune system.

The invention disclosed herein also relates to a product described above whereby the allogeneic cells are chosen without regard for HLA-match with the recipient, or to allow for the maximum mismatch of HLA haplotype with the intended patient population, thereby ensuring the maximum allogeneic potential and subsequent host immune response to the product.

The invention disclosed herein also relates to a product described above whereby the allogeneic cells are capable of stimulating an effective host immune response against a tumor when infused into patients that have not received a prior allogeneic BMT.

The invention disclosed herein also relates to a product described above whereby the allogeneic cells are capable of stimulating an effective host immune response against a tumor when infused into a patient that has not been subjected to immunosuppressive conditioning regimens.

The invention disclosed herein also relates to a product described above whereby the allogeneic cell therapy stimulates an immune response in patients by stimulating the production of inflammatory "Type 1" monokines and lymphokines in the host.

The invention disclosed herein also relates to a product described above whereby the allogeneic cell therapy stimulates an immune response in patients by activating components of host innate and/or Th1 adaptive immunity.

The invention disclosed herein also relates to a product described above whereby the allogeneic cell therapy stimulates the production of cytokines which enhance the immunogenicity of tumors.

The invention disclosed herein also relates to a product described above whereby the allogeneic cells directly kill tumors so as to cause the tumor associated antigens to be available for stimulating host Type 1 adaptive immunity.

The invention disclosed herein also relates to a method of producing a product as described above, whereby the allogeneic T-cells contained in the product are in a state of enhanced activation.

The invention disclosed herein also relates to a method for stimulating a host immune system by collecting the mononuclear cells from an unrelated donor, activating T-cells within the mononuclear cell population, and administering the activated T-cells to a host having a host immune system whereby the activated T-cells are rejected by the host immune system while stimulating the host immune system to mediate an effective immune response against a resident disease. The host may have a resident disease such as hematological malignancy, a solid tumor, a solid tumor that has metastasized or a viral infection. The donor is selected without regard to histocompatibility to the host, and maximum histocompatibility mismatch is preferred. The host also preferably should not have had a prior bone marrow transplant and should not preferably have received any immunosuppressive chemotherapy and/or radiation conditioning regimens designed to allow engraftment of the allogeneic donor cell infusions.

The method further includes that the T-cells are preferably CD4+ T-cells and that a majority of the CD4+ T-cells differentiate after ex-vivo activation from CD45RA+, CD62Lhi naïve cells into CD45RO+, CD62Llo memory cells, and wherein such cells produce Type 1 cytokines such as IL-2, IFN-gamma, TNF-alpha and do not produce Type 2 cytokines such as IL-4, IL-10 and TGF-beta.

The invention disclosed herein also includes such CD4+ T-cells which after ex-vivo activation express CD40L and/or TRAIL on the cell surface. Preferably, the T-cells are activated by cross-linking of anti-CD3 and anti-CD28 mAbs applied to the cell surface of the T-cells. Preferably anti-CD3 and anti-CD28 mAbs applied to the surface of said T-cells are cross-linked by association with biodegradable microspheres coated with an agent reactive against said mAbs.

The invention disclosed herein also includes wherein greater than 90% of the T-cells are in a state of activation just prior to and at the time of contacting the host immune system, and in the preferred embodiment greater than 95% of the T-cells are activated at the time of administration to the host and just prior to contacting the host.

The method also includes wherein T-cells are continuously exposed to an activating stimulus for at least six days prior to infusion in the host. T-cells are preferably activated while being maintained at cell densities of at least 107 cells/ml to maximize cell to cell contact. Such cell to cell contact serves to enhance the state of activation of the allogeneic T-cells.

In another embodiment, the method includes wherein the T-cells are administered with anti-CD3 and anti-CD28 mAbs applied to the surface of the allogeneic T-cells and wherein the mAbs are cross-linked by association with and inclusion of biodegradable microspheres coated with an agent reactive against the mAbs.

The method also includes wherein T-cell administration stimulates production of Type 1 cytokines, and such cytokines include at least one of the following: IL-1, IL-2, IL-12, IL-15, IFN-gamma, IFN-alpha, IFN-beta, TNF-alpha, and TNF-beta. Such cytokines stimulate immunity including host innate immune function. The method also includes wherein the activated T-cell administration activates host dendritic and/or macrophage cells.

The invention also includes wherein the activated allogeneic T-cell administration and subsequent rejection of the activated T-cells stimulates an immune response against a host resident disease.

The invention also includes a method wherein the ex-vivo activated allogeneic T-cells are cryopreserved prior to formulation and administration to the host.

The invention also includes a composition of allogeneic T-cells labeled with anti-CD3 and anti-CD28 mAbs cross-linked with biodegradable microspheres coated with an agent reactive against said mAbs. The labeled allogeneic T-cells and associated biodegradable microspheres are suspended in a media suitable for intravenous infusion. Such T-cells and associated biodegradable microspheres are suspended at a cell density of 107 cells/ml or greater, and preferably in a flexible container or in a syringe. The T-cells labeled with anti-CD3 and anti-CD28 may also be cryopreserved prior to formulation and administration.

The present invention also includes an allogeneic cell material that elicits a host vs. tumor (HVT) and host vs. graft (HVG) response when contacted with a tumor-bearing host immune system without eliciting a toxic graft vs. host (GVH) response. The allogeneic cell material contains ex-vivo activated T-cells and wherein said activated T-cells are preferably CD4+ T-cells.

The present invention also includes an allogeneic cell material that causes apoptosis of tumors when administered to a tumor-bearing host. The allogeneic cell material contains activated allogeneic T-cells, and such T-cells are preferably CD4+ cells. Such CD4+ cells should express FasL and/or TRAIL on the cell surface, preferably at high density. Such activated T-cells preferably differentiate into memory cells expressing CD45RO and CD63Llo after ex-vivo activation. Such allogeneic T-cells should express one or more of the following cytokines: IL-2, IL-15, IFN-gamma, and TNF-alpha and express surface FasL and/or TRAIL upon administration to the host.

The present invention also includes a composition comprising a treatment effective amount of a population of allogeneic cells, of which at least a portion are T-cells, and whereby said T-cells are labeled with an activating effective amount of one or more monoclonal antibodies, or portions thereof, and a cross-linking effective amount of an agent reactive against the monoclonal antibodies. T-cells of such composition are preferably labeled with anti-CD3 and anti-CD28 mAbs. The agent reactive against the mAbs is preferably coated on biodegradable microspheres. The allogeneic T-cells and associated biodegradable microspheres are suspended in a media suitable for intravenous infusion. Such labeled T-cells and associated cross-linking biodegradable microspheres are suspended at a cell density of 107 cells/ml or greater in a flexible container or in a syringe. The composition may be cryopreserved prior to infusion.

In preferred embodiments, the allogeneic cells used in the present invention are purified T-cells which have been activated ex-vivo, preferably CD4+ T-cells, more preferably CD4+ T-cells that have differentiated into effector or memory cells and produce high levels of Type 1 cytokines, such as IL-2, IL-15, IFN-gamma, TNF-alpha and also express, preferably at high density, effector molecules such as CD40L, TRAIL and FasL on the cell surface.

In another preferred embodiment, the allogeneic T-cells for infusion are processed ex-vivo by a method which maintains the cells at high cell density (107 cells/ml or greater) in continuous contact with T-cell activating agents.

In another preferred embodiment, the allogeneic T-cells for infusion are formulated in media suitable for infusion containing activating agents as a means to maintain the activation state of the T-cells from harvest through infusion.

In another preferred embodiment, greater than 90%, or preferably greater than 95% of the infused allogeneic T-cells continue in a state of enhanced activation at the time of infusion into the patient.

VI. EXAMPLES OF THE INVENTION

Example 1

Novel Ionizable Lipids have High Delivery Efficiency at 200 ng/Well Dose In Vitro (Study TRANS-14)

Summary: LNPs were formulated using total lipid concentration of 50 mM comprised of ionizable lipids/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively) and serial dilutions to get 27.74 mM. Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach a concentration of 1 mg/ml. FLuc mRNA stock was diluted in serial dilutions from a higher concentration solution to lower concentrations to reach 0.56 mg/ml in 25 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 µl Lipid Mix and 32 µl mRNA solution were mixed on Setting 3 and ejected into 48 µl 1×DPBS pH 7.4. The formed LNPS were then diluted into an additional 96 µl 1×DPBS pH 7.4. LNPs were then dialyzed against 1×DPBS pH 7.4 for 6×1 hr. LNPs were then diluted so that 32 ul contained 200 ng and 12K HEK293 cells were transfected with the same 50-200 ng dose.

Figure 7:
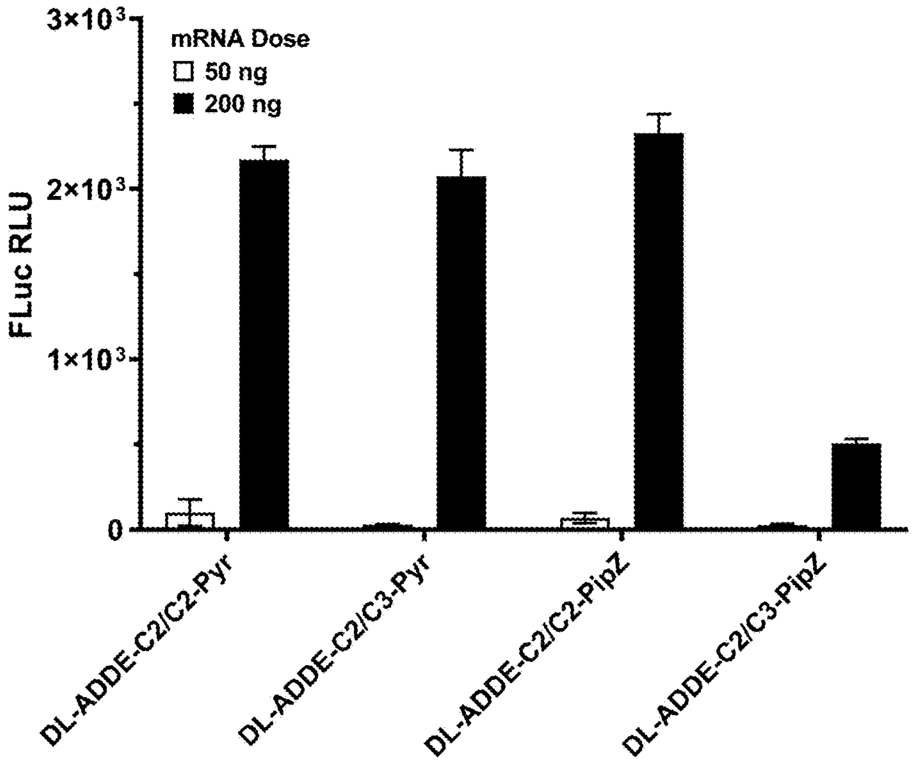
FIG. 7 illustrates a graph of Firefly Luciferase Assay for mRNA Delivery Efficiency as exemplified in Example 1A.

A: Firefly Luciferase Assay for mRNA Delivery Efficiency. After 24 hours of transfection, transfected cells were conditioned to room temperature for 30 minutes prior to the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The results are illustrated in FIG. 7.

Figure 8:
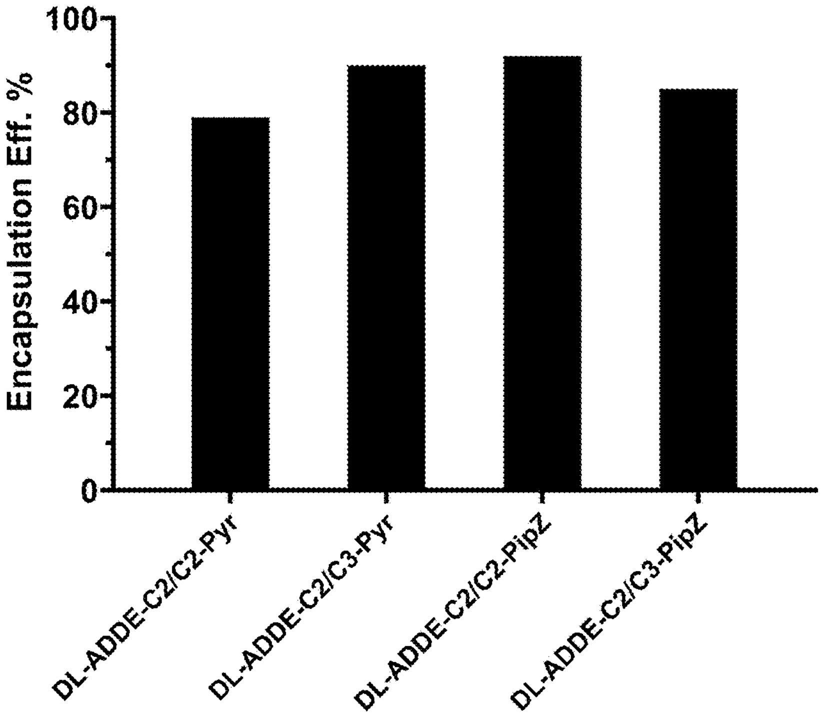
FIG. 8 illustrates a graph of Ribogreen Assay for mRNA Encapsulation Efficiency as exemplified in Example 1B.

B: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 8.

Figure 9:
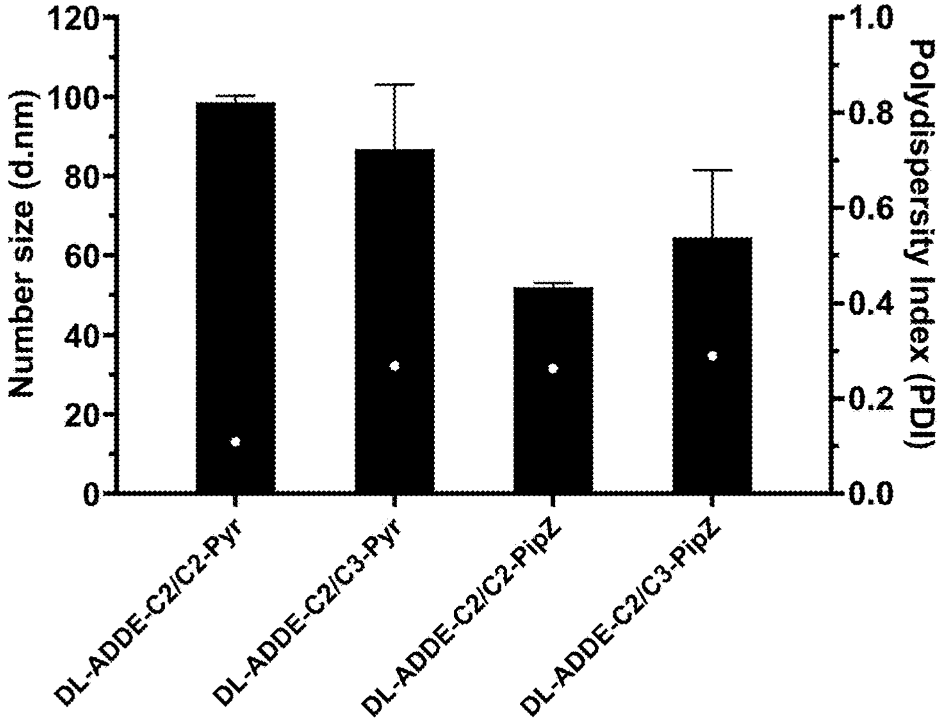
FIG. 9 illustrates a graph of Dynamic Light Scattering for LNP Size (white dots are PDI right y axis) as exemplified in Example 1C.

C: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 9.

Figure 10:
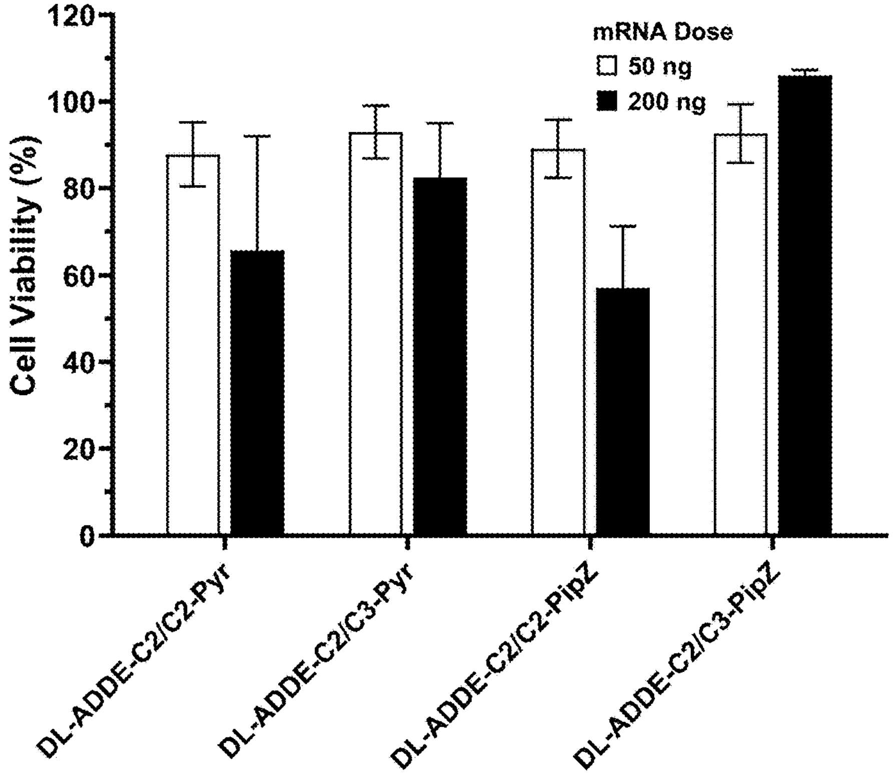
FIG. 10 illustrates a graph of Toxicity Assay based on Presto Blue HS viability reagent as exemplified in Example 1D.

D: Toxicity Assay based on Presto Blue HS viability reagent. After 24 hours of transfection, transfected cells are incubated with pre-warmed Presto Blue HS reagent (10% v/v) for 15 minutes at 37° C. Microplates were immediately introduced into the Cytation 5 Cell Imaging Multi-Mode Reader (Biotek) to read Fluorescence (Ex540/Em590). The results are illustrated in FIG. 10.

Example 2

Exemplary Ionizable Lipids have High Delivery Efficiency at 200 ng/Well Dose In Vitro (Study TRANS-16)

Summary: LNPs were formulated using total lipid concentration of 50 mM comprised of ionizable lipids/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively) and serial dilutions to get 27.74 mM. Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 1 mg/mL. FLuc mRNA stock was diluted in serial dilutions from a higher concentration solution to lower concentrations to reach 0.56 mg/ml in 25 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 µl Lipid Mix and 32 µl mRNA solution were mixed on Setting 3 and ejected into 48 µl 1×DPBS pH 7.4. The formed LNPS were then diluted into an additional 96 µl 1×DPBS pH 7.4. LNPs were then dialyzed against 1×DPBS pH 7.4 for 6×1 hr. LNPs were then diluted so that 32 ul contained 200 ng and 12K HEK293 cells were transfected with the same 50-200 ng dose.

Figure 11:
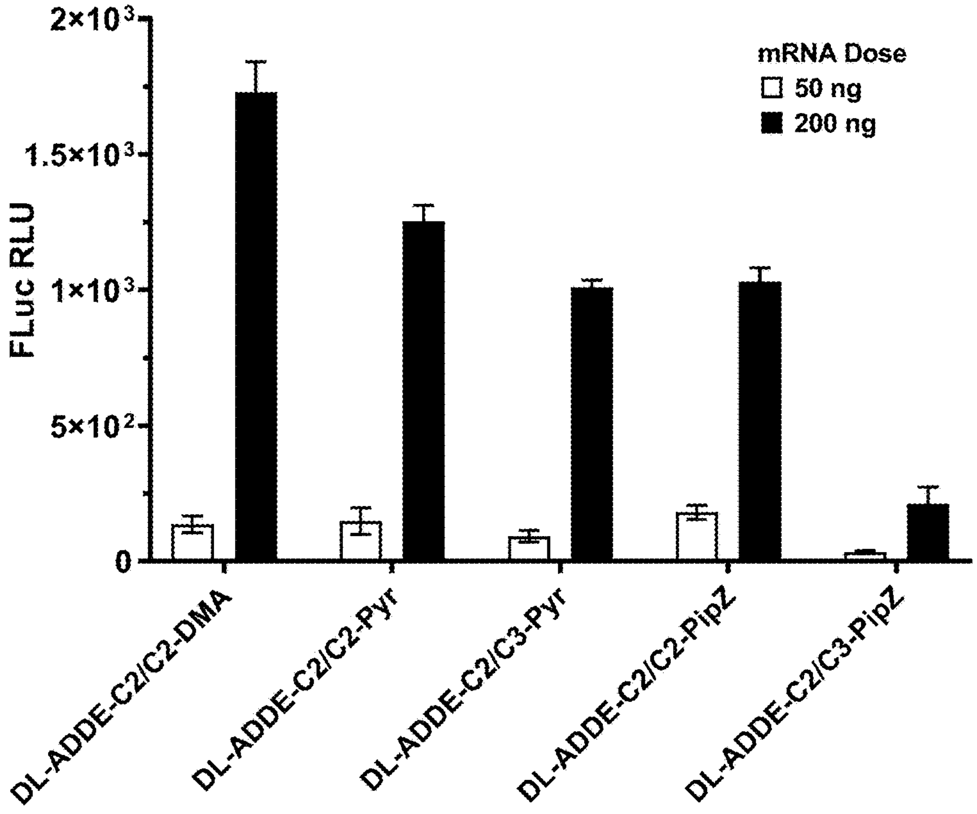
FIG. 11 illustrates a graph of Firefly Luciferase Assay for mRNA Delivery Efficiency as exemplified in Example 2A.

A: Firefly Luciferase Assay for mRNA Delivery Efficiency. After 24 hours of transfection, transfected cells were conditioned to room temperature for 30 minutes prior to the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The results are illustrated in FIG. 11.

Figure 12:
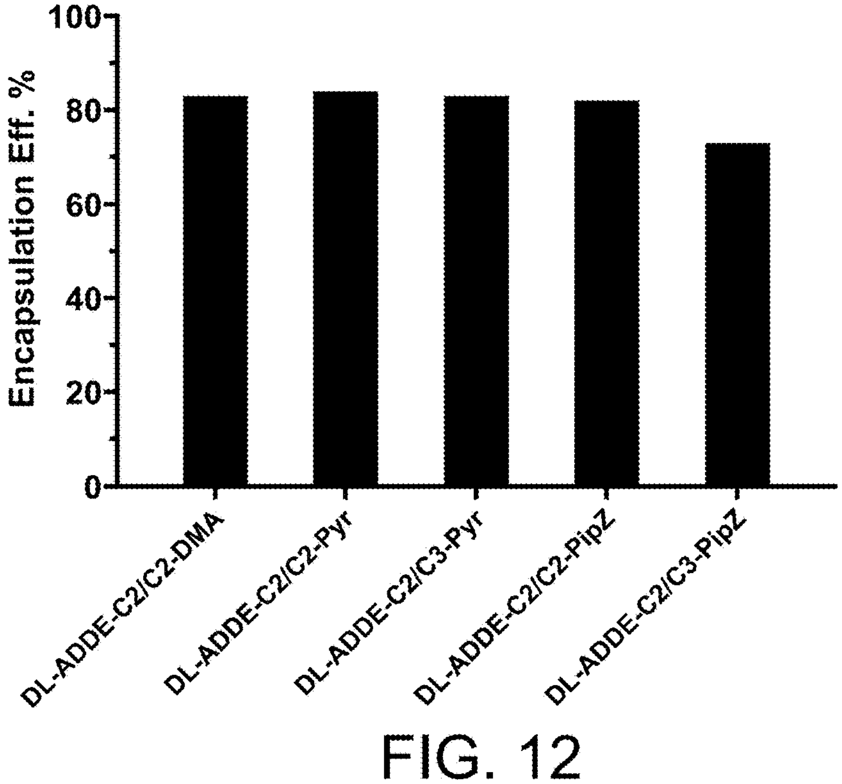
FIG. 12 illustrates a graph of Ribogreen Assay for mRNA Encapsulation Efficiency as exemplified in Example 2B.

B: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 12.

Figure 13:
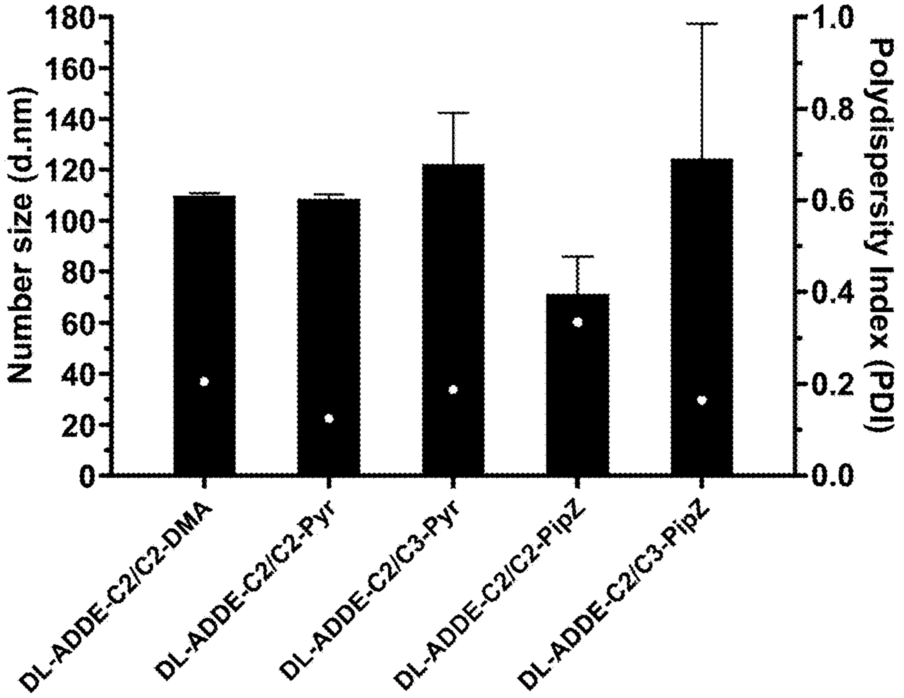
FIG. 13 illustrates a graph of Dynamic Light Scattering for LNP Size (white dots are PDI right y axis) as exemplified in Example 2C.

C: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 13.

Example 3

Exemplary Ionizable Lipids have High Delivery Efficiency at 200 ng/Well Dose In Vitro (Study TRANS-18)

Summary: LNPs were formulated using total lipid concentration of 50 mM comprised of ionizable lipids/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively). Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 3.6 mg/ml. FLuc mRNA stock was diluted in serial dilutions from a higher concentration solution to lower concentrations to reach 1 mg/ml in 25 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 6×1 hr. LNPs were then diluted so that 32 ul contained 200 ng and 12K HEK293 cells were transfected with the same 200 ng dose.

Figure 14:
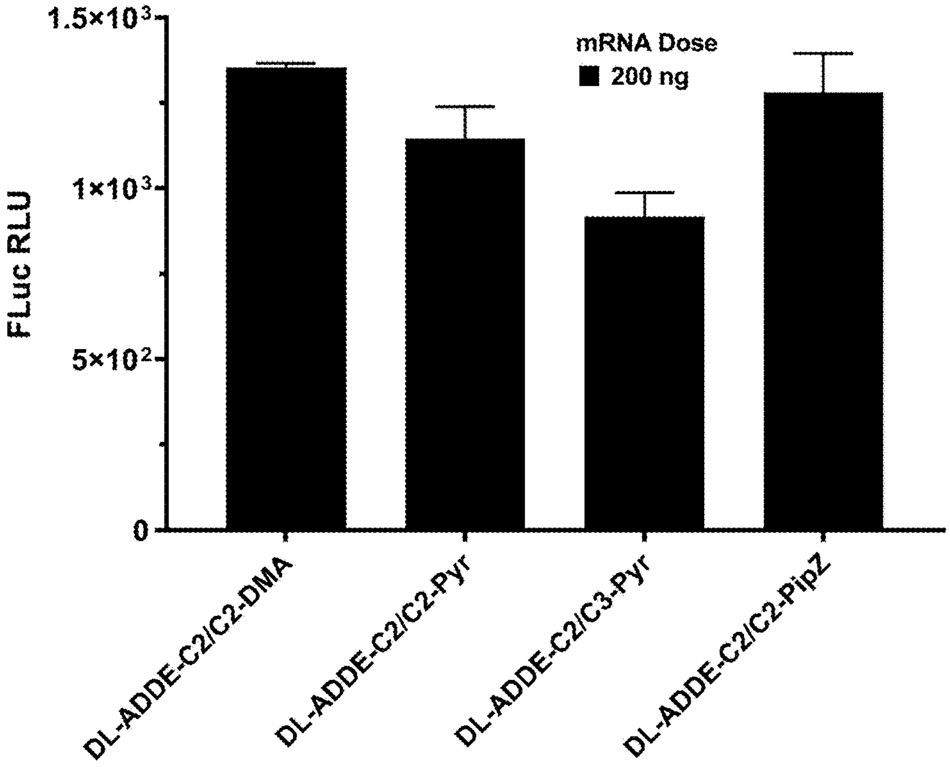
FIG. 14 illustrates a graph of Firefly Luciferase Assay for mRNA Delivery Efficiency as exemplified in Example 3A.

A: Firefly Luciferase Assay for mRNA Delivery Efficiency. After 24 hours of transfection, transfected cells were conditioned to room temperature for 30 minutes prior to the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of $10^7$ RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The results are illustrated in FIG. 14.

Figure 15:
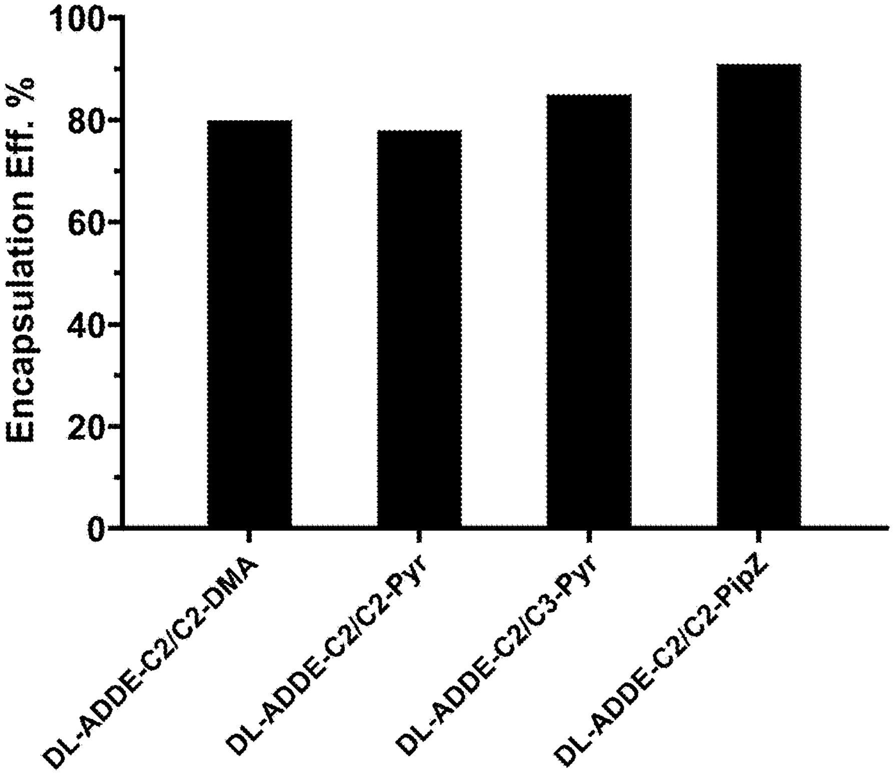
FIG. 15 illustrates a graph of Ribogreen Assay for mRNA Encapsulation Efficiency as exemplified in Example 3B.

B: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 15.

Figure 16:
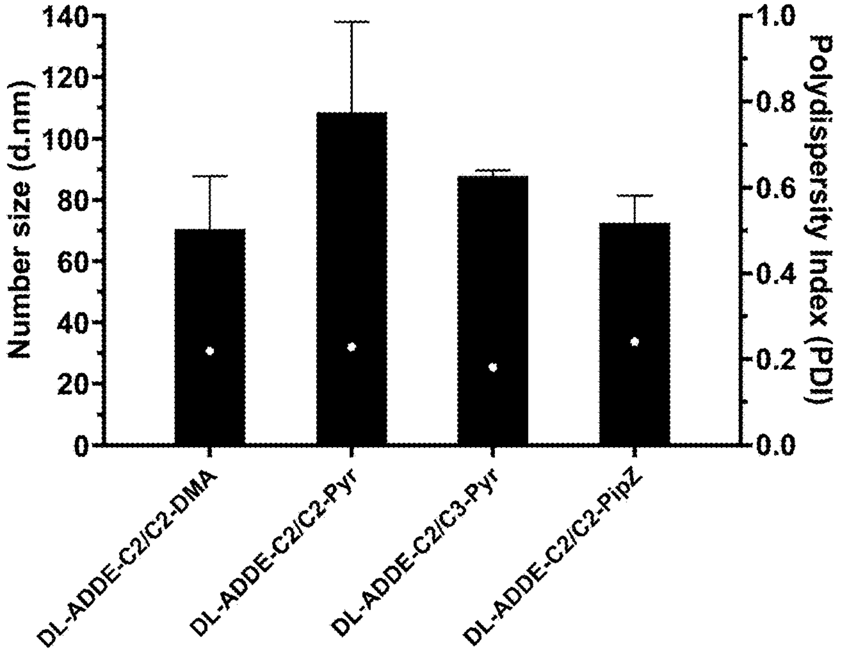
FIG. 16 illustrates a graph of Dynamic Light Scattering for LNP Size (white dots are PDI right y axis) as exemplified in Example 3C.

C: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 16.

Figure 17:
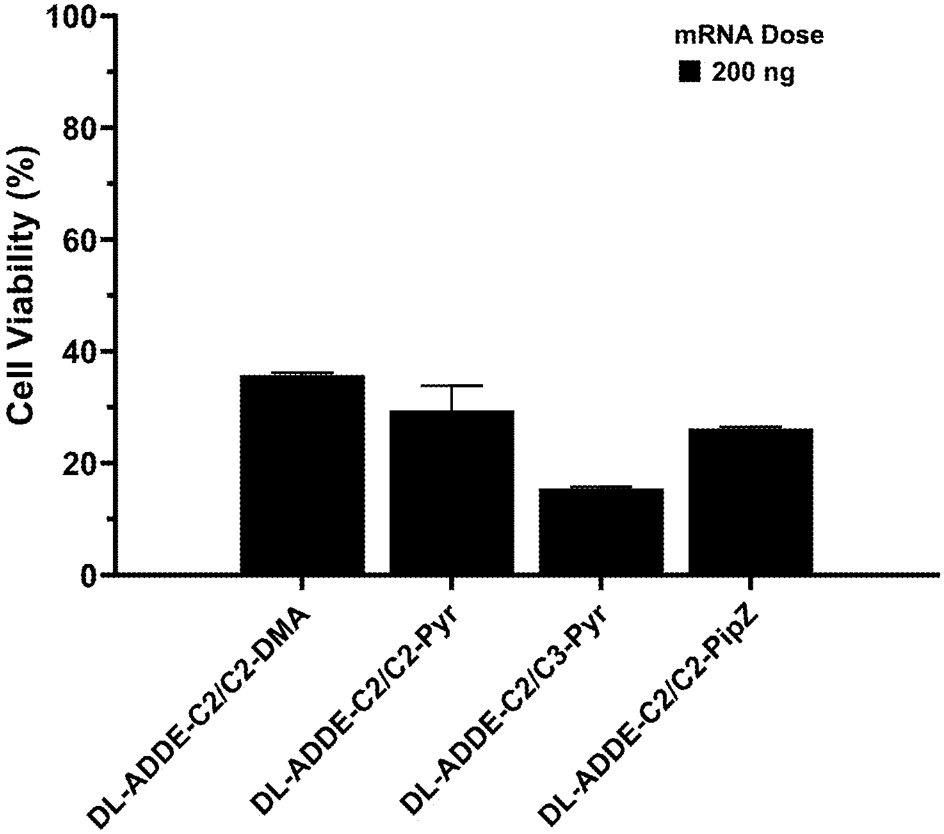
FIG. 17 illustrates a graph of Toxicity Assay based on Presto Blue HS viability reagent as exemplified in Example 3D.

D: Toxicity Assay based on Presto Blue HS viability reagent. After 24 hours of transfection, transfected cells are incubated with pre-warmed Presto Blue HS reagent (10% v/v) for 15 minutes at 37° C. Microplates were immediately introduced into the Cytation 5 Cell Imaging Multi-Mode Reader (Biotek) to read Fluorescence (Ex540/Em590). The results are illustrated in FIG. 17.

Example 4

Exemplary Ionizable Lipids have High Delivery Efficiency at 100-200 ng/Well Dose In Vitro (Study TRANS-22)

Summary: LNPs were formulated using total lipid concentration of 50 mM comprised of ionizable lipids/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively).

Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 3.6 mg/ml. FLuc mRNA stock was diluted in serial dilutions from a higher concentration solution to lower concentrations to reach 1 mg/ml in 50 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 6×1 hr. LNPs were then diluted so that 32 ul contained 200 ng and 12K HEK293 cells were transfected with the same 50-200 ng dose.

Figure 18:
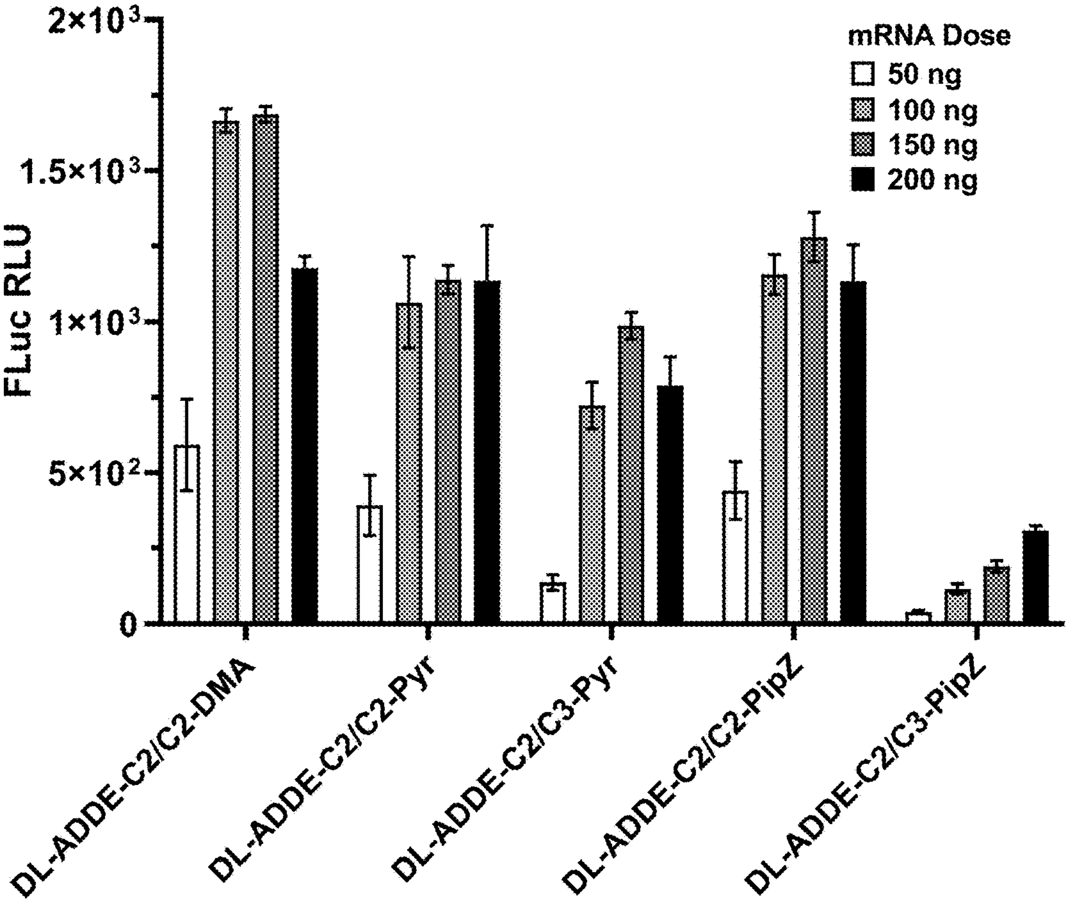
FIG. 18 illustrates a graph of Firefly Luciferase Assay for mRNA Delivery Efficiency as exemplified in Example 4A.

A: Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The results are illustrated in FIG. 18.

Figure 19:
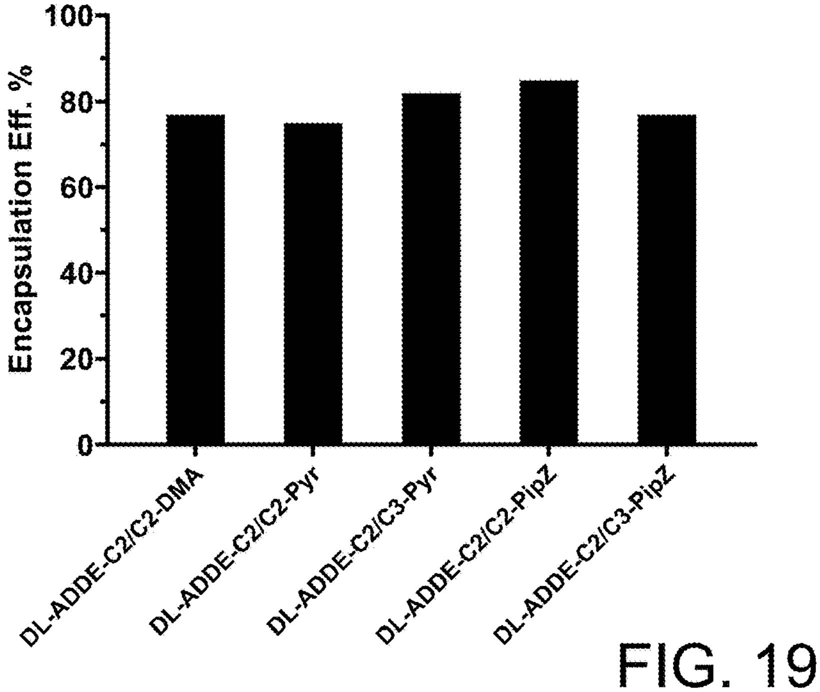
FIG. 19 illustrates a graph of Ribogreen Assay for mRNA Encapsulation Efficiency as exemplified in Example 4B.

B: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 19.

Figure 20:
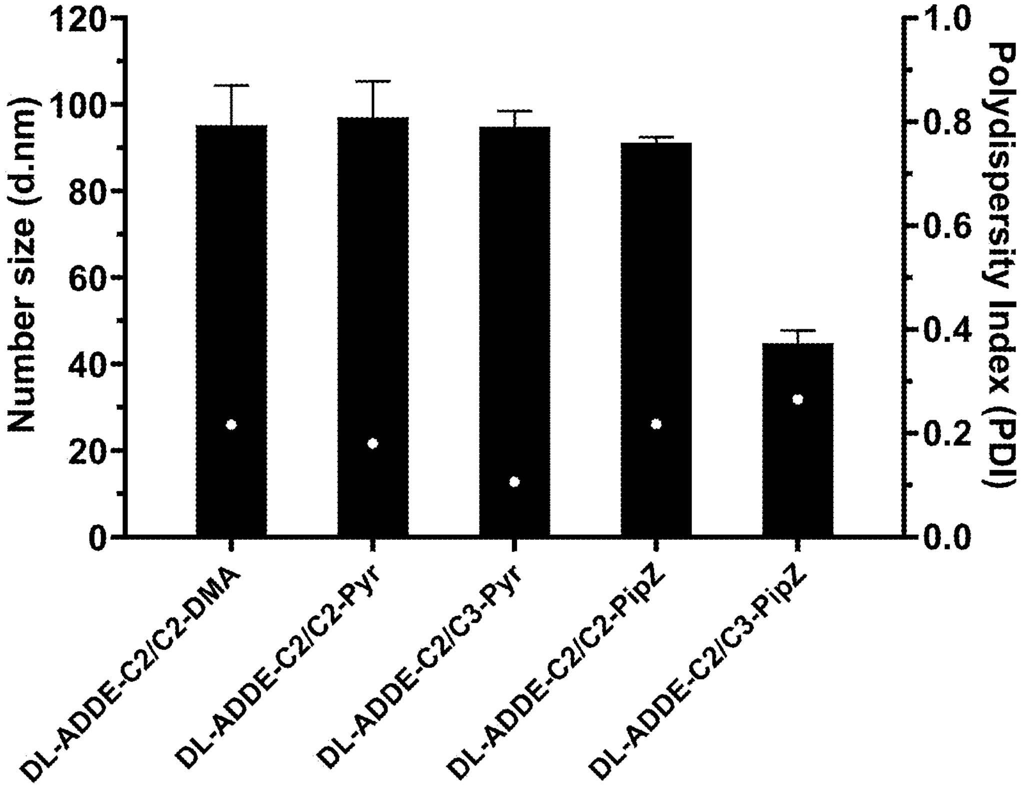
FIG. 20 illustrates a graph of Dynamic Light Scattering for LNP Size (white dots are PDI right y axis) as exemplified in Example 4C.

C: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 20.

Example 5

Exemplary Ionizable Lipids have High Delivery Efficiency at 100-200 ng/Well Dose In Vitro and In Vivo at 2.5 μg Dose (Study In Vivo-1)

Summary: LNPs were formulated using total lipid concentration of 50 mM comprised of ionizable lipids/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively). Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 3.6 mg/ml. mRNA stock was diluted in serial dilutions from a higher concentration solution to lower concentrations to reach 1 mg/ml in 50 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 24 μl Lipid Mix and 48 μl mRNA solution were mixed on Setting 5 and ejected into 72 μl 1×DPBS pH 7.4. The formed LNPs were then diluted into an additional 144 μl 1×DPBS pH 7.4. LNPs were then dialyzed against 1×DPBS pH 7.4 for 6×1 hr. LNPs were then diluted so that 32 ul contained 200 ng and 12K HEK293 cells were transfected with the same 50-200 ng dose. The first-generation DL-ADDE LNPs had similar efficiency in vitro and in vivo as MC3, the standard reference lipid used in prior art LNPs.

Figure 21:
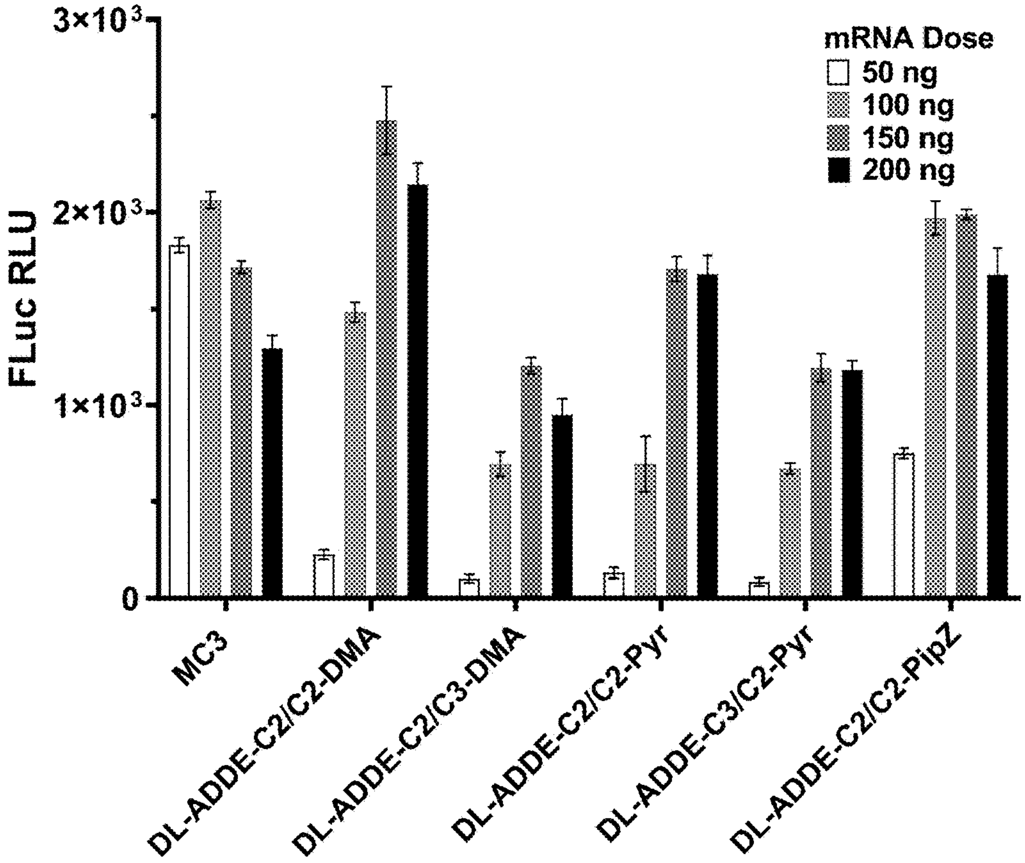
FIG. 21 illustrates a graph of Firefly Luciferase Assay for mRNA Delivery Efficiency as exemplified in Example 5A.

A: Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The results are illustrated in FIG. 21.

Figure 22:
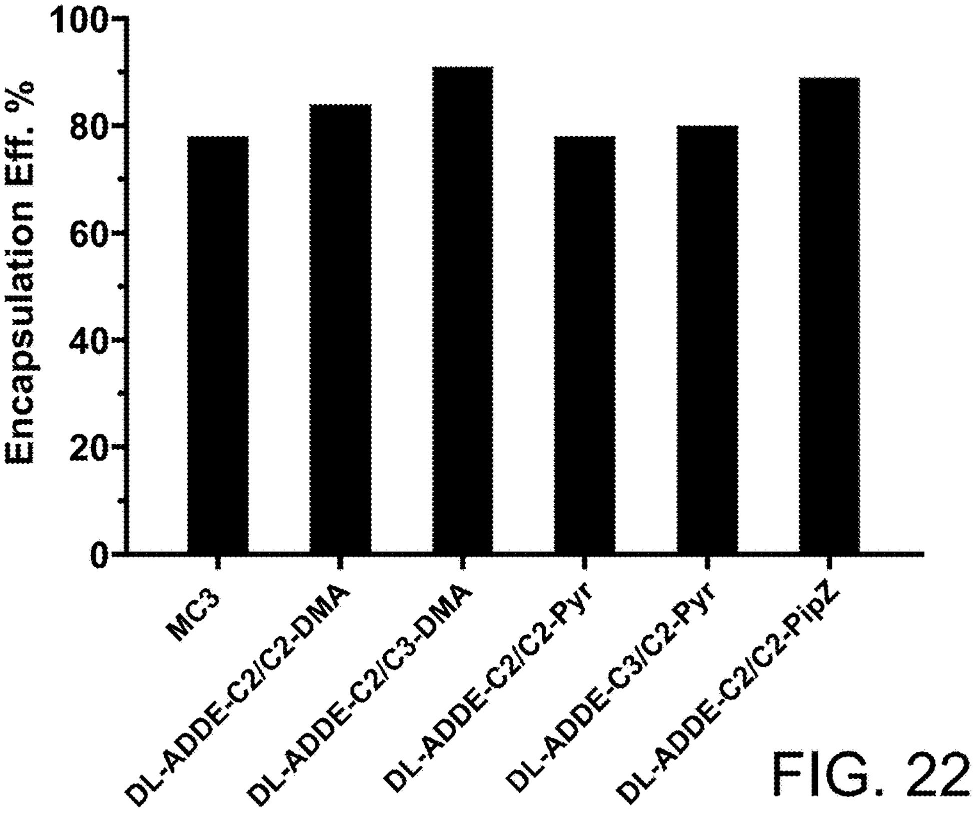
FIG. 22 illustrates a graph of Ribogreen Assay for mRNA Encapsulation Efficiency as exemplified in Example 5B.

B: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 22.

Figure 23:
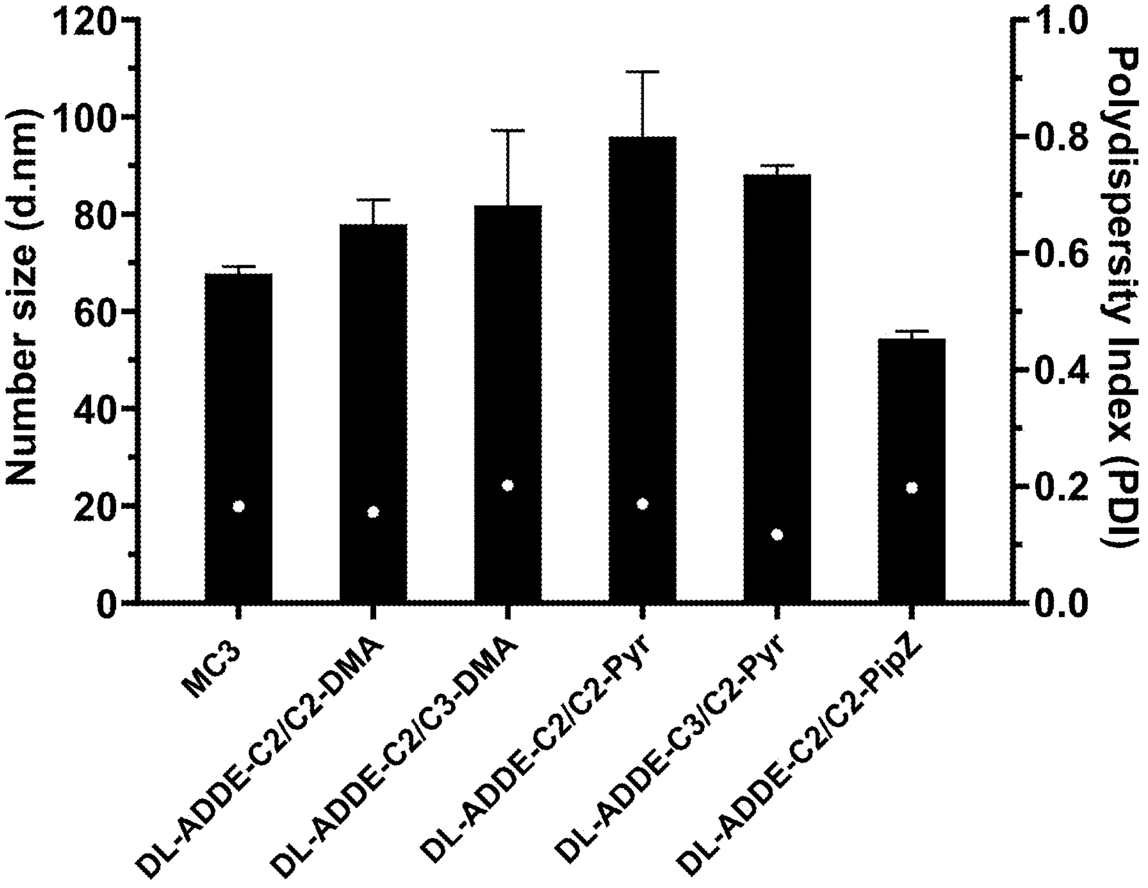
FIG. 23 illustrates a graph of Dynamic Light Scattering for LNP Size (white dots are PDI right y axis) as exemplified in Example 5C.

C: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 23.

Figure 24:
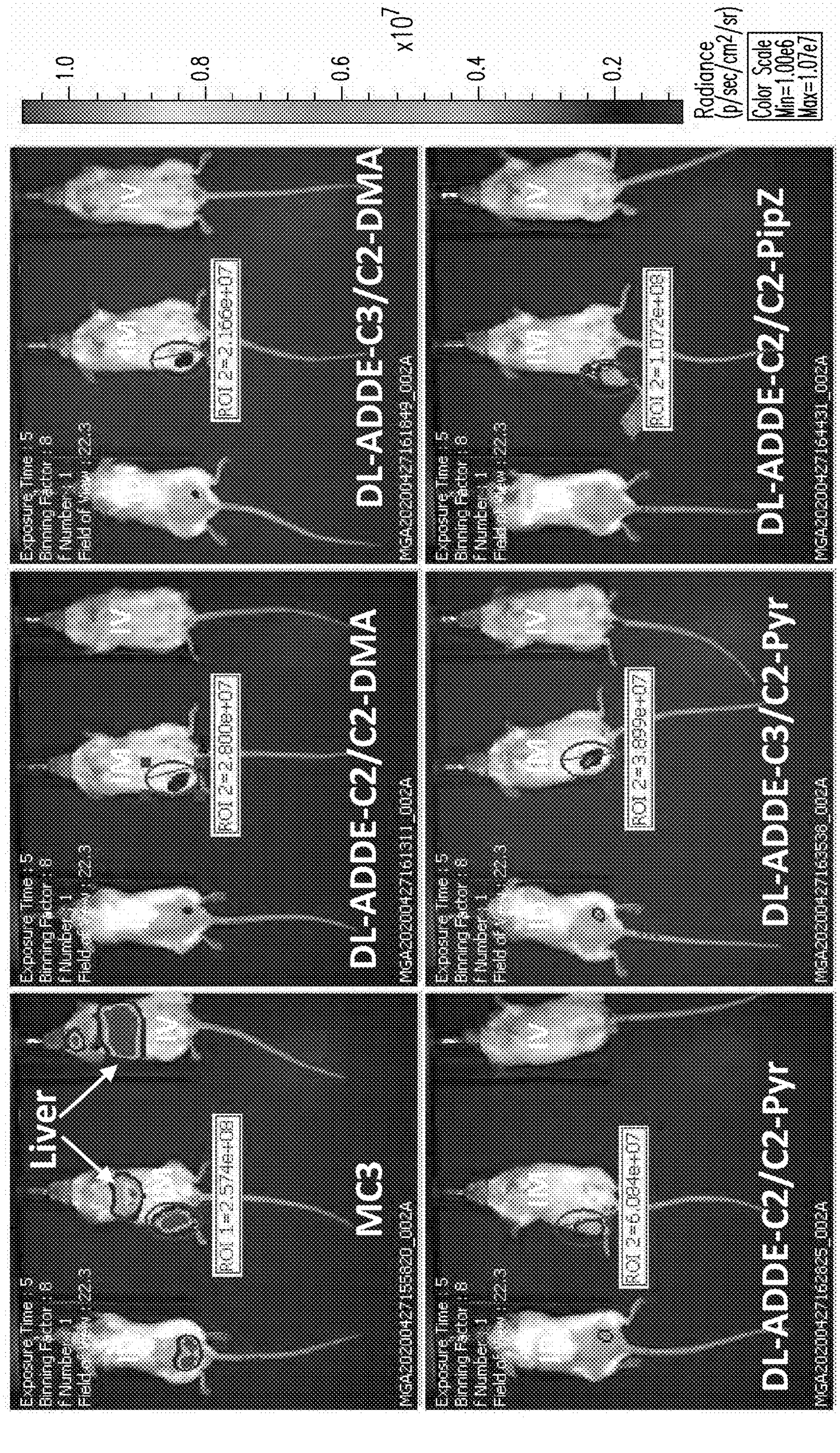
FIG. 24 illustrates a graph of In vivo Translation of mRNA Fluc at 4 hours post-injection in BALB/c mice as exemplified in Example 5D.

D: In vivo Translation of mRNA Fluc at 4 hours post-injection in BALB/c mice. Dialyzed DL-ADDE LNPs and MC3 LNP were injected via 3 routes of administration—intravascular (IV), intramuscular (IM), intradermal (ID). 50 μL total volume containing 2.5 μg of LNP with Fluc mRNA was injected (2×25 μL for MC3 ID). Luciferin was administrated intraperitoneally at 4 hours post-injection and luciferase expression monitored by live animal imaging. DL-ADDE-C2/C2-PipZ LNPs localize expression 4 hours post-injection to the IM injection site and express luciferase at ~50% the level of MC3 according to region of interest (ROI) analyses of radiance. In contrast to DL-ADDE expression localized to muscle, MC3 and other published lipids result in rapid disseminated expression in liver 4 hours after IM injection. The IM localized expression for DL-ADDE LNPs is likely due to their slight positive charge at physiological pH versus negative for MC3 and other published LNPs and could result in greater immunogenicity with reduced reactogenicity and reduced systemic adverse events. Notably DL-ADDE LNPs do not express in liver even when injected IV. Two LNPs below (DL-ADDE-C2/C2-PYR, DL-ADDE-C2/C2-PIPZ) met the go/no-go criteria to proceed to immunogenicity testing using mRNA expressing a SARS-CoV-2 shown further below in Example 9. The results are illustrated in FIG. 24.

Example 6

Exemplary DL-ADDE Ionizable Lipids have High Delivery Efficiency at 100-200 ng/Well Dose while BOD-ADDE Ionizable Lipids are Potent at 25-200 ng In Vitro (Study TRANS-30)

Summary: LNPs were formulated using total lipid concentration of 50 mM comprised of ionizable lipids/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively) and serial dilutions to get 27.74 mM. Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 3.6 mg/ml. FLuc mRNA stock was diluted in serial dilutions from a higher concentration solution to lower concentrations to reach 0.56 mg/ml in 25 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 6×1 hr. LNPs were then diluted so that 32 ul contained 200 ng and 12K HEK293 cells were transfected with the same 25-200 ng dose.

Figure 25:
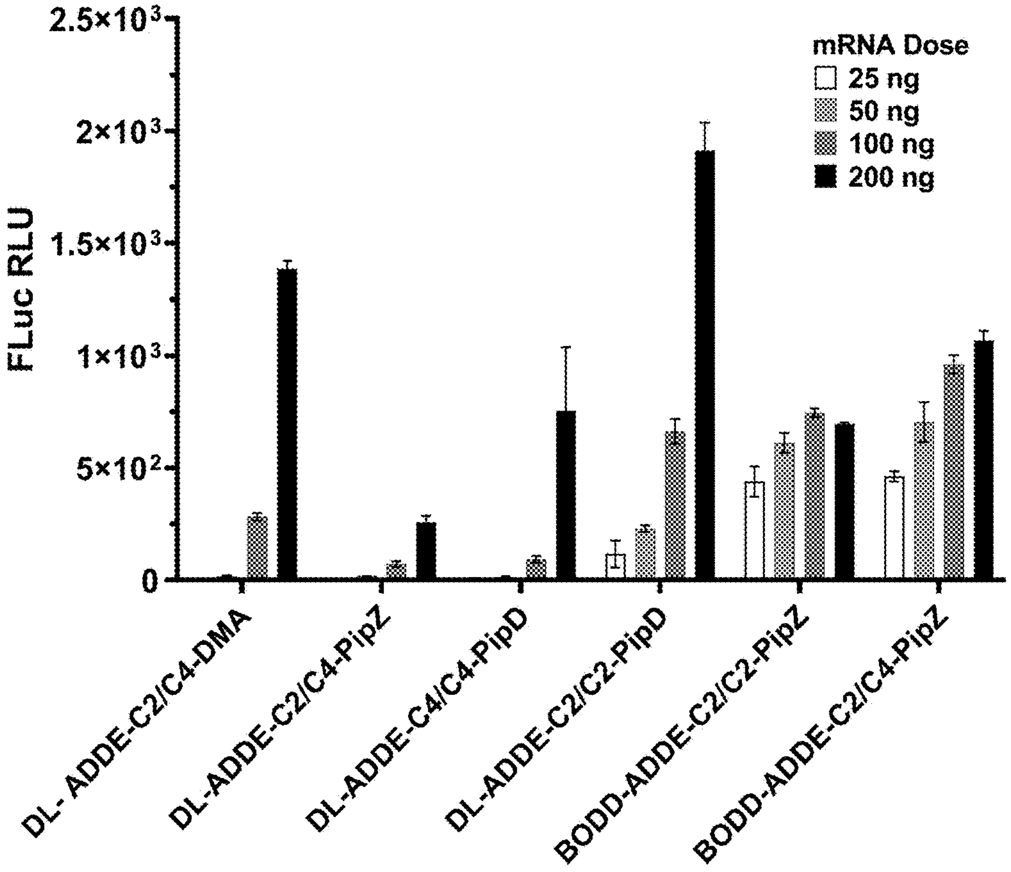
FIG. 25 illustrates a graph of Firefly Luciferase Assay for mRNA Delivery Efficiency as exemplified in Example 6A.

A: Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The results are illustrated in FIG. 25.

Figure 26:
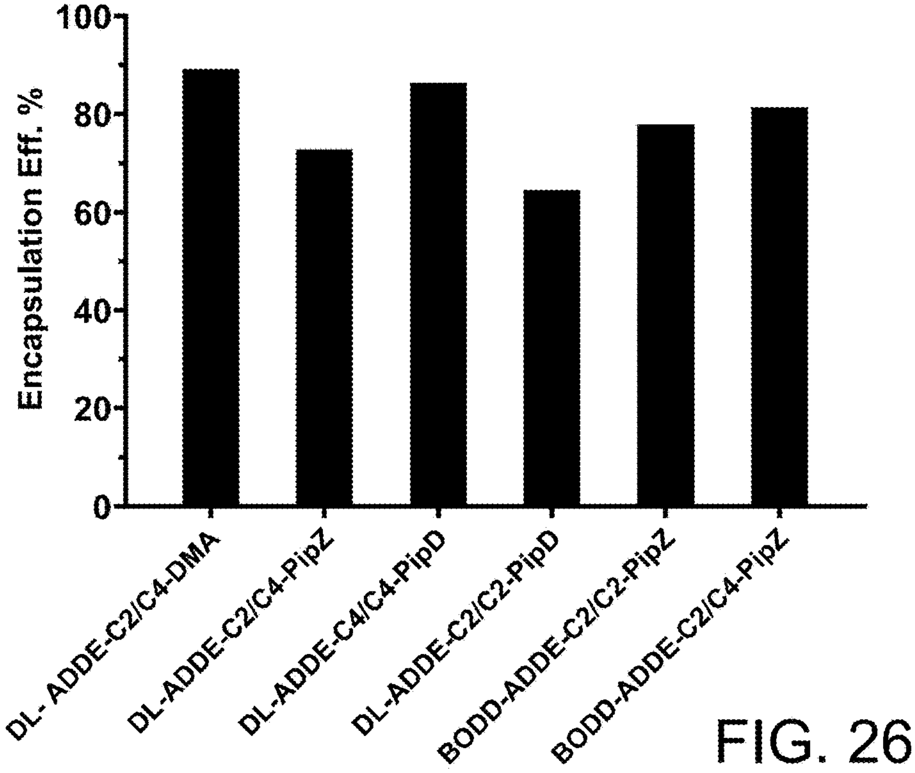
FIG. 26 illustrates a graph of Ribogreen Assay for mRNA Encapsulation Efficiency as exemplified in Example 6B.

B: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 26.

Figure 27:
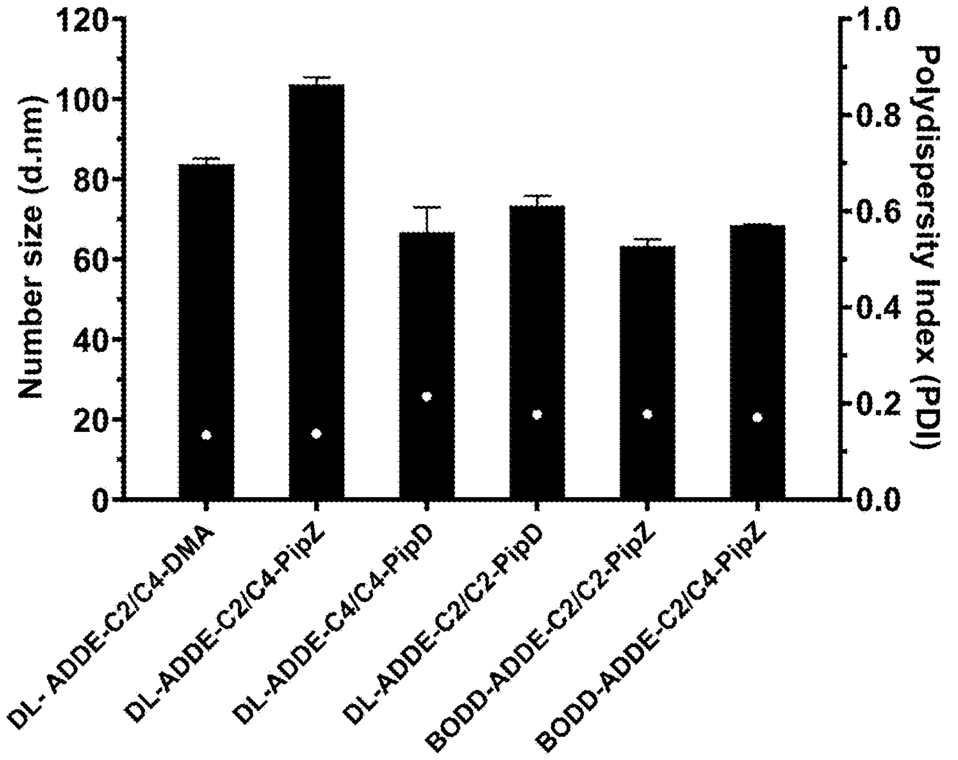
FIG. 27 illustrates a graph of Dynamic Light Scattering for LNP Size (white dots are PDI right y axis) as exemplified in Example 6C.

C: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 27.

Example 7

Exemplary DL-ADDE Ionizable Lipids have High Delivery Efficiency at 100-200 ng/Well Dose while BOD-ADDE Ionizable Lipids are Potent at 25-200 ng In Vitro (Study TRANS-31)

Summary: LNPs were formulated using total lipid concentration of 50 mM comprised of ionizable lipids/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively) and serial dilutions to get 27.74 mM. Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 3.6 mg/ml. FLuc mRNA stock was diluted in serial dilutions from a higher concentration solution to lower concentrations to reach 0.56 mg/ml in 25 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 6×1 hr. LNPs were then diluted so that 32 ul contained 200 ng and 12K HEK293 cells were transfected with the same 25-200 ng dose. The first-generation DL-ADDE LNPs had similar efficiency as MC3 and KC2, the standard reference lipid used in the mRNA LNP literature.

Figure 28:
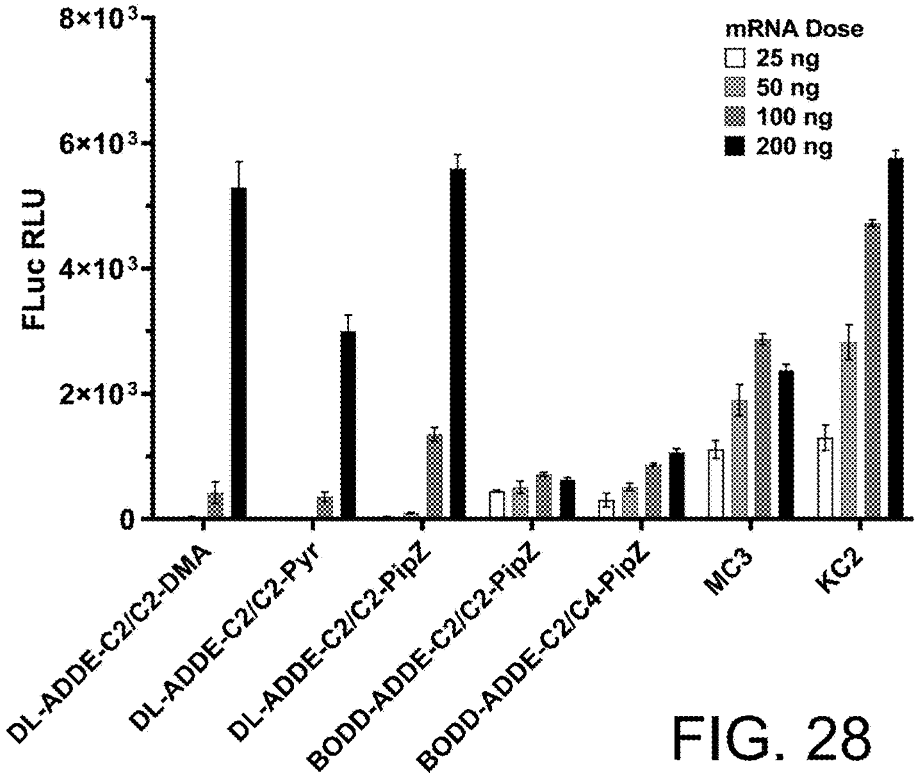
FIG. 28 illustrates a graph of Firefly Luciferase Assay for mRNA Delivery Efficiency as exemplified in Example 7A.

A: Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The results are illustrated in FIG. 28.

Figure 29:
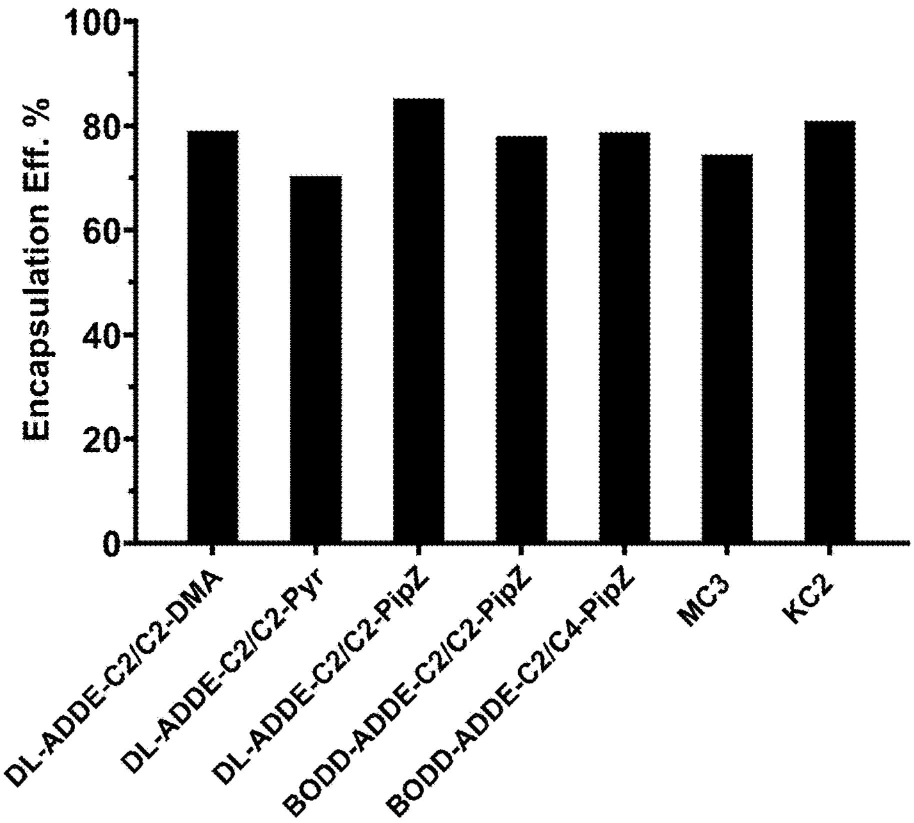
FIG. 29 illustrates a graph of Ribogreen Assay for mRNA Encapsulation Efficiency as exemplified in Example 7B.

B: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 29.

Figure 30:
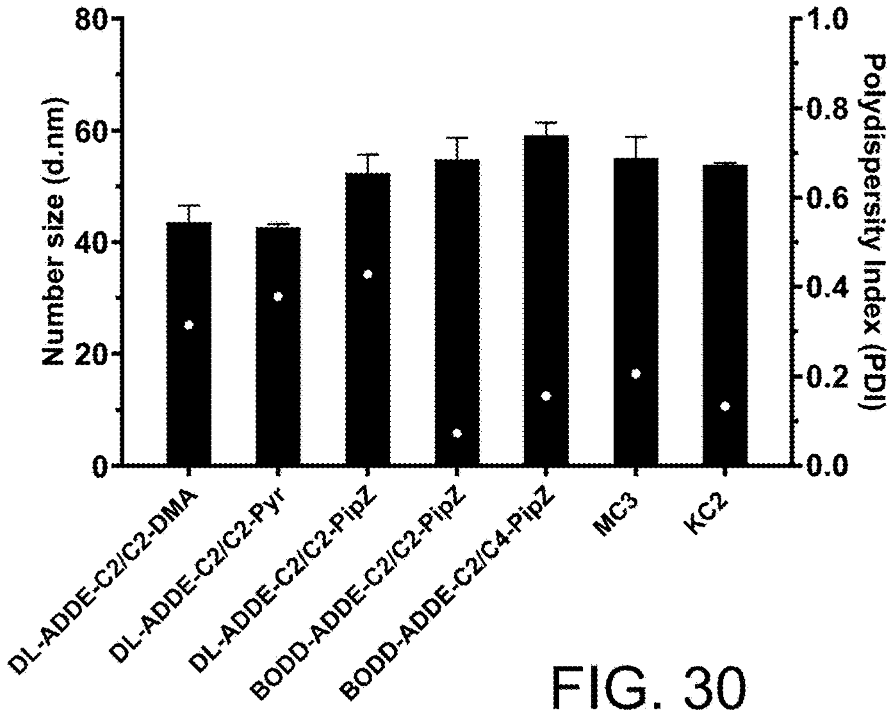
FIG. 30 illustrates a graph of Dynamic Light Scattering for LNP Size (white dots are PDI right y axis) as exemplified in Example 7C.

C: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 30.

Example 8

Novel Ionizable Lipids at 50 mM and mRNA at 1 mg/ml for Rapid Microfluidic Mixing Shows Distinct Colloidal Ionization Properties (Study LNP-19), High In Vitro Delivery Efficiency (Study Trans 31) and High Immunogenicity when Delivering a SARS-CoV-2 Immunogen (Study In Vivo 2)

Summary: LNPs were formulated using total lipid concentration of 50 mM comprised of ionizable lipids/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively). Codon optimized firefly luciferase (Fluc), and 2019-nCoV Wuhan S-2P (Covid) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations >3 mg/ml. mRNA stock was diluted in serial dilutions from a higher concentration solution to lower concentrations to reach 1 mg/ml in 50 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 6×1 hr. ADDE lipids were compared to standard lipids like KC2 and MC3. FIGS. 31-33

Exemplary ADDE ionizable lipids. pKas were obtained from ACDLabs Percepta for the ionizable lipid, and by zeta potential and TNS for LNPs containing the ionizable lipids. LNP isoelectric pI was obtained from the zeta potential. LNP diameter is number-average from DLS. Average mRNA copies per LNP was calculated using a molecular volume model and the DLS diameter and is proportional to LNP volume.

TABLE 14
| Lipid | Structure | pKa, ACD | pKa,ZP | pI, ZP | pKa, TNS | Diameter (nm) | mRNA copies |
|---|---|---|---|---|---|---|---|
| DL-C2/C2-DMA | 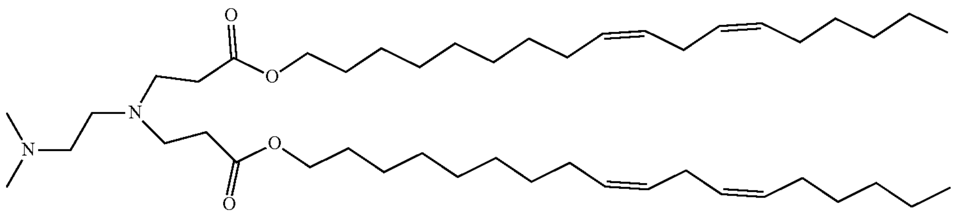 [SMILES: CCCCC/C=C\C/C=C\CCCCCCCCOC(=O)CCN(CCC(=O)OCCCCCCCC/C=C\C/C=C\CCCCC)CCN(C)C] | 8.4, 3.9 | 6.9 | 7.1 | 8.0 | 40 | 1.1 |
| DL-C2/C2-Pyr | 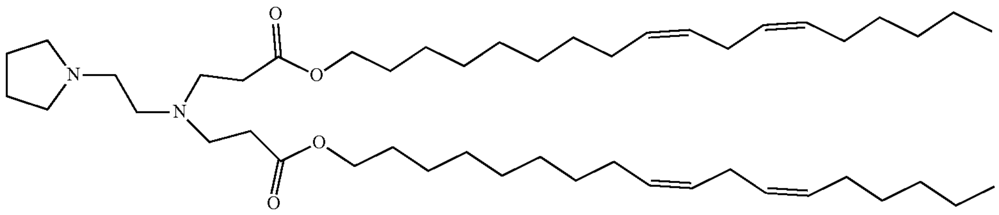 [SMILES: CCCCC/C=C\C/C=C\CCCCCCCCOC(=O)CCN(CCC(=O)OCCCCCCCC/C=C\C/C=C\CCCCC)CCN1CCCC1] | 8.6, 5.9 | 6.8 | 7.2 | 7.9 | 48 | 1.5 |
| DL-C2/C2-PipZ | 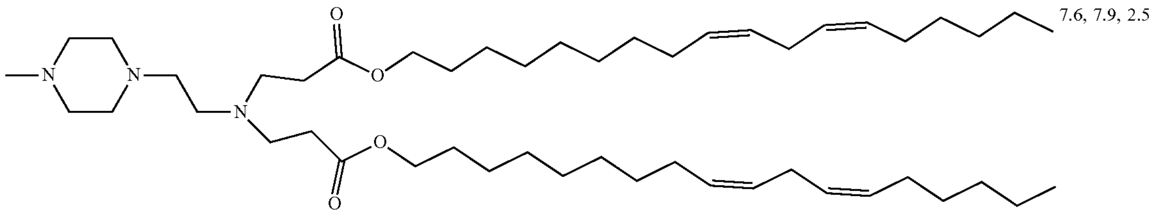 | 7.6, 7.9, 2.5 | 6.2 | 7.6 | 7.8 | 64 | 4.3 |

TABLE 14-continued
| Lipid | Structure | pKa, ACD | pKa,ZP | pI, ZP | pKa, TNS | Diameter (nm) | mRNA copies |
|---|---|---|---|---|---|---|---|
| BODD-C2/C4-PipZ | 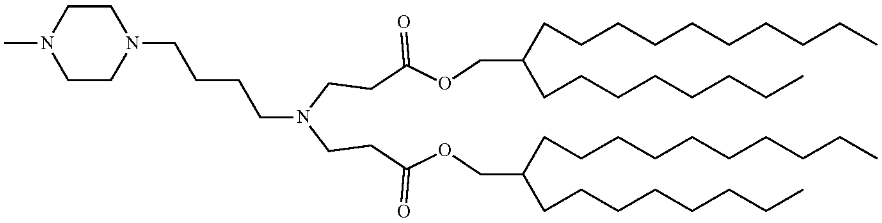 [SMILES: CCCCCCCCCCC(CCCCCCCC)COC(=O)CCN(CCCCN1CCN(C)CC1)CCC(=O)OCC(CCCCCCCC)CCCCCCCCCC] | 7.8, 7.3, 2.4 | 4.9* | 5.8 | 7.0 | 55 | 3.3 |
| BODD-C2/C2-PipZ | 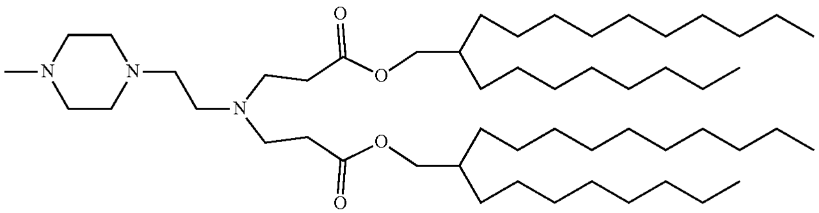 | 7.6, 2.3, 2.4 | 5.4 | 5.9 | 6.6 | 49 | 1.9 |
*did not fit HH
[1]pKa of the N atoms starting from the N atom furtherest on left in the above structures.

A: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 34.

B: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 35.

C: Zeta Potential for LNP charge, pKa and pI. LNPs were diluted in a 75 mM TNS Buffer (10 mM of each of glycylglycine, acetate, imidazole, 20 mM borate, 25 mM NaCl) to contain 0.8 mg of total mRNA in 800 ul of the TNS Buffer and transferred into a Folded Capillary Zeta Cell (DTS1070) to measure size by Dynamic Light Scattering (DLS) and electrophoretic mobility by Electrophoretic Light Scattering (ELS) in the Zetasizer Nano ZS (Malvern Panalytical). Zeta potential is measured under conditions of controlled voltage to limit ohmic heating in a solution with 4 buffers with pKas spread across the pH range 3-10 with 0.5 intervals. LNP pKa is calculated by fitting the Henderson Hasselbalch equation to zeta potential data. LNP pI is found by interpolating zeta potential to zero. We use electrokinetic models to calculate Henry's function and charge of the LNP. The results are illustrated in FIG. 36.

D: TNS Assay for LNP pKa. LNPs were diluted to keep a final concentration of 75 uM of the ionizable lipid and 6 uM of TNS in a 75 mM TNS Buffer (10 mM of each of glycylglycine, acetate, imidazole, 20 mM borate, 25 mM NaCl) in order to keep a ratio TNS/ionizable of 0.08. Fluorescence TNS is measured in a solution with 4 buffers with pKas spread across the pH range 3-10 with 0.5 intervals. The pKa of the LNP was measured using the pH-dependence of fluorescence enhancement of the anionic dye TNS, higher intensity at lower pH and lower at high pH. LNP pKa is calculated by fitting the Henderson Hasselbalch equation to fluorescence data from the TNS Assay. The results are illustrated in FIG. 37.

Example 9

Exemplary Ionizable Lipids have High Delivery Efficiency In Vivo (Study In Vivo-4)

Summary: LNPs were formulated using total lipid concentration of 50 mM comprised of ionizable lipids/DSPC/Cholesterol/PEG-DMG (50:10:38.5:1.5 mol %). Each one of the lipids were solubilized in ethanol until a clear solution was observed. The four lipids were combined to get 50 mM total lipid concentration (25/5/19.25/0.75 mM respectively). Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 4 mg/ml. mRNA stock was diluted in serial dilutions from a higher concentration solution to lower concentrations to reach 1 mg/ml in 50 mM Sodium acetate buffer pH 4, keeping the NP ratio constant at 4, prior to mixing in the Spark NanoAssmblr (Precision NanoSystems), which allows high reproducibility in formulations using a microfluidic mixing technology. 24 μl Lipid Mix and 48 μl mRNA solution were mixed on Setting 5 and ejected into 72 μl 1×DPBS pH 7.4. The formed LNPs were then diluted into an additional 144 μl 1×DPBS pH 7.4. LNPs were then dialyzed against 1×DPBS pH 7.4 for 6×1 hr. LNPs were concentrated in order to inject 5 ug of encapsulated mRNA in 50 ul for an intramuscular administration.

A: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 38.

B: Dynamic Light Scattering for LNP Size (red dots are PDI right y axis). LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 39.

C: In vivo Firefly Luciferase expression in IM administration. 5 ug of encapsulated mRNA was injected in mice in intramuscular (I.M.) injections. Luciferin was administrated intraperitoneally at 4 hours post-injection and luciferase expression monitored by live animal imaging at 4 and 24 hours. ROIs were calculated using the IVIS system. The results are illustrated in FIGS. 40A-40H.

D: SARS-CoV-2 S-specific binding antibody titers. BALB/c mice (n=5/group) were immunized at weeks 0 and 3 with 0.1 μg and 1 μg dose of S-2P mRNA-encoded immunogen in 3 different LNPs MC3/DL-ADDE-C2C2-4Me-PipZ/BOD-ADDE-C2C4-4Me-PipZ. Sera were assessed for SARS-CoV-2 S-specific IgG by ELISA at 3 weeks after the Prime and at 5 weeks after the Boost. Dose-dependent and high binding antibody titers were found after the prime for MC3 and BOD-ADDE-C2C4-4Me-PipZ. High titers were found for all LNPs after the boost in these young animals.

Example 10

Further Optimization in LNP Delivery Efficiency In Vitro Through Mole Ratio Adjustment. (TRANS-36)

Summary: LNPs were formulated using total lipid concentration of 50-52 mM comprised of the ionizable BODD-C2C4-PipZ/DSPC/Cholesterol/PEG-DMG (47-70:8-14:29-49:1-2 mol %). Each one of the lipids were solubilized in ethanol until a clear solution was observed. The four lipids were combined to achieve 50-52 mM total lipid concentration. Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 4.6 mg/ml. Fluc mRNA stock was diluted in serial dilutions from a higher concentration solution to lower concentrations to reach 1 mg/ml in 20 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 6×1 hr. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The results are illustrated in FIG. 41.

B: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 42.

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 43.

Example 11

Screening of Ionizable Lipids Mixed at 50 mM Total Lipid Concentration and mRNA from 1 mg/ml for Rapid Microfluidic Mixing Increases LNP Delivery Efficiency In Vitro (TRANS-40)

Summary: LNPs were formulated using total lipid concentration of 50 mM comprised of several ionizable-lipid/DSPC/Cholesterol/PEG-DMG (47:13:37:2 mol %). Each one of the lipids were solubilized in ethanol until a clear solution was observed. The four lipids were combined to get 50 mM total lipid concentration (24/6.5/18.5/1 mM respectively). Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 1 mg/ml in 15 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPs were then diluted into an additional 96 μl 1×DPBS pH 7.4. LNPs were then dialyzed against 1×DPBS pH 7.4 for hr. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The results are illustrated in FIG. 44.

B: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 45.

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 46.

Example 12

Exemplary Ionizable Lipid Formulations Stability in Liquid Format at 4 C and Room Temperature (TRANS-42)

Summary: LNPs were formulated using total lipid concentration of ~75 mM comprised of several ionizable/DSPC/Cholesterol/PEG-DMG (47-50:10-13:37-38.5:1.5-2 mol %). Each one of the lipids were solubilized in ethanol until a clear solution was observed. The four lipids were combined to get 75 mM total lipid concentration. Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 1.5 mg/ml in 15-25 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPs were then diluted into an additional 96 μl 1×DPBS pH 7.4. LNPs were then dialyzed against 1×DPBS pH 7.4 for 6×1 hr. LNPs were then diluted so that 32 ul contained 25-200 ng and 12K HEK293 cells were transfected with the same dose but manufactured at different concentrations in the microfluidic mixer.

A: Stability Assay based on in vitro potency using Firefly Luciferase Assay. Cells were transfected in Day 0, 2, 4, 7, 14 and 28. Firefly Assay was done for each day and recorded. The results are illustrated in FIG. 47.

B: Dynamic Light Scattering (DLS) for LNP size and Ribogreen Assay for LNP Encapsulation efficiency. LNPs were assayed at Day 0, 2, 4, 7, 14 and 28, and recorded.

The results are illustrated in FIG. 48.

Example 13

Exemplary Ionizable Lipid Formulations at Low 0.25 mg/ml and High 1.5 mg/ml Mixing Concentration for Rapid Microfluidic Mixing Show High Delivery Efficiency and Potency In Vitro (TRANS-43)

Summary: LNPs were formulated using total lipid concentration of 12.5-75 mM comprised of several ionizable/DSPC/Cholesterol/PEG-DMG (47:13:37:2 mol %). Each one of the lipids were solubilized in ethanol until a clear solution was observed. The four lipids were combined to get 75 mM total lipid concentration then serial dilutions were done to reach 12.5 mM. Codon optimized firefly luciferase (Fluc) sequence was cloned into an mRNA plasmid (optimized 3' and 5' UTR and containing a 101 polyA tail (SEQ ID NO: 4)) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 0.25-1.5 mg/ml in 15 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 µl Lipid Mix and 32 µl mRNA solution were mixed on Setting 3 and ejected into 48 µl 1×DPBS pH 7.4. The formed LNPS were then diluted into an additional 96 µl 1×DPBS pH 7.4. LNPs were then dialyzed against 1×DPBS pH 7.4 for 6×1 hr. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The results are illustrated in FIG. 49.

B: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 50.

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 51.

Example 14

Moderna Buffer Helps to Freeze Ionizable Lipid Formulations Better than PBS and Shows Same Delivery Efficiency and Potency In Vitro (TRANS-45)

Summary: LNPs were formulated using total lipid concentration of 12.33-77 mM comprised of several ionizable/DSPC/Cholesterol/PEG-DMG (50-47:10-13:37-38.5:1.5-2 mol %). Each one of the lipids were solubilized in ethanol until a clear solution was observed. The four lipids were combined to get 77 mM total lipid concentration then serial dilutions were done to reach 12.33 mM. Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 6.3 mg/ml. Fluc mRNA stock was diluted in serial dilutions from a higher concentration solution to lower concentrations to reach 0.25-1.5 mg/ml in 15 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 µl Lipid Mix and 32 µl mRNA solution were mixed on Setting 3 and ejected into 48 µl 1×DPBS pH 7.4. The formed LNPs were then diluted into an additional 96 µl 1×DPBS pH 7.4. The formed LNPS were then diluted into an additional 96 µl 1× DPBS pH 7.4. LNPs were then dialyzed against 1×DPBS pH 7.4 for 6×1 hr. LNPs were split to dialyze half in Moderna freezing Buffer 20 mM Tris buffer containing 87 mg/mL (254 mM) sucrose and 10.7 mM sodium acetate at pH 7.5 (page 47 of Moderna Protocol) for 6 hours. Each set LNPs (Fresh PBS, Fresh Moderna, Freezing PBS, Freezing Moderna) were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The results are illustrated in FIG. 52.

B: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 53.

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 54.

Example 15

Exemplary Ionizable Lipid Formulation BODD C2C4 PipZ at High 1.5 mg/ml mRNA Mixing Concentration for Rapid Microfluidic Mixing Show High Delivery Efficiency and Potency In Vivo Versus Reference Lipid MC3 at Standard Mixing Concentration 0.2 mg/ml (In Vivo-7)

Summary: LNPs were formulated using total lipid concentration of 10-75 mM comprised of several ionizable/DSPC/Cholesterol/PEG-DMG (47-50:10-13:37-38.5:1.5-2 mol %). Each one of the lipids were solubilized in ethanol until a clear solution was observed. The four lipids were combined to get 75 mM total lipid concentration then serial dilutions were done to reach 10 mM. Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 0.2-1.5 mg/ml in 15-25 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 µl Lipid Mix and 32 µl mRNA solution were mixed on Setting 3 and ejected into 48 µl 1×DPBS pH 7.4. The formed LNPS were then diluted into an additional 96 µl 1×DPBS pH 7.4. LNPs were then dialyzed against 1×DPBS pH 7.4 for 6×1 hr. LNPs were then diluted so that 32 ul contained 25-200 ng and 12K HEK293 cells were transfected with the same dose but manufactured at different concentrations in the microfluidic mixer.

A: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 55.

B: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 56.

C: In vivo Firefly Luciferase expression in IM administration. 0.5-5 ug of total mRNA was injected in mice in intramuscular (I.M.) injections. Luciferin was administrated intraperitoneally at 4 hours post-injection and luciferase expression monitored by live animal imaging at 4 and 24 hours. ROIs were calculated using the IVIS system. The results are illustrated in FIGS. 57A-57I.

Example 16

Exemplary Ionizable Lipid Formulation BODD C2C4 PipZ at High 1.5 mg/ml mRNA Mixing Concentration Show High Delivery Efficiency and Immunogenicity Potency In Vivo when Delivering SARS-CoV-2 Immunogen Versus the Reference Lipid MC3 at Standard Mixing Concentration 0.2 mg/ml (In Vivo-8)

Summary: LNPs were formulated using total lipid concentration of 10-75 mM comprised of several ionizable/DSPC/Cholesterol/PEG-DMG (47-50:10-13:37-38.5:1.5-2 mol %). Each one of the lipids were solubilized in ethanol until a clear solution was observed. The four lipids were combined to get 75 mM total lipid concentration then serial dilutions were done to reach 10 mM. Codon optimized 2019-nCoV Wuhan S-2P (Covid) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 0.2-1.5 mg/ml in 15-25 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPs were then diluted into an additional 96 μl 1×DPBS pH 7.4. LNPs were then dialyzed against 1×DPBS pH 7.4 for 6×1 hr. LNPs were then diluted so that 32 ul contained 25-200 ng and 12K HEK293 cells were transfected with the same dose but manufactured at different concentrations in the microfluidic mixer.

A: In vivo immunogenicity Endpoint ELISA Anti-RBD titers. 0.1, 0.25, 0.5, 1 ug of total mRNA was injected in mice in intramuscular (I.M.) injections. Pre boost and Post boost (after 3 weeks) shown below. The results are illustrated in FIG. 58A-58B.

B: In vivo immunogenicity FRNT50 titer for Psuedoneutralisation assay. 0.1, 0.25, 0.5, 1 ug of total mRNA was injected in mice in intramuscular (I.M.) injections. Pre boost and Post boost (after 3 weeks) shown below. The results are illustrated in FIG. 59.

Example 17

Mouse Challenge Using Exemplary Ionizable Lipid Formulations BODD C2C4 PipZ at High 1.5 mg/ml mRNA Mixing Concentration for Rapid Microfluidic Mixing Shows Delivery Efficiency and Immunogenicity Potency In Vivo when Deliver SARS-CoV-2 Immunogen for 100% Protection at 0.25 Ug Dose Higher than Standard Lipid MC3 at Standard Mixing Concentration 0.2 mg/ml for 100% Protection at 0.5 Ug (In Vivo-9)

Summary: LNPs were formulated using total lipid concentration of 10-75 mM comprised of several ionizable/DSPC/Cholesterol/PEG-DMG (47-50:10-13:37-38.5:1.5-2 mol %). Each one of the lipids were solubilized in ethanol until a clear solution was observed. The four lipids were combined to get 75 mM total lipid concentration then serial dilutions were done to reach 10 mM. Codon optimized 2019-nCoV Wuhan S-2P (Covid) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 0.2-1.5 mg/ml in 15-25 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 6×1 hr. LNPs were then diluted so that 32 ul contained 25-200 ng and 12K HEK293 cells were transfected with the same dose but manufactured at different concentrations in the microfluidic mixer.

A: In vivo protection against viral challenge—Survival proportion, Weight and Temperature in Challenge model. 0.1, 0.25, 0.5, 1 ug of total mRNA was injected in mice in intramuscular (I.M.) injections Pre boost and Post boost (after 5 weeks). The challenge used with the Italian strain at $5\times10^4$ PFU. The results are illustrated in FIGS. 60A-60B.

B: In vivo weight and temperature in Challenge model. 0.1, 0.25, 0.5, 1 ug of total mRNA was injected in mice in intramuscular (I.M.) injections Pre boost and Post boost (after 5 weeks). The challenge used with the Italian strain at $5\times10^4$ PFU. The results are illustrated in FIG. 61A-61D.

Example 18

Exemplary Ionizable Lipid Formulations at High 1.5 mg/ml mRNA Mixing Concentration for Rapid Microfluidic Mixing Shows Delivery Efficiency and Potency In Vivo Higher than Standard Lipid MC3 (In Vivo-10)

Summary: LNPs were formulated using total lipid concentration of 77 mM comprised of several ionizable/DSPC/Cholesterol/PEG-DMG (47:13:37:2 mol %). Each one of the lipids were solubilized in ethanol until a clear solution was observed. The four lipids were combined to get 77 mM total lipid concentration. Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 1.5 mg/ml in 15 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 6×1 hr. LNPs were then diluted so that 32 ul contained 25-200 ng and 12K HEK293 cells were transfected with the same dose but manufactured at different concentrations in the microfluidic mixer.

A: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 62.

B: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 63.

C: In vivo Firefly Luciferase expression in IM and IV administration. 1 ug of total mRNA was injected in mice in intramuscular (I.M.) and Intravenous (I.V.) injections. Luciferin was administrated intraperitoneally at 4 hours post-injection and luciferase expression monitored by live animal imaging at 4 and 24 hours. ROIs were calculated using the IVIS system. The results are illustrated in FIG. 64A-64J.

Example 19

Increasing Concentrations of Lipids from 10.2 to 77 mM and mRNA from 0.2 to 1.5 mg/ml for Rapid Microfluidic Mixing Increases LNP Delivery Efficiency In Vitro. (TRANS-49)

Summary: LNPs were formulated using total lipid concentration of 10.2-77 mM comprised of several ionizable-lipids and DSPC/Cholesterol/PEG-DMG (47:13:37:2 mol %). Each one of the lipids were solubilized in ethanol until a clear solution was observed. The four lipids were combined to obtain 77 mM total lipid concentration then serial dilutions were done to reach 10.2 mM. Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 0.2-1.5 mg/ml in 15 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The results are illustrated in FIG. 65 and FIG. 66.

B: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 67.

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 68.

Example 20

Increasing Concentrations of Lipids to 77 mM and mRNA to 1.5 Mg/Ml for Rapid Microfluidic Mixing Shows LNP Delivery Efficiency In Vitro. (TRANS-52)

Summary: LNPs were formulated using total lipid concentration of 77 mM comprised of several ionizable-lipids and DSPC/Cholesterol/PEG-DMG (47:13:37:2 mol %). Each one of the lipids were solubilized in ethanol until a clear solution was observed. The four lipids were combined to obtain 77 mM total lipid concentration. Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed, and resuspended in nuclease-free water to reach concentrations of 5.5 mg/ml. Fluc mRNA stock was diluted in serial dilutions from a higher concentration solution to lower concentrations to reach 1.5 mg/ml in 15 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The results are illustrated in FIG. 69.

B: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 70.

C: Dynamic Light Scattering for LNP Size (red dots are PDI right y axis). Dialyzed LNPs were diluted to 6.25 ng/ul in 1×DPBS pH 7.4 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in 1×PBS at 25° C. with viscosity of 1.02 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 71

Example 21

Exemplary Lipids Assembled at ~25 mM Total Concentrations of Lipids and mRNA at 0.5 mg/ml for Rapid Microfluidic Mixing Show LNP Delivery Efficiency In Vitro. (TRANS-59)

Summary: LNPs were formulated using total lipid concentration of ~25 mM comprised of several ionizable-lipids and DSPC/Cholesterol/PEG-DMG (47:13:37:2 mol %). Each one of the lipids were solubilized in ethanol until a clear solution was observed. The four lipids were combined to obtain –25 mM total lipid concentration. Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed, and resuspended in nuclease-free water to reach concentrations of 5.5 mg/ml. Fluc mRNA stock was diluted in serial dilutions from a higher concentration solution to lower concentrations to reach 0.5 mg/ml in 25 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 4×1 hr. LNPs were then diluted so that 32 ul contained 25-200 ng and 12K HEK293 cells were transfected with the same dose but manufactured at different concentrations in the microfluidic mixer.

A. Firefly Luciferase Assay for mRNA Delivery Efficiency. After 24 hours of transfection, transfected cells were conditioned to room temperature for 30 minutes prior the Firefly Luciferase Assay. Quantilum Recombinant Luciferase standard curve was prepared in 10% EMEM in 5-fold serial dilutions. 50 ul of each standard point from the range of $3.9\times10^{-5}$ mg/ml to $4.88\times10^{-3}$ mg/ml were included in the microplate as a positive enzyme activity control (data not shown) to maintain a linearity of 107 RLU/mg/ml. The ONE-Glo substrate, previously conditioned to room temperature for at least 4 hours, was added to each untransfected, transfected and Quantilum wells in a ratio 1:1. Assay plates were incubated for 3 minutes in darkness and immediately introduced into the Cytation 5 Cell Imaging Multi-Mode Reader (Biotek) to read luminescence. The results are illustrated in FIG. 72.

B: Ribogreen Assay for mRNA Encapsulation Efficiency. 1×TE Buffer and Triton Buffer (2% v/v in 1×TE Buffer) were added in duplicates into a black microplate per LNP. LNPs were diluted to 4 ng/ul in 1×DPBS pH 7.4 and added to each TE/Triton well in a ratio 1:1. Two standard curves were included in the Ribogreen Assay, one containing mRNA and 1×TE Buffer and other containing mRNA and Triton Buffer. Each one of these standard curves were used to calculate the mRNA concentration in each TE Buffer or Triton Buffer. This approach using two standard curves is more accurate for calculating the encapsulation efficiency and mRNA concentrations, in comparison to a single standard curve. Standards were included in the microplate after diluted LNPs were added to the plate. Microplates were incubated at 37° C. for 10 minutes to extract LNPs with Triton. Ribogreen reagent was diluted 1:100 in 1×TE Buffer and added to each well in a ratio 1:1. Microplates were immediately introduced into the Cytation 5 Cell Imaging Multi-Mode Reader (Biotek) to read Fluorescence (Ex485/Em528). The results are illustrated in FIG. 73.

C: Dynamic Light Scattering for LNP Size (red dots are PDI right y axis). Dialyzed LNPs were diluted to 6.25 ng/ul in Sucrose Buffer pH 7.5 and transferred into a quartz cuvette (ZEN2112) to measure size by Dynamic Light Scattering (DLS) in the Zetasizer Nano ZS (Malvern Panalytical) using particle RI of 1.45 and Absorption of 0.001 in Sucrose at 25° C. with viscosity of 1.1 cP and RI of 1.335. Measurements were made using a 173° Backscatter angle of detection previously equilibrated to 25° C. for 30 seconds in duplicates, each with 5 runs and 10 second run duration, without delay between measurements. Each measurement had a fixed position of 4.65 in the quartz cuvette with an automatic attenuation selection. Data was analyzed using a General-Purpose model with normal resolution. The results are illustrated in FIG. 74.

Example 22

Assembly of LNPs with total lipid concentrations 77 mM and mRNA concentration 1.5 mg/ml for Rapid Microfluidic Mixing shows LNP Delivery Efficiency in Vivo. (In Vivo-11)

Summary: LNPs were formulated using total lipid concentration of 77 mM comprised of several ionizable-lipids and DSPC/Cholesterol/PEG-DMG (47:13:37:2 mol %). Dual lipid stocks (ionizable/Cholesterol, DSPC/PEG-DMG) were solubilized in ethanol until a clear solution was observed. The four lipids were combined to get 77 mM total lipid concentration. Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 1.5 mg/ml in 20 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against 1×DPBS pH 7.4 for 6×1 hr. LNPs were then diluted so that 32 ul contained 25-200 ng and 12K HEK293 cells were transfected with the same dose but manufactured at different concentrations in the microfluidic mixer.

A: In vivo Firefly Luciferase expression of the Injection site in IM administration. 1 ug of total mRNA was injected in mice in intramuscular (I.M.) injections. Luciferin was administrated intraperitoneally at 4 hours post-injection and luciferase expression monitored by live animal imaging of the injection site at 4 hours. ROIs were calculated using the IVIS system. The results are illustrated in FIG. 75 and FIG. 76.

B: Ex Vivo Firefly Luciferase expression in IM administration. 1 ug of total mRNA was injected in mice in intramuscular (I.M.) injections. Luciferin was administrated intraperitoneally at 4 hours post-injection and luciferase expression monitored by live animal imaging at 4 hours. ROIs were calculated using the IVIS system. For Ex Vivo, organs were extracted and imaged immediately after In Vivo imaging. The results are illustrated in FIG. 77 and FIG. 78.

Example 23

Assembly of LNPs with Total Lipid Concentrations 77 mM and mRNA Concentration 1.5 mg/ml for Rapid Microfluidic Mixing Shows LNP Delivery Efficiency In Vivo. (In Vivo-13)

Summary: LNPs were formulated using total lipid concentration of 77 mM comprised of several ionizable lipids and DSPC/Cholesterol/PEG-DMG (47:13:37:2 mol %). Dual lipid stocks (ionizable/Cholesterol, DSPC/PEG-DMG) were solubilized in ethanol until a clear solution was observed. The four lipids were combined to get 77 mM total lipid concentration. Codon optimized firefly luciferase (Fluc) sequence was cloned into an mRNA plasmid (optimized 3' and 5' UTR and containing a 101 polyA tail) for co-transcriptional capping, in vitro transcribed using N1 methyl pseudouridine modified nucleoside and cellulose purified to remove dsRNA. Purified mRNA was ethanol precipitated, washed and resuspended in nuclease-free water to reach concentrations of 5.5 mg/ml. Fluc mRNA stock was diluted in serial dilutions from a higher concentration solution to lower concentrations to reach 1.5 mg/ml in 15 mM Sodium acetate buffer pH 4 keeping the NP ratio constant at 4, prior to mixing in the Spark NanoAssmblr (Precision NanoSystems), which allows high reproducibility in formulations using a microfluidic mixing technology. 16 μl Lipid Mix and 32 μl mRNA solution were mixed on Setting 3 and ejected into 48 μl 1×DPBS pH 7.4. The formed LNPS were then diluted into an additional 96 μl 1×DPBS pH 7.4. LNPs were then dialyzed against Sucrose Buffer pH 7.5 for 6×1 hr. Frozen LNPs were kept at −80 C for In Vivo injections. LNPs were then diluted so that 32 ul contained 25-200 ng and 12K HEK293 cells were transfected with the same dose but manufactured at different concentrations in the microfluidic mixer.

A: In vivo Firefly Luciferase expression of the injection sites in IM administration. 1 ug of total mRNA was injected in mice in intramuscular (I.M.) injections. Luciferin was administrated intraperitoneally at 4 hours post-injection and luciferase expression monitored by live animal imaging at 4 hours. ROIs were calculated using the IVIS system. The results are illustrated in FIG. 79 and FIG. 80.

B: Ex Vivo Firefly Luciferase expression in IM administration. 1 ug of total mRNA was injected in mice in intramuscular (I.M.) injections. Luciferin was administrated intraperitoneally at 4 hours post-injection and luciferase expression monitored by live animal imaging at 4 hours. ROIs were calculated using the IVIS system. For Ex Vivo, organs were extracted and imaged immediately after In Vivo imaging. The results are illustrated in FIG. 81, FIG. 82, and FIG. 83.

Example 24

Figure 84A:
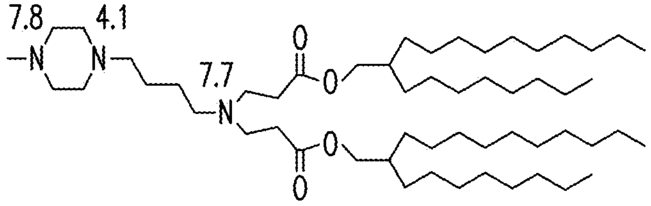
Figure 84A:
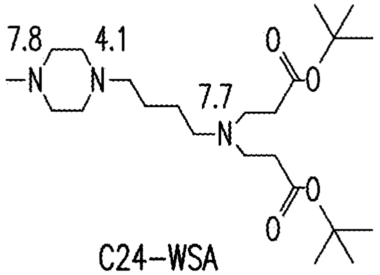
Figure 84A:
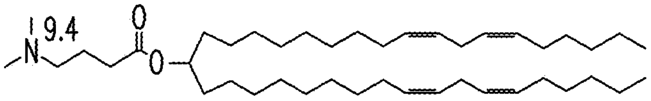
Figure 84A:
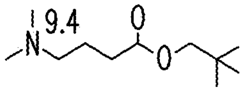
Figure 84B:
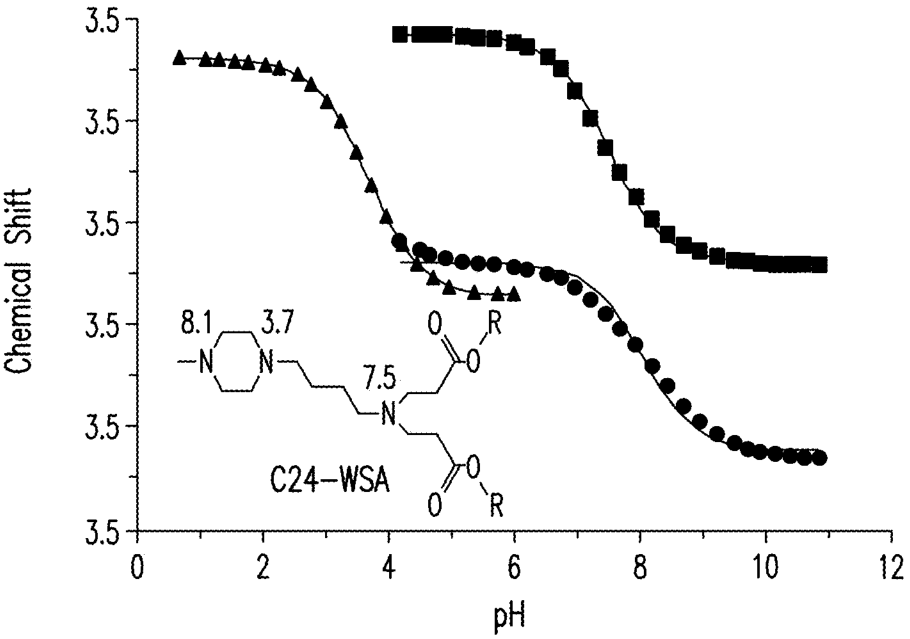
Figure 84C:
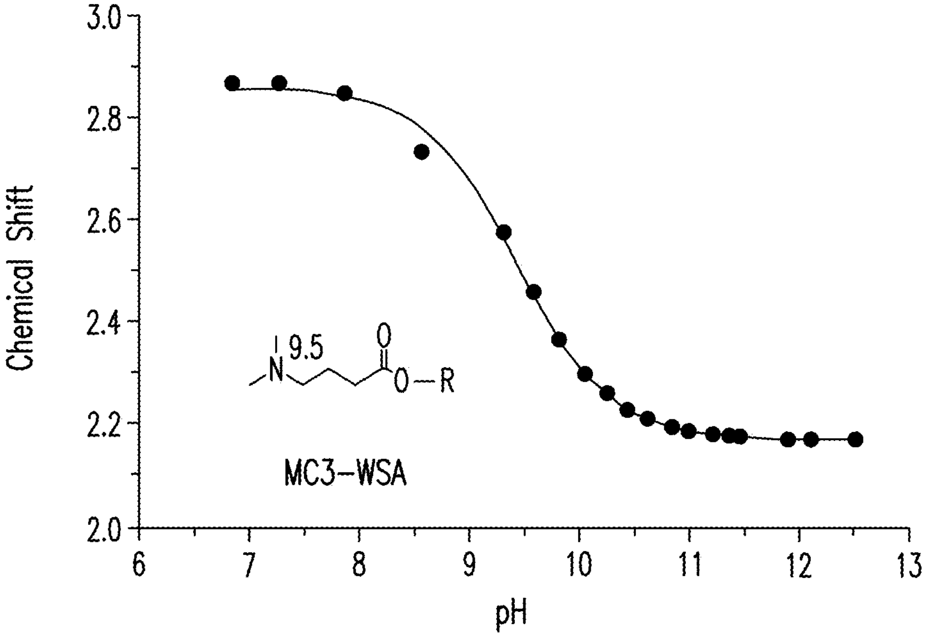
Figure 84D:
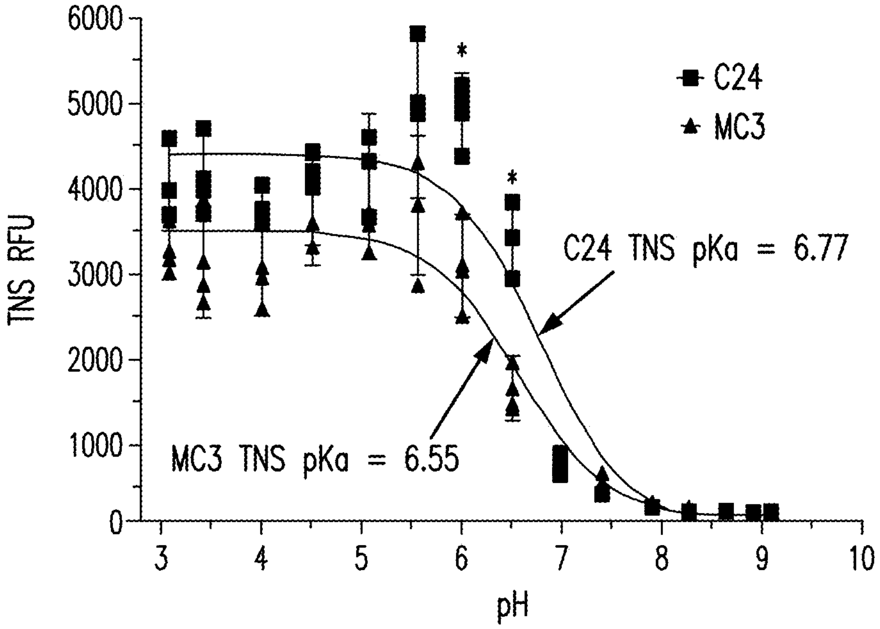
Figure 84E:
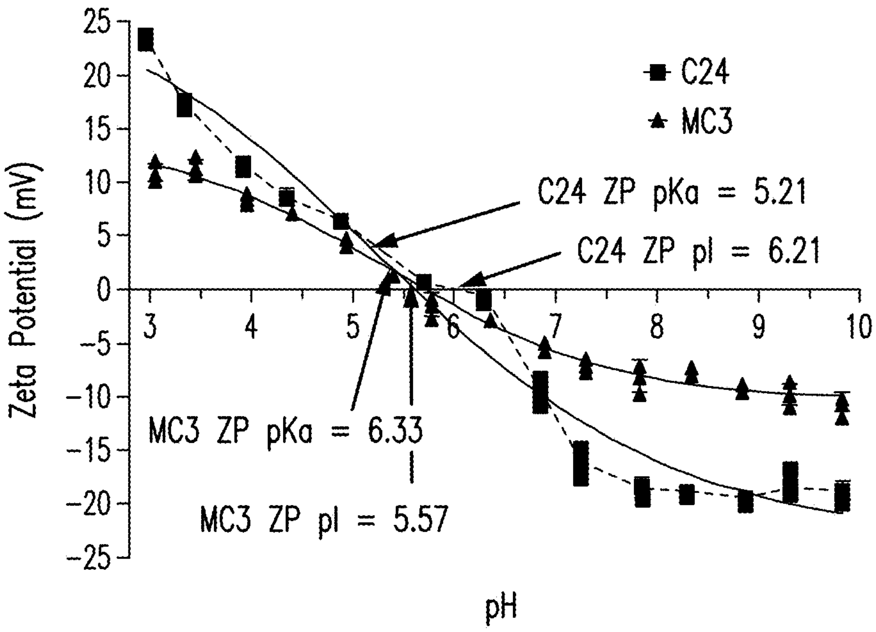

Trivalent Head Group of C24 Ionizable Lipid Displays Molecular and LNP Ionization Properties that Augment Protonation in the Endosomal pH Range The initial screening of our ionizable lipid design space included more than 100 head groups, 10 linkers and 50 alkyl tails that combine for over 50,000 potential ionizable lipid candidates. We calculated aqueous phase pKas for ~500 candidates that sampled this design space and selected several head groups for synthesis with acrylate bearing alkyl tails using a synthetic procedure that involved only 2 reactions and one catalyst versus more than 5 reactions and 7 catalysts for the ionizable lipids in the current COVID-19 mRNA vaccines. The simplicity of the reaction scheme resulted in much fewer purification steps, much shorter synthetic time, and over 80% yield producing an estimated 10 fold reduction in cost that could facilitate global vaccination campaigns. More than 30 candidate ionizable lipids were initially synthesized and characterized physicochemically and for certain biological performance indicators resulting in the selection of C24 (FIG. 84*a*) for further investigation in the current study. C24 bears a trivalent 4-methyl-1-piperazinebutanamide head group with theoretical aqueous phase pKas ranging from 4 to 8, two of which were close in predicted values (7.7 and 7.8). We synthesized a water soluble analogue (C24-WSA) and measured the pKa of each nitrogen using an established 1H NMR method20 confirming theoretical pKas to within 0.4 units (FIG. 84*b*). A slightly stretched deviation from an ideal Henderson-Hasselbalch behavior was observed for the terminal nitrogen (pKa 8.1, red in FIG. 84*b*) consistent with an interaction with the nitrogen atom with a slightly lower pKa (7.5 in FIG. 84b) that protonates almost simultaneously. This observation also indicates the potential for proton co-ordination between these two sites and the formation of a dative bond during initial protonation stages. NMR analyses of the water soluble MC3 analogue revealed a pKa of 9.5 (FIG. 84*c*) that is very similar to the predicted value of 9.4 (FIG. 84*a*). Protonation of LNPs made with C24 and MC3 was assessed using the TNS dye-binding assay that measures surface charge and with zeta potential by electrophoretic mobility that measures net charge of the LNP, as we described recently. The TNS dye-binding assay revealed a higher pKa for C24 (6.77) than MC3 (6.55) and a larger increase in surface protonation when pH drops from 7.4 to 6 (4517 versus 2559 RFU in FIG. 84*f*) indicating greater surface protonation in the endosomal pH range for C24 versus MC3. The lower pH limit in calculating endosomal protonation was taken as 6 for the TNS dye-binding assay since there is no change in surface charge below this pH. Electrophoretic mobility measurements, in contrast to the TNS dye-binding assay, measure net charge of the LNP and show broader changes in LNP net charge reflected by zeta potential increasing down to pH 3 (FIG. 84*e*). MC3 followed very closely the behavior of the extended Henderson-Hasselbalch model originally proposed for polyelectrolytes34 since it accounts for ionization-state-dependent pKa of closely interacting ionizable sites such as the thousands of dimethylamine MC3 head groups that are in close proximity within the LNP. The extended Henderson-Hasselbalch analyses revealed a zeta potential pKa of 5.33 and a pI of 5.57 for the MC3 LNP (FIG. 84*f*). The ionization behavior of the C24 LNP was more complex where a rapidly rising zeta potential occurred from pH 7.4 to pH 6 corresponding to simultaneous protonation of 2 of the 3 nitrogens in the head group with aqueous phase pKas of 8.1 and 7.5 (FIG. 84*b*) below which the zeta potential continued to rise with the contribution of the central nitrogen with a pKa of 3.7 (FIG. 84*b*). This multiprotic ionization behavior for C24 was not well represented by the extended Henderson-Hasselbalch model (dashed versus solid red line in FIG. 84*e*) that resulted in a zeta potential pKa of 5.21 and pI of 6.12 (FIG. 84*f*). The calculation of zeta potential increase from pH 7.4 to pH 4.5 where endosomes are considered to fuse with lysosomes was higher for the C24 LNP than MC3 LNP (25.1 mV versus 14.3 mV in FIG. 84*f*) again indicating a greater level of protonation of C24 versus MC3 in the endosomal pH range. Taken together, the above analyses relate molecular protonation events on monoprotic versus multiprotic head groups to their protonation in the condensed LNP environment and demonstrates an approximately 2 fold increase in protonation of the C24 LNP versus MC3 in the endosomal pH range.

Figure 1:
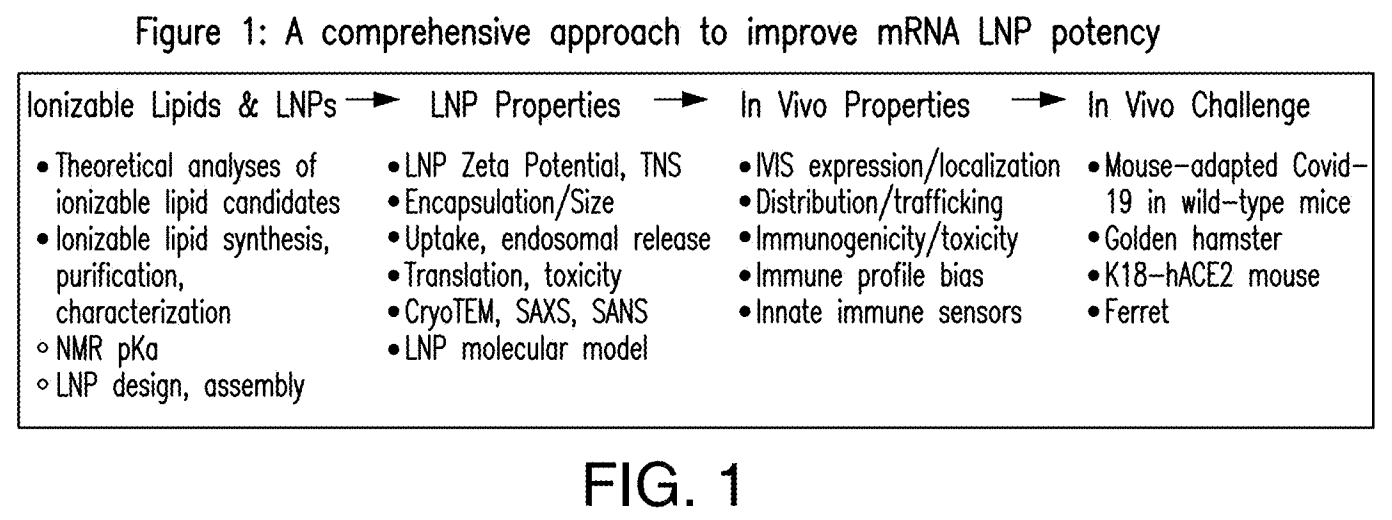
Figure 2A:
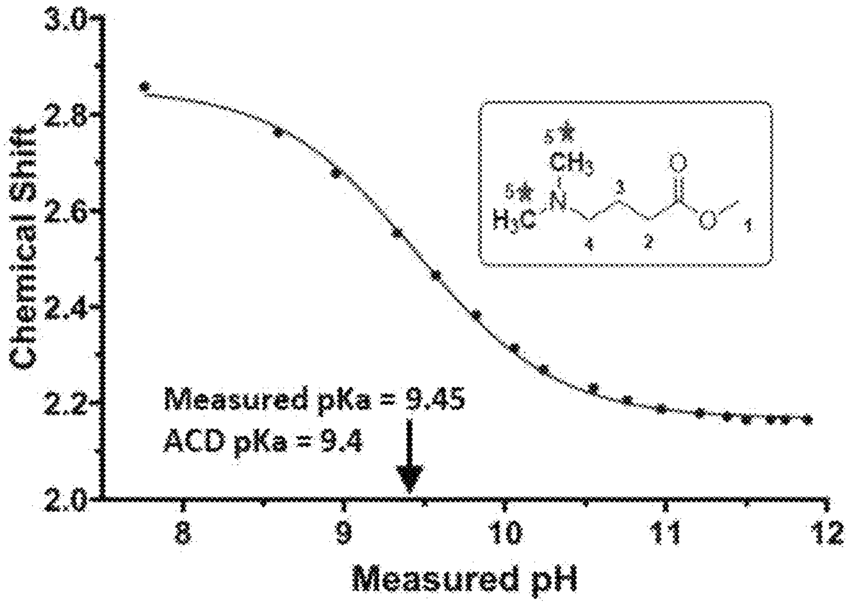
Figure 2B:
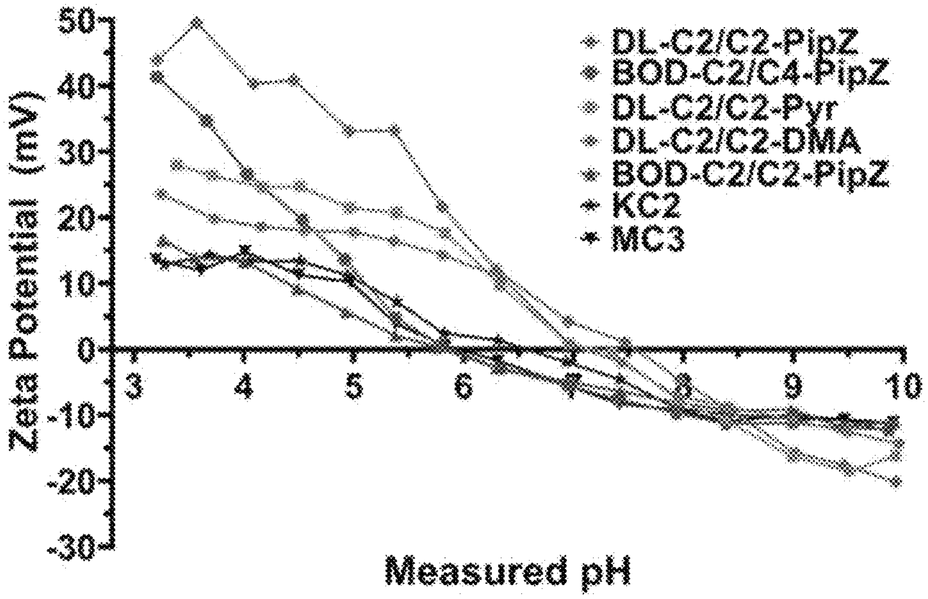
Figure 2C:
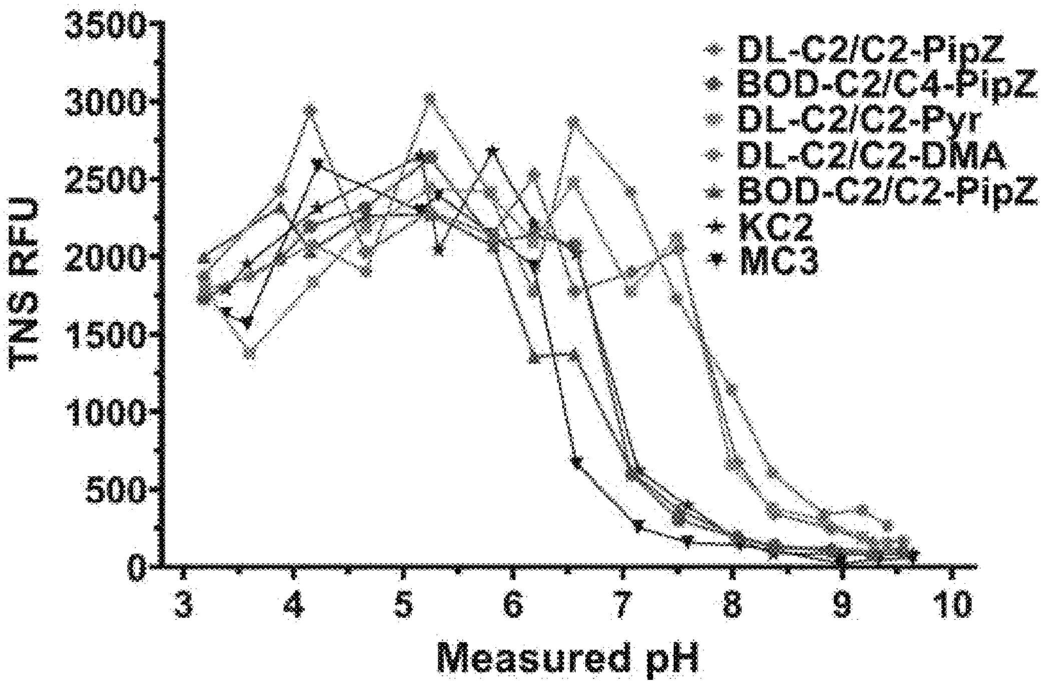
Figure 85D:
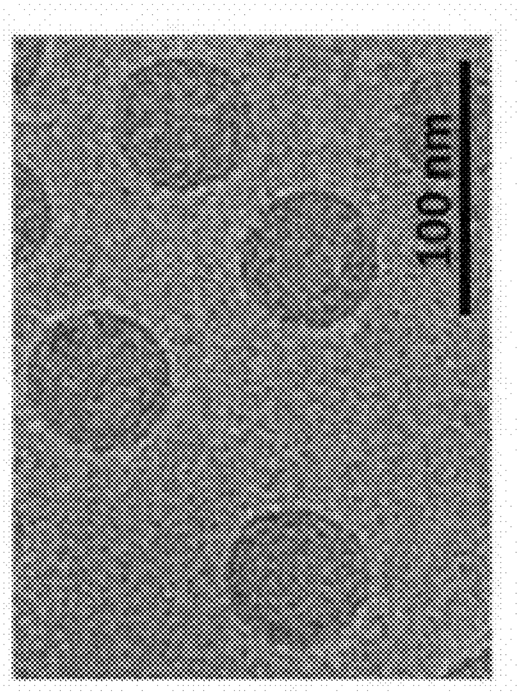

Size characterization showed C24 LNPs to be slightly larger than MC3 (80 nm versus 64 nm diameter in FIG. 85*a*) and to have a slightly lower fraction of mRNA that is inaccessible to ribogreen dye-binding (68% versus 79% in FIG. 85*b*). The fraction of mRNA that is inaccessible to ribogreen is often called encapsulation efficiency, however it is now known that the accessible portion is not a free fraction of mRNA since it may not migrate on a gel-based assay. We used our recently published molecular volume model of the LNP to estimate the number of copies of the Firefly Luciferase (FLuc) encoding mRNA in each LNP finding 4.5 copies in the MC3 LNP and 6 for the C24 LNP (FIG. 2*c*), on average, due to its larger size. CyroTEM analyses revealed a larger size for the C24 LNP consistent with DLS measurements and both LNPs had a similar structure showing a peripheral bilayer and an internal electron dense amorphous core (FIG. 85*d,e*).

Example 25

Luciferase Expression of C24 LNP is 4 Fold Higher than the MC3 LNP Upon Intramuscular Injection and Displays 6 Fold Less Off-Target Expression in Liver than MC3

Figure 86A:
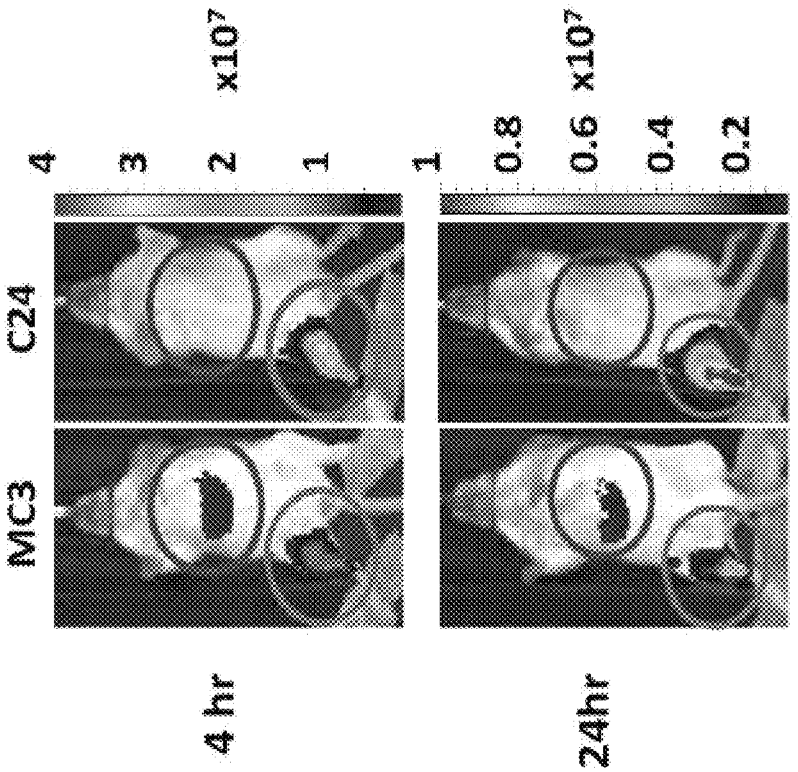
Figure 86B:
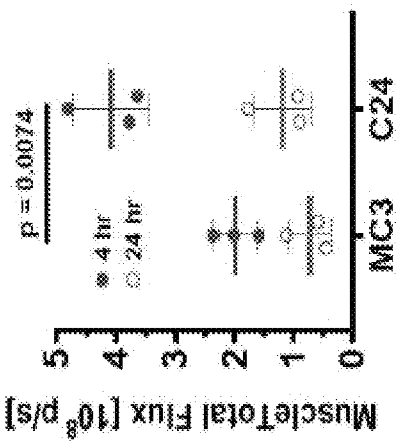
Figure 86C:
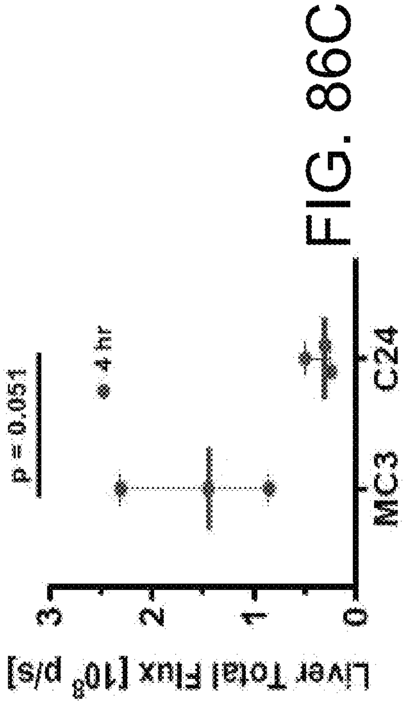
Figure 86E:
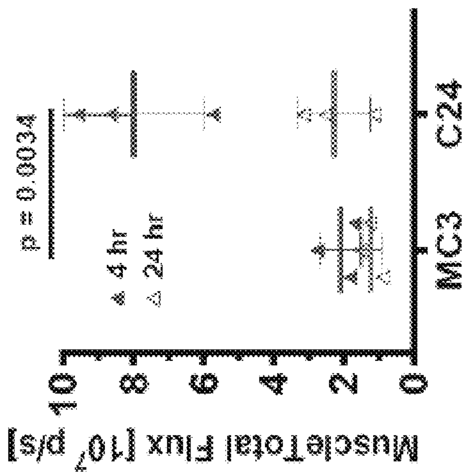
Figure 86D:
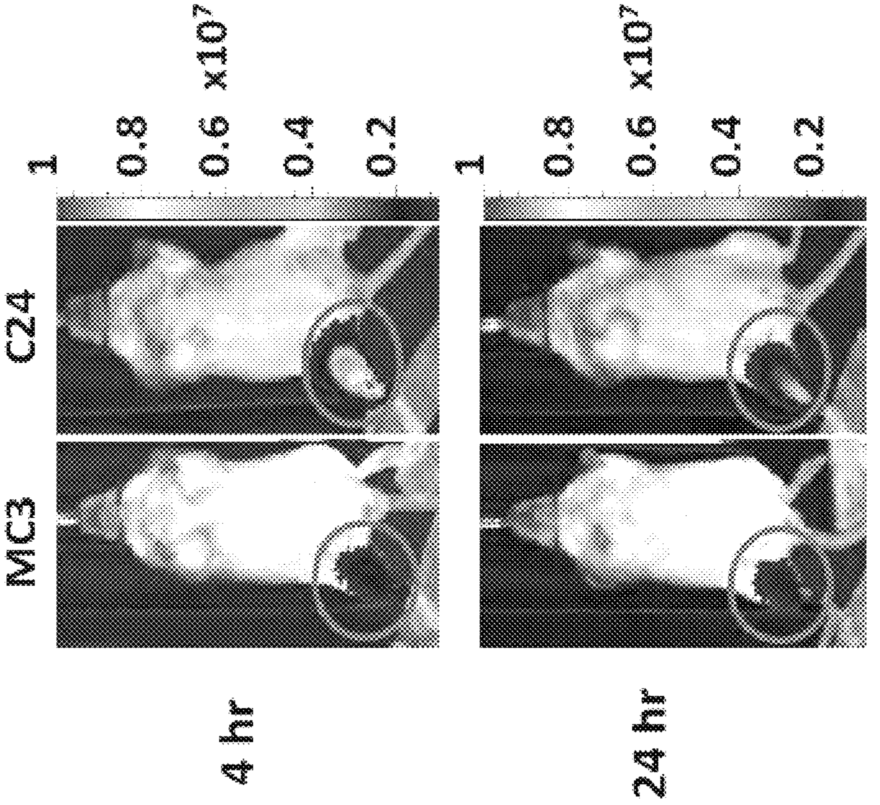
Figure 86F:
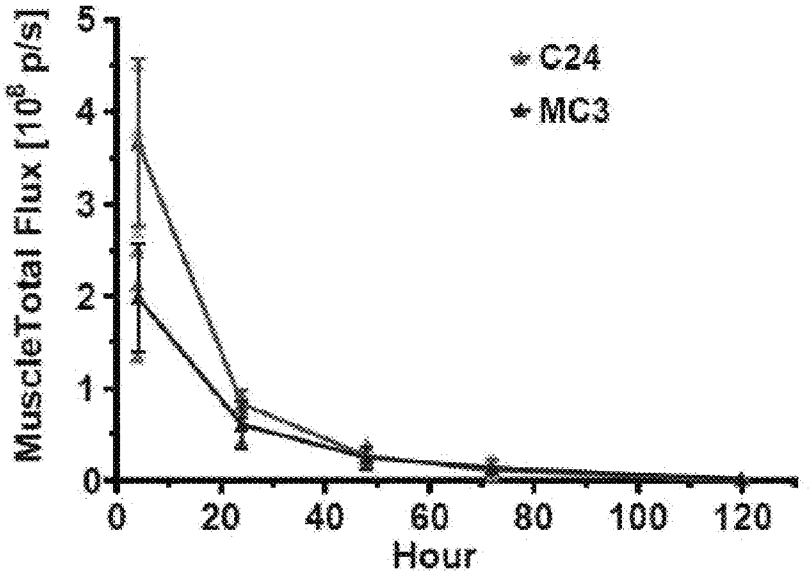

In vivo expression of the mRNA FLuc encoding reporter after intramuscular (IM) administration of the LNPs in mice at a relatively high dose of 5 μg mRNA showed 2 fold higher expression at the injection site for C24 at 4 hrs and 24 hrs (FIGS. 86*a* and 86*b*). Systemic biodistribution and off-target expression in liver was high for MC3 (FIG. 86). In contrast, C24 at this high dose virtually eliminated systemic biodistribution with a 6 fold reduction of off-target expression in liver compared to MC3 (FIG. 86C), an important finding since systemic reactogenicity and adverse events associated with mRNA-LNP vaccines may be linked to systemic biodistribution and off-target expression in sites other than the injection site and draining lymph nodes. The high off-target expression seen here for MC3 is consistent with previous findings for MC3 and regulatory documentation suggest it also occurs in rodent models for the current emergency authorized COVID-19 mRNA vaccines. The mechanism that significantly limits systemic biodistribution for the C24 LNP could be related to its rapid increase in surface charge and net charge near neutral pH (FIGS. 86*d* and 86*e*), since we found previously that a less negatively charged LNP was more locally contained upon IM administration. IM administration of Fluc-encoding mRNA-LNPs at a lower 0.5 μg dose that is more representative of vaccination doses in mice showed C24 to express 4 fold higher than MC3 at the injection site (FIGS. 86*d* and 86*e*). Off target expression could not be detected by IVIS at this 10 fold lower dose due to low signal to noise at the liver site. Daily imaging of mice showed an initial burst of expression lasting 48 hours with a gradual decline to baseline over 5 days (FIG. 86*f*).

Example 26

Figure 87A:
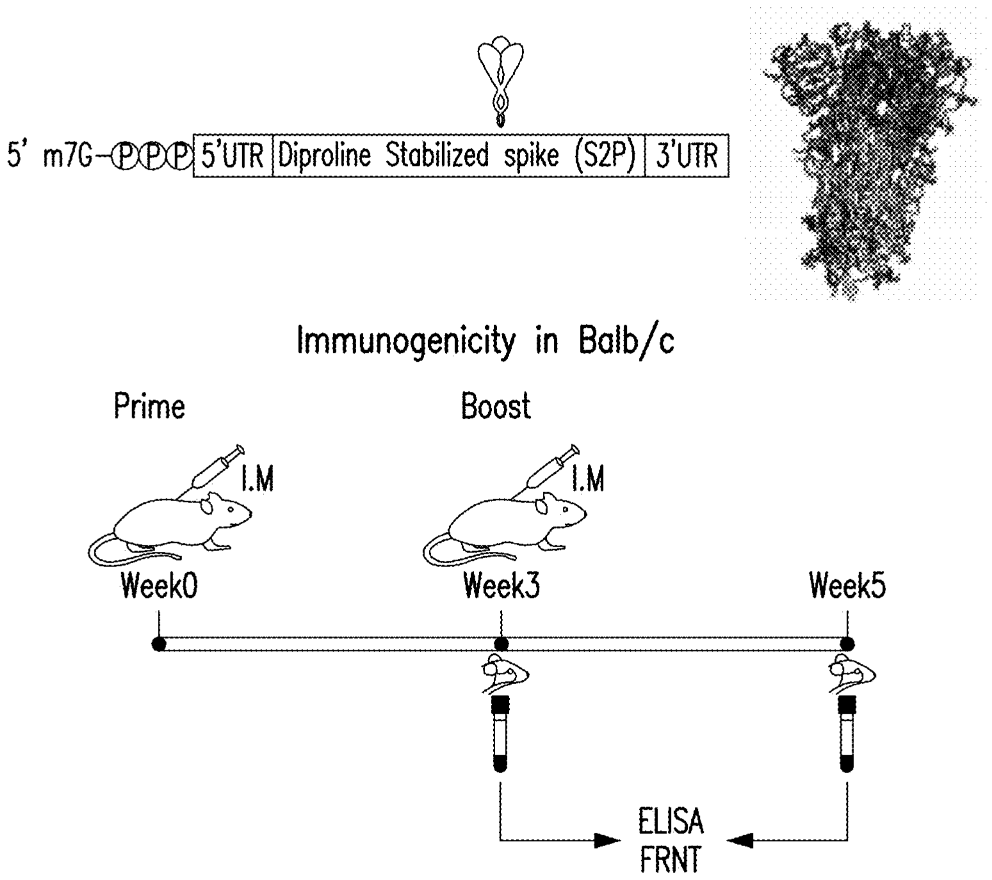
Figure 87B:
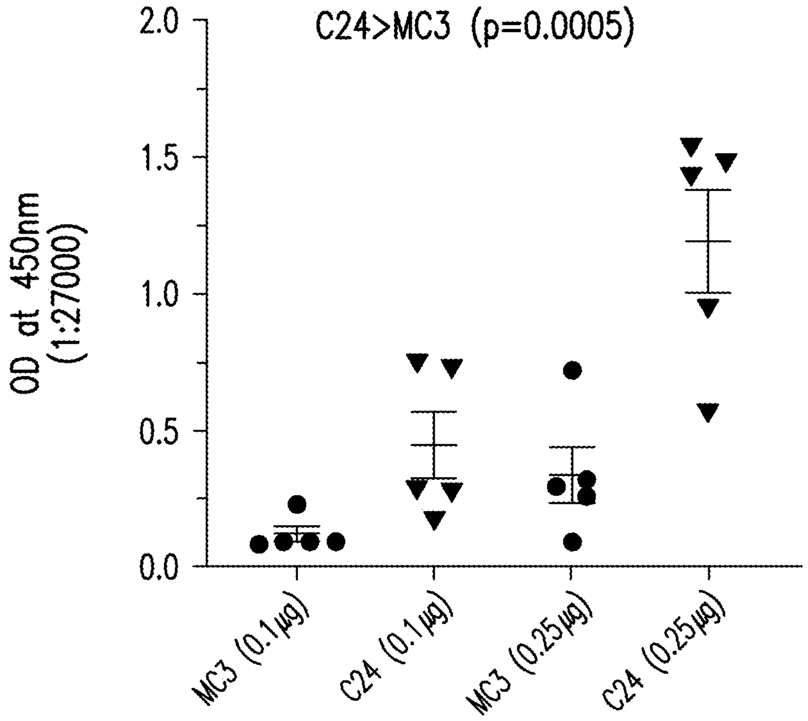
Figure 87C:
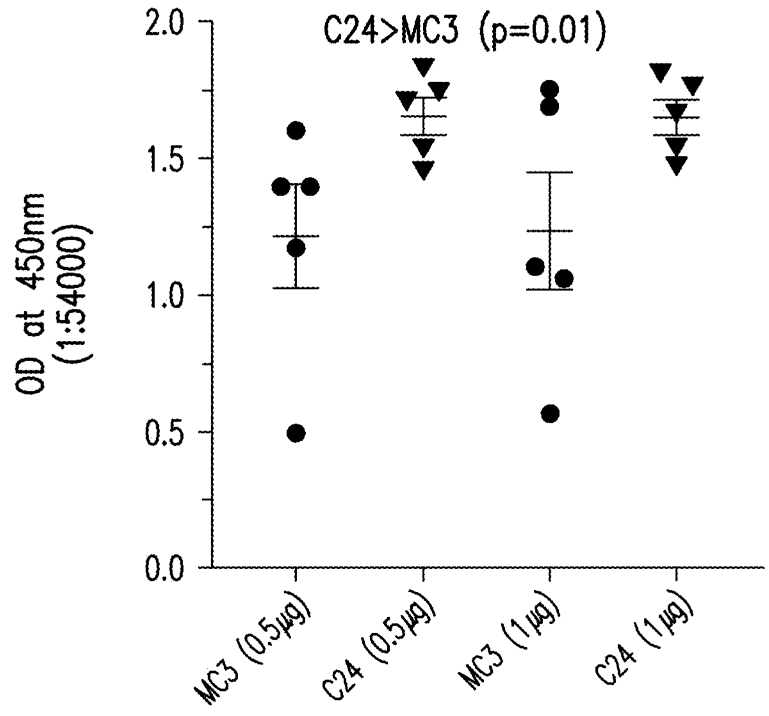
Figure 87D:
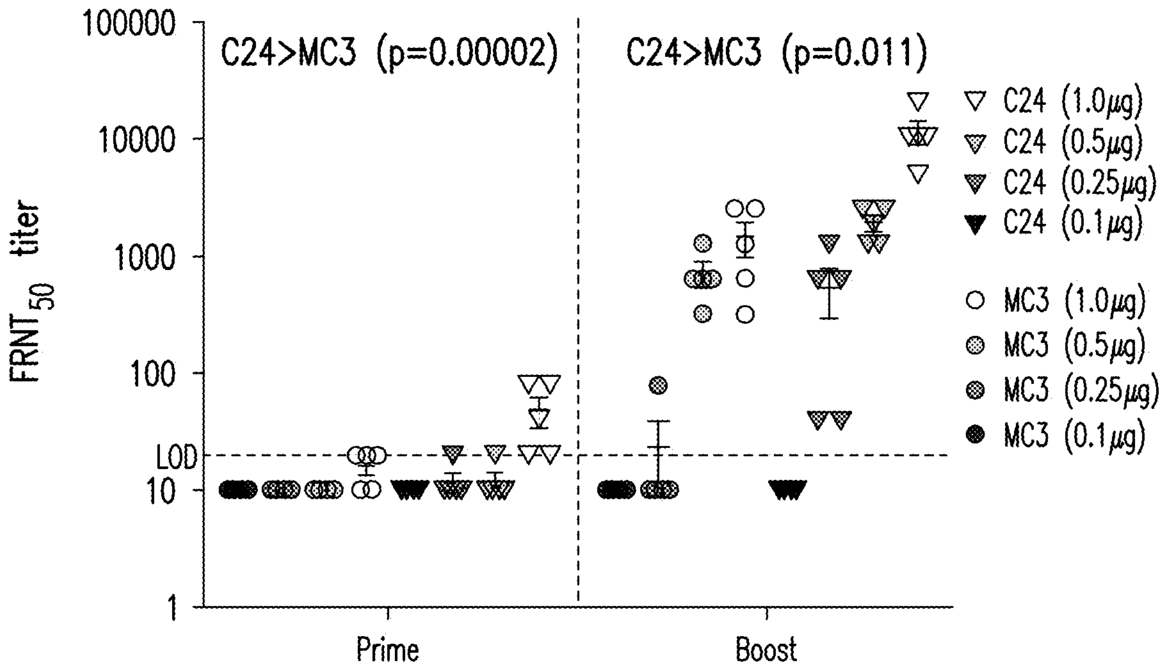
Figure 87E:
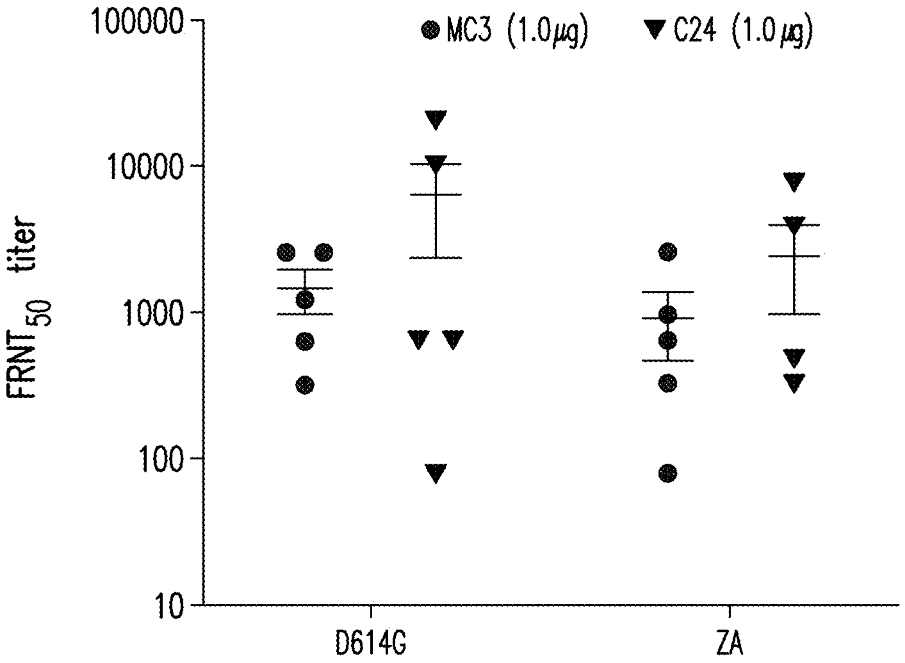

Immunogenicity Towards mRNA-Encoded SARS-CoV-2 Spike Protein Shows Higher Binding Titers and 10 Fold Higher Pseudoneutralization Titers for C24 LNP Versus MC3 LNP Against the Original Wuhan Strain and Against Two Prominent Variants LNPs were assembled with nucleoside-modified mRNA encoding for the diproline-stabilized membrane-bound spike protein immunogen (S2P) that is in the current emergency-authorized COVID-19 mRNA vaccines. We performed immunogenicity studies in Balb/c mice by IM administration of two immunizations with dose ranging from 0.1 μg to 1 μg with 3 weeks between prime and boost and serum analyses for binding antibodies to the receptor-binding domain of the spike protein, as well as neutralization assays to a SARS-CoV-2 pseudovirus. Optical density of the ELISA binding assay at transitional dilutions showed binding antibodies were significantly higher for the C24 LNP versus MC3 at all doses (FIGS. 87*a* and 87*b*). Neutralization assays to a SARS-CoV-2 pseudovirus showed C24 LNPs with significant ~10 fold increases of neutralization titers versus MC3 at all doses after the boost (FIG. 87C). A very similar assay done in Balb/c mice with an identical mRNA-encoded immunogen (other mRNA structures differed) in the SM-102 LNP of Moderna revealed titers similar to those of MC3 (1,000 at 1 pg) suggesting that the C24 LNP may also be more potent than the SM-102 LNP. The 1 μg dose delivered in the C24 LNP was also capable of inducing neutralization after a single dose where MC3 did not produce neutralization (Prime in FIG. 87*c*). Finally, we found that serum from animals vaccinated with the highest 1 pg dose were capable of neutralizing two variants of SARS-CoV-2 and that titers of C24 were higher than those of MC3 for the tested variants (FIG. 87*d*).

Example 27

Figure 88A:
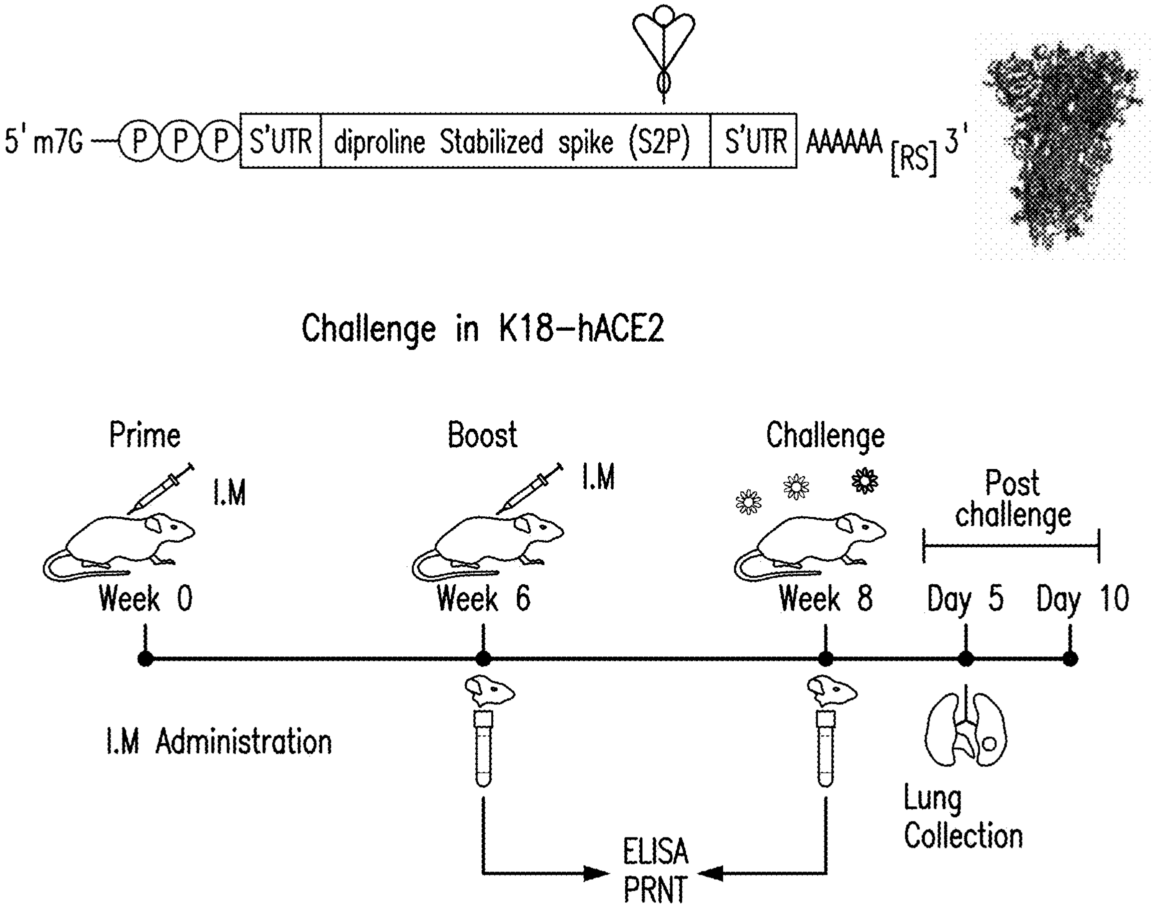
Figure 88B:
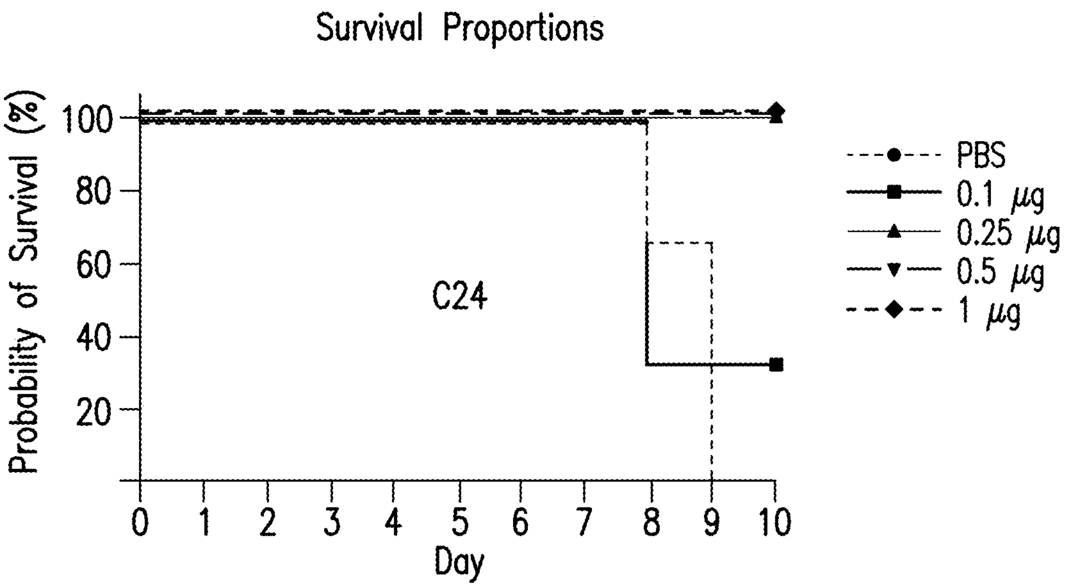
Figure 88C:
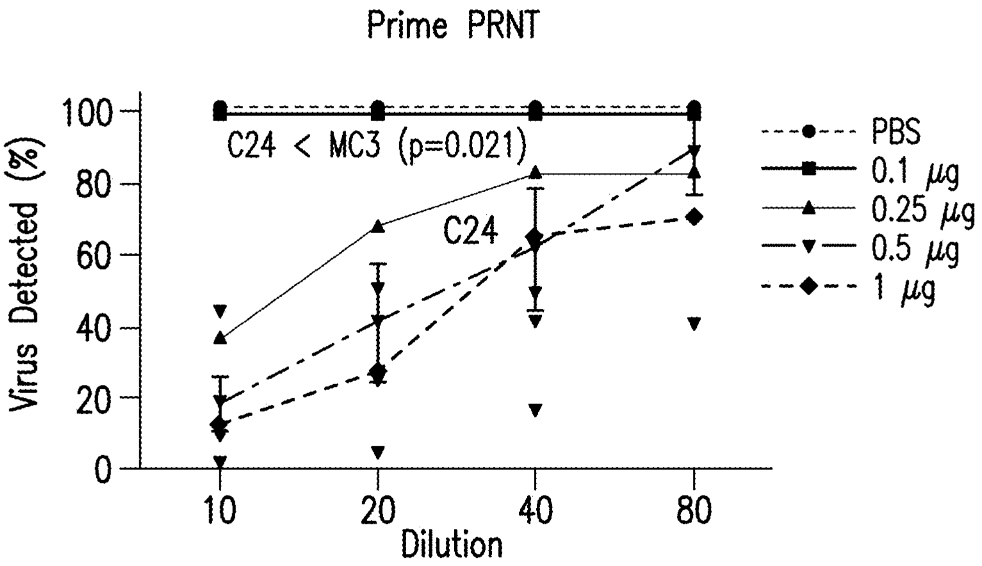
Figure 88D:
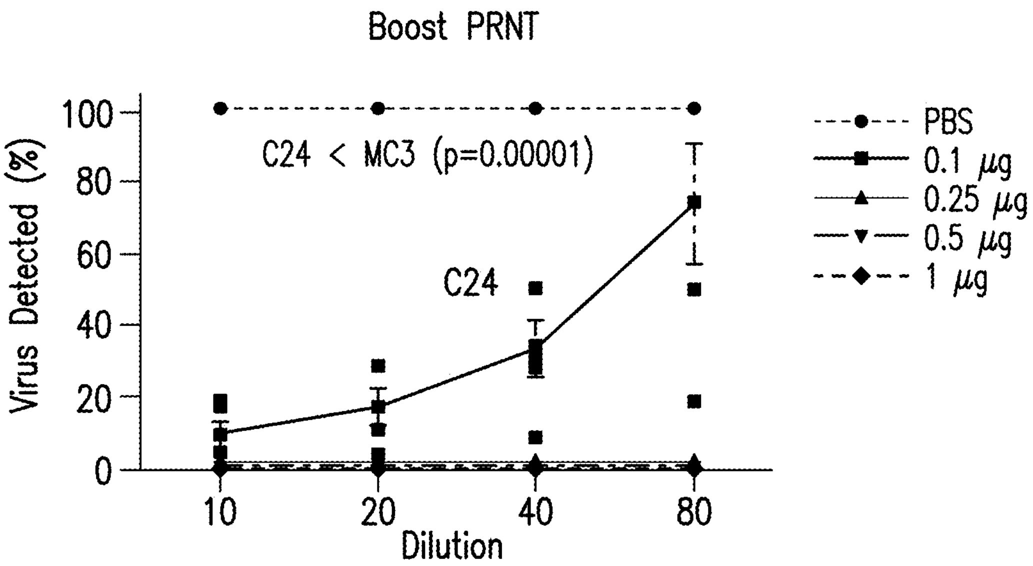
Figure 88E:
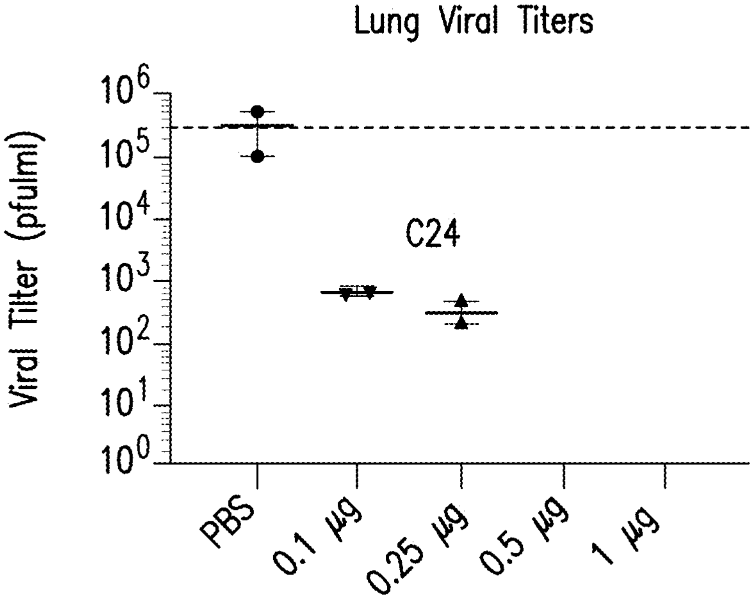
Figure 88F:
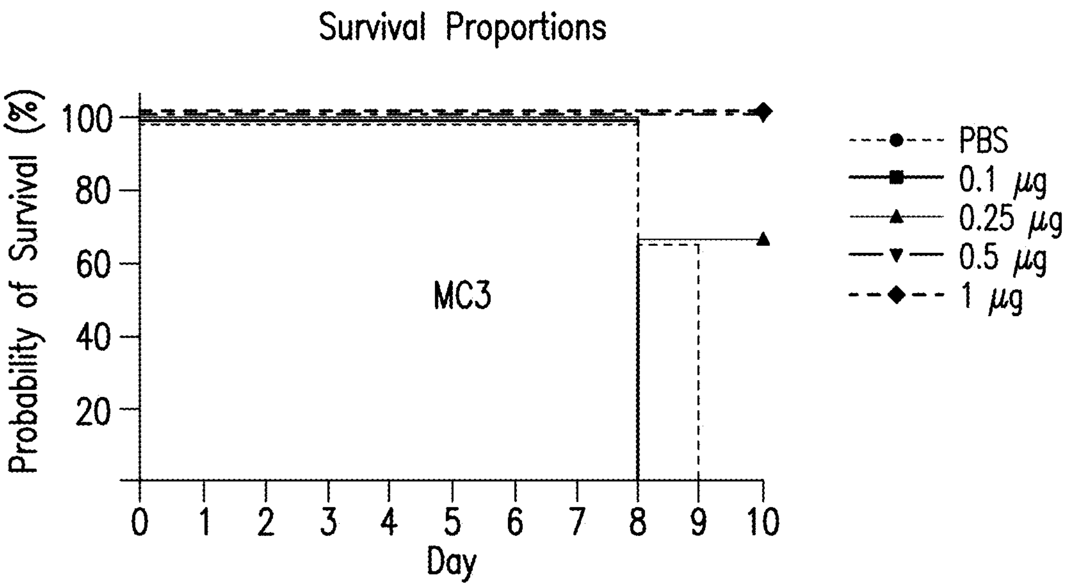
Figure 88G:
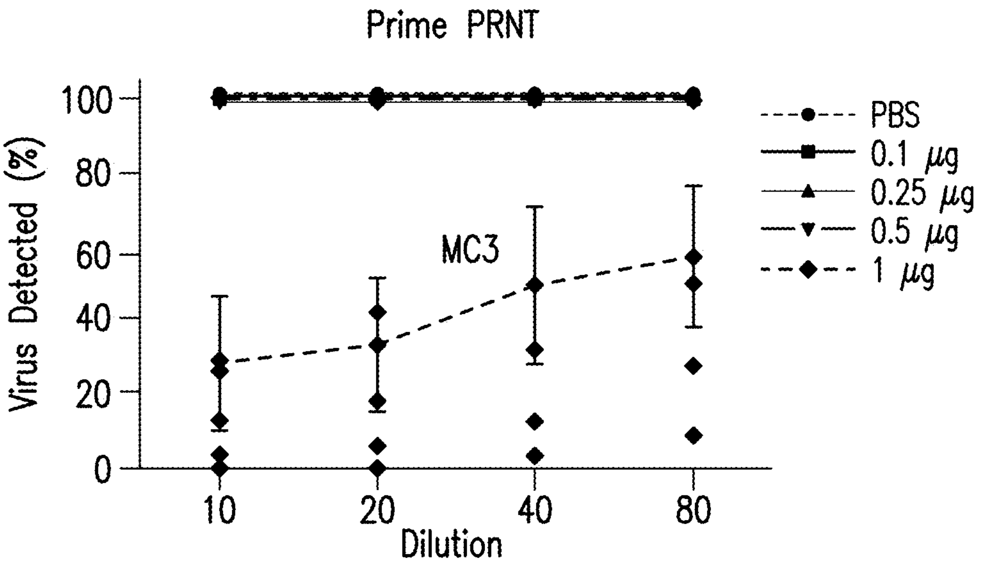
Figure 88H:
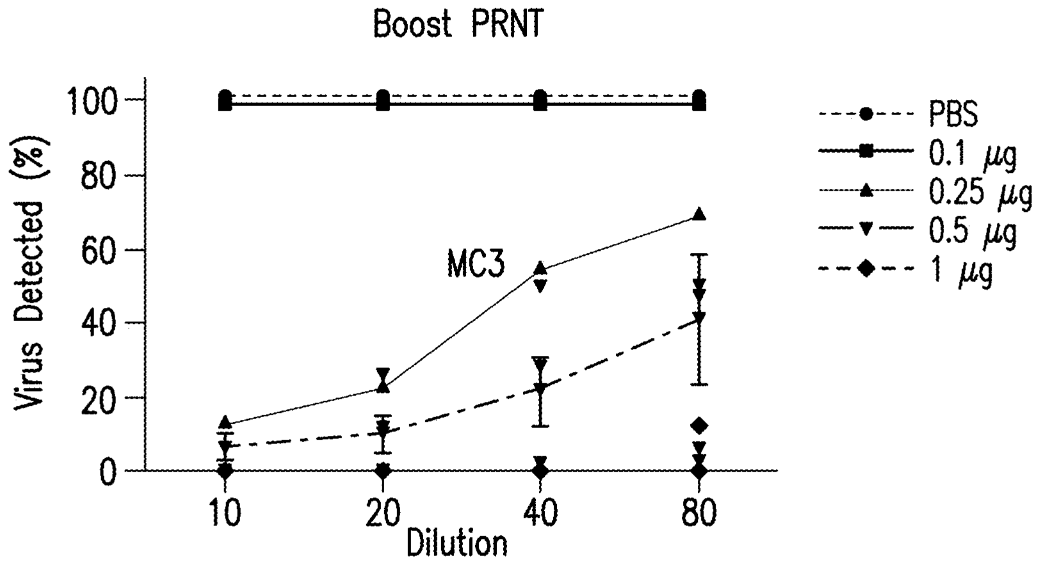
Figure 88I:
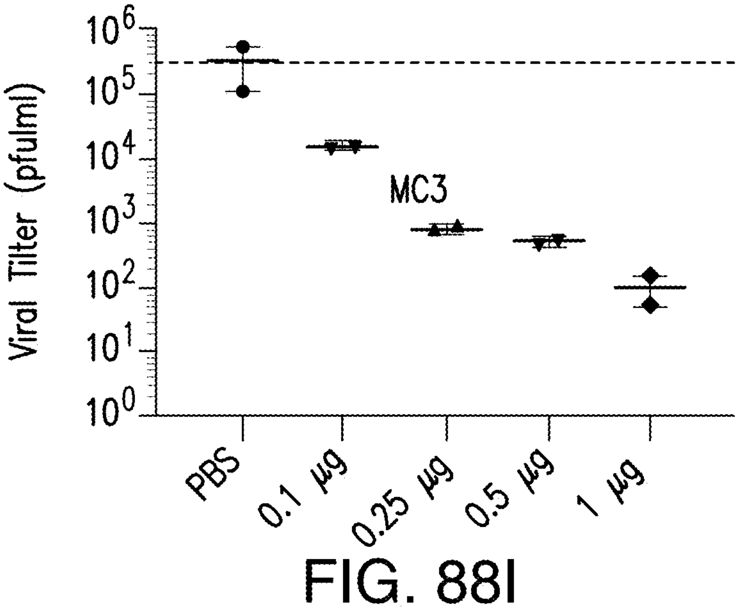

Lethal Challenge in the K18-hACE2 Mouse Reveals Complete Protection for the C24 LNP at a Low, 0.25 μg, Prime/Boost Dose of Nucleoside-Modified S2P mRNA and Complete Elimination of Lung Infection at 0.5 μg Dose Protection against lethal infection with SARS-CoV-2 after vaccination with mRNA-LNPs containing the S2P immunogen was investigated in the K18-hACE2 transgenic mouse bearing the human ACE2 receptor. C24 and MC3 LNPs containing the S2P immunogen were administered twice at mRNA dose levels ranging from 0.1 to 1 μg, each with a group of 5 animals, and then challenged with a lethal intranasal dose of the Italian strain (Isolate Italy-INMI1) of SARS-CoV-2. Two of the five animals in each group were sacrificed on day 5 to assess viral titers in the lung and the remaining 3 followed until euthanasia criteria were met. We found C24 mRNA LNPs completely protected mice at 0.25 μg with one of 3 animals at 0.1 μg dose also surviving versus MC3 where protection occurred at 0.5 μg dose (FIG. 88*a*). Neutralization titers in a plaque assay showed C24 LNPs achieved titers at 0.25 μg that were equivalent to those of MC3 at 1 μg dose after both the prime and the boost (FIGS. 88*b* and 88*c*). Lung viral titers examined 5 days after infection found C24 mRNA LNPs entirely blocked lung infection at 0.5 μg dose and that MC3 did not block infection entirely even at the highest 1 μg dose. Taken together, these results indicate that C24 LNPs achieve protection against infection at a dose-4× lower than MC3. The 0.25 μg protective dose applied twice in our study is 60× lower than the single effective dose (15 μg) found in an LNP38 containing a self-replicating mRNA for the spike protein and 10× lower than another single dose found with a different LNP also containing a self-replicating mRNA. Although these latter studies with self-replicating mRNA are single dose, the required dose is much greater and at a level that would be expected to generate unacceptable reactogenicity in humans. The study that is most similar to ours is prime/boost nucleoside modified approach using the S2P immunogen in the SM-102 LNP of Moderna where doses as high as 1 μg of the S2P immunogen in the SM-102 LNP were not capable of blocking lung infection, although they did reduce lung infection compared to PBS controls. The potency of the SM-102 LNP for blocking lung infection in mice therefore appears similar to that of MC3 in our study supporting with the similar potency we found for SM-102 and MC3 neutralization titers against a SARS-CoV-2 pseudovirus (both at ~1,000 FIG. 87*c*). Taken together these results suggest the C24 LNP system exceeds the potency of MC3 and of SM-102 LNP in mice models. Often, translation to non-human primates and humans is not predictable from mouse models so that results in larger animal models and clinical studies are required to further assess C24 mRNA LNP vaccines.

Example 28

Injection Site Inflammation for the C24 LNP is Milder than for the MC3 LNP

Figure 89D:
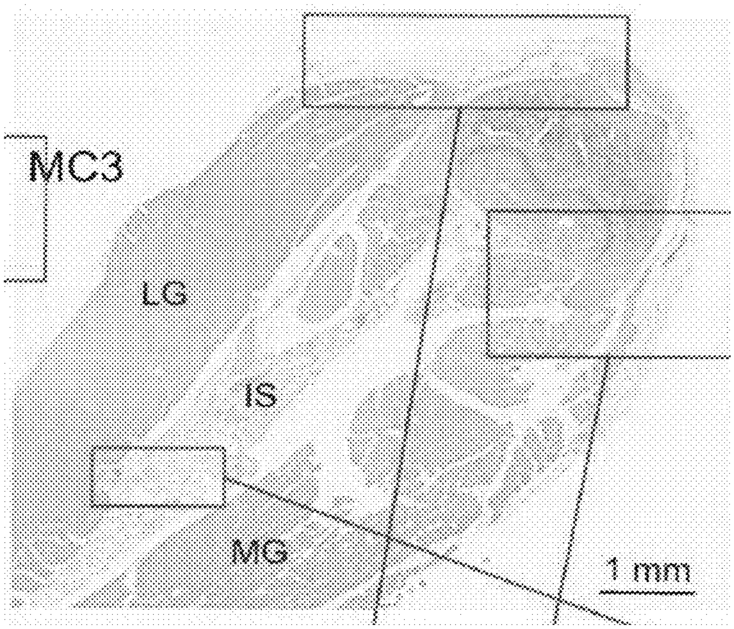
Figure 89E:
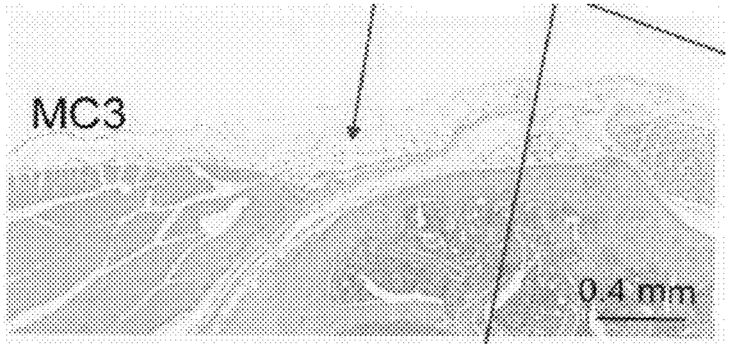
Figure 89F:
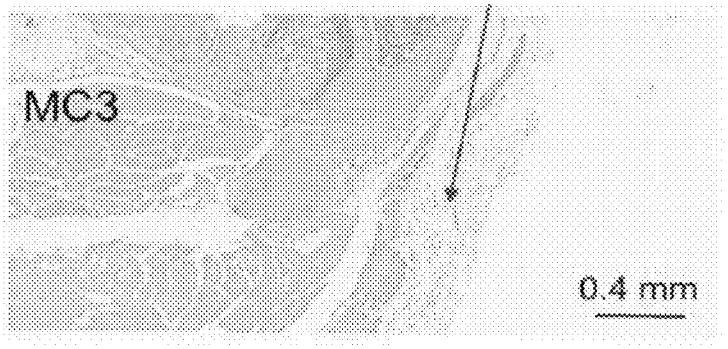
Figure 89G:
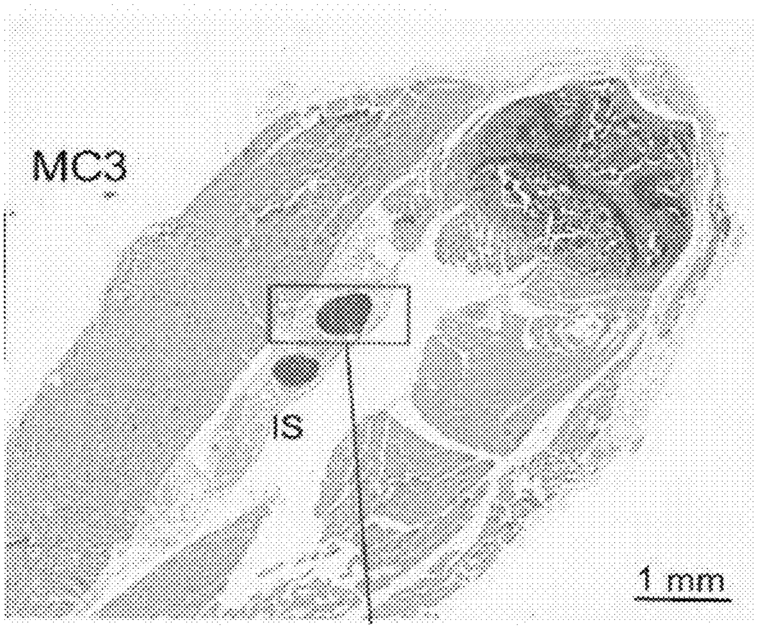
Figure 89H:
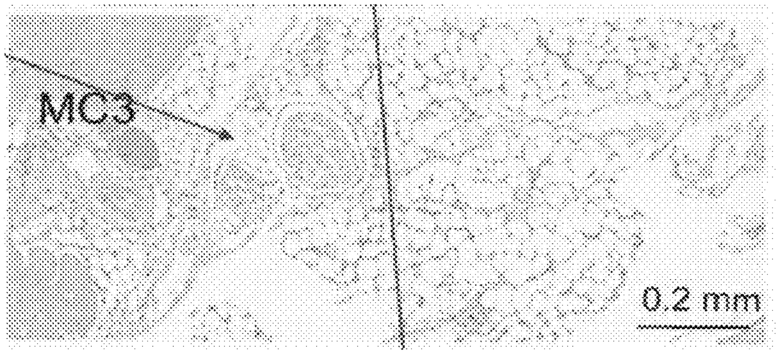
Figure 89I:
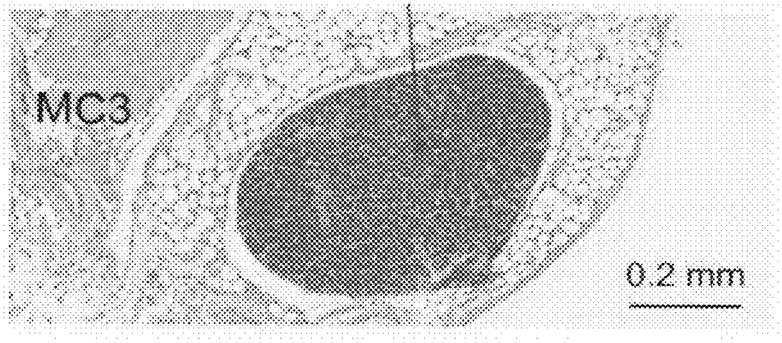

Injection site inflammation for MC3 mRNA LNPs was visually evident 24 hrs post IM administration by macroscopic swelling and a high level of stiffness of the injected leg. Injection site inflammation of C24 mRNA LNPs injected at a 5 μg dose was macroscopically lower than the swelling of MC3 LNP injected sites. We therefore fixed and processed the injected legs for standard histological analyses (Paraffin and H&E staining). We found that the injected 50 μL depot of mRNA LNPs was not inside the muscle tissue but was rather deposited mainly in the facial plane between the medial and lateral gastrocnemius (IS in FIGS. 89*a*, 89*d*, and 89*g*) and was difficult to distinguish from adipose tissue at these sites. This non-intramuscular site for the LNP depot was due to the standard 3 mm injection depth passing through the medial gastrocnemius that is –2 mm thick. The volume of the medial gastrocnemius is only ~150 μL41 so that the standard 50 μL LNP volume would not likely be contained inside the muscle even if the injection depth were reduced. In comparing C24 histology to MC3 we observed greater levels of inflammation for MC3, for example in the synovium which was multicellular and thickened for MC3 versus a normal appearance for C24 (FIG. 89*e*, 89*f* versus 89*b*, 89*c*). In addition to infiltration of leukocytes and vasculature at the injected site, we observed the presence of mixed cell-type lymphoid structures (FIG. 89 *a,g,i*) at 24 hrs post administration for both C24 and MC3 LNPs that were absent in control uninjected legs. These rapidly forming (in 24 hrs) lymphoid structures may play an important role in the immune response in mice and are being further characterized.

Example 29

Figure 90A:
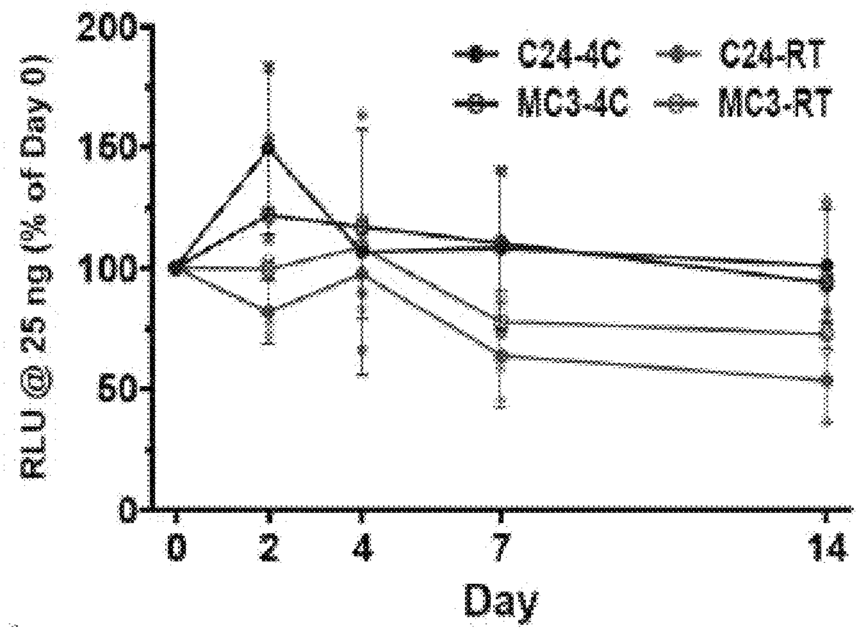
Figure 90B:
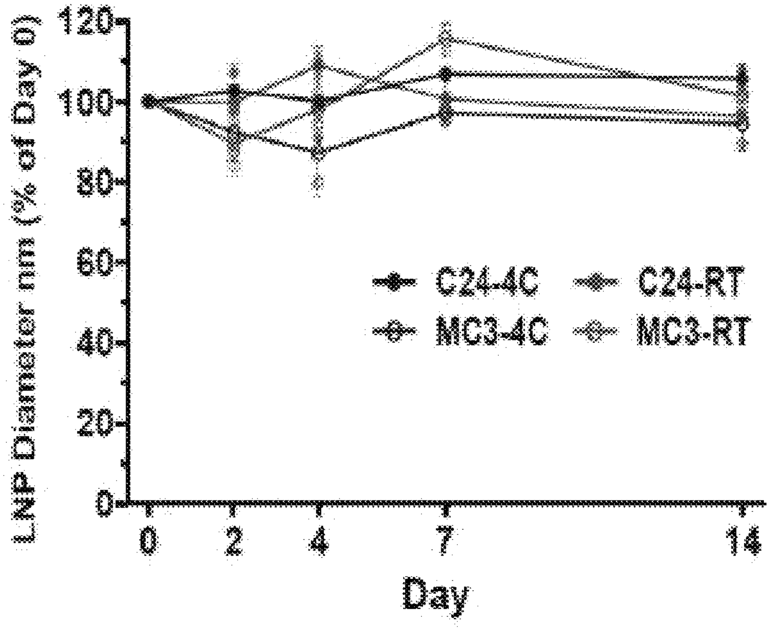
Figure 90C:
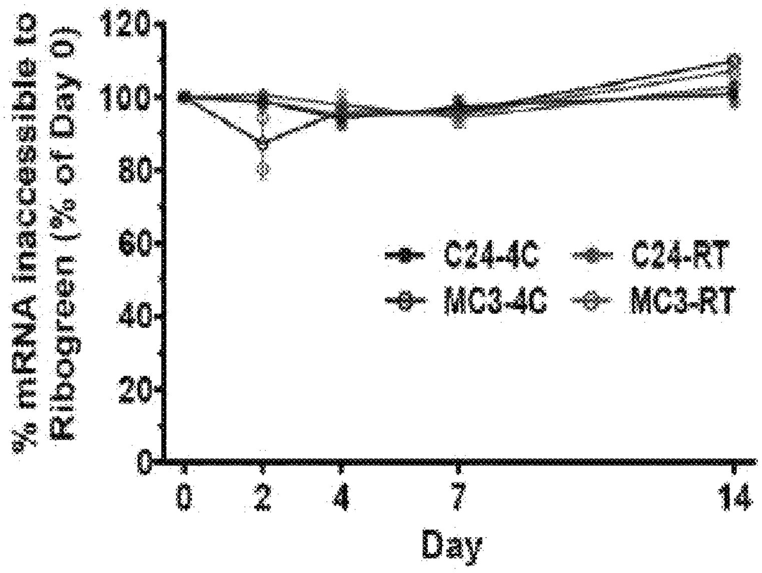
Figure 90D:
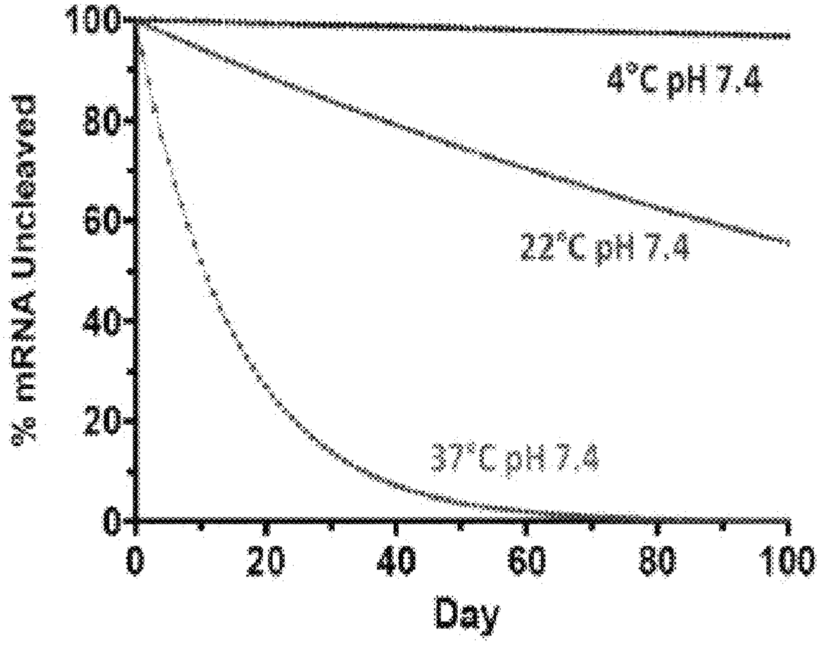
Figure 90E:
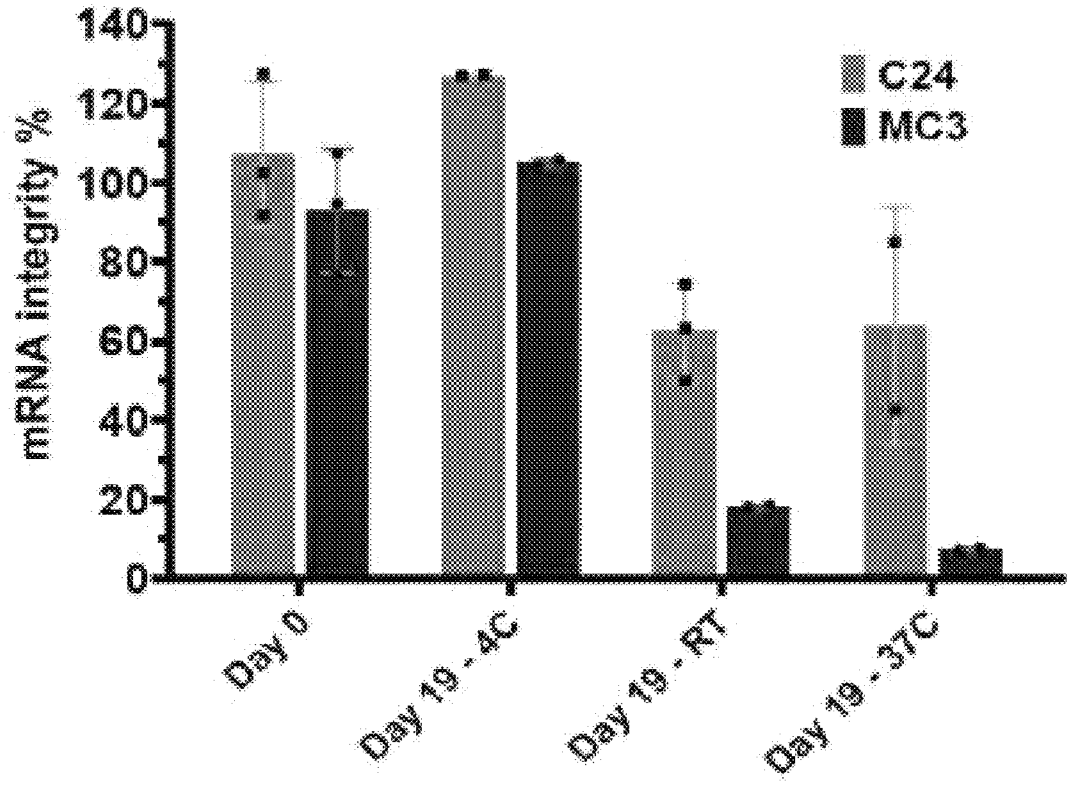
Figure 90F:
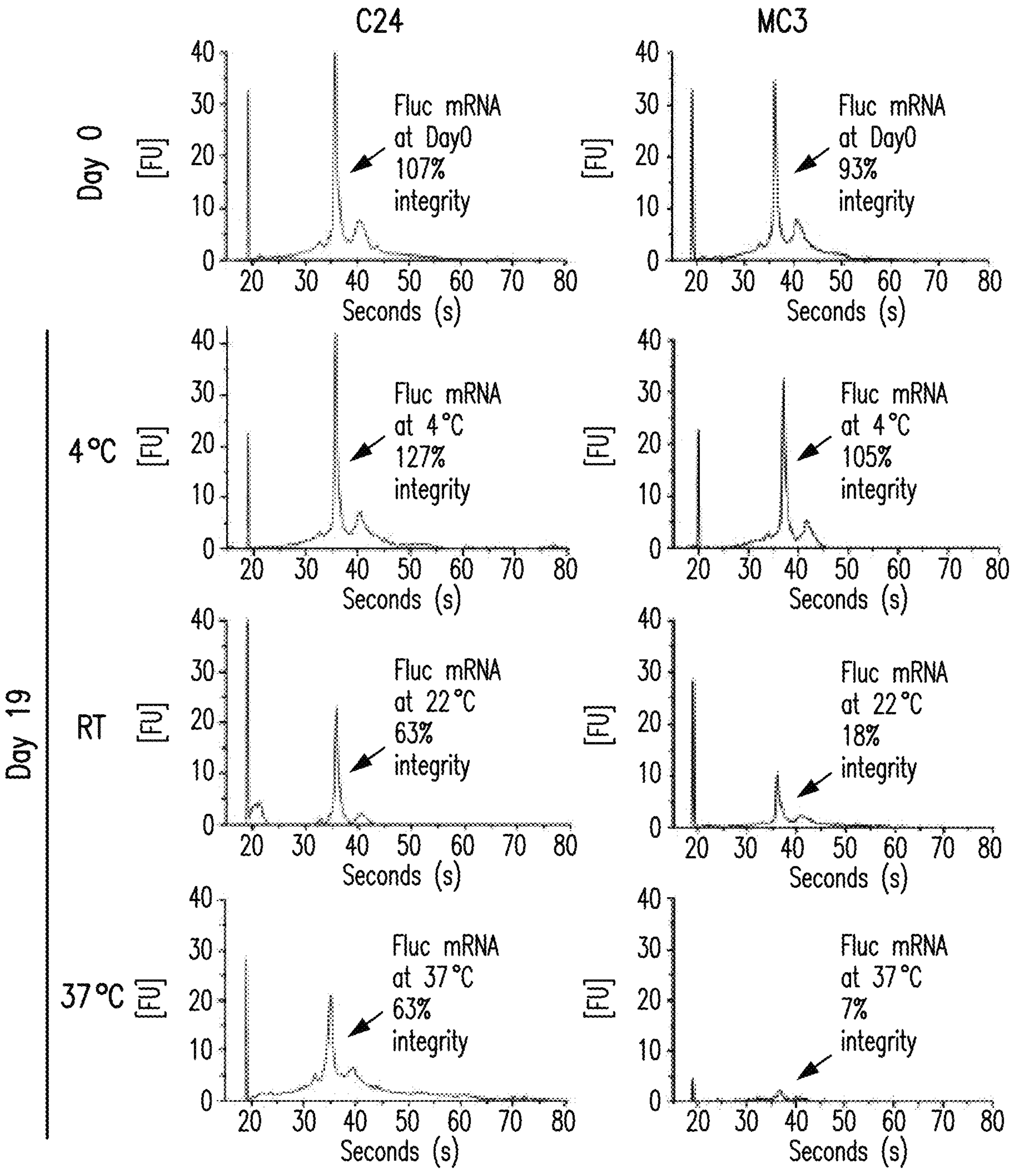

Storage of LNPs at 4° C. Reveal C24 LNPs are Stable for at Least 19 Days while Storage at Higher Temperatures Induces Loss of Bioactivity and mRNA Cleavage that is Consistent with the Phosphodiester Transesterification Reaction Mechanism of mRNA Cleavage mRNA LNPs generally require frozen storage and can be stored at refrigerated temperatures for up to 30 days according to instructions for use of the emergency authorized LNPs. Recent reviews have highlighted a nearly total lack of information on mechanisms contributing to instability during storage of mRNA LNPs although European regulatory documentation states that instability is temperature-dependent and involves a loss of mRNA integrity as well as changes in LNP size and generation of impurities. We therefore stored C24 and MC3 FLuc mRNA LNPs for 2 weeks at one of 2 temperatures, 4° C. or room temperature (RT≈22° C.) in PBS and tested bioactivity by Luciferase expression in vitro. We found that bioactivity was stable (to within the high variability of this bioactivity assay performed on cells seeded on different days) for both C24 and MC3 LNPs for 2 weeks when stored at 4° C. but declined by 20-40% when stored at room temperature (FIG. 90*a*). We did not find any change in LNP size or accessibility to Ribogreen for either storage temperature over 2 weeks (FIGS. 90*b* and 90*c*). We calculated the loss of mRNA integrity of the 2,061 nucleotide long FLuc over time using a model derived from data characterizing the temperature- and pH-dependence of the base-catalyzed phosphodiester transesterification and cleavage of mRNA backbone. The model predicted half-lives of 2,300 days at 4° C. and 125 days at 22° C. (RT) and 11 days at 37° C., all at pH 7.4 (FIG. 90*d*). mRNA backbone cleavage is thereby expected to be exquisitely sensitive to temperature and these trends are qualitatively consistent with previous findings for free mRNA. We then stored additional mRNA LNPs in PBS at 4° C. and at 22° C. (RT) as well as at 37° C. to accelerate degradation and extracted mRNA in chloroform/methanol to analyze mRNA integrity on a microfluidic electrophoresis device. We found mRNA integrity to be maintained for at least 19 days when stored at 4° C. while the higher temperatures could produce mRNA cleavage (FIG. 90*e*). mRNA integrity was estimated by the area under the curve (AUC) corresponding to the FLuc mRNA peak normalized to the day 0 value of C24 and MC3 LNPs taken together. The C24 LNP appeared to maintain higher levels of mRNA integrity than the MC3 LNP at the higher temperatures although sample numbers were too low to permit statistical analyses (FIG. 90*f*). Increased mRNA cleavage at higher temperatures is consistent with the model of based-mediated phosphodiester transesterification reaction mechanism of mRNA cleavage42 (FIG. 90*d*) but may exhibit a dependence on the LNP environment and on the specific structure of the ionizable lipid in the LNP. The LNP environment may for example accelerate mRNA degradation by the proton partitioning phenomena we found to be responsible for the difference in pKa of the ionizable lipid in aqueous media versus in the LNP. Namely, the higher proton solvation energy in the lipid environment will exclude protons and raise the pH in the LNP compared to the external aqueous phase and could thereby accelerate base-mediated mRNA cleavage as predicted by the pH-dependence of the model of base-catalyzed phosphodiester transesterification and cleavage of the mRNA backbone.

Example 30

Materials and Methods

Materials

DMG-PEG (MW 2000 Da) (DMG-PEG2000) was purchased from NOF America. Cholesterol was purchased from Combi Blocks. 1,2-distearoyl-sn-glycero-3-phosphocholine (18:0 PC, DSPC) was purchased from Avanti Polar Lipids. 4-Methyl-1-piperazinebutanamine was purchased from Enamine. Acryloyl chloride, sodium trimethylsilylpropanesulfonate (DSS) were purchased from Sigma Aldrich. 2-Octyl-1-dodecanol was purchased from BOC sciences. Tertiary butyl alcohol and neopentyl alcohol were purchased from combi-blocks. Unless otherwise noted, all reactions were carried out under ambient air atmosphere. All commercial reagents were used without further purification unless otherwise indicated. Bis(2-octyldodecyl) 3,3'-((4-(4-methylpiperazin-1-yl)butyl)azanediyl)dipropionate (C24), and water-soluble analogues of C24 and MC3 were synthesized and purified as described below. Microfluidic cartridges compatible with the Spark NanoAssmblr™ were purchased from Precision Nanosystems. 3M sodium acetate pH=5.5 was purchased from Thermofisher Scientific. The ONE-Glo Luciferase Assay System was purchased from Promega Corporation. Slide-A-Lyzer™ MINI Dialysis Device 0.5 ml (MWCO, 10 KDa), 20×TE Buffer, RNAse-free and Quanti-iT Ribogreen RNA reagent were purchased from Thermo Fisher Scientific. Triton X-100 and 6-(p-toluidino)-2-naphthalenesulfonic acid sodium salt (TNS) was purchased from Sigma. The firefly luciferase (FLuc) sequence was cloned into an mRNA production plasmid (optimized 3' and 5' UTR and containing a 101 polyA tail), in vitro transcribed using N1-methylpseudouridine modified nucleoside, co-transcriptionally capped using the CleanCap technology (TriLink) and cellulose purified45 to remove dsRNA. The prefusion di-proline stabilized SARS-CoV-2 Spike protein (S2P) sequence was codon optimized, and produced as described above. Purified mRNA was ethanol precipitated, washed, resuspended in nuclease-free water, and subjected to quality control (electrophoresis, dot blot, and transfection into human DCs). D-Luciferin (sodium salt) was purchased from REGIS technologies, INC. HEK293 cells were purchased from ATCC.

Synthesis of Ionizable Lipids and Ionizable Lipid Analogues

Solvents were purchased from Sigma Aldrich, Combi blocks, Oakwood chemicals, Alfa Aesar, VWR and Thermofisher. Anhydrous methylene chloride (DCM), anhydrous tetrahydrofuran (THF) and anhydrous DMF were purchased from Sigma Aldrich. Reactions were monitored using Opt. KMnO4 glass-based Silica Plates, F254 thin layer chromatography plates (TLC) and column purification was done using silica gel chromatography (TLG-R10014BK-323) purchased from Silicycle. NMR spectra were recorded on a Bruker 400 MHz Spectrometer using CDCl3, D20 (Sigma Aldrich), as d-solvents and internal standards (δ 7.26 for 1H NMR and δ 77.00 for 13C NMR). Solutions of 1 M NaOH and 1 M HCl were purchased from Sigma Aldrich. Four internal NMR standards, piperazine, imidazole, chloroacetic acid, and acetic acid, were purchased from Sigma Aldrich and were selectively used for in situ NMR pH measurements.

C24 Ionizable Lipid and Water-Soluble Analogue

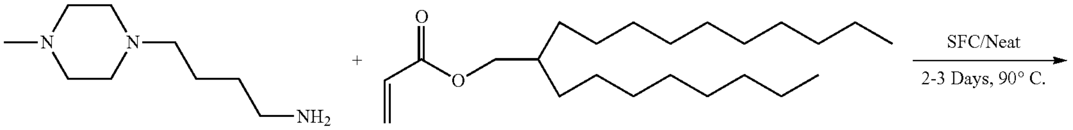

1 2

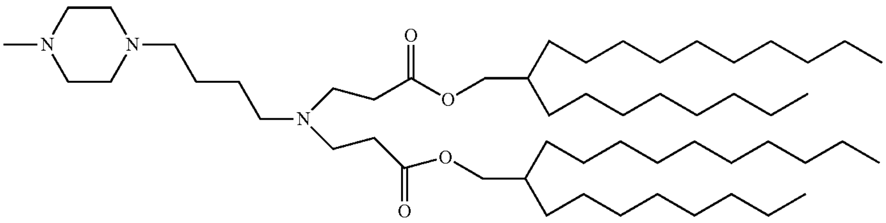

3

2-octyldodecyl acrylate2 (2) (3.4 mmol, 1.2 g, 1.48 ml) was added to an oven dried 5 ml biotage microwave vial and 4-Methyl-1-piperazinebutanamine (1) (1.31 mmol; 0.224 g) was added dropwise46. Solvent free conditions were maintained and the sealed microwave vial was stirred for 2-3 days at 90° C. Reaction progress was monitored by TLC (chloroform/methanol 9:1 v/v, can be visualized with iodine stain, and Phospomolybdic Acid stain) until complete consumption of 1. The crude product was purified on a silica gel column eluted with chloroform containing 0-5% methanol. Column fractions were analyzed by thin layer chromatography (TLC) and fractions containing pure product (Rf=0.3) were concentrated, to obtain product (bis(2-octyldodecyl) 3,3'-((4-(4-methylpiperazin-1-yl)butyl)azanediyl)dipropionate) as yellow oil (3). (0.77 g, 72% yield). 1H-NMR: (400 MHz, CDCl3, δ=7.26 ppm as standard): δ 3.95 (d, 6.0 Hz, 4H), 2.76 (t, 7.4 Hz, 4H), 2.49-2.40 (m, 12H), 2.34 (t, 7.2 Hz, 2H), 2.30 (s, 3H), 1.60 (s, br, 2H), 1.44-1.435 (m, 4H), 1.25 (m, 64H), 0.87 (t, 6.8 Hz, 12H). 13C NMR: (100 MHz, CDCl3, δ=77.0 ppm as standard): S 172.8 (C), 67.2 (CH2), 58.5 (CH2), 55.1 (CH2), 53.6 (CH2), 53.2 (CH2), 49.2 (CH2), 46.0 (CH3), 37.3 (CH), 32.6 (CH2), 31.94 (CH2), 31.92 (CH2), 31.2 (CH2), 30.0 (CH2), 29.7 (CH2), 29.67 (CH2), 29.60 (CH2), 29.38 (CH2), 29.35 (CH2), 26.7 (CH2), 25.2 (CH2), 24.7 (CH2), 22.7 (CH3).

C24-Water-Soluble Analogue

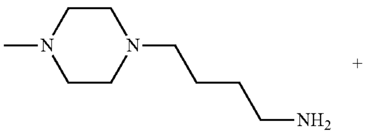

1

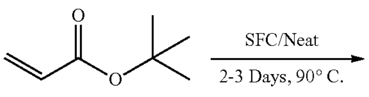

4

-continued

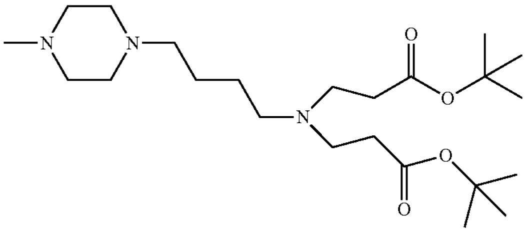

5

A mixture of 4-(4-methylpiperazin-1-yl)butan-1-amine (1) (1.16 mmol, 0.2 g) and tert-Butyl acrylate46 (4) (3.13 mmol, 0.40 g), were added to an oven dried 5 ml biotage microwave vial and solvent free conditions were maintained46. The sealed microwave vial was stirred for 2-3 days at 90° C. Reaction progress was monitored by TLC (chloroform/methanol 9:1 v/v, can be visualized with iodine stain, and Phospomolybdic Acid stain), until complete consumption of 1. The crude product was purified on a silica gel column eluted with chloroform containing 0-5% methanol. Column fractions were analyzed by thin layer chromatography (TLC) and fractions containing pure product (Rf=0.34) were concentrated, to obtain product as yellow oil (5). (0.30 g, 53% yield). 1H-NMR: (400 MHz, CDCl3, 8=7.26 ppm as standard): δ 2.67 (t, 7.2 Hz, 4H), 2.44-2.42 (m, 9H), 2.37-2.27 (m, 7H), 2.25 (s, 3H), 1.84-1.78 (m, 2H), 1.44-1.39 (m, 22H). 13C NMR: (100 MHz, CDCl3, 6=77.0 ppm as standard): δ 172.0 (C), 80.1 (C), 58.3 (CH2), 54.9 (2×CH2), 53.5 (CH2), 52.9 (2×CH2), 49.2 (2×CH2), 45.8 (CH3), 33.6 (2×CH3), 28.0 (9×CH3), 25.2 (CH2), 24.5 (CH2).

DLin-MC3-DMA Water-Soluble Analogue

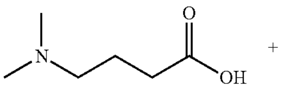

HCl
6

-continued

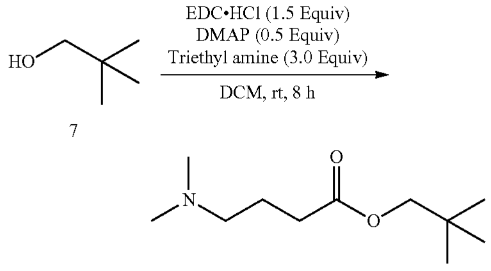

7

8

DLin-MC3-DMA water soluble analogue was synthesized as per the previous literature reports. A mixture of 4-(dimethylamino)butanoic acid hydrochloride salt (6) (59.7 mmol, 1.0 g), 1-(3-dimethylaminopropyl)-3-ethylcarbodiimide hydrochloride (EDC.HCl) (7.16 mmol, 0.63 g), 4-(dimethylamino)pyridine (DMAP) (1.49 mmol, 0.18 g), triethylamine (42.0 mmol, 4.25 g, 5.83 mL), and CH2Cl2 (100 mL) were placed in a 250-mL two-neck round bottom flask. The reaction was stirred for 20 minutes at room temperature and neopentyl alcohol (7) (7.16 mmol, 0.78 mL) was added dropwise and the reaction stirred overnight. Reaction progress was monitored by TLC (chloroform/methanol 9:1 v/v, can be visualized with iodine stain) until complete consumption of 6 and the solvent CH2Cl2 was removed by rotary evaporation. The mixture was dissolved in 100 mL of CH2Cl2 and washed with 150 mL of water and 150 mL of saturated $NaHCO_3$solution. The organic phase was dried over magnesium sulphate and evaporated. The crude product was purified on a silica gel column eluted with chloroform containing 0-1% methanol. Column fractions were analyzed by thin layer chromatography (TLC) and fractions containing pure product (Rf=0.4) were concentrated, to obtain product as yellow oil (8). (0.58 g, 48% yield). 1H-NMR: (400 MHz, CDCl3, δ=7.26 ppm as standard): δ 2.36 (t, 7.4 Hz, 2H), 2.31 (t, 7.2 Hz, 2H), 2.22 (s, 6H, 2×NCH3), 1.84-1.78 (m, 2H), 0.86 (s, 9H, 2×CH3). 13C NMR: (100 MHz, CDCl3, δ=77.0 ppm as standard): δ 173.6 (C), 73.6 (CH2), 58.8 (CH2), 45.3 (2×CH3), 32.1 (CH2), 31.2 (C), 26.4 (9×CH3), 22.9 (2×CH2).

NMR Measurement of pKa of Water-Soluble Ionizable Lipid Analogues.

The pH-dependence of proton NMR chemical shifts was used to measure the pKa's of the ionizable lipid water-soluble analogues (WSA) following published methods5,6. Chemical shifts of piperazine, imidazole, 2-chloroacetic acid and acetic acid were used as internal pH indicators. Solutions for MC3-WSA were prepared with 100 mM KCl, 2 mM piperazine, 2 mM imidazole, and 5 mM water soluble ionizable lipid analogue in 95% H2O-5% D2O. Solutions for the terminal(N1) and aza amines(N2) at the p-position of carboxylic esters of C24-WSA were prepared with 100 mM KCl, 2 mM piperazine, 2 mM imidazole, 0.2 mM DSS, and 5 mM water soluble ionizable lipid analogue in 95% H2O-5% D2O. Solutions for the internal amine (N3) of C24-WSA were prepared with 100 mM KCl, 2 mM chloroacetic acid, 2 mM acetic acid, 0.2 mM DSS, and 5 mM water soluble ionizable lipid analogue in 95% H2O-5% D2O. Solutions were split into two equal volumes and one titrated to a lower pH using 0.1 M HCl and the other to an upper pH using 0.1 M NaOH where the lower and upper pH bracketed the desired range of pH. Intermediate pH values were obtained by mixing different proportions of these two solutions. NMR measurements were performed on a Bruker 400 MHz spectrometer where 1H spectra were acquired at each of ~24 pH values ranging from the lower to upper pH. Peaks for MC3 were calibrated to D20 (400 MHz, D20, δ=4.79 ppm as standard) and the peaks for C24 were calibrated to DSS (400 MHz, DSS, δ=0.00 ppm as standard). Chemical shifts from piperazine, imidazole, 2-chloroacetic acid, and acetic acid were then used to calculate the pH of each solution according to published methods5,6 and the chemical shifts of protons adjacent to each nitrogen in the ionizable lipid water sluble analogue headgroup were fit to the Henderson-Hasselbalch equation to provide the pKa of each Nitrogen. Spectra are in Supplementary FIG. 2.

Theoretical Calculation of pKa

Experimentally determined pKa values from NMR, Zeta Potential and TNS assays were compared against theoretically calculated values using Advanced Chemistry Development, Inc. (ACD/Labs) software. The ACD/pKa database algorithmically estimates pKa values of whole molecules in an aqueous environment based on their constituent fragments using two approaches. The Classic algorithm employs a database of Hammett-type equations parameterized to cover most ionizable functional groups, each characterized by several equations involving variations of sigma constants. The Galas algorithm estimates pKa microconstants for all possible ionization centers in a hypothetical uncharged state based on the surroundings of the reaction center and neighboring ionization centers to produce microconstants from which pKa macroconstants are obtained. Classic algorithm calculations were used in this study.

Preparation of mRNA Lipid Nanoparticles mRNA-loaded LNPs were formulated by preparing lipids in ethanol using % mole ratios for ionizable-lipid/DSPC/Cholesterol/DMG-PEG2000 of 50/10/38.5/1.5 for MC3 and 48/13/37/2 for C24 and preparing mRNA in aqueous buffers. These two solutions were mixed in a Spark NanoAssmblr™ (Precision NanoSystems) at volumes and concentrations to achieve a molar ratio of ionizable lipid to phosphate on the mRNA backbone of 4 and ejected into PBS pH 7.4. The MC3 LNP was prepared using standard procedures described previously while C24 LNP assembly optimized some parameters for this specific formulation. The resulting mixtures were diluted 1:1 into PBS pH 7.4 and dialyzed against PBS to reach pH 7.3-7.4 after 6 buffer exchanges over 6 hours using a Slide-A-Lyzer MINI Dialysis Device (MWCO, 10 kDa).

Assay of mRNA Inaccessibility to Ribogreen

Tris(10 mM, pH=7.5)/EDTA (1 mM) (TE) and Triton/TE (2% v/v Triton in TE Buffer) were added in duplicates to a black microplate. Total mRNA in the LNP was diluted to ~4 ng/μL in TE and added to each TE and TE/Triton well in a 1:1 volume ratio. Two standard curves were included in the Ribogreen Assay, one containing mRNA and TE, and the other containing mRNA and Triton/TE. Each standard curve was used to calculate the mRNA accessibility to ribogreen in each respective buffer. This approach using two standard curves is required, in comparison to a single standard curve in Triton/TE, which can overestimate inaccessibility by 5-10%, since Ribogreen has higher background fluorescence in Triton/TE versus TE. Microplates were incubated at 37° C. for 10 minutes to extract LNPs with Triton. Ribogreen reagent in DMSO was diluted 1:100 in TE Buffer and added to each well in a 1:1 volume ratio. Microplates were immediately introduced into the Cytation 5 Cell Imaging Multi-Mode Reader (Biotek) to read Fluorescence (Ex485/Em528).

TNS Assay

LNP pKa was determined using the TNS assay. The TNS reagent was prepared as a 300 μM stock solution in DMSO. LNPs were diluted to 24 μM ionizable lipid, TNS to 6.3 μM in a total volume of ~103 μL of buffered solutions containing 20 mM boric Acid, 10 mM imidazole, 10 mM sodium acetate, 10 mM glycylglycine, 25 mM NaCl, where the pH ranged from 3 to 10. The Cytation 5 Cell Imaging Multi-Mode Reader (Biotek) was used to read Fluorescence (Ex321/Em445). The pH was measured in each well after TNS addition. Mathematica (Wolfram Research) was used to fit the fluorescence data to the Henderson-Hasselbalch equation RFU=RFU_max−((RFU_max−RFU_min))((1+10^(pKa−pH))) to provide the pKa.

mRNA LNP Size, Zeta Potential (ZP), ZP pKa and pI, Number of mRNA Copies Using Dynamic Light Scattering and Electrophoretic Mobility.

LNPs were diluted to 6.25 ng/μL total mRNA in PBS pH=7.4 and transferred into a quartz cuvette (ZEN2112) to measure size by Dynamic Light Scattering (DLS) in the Zetasizer Nano ZS (Malvern Panalytical) using particle RI of 1.45 and absorption of 0.001 in PBS at 25° C. with viscosity of 0.888 cP and RI of 1.335. Measurements were made using a 1730 backscatter angle of detection previously equilibrated to 25° C. for 30 seconds in duplicates, each with 5 runs and 10 second run duration, without delay between measurements. Each measurement had a fixed position of 4.65 mm in the quartz cuvette with an automatic attenuation selection. Data was analyzed using a General-Purpose model with normal resolution. Diameter are reported as the number-average that corresponds more closely to physical size seen in electron microscopy versus the zeta-average. A molecular volume model described previously was used to estimate the number of mRNA copies in the LNP using the number average diameter to calculate LNP volume. LNPs were diluted into the TNS buffer described above at pH ranging from 3-10 for zeta potential measurement by Electrophoretic Light Scattering (ELS) in the Zetasizer Nano ZP (Malvern Panalytical) using the same material and dispersant parameters described above and the Smoluchowski model. Each measurement had voltage set manually at 80 Volts to avoid ohmic heating that occurred if voltage was set automatically. Measurements in the disposable folded capillary cuvette with an automatic attenuation selection for photon counts were made in triplicates for 20 runs each, and 30 second delay between each replicate. Mathematica was used to fit zeta potential data to the data to the extended Henderson-Hasselbalch equation $$\Psi=\Psi\_max-((\Psi\_max-\Psi\_min))/((1+10\hat{}(((pKa-pH))/n)))$$

to provide the pKa, n and low pH and high pH zeta potential limits Ψ_max and Ψ_min, respectively. The extended model is used here, since the LNP pKa is ionization-state-dependent in a way similar to a polyelectrolyte. TNS data did not require the extended model since TNS dye binding only detects LNP surface charge. The isoelectric pI was the pH found by interpolating zeta potential to zero.

Cryoelectron Microscopy

Grids for electron microscopy were plunge-frozen using a Vitrobot Mark IV system. The chamber was set to 25° C. and 100% humidity. LNPs (3 μL) were applied to grids (ultrathin carbon film on lacey carbon support, Ted Pella #01824G), incubated for 1 minute, and blotted twice for 3 s each time at a blot force of 25 before plunging into liquid ethane. Grids were imaged on a Talos Arctica system (Thermo Fisher Scientific) at 200 kV with a Falcon 3EC detector, using EPU for data collection. The nominal magnification was 45,000×, with a calibrated pixel size of 0.223 nm. Images were collected in integrating mode using 5 s exposures, with a total dose of 60 e/Å2, and 66 fractions which were motion-corrected using Motioncor252.

In Vivo Live Animal Imaging for Luciferase Expression Following Intramuscular Administration of C24 and MC3 LNPs Containing FLuc mRNA.

The investigators adhered to the "Guide for the Care and Use of Laboratory Animals" by the Committee on Care of Laboratory Animal Resources Commission on Life Sciences, National Research Council. Mouse studies were conducted under protocols approved by the Institutional Animal Care and Use Committees (IACUC) of the University of Pennsylvania (UPenn). All animals were housed and cared for according to local, state, and federal policies in an Association for Assessment and Accreditation of Laboratory Animal Care International (AAALAC)-accredited facility. 8-week old female Balb/c mice purchased from Charles Rivers and acclimatized at the University of Pennsylvania for 7 days before experiments. Mice were injected with 5 μg or 0.5 μg FLuc mRNA-LNP using a 3/10 cm3 29G insulin syringe (BD Biosciences). mRNA-LNPs were diluted in PBS and injected into the gastrocnemius muscle (50 μL injection volume). At 4 hours post-injection, mice were anesthetized with 2% isofluorane in oxygen and imaged 10 min after intraperitoneal injection of 250 μL D-Luciferin (15 mg/ml). Bioluminescence imaging was performed using an IVIS Spectrum imaging system (Caliper Life Sciences). Imaging was repeated at 24 hours and animals were euthanized. A longevity experiment imaged animals each day for 5 days. Legs were also fixed at 24 hrs post administration and injection sites fixed in neutral buffered formalin, processed in paraffin, and stained with hematoxylin and eosin.

Immunogenicity in Balb/c Mice of C24 and MC3 LNPs Containing the Nucleoside-Modified S2P SARS-CoV-2 Immunogen.

Balb/c mice (Charles rivers) were administered C24 and MC3 LNPs containing 0.1, 0.25, 0.5, 1.0 μg of the nucleoside-modified mRNA-encoded S2P immunogen (N=5 animals per dose per LNP) in 50 μl injected into the medial gastrocnemius muscle The two injections were spaced 3 weeks apart and blood was collected through the retro-orbital route one day prior to the first injection (Pre-bleed), prior to the second injection (Prime) and 2 weeks after the second injection (Boost). Serum was separated from blood following an incubation period of 30 minutes at room temperature, and samples were centrifuged at 10,000 g for 5 minutes in a non-refrigerated Eppendorf 54 centrifuge (Eppendorf, Enfield, CT, USA). Separated serum was stored at −20° C. until used. Total antibody titers were determined using an Endpoint Enzyme Linked ImmunoSorbent Assay (ELISA). Briefly, High Bind Stripwell™ Corning 96 Well Clear Polystyrene Microplates were coated overnight with 1 μg/ml purified SARS-CoV-2 RBD (cat #Z03501), washed once with wash buffer (0.05% Tween-20 in PBS), and blocked for two hours at room temperature using 2% w/v BSA in PBS. Plates were then washed three times, and mouse sera was added at 1:27,000 (prime sera) and 1:54,000 (boost sera) and in the blocking solution and incubated for 2 hours at room temperature, washed three times before incubation with (HRP)-conjugated anti-mouse secondary antibody in blocking buffer (1:10 000) for 1.5 hours. After incubation, plates were washed three times before the addition of 100 μl per well of KPL TMB substrate for 8 minutes. The reaction was stopped using 2N sulfuric acid, and the absorbance measured at 450 nm using a SpectraMax™ 190 microplate reader. To determine neutralization potential, a VSVΔG-RFP pseudotyped virus (50-200 focus forming units/well) was incubated with 2-fold serially diluted serum samples and incubated for 1 h at 37° C. prior to addition of the virus-antibody mixture to VeroE6 TMPRSS2 cells. 20 hours post infection, the cells were washed and fixed with 4% paraformaldehyde before visualization on an S6 FluoroSpot Analyzer (CTL, Shaker Heights OH). Individual infected foci were enumerated and the values compared to control wells without antibody. The Focus Reduction Neutralization Titer 50% (FRNT50) was measured as the greatest serum dilution at which focus count was reduced by at least 50% relative to control cells that were infected with pseudotype virus in the absence of mouse serum. FRNT50 titers for each sample were measured in two technical replicates performed on separate days.

Protection Against SARS-CoV-2 Lethal Challenge in K18-hACE2 Mice by Immunization with C24 and MC3 LNPs Containing the Nucleoside Modified S2P SARS-CoV-2 Immunogen Female B6; SJL-Tg(K18-hACE2)2Prlmn/J (hACE2) mice purchased from Jackson Laboratory K18-hACE2 mice were administered C24 and MC3 LNPs containing 0.1, 0.25, 0.5, 1.0 μg of the nucleoside-modified mRNA-encoded S2P immunogen (N=5 animals per dose per LNP) in 50 μl injected into the medial gastrocnemius muscle. The mice received a prime and a boost injection of the mRNA LNPs and the two injections were spaced 6 weeks apart. Blood was collected by mandibular bleeds prior to the first injection (Pre-bleed), prior to the second injection (Prime) and 2 weeks after the second injection (Boost). Neutralizing antibodies were assessed by Plaque Reduction Neutralization Titer Assay (PRNT) (described below). SARS-CoV-2 propagation was done in a cell culture flask seeded with Vero cells at 60-75% confluency. The cells were infected with SARS-CoV-2 Italy Isolate-INMI1 (from BEI Resources). Infection was carried out for 48-72 hours after which the supernatant was recovered, and viral titer assessed by plaque assay. Mice were challenged 2 weeks after the second immunization with SARS-CoV-2 by intranasal administration at dose of 5×105 pfu and followed until death or euthanasia criteria were met. Weight and temperature were recorded daily. Two of the 5 mice in each group were sacrificed on day 5 post-challenge to assess lung viral titers by plaque assay. Lung tissues were homogenized and spun down. The supernatant recovered for assessment of viral load by plaque assay. The remaining three mice were monitored daily for signs of morbidity and mortality. Weight and temperature reading were also recorded daily for the surviving mice until the end of the study.

For PRNT50 assays, mouse sera were diluted 1:10 in DMEM (supplemented with 5% FBE, 1% L-glutamate and 20 U/mL penicillin, and 20 μg/mL streptomycin). Serial two-fold dilutions were then prepared from the 1:10 dilution and mixed with 100 pfu of SARS-CoV-2 virus and incubated at 37° C. for 1 h. The sera/virus mixture was then overlayed onto a confluent layer of Vero cells in a 12-well plate format and incubated for 1 h at 37° C. incubator with 5% CO2. The inoculated wells were then overlaid with a 1:1 mixture of Eagle's Minimum Essential Medium (without phenol red, supplemented with 5% FBE, nonessential amino acids, 1 mM sodium pyruvate (VWR, 45000-710, Dixon, CA, USA), 2 mM L-glutamine, 20 U/mL penicillin, and 20 μg/mL streptomycin) and 0.6% agarose (ThermoFisher, 16500100) and incubated for 48h at 37° C. with 5% CO2. Cells were then fixed with 10% formaldehyde (FisherSci, F79p-4) for 1 h. Media was removed, cells were washed with diH2O and stained with 1% crystal violet (FisherSci, C581-25) and 20% ethanol solution (FisherSci, BP2818-4). Plaques were counted and plotted as pfu/dilution.

For plaque assays, the Vero cells (WT Veros, ATCC) were plated in 12-well plates at a density of 2×105 cells per well and incubated overnight. Supernatants from tissue homogenates were serially diluted to 10-6 and overlaid on cells for 1 h (37° C., 5% CO2O). Cells were then overlaid with Eagle's Minimum Essential Medium (without phenol red, supplemented with 5% FBE, nonessential amino acids, 1 mM sodium pyruvate (VWR, 45000-710, Dixon, CA, USA), 2 mM L-glutamine, 20 U/mL penicillin, and 20 μg/mL streptomycin) with 0.6% agarose (ThermoFisher, 16500100) and incubated for 48h. Cells were then fixed with 10% formaldehyde (FisherSci, F79p-4) for 1 h. Medium was removed, cells were washed with diH2O and stained with 1% crystal violet (FisheSci, C581-25) and 20% ethanol solution (FisherSci, BP2818-4). Plaques were manually counted and datasets represent plaque forming units per milliliter (PFU/mL).

Storage/Stability Studies of mRNA LNPs

C24 and MC3 LNPs containing FLuc mRNA were stored in PBS at 4° C. or at room temperature (RT≈22° C.). They were assayed on days 0, 2, 4, 7, 14 of storage for size by DLS as described above, mRNA encapsulation as described above and for bioactivity via transfection into HEK293 cells and assessment of luciferase expression. For bioactivity, HEK293 cells were seeded in white 96-well plates at a density of 12×10' cells per well in 100 μL EMEM medium (10% FBS) the day before transfection and incubated at 37° C. 5% CO2. FLuc mRNA-loaded LNPs were diluted so that 8 μL contained 25 ng mRNA FLuc and HEK293 cells were transfected at this dose using triplicates 24 hours after seeding. After a further 24 hours for transfection, 100 μL of One-Glo substrate was added directly to the wells to detect luciferase expression based on luminescence in Cytation 5 luminometer plate reader. Additional C24 and MC3 LNPs containing FLuc mRNA were stored for 19 days in PBS at 4° C., RT and 37° C. FLuc mRNA was extracted from LNPs using chloroform/methanol and analyzed for mRNA integrity via microfluidic electrophoresis on a 2100 Bioanalyser (Agilent) following manufacturer's instructions. mRNA concentration was quantified by Nanodrop, then diluted to 1 ng/ul to loading mRNA of each sample in the Bioanalyser. The % mRNA integrity was calculated by integrating the area under the curve (AUC) of the main mRNA FLuc peak and normalizing to the average day 0 value for C24 and MC3 LNPs taken together.

Statistics and Reproducibility

The Linear Least Squares Multivariate Model in the JMP Pro 15.1.0 software was used to perform comparisons between groups in FIGS. 84 and 86. For In Vivo IVIS imaging data the 4 and 20/24 hour time points were considered repeated measures. Log 10 transformations were applied to FRNT50 and viral titers. Linear regression models were used to compare OD and transformed FRNT50 and viral titers by LNP adjusted for dose in FIGS. 87*a*-87*c*, 88*d*, and 8*h*. Unadjusted linear regression with LNP as a predictor was used to compare neutralization of pseudovirus in FIG. 87*d*. The proportion of mice dead after lethal challenge of SARS-CoV-2 was compared by LNP using Fishers Exact Test, excluding PBS (FIG. 88*a*). Linear mixed effects models with dose, dilution, and LNP as fixed effects and a random intercept for mouse evaluated the effect of LNP on the percent of virus detected (FIGS. 88*b,c,f,g*). Linear regression and mixed effects models were run in R version 3.6.3.

Example 31

FIG. 84

The multiprotic C24 ionizable lipid produces multistage protonation in the LNP and greater protonation in the endosomal pH range than the MC3 LNP. a) Structures of C24 and MC3 and their water-soluble analogues showing theoretical pKas. The C24 ionizable lipid (MW 876.49) has two rapidly degradable ester bonds each linked to an asymmetric branched C8-C10 (bis 2-octyldodecyl) alkyl tail. The headgroup of C24 is trivalent with theoretical pKas of 7.8, 4.1 and 7.7 calculated using the ACDLabs Percepta Classic algorithm. MC3 (MW 642.11) has one slowly degradable ester linked to a di-linoleic tail and a monovalent head group with a theoretical pKa of 9.4. b) The pKa of each nitrogen in the C24 ionizable lipid was measured using the pH-dependence of the 1H NMR chemical shift of protons adjacent to each nitrogen using the water soluble analogue in the inset. Fitting of the chemical shifts versus pH to the Henderson Hasselbalch equation provides the pKa of each nitrogen and are similar to within 0.4 units of the pKas predicted by ACDLabs Percepta Classic algorithm shown in 84(a). The stretched appearance of the titration of the terminal nitrogen (red) suggests interaction of its protonated form with the nitrogen closest to the linker (blue) that protonates simultaneously possibly coordinating these two nitrogen atoms. c) The pKa of the dimethylamine nitrogen of MC3 was measured using the pH-dependence of the 1H NMR chemical shift of dimethylamine protons and fitting to the Henderson Hasselbalch equation. The measured pKa of 9.5 agreed with the value 9.4 predicted by ACDLabs Percepta Classic algorithm shown in (a). d) The LNP pKa was measured with the TNS dye-binding assay for C24 and MC3. The TNS pKa measures surface charge and cannot reflect protonation below pH~6. Equal amounts of ionizable lipid were used in the assay for C24 and MC3 so that the higher RFU of C24 for pH below 7 indicates a higher level of surface protonation of the C24 LNP in the endosomal pH range where t-tests comparing RFU of C24 to MC3 at pH 6 and 6.5 showed significant differences $p<0.05$ (*) (mean+/−SD for N=3). e) Net LNP charge and ionization was measured using electrophoretic mobility to provide Zeta Potential over the pH range 3-10. Electrophoretic mobility depends on net charge of the LNP and can detect protonation through the entire pH range including endosomal pH values down to 4.5 when endosomes fuse with lysosomes. For the monoprotic MC3 ionizable lipid, the Zeta Potential fits the extended Henderson Hasselbalch equation (solid line) developed originally for polyelectrolytes since it captures the ionization state dependence of pKa of the multivalent LNP containing thousands of strongly interacting MC3 molecules in close proximity within the LNP. For C24, the zeta potential does not fit well the extended Henderson Hasselbalch model accurately (dotted versus solid red lines) since each C24 has 3 nitrogens with different pKa shown in b. The two peripheral nitrogens will protonate at higher pH values while the internal, central nitrogen creates the steeply increasing zeta potential at pH values below 4.5. The C24 LNP produces a more negative zeta potential at neutral pH that rises rapidly as pH drops in the endosomal pH range indicating greater endosomal protonation for C24 than for MC3 and t-tests comparing ZP (mV) of C24 to MC3 at pH 7.4 showed significant differences $p<0.001$ (*) (mean+/−SD for N=3). f) pKa predicted from the ACD Percepta Classic algorithm compared to that measured by NMR on water soluble analogues and the TNS pKa, Zeta Potential (ZP) pKa, ZP isoelectric pI, the increase in TNS RFU from pH 7.4 to 6 and the increase in Zeta Potential from pH 7.4 to 4.5. The NMR pKa agrees with the theoretically predicted pKa and are significantly higher than the LNP pKa measured by both TNS and Zeta Potential. We recently explained this difference between molecular and colloidal pKa as mainly due to proton partitioning between the lipid phase of the LNP and the aqueous medium20. The increase in TNS RFU from pH 7.4 to 6 and the increase in Zeta Potential from pH 7.4 to 4.5 for C24 are nearly double that of MC3 indicating that both surface LNP protonation (TNS) and net LNP charge (ZP) increase more for C24 than MC3 in the endosomal pH range.

Example 32

FIG. 85

Structural properties of C24 and MC3 lipid nanoparticles. a) DLS number-averaged size showed C24 LNPs were slightly larger and with lower polydispersity index than MC3 LNPs. b) The ribogreen assay showed slightly lower levels of mRNA inaccessible to ribogreen for C24 versus MC3. We performed this assay using 2 standard curves, with and without triton. When only one standard curve with triton is used (such as in most publications to date) the mRNA inaccessible to ribogreen increases by ~8% shown in the yellow hatched portions. This assay is often interpreted as % encapsulation efficiency versus % mRNA inaccessible to ribogreen shown here. The latter is more accurate since it has been shown that dye accessibility of mRNA does not indicate that the mRNA is free and unencapsulated. It may however reflect a different packing and internal structure of the LNP. c) mRNA copy number was calculated using a previously published molecular volume model and the number-weighted average diameter of each LNP. We estimated the molecular volume of the C24 ionizable lipid as proportional to its MW at 1.76 nm3 versus 1.29 nm3 for MC3. d) CryoTEM of MC3 and C24 (E) revealed sizes consistent with DLS number-averaged size. Both LNPs have a peripheral bilayer consistent with DSPC localization in this zone as described previously.

Example 33

FIG. 86

Luciferase expression after intramuscular (IM) administration in Balb/c mice shows significantly higher on-target and lower off-target mRNA expression with the C24 LNP than for MC3. a) In vivo imaging at 4h and 24h after IM administration of a 5 μg dose of FLuc in LNPs show higher intramuscular expression (green ROIs) of Fluc delivered using C24 compared to MC3 and also revealed significant systemic distribution of MC3 resulting in off-target expression in liver (red ROIs). b) At this high 5 μg dose C24 has a significantly higher intramuscular expression than MC3 where p=0.0074 for the effect of LNP in a multivariate analyses of photon Flux as a function of LNP (MC3/C24) and time (4 hr/24h). c) Off-target Fluc expression in liver after IM administration is 6× lower for C24 versus MC3 where p=0.051 in a t-test comparing LNPs. d) When a low dose (0.5 μg) more representative of vaccinations is administered, FLuc in the muscle at 4 hrs is ~4 fold higher for C24 versus MC3 where p=0.0034 (in e) for the effect of LNP in a multivariate analysis of Flux as a function of LNP (MC3/C24) and time (4 hr/24h). f) The duration of Luciferase expression for a 5 μg dose administered IM was followed over 5 days showing a rapid decrease over the first 2 days followed by a slower decline in expression.

Example 34

FIG. 87

C24 LNPs generate 10 fold higher binding and pseudoneutralizing antibody titers than MC3 LNPs in immunogenicity studies with Balb/c mice. C24 and MC3 LNPs containing a nucleoside-modified mRNA encoding for a diproline stabilized membrane-bound spike protein (S2P) of SARS-CoV-2 were administered to Balb/c mice at 4 doses ranging from 0.1 to 1 μg. a) ELISA optical density at the transitional dilution of 27,000 for S2P binding antibody assays for low doses 0.1 μg and 0.25 μg of mRNA-encoded S2P immunogen for serum collected 2 weeks after the boost. A Linear Regression Model analysis including LNP and dose as predictors showed that C24 binding antibody OD were significantly higher than MC3 (p=0.0005). Mean+/−SEM. b) ELISA optical density at the transitional dilution of 54,000 for S2P binding antibody assays for higher doses 0.5 μg and 1.0 μg of mRNA-encoded S2P immunogen for serum collected 2 weeks after the boost. A Linear Regression Model analyses including LNP and dose as predictors showed that C24 binding antibody OD were significantly higher than MC3 (p=0.01). Mean+/−SEM. c) C24 LNPs generated a detectable FRNT50 titer against VSVΔG-RFP SARS-CoV-2 pseudovirus 3 weeks after a single Prime injection of a 1 μg dose while MC3 LNPs did not (left Prime panel). Two weeks after the Boost (right Boost panel), C24 LNPs at 0.25 to 1 μg dose revealed FRNT50 titers that were ~10 fold higher than MC3 LNPs at the same doses. A Linear Regression Model analysis of log-transformed FRNT50 titers including dose and LNP as predictors showed that C24 FRNT50 titers were significantly higher than MC3 for the Prime (p=0.00002) and for the Boost (p=0.011). Mean+/−SEM. d) Neutralization of pseudovirus variants representing the variants D614G and ZA suggested FRNT50 titers were higher for C24 than the MC3 LNP, although statistical analyses did not find significant differences. Mean+/−SEM.

Example 35

FIG. 88

Figure 3A:
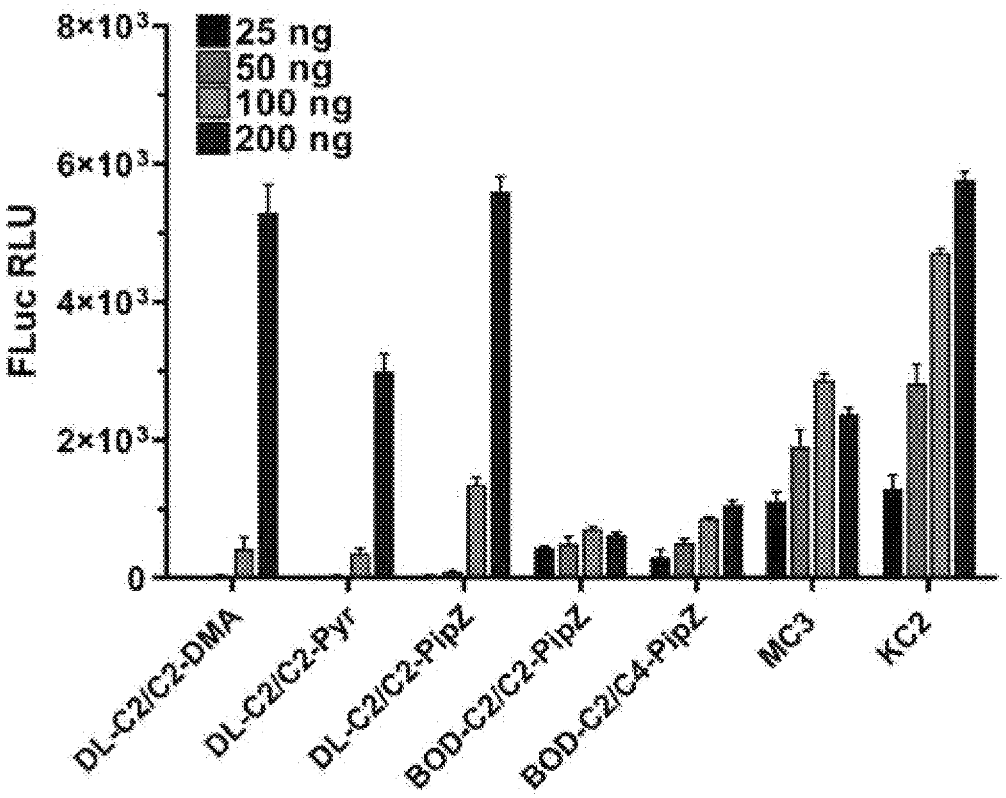
Figure 3B:
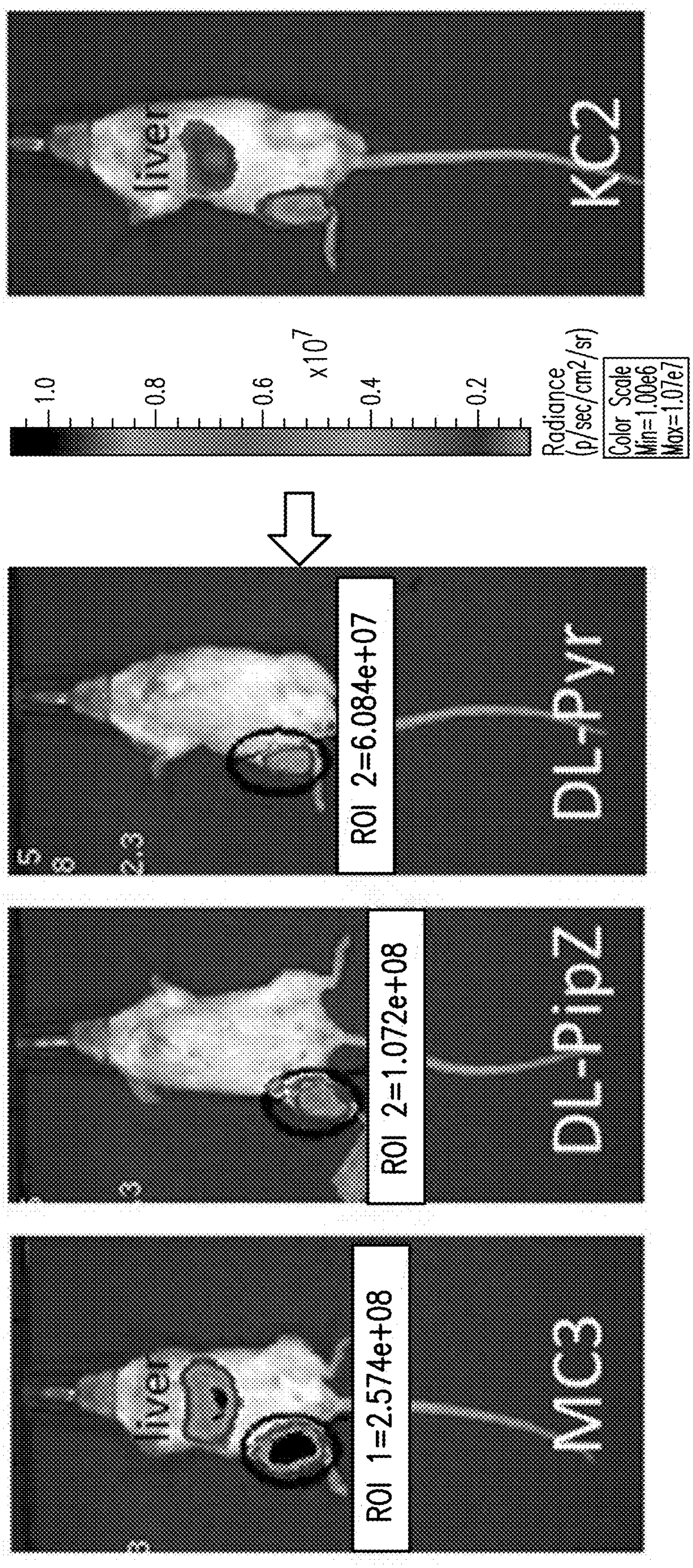
Figure 3C:
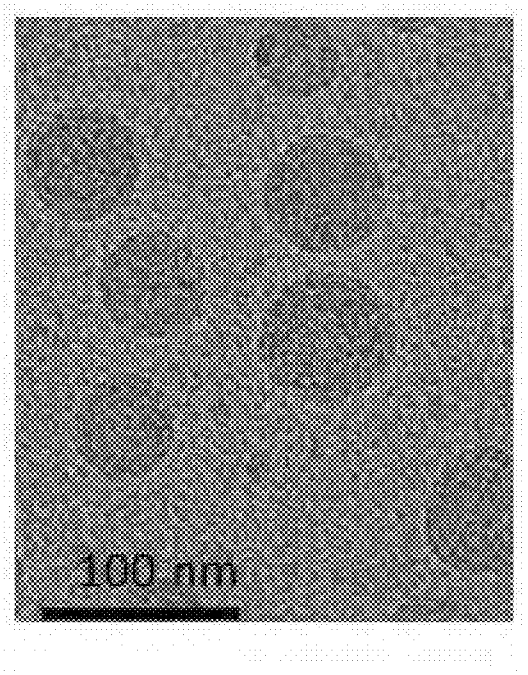
Figure 4A:
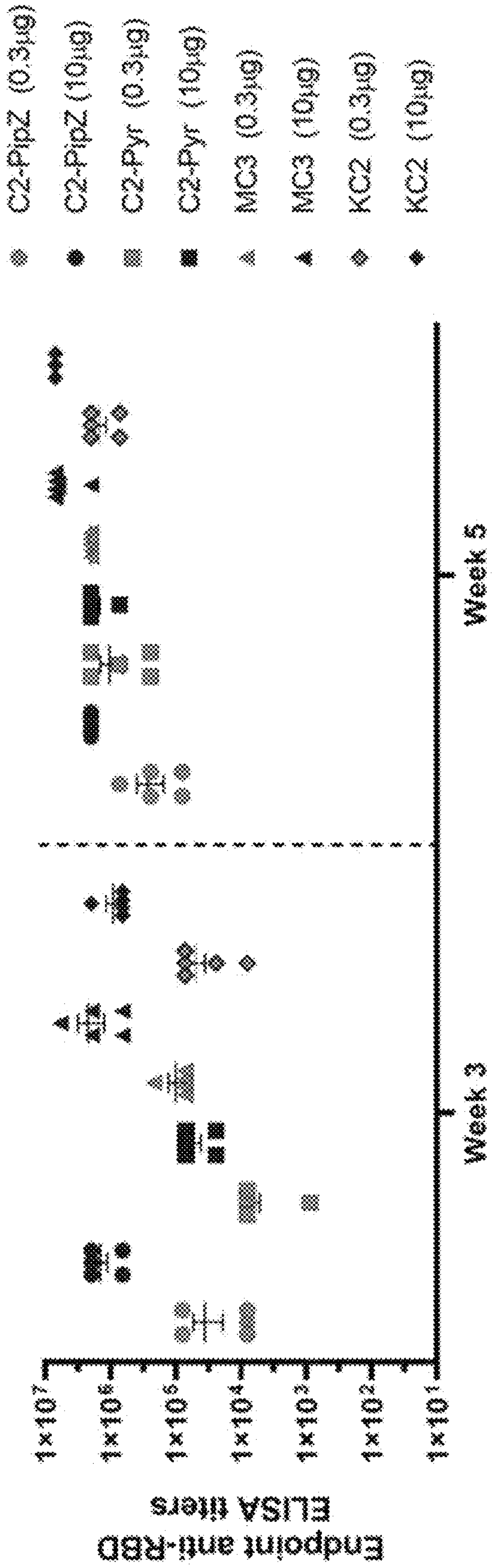
Figure 4B:
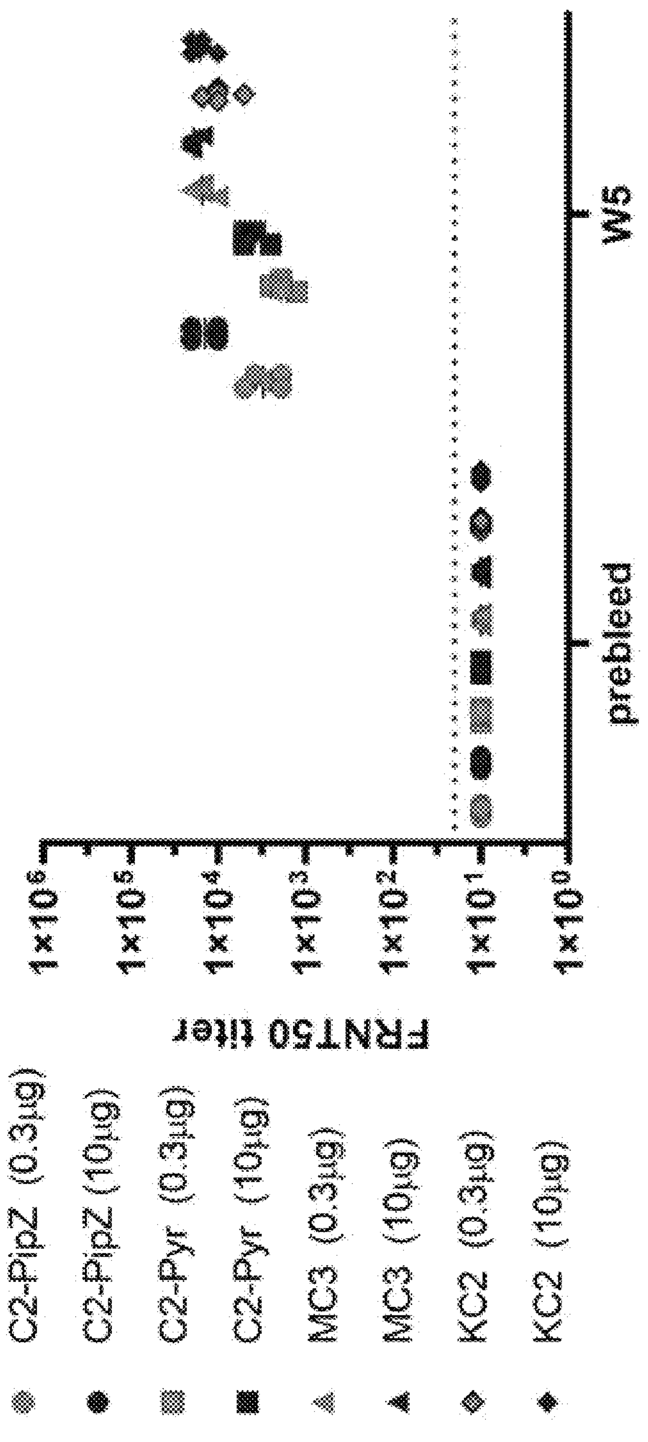
Figure 5:
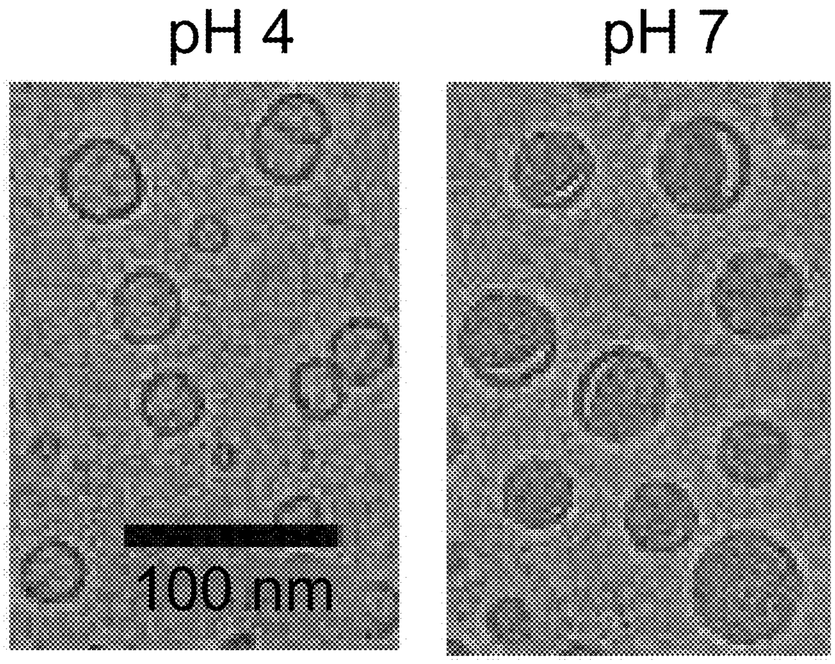
FIG. 5 illustrates cryoTEM images of empty LNPs. KC2 LNPs without mRNA were mixed and ejected into pH 4 buffer showing small electron lucent structures vs electron dense at pH 7.
Figure 6A:
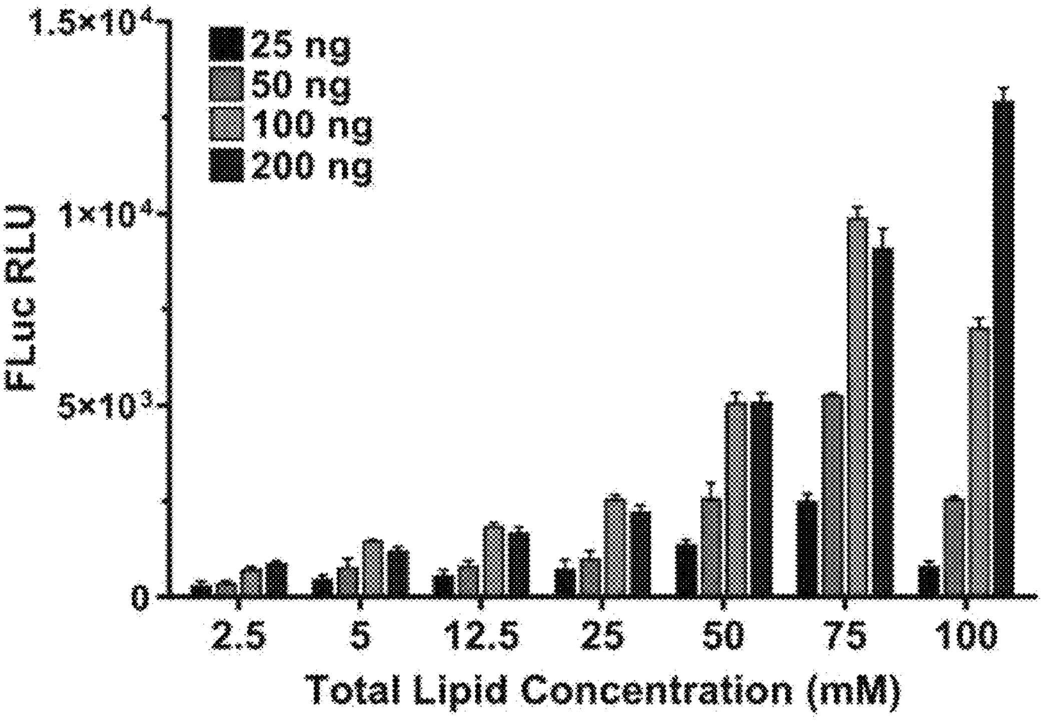
FIG. 6A illustrates the increase in LNP potency when the concentration of lipids and mRNA are increased during microfluidic mixing.
Figure 6B:
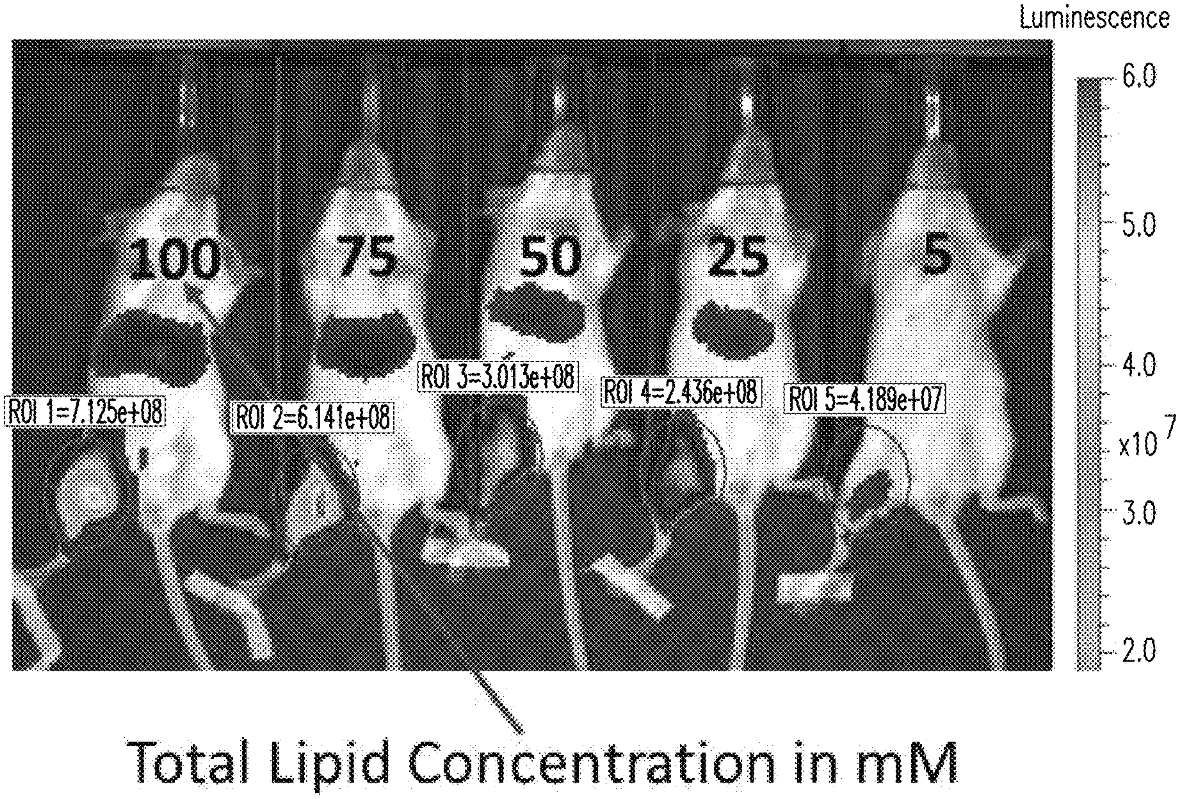
FIG. 6B illustrates in vivo targeting of LNP's of the invention.

C24 LNPs are protective against lethal SARS-CoV-2 challenge at low doses of the S2P immunogen and completely eliminate lung infection. C24 LNPs containing 0.25 μg of mRNA encoded S2P immunogen were entirely protective (a) against a lethal challenge of SARS-CoV-2 while MC3 LNPs were protective at a higher 0.5 μg dose (e) in the K18-hACE2 mouse (N=3 per group from N=5 at day zero since 2 animals per group were taken on day 5 to assess lung viral titers). One of 3 animals in the C24 group also survived at the very low dose of 0.1 μg. Statistical analyses did not show a significant difference with the small numbers of animals per dose (n=3). Neutralization of SARS-CoV-2 in a plaque assay by PRNT (N=5 per group) demonstrated C24 LNPs had neutralizing activity at 0.25 μg dose (b) while MC3 only at 1 μg dose (f) after the Prime. A Linear Mixed Effects Model analysis including LNP, dose and dilution as predictors showed that C24 significantly reduced % Virus Detected more than MC3 (p=0.021 for b versus f). C24 had 100% neutralizing activity at 0.25 μg dose after the Boost for the dilutions tested (c) while MC3 only at 1 μg (g). A Linear Mixed Effects Model analysis including LNP, dose and dilution as predictors showed that C24 significantly reduced % Virus Detected more than MC3 (p<0.00001 for c) versus g). Assessment of lung viral titers at day 5 post infection in a plaque assay (N=2) found that C24 LNPs completely eliminated lung infection at a 0.5 μg dose (d) while MC3 LNPs were not able to entirely eliminate lung infection even at the highest 1 μg dose tested (h). A Linear Regression Model analyses of log transformed Viral Titers including LNP and dose as predictors showed that C24 significantly reduced Lung Viral Titers more than MC3 (p=0.00008). SEM is shown for one dose only for clarity in b, c, f, g. Weight and temperature recordings post-challenge are in Supplementary FIG. 3. Mean+/−SEM.

Example 36

FIG. 89

Local injection site inflammation is lower for C24 than MC3 mRNA LNPs. C24 LNPs (a-c) elicited less inflammation at the injection site than MC3 LNPs (d-i) 24 hours after injection that was consistent with lower levels of macroscopically observed swelling of C24 than MC3, assessed visually and by manual palpation. The 50 μl injection into the medial gastrocnemius (MG) containing 5 μg of mRNA and ~65 μg total lipids was mainly found at the injection site (IS) between the medial gastrocnemius and lateral gastrocnemius (LG) in a, d and g. The lipid was difficult to distinguish from local adipose tissue. MC3 elicited a strong inflammatory response throughout the leg inducing macroscopically evident swelling and histologically observed inflammation of the synovial tissue (e, f) that was absent in C24 injected legs (b, c). The inflammatory response at the injection site involved infiltration of neutrophils and blood vessels (h) and generated mixed cell-type lymphoid structures (i) at the injection site that were not observed in non-injected controls. These responses are representative of a group of 3 animals for each of MC3 and C24. Staining is hematoxylin and eosin.

Example 37

FIG. 90

Bioactivity and mRNA integrity of C24 and MC3 LNPs are stable at 4° C. but decline at higher temperatures over 2 weeks. a) Bioactivity was measured at Day 0, 2, 4, 7 and 14 by luciferase expression in HEK 293 cells at 25 ng per well containing 12,000 cells. Bioactivity was stable for both C24 and MC3 LNPs stored in PBS at 4° C. but declined by ~20-40% when stored at room temperature (RT) over a 2-week period. b) There was no detectable change in LNP size by DLS nor in % mRNA inaccessible to Ribogreen (c). d) Theoretical calculation of mRNA integrity (% uncleaved) using the model in equation "e" of Li and Breaker 1999 suggests free FLuc mRNA half-lives at pH 7.4 of 2,300 days at 4° C., 125 days at RT and 11 days at 37° C. e) mRNA was extracted from LNPs using chloroform/methanol just after being produced on day 0 as well as after 19 days of storage in PBS at 4° C., RT and 37° C. and analyzed by microfluidic electrophoresis. No detectable degradation was found after 19 days at 4° C. (compared to day 0) while storage at higher temperatures (RT and 37° C.) produced increasing amounts of mRNA cleavage that was qualitatively consistent with higher degradation at higher temperature predicted by the model in (d). The least degraded example of the 3 LNPs measured for each condition is shown in (e). The peak below 20s is a standard while the peak near 40s above the main mRNA Fluc peak is the product of an untemplated extension that is not amenable to elimination using the cellulose method used to purify the mRNA45. mRNA integrity was estimated by the area under the curve (AUC) corresponding to the FLuc mRNA peak and was normalized to the average day 0 value for C24 and MC3 LNPs taken together. f) mRNA integrity was stable for at least 19 days at 4° C. and declined at higher temperatures but less so for C24 than for MC3. N=3 or for some N=2 due to technical irregularities in the trace of some samples that precluded quantification.

Example 38

Rational Design Approach by Developing Models that Use Ionizable Lipid Structure to Predict LNP Ionization and the Ability of the Ionizable Lipid to Disrupt the Endosomal Membrane and Release the mRNA.

mRNA-LNPs are manufactured using a microfluidic or a larger scale T-mixer through a self-assembly process where the 4 lipids in ethanol are mixed rapidly with the mRNA that is in a low pH buffer. The formation of the mRNA LNP occurs through electrostatic binding of the protonated cationic ionizable lipid with the anionic mRNA phosphate backbone followed by the lipids segregating from the aqueous phase to form the nanoparticle that is stabilized by the hydrophilic PEG interface. Many factors may be changed in the manufacturing process including the absolute and relative concentrations of the lipids and mRNA, the type of buffer, its concentration and pH, the ratio of the organic to aqueous phases, and the flow rate. We have discovered that increasing the absolute concentrations of the lipids and mRNA jointly, without changing relative concentrations, can increase the delivery efficiency of the resulting mRNA LNP typically by 4× (FIG. 92). All patent and scientific literature use mixing concentrations near 12.5 mM for total lipids which corresponds to mRNA concentrations near 0.25 mg/ml. We found methods to increase these mixing concentrations, for example, by 6× to 75 mM total lipid and 1.5 mg/ml mRNA resulting in a 4× boost in delivery efficiency in vitro and in vivo at identical doses (FIG. 92). By measuring the zeta potential increase from pH 7.4 to 5, we found these more potent LNPs to exhibit a 2 fold greater increase in zeta potential compared to those assembled under the standard conditions (FIG. 92C). This result suggests the improved potency is partly due to a greater level of unprotonated ionizable lipid in the LNPs that increases endosomal protonation. In a more recent innovation, we performed the mRNA LNP assembly in a buffer-free environment. Rather than use a low pH buffer in the mRNA solution to protonate the ionizable lipid upon mixing, we proportionated the ionizable lipid by adding HCl to the lipid mix prior to mixing with mRNA in buffer-free water, We verified by TLC-MS and 1H NMR that lipid degradation did not occur. Using our C24 ionizable lipid that has 3 nitrogens, and adding 0.25 protons per ionizable lipid, we protonated, on average, 1 nitrogen on every 4 lipids so that the protonated nitrogens are at a 1:1 ratio with the phosphates of mRNA (NP ratio was 4). Our buffer-free assembly method produced yet higher potency in vivo, by 3× by IVIS for both IM and IV administration, compared to using a buffer, both using the high lipid and mRNA mixing concentrations. The buffer-free, high absolute lipid/mRNA concentration assembly method can therefore create LNPs that are 10× more potent than current manufacturing methods that use low concentrations and low pH buffers, yet does not change the composition of the final formulation. The preprotonation method more accurately targets a specific level of ionizable lipid protonation versus the buffer which requires convection and diffusion to contact and protonate the lipid that is an inherently fast and inhomogeneous process. These proprietary manufacturing innovations to achieve high potency LNPs are expected to be easily implemented at all manufacturing scales and with both microfluidic and T-mixing geometries. We aim to predictively model the dependence of LNP potency on manufacturing process parameters in order to further increase delivery efficiency to significantly reduce dose and toxicity as well as augment supply of mRNA LNPs.

Distribution, Targeting and Expression of mRNA LNPs Depend on LNP Charge and Ligand Conjugation mRNA-LNPs display biodistribution and expression patterns that can be linked to their ionization properties. Cell-targeting ligands on the surface of LNPs can also increase cell-specific uptake. In IV administration it has been demonstrated that positively charged LNPs target the lung, near-neutral LNPs target the liver and negatively charged LNPs target the spleen. The charge of the LNP in these studies was controlled by changing the ratio of the positively charged ionizable/cationic lipid to the negatively charged mRNA or by leaving this ratio constant and adding a 5th anionic or cationic lipid to adjust LNP charge. One mechanism behind charge-mediated targeting is charge-dependent binding of serum proteins such as ApoE that is recognized by the LDL receptor in hepatocytes. The MC3 LNP, and others that are liver directed, have a slightly negative charge that promotes ApoE binding. In contrast, a strongly negative or positive charge on the LNP will prevent ApoE binding thereby prevent liver targeting. In the case of spleen targeting by negative LNPs, another mechanism may be at play since spleen macrophages and dendritic cells recognize phosphatidylserine to engulf apoptotic cells and aged erythrocytes. Thus coating LNPs with analogues of phosphatidylserine or other negative lipids enhances spleen delivery. An ionizable lipid that generates an LNP with a low pKa of 5.7 will also make the LNP negative and was shown to target spleen and express mRNA in splenic B Lymphocytes, macrophages and neutrophils. Size has also been cited as having a role in spleen targeting where larger sizes can distribute to spleen presumably due to the large size of pores (200-500 nm) in splenic sinusoids delivering arterial blood to parenchymal cells.

Cell-specific targeting within organs may also be achieved by adjusting LNP charge. The MC3 and Acuitas LNPs that have pKas near 6.4 exhibit ApoE-mediated targeting resulting in expression mainly in hepatocytes with some minor expression in liver sinusoidal endothelial cells (LSECs), hematopoetic and Kupffer cells. Cell-targeting could be shifted however from hepatocytes to LSECs by adding a second ionizable lipid with a higher pKa to generate an LNP with pKa 7.15 for LSEC targeting versus 6.4 for hepatocyte targeting. When injecting mRNA-LNPs intramuscularly for vaccines, many cell types express mRNA including monocytes and dendritic cells, myocytes, and adipocytes. Our group was the first to show that LNP charge in IM administration influences biodistribution where MC3 LNPs distribute to vasculature and express in liver while less negative LNPs with a higher pKa remain at the injection site and in draining lymph nodes. The goal of cell-specific targeting has also been pursued by conjugating ligands to LNPs. For example lung endothelial cells were targeted with an antibody to vascular cell adhesion molecule PECAM-121 and splenic CD4+ T lymphocytes were targeted with an antibody to the CD4 receptor. Short peptides have also been used for LNP targeting, for example the influenza derived GALA peptide targeted lung endothelium and a 14 amino acid peptide of neural cell adhesion molecule (NCAM) permitted targeting of skeletal muscle. The third goal of this proposal is to develop models for predicting organ- and cell-specific targeting based on designing and manufacturing LNPs with specific ionization/charge properties and with specific density and affinity/avidity of ligands on the LNP surface.

Predictive models are designed to manufacture mRNA LNPs that have the required expression efficiency, organ- and cell-targeting, low toxicity/reactogenicity, and in the case of vaccines appropriate adjuvanticity and immunogenicity. Using our current library of ionizable lipids described in A below, section B is designed to develop models that use LNP formulation and manufacturing parameters to predict LNP features such as charge, endosomal protonation, ligand density/affinity, that are known to determine efficiency, targeting, toxicity, and immunogenicity. In section C in vitro studies characterize delivery to specific cell types and reactogenic/toxic responses. In section D, animal studies to relate these LNP features to experimentally determined efficiency, targeting, toxicity and immunogenicity will be done. In section E we describe use of machine learning and multi-level functional simulation modules to relate parametric data collected at multiple levels using statistical models. These results will then provide feedback to propose ionizable lipid designs and manufacturing processes for improved performance. A critical difference in our approach compared to prior work is the precise measurement and modeling of the features known to determine LNP performance rather than attempting to link performance directly to chemical structures, formulation and manufacturing. One exception is for degradability which is known to mainly depend on ionizable lipid structure.

A) Synthesis of ionizable lipids. An ionizable lipid library was designed using the approaches described above to create mRNA LNPs with high delivery efficiency. We account for degradability of the ionizable lipid, the complexity and cost of the synthetic pathway and avoid formation of stereoisomeric mixtures. Our current ionizable lipids require fewer synthetic steps and are 10-fold less costly to obtain than the ionizable lipids in the current authorized vaccines. Our current library that has >100 synthesized ionizable lipids, which we perform the analyses and model developments described below. Our synthesized products are fully characterized for identity and purity using NMR spectroscopy, FTIR, LC/MS/MS, and combustion analysis.

B) Develop models predicting LNP charge, endosomal protonation, size, membrane-disrupting and RNA release ability, conjugated lipid density and binding affinity from lipid structures, formulation and manufacturing process parameters. The determinants of mRNA-LNP expression and targeting in vivo that we will characterize and model in this proposal are LNP net charge (NCLNP), surface charge (SCLNP), endosomal protonation (EPLNP), size (DLNP), ionizable lipid membrane-disrupting ability (MDIL), ionizable lipid RNA-release ability (RRIL), targeting ligand density (ρL) and binding affinity (KL) (FIG. 93). These parameters are in turn determined by ionizable lipid ionization and structural properties as well as by formulation parameters (lipid types and mole ratios), manufacturing processes (concentrations, buffer, pH, solvent ratios, flow rates) and ligand conjugation. We will develop several models to predict NCLNP, SCLNP, EPLNP, DLNP, MDIL, RRIL, ρL and KL from ionizable lipid properties, formulation parameters and manufacturing process parameters. These primary determinants of performance (NCLNP, SCLNP, EPLNP, DLNP, MDIL, RRIL, ρL, KL) along with ionizable lipid ionization/structural parameters (pKas, structural descriptors), formulation parameters (5th lipid structure/addition-method/mole-fraction, PEG lipid structure/addition-method/mole-fraction, conjugated-lipid structure/addition-method/mole-fraction) and manufacturing process parameters (lipid/mRNA concentration, buffer type/concentration), will then be used to correlate to, and predict, in vivo mRNA distribution and expression levels in specific organs and cell-types as well as predict toxicity, and for vaccines reactogenicity and immunogenicity.

B1) LNP net charge (NCLNP), surface charge (SCLNP), and endosomal protonation (EPLNP) prediction from ionizable lipid structure and ionization properties. Initially this model will be for a fixed formulation and manufacturing process where only the ionizable lipid will be changed, initially using the members of the BODD PipZ family (FIG. 94) along with DSPC, cholesterol, PEG-DMG-2000 and a 2,069 base FLuc mRNA. We have synthesized 12 members of the BODD PipZ family using different carbon spacers to provide a range of molecular pKa macroconstants. In vitro transfection showed a systematic pattern in dose-response as a consequence of these predictably altered macroconstants. The systematic variation of molecular ionization constants for the members of the BODD PipZ family are expected to change the resulting LNP pKas and pIs over a range of ~2 units which will dramatically influence in vivo efficiency and targeting. We will relate calculated ionizable lipid molecular ionization constants as well as NMR-measured molecular ionization constants4 and structural descriptors (# and types of polar atoms, 2D topology descriptors for the head groups) to measured pH-dependent LNP net charge (NCLNP by zeta potential) and surface charge (SCLNP by TNS and other surface indicators) and derive EPLNP=NCLNP(pH5)−NCLNP (pH 7.4). Our methods to measure pH-dependent (NCLNP, SCLNP, EPLNP) are published. The general form of the model will be:

(NCLNP, SCLNP, EPLNP)=f(ionizable lipid ionization/structural parameters, pH)

where the pH-dependence will follow Henderson-Hasselbalch (HH) and its extended version and the ionization parameters will incorporate lipid/water proton solvation energy differences and ionization-state dependence. This model will predict and design LNP charge and protonation properties that are known to influence expression efficiency and targeting, based on ionizable lipid molecular ionization and structure.

B2) Thermostability characterization and modeling. Our recent mRNA LNP stability studies have confirmed findings in the European Medicines Agency public assessment documents for the Pfizer and Moderna vaccines describing loss of mRNA integrity as the main mechanism of instability during storage. We stored MC3 and our first generation C24 mRNA LNPs and found them stable at 4° C. over 3 weeks. Accelerated degradation at higher temperatures showed loss of mRNA integrity in our C24 LNPs was minimal compared to the complete loss of integrity in MC3 LNPs. This difference is possibly due to pKa differences of each lipid inside the LNP where MC3 is 9.4 and C24 is 8.1. The lower C24 pKa may create a lower pH in the C24 LNP compared to MC3 and slow the kinetics of base-mediated mRNA cleavage. In this section we will start with the current model of mRNA stability that includes pH and temperature dependence and compare predictions to stability analyses of free mRNA and mRNA in LNPs at a range of temperature and pH conditions. mRNA in LNPs will be extracted using chloroform/methanol for fragment analyses. Lipid stability will also be measured. A range of ionizable lipids with distinct pKa macroconstants will be formulated into LNPs to assess the role of this parameter as well as temperature and pH on mRNA degradation kinetics. We will establish a model of the form:

(mRNA degradation)=f(temperature, pH, ionizable lipid ionization/structural parameters)

This model enables predictive design of mRNA stability, a critical feature in manufacturing and distribution.

B3) LNP net charge ($NC_{LNP}$), surface charge ($SC_{LNP}$), endosomal protonation ($EP_{LNP}$), size ($D_{LNP}$), ionizable lipid membrane disrupting ability ($MD_{IL}$) and RNA release ability ($RR_{IL}$) prediction from LNP formulation parameters. This model will be for a fixed NP ratio (4) and ionizable lipid such as C24 initially and will relate lipid components/ratios to pH-dependent NCLNP, SCLNP, EPLNP, DLNP, MDIL and RRIL. For lipid components we will initially use C24, DSPC, cholesterol, PEG-DMG-2000 and add a 5th lipid that is negatively or positively charged following Cheng. We have found that by adding the negative 18-1PA to the lipids prior to mixing with mRNA that there is a large reduction of liver expression accompanied by a 2-3 fold increase in spleen expression upon IV administration of a luciferase reporter (FIG. 96). Although these effects are thought to be due to 18-1PA creating a negatively charged LNP, to date no measurement of the surface- or net-charge of these LNPs has been made. We propose to perform these measurements to develop this simulation module. We will use several negative lipids such as 18-OPA, 18-IPA, 18-2PA, wherein reducing double bonds from 2 to 0 is expected to move the lipid more to the surface of the LNP and away from the LNP interior. We will also place 18PAs directly on the LNP surface by incubation of LNPs in the post-mixing dilution well in a mixed aqueous/organic/electrolyte solvent that promotes insertion of 18PAs into the LNP surface rather than adding 18PAs to the other 4 lipids in ethanol prior to mixing. We will use positively charged lipids such as DOTMA and DOTAP as a 5th lipid to drive distribution to lung. We will also use positively or negatively charged PEG lipids. Changing the length of the PEG alkyl tails will be done since this strongly influences shedding and cell uptake as does length of the PEG chain itself. Finally, analogues will also be substituted for PEG-DMG-2000 in order to more effectively transfect T cells. NCLNP, SCLNP, EPLNP, DLNP, MDIL, RRIL will be measured as described above and related to 5th lipid and PEG lipid structure/addition-method/mole-fraction via the general form:

(NCLNP, SCLNP, EPLNP, DLNP, MDIL, RRIL)=f (5th lipid structure/addition-method/mole-fraction, PEG lipid structure/addition-method/mole-fraction, pH)

This model will enable predictive LNP targeting and expression by relating charge, size, membrane destabilization and RNA release parameters to the type of 5th lipid and PEG lipid in the LNP as well as their proportion and addition method. In a second stage we will design the ionizable lipid to also modify LNP charge.

B4) LNP net charge (NCLNP), surface charge (SCLNP), endosomal protonation (EPLNP), size (DLNP), ionizable lipid membrane disrupting ability (MDIL) and RNA release ability (RRIL) prediction from LNP manufacturing process parameters. This model will be based on experiments using a limited number (~5) of fixed formulations and ionizable lipids beginning with C24/DSPC/Cholesterol/PEG-DMG-2000 at standard mole ratios and NP ratio 4 with the 2,069 nucleotide FLuc mRNA. We have discovered two novel LNP assembly methods that increase potency of mRNA LNPs. As described above in the introduction, both methods require increased concentrations of lipids and mRNA prior to mixing. The second more recently discovered method removes the buffer from the mRNA solution and directly protonates the ionizable lipid by controlled HCl addition to the ionizable lipid in ethanol and, as shown above, can already provide a nearly 10× increase in potency. We measured zeta potential for the buffer-containing method and found a more negative high pH plateau and a consequently greater increase in zeta potential during a pH drop (7→5) representing endosomal protonation. This buffer-containing method increased DLNP by ~20 nm while the buffer-free method with yet higher potency does not change DLNP. We have no data on MDIL and RRIL for these process changes and have only limited ultrastructural information from CryoTEM. Here we propose to complete our characterization of these novel LNP assembly and manufacturing processes using the C24 LNP and assembling it using a range of lipid/mRNA concentrations, buffer concentrations, and levels of ionizable lipid protonation in the absence of buffer. We will measure NCLNP, SCLNP, EPLNP, DLNP, MDIL, RRIL as well as obtain ultrastructural information from CryoTEM imaging and scattering methods using SAXS (small angle x-ray scattering) and SANS (small angle neutron scattering). We have established these ultrastructural methods including contrast-variation SANS using deuterated lipids to obtain specific information on the distribution of lipid components and will define parameters/descriptors from these ultrastructural data to relate to assembly process parameters. Once the C24 LNP is characterized for these different assembly conditions, we will characterize further LNPs of interest. For a specific LNP we will obtain the model in the following general form:

(NCLNP, SCLNP, EPLNP, DLNP, MDIL, RRIL, Ultrastructural parameters)=f(lipid/mRNA concentration, buffer type/concentration, protonation level without buffer, pH)

This model will enable prediction of charge, size, membrane destabilization, RNA release and ultrastructural parameters from assembly and manufacturing conditions that change lipid/mRNA/buffer concentrations and the level of protonation of the ionizable lipid in a buffer-free environment.

B5) Continuum and molecular dynamics models of mRNA LNP. The purpose of this module is to provide insight into the mixing and assembly processes that give rise to mRNA LNP structures and properties that are related to LNP potency. We will model microfluidic and T-mixing geometries using continuum fluid mechanics combined with diffusion and chemical reaction equations. The ethanol and aqueous Newtonian fluids will mix in a manner that depends on the geometry of mixing and flow rates and ratios of the two solvents. The mixed solvent ethanol/water has a higher viscosity by ~3× than either solvent alone due to non-ideality and will be accounted for. The mRNA, lipid components and buffer will be treated as continuum solutes with diffusion constants drawn from literature that will have concentration dependence. Solutes that can be charged depending on pH (buffer, ionizable lipid) and the mRNA that is permanently charged will obey local net electroneutrality as well as the HH equation for the buffer and ionizable lipid with appropriate pKas. The initial simulations will determine flow and mixing patterns of the two fluids and, accounting for diffusion and electroneutrality and HH equations, we will calculate spatial concentrations of mRNA, the 4 lipids, ionizable lipid protonation and pH. LNP assembly during mixing is expected to be nucleated by thresholds of lipid and mRNA concentrations and ionizable lipid protonation as well as increased local water content creating lipid insolubility, i.e. when all 4 of these features occur at the same location. Simulations will be run for different values of lipid, mRNA and buffer concentrations that we know to influence final LNP potency. Spatial concentrations of lipids, mRNA, ionizable lipid protonation, local water content, and pH will be compared for high versus low potency assembly conditions. We have observed mixed populations of empty liposomes and RNA containing structures in the microfluidic channel for low concentration mixing while at high concentrations these structures appear fused (FIG. 97C). We hypothesize that these features can be explained by the extent of spatial overlap of lipids, mRNA, protonated ionizable lipid and local water content during mixing. We will remove the buffer and run simulations with predetermined ionizable lipid protonation to model the second high potency assembly method. We will examine both microfluidic and T-junction mixing geometries with conditions that produce a range of mRNA LNP potencies. Important parameters that will be calculated are:

FNML, the frequency of mRNA-LNP nucleation events characterized by the overlap of high lipid and mRNA concentrations along with ionizable lipid protonation and water content above critical thresholds (initially >25% and >50% respectively).

PNIL, the level of protonation at nucleation associated with FNML events (in the range 25-100%).

FNL, the frequency of empty LNP nucleation events characterized by the absence of either high mRNA concentration or ionizable lipid protonation remaining below a critical threshold (<25%).

We believe that high FNML will create more potent LNPs and high FNL less potent LNPs. We also hypothesize that PNIL needs to be above a critical threshold (i.e. 25%) for protonated ionizable lipid to ionically complex with mRNA, but below an upper threshold (i.e. 75%) so that unprotonated ionizable lipid is within the complex to protonate in the endosome as indicated by our zeta potential measurements. Here it is important to note that even though the LNP is neutralized up to pH 7.4 by dialysis or TFF that the pKa of the protonated ionizable lipid bound to the anionic mRNA phosphate backbone can be shifted upwards by as much as 2 points versus the unbound protonated ionizable lipid due to electrostatics. This will strongly favor maintaining protonation when bound thus making the presence of additional unprotonated unbound ionizable lipid within the LNP a necessity for endosomal release. We will derive general relationships of the following form for both the laminar microfluidic and turbulent T-mixing geometries and for different flow rates and solvent ratios:

(FNML, PNIL FNL)=f(mRNA/lipid concentrations, buffer concentration, preprotonation level without buffer)

As a second complementary aspect of this module we will use molecular dynamics simulations to model local molecular ionizable lipid/mRNA binding and LNP assembly under conditions known to affect LNP potency with high versus low concentrations of lipid/mRNA and with different levels of ionizable lipid protonation and buffer concentration that result from the above continuum simulations. Here we believe that low lipid/mRNA concentrations with high levels of ionizable lipid protonation will produce homogeneous assemblies with highly protonated ionizable lipid covering the mRNA backbone and excess protonated ionizable lipid aggregated around these structures. At higher concentrations, courser structures may be observed with internal parts of the mRNA backbone not bound to protonated ionizable lipid while external mRNA domains are bound to protonated ionizable lipid and excess unprotonated ionizable lipid surrounding these structures. We will model the latter structures interacting with bilayers and cytosolic conditions to determine if they are more readily released intracellularly. We will explicitly model pKa shifts upon binding to assess the magnitude of this potentially critical feature. To model our second method of high potency assembly, we will remove the buffer and preprotonate the ionizable lipid to different levels to observe resulting structures and distributions of the protonated and unprotonated fractions of ionizable lipid in both the high and low concentration regimes.

We believe that 1) high concentration mixing can produce courser ionic aggregates where mRNA is more easily released and 2) that lower levels of preprotonation of the ionizable lipid are more potent due to the presence of defined buffer-independent levels of unprotonated species able to participate in endosomal release. The models in this section will provide understanding of manufacturing process parameters that produce high potency mRNA LNPs.

B6) cGMP compatible production of ligand targeted LNPs and measurement of ligand density ρL and binding affinity. Current ligand conjugated LNPs increase cell specific targeting by at least 10× but suffer from a production method (direct chemical conjugation or post-insertion to the LNP) that is difficult to control and render compatible with cGMP manufacturing. High levels of non-specific expression in organs like the liver remain and are also problematic. Here we propose to develop a cGMP compatible self-assembly method to produce ligand-bearing LNPs and to quantify ligand density (pL) and binding affinity (KDL) to the target and to reduce off-target expression by controlling LNP charge. We will start with the CD4 T cell targeting antibody that we have successfully conjugated to LNPs and use an scFv anti-CD4 protein that can be site-specifically linked to the PEG moiety. Rather than employ the micellar post-insertion method, we will chemically conjugate the anti-mouse CD4 scFv directly to monomeric DSPE-PEG2000-malemide and identify organic/aqueous/electrolyte solvent conditions that maintain the monomeric state for placement in the dilution well post-microfluidic mixing of LNPs and incorporation into the LNP surface. We have already altered the organic/aqueous/electrolyte solvent conditions to maintain the structure of the LNPs produced in the microfluidic channel or to induce LNP fusion as typically occurs. We will therefore be able to perform a screening study of multiple organic/aqueous/electrolyte solvent conditions in the dilution well capable of controlling LNP stability and controlling incorporation of the conjugated lipid into the LNP surface. The resultant LNPs will be separated from unbound scFv by centrifugal filtration or by size-exclusion chromatography (Sepharose CL-4B) and protein content measured in the LNP-containing concentrate and in the filtrate to assess the amount of ligand associated with the LNP. This bound ligand amount will be normalized to particle number obtained by nanoparticle tracking and to mRNA content obtained by the ribogreen assay to provide ligand density ρL content as number of scFv per LNP and alternatively the mass or mole ratio of scFv to mRNA. The binding affinity of the anti-CD4 conjugated LNP with the CD4 ligand, KDL will be measured using surface plasmon resonance (SPR) and isothermal titration calorimetry (ITC44) using methods we developed previously in our laboratories. In addition to these quantitative assessments of ligand density and binding affinity, we will image ligand distribution by CryoTEM (DTEML) in order to visualize scFv distribution using both negative staining with contrast enhancement by incubation and binding of CD4 to the ligand as well as gold-labelled antibody immunostaining. Once the production methods have been selected, we will produce a range of ligand densities and affinity/avidity by modifying solvent conditions and conjugated lipid concentration in the dilution well. Final LNPs for cell and animal testing will then be characterized for net charge and surface charge. In a later stage, we will modify the charge of ligand conjugated LNPs using the methods in B1 and B4 above in order to combine and co-ordinate charge-mediated targeting with ligand-mediated targeting. For example, the charge adjustment promises to remove off-target expression in liver for LNPs that target splenic T-cells (FIG. 96). Our use of this published CD4 targeting LNP with cGMP production and eliminated liver expression will be an initial proof of concept for this approach. The second proof of concept will be to apply these methods to display the peptide ligand of neural cell adhesion molecule (NCAM) to target skeletal muscle. The smaller protein component here will significantly alter organic/aqueous/electrolyte solvent conditions required for its incorporation in the LNP surface. The specific model outcomes to be derived in the initial stages of this module for a prototype C24 LNP and anti-CD4 PEG lipid are represented by the general form:

(ρL, KDL, DTEML)=f(organic/aqueous/electrolyte solvent conditions, ligand type/concentration)

The methods and model derived in this section will permit the controlled manufacturing of LNPs displaying a range of ligand types (Abs, peptides) with characterized ligand density and affinity.

C) Assessment of Delivery Efficiency, Toxicity and Reactogenicity In Vitro.

C1) In vitro assessment of delivery efficiency. Methods of mRNA LNP transfection using a luciferase reporter will be carried out on cell types that represent easily transfectable cells (HEK293), suspension cells (CHO), endothelial cells (HUVEC), muscle cells (C212), macrophages (RAW), hepatocytes (Hep G2) and T cells (Jurkat) and primary human CD4+ T cells. Metabolic toxicity will be assessed by Alamar Blue. The relationships we will establish here are as follows:

(efficiency, toxicity) in Cell(j)=f(NCLNP, SCLNP, EPLNP, DLNP, MDIL, RRIL, ρL, KDL, dose)

C2) In vitro predictors of toxicity and reactogenicity. To relate innate immune reactogenicity to LNP structure and mRNA LNP formulations, high throughput screening will be carried out with cell-free and cell-based assays of innate immune activation. Complement and FXIIa activation in blood plasma are considered to be potential drivers of LNP-induced acute anaphylactoid reactions. Complement activation will be measured by exposing human citrated blood plasma to LNPs followed by Western blot analysis of C3 zymogen conversion to C3b. If anionic RNA surfaces become exposed after LNP are in contact with blood plasma, this could potentially lead to Factor XII (FXII) activation which generates bradykinin, a vasodilator linked to anaphylaxis. As the initiating step of the contact pathway, FXII activation is followed by thrombin generation which could enhance the risk of coagulopathy. FXII activation by RNA LNPs will be measured using a thromboelastography (TEG) assay developed in our laboratory, where anionic surfaces can induce burst coagulation of microparticle-depleted plasma that otherwise fails to clot after addition of calcium. Cell-based reactions will include hemolysis and osmotic fragility of red blood cells with increasing LNP dosage at pH levels seen in the lung (~pH 7.4) and the extravascular space (~pH 6.7). We have already assessed the potential for LNPs to induce innate immune activation in peripheral white blood cells by incubating LNPs encoding eGFP with heparinized human blood for 4 hours at 37° C. then measured the generation of reactogenicity cytokines (IL-6, IL-8). LNPs were also tested in a novel cultured clot assay, with unmodified human whole blood where C24 LNPs had lower reactogenicity than MC3 LNPs. Cultured clot cells expressed eGFP after 24 hours but no eGFP expression was seen in heparinized blood, suggesting that our novel cultured clot assay was superior for screening toxicity and expression of LNP formulations. RNAseq of LNP-spiked cultured clots will allow us to test the hypothesis that LNP mRNA expression is associated with specific innate immune responses that precede successful adaptive immune responses. The general form of the relationship we will establish here is the following:

(FXII activation, complement activation, inflammatory/antigen-presentation cytokines)=f(NCLNP, SCLNP, EPLNP, DLNP, MDIL, RRIL, ρL, KDL, ionizable lipid descriptors, dose, pH)

This model will predict toxicity and reactogenic responses based on LNP features.

D) Assessment of delivery efficiency, targeting and toxicity/reactogenicity in rodent and non-human primate (NHP) models. The mRNA LNPs designed using the above predictive models will be characterized in mice, rat and NHP models for organ- and cell-specific delivery efficiency, as well as for toxicity.

D1) Mouse model assessments of expression and targeting. In IV administration to mice, we will assess mRNA expression and biodistribution independent of expression to liver, lung, spleen, lymph nodes, heart, bone marrow, skeletal muscle, eye, brain, testes and ovaries using 3 mRNA encoded reporters: luciferase, mCherry and a Cre recombinase reporter in Ai6 RCL-ZsGreen1 transgenic mice. Ex vivo IVIS imaging will be used for the luciferase reporter while histology and flow cytometry will be used for mCherry and Cre-activated ZsGreen. During the first 72 hours post-administration, organs from animals receiving the mCherry and Cre reporters will be homogenized and cells released enzymatically for flow cytometry as previously described. These two reporters are complementary since once Cre-R is expressed in the Ai6 model, a cell is permanently green but at levels that can be cell-type dependent with some heterogeneity. mCherry expression is transient but can indicate intensity of mRNA translation.

We will derive 5 measures of organ-specific targeting:

Organ (i) IVIS_expression=integrated organ IVIS signal (photons/s) at 4 hours

Organ (i) mCherryF_expression=summed cell mCherry fluorescence intensity per organ (Fluo/organ)

Organ (i) ZsGreenF_expression=summed cell ZsGreen fluorescence intensity per organ (Fluo/organ)

Organ (i) mCherryC_expression=summed mCherry positive cells per organ (Fluo/organ)

Organ (i) ZsGreenC_expression=summed ZsGreen positive cells per organ (Fluo/organ)

In flow cytometry, specific markers for stromal cells, hematological cells, antigen-presenting cells and organ-specific cell types will indicate expression of mCherry and ZsGreen per cell type providing the indicators:

Cell (j) in Organ (i) mCherryF_expression=summed mCh fluorescence intensity (j) cells/total intensity Cell (j) in Organ (i) ZsGreenF_expression=summed ZsG fluorescence intensity (j) cells/total intensity Cell (j) in Organ (i) mCherryC_expression=summed mCh positive (j) cells/total positive cells.

Cell (j) in Organ (i) ZsGreenC_expression=summed ZsG positive (j) cells/total positive cells For IV administration, IVIS indicators will be obtained for all dissected organs while cell specific expression will be limited to spleen and liver initially. In liver single cell suspensions, cell surface markers will used to indicate hepatocytes, sinusoidal endothelial cells, Kupffer cells, neutrophils and dendritic cells using the markers: (ASGR1, CD16/CD32, CD31, CD11c, CD11b, CD209, CD64, CD45, ESAM, Ly-6g, CD49b, CD19, CD3e, I-A/I-E, Tim-4, CD206, F4/80, CD24, CD86, OX40L). In spleen single cell suspensions, cell surface markers will indicate T lymphocytes, B lymphocytes, macrophages, dendritic cells using the markers: (B220, CCR2, CD3, CD14, CD19, CD49b, CD68, CD71, CD103, CD117, CD169, CD206, Mac2, Mac3, MerTK, Siglec F, CD24, CD86, OX40L). In histology, we will use quantitative histomorphometry image analyses to assess cell-type specific expression as % area per cell type with positive expression. To assess biodistribution that is independent of expression we will use a branched DNA (bDNA) assay on organ homogenates. Additional organs will also be perfused prior to processing to remove interstitial LNPs and then assayed by bDNA on single cell suspensions of the organ and measure bDNA and expression in the suspension. The above organ- and cell-specific expression and distribution data will be related to LNP parameters characterized in the previous section through generalized models of the following type:

Organ(i) expression/distribution=f(NCLNP, SCLNP, EPLNP, DLNP, MDIL, RRIL, ρL, KDL, dose)

Cell(j) Organ(i) expression/distribution=f(NCLNP, SCLNP, EPLNP, DLNP, MDIL, RRIL, ρL, KDL, dose)

We expect the above relationships to be generalizable and to guide us in LNP design since the features of LNPs that are known to drive expression and targeting are on the right hand side of the above expressions. We will also explore potential relationships with ionizable lipid structural descriptors, formulation and manufacturing parameters in a second stage of multi-level models to fully exploit this data set. Our very diverse ionizable lipid library combined with a large space of formulation and manufacturing modifications is likely to provide the ability to change targeting dramatically. We will use initial findings with the ionizable lipid family in FIG. 94 to set our baseline and then sample other library families and candidates to map out targeting our design space. These results with then guide us in further ionizable lipid design and formulation/manufacturing changes.

In IM administration to mice we will use the same assessments described above but in addition we will add ex vivo IVIS imaging of the injection site and draining lymph nodes. The injection site and draining lymph nodes will be analyzed in flow cytometry for mCherry and ZsGreen expression as above to identify neutrophils, monocytes, eosinophils, basophils, mast cells and dendritic cells using the markers listed above for spleen cells. Histological analyses of the injection site will be as above for IV administration and specifically include myocytes and adipocytes. The outcomes of this section will predict organ and cell-specific targeting and expression to LNP features that are expected to strongly influence these performance parameters but have never been previously related to targeting and expression. The results should clarify these dependencies and provide guidance in designing new ionizable lipids, formulations and manufacturing processes to further improve targeted expression of mRNA LNPs.

D2) Mouse model assessments of toxicity and reactogenicity. Toxicity of LNPs has been reduced by the incorporation of degradable esters into the ionizable lipid that are cleaved by in vivo hydrolases and produce fragments that are small enough and hydrophilic enough to be excreted in urine and feces. The single slowly degrading secondary ester in MC3 produces a dilinoleic acid with very slow elimination time and a strong tendency to accumulate in tissues. Incorporating additional degradable esters into the alkyl tails accelerated degradation. Incorporating the quickly degraded primary ester into the branched chains of the ionizable lipids of Moderna also produced much faster degradation than MC3 and reduced systemic toxicity in rodents after IV administration6l as well as reducing injection site inflammation after IM administration. Similar findings were reported from another group comparing another ionizable lipid with multiple primary esters that generated lower toxicity than MC3. The rate of in vivo degradation is therefore a significant factor in determining toxicity and reactogenicity. Our current ionizable lipid library contains >100 synthesized proprietary compounds with structures that contain between 0 and 6 degradable esters producing fragments with a range of predictable sizes. Chemical descriptors describing these degradability features will be related to in vivo measurements of toxicity and degradability. We will measure degradability in vivo using published LC-MS methods applied to extracted tissue homogenates. We will assess toxicity using established methods that measure systemic cytokines in serum as well as ALT and AST levels in blood and liver/spleen histopathology. For IM administration, we will also assess pro-inflammatory cytokines in tissue homogenates of the injection site and the draining lymph nodes to correlate with toxicity and APC activation. Histological analyses will include immunostaining to identify cell types involved in the inflammatory response at the injection site and draining lymph nodes. These results will allow us to build the following relationship:

(degradability, inflammation/APC activation)=f(ionizable lipid descriptors, LNP descriptors, dose)

D3) Mouse model assessments of immunogenicity and adjuvanticity. In addition to providing high delivery efficiency, LNPs used for mRNA vaccines need to act as an adjuvant that enhances the number of antigen specific T follicular helper (Tfh) cells and germinal center B (GC B) cells in draining lymph nodes. This LNP specific adjuvant activity helps drive immunoglobulin class switching, affinity maturation, and development of long-term B cell memory and plasma cells64. Since these effects are known to depend on the ionizable lipid, we will measure antigen-specific Tfh and GC B cells responses in the draining lymph nodes and spleen and relate them to structural features of the ionizable lipid. Immmunogenicity will also be assessed using the current mRNA-encoded nucleoside modified immunogen for SARS-CoV-2, the diproline-stabilized spike protein (S2P). Binding titers and neutralization titers against a SARS-CoV-2 pseudovirus will be measured after a prime and a boost at low doses in Balb/c mice from 0.1 to 1 μg as recently published5. The relationships determined here are:

(Titers, Tfh, GC B)=f(ionizable lipid descriptors, NCLNP, SCLNP, EPLNP, DLNP, MDIL, RRIL, ρL, KDL, dose)

We will complement the above analyses of cellular responses and cytokine responses at the injection site and draining lymph nodes with spatial transcriptomics. Transcriptome profiles will indicate immune activation, lipid metabolism and toxicity and portray the dynamics of molecular events induced by specific ionizable lipid features.

D4) Rat and non-human primate model assessments of expression, targeting, toxicity, reactogenicity, immunogenicity. The relatively high throughput mouse models above will be followed up with select studies done in rats and non-human primates since these are necessary prerequisites for human studies and can reveal species dependencies. Non-human primates often show distinct differences from rodent models and anecdotal reports of LNP targeting in rats suggest that rats may more closely represent non-human primates than mice. We will therefore carry out select rat studies for targeting in the second year of this project, in a similar manner as described above. A limited number of non-human primate studies will be performed in year 3 based on the totality of data obtained to date at that point.

E) Predictive model development. Data sets generated in the above studies will be used to develop predictive models that relate mRNA LNP performance measured in sections C and D to the LNP features that are currently expected to strongly influence performance as described in section B above. These LNP features in turn depend on chemical structures, formulation parameters, and manufacturing processes, creating a multi-layered interdependent set of models and underlying data used to develop those models. We will therefore develop machine learning, knowledge-networks and multi-level functional simulation modules relating parametric data collected at multiple levels that will be statistically and mechanistically modelled (using the in silico tools developed above) to understand potential relationships. Molecular, formulation, and manufacturing parameters will be used to predict LNP features known to influence performance, and these LNP features will be used to predict performance such as expression, targeting and toxicity in animal models. In silico models will be guided and tuned with data generated from in vitro and in vivo experiments. These predictive models will be trained using state-of-the-art machine learning algorithms that will help to identify relevant variables from the different domains (molecular, formulation, manufacturing, LNP, performance). The predictive performance and the importance of individual variables will be rigorously evaluated based on cross-validation strategies.

The foregoing detailed description and accompanying examples are merely illustrative and are not to be construed as limitations on the scope of the invention, which is to be determined solely by the appended claims and their equivalents.

Various changes and modifications to the disclosed embodiments will be apparent to those skilled in the art. Such alterations and modifications, including, but not limited to, chemical structures, substituents, derivatives, intermediates, syntheses, compositions, formulations, or methods of use of the invention, are intended to be within the spirit and scope of the invention.

For all patents, applications, or other reference cited herein, such as non-patent literature and reference sequence information, it should be understood that they are incorporated by reference in their entirety for all purposes as well as for the proposition that is recited. Where any conflict exists between a document incorporated by reference and the present application, this application will control. All information associated with reference gene sequences disclosed in this application, such as GeneIDs or accession numbers (typically referencing NCBI accession numbers), including, for example, genomic loci, genomic sequences, functional annotations, allelic variants, and reference mRNA (including, e.g., exon boundaries or response elements) and protein sequences (such as conserved domain structures), as well as chemical references (e.g., PubChem compound, PubChem substance, or PubChem Bioassay entries, including the annotations therein, such as structures and assays, et cetera), are hereby incorporated by reference in their entirety.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g., elements, including numerical ranges and exemplary embodiments) of particular embodiments and aspects of the invention, including the working examples. For example, particular experimental parameters exemplified in the working examples can be adapted for use in the claimed invention piecemeal without departing from the invention. For example, for materials that are disclosed, while specific reference of each of the various individual and collective combinations and permutations of these compounds may not be explicitly disclosed, each is specifically contemplated and described herein. Thus, if a class of elements A, B, and C are disclosed as well as a class of elements D, E, and F and an example of a combination of elements A-D is disclosed, then, even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-groups of A-E, B-F, and C-E are specifically contemplated and should be considered disclosed from disclosure of A, B, and C; D, E, and F; and the example combination A-D. This concept applies to all aspects of this application, including elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art-thus, to the extent an element is described in one or more references known to the person having ordinary skill in the art, they may be excluded from the claimed invention by, inter alia, a negative proviso or disclaimer of the feature or combination of features.

What is claimed is:

1. A compound of Formula III:

Formula III

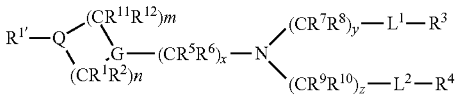

wherein each of $R^1$, $R^2$, $R^{11}$, and $R^{12}$ is independently selected from the group consisting of H, optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C_6$ heteroaryl, optionally substituted $C_4$-$C_8$ aryloxy, optionally substituted $C_7$-$C_{10}$ arylalkyl; optionally substituted $C_5$-$C_{10}$ heteroarylalkyl group, and optionally substituted amine;

wherein $R^{1'}$ is selected from the group consisting of H, $C_1$-$C_{12}$ alkyl, optionally substituted $C_2$-$C_{12}$ alkenyl, optionally substituted $C_2$-$C_{12}$ alkynyl, optionally substituted $C_3$-$C_6$ cycloalkyl, optionally substituted $C_4$-$C_6$ heterocycloalkyl, optionally substituted $C_4$-$C_6$ alkylcycloalkyl, optionally substituted $C_4$-$C_6$ aryl, optionally substituted $C_3$-$C_6$ heteroaryl, optionally substituted $C_4$-$C_8$ aryloxy, optionally substituted $C_7$-$C_{10}$ arylalkyl; optionally substituted $C_5$-$C_{10}$ heteroarylalkyl group, and optionally substituted amine;

wherein each of $R^3$ and $R^4$ is independently selected from the group consisting of optionally substituted branched $C_1$-$C_{22}$ alkyl and optionally substituted $C_2$-$C_{22}$ alkenyl;

wherein each of $R^5$, $R^6$, $R^7$, $R^8$, $R^9$, and $R^{10}$ is independently selected from the group consisting of H, OH, halo, phenyl, benzyl, optionally substituted $C_1$-$C_{22}$ alkyl, optionally substituted $C_2$-$C_{22}$ alkenyl, and optionally substituted $C_2$-$C_{22}$ alkynyl;

wherein each of x, y, and z is independently an integer selected from 0-10;

wherein G and Q are each N;

wherein each of m and n is 2; and wherein each of $L^1$ and $L^2$ is independently selected from the group consisting of OC(═O)— and C(═O)O—.

2. The compound of claim 1, wherein the compound has the following structure:

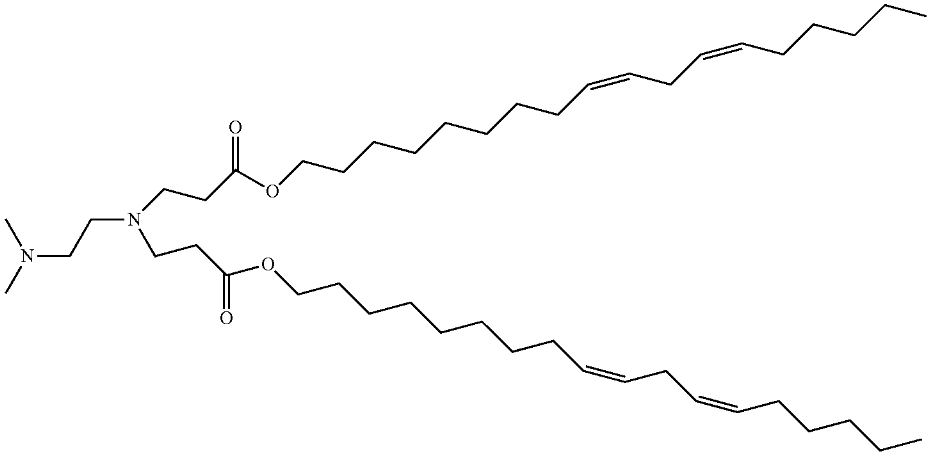 [SMILES: CCCCC/C=C\C/C=C\CCCCCCCCOC(=O)CCN(CCC(=O)OCCCCCCCC/C=C\C/C=C\CCCCC)CCN(C)C]

3. The compound of claim 1, wherein the compound has the following structure:

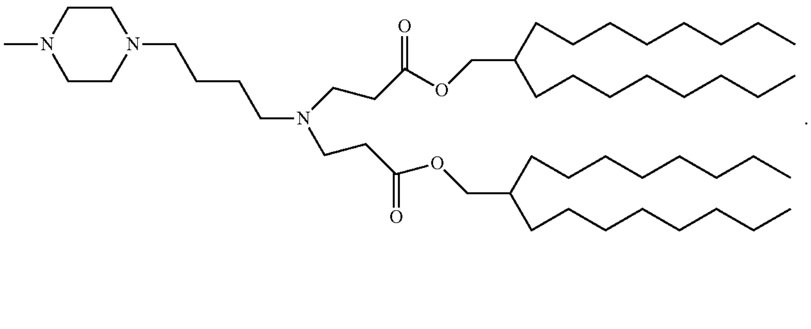 [SMILES: CCCCCCCCC(CCCCCCCC)COC(=O)CCN(CCCCN1CCN(C)CC1)CCC(=O)OCC(CCCCCCCC)CCCCCCCC]

4. The compound of claim 1, wherein the compound has the following structure:
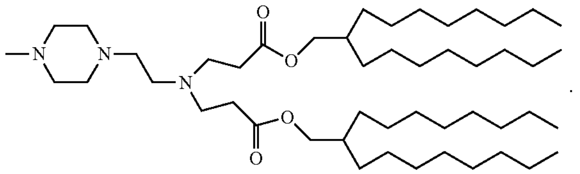 [SMILES: CCCCCCCCC(CCCCCCCC)COC(=O)CCN(CCC(=O)OCC(CCCCCCCC)CCCCCCCC)CCN1CCN(C)CC1]
5. The compound of claim 1, wherein the compound has the following structure:
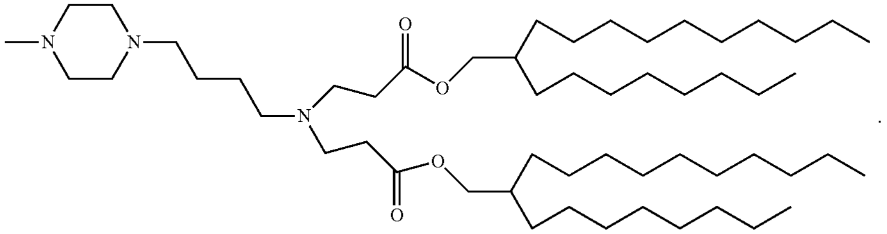 [SMILES: CCCCCCCCCCC(CCCCCCCC)COC(=O)CCN(CCCCN1CCN(C)CC1)CCC(=O)OCC(CCCCCCCC)CCCCCCCCCC]
6. The compound of claim 1, wherein the compound has the following structure:
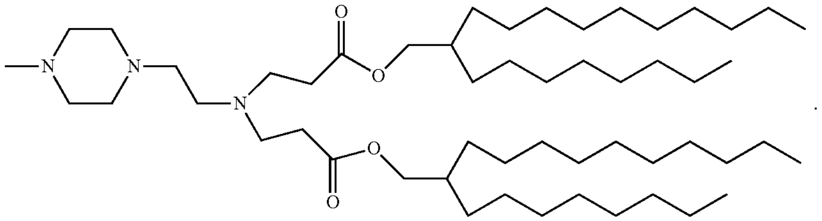 [SMILES: CCCCCCCCCCC(CCCCCCCC)COC(=O)CCN(CCC(=O)OCC(CCCCCCCC)CCCCCCCCCC)CCN1CCN(C)CC1]
7. The compound of claim 1, wherein the compound has the following structure:
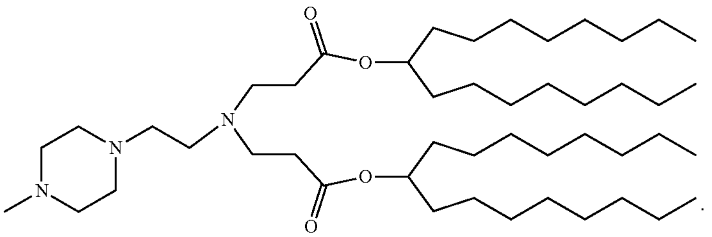 [SMILES: CCCCCCCCC(CCCCCCCC)OC(=O)CCN(CCC(=O)OC(CCCCCCCC)CCCCCCCC)CCN1CCN(C)CC1]

8. The compound of claim 1 wherein x is 2, 3, or 4.

9. The compound of claim 1, wherein y is 2, 3, or 4.

10. The compound of claim 1, wherein z is 2, 3, or 4.

11. The compound of claim 1, wherein $R^3$ and $R^4$ are each optionally substituted branched $C_1$-$C_{22}$ alkyl.

12. The compound of claim 2, wherein $R^3$ and $R^4$ are each optionally substituted branched $C_1$-$C_{22}$ alkyl;

$R^{1'}$ is $C_1$-$C_{12}$ alkyl;

x is 2, 3, or 4;

y is 2, 3, or 4; and z is 2, 3, or 4.

13. The compound of claim 1, wherein $R^{1'}$ is $C_1$-$C_{12}$ alkyl.

* * * * *